US009726666B2

(12) United States Patent
Winqvist et al.

(10) Patent No.: US 9,726,666 B2
(45) Date of Patent: Aug. 8, 2017

(54) DIAGNOSING AND TREATING INFLAMMATORY DISEASES

(71) Applicant: TLA Targeted Immunotherapies AB, Stockholm (SE)

(72) Inventors: Ola Winqvist, Uppsala (SE); Graham Cotton, Edinburgh (GB)

(73) Assignee: TLA Targeted Immunotherapies AB, Stockholm (SE)

( * ) Notice: Subject to any disclaimer, the term of this patent is extended or adjusted under 35 U.S.C. 154(b) by 440 days.

(21) Appl. No.: 14/105,628

(22) Filed: Dec. 13, 2013

(65) Prior Publication Data

US 2014/0175018 A1    Jun. 26, 2014

Related U.S. Application Data

(63) Continuation-in-part of application No. PCT/GB2012/051357, filed on Jun. 13, 2012, and a continuation-in-part of application No. PCT/GB2012/051349, filed on Jun. 13, 2012, and a continuation-in-part of application No. PCT/GB2012/051348, filed on Jun. 13, 2012, and a continuation-in-part of application No. PCT/GB2012/051351, filed on Jun. 13, 2012, and a continuation-in-part of application No. PCT/GB2012/051350, filed on Jun. 13, 2012, and a continuation-in-part of application No. PCT/GB2012/051355, filed on Jun. 13, 2012, and a continuation-in-part of application No. PCT/GB2012/051345, filed on Jun. 13, 2012, and a continuation-in-part of application No. PCT/GB2012/051352, filed on Jun. 13, 2012, and a continuation-in-part of application No. PCT/GB2012/051346, filed on Jun. 13, 2012, and a continuation-in-part of application No. PCT/GB2012/051353, filed on Jun. 13, 2012, and a continuation-in-part of application No. PCT/GB2012/051356, filed on Jun. 13, 2012, and a continuation-in-part of application No. PCT/GB2012/051354, filed on Jun. 13, 2012.

(60) Provisional application No. 61/496,442, filed on Jun. 13, 2011, provisional application No. 61/496,167, filed on Jun. 13, 2011, provisional application No. 61/496,288, filed on Jun. 13, 2011, provisional application No. 61/496,242, filed on Jun. 13, 2011, provisional application No. 61/496,209, filed on Jun. 13, 2011, provisional application No. 61/496,195, filed on Jun. 13, 2011, provisional application No. 61/496,228, filed on Jun. 13, 2011, provisional application No. 61/496,264, filed on Jun. 13, 2011,
(Continued)

(51) Int. Cl.
*A61K 39/00* (2006.01)
*A61M 37/00* (2006.01)
*A61K 39/395* (2006.01)
*A61K 39/40* (2006.01)
*G01N 33/566* (2006.01)
*A61M 1/36* (2006.01)
*G01N 33/569* (2006.01)

(52) U.S. Cl.
CPC ......... *G01N 33/566* (2013.01); *A61M 1/3679* (2013.01); *G01N 33/56972* (2013.01); *G01N 2333/70596* (2013.01); *G01N 2333/7158* (2013.01); *G01N 2800/065* (2013.01)

(58) Field of Classification Search
None
See application file for complete search history.

(56) References Cited

U.S. PATENT DOCUMENTS

2003/0017979 A1    1/2003    Mack
2003/0215421 A1    11/2003   McDonald
(Continued)

FOREIGN PATENT DOCUMENTS

DE    102005036505 A1    6/2006
EP        1255112 A2     11/2002
(Continued)

OTHER PUBLICATIONS

Terada, et al., "Stromal Cell-Derived Factor-1 from Biliary Epithelial Cells Recruits CXCR4-Positive Cells: Implications for Inflammatory Liver Disease", Laboratory Investigation, vol. 83, No. 5, May 1, 2003, 665-672.
Teraki, et al., "Homing Receptor and Chemokine Receptor on Intraedidermal T Cells in Psoriasis Vulgaris", Clinical and Experimental Dermatology, vol. 29, No. 6, Nov. 1, 2004, 658-663.
Tylaska, "CCR2 Regulates the Level of MCP-1/CCL2 in Vitro and at Inflammatory Sites and Controls T Cell Activation in Response to Alloantigen", Cytokine, vol. 18, No. 4, May 1, 2002, 184-190.
(Continued)

*Primary Examiner* — Shulamith H Shafer
(74) *Attorney, Agent, or Firm* — Johnson, Marcou & Isaacs, LLC

(57) ABSTRACT

A method of diagnosing, monitoring progression of, or monitoring treatment of inflammatory bowel disease comprises determining the levels of $CD14^+HLA\text{-}DR^{hi}$ monocytes or monocytes expressing CCR7 or CCR9 or both CCR7 and CCR9 in a sample obtained from a subject, wherein high levels of $CD14^+HLA\text{-}DR^{hi}$ monocytes or monocytes expressing CCR7 or CCR9 or both CCR7 and CCR9, or increased levels of $CD14^+HLA\text{-}DR^{hi}$ monocytes or monocytes expressing CCR7 or CCR9 or both CCR7 and CCR9 compared to control, indicate the presence or progression of inflammatory bowel disease. Similar methods for diagnosing irritable bowel syndrome are also described. Various companion therapeutic methods and useful binding reagents are also described.

9 Claims, 139 Drawing Sheets

Related U.S. Application Data provisional application No. 61/496,184, filed on Jun. 13, 2011, provisional application No. 61/496,329, filed on Jun. 13, 2011, provisional application No. 61/496,377, filed on Jun. 13, 2011, provisional application No. 61/496,352, filed on Jun. 13, 2011.

(56) References Cited

U.S. PATENT DOCUMENTS

| | | | |
|---|---|---|---|
| 2004/0077835 A1* | 4/2004 | Offord | C07K 14/521 530/351 |
| 2007/0092484 A1 | 4/2007 | Levine | |
| 2010/0029753 A1 | 2/2010 | Anderson | |

FOREIGN PATENT DOCUMENTS

| | | |
|---|---|---|
| EP | 1783227 A1 | 5/2007 |
| EP | 2067495 A1 | 6/2009 |
| EP | 2118060 A1 | 11/2009 |
| WO | 0050088 A2 | 8/2000 |
| WO | 0125492 A1 | 4/2001 |
| WO | 0140306 A1 | 6/2001 |
| WO | 2004026893 A2 | 4/2004 |
| WO | 2004045526 A2 | 6/2004 |
| WO | 2005037305 A1 | 4/2005 |
| WO | 2006052723 A2 | 5/2006 |
| WO | 2006125201 A2 | 11/2006 |
| WO | 2006126209 A1 | 11/2006 |
| WO | 2007024705 A2 | 3/2007 |
| WO | 2007133147 A1 | 11/2007 |
| WO | 2008059066 A1 | 5/2008 |
| WO | 2008142405 A1 | 11/2008 |
| WO | 2010021697 A2 | 2/2010 |
| WO | 2010029317 A2 | 3/2010 |
| WO | 2010103517 A1 | 9/2010 |
| WO | 2010142952 A2 | 12/2010 |
| WO | 2011017120 A1 | 2/2011 |
| WO | 2012112724 A1 | 8/2012 |

OTHER PUBLICATIONS

Vergunst, et al., "Modulation of CCR2 in Rheumatoid Arthritis—A Double-Blind, Randomized, Placebo-Controlled Clinical Trial", Arthritis & Rheumatism, vol. 58, No. 7, Jul. 1, 2008, 1931-1939.
Walters, et al., "Characterization of CCX282-B, and Orally Bioavailable Antagonist of the CCR9 Chemokine Receptor, for Treatment of Inflammatory Bowel Disease", Journal of Pharmacology and Experimental Therapeutics, vol. 335, No. 1, Oct. 1, 2010, 61-69.
Williams, et al., "Eotaxin and CCR3 as Therapeutic Targets in Asthma and Allergy", Chemokines 2, retrieved from the Internet on Sep. 17, 2012: http://www.pasteur.fr/applications/euroconf/chemokines2/Williams.pdf Jan. 1, 2003, 4.
Yawalkar, et al., "Enhanced Expression of Eotaxin and CCR3 in Atopic Dermatitis", Journal of Investigative Dermatology, vol. 113, No. 1, Jul. 1, 1999, 43-48.
International Search Report and Written Opinion for PCT/GB2012/051346, Jan. 11, 2013, 22 pages.
International Search Report and Written Opinion for PCT/GB2012/051353, Jan. 11, 2013, 22 pages.
International Search Report and Written Opinion for PCT/GB2012/051355, Jan. 11, 2013, 22 pages.
International Search Report and Written Opinion for PCT/GB2012/051348, Jan. 11, 2013, 23 pages.
International Search Report for PCT/GB2012/051356, Jan. 11, 2013, 6 pages.
International Search Report for PCT/GB2012/051352, Jan. 11, 2013, 7 pages.
International Search Report for PCT/GB2012/051354, Jan. 11, 2013, 7 pages.
International Search Report for PCT/GB2012/051351, Jan. 2, 2013, 5 pages.
International Search Report for PCT/GB2012/051349, Jan. 2, 2013, 7 pages.
European Office Action for European Patent Application No. 12727915.6, Oct. 13, 2015, 3 pages.
International Search Report for PCT/GB2012/051357, Nov. 19, 2012, 6 pages.
European Office Action for European Patent Application No. 1272680.6, Mar. 16, 2015, 6 pages.
Chinese Office Action for Chinese Patent Application No. 2012800396667, English translation only provided to Applicant, Jun. 17, 2015, 8 pages.
International Search Report and Written Opinion for PCT/GB2012/051345, Jan. 11, 2013, 24 pages.
International Search Report for PCT/GB2012/051350, Jan. 11, 2013, 6 pages.
An, et al., "Immunohistochemical Detection of CCR2 and CX3CR1 in Sepsis-Induced Lung Injury", Forensic Science International, Nov. 20, 2009, e21-e25.
Autschbach, et al., "Expression of Chemokine Receptors in Normal and Inflamed Human Intestine, Tonsil, and Liver", Cellular Immunology, vol. 236, Sep. 23, 2005, 110-114.
Bellani, et al., "Altered MRNA Levels of Chemokines and Cytokines in Schizophrenia and Bipolar Disorder", Schizophrenia Research, vol. 117, No. 2-3, Apr. 1, 2010, 251-252.
Beumer, et al., "Increased Level of Serum Cytokines, Chemokines and Adipokines in Patients with Schizophrenia is Associated with Disease and Metabolic Syndrome", Psychoneuroendocrinology, Apr. 1, 2012, 1901-1911.
Borchers, et al., "Lymphocyte Recruitment and Homing to the Liver in Primary Biliary Cirrhosis and Primary Sclerosing Cholangitis", Seminars in Immunopathology, vol. 31, No. 3, Jun. 17, 2009, 309-322.
Bossink, et al., "Plasma Levels of the Chemokines Monocyte Chemotactic Protein-1 and -2 are Elevated in Human Sepsis", Blood, vol. 86, No. 10, Nov. 15, 1995, 3841-3847.
Cancello, et al., "Review Article: Is Obesity an Inflammatory Illness? Role of Low-Grade Inflammation and Macrophage Infiltration in Human White Adipose Tissue", BJOG: An International Journal of Obstetrics and Gynecology, vol. 113, No. 10, Oct. 1, 2006, 1141-1147.
Chantry, et al., "Chemokines in Allergy", Current Drug Targets—Inflammation & Allergy, vol. 1, No. 1, Jan. 1, 2002, 109-116.
Charo, et al., "Chemokines in the Pathogenesis of Vascular Disease", Circulation Research, vol. 95, No. 9, Oct. 29, 2004, 858-866.
De Boer, et al., "Cytokines and Therapy in COPD: A Promising Combination?", Chest, vol. 121, No. 90050, May 1, 2002, 209S-218.
Eksteen, et al., "Hepatic Endothelial CCL25 Mediates the Recruitment of CCR9+ Gut-Homing Lymphocytes to the Sclerosing Cholangitis", Journal of Experimental Medicine, vol. 200, No. 11, Dec. 6, 2004, 1511-1517.
Feng, "Involvement of a Novel Chemokine Decoy Receptor CCX-CKRin Breast Cancer Growth Metastasis and Patient Survival", Clinical Cancer Research, vol. 15, No. 9, May 1, 2009, 2962-2970.
Grant, et al., "Hepatic Expression of Secondary Lymphoid Chemokine (CCL21) Promotes the Development of Portal-Associated Lymphoid Tissue in Chronic Inflammatory Liver Disease", American Journal of Pathology, vol. 160, No. 4, Apr. 2002, 1445-1455.
Hanai, et al., "The Mode of Actions of Adacolumn Therapeutic Leucocytapheresis in Patients with Inflammatory Bowel Disease: A Concise Review", Clinical & Experimental Immunology, vol. 163, No. 1, Nov. 16, 2010, 50-58.
Hsing-Cheng, et al., "Immunologic Variables in Acute Mania of Bipolar Disorder", Journal of Neuroimmunology, vol. 150, No. 1-2, May 1, 2004, 116-122.
Hu, "Schizophrenia is a TH2 Dominant Autoimmune Disease Possibly Against Acetylcholine Receptors of CNS", ViXra.org, vol. 1204, Apr. 30, 2012, 0070.
Iarlori, et al., "Interferon beta-1b Modulates MCP-1 Expression and Production in Relapsing-Remitting Multiple Sclerosis", Journal of Neuroimmunology, vol. 123, No. 1-2, Feb. 1, 2002, 170-179.

(56) References Cited

OTHER PUBLICATIONS

Iwamoto, et al., "Molecular Aspects of Rheumatoid Arthritis: Chemokines in the Joints of Patients", FEBS Journal, vol. 275. No. 18, Sep. 1, 2008, 4448-4455.
Linton, et al., "CCR9-Expressing CD14+HLA-DRhi Blood Monocytes Promote Intestinal Inflammation in IBD", Journal of Translational Medicine, vol. 9, No. Supply 2, Nov. 23, 2011, P32.
Liu, et al., "Correlation Effect of EGFR and CXCR4 and CCR7 Chemokine Receptors in Predicting Breast Cancer Vletastasis and Prognosis", Journal of Experimental & Clinical Cancer Research, vol. 29, No. 16, 2010, 9 pages.
Lumeng et al. "Obesity Induces a Phenotypic Switch in Adipose Tissue Macrophage Polarization", Journal of Clinical Investigation, American Society for Clinical Investigation, vol. 117, No. 1, Jan. 1, 2007, 175-184.
Maury, et al., "Adipokine Dysregulation, Adipose Tissue Inflammation and Metabolic Syndrome", Molecular and Cellular Endocrinology, vol. 314, No. 1, Jan. 15, 2010, 1-16.
Nakajima, "Increased Intrathecal Chemokine Receptor CCR2 Expression in Multiple Sclerosis", Biomarker Insights, Jan. 1, 2007, 463.
Nakatani, et al., "CCR4+ Memory CD4+ T Lymphocytes are Increased in Peripheral Blood and Lesional Skin from Patients with Atopic Dermatitis", Journal of Allergy and Clinical Immunology, vol. 107, No. 2, Feb. 1, 2001, 353-358.
Niu, et al., "Role of MCP-1 in Cardiovascular Disease: Molecular Mechanisms and Clinical Implications", Clinical Science, vol. 117, No. 3, Aug. 2009, 95-109.
Pease, et al., "Asthma, Allergy and Chemokines", Current Drug Targets, vol. 7, No. 1, retrieved from the Internet on Sep. 13, 2012: http://www.benthamdirect.org/pages/article/1/117/asthma-allergy-and-chemokines.html, Jan. 1, 2006, 3-12.
Petrek, et al., "CC and C Chemokine Expression in Pulmonary Sarcoidosis", European Respiratory Journal, vol. 20, No. 5, Nov. 1, 2002, 1206-1212.
Reale, et al., "Dysregulation of Chemo-Cytokine Production in Schizophrenic Patients Versus Healthy Controls", BMC Neuroscience, Biomed Central, vol. 12, No. 1, Jan. 25, 2011, 13 pages.
Reape, et al., "Chemokines and Atherosclerosis", Atherosclerosis, vol. 147, No. 2, Dec. 1, 1999, 213-225.
Rottman, et al., "Potential Role of the Chemokine Receptors CXCR3, CCR4, and the Integrin AlphaEbeta7 in the Pathogenesis of Psoriasis Vulgaris", Laboratory Investigation, vol. 81, No. 3, Mar. 2001, 335-347.
Sarafi, et al., "Murine Monocyte Chemoattractant Protein (MCP)-5: A Novel CC Chemokine that is a Structural and Functional Homologue of Human MCP-1", Journal of Experimental Medicine, vol. 185, No. 1, Jan. 1, 1997, 99-110.
Souto, et al., "Essential Role of CCR2 in Neutrophil Tissue Infiltration and Multiple Organ Dysfunction in Sepsis", American Journal of Respiratory and Critical Care Medicine, vol. 183, No. 2, Jan. 15, 2011, 234-242.
Speyer, "Novel Chemokine Responsiveness and Mobilization of Neutrophils During Sepsis", American Journal of Pathology, vol. 165, No. 6, Dec. 2004, 2187-2196.
Takanami, "Overexpression of CCR7 mRNA in Nonsmall Cell Lung Cancer: Correlation with Lymph Node Metastasis", International Journal of Cancer, vol. 105, No. 2, Jun. 10, 2003, 186-189.
Teixeira, et al., "Increased Serum Levels of CCL11/eotaxin in Schizophrenia", Progress in Neuro-Psychopharmacology & Biological Psychiatry, vol. 32, No. 3, Nov. 23, 2007, 710-714.
European Search Report for European Patent Application No. 12727921, May 24, 2016, 4.
Allen, et al., "A Rapid and Efficient Way to Obtain Modified Chemokines for Functional and Biophysical Studies", Cytokine, vol. 55, No. 2, May 2, 2011, 168-173.
Coillie, et al., "Functional Comparison of Two Human Monocyte Chemotactin Protein-2 Isoforms, Role of the Amino-Terminal Pyroglutamic Acid and Processing by CD26/Dipeptidyl Peptidase IV", Biochemistry, vol. 37, No. 36, Jan. 1, 1998, 12672-12680.
Kruszynski, et al., "Synthetic, Site-Specific Biotinylated Analogs of Human MCP-1", Journal of Peptide Science, vol. 12, May 1, 2006, 354-360.
Vita, et al., "Synthesis and Characterization of Biologically Functional Biotinylated RANTES", Journal of Immunological Methods, Aug. 1, 2002, 53-65.

* cited by examiner

H-pyroGluPDAINAPVTCCYNFTNRKISVQRLASYRRITSS
KCPKEAVIFKTIVAKEICADPKQKWVQDSMDHLDKQTQTPKT-CONH₂

H-pyroGluPDAINAPVTCCYNFTNRKISVQRLASYRRITSS
KCPKEAVIFKTIVAKEICADPKQKWVQDS*Nleu*DHLDKQTQTPKT-CONH₂

H-VTCCYNFTNRKISVQRLASYRRITSS
KCPKEAVIFKTIVAKEICADPKQKWVQDS*Nleu*DHLDKQTQTPKT-CONH₂ ulimit -t 30; /usr/molbio/bin/lalign -f -14 -g -4 -K 3 ./wwwtmp/.11134.1.seq ./wwwtmp/.11134.2.seq > ./wwwtmp/.11134.out LALIGN finds the best local alignments between two sequences version 2.1u09 December 2006 Please cite: X. Huang and W. Miller (1991) Adv. Appl. Math. 12:373-381 alignments < E( 0.05):score: 38 (3 max)

```
 Comparison of:
(A) ./wwwtmp/.11134.1.seq MCP1 (human) 76 bp
 - 76 aa
(B) ./wwwtmp/.11134.2.seq MCP-5 (mouse) 82 bp
 - 82 aa
 using matrix file: BL50 (15/-5), gap-open/ext: -14/-4 E(limit)
0.05

68.1% identity in 72 aa overlap (2-73:2-73); score:   370 E(10000):
1.6e-31

10        20        30        40        50        60
MCP1     PDAINAPVTCCYNFTNRKISVQRLASYRRITSSKCPKEAVIFKTIVAKEICADPKQKWVQ
         :::...:::::::: ...:: :...: :::::::::.::.::::.::. :::::::.:::.
MCP-5    PDAVSTPVTCCYNVVKQKIHVRKLKSYRRITSSQCPREAVIFRTILDKEICADPKEKWVK
                10        20        30        40        50        60

70
MCP1     DSMDHLDKQTQTPKT
         .:..:::: :::
MCP-5    NSINHLDKTSQTFILEPSCLG
                70
```

*FIG. 32* ulimit -t 30; /usr/molbio/bin/lalign -f -14 -g -4 -K 3 ./wwwtmp/.11134.1.seq ./wwwtmp/.11134.2.seq > ./wwwtmp/.11134.out LALIGN finds the best local alignments between two sequences version 2.1u09 December 2006 Please cite: X. Huang and W. Miller (1991) Adv. Appl. Math. 12:373-381 alignments < E( 0.05):score: 38 (3 max)

```
 Comparison of:
(A) ./wwwtmp/.11134.1.seq MCP1 (human) 76 bp
- 76 aa
(B) ./wwwtmp/.11134.2.seq MCP-5 (mouse) 82 bp
- 82 aa
 using matrix file: BL50 (15/-5), gap-open/ext: -14/-4 E(limit)
0.05

68.1% identity in 72 aa overlap (2-73:2-73); score:   370 E(10000):
1.6e-31

10        20        30        40        50        60
MCP1    PDAINAPVTCCYNFTNRKISVQRLASYRRITSSKCPKEAVIFKTIVAKEICADPKQKWVQ
        ::...::::::: ...:: :..: ::::::::.::.::::::.:.  ::::::::.::.
MCP-5   PDAVSTPVTCCYNVVKQKIHVRKLKSYRRITSSQCPREAVIFRTILDKEICADPKEKWVK
              10        20        30        40        50        60

70
MCP1    DSMDHLDKQTQTPKT
        .:...:::: .::
MCP-5   NSINHLDKTSQTFILEPSCLG
              70
```

FIG. 52

H-GPASVPTTCCFNLANRKIPLQRLESYRRITSGK
CPQKAVIFKTKLAKDICADPKKKWVQDSMKYLDQKSPTPKP-CONH₂

H₂N-SPYSSDTTPCCFAYIARPLPRAHIKEYFYTSGKCSNP
AVVFVTRKNRQVCANPEKKWVREYINSLEKS-CO₂H

H-GPASVPTTCCFNLANRKIPLQRLESYRRITSGK
CPQKAVIFKTKLAKDICADPKKKWVQDSMKYLDQKSPTPKP-CONH₂

H₂N-SPYSSDTTPCCFAYIARPLPRAHIKEYFYTSGKCSNP
AVVFVTRKNRQVCANPEKKWVREYINSLEKS-CO₂H ulimit -t 30; /usr/molbio/bin/lalign -f -14 -g -4 -K 3 ./wwwtmp/.11134.1.seq ./wwwtmp/.11134.2.seq > ./wwwtmp/.11134.out LALIGN finds the best local alignments between two sequences version 2.1u09 December 2006 Please cite: X. Huang and W. Miller (1991) Adv. Appl. Math. 12:373-381 alignments < E( 0.05):score: 38 (3 max)

```
 Comparison of:
(A) ./wwwtmp/.11134.1.seq MCP1 (human) 76 bp
- 76 aa
(B) ./wwwtmp/.11134.2.seq MCP-5 (mouse) 82 bp
- 82 aa
 using matrix file: BL50 (15/-5), gap-open/ext: -14/-4 E(limit)
0.05

68.1% identity in 72 aa overlap (2-73:2-73); score:   370 E(10000):
1.6e-31

10        20        30        40        50        60
MCP1    PDAINAPVTCCYNFTNRKISVQRLASYRRITSSKCPKEAVIFKTIVAKEICADPKQKWVQ
        :::...::::::: ....:: ...: ::::::::::.:.:::::.::. ::::::::.::.
MCP-5   PDAVSTPVTCCYNVVKQKIHVRKLKSYRRITSSQCPREAVIFRTILDKEICADPKEKWVK
               10        20        30        40        50        60

70
MCP1    DSMDHLDKQTQTPKT
        .:...::::  .::
MCP-5   NSINHLDKTSQTFILEPSCLG
               70
```

FIG. 95 ulimit -t 30; /usr/molbio/bin/lalign -f -14 -g -4 -K 3 ./wwwtmp/.11134.1.seq
./wwwtmp/.11134.2.seq > ./wwwtmp/.11134.out LALIGN finds the best local
alignments between two sequences version 2.1u09 December 2006 Please cite: X.
Huang and W. Miller (1991) Adv. Appl. Math. 12:373-381 alignments < E(
0.05):score: 38 (3 max)
```
 Comparison of:
(A) ./wwwtmp/.11134.1.seq MCP1 (human) 76 bp
 - 76 aa
(B) ./wwwtmp/.11134.2.seq MCP-5 (mouse) 82 bp
 - 82 aa
 using matrix file: BL50 (15/-5), gap-open/ext: -14/-4 E(limit)
0.05

68.1% identity in 72 aa overlap (2-73:2-73); score:   370 E(10000):
1.6e-31

10        20        30        40        50        60
MCP1    PDAINAPVTCCYNFTNRKISVQRLASYRRITSSKCPKEAVIFKTIVAKEICADPKQKWVQ
        ::...:::::::  ..::  :...::::::::.:::.:::::: :....:::::::.::.
MCP-5   PDAVSTPVTCCYNVVKQKIHVRKLKSYRRITSSQCPREAVIFRTILDKEICADPKEKWVK
              10        20        30        40        50        60

70
MCP1    DSMDHLDKQTQTPKT
        .:..::: .::
MCP-5   NSINHLDKTSQTFILEPSCLG
              70
```

FIG. 113

H-pyroGluPDAINAPVTCCYNFTNRKISVQRLASYRRITSS
KCPKEAVIFKTIVAKEICADPKQKWVQDSMDHLDKQTQTPKT-CONH₂

H-pyroGluPDAINAPVTCCYNFTNRKISVQRLASYRRITSS
KCPKEAVIFKTIVAKEICADPKQKWVQDS*Nleu*DHLDKQTQTPKT-CONH₂

H-VTCCYNFTNRKISVQRLASYRRITSS
KCPKEAVIFKTIVAKEICADPKQKWVQDS*Nleu*DHLDKQTQTPKT-CONH₂

```
ulimit -t 30; /usr/molbio/bin/lalign -f -14 -g -4 -K 3 ./wwwtmp/.11134.1.seq
./wwwtmp/.11134.2.seq > ./wwwtmp/.11134.out LALIGN finds the best local
alignments between two sequences version 2.1u09 December 2006 Please cite: X.
Huang and W. Miller (1991) Adv. Appl. Math. 12:373-381 alignments < E(
0.05):score: 38 (3 max)
 Comparison of:
(A) ./wwwtmp/.11134.1.seq MCP1 (human) 76 bp
- 76 aa
(B) ./wwwtmp/.11134.2.seq MCP-5 (mouse) 82 bp
- 82 aa
 using matrix file: BL50 (15/-5), gap-open/ext: -14/-4 E(limit)
0.05

68.1% identity in 72 aa overlap (2-73:2-73); score:   370 E(10000):
1.6e-31

10        20        30        40        50        60
MCP1    PDAINAPVTCCYNFTNRKISVQRLASYRRITSSKCPKEAVIFKTIVAKEICADPKQKWVQ
        ::...::::::: ...:: :...: ::::::::::.::.::::::.::. :::::::::..
MCP-5   PDAVSTPVTCCYNVVKQKIHVRKLKSYRRITSSQCPREAVIFRTILDKEICADPKEKWVK
                10        20        30        40        50        60

70
MCP1    DSMDHLDKQTQTPKT
        .:..:::: .::
MCP-5   NSINHLDKTSQTFILEPSCLG
                70
```

FIG. 126

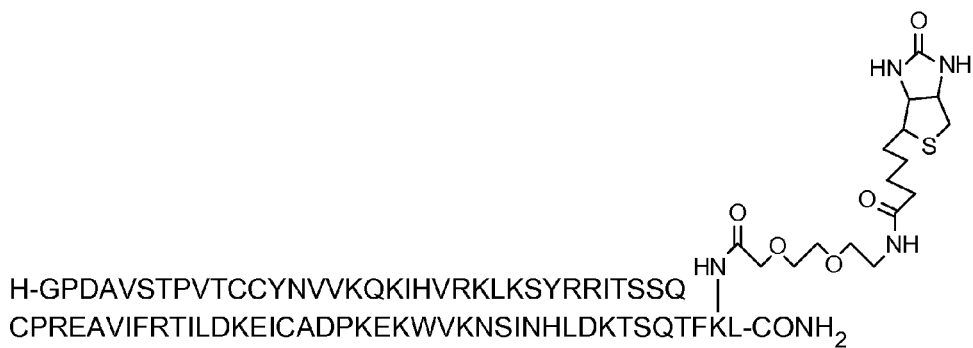

H-GPDAVSTPVTCCYNVVKQKIHVRKLKSYRRITSSQ
CPREAVIFRTILDKEICADPKEKWVKNSINHLDKTSQTFKL-CONH$_2$

FIG. 127

H₂N-SPYSSDTTPCCFAYIARPLPRAHIKEYFYTSGKCSNP
AVVFVTRKNRQVCANPEKKWVREYINSLEKS-CO₂H

H-pyroGluPDAINAPVTCCYNFTNRKISVQRLASYRRITSS
KCPKEAVIFKTIVAKEICADPKQKWVQDS*Nleu*DHLDKQTQTPKT-CONH₂

H-VTCCYNFTNRKISVQRLASYRRITSS
KCPKEAVIFKTIVAKEICADPKQKWVQDS*Nleu*DHLDKQTQTPKT-CONH₂ ulimit -t 30; /usr/molbio/bin/lalign -f -14 -g -4 -K 3 ./wwwtmp/.11134.1.seq ./wwwtmp/.11134.2.seq > ./wwwtmp/.11134.out LALIGN finds the best local alignments between two sequences version 2.1u09 December 2006 Please cite: X. Huang and W. Miller (1991) Adv. Appl. Math. 12:373-381 alignments < E( 0.05):score: 38 (3 max)

```
 Comparison of:
(A) ./wwwtmp/.11134.1.seq MCP1 (human) 76 bp
- 76 aa
(B) ./wwwtmp/.11134.2.seq MCP-5 (mouse) 82 bp
- 82 aa
 using matrix file: BL50 (15/-5), gap-open/ext: -14/-4 E(limit)
0.05

68.1% identity in 72 aa overlap (2-73:2-73); score:   370 E(10000):
1.6e-31

10        20        30        40        50        60
MCP1    PDAINAPVTCCYNFTNRKISVQRLASYRRITSSKCPKEAVIFKTIVAKEICADPKQKWVQ
        :::...::::::  ...::  ...: :::::::::.:.:::::.:.  :::::::::::.
MCP-5   PDAVSTPVTCCYNVVKQKIHVRKLKSYRRITSSQCPREAVIFRTILDKEICADPKEKWVK
              10        20        30        40        50        60

70
MCP1    DSMDHLDKQTQTPKT
        .:...::: .::
MCP-5   NSINHLDKTSQTFILEPSCLG
              70
```

FIG. 156

H-GPDAVSTPVTCCYNVVKQKIHVRKLKSYRRITSSQ
CPREAVIFRTILDKEICADPKEKWVKNSINHLDKTSQTFKL-CONH₂

H₂N-SPYSSDTTPCCFAYIARPLPRAHIKEYFYTSGKCSNP
AVVFVTRKNRQVCANPEKKWVREYINSLEKS-CO₂H

H-GPASVPTTCCFNLANRKIPLQRLESYRRITSGK
CPQKAVIFKTKLAKDICADPKKKWVQDSMKYLDQKSPTPKP-CONH₂

H-pyroGluPDAINAPVTCCYNFTNRKISVQRLASYRRITSS
KCPKEAVIFKTIVAKEICADPKQKWVQDS*Nleu*DHLDKQTQTPKT-CONH₂

H-VTCCYNFTNRKISVQRLASYRRITSS
KCPKEAVIFKTIVAKEICADPKQKWVQDS*Nleu*DHLDKQTQTPKT-CONH₂ ulimit -t 30; /usr/molbio/bin/lalign -f -14 -g -4 -K 3 ./wwwtmp/.11134.1.seq ./wwwtmp/.11134.2.seq > ./wwwtmp/.11134.out LALIGN finds the best local alignments between two sequences version 2.1u09 December 2006 Please cite: X. Huang and W. Miller (1991) Adv. Appl. Math. 12:373-381 alignments < E( 0.05):score: 38 (3 max)
```
 Comparison of:
(A) ./wwwtmp/.11134.1.seq MCP1 (human) 76 bp
- 76 aa
(B) ./wwwtmp/.11134.2.seq MCP-5 (mouse) 82 bp
- 82 aa
 using matrix file: BL50 (15/-5), gap-open/ext: -14/-4 E(limit)
0.05

68.1% identity in 72 aa overlap (2-73:2-73); score:  370 E(10000):
1.6e-31

10        20        30        40        50        60
MCP1   PDAINAPVTCCYNFTNRKISVQRLASYRRITSSKCPKEAVIFKTIVAKEICADPKQKWVQ
       ::...:::::::   ..::   ..:  :::::::::::.:::::::.::::::::. :.
MCP-5  PDAVSTPVTCCYNVVKQKIHVRKLKSYRRITSSQCPREAVIFRTILDKEICADPKEKWVK
               10        20        30        40        50        60

70
MCP1   DSMDHLDKQTQTPKT
       .:...:::: .::
MCP-5  NSINHLDKTSQTFILEPSCLG
               70
```

FIG. 175

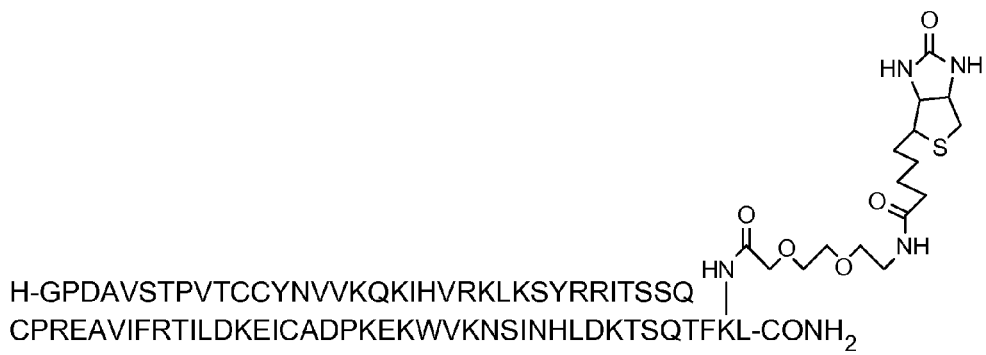

H-GPDAVSTPVTCCYNVVKQKIHVRKLKSYRRITSSQ
CPREAVIFRTILDKEICADPKEKWVKNSINHLDKTSQTFKL-CONH$_2$

FIG. 176

SEQUENCE LISTING

```
<160> NUMBER OF SEQ ID NOS: 267

<210> SEQ ID NO 1
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine

<400> SEQUENCE: 1

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Xaa
    50                  55                  60

Lys Leu Leu Asp Ala Arg Asn Lys Val Phe
65                  70
```

```
<210> SEQ ID NO 2
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine
<220> FEATURE:
<221> NAME/KEY: X
<222> LOCATION: (72)..(72)
<223> OTHER INFORMATION: X is K(ivDde)

<400> SEQUENCE: 2

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Xaa
    50                  55                  60

Lys Leu Leu Asp Ala Arg Asn Xaa Val Phe
65                  70

<210> SEQ ID NO 3
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine
<220> FEATURE:
<221> NAME/KEY: X
<222> LOCATION: (72)..(72)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 3

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Xaa
    50                  55                  60

Lys Leu Leu Asp Ala Arg Asn Xaa Val Phe
65                  70
```

```
<210> SEQ ID NO 4
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 4

Gly Thr Asn Asp Ala Glu Asp Cys Cys Leu Ser Val Thr Gln Lys Pro
1               5                  10                  15

Ile Pro Gly Tyr Ile Val Arg Asn Phe His Tyr Leu Leu Ile Lys Asp
            20                  25                  30

Gly Cys Arg Val Pro Ala Val Val Phe Thr Thr Leu Arg Gly Arg Gln
        35                  40                  45

Leu Cys Ala Pro Pro Asp Gln Pro Trp Val Glu Arg Ile Ile Gln Arg
    50                  55                  60

Leu Gln Arg Thr Ser Ala Lys Met Lys Arg Arg Ser Ser Xaa
65                  70                  75

<210> SEQ ID NO 5
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is K(ivDde)

<400> SEQUENCE: 5

Gly Thr Asn Asp Ala Glu Asp Cys Cys Leu Ser Val Thr Gln Lys Pro
1               5                  10                  15

Ile Pro Gly Tyr Ile Val Arg Asn Phe His Tyr Leu Leu Ile Lys Asp
            20                  25                  30

Gly Cys Arg Val Pro Ala Val Val Phe Thr Thr Leu Arg Gly Arg Gln
        35                  40                  45

Leu Cys Ala Pro Pro Asp Gln Pro Trp Val Glu Arg Ile Ile Gln Arg
    50                  55                  60

Leu Gln Arg Thr Ser Ala Lys Met Lys Arg Arg Ser Ser Xaa
65                  70                  75

<210> SEQ ID NO 6
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is K(Biotin)

<400> SEQUENCE: 6

Gly Thr Asn Asp Ala Glu Asp Cys Cys Leu Ser Val Thr Gln Lys Pro
1               5                  10                  15

Ile Pro Gly Tyr Ile Val Arg Asn Phe His Tyr Leu Leu Ile Lys Asp
            20                  25                  30
```

Gly Cys Arg Val Pro Ala Val Val Phe Thr Thr Leu Arg Gly Arg Gln
            35                  40                  45

Leu Cys Ala Pro Pro Asp Gln Pro Trp Val Glu Arg Ile Ile Gln Arg
 50                  55                  60

Leu Gln Arg Thr Ser Ala Lys Met Lys Arg Arg Ser Ser Xaa
 65                  70                  75

<210> SEQ ID NO 7
<211> LENGTH: 99
<212> TYPE: PRT
<213> ORGANISM: Artificial sequence
<220> FEATURE:
<223> OTHER INFORMATION: Synthesized peptide

<400> SEQUENCE: 7

Met Lys Val Ser Ala Ala Leu Leu Cys Leu Leu Leu Ile Ala Ala Thr
 1               5                  10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
 50                  55                  60

Ile Phe Lys Thr Ile Val Ala Lys Glu Ile Cys Ala Asp Pro Lys Gln
 65                  70                  75                  80

Lys Trp Val Gln Asp Ser Met Asp His Leu Asp Lys Gln Thr Gln Thr
                85                  90                  95

Pro Lys Thr

<210> SEQ ID NO 8
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (64)..(64)
<223> OTHER INFORMATION: X = methionine or norleucine

<400> SEQUENCE: 8

Gln Pro Asp Ala Ile Asn Ala Pro Val Thr Cys Cys Tyr Asn Phe Thr
 1               5                  10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Xaa
 50                  55                  60

Asp His Leu Asp Lys Gln Thr Gln Thr Pro Lys Thr
 65                  70                  75

<210> SEQ ID NO 9
<211> LENGTH: 68
<212> TYPE: PRT
<213> ORGANISM: Artificial sequence
<220> FEATURE:
<223> OTHER INFORMATION: Synthesized peptide

<400> SEQUENCE: 9

-continued

```
Val Thr Cys Cys Tyr Asn Phe Thr Asn Arg Lys Ile Ser Val Gln Arg
1               5                   10                  15

Leu Ala Ser Tyr Arg Arg Ile Thr Ser Ser Lys Cys Pro Lys Glu Ala
            20                  25                  30

Val Ile Phe Lys Thr Ile Val Ala Lys Glu Ile Cys Ala Asp Pro Lys
        35                  40                  45

Gln Lys Trp Val Gln Asp Ser Met Asp His Leu Asp Lys Gln Thr Gln
    50                  55                  60

Thr Pro Lys Thr
65
```

<210> SEQ ID NO 10
<211> LENGTH: 104
<212> TYPE: PRT
<213> ORGANISM: Artificial sequence
<220> FEATURE:
<223> OTHER INFORMATION: Synthesized peptide

<400> SEQUENCE: 10

```
Met Lys Ile Ser Thr Leu Leu Cys Leu Leu Leu Ile Ala Thr Thr Ile
1               5                   10                  15

Ser Pro Gln Val Leu Ala Gly Pro Asp Ala Val Ser Thr Pro Val Thr
            20                  25                  30

Cys Cys Tyr Asn Val Val Lys Gln Lys Ile His Val Arg Lys Leu Lys
        35                  40                  45

Ser Tyr Arg Arg Ile Thr Ser Ser Gln Cys Pro Arg Glu Ala Val Ile
    50                  55                  60

Phe Arg Thr Ile Leu Asp Lys Glu Ile Cys Ala Asp Pro Lys Glu Lys
65                  70                  75                  80

Trp Val Lys Asn Ser Ile Asn His Leu Asp Lys Thr Ser Gln Thr Phe
                85                  90                  95

Ile Leu Glu Pro Ser Cys Leu Gly
                100
```

<210> SEQ ID NO 11
<211> LENGTH: 82
<212> TYPE: PRT
<213> ORGANISM: Artificial sequence
<220> FEATURE:
<223> OTHER INFORMATION: Synthesized peptide

<400> SEQUENCE: 11

```
Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
            20                  25                  30

Ser Ser Gln Cys Pro Arg Glu Ala Val Ile Phe Arg Thr Ile Leu Asp
        35                  40                  45

Lys Glu Ile Cys Ala Asp Pro Lys Glu Lys Trp Val Lys Asn Ser Ile
    50                  55                  60

Asn His Leu Asp Lys Thr Ser Gln Thr Phe Ile Leu Glu Pro Ser Cys
65                  70                  75                  80

Leu Gly
```

<210> SEQ ID NO 12
<211> LENGTH: 76
<212> TYPE: PRT
<213> ORGANISM: Artificial sequence
<220> FEATURE:

<223> OTHER INFORMATION: Synthesized peptide

<400> SEQUENCE: 12

Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
            20                  25                  30

Ser Ser Gln Cys Pro Arg Glu Ala Val Ile Phe Arg Thr Ile Leu Asp
        35                  40                  45

Lys Glu Ile Cys Ala Asp Pro Lys Glu Lys Trp Val Lys Asn Ser Ile
    50                  55                  60

Asn His Leu Asp Lys Thr Ser Gln Thr Phe Ile Leu
65                  70                  75

<210> SEQ ID NO 13
<211> LENGTH: 76
<212> TYPE: PRT
<213> ORGANISM: Artificial sequence
<220> FEATURE:
<223> OTHER INFORMATION: Synthesized peptide

<400> SEQUENCE: 13

Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
            20                  25                  30

Ser Ser Gln Cys Pro Arg Glu Ala Val Ile Phe Arg Thr Ile Leu Asp
        35                  40                  45

Lys Glu Ile Cys Ala Asp Pro Lys Glu Lys Trp Val Lys Asn Ser Ile
    50                  55                  60

Asn His Leu Asp Lys Thr Ser Gln Thr Phe Lys Leu
65                  70                  75

<210> SEQ ID NO 14
<211> LENGTH: 68
<212> TYPE: PRT
<213> ORGANISM: Artificial sequence
<220> FEATURE:
<223> OTHER INFORMATION: Synthesized peptide

<400> SEQUENCE: 14

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Lys Ser
65

<210> SEQ ID NO 15
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)

<223> OTHER INFORMATION: X = pyroGlu or Gln

<400> SEQUENCE: 15

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75

<210> SEQ ID NO 16
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X = K(ivDde)

<400> SEQUENCE: 16

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Xaa Thr
65                  70                  75

<210> SEQ ID NO 17
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is an amino acid residue that can be
    biotinylated, such as lysine, ornithine or diaminopropionic acid
    and optionally is biotinylated, optionally via a spacer molecule
    such as PEG

<400> SEQUENCE: 17

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

```
Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
 50                  55                  60

Asp His Leu Asp Lys Gln Thr Gln Thr Pro Xaa Thr
 65                  70                  75
```

<210> SEQ ID NO 18
<211> LENGTH: 68
<212> TYPE: PRT
<213> ORGANISM: Artificial sequence
<220> FEATURE:
<223> OTHER INFORMATION: Synthesized peptide

<400> SEQUENCE: 18

```
Ser Pro Tyr Ser Ser Asp Thr Thr Pro Cys Cys Phe Ala Tyr Ile Ala
 1               5                  10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Lys Ser
 65
```

<210> SEQ ID NO 19
<211> LENGTH: 68
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (67)..(67)
<223> OTHER INFORMATION: X is K(ivDde)

<400> SEQUENCE: 19

```
Ser Pro Tyr Ser Ser Asp Thr Thr Pro Cys Cys Phe Ala Tyr Ile Ala
 1               5                  10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Xaa Ser
 65
```

<210> SEQ ID NO 20
<211> LENGTH: 68
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (67)..(67)
<223> OTHER INFORMATION: X is an amino acid residue that can be
      biotinylated, such as lysine, ornithine or diaminopropionic acid
      and optionally is biotinylated, optionally via a spacer molecule
      such as PEG (e.g. K(Biotin))

<400> SEQUENCE: 20

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
            35                  40                  45

Val Cys Ala Asn Pro Glu Lys Lys Trp Val Arg Glu Tyr Ile Asn Ser
    50                  55                  60

Leu Glu Xaa Ser
65

<210> SEQ ID NO 21
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln

<400> SEQUENCE: 21

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
            35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro
65                  70                  75

<210> SEQ ID NO 22
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X = K(ivDde)

<400> SEQUENCE: 22

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
            35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Xaa Pro
65                  70                  75

```
<210> SEQ ID NO 23
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is an amino acid residue that can be
      biotinylated, such as lysine, ornithine or diaminopropionic acid
      and optionally is biotinylated, optionally via a spacer molecule
      such as PEG

<400> SEQUENCE: 23

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Xaa Pro
65                  70                  75

<210> SEQ ID NO 24
<211> LENGTH: 99
<212> TYPE: PRT
<213> ORGANISM: Artificial sequence
<220> FEATURE:
<223> OTHER INFORMATION: Synthesized peptide

<400> SEQUENCE: 24

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 25
<211> LENGTH: 76
<212> TYPE: PRT
<213> ORGANISM: Artificial sequence
<220> FEATURE:
<223> OTHER INFORMATION: Synthesized peptide

<400> SEQUENCE: 25

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
```

```
                    20                  25                  30
Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
 50                  55                  60

Asp His Leu Asp Lys Gln Thr Gln Thr Pro Lys Thr
65                  70                  75

<210> SEQ ID NO 26
<211> LENGTH: 68
<212> TYPE: PRT
<213> ORGANISM: Artificial sequence
<220> FEATURE:
<223> OTHER INFORMATION: Synthesized peptide

<400> SEQUENCE: 26

Val Thr Cys Cys Tyr Asn Phe Thr Asn Arg Lys Ile Ser Val Gln Arg
1               5                   10                  15

Leu Ala Ser Tyr Arg Arg Ile Thr Ser Ser Lys Cys Pro Lys Glu Ala
                20                  25                  30

Val Ile Phe Lys Thr Ile Val Ala Lys Glu Ile Cys Ala Asp Pro Lys
            35                  40                  45

Gln Lys Trp Val Gln Asp Ser Met Asp His Leu Asp Lys Gln Thr Gln
        50                  55                  60

Thr Pro Lys Thr
65

<210> SEQ ID NO 27
<211> LENGTH: 104
<212> TYPE: PRT
<213> ORGANISM: Artificial sequence
<220> FEATURE:
<223> OTHER INFORMATION: Synthesized peptide

<400> SEQUENCE: 27

Met Lys Ile Ser Thr Leu Leu Cys Leu Leu Leu Ile Ala Thr Thr Ile
1               5                   10                  15

Ser Pro Gln Val Leu Ala Gly Pro Asp Ala Val Ser Thr Pro Val Thr
                20                  25                  30

Cys Cys Tyr Asn Val Val Lys Gln Lys Ile His Val Arg Lys Leu Lys
            35                  40                  45

Ser Tyr Arg Arg Ile Thr Ser Ser Gln Cys Pro Arg Glu Ala Val Ile
        50                  55                  60

Phe Arg Thr Ile Leu Asp Lys Glu Ile Cys Ala Asp Pro Lys Glu Lys
65                  70                  75                  80

Trp Val Lys Asn Ser Ile Asn His Leu Asp Lys Thr Ser Gln Thr Phe
                85                  90                  95

Ile Leu Glu Pro Ser Cys Leu Gly
            100

<210> SEQ ID NO 28
<211> LENGTH: 82
<212> TYPE: PRT
<213> ORGANISM: Artificial sequence
<220> FEATURE:
<223> OTHER INFORMATION: Synthesized peptide

<400> SEQUENCE: 28

Gly Pro Asp Ala Val Ser Thr Pro Val Thr Cys Cys Tyr Asn Val Val
1               5                   10                  15
```

-continued

```
Lys Gln Lys Ile His Val Arg Lys Leu Lys Ser Tyr Arg Arg Ile Thr
         20                  25                  30

Ser Ser Gln Cys Pro Arg Glu Ala Val Ile Phe Arg Thr Ile Leu Asp
         35                  40                  45

Lys Glu Ile Cys Ala Asp Pro Lys Glu Lys Trp Val Lys Asn Ser Ile
         50                  55                  60

Asn His Leu Asp Lys Thr Ser Gln Thr Phe Ile Leu Glu Pro Ser Cys
65                   70                  75                  80

Leu Gly

<210> SEQ ID NO 29
<211> LENGTH: 76
<212> TYPE: PRT
<213> ORGANISM: Artificial sequence
<220> FEATURE:
<223> OTHER INFORMATION: Synthesized peptide

<400> SEQUENCE: 29

Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
         20                  25                  30

Ser Ser Gln Cys Pro Arg Glu Ala Val Ile Phe Arg Thr Ile Leu Asp
         35                  40                  45

Lys Glu Ile Cys Ala Asp Pro Lys Glu Lys Trp Val Lys Asn Ser Ile
         50                  55                  60

Asn His Leu Asp Lys Thr Ser Gln Thr Phe Ile Leu
65                   70                  75

<210> SEQ ID NO 30
<211> LENGTH: 76
<212> TYPE: PRT
<213> ORGANISM: Artificial sequence
<220> FEATURE:
<223> OTHER INFORMATION: Synthesized peptide

<400> SEQUENCE: 30

Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
         20                  25                  30

Ser Ser Gln Cys Pro Arg Glu Ala Val Ile Phe Arg Thr Ile Leu Asp
         35                  40                  45

Lys Glu Ile Cys Ala Asp Pro Lys Glu Lys Trp Val Lys Asn Ser Ile
         50                  55                  60

Asn His Leu Asp Lys Thr Ser Gln Thr Phe Lys Leu
65                   70                  75

<210> SEQ ID NO 31
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln

<400> SEQUENCE: 31
```

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75

<210> SEQ ID NO 32
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is K(ivDde)

<400> SEQUENCE: 32

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Xaa Thr
65                  70                  75

<210> SEQ ID NO 33
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 33

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met

```
                    50                  55                  60
Asp His Leu Asp Lys Gln Thr Gln Thr Pro Xaa Thr
65                  70                  75

<210> SEQ ID NO 34
<211> LENGTH: 68
<212> TYPE: PRT
<213> ORGANISM: Artificial sequence
<220> FEATURE:
<223> OTHER INFORMATION: Synthesized peptide

<400> SEQUENCE: 34

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
                20                  25                  30

Lys Cys Ser Asn Pro Ala Val Val Phe Val Thr Arg Lys Asn Arg Gln
                35                  40                  45

Val Cys Ala Asn Pro Glu Lys Lys Trp Val Arg Glu Tyr Ile Asn Ser
                50                  55                  60

Leu Glu Lys Ser
65

<210> SEQ ID NO 35
<211> LENGTH: 68
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (67)..(67)
<223> OTHER INFORMATION: X is K(ivDde)

<400> SEQUENCE: 35

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
                20                  25                  30

Lys Cys Ser Asn Pro Ala Val Val Phe Val Thr Arg Lys Asn Arg Gln
                35                  40                  45

Val Cys Ala Asn Pro Glu Lys Lys Trp Val Arg Glu Tyr Ile Asn Ser
                50                  55                  60

Leu Glu Xaa Ser
65

<210> SEQ ID NO 36
<211> LENGTH: 68
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (67)..(67)
<223> OTHER INFORMATION: X is an amino acid residue that can be
      biotinylated, such as lysine, ornithine or diaminopropionic acid
      and optionally is biotinylated, optionally via a spacer molecule
      such as PEG (e.g. K(Biotin))

<400> SEQUENCE: 36

Ser Pro Tyr Ser Ser Asp Thr Thr Pro Cys Cys Phe Ala Tyr Ile Ala
1               5                   10                  15
```

```
Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
            35                  40                  45

Val Cys Ala Asn Pro Glu Lys Lys Trp Val Arg Glu Tyr Ile Asn Ser
        50                  55                  60

Leu Glu Xaa Ser
65

<210> SEQ ID NO 37
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln

<400> SEQUENCE: 37

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro
65                  70                  75

<210> SEQ ID NO 38
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is K(ivDde)

<400> SEQUENCE: 38

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Xaa Pro
65                  70                  75

<210> SEQ ID NO 39
<211> LENGTH: 76
<212> TYPE: PRT
<213> ORGANISM: Artificial sequence
```

```
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 39

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Xaa Pro
65                  70                  75

<210> SEQ ID NO 40
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 40

Gly Pro Ala Ser Val Pro Thr Thr Cys Cys Phe Asn Leu Ala Asn Arg
1               5                   10                  15

Lys Ile Pro Leu Gln Arg Leu Glu Ser Tyr Arg Arg Ile Thr Ser Gly
            20                  25                  30

Lys Cys Pro Gln Lys Ala Val Ile Phe Lys Thr Lys Leu Ala Lys Asp
        35                  40                  45

Ile Cys Ala Asp Pro Lys Lys Lys Trp Val Gln Asp Ser Met Lys Tyr
    50                  55                  60

Leu Asp Gln Lys Ser Pro Thr Pro Xaa Pro
65                  70

<210> SEQ ID NO 41
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is K(ivDde)

<400> SEQUENCE: 41

Gly Pro Ala Ser Val Pro Thr Thr Cys Cys Phe Asn Leu Ala Asn Arg
1               5                   10                  15
```

```
Lys Ile Pro Leu Gln Arg Leu Glu Ser Tyr Arg Arg Ile Thr Ser Gly
             20                  25                  30

Lys Cys Pro Gln Lys Ala Val Ile Phe Lys Thr Lys Leu Ala Lys Asp
         35                  40                  45

Ile Cys Ala Asp Pro Lys Lys Lys Trp Val Gln Asp Ser Met Lys Tyr
 50                  55                  60

Leu Asp Gln Lys Ser Pro Thr Pro Xaa Pro
 65                  70

<210> SEQ ID NO 42
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is K(PEG-Biotin)

<400> SEQUENCE: 42

Gly Pro Ala Ser Val Pro Thr Thr Cys Cys Phe Asn Leu Ala Asn Arg
 1               5                  10                  15

Lys Ile Pro Leu Gln Arg Leu Glu Ser Tyr Arg Arg Ile Thr Ser Gly
             20                  25                  30

Lys Cys Pro Gln Lys Ala Val Ile Phe Lys Thr Lys Leu Ala Lys Asp
         35                  40                  45

Ile Cys Ala Asp Pro Lys Lys Lys Trp Val Gln Asp Ser Met Lys Tyr
 50                  55                  60

Leu Asp Gln Lys Ser Pro Thr Pro Xaa Pro
 65                  70

<210> SEQ ID NO 43
<211> LENGTH: 76
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (1)..(1)
<223> OTHER INFORMATION: X is pyroglutamine or Gln
<220> FEATURE:
<221> NAME/KEY: X
<222> LOCATION: (75)..(75)
<223> OTHER INFORMATION: X is an amino acid residue that can be
      biotinylated, such as lysine, ornithine or diaminopropionic acid
      and optionally is biotinylated, optionally via a spacer molecule
      such as PEG, in particular K(PEG-Biotin)

<400> SEQUENCE: 43

Xaa Pro Asp Ser Val Ser Ile Pro Ile Thr Cys Cys Phe Asn Val Ile
 1               5                  10                  15

Asn Arg Lys Ile Pro Ile Gln Arg Leu Glu Ser Tyr Thr Arg Ile Thr
             20                  25                  30

Asn Ile Gln Cys Pro Lys Glu Ala Val Ile Phe Lys Thr Lys Arg Gly
         35                  40                  45

Lys Glu Val Cys Ala Asp Pro Lys Glu Arg Trp Val Arg Asp Ser Met
 50                  55                  60

Lys His Leu Asp Gln Ile Phe Gln Asn Leu Xaa Pro
 65                  70                  75
```

-continued

```
<210> SEQ ID NO 44
<211> LENGTH: 76
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (1)..(1)
<223> OTHER INFORMATION: X is pyroglutamine or Gln
<220> FEATURE:
<221> NAME/KEY: X
<222> LOCATION: (75)..(75)
<223> OTHER INFORMATION: X is FmocLys(ivDde)

<400> SEQUENCE: 44

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Xaa Pro
65                  70                  75

<210> SEQ ID NO 45
<211> LENGTH: 76
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (1)..(1)
<223> OTHER INFORMATION: X is pyroglutamine
<220> FEATURE:
<221> NAME/KEY: X
<222> LOCATION: (1)..(1)
<223> OTHER INFORMATION: X is pyroglutamine or Gln
<220> FEATURE:
<221> NAME/KEY: X
<222> LOCATION: (75)..(75)
<223> OTHER INFORMATION: X is K(PEG-Biotin)

<400> SEQUENCE: 45

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Xaa Pro
65                  70                  75

<210> SEQ ID NO 46
<211> LENGTH: 68
<212> TYPE: PRT
<213> ORGANISM: Artificial sequence
<220> FEATURE:
<223> OTHER INFORMATION: Synthetic peptide

<400> SEQUENCE: 46
```

```
Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
            35                  40                  45

Val Cys Ala Asn Pro Glu Lys Lys Trp Val Arg Glu Tyr Ile Asn Ser
        50                  55                  60

Leu Glu Lys Ser
65

<210> SEQ ID NO 47
<211> LENGTH: 68
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (67)..(67)
<223> OTHER INFORMATION: X is FmocLys(ivDde)

<400> SEQUENCE: 47

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
            35                  40                  45

Val Cys Ala Asn Pro Glu Lys Lys Trp Val Arg Glu Tyr Ile Asn Ser
        50                  55                  60

Leu Glu Xaa Ser
65

<210> SEQ ID NO 48
<211> LENGTH: 68
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (67)..(67)
<223> OTHER INFORMATION: X is an amino acid residue that can be
      biotinylated, such as lysine, ornithine or diaminopropionic acid
      and optionally is biotinylated (e.g. K-biotin), optionally via a
      spacer molecule such as PEG, in particular K(PEG-Biotin)

<400> SEQUENCE: 48

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
            35                  40                  45

Val Cys Ala Asn Pro Glu Lys Lys Trp Val Arg Glu Tyr Ile Asn Ser
        50                  55                  60

Leu Glu Xaa Ser
65

<210> SEQ ID NO 49
<211> LENGTH: 70
```

```
<212> TYPE: PRT
<213> ORGANISM: Artificial sequence
<220> FEATURE:
<223> OTHER INFORMATION: Synthetic peptide

<400> SEQUENCE: 49

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Leu Ser Val Cys
        35                  40                  45

Ala Asn Pro Lys Gln Thr Trp Val Lys Tyr Ile Val Arg Leu Leu Ser
    50                  55                  60

Lys Lys Val Lys Asn Met
65                  70

<210> SEQ ID NO 50
<211> LENGTH: 70
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (68)..(68)
<223> OTHER INFORMATION: X is FmocLys(ivDde)

<400> SEQUENCE: 50

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Leu Ser Val Cys
        35                  40                  45

Ala Asn Pro Lys Gln Thr Trp Val Lys Tyr Ile Val Arg Leu Leu Ser
    50                  55                  60

Lys Lys Val Xaa Asn Met
65                  70

<210> SEQ ID NO 51
<211> LENGTH: 70
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (68)..(68)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 51

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Leu Ser Val Cys
        35                  40                  45

Ala Asn Pro Lys Gln Thr Trp Val Lys Tyr Ile Val Arg Leu Leu Ser
    50                  55                  60
```

Lys Lys Val Xaa Asn Met
65              70

<210> SEQ ID NO 52
<211> LENGTH: 67
<212> TYPE: PRT
<213> ORGANISM: Artificial sequence
<220> FEATURE:
<223> OTHER INFORMATION: Synthesized peptide

<400> SEQUENCE: 52

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
            35                  40                  45

Val Cys Ile Asp Pro Lys Leu Lys Trp Ile Gln Glu Tyr Leu Glu Lys
    50                  55                  60

Ala Leu Asn
65

<210> SEQ ID NO 53
<211> LENGTH: 66
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (64)..(64)
<223> OTHER INFORMATION: X is FmocLys(ivDde)

<400> SEQUENCE: 53

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
            35                  40                  45

Val Cys Ile Asp Pro Lys Leu Lys Trp Ile Gln Glu Tyr Leu Glu Ala
    50                  55                  60

Leu Asn
65

<210> SEQ ID NO 54
<211> LENGTH: 67
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (64)..(64)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 54

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro

```
                20                  25                  30
Asn Cys Ala Leu Gln Ile Val Ala Arg Leu Lys Asn Asn Arg Gln
            35                  40                  45

Val Cys Ile Asp Pro Lys Leu Lys Trp Ile Gln Glu Tyr Leu Glu Xaa
        50                  55                  60

Ala Leu Asn
65
```

<210> SEQ ID NO 55
<211> LENGTH: 69
<212> TYPE: PRT
<213> ORGANISM: Artificial sequence
<220> FEATURE:
<223> OTHER INFORMATION: Synthetic peptide

<400> SEQUENCE: 55

```
Gly Pro Tyr Gly Ala Asn Met Glu Asp Ser Val Cys Cys Arg Asp Tyr
1               5                   10                  15

Val Arg Tyr Arg Leu Pro Leu Arg Val Val Lys His Phe Tyr Trp Thr
                20                  25                  30

Ser Asp Ser Cys Pro Arg Pro Gly Val Val Leu Leu Thr Phe Arg Asp
            35                  40                  45

Lys Glu Ile Cys Ala Asp Pro Arg Val Pro Trp Val Lys Met Ile Leu
        50                  55                  60

Asn Lys Leu Ser Gln
65
```

<210> SEQ ID NO 56
<211> LENGTH: 69
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (66)..(66)
<223> OTHER INFORMATION: X is FmocLys(ivDde)

<400> SEQUENCE: 56

```
Gly Pro Tyr Gly Ala Asn Met Glu Asp Ser Val Cys Cys Arg Asp Tyr
1               5                   10                  15

Val Arg Tyr Arg Leu Pro Leu Arg Val Val Lys His Phe Tyr Trp Thr
                20                  25                  30

Ser Asp Ser Cys Pro Arg Pro Gly Val Val Leu Leu Thr Phe Arg Asp
            35                  40                  45

Lys Glu Ile Cys Ala Asp Pro Arg Val Pro Trp Val Lys Met Ile Leu
        50                  55                  60

Asn Xaa Leu Ser Gln
65
```

<210> SEQ ID NO 57
<211> LENGTH: 69
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (66)..(66)
<223> OTHER INFORMATION: X is an amino acid residue that can be
      biotinylated, such as lysine, ornithine or diaminopropionic acid
      and optionally is biotinylated, optionally via a spacer molecule
      such as PEG, especially K(PEG-Biotin)

<400> SEQUENCE: 57

```
Gly Pro Tyr Gly Ala Asn Met Glu Asp Ser Val Cys Cys Arg Asp Tyr
1               5                   10                  15

Val Arg Tyr Arg Leu Pro Leu Arg Val Val Lys His Phe Tyr Trp Thr
            20                  25                  30

Ser Asp Ser Cys Pro Arg Pro Gly Val Val Leu Leu Thr Phe Arg Asp
        35                  40                  45

Lys Glu Ile Cys Ala Asp Pro Arg Val Pro Trp Val Lys Met Ile Leu
50                  55                  60

Asn Xaa Leu Ser Gln
65
```

<210> SEQ ID NO 58
<211> LENGTH: 72
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (72)..(72)
<223> OTHER INFORMATION: X is an amino acid residue that can be
      biotinylated, such as lysine, ornithine or diaminopropionic acid
      and optionally is biotinylated (e.g. K-biotin), optionally via a
      spacer molecule such as PEG, in particular K(PEG-Biotin)

<400> SEQUENCE: 58

```
Ala Arg Gly Thr Asn Val Gly Arg Glu Cys Cys Leu Glu Tyr Phe Lys
1               5                   10                  15

Gly Ala Ile Pro Leu Arg Lys Leu Lys Thr Trp Tyr Gln Thr Ser Glu
            20                  25                  30

Asp Cys Ser Arg Asp Ala Ile Val Phe Val Thr Val Gln Gly Arg Ala
        35                  40                  45

Ile Cys Ser Asp Pro Asn Asn Lys Arg Val Lys Asn Ala Val Lys Tyr
    50                  55                  60

Leu Gln Ser Leu Glu Arg Ser Xaa
65                  70
```

<210> SEQ ID NO 59
<211> LENGTH: 72
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (72)..(72)
<223> OTHER INFORMATION: X is FmocLys(ivDde)

<400> SEQUENCE: 59

```
Ala Arg Gly Thr Asn Val Gly Arg Glu Cys Cys Leu Glu Tyr Phe Lys
1               5                   10                  15

Gly Ala Ile Pro Leu Arg Lys Leu Lys Thr Trp Tyr Gln Thr Ser Glu
            20                  25                  30

Asp Cys Ser Arg Asp Ala Ile Val Phe Val Thr Val Gln Gly Arg Ala
        35                  40                  45

Ile Cys Ser Asp Pro Asn Asn Lys Arg Val Lys Asn Ala Val Lys Tyr
    50                  55                  60

Leu Gln Ser Leu Glu Arg Ser Xaa
65                  70
```

<210> SEQ ID NO 60
<211> LENGTH: 72
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (72)..(72)
<223> OTHER INFORMATION: X is K(PEG-Biotin)

<400> SEQUENCE: 60

Ala Arg Gly Thr Asn Val Gly Arg Glu Cys Cys Leu Glu Tyr Phe Lys
1               5                   10                  15

Gly Ala Ile Pro Leu Arg Lys Leu Lys Thr Trp Tyr Gln Thr Ser Glu
            20                  25                  30

Asp Cys Ser Arg Asp Ala Ile Val Phe Val Thr Val Gln Gly Arg Ala
        35                  40                  45

Ile Cys Ser Asp Pro Asn Asn Lys Arg Val Lys Asn Ala Val Lys Tyr
    50                  55                  60

Leu Gln Ser Leu Glu Arg Ser Xaa
65                  70

<210> SEQ ID NO 61
<211> LENGTH: 78
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (78)..(78)
<223> OTHER INFORMATION: X is an amino acid residue that can be
      biotinylated, such as lysine, ornithine or diaminopropionic acid
      and optionally is biotinylated (e.g. K-biotin), optionally via a
      spacer molecule such as PEG, in particular K(PEG-Biotin)

<400> SEQUENCE: 61

Gly Thr Asn Asp Ala Glu Asp Cys Cys Leu Ser Val Thr Gln Lys Pro
1               5                   10                  15

Ile Pro Gly Tyr Ile Val Arg Asn Phe His Tyr Leu Leu Ile Lys Asp
            20                  25                  30

Gly Cys Arg Val Pro Ala Val Val Phe Thr Thr Leu Arg Gly Arg Gln
        35                  40                  45

Leu Cys Ala Pro Pro Asp Gln Pro Trp Val Glu Arg Ile Ile Gln Arg
    50                  55                  60

Leu Gln Arg Thr Ser Ala Lys Met Lys Arg Arg Ser Ser Xaa
65                  70                  75

<210> SEQ ID NO 62
<211> LENGTH: 78
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (78)..(78)
<223> OTHER INFORMATION: X is FmocLys(ivDde)

<400> SEQUENCE: 62

Gly Thr Asn Asp Ala Glu Asp Cys Cys Leu Ser Val Thr Gln Lys Pro
1               5                   10                  15

Ile Pro Gly Tyr Ile Val Arg Asn Phe His Tyr Leu Leu Ile Lys Asp

```
                20                  25                  30
Gly Cys Arg Val Pro Ala Val Val Phe Thr Thr Leu Arg Gly Arg Gln
            35                  40                  45

Leu Cys Ala Pro Pro Asp Gln Pro Trp Val Glu Arg Ile Ile Gln Arg
        50                  55                  60

Leu Gln Arg Thr Ser Ala Lys Met Lys Arg Arg Ser Ser Xaa
65                  70                  75

<210> SEQ ID NO 63
<211> LENGTH: 78
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (78)..(78)
<223> OTHER INFORMATION: X is biotinylated lysine

<400> SEQUENCE: 63

Gly Thr Asn Asp Ala Glu Asp Cys Cys Leu Ser Val Thr Gln Lys Pro
1               5                   10                  15

Ile Pro Gly Tyr Ile Val Arg Asn Phe His Tyr Leu Leu Ile Lys Asp
            20                  25                  30

Gly Cys Arg Val Pro Ala Val Val Phe Thr Thr Leu Arg Gly Arg Gln
            35                  40                  45

Leu Cys Ala Pro Pro Asp Gln Pro Trp Val Glu Arg Ile Ile Gln Arg
        50                  55                  60

Leu Gln Arg Thr Ser Ala Lys Met Lys Arg Arg Ser Ser Xaa
65                  70                  75

<210> SEQ ID NO 64
<211> LENGTH: 73
<212> TYPE: PRT
<213> ORGANISM: Artificial sequence
<220> FEATURE:
<223> OTHER INFORMATION: Synthetic peptide

<400> SEQUENCE: 64

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
            35                  40                  45

Lys Gly Gln Arg Cys Leu Asn Pro Lys Ser Lys Gln Ala Arg Leu Ile
        50                  55                  60

Ile Lys Lys Val Glu Arg Lys Asn Phe
65                  70

<210> SEQ ID NO 65
<211> LENGTH: 74
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (74)..(74)
<223> OTHER INFORMATION: X =a residue that can be biotinylated, such
      as lysine, ornithine or diaminopropionic acid and optionally is
      biotinylated, optionally via a spacer molecule such as PEG. The
      amino acid residue may be added via a spacer molecule such as PEG.
```

```
<400> SEQUENCE: 65

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe Xaa
65                  70

<210> SEQ ID NO 66
<211> LENGTH: 74
<212> TYPE: PRT
<213> ORGANISM: Artificial sequence
<220> FEATURE:
<223> OTHER INFORMATION: Synthetic peptide
<220> FEATURE:
<221> NAME/KEY: X
<222> LOCATION: (74)..(74)
<223> OTHER INFORMATION: X is PEG-K(ivDde)

<400> SEQUENCE: 66

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe Xaa
65                  70

<210> SEQ ID NO 67
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (74)..(74)
<223> OTHER INFORMATION: X is PEG-K(Biotin)

<400> SEQUENCE: 67

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe Xaa
65                  70

<210> SEQ ID NO 68
<211> LENGTH: 74
```

```
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine
<220> FEATURE:
<221> NAME/KEY: X
<222> LOCATION: (72)..(72)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 68

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Xaa
    50                  55                  60

Lys Leu Leu Asp Ala Arg Asn Xaa Val Phe
65                  70

<210> SEQ ID NO 69
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine
<220> FEATURE:
<221> NAME/KEY: X
<222> LOCATION: (72)..(72)
<223> OTHER INFORMATION: X is K(ivDde)

<400> SEQUENCE: 69

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Xaa
    50                  55                  60

Lys Leu Leu Asp Ala Arg Asn Xaa Val Phe
65                  70

<210> SEQ ID NO 70
<211> LENGTH: 74
<212> TYPE: PRT
<213> ORGANISM: Artificial sequence
```

```
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine
<220> FEATURE:
<221> NAME/KEY: X
<222> LOCATION: (72)..(72)
<223> OTHER INFORMATION: X is K(PEG-Biotin)

<400> SEQUENCE: 70

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Xaa
    50                  55                  60

Lys Leu Leu Asp Ala Arg Asn Xaa Val Phe
65                  70

<210> SEQ ID NO 71
<211> LENGTH: 88
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (87)..(87)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 71

Phe Leu Leu Pro Pro Ser Thr Ala Cys Cys Thr Gln Leu Tyr Arg Lys
1               5                   10                  15

Pro Leu Ser Asp Lys Leu Leu Arg Lys Val Ile Gln Val Glu Leu Gln
            20                  25                  30

Glu Ala Asp Gly Asp Cys His Leu Gln Ala Phe Val Leu His Leu Ala
        35                  40                  45

Gln Arg Ser Ile Cys Ile His Pro Gln Asn Pro Ser Leu Ser Gln Trp
    50                  55                  60

Phe Glu His Gln Glu Arg Lys Leu His Gly Thr Leu Pro Lys Leu Asn
65                  70                  75                  80

Phe Gly Met Leu Arg Lys Xaa Gly
                85

<210> SEQ ID NO 72
<211> LENGTH: 88
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (87)..(87)
<223> OTHER INFORMATION: X is K(ivDde)
```

<400> SEQUENCE: 72

Phe Leu Leu Pro Pro Ser Thr Ala Cys Cys Thr Gln Leu Tyr Arg Lys
1               5                   10                  15

Pro Leu Ser Asp Lys Leu Leu Arg Lys Val Ile Gln Val Glu Leu Gln
            20                  25                  30

Glu Ala Asp Gly Asp Cys His Leu Gln Ala Phe Val Leu His Leu Ala
        35                  40                  45

Gln Arg Ser Ile Cys Ile His Pro Gln Asn Pro Ser Leu Ser Gln Trp
    50                  55                  60

Phe Glu His Gln Glu Arg Lys Leu His Gly Thr Leu Pro Lys Leu Asn
65                  70                  75                  80

Phe Gly Met Leu Arg Lys Xaa Gly
                85

<210> SEQ ID NO 73
<211> LENGTH: 88
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (87)..(87)
<223> OTHER INFORMATION: X is K(PEG-Biotin)

<400> SEQUENCE: 73

Phe Leu Leu Pro Pro Ser Thr Ala Cys Cys Thr Gln Leu Tyr Arg Lys
1               5                   10                  15

Pro Leu Ser Asp Lys Leu Leu Arg Lys Val Ile Gln Val Glu Leu Gln
            20                  25                  30

Glu Ala Asp Gly Asp Cys His Leu Gln Ala Phe Val Leu His Leu Ala
        35                  40                  45

Gln Arg Ser Ile Cys Ile His Pro Gln Asn Pro Ser Leu Ser Gln Trp
    50                  55                  60

Phe Glu His Gln Glu Arg Lys Leu His Gly Thr Leu Pro Lys Leu Asn
65                  70                  75                  80

Phe Gly Met Leu Arg Lys Xaa Gly
                85

<210> SEQ ID NO 74
<211> LENGTH: 77
<212> TYPE: PRT
<213> ORGANISM: Artificial sequence
<220> FEATURE:
<223> OTHER INFORMATION: Synthesized peptide

<400> SEQUENCE: 74

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Arg Ser Pro
65                  70                  75

<210> SEQ ID NO 75

```
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is K(ivDde), optionally attached via a spacer
      such as PEG, e.g. -PEG-K(ivDde)

<400> SEQUENCE: 75

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Arg Ser Pro Xaa
65                  70                  75

<210> SEQ ID NO 76
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X =a residue that can be biotinylated, such
      as lysine, ornithine or diaminopropionic acid and optionally is
      biotinylated, optionally via a spacer molecule such as PEG. The
      amino acid residue may be added via a spacer molecule such as PEG.

<400> SEQUENCE: 76

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Arg Ser Pro Xaa
65                  70                  75

<210> SEQ ID NO 77
<211> LENGTH: 97
<212> TYPE: PRT
<213> ORGANISM: Artificial sequence
<220> FEATURE:
<223> OTHER INFORMATION: Synthesized peptide

<400> SEQUENCE: 77

Met Lys Val Ser Ala Ala Leu Leu Trp Leu Leu Leu Ile Ala Ala Ala
1               5                   10                  15

Phe Ser Pro Gln Gly Leu Ala Gly Pro Ala Ser Val Pro Thr Thr Cys
            20                  25                  30

Cys Phe Asn Leu Ala Asn Arg Lys Ile Pro Leu Gln Arg Leu Glu Ser
        35                  40                  45
```

Tyr Arg Arg Ile Thr Ser Gly Lys Cys Pro Gln Lys Ala Val Ile Phe
            50                  55                  60

Lys Thr Lys Leu Ala Lys Asp Ile Cys Ala Asp Pro Lys Lys Trp
 65                  70                  75                  80

Val Gln Asp Ser Met Lys Tyr Leu Asp Gln Lys Ser Pro Thr Pro Lys
                 85                  90                  95

Pro

<210> SEQ ID NO 78
<211> LENGTH: 74
<212> TYPE: PRT
<213> ORGANISM: Artificial sequence
<220> FEATURE:
<223> OTHER INFORMATION: Synthesized peptide

<400> SEQUENCE: 78

Gly Pro Ala Ser Val Pro Thr Thr Cys Cys Phe Asn Leu Ala Asn Arg
 1               5                  10                  15

Lys Ile Pro Leu Gln Arg Leu Glu Ser Tyr Arg Arg Ile Thr Ser Gly
                 20                  25                  30

Lys Cys Pro Gln Lys Ala Val Ile Phe Lys Thr Lys Leu Ala Lys Asp
             35                  40                  45

Ile Cys Ala Asp Pro Lys Lys Lys Trp Val Gln Asp Ser Met Lys Tyr
 50                  55                  60

Leu Asp Gln Lys Ser Pro Thr Pro Lys Pro
 65                  70

<210> SEQ ID NO 79
<211> LENGTH: 68
<212> TYPE: PRT
<213> ORGANISM: Artificial sequence
<220> FEATURE:
<223> OTHER INFORMATION: Synthesized peptide

<400> SEQUENCE: 79

Ser Pro Tyr Ser Ser Asp Thr Thr Pro Cys Cys Phe Ala Tyr Ile Ala
 1               5                  10                  15

Arg Pro Leu Pro Arg Ala His Ile Lys Glu Tyr Phe Tyr Thr Ser Gly
                 20                  25                  30

Lys Cys Ser Asn Pro Ala Val Val Phe Val Thr Arg Lys Asn Arg Gln
             35                  40                  45

Val Cys Ala Asn Pro Glu Lys Lys Trp Val Arg Glu Tyr Ile Asn Ser
 50                  55                  60

Leu Glu Lys Ser
 65

<210> SEQ ID NO 80
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln

<400> SEQUENCE: 80

Xaa Pro Asp Ser Val Ser Ile Pro Ile Thr Cys Cys Phe Asn Val Ile
 1               5                  10                  15

Asn Arg Lys Ile Pro Ile Gln Arg Leu Glu Ser Tyr Thr Arg Ile Thr

```
                  20                  25                  30

Asn Ile Gln Cys Pro Lys Glu Ala Val Ile Phe Lys Thr Lys Arg Gly
             35                  40                  45

Lys Glu Val Cys Ala Asp Pro Lys Glu Arg Trp Val Arg Asp Ser Met
 50                  55                  60

Lys His Leu Asp Gln Ile Phe Gln Asn Leu Lys Pro
 65                  70                  75

<210> SEQ ID NO 81
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is K(ivDde)

<400> SEQUENCE: 81

Xaa Pro Asp Ser Val Ser Ile Pro Ile Thr Cys Cys Phe Asn Val Ile
 1               5                  10                  15

Asn Arg Lys Ile Pro Ile Gln Arg Leu Glu Ser Tyr Thr Arg Ile Thr
             20                  25                  30

Asn Ile Gln Cys Pro Lys Glu Ala Val Ile Phe Lys Thr Lys Arg Gly
             35                  40                  45

Lys Glu Val Cys Ala Asp Pro Lys Glu Arg Trp Val Arg Asp Ser Met
 50                  55                  60

Lys His Leu Asp Gln Ile Phe Gln Asn Leu Xaa Pro
 65                  70                  75

<210> SEQ ID NO 82
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 82

Xaa Pro Asp Ser Val Ser Ile Pro Ile Thr Cys Cys Phe Asn Val Ile
 1               5                  10                  15

Asn Arg Lys Ile Pro Ile Gln Arg Leu Glu Ser Tyr Thr Arg Ile Thr
             20                  25                  30

Asn Ile Gln Cys Pro Lys Glu Ala Val Ile Phe Lys Thr Lys Arg Gly
             35                  40                  45

Lys Glu Val Cys Ala Asp Pro Lys Glu Arg Trp Val Arg Asp Ser Met
 50                  55                  60

Lys His Leu Asp Gln Ile Phe Gln Asn Leu Xaa Pro
 65                  70                  75
```

```
<210> SEQ ID NO 83
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 83

Gly Pro Ala Ser Val Pro Thr Thr Cys Cys Phe Asn Leu Ala Asn Arg
1               5                   10                  15

Lys Ile Pro Leu Gln Arg Leu Glu Ser Tyr Arg Arg Ile Thr Ser Gly
            20                  25                  30

Lys Cys Pro Gln Lys Ala Val Ile Phe Lys Thr Lys Leu Ala Lys Asp
        35                  40                  45

Ile Cys Ala Asp Pro Lys Lys Lys Trp Val Gln Asp Ser Met Lys Tyr
    50                  55                  60

Leu Asp Gln Lys Ser Pro Thr Pro Xaa Pro
65                  70

<210> SEQ ID NO 84
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is K(ivDde)

<400> SEQUENCE: 84

Gly Pro Ala Ser Val Pro Thr Thr Cys Cys Phe Asn Leu Ala Asn Arg
1               5                   10                  15

Lys Ile Pro Leu Gln Arg Leu Glu Ser Tyr Arg Arg Ile Thr Ser Gly
            20                  25                  30

Lys Cys Pro Gln Lys Ala Val Ile Phe Lys Thr Lys Leu Ala Lys Asp
        35                  40                  45

Ile Cys Ala Asp Pro Lys Lys Lys Trp Val Gln Asp Ser Met Lys Tyr
    50                  55                  60

Leu Asp Gln Lys Ser Pro Thr Pro Xaa Pro
65                  70

<210> SEQ ID NO 85
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is K(PEG-Biotin)

<400> SEQUENCE: 85

Gly Pro Ala Ser Val Pro Thr Thr Cys Cys Phe Asn Leu Ala Asn Arg
1               5                   10                  15
```

```
Lys Ile Pro Leu Gln Arg Leu Glu Ser Tyr Arg Arg Ile Thr Ser Gly
                20                  25                  30

Lys Cys Pro Gln Lys Ala Val Ile Phe Lys Thr Lys Leu Ala Lys Asp
            35                  40                  45

Ile Cys Ala Asp Pro Lys Lys Lys Trp Val Gln Asp Ser Met Lys Tyr
50                  55                  60

Leu Asp Gln Lys Ser Pro Thr Pro Xaa Pro
65                  70
```

```
<210> SEQ ID NO 86
<211> LENGTH: 68
<212> TYPE: PRT
<213> ORGANISM: Artificial sequence
<220> FEATURE:
<223> OTHER INFORMATION: Synthesized peptide

<400> SEQUENCE: 86

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
                20                  25                  30

Lys Cys Ser Asn Pro Ala Val Val Phe Val Thr Arg Lys Asn Arg Gln
            35                  40                  45

Val Cys Ala Asn Pro Glu Lys Lys Trp Val Arg Glu Tyr Ile Asn Ser
50                  55                  60

Leu Glu Lys Ser
65
```

```
<210> SEQ ID NO 87
<211> LENGTH: 68
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (67)..(67)
<223> OTHER INFORMATION: X is K(ivDde)

<400> SEQUENCE: 87

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
                20                  25                  30

Lys Cys Ser Asn Pro Ala Val Val Phe Val Thr Arg Lys Asn Arg Gln
            35                  40                  45

Val Cys Ala Asn Pro Glu Lys Lys Trp Val Arg Glu Tyr Ile Asn Ser
50                  55                  60

Leu Glu Xaa Ser
65
```

```
<210> SEQ ID NO 88
<211> LENGTH: 68
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (67)..(67)
<223> OTHER INFORMATION: X is an amino acid residue that can be
      biotinylated, such as lysine, ornithine or diaminopropionic acid
      and optionally is biotinylated, optionally via a spacer molecule
``` such as PEG, e.g. K(PEG-Biotin)

<400> SEQUENCE: 88

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Xaa Ser
65

<210> SEQ ID NO 89
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine

<400> SEQUENCE: 89

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Xaa
    50                  55                  60

Lys Leu Leu Asp Ala Arg Asn Lys Val Phe
65                  70

<210> SEQ ID NO 90
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine
<220> FEATURE:
<221> NAME/KEY: X
<222> LOCATION: (72)..(72)
<223> OTHER INFORMATION: X is K(ivDde)

<400> SEQUENCE: 90

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

```
Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Xaa
    50                  55                  60

Lys Leu Leu Asp Ala Arg Asn Xaa Val Phe
65                  70

<210> SEQ ID NO 91
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine
<220> FEATURE:
<221> NAME/KEY: X
<222> LOCATION: (72)..(72)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 91

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
                20                  25                  30

Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Xaa
    50                  55                  60

Lys Leu Leu Asp Ala Arg Asn Xaa Val Phe
65                  70

<210> SEQ ID NO 92
<211> LENGTH: 97
<212> TYPE: PRT
<213> ORGANISM: Artificial sequence
<220> FEATURE:
<223> OTHER INFORMATION: Synthesized peptide

<400> SEQUENCE: 92

Met Lys Val Ser Ala Ala Leu Leu Trp Leu Leu Leu Ile Ala Ala Ala
1               5                   10                  15

Phe Ser Pro Gln Gly Leu Ala Gly Pro Ala Ser Val Pro Thr Thr Cys
                20                  25                  30

Cys Phe Asn Leu Ala Asn Arg Lys Ile Pro Leu Gln Arg Leu Glu Ser
        35                  40                  45

Tyr Arg Arg Ile Thr Ser Gly Lys Cys Pro Gln Lys Ala Val Ile Phe
    50                  55                  60

Lys Thr Lys Leu Ala Lys Asp Ile Cys Ala Asp Pro Lys Lys Lys Trp
65                  70                  75                  80

Val Gln Asp Ser Met Lys Tyr Leu Asp Gln Lys Ser Pro Thr Pro Lys
                85                  90                  95

Pro
```

-continued

<210> SEQ ID NO 93
<211> LENGTH: 74
<212> TYPE: PRT
<213> ORGANISM: Artificial sequence
<220> FEATURE:
<223> OTHER INFORMATION: Synthesized peptide

<400> SEQUENCE: 93

Gly Pro Ala Ser Val Pro Thr Thr Cys Cys Phe Asn Leu Ala Asn Arg
1               5                   10                  15

Lys Ile Pro Leu Gln Arg Leu Glu Ser Tyr Arg Arg Ile Thr Ser Gly
            20                  25                  30

Lys Cys Pro Gln Lys Ala Val Ile Phe Lys Thr Lys Leu Ala Lys Asp
        35                  40                  45

Ile Cys Ala Asp Pro Lys Lys Lys Trp Val Gln Asp Ser Met Lys Tyr
    50                  55                  60

Leu Asp Gln Lys Ser Pro Thr Pro Lys Pro
65                  70

<210> SEQ ID NO 94
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln

<400> SEQUENCE: 94

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro
65                  70                  75

<210> SEQ ID NO 95
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is K(ivDde)

<400> SEQUENCE: 95

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
            35                  40                  45

Lys Glu Val Cys Ala Asp Pro Lys Glu Arg Trp Val Arg Asp Ser Met
 50                  55                  60

Lys His Leu Asp Gln Ile Phe Gln Asn Leu Xaa Pro
 65                  70                  75

<210> SEQ ID NO 96
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 96

Xaa Pro Asp Ser Val Ser Ile Pro Ile Thr Cys Cys Phe Asn Val Ile
 1               5                  10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
            35                  40                  45

Lys Glu Val Cys Ala Asp Pro Lys Glu Arg Trp Val Arg Asp Ser Met
 50                  55                  60

Lys His Leu Asp Gln Ile Phe Gln Asn Leu Xaa Pro
 65                  70                  75

<210> SEQ ID NO 97
<211> LENGTH: 68
<212> TYPE: PRT
<213> ORGANISM: Artificial sequence
<220> FEATURE:
<223> OTHER INFORMATION: Synthesized peptide

<400> SEQUENCE: 97

Ser Pro Tyr Ser Ser Asp Thr Thr Pro Cys Cys Phe Ala Tyr Ile Ala
 1               5                  10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
            35                  40                  45

Val Cys Ala Asn Pro Glu Lys Lys Trp Val Arg Glu Tyr Ile Asn Ser
 50                  55                  60

Leu Glu Lys Ser
 65

<210> SEQ ID NO 98
<211> LENGTH: 68
<212> TYPE: PRT
<213> ORGANISM: Artificial sequence
<220> FEATURE:
<223> OTHER INFORMATION: Synthesized peptide
<220> FEATURE:
<221> NAME/KEY: X

```
<222> LOCATION: (67)..(67)
<223> OTHER INFORMATION: X is K(ivDde)

<400> SEQUENCE: 98

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Xaa Ser
65

<210> SEQ ID NO 99
<211> LENGTH: 68
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (67)..(67)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 99

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Xaa Ser
65

<210> SEQ ID NO 100
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln

<400> SEQUENCE: 100

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
```

65            70           75

<210> SEQ ID NO 101
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is K(ivDde)

<400> SEQUENCE: 101

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Xaa Thr
65                  70                  75

<210> SEQ ID NO 102
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 102

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Xaa Thr
65                  70                  75

<210> SEQ ID NO 103
<211> LENGTH: 78
<212> TYPE: PRT
<213> ORGANISM: Artificial sequence
<220> FEATURE:
<223> OTHER INFORMATION: Synthesized peptide
<220> FEATURE:

```
<221> NAME/KEY: X
<222> LOCATION: (78)..(78)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 103

Ala Val Leu Pro Arg Ser Ala Lys Glu Leu Arg Cys Gln Cys Ile Lys
1               5                   10                  15

Thr Tyr Ser Lys Pro Phe His Pro Lys Phe Ile Lys Glu Leu Arg Val
            20                  25                  30

Ile Glu Ser Gly Pro His Cys Ala Asn Thr Glu Ile Ile Val Lys Leu
        35                  40                  45

Ser Asp Gly Arg Glu Leu Cys Leu Asp Pro Lys Glu Asn Trp Val Gln
    50                  55                  60

Arg Val Val Glu Lys Phe Leu Lys Arg Ala Glu Asn Ser Xaa
65                  70                  75

<210> SEQ ID NO 104
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is K(ivDde)

<400> SEQUENCE: 104

Ala Val Leu Pro Arg Ser Ala Lys Glu Leu Arg Cys Gln Cys Ile Lys
1               5                   10                  15

Thr Tyr Ser Lys Pro Phe His Pro Lys Phe Ile Lys Glu Leu Arg Val
            20                  25                  30

Ile Glu Ser Gly Pro His Cys Ala Asn Thr Glu Ile Ile Val Lys Leu
        35                  40                  45

Ser Asp Gly Arg Glu Leu Cys Leu Asp Pro Lys Glu Asn Trp Val Gln
    50                  55                  60

Arg Val Val Glu Lys Phe Leu Lys Arg Ala Glu Asn Ser Xaa
65                  70                  75

<210> SEQ ID NO 105
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is K(PEG-Biotin)

<400> SEQUENCE: 105

Ala Val Leu Pro Arg Ser Ala Lys Glu Leu Arg Cys Gln Cys Ile Lys
1               5                   10                  15

Thr Tyr Ser Lys Pro Phe His Pro Lys Phe Ile Lys Glu Leu Arg Val
            20                  25                  30

Ile Glu Ser Gly Pro His Cys Ala Asn Thr Glu Ile Ile Val Lys Leu
        35                  40                  45

Ser Asp Gly Arg Glu Leu Cys Leu Asp Pro Lys Glu Asn Trp Val Gln
    50                  55                  60
```

```
Arg Val Val Glu Lys Phe Leu Lys Arg Ala Glu Asn Ser Xaa
 65                  70                  75
```

<210> SEQ ID NO 106
<211> LENGTH: 73
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 106

```
Ser Ala Lys Glu Leu Arg Cys Gln Cys Ile Lys Thr Tyr Ser Lys Pro
 1               5                  10                  15

Phe His Pro Lys Phe Ile Lys Glu Leu Arg Val Ile Glu Ser Gly Pro
             20                  25                  30

His Cys Ala Asn Thr Glu Ile Ile Val Lys Leu Ser Asp Gly Arg Glu
         35                  40                  45

Leu Cys Leu Asp Pro Lys Glu Asn Trp Val Gln Arg Val Val Glu Lys
     50                  55                  60

Phe Leu Lys Arg Ala Glu Asn Ser Xaa
 65                  70
```

<210> SEQ ID NO 107
<211> LENGTH: 73
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is K(ivDde)

<400> SEQUENCE: 107

```
Ser Ala Lys Glu Leu Arg Cys Gln Cys Ile Lys Thr Tyr Ser Lys Pro
 1               5                  10                  15

Phe His Pro Lys Phe Ile Lys Glu Leu Arg Val Ile Glu Ser Gly Pro
             20                  25                  30

His Cys Ala Asn Thr Glu Ile Ile Val Lys Leu Ser Asp Gly Arg Glu
         35                  40                  45

Leu Cys Leu Asp Pro Lys Glu Asn Trp Val Gln Arg Val Val Glu Lys
     50                  55                  60

Phe Leu Lys Arg Ala Glu Asn Ser Xaa
 65                  70
```

<210> SEQ ID NO 108
<211> LENGTH: 73
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is K(PEG-Biotin)

<400> SEQUENCE: 108

```
Ser Ala Lys Glu Leu Arg Cys Gln Cys Ile Lys Thr Tyr Ser Lys Pro
```

```
                1               5                   10                  15
Phe His Pro Lys Phe Ile Lys Glu Leu Arg Val Ile Glu Ser Gly Pro
                20                  25                  30

His Cys Ala Asn Thr Glu Ile Ile Val Lys Leu Ser Asp Gly Arg Glu
            35                  40                  45

Leu Cys Leu Asp Pro Lys Glu Asn Trp Val Gln Arg Val Val Glu Lys
    50                  55                  60

Phe Leu Lys Arg Ala Glu Asn Ser Xaa
65                  70
```

<210> SEQ ID NO 109
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 109

```
Gly Pro Ala Ser Val Pro Thr Thr Cys Cys Phe Asn Leu Ala Asn Arg
1               5                   10                  15

Lys Ile Pro Leu Gln Arg Leu Glu Ser Tyr Arg Arg Ile Thr Ser Gly
                20                  25                  30

Lys Cys Pro Gln Lys Ala Val Ile Phe Lys Thr Lys Leu Ala Lys Asp
            35                  40                  45

Ile Cys Ala Asp Pro Lys Lys Lys Trp Val Gln Asp Ser Met Lys Tyr
    50                  55                  60

Leu Asp Gln Lys Ser Pro Thr Pro Xaa Pro
65                  70
```

<210> SEQ ID NO 110
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is K(ivDde)

<400> SEQUENCE: 110

```
Gly Pro Ala Ser Val Pro Thr Thr Cys Cys Phe Asn Leu Ala Asn Arg
1               5                   10                  15

Lys Ile Pro Leu Gln Arg Leu Glu Ser Tyr Arg Arg Ile Thr Ser Gly
                20                  25                  30

Lys Cys Pro Gln Lys Ala Val Ile Phe Lys Thr Lys Leu Ala Lys Asp
            35                  40                  45

Ile Cys Ala Asp Pro Lys Lys Lys Trp Val Gln Asp Ser Met Lys Tyr
    50                  55                  60

Leu Asp Gln Lys Ser Pro Thr Pro Xaa Pro
65                  70
```

<210> SEQ ID NO 111
<211> LENGTH: 74
<212> TYPE: PRT

```
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is K(PEG-Biotin)

<400> SEQUENCE: 111
```

Gly Pro Ala Ser Val Pro Thr Thr Cys Cys Phe Asn Leu Ala Asn Arg
1               5                   10                  15

Lys Ile Pro Leu Gln Arg Leu Glu Ser Tyr Arg Arg Ile Thr Ser Gly
            20                  25                  30

Lys Cys Pro Gln Lys Ala Val Ile Phe Lys Thr Lys Leu Ala Lys Asp
        35                  40                  45

Ile Cys Ala Asp Pro Lys Lys Lys Trp Val Gln Asp Ser Met Lys Tyr
50                  55                  60

Leu Asp Gln Lys Ser Pro Thr Pro Xaa Pro
65                  70

```
<210> SEQ ID NO 112
<211> LENGTH: 99
<212> TYPE: PRT
<213> ORGANISM: Artificial sequence
<220> FEATURE:
<223> OTHER INFORMATION: Synthesized peptide

<400> SEQUENCE: 112
```

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

```
<210> SEQ ID NO 113
<211> LENGTH: 76
<212> TYPE: PRT
<213> ORGANISM: Artificial sequence
<220> FEATURE:
<223> OTHER INFORMATION: Synthesized peptide

<400> SEQUENCE: 113
```

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
50                  55                  60

Asp His Leu Asp Lys Gln Thr Gln Thr Pro Lys Thr
65                  70                  75

<210> SEQ ID NO 114
<211> LENGTH: 68
<212> TYPE: PRT
<213> ORGANISM: Artificial sequence
<220> FEATURE:
<223> OTHER INFORMATION: Synthesized peptide

<400> SEQUENCE: 114

Val Thr Cys Cys Tyr Asn Phe Thr Asn Arg Lys Ile Ser Val Gln Arg
1               5                   10                  15

Leu Ala Ser Tyr Arg Arg Ile Thr Ser Ser Lys Cys Pro Lys Glu Ala
            20                  25                  30

Val Ile Phe Lys Thr Ile Val Ala Lys Glu Ile Cys Ala Asp Pro Lys
        35                  40                  45

Gln Lys Trp Val Gln Asp Ser Met Asp His Leu Asp Lys Gln Thr Gln
    50                  55                  60

Thr Pro Lys Thr
65

<210> SEQ ID NO 115
<211> LENGTH: 104
<212> TYPE: PRT
<213> ORGANISM: Artificial sequence
<220> FEATURE:
<223> OTHER INFORMATION: Synthesized peptide

<400> SEQUENCE: 115

Met Lys Ile Ser Thr Leu Leu Cys Leu Leu Leu Ile Ala Thr Thr Ile
1               5                   10                  15

Ser Pro Gln Val Leu Ala Gly Pro Asp Ala Val Ser Thr Pro Val Thr
            20                  25                  30

Cys Cys Tyr Asn Val Val Lys Gln Lys Ile His Val Arg Lys Leu Lys
        35                  40                  45

Ser Tyr Arg Arg Ile Thr Ser Ser Gln Cys Pro Arg Glu Ala Val Ile
    50                  55                  60

Phe Arg Thr Ile Leu Asp Lys Glu Ile Cys Ala Asp Pro Lys Glu Lys
65                  70                  75                  80

Trp Val Lys Asn Ser Ile Asn His Leu Asp Lys Thr Ser Gln Thr Phe
                85                  90                  95

Ile Leu Glu Pro Ser Cys Leu Gly
            100

<210> SEQ ID NO 116
<211> LENGTH: 82
<212> TYPE: PRT
<213> ORGANISM: Artificial sequence
<220> FEATURE:
<223> OTHER INFORMATION: Synthesized peptide

<400> SEQUENCE: 116

Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
            20                  25                  30

Ser Ser Gln Cys Pro Arg Glu Ala Val Ile Phe Arg Thr Ile Leu Asp
        35                  40                  45

Lys Glu Ile Cys Ala Asp Pro Lys Glu Lys Trp Val Lys Asn Ser Ile
    50                  55                  60

Asn His Leu Asp Lys Thr Ser Gln Thr Phe Ile Leu Glu Pro Ser Cys
65                  70                  75                  80

Leu Gly

<210> SEQ ID NO 117
<211> LENGTH: 76
<212> TYPE: PRT
<213> ORGANISM: Artificial sequence
<220> FEATURE:
<223> OTHER INFORMATION: Synthesized peptide

<400> SEQUENCE: 117

Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
            20                  25                  30

Ser Ser Gln Cys Pro Arg Glu Ala Val Ile Phe Arg Thr Ile Leu Asp
        35                  40                  45

Lys Glu Ile Cys Ala Asp Pro Lys Glu Lys Trp Val Lys Asn Ser Ile
    50                  55                  60

Asn His Leu Asp Lys Thr Ser Gln Thr Phe Ile Leu
65                  70                  75

<210> SEQ ID NO 118
<211> LENGTH: 76
<212> TYPE: PRT
<213> ORGANISM: Artificial sequence
<220> FEATURE:
<223> OTHER INFORMATION: Synthesized peptide

<400> SEQUENCE: 118

Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
            20                  25                  30

Ser Ser Gln Cys Pro Arg Glu Ala Val Ile Phe Arg Thr Ile Leu Asp
        35                  40                  45

Lys Glu Ile Cys Ala Asp Pro Lys Glu Lys Trp Val Lys Asn Ser Ile
    50                  55                  60

Asn His Leu Asp Lys Thr Ser Gln Thr Phe Lys Leu
65                  70                  75

<210> SEQ ID NO 119
<211> LENGTH: 68
<212> TYPE: PRT
<213> ORGANISM: Artificial sequence
<220> FEATURE:
<223> OTHER INFORMATION: Synthesized peptide

<400> SEQUENCE: 119

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Lys Ser
65

```
<210> SEQ ID NO 120
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine
<220> FEATURE:
<221> NAME/KEY: X
<222> LOCATION: (72)..(72)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 120

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Xaa
    50                  55                  60

Lys Leu Leu Asp Ala Arg Asn Xaa Val Phe
65                  70

<210> SEQ ID NO 121
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine
<220> FEATURE:
<221> NAME/KEY: X
<222> LOCATION: (72)..(72)
<223> OTHER INFORMATION: X is K(ivDde)

<400> SEQUENCE: 121

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Xaa
    50                  55                  60

Lys Leu Leu Asp Ala Arg Asn Xaa Val Phe
65                  70
```

<210> SEQ ID NO 122
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine
<220> FEATURE:
<221> NAME/KEY: X
<222> LOCATION: (72)..(72)
<223> OTHER INFORMATION: X is K(PEG-Biotin)

<400> SEQUENCE: 122

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Xaa
    50                  55                  60

Lys Leu Leu Asp Ala Arg Asn Xaa Val Phe
65                  70

<210> SEQ ID NO 123
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln

<400> SEQUENCE: 123

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75

<210> SEQ ID NO 124
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)

<223> OTHER INFORMATION: X is K(ivDde)

<400> SEQUENCE: 124

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
50                  55                  60

Asp His Leu Asp Lys Gln Thr Gln Thr Pro Xaa Thr
65                  70                  75

<210> SEQ ID NO 125
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 125

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
50                  55                  60

Asp His Leu Asp Lys Gln Thr Gln Thr Pro Xaa Thr
65                  70                  75

<210> SEQ ID NO 126
<211> LENGTH: 68
<212> TYPE: PRT
<213> ORGANISM: Artificial sequence
<220> FEATURE:
<223> OTHER INFORMATION: Synthesized peptide

<400> SEQUENCE: 126

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
50                  55                  60

Leu Glu Lys Ser
65

```
<210> SEQ ID NO 127
<211> LENGTH: 68
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (67)..(67)
<223> OTHER INFORMATION: X is K(ivDde)

<400> SEQUENCE: 127
```

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Xaa Ser
65

```
<210> SEQ ID NO 128
<211> LENGTH: 68
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (67)..(67)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 128
```

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Xaa Ser
65

```
<210> SEQ ID NO 129
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln

<400> SEQUENCE: 129
```

Xaa Pro Asp Ser Val Ser Ile Pro Ile Thr Cys Cys Phe Asn Val Ile
1               5                   10                  15

```
Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
 50                  55                  60

Lys His Leu Asp Gln Ile Phe Gln Asn Leu Lys Pro
 65                  70                  75

<210> SEQ ID NO 130
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is K(ivDde)

<400> SEQUENCE: 130

Xaa Pro Asp Ser Val Ser Ile Pro Ile Thr Cys Cys Phe Asn Val Ile
 1               5                  10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
 50                  55                  60

Lys His Leu Asp Gln Ile Phe Gln Asn Leu Xaa Pro
 65                  70                  75

<210> SEQ ID NO 131
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 131

Xaa Pro Asp Ser Val Ser Ile Pro Ile Thr Cys Cys Phe Asn Val Ile
 1               5                  10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
 50                  55                  60

Lys His Leu Asp Gln Ile Phe Gln Asn Leu Xaa Pro
```

-continued

```
                65                  70                  75

<210> SEQ ID NO 132
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 132

Ala Val Leu Pro Arg Ser Ala Lys Glu Leu Arg Cys Gln Cys Ile Lys
1               5                   10                  15

Thr Tyr Ser Lys Pro Phe His Pro Lys Phe Ile Lys Glu Leu Arg Val
                20                  25                  30

Ile Glu Ser Gly Pro His Cys Ala Asn Thr Glu Ile Ile Val Lys Leu
            35                  40                  45

Ser Asp Gly Arg Glu Leu Cys Leu Asp Pro Lys Glu Asn Trp Val Gln
        50                  55                  60

Arg Val Val Glu Lys Phe Leu Lys Arg Ala Glu Asn Ser Xaa
65                  70                  75

<210> SEQ ID NO 133
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is K(ivDde)

<400> SEQUENCE: 133

Ala Val Leu Pro Arg Ser Ala Lys Glu Leu Arg Cys Gln Cys Ile Lys
1               5                   10                  15

Thr Tyr Ser Lys Pro Phe His Pro Lys Phe Ile Lys Glu Leu Arg Val
                20                  25                  30

Ile Glu Ser Gly Pro His Cys Ala Asn Thr Glu Ile Ile Val Lys Leu
            35                  40                  45

Ser Asp Gly Arg Glu Leu Cys Leu Asp Pro Lys Glu Asn Trp Val Gln
        50                  55                  60

Arg Val Val Glu Lys Phe Leu Lys Arg Ala Glu Asn Ser Xaa
65                  70                  75

<210> SEQ ID NO 134
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is K(PEG-Biotin)

<400> SEQUENCE: 134

Ala Val Leu Pro Arg Ser Ala Lys Glu Leu Arg Cys Gln Cys Ile Lys
1               5                   10                  15
```

```
Thr Tyr Ser Lys Pro Phe His Pro Lys Phe Ile Lys Glu Leu Arg Val
            20                  25                  30

Ile Glu Ser Gly Pro His Cys Ala Asn Thr Glu Ile Ile Val Lys Leu
        35                  40                  45

Ser Asp Gly Arg Glu Leu Cys Leu Asp Pro Lys Glu Asn Trp Val Gln
50                  55                  60

Arg Val Val Glu Lys Phe Leu Lys Arg Ala Glu Asn Ser Xaa
65                  70                  75

<210> SEQ ID NO 135
<211> LENGTH: 73
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 135

Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Glu Ser Gly Pro
            20                  25                  30

His Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser Xaa
65                  70

<210> SEQ ID NO 136
<211> LENGTH: 73
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is K(ivDde)

<400> SEQUENCE: 136

Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Glu Ser Gly Pro
            20                  25                  30

His Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser Xaa
65                  70

<210> SEQ ID NO 137
<211> LENGTH: 73
<212> TYPE: PRT
<213> ORGANISM: Artificial sequence
```

```
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is K(PEG-Biotin)

<400> SEQUENCE: 137

Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Glu Ser Gly Pro
            20                  25                  30

His Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser Xaa
65                  70

<210> SEQ ID NO 138
<211> LENGTH: 70
<212> TYPE: PRT
<213> ORGANISM: Artificial sequence
<220> FEATURE:
<223> OTHER INFORMATION: Synthesized peptide

<400> SEQUENCE: 138

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Lys Leu Ser Val Cys
        35                  40                  45

Ala Asn Pro Lys Gln Thr Trp Val Lys Tyr Ile Val Arg Leu Leu Ser
    50                  55                  60

Lys Lys Val Lys Asn Met
65                  70

<210> SEQ ID NO 139
<211> LENGTH: 70
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (68)..(68)
<223> OTHER INFORMATION: X is K(ivDde)

<400> SEQUENCE: 139

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Lys Leu Ser Val Cys
        35                  40                  45

Ala Asn Pro Lys Gln Thr Trp Val Lys Tyr Ile Val Arg Leu Leu Ser
    50                  55                  60

Lys Lys Val Xaa Asn Met
65                  70
```

```
<210> SEQ ID NO 140
<211> LENGTH: 70
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (68)..(68)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 140

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Lys Leu Ser Val Cys
        35                  40                  45

Ala Asn Pro Lys Gln Thr Trp Val Lys Tyr Ile Val Arg Leu Leu Ser
    50                  55                  60

Lys Lys Val Xaa Asn Met
65                  70

<210> SEQ ID NO 141
<211> LENGTH: 69
<212> TYPE: PRT
<213> ORGANISM: Artificial sequence
<220> FEATURE:
<223> OTHER INFORMATION: Synthesized peptide

<400> SEQUENCE: 141

Gly Pro Tyr Gly Ala Asn Met Glu Asp Ser Val Cys Cys Arg Asp Tyr
1               5                   10                  15

Val Arg Tyr Arg Leu Pro Leu Arg Val Val Lys His Phe Tyr Trp Thr
            20                  25                  30

Ser Asp Ser Cys Pro Arg Pro Gly Val Val Leu Leu Thr Phe Arg Asp
        35                  40                  45

Lys Glu Ile Cys Ala Asp Pro Arg Val Pro Trp Val Lys Met Ile Leu
    50                  55                  60

Asn Lys Leu Ser Gln
65

<210> SEQ ID NO 142
<211> LENGTH: 69
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (66)..(66)
<223> OTHER INFORMATION: X is K(ivDde)

<400> SEQUENCE: 142

Gly Pro Tyr Gly Ala Asn Met Glu Asp Ser Val Cys Cys Arg Asp Tyr
1               5                   10                  15

Val Arg Tyr Arg Leu Pro Leu Arg Val Val Lys His Phe Tyr Trp Thr
            20                  25                  30

Ser Asp Ser Cys Pro Arg Pro Gly Val Val Leu Leu Thr Phe Arg Asp
        35                  40                  45
```

```
Lys Glu Ile Cys Ala Asp Pro Arg Val Pro Trp Val Lys Met Ile Leu
 50                  55                  60

Asn Xaa Leu Ser Gln
 65
```

<210> SEQ ID NO 143
<211> LENGTH: 69
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (66)..(66)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 143

```
Gly Pro Tyr Gly Ala Asn Met Glu Asp Ser Val Cys Cys Arg Asp Tyr
  1               5                  10                  15

Val Arg Tyr Arg Leu Pro Leu Arg Val Val Lys His Phe Tyr Trp Thr
                 20                  25                  30

Ser Asp Ser Cys Pro Arg Pro Gly Val Val Leu Leu Thr Phe Arg Asp
             35                  40                  45

Lys Glu Ile Cys Ala Asp Pro Arg Val Pro Trp Val Lys Met Ile Leu
 50                  55                  60

Asn Xaa Ser Leu Gln
 65
```

<210> SEQ ID NO 144
<211> LENGTH: 99
<212> TYPE: PRT
<213> ORGANISM: Artificial sequence
<220> FEATURE:
<223> OTHER INFORMATION: Synthesized peptide

<400> SEQUENCE: 144

```
Met Lys Val Ser Ala Ala Leu Leu Cys Leu Leu Leu Ile Ala Ala Thr
  1               5                  10                  15

Phe Ile Pro Gln Gly Leu Ala Gln Pro Asp Ala Ile Asn Ala Pro Val
                 20                  25                  30

Thr Cys Cys Tyr Asn Phe Thr Asn Arg Lys Ile Ser Val Gln Arg Leu
             35                  40                  45

Ala Ser Tyr Arg Arg Ile Thr Ser Ser Lys Cys Pro Lys Glu Ala Val
 50                  55                  60

Ile Phe Lys Thr Ile Val Ala Lys Glu Ile Cys Ala Asp Pro Lys Gln
 65                  70                  75                  80

Lys Trp Val Gln Asp Ser Met Asp His Leu Asp Lys Gln Thr Gln Thr
                 85                  90                  95

Pro Lys Thr
```

<210> SEQ ID NO 145
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (64)..(64)
<223> OTHER INFORMATION: X = Met or Nleu

<400> SEQUENCE: 145

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Xaa
50                  55                  60

Asp His Leu Asp Lys Gln Thr Gln Thr Pro Lys Thr
65                  70                  75

<210> SEQ ID NO 146
<211> LENGTH: 68
<212> TYPE: PRT
<213> ORGANISM: Artificial sequence
<220> FEATURE:
<223> OTHER INFORMATION: Synthesized peptide

<400> SEQUENCE: 146

Val Thr Cys Cys Tyr Asn Phe Thr Asn Arg Lys Ile Ser Val Gln Arg
1               5                   10                  15

Leu Ala Ser Tyr Arg Arg Ile Thr Ser Ser Lys Cys Pro Lys Glu Ala
            20                  25                  30

Val Ile Phe Lys Thr Ile Val Ala Lys Glu Ile Cys Ala Asp Pro Lys
        35                  40                  45

Gln Lys Trp Val Gln Asp Ser Met Asp His Leu Asp Lys Gln Thr Gln
50                  55                  60

Thr Pro Lys Thr
65

<210> SEQ ID NO 147
<211> LENGTH: 104
<212> TYPE: PRT
<213> ORGANISM: Artificial sequence
<220> FEATURE:
<223> OTHER INFORMATION: Synthesized peptide

<400> SEQUENCE: 147

Met Lys Ile Ser Thr Leu Leu Cys Leu Leu Leu Ile Ala Thr Thr Ile
1               5                   10                  15

Ser Pro Gln Val Leu Ala Gly Pro Asp Ala Val Ser Thr Pro Val Thr
            20                  25                  30

Cys Cys Tyr Asn Val Val Lys Gln Lys Ile His Val Arg Lys Leu Lys
        35                  40                  45

Ser Tyr Arg Arg Ile Thr Ser Ser Gln Cys Pro Arg Glu Ala Val Ile
50                  55                  60

Phe Arg Thr Ile Leu Asp Lys Glu Ile Cys Ala Asp Pro Lys Glu Lys
65                  70                  75                  80

Trp Val Lys Asn Ser Ile Asn His Leu Asp Lys Thr Ser Gln Thr Phe
                85                  90                  95

Ile Leu Glu Pro Ser Cys Leu Gly
            100

<210> SEQ ID NO 148
<211> LENGTH: 82
<212> TYPE: PRT
<213> ORGANISM: Artificial sequence
<220> FEATURE:
<223> OTHER INFORMATION: Synthesized peptide

<400> SEQUENCE: 148

Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
            20                  25                  30

Ser Ser Gln Cys Pro Arg Glu Ala Val Ile Phe Arg Thr Ile Leu Asp
        35                  40                  45

Lys Glu Ile Cys Ala Asp Pro Lys Glu Lys Trp Val Lys Asn Ser Ile
    50                  55                  60

Asn His Leu Asp Lys Thr Ser Gln Thr Phe Ile Leu Glu Pro Ser Cys
65                  70                  75                  80

Leu Gly

<210> SEQ ID NO 149
<211> LENGTH: 76
<212> TYPE: PRT
<213> ORGANISM: Artificial sequence
<220> FEATURE:
<223> OTHER INFORMATION: Synthesized peptide

<400> SEQUENCE: 149

Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
            20                  25                  30

Ser Ser Gln Cys Pro Arg Glu Ala Val Ile Phe Arg Thr Ile Leu Asp
        35                  40                  45

Lys Glu Ile Cys Ala Asp Pro Lys Glu Lys Trp Val Lys Asn Ser Ile
    50                  55                  60

Asn His Leu Asp Lys Thr Ser Gln Thr Phe Ile Leu
65                  70                  75

<210> SEQ ID NO 150
<211> LENGTH: 76
<212> TYPE: PRT
<213> ORGANISM: Artificial sequence
<220> FEATURE:
<223> OTHER INFORMATION: Synthesized peptide

<400> SEQUENCE: 150

Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
            20                  25                  30

Ser Ser Gln Cys Pro Arg Glu Ala Val Ile Phe Arg Thr Ile Leu Asp
        35                  40                  45

Lys Glu Ile Cys Ala Asp Pro Lys Glu Lys Trp Val Lys Asn Ser Ile
    50                  55                  60

Asn His Leu Asp Lys Thr Ser Gln Thr Phe Lys Leu
65                  70                  75

<210> SEQ ID NO 151
<211> LENGTH: 76
<212> TYPE: PRT
<213> ORGANISM: Artificial sequence
<220> FEATURE:
<223> OTHER INFORMATION: Synthesized peptide

```
<220> FEATURE:
<221> NAME/KEY: X
<222> LOCATION: (1)..(1)
<223> OTHER INFORMATION: X = pyroGlu

<400> SEQUENCE: 151

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
50                  55                  60

Asp His Leu Asp Lys Gln Thr Gln Thr Pro Lys Thr
65                  70                  75

<210> SEQ ID NO 152
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu
<220> FEATURE:
<221> NAME/KEY: X
<222> LOCATION: (75)..(75)
<223> OTHER INFORMATION: X is K(ivDde)

<400> SEQUENCE: 152

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
50                  55                  60

Asp His Leu Asp Lys Gln Thr Gln Thr Pro Xaa Thr
65                  70                  75

<210> SEQ ID NO 153
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu
<220> FEATURE:
<221> NAME/KEY: X
<222> LOCATION: (75)..(75)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 153

Xaa Pro Asp Ala Ile Asn Ala Pro Val Thr Cys Cys Tyr Asn Phe Thr
1               5                   10                  15
```

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
            35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Xaa Thr
65                  70                  75

<210> SEQ ID NO 154
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu

<400> SEQUENCE: 154

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
            35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro
65                  70                  75

<210> SEQ ID NO 155
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu
<220> FEATURE:
<221> NAME/KEY: X
<222> LOCATION: (75)..(75)
<223> OTHER INFORMATION: X is K(ivDde)

<400> SEQUENCE: 155

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
            35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Xaa Pro
65                  70                  75

<210> SEQ ID NO 156
<211> LENGTH: 76
<212> TYPE: PRT
<213> ORGANISM: Artificial sequence

```
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu
<220> FEATURE:
<221> NAME/KEY: X
<222> LOCATION: (75)..(75)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 156

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Xaa Pro
65                  70                  75

<210> SEQ ID NO 157
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 157

Gly Pro Ala Ser Val Pro Thr Thr Cys Cys Phe Asn Leu Ala Asn Arg
1               5                   10                  15

Lys Ile Pro Leu Gln Arg Leu Glu Ser Tyr Arg Arg Ile Thr Ser Gly
            20                  25                  30

Lys Cys Pro Gln Lys Ala Val Ile Phe Lys Thr Lys Leu Ala Lys Asp
        35                  40                  45

Ile Cys Ala Asp Pro Lys Lys Lys Trp Val Gln Asp Ser Met Lys Tyr
    50                  55                  60

Leu Asp Gln Lys Ser Pro Thr Pro Xaa Pro
65                  70

<210> SEQ ID NO 158
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is K(ivDde)

<400> SEQUENCE: 158

Gly Pro Ala Ser Val Pro Thr Thr Cys Cys Phe Asn Leu Ala Asn Arg
1               5                   10                  15
```

```
Lys Ile Pro Leu Gln Arg Leu Glu Ser Tyr Arg Arg Ile Thr Ser Gly
             20                  25                  30

Lys Cys Pro Gln Lys Ala Val Ile Phe Lys Thr Lys Leu Ala Lys Asp
             35                  40                  45

Ile Cys Ala Asp Pro Lys Lys Lys Trp Val Gln Asp Ser Met Lys Tyr
 50                  55                  60

Leu Asp Gln Lys Ser Pro Thr Pro Xaa Pro
 65                  70

<210> SEQ ID NO 159
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is K(PEG-Biotin)

<400> SEQUENCE: 159

Gly Pro Ala Ser Val Pro Thr Thr Cys Cys Phe Asn Leu Ala Asn Arg
 1               5                  10                  15

Lys Ile Pro Leu Gln Arg Leu Glu Ser Tyr Arg Arg Ile Thr Ser Gly
             20                  25                  30

Lys Cys Pro Gln Lys Ala Val Ile Phe Lys Thr Lys Leu Ala Lys Asp
             35                  40                  45

Ile Cys Ala Asp Pro Lys Lys Lys Trp Val Gln Asp Ser Met Lys Tyr
 50                  55                  60

Leu Asp Gln Lys Ser Pro Thr Pro Xaa Pro
 65                  70

<210> SEQ ID NO 160
<211> LENGTH: 68
<212> TYPE: PRT
<213> ORGANISM: Artificial sequence
<220> FEATURE:
<223> OTHER INFORMATION: Synthesized peptide

<400> SEQUENCE: 160

Ser Pro Tyr Ser Ser Asp Thr Thr Pro Cys Cys Phe Ala Tyr Ile Ala
 1               5                  10                  15

Arg Pro Leu Pro Arg Ala His Ile Lys Glu Tyr Phe Tyr Thr Ser Gly
             20                  25                  30

Lys Cys Ser Asn Pro Ala Val Val Phe Val Thr Arg Lys Asn Arg Gln
             35                  40                  45

Val Cys Ala Asn Pro Glu Lys Lys Trp Val Arg Glu Tyr Ile Asn Ser
 50                  55                  60

Leu Glu Lys Ser
 65

<210> SEQ ID NO 161
<211> LENGTH: 68
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (67)..(67)
<223> OTHER INFORMATION: X is K(ivDde)
```

-continued

```
<400> SEQUENCE: 161

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Xaa Ser
65

<210> SEQ ID NO 162
<211> LENGTH: 68
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (67)..(67)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 162

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Xaa Ser
65

<210> SEQ ID NO 163
<211> LENGTH: 70
<212> TYPE: PRT
<213> ORGANISM: Artificial sequence
<220> FEATURE:
<223> OTHER INFORMATION: Synthesized peptide

<400> SEQUENCE: 163

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Lys Leu Ser Val Cys
        35                  40                  45

Ala Asn Pro Lys Gln Thr Trp Val Lys Tyr Ile Val Arg Leu Leu Ser
    50                  55                  60

Lys Lys Val Lys Asn Met
65                  70

<210> SEQ ID NO 164
<211> LENGTH: 70
<212> TYPE: PRT
<213> ORGANISM: Artificial sequence
```

<220> FEATURE:
<223> OTHER INFORMATION: Synthesized peptide
<220> FEATURE:
<221> NAME/KEY: X
<222> LOCATION: (68)..(68)
<223> OTHER INFORMATION: X is K(ivDde)

<400> SEQUENCE: 164

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Lys Leu Ser Val Cys
        35                  40                  45

Ala Asn Pro Lys Gln Thr Trp Val Lys Tyr Ile Val Arg Leu Leu Ser
    50                  55                  60

Lys Lys Val Xaa Asn Met
65                  70

<210> SEQ ID NO 165
<211> LENGTH: 70
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (68)..(68)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 165

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Lys Leu Ser Val Cys
        35                  40                  45

Ala Asn Pro Lys Gln Thr Trp Val Lys Tyr Ile Val Arg Leu Leu Ser
    50                  55                  60

Lys Lys Val Xaa Asn Met
65                  70

<210> SEQ ID NO 166
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine

<400> SEQUENCE: 166

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

```
Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Xaa
    50                  55                  60

Lys Leu Leu Asp Ala Arg Asn Lys Val Phe
65                  70

<210> SEQ ID NO 167
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine
<220> FEATURE:
<221> NAME/KEY: X
<222> LOCATION: (72)..(72)
<223> OTHER INFORMATION: X is K(ivDde)

<400> SEQUENCE: 167

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Xaa
    50                  55                  60

Lys Leu Leu Asp Ala Arg Asn Xaa Val Phe
65                  70

<210> SEQ ID NO 168
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine
<220> FEATURE:
<221> NAME/KEY: X
<222> LOCATION: (72)..(72)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 168

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
```

-continued

```
                35                  40                  45
Arg Lys Val Cys Gly Asn Pro Lys Ser Arg Glu Val Gln Arg Ala Xaa
        50                  55                  60

Lys Leu Leu Asp Ala Arg Asn Xaa Val Phe
 65                  70

<210> SEQ ID NO 169
<211> LENGTH: 73
<212> TYPE: PRT
<213> ORGANISM: Artificial sequence
<220> FEATURE:
<223> OTHER INFORMATION: Synthesized peptide

<400> SEQUENCE: 169

Phe Pro Met Phe Lys Arg Gly Arg Cys Leu Cys Ile Gly Pro Gly Val
  1               5                  10                  15

Lys Ala Val Lys Val Ala Asp Ile Glu Lys Ala Ser Ile Met Tyr Pro
             20                  25                  30

Ser Asn Asn Cys Asp Lys Ile Glu Val Ile Ile Thr Leu Lys Glu Asn
         35                  40                  45

Lys Gly Gln Arg Cys Leu Asn Pro Lys Ser Lys Gln Ala Arg Leu Ile
     50                  55                  60

Ile Lys Lys Val Glu Arg Lys Asn Phe
 65                  70

<210> SEQ ID NO 170
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (74)..(74)
<223> OTHER INFORMATION: X is PEG-K(ivDde)

<400> SEQUENCE: 170

Phe Pro Met Phe Lys Arg Gly Arg Cys Leu Cys Ile Gly Pro Gly Val
  1               5                  10                  15

Lys Ala Val Lys Val Ala Asp Ile Glu Lys Ala Ser Ile Met Tyr Pro
             20                  25                  30

Ser Asn Asn Cys Asp Lys Ile Glu Val Ile Ile Thr Leu Lys Glu Asn
         35                  40                  45

Lys Gly Gln Arg Cys Leu Asn Pro Lys Ser Lys Gln Ala Arg Leu Ile
     50                  55                  60

Ile Lys Lys Val Glu Arg Lys Asn Phe Xaa
 65                  70

<210> SEQ ID NO 171
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (74)..(74)
<223> OTHER INFORMATION: X = residue that can be biotinylated, e.g.
      lysine, ornithine or diaminopropionic acid and optionally is
      biotinylated, optionally via a spacer molecule such as PEG, e.g.
      K(PEG-Biotin) and may be attached via a spacer molecule,
      e.g.PEG-K(Biotin)

<400> SEQUENCE: 171
```

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
                20                  25                  30

Ser Asn Asn Cys Asp Lys Ile Glu Val Ile Ile Thr Leu Lys Glu Asn
            35                  40                  45

Lys Gly Gln Arg Cys Leu Asn Pro Lys Ser Gln Ala Arg Leu Ile
        50                  55                  60

Ile Lys Lys Val Glu Arg Lys Asn Phe Xaa
65                  70

<210> SEQ ID NO 172
<211> LENGTH: 77
<212> TYPE: PRT
<213> ORGANISM: Artificial sequence
<220> FEATURE:
<223> OTHER INFORMATION: Synthesized peptide

<400> SEQUENCE: 172

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
                20                  25                  30

Ser Gln Phe Cys Pro Arg Val Glu Ile Ile Ala Thr Met Lys Lys Lys
            35                  40                  45

Gly Glu Lys Arg Cys Leu Asn Pro Glu Ser Lys Ala Ile Lys Asn Leu
        50                  55                  60

Leu Lys Ala Val Ser Lys Glu Arg Ser Lys Arg Ser Pro
65                  70                  75

<210> SEQ ID NO 173
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (77)..(77)
<223> OTHER INFORMATION: X is K(ivDde), optionally attached via a spacer
      such as PEG, e.g. -PEG-K(ivDde)
<220> FEATURE:
<221> NAME/KEY: misc_feature
<222> LOCATION: (78)..(78)
<223> OTHER INFORMATION: Xaa can be any naturally occurring amino acid

<400> SEQUENCE: 173

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
                20                  25                  30

Ser Gln Phe Cys Pro Arg Val Glu Ile Ile Ala Thr Met Lys Lys Lys
            35                  40                  45

Gly Glu Lys Arg Cys Leu Asn Pro Glu Ser Lys Ala Ile Lys Asn Leu
        50                  55                  60

Leu Lys Ala Val Ser Lys Glu Arg Ser Lys Arg Ser Pro Xaa
65                  70                  75

<210> SEQ ID NO 174
<211> LENGTH: 78
<212> TYPE: PRT

```
<213> ORGANISM: Artificial sequence
<220> FEATURE:
<223> OTHER INFORMATION: Synthesized peptide
<220> FEATURE:
<221> NAME/KEY: X
<222> LOCATION: (77)..(77)
<223> OTHER INFORMATION: X = residue that can be biotinylated, e.g.
      lysine, ornithine or diaminopropionic acid and optionally is
      biotinylated, optionally via a spacer molecule such as PEG, e.g.
      K(PEG-Biotin) and may be attached via a spacer molecule,
      e.g.PEG-K(Biotin)
<220> FEATURE:
<221> NAME/KEY: misc_feature
<222> LOCATION: (78)..(78)
<223> OTHER INFORMATION: Xaa can be any naturally occurring amino acid

<400> SEQUENCE: 174
```

Val Pro Leu Ser Arg Thr Val Arg Cys Thr Cys Ile Ser Ile Ser Asn
1               5                  10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Arg Ser Pro Xaa
65                  70                  75

```
<210> SEQ ID NO 175
<211> LENGTH: 99
<212> TYPE: PRT
<213> ORGANISM: Artificial sequence
<220> FEATURE:
<223> OTHER INFORMATION: Synthesized peptide

<400> SEQUENCE: 175
```

Met Lys Val Ser Ala Ala Leu Leu Cys Leu Leu Leu Ile Ala Ala Thr
1               5                  10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

```
<210> SEQ ID NO 176
<211> LENGTH: 76
<212> TYPE: PRT
<213> ORGANISM: Artificial sequence
<220> FEATURE:
<223> OTHER INFORMATION: Synthesized peptide

<400> SEQUENCE: 176
```

Gln Pro Asp Ala Ile Asn Ala Pro Val Thr Cys Cys Tyr Asn Phe Thr
1               5                  10                  15

Asn Arg Lys Ile Ser Val Gln Arg Leu Ala Ser Tyr Arg Arg Ile Thr
            20                  25                  30

```
Ser Ser Lys Cys Pro Lys Glu Ala Val Ile Phe Lys Thr Ile Val Ala
         35                  40                  45

Lys Glu Ile Cys Ala Asp Pro Lys Gln Lys Trp Val Gln Asp Ser Met
 50                  55                  60

Asp His Leu Asp Lys Gln Thr Gln Thr Pro Lys Thr
 65                  70                  75

<210> SEQ ID NO 177
<211> LENGTH: 68
<212> TYPE: PRT
<213> ORGANISM: Artificial sequence
<220> FEATURE:
<223> OTHER INFORMATION: Synthesized peptide

<400> SEQUENCE: 177

Val Thr Cys Cys Tyr Asn Phe Thr Asn Arg Lys Ile Ser Val Gln Arg
 1               5                  10                  15

Leu Ala Ser Tyr Arg Arg Ile Thr Ser Ser Cys Pro Lys Glu Ala
             20                  25                  30

Val Ile Phe Lys Thr Ile Val Ala Lys Glu Ile Cys Ala Asp Pro Lys
             35                  40                  45

Gln Lys Trp Val Gln Asp Ser Met Asp His Leu Asp Lys Gln Thr Gln
 50                  55                  60

Thr Pro Lys Thr
 65

<210> SEQ ID NO 178
<211> LENGTH: 104
<212> TYPE: PRT
<213> ORGANISM: Artificial sequence
<220> FEATURE:
<223> OTHER INFORMATION: Synthesized peptide

<400> SEQUENCE: 178

Met Lys Ile Ser Thr Leu Leu Cys Leu Leu Leu Ile Ala Thr Thr Ile
 1               5                  10                  15

Ser Pro Gln Val Leu Ala Gly Pro Asp Ala Val Ser Thr Pro Val Thr
             20                  25                  30

Cys Cys Tyr Asn Val Val Lys Gln Lys Ile His Val Arg Lys Leu Lys
             35                  40                  45

Ser Tyr Arg Arg Ile Thr Ser Ser Gln Cys Pro Arg Glu Ala Val Ile
 50                  55                  60

Phe Arg Thr Ile Leu Asp Lys Glu Ile Cys Ala Asp Pro Lys Glu Lys
 65                  70                  75                  80

Trp Val Lys Asn Ser Ile Asn His Leu Asp Lys Thr Ser Gln Thr Phe
                 85                  90                  95

Ile Leu Glu Pro Ser Cys Leu Gly
             100

<210> SEQ ID NO 179
<211> LENGTH: 82
<212> TYPE: PRT
<213> ORGANISM: Artificial sequence
<220> FEATURE:
<223> OTHER INFORMATION: Synthesized peptide

<400> SEQUENCE: 179

Gly Pro Asp Ala Val Ser Thr Pro Val Thr Cys Cys Tyr Asn Val Val
 1               5                  10                  15

Lys Gln Lys Ile His Val Arg Lys Leu Lys Ser Tyr Arg Arg Ile Thr
```

-continued

```
                20                  25                  30

Ser Ser Gln Cys Pro Arg Glu Ala Val Ile Phe Arg Thr Ile Leu Asp
        35                  40                  45

Lys Glu Ile Cys Ala Asp Pro Lys Glu Lys Trp Val Lys Asn Ser Ile
 50                  55                  60

Asn His Leu Asp Lys Thr Ser Gln Thr Phe Ile Leu Glu Pro Ser Cys
 65                  70                  75                  80

Leu Gly

<210> SEQ ID NO 180
<211> LENGTH: 76
<212> TYPE: PRT
<213> ORGANISM: Artificial sequence
<220> FEATURE:
<223> OTHER INFORMATION: Synthesized peptide

<400> SEQUENCE: 180

Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
                20                  25                  30

Ser Ser Gln Cys Pro Arg Glu Ala Val Ile Phe Arg Thr Ile Leu Asp
        35                  40                  45

Lys Glu Ile Cys Ala Asp Pro Lys Glu Lys Trp Val Lys Asn Ser Ile
 50                  55                  60

Asn His Leu Asp Lys Thr Ser Gln Thr Phe Ile Leu
 65                  70                  75

<210> SEQ ID NO 181
<211> LENGTH: 76
<212> TYPE: PRT
<213> ORGANISM: Artificial sequence
<220> FEATURE:
<223> OTHER INFORMATION: Synthesized peptide

<400> SEQUENCE: 181

Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
                20                  25                  30

Ser Ser Gln Cys Pro Arg Glu Ala Val Ile Phe Arg Thr Ile Leu Asp
        35                  40                  45

Lys Glu Ile Cys Ala Asp Pro Lys Glu Lys Trp Val Lys Asn Ser Ile
 50                  55                  60

Asn His Leu Asp Lys Thr Ser Gln Thr Phe Lys Leu
 65                  70                  75

<210> SEQ ID NO 182
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln

<400> SEQUENCE: 182

Xaa Pro Asp Ala Ile Asn Ala Pro Val Thr Cys Cys Tyr Asn Phe Thr
1               5                   10                  15
```

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75

<210> SEQ ID NO 183
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is K(ivDde)

<400> SEQUENCE: 183

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Xaa Thr
65                  70                  75

<210> SEQ ID NO 184
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 184

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

```
Asp His Leu Asp Lys Gln Thr Gln Thr Pro Xaa Thr
65                  70                  75
```

<210> SEQ ID NO 185
<211> LENGTH: 68
<212> TYPE: PRT
<213> ORGANISM: Artificial sequence
<220> FEATURE:
<223> OTHER INFORMATION: Synthesized peptide

<400> SEQUENCE: 185

```
Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Lys Ser
65
```

<210> SEQ ID NO 186
<211> LENGTH: 68
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (67)..(67)
<223> OTHER INFORMATION: X is K(ivDde)

<400> SEQUENCE: 186

```
Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Xaa Ser
65
```

<210> SEQ ID NO 187
<211> LENGTH: 68
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (67)..(67)
<223> OTHER INFORMATION: X is an amino acid residue that can be
      biotinylated, such as lysine, ornithine or diaminopropionic acid
      and optionally is biotinylated, optionally via a spacer molecule
      such as PEG (e.g. K(Biotin))

<400> SEQUENCE: 187

```
Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30
```

Lys Cys Ser Asn Pro Ala Val Val Phe Val Thr Arg Lys Asn Arg Gln
            35                  40                  45

Val Cys Ala Asn Pro Glu Lys Lys Trp Val Arg Glu Tyr Ile Asn Ser
    50                  55                  60

Leu Glu Xaa Ser
65

<210> SEQ ID NO 188
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln

<400> SEQUENCE: 188

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro
65                  70                  75

<210> SEQ ID NO 189
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is K(ivDde)

<400> SEQUENCE: 189

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Xaa Pro
65                  70                  75

<210> SEQ ID NO 190
<211> LENGTH: 76
<212> TYPE: PRT
<213> ORGANISM: Artificial sequence
<220> FEATURE:
<223> OTHER INFORMATION: Synthesized peptide

```
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 190

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
50                  55                  60

Lys His Leu Asp Gln Ile Phe Gln Asn Leu Xaa Pro
65                  70                  75

<210> SEQ ID NO 191
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is an amino acid residue that can be
      biotinylated, such as lysine, ornithine or diaminopropionic acid
      and optionally is biotinylated (e.g. K-biotin), optionally via a
      spacer molecule such as PEG, in particular K(PEG-Biotin)

<400> SEQUENCE: 191

Gly Thr Asn Asp Ala Glu Asp Cys Cys Leu Ser Val Thr Gln Lys Pro
1               5                   10                  15

Ile Pro Gly Tyr Ile Val Arg Asn Phe His Tyr Leu Leu Ile Lys Asp
            20                  25                  30

Gly Cys Arg Val Pro Ala Val Val Phe Thr Thr Leu Arg Gly Arg Gln
        35                  40                  45

Leu Cys Ala Pro Pro Asp Gln Pro Trp Val Glu Arg Ile Ile Gln Arg
50                  55                  60

Leu Gln Arg Thr Ser Ala Lys Met Lys Arg Arg Ser Ser Xaa
65                  70                  75

<210> SEQ ID NO 192
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is K(ivDde)

<400> SEQUENCE: 192

Gly Thr Asn Asp Ala Glu Asp Cys Cys Leu Ser Val Thr Gln Lys Pro
1               5                   10                  15

Ile Pro Gly Tyr Ile Val Arg Asn Phe His Tyr Leu Leu Ile Lys Asp
```

-continued

```
                20                  25                  30

Gly Cys Arg Val Pro Ala Val Val Phe Thr Thr Leu Arg Gly Arg Gln
            35                  40                  45

Leu Cys Ala Pro Pro Asp Gln Pro Trp Val Glu Arg Ile Ile Gln Arg
        50                  55                  60

Leu Gln Arg Thr Ser Ala Lys Met Lys Arg Arg Ser Ser Xaa
65                  70                  75

<210> SEQ ID NO 193
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is K(Biotin)

<400> SEQUENCE: 193

Gly Thr Asn Asp Ala Glu Asp Cys Cys Leu Ser Val Thr Gln Lys Pro
1               5                   10                  15

Ile Pro Gly Tyr Ile Val Arg Asn Phe His Tyr Leu Leu Ile Lys Asp
                20                  25                  30

Gly Cys Arg Val Pro Ala Val Val Phe Thr Thr Leu Arg Gly Arg Gln
            35                  40                  45

Leu Cys Ala Pro Pro Asp Gln Pro Trp Val Glu Arg Ile Ile Gln Arg
        50                  55                  60

Leu Gln Arg Thr Ser Ala Lys Met Lys Arg Arg Ser Ser Xaa
65                  70                  75

<210> SEQ ID NO 194
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine

<400> SEQUENCE: 194

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
                20                  25                  30

Gly Ser Cys Asn Leu Pro Ala Ala Ile Phe Tyr Leu Pro Lys Arg His
            35                  40                  45

Arg Lys Val Cys Gly Asn Pro Lys Ser Arg Glu Val Gln Arg Ala Xaa
        50                  55                  60

Lys Leu Leu Asp Ala Arg Asn Lys Val Phe
65                  70

<210> SEQ ID NO 195
<211> LENGTH: 68
<212> TYPE: PRT
<213> ORGANISM: Artificial sequence
<220> FEATURE:
```

<223> OTHER INFORMATION: Synthesized peptide

<400> SEQUENCE: 195

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Lys Ser
65

<210> SEQ ID NO 196
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine
<220> FEATURE:
<221> NAME/KEY: X
<222> LOCATION: (72)..(72)
<223> OTHER INFORMATION: X = K(Dde)

<400> SEQUENCE: 196

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Xaa
    50                  55                  60

Lys Leu Leu Asp Ala Arg Asn Xaa Val Phe
65                      70

<210> SEQ ID NO 197
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (64)..(64)
<223> OTHER INFORMATION: X = Norleucine
<220> FEATURE:
<221> NAME/KEY: X
<222> LOCATION: (72)..(72)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 197

Xaa Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
        35                  40                  45

Arg Lys Val Cys Gly Asn Pro Lys Ser Arg Val Gln Arg Ala Xaa
    50                  55                  60

Lys Leu Leu Asp Ala Arg Asn Xaa Val Phe
65                  70

<210> SEQ ID NO 198
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln

<400> SEQUENCE: 198

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro
65                  70                  75

<210> SEQ ID NO 199
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is K(ivDde)

<400> SEQUENCE: 199

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Xaa Pro
65                  70                  75

```
<210> SEQ ID NO 200
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 200

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Xaa Pro
65                  70                  75

<210> SEQ ID NO 201
<211> LENGTH: 68
<212> TYPE: PRT
<213> ORGANISM: Artificial sequence
<220> FEATURE:
<223> OTHER INFORMATION: Synthesized peptide

<400> SEQUENCE: 201

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Met Ser
65

<210> SEQ ID NO 202
<211> LENGTH: 68
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (67)..(67)
<223> OTHER INFORMATION: X is K(ivDde)

<400> SEQUENCE: 202

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
```

```
                     20                  25                  30

Lys Cys Ser Asn Pro Ala Val Val Phe Val Thr Arg Lys Asn Arg Gln
            35                  40                  45

Val Cys Ala Asn Pro Glu Lys Lys Trp Val Arg Glu Tyr Ile Asn Ser
        50                  55                  60

Leu Glu Xaa Ser
65

<210> SEQ ID NO 203
<211> LENGTH: 68
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (67)..(67)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 203

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Xaa Ser
65

<210> SEQ ID NO 204
<211> LENGTH: 67
<212> TYPE: PRT
<213> ORGANISM: Artificial sequence
<220> FEATURE:
<223> OTHER INFORMATION: Synthesized peptide

<400> SEQUENCE: 204

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn
65

<210> SEQ ID NO 205
<211> LENGTH: 67
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (64)..(64)
<223> OTHER INFORMATION: X is K(ivDde)
```

<400> SEQUENCE: 205

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Xaa
    50                  55                  60

Ala Leu Asn
65

<210> SEQ ID NO 206
<211> LENGTH: 67
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (64)..(64)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 206

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Xaa
    50                  55                  60

Ala Leu Asn
65

<210> SEQ ID NO 207
<211> LENGTH: 78
<212> TYPE: PRT
<213> ORGANISM: Artificial sequence
<220> FEATURE:
<223> OTHER INFORMATION: Synthesized peptide

<400> SEQUENCE: 207

Gly Thr Asn Asp Ala Glu Asp Cys Cys Leu Ser Val Thr Gln Lys Pro
1               5                   10                  15

Ile Pro Gly Tyr Ile Val Arg Asn Phe His Tyr Leu Leu Ile Lys Asp
            20                  25                  30

Gly Cys Arg Val Pro Ala Val Val Phe Thr Thr Leu Arg Gly Arg Gln
        35                  40                  45

Leu Cys Ala Pro Pro Asp Gln Pro Trp Val Glu Arg Ile Ile Gln Arg
    50                  55                  60

Leu Gln Arg Thr Ser Ala Lys Met Lys Arg Arg Ser Ser Lys
65                  70                  75

<210> SEQ ID NO 208
<211> LENGTH: 78
<212> TYPE: PRT

```
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is K(ivDde)

<400> SEQUENCE: 208

Gly Thr Asn Asp Ala Glu Asp Cys Cys Leu Ser Val Thr Gln Lys Pro
1               5                   10                  15

Ile Pro Gly Tyr Ile Val Arg Asn Phe His Tyr Leu Leu Ile Lys Asp
            20                  25                  30

Gly Cys Arg Val Pro Ala Val Val Phe Thr Thr Leu Arg Gly Arg Gln
        35                  40                  45

Leu Cys Ala Pro Pro Asp Gln Pro Trp Val Glu Arg Ile Ile Gln Arg
    50                  55                  60

Leu Gln Arg Thr Ser Ala Lys Met Lys Arg Arg Ser Ser Xaa
65                  70                  75

<210> SEQ ID NO 209
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 209

Gly Thr Asn Asp Ala Glu Asp Cys Cys Leu Ser Val Thr Gln Lys Pro
1               5                   10                  15

Ile Pro Gly Tyr Ile Val Arg Asn Phe His Tyr Leu Leu Ile Lys Asp
            20                  25                  30

Gly Cys Arg Val Pro Ala Val Val Phe Thr Thr Leu Arg Gly Arg Gln
        35                  40                  45

Leu Cys Ala Pro Pro Asp Gln Pro Trp Val Glu Arg Ile Ile Gln Arg
    50                  55                  60

Leu Gln Arg Thr Ser Ala Lys Met Lys Arg Arg Ser Ser Xaa
65                  70                  75

<210> SEQ ID NO 210
<211> LENGTH: 99
<212> TYPE: PRT
<213> ORGANISM: Artificial sequence
<220> FEATURE:
<223> OTHER INFORMATION: Synthesized peptide

<400> SEQUENCE: 210

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60
```

-continued

```
Ile Phe Lys Thr Ile Val Ala Lys Glu Ile Cys Ala Asp Pro Lys Gln
 65                  70                  75                  80

Lys Trp Val Gln Asp Ser Met Asp His Leu Asp Lys Gln Thr Gln Thr
                 85                  90                  95

Pro Lys Thr

<210> SEQ ID NO 211
<211> LENGTH: 76
<212> TYPE: PRT
<213> ORGANISM: Artificial sequence
<220> FEATURE:
<223> OTHER INFORMATION: Synthesized peptide

<400> SEQUENCE: 211

Gln Pro Asp Ala Ile Asn Ala Pro Val Thr Cys Cys Tyr Asn Phe Thr
 1               5                  10                  15

Asn Arg Lys Ile Ser Val Gln Arg Leu Ala Ser Tyr Arg Arg Ile Thr
                20                  25                  30

Ser Ser Lys Cys Pro Lys Glu Ala Val Ile Phe Lys Thr Ile Val Ala
                35                  40                  45

Lys Glu Ile Cys Ala Asp Pro Lys Gln Lys Trp Val Gln Asp Ser Met
 50                  55                  60

Asp His Leu Asp Lys Gln Thr Gln Thr Pro Lys Thr
 65                  70                  75

<210> SEQ ID NO 212
<211> LENGTH: 68
<212> TYPE: PRT
<213> ORGANISM: Artificial sequence
<220> FEATURE:
<223> OTHER INFORMATION: Synthesized peptide

<400> SEQUENCE: 212

Val Thr Cys Cys Tyr Asn Phe Thr Asn Arg Lys Ile Ser Val Gln Arg
 1               5                  10                  15

Leu Ala Ser Tyr Arg Arg Ile Thr Ser Ser Lys Cys Pro Lys Glu Ala
                20                  25                  30

Val Ile Phe Lys Thr Ile Val Ala Lys Glu Ile Cys Ala Asp Pro Lys
                35                  40                  45

Gln Lys Trp Val Gln Asp Ser Met Asp His Leu Asp Lys Gln Thr Gln
 50                  55                  60

Thr Pro Lys Thr
 65

<210> SEQ ID NO 213
<211> LENGTH: 104
<212> TYPE: PRT
<213> ORGANISM: Artificial sequence
<220> FEATURE:
<223> OTHER INFORMATION: Synthesized peptide

<400> SEQUENCE: 213

Met Lys Ile Ser Thr Leu Leu Cys Leu Leu Leu Ile Ala Thr Thr Ile
 1               5                  10                  15

Ser Pro Gln Val Leu Ala Gly Pro Asp Ala Val Ser Thr Pro Val Thr
                20                  25                  30

Cys Cys Tyr Asn Val Val Lys Gln Lys Ile His Val Arg Lys Leu Lys
                35                  40                  45

Ser Tyr Arg Arg Ile Thr Ser Ser Gln Cys Pro Arg Glu Ala Val Ile
 50                  55                  60
```

Phe Arg Thr Ile Leu Asp Lys Glu Ile Cys Ala Asp Pro Lys Glu Lys
65                  70                  75                  80

Trp Val Lys Asn Ser Ile Asn His Leu Asp Lys Thr Ser Gln Thr Phe
                85                  90                  95

Ile Leu Glu Pro Ser Cys Leu Gly
            100

<210> SEQ ID NO 214
<211> LENGTH: 82
<212> TYPE: PRT
<213> ORGANISM: Artificial sequence
<220> FEATURE:
<223> OTHER INFORMATION: Synthesized peptide

<400> SEQUENCE: 214

Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
            20                  25                  30

Ser Ser Gln Cys Pro Arg Glu Ala Val Ile Phe Arg Thr Ile Leu Asp
        35                  40                  45

Lys Glu Ile Cys Ala Asp Pro Lys Glu Lys Trp Val Lys Asn Ser Ile
    50                  55                  60

Asn His Leu Asp Lys Thr Ser Gln Thr Phe Ile Leu Glu Pro Ser Cys
65                  70                  75                  80

Leu Gly

<210> SEQ ID NO 215
<211> LENGTH: 76
<212> TYPE: PRT
<213> ORGANISM: Artificial sequence
<220> FEATURE:
<223> OTHER INFORMATION: Synthesized peptide

<400> SEQUENCE: 215

Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
            20                  25                  30

Ser Ser Gln Cys Pro Arg Glu Ala Val Ile Phe Arg Thr Ile Leu Asp
        35                  40                  45

Lys Glu Ile Cys Ala Asp Pro Lys Glu Lys Trp Val Lys Asn Ser Ile
    50                  55                  60

Asn His Leu Asp Lys Thr Ser Gln Thr Phe Ile Leu
65                  70                  75

<210> SEQ ID NO 216
<211> LENGTH: 76
<212> TYPE: PRT
<213> ORGANISM: Artificial sequence
<220> FEATURE:
<223> OTHER INFORMATION: Synthesized peptide

<400> SEQUENCE: 216

Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
            20                  25                  30

Ser Ser Gln Cys Pro Arg Glu Ala Val Ile Phe Arg Thr Ile Leu Asp

```
                35                  40                  45
Lys Glu Ile Cys Ala Asp Pro Lys Glu Lys Trp Val Lys Asn Ser Ile
 50                  55                  60

Asn His Leu Asp Lys Thr Ser Gln Thr Phe Lys Leu
 65                  70                  75
```

<210> SEQ ID NO 217
<211> LENGTH: 97
<212> TYPE: PRT
<213> ORGANISM: Artificial sequence
<220> FEATURE:
<223> OTHER INFORMATION: Synthesized peptide

<400> SEQUENCE: 217

```
Met Lys Val Ser Ala Ala Leu Leu Trp Leu Leu Leu Ile Ala Ala Ala
 1               5                  10                  15

Phe Ser Pro Gln Gly Leu Ala Gly Pro Ala Ser Val Pro Thr Thr Cys
                20                  25                  30

Cys Phe Asn Leu Ala Asn Arg Lys Ile Pro Leu Gln Arg Leu Glu Ser
                35                  40                  45

Tyr Arg Arg Ile Thr Ser Gly Lys Cys Pro Gln Lys Ala Val Ile Phe
 50                  55                  60

Lys Thr Lys Leu Ala Lys Asp Ile Cys Ala Asp Pro Lys Lys Lys Trp
 65                  70                  75                  80

Val Gln Asp Ser Met Lys Tyr Leu Asp Gln Lys Ser Pro Thr Pro Lys
                85                  90                  95

Pro
```

<210> SEQ ID NO 218
<211> LENGTH: 74
<212> TYPE: PRT
<213> ORGANISM: Artificial sequence
<220> FEATURE:
<223> OTHER INFORMATION: Synthesized peptide

<400> SEQUENCE: 218

```
Gly Pro Ala Ser Val Pro Thr Thr Cys Cys Phe Asn Leu Ala Asn Arg
 1               5                  10                  15

Lys Ile Pro Leu Gln Arg Leu Glu Ser Tyr Arg Arg Ile Thr Ser Gly
                20                  25                  30

Lys Cys Pro Gln Lys Ala Val Ile Phe Lys Thr Lys Leu Ala Lys Asp
                35                  40                  45

Ile Cys Ala Asp Pro Lys Lys Lys Trp Val Gln Asp Ser Met Lys Tyr
 50                  55                  60

Leu Asp Gln Lys Ser Pro Thr Pro Lys Pro
 65                  70
```

<210> SEQ ID NO 219
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln

<400> SEQUENCE: 219

```
Xaa Pro Asp Ala Ile Asn Ala Pro Val Thr Cys Cys Tyr Asn Phe Thr
 1               5                  10                  15
```

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75

<210> SEQ ID NO 220
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is K(ivDde)

<400> SEQUENCE: 220

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Xaa Thr
65                  70                  75

<210> SEQ ID NO 221
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 221

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Xaa Thr
65                  70                  75

<210> SEQ ID NO 222
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln

<400> SEQUENCE: 222

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro
65                  70                  75

<210> SEQ ID NO 223
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is K(ivDde)

<400> SEQUENCE: 223

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Xaa Pro
65                  70                  75

<210> SEQ ID NO 224
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)

-continued

<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 224

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
50                  55                  60

Lys His Leu Asp Gln Ile Phe Gln Asn Leu Xaa Pro
65                  70                  75

<210> SEQ ID NO 225
<211> LENGTH: 68
<212> TYPE: PRT
<213> ORGANISM: Artificial sequence
<220> FEATURE:
<223> OTHER INFORMATION: Synthesized peptide

<400> SEQUENCE: 225

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
50                  55                  60

Leu Glu Lys Ser
65

<210> SEQ ID NO 226
<211> LENGTH: 68
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (67)..(67)
<223> OTHER INFORMATION: X is K(ivDde)

<400> SEQUENCE: 226

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
50                  55                  60

Leu Glu Xaa Ser
65

<210> SEQ ID NO 227
<211> LENGTH: 68

```
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (67)..(67)
<223> OTHER INFORMATION: X is an amino acid residue that can be
      biotinylated, such as lysine, ornithine or diaminopropionic acid
      and optionally is biotinylated, optionally via a spacer molecule
      such as PEG (e.g. K(Biotin))

<400> SEQUENCE: 227

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Xaa Ser
65

<210> SEQ ID NO 228
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is an amino acid residue that can be
      biotinylated, such as lysine, ornithine or diaminopropionic acid
      and optionally is biotinylated (e.g. K-biotin), optionally via a
      spacer molecule such as PEG, in particular K(PEG-Biotin)

<400> SEQUENCE: 228

Gly Thr Asn Asp Ala Glu Asp Cys Cys Leu Ser Val Thr Gln Lys Pro
1               5                   10                  15

Ile Pro Gly Tyr Ile Val Arg Asn Phe His Tyr Leu Leu Ile Lys Asp
            20                  25                  30

Gly Cys Arg Val Pro Ala Val Val Phe Thr Thr Leu Arg Gly Arg Gln
        35                  40                  45

Leu Cys Ala Pro Pro Asp Gln Pro Trp Val Glu Arg Ile Ile Gln Arg
    50                  55                  60

Leu Gln Arg Thr Ser Ala Lys Met Lys Arg Arg Ser Ser Xaa
65                  70                  75

<210> SEQ ID NO 229
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is K(ivDde)

<400> SEQUENCE: 229

Gly Thr Asn Asp Ala Glu Asp Cys Cys Leu Ser Val Thr Gln Lys Pro
1               5                   10                  15

Ile Pro Gly Tyr Ile Val Arg Asn Phe His Tyr Leu Leu Ile Lys Asp
```

```
                    20                  25                  30

Gly Cys Arg Val Pro Ala Val Val Phe Thr Thr Leu Arg Gly Arg Gln
            35                  40                  45

Leu Cys Ala Pro Pro Asp Gln Pro Trp Val Glu Arg Ile Ile Gln Arg
        50                  55                  60

Leu Gln Arg Thr Ser Ala Lys Met Lys Arg Arg Ser Ser Xaa
65                  70                  75
```

<210> SEQ ID NO 230
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is K(Biotin)

<400> SEQUENCE: 230

```
Gly Thr Asn Asp Ala Glu Asp Cys Cys Leu Ser Val Thr Gln Lys Pro
1               5                   10                  15

Ile Pro Gly Tyr Ile Val Arg Asn Phe His Tyr Leu Leu Ile Lys Asp
            20                  25                  30

Gly Cys Arg Val Pro Ala Val Val Phe Thr Thr Leu Arg Gly Arg Gln
        35                  40                  45

Leu Cys Ala Pro Pro Asp Gln Pro Trp Val Glu Arg Ile Ile Gln Arg
    50                  55                  60

Leu Gln Arg Thr Ser Ala Lys Met Lys Arg Arg Ser Ser Xaa
65                  70                  75
```

<210> SEQ ID NO 231
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 231

```
Ala Val Leu Pro Arg Ser Ala Lys Glu Leu Arg Cys Gln Cys Ile Lys
1               5                   10                  15

Thr Tyr Ser Lys Pro Phe His Pro Lys Phe Ile Lys Glu Leu Arg Val
            20                  25                  30

Ile Glu Ser Gly Pro His Cys Ala Asn Thr Glu Ile Ile Val Lys Leu
        35                  40                  45

Ser Asp Gly Arg Glu Leu Cys Leu Asp Pro Lys Glu Asn Trp Val Gln
    50                  55                  60

Arg Val Val Glu Lys Phe Leu Lys Arg Ala Glu Asn Ser Xaa
65                  70                  75
```

<210> SEQ ID NO 232
<211> LENGTH: 78
<212> TYPE: PRT
<213> ORGANISM: Artificial sequence
<220> FEATURE:
<223> OTHER INFORMATION: Synthesized peptide

```
<220> FEATURE:
<221> NAME/KEY: X
<222> LOCATION: (78)..(78)
<223> OTHER INFORMATION: X is K(ivDde)

<400> SEQUENCE: 232

Ala Val Leu Pro Arg Ser Ala Lys Glu Leu Arg Cys Gln Cys Ile Lys
1               5                   10                  15

Thr Tyr Ser Lys Pro Phe His Pro Lys Phe Ile Lys Glu Leu Arg Val
            20                  25                  30

Ile Glu Ser Gly Pro His Cys Ala Asn Thr Glu Ile Ile Val Lys Leu
        35                  40                  45

Ser Asp Gly Arg Glu Leu Cys Leu Asp Pro Lys Glu Asn Trp Val Gln
    50                  55                  60

Arg Val Val Glu Lys Phe Leu Lys Arg Ala Glu Asn Ser Xaa
65                  70                  75

<210> SEQ ID NO 233
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is K(PEG-Biotin)

<400> SEQUENCE: 233

Ala Val Leu Pro Arg Ser Ala Lys Glu Leu Arg Cys Gln Cys Ile Lys
1               5                   10                  15

Thr Tyr Ser Lys Pro Phe His Pro Lys Phe Ile Lys Glu Leu Arg Val
            20                  25                  30

Ile Glu Ser Gly Pro His Cys Ala Asn Thr Glu Ile Ile Val Lys Leu
        35                  40                  45

Ser Asp Gly Arg Glu Leu Cys Leu Asp Pro Lys Glu Asn Trp Val Gln
    50                  55                  60

Arg Val Val Glu Lys Phe Leu Lys Arg Ala Glu Asn Ser Xaa
65                  70                  75

<210> SEQ ID NO 234
<211> LENGTH: 73
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 234

Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Glu Ser Gly Pro
            20                  25                  30

His Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60
```

```
Phe Leu Lys Arg Ala Glu Asn Ser Xaa
 65                  70
```

<210> SEQ ID NO 235
<211> LENGTH: 73
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is K(ivDde)

<400> SEQUENCE: 235

```
Ser Ala Lys Glu Leu Arg Cys Gln Cys Ile Lys Thr Tyr Ser Lys Pro
  1               5                  10                  15

Phe His Pro Lys Phe Ile Lys Glu Leu Arg Val Ile Glu Ser Gly Pro
             20                  25                  30

His Cys Ala Asn Thr Glu Ile Ile Val Lys Leu Ser Asp Gly Arg Glu
         35                  40                  45

Leu Cys Leu Asp Pro Lys Glu Asn Trp Val Gln Arg Val Val Glu Lys
     50                  55                  60

Phe Leu Lys Arg Ala Glu Asn Ser Xaa
 65                  70
```

<210> SEQ ID NO 236
<211> LENGTH: 73
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is K(PEG-Biotin)

<400> SEQUENCE: 236

```
Ser Ala Lys Glu Leu Arg Cys Gln Cys Ile Lys Thr Tyr Ser Lys Pro
  1               5                  10                  15

Phe His Pro Lys Phe Ile Lys Glu Leu Arg Val Ile Glu Ser Gly Pro
             20                  25                  30

His Cys Ala Asn Thr Glu Ile Ile Val Lys Leu Ser Asp Gly Arg Glu
         35                  40                  45

Leu Cys Leu Asp Pro Lys Glu Asn Trp Val Gln Arg Val Val Glu Lys
     50                  55                  60

Phe Leu Lys Arg Ala Glu Asn Ser Xaa
 65                  70
```

<210> SEQ ID NO 237
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 237

-continued

Gly Pro Ala Ser Val Pro Thr Thr Cys Cys Phe Asn Leu Ala Asn Arg
1               5                   10                  15

Lys Ile Pro Leu Gln Arg Leu Glu Ser Tyr Arg Arg Ile Thr Ser Gly
            20                  25                  30

Lys Cys Pro Gln Lys Ala Val Ile Phe Lys Thr Lys Leu Ala Lys Asp
        35                  40                  45

Ile Cys Ala Asp Pro Lys Lys Lys Trp Val Gln Asp Ser Met Lys Tyr
    50                  55                  60

Leu Asp Gln Lys Ser Pro Thr Pro Xaa Pro
65                  70

<210> SEQ ID NO 238
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is K(ivDde)

<400> SEQUENCE: 238

Gly Pro Ala Ser Val Pro Thr Thr Cys Cys Phe Asn Leu Ala Asn Arg
1               5                   10                  15

Lys Ile Pro Leu Gln Arg Leu Glu Ser Tyr Arg Arg Ile Thr Ser Gly
            20                  25                  30

Lys Cys Pro Gln Lys Ala Val Ile Phe Lys Thr Lys Leu Ala Lys Asp
        35                  40                  45

Ile Cys Ala Asp Pro Lys Lys Lys Trp Val Gln Asp Ser Met Lys Tyr
    50                  55                  60

Leu Asp Gln Lys Ser Pro Thr Pro Xaa Pro
65                  70

<210> SEQ ID NO 239
<211> LENGTH: 74
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is K(PEG-Biotin)

<400> SEQUENCE: 239

Gly Pro Ala Ser Val Pro Thr Thr Cys Cys Phe Asn Leu Ala Asn Arg
1               5                   10                  15

Lys Ile Pro Leu Gln Arg Leu Glu Ser Tyr Arg Arg Ile Thr Ser Gly
            20                  25                  30

Lys Cys Pro Gln Lys Ala Val Ile Phe Lys Thr Lys Leu Ala Lys Asp
        35                  40                  45

Ile Cys Ala Asp Pro Lys Lys Lys Trp Val Gln Asp Ser Met Lys Tyr
    50                  55                  60

Leu Asp Gln Lys Ser Pro Thr Pro Xaa Pro
65                  70

<210> SEQ ID NO 240
<211> LENGTH: 99
<212> TYPE: PRT
<213> ORGANISM: Artificial sequence
<220> FEATURE:

<223> OTHER INFORMATION: Synthesized peptide

<400> SEQUENCE: 240

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 241
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (64)..(64)
<223> OTHER INFORMATION: X = methionine or norleucine

<400> SEQUENCE: 241

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Xaa
    50                  55                  60

Asp His Leu Asp Lys Gln Thr Gln Thr Pro Lys Thr
65                  70                  75

<210> SEQ ID NO 242
<211> LENGTH: 68
<212> TYPE: PRT
<213> ORGANISM: Artificial sequence
<220> FEATURE:
<223> OTHER INFORMATION: Synthesized peptide

<400> SEQUENCE: 242

Val Thr Cys Cys Tyr Asn Phe Thr Asn Arg Lys Ile Ser Val Gln Arg
1               5                   10                  15

Leu Ala Ser Tyr Arg Arg Ile Thr Ser Ser Lys Cys Pro Lys Glu Ala
            20                  25                  30

Val Ile Phe Lys Thr Ile Val Ala Lys Glu Ile Cys Ala Asp Pro Lys
        35                  40                  45

Gln Lys Trp Val Gln Asp Ser Met Asp His Leu Asp Lys Gln Thr Gln
    50                  55                  60

Thr Pro Lys Thr
65

```
<210> SEQ ID NO 243
<211> LENGTH: 104
<212> TYPE: PRT
<213> ORGANISM: Artificial sequence
<220> FEATURE:
<223> OTHER INFORMATION: Synthesized peptide

<400> SEQUENCE: 243

Met Lys Ile Ser Thr Leu Leu Cys Leu Leu Leu Ile Ala Thr Thr Ile
1               5                   10                  15

Ser Pro Gln Val Leu Ala Gly Pro Asp Ala Val Ser Thr Pro Val Thr
            20                  25                  30

Cys Cys Tyr Asn Val Val Lys Gln Lys Ile His Val Arg Lys Leu Lys
        35                  40                  45

Ser Tyr Arg Arg Ile Thr Ser Ser Gln Cys Pro Arg Glu Ala Val Ile
    50                  55                  60

Phe Arg Thr Ile Leu Asp Lys Glu Ile Cys Ala Asp Pro Lys Glu Lys
65                  70                  75                  80

Trp Val Lys Asn Ser Ile Asn His Leu Asp Lys Thr Ser Gln Thr Phe
                85                  90                  95

Ile Leu Glu Pro Ser Cys Leu Gly
            100

<210> SEQ ID NO 244
<211> LENGTH: 82
<212> TYPE: PRT
<213> ORGANISM: Artificial sequence
<220> FEATURE:
<223> OTHER INFORMATION: Synthesized peptide

<400> SEQUENCE: 244

Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
            20                  25                  30

Ser Ser Gln Cys Pro Arg Glu Ala Val Ile Phe Arg Thr Ile Leu Asp
        35                  40                  45

Lys Glu Ile Cys Ala Asp Pro Lys Glu Lys Trp Val Lys Asn Ser Ile
    50                  55                  60

Asn His Leu Asp Lys Thr Ser Gln Thr Phe Ile Leu Glu Pro Ser Cys
65                  70                  75                  80

Leu Gly

<210> SEQ ID NO 245
<211> LENGTH: 76
<212> TYPE: PRT
<213> ORGANISM: Artificial sequence
<220> FEATURE:
<223> OTHER INFORMATION: Synthesized peptide

<400> SEQUENCE: 245

Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
            20                  25                  30

Ser Ser Gln Cys Pro Arg Glu Ala Val Ile Phe Arg Thr Ile Leu Asp
        35                  40                  45

Lys Glu Ile Cys Ala Asp Pro Lys Glu Lys Trp Val Lys Asn Ser Ile
    50                  55                  60
```

```
Asn His Leu Asp Lys Thr Ser Gln Thr Phe Ile Leu
 65                  70                  75
```

<210> SEQ ID NO 246
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (75)..(75)
<223> OTHER INFORMATION: X is an amino acid residue that can be
      biotinylated, such as lysine, ornithine or diaminopropionic acid
      and optionally is biotinylated, optionally via a spacer molecule
      such as PEG, e.g. K(PEG-Biotin)

<400> SEQUENCE: 246

```
Gly Pro Asp Ala Val Ser Thr Pro Val Thr Cys Cys Tyr Asn Val Val
 1               5                  10                  15

Lys Gln Lys Ile His Val Arg Lys Leu Lys Ser Tyr Arg Arg Ile Thr
            20                  25                  30

Ser Ser Gln Cys Pro Arg Glu Ala Val Ile Phe Arg Thr Ile Leu Asp
        35                  40                  45

Lys Glu Ile Cys Ala Asp Pro Lys Glu Lys Trp Val Lys Asn Ser Ile
 50                  55                  60

Asn His Leu Asp Lys Thr Ser Gln Thr Phe Xaa Leu
 65                  70                  75
```

<210> SEQ ID NO 247
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln

<400> SEQUENCE: 247

```
Xaa Pro Asp Ala Ile Asn Ala Pro Val Thr Cys Cys Tyr Asn Phe Thr
 1               5                  10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
 50                  55                  60

Asp His Leu Asp Lys Gln Thr Gln Thr Pro Lys Thr
 65                  70                  75
```

<210> SEQ ID NO 248
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X = pyroGlu or Gln
<220> FEATURE:
<221> NAME/KEY: X
<222> LOCATION: (75)..(75)
<223> OTHER INFORMATION: X is K(ivDde)

<400> SEQUENCE: 248

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
50                  55                  60

Asp His Leu Asp Lys Gln Thr Gln Thr Pro Xaa Thr
65                  70                  75

<210> SEQ ID NO 249
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X is pyroGlu or Gln
<220> FEATURE:
<221> NAME/KEY: X
<222> LOCATION: (75)..(75)
<223> OTHER INFORMATION: X is an amino acid residue that can be
      biotinylated, such as lysine, ornithine or diaminopropionic acid
      and optionally is biotinylated, optionally via a spacer molecule
      such as PEG

<400> SEQUENCE: 249

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
50                  55                  60

Asp His Leu Asp Lys Gln Thr Gln Thr Pro Xaa Thr
65                  70                  75

<210> SEQ ID NO 250
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X is pyroGlu or Gln

<400> SEQUENCE: 250

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
50                  55                  60

```
Lys His Leu Asp Gln Ile Phe Gln Asn Leu Lys Pro
65                  70                  75

<210> SEQ ID NO 251
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X is pyroGlu or Gln
<220> FEATURE:
<221> NAME/KEY: X
<222> LOCATION: (75)..(75)
<223> OTHER INFORMATION: X is FmocLys(ivDde)

<400> SEQUENCE: 251

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Xaa Pro
65                  70                  75

<210> SEQ ID NO 252
<211> LENGTH: 76
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (1)..(1)
<223> OTHER INFORMATION: X is pyroGlu or Gln
<220> FEATURE:
<221> NAME/KEY: X
<222> LOCATION: (75)..(75)
<223> OTHER INFORMATION: X is an amino acid residue that can be
      biotinylated, such as lysine, ornithine or diaminopropionic acid
      and optionally is biotinylated, optionally via a spacer molecule
      such as PEG

<400> SEQUENCE: 252

Xaa Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Xaa Pro
65                  70                  75

<210> SEQ ID NO 253
<211> LENGTH: 68
<212> TYPE: PRT
<213> ORGANISM: Artificial sequence
<220> FEATURE:
```

<223> OTHER INFORMATION: Synthesized peptide

<400> SEQUENCE: 253

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Lys Ser
65

<210> SEQ ID NO 254
<211> LENGTH: 68
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (67)..(67)
<223> OTHER INFORMATION: X is K(ivDde)

<400> SEQUENCE: 254

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Xaa Ser
65

<210> SEQ ID NO 255
<211> LENGTH: 68
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (67)..(67)
<223> OTHER INFORMATION: X is an amino acid residue that can be
      biotinylated, such as lysine, ornithine or diaminopropionic acid
      and optionally is biotinylated, optionally via a spacer molecule
      such as PEG

<400> SEQUENCE: 255

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Xaa Ser
65

```
<210> SEQ ID NO 256
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is an amino acid residue that can be
      biotinylated, such as lysine, ornithine or diaminopropionic acid
      and optionally is biotinylated, optionally via a spacer molecule
      such as PEG

<400> SEQUENCE: 256

Ala Val Leu Pro Arg Ser Ala Lys Glu Leu Arg Cys Gln Cys Ile Lys
1               5                   10                  15

Thr Tyr Ser Lys Pro Phe His Pro Lys Phe Ile Lys Glu Leu Arg Val
            20                  25                  30

Ile Glu Ser Gly Pro His Cys Ala Asn Thr Glu Ile Ile Val Lys Leu
        35                  40                  45

Ser Asp Gly Arg Glu Leu Cys Leu Asp Pro Lys Glu Asn Trp Val Gln
    50                  55                  60

Arg Val Val Glu Lys Phe Leu Lys Arg Ala Glu Asn Ser Xaa
65                  70                  75

<210> SEQ ID NO 257
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is K(ivDde)

<400> SEQUENCE: 257

Ala Val Leu Pro Arg Ser Ala Lys Glu Leu Arg Cys Gln Cys Ile Lys
1               5                   10                  15

Thr Tyr Ser Lys Pro Phe His Pro Lys Phe Ile Lys Glu Leu Arg Val
            20                  25                  30

Ile Glu Ser Gly Pro His Cys Ala Asn Thr Glu Ile Ile Val Lys Leu
        35                  40                  45

Ser Asp Gly Arg Glu Leu Cys Leu Asp Pro Lys Glu Asn Trp Val Gln
    50                  55                  60

Arg Val Val Glu Lys Phe Leu Lys Arg Ala Glu Asn Ser Xaa
65                  70                  75

<210> SEQ ID NO 258
<211> LENGTH: 78
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (78)..(78)
<223> OTHER INFORMATION: X is K(PEG-Biotin)

<400> SEQUENCE: 258

Ala Val Leu Pro Arg Ser Ala Lys Glu Leu Arg Cys Gln Cys Ile Lys
1               5                   10                  15
```

```
Thr Tyr Ser Lys Pro Phe His Pro Lys Phe Ile Lys Glu Leu Arg Val
            20                  25                  30

Ile Glu Ser Gly Pro His Cys Ala Asn Thr Glu Ile Ile Val Lys Leu
            35                  40                  45

Ser Asp Gly Arg Glu Leu Cys Leu Asp Pro Lys Glu Asn Trp Val Gln
50                  55                  60

Arg Val Val Glu Lys Phe Leu Lys Arg Ala Glu Asn Ser Xaa
65                  70                  75

<210> SEQ ID NO 259
<211> LENGTH: 73
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is an amino acid residue that can be
      biotinylated, such as lysine, ornithine or diaminopropionic acid
      and optionally is biotinylated, optionally via a spacer molecule
      such as PEG

<400> SEQUENCE: 259

Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Glu Ser Gly Pro
            20                  25                  30

His Cys Ala Asn Thr Glu Ile Ile Val Lys Leu Ser Asp Gly Arg Glu
            35                  40                  45

Leu Cys Leu Asp Pro Lys Glu Asn Trp Val Gln Arg Val Val Glu Lys
        50                  55                  60

Phe Leu Lys Arg Ala Glu Asn Ser Xaa
65                  70

<210> SEQ ID NO 260
<211> LENGTH: 73
<212> TYPE: PRT
<213> ORGANISM: Artificial sequence
<220> FEATURE:
<223> OTHER INFORMATION: Synthesized peptide
<220> FEATURE:
<221> NAME/KEY: X
<222> LOCATION: (73)..(73)
<223> OTHER INFORMATION: X is K(ivDde)

<400> SEQUENCE: 260

Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Glu Ser Gly Pro
            20                  25                  30

His Cys Ala Asn Thr Glu Ile Ile Val Lys Leu Ser Asp Gly Arg Glu
            35                  40                  45

Leu Cys Leu Asp Pro Lys Glu Asn Trp Val Gln Arg Val Val Glu Lys
        50                  55                  60

Phe Leu Lys Arg Ala Glu Asn Ser Xaa
65                  70

<210> SEQ ID NO 261
<211> LENGTH: 73
<212> TYPE: PRT
<213> ORGANISM: Artificial sequence
<220> FEATURE:
```

-continued

<223> OTHER INFORMATION: Synthesized peptide
<220> FEATURE:
<221> NAME/KEY: X
<222> LOCATION: (73)..(73)
<223> OTHER INFORMATION: X is K(PEG-Biotin)

<400> SEQUENCE: 261

Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Glu Ser Gly Pro
            20                  25                  30

His Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser Xaa
65                  70

<210> SEQ ID NO 262
<211> LENGTH: 20
<212> TYPE: DNA
<213> ORGANISM: Artificial Sequence
<220> FEATURE:
<223> OTHER INFORMATION: Synthetic DNA Primer

<400> SEQUENCE: 262
ctctctcccc tggaaaggac                                               20

<210> SEQ ID NO 263
<211> LENGTH: 20
<212> TYPE: DNA
<213> ORGANISM: Artificial Sequence
<220> FEATURE:
<223> OTHER INFORMATION: Synthetic DNA Primer

<400> SEQUENCE: 263
gccagagggc tgattagaga                                               20

<210> SEQ ID NO 264
<211> LENGTH: 20
<212> TYPE: DNA
<213> ORGANISM: Artificial Sequence
<220> FEATURE:
<223> OTHER INFORMATION: Synthetic DNA Primer

<400> SEQUENCE: 264 aaggttttg caaagctcca                                                20

<210> SEQ ID NO 265
<211> LENGTH: 20
<212> TYPE: DNA
<213> ORGANISM: Artificial Sequence
<220> FEATURE:
<223> OTHER INFORMATION: Synthetic DNA Primer

<400> SEQUENCE: 265
tactgctgct gatgggattg                                               20

<210> SEQ ID NO 266
<211> LENGTH: 19
<212> TYPE: DNA
<213> ORGANISM: Artificial Sequence
<220> FEATURE:
<223> OTHER INFORMATION: Synthetic DNA Primer

```
<400> SEQUENCE: 266
gcaccacgtc caatgacat                                              19

<210> SEQ ID NO 267
<211> LENGTH: 18
<212> TYPE: DNA
<213> ORGANISM: Artificial Sequence
<220> FEATURE:
<223> OTHER INFORMATION: Synthetic DNA Primer

<400> SEQUENCE: 267
gtgcggctgc ttccataa                                               18
```

DIAGNOSING AND TREATING INFLAMMATORY DISEASES

CROSS REFERENCE TO RELATED APPLICATIONS

This application is a continuation-in-part of International Application No. PCT/GB2012/051357, filed Jun. 13, 2012, which claims the benefit of the earlier filing date of U.S. Provisional Application No. 61/496,442, filed Jun. 13, 2011, International Application No. PCT/GB2012/051349, filed Jun. 13, 2012, which claims the benefit of the earlier filing date of U.S. Provisional Application No. 61/496,167, filed Jun. 13, 2011, International Application No. PCT/GB2012/051348, filed Jun. 13, 2012, which claims the benefit of the earlier filing date of U.S. Provisional Application No. 61/496,288, filed Jun. 13, 2011, International Application No. PCT/GB2012/051351, filed Jun. 13, 2012, which claims the benefit of the earlier filing date of U.S. Provisional Application No. 61/496,242, filed Jun. 13, 2011, International Application No. PCT/GB2012/051350, filed Jun. 13, 2012, which claims the benefit of the earlier filing date of U.S. Provisional Application No. 61/496,209, filed Jun. 13, 2011, International Application No. PCT/GB2012/051355, filed Jun. 13, 2012, which claims the benefit of the earlier filing date of U.S. Provisional Application No. 61/496,195, filed Jun. 13, 2011, International Application No. PCT/GB2012/051345, filed Jun. 13, 2012, which claims the benefit of the earlier filing date of U.S. Provisional Application No. 61/496,228, filed Jun. 13, 2011, International Application No. PCT/GB2012/051352, filed Jun. 13, 2012, which claims the benefit of the earlier filing date of U.S. Provisional Application No. 61/496,264, filed Jun. 13, 2011, International Application No. PCT/GB2012/051346, filed Jun. 13, 2012, which claims the benefit of the earlier filing date of U.S. Provisional Application No. 61/496,184, filed Jun. 13, 2011, International Application No. PCT/GB2012/051353, filed Jun. 13, 2012, which claims the benefit of the earlier filing date of U.S. Provisional Application No. 61/496,329, filed Jun. 13, 2011, International Application No. PCT/GB2012/051356, filed Jun. 13, 2012, which claims the benefit of the earlier filing date of U.S. Provisional Application No. 61/496,377, filed Jun. 13, 2011, and International Application No. PCT/GB2012/051354, filed Jun. 13, 2012, which claims the benefit of the earlier filing date of U.S. Provisional Application No. 61/496,352, filed Jun. 13, 2011. All of the above listed applications are specifically incorporated by reference herein in their entirety.

FIELD OF THE INVENTION

The various embodiments of the present invention relate to products for and methods of treating inflammatory conditions, such as: inflammatory bowel disease, including Crohn's disease (CD) and ulcerative colitis (UC); conditions associated with metabolic syndrome, in particular diabetes, obesity, insulin resistance, increased serum triacylglycerol concentrations and hypertension; inflammatory arthritis, in particular rheumatoid arthritis, psoriatic arthritis and eosinophilic arthritis; allergic conditions, in particular asthma, allergic rhinitis, allergic ocular disease, atopic dermatitis, food allergies and allergic inflammation; mental disorders such as schizophrenia, depression and bipolar disorder; inflammatory skin diseases, in particular psoriasis and atopic dermatitis; multiple sclerosis, in particular active and stable relapsing-remitting multiple sclerosis, primary progressive, secondary progressive and progressive relapsing multiple sclerosis; cardiovascular disease, including arteriosclerosis and in particular atherosclerosis; primary sclerosing cholangitis; and respiratory conditions, in particular sarcoidosis and Chronic Obstructive Pulmonary Disease (COPD); sepsis and Respiratory Distress Syndrome (RDS) (including but not limited to sepsis associated RDS). The various embodiments of the present invention relate to products for and methods of treating cancer, in particular by reducing levels of circulating tumour cells, reducing the incidence of tumour metastasis, removing regulatory T lymphocytes from the peripheral blood, or treating leukaemias such as chronic lymphocytic leukaemia and chronic myeloic leukemia. The products and methods may also be used for debulking in Acute Myeloid Leukemia (AML), Acute Lymphoblastic Leukemia (ALL) and before harvest for autologous bone marrow/stem cell transplantation and for treating the leukemic phase of lymphoma. Companion diagnostics are also described.

BACKGROUND OF THE INVENTION

A. Diagnosing and Treating Inflammatory Bowel Disease and Irritable Bowel Syndrome Fulminant ulcerative colitis is a worsening of ulcerative colitis characterized by a high white blood cell count and severe abdominal pain. At present, patients with fulminant ulcerative colitis are treated with high doses of steroids. In phase III-studies treatment with anti-TNFα has been investigated. Both drugs are general inhibitors of inflammation. They are effective in about 50% of cases but have serious adverse effects. Even if successfully treated fulminant ulcerative colitis has a tendency of recurring.

In patients with fulminant ulcerative colitis not responding to medical treatment prompt surgical intervention is mandatory. Ulcerative colitis is always restricted to the large intestine (colon). As a last measure the colon is resected, and an external ileostoma constructed. After a recovery period of at least 6 months and sometimes further medical treatment of rectal stump inflammation either ileorectal anastomosis or reconstructive surgery with a pelvic pouch will be performed in most patients to restore intestinal continuity. Both procedures entail loose stools about six times daily and disturbances in water- and mineral balances. There may also be fulminant episodes in Crohn's disease (fulminant Crohn's colitis), which are also serious conditions necessitating immediate medical and/or surgical intervention.

While the inflammation can be located in any part of the gastrointestinal tract in patients with Crohn's disease, it is usually confined to the most distal part of the small intestine and the first part of the large intestine (ileocaecal region). Medical treatment cannot cure the disease although anti-inflammatory drugs such as steroids and aza-thioprine relieve symptoms. Surgery with resection of stenotic and fistulating bowel segments is indicated in about 50% of patients; half of them will have recurrences and need further surgery. A method which can specifically turn off the inflammation in IBD and prevent recurrent disease in the individual patient thus is highly warranted.

B. Treating Conditions Associated with Metabolic Syndrome

The International Diabetes Foundation (IDF) define metabolic syndrome as follows:

For a person to be defined as having the metabolic syndrome they must have: Central obesity (defined as waist circumference ≥94 cm for Europid men and ≥80 cm for Europid women, with ethnicity specific values for other groups) plus any two of the following four factors:

raised triglyceride (TG) level: ≥150 mg/dL (1.7 mmol/L), or specific treatment for this lipid abnormality reduced high-density lipoprotein (HDL) cholesterol: <40 mg/dL (1.03 mmol/L*) in males and <50 mg/dL (1.29 mmol/L*) in females, or specific treatment for this lipid abnormality raised blood pressure (BP): systolic BP≥130 or diastolic BP≥85 mm Hg, or treatment of previously diagnosed hypertension raised fasting plasma glucose (FPG)≥100 mg/dL (5.6 mmol/L), or previously diagnosed type 2 diabetes If above 5.6 mmol/L or 100 mg/dL, oral glucose tolerance test (OGTT) is strongly recommended but is not necessary to define presence of the syndrome.

While the pathogenesis of the metabolic syndrome and each of its components is complex and not well understood, central obesity and insulin resistance are acknowledged as important causative factors.

Adiposis dolorosa, or Dercum's disease, is a rare progressive condition characterized by multiple, painful, subcutaneous lipomas that usually occur in obese, postmenopausal women (Dercum FX. Three cases of a hitherto unclassified affection resembling in its grosser aspects obesity, but associated with special symptoms: adiposis dolorosa. Am J Med Sci 1892; 104:521-35, incorporated herein by reference in its entirety).

C. Treating Inflammatory Arthritis

Inflammatory arthritis describes a range of conditions, including rheumatoid arthritis, ankylosing spondylitis, psoriatic arthritis and gout, characterised by severe damage to joints throughout the body. Rheumatoid arthritis (RA) is the most common form of inflammatory arthritis affecting about 1% of the total world population.

RA, similar to other forms of inflammatory arthritis is characterised by "synovitis" or inflammation of the synovial membrane, which lines the cavity of synovial joints. As the disease progresses, ongoing inflammation can lead to erosion and destruction of the joint causing significant pain, swelling and potentially deformity.

In many cases, the precise etiology of inflammatory arthritis is not well understood. However, all of these disorders fall within the category of "autoimmune conditions", wherein disease pathogenesis is attributable in large part, to immune system dysregulation. RA in particular, is characterised by the presence of autoantibodies to "rheumatoid factor" and to "citrullinated peptides". Moreover, the presence of inflammatory mediators, for example cytokines, is known to play a key role in fuelling disease progression. In this regard, TNFα has been identified as a central mediator of inflammation in RA, and therapies that block the activity of this molecule are being used successfully to alleviate the symptoms of this disease.

D. Treating Cancer

Cancer is a disease characterised by uncontrolled cell growth caused by accumulation of genetic mutations in the cellular DNA. There are over 200 types of different cancer classified according to the cell of origin from which the cancer or tumour first developed. Furthermore, cancers can be classified broadly as either solid tumours, for example breast cancer, colorectal cancer and melanoma, or as haematological malignancies such as leukaemias and lymphomas.

Solid tumours typically initiate and grow as an abnormal mass at a local site. However, during the course of cancer progression, the cells may acquire the ability to invade the underlying tissue and thereby enter the circulatory and/or lymphatic systems. These invasive properties ultimately allow solid tumours to metastasise to distal sites within the body, and it is metastasis combined with growth at secondary sites that accounts for the vast majority of cancer deaths.

In contrast to solid tumours, cancers such as leukaemias and lymphomas derive from cells of haematological origin, and therefore manifest as systemic diseases. In particular, chronic lymphocytic leukaemia, the most common form of leukaemia, develops from malignant lymphocytes originating in the bone marrow.

The body has many intrinsic mechanisms intended to guard against cancer development. In this regard, the immune system is thought to play a key role in eradicating cells harbouring genetic mutations. It follows therefore, that cancer cells often persist by evolving ways to avoid recognition by the cells of the immune system. In particular, it has been shown that elevated levels of T regulatory cells, both within the peripheral circulation and within the tumour microenvironment, underlie the immune suppression seen in cancer patients. The presence of increased numbers of regulatory T cells has also been identified as a barrier to the successful implementation of cancer immunotherapies.

E. Treating Mental Disorders

Schizophrenia is a mental disorder characterized by disintegration of thought processes and of emotional responsiveness. It most commonly manifests as auditory hallucinations, paranoid or bizarre delusions, or disorganized speech and thinking, and it is accompanied by significant social or occupational dysfunction. The onset of symptoms typically occurs in young adulthood, with a global lifetime prevalence of about 0.3-0.7%. Diagnosis is typically based on observed behaviour and the patient's reported experiences.

Current treatments include antipsychotic medication, which primarily suppresses dopamine, and sometimes serotonin, receptor activity. Psychotherapy and vocational and social rehabilitation may also be important in treatment.

F. Treating Conditions Associated with Allergy

Allergy is a hypersensitivity disorder of the immune system. Allergic reactions occur to normally harmless environmental substances known as allergens; these reactions are acquired, predictable, and rapid. Allergy is a type I (or immediate) hypersensitivity and may be characterized by excessive activation of certain white blood cells, resulting in an extreme inflammatory response. Common allergic reactions include eczema, hives, hay fever, asthma attacks, food allergies, and reactions to the venom of stinging insects such as wasps and bees.

Mild allergies, such as hay fever, are highly prevalent in the human population. Allergies can play a major role in a range of conditions such as asthma.

A variety of tests now exist to diagnose allergic conditions; these include testing the skin for responses to known allergens or analyzing the blood for the presence and levels of allergen-specific IgE. Treatments for allergies include allergen avoidance, use of anti-histamines, steroids or other oral medications, immunotherapy to desensitize the response to allergen, and targeted therapy.

Allergic inflammation is an important pathophysiological feature of several medical conditions including allergic asthma, atopic dermatitis, allergic rhinitis and several ocular allergic diseases. Allergic reactions may generally be divided into two components; the early phase reaction, and the late phase reaction. While the contribution to the development of symptoms from each of the phases varies greatly between diseases, both are usually present and provide a framework for understanding allergic disease.

The early phase of the allergic reaction typically occurs within minutes following allergen exposure and may be referred to as the immediate allergic reaction or as a Type I allergic reaction. The reaction is caused by the release of histamine and mast cell granule proteins by a process called degranulation, as well as the production of leukotrienes, prostaglandins and cytokines, by mast cells following the cross-linking of allergen specific IgE molecules bound to mast cell FcϵRI receptors. These mediators affect nerve cells causing itching, smooth muscle cells causing contraction (leading to the airway narrowing seen in allergic asthma), goblet cells causing mucus production, and endothelial cells causing vasodilatation and edema.

The products of the early phase reaction include chemokines and molecules that act on endothelial cells and cause them to express intercellular adhesion molecules (such as vascular cell adhesion molecule and selectins), which together result in the recruitment and activation of leukocytes from the blood into the site of the allergic reaction. Typically, the infiltrating cells observed in allergic reactions contain a high proportion of lymphocytes, and especially, of eosinophils. The recruited eosinophils will degranulate releasing a number of cytotoxic molecules (including Major Basic Protein and eosinophil peroxidase) as well as produce a number of cytokines such as IL-5. The recruited T-cells are typically of the Th2 variety and the cytokines they produce lead to further recruitment of mast cells and eosinophils as well as plasma cell isotype switching to IgE. The IgE binds to the mast cell FcϵRI receptors and primes the individual for further allergic responses.

G. Treating Inflammatory Skin Diseases

Inflammatory skin disease defines a broad category of disorders characterised by mild to severe irritation and inflammation of the skin. These disorders can affect people of all ages, and include conditions such as acne, eczema or dermatitis, Rosacea and psoriasis. In most cases, there is no cure and patients with such conditions receive treatments to manage their symptoms.

Psoriasis and atopic dermatitis represent two of the commonest chronic inflammatory disorders of the skin, although, in both cases, the precise etiology of these diseases remains unknown. Psoriasis is characterised clinically by keratinocyte hyperproliferation and increased migration of inflammatory cells into the skin leading to epithelial hyperplasia and an excessive inflammatory response at the site of psoriatic plaques or lesions. Atopic dermatitis typically develops as an allergic reaction following exposure to irritants and/or environmental allergens and is associated with a dysregulated immune response occurring at the affected site.

In all inflammatory disorders of the skin, including psoriasis and atopic dermatitis, crosstalk between epidermal keratinocytes and cells of the immune system appears to play a central role in the pathogenesis of disease. For example, dendritic cells and effector T cells have been identified as key players in the development of psoriasis, and cytokines produced by these cells are known to stimulate keratinocyte proliferation and increase migration of inflammatory cells in the skin. In atopic dermatitis, cytokines released by immune cells trigger the inflammatory activation of keratinocytes.

H. Treating Multiple Sclerosis

Multiple sclerosis is a neurodegenerative disease affecting the central nervous system (CNS). Disease onset usually occurs in young adults between the ages of 20 and 40, however, the precise underlying cause of MS is unknown. There is currently no cure for this disabling disease and treatment is primarily focussed on management of symptoms.

Irrespective of disease etiology, the immune system has been found to play a central role in the pathogenesis of MS. In particular, the lesions that develop in the brain and/or spinal cord during disease progression are frequently characterised by an excessive inflammatory infiltrate and the presence of autoreactive CD4+/CD8+ T cells and autoreactive B cells. Furthermore, ongoing assault of the CNS mediated by a variety of inflammatory and/or immune cell types appears to be the primary cause of the nerve damage and in particular, the axon demyelination, associated with this disease.

I. Treating Cardiovascular Disease

Heart or cardiovascular diseases are the class of diseases that involve the heart or blood vessels. Thus disease may relate to the arteries and/or veins.

Obesity and diabetes mellitus are often linked to cardiovascular disease. C-reactive protein (CRP) is a common inflammatory marker that has been found to be present in increased levels in patients at risk for cardiovascular disease. Also osteoprotegerin, which is involved with regulation of a key inflammatory transcription factor called NF-κB has been found to be a risk factor of cardiovascular disease and mortality.

Atherosclerosis is a condition in which fatty material collects along the walls of arteries. This fatty material thickens, hardens to form a plaque, and may eventually block the arteries resulting in myocardial infarction. Atherosclerosis is a type of arteriosclerosis (which refers to any stiffening of the arteries).

Pieces of plaque can break off and move through the affected artery to smaller blood vessels, blocking them and causing tissue damage or death (embolization). This is a common cause of heart attack and stroke. Blood clots can also form around a tear (fissure) in the plaque leading to blocked blood flow. If the clot moves into an artery in the heart, lungs, or brain, it can cause a stroke, heart attack, or pulmonary embolism. In some cases, the atherosclerotic plaque is associated with a weakening of the wall of an artery leading to an aneurysm.

J. Treating Primary Sclerosing Cholangitis

Primary sclerosing cholangitis (PSC) is a chronic liver disease characterised by excessive inflammation and fibrosis of intra- and extra-hepatic bile ducts. Although the precise etiology of this disease remains unclear, PSC is considered to be an 'autoimmune condition' associated with immune system dysfunction. In particular, inflammation of the bile ducts plays a key role in disease progression. This excessive inflammation ultimately causes bile duct damage, which severely impairs the flow of bile from the liver to the duodenum resulting in a condition referred to as cholestasis. As the disease progresses, patients ultimately develop liver cancer or suffer from liver failure.

PSC is associated with an increased incidence of other forms of cancer, in particular cholangiosarcoma, cancer of the biliary tree, and colorectal cancer. The majority of patients with PSC also suffer with inflammatory bowel disease, in particular the form of this disease known as ulcerative colitis.

Many drugs have been found to be ineffective at halting PSC disease progression and treatment options are currently focussed around management of the complications associated with cholestasis. The only essentially curative treatment is liver transplantation.

K. Treating Respiratory Conditions

Respiratory tract disorders such as asthma and chronic obstructive pulmonary disease (COPD) are typically characterised by breathing difficulties as a result of reduced airflow to the lungs. These symptoms are often caused by inflammation of the airways; for example, chronic bronchitis is a form of COPD associated with excessive inflammation of the bronchi.

In addition to breathing difficulties, airway obstruction and associated inflammation can cause progressive lung damage. In the case of patients with COPD, permanent narrowing of the airways can lead to complications such as chest infections, heart failure and ultimately pulmonary failure.

COPD is a very common respiratory disease and in the majority of cases, smoking is the cause.

Patients are typically treated using inhalers containing "bronchodilator" drugs. However, these are of limited use for patients with permanently-constricted airways and/or end-stage disease characterised by extensive damage to the lungs.

L. Treating Conditions Associated with Sepsis

Sepsis is a severe clinical condition wherein the body undergoes a systemic inflammatory response to a known or suspected infection. Sepsis causes serious illness which can lead to multiple organ failure and death.

Sepsis is typically triggered as a result of the body's aberrant physiologic response to a blood-borne infection. In particular, a cascade of immunological activity involving rapid activation of neutrophils and macrophages, up-regulation of lymphocyte co-stimulatory molecules and rapid lymphocyte apoptosis, contributes significantly to the pathogenesis of this condition. The systemic release of cytokines, such as TNF-$\alpha$, also causes dysregulation of the coagulation system and associated collapse of blood vessels. At the same time, disseminated activation of immunological pathways, such as the complement cascade, leads to wide-spread tissue and organ damage. A specific example of end-organ dysfunction is acute respiratory distress syndrome (ARDS). ARDS is characterized by inflammation of the lung parenchyma leading to impaired gas exchange with concomitant systemic release of inflammatory mediators causing inflammation, hypoxemia and frequently resulting in multiple organ failure.

The incidence of sepsis continues to increase worldwide, yet the mortality rate for this condition remains relatively high at between 20-40%. Improved knowledge of this complex condition is facilitating the development of new strategies for treatment; however, improved treatment options are still in high demand.

M. Apheresis

Apheresis is a treatment used for depletion of blood components, such as antibodies, low-density lipoproteins (LDL) and blood cells. Leukapheresis is the apheresis treatment used for removal of white blood cells, leukocytes. The patient is connected to an extracorporeal blood circulating system; the blood is drawn from a vein in one arm, passed through a column device and returned into the other arm of the patient. WO2010/029317 describes apheresis columns useful for treating inflammatory conditions including a chemokine immobilised on a solid support.

SUMMARY OF THE INVENTION

A. Diagnosing and Treating Inflammatory Bowel Disease and Irritable Bowel Syndrome Chemokines are a class of cytokine molecules involved in cell recruitment and activation in inflammation. Chemokines cause chemotaxis and activation of various subpopulations of cells in the immune system. The activity of chemokines is mediated primarily through tight binding to their receptors on the surface of leukocytes. In certain embodiments the present invention is based on the realisation that the interaction between (specific) chemokines and (specific) cells expressing their receptors may be exploited for the treatment of inflammatory bowel disease, including Crohn's disease (CD) and ulcerative cholitis (UC). The inventors have determined that targeting increased recruitment of specific chemokine receptor-expressing cells to the site of inflammation presents a new therapeutic approach to treat such conditions. Moreover, in such conditions, chemokine receptor expression on each cell may be increased again providing a therapeutic approach to treat such conditions.

The inventors have also determined that the frequency of circulating CD14+HLA-DR$^{hi}$ monocytes was significantly higher in IBD patients with moderate-to-severe disease compared to healthy controls. Furthermore, the presence of these monocytes correlated significantly to disease activity in patients with ulcerative colitis and Crohn's disease. This provides a further target for treatment of IBD which may be utilised in combination with targeting cells expressing chemokine receptors. This population of monocytes expresses high levels of CCR7 and CCR9.

Thus, in certain embodiments the invention serves to reduce the recruitment of inflammatory leukocytes, which express characteristic receptors, including chemokine receptors, and possibly express characteristic receptors, in particular chemokine receptors at increased levels, to sites of inflammation linked to disorders such as inflammatory bowel disease, including Crohn's disease (CD) and ulcerative cholitis (UC). This is achieved using specific binding reagents to capture specific receptor-expressing inflammatory leukocytes from the patient. Accordingly, in certain embodiments the invention provides in a first aspect a method for treating inflammatory bowel disease, including Crohn's disease (CD) and ulcerative cholitis (UC) comprising applying peripheral blood from a patient to an apheresis column loaded with a solid support comprising one or more binding reagents capable of specifically binding to a marker of CD14+HLA-DRhi monocytes selected from CD14, CCR7 and CCR9 immobilized directly or indirectly on the support thus removing CD14+HLA-DRhi monocytes from the peripheral blood of the patient. Combinations of binding reagents targeting at least two and possibly three of these markers are specifically contemplated. The peripheral blood from which the chemokine receptor expressing cells have been removed may then be returned to the patient in order to complete the treatment. In certain embodiments the invention may thus rely on a continuous extracorporeal circuit in some embodiments. Alternatively, in certain embodiments the invention may comprise steps of obtaining peripheral blood from the patient, applying the peripheral blood to the column and subsequently returning the peripheral blood from which the chemokine receptor expressing cells have been removed to the patient.

As shown herein, suitable binding reagents can be immobilized onto a solid support, either directly or indirectly, to generate an apheresis column suitable for capturing relevant receptor-expressing cells. Where increased levels of receptor expression are observed, such cells may be preferably removed from the peripheral blood using the columns of the various embodiments of the invention. Thus, the methods of various embodiments of the invention preferably target CD14+HLA-DRhi cells as defined herein for removal from the peripheral blood. "High" expression may be determined according to standard flow cytometry techniques, as discussed in further detail herein. An example is shown in FIG. 1 and FIG. 16 herein of a gating strategy. HLA-DR is a MHC class II cell surface receptor encoded by the human leukocyte antigen complex on chromosome 6 region 6p21.31.

The inventors have also surprisingly found that Irritable Bowel Syndrome (IBS) patients, or subject suffering from IBS, display an increased frequency (or level) of chemokine receptor expressing cells, in particular monocytes, more specifically CCR9 expressing monocytes. Thus, IBS patients may display inflammation that is comparable to that shown by patients suffering from IBD (levels of CCR9 expression may be similar to those found in UC and CD as discussed herein). Irritable bowel syndrome (IBS) is a condition characterized by chronic abdominal pain, discomfort, bloating, and alteration of bowel habits. It is currently diagnosed on the basis of symptoms only. Accordingly, identification of a pro-inflammatory component provides new avenues for treatment and diagnosis of this debilitating condition. In particular, it is shown herein that the CCR9 expressing cells increased in IBS patients can be depleted using a leukapheresis approach and/or a monocyte reduction therapy. This may be based upon use of a suitable binding reagent such as a CCL25 chemokine, as described in greater detail herein.

Thus, in certain embodiments the invention serves to reduce the recruitment of inflammatory leukocytes, which express characteristic receptors, including chemokine receptors, and possibly express characteristic receptors, in particular chemokine receptors at increased levels, to sites of inflammation linked to IBS. This is achieved using specific binding reagents to capture specific receptor-expressing inflammatory leukocytes from the patient. Accordingly, in certain embodiments the invention provides a method for treating IBS comprising applying peripheral blood from a patient to an apheresis column loaded with a solid support comprising one or more binding reagents capable of specifically binding to chemokine receptor expressing cells, in particular CCR9 expressing cells immobilized directly or indirectly on the support thus removing the chemokine receptor expressing cells from the peripheral blood of the patient. The peripheral blood from which the chemokine receptor expressing cells have been removed may then be returned to the patient in order to complete the treatment. In certain embodiments the invention may thus rely on a continuous extracorporeal circuit in some embodiments. Alternatively, in certain embodiments the invention may comprise steps of obtaining peripheral blood from the patient, applying the peripheral blood to the column and subsequently returning the peripheral blood from which the chemokine receptor expressing cells have been removed to the patient.

As shown herein, suitable binding reagents can be immobilized onto a solid support, either directly or indirectly, to generate an apheresis column suitable for capturing relevant receptor-expressing cells. Where increased levels of receptor expression are observed, such cells may be preferably removed from the peripheral blood using the columns of the various embodiments of the invention. Thus, the methods of various embodiments of the invention preferably target "CCR9hi" expressing cells as defined herein for removal from the peripheral blood. "High" expression may be determined according to standard flow cytometry techniques, as discussed in further detail herein. An example is shown in FIG. 1 and FIG. 16 herein of a gating strategy.

In other embodiments the invention further provides a/one or more binding reagent(s) capable of specifically binding to a marker of CD14+HLA-DRhi monocytes selected from CD14, CCR7 and CCR9 for use in the treatment of inflammatory bowel disease, including Crohn's disease (CD) and ulcerative cholitis (UC), wherein the binding reagent is immobilized, directly or indirectly, on a solid support contained within an apheresis column, to which is applied peripheral blood from a patient thus removing CD14+HLA-DRhi monocytes from the peripheral blood of the patient. In certain embodiments the invention also provides for use of one or more binding reagents capable of specifically binding to a marker of CD14+HLA-DRhi monocytes selected from CD14, CCR7 and CCR9 for use in the manufacture of an apheresis column for treatment of inflammatory bowel disease, including Crohn's disease (CD) and ulcerative cholitis (UC), wherein the one or more binding reagents is immobilized on a solid support contained within an apheresis column, to which is applied peripheral blood from a patient thus removing CD14+HLA-DRhi monocytes from the peripheral blood of the patient.

In other embodiments the invention further provides a/one or more binding reagent(s) capable of specifically binding to chemokine receptor expressing cells, in particular monocytes, more specifically CCR9 expressing cells/monocytes for use in the treatment of IBS, wherein the binding reagent is immobilized, directly or indirectly, on a solid support contained within an apheresis column, to which is applied peripheral blood from a patient thus removing chemokine receptor expressing cells, in particular monocytes, more specifically CCR9 expressing cells/monocytes from the peripheral blood of the patient. In certain embodiments the invention also provides for use of one or more binding reagents capable of specifically binding to chemokine receptor expressing cells, in particular monocytes, more specifically CCR9 expressing cells/monocytes for use in the manufacture of an apheresis column for treatment of IBS, wherein the one or more binding reagents is immobilized on a solid support contained within an apheresis column, to which is applied peripheral blood from a patient thus removing chemokine receptor expressing cells, in particular monocytes, more specifically CCR9 expressing cells/monocytes from the peripheral blood of the patient.

All embodiments described in respect of the methods of treatment of the various embodiments of the invention apply to these aspects mutatis mutandis and are not repeated for reasons of conciseness. Thus, the following discussion made with reference to the methods of treatment is also applicable to the medical use aspects of the various embodiments of the invention.

In certain embodiments the invention aims to treat inflammatory bowel disease, including Crohn's disease (CD) and ulcerative cholitis (UC). By treatment is meant a reduction in the specific receptor, including chemokine receptor, expressing cells in the peripheral blood of the patient. The reduction may comprise a reduction in cells that express receptors, including chemokine receptors, in particular CD14, HLA-DR, CCR9 and/or CCR7, at increased levels in diseased patients. The patient is typically a human patient but the term patient may include both human and non-human animal subjects in some embodiments. In the context of the various embodiments of the present invention, this typically involves a reduction in CD14, HLA-DR, CCR9 and/or CCR7 expressing cells, such as CD14 hi, HLA-DR hi, CCR9 hi and/or CCR7hi expressing cells, in the peripheral blood of the patient. The CD14, HLA-DR, CCR9 and/or CCR7 expressing cells comprise, consist essentially of or consist of monocytes, in particular CD14+HLA-DRhi monocytes, in certain embodiments. This cell type can be characterized according to the techniques disclosed herein (for example using flow cytometry).

In other embodiments the invention aims to treat IBS. By treatment is meant a reduction in the specific receptor, including chemokine receptor, expressing cells in the peripheral blood of the patient. The reduction may comprise a reduction in cells that express receptors, including chemokine receptors, in particular CCR9, at increased levels in diseased patients. The patient is typically a human patient but the term patient may include both human and non-human animal subjects in some embodiments. In the context of the various embodiments of the present invention, this typically involves a reduction in CCR9 expressing cells, CCR9 hi expressing cells, in the peripheral blood of the patient. The CCR9 expressing cells comprise, consist essentially of or consist of monocytes, in particular CD14+HLA-DRhi monocytes, in certain embodiments. This cell type can be characterized according to the techniques disclosed herein (for example using flow cytometry).

Monocytes are produced by the bone marrow from haematopoietic stem cell precursors called monoblasts. Monocytes may differentiate into macrophages or dendritic cells. Monocytes and their macrophage and dendritic cell progeny serve a number of functions in the immune system including phagocytosis, antigen presentation and cytokine production. Monocytes may be characterized with reference to expression of the cell surface marker CD14, optionally together with CD16. Classical monocytes may be characterized by high level expression of the CD14 cell surface receptor (CD14++CD16− monocyte). Non-classical monocytes may be characterized by low level expression of CD14 and with additional co-expression of the CD16 receptor (CD14+CD16++ monocyte). Intermediate monocytes may be characterized by high level expression of CD14 and low level expression of CD16 (CD14++CD16+ monocytes). Macrophages are derived from monocytes and are responsible for protecting tissues from foreign substances. They are cells that possess a large smooth nucleus, a large area of cytoplasm and internal vesicles for processing foreign material. The term "macrophage" may refer to a monocyte-derived cell expressing one or more of the following cell surface markers CD14, CD11b, Lysozyme M, MAC-1/MAC-3 and CD68. The term macrophage includes both activated and un-activated macrophages. Activated macrophages may be characterized by expression of CD69, ENG, FCER2 and IL2RA, HLA-DR, CD86. Un-activated macrophages have not yet received activating signals through for example TLR receptors and therefore they express less activation markers on the cell surface which correlates with lesser maturation. M1 macrophages may be characterized by expression of one or more of CD16+CD32+CD64+ and secrete mainly IL-23 and IL-1, TNF, IL-6 and high levels of IL-12 and in addition effector molecules such as iNOS and ROI. M1 macrophages have cytotoxic features as opposed to M2 macrophages. M2 macrophages may be characterized by expression of one or more of SRA/B+CD163+MR+CD14+ and express TGFβ, IL-10 and IL-1Ra. Tumour associated macrophages (TAMs) share many characteristics with the M2 macrophages and are considered as M2 polarised macrophages. The M1/M2 paradigm can also be found in monocyte subsets where CD14+CD16-CXC3R1low monocytes are considered the "inflammatory" subset and the CD14lowCD16+CXC3R1high are "resident" monocytes.

CCR9 and/or CCR7 expressed on these aforementioned cells binds to chemokines such as CCL25, CCL21 and CCL19. CCR9 is the gene symbol approved by the HUGO Gene Nomenclature Committee for chemokine (C—C motif) receptor 9. The HGNC ID for this gene is 1610. The gene is located at chromosome position 3p22. The previous symbol and name for the gene is GPR28. Synonyms for this gene include CDw199, GPR-9-6. The Genbank reference sequence for CCR9 is AJ132337.1 as available on 13 Jun. 2011, which is incorporated herein by reference in its entirety.

CCR7 is the gene symbol approved by the HUGO Gene Nomenclature Committee for chemokine (C—C motif) receptor 7. The HGNC ID for this gene is 1608. The gene is located at chromosome position 17q12-q21.2. The previous symbol and name for the gene is CMKBR7, EBI1. Synonyms for this gene include BLR2, CD197 and CDw197. The RefSeq reference sequence for CCR1 is NM_001838.3 as available on 13 Jun. 2011, which is incorporated herein by reference in its entirety.

CD14 is the gene symbol approved by the HUGO Gene Nomenclature Committee for CD14 molecule. The HGNC ID for this gene is 1628. The gene is located at chromosome position 5q22-q32. The previous symbol and name for the gene is "CD14 antigen". The RefSeq reference sequence for CD14 is NM_000591.3 as available on 13 Jun. 2011, which is incorporated herein by reference in its entirety.

The various embodiments of the methods of the invention may involve specific binding interactions with any of these further cell-surface markers in addition to the removal based upon binding to CD14, HLA-DR, CCR9 and/or CCR7. Suitable binding reagents can be prepared to specifically bind to these cell-surface markers. The discussion of CD14, HLA-DR, CCR9 and/or CCR7 specific binding reagents thus applies mutatis mutandis.

Treatment of IBD according to the various embodiments of the invention may result in alleviation or amelioration of symptoms, prevention of progression, regression of the condition, or complete recovery. Measurable parameters of successful treatment include one or more, up to all, of improved Mayo score or UCDAI (for UC) or improvement in CDAI index (CD). In specific embodiments, a single treatment is sufficient to cause a depletion of around 10%, 20%, 30%, 40%, 50%, 60% or 70%, or higher up to 80%, 90%, 95% or more, or any range of values between and including these amounts, of a specific receptor, including chemokine receptor, in particular CD14, HLA-DR, CCR9 and/or CCR7, expressing cells, in particular CD14+HLA-DRhi monocytes from the peripheral blood of the patient. In specific embodiments, at least around 50% depletion is achieved in a single treatment. Thus, successful treatment may be defined with reference to depletion of CD14, HLA-DR, CCR9 and/or CCR7 expressing cells, in particular CD14+HLA-DRhi monocytes. Treatment may lead to depletion of between approximately 100 and 500 million CD14, HLA-DR, CCR9 and/or CCR7 expressing cells, in particular CD14+HLA-DRhi monocytes, in certain embodiments and more particularly to about 100, 150, 200, 250, 300, 350, 400, 450, or 500 million CD14, HLA-DR, CCR9 and/or CCR7 expressing cells.

Treatment of IBS according to the various embodiments of the invention may result in alleviation or amelioration of symptoms, prevention of progression, regression of the condition, or complete recovery. In specific embodiments, a single treatment is sufficient to cause a depletion of around 10%, 20%, 30%, 40%, 50%, 60% or 70%, or higher up to 80%, 90%, 95% or more, or any range of values between and including these amounts, of a specific receptor, including chemokine receptor, in particular CCR9, expressing cells, in particular CCR9 expressing monocytes from the peripheral blood of the patient. In specific embodiments, at least around 50% depletion is achieved in a single treatment. Thus, successful treatment may be defined with reference to depletion of CCR9 expressing cells, in particular CCR9 expressing monocytes, such as CD14+HLA-DRhi monocytes. Treatment may lead to depletion of between approximately 100 and 500 million CCR9 expressing cells, in particular CCR9 expressing monocytes, such as CD14+HLA-DRhi monocytes, in certain embodiments and more particularly to about 100, 150, 200, 250, 300, 350, 400, 450, or 500 million CCR9 expressing cells.

By binding to the column through the binding reagent-receptor, including chemokine receptor, interaction, receptor, including chemokine receptor, expressing cells are immobilized. These immobilized cells express further unoccupied chemokine receptors, which may be of the same or different type to those used for capture. These additional chemokine receptors may permit circulating chemokines which contribute to the inflammatory condition to be captured from the peripheral blood. Thus, a reduction in circulating (specific) chemokine levels may provide a measure of successful treatment.

The duration of treatment may be readily determined by one skilled in the art and will depend upon factors such as the flow rate of the peripheral blood. Duration of treatment may be tied into monitoring of the treatment itself, with the treatment considered complete once a measurable parameter of treatment has reached a defined threshold. Any suitable parameter may be employed as discussed herein. Thus, for example, treatment may be considered complete when a reduction in CD14, HLA-DR, CCR9 and/or CCR7 expressing cells for IBD, or CCR9 expressing cells for IBS such as a 50% reduction in CD14, HLA-DR, CCR9 and/or CCR7 expressing cells for IBD or CCR9 expressing cells for IBS, in particular CD14+HLA-DRhi monocytes has been achieved. The apheresis system may be operated at a flow rate of around 10-80 mL/min, or more specifically between around 20-70 mL/min, or between around 30-60 mL/min. In specific embodiments, the treatment is performed for a period of around 10, 20, 30, 40, 50, 60, 70, 80, 90, 100, 110, 120 etc., or any range of values between and including these amounts, minutes. The treatment is typically not aimed to remove all of the cells expressing the receptor, including chemokine receptor, in the peripheral blood, as a basal level of those cells, in particular CD14+HLA-DRhi monocytes is required in healthy subjects. However, it has been found that only low blood volumes need to be applied to the columns of the various embodiments of the invention in order to achieve effective levels of depletion of the receptor, including chemokine receptor, -expressing cells. Thus, in certain embodiments, around 10-80% or more specifically around 20, 30, 40 or 50%, or any range of values between and including these amounts, of the patient's blood is applied to the column in a single treatment. The volume of blood circulated through the apheresis column or system may be in the region of around 1000-3000 ml, such as around 1000, 1200, 1400, 1600, 1800 or 2000 ml or any range of values between and including these amounts. The treatment may be considered complete once this volume of blood has been circulated. The patient may be administered anticoagulants prior to each treatment session. A suitable solution, such as a sterile saline solution, optionally including an anticoagulant such as Heparin, may be used for priming the apheresis (extracorporeal) system. An additional volume of anticoagulant may be added to the circuit at the start of each treatment session, for example as a bolus injection.

In certain embodiments the invention relies upon one or more binding reagents which is/are capable of specifically binding to a receptor, including chemokine receptor. This specific binding reaction permits cells expressing the receptor, including chemokine receptor, to be removed from the peripheral blood of the patient when the blood is passed over the solid support upon or within which the binding reagent is immobilized. Specific receptors, including chemokine receptors of interest, include CD14, HLA-DR, CCR9 and/or CCR7, particularly CD14, CCR9 and CCR7 and specifically CCR9 in the case of IBS. The binding reagent can be any binding reagent capable of specifically binding to the receptor in question. By "specific binding" is meant that the binding reagent displays sufficient specificity of binding and appropriate binding affinity/kinetics to permit removal of cells expressing one or more of CD14, HLA-DR, CCR9 and/or CCR7, and specifically CCR9 in the case of IBS in particular CD14+HLA-DRhi monocytes from the peripheral blood. Whilst it is not precluded that the binding reagent is capable of binding to other molecules, such as other receptor, including chemokine receptors, the binding reagent will preferentially bind to cells expressing one or more of CD14, HLA-DR, CCR9 and/or CCR7 and specifically CCR9 in the case of IBS and in particular to cells expressing increased levels of CD14, HLA-DR, CCR9 and/or CCR7 and specifically CCR9 in the case of IBS (as defined further herein), in particular CD14+HLA-DRhi monocytes.

It is specifically envisaged that combinations of binding reagents may be employed in order to deplete levels of CD14+HLA-DRhi monocytes or monocytes expressing CCR7 or CCR9 or both CCR7 and CCR9 from peripheral blood. In particular, binding reagents capable of specifically binding CD14 together with one or both of CCR7 and CCR9 may be employed. Similarly, binding reagents capable of specifically binding CCR7 and CCR9 respectively may be utilized in some embodiments.

The binding reagent capable of specifically binding to CD14, HLA-DR, CCR9 and/or CCR7 and specifically CCR9 in the case of IBS may be either an agonist or an antagonist of CD14, HLA-DR, CCR9 and/or CCR7, respectively. As the disease condition relies upon up-regulation of expression of or signaling via CD14, HLA-DR, CCR9 and/or CCR7, in certain embodiments the binding reagent capable of specifically binding to CD14, HLA-DR, CCR9 and/or CCR7 is an antagonist of CD14, HLA-DR, CCR9 and/or CCR7, respectively. In the case of IBS, the disease condition relies upon up-regulation of expression of or signaling via CCR9 and thus, in certain embodiments the binding reagent capable of specifically binding to CCR9 is an antagonist of CCR9. Chemokines are typically, although not necessarily exclusively (particularly in the case of truncated or modified forms) agonists of their cognate receptor and serve to activate the cells expressing the relevant receptor, as would be appreciated by one skilled in the art. Antibodies against the relevant chemokine receptor are generally considered to be antagonists, as would be appreciated by one skilled in the art. Specific examples of binding reagents include proteins or polypeptides, such as antibodies and receptor ligands, in particular chemokines. The binding reagent may be a nucleic acid molecule in certain embodiments. In some embodiments, the nucleic acid is an aptamer. Nucleic acid aptamers are polynucleotides of approximately 15-40 nucleotides long. Nucleic acid aptamers can be made using the SELEX process (systemic evolution of ligands by exponential enrichment) or any other process known to those of skill in the art.

In other embodiments, the binding reagent may be a peptide, and in certain instances, a peptide aptamer. Peptide aptamers are artificial recognition molecules that consist of a variable peptide sequence inserted into a constant scaffold protein (Baines I C, Colas P. Peptide aptamers as guides for small molecule drug discovery. Drug Discov Today. 2006; 11:334-341, incorporated herein by reference). A number of methodologies, such as phage display, ribosome display and yeast two-hybrid screening systems are available for screening a library of potential peptide-based binding agents. Similarly protein scaffolds based on domains such as fibronectins, ankyrin repeats, protein A, SH3 domains, lipocalins and ubiquitin can be used as the binding agent. Again a number of technologies such as phage display and ribosome display are available for screening a library of protein—based binding agents. Similarly, libraries of candidate chemical compounds can be screened for specific binding to the relevant receptor, including chemokine receptor, using suitable screening techniques known in the art, which may be high throughput screens in certain embodiments. The candidate binding agent may be immobilized on a solid support and the ability of the agent to specifically retain cells expressing the receptor, including chemokine receptor, of interest or labelled receptor, including chemokine receptor, is determined. A range of cell types may be applied to the solid supports to confirm specificity of binding, or alternatively a mixed sample (such as peripheral blood) may be applied to the solid support. Retention of the cell type of interest (expressing the appropriate receptor, including chemokine receptor,) can be confirmed to identify suitable binding agents.

CD14 binds to lipopolysaccharide (LPS) and other pathogen-associated molecules. This binding requires the additional presence of lipopolysaccharide binding protein (LBP). Thus, suitable binding reagents to specifically bind to CD14 expressing cells may be based upon CD14 as associated with LBP. For example, the combination may be utilised as an immunogen in order to raise suitable antibody based binding reagents, as discussed in further detail herein. However, in other embodiments, antibodies are produced which bind solely to CD14. These antibodies should preferably be able to effectively compete with LBP for binding to CD14 expressing cells. Suitable binding reagents may, in certain embodiments, be based upon LPS as a molecule to which CD14 is known to bind.

In the context of the various embodiments of the present invention the term "chemokine" also comprises biotinylated or otherwise labelled chemokines. The term "chemokine" also comprises modified and truncated versions of the chemokine and chemokine fragments with the proviso that the modified or truncated form retains its ability to bind to its cognate receptor (and thus remains functional in the context of the various embodiments of the invention). The chemokine does not necessarily need to retain biological activity as it is specific binding affinity for CCR9 and/or CCR7 that is required. In certain embodiments, the chemokine lacks biological activity, for example in terms of activation of the (CCR9 and/or CCR7) receptor. Modifications may be made to improve protein synthesis, for example uniformity of product and yield. Modifications may comprise amino acid additions, substitutions, deletions or other modifications to one or more amino acids in the chemokine. As known to those skilled in the art, exemplary modifications may comprise substitution of the wild type amino acid with non-natural amino acids such as norleucine (NLeu) and derivatized amino acids such as pyroglutamic acid (pyro-Glu). Such modifications may be made to minimize side-product formation during storage and use of the columns of the various embodiments of the invention. Modifications may be made to improve labelling, for example inclusion of a polyethylene glycol (PEG) spacer to facilitate biotinylation. The biotinylation and/or conjugation with fluorochromes or other labelling groups of the chemokine is performed in a manner which does not substantially affect the receptor binding capacity. Site specific biotinylation or other labelling is preferred as non-selective labelling of chemokines may compromise receptor binding activity. Biotinylation or other labelling is generally preferred at or towards the C-terminus of the protein as the inventors have found that modifications in this area are generally well tolerated (in terms of a minimal effect on receptor binding capability). Biotinylation may be carried out site-specifically at any suitable amino acid. Examples of suitable amino acids include lysine, diaminopropionic acid and ornithine. Generally, reference may be made to Natarajan S et al, Int. J. Pept. Protein Res., 1992, 40, 567-74; Baumeister B, Int. J. Peptide Res. And Therapeutics, 2005, 11, 139-141; Bioconjugate techniques 2nd edition, Greg T. Hermanson, incorporated by reference herein in its entirety.

Truncations may involve deletion of either N or C terminal amino acids as appropriate, or both. Typically, the truncated version will retain the residues required for the chemokine to fold correctly, for example to retain a chemokine fold structure, consistent with the requirement that a truncated version must retain the ability to bind to the relevant receptor (expressed by (on the surface of) a leukocyte). Chemokine molecules typically include disulphide bonds between the 1st and 3rd and 2nd and 4th cysteine residues respectively, as would be understood by one skilled in the art. Where sequences are presented herein, it is assumed that these disulphide bonds will form in the folded protein (unless otherwise stated). Truncated versions may comprise anywhere between 1 and 100 less amino acids, such as 1, 2, 3, 4, 5 etc amino acids, than the wild type amino acid sequence in certain embodiments. Of course, truncated versions may comprise further modification as detailed herein. The modified or truncated version may have 40%, 45%, 50%, 55%, 60%, 65%, 70%, 75%, 80%, 85%, 90%, 95% or more overall amino acid sequence identity with the full length wild type chemokine (where a deletion is counted as a difference in amino acid sequence) in certain embodiments. Over the common sequence between the molecules (i.e the amino acids that have not been deleted), there may be 80%, 85%, 90%, 91%, 92%, 93%, 94%, 95%, 96%, 97%, 98% or 99% amino acid sequence identity in certain embodiments. Sequence identity may be determined using known algorithms, such as BLAST or GAP analysis (GCG Program) (applying default settings), which are freely available. Chemokines may lack the N-terminal signal peptide which is cleaved off during synthesis in vivo.

Specific chemokines useful in the various embodiments of the present invention for binding to CCR9 and/or CCR7 include CCL25, CCL19 and CCL21. CCL25, CCL21 and CCL19 are able to bind to chemokine receptors implicated in inflammatory bowel disease, including Crohn's disease (CD) and ulcerative cholitis (UC). More specifically, CCL25, CCL21 and CCL19 are useful for removing CD14, HLA-DR, CCR9 and/or CCR7 expressing cells, in particular CD14+HLA-DRhi monocytes from the blood of a patient. CCL25, which specifically binds CCR9, is relevant for the treatment of IBS. The chemokines described in greater detail herein (with reference to the relevant figures and amino acid sequences, as set forth in the SEQ ID NOs) may each be applied according to the various embodiments of the present invention.

CCL25 is the gene symbol approved by the HUGO Gene Nomenclature Committee for chemokine (C—C motif) ligand 25. The HGNC ID for this gene is 10624. The gene is located at chromosome position 19p13.2. The previous symbol and name for the gene is SCYA25, "small inducible cytokine subfamily A (Cys-Cys), member 25". Synonyms for this gene include "Ck beta-15", Ckb15, TECK, "TECK-var", "thymus expressed chemokine". The Genbank reference sequence for CCL25 is U86358.1 as available on 13 Jun. 2011, which is incorporated herein by reference in its entirety.

CCL21 is the gene symbol approved by the HUGO Gene Nomenclature Committee for chemokine (C—C motif) ligand 21. The HGNC ID for this gene is 10620. The gene is located at chromosome position 9p13. The previous symbol and name for the gene is SCYA21, "small inducible cytokine subfamily A (Cys-Cys), member 21". Synonyms for this gene include 6Ckine, "beta chemokine exodus-2", CKb9, ECL, "Efficient Chemoattractant for Lymphocytes", exodus-2, "secondary lymphoid tissue chemokine", SLC, TCA4. The Genbank reference sequence for CCL21 is AB002409.1 as available on 13 Jun. 2011, which is incorporated herein by reference in its entirety.

CCL19 is the gene symbol approved by the HUGO Gene Nomenclature Committee for chemokine (C—C motif) ligand 19, also known as MIP-3b. The HGNC ID for this gene is 10617. The gene is located at chromosome position 9p13. The previous symbol and name for the gene is SCYA19, "small inducible cytokine subfamily A (Cys-Cys), member 19". Synonyms for this gene include "beta chemokine exodus-3", "CC chemokine ligand 19", "CK beta-11", CKb11, "EBI1-ligand chemokine", ELC, exodus-3, "macrophage inflammatory protein 3-beta", MIP-3b. The Genbank reference sequence for CCL19 is AB000887.1 as available on 13 Jun. 2011, which is incorporated herein by reference in its entirety.

An example of a chemokine of the various embodiments of the invention containing both modifications and a truncation and specifically adapted for use in the invention is described in detail herein. The truncated CCL25 corresponds to residues 1 to 74 of the full length mature protein (and thus lacks amino acids 75 to 127 and the N-terminal signal peptide of 23 amino acids) and thus retains the chemokine fold. In addition, a methionine to Norleucine substitution is incorporated, to prevent oxidation of the residue during chain assembly. The N terminal glutamine residue is substituted with pyroglutamine to permit uniformity of product during synthesis. Biotinylation is achieved via a PEG spacer at the r-functionality of the lysine residue found at position 72. The amino acid sequence of the linear molecule (i.e. without the PEG spacer and biotin molecule at amino acid 72 shown) comprises, consists essentially of or consists of the amino acid sequence presented as SEQ ID NO: 1. The final protein may thus comprise, consist essentially of or consist of the amino acid sequence of SEQ ID NO: 3.

A further example of a chemokine of the various embodiments of the invention containing modifications and specifically adapted for use in the invention is described in detail herein (see Examples below). The modified CCL19 (MIP-3β) corresponds to residues 1 to 77 of the full length mature protein (and lacks the N-terminal signal peptide of 21 amino acids, which is cleaved off) and thus retains the chemokine fold. An additional lysine is inserted at the C-terminus, at position 78. The chemokine may thus comprise, consist essentially of or consist of the amino acid sequence of SEQ ID NO: 4. FmocLys(ivDde)-OH is incorporated as residue 78 to facilitate site-specific labelling at this position of the protein (SEQ ID NO: 5). The e-amino side chain functionality of Lys(78) is modified through biotinylation. The final protein may thus comprise, consist essentially of or consist of the amino acid sequence of SEQ ID NO: 6.

Thus, in certain embodiments the invention also relates to a modified chemokine comprising, consisting essentially of or consisting of the amino acid sequence of SEQ ID NO: 4 or 6:

```
                                              SEQ ID NO: 4
GTNDAEDCCLSVTQKPIPGYIVRNFHYLLIKDGCRVPAVVFTTLRGRQLC

APPDQPWVERIIQRLQRTSAKMKRRSSX
```

X is an amino acid residue that can be biotinylated, such as lysine, ornithine or diaminopropionic acid and optionally is biotinylated, optionally via a spacer molecule such as PEG

```
                                              SEQ ID NO: 6
GTNDAEDCCLSVTQKPIPGYIVRNFHYLLIKDGCRVPAVVFTTLRGRQLC

APPDQPWVERIIQRLQRTSAKMKRRSSX
```

X is K(Biotin)

Chemokines useful in the various embodiments of the invention may be synthesised through any suitable means known in the art. Preferably, the chemokines are chemically synthesised as this facilitates modification and labelling etc. However, recombinant DNA based approaches may also be employed in combination with appropriate labelling and modification technologies as required. Thus, in certain embodiments the invention also provides a nucleic acid molecule encoding the chemokines of the various embodiments of the invention. In certain embodiments the invention also relates to a vector containing such a nucleic acid molecule and a host cell containing the vector. The vector may additionally comprise a suitable promoter operably linked to the nucleic acid molecule, to facilitate transcription of the corresponding mRNA molecule. The host cell may be capable of expressing the protein by transcription and translation of the nucleic acid molecule encoding a chemokine of the various embodiments of the invention.

The chemokines useful in the various embodiments of the invention can be biotinylated by methods known in the art such as described in WO 00/50088 A2, which is incorporated herein by reference in its entirety. As indicated above, site-specific labelling of the chemokines of the various embodiments of the invention is preferable, although any labelling technique which does not significantly affect the receptor-binding capacity of the chemokine may be employed. Various site-specifically biotinylated chemokines and native chemokines are available commercially, for instance from Almac, Craigavon, UK. In specific embodiments the one or more chemokines are biotinylated via a spacer group. The spacer may be employed to prevent the biotin group from impacting on the activity of the chemokine, in particular binding of the chemokine to its cognate receptor. Any suitable spacer that facilitates retention of receptor binding properties of the chemokine may be employed in the various embodiments of the invention. Thus, in the specific embodiments described above, spacers other than PEG spacers may be employed as appropriate. In specific embodiments, the spacer is a polyethylene glycol (PEG) spacer. PEG has been shown to be an effective spacer permitting attachment of biotin to the chemokine (which can then be immobilized on the solid support through interaction with streptavidin) without compromising receptor binding capability.

In the context of the various embodiments of the present invention the term "antibody" includes all immunoglobulins or immunoglobulin-like molecules with specific binding affinity for the relevant receptor, including chemokine receptor (including by way of example and without limitation, IgA, IgD, IgE, IgG and IgM, combinations thereof, and similar molecules produced during an immune response in any vertebrate, for example, in mammals such as humans, goats, rabbits and mice). Specific immunoglobulins useful in the various embodiments of the invention include IgG isotypes. The antibodies useful in the various embodiments of the invention may be monoclonal or polyclonal in origin, but are typically monoclonal antibodies. Antibodies may be human antibodies, non-human antibodies, or humanized versions of non-human antibodies or chimeric antibodies. Various techniques for antibody humanization are well established and any suitable technique may be employed. The term "antibody" also refers to a polypeptide ligand comprising at least a light chain or heavy chain immunoglobulin variable region which specifically recognizes and binds an epitope of an antigen, and it extends to all antibody derivatives and fragments that retain the ability to specifically bind to the relevant receptor, including chemokine receptor. These derivative and fragments may include Fab fragments, F(ab')2 fragments, Fv fragments, single chain antibodies, single domain antibodies, Fc fragments etc. The term antibody encompasses antibodies comprised of both heavy and light chains, but also heavy chain (only) antibodies. In specific embodiments, the antibodies may be engineered so as to be specific for more than one receptor, including chemokine receptor, for example bi-specific to permit binding to two different receptors, including chemokine receptors. Suitable commercially available antibodies which bind to the chemokine receptors of interest are listed in table 1. They may or may not be labelled. General reference may be made to "Antibodies a laboratory manual: By E Harlow and D Lane. pp 726. Cold Spring Harbor Laboratory. 1988", which reference is incorporated herein in its entirety.

TABLE 1

Commercially available fluorophore labelled antibodies against specific chemokine receptors

| Antibody | Fluorophore | Supplier |
| --- | --- | --- |
| CCR9 | APC | R&D Systems |
| CD14 | FITC | Beckman Coulter |
| CCR7 | PerCP Cy5.5 | Biolegend |
| HLA-DR | APC Cy7 | Biolegend |

The chemokine receptor expressing cells may thus be targeted using alternative binding agents, such as antibodies or other chemical compounds, as defined herein, rather than the natural chemokine binding partner. This approach is a new approach to treating inflammatory conditions, such as IBD, in particular UC or CD and IBS.

Thus, in certain embodiments the invention also provides an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine. The binding reagent capable of specifically binding to the chemokine receptor may be an agonist or an antagonist of the chemokine receptor. In specific embodiments, the binding reagent capable of specifically binding to the chemokine receptor is selected from an antibody and a chemical compound.

In other embodiments the invention thus also provides a method for treating an inflammatory condition, in particular IBD and IBS, comprising applying peripheral blood from a patient/subject to an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine) thus removing chemokine receptor expressing cells from the peripheral blood of the patient/subject. The method may comprise returning the blood depleted of the chemokine receptor expressing cells to the patient/subject.

Similarly, in other embodiments the invention provides a binding reagent capable of specifically binding to a chemokine receptor for use in the treatment of an inflammatory condition, in particular IBD and IBS, wherein the binding reagent is immobilized on a solid support contained within an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient/subject, wherein the binding reagent is not a chemokine), to which is applied peripheral blood from a patient thus removing chemokine receptor expressing cells from the peripheral blood of the patient.

These aspects of the various embodiments of the invention may be integrated into the more focussed therapeutic aspects of the various embodiments of the invention and thus, the remainder of the disclosure, including all specific embodiments applies mutatis mutandis.

Solid support materials for immobilizing the binding reagents of the various embodiments of the invention are known in the art. "Solid support" refers to, for example, materials having a rigid or semi-rigid surface or surfaces, and may take the form of beads, resins, gels, microspheres, or other geometric configurations. A useful support material is one that does not activate blood cells so as to make them coagulate or adhere to the support as peripheral whole blood is applied to the device. In certain embodiments, a support treated with an agent to provide it with anti-coagulation properties, in particular a heparinized support is employed. Alternatively, the blood of the patient may be treated with an anti-coagulant such as heparin prior to application to the support. Useful support materials comprise high molecular weight carbohydrates, in particular carbohydrates having a molecular weight of 100 kDa or more, such as agarose, in particulate form, optionally cross-linked, and cellulose. Other preferred support materials are polymers, such as carboxylated polystyrene, and glass. The support of the various embodiments of the invention may be provided in the form of particles or fibres. The support particles may have regular form, such as spheres or beads, or irregular form. They may be porous or non-porous. A preferred average particle size of the support is from 50 μm to 2 mm.

In certain embodiments Sepharose™, a cross linked, beaded-form of agarose, is used as column matrix. It is chosen for its optimal distribution capacity and can provide a large available area for affinity binding. Solid supports may be provided in the form of magnetic beads, with the specific binding reagent immobilized on the magnetic beads. Following capture of the (CD14, HLA-DR, CCR9 and/or CCR7) receptor, including chemokine receptor, expressing cells, in particular CD14+HLA-DRhi monocytes from the blood, the beads can be removed from the blood with the aid of an appropriate magnetic separator.

Methods for immobilizing binding reagents on a solid support are known in the art. A binding reagent, such as a chemokine, antibody, peptide, nucleic acid or chemical compound, can be immobilized on the support in a direct or indirect manner. Immobilization can be by means of a suitable linker in some embodiments. A preferred method of indirect immobilization of a binding reagent, such as a chemokine, relies upon the interaction between biotin and avidin molecules. "Avidin" or "avidin molecule" refers to any type of protein that specifically binds biotin to the substantial exclusion of other (small) molecules that might be present in a biological sample. Examples of avidin include avidins that are naturally present in egg white, oilseed protein (e.g., soybean meal), and grain (e.g., corn/maize), and streptavidin, which is a protein of bacterial origin. Thus, biotinylation of the binding reagent and use of an avidin molecule such as streptavidin immobilized on the solid support allows reliable attachment of the binding reagent to the solid support according to methods known in the art. Specifically, such a method may comprise providing the binding reagent in biotinylated form, providing a solid support having streptavidin immobilized on its surface, contacting the support with an aqueous solution of the biotinylated binding reagent, and rinsing the support with an aqueous solvent. In addition, binding pair interactions, such as antibody-antigen interactions, may also be utilised for indirect immobilisation of binding reagent onto a support. In such embodiments the support may be derivatised with one member of a binding pair, such as an antibody or fragment or derivative thereof, as defined herein, which has known affinity for a particular peptide sequence or small molecule hapten. Incorporating the other member of the binding pair, such as an antigen, peptide sequence or the hapten onto or into the binding reagent facilitates immobilisation onto a solid support coated with the corresponding antibody or fragment or derivative thereof. Thus, the binding reagent may be modified to include the peptide sequence or hapten into the linear molecule or may be added as a side chain or label. Any suitable antibody-antigen pair may be employed. The antibody fragment or derivative may be any fragment or derivative that retains specific binding affinity for the appropriate antigen. Examples include Fab, F(ab')2 fragments, scFV, VH domains, single domain antibodies (such as nanobodies), heavy chain antibodies and humanized version of non-human antibodies etc. Other high affinity interactions can be utilised for immobilisation of binding reagents, as long as the binding reagent can be synthesised or derivatised with one of the interacting partners and the solid support synthesised or derivatised with the other interacting partner without loss of binding activity (i.e. binding of the binding reagent to the appropriate receptor, including chemokine receptor). Immobilization may occur via essentially the same interaction in reverse in some embodiments. Thus, the binding reagent which may be a chemokine for example, may be attached to an antibody as defined herein, and the solid support derivatised with the antigen. The chemokine may be produced as a fusion protein with the antibody.

Alternatively binding reagents, such as chemokines and antibodies, can be immobilised directly onto a solid support using bioconjugation techniques established in the field. For example direct immobilisation of proteins onto cyanogen bromide activated solid supports via amino functionalities within the primary sequence of the protein. Alternatively, sulphydryl functionalities within proteins can be used to directly immobilise the protein to alkyl halide derivatised supports or supports containing free thiol functionalities. In further embodiments, proteins containing α-thioester functionalities can be directly immobilised on supports containing 1,2 amino thiol moieties (eg N-terminal cysteine) using the native chemical ligation reaction. Alternatively proteins modified with ketones and aldehydes can be immobilised on solid supports derivatised with hydrazinyl, hydrazide and aminoxy functionalities using hydrazone/oxime bond forming ligation reactions (and vice versa). Alternatively 'Click' chemistry can be used to immobilise proteins onto solid supports, whereby the protein and the support are derivatised with the appropriate mutually reactive chemical functionalities (azides and alkynes). In other embodiments Staudinger ligation chemistry can be used to immobilise appropriately derivatised proteins onto the appropriately derivatised solid supports.

The solid support is contained within or carried by the apheresis column. Thus, by "loaded" is meant that the column carries or contains the solid support in a manner such that (peripheral) blood can flow through the column in contact with the solid support. Thus, the solid support provides a matrix within the column through which blood flows, in continuous fashion in certain embodiments. This permits cells expressing the specific receptor, including chemokine receptor, to be removed from the blood passing through the column, such that blood exiting the column is depleted of the specific receptor, including chemokine receptor, -expressing cells. In specific embodiments, the apheresis column is loaded with a support comprising streptavidin immobilized on the support and one or more biotinylated binding reagents, such as chemokines, bound to the streptavidin on the support. The solid support may be comprised of a high-molecular weight carbohydrate, optionally cross-linked, such as agarose.

As discussed above, the binding reagent is coupled to the solid support. The relative amounts of binding reagent may be controlled to ensure that coupling between the solid support and the binding reagent will be immediate, minimising the risk of binding reagent decoupling from the solid support. Thus, it may be ensured that there is a relative excess of immobilization sites for the binding reagent on the solid support. Alternatively, or additionally, following immobilization of the binding reagent on the solid support, the solid support may be washed to remove any unbound binding reagent.

The apheresis column utilised in the various embodiments of the present invention acts as a leukapheresis treatment for inflammatory bowel disease, including Crohn's disease (CD) and ulcerative cholitis (UC). The column acts to specifically remove CD14, HLA-DR, CCR9 and/or CCR7-expressing monocytes, in particular CD14+HLA-DRhi monocytes by exploiting the interaction between CD14, HLA-DR, CCR9 and/or CCR7 expressed on the cell surface and a specific binding reagent immobilized on a solid support contained within or carried by the column. Similarly, the apheresis column utilised in the various embodiments of the present invention acts as a leukapheresis treatment for IBS. The column acts to specifically remove CCR9-expressing monocytes, in particular CD14+HLA-DRhi monocytes by exploiting the interaction between CCR9 expressed on the cell surface and a specific binding reagent immobilized on a solid support contained within or carried by the column.

The overall column typically comprises, consists of, or consists essentially of three combined components; 1) a housing which contains or carries 2) the solid support and 3) one or more binding reagents (immobilized thereon) which specifically bind one or more chemokine receptors. The housing may be manufactured from any suitable material for clinical use. In certain embodiments the housing is composed of a plastic material. The housing includes an in flow site for entry of blood and an out flow site for blood (depleted of target cells) to exit the column. The housing may be designed to maintain a continuous blood flow through the solid support matrix. The housing (as shown for example in FIG. 9)) may include a top portion which comprises a distribution plate (2) at the inflow site (1) to spread the blood evenly over the entire matrix area. The distribution plate may act as a first safety barrier preventing larger particles flowing through the column and into the patient. However, the distribution plate is not essential and may be removed in some embodiments to decrease the overall resistance in the system. The column may contain one or more safety filter units (3 and 4) placed at the inflow (1) and/or outflow (5) sites of the plastic housing. Such filter units may act to prevent particles larger than blood cells passing in and/or out of the column. The safety filter units may contain a plurality of filters, such as two, three or four filters designed to be a robust barrier and stop all particles larger than blood cells passing through the column. Inclusion of safety filters (3 and 4) at both ends of the column serves to minimize the risk of leakage of particles into the patient, including in the event that the device is incorrectly connected resulting in blood flow in the opposite direction to that intended. The safety filters may comprise of any suitable pore size to prevent particles larger than blood cells from passing through the column, as would be readily understood by one skilled in the art. Suitable filters are commercially available. In specific embodiments, the pore size of the filter(s) is between approximately 60 µm and 100 µm, more specifically approximately 80 µm. The solid support and binding reagent components are discussed in further detail herein.

The volume of the housing may be varied depending upon the blood volumes intended to pass through the column. Typically, the volume of the housing is between approximately 40 ml and 200 ml, more specifically 50 ml to 150 ml or 60 ml to 120 ml.

The column is generally applied in the form of an apheresis circuit. In this context, the overall system includes the apheresis column, tubing and an appropriate pump to pump the blood around the circuit. The system is illustrated in FIG. 10. The patient (1) is connected to the extracorporeal circuit via sterile needles to veins in the right and the left arms. A saline bag (3) is also connected and the saline solution is pumped with a suitable pump (2). Blood is drawn from one arm of the patient through the sterile tubing system by the blood pump (4) and passed through the column (6) and back to the patient. The tubing system may be connected to the column via any suitable coupling, such as standard dialysis luer-lock couplings. The couplings on the column may be colour-coded for correct assembly. For example, red tubing for inflow to the red column top and blue tubing for outflow back to the patient. An air detector (8) may be present in the circuit. Inlet pressure (5) and/or Pven sensors (7) may additionally be employed to monitor the pressure in the circuit.

An apheresis pump, such as the 4008 ADS pump manufactured by Fresenius Medical Care or the Adamonitor pump, may monitor the patient's inflow and outflow. The pump may also monitor the pressure in the extracorporeal circulation. The pump may be able to discriminate air by a bubble catcher and air detector. A clot catcher filter may be positioned inside the bubble catcher. The pump may also incorporate an optical detector to distinguish between light, e.g. saline solution or air present in the tubing system and dark e.g. blood present in the tubing system.

A schematic diagram of a suitable pump, showing the air detector and optical filter is shown in FIG. 11. If the pump system detects air bubbles and optical fluctuations or if extracorporeal pressure values are out of the set range, then the pump may stop immediately. Alternatively or additionally a visual/audible alarm may be emitted.

The treatment methods of the various embodiments of the invention may thus rely upon an extracorporeal circuit. The methods may be considered as ex vivo or in vitro methods and be defined solely with reference to steps performed outside of the patient. In some embodiments, however, the method further comprises, prior to application of the blood to the column, collecting peripheral blood from the patient. In a further embodiment, the method further comprises, following the application of the blood to the column, infusing the blood depleted of (CD14, HLA-DR, CCR9 and/or CCR7) receptor, including chemokine receptor, expressing cells to the patient. This is then a complete leukapheresis treatment method. Thus, a leukapheresis method, for treating inflammatory bowel disease, including Crohn's disease (CD) and ulcerative cholitis (UC), comprises collecting peripheral blood from the patient; applying the peripheral blood to an apheresis column loaded with a solid support comprising one or more binding reagents capable of specifically binding to one or more receptor, including chemokine receptors, in particular the receptor, including chemokine receptor, CD14, HLA-DR, CCR9 and/or CCR7, particularly CD14, CCR9 and/or CCR7 immobilized directly or indirectly on the support thus removing CD14, HLA-DR, CCR9 and/or CCR7 expressing cells from the peripheral blood of the patient; and infusing the depleted blood (of receptor, including chemokine receptor, expressing cells) to the patient. Similarly, a leukapheresis method, for treating IBS, comprises collecting peripheral blood from the patient; applying the peripheral blood to an apheresis column loaded with a solid support comprising one or more binding reagents capable of specifically binding to one or more receptors, including chemokine receptors, in particular the receptor, including chemokine receptor, CCR9 immobilized directly or indirectly on the support thus removing CCR9 expressing cells from the peripheral blood of the patient; and infusing the depleted blood (of receptor, including chemokine receptor, expressing cells) to the patient.

The peripheral blood may be continuously collected from the patient. Similarly, the depleted blood may be continuously infused to the patient, through use of an appropriate circuit as described herein. Thus, the support may be disposed in a column through which the blood is made to flow. This may be achieved using a suitable pump for example, as also described herein. Blood flow through the column enables the binding reagent(s) immobilized on the solid support to capture the cells expressing the receptor, including chemokine receptor, thus depleting them from the blood and preventing their contribution to the inflammatory bowel disease, including Crohn's disease (CD) and ulcerative cholitis (UC) or IBS.

The methods of the various embodiments of the invention and binding reagents for use in the methods of the various embodiments of the invention may require that the patient has been selected for treatment on the basis of detecting an increase in the level of receptor, including chemokine receptor, in particular, CD14, HLA-DR, CCR9 and/or CCR7 expressing cells, in particular CD14+HLA-DRhi monocytes in a sample obtained from the patient. Such companion diagnostic methods are described in greater detail herein and are based, for example, on the observation that CD14+HLA-DRhi monocytes are up-regulated in active IBD.

Thus, (in this context) in certain embodiments the invention also provides a method of diagnosing, monitoring progression of, or monitoring treatment of inflammatory bowel disease, including Crohn's disease (CD) and ulcerative cholitis (UC) comprising determining:
  a) the levels of CD14, HLA-DR, CCR9 and/or CCR7 expressing cells, particularly levels of CD14+HLA-DRhi monocytes or monocytes expressing CCR7 or CCR9 or both CCR7 and CCR9
  b) levels of expression of CD14, HLA-DR, CCR9 and/or CCR7; and/or
  c) levels of cells with high expression of CD14, HLA-DR, CCR9 and/or CCR7 in a sample obtained from a subject, wherein high levels of CD14+HLA-DRhi monocytes or monocytes expressing CCR7 or CCR9 or both CCR7 and CCR9, high levels of expression of CD14, HLA-DR, CCR9 and/or CCR7 or high levels of cells with high expression of CD14, HLA-DR, CCR9 and/or CCR7 or increased levels of CD14+HLA-DRhi monocytes or monocytes expressing CCR7 or CCR9 or both CCR7 and CCR9 compared to control, increased levels of expression of CD14, HLA-DR, CCR9 and/or CCR7 compared to a control or increased levels of cells with high expression of CD14, HLA-DR, CCR9 and/or CCR7 compared to a control indicate the presence or progression of inflammatory bowel disease, including Crohn's disease (CD) and ulcerative cholitis (UC). Levels of receptor, including chemokine receptor, expression, as opposed to cell numbers, may also be investigated as increased levels of receptor, including chemokine receptor, expression per cell may also be diagnostically relevant.

Similarly, the methods of the various embodiments of the invention and binding reagents for use in the methods of the various embodiments of the invention may require that the patient has been selected for treatment on the basis of detecting an increase in the level of receptor, including chemokine receptor, in particular, CCR9 expressing cells, in particular CCR9 expressing monocytes in a sample obtained from the patient. Such companion diagnostic methods are described in greater detail herein and are based, for example, on the observation that CCR9 expressing monocytes are up-regulated in IBS, suggesting IBS has an inflammatory component that may be diagnostically and therapeutically relevant.

Thus, (in this context) in certain embodiments the invention also provides a method of diagnosing, monitoring progression of, or monitoring treatment of IBS comprising determining:
  a) the levels of CCR9 expressing cells, particularly levels of CCR9 expressing monocytes
  b) levels of expression of CCR9; and/or
  c) levels of cells with high expression of CCR9 in a sample obtained from a subject, wherein high levels of CD14+HLA-DRhi monocytes or monocytes expressing, high levels of expression of CCR9 or high levels of cells with high expression of CCR9 or increased levels of CD14+ HLA-DRhi monocytes or monocytes expressing CCR9 compared to control, increased levels of expression of CCR9 compared to a control or increased levels of cells with high expression of CCR9 compared to a control indicate the presence or progression of IBS. Levels of receptor, including chemokine receptor, expression, as opposed to cell numbers, may also be investigated as increased levels of receptor, including chemokine receptor, expression per cell may also be diagnostically relevant.

"Diagnosing" is defined herein to include screening for a disease/condition or pre-indication of a disease/condition, identifying a disease/condition or pre-indication of a disease/condition and checking for recurrence of disease/condition following treatment. The methods of the various embodiments of the invention may also have prognostic value, and this is included within the definition of the term "diagnosis". The prognostic value of the methods of the various embodiments of the invention may be used as a marker of potential susceptibility to inflammatory bowel disease, including Crohn's disease (CD) and ulcerative cholitis (UC) by identifying levels of CD14, HLA-DR, CCR9 and/or CCR7 expression or levels of CD14+HLA-DRhi monocytes or monocytes expressing CCR7 or CCR9 or both CCR7 and CCR9 linked to inflammatory bowel disease, including Crohn's disease (CD) and ulcerative cholitis (UC). Similarly, the prognostic value of the methods of the various embodiments of the invention may be used as a marker of potential susceptibility to IBS by identifying levels of CCR9 expression or levels of CD14+HLA-DRhi monocytes or monocytes expressing CCR9 linked to IBS. Thus patients at risk may be identified before the disease has a chance to manifest itself in terms of symptoms identifiable in the patient. In certain embodiments, diagnosis may be made in conjunction with other objective indicators of inflammatory bowel disease, including Crohn's disease (CD) and ulcerative cholitis (UC) or IBS respectively. Thus, in specific embodiments, diagnosis is made in conjunction with the following indicators:

The diagnosis may be based on known clinical parameters for IBD. Histopathological assessment may be made in order to determine UC or CD. For staging of inflammation determination of pro inflammatory cells and expression of chemokine receptors may provide guidance to proper treatment such as tailored leukapheresis, according to the methods of the various embodiments of the invention.

"Monitoring progression of" includes performing the methods to monitor the stage and/or the state and progression of the inflammatory bowel disease, including Crohn's disease (CD) and ulcerative cholitis (UC) or IBS respectively. Monitoring progression may involve performing the diagnostic methods multiple times on the same patient to determine whether the levels of CD14, HLA-DR, CCR9 and/or CCR7 expressing cells, or CCR9 expressing cells in the case of IBS, or levels of CD14+HLA-DRhi monocytes or monocytes expressing CCR7 or CCR9 or both CCR7 and CCR9 or CCR9 in the case of IBS are increasing, decreasing or remaining stable over a certain time period. This may be in the context of a treatment regime.

"Monitoring the success of a particular treatment" is defined to include determining the levels of CD14, HLA-DR, CCR9 and/or CCR7 expressing cells or levels of CD14+HLA-DRhi monocytes or monocytes expressing CCR7 or CCR9 or both CCR7 and CCR9 before and after a treatment. The treatment is generally one aimed at treating inflammatory bowel disease, including Crohn's disease (CD) and ulcerative cholitis (UC) and may be a treatment according to one of the methods of the various embodiments of the invention as defined herein. Successful treatment may be determined with reference to a decrease in CD14, HLA-DR, CCR9 and/or CCR7 expressing cells or levels of CD14+HLA-DRhi monocytes or monocytes expressing CCR7 or CCR9 or both CCR7 and CCR9 as a result of, or following, the treatment. Thus, in such methods a level of CD14, HLA-DR, CCR9 and/or CCR7 expressing cells or levels of CD14+HLA-DRhi monocytes or monocytes expressing CCR7 or CCR9 or both CCR7 and CCR9 is determined prior to treatment. This level is recorded and a further assessment made at a predetermined time following the treatment. The comparison of levels of CD14, HLA-DR, CCR9 and/or CCR7 expressing cells or levels of CD14+HLA-DRhi monocytes or monocytes expressing CCR7 or CCR9 or both CCR7 and CCR9 permits the success of the treatment to be monitored. In specific embodiments, a single treatment is sufficient to cause a depletion of around 10%, 20%, 30%, 40%, 50%, 60% or 70%, or higher, up to 80%, 90%, 95% or more, or any range of values between and including these amounts, of one or more specific receptor, including chemokine receptors, in particular CD14, HLA-DR, CCR9 and/or CCR7, expressing cells or levels of CD14+HLA-DRhi monocytes or monocytes expressing CCR7 or CCR9 or both CCR7 and CCR9 from the peripheral blood of the patient. In specific embodiments, at least around 50% depletion is achieved in a single treatment. Thus, successful treatment may be defined with reference to depletion of CD14, HLA-DR, CCR9 and/or CCR7 expressing cells or levels of CD14+HLA-DRhi monocytes or monocytes expressing CCR7 or CCR9 or both CCR7 and CCR9. Treatment may lead to depletion of between approximately 100 and 500 million of one or more of CD14, HLA-DR, CCR9 and/or CCR7 expressing cells, such as CD14+HLA-DRhi monocytes or monocytes expressing CCR7 or CCR9 or both CCR7 and CCR9, in certain embodiments. Additional factors may be included to determine successful treatment. For example, a lack of increase in CD14, HLA-DR, CCR9 and/or CCR7 expressing cells or levels of CD14+HLA-DRhi monocytes or monocytes expressing CCR7 or CCR9 or both CCR7 and CCR9 following treatment may indicate successful treatment in terms of preventing further progression of the condition, optionally combined with an improvement in other markers or staging of the inflammatory bowel disease, including Crohn's disease (CD) and ulcerative cholitis (UC).

In the case of IBS, "Monitoring the success of a particular treatment" is defined to include determining the levels of CCR9 expressing cells or levels of CD14+HLA-DRhi monocytes or monocytes expressing CCR9 before and after a treatment. The treatment is generally one aimed at treating IBS and may be a treatment according to one of the methods of the various embodiments of the invention as defined herein. Successful treatment may be determined with reference to a decrease in CCR9 expressing cells or levels of CD14+HLA-DRhi monocytes or monocytes expressing CCR9 as a result of, or following, the treatment. Thus, in such methods a level of CCR9 expressing cells or levels of CD14+HLA-DRhi monocytes or monocytes expressing CCR9 is determined prior to treatment. This level is recorded and a further assessment made at a predetermined time following the treatment. The comparison of levels of CCR9 expressing cells or levels of CD14+HLA-DRhi monocytes or monocytes expressing CCR9 permits the success of the treatment to be monitored. In specific embodiments, a single treatment is sufficient to cause a depletion of around 10%, 20%, 30%, 40%, 50%, 60% or 70%, or higher, up to 80%, 90%, 95% or more, or any range of values between and including these amounts, of one or more specific receptor, including chemokine receptors, in particular CCR9 expressing cells or levels of CD14+HLA-DRhi monocytes or monocytes expressing CCR9 from the peripheral blood of the patient. In specific embodiments, at least around 50% depletion is achieved in a single treatment. Thus, successful treatment may be defined with reference to depletion of CCR9 expressing cells or levels of CD14+HLA-DRhi monocytes or monocytes expressing CCR9. Treatment may lead to depletion of between approximately 100 and 500 million of one or more of CCR9 expressing cells, such as CD14+HLA-DRhi monocytes or monocytes expressing CCR9, in certain embodiments. Additional factors may be included to determine successful treatment. For example, a lack of increase in CCR9 expressing cells or levels of CD14+HLA-DRhi monocytes or monocytes expressing CCR9 following treatment may indicate successful treatment in terms of preventing further progression of the condition, optionally combined with an improvement in other markers or staging of the IBS.

By binding to the column through the binding reagent-receptor, including chemokine receptor, interaction, receptor, including chemokine receptor, expressing cells are immobilized. These immobilized cells express further unoccupied receptors, including chemokine receptors, which may be of the same or different type to those used for capture. These additional receptors, including chemokine receptors may permit circulating chemokines which contribute to the inflammatory condition to be captured from the peripheral blood. Thus, a reduction in circulating (specific) chemokine levels may provide a measure of successful treatment.

The sample in which CD14, HLA-DR, CCR9 and/or CCR7 expressing cell levels, levels of CD14+HLA-DRhi monocytes or monocytes expressing CCR7 or CCR9 or both CCR7 and CCR9, levels of expression of CD14, HLA-DR, CCR9 and/or CCR7 and/or levels of cells with high expression of CD14, HLA-DR, CCR9 and/or CCR7 (defined as CD14 hi, HLA-DR hi, CCR9 hi and/or CCR7hi) are determined may comprise any suitable tissue sample or body fluid sample. Generally, the test sample is obtained from a human subject. Typically, the sample is a blood sample, in particular a peripheral blood sample. The sample may comprise a mucosal biopsy in certain embodiments. The methods may involve determining levels of CD14, HLA-DR, CCR9 and/or CCR7 expressing monocytes, in particular levels of CD14+HLA-DRhi monocytes or monocytes expressing CCR7 or CCR9 or both CCR7 and CCR9 in certain embodiments.

Similarly, in the case of IBS, the sample in which CCR9 expressing cell levels, levels of CD14+HLA-DRhi monocytes or monocytes expressing CCR9, levels of expression of CCR9 and/or levels of cells with high expression of CCR9 (defined as CCR9 hi) are determined may comprise any suitable tissue sample or body fluid sample. Generally, the test sample is obtained from a human subject. Typically, the sample is a blood sample, in particular a peripheral blood sample. The sample may comprise a mucosal biopsy in certain embodiments. The methods may involve determining levels of CCR9 expressing monocytes, in particular levels of CD14+HLA-DRhi monocytes or monocytes expressing CCR9 in certain embodiments.

Levels of CD14, HLA-DR, CCR9 and/or CCR7 expressing cells, levels of CD14+HLA-DRhi monocytes or monocytes expressing CCR7 or CCR9 or both CCR7 and CCR9, levels of expression of CD14, HLA-DR, CCR9 and/or CCR7 and/or levels of cells with high expression of CD14, HLA-DR, CCR9 and/or CCR7 (defined as CD14 hi, HLA-DR hi, CCR9 hi and/or CCR7hi) may be determined according to any suitable method. For example, flow cytometry may be employed in order to determine the number of cells expressing CD14, HLA-DR, CCR9 and/or CCR7 in the sample, to determine levels of CD14+HLA-DRhi monocytes or monocytes expressing CCR7 or CCR9 or both CCR7 and CCR9, to determine levels of CD14, HLA-DR, CCR9 and/or CCR7 expression and/or to identify levels of CD14hi, HLA-DRhi, CCR9hi and/or CCR7hi cells. Flow cytometric techniques are described herein and examples of commercially available antibodies suitably labelled for use in flow cytometry are set out in Table 1 for example. Alternatively, the method may involve steps of collecting and fixing the cells in the sample, followed by incubation with a suitable binding reagent that binds specifically to the CD14, HLA-DR, CCR9 and/or CCR7 receptor expressing cells in the sample. Any suitable binding reagent, as defined herein, may be employed. For example, a CD14, HLA-DR, CCR9 and/or CCR7 specific antibody may be employed. A wash step may be adopted following an incubation period to remove any unbound reagent. Suitable wash steps and incubation conditions would be well known to one skilled in the art. The binding reagent may be directly labeled in order to permit antibody binding to be directly determined. Alternatively a secondary binding reagent, such as an antibody, may be employed which binds to the first binding reagent and carries a label. Again, suitable incubation conditions and wash steps would be apparent to one skilled in the art. The primary and secondary binding reagents may form two halves of a binding pair. The binding interaction should not prevent the primary binding reagent binding to the CD14, HLA-DR, CCR9 and/or CCR7 receptor expressing cells, unless a competition assay is being employed. The two halves of a binding pair may comprise an antigen-antibody, antibody-antibody, receptor-ligand, biotin-streptavidin pair etc. in certain embodiments. Other techniques used to quantify chemokine (CD14, HLA-DR, CCR9 and/or CCR7) receptor expressing cell levels, to quantify levels of CD14, HLA-DR, CCR9 and/or CCR7 expression, to quantify levels of CD14+HLA-DRhi monocytes or monocytes expressing CCR7 or CCR9 or both CCR7 and CCR9 and/or to quantify levels of CD14 hi, HLA-DR hi, CCR9 hi and/or CCR7hi cells include PCR-based techniques such as QT-PCR and protein based methods such as western blot. Quantitation may be achieved with reference to fixed cell lines carrying known numbers of various receptor expressing cells and/or known levels of receptor expression per cell. Such fixed cell lines are available commercially (for example ChemiScreen™ cell lines from Millipore). Methods analogous to the treatment methods of the various embodiments of the invention may also be employed, with binding of CCR expressing cells to the solid support being determined following peripheral blood being passed through the column.

Similarly, in the case of IBS, levels of CCR9 expressing cells, levels of CD14+HLA-DRhi monocytes or monocytes expressing CCR9, levels of expression of CCR9 and/or levels of cells with high expression of CCR9 (defined as CCR9 hi) may be determined according to any suitable method. For example, flow cytometry may be employed in order to determine the number of cells expressing CCR9 in the sample, to determine levels of CD14+HLA-DRhi monocytes or monocytes expressing CCR9, to determine levels of CCR9 expression and/or to identify levels of CCR9hi cells. Flow cytometric techniques are described herein and examples of commercially available antibodies suitably labelled for use in flow cytometry are set out in Table 1 for example. Alternatively, the method may involve steps of collecting and fixing the cells in the sample, followed by incubation with a suitable binding reagent that binds specifically to the CCR9 receptor expressing cells in the sample. Any suitable binding reagent, as defined herein, may be employed. For example, a CCR9 specific antibody may be employed. A wash step may be adopted following an incubation period to remove any unbound reagent. Suitable wash steps and incubation conditions would be well known to one skilled in the art. The binding reagent may be directly labeled in order to permit antibody binding to be directly determined. Alternatively a secondary binding reagent, such as an antibody, may be employed which binds to the first binding reagent and carries a label. Again, suitable incubation conditions and wash steps would be apparent to one skilled in the art. The primary and secondary binding reagents may form two halves of a binding pair. The binding interaction should not prevent the primary binding reagent binding to the CCR9 receptor expressing cells, unless a competition assay is being employed. The two halves of a binding pair may comprise an antigen-antibody, antibody-antibody, receptor-ligand, biotin-streptavidin pair etc. in certain embodiments. Other techniques used to quantify chemokine receptor expressing cell levels, to quantify levels of CCR9 expression, to quantify levels of CD14+HLA-DRhi monocytes or monocytes expressing CCR9 and/or to quantify levels of CCR9 hi cells include PCR-based techniques such as QT-PCR and protein based methods such as western blot. Quantitation may be achieved with reference to fixed cell lines carrying known numbers of various receptor expressing cells and/or known levels of receptor expression per cell. Such fixed cell lines are available commercially (for example ChemiScreen™ cell lines from Millipore). Methods analogous to the treatment methods of the various embodiments of the invention may also be employed, with binding of CCR expressing cells to the solid support being determined following peripheral blood being passed through the column.

The levels of CD14, HLA-DR, CCR9 and/or CCR7 expressing cells, levels of CD14+HLA-DRhi monocytes or monocytes expressing CCR7 or CCR9 or both CCR7 and CCR9, levels of expression of CD14, HLA-DR, CCR9 and/or CCR7 and/or levels of cells with high expression of CD14, HLA-DR, CCR9 and/or CCR7 (defined as CD14 hi, HLA-DR hi, CCR9 hi and/or CCR7hi) may be determined relative to a suitable control. When diagnosing inflammatory bowel disease, including Crohn's disease (CD) and ulcerative cholitis (UC), a threshold level of cells, levels of CD14+HLA-DRhi monocytes or monocytes expressing CCR7 or CCR9 or both CCR7 and CCR9, level of expression of CD14, HLA-DR, CCR9 and/or CCR7 and/or level of cells with high expression of CD14, HLA-DR, CCR9 and/or CCR7 (defined as CD14 hi, HLA-DR hi, CCR9 hi and/or CCR7hi) may be set at or over which a positive diagnosis is made. This threshold may be determined based upon measuring levels of CD14, HLA-DR, CCR9 and/or CCR7 expressing cells, levels of CD14+HLA-DRhi monocytes or monocytes expressing CCR7 or CCR9 or both CCR7 and CCR9, levels of expression of CD14, HLA-DR, CCR9 and/or CCR7 and/or levels of cells with high expression of CD14, HLA-DR, CCR9 and/or CCR7 (defined as CD14 hi, HLA-DR hi, CCR9 hi and/or CCR7hi) in samples obtained from diseased patients and comparing these levels with levels of CD14, HLA-DR, CCR9 and/or CCR7 expressing cells, levels of CD14+HLA-DRhi monocytes or monocytes expressing CCR7 or CCR9 or both CCR7 and CCR9, levels of expression of CD14, HLA-DR, CCR9 and/or CCR7 and/or levels of cells with high expression of CD14, HLA-DR, CCR9 and/or CCR7 (defined as CD14 hi, HLA-DR hi, CCR9 hi and/or CCR7hi) in samples obtained from healthy subjects. Suitable software is freely available (such as the R project for statistical computing) to perform the necessary statistical analysis of the data obtained to calculate a useful threshold. The threshold may be set to maximize sensitivity and/or specificity of the test. Performance of the test in these respects may be measured by plotting a receiver operating characteristics (ROC) curve (sensitivity versus specificity). The area under the curve provides an indication of the overall performance of the test. Thus, once thresholds have been set for diagnosing the condition, a separate control experiment does not necessarily have to be run each time a sample is tested. Rather reference can simply be made to the pre-existing thresholds to determine the diagnosis. However, in certain embodiments, the sample is tested together with a control sample taken from a healthy subject to provide a comparator based upon essentially identical experimental conditions. The test sample is generally tested in parallel with the control sample. The test sample level of CD14, HLA-DR, CCR9 and/or CCR7 expressing cells, levels of CD14+HLA-DRhi monocytes or monocytes expressing CCR7 or CCR9 or both CCR7 and CCR9, levels of expression of CD14, HLA-DR, CCR9 and/or CCR7 and/or levels of cells with high expression of CD14, HLA-DR, CCR9 and/or CCR7 (defined as CD14 hi, HLA-DR hi, CCR9 hi and/or CCR7hi) can then be compared with that of the control sample to make the diagnosis. A control sample from a disease patient may also be tested in certain embodiments. Reference to controls permits relative levels ("high", "low" etc.) of CD14, HLA-DR, CCR9 and/or CCR7 expressing cells in the test sample to be readily identified and the significance thereof interpreted. Reference to controls also permits relative levels of CD14, HLA-DR, CCR9 and/or CCR7 expression ("high", "low" etc.) within the cell population to be determined and the significance thereof interpreted. Such determination may, for example, indicate the average levels of CD14, HLA-DR, CCR9 and/or CCR7 expression per cell in the test sample.

Thus, in specific embodiments, high or higher levels of CD14, HLA-DR, CCR9 and/or CCR7 expressing cells, high or higher levels of CD14+HLA-DRhi monocytes or monocytes expressing CCR7 or CCR9 or both CCR7 and CCR9 or high or higher levels of CD14, HLA-DR, CCR9 and/or CCR7 expression, for example average CD14, HLA-DR, CCR9 and/or CCR7 expression per cell, or high or higher levels of CD14 hi, HLA-DR hi, CCR9 hi and/or CCR7hi cells correlate with active disease or more active disease. Similarly, lower or low levels of CD14, HLA-DR, CCR9 and/or CCR7 expressing cells, low or lower levels of CD14+HLA-DRhi monocytes or monocytes expressing CCR7 or CCR9 or both CCR7 and CCR9 or low or lower levels of CD14, HLA-DR, CCR9 and/or CCR7 expression, for example average CD14, HLA-DR, CCR9 and/or CCR7 expression per cell, or low or lower levels of CD14 hi, HLA-DR hi, CCR9 hi and/or CCR7hi cells may correlate with a lack of active inflammation or disease. This may be defined as "less active disease". It can readily be envisaged that control samples may be assessed and levels of CD14, HLA-DR, CCR9 and/or CCR7 expressing cells, levels of CD14+HLA-DRhi monocytes or monocytes expressing CCR7 or CCR9 or both CCR7 and CCR9, levels of expression of CD14, HLA-DR, CCR9 and/or CCR7 and/or levels of cells with high expression of CD14, HLA-DR, CCR9 and/or CCR7 (defined as CD14 hi, HLA-DR hi, CCR9 hi and/or CCR7hi) determined across the range of severities of inflammatory bowel disease, including Crohn's disease (CD) and ulcerative cholitis (UC). This may assist in correlating the levels of CD14, HLA-DR, CCR9 and/or CCR7 expressing cells, levels of CD14+HLA-DRhi monocytes or monocytes expressing CCR7 or CCR9 or both CCR7 and CCR9, levels of expression of CD14, HLA-DR, CCR9 and/or CCR7 and/or levels of cells with high expression of CD14, HLA-DR, CCR9 and/or CCR7 (defined as CD14 hi, HLA-DR hi, CCR9 hi and/or CCR7hi) in the test sample with the relative severity of the condition.

When monitoring progression of, or monitoring treatment of inflammatory bowel disease, including Crohn's disease (CD) and ulcerative cholitis (UC), the control samples may be taken from the subject at an earlier time point. They may, however, be based upon known reference values as discussed above. Thus, relative levels of CD14, HLA-DR, CCR9 and/or CCR7 expressing cells, relative levels of CD14+HLA-DRhi monocytes or monocytes expressing CCR7 or CCR9 or both CCR7 and CCR9, relative levels of CD14, HLA-DR, CCR9 and/or CCR7 expression including relative levels of average CD14, HLA-DR, CCR9 and/or CCR7 expression per cell or relative levels of CD14 hi, HLA-DR hi, CCR9 hi and/or CCR7hi cells may be with reference to samples taken from the same subject at a different point in time. In certain embodiments, decreased levels of CD14, HLA-DR, CCR9 and/or CCR7 expressing cells, decreased levels of CD14+HLA-DRhi monocytes or monocytes expressing CCR7 or CCR9 or both CCR7 and CCR9, decreased relative levels of CD14, HLA-DR, CCR9 and/or CCR7 expression including decreased relative levels of average CD14, HLA-DR, CCR9 and/or CCR7 expression per cell, or decreased relative levels of CD14 hi, HLA-DR hi, CCR9 hi and/or CCR7hi cells correlate with successful treatment. The treatment may be any suitable treatment, but in specific embodiments is a treatment according to the various embodiments of the invention.

When monitoring progression of inflammatory bowel disease, including Crohn's disease (CD) and ulcerative cholitis (UC), increased levels of CD14, HLA-DR, CCR9 and/or CCR7 expressing cells, increased levels of CD14+HLA-DRhi monocytes or monocytes expressing CCR7 or CCR9 or both CCR7 and CCR9, increased relative levels of CD14, HLA-DR, CCR9 and/or CCR7 expression including increased relative levels of average CD14, HLA-DR, CCR9 and/or CCR7 expression per cell or increased relative levels of CD14 hi, HLA-DR hi, CCR9 hi and/or CCR7hi cells may indicate the progression of condition or disease. Thus, if levels of CD14, HLA-DR, CCR9 and/or CCR7 expressing cells, levels of CD14+HLA-DRhi monocytes or monocytes expressing CCR7 or CCR9 or both CCR7 and CCR9, levels of expression of CD14, HLA-DR, CCR9 and/or CCR7 and/or levels of cells with high expression of CD14, HLA-DR, CCR9 and/or CCR7 (defined as CD14 hi, HLA-DR hi, CCR9 hi and/or CCR7hi) are increased in a sample taken later than a sample from the same patient this may indicate progression of the condition.

Similarly in the case of IBS, the levels of CCR9 expressing cells, levels of CD14+HLA-DRhi monocytes or monocytes expressing CCR9, levels of expression of CCR9 and/or levels of cells with high expression of CCR9 (defined as CCR9 hi) may be determined relative to a suitable control. When diagnosing IBS, a threshold level of cells, levels of CD14+HLA-DRhi monocytes or monocytes expressing CCR9, level of expression of CCR9 and/or level of cells with high expression of CCR9 (defined as CCR9 hi)

may be set at or over which a positive diagnosis is made. This threshold may be determined based upon measuring levels of CCR9 expressing cells, levels of CD14+HLA-DRhi monocytes or monocytes expressing CCR9, levels of expression of CCR9 and/or levels of cells with high expression of CCR9 (defined as CCR9 hi) in samples obtained from diseased patients and comparing these levels with levels of CCR9 expressing cells, levels of CD14+HLA-DRhi monocytes or monocytes expressing CCR9, levels of expression of CCR9 and/or levels of cells with high expression of CCR9 (defined as CCR9 hi) in samples obtained from healthy subjects. Suitable software is freely available (such as the R project for statistical computing) to perform the necessary statistical analysis of the data obtained to calculate a useful threshold. The threshold may be set to maximize sensitivity and/or specificity of the test. Performance of the test in these respects may be measured by plotting a receiver operating characteristics (ROC) curve (sensitivity versus specificity). The area under the curve provides an indication of the overall performance of the test. Thus, once thresholds have been set for diagnosing the condition, a separate control experiment does not necessarily have to be run each time a sample is tested. Rather reference can simply be made to the pre-existing thresholds to determine the diagnosis. However, in certain embodiments, the sample is tested together with a control sample taken from a healthy subject to provide a comparator based upon essentially identical experimental conditions. The test sample is generally tested in parallel with the control sample. The test sample level of CCR9 expressing cells, levels of CD14+HLA-DRhi monocytes or monocytes expressing CCR9, levels of expression of CCR9 and/or levels of cells with high expression of CCR9 (defined as CCR9 hi) can then be compared with that of the control sample to make the diagnosis. A control sample from a disease patient may also be tested in certain embodiments. Reference to controls permits relative levels ("high", "low" etc.) of CCR9 expressing cells in the test sample to be readily identified and the significance thereof interpreted. Reference to controls also permits relative levels of CCR9 expression ("high", "low" etc.) within the cell population to be determined and the significance thereof interpreted. Such determination may, for example, indicate the average levels of CCR9 expression per cell in the test sample.

Thus, in specific embodiments, high or higher levels of CCR9 expressing cells, high or higher levels of CD14+HLA-DRhi monocytes or monocytes expressing CCR9 or high or higher levels of CCR9 expression, for example average CCR9 expression per cell, or high or higher levels of CCR9 hi cells correlate with active disease or more active disease. Similarly, lower or low levels of CCR9 expressing cells, low or lower levels of CD14+HLA-DRhi monocytes or monocytes expressing CCR9 or low or lower levels of CCR9 expression, for example average CCR9 expression per cell, or low or lower levels of CCR9 hi cells may correlate with a lack of active inflammation or disease. This may be defined as "less active disease". It can readily be envisaged that control samples may be assessed and levels of CCR9 expressing cells, levels of CD14+HLA-DRhi monocytes or monocytes expressing CCR9, levels of expression of CCR9 and/or levels of cells with high expression of CCR9 (defined as CCR9 hi) determined across the range of severities of IBS. This may assist in correlating the levels of CCR9 expressing cells, levels of CD14+HLA-DRhi monocytes or monocytes expressing CCR9, levels of expression of CCR9 and/or levels of cells with high expression of CCR9 (defined as CCR9 hi) in the test sample with the relative severity of the condition.

When monitoring progression of, or monitoring treatment of IBS the control samples may be taken from the subject at an earlier time point. They may, however, be based upon known reference values as discussed above. Thus, relative levels of CCR9 expressing cells, relative levels of CD14+HLA-DRhi monocytes or monocytes expressing CCR9, relative levels of CCR9 expression including relative levels of average CCR9 expression per cell or relative levels of CCR9 hi cells may be with reference to samples taken from the same subject at a different point in time. In certain embodiments, decreased levels of CCR9 expressing cells, decreased levels of CD14+HLA-DRhi monocytes or monocytes expressing CCR9, decreased relative levels of CCR9 expression including decreased relative levels of average CCR9 expression per cell, or decreased relative levels of CCR9 hi cells correlate with successful treatment. The treatment may be any suitable treatment, but in specific embodiments is a treatment according to the various embodiments of the invention.

When monitoring progression of IBS, increased levels of CCR9 expressing cells, increased levels of CD14+HLA-DRhi monocytes or monocytes expressing CCR9, increased relative levels of CCR9 expression including increased relative levels of average CCR9 expression per cell or increased relative levels of CCR9 hi cells may indicate the progression of condition or disease. Thus, if levels of CCR9 expressing cells, levels of CD14+HLA-DRhi monocytes or monocytes expressing CCR9, levels of expression of CCR9 and/or levels of cells with high expression of CCR9 (defined as CCR9 hi) are increased in a sample taken later than a sample from the same patient this may indicate progression of the condition.

In certain embodiments, IBD or IBS is diagnosed on the basis of levels of the relevant chemokine (or other, i.e. CD14 or HLA-DR in the case of IBD) receptor expressing cells, such as CD14, HLA-DR, CCR9 and/or CCR7 expressing cells. A positive diagnosis may be made in subjects based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, IBD or IBS is diagnosed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, such as CD14, HLA-DR, CCR9 and/or CCR7 expressing cells, relative to healthy controls.

In specific embodiments, IBS is diagnosed on the basis of levels of CCR9 expressing cells. A positive diagnosis may be made based upon the presence of greater than about 8%, greater than about 9%, greater than about 10%, greater than about 12%, greater than about 15% or more CCR9 expressing cells in the sample, as a percentage of total cells in the sample.

In certain embodiments, progression of IBD or IBS, which may be in the context of a treatment regime, is monitored on the basis of levels of chemokine (or other) receptor expressing cells at different time points, such as CD14, HLA-DR, CCR9 and/or CCR7 expressing cells. Progression of IBD or IBS may be indicated in subjects based upon an increase of greater than about 10%, such as an increase of greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more chemokine receptor expressing cells in the sample, as a percentage of total cells in the sample, compared to a sample taken from the same subject at an earlier time point. In other embodiments, progression of IBD or IBS is confirmed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, such as CD14, HLA-DR, CCR9 and/or CCR7 expressing cells, relative to a sample taken from the same subject at an earlier time point.

In specific embodiments, IBS is monitored on the basis of levels of CCR9 expressing cells. Progression of the disease, which may be in the context of a treatment regime, may be indicated based upon the presence of greater than about 10%, or greater than about 15% or more CCR9 expressing cells in the sample, as a percentage of total cells in the sample or by an increase of greater than about 10%, such as greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more CCR9 expressing cells in the sample, as a percentage of total cells in the sample, compared to a sample taken from the same subject at an earlier time point.

Regression or successful treatment may be monitored based upon similar decreases over various time points. For example, regression or successful treatment may be indicated in subjects based upon a decrease of about 10%, such as a decrease of about 15%, about 20%, about 25%, about 30%, about 35%, about 40%, about 45%, about 50%, about 55%, about 60%, about 65%, about 70%, about 75% or more chemokine receptor expressing cells in the sample, such as CD14, HLA-DR, CCR9 and/or CCR7 expressing cells, as a percentage of total cells in the sample, compared to a sample taken from the same subject at an earlier time point. In other embodiments, regression of IBD or IBS is confirmed on the basis of the presence of a about a 1.2 fold or greater decrease, such as about a 1.5, 2, 2.5, 3, 3.5, 4, 4.5, 5, 10, 20, 50 or 100 or greater fold decrease in chemokine receptor expressing cells, such as CD14, HLA-DR, CCR9 and/or CCR7 expressing cells, relative to a sample taken from the same subject at an earlier time point.

In specific embodiments, IBS is monitored on the basis of levels of CCR9 expressing cells. Regression or successful treatment of the disease may be indicated based upon a decrease of about 50%, such as such as a decrease of about 55%, about 60%, about 65%, about 70%, about 75%, about 80%, about 85%, about 90%, about 95% or more CCR9 expressing cells in the sample, as a percentage of total cells in the sample or by a decrease of about 10%, such as a decrease of about 15%, about 20%, about 25%, about 30%, about 35%, about 40%, about 45%, about 50%, about 55%, about 60%, about 65%, about 70%, about 75% or more chemokine receptor expressing cells in the sample, as a percentage of total cells in the sample, compared to a sample taken from the same subject at an earlier time point.

Since the levels of CD14, HLA-DR, CCR9 and/or CCR7 expressing cells, levels of CD14+HLA-DRhi monocytes or monocytes expressing CCR7 or CCR9 or both CCR7 and CCR9, levels of CD14, HLA-DR, CCR9 and/or CCR7 expression or levels of CD14 hi, HLA-DR hi, CCR9 hi and/or CCR7hi cells are diagnostically relevant, determining such levels in a sample obtained from a subject may influence treatment selection for that subject. Accordingly, in certain embodiments the invention provides a method of selecting a suitable treatment for inflammatory bowel disease, including Crohn's disease (CD) and ulcerative cholitis (UC) comprising determining:

a) the levels of CD14, HLA-DR, CCR9 and/or CCR7 expressing cells, particularly levels of CD14+HLA-DRhi monocytes or monocytes expressing CCR7 or CCR9 or both CCR7 and CCR9 b) levels of expression of CD14, HLA-DR, CCR9 and/or CCR7; and/or c) levels of cells with high expression of CD14, HLA-DR, CCR9 and/or CCR7 in a sample obtained from a subject, wherein high levels of CD14, HLA-DR, CCR9 and/or CCR7 expressing cells, high levels of CD14+HLA-DRhi monocytes or monocytes expressing CCR7 or CCR9 or both CCR7 and CCR9, high levels of expression of CD14, HLA-DR, CCR9 and/or CCR7 or high levels of cells with high expression of CD14, HLA-DR, CCR9 and/or CCR7 or increased levels of CD14, HLA-DR, CCR9 and/or CCR7 expressing cells compared to control, increased levels of CD14+HLA-DRhi monocytes or monocytes expressing CCR7 or CCR9 or both CCR7 and CCR9 compared to control, increased levels of expression of CD14, HLA-DR, CCR9 and/or CCR7 compared to a control or increased levels of cells with high expression of CD14, HLA-DR, CCR9 and/or CCR7 compared to a control, result in selection of a treatment as defined herein for treatment of the inflammatory bowel disease, including Crohn's disease (CD) and ulcerative cholitis (UC). In certain embodiments, the receptor, including chemokine receptor, expressing cells are high receptor, including chemokine receptor, expressing cells, in particular, high CD14, HLA-DR, CCR9 and/or CCR7 expressing cells, in particular CD14+HLA-DRhi monocytes or monocytes expressing CCR7 or CCR9 or both CCR7 and CCR9.

Similarly, since the levels of CCR9 expressing cells, levels of CD14+HLA-DRhi monocytes or monocytes expressing CCR9, levels of CCR9 expression or levels of CCR9 hi cells are diagnostically relevant, determining such levels in a sample obtained from a subject may influence treatment selection for that subject. Accordingly, in certain embodiments the invention provides a method of selecting a suitable treatment for IBS comprising determining:

a) the levels of CCR9 expressing cells, particularly levels of CD14+HLA-DRhi monocytes or monocytes expressing CCR9 b) levels of expression of CCR9; and/or c) levels of cells with high expression of CCR9 in a sample obtained from a subject, wherein high levels of CCR9 expressing cells, high levels of CD14+HLA-DRhi monocytes or monocytes expressing CCR9, high levels of expression of CCR9 or high levels of cells with high expression of CCR9 or increased levels of CCR9 expressing cells compared to control, increased levels of CD14+HLA-DRhi monocytes or monocytes expressing CCR9 compared to control, increased levels of expression of CCR9 compared to a control or increased levels of cells with high expression of CCR9 compared to a control, result in selection of a treatment as defined herein for treatment of the IBS. In certain embodiments, the receptor, including chemokine receptor, expressing cells are high receptor, including chemokine receptor, expressing cells, in particular, high CCR9 expressing cells, in particular CD14+HLA-DRhi monocytes or monocytes expressing CCR9.

In specific embodiments, IBD or IBS is treated on the basis of measuring levels of chemokine (or other) receptor expressing cells, such as CD14, HLA-DR, CCR9 and/or CCR7 expressing cells. Thus, a treatment according to the various embodiments of the invention may be applied based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, IBD or IBS is treated according to the various embodiments of the invention on the basis of the presence of a about a 1.5 fold or greater increase, such as about a 2, 2.5, 3, 3.5, 4, 4.5, 5, 10, 20, 50 or 100 or greater fold increase in chemokine (or other) receptor expressing cells, such as CD14, HLA-DR, CCR9 and/or CCR7 expressing cells, relative to healthy controls.

In specific embodiments, IBS is treated on the basis of measuring levels of CCR9 expressing cells. A positive decision to treat the subject may be made based upon the presence of greater than about 10%, or greater than about 15% or more CCR9 expressing cells in the sample, as a percentage of total cells in the sample.

For the avoidance of doubt, all embodiments described in respect of the methods of the various embodiments of the invention apply to these aspects mutatis mutandis and are not repeated for reasons of conciseness. Specifically, inflammatory bowel disease, including Crohn's disease (CD) and ulcerative cholitis (UC) may be indicated in conjunction with the following indicators:

The diagnosis may be based on known clinical parameters for IBD. Histopathological assessment may be made in order to determine UC or CD. For staging of inflammation determination of pro inflammatory cells and expression of chemokine receptors may provide guidance to proper treatment such as tailored leukapheresis, according to the methods of the various embodiments of the invention.

The inventors have shown that levels of CD14+HLA-DRhi monocytes or monocytes expressing CCR7 or CCR9 or both CCR7 and CCR9 may be linked to improved success with certain treatments for inflammatory bowel disease. Thus, in some embodiments, the treatment may be selected from an immunosuppression treatment or a monocyte reduction therapy. More specifically, the immunosuppression treatment may comprise a corticosteroid treatment.

The methods and medical uses of the various embodiments of the invention thus can be tailored to the need of individual patients or groups of patients on the basis of the various diagnostic methods of the various embodiments of the invention. By removing from the circulation CD14, HLA-DR, CCR9 and/or CCR7 expressing cells, such as monocytes, in particular CD14+HLA-DRhi monocytes or monocytes expressing CCR7 or CCR9 or both CCR7 and CCR9, upregulated in various inflammatory conditions associated with inflammatory bowel disease, including Crohn's disease (CD) and ulcerative cholitis (UC), an important factor in the inflammatory process of inflammatory bowel disease, including Crohn's disease (CD) and ulcerative cholitis (UC) can be controlled. Similarly, the methods and medical uses of the various embodiments of the invention thus can be tailored to the need of individual patients or groups of patients on the basis of the various diagnostic methods of the various embodiments of the invention. By removing from the circulation CCR9 expressing cells, such as monocytes, in particular CD14+HLA-DRhi monocytes or monocytes expressing CCR9, upregulated in IBS, an important factor in the inflammatory process of IBS can be controlled.

B. Treating Conditions Associated with Metabolic Syndrome

Chemokines are a class of cytokine molecules involved in cell recruitment and activation in inflammation. Chemokines cause chemotaxis and activation of various subpopulations of cells in the immune system. The activity of chemokines is mediated primarily through tight binding to their receptors on the surface of leukocytes. In certain embodiments the present invention is based on the realisation that the interaction between chemokines and cells expressing their receptors may be exploited for the treatment of specific inflammatory conditions associated with metabolic syndrome. In particular, various conditions associated with metabolic syndrome, such as diabetes, in particular type 2 diabetes, obesity, insulin resistance, increased serum triacylglycerol concentrations and hypertension include an inflammatory component. The inventors have determined that targeting increased recruitment of specific chemokine receptor-expressing cells to the site of inflammation presents a new therapeutic approach to treat such conditions. Moreover, in such conditions, chemokine receptor expression on each cell may be increased again providing a therapeutic approach to treat such conditions. Adiposis dolorosa (AD), or Dercum's disease, is a rare progressive condition characterized by multiple, painful, subcutaneous lipomas that usually occur in obese, postmenopausal women (Dercum FX. Three cases of a hitherto unclassified affection resembling in its grosser aspects obesity, but associated with special symptoms: adiposis dolorosa. Am J Med Sci 1892; 104:521-35, incorporated herein by reference in its entirety). AD may be treated and diagnosed according to the invention, optionally as a condition associated with metabolic syndrome. It is shown herein that levels of CCR2 expressing leukocytes in particular B lymphocytes are increased in AD patients. It is shown herein that levels of CCR1 expressing monocytes are increased in AD patients. This provides a target for leukapheresis treatment and diagnosis according to the invention.

It is also shown herein that pro-inflammatory CCR2 expressing monocytes (such as macrophages) can be depleted from diabetes patients using a suitable chemokine such as MCP-1 (CCL2), in particular biotinylated MCP-1. This provides inflamed tissue, such as adipose and liver tissue, with the opportunity to heal and helps to prevent the development of insulin resistance. Moreover, it is shown herein that levels of CCR4 and CCR5 expressing leukocytes in particular T lymphocytes are increased in diabetes patients and can be depleted according to various embodiments of the invention.

Thus, in certain embodiments the invention serves to reduce the recruitment of inflammatory leukocytes, which express characteristic chemokine receptors, and possibly express characteristic chemokine receptors at increased levels, to sites of inflammation linked to disorders such as diabetes, in particular type 2 diabetes, obesity, insulin resistance, increased serum triacylglycerol concentrations and hypertension and AD. This is achieved using specific binding reagents to capture specific chemokine receptor-expressing inflammatory leukocytes from the patient. Accordingly, in certain embodiments the invention provides in a first aspect a method for treating a condition associated with metabolic syndrome comprising applying peripheral blood from a patient to an apheresis column loaded with a solid support comprising one or more binding reagents capable of specifically binding to one or more chemokine receptors, in particular the chemokine receptors CCR2, CCR1, CCR3, CCR4 and/or CCR5, immobilized directly or indirectly on the support thus removing one or more chemokine receptor, in particular one or more of CCR2, CCR1, CCR3, CCR4 and CCR5, expressing cells from the peripheral blood of the patient. The peripheral blood from which the chemokine receptor expressing cells have been removed may then be returned to the patient in order to complete the treatment. The invention may thus rely on a continuous extracorporeal circuit in some embodiments. Alternatively, in certain embodiments the invention may comprise steps of obtaining peripheral blood from the patient, applying the peripheral blood to the column and subsequently returning the peripheral blood from which the chemokine receptor expressing cells have been removed to the patient.

In certain embodiments the invention also provides a method for treating adiposis dolorosa (AD) comprising applying peripheral blood from a patient to an apheresis column loaded with a solid support comprising one or more binding reagents capable of specifically binding to one or more chemokine receptors, in particular the chemokine receptors CCR2, CCR1, CCR3, CCR4 and/or CCR5, immobilized directly or indirectly on the support thus removing one or more chemokine receptor, in particular one or more of CCR2, CCR1, CCR3, CCR4 and CCR5, expressing cells from the peripheral blood of the patient. The peripheral blood from which the chemokine receptor expressing cells have been removed may then be returned to the patient in order to complete the treatment. The invention may thus rely on a continuous extracorporeal circuit in some embodiments. Alternatively, in certain embodiments the invention may comprise steps of obtaining peripheral blood from the patient, applying the peripheral blood to the column and subsequently returning the peripheral blood from which the chemokine receptor expressing cells have been removed to the patient. Specific embodiments target CCR2 expressing cells, in particular CCR2 expressing B cells.

As shown herein, suitable binding reagents can be immobilized onto a solid support, either directly or indirectly, to generate an apheresis column suitable for capturing relevant chemokine receptor-expressing cells. Where increased levels of chemokine receptor expression are observed, such cells may be preferably removed from the peripheral blood using the columns of the various embodiments of the invention. Thus, the methods of the various embodiments of the invention may preferably target one or more of CCR2hi, CCR1hi, CCR3hi, CCR4hi and CCR5hi cells as defined herein for removal from the peripheral blood. "High" expression may be determined according to standard flow cytometry techniques. The level may be measured relative to levels of expression of the chemokine receptor in cells taken from a healthy subject. The attached FIG. 35 provides an example of a gating strategy.

In other embodiments the invention further provides a binding reagent capable of specifically binding to one or more chemokine receptors, in particular to a chemokine receptor/the chemokine receptor CCR2, CCR1, CCR3, CCR4 and/or CCR5, for use in the treatment of a condition associated with metabolic syndrome, wherein the one or more binding reagents is immobilized, directly or indirectly, on a solid support contained within an apheresis column, to which is applied peripheral blood from a patient thus removing one or more chemokine receptor/CCR2, CCR1, CCR3, CCR4 and/or CCR5 expressing cells from the peripheral blood of the patient. In certain embodiments the invention also provides for use of one or more binding reagents capable of specifically binding to a chemokine receptor/the chemokine receptor CCR2, CCR1, CCR3, CCR4 and/or CCR5 for use in the manufacture of an apheresis column for treatment of a condition associated with metabolic syndrome, wherein the one or more binding reagents is immobilized on a solid support contained within the apheresis column, to which is applied peripheral blood from a patient thus removing one or more of chemokine receptor/CCR2, CCR1, CCR3, CCR4 and/or CCR5 expressing cells from the peripheral blood of the patient.

Similarly, the various embodiments of the invention further provide a binding reagent capable of specifically binding to one or more chemokine receptors, in particular to a chemokine receptor/the chemokine receptor CCR2, CCR1, CCR3, CCR4 and/or CCR5, for use in the treatment of AD, wherein the one or more binding reagents is immobilized, directly or indirectly, on a solid support contained within an apheresis column, to which is applied peripheral blood from a patient thus removing one or more chemokine receptor/CCR2, CCR1, CCR3, CCR4 and/or CCR5 expressing cells from the peripheral blood of the patient. The invention also provides for use of one or more binding reagents capable of specifically binding to a chemokine receptor/the chemokine receptor CCR2, CCR1, CCR3, CCR4 and/or CCR5 for use in the manufacture of an apheresis column for treatment of AD, wherein the one or more binding reagents is immobilized on a solid support contained within the apheresis column, to which is applied peripheral blood from a patient thus removing one or more of chemokine receptor/CCR2, CCR1, CCR3, CCR4 and/or CCR5 expressing cells from the peripheral blood of the patient.

All embodiments described in respect of the methods of treatment of the various embodiments of the invention apply to these aspects mutatis mutandis and are not repeated for reasons of conciseness. Thus, the following discussion made with reference to the methods of treatment is also applicable to the medical use aspects of the various embodiments of the invention.

In certain embodiments the invention aims to treat a range of specific conditions associated with metabolic syndrome. Metabolic syndrome represents a group of risk factors that occur together and increase the risk for coronary artery disease, stroke, and type 2 diabetes. Generally, the syndrome's risk factors are related to obesity. The two most important risk factors are central obesity and insulin resistance. In this context, adipose tissue inflammation and other inflammatory damage, such as to organs, represent a central target of treatment according to the invention. Any relevant condition including an inflammatory component may be treated according to the methods of the invention. Specific conditions including an inflammatory component may be selected from diabetes, in particular type 2 diabetes, obesity, insulin resistance, increased serum triacylglycerol concentrations and hypertension. AD may also be treated, as discussed herein.

By treatment is meant a reduction in the specific chemokine receptor expressing cells in the peripheral blood of the patient. The reduction may comprise a reduction in cells that express chemokine receptors, in particular one or more of CCR2, CCR1, CCR3, CCR4 and CCR5, at increased levels in diseased patients. The patient is typically a human patient but the term patient may include both human and non-human animal subjects in some embodiments. In the context of the various embodiments of the present invention, this typically involves a reduction in one or more of CCR2, CCR1, CCR3, CCR4 and CCR5 expressing cells, such as one or more of "CCR2hi, CCR1hi, CCR3hi, CCR4hi and CCR5hi" expressing cells, in the peripheral blood of the patient. The CCR2, CCR1, CCR3, CCR4 or CCR5 expressing cells comprise, consist essentially of or consist of monocytes, macrophages and/or lymphocytes, in particular T-lymphocytes, in certain embodiments. CCR2 expressing monocytes, such as macrophages, may be specifically targeted for the treatment of diabetes. CCR4 and CCR5 expressing leukocytes in particular T lymphocytes may be specifically targeted for treatment of diabetes patients. B lymphocyte reduction may be particularly pertinent in the case of AD treatment. CCR2 expressing B cells may targeted. AD may also be treated by targeting CCR1 expressing monocytes Monocytes are produced by the bone marrow from haematopoietic stem cell precursors called monoblasts. Monocytes may differentiate into macrophages or dendritic cells. Monocytes and their macrophage and dendritic cell progeny serve a number of functions in the immune system including phagocytosis, antigen presentation and cytokine production. Monocytes may be characterized with reference to expression of the cell surface marker CD14, optionally together with CD16. Classical monocytes may be characterized by high level expression of the CD14 cell surface receptor (CD14++CD16− monocyte). Non-classical monocytes may be characterized by low level expression of CD14 and with additional co-expression of the CD16 receptor (CD14+CD16++ monocyte). Intermediate monocytes may be characterized by high level expression of CD14 and low level expression of CD16 (CD14++CD16+ monocytes). Macrophages are derived from monocytes and are responsible for protecting tissues from foreign substances. They are cells that possess a large smooth nucleus, a large area of cytoplasm and internal vesicles for processing foreign material. The term "macrophage" may refer to a monocyte-derived cell expressing one or more of the following cell surface markers CD14, CD11b, Lysozyme M, MAC-1/MAC-3 and CD68. The term macrophage includes both activated and un-activated macrophages. Activated macrophages may be characterized by expression of one or more of CD69, ENG, FCER2 and IL2RA, HLA-DR, CD86. Un-activated macrophages have not yet received activating signals through for example TLR receptors and therefore they express less activation markers on the cell surface which correlates with lesser maturation. M1 macrophages may be characterized by expression of one or more of CD16+CD32+CD64+ and secrete mainly IL-23 and IL-1, TNF, IL-6 and high levels of IL-12 and in addition effector molecules such as iNOS and ROI. M1 macrophages have cytotoxic features as opposed to M2 macrophages. M2 macrophages may be characterized by expression of one or more of SRA/B+CD163+MR+CD14+ and express TGFβ, IL-10 and IL-1Ra. Tumour associated macrophages (TAMs) share many characteristics with the M2 macrophages and are considered as M2 polarised macrophages. The M1/M2 paradigm can also be found in monocyte subsets where CD14+CD16−CXC3R1low monocytes are considered the "inflammatory" subset and the CD14lowCD16+CXC3R1high are "resident" monocytes.

The three major types of lymphocyte are T cells, B cells and natural killer (NK) cells. The term "T-lymphocyte" includes CD4+ T cells such as T helper cells (Th1 cells and Th2 cells), and CD8+ T cells such as cytotoxic T cells. Th1 cells may be characterized by expression of CCR5 and/or by production of IFN-γ. Th2 cells may be characterized by expression of CCR3 and/or by production of IL-4.

CCR2, CCR1, CCR3, CCR4 or CCR5 expressed on these aforementioned cells binds to chemokines such as monocyte chemoattractant protein-1 (MCP-1, CCL2) or CCL5. MCP-1 is a major chemoattractant for monocytes and memory T cells by means of their binding to its specific cell-surface receptor, CC-chemokine receptor-2. CCL5 is the gene symbol approved by the HUGO Gene Nomenclature Committee for chemokine (C—C motif) ligand 5, also known as RANTES. The HGNC ID for this gene is 10632. The gene is located at chromosome position 17q11.2-q12. The previous symbol and name for the gene is D17S136E, SCYA5, "small inducible cytokine A5 (RANTES)". Synonyms for this gene include "beta-chemokine RANTES", MGC17164, RANTES, "regulated upon activation, normally T-expressed, and presumably secreted", "SIS-delta", SISd, "small inducible cytokine subfamily A (Cys-Cys), member 5", "T-cell specific protein p288", "T-cell specific RANTES protein", and TCP228. The Genbank reference sequence for CCL5 is AF043341.1. RANTES binds to CCR1, CCR3 or CCR5.

CCR1 is the gene symbol approved by the HUGO Gene Nomenclature Committee for chemokine (C—C motif) receptor 1. The HGNC ID for this gene is 1602. The gene is located at chromosome position 3p21. The previous symbol and name CMKBR1, SCYAR1. Synonyms for this gene include CD191, CKR-1, MIP1α R. The Entrez Gene reference sequence for CCR1 is 1230 as available on 13 Jun. 2011, which is incorporated herein by reference in its entirety.

CCR2 is the gene symbol approved by the HUGO Gene Nomenclature Committee for chemokine (C—C motif) receptor 2. The HGNC ID for this gene is 1603. The gene is located at chromosome position 3p21. The previous symbol and name for the gene is CMKBR2. Synonyms for this gene include CC-CKR-2, CD192, CKR2, FLJ78302, MCP-1-R. The NCBI Reference Sequence is NM_001123041.2 as available on 13 Jun. 2011, which is incorporated herein by reference in its entirety.

CCR3 is the gene symbol approved by the HUGO Gene Nomenclature Committee for chemokine (C—C motif) receptor 3. The HGNC ID for this gene is 1604. The gene is located at chromosome position 3p21.3. The previous symbol and name for the gene is CMKBR3. Synonyms for this gene include CC-CKR-3, CD193 and CKR3. The Genbank reference sequence for CCR3 is AF247361.1 as available on 13 Jun. 2011, which is incorporated herein by reference in its entirety.

CCR5 is the gene symbol approved by the HUGO Gene Nomenclature Committee for chemokine (C—C motif) receptor 5. The HGNC ID for this gene is 1605. The gene is located at chromosome position 3p21. The previous symbol and name for the gene is CMKBR5. Synonyms for this gene include CC-CKR-5, CD195 CKR-5, IDDM22 and CKR5. The Entrez Gene reference sequence for CCR5 is 1234 as available on 13 Jun. 2011, which is incorporated herein by reference in its entirety.

CCR4 is the gene symbol approved by the HUGO Gene Nomenclature Committee for chemokine (C—C motif) receptor 4. The HGNC ID for this gene is 1605. The gene is located at chromosome position 3p24-p21.3. Synonyms for this gene include CC-CKR-4, CD194, ChemR13, CKR4, CMKBR4, k5-5. The Genbank reference sequence for CCR4 is X85740.1 as available on 13 Jun. 2011, which is incorporated herein by reference in its entirety.

The various embodiments of the methods of the invention may involve specific binding interactions with any one or more of these further cell-surface markers in addition to the removal based upon binding to CCR2, CCR1, CCR3, CCR4 or CCR5. Suitable binding reagents can be prepared to specifically bind to these cell-surface markers. The discussion of CCR2, CCR1, CCR3, CCR4 or CCR5 specific binding reagents thus applies mutatis mutandis.

It has been shown that CCR2 expression on monocytes is elevated in diabetic patients. Furthermore, transgenic mice with an adipose-tissue-specific expression of MCP-1 have macrophage infiltration into adipose tissue, increased hepatic triacylglycerol content and insulin resistance. MCP-1-knockout mice fed a high-fat diet have a drastically reduced macrophage accumulation into adipose tissue and hepatic steatosis when compared with high-fat fed wild-type mice. Inhibition of MCP-1 function by the acute expression of a dominant negative mutant of MCP-1 ameliorated insulin resistance in db/db mice and in high-fat-fed wild-type mice. Moreover, an increased level of serum MCP-1 correlates with conditions associated with metabolic syndrome, including obesity, insulin resistance, Type 2 diabetes, hypertension and increased serum triacylglycerol concentrations. It is shown herein that MCP-1 can be used to reduce CCR2-expressing monocyte levels in diabetic subjects. This provides inflamed tissue, such as adipose and liver tissue, with the opportunity to heal and helps to prevent the development of insulin resistance. It is also shown herein that MCP-1 can be used to reduce CCR2-expressing B cell levels in subjects suffering from AD.

Treatment according to the various embodiments of the invention may result in alleviation or amelioration of symptoms, prevention of progression, regression of the condition, or complete recovery. Measurable parameters of successful treatment include one or more, up to all, of a decrease in central obesity, which may be defined with reference to waist circumference. A decrease in glycated/glycosylated hemoglobin (HbA1C), a decrease in triglycerides, a decrease in glucose measured for example as FPG or a decrease in blood pressure. Measurable parameters of successful treatment may also include one or more, up to all, of an increase in HDL cholesterol or improved glucose tolerance, which may be measured by OGTT. Measurable parameters of successful treatment of AD may comprise a reduction in pain symptoms and/or a reduction in the extent and/or size of subcutaneous lipomas (or fatty deposits).

In specific embodiments, a single treatment is sufficient to cause a depletion of around 10%, 20%, 30%, 40%, 50%, 60% or 70%, or higher up to 80%, 90%, 95% or more, or any range of values between and including these amounts, of one or more of a specific chemokine receptor, in particular one or more of CCR2, CCR1, CCR3, CCR4 and CCR5, expressing cells from the peripheral blood of the patient. In specific embodiments, at least around 50% depletion is achieved in a single treatment. Thus, successful treatment may be defined with reference to depletion of one or more of CCR2, CCR1, CCR3, CCR4 and CCR5 expressing cells. Treatment may lead to depletion of between approximately 100 and 500 million CCR2, CCR1, CCR3, CCR4 and/or CCR5 expressing cells, such as monocytes, in certain embodiments and more particularly to about 100, 150, 200, 250, 300, 350, 400, 450, or 500 million CCR2, CCR1, CCR3, CCR4 and/or CCR5 expressing cells.

By binding to the column through the binding reagent-chemokine receptor interaction, chemokine receptor expressing cells are immobilized. These immobilized cells express further unoccupied chemokine receptors, which may be of the same or different type to those used for capture. These additional chemokine receptors may permit circulating chemokines which contribute to the inflammatory condition to be captured from the peripheral blood. Thus, a reduction in circulating (specific) chemokine levels may provide a measure of successful treatment.

The duration of treatment may be readily determined by one skilled in the art and will depend upon factors such as the flow rate of the peripheral blood. Duration of treatment may be tied into monitoring of the treatment itself, with the treatment considered complete once a measurable parameter of treatment has reached a defined threshold. Any suitable parameter may be employed as discussed herein. Thus, for example, treatment may be considered complete when a reduction in one or more of CCR2, CCR1, CCR3, CCR4 and CCR5 expressing cells, such as a 50% reduction in one or more of CCR2, CCR1, CCR3, CCR4 and CCR5 expressing cells, has been achieved. The apheresis system may be operated at a flow rate of around 10-80 mL/min, or more specifically between around 20-70 mL/min, or between around 30-60 mL/min. In specific embodiments, the treatment is performed for a period of around 10, 20, 30, 40, 50, 60, 70, 80, 90, 100, 110, 120 etc., or any range of values between and including these amounts, minutes. The treatment is typically not aimed to remove all of the cells expressing the chemokine receptor in the peripheral blood, as a basal level of those cells is required in healthy subjects. However, it has been found that only low blood volumes need to be applied to the columns of the various embodiments of the invention in order to achieve effective levels of depletion of the chemokine receptor-expressing cells. Thus, in certain embodiments, around 10-80% or more specifically around 20, 30, 40 or 50%, or any range of values between and including these amounts, of the patient's blood is applied to the column in a single treatment. The volume of blood circulated through the apheresis column or system may be in the region of around 1000-3000 ml, such as around 1000, 1200, 1400, 1600, 1800 or 2000 ml or any range of values between and including these amounts. The treatment may be considered complete once this volume of blood has been circulated. The patient may be administered anticoagulants prior to each treatment session. A suitable solution, such as a sterile saline solution, optionally including an anticoagulant such as Heparin, may be used for priming the apheresis (extracorporeal) system. An additional volume of anticoagulant may be added to the circuit at the start of each treatment session, for example as a bolus injection.

In certain embodiments the invention relies upon a binding reagent which is capable of specifically binding to a chemokine receptor. This specific binding reaction permits cells expressing the chemokine receptor to be removed from the peripheral blood of the patient when the blood is passed over the solid support upon or within which the binding reagent is immobilized. Specific chemokine receptors of interest include CCR2, CCR1, CCR3, CCR4 and CCR5, particularly CCR2. The binding reagent can be any binding reagent capable of specifically binding to the receptor in question. By "specific binding" is meant that the binding reagent displays sufficient specificity of binding and appropriate binding affinity/kinetics to permit removal of cells expressing one or more of CCR2, CCR1, CCR3, CCR4 and CCR5 from the peripheral blood. Whilst it is not precluded that the binding reagent is capable of binding to other molecules, such as other chemokine receptors, the binding reagent will preferentially bind to cells expressing one or more of CCR2, CCR1, CCR3, CCR4 and CCR5 and in particular to cells expressing increased levels of one or more of CCR2, CCR1, CCR3, CCR4 and CCR5 (as defined further herein). The binding reagent capable of specifically binding to CCR2, CCR1, CCR3, CCR4 or CCR5 may be either an agonist or an antagonist of CCR2, CCR1, CCR3, CCR4 or CCR5, respectively. As the disease condition relies upon up-regulation of expression of or signaling via CCR2, CCR1, CCR3, CCR4 or CCR5, in certain embodiments the binding reagent capable of specifically binding to CCR2, CCR1, CCR3, CCR4 or CCR5 is an antagonist of CCR2, CCR1, CCR3, CCR4 or CCR5, respectively. Chemokines are typically, although not necessarily exclusively (particularly in the case of truncated or modified forms) agonists of their cognate receptor and serve to activate the cells expressing the relevant receptor, as would be appreciated by one skilled in the art. Antibodies against the relevant chemokine receptor are generally considered to be antagonists, as would be appreciated by one skilled in the art. Specific examples of binding reagents include proteins or polypeptides, such as antibodies and receptor ligands, in particular chemokines. The binding reagent may be a nucleic acid molecule in certain embodiments. In some embodiments, the nucleic acid is an aptamer. Nucleic acid aptamers are polynucleotides of approximately 15-40 nucleotides long. Nucleic acid aptamers can be made using the SELEX process (systemic evolution of ligands by exponential enrichment) or any other process known to those of skill in the art.

In other embodiments, the binding reagent may be a peptide, and in certain instances, a peptide aptamer. Peptide aptamers are artificial recognition molecules that consist of a variable peptide sequence inserted into a constant scaffold protein (Baines I C, Colas P. Peptide aptamers as guides for small molecule drug discovery. Drug Discov Today. 2006; 11:334-341, incorporated herein by reference). A number of methodologies, such as phage display, ribosome display and yeast two-hybrid screening systems are available for screening a library of potential peptide-based binding agents. Similarly protein scaffolds based on domains such as fibronectins, ankyrin repeats, protein A, SH3 domains, lipocalins, ubiquitin can be used as the binding agent. Again a number of technologies such as phage display, ribosome display are available for screening a library of protein—based binding agents. Similarly, libraries of candidate chemical compounds can be screened for specific binding to the relevant chemokine receptor using suitable screening techniques known in the art, which may be high throughput screens in certain embodiments. The candidate binding agent may be immobilized on a solid support and the ability of the agent to specifically retain cells expressing the chemokine receptor of interest or labelled chemokine receptors determined. A range of cell types may be applied to the solid supports to confirm specificity of binding, or alternatively a mixed sample (such as peripheral blood) may be applied to the solid support. Retention of the cell type of interest (expressing the appropriate chemokine receptor) can be confirmed to identify suitable binding agents. A range of small-molecule antagonists of CCR-2 are discussed by Xia M and Sui Z in Expert Opin Ther Pat. 2009 March; 19 (3):295-303—Recent developments in CCR2 antagonists, and incorporated herein by reference.

In the context of the various embodiments of the present invention the term "chemokine" also comprises biotinylated or otherwise labeled chemokines. The term "chemokine" also comprises modified and truncated versions of the chemokine and chemokine fragments with the proviso that the modified or truncated form retains its ability to bind to its cognate receptor (and thus remains functional in the context of the various embodiments of the invention). The chemokine does not necessarily need to retain biological activity as it is specific binding affinity for CCR2, CCR1, CCR3, CCR4 or CCR5 that is required. In certain embodiments, the chemokine lacks biological activity, for example in terms of activation of the (CCR2, CCR1, CCR3, CCR4 or CCR5) receptor. Modifications may be made to improve protein synthesis, for example uniformity of product and yield. As known to those skilled in the art, exemplary modifications may comprise amino acid additions, substitutions, deletions or other modifications to one or more amino acids in the chemokine. Modifications may comprise substitution of the wild type amino acid with non-natural amino acids such as norleucine (NLeu) and derivatized amino acids such as pyroglutamic acid (pyroGlu). Such modifications may be made to minimize side-product formation during storage and use of the columns of the various embodiments of the invention. Modifications may be made to improve labelling, for example inclusion of a polyethylene glycol (PEG) spacer to facilitate biotinylation. The biotinylation and/or conjugation with fluorochromes or other labelling groups of the chemokine is performed in a manner which does not substantially affect the receptor binding capacity. Site specific biotinylation or other labelling is preferred as non-selective labelling of chemokines may compromise receptor binding activity. Biotinylation or other labelling is generally preferred at or towards the C-terminus of the protein as the inventors have found that modifications in this area are generally well tolerated (in terms of a minimal effect on receptor binding capability). Biotinylation may be carried out site-specifically at any suitable amino acid. Examples of suitable amino acids include lysine, diaminopropionic acid and ornithine. Generally, reference may be made to Natarajan S et al, Int. J. Pept. Protein Res., 1992, 40, 567-74; Baumeister B, Int. J. Peptide Res. And Therapeutics, 2005, 11, 139-141; Bioconjugate techniques 2nd edition, Greg T. Hermanson, incorporated by reference herein in its entirety.

Truncations may involve deletion of either N or C terminal amino acids as appropriate, or both. Typically, the truncated version will retain the residues required for the chemokine to fold correctly, for example to retain a chemokine fold structure, consistent with the requirement that a truncated version must retain the ability to bind to the relevant receptor (expressed by (on the surface of) a leukocyte). Chemokine molecules typically include disulphide bonds between the 1st and 3rd and 2nd and 4th cysteine residues respectively, as would be understood by one skilled in the art. Where sequences are presented herein, it is assumed that these disulphide bonds will form in the folded protein (unless otherwise stated). Truncated versions may comprise anywhere between 1 and 100 less amino acids, such as 1, 2, 3, 4, 5 etc amino acids, than the wild type amino acid sequence in certain embodiments. Of course, truncated versions may comprise further modification as detailed herein. The modified or truncated version may have 40%, 45%, 50%, 55%, 60%, 65%, 70%, 75%, 80%, 85%, 90%, 95% or more overall amino acid sequence identity with the full length wild type chemokine (where a deletion is counted as a difference in amino acid sequence) in certain embodiments. Over the common sequence between the molecules (i.e the amino acids that have not been deleted), there may be 80%, 85%, 90%, 91%, 92%, 93%, 94%, 95%, 96%, 97%, 98% or 99% amino acid sequence identity in certain embodiments. Sequence identity may be determined using known algorithms, such as BLAST or GAP analysis (GCG Program) (applying default settings), which are freely available. Chemokines may lack the N-terminal signal peptide which is cleaved off during synthesis in vivo.

Specific chemokines useful in the various embodiments of the present invention for binding to CCR2 include MCP-1, MCP-2, MCP-3, MCP-4 and MCP-5. Both MCP-1 and MCP-5 bind solely to the chemokine receptor CCR2 and so these chemokines may be preferred in some embodiments. Each chemokine is able to bind to a chemokine receptor implicated in a metabolic syndrome associated disorder or condition. More specifically, each of MCP-1, MCP-2, MCP-3, MCP-4 and MCP-5 are useful for removing CCR2 expressing cells from the blood of a patient. Specific chemokines useful in the present invention for binding to CCR1, CCR3 and/or CCR5 include RANTES. RANTES is able to bind to chemokine receptors implicated in a metabolic syndrome associated disorder or condition. More specifically, RANTES is useful for removing CCR1, CCR3 and/or CCR5 expressing cells from the blood of a patient. The chemokines described in greater detail herein (with reference to the relevant figures and amino acid sequences, as set forth in the SEQ ID NOs) may each be applied according to the various embodiments of the present invention. CCL17 (TARC) and CCL22 (MDC) bind CCR4 only and may be useful in certain embodiments of the invention.

CCL2 is the gene symbol approved by the HUGO Gene Nomenclature Committee for chemokine (C—C motif) ligand 2, also known as MCP-1. The HGNC ID for this gene is 10618. The gene is located at chromosome position 17q11.2-q21.1. The previous symbol and name for the gene is SCYA2 "small inducible cytokine A2 (monocyte chemotatic protein 1, homologus to mouse Sig-je)". Synonyms for this gene include GDCF-2, HC11, MCP1, MGC9434, SMC-CF, "monocyte chemoattractant protein-1", "monocyte chemotactic and activating factor", "monocyte chemotactic protein 1, homologous to mouse Sig-je", "monocyte secretory protein JE", "small inducible cytokine subfamily A (Cys-Cys), member 2". The Genbank reference sequence for CCL2 is BC009716.1 as available on 13 Jun. 2011, which is incorporated herein by reference in its entirety.

CCL8 is the gene symbol approved by the HUGO Gene Nomenclature Committee for chemokine (C—C motif) ligand 8, also known as MCP-2. The HGNC ID for this gene is 10635. The gene is located at chromosome position 17q11.2. The previous symbol and name for the gene is SCYA8, "small inducible cytokine subfamily A (Cys-Cys), member 8 (monocyte chemotactic protein 2)". Another synonym for this gene is HC14. The Genbank reference sequence for CCL8 is X99886.1 as available on 13 Jun. 2011, which is incorporated herein by reference in its entirety.

CCL7 is the gene symbol approved by the HUGO Gene Nomenclature Committee for chemokine (C—C motif) ligand 7, also known as MCP-3. The HGNC ID for this gene is 10634. The gene is located at chromosome position 17q11.2-q12. The previous symbol and name for the gene is SCYA6, SCYA7, "small inducible cytokine A7 (monocyte chemotactic protein 3)". Synonyms for this gene include FIC, MARC, MCP-3, MCP3, NC28, "monocyte chemoattractant protein 3", "monocyte chemotactic protein 3". The Genbank reference sequence for CCL7 is AF043338 as available on 13 Jun. 2011, which is incorporated herein by reference in its entirety.

CCL13 is the gene symbol approved by the HUGO Gene Nomenclature Committee for chemokine (C—C motif) ligand 13, also known as MCP-4. The HGNC ID for this gene is 10611. The gene is located at chromosome position 17q11.2. The previous symbol and name for the gene is SCYA13, "small inducible cytokine subfamily A (Cys-Cys), member 13". Synonyms for this gene include CKb10, MCP-4, MGC17134, NCC-1, SCYL1. The Genbank reference sequence for CCL13 is AJ001634 as available on 13 Jun. 2011, which is incorporated herein by reference in its entirety.

MCP-5 is a mouse chemokine in the CC chemokine family. It is also known as Chemokine (C—C motif) ligand 12 (CCL12) and, due to its similarity with the human chemokine MCP-1, sometimes it is called MCP-1-related chemokine. The gene for MCP-5 is found in a cluster of CC chemokines on mouse chromosome 11. The NCBI reference sequence for CCL12 is NC_000077.5. The previous symbol for MCP-5 is SCYA12. The NCBI reference sequence for CCL12 is NC_000077.5 as available on 13 Jun. 2011, which is incorporated herein by reference in its entirety.

CCL5 is the gene symbol approved by the HUGO Gene Nomenclature Committee for chemokine (C—C motif) ligand 5, also known as RANTES. The HGNC ID for this gene is 10632. The gene is located at chromosome position 17q11.2-q12. The previous symbol and name for the gene is D17S136E, SCYA5, "small inducible cytokine A5 (RANTES)". Synonyms for this gene include "beta-chemokine RANTES", MGC17164, RANTES, "regulated upon activation, normally T-expressed, and presumably secreted", "SIS-delta", SISd, "small inducible cytokine subfamily A (Cys-Cys), member 5", "T-cell specific protein p288", "T-cell specific RANTES protein", TCP228. The Genbank reference sequence for CCL5 is AF043341.1 as available on 13 Jun. 2011, which is incorporated herein by reference in its entirety.

CCL17 is the gene symbol approved by the HUGO Gene Nomenclature Committee for chemokine (C—C motif) ligand 17. The HGNC ID for this gene is 10615. The gene is located at chromosome position 16q113. The previous symbol and name for the gene is SCYA17, "small inducible cytokine subfamily A (Cys-Cys), member 17". Synonyms for this gene include ABCD-2, TARC. The Genbank reference sequence for CCL17 is D43767.1 as available on 13 Jun. 2011, which is incorporated herein by reference in its entirety.

CCL21 is the gene symbol approved by the HUGO Gene Nomenclature Committee for chemokine (C—C motif) ligand 21. The HGNC ID for this gene is 10620. The gene is located at chromosome position 9p13. The previous symbol and name for the gene is SCYA21, "small inducible cytokine subfamily A (Cys-Cys), member 21". Synonyms for this gene include 6Ckine, "beta chemokine exodus-2", CKb9, ECL, "Efficient Chemoattractant for Lymphocytes", exodus-2, "secondary lymphoid tissue chemokine", SLC, TCA4. The Genbank reference sequence for CCL21 is AB002409.1 as available on 13 Jun. 2011, which is incorporated herein by reference in its entirety.

Examples of suitable modified chemokines of the various embodiments of the invention containing modifications and/or truncations and specifically adapted for use in the invention are described in detail herein. MCP-1 has been produced with residue 75, which may be a lysine, as the site of biotinylation on the chemokine (numbering based upon the mature protein having the amino acid sequence of SEQ ID NO: 8). Biotinylation permits immobilization of MCP-1 on a solid support (via a biotin-avidin interaction). The basic amino acid sequence of MCP-1, including a 23 amino acid leader sequence is set forth as SEQ ID NO: 7. The amino acid sequence of the mature protein is set forth as SEQ ID NO: 8. The inventors have determined that chemokines may display improved binding properties where the chemokine is biotinylated via a spacer group. The spacer may prevent the biotin group from impacting on the binding affinity of the chemokine. Any suitable spacer group may be employed.

Further modifications may provide the molecule with advantageous properties. The invention also relates to derivatives of truncated MCP-1 chemokines. The amino acid sequence of the truncated version is set forth as SED ID NO: 9.

Accordingly, in certain embodiments the invention also provides a modified MCP-1 chemokine comprising, consisting essentially of or consisting of the amino acid sequence set forth as SEQ ID NO: 7, SEQ ID NO: 14 or SEQ ID NO: 15 in which one or more of the following modifications have been made:

a) the glutamine residue 1 of SEQ ID NO: 14 has been replaced with pyroglutamine b) the C terminus is produced as an amide derivative (this may be achieved by synthesis on an amide linker)

c) the (C terminal region) residue at position 98 of SEQ ID NO: 13 or position 75 of SEQ ID NO: 8 or position 67 of SEQ ID NO: 9, which may be a lysine or ornithine residue, is biotinylated, optionally via a spacer group, in order to permit immobilization of the chemokine on a solid support; and/or d) the methionine residue at position 87 of SEQ ID NO: 7 or position 64 of SEQ ID NO: 8 or position 56 of SEQ ID NO: 9 has been replaced with norleucine.

The (C terminal region) amino acid, which may be a lysine residue or a functional equivalent, at position 98 of SEQ ID NO: 7 or position 75 of SEQ ID NO: 8 or position 67 of SEQ ID NO: 9 may be biotinylated via a suitable spacer group, such as a polyethylene glycol (PEG) spacer group, in order to permit immobilization of the chemokine on a solid support. In specific embodiments, the PEG spacer is 3,6-dioxo aminooctanoic acid. The sequence and biotinylation of the modified MCP-1 chemokines of the invention are shown in FIGS. 29 to 31 respectively. The modified MCP-1 chemokines may be agonists or antagonists of CCR2 activity. They can be tested for activity in a suitable assay, such as cell-based assays. In particular, agonist and antagonist properties may be determined in functional cell-based assay on human CCR2 receptor.

MCP-5 only binds CCR2 and should be selective in its removal of CCR2 expressing cells. The full length amino acid sequence, including the signal peptide, is set forth as SEQ ID NO: 10. The amino acid sequence of N-terminal processed MCP-5 chemokine is 82 amino acids long and is set forth as SEQ ID NO: 11. An amino acid sequence alignment suggests that MCP-5 has a C-terminal extension when compared to the amino acid sequence of MCP-1. The results of this alignment are shown in FIG. 32. C-terminal truncated versions of MCP-5 can thus be synthesised. This truncated version will comprise, consist essentially of or consist of MCP-5 residues 1-76, set forth as SEQ ID NO: 12.

Accordingly, in certain embodiments the invention also provides a modified MCP-5 chemokine comprising the amino acid sequence set forth as SEQ ID NO: 10, SEQ ID NO: 11 or SEQ ID NO: 12 in which the isoleucine residue at position 97 of SEQ ID NO: 10 or at position 75 of SEQ ID NO: 11 or SEQ ID NO: 12 has been replaced with lysine. In certain embodiments, the modified MCP-5 chemokine comprises, consists essentially of or consists of the amino acid sequence of SEQ ID NO: 13. The modified MCP-5 chemokine may be biotinylated at the lysine (or a functional equivalent) residue at position 97 of SEQ ID NO: 10 or at position 75 of SEQ ID NO: 11 or SEQ ID NO: 11. Biotinylation may be via a suitable spacer group. Specific examples of the spacer group include a PEG spacer, optionally 3,6-dioxo aminooctanoic acid. In some embodiments, the C terminus is produced as an amide derivative. This may be achieved by synthesis on an amide linker. In certain embodiments, the modified MCP-5 chemokine comprises, consists essentially of or consists of the sequence and biotinylation shown in FIG. 33. The modified MCP-5 chemokine may be an agonist or an antagonist of CCR2 activity. They can be tested for activity in a suitable assay, such as cell-based assays. In particular, agonist and antagonist properties may be determined in a functional cell-based assay on human CCR2 receptor.

A further example of a chemokine of the various embodiments of the invention containing modifications and specifically adapted for use in the invention is described in detail herein (see Example below). The modified CCL2 (MCP-1) corresponds to residues 1 to 76 of the full length mature protein (and lacks the N-terminal signal peptide of 23 amino acids, which is cleaved off) and thus retains the chemokine fold. The Gln at the N-terminus of the protein (Gln1) is substituted with pyroglutamine to prevent mixed species of N-terminal Gln and pyroGlu being generated. This improves the yield of synthesis and ensures a homogeneous chemokine preparation through column manufacture and use. FmocLys(ivDde)-OH is incorporated as residue 75 to facilitate site-specific labelling at this position of the protein (SEQ ID NO: 16). A suitable spacer, such as a PEG spacer, may be incorporated between the ϵ-amino functionality and the biotin. The biotinylated version comprises, consists essentially of or consists of the amino acid sequence of SEQ ID NO: 17.

Thus, in certain embodiments the invention also relates to a modified chemokine comprising, consisting essentially of or consisting of the amino acid sequence of:

```
SEQ ID NO: 15:
XPDAINAPVTCCYNFTNRKISVQRLASYRRITSSKCPKEAVIFKTIVAKE

ICADPKQKWVQDSMDHLDKQTQTPKT
```

X=pyroGlu or Gln

```
And/or SEQ ID NO: 17:
XPDAINAPVTCCYNFTNRKISVQRLASYRRITSSKCPKEAVIFKTIVAK

EICADPKQKWVQDSMDHLDKQTQTPXT
```

X1=pyroGlu or Gln

X75 is an amino acid residue that can be biotinylated, such as lysine, ornithine or diaminopropionic acid and optionally is biotinylated, optionally via a spacer molecule such as PEG, optionally K(PEG-Biotin)

A further example of a chemokine of the various embodiments of the invention containing modifications and specifically adapted for use in the invention is described in detail herein (see Examples below). The modified CCL5 (RANTES) corresponds to residues 1 to 68 of the full length mature protein (and lacks the N-terminal signal peptide of 23 amino acids, which is cleaved off) and thus retains the chemokine fold. The single methionine (Met67) within the sequence is mutated to lysine, to mitigate against oxidation of this residue during the chain assembly (SEQ ID NO: 18). This Met to Lys substitution provides a lysine at position 67 which can be modified through biotinylation. FmocLys (ivDde)-OH is incorporated as residue 67 to facilitate site-specific labelling at this position of the protein (SEQ ID NO: 19). The biotinylated version comprises, consists essentially of or consists of the amino acid sequence of SEQ ID NO: 20.

Thus, in other embodiments the invention also relates to a modified chemokine comprising, consisting essentially of or consisting of the amino acid sequence of SEQ ID NO: 20:

```
SPYSSDTTPCCFAYIARPLPRAHIKEYFYTSGKCSNPAVVFVTRKNRQVC
ANPEKKWVREYINSLEXS
```

X is an amino acid residue that can be biotinylated, such as lysine, ornithine or diaminopropionic acid and optionally is biotinylated, optionally via a spacer molecule such as PEG (e.g. K(Biotin))

A further example of a chemokine of the various embodiments of the invention containing modifications and specifically adapted for use in the invention is described in detail herein (see Examples below). The modified CCL8 (MCP-2) corresponds to residues 1 to 76 of the full length mature protein (and lacks the N-terminal signal peptide of 23 amino acids, which is cleaved off) and thus retains the chemokine fold. The Gln at the N-terminus of the protein is subject to pyroGlu formation under physiological conditions. Thus Gln1 of the sequence is substituted with pyroglutamine to prevent mixed species of N-terminal Gln and pyroGlu being generated (SEQ ID NO: 21). This improves the yield of synthesis and ensures a homogeneous chemokine preparation through column manufacture and use. FmocLys(ivDde)-OH is incorporated as residue 75 to facilitate site-specific labelling at this position of the protein (SEQ ID NO: 22). The naturally occurring lysine at position 75 is modified through biotinylation. A suitable spacer, such as a PEG spacer, may be incorporated between the ε-amino functionality and the biotin (SEQ ID NO: 23):

Thus, in other embodiments the invention also relates to a modified chemokine comprising, consisting essentially of or consisting of the amino acid sequence of SEQ ID NO: 23:

```
XPDSVSIPITCCFNVINRKIPIQRLESYTRITNIQCPKEAVIFKTKRGKE
VCADPKERWVRDSMKHLDQIFQNLXP
```

X1=pyroGlu (but may remain as Gln in some embodiments)

X75=an amino acid residue that can be biotinylated, such as lysine, ornithine or diaminopropionic acid and optionally is biotinylated, optionally via a spacer molecule such as PEG, e.g. K(PEG-Biotin).

Chemokines useful in the various embodiments of the invention may be synthesised through any suitable means known in the art. Preferably, the chemokines are chemically synthesised as this facilitates modification and labelling etc. However, recombinant DNA based approaches may also be employed in combination with appropriate labelling and modification technologies as required. Thus, in certain embodiments the invention also provides a nucleic acid molecule encoding the chemokines of the various embodiments of the invention. In certain embodiments the invention also relates to a vector containing such a nucleic acid molecule and a host cell containing the vector. The vector may additionally comprise a suitable promoter operably linked to the nucleic acid molecule, to facilitate transcription of the corresponding mRNA molecule. The host cell may be capable of expressing the protein by transcription and translation of the nucleic acid molecule encoding a chemokine of the various embodiments of the invention.

The chemokines useful in the various embodiments of the invention can be biotinylated by methods known in the art such as described in WO 00/50088 A2, which is incorporated herein by reference in its entirety. As indicated above, site-specific labelling of the chemokines of the various embodiments of the invention is preferable, although any labelling technique which does not significantly affect the receptor-binding capacity of the chemokine may be employed. Various site-specifically biotinylated chemokines and native chemokines are available commercially, for instance from Almac, Craigavon, UK. In specific embodiments the one or more chemokines are biotinylated via a spacer group. The spacer may be employed to prevent the biotin group from impacting on the activity of the chemokine, in particular binding of the chemokine to its cognate receptor. Any suitable spacer that facilitates retention of receptor binding properties of the chemokine may be employed in the various embodiments of the invention. Thus, in the specific embodiments described above, spacers other than PEG spacers may be employed as appropriate. In specific embodiments, the spacer is a polyethylene glycol (PEG) spacer. PEG has been shown to be an effective spacer permitting attachment of biotin to the chemokine (which can then be immobilized on the solid support through interaction with streptavidin) without compromising receptor binding capability.

In the context of the various embodiments of the present invention the term "antibody" includes all immunoglobulins or immunoglobulin-like molecules with specific binding affinity for the relevant chemokine receptor (including by way of example and without limitation, IgA, IgD, IgE, IgG and IgM, combinations thereof, and similar molecules produced during an immune response in any vertebrate, for example, in mammals such as humans, goats, rabbits and mice). Specific immunoglobulins useful in the various embodiments of the invention include IgG isotypes. The antibodies useful in the various embodiments of the invention may be monoclonal or polyclonal in origin, but are typically monoclonal antibodies. Antibodies may be human antibodies, non-human antibodies, or humanized versions of non-human antibodies, or chimeric antibodies. Various techniques for antibody humanization are well established and any suitable technique may be employed. The term "antibody" also refers to a polypeptide ligand comprising at least a light chain or heavy chain immunoglobulin variable region which specifically recognizes and binds an epitope of an antigen, and it extends to all antibody derivatives and fragments that retain the ability to specifically bind to the relevant chemokine receptor. These derivative and fragments may include Fab fragments, F(ab')2 fragments, Fv fragments, single chain antibodies, single domain antibodies, Fc fragments etc. The term antibody encompasses antibodies comprised of both heavy and light chains, but also heavy chain (only) antibodies. In specific embodiments, the antibodies may be engineered so as to be specific for more than one chemokine receptor, for example bi-specific to permit binding to two different chemokine receptors. Suitable commercially available antibodies which bind to the chemokine receptors of interest are listed in table 2. They may or may not be labelled. General reference may be made to "Antibodies a laboratory manual: By E Harlow and D Lane. pp 726. Cold Spring Harbor Laboratory. 1988", which reference is incorporated herein in its entirety. Anti-CCR2 antibodies are described for example in WO 2010/021697, incorporated herein by reference. Further examples of potentially useful antibodies include MLN-1202, an anti-CCR2 monoclonal antibody currently undergoing clinical trials (Millennium Pharmaceuticals).

TABLE 2

Commercially available fluorophore labelled antibodies against specific chemokine receptors

| Antibody | Fluorophore | Supplier |
|---|---|---|
| CCR5 | PE | Biolegend |
| CCR3 | PE | Biolegend |
| CCR1 | Alexa Fluor 647 | Biolegend |
| CCR2 | PerCP Cy5.5 | BD Biosciences |
| CCR4 | PerCP Cy5.5 | BD Biosciences |

The chemokine receptor expressing cells may thus be targeted using alternative binding agents, such as antibodies or other chemical compounds, as defined herein, rather than the natural chemokine binding partner. This approach is a new approach to treating inflammatory conditions.

Thus, in certain embodiments the invention also provides an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine. The binding reagent capable of specifically binding to the chemokine receptor may be an agonist or an antagonist of the chemokine receptor. In specific embodiments, the binding reagent capable of specifically binding to the chemokine receptor is selected from an antibody and a chemical compound.

In other embodiments the invention thus also provides a method for treating an inflammatory condition comprising applying peripheral blood from a patient/subject to an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine) thus removing chemokine receptor expressing cells from the peripheral blood of the patient/subject. The method may comprise returning the blood depleted of the chemokine receptor expressing cells to the patient/subject.

Similarly, in other embodiments the invention provides a binding reagent capable of specifically binding to a chemokine receptor for use in the treatment of an inflammatory condition, wherein the binding reagent is immobilized on a solid support contained within an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient/subject, wherein the binding reagent is not a chemokine), to which is applied peripheral blood from a patient thus removing chemokine receptor expressing cells from the peripheral blood of the patient.

These aspects of the various embodiments of the invention may be integrated into the more focussed therapeutic aspects of the various embodiments of the invention (i.e. treating metabolic syndrome disorders and various aspects thereof including diabetes and Adioposis Dolorosa (AD)) and thus, the remainder of the disclosure, including all specific embodiments applies mutatis mutandis.

Solid support materials for immobilizing the binding reagents of the various embodiments of the invention are known in the art. "Solid support" refers to, for example, materials having a rigid or semi-rigid surface or surfaces, and may take the form of beads, resins, gels, microspheres, or other geometric configurations. A useful support material is one that does not activate blood cells so as to make them coagulate or adhere to the support as peripheral whole blood is applied to the device. In certain embodiments, a support treated with an agent to provide it with anti-coagulation properties, in particular a heparinized support is employed. Alternatively, the blood of the patient may be treated with an anti-coagulant such as heparin prior to application to the support. Useful support materials comprise high molecular weight carbohydrates, in particular carbohydrates having a molecular weight of 100 kDa or more, such as agarose, in particulate form, optionally cross-linked, and cellulose. Other preferred support materials are polymers, such as carboxylated polystyrene, and glass. The support of the various embodiments of the invention may be provided in the form of particles or fibres. The support particles may have regular form, such as spheres or beads, or irregular form. They may be porous or non-porous. A preferred average particle size of the support is from 50 μm to 2 mm. In certain embodiments Sepharose™, a cross linked, beaded-form of agarose, is used as column matrix. It is chosen for its optimal distribution capacity and can provide a large available area for affinity binding. Solid supports may be provided in the form of magnetic beads, with the specific binding reagent immobilized on the magnetic beads. Following capture of the (CCR2, CCR1, CCR3, CCR4 and/or CCR5) chemokine receptor expressing cells from the blood, the beads can be removed from the blood with the aid of an appropriate magnetic separator.

Methods for immobilizing binding reagents on a solid support are known in the art. A binding reagent, such as a chemokine, antibody, peptide, nucleic acid or chemical compound, can be immobilized on the support in a direct or indirect manner. Immobilization can be by means of a suitable linker in some embodiments. A preferred method of indirect immobilization of a binding reagent, such as a chemokine, relies upon the interaction between biotin and avidin molecules. "Avidin" or "avidin molecule" refers to any type of protein that specifically binds biotin to the substantial exclusion of other (small) molecules that might be present in a biological sample. Examples of avidin include avidins that are naturally present in egg white, oilseed protein (e.g., soybean meal), and grain (e.g., corn/maize), and streptavidin, which is a protein of bacterial origin. Thus, biotinylation of the binding reagent and use of an avidin molecule such as streptavidin immobilized on the solid support allows reliable attachment of the binding reagent to the solid support according to methods known in the art. Specifically, such a method may comprise providing the binding reagent in biotinylated form, providing a solid support having streptavidin immobilized on its surface, contacting the support with an aqueous solution of the biotinylated binding reagent, and rinsing the support with an aqueous solvent. In addition, binding pair interactions, such as antibody-antigen interactions, may also be utilised for indirect immobilisation of binding reagent onto a support. In such embodiments the support may be derivatised with one member of a binding pair, such as an antibody or fragment or derivative thereof, as defined herein, which has known affinity for a particular peptide sequence or small molecule hapten. Incorporating the other member of the binding pair, such as an antigen, peptide sequence or the hapten onto or into the binding reagent facilitates immobilisation onto a solid support coated with the corresponding antibody or fragment or derivative thereof. Thus, the binding reagent may be modified to include the peptide sequence or hapten into the linear molecule or may be added as a side chain or label. Any suitable antibody-antigen pair may be employed. The antibody fragment or derivative may be any fragment or derivative that retains specific binding affinity for the appropriate antigen. Examples include Fab, F(ab')2 fragments, scFV, VH domains, single domain antibodies (such as nanobodies), heavy chain antibodies and humanized version of non-human antibodies etc. Other high affinity interactions can be utilised for immobilisation of binding reagents, as long as the binding reagent can be synthesised or derivatised with one of the interacting partners and the solid support synthesised or derivatised with the other interacting partner without loss of binding activity (i.e. binding of the binding reagent to the appropriate chemokine receptor). Immobilization may occur via essentially the same interaction in reverse in some embodiments. Thus, the binding reagent which may be a chemokine for example, may be attached to an antibody as defined herein, and the solid support derivatised with the antigen. The chemokine may be produced as a fusion protein with the antibody.

Alternatively binding reagents, such as chemokines and antibodies, can be immobilised directly onto a solid support using bioconjugation techniques established in the field. For example direct immobilisation of proteins onto cyanogen bromide activated solid supports via amino functionalities within the primary sequence of the protein. Alternatively, sulphydryl functionalities within proteins can be used to directly immobilise the protein to alkyl halide derivatised supports or supports containing free thiol functionalities. In further embodiments, proteins containing α-thioester functionalities can be directly immobilised on supports containing 1,2 amino thiol moieties (eg N-terminal cysteine) using the native chemical ligation reaction. Alternatively proteins modified with ketones and aldehydes can be immobilised on solid supports derivatised with hydrazinyl, hydrazide and aminoxy functionalities using hydrazone/oxime bond forming ligation reactions (and vice versa). Alternatively 'Click' chemistry can be used to immobilise proteins onto solid supports, whereby the protein and the support are derivatised with the appropriate mutually reactive chemical functionalities (azides and alkynes). In other embodiments Staudinger ligation chemistry can be used to immobilise appropriately derivatised proteins onto the appropriately derivatised solid supports.

The solid support is contained within or carried by the apheresis column. Thus, by "loaded" is meant that the column carries or contains the solid support in a manner such that (peripheral) blood can flow through the column in contact with the solid support. Thus, the solid support provides a matrix within the column through which blood flows, in continuous fashion in certain embodiments. This permits cells expressing the specific chemokine receptor to be removed from the blood passing through the column, such that blood exiting the column is depleted of the specific chemokine receptor-expressing cells. In specific embodiments, the apheresis column is loaded with a support comprising streptavidin immobilized on the support and one or more biotinylated binding reagents, such as chemokines, bound to the streptavidin on the support. The solid support may be comprised of a high-molecular weight carbohydrate, optionally cross-linked, such as agarose.

As discussed above, the binding reagent is coupled to the solid support. The relative amounts of binding reagent may be controlled to ensure that coupling between the solid support and the binding reagent will be immediate, minimising the risk of binding reagent decoupling from the solid support. Thus, it may be ensured that there is a relative excess of immobilization sites for the binding reagent on the solid support. Alternatively, or additionally, following immobilization of the binding reagent on the solid support, the solid support may be washed to remove any unbound binding reagent.

The apheresis column utilised in the various embodiments of the present invention acts as a leukapheresis treatment for conditions associated with metabolic syndrome. The column acts to specifically remove one or more of CCR2, CCR1, CCR3, CCR4 and CCR5-expressing monocytes or leukocytes by exploiting the interaction between CCR2, CCR1, CCR3, CCR4 or CCR5 expressed on the cell surface and a specific binding reagent immobilized on a solid support contained within or carried by the column. The overall column typically comprises, consists of, or consists essentially of three combined components; 1) a housing which contains or carries 2) the solid support and 3) one or more binding reagents (immobilized thereon) which specifically bind one or more chemokine receptors. The housing may be manufactured from any suitable material for clinical use. In certain embodiments the housing is composed of a plastic material. The housing includes an in flow site for entry of blood and an out flow site for blood (depleted of target cells) to exit the column. The housing may be designed to maintain a continuous blood flow through the solid support matrix. The housing (as shown for example in FIG. 9) may include a top portion which comprises a distribution plate (2) at the inflow site (1) to spread the blood evenly over the entire matrix area. The distribution plate may act as a first safety barrier preventing larger particles flowing through the column and into the patient. However, the distribution plate is not essential and may be removed in some embodiments to decrease the overall resistance in the system. The column may contain one or more safety filter units (3 and 4) placed at the inflow (1) and/or outflow (5) sites of the plastic housing. Such filter units may act to prevent particles larger than blood cells passing in and/or out of the column. The safety filter units may contain a plurality of filters, such as two, three or four filters designed to be a robust barrier and stop all particles larger than blood cells passing through the column. Inclusion of safety filters (3 and 4) at both ends of the column serves to minimize the risk of leakage of particles into the patient, including in the event that the device is incorrectly connected resulting in blood flow in the opposite direction to that intended. The safety filters may comprise of any suitable pore size to prevent particles larger than blood cells from passing through the column, as would be readily understood by one skilled in the art. Suitable filters are commercially available. In specific embodiments, the pore size of the filter(s) is between approximately 60 μm and 100 μm, more specifically approximately 80 μm. The solid support and binding reagent components are discussed in further detail herein.

The volume of the housing may be varied depending upon the blood volumes intended to pass through the column. Typically, the volume of the housing is between approximately 40 ml and 200 ml, more specifically 50 ml to 150 ml or 60 ml to 120 ml.

The column is generally applied in the form of an apheresis circuit. In this context, the overall system includes the apheresis column, tubing and an appropriate pump to pump the blood around the circuit. The system is illustrated in FIG. 10. The patient (1) is connected to the extracorporeal circuit via sterile needles to veins in the right and the left arms. A saline bag (3) is also connected and the saline solution is pumped with a suitable pump (2). Blood is drawn from one arm of the patient through the sterile tubing system by the blood pump (4) and passed through the column (6) and back to the patient. The tubing system may be connected to the column via any suitable coupling, such as standard dialysis luer-lock couplings. The couplings on the column may be colour-coded for correct assembly. For example, red tubing for inflow to the red column top and blue tubing for outflow back to the patient. An air detector (8) may be present in the circuit. Inlet pressure (5) and/or Pven sensors (7) may additionally be employed to monitor the pressure in the circuit.

An apheresis pump, such as the 4008 ADS pump manufactured by Fresenius Medical Care or the Adamonitor pump, may monitor the patient's inflow and outflow. The pump may also monitor the pressure in the extracorporeal circulation. The pump may be able to discriminate air by a bubble catcher and air detector. A clot catcher filter may be positioned inside the bubble catcher. The pump may also incorporate an optical detector to distinguish between light, e.g. saline solution or air present in the tubing system and dark e.g. blood present in the tubing system.

A schematic diagram of a suitable pump, showing the air detector and optical filter is shown in FIG. 11. If the pump system detects air bubbles and optical fluctuations or if extracorporeal pressure values are out of the set range, then the pump may stop immediately. Alternatively or additionally a visual/audible alarm may be emitted.

The treatment methods of the various embodiments of the invention may thus rely upon an extracorporeal circuit. The methods may be considered as ex vivo or in vitro methods and be defined solely with reference to steps performed outside of the patient. In some embodiments, however, the method further comprises, prior to application of the blood to the column, collecting peripheral blood from the patient. In a further embodiment, the method further comprises, following the application of the blood to the column, infusing the blood depleted of (CCR2, CCR1, CCR3, CCR4 and/or CCR5) chemokine receptor expressing cells to the patient. This is then a complete leukapheresis treatment method. Thus, a leukaphereis method, for treating a condition associated with metabolic syndrome, comprises collecting peripheral blood from the patient; applying the peripheral blood to an apheresis column loaded with a solid support comprising one or more binding reagents capable of specifically binding to one or more chemokine receptors, in particular the chemokine receptor CCR2, CCR1, CCR3, CCR4 or CCR5, immobilized directly or indirectly on the support thus removing one or more of CCR2, CCR1, CCR3 and CCR5 expressing cells from the peripheral blood of the patient; and infusing the depleted blood (of chemokine receptor expressing cells) to the patient.

The peripheral blood may be continuously collected from the patient. Similarly, the depleted blood may be continuously infused to the patient, through use of an appropriate circuit as described herein. Thus, the support may be disposed in a column through which the blood is made to flow. This may be achieved using a suitable pump for example, as also described herein. Blood flow through the column enables the binding reagent(s) immobilized on the solid support to capture the cells expressing the chemokine receptor, thus depleting them from the blood and preventing their contribution to the inflammatory condition associated with metabolic syndrome.

The methods of the various embodiments of the invention and binding reagents for use in the methods of the various embodiments of the invention may require that the patient has been selected for treatment on the basis of detecting an increase in the level of chemokine receptor, in particular, one or more of CCR2, CCR1, CCR3, CCR4 and CCR5 expressing cells in a sample obtained from the patient. Such companion diagnostic methods are described in greater detail herein and are based, for example, on the observation that CCR2, CCR1, CCR3, CCR4 and/or CCR5 expression on monocytes is elevated in patients with type 2 diabetes.

Thus, (in this context) in certain embodiments the invention also provides a method of diagnosing, monitoring progression of, or monitoring treatment of a condition associated with metabolic syndrome comprising determining:

a) the levels of one or more of the chemokine receptor CCR2, CCR1, CCR3, CCR4 and CCR5 expressing cells b) levels of expression of one or more of CCR2, CCR1, CCR3, CCR4 and CCR5; and/or c) levels of cells with high expression of one or more of CCR2, CCR1, CCR3, CCR4 and CCR5 in a sample obtained from a subject, wherein high levels of one or more of CCR2, CCR1, CCR3, CCR4 and CCR5 expressing cells, high levels of expression of one or more of CCR2, CCR1, CCR3, CCR4 and CCR5 or high levels of cells with high expression of one or more of CCR2, CCR1, CCR3, CCR4 and CCR5 or increased levels of one or more of CCR2, CCR1, CCR3, CCR4 and CCR5 expressing cells compared to control, increased levels of expression of one or more of CCR2, CCR1, CCR3, CCR4 and CCR5 compared to a control or increased levels of cells with high expression of one or more of CCR2, CCR1, CCR3, CCR4 and CCR5 compared to a control indicate the presence or progression of a condition associated with metabolic syndrome. Levels of chemokine receptor expression, as opposed to cell numbers, may also be investigated as increased levels of chemokine receptor expression per cell may also be diagnostically relevant. These methods may be specifically applied to monocytes, in particular CCR2 expressing monocytes. They may also be applied to CCR4 and/or CCR5 expressing T lymphocytes.

The invention also specifically provides a method of diagnosing, monitoring progression of, or monitoring treatment of adiposis dolorosa (AD) comprising determining:

a) the levels of one or more of the chemokine receptor CCR2, CCR1, CCR3, CCR4 and CCR5 expressing cells b) levels of expression of one or more of CCR2, CCR1, CCR3, CCR4 and CCR5; and/or c) levels of cells with high expression of one or more of CCR2, CCR1, CCR3, CCR4 and CCR5 in a sample obtained from a subject, wherein high levels of one or more of CCR2, CCR1, CCR3, CCR4 and CCR5 expressing cells, high levels of expression of one or more of CCR2, CCR1, CCR3, CCR4 and CCR5 or high levels of cells with high expression of one or more of CCR2, CCR1, CCR3, CCR4 and CCR5 or increased levels of one or more of CCR2, CCR1, CCR3, CCR4 and CCR5 expressing cells compared to control, increased levels of expression of one or more of CCR2, CCR1, CCR3, CCR4 and CCR5 compared to a control or increased levels of cells with high expression of one or more of CCR2, CCR1, CCR3, CCR4 and CCR5 compared to a control indicate the presence or progression of AD. Levels of chemokine receptor expression, as opposed to cell numbers, may also be investigated as increased levels of chemokine receptor expression per cell may also be diagnostically relevant. These methods may be specifically applied to lymphocytes, in particular B cells and more specifically CCR2 expressing B cells. These methods may also be applied to monocytes, in particular CCR1 expressing monocytes.

"Diagnosing" is defined herein to include screening for a disease/condition or pre-indication of a disease/condition, identifying a disease/condition or pre-indication of a disease/condition and checking for recurrence of disease/condition following treatment. The methods of the various embodiments of the invention may also have prognostic value, and this is included within the definition of the term "diagnosis". The prognostic value of the methods of the various embodiments of the invention may be used as a marker of potential susceptibility to a condition associated with metabolic syndrome or AD by identifying levels of one or more of CCR2, CCR1, CCR3, CCR4 and CCR5 expression linked to conditions associated with that syndrome or AD. Thus patients at risk may be identified before the disease has a chance to manifest itself in terms of symptoms identifiable in the patient. In certain embodiments, diagnosis may be made in conjunction with other objective indicators of metabolic syndrome or AD. Thus, in specific embodiments, diagnosis is made in conjunction with one or more of the following indicators:

1. Central obesity, which may be defined as waist circumference ≥94 cm for Europid men and ≥80 cm for Europid women, with ethnicity specific values for other groups 2. Raised triglyceride (TG) level, which may be defined as ≥150 mg/dL (1.7 mmol/L), or specific treatment for this lipid abnormality 3. Reduced high-density lipoprotein (HDL) cholesterol, which may be defined as <40 mg/dL (1.03 mmol/L*) in males and <50 mg/dL (1.29 mmol/L*) in females, or specific treatment for this lipid abnormality 4. Raised blood pressure (BP), which may be defined as systolic BP≥130 or diastolic BP≥85 mm Hg, or treatment of previously diagnosed hypertension 5. Raised fasting plasma glucose (FPG), which may be defined as ≥100 mg/dL (5.6 mmol/L), or previously diagnosed type 2 diabetes Factor 1 may be combined with any two of factors 2 to 5 in specific embodiments in conjunction with one or more of CCR2, CCR1, CCR3, CCR4 and CCR5 levels. In further specific embodiments, where FPG is above the threshold, which may be above 5.6 mmol/L or 100 mg/dL, an oral glucose tolerance test (OGTT) may be employed to define or confirm presence of the syndrome.

In the case of AD, diagnosis may be made in conjunction with one or more of the following indicators:

Levels of pain out of proportion to physical findings (Brodovsky S, Westreich M, Leibowitz A, Schwartz Y. Adiposis dolorosa (Dercum's disease): 10-year follow-up. Ann Plast Surg 1994; 33:664-8 and DeFranzo A J, Hall J H Jr, Herring S M. Adiposis dolorosa (Dercum's disease): liposuction as an effective form of treatment. Plast Reconstr Surg 1990; 85:289-92; incorporated herein by reference in their entirety). Pain increases with BMI, and patients are usually 50% above normal weight for their age.

Other findings in adiposis dolorosa include:

hyperalgesia to light pressure, acral swelling, bruising, and telangiectasia, fatigability and weakness, depression, confusion, and dementia.

Diagnosis may be made by ultrasonography and magnetic resonance imaging (Amine B, Leguilchard F, Benhamou C L. Dercum's disease (adiposis dolorosa): a new case-report. Joint Bone Spine 2004; 71:147-9, incorporated herein by reference in its entirety).

"Monitoring progression of" includes performing the methods to monitor the stage and/or the state and progression of the condition associated with metabolic syndrome and/or AD. Monitoring progression may involve performing the diagnostic methods multiple times on the same patient to determine whether the levels of one or more of CCR2, CCR1, CCR3, CCR4 and CCR5 expressing cells are increasing, decreasing or remaining stable over a certain time period. This may be in the context of a treatment regime.

"Monitoring the success of a particular treatment" is defined to include determining the levels of one or more of CCR2, CCR1, CCR3, CCR4 and CCR5 expressing cells before and after a treatment. The treatment is generally one aimed at treating a condition associated with metabolic syndrome and/or AD and may be a treatment according to one of the methods of the various embodiments of the invention as defined herein. Successful treatment may be determined with reference to a decrease in one or more of CCR2, CCR1, CCR3, CCR4 and CCR5 expressing cells as a result of, or following, the treatment. Thus, in such methods a level of one or more of CCR2, CCR1, CCR3, CCR4 and CCR5 expressing cells is determined prior to treatment. This level is recorded and a further assessment made at a predetermined time following the treatment. The comparison of levels of one or more of CCR2, CCR1, CCR3, CCR4 and CCR5 expressing cells permits the success of the treatment to be monitored. In specific embodiments, a single treatment is sufficient to cause a depletion of around 10%, 20%, 30%, 40%, 50%, 60% or 70%, or higher, up to 80%, 90%, 95% or more, or any range of values between and including these amounts, of one or more specific chemokine receptors, in particular one or more of CCR2, CCR1, CCR3, CCR4 and CCR5, expressing cells from the peripheral blood of the patient. In specific embodiments, at least around 50% depletion is achieved in a single treatment. Thus, successful treatment may be defined with reference to depletion of one or more of CCR2, CCR1, CCR3, CCR4 and CCR5 expressing cells. Treatment may lead to depletion of between approximately 100 and 500 million of one of more of CCR2, CCR1, CCR3, CCR4 and CCR5 expressing cells, such as monocytes, in certain embodiments. Additional factors may be included to determine successful treatment. For example, a lack of increase in one or more of CCR2, CCR1, CCR3, CCR4 and CCR5 expressing cells following treatment may indicate successful treatment in terms of preventing further progression of the condition, optionally combined with an improvement in other markers or staging of the condition associated with metabolic syndrome and/or AD. By binding to the column through the binding reagent-chemokine receptor interaction, chemokine receptor expressing cells are immobilized. These immobilized cells express further unoccupied chemokine receptors, which may be of the same or different type to those used for capture. These additional chemokine receptors may permit circulating chemokines which contribute to the inflammatory condition to be captured from the peripheral blood. Thus, a reduction in circulating (specific) chemokine levels may provide a measure of successful treatment.

In specific embodiments, the condition associated with metabolic syndrome is selected from diabetes; in particular type 2 diabetes, obesity, insulin resistance, increased serum triacylglycerol concentrations and hypertension or AD. In the case of diabetes, changes in levels of CCR2 expressing monocytes, including CCR2 expression on monocytes, (such as macrophages) may be monitored. In the case of AD, changes in levels of CCR2 expressing lymphocytes, including CCR2 expression on lymphocytes, (such as B-cells) may be monitored.

The sample in which one or more of CCR2, CCR1, CCR3, CCR4 and CCR5 expressing cell levels, levels of expression of one or more of CCR2, CCR1, CCR3, CCR4 and CCR5 and/or levels of cells with high expression of one or more of CCR2, CCR1, CCR3, CCR4 and CCR5 (defined as CCR2 hi, CCR1 hi, CCR3 hi or CCR5hi) are determined may comprise any suitable tissue sample or body fluid sample. Generally, the test sample is obtained from a human subject. Typically, the sample is a blood sample, in particular a peripheral blood sample. The sample may comprise an adipose tissue biopsy in certain embodiments. The methods may involve determining levels of one or more of CCR2, CCR1, CCR3, CCR4 and CCR5 expressing monocytes, macrophages or lymphocytes in certain embodiments. In the case of diabetes, changes in levels of CCR2 expressing monocytes, including CCR2 expression on monocytes, (such as macrophages) may be monitored. In the case of AD, changes in levels of CCR2 expressing lymphocytes, including CCR2 expression on lymphocytes, (such as B-cells) may be monitored.

Levels of CCR2, CCR1, CCR3, CCR4 or CCR5 expressing cells, levels of expression of CCR2, CCR1, CCR3, CCR4 or CCR5 and/or levels of cells with high expression of CCR2, CCR1, CCR3, CCR4 or CCR5 (defined as CCR2 hi, CCR1 hi, CCR3 hi or CCR5hi) may be determined according to any suitable method. For example, flow cytometry may be employed in order to determine the number of cells expressing CCR2, CCR1, CCR3, CCR4 or CCR5 in the sample, to determine levels of CCR2, CCR1, CCR3, CCR4 or CCR5 expression and/or to identify levels of CCR2hi, CCR1hi, CCR3hi or CCR5hi cells. Flow cytometric techniques are described herein and examples of commercially available antibodies suitably labelled for use in flow cytometry are set out in Table 2 for example. Alternatively, the method may involve steps of collecting and fixing the cells in the sample, followed by incubation with a suitable binding reagent that binds specifically to the CCR2, CCR1, CCR3, CCR4 or CCR5 chemokine receptor expressing cells in the sample. Any suitable binding reagent, as defined herein, may be employed. For example, a CCR-2 specific antibody may be employed. A wash step may be adopted following an incubation period to remove any unbound reagent. Suitable wash steps and incubation conditions would be well known to one skilled in the art. The binding reagent may be directly labeled in order to permit antibody binding to be directly determined. Alternatively a secondary binding reagent, such as an antibody, may be employed which binds to the first binding reagent and carries a label. Again, suitable incubation conditions and wash steps would be apparent to one skilled in the art. The primary and secondary binding reagents may form two halves of a binding pair. The binding interaction should not prevent the primary binding reagent binding to the CCR2, CCR1, CCR3, CCR4 or CCR5 receptor expressing cells, unless a competition assay is being employed. The two halves of a binding pair may comprise an antigen-antibody, antibody-antibody, receptor-ligand, biotin-streptavidin pair etc. in certain embodiments. Other techniques used to quantify chemokine (CCR2, CCR1, CCR3, CCR4 or CCR5) receptor expressing cell levels, to quantify levels of CCR2, CCR1, CCR3, CCR4 or CCR5 expression and/or to quantify levels of CCR2 hi, CCR1 hi, CCR3 hi or CCR5hi cells include PCR-based techniques such as QT-PCR and protein based methods such as western blot. Quantitation may be achieved with reference to fixed cell lines carrying known numbers of various receptor expressing cells and/or known levels of receptor expression per cell. Such fixed cell lines are available commercially (for example ChemiScreen™ cell lines from Millipore). Methods analogous to the treatment methods of the various embodiments of the invention may also be employed, with binding of CCR expressing cells to the solid support being determined following peripheral blood being passed through the column.

The levels of CCR2, CCR1, CCR3, CCR4 or CCR5 expressing cells, levels of expression of CCR2, CCR1, CCR3, CCR4 or CCR5 and/or levels of cells with high expression of CCR2, CCR1, CCR3, CCR4 or CCR5 (defined as CCR2, CCR1, CCR3, CCR4 or CCR5hi) may be determined relative to a suitable control. When diagnosing a condition associated with a metabolic syndrome, a threshold level of cells, level of expression of CCR2, CCR1, CCR3, CCR4 or CCR5 and/or level of cells with high expression of CCR2, CCR1, CCR3, CCR4 or CCR5 (defined as CCR2 hi, CCR1 hi, CCR3 hi or CCR5hi) may be set at or over which a positive diagnosis is made. This threshold may be determined based upon measuring levels of CCR2, CCR1, CCR3, CCR4 or CCR5 expressing cells, levels of expression of CCR2, CCR1, CCR3, CCR4 or CCR5 and/or levels of cells with high expression of CCR2, CCR1, CCR3, CCR4 or CCR5 (defined as CCR2 hi, CCR1 hi, CCR3 hi or CCR5hi) in samples obtained from diseased patients and comparing these levels with levels of CCR2, CCR1, CCR3, CCR4 or CCR5 expressing cells, levels of expression of CCR2, CCR1, CCR3, CCR4 or CCR5 and/or levels of cells with high expression of CCR2, CCR1, CCR3, CCR4 or CCR5 (defined as CCR2 hi, CCR1 hi, CCR3 hi or CCR5hi) in samples obtained from healthy subjects.

In certain embodiments, a metabolic syndrome such as diabetes is diagnosed on the basis of levels of chemokine receptor expressing cells. A positive diagnosis may be made in subjects based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, a metabolic syndrome such as diabetes is diagnosed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to healthy controls.

In specific embodiments, diabetes is diagnosed on the basis of levels of CCR2, CCR4 or CCR5 expressing cells. A positive diagnosis may be made in subjects based upon the presence of greater than about 10%, greater than about 15% or greater than about 20% CCR4 expressing T cells in the sample, as a percentage of total cells in the sample. A positive diagnosis may be made in subjects based upon the presence of greater than about 40%, greater than about 45% or greater than about 50% CCR5 expressing T cells in the sample, as a percentage of total cells in the sample. A positive diagnosis may be made in subjects based upon the presence of greater than about 80%, greater than about 85% or greater than about 90% CCR2 expressing monocytes in the sample, as a percentage of total cells in the sample. Diabetes may also be diagnosed on the basis of the presence of a about a 1.2 fold or greater increase, such as about a 1.5, 2, 2.5, 3, 3.5, 4, 4.5, 5, 10, 20, 50 or 100 or greater fold increase in the specific chemokine receptor expressing cells, relative to healthy controls.

In other embodiments, AD is diagnosed on the basis of measuring levels of chemokine receptor expressing cells. Thus, a positive diagnosis according to the various embodiments of the invention may be made based upon the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to healthy controls. In specific embodiments, AD is diagnosed on the basis of measuring levels of CCR1 expressing cells. A positive diagnosis may be made in subjects where the levels of CCR1 expressing cells, in particular CCR1 expressing monocytes, are increased relative to healthy controls. Thus, a diagnosis according to the various embodiments of the invention may be made based upon the presence of about a 1.2-fold or greater increase, such as about a 1.5, 2, 2.5, 3, 3.5, 4, 4.5, 5, 10, 20, 50 or 100 or greater fold increase in CCR1 expressing cells, in particular CCR1 expressing monocytes, relative to healthy controls. AD may be diagnosed on the basis of the presence of greater than about 70%, greater than about 75% or greater than about 80% CCR1 expressing monocytes in the sample, as a percentage of total cells in the sample.

In specific embodiments, AD is diagnosed on the basis of measuring levels of CCR2 expressing cells. A positive diagnosis may be made in subjects where the levels of CCR2 expressing cells, in particular CCR2 expressing B cells, are increased relative to healthy controls. Thus, a diagnosis according to the various embodiments of the invention may be made based upon the presence of about a 1.2-fold or greater increase, such as about a 1.5, 2, 2.5, 3, 3.5, 4, 4.5, 5, 10, 20, 50 or 100 or greater fold increase in CCR2 expressing cells, in particular CCR2 expressing B cells, relative to healthy controls. AD may be diagnosed on the basis of the presence of greater than about 1%, greater than about 1.5% or greater than about 2% CCR2 expressing B cells in the sample, as a percentage of total cells in the sample.

In certain embodiments, progression of metabolic syndrome conditions such as diabetes, which may be in the context of a treatment regime, is monitored on the basis of levels of chemokine receptor expressing cells at different time points. Progression of metabolic syndrome conditions such as diabetes may be indicated in subjects based upon an increase of greater than about 10%, such as an increase of greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more chemokine receptor expressing cells in the sample, as a percentage of total cells in the sample, compared to a sample taken from the same subject at an earlier time point. In other embodiments, progression of metabolic syndrome conditions such as diabetes is confirmed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to a sample taken from the same subject at an earlier time point.

In specific embodiments, diabetes is monitored on the basis of levels of CCR2, CCR4 and/or CCR5 expressing cells. Progression of the disease, which may be in the context of a treatment regime, may be indicated in subjects based upon the presence of an increase of greater than about 10%, such as greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more chemokine receptor expressing cells in the sample, as a percentage of total cells in the sample, compared to a sample taken from the same subject at an earlier time point.

Regression or successful treatment may be monitored based upon similar decreases over various time points. For example, regression or successful treatment may be indicated in subjects based upon a decrease of about 10%, such as a decrease of about 15%, about 20%, about 25%, about 30%, about 35%, about 40%, about 45%, about 50%, about 55%, about 60%, about 65%, about 70%, about 75% or more chemokine receptor expressing cells in the sample, as a percentage of total cells in the sample, compared to a sample taken from the same subject at an earlier time point. In other embodiments, regression of metabolic syndrome conditions such as diabetes is confirmed on the basis of the presence of a about a 1.2 fold or greater decrease, such as about a 1.5, 2, 2.5, 3, 3.5, 4, 4.5, 5, 10, 20, 50 or 100 or greater fold decrease in chemokine receptor expressing cells, relative to a sample taken from the same subject at an earlier time point.

In specific embodiments, diabetes is monitored on the basis of levels of CCR2, CCR4 and/or CCR5 expressing cells. Regression or successful treatment of the disease may be made in subjects based upon a decrease of about 50%, such as such as a decrease of about 55%, about 60%, about 65%, about 70%, about 75%, about 80%, about 85%, about 90%, about 95% or more CCR2, CCR4 and/or CCR5 expressing cells in the sample, as a percentage of total cells in the sample or by a decrease of about 10%, such as a decrease of about 15%, about 20%, about 25%, about 30%, about 35%, about 40%, about 45%, about 50%, about 55%, about 60%, about 65%, about 70%, about 75% or more chemokine receptor expressing cells in the sample, as a percentage of total cells in the sample, compared to a sample taken from the same subject at an earlier time point.

In other embodiments, progression of AD, which may be in the context of a treatment regime, is monitored on the basis of measuring levels of chemokine receptor expressing cells. Progression of AD may be indicated based upon the presence of about a 1.2-fold or greater increase, such as about a 1.5, 2, 2.5, 3, 3.5, 4, 4.5, 5, 10, 20, 50 or 100 or greater fold increase in chemokine receptor expressing cells, relative to a sample taken from the same subject at an earlier time point. In specific embodiments, AD is monitored on the basis of measuring levels of CCR2 and/or CCR1 expressing cells. In certain embodiments, progression of AD, which may be in the context of a treatment regime, is monitored on the basis of levels of chemokine receptor expressing cells at different time points. Progression of AD may be indicated in subjects based upon an increase of greater than about 10%, such as an increase of greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more chemokine receptor expressing cells in the sample, as a percentage of total cells in the sample, compared to a sample taken from the same subject at an earlier time point.

Progression of AD, which may be in the context of a treatment regime, may be identified in subjects where the levels of CCR2 expressing cells, in particular CCR2 expressing B cells, are increased relative to a sample taken from the same subject at an earlier time point. Thus, progression according to the various embodiments of the invention may be indicated based upon the presence of a about a 1.2-fold or greater increase, such as about a 1.5, 2, 2.5, 3, 3.5, 4, 4.5, 5, 10, 20, 50 or 100 or greater fold increase in CCR2 expressing cells, in particular CCR2 expressing B cells, relative to a sample taken from the same subject at an earlier time point.

Progression of AD, which may be in the context of a treatment regime, may be identified in subjects where the levels of CCR1 expressing cells, in particular CCR1 expressing monocytes, are increased relative to a sample taken from the same subject at an earlier time point. Thus, progression according to the various embodiments of the invention may be indicated based upon the presence of a about a 1.2-fold or greater increase, such as about a 1.5, 2, 2.5, 3, 3.5, 4, 4.5, 5, 10, 20, 50 or 100 or greater fold increase in CCR1 expressing cells, in particular CCR1 expressing monocytes, relative to a sample taken from the same subject at an earlier time point.

Regression or successful treatment may be monitored based upon similar decreases over various time points. For example, in some embodiments regression or successful treatment of AD may be indicated based upon a 1.2-fold or greater decrease, such as about a 1.5, 2, 2.5, 3, 3.5, 4, 4.5, 5, 10, 20, 50 or 100 or greater fold decrease in chemokine receptor expressing cells, relative to a sample taken from the same subject at an earlier time point. In other embodiments, regression or successful treatment may be indicated in subjects based upon a decrease of about 10%, such as a decrease of about 15%, about 20%, about 25%, about 30%, about 35%, about 40%, about 45%, about 50%, about 55%, about 60%, about 65%, about 70%, about 75% or more chemokine receptor expressing cells in the sample, as a percentage of total cells in the sample, compared to a sample taken from the same subject at an earlier time point.

In specific embodiments, AD is monitored on the basis of measuring levels of CCR2 expressing cells. Regression or successful treatment may be identified in subjects where the levels of CCR2 expressing cells, in particular CCR2 expressing B cells, are decreased relative to a sample taken from the same subject at an earlier time point. Thus, regression or successful treatment according to the various embodiments of the invention may be indicated based upon the presence of about a 1.2-fold or greater decrease, such as about a 1.5, 2, 2.5, 3, 3.5, 4, 4.5, 5, 10, 20, 50 or 100 or greater fold decrease in CCR2 expressing cells, in particular CCR2 expressing B cells, relative to a sample taken from the same subject at an earlier time point.

In specific embodiments, AD is monitored on the basis of measuring levels of CCR1 expressing cells. Regression or successful treatment may be identified in subjects where the levels of CCR1 expressing cells, in particular CCR1 expressing monocytes, are decreased relative to a sample taken from the same subject at an earlier time point. Thus, regression or successful treatment according to the various embodiments of the invention may be indicated based upon the presence of about a 1.2-fold or greater decrease, such as about a 1.5, 2, 2.5, 3, 3.5, 4, 4.5, 5, 10, 20, 50 or 100 or greater fold decrease in CCR1 expressing cells, in particular CCR1 expressing monocytes, relative to a sample taken from the same subject at an earlier time point.

Suitable software is freely available (such as the R project for statistical computing) to perform the necessary statistical analysis of the data obtained to calculate a useful threshold. The threshold may be set to maximize sensitivity and/or specificity of the test. Performance of the test in these respects may be measured by plotting a receiver operating characteristics (ROC) curve (sensitivity versus specificity). The area under the curve provides an indication of the overall performance of the test. Thus, once thresholds have been set for diagnosing the condition, a separate control experiment does not necessarily have to be run each time a sample is tested. Rather reference can simply be made to the pre-existing thresholds to determine the diagnosis. However, in certain embodiments, the sample is tested together with a control sample taken from a healthy subject to provide a comparator based upon essentially identical experimental conditions. The test sample is generally tested in parallel with the control sample. The test sample level of CCR2, CCR1, CCR3, CCR4 or CCR5 expressing cells, levels of expression of CCR2, CCR1, CCR3, CCR4 or CCR5 and/or levels of cells with high expression of CCR2, CCR1, CCR3, CCR4 or CCR5 (defined as CCR2 hi, CCR1 hi, CCR3 hi or CCR5hi) can then be compared with that of the control sample to make the diagnosis. A control sample from a disease patient may also be tested in certain embodiments. Reference to controls permits relative levels ("high", "low" etc.) of CCR2, CCR1, CCR3, CCR4 or CCR5 expressing cells in the test sample to be readily identified and the significance thereof interpreted. Reference to controls also permits relative levels of CCR2, CCR1, CCR3, CCR4 or CCR5 expression ("high", "low" etc.) within the cell population to be determined and the significance thereof interpreted. Such determination may, for example, indicate the average levels of CCR2, CCR1, CCR3, CCR4 or CCR5 expression per cell in the test sample.

Thus, in specific embodiments, high or higher levels of one or more of CCR2, CCR1, CCR3, CCR4 and CCR5 expressing cells or high or higher levels of one or more of CCR2, CCR1, CCR3, CCR4 and CCR5 expression, for example average CCR2, CCR1, CCR3, CCR4 or CCR5 expression per cell, or high or higher levels of one or more of CCR2hi, CCR1hi, CCR3hi, CCR4hi and CCR5hi cells correlate with active disease or more active disease associated with metabolic syndrome or AD. Similarly, lower or low levels of one or more of CCR2, CCR1, CCR3, CCR4 and CCR5 expressing cells, or low or lower levels of one or more of CCR2, CCR1, CCR3, CCR4 and CCR5 expression, for example average CCR2, CCR1, CCR3, CCR4 or CCR5 expression per cell, or low or lower levels of one or more of CCR2hi, CCR1hi, CCR3hi, CCR4hi and CCR5hi cells may correlate with a lack of active inflammation or disease associated with metabolic syndrome or AD. This may be defined as "less active disease". It can readily be envisaged that control samples may be assessed and levels of CCR2, CCR1, CCR3, CCR4 or CCR5 expressing cells, levels of expression of CCR2, CCR1, CCR3, CCR4 or CCR5 and/or levels of cells with high expression of CCR2, CCR1, CCR3, CCR4 or CCR5 (defined as CCR2 hi, CCR1 hi, CCR3 hi or CCR5hi) determined across the range of severities of conditions associated with metabolic syndrome or across the range of severities of AD. This may assist in correlating the levels of CCR2, CCR1, CCR3, CCR4 or CCR5 expressing cells, levels of expression of CCR2, CCR1, CCR3, CCR4 or CCR5 and/or levels of cells with high expression of CCR2, CCR1, CCR3, CCR4 or CCR5 (defined as CCR2 hi, CCR1 hi, CCR3 hi or CCR5hi) in the test sample with the relative severity of the condition.

When monitoring progression of, or monitoring treatment of a condition associated with metabolic syndrome or AD, the control samples may be taken from the subject at an earlier time point. They may, however, be based upon known reference values as discussed above. Thus, relative levels of CCR2, CCR1, CCR3, CCR4 or CCR5 expressing cells, relative levels of CCR2, CCR1, CCR3, CCR4 or CCR5 expression including relative levels of average CCR2, CCR1, CCR3, CCR4 or CCR5 expression per cell or relative levels of CCR2 hi, CCR1 hi, CCR3 hi or CCR5hi cells may be with reference to samples taken from the same subject at a different point in time. In certain embodiments, decreased levels of one or more of CCR2, CCR1, CCR3, CCR4 and CCR5 expressing cells, decreased relative levels of one or more of CCR2, CCR1, CCR3, CCR4 and CCR5 expression including decreased relative levels of average CCR2, CCR1, CCR3, CCR4 or CCR5 expression per cell, or decreased relative levels of one or more of CCR2hi, CCR1hi, CCR3hi, CCR4hi and CCR5hi cells correlate with successful treatment. The treatment may be any suitable treatment, but in specific embodiments is a treatment according to the various embodiments of the invention.

When monitoring progression of a condition associated with metabolic syndrome or progression of AD, increased levels of one or more of CCR2, CCR1, CCR3, CCR4 and CCR5 expressing cells increased relative levels of one or more of CCR2, CCR1, CCR3, CCR4 and CCR5 expression including increased relative levels of average CCR2, CCR1, CCR3, CCR4 or CCR5 expression per cell or increased relative levels of one or more of CCR2 hi, CCR1 hi, CCR3 hi or CCR5hi cells may indicate the progression of condition or disease. Thus, if levels of one or more of CCR2, CCR1, CCR3, CCR4 and CCR5 expressing cells, levels of expression of one or more of CCR2, CCR1, CCR3, CCR4 and CCR5 and/or levels of cells with high expression of one or more of CCR2, CCR1, CCR3, CCR4 and CCR5 (defined as CCR2 hi, CCR1 hi, CCR3 hi or CCR5hi) are increased in a sample taken later than a sample from the same patient this may indicate progression of the condition.

Since the levels of one or more of CCR2, CCR1, CCR3, CCR4 and CCR5 expressing cells, levels of one or more of CCR2, CCR1, CCR3, CCR4 and CCR5 expression or levels of one or more of CCR2hi, CCR1hi, CCR3hi, CCR4hi and CCR5hi cells are diagnostically relevant, determining such levels in a sample obtained from a subject may influence treatment selection for that subject. Accordingly, in certain embodiments the invention provides a method of selecting a suitable treatment for a condition associated with metabolic syndrome comprising determining:

a) the levels of one or more of the chemokine receptor CCR2, CCR1, CCR3, CCR4 and CCR5 expressing cells b) levels of expression of one or more of CCR2, CCR1, CCR3, CCR4 and CCR5; and/or c) levels of cells with high expression of one or more of CCR2, CCR1, CCR3, CCR4 and CCR5 in a sample obtained from a subject, wherein high levels of one or more of CCR2, CCR1, CCR3, CCR4 and CCR5 expressing cells, high levels of expression of one or more of CCR2, CCR1, CCR3, CCR4 and CCR5 or high levels of cells with high expression of CCR2, CCR1, CCR3, CCR4 or CCR5 or increased levels of one or more of CCR2, CCR1, CCR3, CCR4 and CCR5 expressing cells compared to control, increased levels of expression of one or more of CCR2, CCR1, CCR3, CCR4 and CCR5 compared to a control or increased levels of cells with high expression of one or more of CCR2, CCR1, CCR3, CCR4 and CCR5 compared to a control, result in selection of a treatment as defined herein for treatment of the condition associated with metabolic syndrome. In certain embodiments, the chemokine receptor expressing cells are high chemokine receptor expressing cells, in particular, high CCR2, CCR1, CCR3, CCR4 or CCR5 expressing cells. In the case of diabetes, changes in levels of CCR2 expressing monocytes, including CCR2 expression on monocytes, (such as macrophages) may be monitored or CCR4 or CCR5 expressing T cells.

In specific embodiments, metabolic syndrome conditions such as diabetes is treated on the basis of measuring levels of chemokine receptor expressing cells. Thus, a treatment according to the various embodiments of the invention may be applied based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, metabolic syndrome conditions such as diabetes is treated according to the various embodiments of the invention on the basis of the presence of a about a 1.5 fold or greater increase, such as about a 2, 2.5, 3, 3.5, 4, 4.5, 5, 10, 20, 50 or 100 or greater fold increase in chemokine receptor expressing cells, relative to healthy controls.

In specific embodiments, diabetes is treated on the basis of measuring levels of CCR2, CCR4 or CCR5 expressing cells. Thus, a treatment according to the various embodiments of the invention may be applied based upon the presence of greater than about 80%, greater than about 85% or greater than about 90% CCR2 expressing monocytes in the sample, as a percentage of total cells in the sample or on the basis of the presence of a about a 1.5 fold or greater increase, such as about a 2, 2.5, 3, 3.5, 4, 4.5, 5, 10, 20, 50 or 100 or greater fold increase in chemokine receptor expressing cells, relative to healthy controls.

Thus, a treatment according to the various embodiments of the invention may be applied based upon the presence of greater than about 10%, greater than about 15% or greater than about 20% CCR4 expressing T cells in the sample, as a percentage of total cells in the sample. Thus, a treatment according to the various embodiments of the invention may be applied based upon the presence of greater than about 40%, greater than about 45% or greater than about 50% CCR5 expressing T cells in the sample, as a percentage of total cells in the sample or on the basis of the presence of a about a 1.5 fold or greater increase, such as about a 2, 2.5, 3, 3.5, 4, 4.5, 5, 10, 20, 50 or 100 or greater fold increase in chemokine receptor expressing cells, relative to healthy controls.

Similarly, the invention provides a method of selecting a suitable treatment for AD comprising determining:

a) the levels of one or more of the chemokine receptor CCR2, CCR1, CCR3, CCR4 and CCR5 expressing cells b) levels of expression of one or more of CCR2, CCR1, CCR3, CCR4 and CCR5; and/or c) levels of cells with high expression of one or more of CCR2, CCR1, CCR3, CCR4 and CCR5 in a sample obtained from a subject, wherein high levels of one or more of CCR2, CCR1, CCR3, CCR4 and CCR5 expressing cells, high levels of expression of one or more of CCR2, CCR1, CCR3, CCR4 and CCR5 or high levels of cells with high expression of CCR2, CCR1, CCR3, CCR4 or CCR5 or increased levels of one or more of CCR2, CCR1, CCR3, CCR4 and CCR5 expressing cells compared to control, increased levels of expression of one or more of CCR2, CCR1, CCR3, CCR4 and CCR5 compared to a control or increased levels of cells with high expression of one or more of CCR2, CCR1, CCR3, CCR4 and CCR5 compared to a control, result in selection of a treatment as defined herein for treatment of AD. In certain embodiments, the chemokine receptor expressing cells are high chemokine receptor expressing cells, in particular, high CCR2, CCR1, CCR3, CCR4 or CCR5 expressing cells. The cells may be lymphocyes, in particular B lymphocytes, especially CCR2 expressing B cells or CCR1 expressing monocytes.

In specific embodiments, AD is treated on the basis of measuring levels of chemokine receptor expressing cells. Thus, a treatment according to the various embodiments of the invention may be applied based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, AD is treated according to the various embodiments of the invention on the basis of the presence of a about a 1.5 fold or greater increase, such as about a 2, 2.5, 3, 3.5, 4, 4.5, 5, 10, 20, 50 or 100 or greater fold increase in chemokine receptor expressing cells, relative to healthy controls.

In specific embodiments, AD is treated on the basis of measuring levels of CCR2 or CCR1 expressing cells. Thus, a treatment according to the various embodiments of the invention may be applied based upon the presence of about a 1.2-fold or greater increase, such as about a 1.5, 2, 2.5, 3, 3.5, 4, 4.5, 5, 10, 20, 50 or 100 or greater fold increase in CCR1 expressing cells, in particular CCR1 expressing monocytes, relative to healthy controls. AD may be treated on the basis of the presence of greater than about 70%, greater than about 75% or greater than about 80% CCR1 expressing monocytes in the sample, as a percentage of total cells in the sample.

Thus, a treatment according to the various embodiments of the invention may be applied based upon the presence of about a 1.2-fold or greater increase, such as about a 1.5, 2, 2.5, 3, 3.5, 4, 4.5, 5, 10, 20, 50 or 100 or greater fold increase in CCR2 expressing cells, in particular CCR2 expressing B cells, relative to healthy controls. AD may be treated on the basis of the presence of greater than about 1%, greater than about 1.5% or greater than about 2% CCR2 expressing B cells in the sample, as a percentage of total cells in the sample.

For the avoidance of doubt, all embodiments described in respect of the methods of the various embodiments of the invention apply to these aspects mutatis mutandis and are not repeated for reasons of conciseness. Specifically, metabolic syndrome may be indicated in conjunction with one or more of the following indicators:

1. Central obesity, which may be defined as waist circumference ≥94 cm for Europid men and ≥80 cm for Europid women, with ethnicity specific values for other groups
2. Raised triglyceride (TG) level, which may be defined as ≥150 mg/dL (1.7 mmol/L), or specific treatment for this lipid abnormality
3. Reduced high-density lipoprotein (HDL) cholesterol, which may be defined as <40 mg/dL (1.03 mmol/L*) in males and <50 mg/dL (1.29 mmol/L*) in females, or specific treatment for this lipid abnormality
4. Raised blood pressure (BP), which may be defined as systolic BP≥130 or diastolic BP≥85 mm Hg, or treatment of previously diagnosed hypertension
5. Raised fasting plasma glucose (FPG), which may be defined as ≥100 mg/dL (5.6 mmol/L), or previously diagnosed type 2 diabetes Factor 1 may be combined with any two of factors 2 to 5 in specific embodiments in conjunction with one or more of CCR2, CCR1, CCR3, CCR4 and CCR5 levels. In further specific embodiments, where FPG is above the threshold, which may be above 5.6 mmol/L or 100 mg/dL, an oral glucose tolerance test (OGTT) may be employed to define or confirm presence of the syndrome. The condition associated with metabolic syndrome may be selected from diabetes, and more particularly type 2 diabetes, obesity, insulin resistance, increased serum triacylglycerol concentrations and hypertension. In specific embodiments, the sample is a peripheral blood sample.

In the case of AD, diagnosis may be made in conjunction with one or more of the following indicators:

Levels of pain out of proportion to physical findings (Brodovsky S, Westreich M, Leibowitz A, Schwartz Y. Adiposis dolorosa (Dercum's disease): 10-year follow-up. Ann Plast Surg 1994; 33:664-8 and DeFranzo A J, Hall J H Jr, Herring S M. Adiposis dolorosa (Dercum's disease): liposuction as an effective form of treatment. Plast Reconstr Surg 1990; 85:289-92; incorporated herein by reference in their entirety). Pain increases with BMI, and patients are usually 50% above normal weight for their age.

Other findings in adiposis dolorosa include:

hyperalgesia to light pressure, acral swelling, bruising, and telangiectasia, fatigability and weakness, depression, confusion, and dementia.

Diagnosis may be made by ultrasonography and magnetic resonance imaging (Amine B, Leguilchard F, Benhamou C L. Dercum's disease (adiposis dolorosa): a new case-report. Joint Bone Spine 2004; 71:147-9, incorporated herein by reference in its entirety).

The methods and medical uses of the various embodiments of the invention thus can be tailored to the need of individual patients or groups of patients on the basis of the various diagnostic methods of the various embodiments of the invention. By removing from the circulation one or more of CCR2, CCR1, CCR3, CCR4 and CCR5 expressing cells, such as monocytes, macrophages and lymphocytes, in particular monocytes, upregulated in various inflammatory conditions associated with metabolic syndrome, an important factor in the inflammatory process of metabolic syndrome associated conditions can be controlled. The method of the invention may be effective in treating or reversing conditions such as diabetes, obesity, insulin resistance, increased serum triacylglycerol concentrations and hypertension. The method of the invention may be effective in treating or reversing AD, in particular by targeting CCR2 expressing B cells shown to be upregulated in the disease condition. The method of the invention may be effective in treating or reversing diabetes by depleting pro-inflammatory CCR2 expressing monocytes (such as macrophages) using a suitable chemokine such as MCP-1 (CCL2), in particular biotinylated MCP-1. This provides inflamed tissue, such as adipose and liver tissue, with the opportunity to heal and helps to prevent the development of insulin resistance.

C. Treating Inflammatory Arthritis

Chemokines are a class of cytokine molecules involved in cell recruitment and activation in inflammation. Chemokines cause chemotaxis and activation of various subpopulations of cells in the immune system. The activity of chemokines is mediated primarily through tight binding to their receptors on the surface of leukocytes. In certain embodiments, the present invention is based on the realisation that the interaction between chemokines and cells expressing their receptors may be exploited for the treatment of specific inflammatory conditions. In particular, various inflammatory arthritis, such as rheumatoid arthritis, psoriatic arthritis and eosinophilic arthritis include an inflammatory component. The inventors have determined that targeting increased recruitment of specific chemokine receptor-expressing cells to the site of inflammation presents a new therapeutic approach to treat such conditions. Moreover, in such conditions, chemokine receptor expression on each cell may be increased again providing a therapeutic approach to treat such conditions. It is shown herein that subjects suffering from rheumatoid arthritis exhibit increased frequency of chemokine receptor expressing cells in the peripheral blood, in particular CCR1 and CCR2 expressing monocytes. It is also shown herein that the CCR2 and CCR1 cells can be removed using a suitable binding reagent, in particular CCL2 to remove CCR2 expressing cells and CCL5 (RANTES) (in biotinylated form) immobilized on a suitable matrix to remove CCR1 expressing cells. Similarly, it is shown herein that CCR5-expressing lymphocytes, in particular T-lymphocytes can be depleted in subjects suffering from rheumatoid arthritis using a suitable binding reagent, in particular CCL5 (RANTES), in biotinylated form, immobilized on a suitable matrix. Leukocytes with pro inflammatory functions are in the circulation and are recruited to the site of inflammation, i.e, the relevant joint, by the expression of local chemokines allowing transmigration of effector leukocytes into the joint. Thus, normal expression levels in the presence of local production of chemokines will promote inflammation. In a healthy subject where there is no production of local chemokines there is no extravasation of leukocytes to the joint. Therefore, subjects may have an increased expression level of chemokine receptor, increased number of chemokine receptor expressing cells or the chemokine receptor expression may be normal but the patient has an increased local chemokine production.

Thus, in certain embodiments the invention serves to reduce the recruitment of inflammatory leukocytes, which express characteristic chemokine receptors, and possibly express characteristic chemokine receptors at increased levels, to sites of inflammation linked to disorders such as rheumatoid arthritis, psoriatic arthritis and eosinophilic arthritis. This is achieved using specific binding reagents to capture specific chemokine receptor-expressing inflammatory leukocytes from the patient. Accordingly, in certain embodiments the invention provides in a first aspect a method for treating inflammatory arthritis comprising applying peripheral blood from a patient to an apheresis column loaded with a solid support comprising one or more binding reagents capable of specifically binding to one or more chemokine receptors, in particular the chemokine receptors CCR2, CCR1, CCR3 and/or CCR5, immobilized directly or indirectly on the support thus removing one or more chemokine receptor, in particular one or more of CCR2, CCR1, CCR3 and CCR5, expressing cells from the peripheral blood of the patient. The peripheral blood from which the chemokine receptor expressing cells have been removed may then be returned to the patient in order to complete the treatment. The invention may thus rely on a continuous extracorporeal circuit in some embodiments. Alternatively, the invention may comprise steps of obtaining peripheral blood from the patient, applying the peripheral blood to the column and subsequently returning the peripheral blood from which the chemokine receptor expressing cells have been removed to the patient.

As shown herein, suitable binding reagents can be immobilized onto a solid support, either directly or indirectly, to generate an apheresis column suitable for capturing relevant chemokine receptor-expressing cells. Where increased levels of chemokine receptor expression are observed, such cells may be preferably removed from the peripheral blood using the columns of the various embodiments of the invention. Thus, the methods of the various embodiments of the invention may preferably target one or more of CCR2hi, CCR1hi, CCR3hi and CCR5hi cells as defined herein for removal from the peripheral blood. "High" expression may be determined according to standard flow cytometry techniques. The level is measured relative to levels of expression of the chemokine receptor in cells taken from a healthy subject. The attached FIG. 55 provides an example of a gating strategy.

Herein, reference to CCR2, CCR1, CCR3 and/or CCR5 is intended to encompass selection of any one or more, up to all, of the chemokine receptors listed.

In other embodiments the invention further provides a binding reagent capable of specifically binding to one or more chemokine receptors, in particular to a chemokine receptor/the chemokine receptor CCR2, CCR1, CCR3 and/or CCR5, for use in the treatment of inflammatory arthritis, wherein the one or more binding reagents is immobilized, directly or indirectly, on a solid support contained within an apheresis column, to which is applied peripheral blood from a patient thus removing one or more chemokine receptor/CCR2, CCR1, CCR3 and/or CCR5 expressing cells from the peripheral blood of the patient. In certain embodiments the invention also provides for use of one or more binding reagents capable of specifically binding to a chemokine receptor/the chemokine receptor CCR2, CCR1, CCR3 and/or CCR5 for use in the manufacture of an apheresis column for treatment of inflammatory arthritis, wherein the one or more binding reagents is immobilized on a solid support contained within the apheresis column, to which is applied peripheral blood from a patient thus removing one or more of chemokine receptor/CCR2, CCR1, CCR3 and/or CCR5 expressing cells from the peripheral blood of the patient.

All embodiments described in respect of the methods of treatment of the various embodiments of the invention apply to these aspects mutatis mutandis and are not repeated for reasons of conciseness. Thus, the following discussion made with reference to the methods of treatment is also applicable to the medical use aspects of the various embodiments of the invention.

In certain embodiments the invention aims to treat a range of specific inflammatory arthritis conditions. Any relevant condition including an inflammatory component may be treated according to the methods of the invention. Specific conditions including an inflammatory component may be selected from rheumatoid arthritis, psoriatic arthritis and eosinophilic arthritis By treatment is meant a reduction in the specific chemokine receptor expressing cells in the peripheral blood of the patient. The reduction may comprise a reduction in cells that express chemokine receptors, in particular one or more of CCR2, CCR1, CCR3 and CCR5, at increased levels in diseased patients. The patient is typically a human patient but the term patient may include both human and non-human animal subjects in some embodiments. In the context of the various embodiments of the present invention, this typically involves a reduction in one or more of CCR2, CCR1, CCR3 and CCR5 expressing cells, such as one or more of "CCR2 hi, CCR1 hi, CCR3 hi and CCR5hi" expressing cells, in the peripheral blood of the patient. The CCR2, CCR1, CCR3 or CCR5 expressing cells comprise, consist essentially of or consist of monocytes, lymphocytes, in particular T lymphocytes neutrophils, macrophages, eosinophils and basophils in certain embodiments. In specific embodiments the cells removed in order to treat rheumatoid arthritis comprise monocytes, in particular CCR1 and/or CCR2 expressing monocytes. In other embodiments the cells removed in order to treat rheumatoid arthritis comprise T lymphocytes, in particular CCR5 expressing T lymphocytes.

Monocytes are produced by the bone marrow from haematopoietic stem cell precursors called monoblasts. Monocytes may differentiate into macrophages or dendritic cells. Monocytes and their macrophage and dendritic cell progeny serve a number of functions in the immune system including phagocytosis, antigen presentation and cytokine production. Monocytes may be characterized with reference to expression of the cell surface marker CD14, optionally together with CD16. Classical monocytes may be characterized by high level expression of the CD14 cell surface receptor (CD14++CD16− monocyte). Non-classical monocytes may be characterized by low level expression of CD14 and with additional co-expression of the CD16 receptor (CD14+CD16++ monocyte). Intermediate monocytes may be characterized by high level expression of CD14 and low level expression of CD16 (CD14++CD16+ monocytes). Macrophages are derived from monocytes and are responsible for protecting tissues from foreign substances. They are cells that possess a large smooth nucleus, a large area of cytoplasm and internal vesicles for processing foreign material. The term "macrophage" may refer to a monocyte-derived cell expressing one or more of the following cell surface markers CD14, CD11b, Lysozyme M, MAC-1/MAC-3 and CD68. The term macrophage includes both activated and un-activated macrophages. Activated macrophages may be characterized by expression of one or more of CD69, ENG, FCER2 and IL2RA, HLA-DR, CD86. Un-activated macrophages have not yet received activating signals through for example TLR receptors and therefore they express less activation markers on the cell surface which correlates with lesser maturation. M1 macrophages may be characterized by expression of one or more of CD16+CD32+CD64+ and secrete mainly IL-23 and IL-1, TNF, IL-6 and high levels of IL-12 and in addition effector molecules such as iNOS and ROI. M1 macrophages have cytotoxic features as opposed to M2 macrophages. M2 macrophages may be characterized by expression of one or more of SRA/B+CD163+MR+CD14+ and express TGFβ, IL-10 and IL-1Ra. Tumour associated macrophages (TAMs) share many characteristics with the M2 macrophages and are considered as M2 polarised macrophages. The M1/M2 paradigm can also be found in monocyte subsets where CD14+CD16−CXC3R1low monocytes are considered the "inflammatory" subset and the CD14lowCD16+CXC3R1high are "resident" monocytes.

The three major types of lymphocyte are T cells, B cells and natural killer (NK) cells. The term "T-lymphocyte" includes CD4+ T cells such as T helper cells (Th1 cells and Th2 cells), and CD8+ T cells such as cytotoxic T cells. Th1 cells may be characterized by expression of CCR5 and/or by production of IFN-γ. Th2 cells may be characterized by expression of CCR3 and/or by production of IL-4.

The claimed methods may, in some embodiments, target eosinophils. Eosinophilia is an important component of certain arthritic conditions, such as eosinophilic arthritis and may be defined as the presence of more than 500 eosinophils/microliter of blood. Thus, reducing numbers of circulating eosinophils represents an important therapeutic approach. Eosinophils, or eosinophil granulocytes, are white blood cells and represent an important immune system component. Along with mast cells, they also control mechanisms associated with allergy and asthma. They are granulocytes that develop during haematopoiesis in the bone marrow before migrating into blood.

The name "eosinophil" derives from the eosinophilic "acid-loving" properties of the cell. Normally transparent, it is this affinity that causes them to appear brick-red after staining with eosin, a red dye, using the Romanowsky method. The staining is concentrated in small granules within the cellular cytoplasm, which contain many chemical mediators, such as histamines and proteins such as eosinophil peroxidase, ribonuclease (RNase), deoxyribonucleases, lipase, plasminogen, and major basic protein. These mediators are released by a process called degranulation following activation of the eosinophil, and are toxic to both parasite and host tissues.

Eosinophils develop and mature in bone marrow. They differentiate from myeloid precursor cells in response to the cytokines interleukin 3 (IL-3), interleukin 5 (IL-5), and granulocyte macrophage colony-stimulating factor (GM-CSF). Eosinophils produce and store many secondary granule proteins prior to their exit from the bone marrow. After maturation, eosinophils circulate in blood and migrate to inflammatory sites in tissues in response to chemokines such as CCL11 (eotaxin-1), CCL24 (eotaxin-2), CCL5 (RANTES) and MCP1/4. Eosinophils may be activated by Type 2 cytokines released from a specific subset of helper T cells (Th2); IL-5, GM-CSF, and IL-3 are important for eosinophil activation as well as maturation. CD44 and CD69 have been shown to represent different types of cell-surface activation markers for human eosinophils. CD69 is absent from "fresh" eosinophils but expressed following activation (using cytokines). CD44 on the other hand is constitutively expressed but expression is significantly up-regulated in response to activation (Matsumoto et al., Am. J. Respir. Cell Mol. Biol., Volume 18, Number 6, June, 1998 860-866). Cell specific markers for eosinophils include CD9 and CDw125.

Basophils may also be known as basophil granulocyte. In contrast to eosinophils, these leukocytes are basophilic, i.e., they are susceptible to staining by basic dyes. Basophils contain large cytoplasmic granules which obscure the cell nucleus under the microscope. However, when unstained, the nucleus is visible and it usually has 2 lobes. Basophils store histamine, which is secreted by the cells upon stimulation.

Basophils have protein receptors on their cell surface that bind IgE, an immunoglobulin involved in macroparasite defense and allergy. It is the bound IgE antibody that confers a selective response of these cells to environmental substances, for example, pollen proteins or helminth antigens. Recent studies in mice suggest that basophils may also regulate the behavior of T cells and mediate the magnitude of the secondary immune response. Basophils may display an immunophenotype based upon expression (or lack thereof, indicated as "+" or "−" respectively of one or more of the following markers: FcεRI+, CD123, CD49b(DX-5)+, CD69+, Thy-1.2+, 2B4+, CD11bdull, CD117(c-kit)−, CD24−, CD19−, CD80−, CD14−, CD23−, Ly49c−, CD122−, CD11c−, Gr-1−, NK1.1−, B220−, CD3−, γδTCR−, αβTCR−, α4 and β4-integrin negative When activated, basophils degranulate to release histamine, proteoglycans (e.g. heparin and chondroitin), and proteolytic enzymes (e.g. elastase and lysophospholipase). They also secrete lipid mediators like leukotrienes, and several cytokines. Histamine and proteoglycans are pre-stored in the cell's granules while the other secreted substances are newly generated. Each of these substances contributes to inflammation. Recent evidence suggests that basophils are an important source of the cytokine, interleukin-4, perhaps more important than T cells. Interleukin-4 is considered one of the critical cytokines in the development of allergies and the production of IgE antibody by the immune system. There are other substances that can activate basophils to secrete which suggests that these cells have other roles in inflammation.

The various embodiments of the methods of the invention may involve specific binding interactions with any one or more of these further cell-surface (and cell-specific) markers in addition to the removal based upon binding to CCR2, CCR1, CCR3 or CCR5. Suitable binding reagents can be prepared to specifically bind to these cell-surface markers. The discussion of CCR2, CCR1, CCR3 or CCR5 specific binding reagents thus applies mutatis mutandis.

CCR2, CCR1, CCR3 or CCR5 expressed on these aforementioned cells binds to chemokines such as monocyte chemoattractant protein-1 (MCP-1) or), CCL5, MCP-2, MCP-3, MCP-4, or MCP-5. MCP-1 is a major chemoattractant for monocytes and memory T cells by means of their binding to its specific cell-surface receptor, CC-chemokine receptor-2 (CCR2). CCR2 also binds MCP-2, MCP-3, MCP-4 and MCP-5. CCL5 is the gene symbol approved by the HUGO Gene Nomenclature Committee for chemokine (C—C motif) ligand 5, also known as RANTES. The HGNC ID for this gene is 10632. The gene is located at chromosome position 17q11.2-q12. The previous symbol and name for the gene is D17S136E, SCYA5, "small inducible cytokine A5 (RANTES)". Synonyms for this gene include "beta-chemokine RANTES", MGC17164, RANTES, "regulated upon activation, normally T-expressed, and presumably secreted", "SIS-delta", SISd, "small inducible cytokine subfamily A (Cys-Cys), member 5", "T-cell specific protein p288", "T-cell specific RANTES protein", and TCP228. The Genbank reference sequence for CCL5 is AF043341.1. RANTES binds to CCR1, CCR3 or CCR5.

CCR1 is the gene symbol approved by the HUGO Gene Nomenclature Committee for chemokine (C—C motif) receptor 1. The HGNC ID for this gene is 1602. The gene is located at chromosome position 3p21. The previous symbol and name CMKBR1, SCYAR1. Synonyms for this gene include CD191, CKR-1, MIP1α R. The Entrez Gene reference sequence for CCR1 is 1230. CCR2 is the gene symbol approved by the HUGO Gene Nomenclature Committee for chemokine (C—C motif) receptor 2. The HGNC ID for this gene is 1603. The gene is located at chromosome position 3p21. The previous symbol and name for the gene is CMKBR2. Synonyms for this gene include CC-CKR-2, CD192, CKR2, FLJ78302, MCP-1-R. The NCBI Reference Sequence is NM_001123041.2 as available on 13 Jun. 2011, which is incorporated herein by reference in its entirety CCR3 is the gene symbol approved by the HUGO Gene Nomenclature Committee for chemokine (C—C motif) receptor 3. The HGNC ID for this gene is 1604. The gene is located at chromosome position 3p21.3. The previous symbol and name for the gene is CMKBR3. Synonyms for this gene include CC-CKR-3, CD193 and CKR3. The Genbank reference sequence for CCR3 is AF247361.1 as available on 13 Jun. 2011, which is incorporated herein by reference in its entirety CCR5 is the gene symbol approved by the HUGO Gene Nomenclature Committee for chemokine (C—C motif) receptor 5. The HGNC ID for this gene is 1605. The gene is located at chromosome position 3p21. The previous symbol and name for the gene is CMKBR5. Synonyms for this gene include CC-CKR-5, CD195 CKR-5, IDDM22 and CKR5. The Entrez Gene reference sequence for CCR5 is 1234 as available on 13 Jun. 2011, which is incorporated herein by reference in its entirety Treatment according to the various embodiments of the invention may result in alleviation or amelioration of symptoms, prevention of progression, regression of the condition, or complete recovery. Measurable parameters of successful treatment include one or more, up to all, of. Diminished ESR, CRP, increased Haemoglobin, American College of Rheumatologists response criteria, EULAR criteria. In specific embodiments, a single treatment is sufficient to cause a depletion of around 10%, 20%, 30%, 40%, 50%, 60% or 70%, or higher up to 80%, 90%, 95% or more, or any range of values between and including these amounts, of one or more of a specific chemokine receptor, in particular one or more of CCR2, CCR1, CCR3 and CCR5, expressing cells from the peripheral blood of the patient. In specific embodiments, at least around 50% depletion is achieved in a single treatment. Thus, successful treatment may be defined with reference to depletion of one or more of CCR2, CCR1, CCR3 and CCR5 expressing cells. Treatment may lead to depletion of between approximately 100 and 500 million CCR2, CCR1, CCR3 and/or CCR5 expressing cells, such as monocytes, in certain embodiments and more particularly to about 100, 150, 200, 250, 300, 350, 400, 450, or 500 million CCR1, CCR3, and/or CCR5 expressing cells.

By binding to the column through the binding reagent-chemokine receptor interaction, chemokine receptor expressing cells are immobilized. These immobilized cells express further unoccupied chemokine receptors, which may be of the same or different type to those used for capture. These additional chemokine receptors may permit circulating chemokines which contribute to the inflammatory condition to be captured from the peripheral blood. Thus, a reduction in circulating (specific) chemokine levels may provide a measure of successful treatment.

The duration of treatment may be readily determined by one skilled in the art and will depend upon factors such as the flow rate of the peripheral blood. Duration of treatment may be tied into monitoring of the treatment itself, with the treatment considered complete once a measurable parameter of treatment has reached a defined threshold. Any suitable parameter may be employed as discussed herein. Thus, for example, treatment may be considered complete when a reduction in one or more of CCR2, CCR1, CCR3 and CCR5 expressing cells, such as a 50% reduction in one or more of CCR2, CCR1, CCR3 and CCR5 expressing cells, has been achieved. The apheresis system may be operated at a flow rate of around 10-80 mL/min, or more specifically between around 20-70 mL/min, or between around 30-60 mL/min. In specific embodiments, the treatment is performed for a period of around 10, 20, 30, 40, 50, 60, 70, 80, 90, 100, 110, 120 etc., or any range of values between and including these amounts, minutes. The treatment is typically not aimed to remove all of the cells expressing the chemokine receptor in the peripheral blood, as a basal level of those cells is required in healthy subjects. However, it has been found that only low blood volumes need to be applied to the columns of the various embodiments of the invention in order to achieve effective levels of depletion of the chemokine receptor-expressing cells. Thus, in certain embodiments, around 10-80% or more specifically around 20, 30, 40 or 50%, or any range of values between and including these amounts, of the patient's blood is applied to the column in a single treatment. The volume of blood circulated through the apheresis column or system may be in the region of around 1000-3000 ml, such as around 1000, 1200, 1400, 1600, 1800 or 2000 ml or any range of values between and including these amounts. The treatment may be considered complete once this volume of blood has been circulated. The patient may be administered anticoagulants prior to each treatment session. A suitable solution, such as a sterile saline solution, optionally including an anticoagulant such as Heparin, may be used for priming the apheresis (extracorporeal) system. An additional volume of anticoagulant may be added to the circuit at the start of each treatment session, for example as a bolus injection.

In certain embodiments the invention relies upon a binding reagent which is capable of specifically binding to a chemokine receptor. This specific binding reaction permits cells expressing the chemokine receptor to be removed from the peripheral blood of the patient when the blood is passed over the solid support upon or within which the binding reagent is immobilized. Specific chemokine receptors of interest include CCR2, CCR1, CCR3 and CCR5, particularly CCR2. The binding reagent can be any binding reagent capable of specifically binding to the receptor in question. By "specific binding" is meant that the binding reagent displays sufficient specificity of binding and appropriate binding affinity/kinetics to permit removal of cells expressing one or more of CCR2, CCR1, CCR3 and CCR5 from the peripheral blood. Whilst it is not precluded that the binding reagent is capable of binding to other molecules, such as other chemokine receptors, the binding reagent will preferentially bind to cells expressing one or more of CCR2, CCR1, CCR3 and CCR5 and in particular to cells expressing increased levels of one or more of CCR2, CCR1, CCR3 and CCR5 (as defined further herein). The binding reagent capable of specifically binding to CCR2, CCR1, CCR3 or CCR5 may be either an agonist or an antagonist of CCR2, CCR1, CCR3 or CCR5, respectively. As the disease condition relies upon up-regulation of expression of or signaling via CCR2, CCR1, CCR3 or CCR5, in certain embodiments the binding reagent capable of specifically binding to CCR2, CCR1, CCR3 or CCR5 is an antagonist of CCR2, CCR1, CCR3 or CCR5, respectively. Chemokines are typically, although not necessarily exclusively (particularly in the case of truncated or modified forms) agonists of their cognate receptor and serve to activate the cells expressing the relevant receptor, as would be appreciated by one skilled in the art. Antibodies against the relevant chemokine receptor are generally considered to be antagonists, as would be appreciated by one skilled in the art. Specific examples of binding reagents include proteins or polypeptides, such as antibodies and receptor ligands, in particular chemokines. The binding reagent may be a nucleic acid molecule in certain embodiments. In some embodiments, the nucleic acid is an aptamer. Nucleic acid aptamers are polynucleotides of approximately 15-40 nucleotides long. Nucleic acid aptamers can be made using the SELEX process (systemic evolution of ligands by exponential enrichment) or any other process known to those of skill in the art.

In other embodiments, the binding reagent may be a peptide, and in certain instances, a peptide aptamer. Peptide aptamers are artificial recognition molecules that consist of a variable peptide sequence inserted into a constant scaffold protein (Baines I C, Colas P. Peptide aptamers as guides for small molecule drug discovery. Drug Discov Today. 2006; 11:334-341, incorporated herein by reference). A number of methodologies, such as phage display, ribosome display and yeast two-hybrid screening systems are available for screening a library of potential peptide-based binding agents. Similarly protein scaffolds based on domains such as fibronectins, ankyrin repeats, protein A, SH3 domains, lipocalins and, ubiquitin can be used as the binding agent. Again a number of technologies such as phage display and, ribosome display are available for screening a library of protein—based binding agents. Similarly, libraries of candidate chemical compounds can be screened for specific binding to the relevant chemokine receptor using suitable screening techniques known in the art, which may be high throughput screens in certain embodiments. The candidate binding agent may be immobilized on a solid support and the ability of the agent to specifically retain cells expressing the chemokine receptor of interest or labelled chemokine receptors determined. A range of cell types may be applied to the solid supports to confirm specificity of binding, or alternatively a mixed sample (such as peripheral blood) may be applied to the solid support. Retention of the cell type of interest (expressing the appropriate chemokine receptor) can be confirmed to identify suitable binding agents. A range of small-molecule antagonists of CCR-2 are discussed by Xia M and Sui Z in Expert Opin Ther Pat. 2009 March; 19 (3):295-303—Recent developments in CCR2 antagonists, and incorporated herein by reference.

In the context of the various embodiments of the present invention the term "chemokine" also comprises biotinylated or otherwise labelled chemokines. The term "chemokine" also comprises modified and truncated versions of the chemokine and chemokine fragments with the proviso that the modified or truncated form retains its ability to bind to its cognate receptor (and thus remains functional in the context of the various embodiments of the invention). The chemokine does not necessarily need to retain biological activity as it is specific binding affinity for CCR2, CCR1, CCR3 or CCR5 that is required. In certain embodiments, the chemokine lacks biological activity, for example in terms of activation of the (CCR2, CCR1, CCR3 or CCR5) receptor. Modifications may be made to improve protein synthesis, for example uniformity of product and yield. As known to those skilled in the art, exemplary modifications may comprise amino acid additions, substitutions, deletions or other modifications to one or more amino acids in the chemokine. Modifications may comprise substitution of the wild type amino acid with non-natural amino acids such as norleucine (NLeu) and derivatized amino acids such as pyroglutamic acid (pyroGlu). Such modifications may be made to minimize side-product formation during storage and use of the various embodiments of the columns of the invention. Modifications may be made to improve labelling, for example inclusion of a polyethylene glycol (PEG) spacer to facilitate biotinylation. The biotinylation and/or conjugation with fluorochromes or other labelling groups of the chemokine is performed in a manner which does not substantially affect the receptor binding capacity. Site specific biotinylation or other labelling is preferred as non-selective labelling of chemokines may compromise receptor binding activity. Bioinylation or other labelling is generally preferred at or towards the C-terminus of the protein as the inventors have found that modifications in this area are generally well tolerated (in terms of a minimal effect on receptor binding capability). Biotinylation may be carried out site-specifically at any suitable amino acid. Examples of suitable amino acids include lysine and ornithine. Generally, reference may be made to Natarajan S et al, Int. J. Pept. Protein Res., 1992, 40, 567-74; Baumeister B, Int. J. Peptide Res. And Therapeutics, 2005, 11, 139-141; Bioconjugate techniques 2nd edition, Greg T. Hermanson, incorporated by reference herein in its entirety.

Truncations may involve deletion of either N or C terminal amino acids as appropriate, or both. Typically, the truncated version will retain the residues required for the chemokine to fold correctly, for example to retain a chemokine fold structure, consistent with the requirement that a truncated version must retain the ability to bind to the relevant receptor (expressed by (on the surface of) a leukocyte). Chemokine molecules typically include disulphide bonds between the 1st and 3rd and 2nd and 4th cysteine residues respectively, as would be understood by one skilled in the art. Where sequences are presented herein, it is assumed that these disulphide bonds will form in the folded protein (unless otherwise stated). Truncated versions may comprise anywhere between 1 and 100 less amino acids, such as 1, 2, 3, 4, 5 etc amino acids, than the wild type amino acid sequence in certain embodiments. Of course, truncated versions may comprise further modification as detailed herein. The modified or truncated version may have 40%, 45%, 50%, 55%, 60%, 65%, 70%, 75%, 80%, 85%, 90%, 95% or more overall amino acid sequence identity with the full length wild type chemokine (where a deletion is counted as a difference in amino acid sequence) in certain embodiments. Over the common sequence between the molecules (i.e the amino acids that have not been deleted), there may be 80%, 85%, 90%, 91%, 92%, 93%, 94%, 95%, 96%, 97%, 98% or 99% amino acid sequence identity in certain embodiments. Sequence identity may be determined using known algorithms, such as BLAST or GAP analysis (GCG Program) (applying default settings), which are freely available. Chemokines may lack the N-terminal signal peptide which is cleaved off during synthesis in vivo.

Specific chemokines useful in the various embodiments of the present invention for binding to CCR2 include MCP-1, MCP-2, MCP-3, MCP-4 and MCP-5. Both MCP-1 and MCP-5 bind solely to the chemokine receptor CCR2 and so these chemokines may be preferred in some embodiments. Each chemokine is able to bind to a chemokine receptor implicated in inflammatory arthritis. More specifically, each of MCP-1, MCP-2, MCP-3, MCP-4 and MCP-5 are useful for removing CCR2 expressing cells from the blood of a patient. Specific chemokines useful in the present invention for binding to CCR1, CCR3 and/or CCR5 include RANTES. RANTES is able to bind to chemokine receptors implicated in inflammatory arthritis. More specifically, RANTES is useful for removing CCR1, CCR3 and/or CCR5 expressing cells from the blood of a patient. The chemokines described in greater detail herein (with reference to the relevant figures and amino acid sequences, as set forth in the SEQ ID NOs) may each be applied according to the various embodiments of the present invention. Chemokines MIP1g (CCL9), MRP-2 (CCL10), MIp-1d (CCL15) and CCL23 may bind CCR1 only, Chemokines Eotaxin (CCL11), Eotaxin-2 (CCL24) only bind CCR3, Chemokine MIP1b (CCL4) only binds CCR5. Each may be useful in the present invention.

CCL2 is the gene symbol approved by the HUGO Gene Nomenclature Committee for chemokine (C—C motif) ligand 2, also known as MCP-1. The HGNC ID for this gene is 10618. The gene is located at chromosome position 17q11.2-q21.1. The previous symbol and name for the gene is SCYA2 "small inducible cytokine A2 (monocyte chemotatic protein 1, homologus to mouse Sig-je)". Synonyms for this gene include GDCF-2, HC11, MCP1, MGC9434, SMC-CF, "monocyte chemoattractant protein-1", "monocyte chemotactic and activating factor", "monocyte chemotactic protein 1, homologous to mouse Sig-je", "monocyte secretory protein JE", "small inducible cytokine subfamily A (Cys-Cys), member 2". The Genbank reference sequence for CCL2 is BC009716.1 as available on 13 Jun. 2011, which is incorporated herein by reference in its entirety.

CCL8 is the gene symbol approved by the HUGO Gene Nomenclature Committee for chemokine (C—C motif) ligand 8, also known as MCP-2. The HGNC ID for this gene is 10635. The gene is located at chromosome position 17q11.2. The previous symbol and name for the gene is SCYA8, "small inducible cytokine subfamily A (Cys-Cys), member 8 (monocyte chemotactic protein 2)". Another synonym for this gene is HC14. The Genbank reference sequence for CCL8 is X99886.1 as available on 13 Jun. 2011, which is incorporated herein by reference in its entirety.

CCL7 is the gene symbol approved by the HUGO Gene Nomenclature Committee for chemokine (C—C motif) ligand 7, also known as MCP-3. The HGNC ID for this gene is 10634. The gene is located at chromosome position 17q11.2-q12. The previous symbol and name for the gene is SCYA6, SCYA7, "small inducible cytokine A7 (monocyte chemotactic protein 3)". Synonyms for this gene include FIC, MARC, MCP-3, MCP3, NC28, "monocyte chemoattractant protein 3", "monocyte chemotactic protein 3". The Genbank reference sequence for CCL7 is AF043338 as available on 13 Jun. 2011, which is incorporated herein by reference in its entirety.

CCL13 is the gene symbol approved by the HUGO Gene Nomenclature Committee for chemokine (C—C motif) ligand 13, also known as MCP-4. The HGNC ID for this gene is 10634. The gene is located at chromosome position 17q11.2-q12. The previous symbol and name for the gene is SCYA6, SCYA7, "small inducible cytokine A7 (monocyte chemotactic protein 3)". Synonyms for this gene include FIC, MARC, MCP-3, MCP3, NC28, "monocyte chemoattractant protein 3", "monocyte chemotactic protein 3". The Genbank reference sequence for CCL13 is AJ001634 as available on 13 Jun. 2011, which is incorporated herein by reference in its entirety.

MCP-5 is a mouse chemokine in the CC chemokine family. It is also known as Chemokine (C—C motif) ligand 12 (CCL12) and, due to its similarity with the human chemokine MCP-1, sometimes it is called MCP-1-related chemokine. The gene for MCP-5 is found in a cluster of CC chemokines on mouse chromosome 11. The NCBI reference sequence for CCL12 is NC_000077.5 as available on 13 Jun. 2011, which is incorporated herein by reference in its entirety.

CCL15 is the gene symbol approved by the HUGO Gene Nomenclature Committee for chemokine (C—C motif) ligand 15, also known as HCC-2 and Lkn-1. The HGNC ID for this gene is 10613. The gene is located at chromosome position 17q11.2. The previous symbol and name for the gene is SCYA15, "small inducible cytokine subfamily A (Cys-Cys), member 15". Synonyms for this gene include "CC chemokine 3", "chemokine CC-2", HCC-2, HMRP-2B, "leukotactin 1", Lkn-1, "macrophage inflammatory protein 5", "MIP-1 delta", MIP-1d, MIP-5, NCC-3, SCYL3. The Genbank reference sequence for CCL15 is AF031587.1 as available on 13 Jun. 2011, which is incorporated herein by reference in its entirety.

CCL23 is the gene symbol approved by the HUGO Gene Nomenclature Committee for chemokine (C—C motif) ligand 23. The HGNC ID for this gene is 10622. The gene is located at chromosome position 17q11.2. The previous symbol and name for the gene is SCYA23, "small inducible cytokine subfamily A (Cys-Cys), member 23". Synonyms for this gene include Ckb-8, CKb8, MIP-3, MPIF-1. The Genbank reference sequence for CCL23 is U58913.1 as available on 13 Jun. 2011, which is incorporated herein by reference in its entirety.

CCL4 is the gene symbol approved by the HUGO Gene Nomenclature Committee for chemokine (C—C motif) ligand 4. The HGNC ID for this gene is 10630. The gene is located at chromosome position 17q12-q23. The previous symbol and name for the gene is LAG1, SCYA4, "small inducible cytokine A4 (homologous to mouse Mip-1b)". Synonyms for this gene include Act-2, AT744.1, MIP-1-beta. The Genbank reference sequence for CCL4 is M23502.1 as available on 13 Jun. 2011, which is incorporated herein by reference in its entirety.

CCL5 is the gene symbol approved by the HUGO Gene Nomenclature Committee for chemokine (C—C motif) ligand 5, also known as RANTES. The HGNC ID for this gene is 10632. The gene is located at chromosome position 17q11.2-q12. The previous symbol and name for the gene is D17S136E, SCYA5, "small inducible cytokine A5 (RANTES)". Synonyms for this gene include "beta-chemokine RANTES", MGC17164, RANTES, "regulated upon activation, normally T-expressed, and presumably secreted", "SIS-delta", SISd, "small inducible cytokine subfamily A (Cys-Cys), member 5", "T-cell specific protein p288", "T-cell specific RANTES protein", TCP228. The Genbank reference sequence for CCL5 is AF043341.1 as available on 13 Jun. 2011, which is incorporated herein by reference in its entirety.

Examples of suitable modified chemokines of the various embodiments of the invention containing modifications and/or truncations and specifically adapted for use in the invention are described in detail herein. MCP-1 has been produced with residue 75, which may be a lysine, as the site of biotinylation on the chemokine (numbering based upon the mature protein having the amino acid sequence of SEQ ID NO: 25). Biotinylation permits immobilization of MCP-1 on a solid support (via a biotin-avidin interaction). The basic amino acid sequence of MCP-1, including a 23 amino acid leader sequence is set forth as SEQ ID NO: 24. The amino acid sequence of the mature protein is set forth as SEQ ID NO: 25. The inventors have determined that chemokines may display improved binding properties where the chemokine is biotinylated via a spacer group. The spacer may prevent the biotin group from impacting on the binding affinity of the chemokine. Any suitable spacer group may be employed. Further modifications may provide the molecule with advantageous properties. The invention also relates to derivatives of truncated MCP-1 chemokines. The amino acid sequence of the truncated version is set forth as SEQ ID NO: 26.

Accordingly, the invention also provides a modified MCP-1 chemokine comprising, consisting essentially of or consisting of the amino acid sequence set forth as SEQ ID NO: 24, SEQ ID NO: 25 or SEQ ID NO: 26 in which one or more of the following modifications have been made:

a) the glutamine residue 1 of SEQ ID NO: 25 has been replaced with pyroglutamine b) the C terminus is produced as an amide derivative (this may be achieved by synthesis on an amide linker)

c) the (C terminal region) residue at position 98 of SEQ ID NO: 24 or position 75 of SEQ ID NO: 25 or position 67 of SEQ ID NO: 26, which may be a lysine or ornithine residue, is biotinylated, optionally via a spacer group, in order to permit immobilization of the chemokine on a solid support; and/or d) the methionine residue at position 87 of SEQ ID NO: 24 or position 64 of SEQ ID NO: 25 or position 56 of SEQ ID NO: 26 has been replaced with norleucine.

The (C terminal region) amino acid, which may be a lysine residue or a functional equivalent, at position 98 of SEQ ID NO: 24 or position 75 of SEQ ID NO: 25 or position 67 of SEQ ID NO: 26 may be biotinylated via a suitable spacer group, such as a polyethylene glycol (PEG) spacer group, in order to permit immobilization of the chemokine on a solid support. In specific embodiments, the PEG spacer is 3,6-dioxo aminooctanoic acid. The sequence and biotinylation of the modified MCP-1 chemokines of the invention are shown in FIGS. 49 to 51 respectively. The modified MCP-1 chemokines may be agonists or antagonists of CCR2 activity. They can be tested for activity in a suitable assay, such as cell-based assays. In particular, agonist and antagonist properties may be determined in functional cell-based assay on human CCR2 receptor.

MCP-5 only binds CCR2 and should be selective in its removal of CCR2 expressing cells. The full length amino acid sequence, including the signal peptide, is set forth as SEQ ID NO: 27. The amino acid sequence of N-terminal processed MCP-5 chemokine is 82 amino acids long and is set forth as SEQ ID NO: 28. An amino acid sequence alignment suggests that MCP-5 has a C-terminal extension when compared to the amino acid sequence of MCP-1. The results of this alignment are shown in FIG. 52. C-terminal truncated versions of MCP-5 can thus be synthesised. This truncated version will comprise, consist essentially of or consist of MCP-5 residues 1-76, set forth as SEQ ID NO: 29.

Accordingly, the invention also provides a modified MCP-5 chemokine comprising the amino acid sequence set forth as SEQ ID NO: 27, SEQ ID NO: 28 or SEQ ID NO: 29 in which the isoleucine residue at position 97 of SEQ ID NO:27 or at position 75 of SEQ ID NO: 28 or SEQ ID NO: 29 has been replaced with lysine. In certain embodiments, the modified MCP-5 chemokine comprises, consists essentially of or consists of the amino acid sequence of SEQ ID NO: 30. The modified MCP-5 chemokine may be biotinylated at the lysine (or a functional equivalent) residue at position 97 of SEQ ID NO: 27 or at position 75 of SEQ ID NO: 28 or SEQ ID NO: 29. Biotinylation may be via a suitable spacer group. Specific examples of the spacer group include a PEG spacer, optionally 3,6-dioxo aminooctanoic acid. In some embodiments, the C terminus is produced as an amide derivative. This may be achieved by synthesis on an amide linker. In certain embodiments, the modified MCP-5 chemokine comprises, consists essentially of or consists of the sequence and biotinylation shown in FIG. 53. The modified MCP-5 chemokine may be an agonist or an antagonist of CCR2 activity. They can be tested for activity in a suitable assay, such as cell-based assays. In particular, agonist and antagonist properties may be determined in a functional cell-based assay on human CCR2 receptor.

An example of a chemokine of the various embodiments of the invention containing modifications and specifically adapted for use in the invention is described in detail herein (see Examples below). The modified CCL8 (MCP-2) corresponds to residues 1 to 76 of the full length mature protein (and lacks the N-terminal signal peptide of 23 amino acids, which is cleaved off) and thus retains the chemokine fold. The Gln at the N-terminus of the protein is subject to pyroGlu formation under physiological conditions. Thus Gln1 of the sequence may thus be substituted with pyroglutamine to prevent mixed species of N-terminal Gln and pyroGlu being generated (SEQ ID NO: 37). This improves the yield of synthesis and ensures a homogeneous chemokine preparation through column manufacture and use. FmocLys(ivDde)-OH is incorporated as residue 75 to facilitate site-specific labelling at this position of the protein (SEQ ID NO: 38). The naturally occurring lysine at position 75 is modified through biotinylation. A PEG spacer may be incorporated between the ε-amino functionality and the biotin (SEQ ID NO: 39).

Thus, in certain embodiments the invention also relates to a modified chemokine comprising, consisting essentially of or consisting of the amino acid sequence of SEQ ID NO: 37:

XPDSVSIPITCCFNVINRKIPIQRLESYTRITNIQCPKEAVIFKTKRGKE

VCADPKERWVRDSMKHLDQIFQNLXP

- X1=pyroGlu (but may remain as Gln in some embodiments)
- X75=an amino acid residue that can be biotinylated, such as lysine, ornithine or diaminopropionic acid and optionally is biotinylated, optionally via a spacer molecule such as PEG, e.g. K(PEG-Biotin).

Or SEQ ID NO: 39
XPDSVSIPITCCFNVINRKIPIQRLESYTRITNIQCPKEAVIFKTKRGKE

VCADPKERWVRDSMKHLDQIFQNLXP

- X1=pyroGlu (but may remain as Gln in some embodiments)
- X75=K(PEG-Biotin).

A further example of a chemokine of the various embodiments of the invention containing modifications and specifically adapted for use in the invention is described in detail herein (see Examples below). The modified CCL5 (RANTES) corresponds to residues 1 to 68 of the full length mature protein (and lacks the N-terminal signal peptide of 23 amino acids, which is cleaved off) and thus retains the chemokine fold. The single methionine (Met67) within the sequence is mutated to lysine, to mitigate against oxidation of this residue during the chain assembly (SEQ ID NO: 34). This Met to Lys substitution provides a lysine at position 67 which can be modified through biotinylation. FmocLys(ivDde)-OH is incorporated as residue 67 to facilitate site-specific labelling at this position of the protein (SEQ ID NO: 35). The biotinylated version comprises, consists essentially of or consists of the amino acid sequence of SEQ ID NO: 36.

Thus, in other embodiments the invention also relates to a modified chemokine comprising, consisting essentially of or consisting of the amino acid sequence of SEQ ID NO: 36:

SPYSSDTTPCCFAYIARPLPRAHIKEYFYTSGKCSNPAVVFVTRKNRQVC

ANPEKKWVREYINSLEXS

X is an amino acid residue that can be biotinylated, such as lysine, ornithine or diaminopropionic acid and optionally is biotinylated, optionally via a spacer molecule such as PEG (e.g. K(Biotin))

A further example of a chemokine of the various embodiments of the invention containing modifications and specifically adapted for use in the invention is described in detail herein (see Examples below). The modified CCL2 (MCP-1) corresponds to residues 1 to 76 of the full length mature protein (and lacks the N-terminal signal peptide of 23 amino acids, which is cleaved off) and thus retains the chemokine fold. The Gln at the N-terminus of the protein (Gln1) is substituted with pyroglutamine to prevent mixed species of N-terminal Gln and pyroGlu being generated. This improves the yield of synthesis and ensures a homogeneous chemokine preparation through column manufacture and use. FmocLys(ivDde)-OH is incorporated as residue 75 to facilitate site-specific labelling at this position of the protein (SEQ ID NO: 32). A suitable spacer, such as a PEG spacer, may be incorporated between the ε-amino functionality and the biotin. The biotinylated version comprises, consists essentially of or consists of the amino acid sequence of SEQ ID NO: 33.

Thus, in other embodiments the invention also relates to a modified chemokine comprising, consisting essentially of or consisting of the amino acid sequence of:

SEQ ID NO: 31:
XPDAINAPVTCCYNFTNRKISVQRLASYRRITSSKCPKEAVIFKTIVAKE

ICADPKQKWVQDSMDHLDKQTQTPKT

X=pyroGlu or Gln

And/or SEQ ID NO: 33:
XPDAINAPVTCCYNFTNRKISVQRLASYRRITSSKCPKEAVIFKTIVAK

EICADPKQKWVQDSMDHLDKQTQTPXT

- X1=pyroGlu or Gln
- X75 is an amino acid residue that can be biotinylated, such as lysine, ornithine or diaminopropionic acid and optionally is biotinylated, optionally via a spacer molecule such as PEG, optionally K(PEG-Biotin)

A further example of a chemokine of the various embodiments of the invention containing modifications and specifically adapted for use in the invention is described in detail herein (see Examples). The modified CCL11 (Eotaxin) corresponds to residues 1 to 74 of the full length mature protein (and lacks the N-terminal signal peptide of 23 amino acids, which is cleaved off) and thus retains the chemokine fold (SEQ ID NO: 40). The lysine at position 73 may be modified through biotinylation. FmocLys(ivDde)-OH is incorporated as residue 73 to facilitate site-specific labelling at this position of the protein (SEQ ID NO: 41). A suitable spacer, such as a PEG spacer, may be incorporated between the ε-amino functionality and the biotin. The biotinylated version comprises, consists essentially of or consists of the amino acid sequence of SEQ ID NO: 42.

Thus, in other embodiments the invention also relates to a modified chemokine comprising, consisting essentially of or consisting of the amino acid sequence of SEQ ID NO: 40 or SEQ ID NO: 42:

SEQ ID NO: 40
GPASVPTTCCFNLANRKIPLQRLESYRRITSGKCPQKAVIFKTKLAKDIC

ADPKKKWVQDSMKYLDQKSPTPXP

X is an amino acid residue that can be biotinylated, such as lysine, ornithine or diaminopropionic acid and optionally is biotinylated, optionally via a spacer molecule such as PEG, e.g. K(PEG-Biotin).

SEQ ID NO: 42
H-GPASVPTTCCFNLANRKIPLQRLESYRRITSGKCPQKAVIFKTKLAKD

ICADPKKKWVQDSMKYLDQKSPTPXP-NH2

X is K(PEG-Biotin)

Chemokines useful in the various embodiments of the invention may be synthesised through any suitable means known in the art. Preferably, the chemokines are chemically synthesised as this facilitates modification and labelling etc. However, recombinant DNA based approaches may also be employed in combination with appropriate labelling and modification technologies as required. Thus, in certain embodiments the invention also provides a nucleic acid molecule encoding the chemokines of the various embodiments of the invention. In certain embodiments the invention also relates to a vector containing such a nucleic acid molecule and a host cell containing the vector. The vector may additionally comprise a suitable promoter operably linked to the nucleic acid molecule, to facilitate transcription of the corresponding mRNA molecule. The host cell may be capable of expressing the protein by transcription and translation of the nucleic acid molecule encoding a chemokine of the invention.

The chemokines useful in the various embodiments of the invention can be biotinylated by methods known in the art such as described in WO 00/50088 A2, which is incorporated herein by reference in its entirety. As indicated above, site-specific labelling of the chemokines of the various embodiments of the invention is preferable, although any labelling technique which does not significantly affect the receptor-binding capacity of the chemokine may be employed. Various site-specifically biotinylated chemokines and native chemokines are available commercially, for instance from Almac, Craigavon, UK. In specific embodiments the one or more chemokines are biotinylated via a spacer group. The spacer may be employed to prevent the biotin group from impacting on the activity of the chemokine, in particular binding of the chemokine to its cognate receptor. Any suitable spacer that facilitates retention of receptor binding properties of the chemokine may be employed in the various embodiments of the invention. Thus, in the specific embodiments described above, spacers other than PEG spacers may be employed as appropriate. In specific embodiments, the spacer is a polyethylene glycol (PEG) spacer. PEG has been shown to be an effective spacer permitting attachment of biotin to the chemokine (which can then be immobilized on the solid support through interaction with streptavidin) without compromising receptor binding capability.

In the context of the various embodiments of the present invention the term "antibody" includes all immunoglobulins or immunoglobulin-like molecules with specific binding affinity for the relevant chemokine receptor (including by way of example and without limitation, IgA, IgD, IgE, IgG and IgM, combinations thereof, and similar molecules produced during an immune response in any vertebrate, for example, in mammals such as humans, goats, rabbits and mice). Specific immunoglobulins useful in the various embodiments of the invention include IgG isotypes. The antibodies useful in the various embodiments of the invention may be monoclonal or polyclonal in origin, but are typically monoclonal antibodies. Antibodies may be human antibodies, non-human antibodies, or humanized versions of non-human antibodies, or chimeric antibodies. Various techniques for antibody humanization are well established and any suitable technique may be employed. The term "antibody" also refers to a polypeptide ligand comprising at least a light chain or heavy chain immunoglobulin variable region which specifically recognizes and binds an epitope of an antigen, and it extends to all antibody derivatives and fragments that retain the ability to specifically bind to the relevant chemokine receptor. These derivative and fragments may include Fab fragments, F(ab')2 fragments, Fv fragments, single chain antibodies, single domain antibodies, Fc fragments etc. The term antibody encompasses antibodies comprised of both heavy and light chains, but also heavy chain (only) antibodies. In specific embodiments, the antibodies may be engineered so as to be specific for more than one chemokine receptor, for example bi-specific to permit binding to two different chemokine receptors. Suitable commercially available antibodies which bind to the chemokine receptors of interest are listed in table 3 below. They may or may not be labelled. General reference may be made to "Antibodies a laboratory manual: By E Harlow and D Lane. pp 726. Cold Spring Harbor Laboratory. 1988", which reference is incorporated herein in its entirety.

TABLE 3

Commercially available fluorophore labelled antibodies against specific chemokine receptors

| Antibody | Fluorophore | Supplier |
|---|---|---|
| CCR5 | PE | Biolegend |
| CCR1 | Alexa Fluor 647 | Biolegend |
| CCR3 | PE | Biolegend |
| CCR2 | PerCP Cy5.5 | BD Biosciences |

Anti-CCR2 antibodies are described for example in WO 2010/021697, incorporated herein by reference. Further examples of potentially useful antibodies include MLN-1202, an anti-CCR2 monoclonal antibody currently undergoing clinical trials (Millennium Pharmaceuticals).

The chemokine receptor expressing cells may thus be targeted using alternative binding agents, such as antibodies or other chemical compounds, as defined herein, rather than the natural chemokine binding partner. This approach is a new approach to treating inflammatory conditions.

Thus, in certain embodiments the invention also provides an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine. The binding reagent capable of specifically binding to the chemokine receptor may be an agonist or an antagonist of the chemokine receptor. In specific embodiments, the binding reagent capable of specifically binding to the chemokine receptor is selected from an antibody and a chemical compound.

In other embodiments the invention thus also provides a method for treating an inflammatory condition comprising applying peripheral blood from a patient/subject to an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine) thus removing chemokine receptor expressing cells from the peripheral blood of the patient/subject. The method may comprise returning the blood depleted of the chemokine receptor expressing cells to the patient/subject.

Similarly, in other embodiments the invention provides a binding reagent capable of specifically binding to a chemokine receptor for use in the treatment of an inflammatory condition, wherein the binding reagent is immobilized on a solid support contained within an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient/subject, wherein the binding reagent is not a chemokine), to which is applied peripheral blood from a patient thus removing chemokine receptor expressing cells from the peripheral blood of the patient.

These aspects of the various embodiments of the invention may be integrated into the more focussed therapeutic aspects of the various embodiments of the invention (i.e. treating inflammatory arthritis and various aspects thereof) and thus, the remainder of the disclosure, including all specific embodiments applies mutatis mutandis.

Solid support materials for immobilizing the binding reagents of the invention are known in the art. "Solid support" refers to, for example, materials having a rigid or semi-rigid surface or surfaces, and may take the form of beads, resins, gels, microspheres, or other geometric configurations. A useful support material is one that does not activate blood cells so as to make them coagulate or adhere to the support as peripheral whole blood is applied to the device. In certain embodiments, a support treated with an agent to provide it with anti-coagulation properties, in particular a heparinized support is employed. Alternatively, the blood of the patient may be treated with an anti-coagulant such as heparin prior to application to the support. Useful support materials comprise high molecular weight carbohydrates, in particular carbohydrates having a molecular weight of 100 kDa or more, such as agarose, in particulate form, optionally cross-linked, and cellulose. Other preferred support materials are polymers, such as carboxylated polystyrene, and glass. The support of the various embodiments of the invention may be provided in the form of particles or fibres. The support particles may have regular form, such as spheres or beads, or irregular form. They may be porous or non-porous. A preferred average particle size of the support is from 50 µm to 2 mm. In certain embodiments Sepharose™, a cross linked, beaded-form of agarose, is used as column matrix. It is chosen for its optimal distribution capacity and can provide a large available area for affinity binding. Solid supports may be provided in the form of magnetic beads, with the specific binding reagent immobilized on the magnetic beads. Following capture of the (CCR2, CCR1, CCR3 and/or CCR5) chemokine receptor expressing cells from the blood, the beads can be removed from the blood with the aid of an appropriate magnetic separator.

Methods for immobilizing binding reagents on a solid support are known in the art. A binding reagent, such as a chemokine, antibody, peptide, nucleic acid or chemical compound, can be immobilized on the support in a direct or indirect manner. Immobilization can be by means of a suitable linker in some embodiments. A preferred method of indirect immobilization of a binding reagent, such as a chemokine, relies upon the interaction between biotin and avidin molecules. "Avidin" or "avidin molecule" refers to any type of protein that specifically binds biotin to the substantial exclusion of other (small) molecules that might be present in a biological sample. Examples of avidin include avidins that are naturally present in egg white, oilseed protein (e.g., soybean meal), and grain (e.g., corn/maize), and streptavidin, which is a protein of bacterial origin. Thus, biotinylation of the binding reagent and use of an avidin molecule such as streptavidin immobilized on the solid support allows reliable attachment of the binding reagent to the solid support according to methods known in the art. Specifically, such a method may comprise providing the binding reagent in biotinylated form, providing a solid support having streptavidin immobilized on its surface, contacting the support with an aqueous solution of the biotinylated binding reagent, and rinsing the support with an aqueous solvent. In addition, binding pair interactions, such as antibody-antigen interactions, may also be utilised for indirect immobilisation of binding reagent onto a support. In such embodiments the support may be derivatised with one member of a binding pair, such as an antibody or fragment or derivative thereof, as defined herein, which has known affinity for a particular peptide sequence or small molecule hapten. Incorporating the other member of the binding pair, such as an antigen, peptide sequence or the hapten onto or into the binding reagent facilitates immobilisation onto a solid support coated with the corresponding antibody or fragment or derivative thereof. Thus, the binding reagent may be modified to include the peptide sequence or hapten into the linear molecule or may be added as a side chain or label. Any suitable antibody-antigen pair may be employed. The antibody fragment or derivative may be any fragment or derivative that retains specific binding affinity for the appropriate antigen. Examples include Fab, F(ab')2 fragments, scFV, VH domains, single domain antibodies (such as nanobodies), heavy chain antibodies and humanized version of non-human antibodies etc. Other high affinity interactions can be utilised for immobilisation of binding reagents, as long as the binding reagent can be synthesised or derivatised with one of the interacting partners and the solid support synthesised or derivatised with the other interacting partner without loss of binding activity (i.e. binding of the binding reagent to the appropriate chemokine receptor). Immobilization may occur via essentially the same interaction in reverse in some embodiments. Thus, the binding reagent which may be a chemokine for example, may be attached to an antibody as defined herein, and the solid support derivatised with the antigen. The chemokine may be produced as a fusion protein with the antibody.

Alternatively binding reagents, such as chemokines and antibodies, can be immobilised directly onto a solid support using bioconjugation techniques established in the field. For example direct immobilisation of proteins onto cyanogen bromide activated solid supports via amino functionalities within the primary sequence of the protein. Alternatively, sulphydryl functionalities within proteins can be used to directly immobilise the protein to alkyl halide derivatised supports or supports containing free thiol functionalities. In further embodiments, proteins containing α-thioester functionalities can be directly immobilised on supports containing 1,2 amino thiol moieties (eg N-terminal cysteine) using the native chemical ligation reaction. Alternatively proteins modified with ketones and aldehydes can be immobilised on solid supports derivatised with hydrazinyl, hydrazide and aminoxy functionalities using hydrazone/oxime bond forming ligation reactions (and vice versa). Alternatively 'Click' chemistry can be used to immobilise proteins onto solid supports, whereby the protein and the support are derivatised with the appropriate mutually reactive chemical functionalities (azides and alkynes). In other embodiments Staudinger ligation chemistry can be used to immobilise appropriately derivatised proteins onto the appropriately derivatised solid supports.

The solid support is contained within or carried by the apheresis column. Thus, by "loaded" is meant that the column carries or contains the solid support in a manner such that (peripheral) blood can flow through the column in contact with the solid support. Thus, the solid support provides a matrix within the column through which blood flows, in continuous fashion in certain embodiments. This permits cells expressing the specific chemokine receptor to be removed from the blood passing through the column, such that blood exiting the column is depleted of the specific chemokine receptor-expressing cells. In specific embodiments, the apheresis column is loaded with a support comprising streptavidin immobilized on the support and one or more biotinylated binding reagents, such as chemokines, bound to the streptavidin on the support. The solid support may be comprised of a high-molecular weight carbohydrate, optionally cross-linked, such as agarose.

As discussed above, the binding reagent is coupled to the solid support. The relative amounts of binding reagent may be controlled to ensure that coupling between the solid support and the binding reagent will be immediate, minimising the risk of binding reagent decoupling from the solid support. Thus, it may be ensured that there is a relative excess of immobilization sites for the binding reagent on the solid support. Alternatively, or additionally, following immobilization of the binding reagent on the solid support, the solid support may be washed to remove any unbound binding reagent.

The apheresis column utilised in the various embodiments of the present invention acts as a leukapheresis treatment for inflammatory arthritis. The column acts to specifically remove one or more of CCR2, CCR1, CCR3 and CCR5-expressing cells, such as monocytes, eosinophils or leukocytes by exploiting the interaction between CCR2, CCR1, CCR3 or CCR5 expressed on the cell surface and a specific binding reagent immobilized on a solid support contained within or carried by the column. The overall column typically comprises, consists of, or consists essentially of three combined components; 1) a housing which contains or carries 2) the solid support and 3) one or more binding reagents (immobilized thereon) which specifically bind one or more chemokine receptors. The housing may be manufactured from any suitable material for clinical use. In certain embodiments the housing is composed of a plastic material. The housing includes an in flow site for entry of blood and an out flow site for blood (depleted of target cells) to exit the column. The housing may be designed to maintain a continuous blood flow through the solid support matrix. The housing (as shown for example in FIG. 9) may include a top portion which comprises a distribution plate (2) at the inflow site (1) to spread the blood evenly over the entire matrix area. The distribution plate may act as a first safety barrier preventing larger particles flowing through the column and into the patient. However, the distribution plate is not essential and may be removed in some embodiments to decrease the overall resistance in the system. The column may contain one or more safety filter units (3 and 4) placed at the inflow (1) and/or outflow (5) sites of the plastic housing. Such filter units may act to prevent particles larger than blood cells passing in and/or out of the column. The safety filter units may contain a plurality of filters, such as two, three or four filters designed to be a robust barrier and stop all particles larger than blood cells passing through the column. Inclusion of safety filters (3 and 4) at both ends of the column serves to minimize the risk of leakage of particles into the patient, including in the event that the device is incorrectly connected resulting in blood flow in the opposite direction to that intended. The safety filters may comprise of any suitable pore size to prevent particles larger than blood cells from passing through the column, as would be readily understood by one skilled in the art. Suitable filters are commercially available. In specific embodiments, the pore size of the filter(s) is between approximately 60 μm and 100 μm, more specifically approximately 80 μm. The solid support and binding reagent components are discussed in further detail herein.

The volume of the housing may be varied depending upon the blood volumes intended to pass through the column. Typically, the volume of the housing is between approximately 40 ml and 200 ml, more specifically 50 ml to 150 ml or 60 ml to 120 ml.

The column is generally applied in the form of an apheresis circuit. In this context, the overall system includes the apheresis column, tubing and an appropriate pump to pump the blood around the circuit. The system is illustrated in FIG. 10. The patient (1) is connected to the extracorporeal circuit via sterile needles to veins in the right and the left arms. A saline bag (3) is also connected and the saline solution is pumped with a suitable pump (2). Blood is drawn from one arm of the patient through the sterile tubing system by the blood pump (4) and passed through the column (6) and back to the patient. The tubing system may be connected to the column via any suitable coupling, such as standard dialysis luer-lock couplings. The couplings on the column may be colour-coded for correct assembly. For example, red tubing for inflow to the red column top and blue tubing for outflow back to the patient. An air detector (8) may be present in the circuit. Inlet pressure (5) and/or Pven sensors (7) may additionally be employed to monitor the pressure in the circuit.

An apheresis pump, such as the 4008 ADS pump manufactured by Fresenius Medical Care or the Adamonitor pump, may monitor the patient's inflow and outflow. The pump may also monitor the pressure in the extracorporeal circulation. The pump may be able to discriminate air by a bubble catcher and air detector. A clot catcher filter may be positioned inside the bubble catcher. The pump may also incorporate an optical detector to distinguish between light, e.g. saline solution or air present in the tubing system and dark e.g. blood present in the tubing system.

A schematic diagram of a suitable pump, showing the air detector and optical filter is shown in FIG. 11. If the pump system detects air bubbles and optical fluctuations or if extracorporeal pressure values are out of the set range, then the pump may stop immediately. Alternatively or additionally a visual/audible alarm may be emitted.

The treatment methods of the various embodiments of the invention may thus rely upon an extracorporeal circuit. The methods may be considered as ex vivo or in vitro methods and be defined solely with reference to steps performed outside of the patient. In some embodiments, however, the method further comprises, prior to application of the blood to the column, collecting peripheral blood from the patient. In a further embodiment, the method further comprises, following the application of the blood to the column, infusing the blood depleted of (CCR2, CCR1, CCR3 and/or CCR5) chemokine receptor expressing cells to the patient. This is then a complete leukapheresis treatment method. Thus, a leukaphereis method, for treating inflammatory arthritis, comprises collecting peripheral blood from the patient; applying the peripheral blood to an apheresis column loaded with a solid support comprising one or more binding reagents capable of specifically binding to one or more chemokine receptors, in particular the chemokine receptor CCR2, CCR1, CCR3 or CCR5, immobilized directly or indirectly on the support thus removing one or more of CCR2, CCR1, CCR3 and CCR5 expressing cells from the peripheral blood of the patient; and infusing the depleted blood (of chemokine receptor expressing cells) to the patient.

The peripheral blood may be continuously collected from the patient. Similarly, the depleted blood may be continuously infused to the patient, through use of an appropriate circuit as described herein. Thus, the support may be disposed in a column through which the blood is made to flow. This may be achieved using a suitable pump for example, as also described herein. Blood flow through the column enables the binding reagent(s) immobilized on the solid support to capture the cells expressing the chemokine receptor, thus depleting them from the blood and preventing their contribution to the inflammatory condition associated with inflammatory arthritis.

The methods of the various embodiments of the invention and binding reagents for use in the methods of the various embodiments of the invention may require that the patient has been selected for treatment on the basis of detecting an increase in the level of chemokine receptor, in particular, one or more of CCR2, CCR1, CCR3 and CCR5 expressing cells in a sample obtained from the patient. Such companion diagnostic methods are described in greater detail herein and are based, for example, on the observation that CCR2, CCR1, CCR3 and/or CCR5 expression may be elevated in patients with inflammatory arthritis. It is shown herein that subjects suffering from rheumatoid arthritis contain chemokine receptor expressing cells in the peripheral blood, in particular CCR1 and CCR2 expressing monocytes. It is also shown herein that the CCR2 and CCR1 cells can be removed using a suitable binding reagent, in particular CCL2 to remove CCR2 expressing cells and CCL5 (RANTES) (in biotinylated form) immobilized on a suitable matrix to remove CCR1 expressing cells. Similarly, it is shown herein that CCR5-expressing lymphocytes, in particular T-lymphocytes can be depleted in subjects suffering from rheumatoid arthritis using a suitable binding reagent, in particular CCL5 (RANTES), in biotinylated form, immobilized on a suitable matrix.

Thus, (in this context) in certain embodiments the invention also provides a method of diagnosing, monitoring progression of, or monitoring treatment of inflammatory arthritis comprising determining:

a) the levels of one or more of the chemokine receptor CCR2, CCR1, CCR3 and CCR5 expressing cells b) levels of expression of one or more of CCR2, CCR1, CCR3 and CCR5; and/or c) levels of cells with high expression of one or more of CCR2, CCR1, CCR3 and CCR5 in a sample obtained from a subject, wherein high levels of one or more of CCR2, CCR1, CCR3 and CCR5 expressing cells, high levels of expression of one or more of CCR2, CCR1, CCR3 and CCR5 or high levels of cells with high expression of one or more of CCR2, CCR1, CCR3 and CCR5 or increased levels of one or more of CCR2, CCR1, CCR3 and CCR5 expressing cells compared to control, increased levels of expression of one or more of CCR2, CCR1, CCR3 and CCR5 compared to a control or increased levels of cells with high expression of one or more of CCR2, CCR1, CCR3 and CCR5 compared to a control indicate the presence or progression of inflammatory arthritis. Levels of chemokine receptor expression, as opposed to cell numbers, may also be investigated as increased levels of chemokine receptor expression per cell may also be diagnostically relevant. In specific embodiments the cells comprise monocytes, in particular CCR1 and/or CCR2 expressing monocytes. In other embodiments the cells comprise T lymphocytes, in particular CCR5 expressing T lymphocytes.

"Diagnosing" is defined herein to include screening for a disease/condition or pre-indication of a disease/condition, identifying a disease/condition or pre-indication of a disease/condition and checking for recurrence of disease/condition following treatment. The methods of the various embodiments of the invention may also have prognostic value, and this is included within the definition of the term "diagnosis". The prognostic value of the methods of the various embodiments of the invention may be used as a marker of potential susceptibility to inflammatory arthritis by identifying levels of one or more of CCR2, CCR1, CCR3 and CCR5 expression linked to conditions associated with that syndrome. Thus patients at risk may be identified before the disease has a chance to manifest itself in terms of symptoms identifiable in the patient. In certain embodiments, diagnosis may be made in conjunction with other objective indicators of inflammatory arthritis. Thus, in specific embodiments, diagnosis is made in conjunction with one or more of the following indicators: Diagnosis may be clinical according to ACR criteria where joints are investigated, ESR, CRP RF, CCP antibodies may be measured. In addition increased number of circulating leukocytes expressing a particular joint homing chemokine receptor.

"Monitoring progression of" includes performing the methods to monitor the stage and/or the state and progression of inflammatory arthritis. Monitoring progression may involve performing the diagnostic methods multiple times on the same patient to determine whether the levels of one or more of CCR2, CCR1, CCR3 and CCR5 expressing cells are increasing, decreasing or remaining stable over a certain time period. This may be in the context of a treatment regime.

"Monitoring the success of a particular treatment" is defined to include determining the levels of one or more of CCR2, CCR1, CCR3 and CCR5 expressing cells before and after a treatment. The treatment is generally one aimed at treating inflammatory arthritis and may be a treatment according to one of the methods of the various embodiments of the invention as defined herein. Successful treatment may be determined with reference to a decrease in one or more of CCR2, CCR1, CCR3 and CCR5 expressing cells as a result of, or following, the treatment. Thus, in such methods a level of one or more of CCR2, CCR1, CCR3 and CCR5 expressing cells is determined prior to treatment. This level is recorded and a further assessment made at a predetermined time following the treatment. The comparison of levels of one or more of CCR2, CCR1, CCR3 and CCR5 expressing cells permits the success of the treatment to be monitored. In specific embodiments, a single treatment is sufficient to cause a depletion of around 10%, 20%, 30%, 40%, 50%, 60% or 70%, or higher, up to 80%, 90%, 95% or more, or any range of values between and including these amounts, of one or more specific chemokine receptors, in particular one or more of CCR2, CCR1, CCR3 and CCR5, expressing cells from the peripheral blood of the patient. In specific embodiments, at least around 50% depletion is achieved in a single treatment. Thus, successful treatment may be defined with reference to depletion of one or more of CCR2, CCR1, CCR3 and CCR5 expressing cells. Treatment may lead to depletion of between approximately 100 and 500 million of one or more of CCR2, CCR1, CCR3 and CCR5 expressing cells, such as monocytes, in certain embodiments. Additional factors may be included to determine successful treatment. For example, a lack of increase in one or more of CCR2, CCR1, CCR3 and CCR5 expressing cells following treatment may indicate successful treatment in terms of preventing further progression of the condition, optionally combined with an improvement in other markers or staging of the inflammatory arthritis. By binding to the column through the binding reagent-chemokine receptor interaction, chemokine receptor expressing cells are immobilized. These immobilized cells express further unoccupied chemokine receptors, which may be of the same or different type to those used for capture. These additional chemokine receptors may permit circulating chemokines which contribute to the inflammatory condition to be captured from the peripheral blood. Thus, a reduction in circulating (specific) chemokine levels may provide a measure of successful treatment.

In specific embodiments, the condition associated with inflammatory arthritis is selected from rheumatoid arthritis, psoriatic arthritis and eosinophilic arthritis.

The sample in which one or more of CCR2, CCR1, CCR3 and CCR5 expressing cell levels, levels of expression of one or more of CCR2, CCR1, CCR3 and CCR5 and/or levels of cells with high expression of one or more of CCR2, CCR1, CCR3 and CCR5 (defined as CCR2hi, CCR1hi, CCR3hi or CCR5hi) are determined may comprise any suitable tissue sample or body fluid sample. Generally, the test sample is obtained from a human subject. Typically, the sample is a blood sample, in particular a peripheral blood sample. The methods may involve determining levels of one or more of CCR2, CCR1, CCR3 and CCR5 expressing monocytes, macrophages or lymphocytes in certain embodiments.

Levels of CCR2, CCR1, CCR3 or CCR5 expressing cells, levels of expression of CCR2, CCR1, CCR3 or CCR5 and/or levels of cells with high expression of CCR2, CCR1, CCR3 or CCR5 (defined as CCR2 hi, CCR1 hi, CCR3 hi or CCR5hi) may be determined according to any suitable method. Flow cytometric techniques are described herein and examples of commercially available antibodies suitably labelled for use in flow cytometry are set out in Table 3 for example. For example, flow cytometry may be employed in order to determine the number of cells expressing CCR2, CCR1, CCR3 or CCR5 in the sample, to determine levels of CCR2, CCR1, CCR3 or CCR5 expression and/or to identify levels of CCR2 hi, CCR1 hi, CCR3 hi or CCR5hi cells. Alternatively, the method may involve steps of collecting and fixing the cells in the sample, followed by incubation with a suitable binding reagent that binds specifically to the CCR2, CCR1, CCR3 or CCR5 chemokine receptor expressing cells in the sample. Any suitable binding reagent, as defined herein, may be employed. For example, a CCR2, CCR1, CCR3 or CCR5-2 specific antibody may be employed. A wash step may be adopted following an incubation period to remove any unbound reagent. Suitable wash steps and incubation conditions would be well known to one skilled in the art. The binding reagent may be directly labeled in order to permit antibody binding to be directly determined. Alternatively a secondary binding reagent, such as an antibody, may be employed which binds to the first binding reagent and carries a label. Again, suitable incubation conditions and wash steps would be apparent to one skilled in the art. The primary and secondary binding reagents may form two halves of a binding pair. The binding interaction should not prevent the primary binding reagent binding to the CCR2, CCR1, CCR3 or CCR5 receptor expressing cells, unless a competition assay is being employed. The two halves of a binding pair may comprise an antigen-antibody, antibody-antibody, receptor-ligand, biotin-streptavidin pair etc. in certain embodiments. Other techniques used to quantify chemokine (CCR2, CCR1, CCR3 or CCR5) receptor expressing cell levels, to quantify levels of CCR2, CCR1, CCR3 or CCR5 expression and/or to quantify levels of CCR2 hi, CCR1 hi, CCR3 hi or CCR5hi cells include PCR-based techniques such as QT-PCR and protein based methods such as western blot. Quantitation may be achieved with reference to fixed cell lines carrying known numbers of various receptor expressing cells and/or known levels of receptor expression per cell. Such fixed cell lines are available commercially (for example ChemiScreen™ cell lines from Millipore). Methods analogous to the treatment methods of the various embodiments of the invention may also be employed, with binding of CCR2, CCR1, CCR3 or CCR5 expressing cells to the solid support being determined following peripheral blood being passed through the column.

The levels of CCR2, CCR1, CCR3 or CCR5 expressing cells, levels of expression of CCR2, CCR1, CCR3 or CCR5 and/or levels of cells with high expression of CCR2, CCR1, CCR3 or CCR5 (defined as CCR2 hi, CCR1 hi, CCR3 hi or CCR5hi) may be determined relative to a suitable control. When diagnosing inflammatory arthritis, a threshold level of cells, level of expression of CCR2, CCR1, CCR3 or CCR5 and/or level of cells with high expression of CCR2, CCR1, CCR3 or CCR5 (defined as CCR2 hi, CCR1 hi, CCR3 hi or CCR5hi) may be set at or over which a positive diagnosis is made. This threshold may be determined based upon measuring levels of CCR2, CCR1, CCR3 or CCR5 expressing cells, levels of expression of CCR2, CCR1, CCR3 or CCR5 and/or levels of cells with high expression of CCR2, CCR1, CCR3 or CCR5 (defined as CCR2 hi, CCR1 hi, CCR3 hi or CCR5hi) in samples obtained from diseased patients and comparing these levels with levels of CCR2, CCR1, CCR3 or CCR5 expressing cells, levels of expression of CCR2, CCR1, CCR3 or CCR5 and/or levels of cells with high expression of CCR2, CCR1, CCR3 or CCR5 (defined as CCR2 hi, CCR1 hi, CCR3 hi or CCR5hi) in samples obtained from healthy subjects.

In certain embodiments, inflammatory arthritis such as rheumatoid arthritis is diagnosed on the basis of levels of chemokine receptor expressing cells, such as CCR2, CCR1, CCR3 or CCR5 expressing cells as discussed herein. A positive diagnosis may be made in subjects based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, inflammatory arthritis such as rheumatoid arthritis is diagnosed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to healthy controls.

In certain embodiments, progression of inflammatory arthritis such as rheumatoid arthritis, which may be in the context of a treatment regime, is monitored on the basis of levels of chemokine receptor expressing cells, such as CCR2, CCR1, CCR3 or CCR5 expressing cells as discussed herein, at different time points. Progression of inflammatory arthritis such as rheumatoid arthritis may be indicated in subjects based upon an increase of greater than about 10%, such as an increase of greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more chemokine receptor expressing cells in the sample, as a percentage of total cells in the sample, compared to a sample taken from the same subject at an earlier time point. In other embodiments, progression of inflammatory arthritis such as rheumatoid arthritis is confirmed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to a sample taken from the same subject at an earlier time point.

Regression or successful treatment may be monitored based upon similar decreases over various time points. For example, regression or successful treatment may be indicated in subjects based upon a decrease of about 10%, such as a decrease of about 15%, about 20%, about 25%, about 30%, about 35%, about 40%, about 45%, about 50%, about 55%, about 60%, about 65%, about 70%, about 75% or more chemokine receptor expressing cells in the sample, as a percentage of total cells in the sample, compared to a sample taken from the same subject at an earlier time point. In other embodiments, regression of inflammatory arthritis such as rheumatoid arthritis is confirmed on the basis of the presence of a about a 1.2 fold or greater decrease, such as about a 1.5, 2, 2.5, 3, 3.5, 4, 4.5, 5, 10, 20, 50 or 100 or greater fold decrease in chemokine receptor expressing cells, relative to a sample taken from the same subject at an earlier time point.

Suitable software is freely available (such as the R project for statistical computing) to perform the necessary statistical analysis of the data obtained to calculate a useful threshold. The threshold may be set to maximize sensitivity and/or specificity of the test. Performance of the test in these respects may be measured by plotting a receiver operating characteristics (ROC) curve (sensitivity versus specificity). The area under the curve provides an indication of the overall performance of the test. Thus, once thresholds have been set for diagnosing the condition, a separate control experiment does not necessarily have to be run each time a sample is tested. Rather reference can simply be made to the pre-existing thresholds to determine the diagnosis. However, in certain embodiments, the sample is tested together with a control sample taken from a healthy subject to provide a comparator based upon essentially identical experimental conditions. The test sample is generally tested in parallel with the control sample. The test sample level of CCR2, CCR1, CCR3 or CCR5 expressing cells, levels of expression of CCR2, CCR1, CCR3 or CCR5 and/or levels of cells with high expression of CCR2, CCR1, CCR3 or CCR5 (defined as CCR2 hi, CCR1 hi, CCR3 hi or CCR5hi) can then be compared with that of the control sample to make the diagnosis.

A control sample from a disease patient may also be tested in certain embodiments. Reference to controls permits relative levels ("high", "low" etc.) of CCR2, CCR1, CCR3 or CCR5 expressing cells in the test sample to be readily identified and the significance thereof interpreted. Reference to controls also permits relative levels of CCR2, CCR1, CCR3 or CCR5 expression ("high", "low" etc.) within the cell population to be determined and the significance thereof interpreted. Such determination may, for example, indicate the average levels of CCR2, CCR1, CCR3 or CCR5 expression per cell in the test sample.

Thus, in specific embodiments, high or higher levels of one or more of CCR2, CCR1, CCR3 and CCR5 expressing cells or high or higher levels of one or more of CCR2, CCR1, CCR3 and CCR5 expression, for example average CCR2, CCR1, CCR3 or CCR5 expression per cell, or high or higher levels of one or more of CCR2 hi, CCR1 hi, CCR3 hi and CCR5hi cells correlate with active disease or more active disease. Similarly, lower or low levels of one or more of CCR2, CCR1, CCR3 and CCR5 expressing cells, or low or lower levels of one or more of CCR2, CCR1, CCR3 and CCR5 expression, for example average CCR2, CCR1, CCR3 or CCR5 expression per cell, or low or lower levels of one or more of CCR2 hi, CCR1 hi, CCR3 hi and CCR5hi cells may correlate with a lack of active inflammation or inflammatory arthritis. This may be defined as "less active disease". It can readily be envisaged that control samples may be assessed and levels of CCR2, CCR1, CCR3 or CCR5 expressing cells, levels of expression of CCR2, CCR1, CCR3 or CCR5 and/or levels of cells with high expression of CCR2, CCR1, CCR3 or CCR5 (defined as CCR2 hi, CCR1 hi, CCR3 hi or CCR5hi) determined across the range of severities of inflammatory arthritis. This may assist in correlating the levels of CCR2, CCR1, CCR3 or CCR5 expressing cells, levels of expression of CCR2, CCR1, CCR3 or CCR5 and/or levels of cells with high expression of CCR2, CCR1, CCR3 or CCR5 (defined as CCR2 hi, CCR1 hi, CCR3 hi or CCR5hi) in the test sample with the relative severity of the condition.

When monitoring progression of, or monitoring treatment of inflammatory arthritis, the control samples may be taken from the subject at an earlier time point. They may, however, be based upon known reference values as discussed above. Thus, relative levels of CCR2, CCR1, CCR3 or CCR5 expressing cells, relative levels of CCR2, CCR1, CCR3 or CCR5 expression including relative levels of average CCR2, CCR1, CCR3 or CCR5 expression per cell or relative levels of CCR2 hi, CCR1 hi, CCR3 hi or CCR5hi cells may be with reference to samples taken from the same subject at a different point in time. In certain embodiments, decreased levels of one or more of CCR2, CCR1, CCR3 and CCR5 expressing cells, decreased relative levels of one or more of CCR2, CCR1, CCR3 and CCR5 expression including decreased relative levels of average CCR2, CCR1, CCR3 or CCR5 expression per cell, or decreased relative levels of one or more of CCR2 hi, CCR1 hi, CCR3 hi and CCR5hi cells correlate with successful treatment. The treatment may be any suitable treatment, but in specific embodiments is a treatment according to the invention. When monitoring progression of inflammatory arthritis, increased levels of one or more of CCR2, CCR1, CCR3 and CCR5 expressing cells increased relative levels of one or more of CCR2, CCR1, CCR3 and CCR5 expression including increased relative levels of average CCR2, CCR1, CCR3 or CCR5 expression per cell or increased relative levels of one or more of CCR2 hi, CCR1 hi, CCR3 hi and/or CCR5hi cells may indicate the progression of condition or disease. Thus, if levels of one or more of CCR2, CCR1, CCR3 and CCR5 expressing cells, levels of expression of one or more of CCR2, CCR1, CCR3 and CCR5 and/or levels of cells with high expression of one or more of CCR2, CCR1, CCR3 and CCR5 (defined as CCR2 hi, CCR1 hi, CCR3 hi or CCR5hi) are increased in a sample taken later than a sample from the same patient this may indicate progression of the condition.

Since the levels of one or more of CCR2, CCR1, CCR3 and CCR5 expressing cells, levels of one or more of CCR2, CCR1, CCR3 and CCR5 expression or levels of one or more of CCR2 hi, CCR1 hi, CCR3 hi and CCR5hi cells are diagnostically relevant, determining such levels in a sample obtained from a subject may influence treatment selection for that subject. Accordingly, in certain embodiments aspect the invention provides a method of selecting a suitable treatment for inflammatory arthritis comprising determining:

a) the levels of one or more of the chemokine receptor CCR2, CCR1, CCR3 and CCR5 expressing cells b) levels of expression of one or more of CCR2, CCR1, CCR3 and CCR5; and/or c) levels of cells with high expression of one or more of CCR2, CCR1, CCR3 and CCR5 in a sample obtained from a subject, wherein high levels of one or more of CCR2, CCR1, CCR3 and CCR5 expressing cells, high levels of expression of one or more of CCR2, CCR1, CCR3 and CCR5 or high levels of cells with high expression of CCR2, CCR1, CCR3 or CCR5 or increased levels of one or more of CCR2, CCR1, CCR3 and CCR5 expressing cells compared to control, increased levels of expression of one or more of CCR2, CCR1, CCR3 and CCR5 compared to a control or increased levels of cells with high expression of one or more of CCR2, CCR1, CCR3 and CCR5 compared to a control, result in selection of a treatment as defined herein for treatment of the condition associated with inflammatory arthritis. In certain embodiments, the chemokine receptor expressing cells are high chemokine receptor expressing cells, in particular, high CCR2, CCR1, CCR3 or CCR5 expressing cells. In specific embodiments the cells comprise monocytes, in particular CCR1 and/or CCR2 expressing monocytes. In other embodiments the cells comprise T lymphocytes, in particular CCR5 expressing T lymphocytes.

In specific embodiments, inflammatory arthritis such as rheumatoid arthritis is treated on the basis of measuring levels of chemokine receptor expressing cells, such as CCR2, CCR1, CCR3 or CCR5 expressing cells as discussed herein. Thus, a treatment according to the various embodiments of the invention may be applied based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, inflammatory arthritis such as rheumatoid arthritis is treated according to the various embodiments of the invention on the basis of the presence of a about a 1.5 fold or greater increase, such as about a 2, 2.5, 3, 3.5, 4, 4.5, 5, 10, 20, 50 or 100 or greater fold increase in chemokine receptor expressing cells, relative to healthy controls.

For the avoidance of doubt, all embodiments described in respect of the methods of the various embodiments of the invention apply to these aspects mutatis mutandis and are not repeated for reasons of conciseness. Specifically, inflammatory arthritis may be indicated in conjunction with one or more of the following indicators: ACR criteria where joints are investigated, ESR, CRP RF, CCP antibodies are measured. In addition increased number of circulating leukocytes expressing a particular joint homing chemokine receptor.

The inflammatory arthritis may be selected from rheumatoid arthritis, psoriatic arthritis and eosinophilic arthritis. In specific embodiments, the sample is a peripheral blood sample.

The methods and medical uses of the various embodiments of the invention thus can be tailored to the need of individual patients or groups of patients on the basis of the various diagnostic methods of the various embodiments of the invention. By removing from the circulation one or more of CCR2, CCR1, CCR3 and CCR5 expressing cells, such as monocytes, macrophages and lymphocytes, in particular monocytes, upregulated in inflammatory arthritis, an important factor in the inflammatory process can be controlled. The method of the invention may be effective in treating or reversing conditions such as rheumatoid arthritis, psoriatic arthritis and eosinophilic arthritis.

D. Treating Cancer

Chemokines are a class of cytokine molecules involved in cell recruitment and activation in inflammation. Chemokines cause chemotaxis and activation of various subpopulations of cells in the immune system. The activity of chemokines is mediated primarily through tight binding to their receptors on the surface of leukocytes. In certain embodiments the present invention is based on the realisation that the interaction between chemokines and cells expressing their receptors may be exploited for the treatment of various cancers and components thereof, such as by reducing levels of circulating tumour cells, reducing the incidence of tumour metastasis, removing regulatory T lymphocytes (which may be referred to herein as "Tregs") from the peripheral blood, or treating leukaemias such as chronic lymphocytic leukaemia, chronic myeloid leukemia, use for debulking in AML, ALL and before harvest for autologous bone marrow/stem cell transplantation and for treating the leukemic phase of lymphoma. The inventors have determined that targeting specific chemokine receptor-expressing cells presents a new therapeutic approach to treat such conditions. Moreover, in such conditions, chemokine receptor expression on each cell may be increased again providing a therapeutic approach to treat such conditions. It is shown herein that cancer patients, in particular subjects suffering from UBC and PC, exhibit an increased frequency of CCR4 expressing circulating Tregs and that this response is specific to Tregs (and does not apply to other T lymphocytes). CCR4 expressing cells may thus be targeted in order to treat cancer. Treatment may rely upon suitable binding reagents such as CCL22 (MDC) and derivatives thereof, as described herein in further detail. It is also shown herein that subject suffering from leukemias, such as CLL, have a highly increased number of circulating (leukemic) B cells. The leukemic B cells express characteristic chemokine receptors, such as CCR7. It is also shown herein that CCR7 expressing B cells may be efficiently depleted using MIP3b as a specific binding reagent in a leukapheresis method.

Thus, in certain embodiments the invention serves to reduce the levels of circulating tumour cells, reduce the incidence of tumour metastasis, remove regulatory T lymphocytes from the peripheral blood or treat leukaemias such as chronic lymphocytic leukaemia, chronic myeloid leukemia. In certain embodiments the invention may also be used for debulking in AML, ALL and before harvest for autologous bone marrow/stem cell transplantation and to treat the leukemic phase of lymphoma. This is achieved using specific binding reagents to capture specific chemokine receptor-expressing cancer cells and regulatory T lymphocytes from the patient. Accordingly, in certain embodiments the invention provides in a first aspect a method for treating cancer comprising applying peripheral blood from a patient to an apheresis column loaded with a solid support comprising one or more binding reagents capable of specifically binding to one or more chemokine receptors, in particular the chemokine receptors CCR5, CCR6, CCR7, CCR8, CXCR4, CXCR7, CCR4, CCR9, CCR10, CXCR3 and/or CXCR5, immobilized directly or indirectly on the support thus removing one or more chemokine receptor, in particular one or more of CCR5, CCR6, CCR7, CCR8, CXCR4, CXCR7, CCR4, CCR9, CCR10, CXCR3 and/or CXCR5, expressing cells from the peripheral blood of the patient. The peripheral blood from which the chemokine receptor expressing cells have been removed may then be returned to the patient in order to complete the treatment. In certain embodiments the invention may thus rely on a continuous extracorporeal circuit in some embodiments. Alternatively, in other embodiments the invention may comprise steps of obtaining peripheral blood from the patient, applying the peripheral blood to the column and subsequently returning the peripheral blood from which the chemokine receptor expressing cells have been removed to the patient.

Herein, reference to CCR5, CCR6, CCR7, CCR8, CXCR4, CXCR7, CCR4, CCR9, CCR10, CXCR3 and/or CXCR5 is intended to encompass selection of any one or more, up to all, of the chemokine receptors listed. In addition, the combination of CCR5, CCR6, CCR7, CCR8, CXCR4 and/or CXCR7 is explicitly contemplated as a separate grouping, to include any one or more of CCR5, CCR6, CCR7, CCR8, CXCR4 and CXCR7.

Thus, the direct treatment of cancer relies upon removal of tumor cells expressing CCRs. The CCRs may be restricted to/accumulated on Leukemic cells. In certain embodiments the invention also reflects (encompasses) the removal of (normal) regulatory T cells that have been induced by the tumor as a tumor escape mechanism as an approach to treatment, which may be performed in addition to or as an alternative to direct treatment.

In certain embodiments the invention therefore also provides a method for treating cancer comprising applying peripheral blood from a patient to an apheresis column loaded with a solid support comprising one or more binding reagents capable of specifically binding to one or more regulatory T cell receptors, which may have been identified as being up-regulated in cancer, in particular the cutaneous lymphocyte antigen (CLA) receptor or chemokine receptors expressed on Tregs such as CCR4 and CCR8, immobilized directly or indirectly on the support thus removing one or more regulatory T cell receptor expressing cells from the peripheral blood of the patient. The peripheral blood from which the regulatory T cell receptor expressing cells have been removed may then be returned to the patient in order to complete the treatment. The invention may thus rely on a continuous extracorporeal circuit in some embodiments. Alternatively, in other embodiments the invention may comprise steps of obtaining peripheral blood from the patient, applying the peripheral blood to the column and subsequently returning the peripheral blood from which the regulatory T cell receptor expressing cells have been removed to the patient.

Herein, reference to CLA, CCR4 and/or CCR8 is intended to encompass selection of any one or more, up to all, of the chemokine receptors listed. In addition, the combination of CLA, CCR4 and/or CCR8 is explicitly contemplated as a separate grouping to the CCR5, CCR6, CCR7, CCR8, CXCR4, CXCR7, CCR4, CCR9, CCR10, CXCR3 and/or CXCR5 grouping also described herein.

Tregs may be recruited to the tumour by chemokines such as CCL17 and CCL22 binding to CCR4 expressed on the Treg, or CCR8 mediated recruitment by CCL1 may occur for example. Thus, in certain embodiments the invention may also rely upon one or more binding reagents capable of specifically binding to one or more chemokine receptors, such as CCR4 and CCR8. As discussed below, the binding reagents may comprise one or more chemokines. CCL17 and CCL22 may be utilised for the removal of CCR4 expressing Tregs and CCL1 may be utilised for the removal of CCR8 expressing Tregs.

The expression of chemokine receptors may vary from leukaemia to leukaemia. For example, the difference between a leukaemia with circulating cells and lymphoma with lymph node malignant cell may lie in the expression of CCR7 allowing entrance into the lymph node. When lymphoma enters into a leukemic phase it is likely due to down-regulation of CCR7. Accordingly, in other embodiments the invention also provides a method for treating leukemia comprising applying peripheral blood from a patient to an apheresis column loaded with a solid support comprising one or more binding reagents capable of specifically binding to one or more chemokine receptors, which have been identified as being linked to leukemia, for example up-regulated in leukemia, immobilized directly or indirectly on the support thus removing one or more chemokine receptor expressing cells from the peripheral blood of the patient. Suitable chemokine receptor expressing cells can be identified by applying the methods described herein.

As shown herein, suitable binding reagents can be immobilized onto a solid support, either directly or indirectly, to generate an apheresis column suitable for capturing relevant chemokine receptor-expressing cells. Where increased levels of chemokine receptor expression are observed, such cells may be preferably removed from the peripheral blood using the columns of the various embodiments of the invention. Thus, the methods of various embodiments of the invention may preferably target one or more of CCR5hi, CCR6hi, CCR7hi, CCR8hi, CXCR4hi, CXCR7hi, CCR4hi, CCR9hi, CCR100hi, CXCR3hi and/or CXCR5hi cells as defined herein for removal from the peripheral blood. "High" expression may be determined according to standard flow cytometry techniques. The level is measured relative to levels of expression of the chemokine receptor in cells taken from a healthy subject. FIG. 60 provides an example of a gating strategy.

In certain embodiments the invention further provides a binding reagent capable of specifically binding to one or more chemokine receptors, in particular to a chemokine receptor/the chemokine receptor CCR5, CCR6, CCR7, CCR8, CXCR4, CXCR7, CCR4, CCR9, CCR10, CXCR3 and/or CXCR5, for use in the treatment of cancer, wherein the one or more binding reagents is immobilized, directly or indirectly, on a solid support contained within an apheresis column, to which is applied peripheral blood from a patient thus removing one or more chemokine receptor/CCR5, CCR6, CCR7, CCR8, CXCR4, CXCR7, CCR4, CCR9, CCR10, CXCR3 and/or CXCR5 expressing cells from the peripheral blood of the patient. In other embodiments the invention also provides for use of one or more binding reagents capable of specifically binding to a chemokine receptor/the chemokine receptor CCR5, CCR6, CCR7, CCR8, CXCR4, CXCR7, CCR4, CCR9, CCR10, CXCR3 and/or CXCR5 (for use) in the manufacture of an apheresis column for treatment of cancer, wherein the one or more binding reagents is immobilized on a solid support contained within the apheresis column, to which is applied peripheral blood from a patient thus removing one or more of chemokine receptor/CCR5, CCR6, CCR7, CCR8, CXCR4, CXCR7, CCR4, CCR9, CCR10, CXCR3 and/or CXCR5 expressing cells from the peripheral blood of the patient.

Similarly, as shown herein, suitable binding reagents can be immobilized onto a solid support, either directly or indirectly, to generate an apheresis column suitable for capturing relevant Treg receptor-expressing cells. Where increased levels of Treg receptor expression are observed, such cells may be preferably removed from the peripheral blood using the columns of the various embodiments of the invention. Thus, in certain embodiments the methods of the various embodiments of the invention may preferably target one or more of CLAhi, CCR4hi and/or CCR8hi cells as defined herein for removal from the peripheral blood. "High" expression may be determined according to standard flow cytometry techniques. The level is measured relative to levels of expression of the Treg receptor in cells taken from a healthy subject. FIG. 60 provides an example of a gating strategy.

In other embodiments the invention further provides a binding reagent capable of specifically binding to one or more Treg receptors, in particular to the Treg receptor CLA, CCR4 and/or CCR8, for use in the treatment of cancer, wherein the one or more binding reagents is immobilized, directly or indirectly, on a solid support contained within an apheresis column, to which is applied peripheral blood from a patient thus removing one or more Treg receptor expressing cells from the peripheral blood of the patient. In certain embodiments the invention also provides for use of one or more binding reagents capable of specifically binding to a Treg receptor/the Treg receptor CLA, CCR4 and/or CCR8 (for use) in the manufacture of an apheresis column for treatment of cancer, wherein the one or more binding reagents is immobilized on a solid support contained within the apheresis column, to which is applied peripheral blood from a patient thus removing one or more of Treg receptor/CLA, CCR4 and/or CCR8 expressing cells from the peripheral blood of the patient.

All embodiments described in respect of the methods of treatment of the various embodiments of the invention apply to these aspects mutatis mutandis and are not repeated for reasons of conciseness. Thus, the following discussion made with reference to the methods of treatment is also applicable to the medical use aspects of the various embodiments of the invention.

In certain embodiments the invention aims to treat a range of specific cancer, or cancer-related, conditions. Specific conditions may be selected from reducing levels of circulating tumour cells, reducing the incidence of tumour metastasis, removing regulatory T lymphocytes from the peripheral blood, or treating leukaemias such as chronic lymphocytic leukaemia, chronic myeloid leukemia, use for debulking in AML, ALL and before harvest for autologous bone marrow/stem cell transplantation and treating the leukemic phase of lymphoma. Reducing levels of circulating tumour cells may be applicable to a range of cancers. This aspect may be relevant to certain solid tumours such as breast cancer, colon cancer or lung cancer. Reducing the incidence of tumour metastasis may rely upon preventing metastatic cell entry at specific locations, since this may be driven via chemokine-chemokine receptor interactions. Thus, in certain embodiments the methods of the invention may be utilized to prevent entry of metastatic cells into any one or more of bone, lungs, lymph nodes, skin and small intestine. In specific embodiments, CXCR4 expressing cells are targeted to prevent metastatic cell entry into the bone and/or lungs. In other embodiments, CCR7 expressing cells are targeted to prevent metastatic cell entry into the lymph nodes. In further embodiments, CCR10 expressing cells are targeted to prevent metastatic cell entry into the skin. In yet further embodiments, CCR9 expressing cells are targeted to prevent metastatic cell entry into the small intestine.

Removal of regulatory T lymphocytes (which may be referred to herein as "Tregs") from the peripheral blood may assist with immune system recognition of the cancer or tumour. T regulatory cells (Tregs) are a subpopulation of T cells that suppress the immune system in order to maintain immune homeostasis. In cancer, the Tregs can inhibit an effective immune response against the tumor and thus removal of the Tregs may lead to an improved immune activation against the cancer cells. In certain embodiments this aspect of the invention may thus be applicable to treating any cancer. Specific examples include pancreatic cancer and bladder cancer, in particular urinirary bladder cancer.

In certain embodiments the methods of the invention may also be utilized in combination with other forms of therapy, such as chemotherapies. Debulking using the leukaphereis procedure may decrease the need for chemotherapy and therefore diminish side effects.

Treating leukaemias such as chronic lymphocytic leukaemia and chronic myeloid leukemia may be based upon direct removal of cancerous cells in the peripheral blood. Use for debulking in AML and ALL may rely upon the targeted cytoreductive effects achieved by the various embodiments of the present invention. Similarly, removal of cancerous cells or cells contributing to the cancerous condition (such as Tregs) may be useful prior to harvest of bone marrow or stem cells from a subject or patient for autologous bone marrow/stem cell transplantation. In certain embodiments the invention may also be useful for treating the leukemic phase of lymphoma, when excess lymphocytes are found in the peripheral blood. The excess lymphocytes, which may include Tregs, can be removed on the basis of the cells expressing particular receptors, especially chemokine receptors.

Leukemia, in particular Acute lymphoblastic leukemia (ALL), may be treated by targeting CXCR4 and/or CXCR3 expressing cells. Leukemia, in particular Chronic myelogenous leukemia (CML), may be treated by targeting CXCR4, CXCR5 and/or CXCR3 expressing cells.

By treatment is meant a reduction in the specific chemokine receptor expressing cells in the peripheral blood of the patient. The reduction may comprise a reduction in cells that express chemokine receptors, in particular one or more of CCR5, CCR6, CCR7, CCR8, CXCR4, CXCR7, CCR4, CCR9, CCR10, CXCR3 and/or CXCR5, at increased levels in diseased patients. The patient is typically a human patient but the term patient may include both human and non-human animal subjects in some embodiments. In the context of the various embodiments of the present invention, this typically involves a reduction in one or more of CCR5, CCR6, CCR7, CCR8, CXCR4, CXCR7, CCR4, CCR9, CCR10, CXCR3 and/or CXCR5 expressing cells, such as one or more of CCR5hi, CCR6hi, CCR7hi, CCR8hi, CXCR4hi, CXCR7hi, CCR4hi, CCR9hi, CCR100hi, CXCR3hi and/or CXCR5hi expressing cells, in the peripheral blood of the patient. The CCR5, CCR6, CCR7, CCR8, CXCR4, CXCR7, CCR4, CCR9, CCR10, CXCR3 and/or CXCR5 expressing cells comprise, consist essentially of or consist of tumour cells, central memory T lymphocytes and regulatory T lymphocytes, in certain embodiments. Tumour cells may be derived from leukemia in certain embodiments, such as chronic lymphocytic leukaemia, in particular B-CLL (B-cell chronic lymphocytic leukemia), chronic myeloid leukemia, AML, ALL and the leukemic phase of lymphoma. In certain embodiments the invention may, for example, rely generally upon the removal of leukemic B-cells. B-cells may be characterised as CD19 positive cells.

Treatment in the context of Treg focused applications specifically relies upon a reduction in the specific Treg receptor expressing cells in the peripheral blood of the patient. The reduction may comprise a reduction in cells that express Treg receptors, in particular one or more of CLA, CCR4 and/or CCR8, at increased levels in diseased patients. The patient is typically a human patient but the term patient may include both human and non-human animal subjects in some embodiments. In the context of the present invention, this typically involves a reduction in one or more of CLA, CCR4 and/or CCR8 expressing cells, such as one or more of "CLAhi, CXCR4hi and/or CXCR8hi" expressing cells, in the peripheral blood of the patient. It is shown herein that cancer patients exhibit an increased frequency of CCR4 expressing circulating Tregs and that this response is specific to Tregs (and does not apply to other T lymphocytes). CCR4 expressing cells may be targeted using suitable binding reagents such as CCL22 (MDC) and derivatives thereof, as described herein in further detail.

The three major types of lymphocyte are T cells, B cells and natural killer (NK) cells. The term "T-lymphocyte" includes CD4+ T cells such as T helper cells (Th1 cells and Th2 cells), and CD8+ T cells such as cytotoxic T cells. Th1 cells may be characterized by expression of CCR5 and/or by production of IFN-γ. Th2 cells may be characterized by expression of CCR3 and/or by production of IL-4. Regulatory T cells (Tregs) express the transcription factor FoxP3 and express high levels of the IL-2Ra (CD25) on the cell surface. In addition they have down-regulated levels of the IL-7a receptor CD127. Thus, Tregs can be defined as CD4+ CD25hiCD127lo/− and Foxp3 positive. The function of Tregs is to regulate and modulate T effector cell responses by direct and indirect contacts mediated by cytokines. Thus, tumors induce Tregs in order to avoid recognition and elimination by T effector cells as a tumor escape mechanism.

In certain embodiments the methods of the invention may involve specific binding interactions with any one or more of these further cell-surface (and cell-specific) markers in addition to the removal based upon binding to chemokine receptors such as CCR5, CCR6, CCR7, CCR8, CXCR4, CXCR7, CCR4, CCR9, CCR10, CXCR3 and/or CXCR5 and/or Treg receptors such as CLA, CCR4 and/or CCR8. Suitable binding reagents can be prepared to specifically bind to these cell-surface markers. The discussion of (chemokine receptor, in particular CCR5, CCR6, CCR7, CCR8, CXCR4, CXCR7, CCR4, CCR9, CCR10, CXCR3 and/or CXCR5; and/or Treg receptor) specific binding reagents thus applies mutatis mutandis.

CCR5 is the gene symbol approved by the HUGO Gene Nomenclature Committee for chemokine (C—C motif) receptor 5. The HGNC ID for this gene is 1605. The gene is located at chromosome position 3p21. The previous symbol and name for the gene is CMKBR5. Synonyms for this gene include CC-CKR-5, CD195 CKR-5, IDDM22 and CKR5. The Entrez Gene reference sequence for CCR5 is 1234 as available on 13 Jun. 2011, which is incorporated herein by reference in its entirety.

CCR6 is the gene symbol approved by the HUGO Gene Nomenclature Committee for chemokine (C—C motif) receptor 6. The HGNC ID for this gene is 1607. The gene is located at chromosome position 6q27. The previous symbol and name for the gene is STRL22. Synonyms for this gene include BN-1, CD196, CKR-L3, CMKBR6, DCR2, DRY-6, GPR-CY4, GPR29. The Genbank reference sequence for CCR6 is U68030.1 as available on 13 Jun. 2011, which is incorporated herein by reference in its entirety.

CCR7 is the gene symbol approved by the HUGO Gene Nomenclature Committee for chemokine (C—C motif) receptor 7. The HGNC ID for this gene is 1608. The gene is located at chromosome position 17q112-q21.2. The previous symbol and name for the gene is CMKBR7, EBI1. Synonyms for this gene include BLR2, CD197 and CDw197. The RefSeq reference sequence for CCR1 is NM_001838.3 as available on 13 Jun. 2011, which is incorporated herein by reference in its entirety.

CCR8 is the gene symbol approved by the HUGO Gene Nomenclature Committee for chemokine (C—C motif) receptor 8. The HGNC ID for this gene is 1609. The gene is located at chromosome position 3p22. The previous symbol and name for the gene is CMKBR8, CMK. Synonyms for this gene include CDw198, CKR-L1, CY6, GPR-CY6, TER1. The Genbank reference sequence for CCR8 is D49919.1 as available on 13 Jun. 2011, which is incorporated herein by reference in its entirety.

CXCR4 is the gene symbol approved by the HUGO Gene Nomenclature Committee for chemokine (C—X—C motif) receptor 4. The HGNC ID for this gene is 2561. The gene is located at chromosome position 2q21. The previous symbol and name for the gene is "chemokine (C—X—C motif), receptor 4 (fusin)". Synonyms for this gene include CD184, D2S201E, fusin, HM89, HSY3RR, LESTR, NPY3R, NPYR, NPYY3R. The Genbank reference sequence for CXCR4 is AJ132337.1 as available on 13 Jun. 2011, which is incorporated herein by reference in its entirety.

CXCR7 is the gene symbol approved by the HUGO Gene Nomenclature Committee for chemokine (C—X—C motif) receptor 7. The HGNC ID for this gene is 23692. The gene is located at chromosome position 2q37.3. The previous symbol and name for the gene is "chemokine orphan receptor 1", CMKOR1. Synonyms for this gene include GPR159 and RDC1. The Genbank reference sequence for CXCR7 is BC008459.1 as available on 13 Jun. 2011, which is incorporated herein by reference in its entirety.

CCR4 is the gene symbol approved by the HUGO Gene Nomenclature Committee for chemokine (C—C motif) receptor 4. The HGNC ID for this gene is 1605. The gene is located at chromosome position 3p24-p21.3. Synonyms for this gene include CC-CKR-4, CD194, ChemR13, CKR4, CMKBR4, k5-5. The Genbank reference sequence for CCR4 is X85740.1 as available on 4 Apr. 2012, which is incorporated herein by reference in its entirety.

Cutaneous lymphocyte antigen (CLA herein) is a specialized form of PSGL-1 expressed on skin-homing T cells, see Fuhlbrigge et al., Nature 389, 978-981 (30 Oct. 1997)|doi: 10.1038/40166 (incorporated herein by reference in its entirety). Memory T cells that infiltrate the skin express a unique skin-homing receptor called cutaneous lymphocyte-associated antigen (CLA), a carbohydrate epitope that facilitates the targeting of T cells to inflamed skin1, CLA is an inducible carbohydrate modification of P-selectin glycoprotein ligand-1 (PSGL-1), a known surface glycoprotein that is expressed constitutively on all human peripheral-blood T cells.

CXCR3 is the gene symbol approved by the HUGO Gene Nomenclature Committee for chemokine (C—X—C motif) receptor 3. The HGNC ID for this gene is 4540. The gene is located at chromosome position Xq13. The previous symbol and name for the gene is "G protein-coupled receptor 9", GPR9. Synonyms for this gene include CD183, CKR-L2, CMKAR3, IP10-R and MigR. The Genbank reference sequence for CXCR3 is U32674.1 as available on 13 Jun. 2011, which is incorporated herein by reference in its entirety.

CXCR5 is the gene symbol approved by the HUGO Gene Nomenclature Committee for chemokine (C—X—C motif) receptor 5. The HGNC ID for this gene is 1060. The gene is located at chromosome position 11q23.3. The previous symbol and name for the gene is BLR1, "Burkitt lymphoma receptor 1, GTP binding protein (chemokine (C—X—C motif) receptor 5)", "Burkitt lymphoma receptor 1, GTP-binding protein". Synonyms for this gene include CD185, MDR15. The Genbank reference sequence for CXCR4 is X68829.1 as available on 29 May 2012, which is incorporated herein by reference in its entirety.

CCR9 is the gene symbol approved by the HUGO Gene Nomenclature Committee for chemokine (C—C motif) receptor 9. The HGNC ID for this gene is 1610. The gene is located at chromosome position 3p22. The previous symbol and name for the gene is GPR28. Synonyms for this gene include CDw199, GPR-9-6. The Genbank reference sequence for CCR9 is AJ132337.1 as available on 13 Jun. 2011, which is incorporated herein by reference in its entirety.

CCR10 is the gene symbol approved by the HUGO Gene Nomenclature Committee for chemokine (C—C motif) receptor 10. The HGNC ID for this gene is 4474. The gene is located at chromosome position 17p21.1-q21.3. The previous symbol and name for the gene is "G protein-coupled receptor 2", GPR2. The Genbank reference sequence for CCR9 is AF215981.1 as available on 29 May 2012, which is incorporated herein by reference in its entirety.

Treatment according to the various embodiments of the invention may result in alleviation or amelioration of symptoms, prevention of progression, regression of the condition, or complete recovery. Measurable parameters of successful treatment include one or more, up to all, of:

The number of circulating CD4+CD25hiCD127lo/− and Foxp3 positive cells will decrease and the functional activation of T effector cells in peripheral blood will increase as a sign of effective treatment. The number of circulating chemokine receptor expressing leukemic or tumor cells may decrease as a sign of effective leukapheresis. In specific embodiments, a single treatment is sufficient to cause a depletion of around 10%, 20%, 30%, 40%, 50%, 60% or 70%, or higher up to 80%, 90%, 95% or more, or any range of values between and including these amounts, of one or more of a specific chemokine receptor, in particular one or more of CCR5, CCR6, CCR7, CCR8, CXCR4, CXCR7, CCR4, CCR9, CCR10, CXCR3 and/or CXCR5, expressing cells from the peripheral blood of the patient. In specific embodiments, at least around 50% depletion is achieved in a single treatment. Thus, successful treatment may be defined with reference to depletion of one or more of CCR5, CCR6, CCR7, CCR8, CXCR4, CXCR7, CCR4, CCR9, CCR10, CXCR3 and/or CXCR5 expressing cells. Treatment may lead to depletion of between approximately 100 and 500 million CCR5, CCR6, CCR7, CCR8, CXCR4, CXCR7, CCR4, CCR9, CCR10, CXCR3 and/or CXCR5 expressing cells, such as cancer cells and regulatory T-lymphocytes, in certain embodiments, and more particularly to about 100, 150, 200, 250, 300, 350, 400, 450, or 500 million CCR5, CCR6, CCR7, CCR8, CXCR4, CXCR7, CCR4, CCR9, CCR10, CXCR3 and/or CXCR5 expressing cells. Similar depletion levels may apply to methods in which Treg receptor expressing cells (CLA, CCR4 and/or CCR8) are targeted.

By binding to the column through the binding reagent-chemokine receptor interaction, chemokine receptor expressing cells are immobilized. These immobilized cells may express further unoccupied chemokine receptors, which may be of the same or different type to those used for capture. These additional chemokine receptors may permit circulating chemokines which may contribute to the condition to be captured from the peripheral blood. Thus, a reduction in circulating (specific) chemokine levels may provide a measure of successful treatment, since for example chemokine down-regulation may diminish Treg recruitment.

The duration of treatment may be readily determined by one skilled in the art and will depend upon factors such as the flow rate of the peripheral blood. Duration of treatment may be tied into monitoring of the treatment itself, with the treatment considered complete once a measurable parameter of treatment has reached a defined threshold. Any suitable parameter may be employed as discussed herein. Thus, for example, treatment may be considered complete when a reduction in one or more of CCR5, CCR6, CCR7, CCR8, CXCR4, CXCR7, CCR4, CCR9, CCR10, CXCR3 and/or CXCR5 expressing cells, such as a 50% reduction in one or more of CCR5, CCR6, CCR7, CCR8, CXCR4, CXCR7, CCR4, CCR9, CCR10, CXCR3 and/or CXCR5 expressing cells, has been achieved. The apheresis system may be operated at a flow rate of around 10-80 mL/min, or more specifically between around 20-70 mL/min, or between around 30-60 mL/min. In specific embodiments, the treatment is performed for a period of around 10, 20, 30, 40, 50, 60, 70, 80, 90, 100, 110, 120 etc., or any range of values between and including these amounts, minutes. The treatment is typically not aimed to remove all of the cells expressing the chemokine receptor in the peripheral blood, as a basal level of those cells is required in healthy subjects. However, it has been found that only low blood volumes need to be applied to the columns of the invention in order to achieve effective levels of depletion of the chemokine receptor-expressing cells. Thus, in certain embodiments, around 10-90% or more specifically around 20, 30, 40, 50, 60, 70, 80 or 90%, or any range of values between and including these amounts, of the patient's blood is applied to the column in a single treatment. The volume of blood circulated through the apheresis column or system may be in the region of around 1000-3000 ml, such as around 1000, 1200, 1400, 1600, 1800 or 2000 ml or any range of values between and including these amounts. The treatment may be considered complete once this volume of blood has been circulated. The patient may be administered anticoagulants prior to each treatment session. A suitable solution, such as a sterile saline solution, optionally including an anticoagulant such as Heparin, may be used for priming the apheresis (extracorporeal) system. An additional volume of anticoagulant may be added to the circuit at the start of each treatment session, for example as a bolus injection. The same factors may be applied mutatis mutandis to aspects of the invention where Treg expressing cells are targeted (such as CLA, CCR4 and/or CCR8 expressing cells).

In certain embodiments the invention relies upon a binding reagent which is capable of specifically binding to a chemokine receptor, or to a regulatory T cell receptor in some embodiments. This specific binding reaction permits cells expressing the chemokine receptor or regulatory T cell receptor to be removed from the peripheral blood of the patient when the blood is passed over the solid support upon or within which the binding reagent is immobilized. Specific chemokine receptors of interest include CCR5, CCR6, CCR7, CCR8, CXCR4, CXCR7, CCR4, CCR9, CCR10, CXCR3 and/or CXCR5 (when treating cancers such as leukemias) and/or regulatory T cell receptors such as CLA, CCR4 and CCR8 (when specifically aiming to remove Tregs). The binding reagent can be any binding reagent capable of specifically binding to the receptor in question. By "specific binding" is meant that the binding reagent displays sufficient specificity of binding and appropriate binding affinity/kinetics to permit removal of cells expressing one or more of CCR5, CCR6, CCR7, CCR8, CXCR4, CXCR7, CCR4, CCR9, CCR10, CXCR3 and/or CXCR5, or a regulatory T cell receptor such as CLA, CCR4 and CCR8 from the peripheral blood (as appropriate). Whilst it is not precluded that the binding reagent is capable of binding to other molecules, such as other chemokine receptors, the binding reagent will preferentially bind to cells expressing one or more of CCR5, CCR6, CCR7, CCR8, CXCR4, CXCR7, CCR4, CCR9, CCR10, CXCR3 and/or CXCR5, or a regulatory T cell receptor such as CLA, CCR4 and CCR8 and in particular to cells expressing increased levels of one or more of CCR5, CCR6, CCR7, CCR8, CXCR4, CXCR7, CCR4, CCR9, CCR10, CXCR3 and/or CXCR5, or a regulatory T cell receptor such as CLA, CCR4 and CCR8 (as defined further herein). The binding reagent capable of specifically binding to CCR5, CCR6, CCR7, CCR8, CXCR4, CXCR7, CCR4, CCR9, CCR10, CXCR3 and/or CXCR5, or a regulatory T cell receptor such as CLA, CCR4 and CCR8 may be either an agonist or an antagonist of CCR5, CCR6, CCR7, CCR8, CXCR4, CXCR7, CCR4, CCR9, CCR10, CXCR3 and/or CXCR5, or a regulatory T cell receptor such as CLA, CCR4 and CCR8, respectively. As the disease condition may rely upon up-regulation of expression of, or signaling via, CCR5, CCR6, CCR7, CCR8, CXCR4, CXCR7, CCR4, CCR9, CCR10, CXCR3 and/or CXCR5, or a regulatory T cell receptor such as CLA, CCR4 and CCR8, in certain embodiments the binding reagent capable of specifically binding to CCR5, CCR6, CCR7, CCR8, CXCR4, CXCR7, CCR4, CCR9, CCR10, CXCR3 and/or CXCR5, or a regulatory T cell receptor such as CLA, CCR4 and CCR8 is an antagonist of CCR5, CCR6, CCR7, CCR8, CXCR4, CXCR7, CCR4, CCR9, CCR10, CXCR3 and/or CXCR5, or a regulatory T cell receptor such as CLA, CCR4 and CCR8, respectively. Chemokines are typically, although not necessarily exclusively (particularly in the case of truncated or modified forms) agonists of their cognate receptor and serve to activate the cells expressing the relevant receptor, as would be appreciated by one skilled in the art. Antibodies against the relevant chemokine receptor are generally considered to be antagonists, as would be appreciated by one skilled in the art. Specific examples of binding reagents include proteins or polypeptides, such as antibodies and receptor ligands, in particular chemokines. The binding reagent may be a nucleic acid molecule in certain embodiments. In some embodiments, the nucleic acid is an aptamer. Nucleic acid aptamers are polynucleotides of approximately 15-40 nucleotides long. Nucleic acid aptamers can be made using the SELEX process (systemic evolution of ligands by exponential enrichment) or any other process known to those of skill in the art. For CLA the binding reagent may be based upon a known binding agent such as vascular lectin endothelial cell-leukocyte adhesion molecule 1 (ELAM-1). The discussion of modified truncated chemokines herein applies mutandis mutandis to the ELAM-1 binding reagent for CLA.

In other embodiments, the binding reagent may be a peptide, and in certain instances, a peptide aptamer. Peptide aptamers are artificial recognition molecules that consist of a variable peptide sequence inserted into a constant scaffold protein (Baines I C, Colas P. Peptide aptamers as guides for small molecule drug discovery. Drug Discov Today. 2006; 11:334-341, incorporated herein by reference). A number of methodologies, such as phage display, ribosome display and yeast two-hybrid screening systems are available for screening a library of potential peptide-based binding agents. Similarly protein scaffolds based on domains such as fibronectins, ankyrin repeats, protein A, SH3 domains, lipocalins and ubiquitin can be used as the binding agent. Again a number of technologies such as phage display and ribosome display are available for screening a library of protein—based binding agents. Similarly, libraries of candidate chemical compounds can be screened for specific binding to the relevant chemokine receptor using suitable screening techniques known in the art, which may be high throughput screens in certain embodiments. The candidate binding agent may be immobilized on a solid support and the ability of the agent to specifically retain cells expressing the chemokine receptor of interest or labelled chemokine receptors determined. A range of cell types may be applied to the solid supports to confirm specificity of binding, or alternatively a mixed sample (such as peripheral blood) may be applied to the solid support. Retention of the cell type of interest (expressing the appropriate chemokine receptor) can be confirmed to identify suitable binding agents.

In the context of the various embodiments of the present invention the term "chemokine" also comprises biotinylated or otherwise labelled chemokines. The term "chemokine" also comprises modified and truncated versions of the chemokine and chemokine fragments with the proviso that the modified or truncated form retains its ability to bind to its cognate receptor (and thus remains functional in the context of the invention). The chemokine does not necessarily need to retain biological activity as it is specific binding affinity for CCR5, CCR6, CCR7, CCR8, CXCR4, CXCR7, CCR4, CCR9, CCR10, CXCR3 and/or CXCR5 and/or for CCR4 and CCR8 where Tregs are specifically targeted that is required. In certain embodiments, the chemokine lacks biological activity, for example in terms of activation of the (CCR5, CCR6, CCR7, CCR8, CXCR4, CXCR7, CCR4, CCR9, CCR10, CXCR3 and/or CXCR5; or CCR4 or CCR8 when specifically targeting Tregs) receptor.

Modifications may be made to improve protein synthesis, for example uniformity of product and yield. As known to those skilled in the art, exemplary modifications may comprise amino acid additions, substitutions, deletions or other modifications to one or more amino acids in the chemokine. Modifications may comprise substitution of the wild type amino acid with non-natural amino acids such as norleucine (NLeu) and derivatized amino acids such as pyroglutamic acid (pyroGlu). Such modifications may be made to minimize side-product formation during storage and use of the columns of the various embodiments of the invention. Modifications may be made to improve labelling, for example inclusion of a polyethylene glycol (PEG) spacer to facilitate biotinylation. The biotinylation and/or conjugation with fluorochromes or other labelling groups of the chemokine is performed in a manner which does not substantially affect the receptor binding capacity. Site specific biotinylation or other labelling is preferred as non-selective labelling of chemokines may compromise receptor binding activity. Bioinylation or other labelling is generally preferred at or towards the C-terminus of the protein as the inventors have found that modifications in this area are generally well tolerated (in terms of a minimal effect on receptor binding capability). Biotinylation may be carried out site-specifically at any suitable amino acid. Examples of suitable amino acids include lysine and ornithine. Generally, reference may be made to Natarajan S et al, Int. J. Pept. Protein Res., 1992, 40, 567-74; Baumeister B, Int. J. Peptide Res. And Therapeutics, 2005, 11, 139-141; Bioconjugate techniques 2nd edition, Greg T. Hermanson, incorporated by reference herein in its entirety.

Truncations may involve deletion of either N or C terminal amino acids as appropriate, or both. Typically, the truncated version will retain the residues required for the chemokine to fold correctly, for example to retain a chemokine fold structure, consistent with the requirement that a truncated version must retain the ability to bind to the relevant receptor (expressed by (on the surface of) a leukocyte). Chemokine molecules typically include disulphide bonds between the 1st and 3rd and 2nd and 4th cysteine residues respectively, as would be understood by one skilled in the art. Where sequences are presented herein, it is assumed that these disulphide bonds will form in the folded protein (unless otherwise stated). Truncated versions may comprise anywhere between 1 and 100 less amino acids, such as 1, 2, 3, 4, 5 etc amino acids, than the wild type amino acid sequence in certain embodiments. Of course, truncated versions may comprise further modification as detailed herein. The modified or truncated version may have 40%, 45%, 50%, 55%, 60%, 65%, 70%, 75%, 80%, 85%, 90%, 95% or more overall amino acid sequence identity with the full length wild type chemokine (where a deletion is counted as a difference in amino acid sequence) in certain embodiments. Over the common sequence between the molecules (i.e the amino acids that have not been deleted), there may be 80%, 85%, 90%, 91%, 92%, 93%, 94%, 95%, 96%, 97%, 98% or 99% amino acid sequence identity in certain embodiments. Sequence identity may be determined using known algorithms, such as BLAST or GAP analysis (GCG Program) (applying default settings), which are freely available. Chemokines may lack the N-terminal signal peptide which is cleaved off during synthesis in vivo.

Specific chemokines useful in the various embodiments of the present invention for binding to CCR5, CCR6, CCR7, CCR8, CXCR4, CXCR7, CCR4, CCR9, CCR10, CXCR3 and/or CXCR5 include MIP-3alpha (CCL20), CCL19, CCL21, CCL1, CXCL11, CXCL12, CCL25 (TECK), CCL27 (CTACK), CCL28 (MEC), CXCL9 (MIG), CXCL10 (IP10), CXCL13 (BCA-1), CCL17 (TARC) and CCL22 (MDC). Herein, reference to MIP-3alpha (CCL20), CCL19, CCL21, CCL1, CXCL11, CXCL12, CCL25 (TECK), CCL27 (CTACK), CCL28 (MEC), CXCL9 (MIG), CXCL10 (IP10), CXCL13 (BCA-1), CCL17 (TARC) and CCL22 (MDC) is intended to encompass selection of any one or more, up to all, of the chemokines listed. In addition, the combination of MIP-3alpha (CCL20), CCL19, CCL21, CCL1, CXCL11 and CXCL12 is explicitly contemplated as a separate grouping, to include any one or more of MIP-3alpha (CCL20), CCL19, CCL21, CCL1, CXCL11 and CXCL12. In addition, the combination of CCL25 (TECK), CCL27 (CTACK), CCL28 (MEC), CXCL9 (MIG), CXCL10 (IP10), CXCL11 (ITAC), CXCL13 (BCA-1), CCL17 (TARC) and CCL22 (MDC) is explicitly contemplated as a separate grouping, to include any one or more of CCL25 (TECK), CCL27 (CTACK), CCL28 (MEC), CXCL9 (MIG), CXCL10 (IP10), CXCL11 (ITAC), CXCL13 (BCA-1), CCL17 (TARC) and CCL22 (MDC).

CCL3, CCL4, CCL5 and CCL8 bind CCR5. CCL20 binds CCR6 (only). CCL19 and CCL21 bind CCR7. CXCL12 bind CXCR4. CCL1 binds CCR8. CXCL11 and CXCL12 bind CXCR7. CCL17 and CCL22 each bind to CCR4. CCL25 (TECK) binds to CCR9. CCL27 (CTACK) and CCL28 (MEC) each bind CCR10. CXCL9 (MIG), CXCL10 (IP10) and CXCL11 (ITAC) bind CXCR3. CXCL13 (BCA-1) binds CXCR5. CCL17 (TARC) and CCL22 (MDC) bind CCR4 only.

CCL20 is the gene symbol approved by the HUGO Gene Nomenclature Committee for chemokine (C—C motif) ligand 20, also known as MIP-3alpha. The HGNC ID for this gene is 10619. The gene is located at chromosome position 2q33-q37. The previous symbol and name for the gene is SCYA20, "small inducible cytokine subfamily A (Cys-Cys), member 20". Synonyms for this gene include CKb4, exodus-1, LARC, MIP-3a, ST38. The Genbank reference sequence for CCL20 is D86955.1 as available on 13 Jun. 2011, which is incorporated herein by reference in its entirety.

CCL19 is the gene symbol approved by the HUGO Gene Nomenclature Committee for chemokine (C—C motif) ligand 19, also known as MIP-3b. The HGNC ID for this gene is 10617. The gene is located at chromosome position 9p13. The previous symbol and name for the gene is SCYA19, "small inducible cytokine subfamily A (Cys-Cys), member 19". Synonyms for this gene include "beta chemokine exodus-3", "CC chemokine ligand 19", "CK beta-11", CKb11, "EBl1-ligand chemokine", ELC, exodus-3, "macrophage inflammatory protein 3-beta", MIP-3b. The Genbank reference sequence for CCL19 is AB000887.1 as available on 13 Jun. 2011, which is incorporated herein by reference in its entirety.

CCL21 is the gene symbol approved by the HUGO Gene Nomenclature Committee for chemokine (C—C motif) ligand 21. The HGNC ID for this gene is 10620. The gene is located at chromosome position 9p13. The previous symbol and name for the gene is SCYA21, "small inducible cytokine subfamily A (Cys-Cys), member 21". Synonyms for this gene include 6Ckine, "beta chemokine exodus-2", CKb9, ECL, "Efficient Chemoattractant for Lymphocytes", exodus-2, "secondary lymphoid tissue chemokine", SLC, TCA4. The Genbank reference sequence for CCL21 is AB002409.1 as available on 13 Jun. 2011, which is incorporated herein by reference in its entirety.

CCL1 is the gene symbol approved by the HUGO Gene Nomenclature Committee for chemokine (C—C motif) ligand 1. The HGNC ID for this gene is 10609. The gene is located at chromosome position 17q11.2. The previous symbol and name for the gene is SCYA1, "small inducible cytokine A1 (I-309, homologous to mouse Tca-3)". Synonyms for this gene include I-309, "inflammatory cytokine I-309", P500, SISe, "T lymphocyte-secreted protein I-309", TCA3. The Genbank reference sequence for CCL1 is M57506.1 as available on 13 Jun. 2011, which is incorporated herein by reference in its entirety.

CXCL11 is the gene symbol approved by the HUGO Gene Nomenclature Committee for chemokine (C—X—C motif) ligand 11. The HGNC ID for this gene is 10638. The gene is located at chromosome position 4q21. The previous symbol and name for the gene is SCYB9B, SCYB11, "small inducible cytokine subfamily B (Cys-X-Cys), member 11". Synonyms for this gene include b-R1, H174, I-TAC, IP-9. The Genbank reference sequence for CXCL11 is U66096.1 as available on 13 Jun. 2011, which is incorporated herein by reference in its entirety.

CXCL12 is the gene symbol approved by the HUGO Gene Nomenclature Committee for chemokine (C—X—C motif) ligand 12. The HGNC ID for this gene is 10672. The gene is located at chromosome position 10q11.1. The previous symbol and name for the gene is SDF1, SDF1A, SDF1B, "stromal cell-derived factor 1". Synonyms for this gene include PBSF, SCYB12, SDF-1a, SDF-1b, TLSF-a, TLSF-b, TPAR1. The Genbank reference sequence for CXCL12 is L36033.1 as available on 13 Jun. 2011, which is incorporated herein by reference in its entirety.

SELE is the gene symbol approved by the HUGO Gene Nomenclature Committee for selectin E, also known as ELAM-1. The HGNC ID for this gene is 10718. The gene is located at chromosome position 1q22-q25. Synonyms for this gene include CD26E, ESEL. The Genbank reference sequence for SELE is M30640.1 as available on 13 Jun. 2011, which is incorporated herein by reference in its entirety.

CCL17 is the gene symbol approved by the HUGO Gene Nomenclature Committee for chemokine (C—C motif) ligand 17. The HGNC ID for this gene is 10615. The gene is located at chromosome position 16q13. The previous symbol and name for the gene is SCYA17, "small inducible cytokine subfamily A (Cys-Cys), member 17". Synonyms for this gene include ABCD-2, TARC. The Genbank reference sequence for CCL17 is D43767.1 as available on 4 Apr. 2012, which is incorporated herein by reference in its entirety.

CCL22 is the gene symbol approved by the HUGO Gene Nomenclature Committee for chemokine (C—C motif) ligand 22. The HGNC ID for this gene is 10621. The gene is located at chromosome position 16q13. The previous symbol and name for the gene is SCYA22, "small inducible cytokine subfamily A (Cys-Cys), member 22". Synonyms for this gene include A-152E5.1, ABCD-1, DC/B-CK, MDC, MGC34554, STCP-1. The Genbank reference sequence for CCL22 is U83171.1 as available on 4 Apr. 2012, which is incorporated herein by reference in its entirety.

CCL25 is the gene symbol approved by the HUGO Gene Nomenclature Committee for chemokine (C—C motif) ligand 25. The HGNC ID for this gene is 10624. The gene is located at chromosome position 19p13.2. The previous symbol and name for the gene is SCYA25, "small inducible cytokine subfamily A (Cys-Cys), member 25". Synonyms for this gene include "Ck beta-15", Ckb15, TECK, "TECK-var", "thymus expressed chemokine". The Genbank reference sequence for CCL25 is U86358.1 as available on 13 Jun. 2011, which is incorporated herein by reference in its entirety.

CCL27 is the gene symbol approved by the HUGO Gene Nomenclature Committee for chemokine (C—C motif) ligand 27. The HGNC ID for this gene is 10626. The previous symbol and name for the gene is SCYA27, "small inducible cytokine subfamily A (Cys-Cys), member 27". The gene is located at chromosome position 9p13. Synonyms for this gene include ALP, "CC chemokine ILC", CTACK, CTAK, "cutaneous T-cell attracting chemokine", ESkine, "IL-11 Ralpha-locus chemokine", ILC, PESKY, skinkine. The Genbank reference sequence for CCL27 is AJ2433542.1 as available on 29 May 2012, which is incorporated herein by reference in its entirety.

CCL28 is the gene symbol approved by the HUGO Gene Nomenclature Committee for chemokine (C—C motif) ligand 28, also known as MEC and CCK1. The HGNC ID for this gene is 17700. The gene is located at chromosome position 5p12. Synonyms for this gene include "CC chemokine CCL28", CCK1, MEC, "mucosae-associated epithelial chemokine", SCYA28, "small inducible cytokine A28", "small inducible cytokine subfamily A (Cys-Cys), member 28". The Genbank reference sequence for CCL28 is AF110384.1 as available on 13 Jun. 2011, which is incorporated herein by reference in its entirety.

CXCL9 is the gene symbol approved by the HUGO Gene Nomenclature Committee for chemokine (C—X—C motif) ligand 9. The HGNC ID for this gene is 7098. The gene is located at chromosome position 4q21. The previous symbol and name for the gene is CMK, MIG, "monokine induced by gamma interferon". Synonyms for this gene include crg-10, Humig, SCYB9. The Genbank reference sequence for CXCL10 is X72755.1 as available on 13 Jun. 2011, which is incorporated herein by reference in its entirety.

CXCL10 is the gene symbol approved by the HUGO Gene Nomenclature Committee for chemokine (C—X—C motif) ligand 10. The HGNC ID for this gene is 10637. The gene is located at chromosome position 4q21. The previous symbol and name for the gene is INP10, SCYB10, "small inducible cytokine subfamily B (Cys-X-Cys), member 10". Synonyms for this gene include C7, crg-2, gIP-10, IFI10, IP-10, mob-1. The Genbank reference sequence for CXCL10 is X02530.1 as available on 13 Jun. 2011, which is incorporated herein by reference in its entirety.

CXCL13 is the gene symbol approved by the HUGO Gene Nomenclature Committee for chemokine (C—X—C motif) ligand 13. The HGNC ID for this gene is 10639. The gene is located at chromosome position 4q21. The previous symbol and name for the gene is SCYB13, "small inducible cytokine B subfamily (Cys-X-Cys motif), member 13 (B-cell chemoattractant)". Synonyms for this gene include ANGIE, ANGIE2, "B-cell chemoattractant", BCA-1, BLC, BLR1L. The Genbank reference sequence for CXCL13 is AJ002211.1 as available on 29 May 2012, which is incorporated herein by reference in its entirety.

An example of a chemokine of the various embodiments of the invention containing modifications and specifically adapted for use in the invention is described in detail herein (see Examples below). The modified CCL8 (MCP-2) corresponds to residues 1 to 76 of the full length mature protein (and lacks the N-terminal signal peptide of 23 amino acids, which is cleaved off) and thus retains the chemokine fold. The Gln at the N-terminus of the protein is subject to pyroGlu formation under physiological conditions. Thus Gln1 of the sequence is substituted with pyroglutamine to prevent mixed species of N-terminal Gln and pyroGlu being generated (SEQ ID NO: 43). This improves the yield of synthesis and ensures a homogeneous chemokine preparation through column manufacture and use. FmocLys (ivDde)-OH is incorporated as residue 75 to facilitate site-specific labelling at this position of the protein (SEQ ID NO: 44). The naturally occurring lysine at position 75 is modified through biotinylation. A PEG spacer may be incorporated between the ε-amino functionality and the biotin (SEQ ID NO: 45).

Thus, in certain embodiments the invention also relates to a modified chemokine comprising, consisting essentially of or consisting of the amino acid sequence of SEQ ID NO: 43:

XPDSVSIPITCCFNVINRKIPIQRLESYTRITNIQCPKEAVIFKTKRGKE

VCADPKERWVRDSMKHLDQIFQNLXP

X1=pyroGlu (but may remain as Gln in some embodiments)

X75=an amino acid residue that can be biotinylated, such as lysine, ornithine or diaminopropionic acid and optionally is biotinylated, optionally via a spacer molecule such as PEG, e.g. K(PEG-Biotin).

Or SEQ ID NO: 45
XPDSVSIPITCCFNVINRKIPIQRLESYTRITNIQCPKEAVIFKTKRGKE

VCADPKERWVRDSMKHLDQIFQNLXP

X1=pyroGlu (but may remain as Gln in some embodiments)
X75=K(PEG-Biotin).

A further example of a chemokine of the various embodiments of the invention containing modifications and specifically adapted for use in the invention is described in detail herein (see Examples below). The modified CCL5 (RANTES) corresponds to residues 1 to 68 of the full length mature protein (and lacks the N-terminal signal peptide of 23 amino acids, which is cleaved off) and thus retains the chemokine fold. The single methionine (Met67) within the sequence is mutated to lysine, to mitigate against oxidation of this residue during the chain assembly (SEQ ID NO: 46). This Met to Lys substitution provides a lysine at position 67 which can be modified through biotinylation. FmocLys (ivDde)-OH is incorporated as residue 67 to facilitate site-specific labelling at this position of the protein (SEQ ID NO: 47). The biotinylated version comprises, consists essentially of or consists of the amino acid sequence of SEQ ID NO: 48.

Thus, in certain embodiments the invention also relates to a modified chemokine comprising, consisting essentially of or consisting of the amino acid sequence of SEQ ID NO: 48:

SPYSSDTTPCCFAYIARPLPRAHIKEYFYTSGKCSNPAVVFVTRKNRQVC

ANPEKKWVREYINSLEXS

X is an amino acid residue that can be biotinylated, such as lysine, ornithine or diaminopropionic acid and optionally is biotinylated, optionally via a spacer molecule such as PEG (e.g. K(Biotin))

A further example of a chemokine of the various embodiments of the invention containing modifications and specifically adapted for use in the invention is described in detail herein (see Examples below). The modified CCL20 (MIP-3a) corresponds to residues 1 to 70 of the full length mature protein (and lacks the N-terminal signal peptide of 26 amino acids, which is cleaved off) and thus retains the chemokine fold (SEQ ID NO: 49). FmocLys(ivDde)-OH is incorporated as residue 68 to facilitate site-specific labelling at this position of the protein (SEQ ID NO: 50). The naturally occurring lysine at position 68 is modified through biotinylation. A PEG spacer may be incorporated between the ε-amino functionality and the biotin. The final protein may thus comprise, consist essentially of or consist of the amino acid sequence of SEQ ID NO: 51.

Thus, in certain embodiments the invention also relates to a modified chemokine comprising, consisting essentially of or consisting of the amino acid sequence of SEQ ID NO: 51:

ASNFDCCLGYTDRILHPKFIVGFTRQLANEGCDINAIIFHTKKKLSVCAN

PKQTWVKYIVRLLSKKVXNM

X is an amino acid residue that can be biotinylated, such as lysine, ornithine or diaminopropionic acid and optionally is biotinylated, optionally via a spacer molecule such as PEG, in particular K(PEG-Biotin)

A further example of a chemokine of the various embodiments of the invention containing truncation and modifications and specifically adapted for use in the invention is described in detail herein (see Examples below). The truncated CXCL12 (SDF-1a) corresponds to residues 1 to 67 of the full length mature protein (and lacks the N-terminal signal peptide of 21 amino acids, which is cleaved off from an immature protein of total length 93 amino acids) and thus retains the chemokine fold (SEQ ID NO: 52). FmocLys (ivDde)-OH is incorporated as residue 64 to facilitate site-specific labelling at this position of the protein (SEQ ID NO: 53). The naturally occurring lysine at position 64 is modified through biotinylation. The final protein may thus comprise, consist essentially of or consist of the amino acid sequence of SEQ ID NO: 54.

Thus, in certain embodiments the invention also relates to a truncated/modified chemokine comprising, consisting essentially of or consisting of the amino acid sequence of

SEQ ID NO: 54:
KPVSLSYRCPCRFFESHVARANVKHLKILNTPNCALQIVARLKNNNRQV

CIDPKLKWIQEYLEXALN

X is an amino acid residue that can be biotinylated, such as lysine, ornithine or diaminopropionic acid and optionally is biotinylated, optionally via a spacer molecule such as PEG, especially K(Biotin)

Or SEQ ID NO: 52:
KPVSLSYRCPCRFFESHVARANVKHLKILNTPNCALQIVARLKNNNRQV

CIDPKLKWIQEYLEKALN

A further example of a chemokine of the various embodiments of the invention containing modifications and specifically adapted for use in the invention is described in detail herein (see Examples below). The modified CCL22 (MDC) corresponds to residues 1 to 69 of the full length mature protein (and lacks the N-terminal signal peptide of 24 amino acids, which is cleaved off) and thus retains the chemokine fold (SEQ ID NO: 55). FmocLys(ivDde)-OH is incorporated as residue 66 to facilitate site-specific labelling at this position of the protein (SEQ ID NO: 56). The naturally occurring lysine at position 66 is modified through biotinylation. A PEG spacer may be incorporated between the ε-amino functionality and the biotin. The final protein may thus comprise, consist essentially of or consist of the amino acid sequence of SEQ ID NO: 57.

Thus, in certain embodiments in certain embodiments the invention also relates to a modified chemokine comprising, consisting essentially of or consisting of the amino acid sequence of SEQ ID NO: 57:

GPYGANMEDSVCCRDYVRYRLPLRVVKHFYWTSDSCPRPGVVLLTFRDK

EICADPRVPWVKMILNXLSQ

X is an amino acid residue that can be biotinylated, such as lysine, ornithine or diaminopropionic acid and optionally is biotinylated, optionally via a spacer molecule such as PEG, especially K(PEG-Biotin)

A further example of a chemokine of the various embodiments of the invention containing modifications and specifically adapted for use in the invention is described in detail herein (see Examples below). The modified CCL17 (TARC) corresponds to residues 1 to 71 of the full length mature protein (and lacks the N-terminal signal peptide of 23 amino acids, which is cleaved off) and thus retains the chemokine fold. An additional lysine or equivalent residue may be inserted at the C-terminus, at position 72. The chemokine may thus comprise, consist essentially of or consist of the amino acid sequence of SEQ ID NO: 58. FmocLys(ivDde)-OH is incorporated as residue 72 to facilitate site-specific labelling at this position of the protein (SEQ ID NO: 59). The ε-amino side chain functionality of Lys(72) is modified through biotinylation. A PEG spacer may be incorporated between the r-amino functionality and the biotin. The final protein may thus comprise, consist essentially of or consist of the amino acid sequence of SEQ ID NO: 60.

Thus, in certain embodiments the invention also relates to a modified chemokine comprising, consisting essentially of or consisting of the amino acid sequence of SEQ ID NO: 58 or 60:

SEQ ID NO: 58
ARGTNVGRECCLEYFKGAIPLRKLKTWYQTSEDCSRDAIVFVTVQGRAI

CSDPNNKRVKNAVKYLQSLERSX

X is an amino acid residue that can be biotinylated, such as lysine, ornithine or diaminopropionic acid and optionally is biotinylated (e.g. K-biotin), optionally via a spacer molecule such as PEG, in particular K(PEG-Biotin)

SEQ ID NO: 60
ARGTNVGRECCLEYFKGAIPLRKLKTWYQTSEDCSRDAIVFVTVQGRAI

CSDPNNKRVKNAVKYLQSLERSK(PEG-Biotin)

A further example of a chemokine of the various embodiments of the invention containing modifications and specifically adapted for use in the invention is described in detail herein (see Examples below). The modified CCL19 (MIP-3β) corresponds to residues 1 to 77 of the full length mature protein (and lacks the N-terminal signal peptide of 21 amino acids, which is cleaved off) and thus retains the chemokine fold. An additional lysine is inserted at the C-terminus, at position 78. The chemokine may thus comprise, consist essentially of or consist of the amino acid sequence of SEQ ID NO: 61. FmocLys(ivDde)-OH is incorporated as residue 78 to facilitate site-specific labelling at this position of the protein (SEQ ID NO: 62). The e-amino side chain functionality of Lys(78) is modified through biotinylation. The final protein may thus comprise, consist essentially of or consist of the amino acid sequence of SEQ ID NO: 63.

Thus, in certain embodiments the invention also relates to a modified chemokine comprising, consisting essentially of or consisting of the amino acid sequence of SEQ ID NO: 61 or 63:

SEQ ID NO: 61
GTNDAEDCCLSVTQKPIPGYIVRNFHYLLIKDGCRVPAVVFTTLRGRQL

CAPPDQPWVERIIQRLQRTSAKMKRRSSX

X is an amino acid residue that can be biotinylated, such as lysine, ornithine or diaminopropionic acid and optionally is biotinylated (e.g. K-biotin), optionally via a spacer molecule such as PEG, in particular K(PEG-Biotin)

SEQ ID NO: 63
GTNDAEDCCLSVTQKPIPGYIVRNFHYLLIKDGCRVPAVVFTTLRGRQL

CAPPDQPWVERIIQRLQRTSAKMKRRSSX

X is K(Biotin)

A further example of a chemokine of the various embodiments of the invention containing modifications and specifically adapted for use in the invention is described in detail herein (see Examples below). The modified CXCL11 (ITAC) corresponds to residues 1 to 73 of the full length mature protein (and lacks the N-terminal signal peptide of 21 amino acids, which is cleaved off) and thus retains the chemokine fold (SEQ ID NO: 64). An additional lysine is inserted at the C-terminus, optionally via a PEG spacer, at position 74. The chemokine may thus comprise, consist essentially of or consist of the amino acid sequence of SEQ ID NO: 65.

SEQ ID NO: 65:
FPMFKRGRCLCIGPGVKAVKVADIEKASIMYPSNNCDKIEVIITLKEN

KGQRCLNPKSKQARLIIKKVERKNFX

X is an amino acid residue that can be biotinylated, such as lysine, ornithine or diaminopropionic acid and optionally is biotinylated, optionally via a spacer molecule such as PEG. The amino acid residue may be added via a spacer molecule such as PEG and may thus be "PEG-K".

FmocLys(ivDde)-OH is incorporated, following Fmoc-12-amino-4,7,10-trioxadodecanoic acid, as residue 74 to facilitate site-specific labelling at this position of the protein (SEQ ID NO: 66). The e-amino side chain functionality of the additional Lys(74) is modified through biotinylation. The final protein may thus comprise, consist essentially of or consist of the amino acid sequence of SEQ ID NO: 67.

SEQ ID NO: 67:
FPMFKRGRCLCIGPGVKAVKVADIEKASIMYPSNNCDKIEVIITLKENK

GQRCLNPKSKQARLIIKKVERKNFX

X is PEG-K(biotin).

Thus, in certain embodiments the invention also relates to a modified chemokine comprising, consisting essentially of or consisting of the amino acid sequence of SEQ ID NO: 65 or 67.

A further example of a chemokine of the various embodiments of the invention containing truncation and modifications and specifically adapted for use in the invention is described in detail herein (see Examples below). The truncated form of human CCL25 (TECK) corresponds to residues 1-74 of the mature protein, which encompasses the sequence corresponding to the chemokine fold. The full length mature protein is 127 amino acids (the signal peptide is 23 amino acids in a 150 amino acid immature protein). The single methionine within the sequence is altered to Norleucine, to mitigate against oxidation of this residue during the chain assembly, which was observed during the synthesis of the natural sequence derivative. The Gln at the N-terminus of the proteins is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 72 was modified through biotinylation on the resin. A PEG spacer was incorporated between the ε-amino functionality and the biotin.

Thus, in certain embodiments the invention also relates to a modified chemokine comprising, consisting essentially of or consisting of the amino acid sequence of SEQ ID NO: 68:

XGVFEDCCLAYHYPIGWAVLRRAWTYRIQEVSGSCNLPAAIFYLPKRHR

KVCGNPKSREVQRAXKLLDARNXVF

X1=pyroGlu or Gln
X64=Norleucine
X72=an amino acid residue that can be biotinylated, such as lysine, ornithine or diaminopropionic acid and optionally is biotinylated, optionally via a spacer molecule such as PEG, e.g. K(PEG-Biotin)

XGVFEDCCLAYHYPIGWAVLRRAWTYRIQEVSGSCNLPAAIFYLPKRHR

KVCGNPKSREVQRAXKLLDARNXVF

X1=pyroGlu or Gln
X64=Norleucine
X72=K(ivDde)

FmocLys(ivDde)-OH may be incorporated as residue 72 to facilitate site-specific labelling at this position of the protein (SEQ ID NO: 69). Subsequent removal of the ivDde protecting group, followed by coupling of the PEG spacer and Biotin, may be carried out as described in the general protocol section. The desired active chemokine may thus comprise, consist essentially of or consist of the amino acid sequence of SEQ ID NO: 70:

XGVFEDCCLAYHYPIGWAVLRRAWTYRIQEVSGSCNLPAAIFYLPKRHR

KVCGNPKSREVQRAXKLLDARNXVF

X1=pyroGlu or Gln
X64=Norleucine
X72 is K(PEG-Biotin)

A further example of a chemokine of the various embodiments of the invention containing modifications and specifically adapted for use in the invention is described in detail herein (see Examples below). Human CCL27 (CTAC) corresponding to residues 1-88, is initially expressed as 112 amino acids comprising the chemokine fold, and a 24 amino acid signal peptide which is cleaved off. The Met(87) within the sequence was mutated to lysine to provide a lysine at position 87 which was modified through biotinylation on the resin. A PEG spacer was incorporated between the ε-amino functionality and the biotin.

Thus, in certain embodiments the invention also relates to a modified chemokine comprising, consisting essentially of or consisting of the amino acid sequence of SEQ ID NO: 71:

FLLPPSTACCTQLYRKPLSDKLLRKVIQVELQEADGDCHLQAFVLHLAQ

RSICIHPQNPSLSQWFEHQERKLHGTLPKLNFGMLRKXG

X is an amino acid residue that can be biotinylated, such as lysine, ornithine or diaminopropionic acid and optionally is biotinylated, optionally via a spacer molecule such as PEG, e.g. K(PEG-Biotin)

FLLPPSTACCTQLYRKPLSDKLLRKVIQVELQEADGDCHLQAFVLHLAQ

RSICIHPQNPSLSQWFEHQERKLHGTLPKLNFGMLRKXG

X=K(ivDde)

FmocLys(ivDde)-OH is incorporated as residue 87 to facilitate site-specific labelling at this position of the protein (SEQ ID NO: 72). Subsequent removal of the ivDde protecting group, followed by coupling of the PEG spacer and Biotin, was carried out as described in the general protocol section. The desired active chemokine may thus comprise, consist essentially of or consist of the amino acid sequence of SEQ ID NO: 73:

FLLPPSTACCTQLYRKPLSDKLLRKVIQVELQEADGDCHLQAFVLHLAQ

RSICIHPQNPSLSQWFEHQERKLHGTLPKLNFGMLRKXG

X=K(PEG-Biotin)

A further example of a chemokine of the various embodiments of the invention containing modifications and specifically adapted for use in the invention is described in detail herein (see Examples below). The modified CXCL10 (IP-10) corresponds to residues 1 to 78 of the full length mature protein (and lacks the N-terminal signal peptide of 21 amino acids, which is cleaved off) and thus retains the chemokine fold. An amino acid which is capable of biotinylation, such as lysine or ornithine for example, may be inserted as residue 78. Insertion may be via a spacer, such as a PEG spacer. The linear amino acid sequence (SEQ ID NO: 74) is shown, prior to attachment of the PEG spacer, additional lysine and biotin molecules:

VPLSRTVRCTCISISNQPVNPRSLEKLEIIPASQFCPRVEIIATMKKKG

EKRCLNPESKAIKNLLKAVSKERSKRSP

Thus, position 78 may be modified through biotinylation. FmocLys(ivDde)-OH may be incorporated as residue 78 to facilitate site-specific labelling at this position of the protein (SEQ ID NO: 75). A suitable spacer, such as a PEG spacer, may be incorporated between the ε-amino functionality and the biotin. The biotinylated version comprises, consists essentially of or consists of the amino acid sequence of SEQ ID NO: 76.

Thus, in certain embodiments the invention also relates to a modified chemokine comprising, consisting essentially of or consisting of the amino acid sequence of SEQ ID NO: 76:

VPLSRTVRCTCISISNQPVNPRSLEKLEIIPASQFCPRVEIIATMKKKG

EKRCLNPESKAIKNLLKAVSKERSKRSPX

X is an amino acid residue that can be biotinylated, such as lysine, ornithine or diaminopropionic acid and optionally is biotinylated, optionally via a spacer molecule such as PEG, e.g. K(PEG-Biotin) and may be attached via a spacer molecule, e.g. PEG-K(Biotin)

The specific chemokines, including derivatives thereof as described herein, newly synthesised for use in the methods of the various embodiments of the invention may in certain embodiments in certain embodiments represent separate aspects of the invention. Biotinylation is positioned so as to permit immobilisation whilst retaining receptor binding capability.

Chemokines useful in the various embodiments of the invention may be synthesised through any suitable means known in the art. Preferably, the chemokines are chemically synthesised as this facilitates modification and labelling etc. However, recombinant DNA based approaches may also be employed in combination with appropriate labelling and modification technologies as required. Thus, in certain embodiments the invention also provides a nucleic acid molecule encoding the chemokines of the various embodiments of the invention. In other embodiments the invention also relates to a vector containing such a nucleic acid molecule and a host cell containing the vector. The vector may additionally comprise a suitable promoter operably linked to the nucleic acid molecule, to facilitate transcription of the corresponding mRNA molecule. The host cell may be capable of expressing the protein by transcription and translation of the nucleic acid molecule encoding a chemokine of the various embodiments of the invention.

The chemokines useful in the various embodiments of the invention can be biotinylated by methods known in the art such as described in WO 00/50088 A2, which is incorporated herein by reference in its entirety. As indicated above, site-specific labelling of the chemokines of the various embodiments of the invention is preferable, although any labelling technique which does not significantly affect the receptor-binding capacity of the chemokine may be employed. Various site-specifically biotinylated chemokines and native chemokines are available commercially, for instance from Almac, Craigavon, UK. In specific embodiments the one or more chemokines are biotinylated via a spacer group. The spacer may be employed to prevent the biotin group from impacting on the activity of the chemokine, in particular binding of the chemokine to its cognate receptor. Any suitable spacer that facilitates retention of receptor binding properties of the chemokine may be employed in the various embodiments of the invention. Thus, in the specific embodiments described above, spacers other than PEG spacers may be employed as appropriate. In specific embodiments, the spacer is a polyethylene glycol (PEG) spacer. PEG has been shown to be an effective spacer permitting attachment of biotin to the chemokine (which can then be immobilized on the solid support through interaction with streptavidin) without compromising receptor binding capability.

In the context of the various embodiments of the present invention the term "antibody" includes all immunoglobulins or immunoglobulin-like molecules with specific binding affinity for the relevant chemokine receptor (including by way of example and without limitation, IgA, IgD, IgE, IgG and IgM, combinations thereof, and similar molecules produced during an immune response in any vertebrate, for example, in mammals such as humans, goats, rabbits and mice). Specific immunoglobulins useful in the various embodiments of the invention include IgG isotypes. The antibodies useful in the various embodiments of the invention may be monoclonal or polyclonal in origin, but are typically monoclonal antibodies. Antibodies may be human antibodies, non-human antibodies, humanized versions of non-human antibodies, or chimeric antibodies. Various techniques for antibody humanization are well established and any suitable technique may be employed. The term "antibody" also refers to a polypeptide ligand comprising at least a light chain or heavy chain immunoglobulin variable region which specifically recognizes and binds an epitope of an antigen, and it extends to all antibody derivatives and fragments that retain the ability to specifically bind to the relevant chemokine receptor. These derivative and fragments may include Fab fragments, F(ab')2 fragments, Fv fragments, single chain antibodies, single domain antibodies, Fc fragments etc. The term antibody encompasses antibodies comprised of both heavy and light chains, but also heavy chain (only) antibodies. In specific embodiments, the antibodies may be engineered so as to be specific for more than one chemokine receptor, for example bi-specific to permit binding to two different chemokine receptors. Suitable commercially available antibodies which bind to the chemokine receptors of interest are listed in table 4. They may or may not be labelled. General reference may be made to "Antibodies a laboratory manual: By E Harlow and D Lane. pp 726. Cold Spring Harbor Laboratory. 1988", which reference is incorporated herein in its entirety.

TABLE 4

Commercially available fluorophore labelled antibodies against specific chemokine receptors

| Antibody | Fluorophore | Supplier |
| --- | --- | --- |
| CCR5 | PE | Biolegend |
| CXCR7 | PE | Biolegend |
| CCR6 | PE | BD Biosciences |
| CCR4 | PerCP Cy5.5 | BD Biosciences |
| CCR7 | PerCP Cy5.5 | Biolegend |
| CCR6 | PerCP Cy5.5 | BD Biosciences |
| CXCR4 | APC | R&D Systems |
| CCR8 | APC | R&D Systems |

The chemokine receptor expressing cells may thus be targeted using alternative binding agents, such as antibodies or other chemical compounds, as defined herein, rather than the natural chemokine binding partner. This approach is a new approach to treating inflammatory conditions.

Thus, in certain embodiments the invention also provides an apheresis column loaded with a solid support comprising a binding reagent capable of specifically binding to a chemokine receptor immobilized directly or indirectly on the support to permit removal of a cell expressing the chemokine receptor from the peripheral blood of a patient/subject, wherein the binding reagent is not a chemokine. The binding reagent capable of specifically binding to the chemokine receptor may be an agonist or an antagonist of the chemokine receptor. In specific embodiments, the binding reagent capable of specifically binding to the chemokine receptor is selected from an antibody and a chemical compound.

In other embodiments the invention thus also provides a method for treating an inflammatory condition comprising applying peripheral blood from a patient/subject to an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine) thus removing chemokine receptor expressing cells from the peripheral blood of the patient/subject. The method may comprise returning the blood depleted of the chemokine receptor expressing cells to the patient/subject.

Similarly, in other embodiments the invention provides a binding reagent capable of specifically binding to a chemokine receptor for use in the treatment of an inflammatory condition, wherein the binding reagent is immobilized on a solid support contained within an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient/subject, wherein the binding reagent is not a chemokine), to which is applied peripheral blood from a patient thus removing chemokine receptor expressing cells from the peripheral blood of the patient.

These aspects of the various embodiments of the invention may be integrated into the more focussed therapeutic aspects of the various embodiments of the invention (i.e. treating cancer and various aspects thereof) and thus the remainder of the disclosure, including all specific embodiments, applies mutatis mutandis.

Solid support materials for immobilizing the binding reagents of the various embodiments of the invention are known in the art. "Solid support" refers to, for example, materials having a rigid or semi-rigid surface or surfaces, and may take the form of beads, resins, gels, microspheres, or other geometric configurations. A useful support material is one that does not activate blood cells so as to make them coagulate or adhere to the support as peripheral whole blood is applied to the device. In certain embodiments, a support treated with an agent to provide it with anti-coagulation properties, in particular a heparinized support is employed. Alternatively, the blood of the patient may be treated with an anti-coagulant such as heparin prior to application to the support. Useful support materials comprise high molecular weight carbohydrates, in particular carbohydrates having a molecular weight of 100 kDa or more, such as agarose, in particulate form, optionally cross-linked, and cellulose. Other preferred support materials are polymers, such as carboxylated polystyrene, and glass. The support of the various embodiments of the invention may be provided in the form of particles or fibres. The support particles may have regular form, such as spheres or beads, or irregular form. They may be porous or non-porous. A preferred average particle size of the support is from 50 µm to 2 mm. In certain embodiments Sepharose™, a cross linked, beaded-form of agarose, is used as the column matrix. It is chosen for its optimal distribution capacity and can provide a large available area for affinity binding. Solid supports may be provided in the form of magnetic beads, with the specific binding reagent immobilized on the magnetic beads. Following capture of the (CCR5, CCR6, CCR7, CCR8, CXCR4, CXCR7, CCR4, CCR9, CCR10, CXCR3 and/or CXCR5; or CCR4, CCR8 or CLA where Tregs are specifically targeted) chemokine receptor and/or Treg receptor expressing cells from the blood, the beads can be removed from the blood with the aid of an appropriate magnetic separator.

Methods for immobilizing binding reagents on a solid support are known in the art. A binding reagent, such as a chemokine, antibody, peptide, nucleic acid or chemical compound, can be immobilized on the support in a direct or indirect manner. Immobilization can be by means of a suitable linker in some embodiments. A preferred method of indirect immobilization of a binding reagent, such as a chemokine, relies upon the interaction between biotin and avidin molecules. "Avidin" or "avidin molecule" refers to any type of protein that specifically binds biotin to the substantial exclusion of other (small) molecules that might be present in a biological sample. Examples of avidin include avidins that are naturally present in egg white, oilseed protein (e.g., soybean meal), and grain (e.g., corn/maize), and streptavidin, which is a protein of bacterial origin. Thus, biotinylation of the binding reagent and use of an avidin molecule such as streptavidin immobilized on the solid support allows reliable attachment of the binding reagent to the solid support according to methods known in the art. Specifically, such a method may comprise providing the binding reagent in biotinylated form, providing a solid support having streptavidin immobilized on its surface, contacting the support with an aqueous solution of the biotinylated binding reagent, and rinsing the support with an aqueous solvent. In addition, binding pair interactions, such as antibody-antigen interactions, may also be utilised for indirect immobilisation of binding reagent onto a support. In such embodiments the support may be derivatised with one member of a binding pair, such as an antibody or fragment or derivative thereof, as defined herein, which has known affinity for a particular peptide sequence or small molecule hapten. Incorporating the other member of the binding pair, such as an antigen, peptide sequence or the hapten onto or into the binding reagent facilitates immobilisation onto a solid support coated with the corresponding antibody or fragment or derivative thereof. Thus, the binding reagent may be modified to include the peptide sequence or hapten into the linear molecule or may be added as a side chain or label. Any suitable antibody-antigen pair may be employed. The antibody fragment or derivative may be any fragment or derivative that retains specific binding affinity for the appropriate antigen. Examples include Fab, F(ab')2 fragments, scFV, VH domains, single domain antibodies (such as nanobodies), heavy chain antibodies and humanized version of non-human antibodies etc. Other high affinity interactions can be utilised for immobilisation of binding reagents, as long as the binding reagent can be synthesised or derivatised with one of the interacting partners and the solid support synthesised or derivatised with the other interacting partner without loss of binding activity (i.e. binding of the binding reagent to the appropriate chemokine receptor). Immobilization may occur via essentially the same interaction in reverse in some embodiments. Thus, the binding reagent which may be a chemokine for example, may be attached to an antibody as defined herein, and the solid support derivatised with the antigen. The chemokine may be produced as a fusion protein with the antibody.

Alternatively binding reagents, such as chemokines and antibodies, can be immobilised directly onto a solid support using bioconjugation techniques established in the field. For example direct immobilisation of proteins onto cyanogen bromide activated solid supports via amino functionalities within the primary sequence of the protein. Alternatively, sulphydryl functionalities within proteins can be used to directly immobilise the protein to alkyl halide derivatised supports or supports containing free thiol functionalities. In further embodiments, proteins containing α-thioester functionalities can be directly immobilised on supports containing 1,2 amino thiol moieties (eg N-terminal cysteine) using the native chemical ligation reaction. Alternatively proteins modified with ketones and aldehydes can be immobilised on solid supports derivatised with hydrazinyl, hydrazide and aminoxy functionalities using hydrazone/oxime bond forming ligation reactions (and vice versa). Alternatively 'Click' chemistry can be used to immobilise proteins onto solid supports, whereby the protein and the support are derivatised with the appropriate mutually reactive chemical functionalities (azides and alkynes). In other embodiments Staudinger ligation chemistry can be used to immobilise appropriately derivatised proteins onto the appropriately derivatised solid supports.

The solid support is contained within or carried by the apheresis column. Thus, by "loaded" is meant that the column carries or contains the solid support in a manner such that (peripheral) blood can flow through the column in contact with the solid support. Thus, the solid support provides a matrix within the column through which blood flows, in continuous fashion in certain embodiments. This permits cells expressing the specific chemokine receptor to be removed from the blood passing through the column, such that blood exiting the column is depleted of the specific chemokine receptor-expressing cells. In specific embodiments, the apheresis column is loaded with a support comprising streptavidin immobilized on the support and one or more biotinylated binding reagents, such as chemokines, bound to the streptavidin on the support. The solid support may be comprised of a high-molecular weight carbohydrate, optionally cross-linked, such as agarose.

As discussed above, the binding reagent is coupled to the solid support. The relative amounts of binding reagent may be controlled to ensure that coupling between the solid support and the binding reagent will be immediate, minimising the risk of binding reagent decoupling from the solid support. Thus, it may be ensured that there is a relative excess of immobilization sites for the binding reagent on the solid support. Alternatively, or additionally, following immobilization of the binding reagent on the solid support, the solid support may be washed to remove any unbound binding reagent.

The apheresis column utilised in the various embodiments of the present invention acts as a leukapheresis treatment for cancer. The column acts to specifically remove one or more of CCR5, CCR6, CCR7, CCR8, CXCR4, CXCR7, CCR4, CCR9, CCR10, CXCR3 and/or CXCR5-expressing cells, by exploiting the interaction between CCR5, CCR6, CCR7, CCR8, CXCR4, CXCR7, CCR4, CCR9, CCR10, CXCR3 and/or CXCR5 expressed on the cell surface and a specific binding reagent immobilized on a solid support contained within or carried by the column. In other embodiments, the column acts to specifically remove one or more of Treg receptor expressing cells, in particular CLA, CCR4 and/or CCR8 expressing cells, by exploiting the interaction between Treg receptors such as CLA, CCR4 and CCR8 expressed on the cell surface and a specific binding reagent immobilized on a solid support contained within or carried by the column. The overall column typically comprises, consists of, or consists essentially of three combined components; 1) a housing which contains or carries 2) the solid support and 3) one or more binding reagents (immobilized thereon) which specifically bind one or more chemokine receptors. The housing may be manufactured from any suitable material for clinical use. In certain embodiments the housing is composed of a plastic material. The housing includes an in flow site for entry of blood and an out flow site for blood (depleted of target cells) to exit the column. The housing may be designed to maintain a continuous blood flow through the solid support matrix. The housing (as shown for example in FIG. 9) may include a top portion which comprises a distribution plate (2) at the inflow site (1) to spread the blood evenly over the entire matrix area. The distribution plate may act as a first safety barrier preventing larger particles flowing through the column and into the patient. However, the distribution plate is not essential and may be removed in some embodiments to decrease the overall resistance in the system. The column may contain one or more safety filter units (3 and 4) placed at the inflow (1) and/or outflow (5) sites of the plastic housing. Such filter units may act to prevent particles larger than blood cells passing in and/or out of the column. The safety filter units may contain a plurality of filters, such as two, three or four filters designed to be a robust barrier and stop all particles larger than blood cells passing through the column. Inclusion of safety filters (3 and 4) at both ends of the column serves to minimize the risk of leakage of particles into the patient, including in the event that the device is incorrectly connected resulting in blood flow in the opposite direction to that intended. The safety filters may comprise of any suitable pore size to prevent particles larger than blood cells from passing through the column, as would be readily understood by one skilled in the art. Suitable filters are commercially available. In specific embodiments, the pore size of the filter(s) is between approximately 60 μm and 100 μm, more specifically approximately 80 μm. The solid support and binding reagent components are discussed in further detail herein.

The volume of the housing may be varied depending upon the blood volumes intended to pass through the column. Typically, the volume of the housing is between approximately 40 ml and 200 ml, more specifically 50 ml to 150 ml or 60 ml to 120 ml. For leukemia treatments housing volumes tend to be higher, due to the large number of cells which are to be removed from the blood. In such embodiments, the housing volume is typically in the region of approximately 100 ml to 500 ml, such as 100 ml to 300 ml or 120 ml to 150 ml. In specific embodiments, the housing volume is approximately 120 ml.

The column is generally applied in the form of an apheresis circuit. In this context, the overall system includes the apheresis column, tubing and an appropriate pump to pump the blood around the circuit. The system is illustrated in FIG. 10. The patient (1) is connected to the extracorporeal circuit via sterile needles to veins in the right and the left arms. A saline bag (3) is also connected and the saline solution is pumped with a suitable pump (2). Blood is drawn from one arm of the patient through the sterile tubing system by the blood pump (4) and passed through the column (6) and back to the patient. The tubing system may be connected to the column via any suitable coupling, such as standard dialysis luer-lock couplings. The couplings on the column may be colour-coded for correct assembly. For example, red tubing for inflow to the red column top and blue tubing for outflow back to the patient. An air detector (8) may be present in the circuit. Inlet pressure (5) and/or Pven sensors (7) may additionally be employed to monitor the pressure in the circuit.

An apheresis pump, such as the 4008 ADS pump manufactured by Fresenius Medical Care or the Adamonitor pump, may monitor the patient's inflow and outflow. The pump may also monitor the pressure in the extracorporeal circulation. The pump may be able to discriminate air by a bubble catcher and air detector. A clot catcher filter may be positioned inside the bubble catcher. The pump may also incorporate an optical detector to distinguish between light, e.g. saline solution or air present in the tubing system and dark e.g. blood present in the tubing system.

A schematic diagram of a suitable pump, showing the air detector and optical filter is shown in FIG. 11. If the pump system detects air bubbles and optical fluctuations or if extracorporeal pressure values are out of the set range, then the pump may stop immediately. Alternatively or additionally a visual/audible alarm may be emitted.

The treatment methods of the various embodiments of the invention may thus rely upon an extracorporeal circuit. The methods may be considered as ex vivo or in vitro methods and be defined solely with reference to steps performed outside of the patient. In some embodiments, however, the method further comprises, prior to application of the blood to the column, collecting peripheral blood from the patient. In a further embodiment, the method further comprises, following the application of the blood to the column, infusing the blood depleted of (CCR5, CCR6, CCR7, CCR8, CXCR4, CXCR7, CCR4, CCR9, CCR10, CXCR3 and/or CXCR5) chemokine receptor expressing cells or of Treg receptor, such as CLA, CCR4 or CCR8 expressing cells (Tregs) to the patient. This is then a complete leukapheresis treatment method. Thus, a leukaphereis method, for treating cancer, comprises collecting peripheral blood from the patient; applying the peripheral blood to an apheresis column loaded with a solid support comprising one or more binding reagents capable of specifically binding to one or more chemokine receptors, in particular the chemokine receptor CCR5, CCR6, CCR7, CCR8, CXCR4, CXCR7, CCR4, CCR9, CCR10, CXCR3 and/or CXCR5; or the Treg receptors CLA, CCR4 and/or CCR8, immobilized directly or indirectly on the support thus removing one or more of CCR5, CCR6, CCR7, CCR8, CXCR4, CXCR7, CCR4, CCR9, CCR10, CXCR3 and/or CXCR5 expressing cells, or specifically Tregs in some embodiments, from the peripheral blood of the patient; and infusing the depleted blood (of chemokine receptor expressing cells) to the patient.

The peripheral blood may be continuously collected from the patient. Similarly, the depleted blood may be continuously infused to the patient, through use of an appropriate circuit as described herein. Thus, the support may be disposed in a column through which the blood is made to flow. This may be achieved using a suitable pump for example, as also described herein. Blood flow through the column enables the binding reagent(s) immobilized on the solid support to capture the cells expressing the chemokine receptor, thus depleting them from the blood and preventing their contribution to the cancer linked condition.

The methods of the various embodiments of the invention and binding reagents for use in the methods of the various embodiments of the invention may require that the patient has been selected for treatment on the basis of detecting an increase in the level of chemokine receptor, in particular, one or more of CCR5, CCR6, CCR7, CCR8, CXCR4, CXCR7, CCR4, CCR9, CCR10, CXCR3 and/or CXCR5 expressing cells and/or Treg receptor expressing cells, for example CLA, CCR4 and/or CCR8 expressing cells in a sample obtained from the patient. Such companion diagnostic methods are described in greater detail herein and are based, for example, on the observation that CCR5, CCR6, CCR7, CCR8, CXCR4, CXCR7, CCR4, CCR9, CCR10, CXCR3 and/or CXCR5 expression may be present on circulating tumour cells and CLA, CCR4 and/or CCR8 expression may be present specifically on regulatory T cells (that contribute to immune system avoidance by a cancer).

Thus, (in this context) in certain embodiments the invention also provides a method of diagnosing, monitoring progression of, or monitoring treatment of cancer comprising determining:

a) the levels of one or more of the chemokine receptor CCR5, CCR6, CCR7, CCR8, CXCR4, CXCR7, CCR4, CCR9, CCR10, CXCR3 and/or CXCR5 expressing cells b) levels of expression of one or more of CCR5, CCR6, CCR7, CCR8, CXCR4, CXCR7, CCR4, CCR9, CCR10, CXCR3 and/or CXCR5; and/or c) levels of cells with high expression of one or more of CCR5, CCR6, CCR7, CCR8, CXCR4, CXCR7, CCR4, CCR9, CCR10, CXCR3 and/or CXCR5 in a sample obtained from a subject, wherein high levels of one or more of CCR5, CCR6, CCR7, CCR8, CXCR4, CXCR7, CCR4, CCR9, CCR10, CXCR3 and/or CXCR5 expressing cells, high levels of expression of one or more of CCR5, CCR6, CCR7, CCR8, CXCR4, CXCR7, CCR4, CCR9, CCR10, CXCR3 and/or CXCR5 or high levels of cells with high expression of one or more of CCR5, CCR6, CCR7, CCR8, CXCR4, CXCR7, CCR4, CCR9, CCR10, CXCR3 and/or CXCR5 or increased levels of one or more of CCR5, CCR6, CCR7, CCR8, CXCR4, CXCR7, CCR4, CCR9, CCR10, CXCR3 and/or CXCR5 expressing cells compared to control, increased levels of expression of one or more of CCR5, CCR6, CCR7, CCR8, CXCR4, CXCR7, CCR4, CCR9, CCR10, CXCR3 and/or CXCR5 compared to a control or increased levels of cells with high expression of one or more of CCR5, CCR6, CCR7, CCR8, CXCR4, CXCR7, CCR4, CCR9, CCR10, CXCR3 and/or CXCR5 compared to a control indicate the presence or progression of cancer. Levels of chemokine receptor expression, as opposed to cell numbers, may also be investigated as increased levels of chemokine receptor expression per cell may also be diagnostically relevant.

Similarly, in other embodiments the invention also provides a method of diagnosing, monitoring progression of, or monitoring treatment of cancer comprising determining:

a) the levels of one or more Treg receptor expressing cells, in particular CLA, CCR4 and/or CCR8 expressing cells b) levels of expression of one or more of Treg receptors in particular CLA, CCR4 and/or CCR8; and/or c) levels of cells with high expression of one or more of Treg receptors in particular CLA, CCR4 and/or CCR8 in a sample obtained from a subject, wherein high levels of one or more of Treg receptors in particular CLA, CCR4 and/or CCR8 expressing cells, high levels of expression of one or more Treg receptors in particular CLA, CCR4 and/or CCR8 or high levels of cells with high expression of one or more of Treg receptors in particular CLA, CCR4 and/or CCR8 or increased levels of one or more of Treg receptors in particular CLA, CCR4 and/or CCR8 expressing cells compared to control, increased levels of expression of one or more of Treg receptors in particular CLA, CCR4 and/or CCR8 compared to a control or increased levels of cells with high expression of one or more of Treg receptors in particular CLA, CCR4 and/or CCR8 compared to a control indicate the presence or progression of cancer. Levels of Treg receptor expression, as opposed to cell numbers, may also be investigated as increased levels of Treg receptor expression per cell may also be diagnostically relevant. For the avoidance of doubt "Treg receptor expressing cells" may comprise, consist essentially of or consist of Tregs, in particular Tregs that express the specific receptor or receptors. This applies to all relevant aspects of the various embodiments of the invention.

"Diagnosing" is defined herein to include screening for a disease/condition or pre-indication of a disease/condition, identifying a disease/condition or pre-indication of a disease/condition and checking for recurrence of disease/condition following treatment. The methods of the various embodiments of the invention may also have prognostic value, and this is included within the definition of the term "diagnosis". The prognostic value of the methods of the various embodiments of the invention may be used as a marker of potential susceptibility to cancer by identifying levels of one or more of CCR5, CCR6, CCR7, CCR8, CXCR4, CXCR7, CCR4, CCR9, CCR10, CXCR3 and/or CXCR5; and/or of Treg receptors in particular CLA, CCR4 and/or CCR8. Thus patients at risk may be identified before the disease has a chance to manifest itself in terms of symptoms identifiable in the patient. In certain embodiments, diagnosis may be made in conjunction with other objective indicators of cancer. Thus, in specific embodiments, diagnosis is made in conjunction with one or more of the following indicators: clinical indications as known in the art. Also increased number of Tregs (CD4+ CD25hiCD127lo/– and Foxp3 positive) is a diagnostic indicator of poor prognosis in cancer. Determining the number of circulating leukemic or tumor cells and their chemokine receptor profile expression may be a further technique used in conjunction with the methods of the various embodiments of the invention.

"Monitoring progression of" includes performing the methods to monitor the stage and/or the state and progression of the cancer. Monitoring progression may involve performing the diagnostic methods multiple times on the same patient to determine whether the levels of one or more of CCR5, CCR6, CCR7, CCR8, CXCR4, CXCR7, CCR4, CCR9, CCR10, CXCR3 and/or CXCR5; and/or Treg receptors in particular CLA, CCR4 and/or CCR8 expressing cells are increasing, decreasing or remaining stable over a certain time period. This may be in the context of a treatment regime.

"Monitoring the success of a particular treatment" is defined to include determining the levels of one or more of CCR5, CCR6, CCR7, CCR8, CXCR4, CXCR7, CCR4, CCR9, CCR10, CXCR3 and/or CXCR5 expressing cells; and/or Treg receptor in particular CLA, CCR4 and/or CCR8 expressing cells before and after a treatment. The treatment is generally one aimed at treating cancer and may be a treatment according to one of the methods of the various embodiments of the invention as defined herein. Successful treatment may be determined with reference to a decrease in one or more of CCR5, CCR6, CCR7, CCR8, CXCR4, CXCR7, CCR4, CCR9, CCR10, CXCR3 and/or CXCR5 expressing cells; and/or Treg receptor in particular CLA, CCR4 and/or CCR8 expressing cells as a result of, or following, the treatment. Thus, in such methods a level of one or more of CCR5, CCR6, CCR7, CCR8, CXCR4, CXCR7, CCR4, CCR9, CCR10, CXCR3 and/or CXCR5 expressing cells; and/or Treg receptor in particular CLA, CCR4 and/or CCR8 expressing cells is determined prior to treatment. This level is recorded and a further assessment made at a predetermined time following the treatment. The comparison of levels of one or more of CCR5, CCR6, CCR7, CCR8, CXCR4, CXCR7, CCR4, CCR9, CCR10, CXCR3 and/or CXCR5 expressing cells; and/or Treg receptor in particular CLA, CCR4 and/or CCR8 expressing cells permits the success of the treatment to be monitored. In specific embodiments, a single treatment is sufficient to cause a depletion of around 10%, 20%, 30%, 40%, 50%, 60% or 70%, or higher, up to 80%, 90%, 95% or more, or any range of values between and including these amounts, of one or more specific chemokine receptors, in particular one or more of CCR5, CCR6, CCR7, CCR8, CXCR4, CXCR7, CCR4, CCR9, CCR10, CXCR3 and/or CXCR5 expressing cells; and/or Treg receptor in particular CLA, CCR4 and/or CCR8 expressing cells from the peripheral blood of the patient. In specific embodiments, at least around 50% depletion is achieved in a single treatment. Thus, successful treatment may be defined with reference to depletion of one or more of CCR5, CCR6, CCR7, CCR8, CXCR4, CXCR7, CCR4, CCR9, CCR10, CXCR3 and/or CXCR5 expressing cells; and/or Treg receptor in particular CLA, CCR4 and/or CCR8 expressing cells. Treatment may lead to depletion of between approximately 100 and 500 million of one of more of CCR5, CCR6, CCR7, CCR8, CXCR4, CXCR7, CCR4, CCR9, CCR10, CXCR3 and/or CXCR5 expressing cells, such as regulatory T lymphocytes and cancer cells; and/or Treg receptor in particular CLA, CCR4 and/or CCR8 expressing cells, in certain embodiments. Additional factors may be included to determine successful treatment. For example, a lack of increase in one or more of CCR5, CCR6, CCR7, CCR8, CXCR4, CXCR7, CCR4, CCR9, CCR10, CXCR3 and/or CXCR5 expressing cells; and/or Treg receptor in particular CLA, CCR4 and/or CCR8 expressing cells following treatment may indicate successful treatment in terms of preventing further progression of the condition, optionally combined with an improvement in other markers or staging of the cancer. By binding to the column through the binding reagent-chemokine receptor interaction, chemokine receptor expressing cells are immobilized. These immobilized cells express further unoccupied chemokine receptors, which may be of the same or different type to those used for capture. These additional chemokine receptors may permit circulating chemokines which contribute to the cancer to be captured from the peripheral blood. Thus, a reduction in circulating (specific) chemokine levels may provide a measure of successful treatment.

In specific embodiments, the condition associated with cancer or cancer treatment is selected from reducing levels of circulating tumour cells, reducing the incidence of tumour metastasis, removing regulatory T lymphocytes from the peripheral blood, or treating leukaemias such as chronic lymphocytic leukaemia, chronic myeloid leukemia, use for debulking in AML, ALL and before harvest for autologous bone marrow/stem cell transplantation and (treating the) leukemic phase of lymphoma.

The sample in which one or more of CCR5, CCR6, CCR7, CCR8, CXCR4, CXCR7, CCR4, CCR9, CCR10, CXCR3 and/or CXCR5 expressing cell levels, levels of expression of one or more of CCR5, CCR6, CCR7, CCR8, CXCR4, CXCR7, CCR4, CCR9, CCR10, CXCR3 and/or CXCR5 and/or levels of cells with high expression of one or more of CCR5, CCR6, CCR7, CCR8, CXCR4, CXCR7, CCR4, CCR9, CCR10, CXCR3 and/or CXCR5 (defined as CCR5hi, CCR6hi, CCR7hi, CCR8hi, CXCR4hi, CXCR7hi, CCR4hi, CCR9hi, CCR100hi, CXCR3hi and/or CXCR5hi) are determined may comprise any suitable tissue sample or body fluid sample. Generally, the test sample is obtained from a human subject. Typically, the sample is a blood sample, in particular a peripheral blood sample. The methods may involve determining levels of one or more of CCR5, CCR6, CCR7, CCR8, CXCR4, CXCR7, CCR4, CCR9, CCR10, CXCR3 and/or CXCR5 expressing tumour cells or regulatory T lymphocytes in certain embodiments.

Similarly, the sample in which one or more of Treg receptor in particular CLA, CCR4 and/or CCR8 expressing cell levels, levels of expression of one or more of Treg receptors in particular CLA, CCR4 and/or CCR8 and/or levels of cells with high expression of one or more of Treg receptors in particular CLA, CCR4 and/or CCR8 (defined as CLAhi, CCR4hi, and/or CCR8hi) are determined may comprise any suitable tissue sample or body fluid sample. Generally, the test sample is obtained from a human subject. Typically, the sample is a blood sample, in particular a peripheral blood sample. The methods may involve determining levels of one or more of Treg receptors in particular CLA, CCR4 and/or CCR8 expressing regulatory T lymphocytes in certain embodiments.

Levels of CCR5, CCR6, CCR7, CCR8, CXCR4, CXCR7, CCR4, CCR9, CCR10, CXCR3 and/or CXCR5 expressing cells, levels of expression of CCR5, CCR6, CCR7, CCR8, CXCR4, CXCR7, CCR4, CCR9, CCR10, CXCR3 and/or CXCR5 and/or levels of cells with high expression of CCR5, CCR6, CCR7, CCR8, CXCR4, CXCR7, CCR4, CCR9, CCR10, CXCR3 and/or CXCR5 (defined as CCR5hi, CCR6hi, CCR7hi, CCR8hi, CXCR4hi, CXCR7hi, CCR4hi, CCR9hi, CCR100hi, CXCR3hi and/or CXCR5hi) may be determined according to any suitable method. Similarly, levels of Treg receptors in particular CLA, CCR4 and/or CCR8 expressing cells, levels of expression of Treg receptors in particular CLA, CCR4 and/or CCR8 and/or levels of cells with high expression of Treg receptors in particular CLA, CCR4 and/or CCR8 (defined as CLAhi, CCR4hi, and/or CCR8hi) may be determined according to any suitable method.

For example, flow cytometry may be employed in order to determine the number of cells expressing CCR5, CCR6, CCR7, CCR8, CXCR4, CXCR7, CCR4, CCR9, CCR10, CXCR3 and/or CXCR5; and/or Treg receptors in particular CLA, CCR4 and/or CCR8 expressing cells in the sample, to determine levels of CCR5, CCR6, CCR7, CCR8, CXCR4, CXCR7, CCR4, CCR9, CCR10, CXCR3 and/or CXCR5 expression; and/or Treg receptors in particular CLA, CCR4 and/or CCR8 expression and/or to identify levels of CCR5hi, CCR6hi, CCR7hi, CCR8hi, CXCR4hi and/or CXCR7hi, optionally and/or CCR4hi; and/or CLAhi, CCR4hi, and/or CCR8hi cells. Flow cytometric techniques are described herein and examples of commercially available antibodies suitably labelled for use in flow cytometry are set out in Table 4 for example. Alternatively, the method may involve steps of collecting and fixing the cells in the sample, followed by incubation with a suitable binding reagent that binds specifically to the CCR5, CCR6, CCR7, CCR8, CXCR4, CXCR7, CCR4, CCR9, CCR10, CXCR3 and/or CXCR5 chemokine receptor expressing cells; and/or Treg receptors in particular CLA, CCR4 and/or CCR8 expressing cells in the sample. Any suitable binding reagent, as defined herein, may be employed. For example, a CCR5, CCR6, CCR7, CCR8, CXCR4, CXCR7, CCR4, CCR9, CCR10, CXCR3 and/or CXCR5; and/or Treg receptor in particular CLA, CCR4 and/or CCR8 specific antibody may be employed. A wash step may be adopted following an incubation period to remove any unbound reagent. Suitable wash steps and incubation conditions would be well known to one skilled in the art. The binding reagent may be directly labeled in order to permit antibody binding to be directly determined. Alternatively a secondary binding reagent, such as an antibody, may be employed which binds to the first binding reagent and carries a label. Again, suitable incubation conditions and wash steps would be apparent to one skilled in the art. The primary and secondary binding reagents may form two halves of a binding pair. The binding interaction should not prevent the primary binding reagent binding to the CCR5, CCR6, CCR7, CCR8, CXCR4, CXCR7, CCR4, CCR9, CCR10, CXCR3 and/or CXCR5; and/or Treg in particular CLA, CCR4 and/or CCR8 receptor expressing cells, unless a competition assay is being employed. The two halves of a binding pair may comprise an antigen-antibody, antibody-antibody, receptor-ligand, biotin-streptavidin pair etc. in certain embodiments. Other techniques used to quantify chemokine (CCR5, CCR6, CCR7, CCR8, CXCR4, CXCR7, CCR4, CCR9, CCR10, CXCR3 and/or CXCR5; and/or Treg receptors in particular CLA, CCR4 and/or CCR8) receptor expressing cell levels, to quantify levels of CCR5, CCR6, CCR7, CCR8, CXCR4, CXCR7, CCR4, CCR9, CCR10, CXCR3 and/or CXCR5; and/or Treg receptor in particular CLA, CCR4 and/or CCR8 expression and/or to quantify levels of CCR5hi, CCR6hi, CCR7hi, CCR8hi, CXCR4hi or CXCR7hi, optionally and/or CCR4hi cells; and/or CLAhi, CCR4hi, and/or CCR8hi cells include PCR-based techniques such as QT-PCR and protein based methods such as western blot. Quantitation may be achieved with reference to fixed cell lines carrying known numbers of various receptor expressing cells and/or known levels of receptor expression per cell. Such fixed cell lines are available commercially (for example ChemiScreen™ cell lines from Millipore). Methods analogous to the treatment methods of the various embodiments of the invention may also be employed, with binding of CCR expressing cells to the solid support being determined following peripheral blood being passed through the column.

The levels of CCR5, CCR6, CCR7, CCR8, CXCR4, CXCR7, CCR4, CCR9, CCR10, CXCR3 and/or CXCR5 expressing cells, levels of expression of CCR5, CCR6, CCR7, CCR8, CXCR4, CXCR7, CCR4, CCR9, CCR10, CXCR3 and/or CXCR5 and/or levels of cells with high expression of CCR5, CCR6, CCR7, CCR8, CXCR4, CXCR7, CCR4, CCR9, CCR10, CXCR3 and/or CXCR5 (defined as CCR5hi, CCR6hi, CCR7hi, CCR8hi, CXCR4hi, CXCR7hi, CCR4hi, CCR9hi, CCR100hi, CXCR3hi and/or CXCR5hi) may be determined relative to a suitable control. Similarly, levels of Treg receptor in particular CLA, CCR4 and/or CCR8 expressing cells, levels of expression of Treg receptors in particular CLA, CCR4 and/or CCR8 and/or levels of cells with high expression of Treg receptors in particular CLA, CCR4 and/or CCR8 (defined as CLAhi, CCR4hi, and/or CCR8hi) may be determined relative to a suitable control. When diagnosing a condition associated with cancer, a threshold level of cells, level of expression of CCR5, CCR6, CCR7, CCR8, CXCR4, CXCR7, CCR4, CCR9, CCR10, CXCR3 and/or CXCR5; and/or Treg receptors in particular CLA, CCR4 and/or CCR8 and/or level of cells with high expression of CCR5, CCR6, CCR7, CCR8, CXCR4, CXCR7, CCR4, CCR9, CCR10, CXCR3 and/or CXCR5 (defined as CCR5hi, CCR6hi, CCR7hi, CCR8hi, CXCR4hi, CXCR7hi, CCR4hi, CCR9hi, CCR100hi, CXCR3hi and/or CXCR5hi); and/or Treg receptors in particular CLA, CCR4 and/or CCR8 expressing cells (defined as CLAhi, CCR4hi, and/or CCR8hi) may be set at or over which a positive diagnosis is made. This threshold may be determined based upon measuring levels of CCR5, CCR6, CCR7, CCR8, CXCR4, CXCR7, CCR4, CCR9, CCR10, CXCR3 and/or CXCR5 expressing cells, levels of expression of CCR5, CCR6, CCR7, CCR8, CXCR4, CXCR7, CCR4, CCR9, CCR10, CXCR3 and/or CXCR5 and/or levels of cells with high expression of CCR5, CCR6, CCR7, CCR8, CXCR4, CXCR7, CCR4, CCR9, CCR10, CXCR3 and/or CXCR5 (defined as CCR5hi, CCR6hi, CCR7hi, CCR8hi, CXCR4hi, CXCR7hi, CCR4hi, CCR9hi, CCR100hi, CXCR3hi and/or CXCR5hi, optionally and/or CCR4hi) in samples obtained from diseased patients and comparing these levels with levels of CCR5, CCR6, CCR7, CCR8, CXCR4, CXCR7, CCR4, CCR9, CCR10, CXCR3 and/or CXCR5 expressing cells, levels of expression of CCR5, CCR6, CCR7, CCR8, CXCR4, CXCR7, CCR4, CCR9, CCR10, CXCR3 and/or CXCR5 and/or levels of cells with high expression of CCR5, CCR6, CCR7, CCR8, CXCR4, CXCR7, CCR4, CCR9, CCR10, CXCR3 and/or CXCR5 (defined as CCR5hi, CCR6hi, CCR7hi, CCR8hi, CXCR4hi, CXCR7hi, CCR4hi, CCR9hi, CCR100hi, CXCR3hi and/or CXCR5hi) in samples obtained from healthy subjects. Similarly, where diagnosis is based upon Tregs specifically, this threshold may be determined based upon measuring levels of Treg receptors in particular CLA, CCR4 and/or CCR8 expressing cells, levels of expression of Treg receptors in particular CLA, CCR4 and/or CCR8 and/or levels of cells with high expression of Treg receptors in particular CLA, CCR4 and/or CCR8 (defined as CLAhi, CCR4hi, and/or CCR8hi) in samples obtained from diseased patients and comparing these levels with levels of Treg receptor in particular CLA, CCR4 and/or CCR8 expressing cells, levels of expression of Treg receptors in particular CLA, CCR4 and/or CCR8 and/or levels of cells with high expression of Treg receptors in particular CLA, CCR4 and/or CCR8 (defined as CLAhi, CCR4hi, and/or CCR8hi) in samples obtained from healthy subjects.

In certain embodiments, cancer is diagnosed on the basis of levels of chemokine receptor expressing cells. A positive diagnosis may be made in subjects based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, cancer is diagnosed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to healthy controls.

In specific embodiments, leukemias such as CLL are diagnosed on the basis of levels of CCR7 expressing cells. A positive diagnosis may be made in subjects where the levels of CCR7 expressing cells are sufficient to interfere with normal hematopoiesis. This may be when the majority of circulating cells are leukemic, and in addition are CCR7 positive. Thus, diagnosis may be made based upon the presence of greater than about 50%, such as greater than about 55%, greater than about 60%, greater than about 65%, greater than about 70%, greater than about 75%, greater than about 80%, greater than about 85%, greater than about 90%, greater than about 95% or more CCR7 expressing cells in the sample, as a percentage of total cells in the sample.

In other embodiments, cancer is diagnosed on the basis of measuring levels of Treg receptor expressing cells. Thus, a positive diagnosis according to the various embodiments of the invention may be made based upon the presence of a about a 1.2 fold or greater increase, such as about a 1.5, 2, 2.5, 3, 3.5, 4, 4.5, 5, 10, 20, 50 or 100 or greater fold increase in Treg receptor expressing cells, relative to healthy controls. In specific embodiments, cancers such as pancreatic cancer and urinirary bladder cancer are diagnosed on the basis of measuring levels of CCR4 expressing cells. A positive diagnosis may be made in subjects where the levels of CCR4 expressing cells, in particular CCR4 expressing Tregs, are increased relative to healthy controls. Thus, a diagnosis according to the various embodiments of the invention may be made based upon the presence of about a 1.2-fold or greater increase, such as about a 1.5, 2, 2.5, 3, 3.5, 4, 4.5, 5, 10, 20, 50 or 100 or greater fold increase in CCR4 expressing cells, in particular CCR4 expressing Tregs, relative to healthy controls.

In certain embodiments, progression of cancer, which may be in the context of a treatment regime, is monitored on the basis of levels of chemokine receptor expressing cells at different time points. Progression of cancer may be indicated in subjects based upon an increase of greater than about 10%, such as an increase of greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more chemokine receptor expressing cells in the sample, as a percentage of total cells in the sample, compared to a sample taken from the same subject at an earlier time point. In other embodiments, progression of cancer is confirmed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to a sample taken from the same subject at an earlier time point.

In specific embodiments, leukemias such as CLL are monitored on the basis of levels of CCR7 expressing cells. Progression of the disease, which may be in the context of a treatment regime, may be indicated in subjects where the levels of CCR7 expressing cells become sufficient to interfere with normal hematopoiesis. This may be when the majority of circulating cells are leukemic, and in addition are CCR7 positive. Thus, progression, which may be in the context of a treatment regime, may be indicated based upon the presence of greater than about 50%, such as greater than about 55%, greater than about 60%, greater than about 65%, greater than about 70%, greater than about 75%, greater than about 80%, greater than about 85%, greater than about 90%, greater than about 95% or more CCR7 expressing cells in the sample, as a percentage of total cells in the sample or by an increase of greater than about 10%, such as greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more chemokine receptor expressing cells in the sample, as a percentage of total cells in the sample, compared to a sample taken from the same subject at an earlier time point.

Regression or successful treatment may be monitored based upon similar decreases over various time points. For example, regression or successful treatment may be indicated in subjects based upon a decrease of about 10%, such as a decrease of about 15%, about 20%, about 25%, about 30%, about 35%, about 40%, about 45%, about 50%, about 55%, about 60%, about 65%, about 70%, about 75% or more chemokine receptor expressing cells in the sample, as a percentage of total cells in the sample, compared to a sample taken from the same subject at an earlier time point. In other embodiments, regression of cancer is confirmed on the basis of the presence of a about a 1.2 fold or greater decrease, such as about a 1.5, 2, 2.5, 3, 3.5, 4, 4.5, 5, 10, 20, 50 or 100 or greater fold decrease in chemokine receptor expressing cells, relative to a sample taken from the same subject at an earlier time point.

In specific embodiments, leukemias such as CLL are monitored on the basis of levels of CCR7 expressing cells. Regression or successful treatment of the disease may be made in subjects where the levels of CCR7 expressing cells are no longer sufficient to interfere with normal hematopoiesis. This may be when the majority of circulating cells are no longer leukemic (and in addition are CCR7 positive). Thus, regression or successful treatment may be indicated based upon a decrease of about 50%, such as such as a decrease of about 55%, about 60%, about 65%, about 70%, about 75%, about 80%, about 85%, about 90%, about 95% or more CCR7 expressing cells in the sample, as a percentage of total cells in the sample or by a decrease of about 10%, such as a decrease of about 15%, about 20%, about 25%, about 30%, about 35%, about 40%, about 45%, about 50%, about 55%, about 60%, about 65%, about 70%, about 75% or more chemokine receptor expressing cells in the sample, as a percentage of total cells in the sample, compared to a sample taken from the same subject at an earlier time point.

In other embodiments, progression of cancer, which may be in the context of a treatment regime, is monitored on the basis of measuring levels of Treg receptor expressing cells. Progression of cancer may be indicated based upon the presence of about a 1.2-fold or greater increase, such as about a 1.5, 2, 2.5, 3, 3.5, 4, 4.5, 5, 10, 20, 50 or 100 or greater fold increase in Treg receptor expressing cells, relative to a sample taken from the same subject at an earlier time point. In specific embodiments, cancers such as pancreatic cancer and urinirary bladder cancer are monitored on the basis of measuring levels of CCR4 expressing cells. In certain embodiments, progression of cancer, which may be in the context of a treatment regime, is monitored on the basis of levels of Treg receptor expressing cells at different time points. Progression of cancer may be indicated in subjects based upon an increase of greater than about 10%, such as an increase of greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more Treg receptor expressing cells in the sample, as a percentage of total cells in the sample, compared to a sample taken from the same subject at an earlier time point.

Progression of cancer, which may be in the context of a treatment regime, may be identified in subjects where the levels of CCR4 expressing cells, in particular CCR4 expressing Tregs, are increased relative to a sample taken from the same subject at an earlier time point. Thus, progression according to the various embodiments of the invention may be indicated based upon the presence of a about a 1.2-fold or greater increase, such as about a 1.5, 2, 2.5, 3, 3.5, 4, 4.5, 5, 10, 20, 50 or 100 or greater fold increase in CCR4 expressing cells, in particular CCR4 expressing Tregs, relative to a sample taken from the same subject at an earlier time point.

Regression or successful treatment may be monitored based upon similar decreases over various time points. For example, in some embodiments regression or successful treatment of cancer may be indicated based upon a 1.2-fold or greater decrease, such as about a 1.5, 2, 2.5, 3, 3.5, 4, 4.5, 5, 10, 20, 50 or 100 or greater fold decrease in Treg receptor expressing cells, relative to a sample taken from the same subject at an earlier time point. In other embodiments, regression or successful treatment may be indicated in subjects based upon a decrease of about 10%, such as a decrease of about 15%, about 20%, about 25%, about 30%, about 35%, about 40%, about 45%, about 50%, about 55%, about 60%, about 65%, about 70%, about 75% or more Treg receptor expressing cells in the sample, as a percentage of total cells in the sample, compared to a sample taken from the same subject at an earlier time point.

In specific embodiments, cancers such as pancreatic cancer and urinirary bladder cancer are monitored on the basis of measuring levels of CCR4 expressing cells. Regression or successful treatment may be identified in subjects where the levels of CCR4 expressing cells, in particular CCR4 expressing Tregs, are decreased relative to a sample taken from the same subject at an earlier time point. Thus, regression or successful treatment according to the various embodiments of the invention may be indicated based upon the presence of about a 1.2-fold or greater decrease, such as about a 1.5, 2, 2.5, 3, 3.5, 4, 4.5, 5, 10, 20, 50 or 100 or greater fold decrease in CCR4 expressing cells, in particular CCR4 expressing Tregs, relative to a sample taken from the same subject at an earlier time point.

Suitable software is freely available (such as the R project for statistical computing) to perform the necessary statistical analysis of the data obtained to calculate a useful threshold. The threshold may be set to maximize sensitivity and/or specificity of the test. Performance of the test in these respects may be measured by plotting a receiver operating characteristics (ROC) curve (sensitivity versus specificity). The area under the curve provides an indication of the overall performance of the test. Thus, once thresholds have been set for diagnosing the condition, a separate control experiment does not necessarily have to be run each time a sample is tested. Rather reference can simply be made to the pre-existing thresholds to determine the diagnosis. However, in certain embodiments, the sample is tested together with a control sample taken from a healthy subject to provide a comparator based upon essentially identical experimental conditions. The test sample is generally tested in parallel with the control sample. The test sample level of CCR5, CCR6, CCR7, CCR8, CXCR4, CXCR7, CCR4, CCR9, CCR10, CXCR3 and/or CXCR5 expressing cells; and/or Treg receptors in particular CLA, CCR4 and/or CCR8 expressing cells, levels of expression of CCR5, CCR6, CCR7, CCR8, CXCR4, CXCR7, CCR4, CCR9, CCR10, CXCR3 and/or CXCR5; and/or Treg receptor in particular CLA, CCR4 and/or CCR8 and/or levels of cells with high expression of CCR5, CCR6, CCR7, CCR8, CXCR4, CXCR7, CCR4, CCR9, CCR10, CXCR3 and/or CXCR5 (defined as CCR5hi, CCR6hi, CCR7hi, CCR8hi, CXCR4hi, CXCR7hi, CCR4hi, CCR9hi, CCR10hi, CXCR3hi and/or CXCR5hi); and/or Treg receptors in particular CLA, CCR4 and/or CCR8 (defined as CLAhi, CCR4hi, and/or CCR8hi) can then be compared with that of the control sample to make the diagnosis. A control sample from a disease patient may also be tested in certain embodiments. Reference to controls permits relative levels ("high", "low" etc.) of CCR5, CCR6, CCR7, CCR8, CXCR4, CXCR7, CCR4, CCR9, CCR10, CXCR3 and/or CXCR5 expressing cells; and/or Treg receptors in particular CLA, CCR4 and/or CCR8 expressing cells in the test sample to be readily identified and the significance thereof interpreted. Reference to controls also permits relative levels of CCR5, CCR6, CCR7, CCR8, CXCR4, CXCR7, CCR4, CCR9, CCR10, CXCR3 and/or CXCR5 expression; and/or Treg receptors in particular CLA, CCR4 and/or CCR8 expression ("high", "low" etc.) within the cell population to be determined and the significance thereof interpreted. Such determination may, for example, indicate the average levels of CCR5, CCR6, CCR7, CCR8, CXCR4, CXCR7, CCR4, CCR9, CCR10, CXCR3 and/or CXCR5 expression per cell; and/or Treg receptors in particular CLA, CCR4 and/or CCR8 expression per cell in the test sample.

Thus, in specific embodiments, high or higher levels of one or more of CCR5, CCR6, CCR7, CCR8, CXCR4, CXCR7, CCR4, CCR9, CCR10, CXCR3 and/or CXCR5 expressing cells; and/or Treg receptors in particular CLA, CCR4 and/or CCR8 expressing cells or high or higher levels of one or more of CCR5, CCR6, CCR7, CCR8, CXCR4, CXCR7, CCR4, CCR9, CCR10, CXCR3 and/or CXCR5 expression; and/or Treg receptors in particular CLA, CCR4 and/or CCR8 expression, for example average CCR5, CCR6, CCR7, CCR8, CXCR4, CXCR7, CCR4, CCR9, CCR10, CXCR3 and/or CXCR5 expression per cell; and/or Treg receptors in particular CLA, CCR4 and/or CCR8 expression per cell, or high or higher levels of one or more of CCR5hi, CCR6hi, CCR7hi, CCR8hi, CXCR4hi, CXCR7hi, CCR4hi, CCR9hi, CCR100hi, CXCR3hi and/or CXCR5hi cells; and/or CLAhi, CCR4hi, and/or CCR8hi cells correlate with active disease or more active cancer. More active disease is generally related to higher levels of cellular proliferation in the case of cancer and so high or higher levels of one or more of CCR5, CCR6, CCR7, CCR8, CXCR4, CXCR7, CCR4, CCR9, CCR10, CXCR3 and/or CXCR5 expressing cells; and/or Treg receptors in particular CLA, CCR4 and/or CCR8 expressing cells or high or higher levels of one or more of CCR5, CCR6, CCR7, CCR8, CXCR4, CXCR7, CCR4, CCR9, CCR10, CXCR3 and/or CXCR5 expression; and/or Treg receptors in particular CLA, CCR4 and/or CCR8 expression, for example average CCR5, CCR6, CCR7, CCR8, CXCR4, CXCR7, CCR4, CCR9, CCR10, CXCR3 and/or CXCR5 expression per cell; and/or Treg receptors in particular CLA, CCR4 and/or CCR8 expression per cell, or high or higher levels of one or more of CCR5hi, CCR6hi, CCR7hi, CCR8hi, CXCR4hi, CXCR7hi, CCR4hi, CCR9hi, CCR100hi, CXCR3hi and/or CXCR5hi cells; and/or CLAhi, CCR4hi, and/or CCR8hi cells may be expected to correlate with progression of the disease. Similarly, lower or low levels of one or more of CCR5, CCR6, CCR7, CCR8, CXCR4, CXCR7, CCR4, CCR9, CCR10, CXCR3 and/or CXCR5 expressing cells; and/or Treg receptors in particular CLA, CCR4 and/or CCR8 expressing cells, or low or lower levels of one or more of CCR5, CCR6, CCR7, CCR8, CXCR4, CXCR7, CCR4, CCR9, CCR10, CXCR3 and/or CXCR5 expression; and/or Treg receptors in particular CLA, CCR4 and/or CCR8 expression, for example average CCR5, CCR6, CCR7, CCR8, CXCR4, CXCR7, CCR4, CCR9, CCR10, CXCR3 and/or CXCR5 expression per cell; and/or Treg receptors in particular CLA, CCR4 and/or CCR8 expression per cell, or low or lower levels of one or more of CCR5hi, CCR6hi, CCR7hi, CCR8hi, CXCR4hi, CXCR7hi, CCR4hi, CCR9hi, CCR100hi, CXCR3hi and/or CXCR5hi cells; and/or CLAhi, CCR4hi, and/or CCR8hi cells may correlate with a lack of active inflammation or cancer. This may be defined as "less active disease". It can readily be envisaged that control samples may be assessed and levels of CCR5, CCR6, CCR7, CCR8, CXCR4, CXCR7, CCR4, CCR9, CCR10, CXCR3 and/or CXCR5 expressing cells; and/or Treg receptor in particular CLA, CCR4 and/or CCR8 expressing cells, levels of expression of CCR5, CCR6, CCR7, CCR8, CXCR4, CXCR7, CCR4, CCR9, CCR10, CXCR3 and/or CXCR5; and/or Treg receptors in particular CLA, CCR4 and/or CCR8 expression and/or levels of cells with high expression of CCR5, CCR6, CCR7, CCR8, CXCR4, CXCR7, CCR4, CCR9, CCR10, CXCR3 and/or CXCR5 (defined as CCR5hi, CCR6hi, CCR7hi, CCR8hi, CXCR4hi, CXCR7hi, CCR4hi, CCR9hi, CCR100hi, CXCR3hi and/or CXCR5hi); and/or Treg receptors in particular CLA, CCR4 and/or CCR8 (defined as CLAhi, CCR4hi, and/or CCR8hi) determined across the range of severities of cancer. This may assist in correlating the levels of CCR5, CCR6, CCR7, CCR8, CXCR4, CXCR7, CCR4, CCR9, CCR10, CXCR3 and/or CXCR5 expressing cells; and/or Treg receptors in particular CLA, CCR4 and/or CCR8 expressing cells, levels of expression of CCR5, CCR6, CCR7, CCR8, CXCR4, CXCR7, CCR4, CCR9, CCR10, CXCR3 and/or CXCR5; and/or Treg receptors in particular CLA, CCR4 and/or CCR8 and/or levels of cells with high expression of CCR5, CCR6, CCR7, CCR8, CXCR4, CXCR7, CCR4, CCR9, CCR10, CXCR3 and/or CXCR5 (defined as CCR5hi, CCR6hi, CCR7hi, CCR8hi, CXCR4hi, CXCR7hi, CCR4hi, CCR9hi, CCR10hi, CXCR3hi and/or CXCR5hi); and/or Treg receptors in particular CLA, CCR4 and/or CCR8 (defined as CLAhi, CCR4hi, and/or CCR8hi) in the test sample with the relative severity of the condition.

When monitoring progression of, or monitoring treatment of cancer, the control samples may be taken from the subject at an earlier time point. They may, however, be based upon known reference values as discussed above. Thus, relative levels of CCR5, CCR6, CCR7, CCR8, CXCR4, CXCR7, CCR4, CCR9, CCR10, CXCR3 and/or CXCR5 expressing cells; and/or Treg receptor in particular CLA, CCR4 and/or CCR8 expressing cells, relative levels of CCR5, CCR6, CCR7, CCR8, CXCR4, CXCR7, CCR4, CCR9, CCR10, CXCR3 and/or CXCR5 expression; and/or Treg receptors in particular CLA, CCR4 and/or CCR8 expression including relative levels of average CCR5, CCR6, CCR7, CCR8, CXCR4, CXCR7, CCR4, CCR9, CCR10, CXCR3 and/or CXCR5 expression per cell; and/or Treg receptors in particular CLA, CCR4 and/or CCR8 expression per cell or relative levels of CCR5hi, CCR6hi, CCR7hi, CCR8hi, CXCR4hi or CXCR7hi, optionally and/or CCR4hi cells; and/or CLAhi, CCR4hi, and/or CCR8hi cells may be with reference to samples taken from the same subject at a different point in time. In certain embodiments, decreased levels of one or more of CCR5, CCR6, CCR7, CCR8, CXCR4, CXCR7, CCR4, CCR9, CCR10, CXCR3 and/or CXCR5 expressing cells; and/or Treg receptors in particular CLA, CCR4 and/or CCR8 expressing cells, decreased relative levels of one or more of CCR5, CCR6, CCR7, CCR8, CXCR4, CXCR7, CCR4, CCR9, CCR10, CXCR3 and/or CXCR5 expression; and/or Treg receptors in particular CLA, CCR4 and/or CCR8 expression including decreased relative levels of average CCR5, CCR6, CCR7, CCR8, CXCR4, CXCR7, CCR4, CCR9, CCR10, CXCR3 and/or CXCR5 expression per cell; and/or Treg receptors in particular CLA, CCR4 and/or CCR8 expression per cell, or decreased relative levels of one or more of CCR5hi, CCR6hi, CCR7hi, CCR8hi, CXCR4hi, CXCR7hi, CCR4hi, CCR9hi, CCR100hi, CXCR3hi and/or CXCR5hi cells; and/or CLAhi, CCR4hi, and/or CCR8hi cells correlate with successful treatment. The treatment may be any suitable treatment, but in specific embodiments is a treatment according to the various embodiments of the invention.

When monitoring progression of cancer, increased levels of one or more of CCR5, CCR6, CCR7, CCR8, CXCR4, CXCR7, CCR4, CCR9, CCR10, CXCR3 and/or CXCR5 expressing cells; and/or Treg receptors in particular CLA, CCR4 and/or CCR8 expressing cells increased relative levels of one or more of CCR5, CCR6, CCR7, CCR8, CXCR4, CXCR7, CCR4, CCR9, CCR10, CXCR3 and/or CXCR5 expression; and/or Treg receptors in particular CLA, CCR4 and/or CCR8 expression including increased relative levels of average CCR5, CCR6, CCR7, CCR8, CXCR4, CXCR7, CCR4, CCR9, CCR10, CXCR3 and/or CXCR5 expression per cell; and/or Treg receptors in particular CLA, CCR4 and/or CCR8 expression per cell or increased relative levels of one or more of CCR5hi, CCR6hi, CCR7hi, CCR8hi, CXCR4hi, CXCR7hi, CCR4hi, CCR9hi, CCR100hi, CXCR3hi and/or CXCR5hi cells; and/or CLAhi, CCR4hi, and/or CCR8hi cells may indicate the progression of condition or disease. Thus, if levels of one or more of CCR5, CCR6, CCR7, CCR8, CXCR4, CXCR7, CCR4, CCR9, CCR10, CXCR3 and/or CXCR5 expressing cells; and/or Treg receptors in particular CLA, CCR4 and/or CCR8 expressing cells, levels of expression of one or more of CCR5, CCR6, CCR7, CCR8, CXCR4, CXCR7, CCR4, CCR9, CCR10, CXCR3 and/or CXCR5; and/or Treg receptors in particular CLA, CCR4 and/or CCR8 and/or levels of cells with high expression of one or more of CCR5, CCR6, CCR7, CCR8, CXCR4, CXCR7, CCR4, CCR9, CCR10, CXCR3 and/or CXCR5 (defined as CCR5hi, CCR6hi, CCR7hi, CCR8hi, CXCR4hi, CXCR7hi, CCR4hi, CCR9hi, CCR100hi, CXCR3hi and/or CXCR5hi); and/or Treg receptors in particular CLA, CCR4 and/or CCR8 expressing cells (defined as CLAhi, CCR4hi, and/or CCR8hi) are increased in a sample taken later than a sample from the same patient this may indicate progression of the condition.

Since the levels of one or more of CCR5, CCR6, CCR7, CCR8, CXCR4, CXCR7, CCR4, CCR9, CCR10, CXCR3 and/or CXCR5 expressing cells, levels of one or more of CCR5, CCR6, CCR7, CCR8, CXCR4, CXCR7, CCR4, CCR9, CCR10, CXCR3 and/or CXCR5 expression or levels of one or more of CCR5hi, CCR6hi, CCR7hi, CCR8hi, CXCR4hi, CXCR7hi, CCR4hi, CCR9hi, CCR100hi, CXCR3hi and/or CXCR5hi cells are diagnostically relevant, determining such levels in a sample obtained from a subject may influence treatment selection for that subject. Accordingly, in certain embodiments the invention provides a method of selecting a suitable treatment for cancer comprising determining:

a) the levels of one or more of the chemokine receptor CCR5, CCR6, CCR7, CCR8, CXCR4, CXCR7, CCR4, CCR9, CCR10, CXCR3 and/or CXCR5 expressing cells b) levels of expression of one or more of CCR5, CCR6, CCR7, CCR8, CXCR4, CXCR7, CCR4, CCR9, CCR10, CXCR3 and/or CXCR5; and/or c) levels of cells with high expression of one or more of CCR5, CCR6, CCR7, CCR8, CXCR4, CXCR7, CCR4, CCR9, CCR10, CXCR3 and/or CXCR5 in a sample obtained from a subject, wherein high levels of one or more of CCR5, CCR6, CCR7, CCR8, CXCR4, CXCR7, CCR4, CCR9, CCR10, CXCR3 and/or CXCR5 expressing cells, high levels of expression of one or more of CCR5, CCR6, CCR7, CCR8, CXCR4, CXCR7, CCR4, CCR9, CCR10, CXCR3 and/or CXCR5 or high levels of cells with high expression of CCR5, CCR6, CCR7, CCR8, CXCR4, CXCR7, CCR4, CCR9, CCR10, CXCR3 and/or CXCR5 or increased levels of one or more of CCR5, CCR6, CCR7, CCR8, CXCR4, CXCR7, CCR4, CCR9, CCR10, CXCR3 and/or CXCR5 expressing cells compared to control, increased levels of expression of one or more of CCR5, CCR6, CCR7, CCR8, CXCR4, CXCR7, CCR4, CCR9, CCR10, CXCR3 and/or CXCR5 compared to a control or increased levels of cells with high expression of one or more of CCR5, CCR6, CCR7, CCR8, CXCR4, CXCR7, CCR4, CCR9, CCR10, CXCR3 and/or CXCR5 compared to a control, result in selection of a treatment as defined herein for treatment of the (condition associated with) cancer. In certain embodiments, the chemokine receptor expressing cells are high chemokine receptor expressing cells, in particular, high CCR5, CCR6, CCR7, CCR8, CXCR4, CXCR7, CCR4, CCR9, CCR10, CXCR3 and/or CXCR5 expressing cells.

In specific embodiments, cancer is treated on the basis of measuring levels of chemokine receptor expressing cells. Thus, a treatment according to the various embodiments of the invention may be applied based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, cancer is treated according to the various embodiments of the invention on the basis of the presence of a about a 1.5 fold or greater increase, such as about a 2, 2.5, 3, 3.5, 4, 4.5, 5, 10, 20, 50 or 100 or greater fold increase in chemokine receptor expressing cells, relative to healthy controls.

In specific embodiments, leukemias such as CLL are treated on the basis of measuring levels of CCR7 expressing cells. A positive decision to treat the subject may be made in subjects where the levels of CCR7 expressing cells are sufficient to interfere with normal hematopoiesis. This may be when the majority of circulating cells are leukemic, and in addition are CCR7 positive. Thus, a treatment according to the various embodiments of the invention may be applied based upon the presence of greater than about 50%, such as greater than about 55%, greater than about 60%, greater than about 65%, greater than about 70%, greater than about 75%, greater than about 80%, greater than about 85%, greater than about 90%, greater than about 95% or more CCR7 expressing cells in the sample, as a percentage of total cells in the sample.

Similarly, since the levels of one or more of Treg receptors in particular CLA, CCR4 and/or CCR8 expressing cells, levels of one or more of Treg receptors in particular CLA, CCR4 and/or CCR8 expression or levels of one or more of CLAhi, CCR4hi, and/or CCR8hi cells are diagnostically relevant, determining such levels in a sample obtained from a subject may influence treatment selection for that subject. Accordingly, in a related aspect the invention provides a method of selecting a suitable treatment for cancer comprising determining:

a) the levels of one or more Treg receptor expressing cells, in particular CLA, CCR4 and/or CCR8 expressing cells b) levels of expression of one or more of Treg receptors in particular CLA, CCR4 and/or CCR8; and/or c) levels of cells with high expression of one or more of Treg receptors in particular CLA, CCR4 and/or CCR8 in a sample obtained from a subject, wherein high levels of one or more of Treg receptors in particular CLA, CCR4 and/or CCR8 expressing cells, high levels of expression of one or more Treg receptors in particular CLA, CCR4 and/or CCR8 or high levels of cells with high expression of one or more of Treg receptors in particular CLA, CCR4 and/or CCR8 or increased levels of one or more of Treg receptors in particular CLA, CCR4 and/or CCR8 expressing cells compared to control, increased levels of expression of one or more of Treg receptors in particular CLA, CCR4 and/or CCR8 compared to a control or increased levels of cells with high expression of one or more of Treg receptors in particular CLA, CCR4 and/or CCR8 compared to a control result in selection of a treatment as defined herein for treatment of the (condition associated with) cancer. In certain embodiments, the chemokine receptor expressing cells are high chemokine receptor expressing cells, in particular, high Treg receptor in particular CLA, CCR4 and/or CCR8 expressing cells.

In some embodiments, cancer is treated on the basis of measuring levels of Treg receptor expressing cells. Thus, a treatment according to the various embodiments of the invention may be applied based upon the presence of about a 1.5-fold or greater increase, such as about a 2, 2.5, 3, 3.5, 4, 4.5, 5, 10, 20, 50 or 100 or greater fold increase in Treg receptor expressing cells, relative to healthy controls. In other embodiments, cancer is treated according to the various embodiments of the invention based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more Treg receptor expressing cells in the sample, as a percentage of total cells in the sample.

In specific embodiments, cancers such as pancreatic cancer and urinary bladder cancer are treated on the basis of measuring levels of CCR4 expressing cells. A positive decision to treat the subject may be made in subjects where the levels of CCR4 expressing cells, in particular CCR4 expressing Tregs, are increased relative to healthy controls. Thus, a treatment according to the various embodiments of the invention may be applied based upon the presence of about a 1.5-fold or greater increase, such as about a 2, 2.5, 3, 3.5, 4, 4.5, 5, 10, 20, 50 or 100 or greater fold increase in CCR4 expressing cells, in particular CCR4 expressing Tregs, relative to healthy controls.

For the avoidance of doubt, all embodiments described in respect of the methods of the various embodiments of the invention apply to these aspects mutatis mutandis and are not repeated for reasons of conciseness. Specifically, cancer may be indicated in conjunction with one or more clinical indications as known in the art. Also increased number of Tregs (CD4+CD25hiCD127lo/– and Foxp3 positive) is a diagnostic indicator of poor prognosis in cancer. Determining the number of circulating leukemic or tumor cells and their chemokine receptor profile expression may be a further technique used in conjunction with the methods of the various embodiments of the invention.

The cancer or cancer treatment may be selected from reducing levels of circulating tumour cells, reducing the incidence of tumour metastasis, removing regulatory T lymphocytes from the peripheral blood, or treating leukaemias such as chronic lymphocytic leukaemia, chronic myeloid leukemia, use for debulking in AML, ALL and before harvest for autologous bone marrow/stem cell transplantation and treatment of the leukemic phase of lymphoma. In specific embodiments, the sample is a peripheral blood sample.

The methods and medical uses of the various embodiments of the invention thus can be tailored to the need of individual patients or groups of patients on the basis of the various diagnostic methods of the various embodiments of the invention. By removing from the circulation one or more of CCR5, CCR6, CCR7, CCR8, CXCR4, CXCR7, CCR4, CCR9, CCR10, CXCR3 and/or CXCR5 expressing cells; and/or Treg receptor in particular CLA, CCR4 and/or CCR8 expressing cells, such as tumour cells and regulatory T lymphocytes, upregulated in cancer, an important factor in the disease can be controlled. The methods of the various embodiments of the invention may be effective in treating or reversing conditions such as by reducing levels of circulating tumour cells, reducing the incidence of tumour metastasis, removing regulatory T lymphocytes from the peripheral blood, or treating leukaemias such as chronic lymphocytic leukaemia, chronic myeloid leukemia, use for debulking in AML, ALL and before harvest for autologous bone marrow/stem cell transplantation and treatment of the leukemic phase of lymphoma.

E. Treating Mental Disorder

Chemokines are a class of cytokine molecules involved in cell recruitment and activation in inflammation. Chemokines cause chemotaxis and activation of various subpopulations of cells in the immune system. The activity of chemokines is mediated primarily through tight binding to their receptors on the surface of leukocytes. Inflammatory and immune alterations occur and may be relevant in patients with mental disorders such as schizophrenia and depression. Teixeira et al., (Prog Neuropsychopharmacol Biol Psychiatry. 2008 Apr. 1; 32 (3):710-4. Epub 2007 Nov. 23) evaluated serum levels of CC and CXC chemokines of schizophrenic patients and age- and gender-matched controls. They showed that serum levels of CCL11 were increased in schizophrenic patients when compared to controls. Mast cells express CCR3 in patients with schizophrenia according to Teixeira et al., (Prog Neuropsychopharmacol Biol Psychiatry. 2008 Apr. 1; 32 (3):710-4. It has been shown in patient plasma samples that high pro-inflammatory cytokine and chemokine expression correlate with depression and fatigue ("Plasma Protein Biomarkers for Depression and Schizophrenia by Multi Analyte Profiling of Case-Control Collections": Domenici E et al, PLoS ONE 5 (2): e9166, 2010).

In certain embodiments the present invention is based on the realisation that the interaction between chemokines and cells expressing their receptors may be exploited for the treatment of mental disorders such as schizophrenia, depression and bipolar disorder and in particular inflammation associated with mental disorders such as schizophrenia, depression and bipolar disorder. The inventors have determined that targeting increased recruitment of specific chemokine receptor-expressing cells to the site of inflammation presents a new therapeutic approach to treat this condition. Moreover, in this condition, chemokine receptor expression on each cell may be increased again providing a therapeutic approach to treat this condition. It is surprisingly shown herein that subjects suffering from mental disorders such as bipolar disorder exhibit highly increased frequency of chemokine receptor expressing cells in the peripheral blood, in particular CCR9 expressing monocytes, compared to healthy controls. It is also shown herein that the CCR9 cells can be removed using a suitable binding reagent, in particular CCL25 (in biotinylated form) immobilized on a suitable matrix.

Thus, in certain embodiments the invention serves to reduce the recruitment of inflammatory leukocytes, which express characteristic chemokine receptors, and possibly express characteristic chemokine receptors at increased levels, to sites of inflammation linked to mental disorders such as schizophrenia, depression and bipolar disorder. This is achieved using specific binding reagents to capture specific chemokine receptor-expressing (inflammatory) leukocytes from the patient. Accordingly, in certain embodiments the invention provides in a first aspect a method for treating mental disorders such as schizophrenia, depression and bipolar disorder comprising applying peripheral blood from a patient to an apheresis column loaded with a solid support comprising one or more binding reagents capable of specifically binding to a chemokine receptor, in particular one or more of the chemokine receptors CCR9, CCR1, CCR3 and/or CCR5, immobilized directly or indirectly on the support thus removing chemokine receptor, in particular CCR9, CCR1, CCR3 and/or CCR5, expressing cells from the peripheral blood of the patient. The peripheral blood from which the chemokine receptor expressing cells have been removed may then be returned to the patient in order to complete the treatment. The invention may thus rely on a continuous extracorporeal circuit in some embodiments. Alternatively, the invention may comprise steps of obtaining peripheral blood from the patient, applying the peripheral blood to the column and subsequently returning the peripheral blood from which the chemokine receptor expressing cells have been removed to the patient.

As shown herein, suitable binding reagents can be immobilized onto a solid support, either directly or indirectly, to generate an apheresis column suitable for capturing relevant chemokine receptor-expressing cells. Where increased levels of chemokine receptor expression are observed, such cells may be preferably removed from the peripheral blood using the columns of the various embodiments of the invention. Thus, the methods of various embodiments of the invention may preferably target CCR9, CCR1, CCR3 and/or CCR5hi cells as defined herein for removal from the peripheral blood. "High" expression may be determined according to standard flow cytometry techniques. The level is measured relative to levels of expression of the chemokine receptor in cells taken from a healthy subject. The attached FIG. 73 provides an example of a gating strategy.

Herein, reference to CCR9, CCR1, CCR3 and/or CCR5 is intended to encompass selection of any one or more, up to all, of the chemokine receptors listed. In addition, the combination of CCR1, CCR3 and/or CCR5 is explicitly contemplated as a separate grouping, to include any one or more of CCR1, CCR3 and/or CCR5.

In other embodiments the invention further provides a binding reagent capable of specifically binding to a chemokine receptor, in particular to a chemokine receptor/the chemokine receptor CCR9, CCR1, CCR3 and/or CCR5, for use in the treatment of mental disorders such as schizophrenia, depression and bipolar disorder, wherein the binding reagent is immobilized, directly or indirectly, on a solid support contained within an apheresis column, to which is applied peripheral blood from a patient thus removing chemokine receptor/CCR9, CCR1, CCR3 and/or CCR5 expressing cells from the peripheral blood of the patient. In certain embodiments the invention also provides for use of a binding reagent capable of specifically binding to a chemokine receptor/the chemokine receptor CCR9, CCR1, CCR3 and/or CCR5 for use in the manufacture of an apheresis column for treatment of mental disorders such as schizophrenia, depression and bipolar disorder, wherein the binding reagent is immobilized on a solid support contained within the apheresis column, to which is applied peripheral blood from a patient thus removing chemokine receptor/CCR9, CCR1, CCR3 and/or CCR5 expressing cells from the peripheral blood of the patient.

All embodiments described in respect of the methods of treatment of the various embodiments of the invention apply to these aspects mutatis mutandis and are not repeated for reasons of conciseness. Thus, the following discussion made with reference to the methods of treatment is also applicable to the medical use aspects of the various embodiments of the invention.

In certain embodiments the invention aims to treat mental disorders such as schizophrenia, depression and bipolar disorder. Inflammation is an important component of mental disorders such as schizophrenia, depression and bipolar disorder and may involve increased levels of CCL11 signalling. CCL11 is a ligand for CCR1, CCR3 and/or CCR5, a receptor expressed preferentially on Th2 lymphocytes, mast cells and eosinophils. Higher serum levels of CCL11 in mental disorders such as schizophrenia, depression and bipolar disorder suggest that this disease may be associated with a Th1/Th2 imbalance with a shift toward a Th2 immune response. The various embodiments of the invention aim to address the inflammatory component of mental disorders such as schizophrenia, depression and bipolar disorder in some embodiments. Any relevant inflammatory component of mental disorders such as schizophrenia, depression and bipolar disorder may be treated according to the methods of the various embodiments of the invention. As aforementioned, it is shown herein that subjects suffering from mental disorders such as bipolar disorder exhibit highly increased frequency of chemokine receptor expressing cells in the peripheral blood, in particular CCR9 expressing monocytes, compared to healthy controls. It is also shown herein that the CCR9 cells can be removed using a suitable binding reagent, in particular CCL25 (in biotinylated form) immobilized on a suitable matrix.

By "treatment" is meant a reduction in the specific chemokine receptor expressing cells in the peripheral blood of the patient. The reduction may comprise a reduction in cells that express chemokine receptors, in particular CCR9, CCR1, CCR3 and/or CCR5, at increased levels in diseased patients. The patient is typically a human patient but the term patient may include both human and non-human animal subjects in some embodiments. In the context of the various embodiments of the present invention, this typically involves a reduction in CCR9, CCR1, CCR3 and/or CCR5 expressing cells, such as "CCR9, CCR1, CCR3 and/or CCR5hi" expressing cells, in the peripheral blood of the patient. The CCR9, CCR1, CCR3 and/or CCR5 expressing cells comprise, consist essentially of or consist of eosinophils, lymphocytes, in particular T lymphocytes and more particularly Th2 lymphocytes, basophils, neutrophils and mast cells, in certain embodiments. The claimed methods may, in particular, target lymphocytes, in particular T lymphocytes and more particularly Th2 lymphocytes or eosinophils. Eosinophilia may be an important component of mental disorders such as schizophrenia, depression and bipolar disorder and may be defined as the presence of more than 500 eosinophils/microliter of blood. Thus, reducing numbers of circulating eosinophils may represent an important therapeutic approach. Eosinophils, or eosinophil granulocytes, are white blood cells and represent an important immune system component. Along with mast cells, they also control mechanisms associated with allergy and asthma. They are granulocytes that develop during haematopoiesis in the bone marrow before migrating into blood. In specific embodiments the cells removed in order to treat mental disorders such as bipolar disorder comprise monocytes or macrophages, in particular CCR9 expressing monocytes or macrophages.

The name "eosinophil" derives from the eosinophilic "acid-loving" properties of the cell. Normally transparent, it is this affinity that causes them to appear brick-red after staining with eosin, a red dye, using the Romanowsky method. The staining is concentrated in small granules within the cellular cytoplasm, which contain many chemical mediators, such as histamines and proteins such as eosinophil peroxidase, ribonuclease (RNase), deoxyribonucleases, lipase, plasminogen, and major basic protein. These mediators are released by a process called degranulation following activation of the eosinophil, and are toxic to both parasite and host tissues.

Eosinophils develop and mature in bone marrow. They differentiate from myeloid precursor cells in response to the cytokines interleukin 3 (IL-3), interleukin 5 (IL-5), and granulocyte macrophage colony-stimulating factor (GM-CSF). Eosinophils produce and store many secondary granule proteins prior to their exit from the bone marrow. After maturation, eosinophils circulate in blood and migrate to inflammatory sites in tissues in response to chemokines such as CCL11 (eotaxin-1), CCL24 (eotaxin-2), CCL5 (RANTES) and MCP1/4. Eosinophils may be activated by Type 2 cytokines released from a specific subset of helper T cells (Th2); IL-5, GM-CSF, and IL-3 are important for eosinophil activation as well as maturation. CD44 and CD69 have been shown to represent different types of cell-surface activation markers for human eosinophils. CD69 is absent from "fresh" eosinophils but expressed following activation (using cytokines). CD44 on the other hand is constitutively expressed but expression is significantly up-regulated in response to activation (Matsumoto et al., Am. J. Respir. Cell Mol. Biol., Volume 18, Number 6, June, 1998 860-866). Cell specific markers for eosinophils include CD9 and CDw125.

The three major types of lymphocyte are T cells, B cells and natural killer (NK) cells. The term "T-lymphocyte" includes CD4+ T cells such as T helper cells (Th1 cells and Th2 cells), and CD8+ T cells such as cytotoxic T cells. Th1 cells may be characterized by expression of CCR5 and production of IFN-γ. Th2 cells may be characterized by expression of CCR9, CCR1, CCR3 and/or CCR5 and production of IL-4. Th2 cells expressing CCR9, CCR1, CCR3 and/or CCR5 may be a particular target cell in the context of the various embodiments of the present invention.

Basophils may also be known as basophil granulocyte. In contrast to eosinophils, these leukocytes are basophilic, i.e., they are susceptible to staining by basic dyes. Basophils contain large cytoplasmic granules which obscure the cell nucleus under the microscope. However, when unstained, the nucleus is visible and it usually has 2 lobes. Basophils store histamine, which is secreted by the cells upon stimulation.

Basophils have protein receptors on their cell surface that bind IgE, an immunoglobulin involved in macroparasite defense and allergy. It is the bound IgE antibody that confers a selective response of these cells to environmental substances, for example, pollen proteins or helminth antigens. Recent studies in mice suggest that basophils may also regulate the behavior of T cells and mediate the magnitude of the secondary immune response. Basophils may display an immunophenotype based upon expression (or lack thereof, indicated as "+" or "−" respectively of one or more of the following markers: FcεRI+, CD123, CD49b(DX-5)+, CD69+, Thy-1.2+, 2B4+, CD11bdull, CD117(c-kit)−, CD24−, CD19−, CD80−, CD14−, CD23−, Ly49c−, CD122−, CD11c−, Gr-1−, NK1.1−, B220−, CD3−, γδTCR−, αβTCR−, α4 and β4-integrin negative.

When activated, basophils degranulate to release histamine, proteoglycans (e.g. heparin and chondroitin), and proteolytic enzymes (e.g. elastase and lysophospholipase). They also secrete lipid mediators like leukotrienes, and several cytokines. Histamine and proteoglycans are pre-stored in the cell's granules while the other secreted substances are newly generated. Each of these substances contributes to inflammation. Recent evidence suggests that basophils are an important source of the cytokine, interleukin-4, and perhaps more important than T cells. Interleukin-4 is considered one of the critical cytokines in the development of allergies and the production of IgE antibody by the immune system. There are other substances that can activate basophils to secrete which suggests that these cells have other roles in inflammation.

Neutrophils, also known as neutrophil granulocytes, may be subdivided into segmented neutrophils (or segs) and banded neutrophils (or bands). Neutrophils form part of the polymorphonuclear cell family (PMNs) together with basophils and eosinophils. Neutrophils staining a neutral pink on hematoxylin and eosin (H&E) histological or cytological preparations. Normally neutrophils contain a nucleus divided into 2-5 lobes.

Neutrophils are one of the first-responders of inflammatory cells to migrate towards the site of inflammation. Neutrophil granulocytes have an average diameter of 12-15 micrometers (μm) in peripheral blood smears. When analyzing a pure neutrophil suspension on an automated cell counter, neutrophils have an average diameter of 8-9 μm.

In addition to recruiting and activating other cells of the immune system, neutrophils play a key role in the front-line defence against invading pathogens. Neutrophils have three strategies for directly attacking micro-organisms: phagocytosis (ingestion), release of soluble anti-microbials (including granule proteins) and generation of neutrophil extracellular traps (NETs). Cell specific markers for neutrophils include CD15 and CD16 (in combination).

Mast cells may also be referred to as mastocytes and labrocytes. They are resident cells of several types of tissues and contains many granules rich in histamine and heparin. Mast cells play a role in allergy, anaphylaxis, wound healing and defense against pathogens. Both mast cells and basophils are thought to originate from bone marrow precursors expressing the CD34 molecule. The basophil leaves the bone marrow already mature, whereas the mast cell circulates in an immature form, only maturing once in a tissue site. Two types of mast cells are recognized, those from connective tissue and a distinct set of mucosal mast cells. The activities of the latter are dependent on T-cells.

Mast cells play a key role in the inflammatory process. When activated, a mast cell rapidly releases its characteristic granules and various hormonal mediators into the interstitium. Mast cells can be stimulated to degranulate by direct injury (e.g. physical or chemical [such as opioids, alcohols, and certain antibiotics such as polymyxins]), cross-linking of Immunoglobulin E (IgE) receptors, or by activated complement proteins.

Mast cells express a high-affinity receptor (FcεRI) for the Fc region of IgE, the least-abundant member of the antibodies. This receptor is of such high affinity that binding of IgE molecules is essentially irreversible. As a result, mast cells are coated with IgE. IgE is produced by Plasma cells (the antibody-producing cells of the immune system). IgE molecules, like all antibodies, are specific to one particular antigen. Cell specific markers for mast cells include c-kit Mast cells may be stained using Toluidine Blue—one of the most common stains for acid mucopolysaccharides and glycoaminoglycans, components of mast cells granules.

Monocytes are produced by the bone marrow from haematopoietic stem cell precursors called monoblasts. Monocytes may differentiate into macrophages or dendritic cells. Monocytes and their macrophage and dendritic cell progeny serve a number of functions in the immune system including phagocytosis, antigen presentation and cytokine production. Monocytes may be characterized with reference to expression of the cell surface marker CD14, optionally together with CD16. Classical monocytes may be characterized by high level expression of the CD14 cell surface receptor (CD14++CD16− monocyte). Non-classical monocytes may be characterized by low level expression of CD14 and with additional co-expression of the CD16 receptor (CD14+CD16++ monocyte). Intermediate monocytes may be characterized by high level expression of CD14 and low level expression of CD16 (CD14++CD16+ monocytes). Macrophages are derived from monocytes and are responsible for protecting tissues from foreign substances. They are cells that possess a large smooth nucleus, a large area of cytoplasm and internal vesicles for processing foreign material. The term "macrophage" may refer to a monocyte-derived cell expressing one or more of the following cell surface markers CD14, CD11b, Lysozyme M, MAC-1/MAC-3 and CD68. The term macrophage includes both activated and un-activated macrophages. Activated macrophages may be characterized by expression of CD69, ENG, FCER2 and IL2RA, HLA-DR, CD86. Un-activated macrophages have not yet received activating signals through for example TLR receptors and therefore they express less activation markers on the cell surface which correlates with lesser maturation. M1 macrophages may be characterized by expression of one or more of CD16+CD32+CD64+ and secrete mainly IL-23 and IL-1, TNF, IL-6 and high levels of IL-12 and in addition effector molecules such as iNOS and ROI. M1 macrophages have cytotoxic features as opposed to M2 macrophages. M2 macrophages may be characterized by expression of one or more of SRA/B+CD163+MR+CD14+ and express TGFβ, IL-10 and IL-1Ra. Tumour associated macrophages (TAMs) share many characteristics with the M2 macrophages and are considered as M2 polarised macrophages. The M1/M2 paradigm can also be found in monocyte subsets where CD14+ CD16−CXC3R1low monocytes are considered the "inflammatory" subset and the CD14lowCD16+CXC3R1high are "resident" monocytes.

CCR9, CCR1, CCR3 and/or CCR5 expressed on these aforementioned cells binds to chemokines such as eotaxin. Eotaxin is a major chemoattractant for eosinophils, lymphocytes, in particular T lymphocytes and more particularly Th2 lymphocytes, basophils and neutrophils and mast cells by means of their binding to its specific cell-surface receptor, CC-chemokine receptor-3 (CCR3). CCR3 is the gene symbol approved by the HUGO Gene Nomenclature Committee for chemokine (C—C motif) receptor 3. The HGNC ID for this gene is 1604. The gene is located at chromosome position 3p21.3. The previous symbol and name for the gene is CMKBR3. Synonyms for this gene include CC-CKR-3, CD193 and CKR3. The Genbank reference sequence for CCR3 is AF247361.1 as available on 13 Jun. 2011, which is incorporated herein by reference in its entirety.

CCR9 is the gene symbol approved by the HUGO Gene Nomenclature Committee for chemokine (C—C motif) receptor 9. The HGNC ID for this gene is 1610. The gene is located at chromosome position 3p22. The previous symbol and name for the gene is GPR28. Synonyms for this gene include CDw199, GPR-9-6. The Genbank reference sequence for CCR9 is AJ132337.1 as available on 13 Jun. 2011, which is incorporated herein by reference in its entirety.

CCR5 is the gene symbol approved by the HUGO Gene Nomenclature Committee for chemokine (C—C motif) receptor 5. The HGNC ID for this gene is 1606. The gene is located at chromosome position 3p21. The previous symbol and name for the gene is CMKBR5. Synonyms for this gene include CC-CKR-5, CD195 CKR-5, IDDM22 and CKR5. The RefSeq reference sequence for CCR1 is NM_000579.3 as available on 13 Jun. 2011, which is incorporated herein by reference in its entirety.

CCR1 is the gene symbol approved by the HUGO Gene Nomenclature Committee for chemokine (C—C motif) receptor 1. The HGNC ID for this gene is 1602. The gene is located at chromosome position 3p21. The previous symbol and name CMKBR1, SCYAR1. Synonyms for this gene include CD191, CKR-1, MIP1aR. The RefSeq reference sequence for CCR1 is NM_001295.2 as available on 13 Jun. 2011, which is incorporated herein by reference in its entirety.

The various embodiments of the methods of the invention may involve specific binding interactions with any one or more of the further cell-surface markers, characteristic of the cell types targeted according to the invention, in addition to the removal based upon binding to CCR9, CCR1, CCR3 and/or CCR5. Suitable binding reagents can be prepared to specifically bind to these cell-surface markers. The discussion of CCR9, CCR1, CCR3 and/or CCR5 specific binding reagents thus applies mutatis mutandis.

Treatment according to the various embodiments of the invention may result in alleviation or amelioration of symptoms, prevention of progression, regression of the condition, or complete recovery. Measurable parameters of successful treatment include one or more, up to all, of a reduction in symptoms and an absence of eosinophilia and/or a measurable decrease in eosinophils, lymphocytes, in particular T lymphocytes and more particularly Th2 lymphocytes, basophils and neutrophils and mast cells. In other embodiments, monocytes or macrophages, in particular CCR9 expressing monocytes or macrophages are removed. Symptoms of mental disorders such as schizophrenia, depression and bipolar disorder which may be measured include hallucinations, delusions and disorganized thinking and speech. According to DSM-IV Two (or more) of the following, each present for a significant portion of time during a 1-month period (or less if successfully treated): (1) delusions (2) hallucinations (3) disorganized speech (e.g., frequent derailment or incoherence) (4) grossly disorganized or catatonic behaviour (5) negative symptoms, i.e., affective flattening, alogia (poverty of speech), or avolition (lack of motivation).

In specific embodiments, a single treatment is sufficient to cause a depletion of around 10%, 20%, 30%, 40%, 50%, 60% or 70%, or higher up to 80%, 90%, 95% or more, or any range of values between and including these amounts, of the specific chemokine receptor, in particular CCR9, CCR1, CCR3 and/or CCR5, expressing cells from the peripheral blood of the patient. In specific embodiments, at least around 50% depletion is achieved in a single treatment. Thus, successful treatment may be defined with reference to depletion of CCR9, CCR1, CCR3 and/or CCR5 expressing cells. Treatment may lead to depletion of between approximately 100 and 500 million CCR9, CCR1, CCR3 and/or CCR5 expressing cells, such as eosinophils and Th2 lymphocytes, in certain embodiments and more particularly to about 100, 150, 200, 250, 300, 350, 400, 450, or 500 million CCR9, CCR1, CCR3 and/or CCR5 expressing cells. In specific embodiments, monocytes or macrophages, in particular CCR9 expressing monocytes or macrophages are removed.

By binding to the column through the binding reagent-chemokine receptor interaction, chemokine receptor expressing cells are immobilized. These immobilized cells express further unoccupied chemokine receptors, which may be of the same or different type to those used for capture. These additional chemokine receptors may permit circulating chemokines which contribute to the inflammatory condition to be captured from the peripheral blood. Thus, a reduction in circulating (specific) chemokine levels may provide a measure of successful treatment.

The duration of treatment may be readily determined by one skilled in the art and will depend upon factors such as the flow rate of the peripheral blood. Duration of treatment may be tied into monitoring of the treatment itself, with the treatment considered complete once a measurable parameter of treatment has reached a defined threshold. Any suitable parameter may be employed as discussed herein. Thus, for example, treatment may be considered complete when a reduction in CCR9, CCR1, CCR3 and/or CCR5 expressing cells, such as a 50% reduction in CCR9, CCR1, CCR3 and/or CCR5 expressing cells, has been achieved. The apheresis system may be operated at a flow rate of around 10-80 mL/min, or more specifically between around 20-70 mL/min, or between around 30-60 mL/min. In specific embodiments, the treatment is performed for a period of around 10, 20, 30, 40, 50, 60, 70, 80, 90, 100, 110, 120 etc., or any range of values between and including these amounts, minutes. The treatment is typically not aimed to remove all of the cells expressing the chemokine receptor in the peripheral blood, as a basal level of those cells is required in healthy subjects. However, it has been found that only low blood volumes need to be applied to the columns of the various embodiments of the invention in order to achieve effective levels of depletion of the chemokine receptor-expressing cells. Thus, in certain embodiments, around 10-80% or more specifically around 20, 30, 40 or 50%, or any range of values between and including these amounts, of the patient's blood is applied to the column in a single treatment. The volume of blood circulated through the apheresis column or system may be in the region of around 1000-3000 ml, such as around 1000, 1200, 1400, 1600, 1800 or 2000 ml or any range of values between and including these amounts. The treatment may be considered complete once this volume of blood has been circulated. The patient may be administered anticoagulants prior to each treatment session. A suitable solution, such as a sterile saline solution, optionally including an anticoagulant such as Heparin, may be used for priming the apheresis (extracorporeal) system. An additional volume of anticoagulant may be added to the circuit at the start of each treatment session, for example as a bolus injection.

In certain embodiments the invention relies upon a binding reagent which is capable of specifically binding to a chemokine receptor. This specific binding reaction permits cells expressing the chemokine receptor to be removed from the peripheral blood of the patient when the blood is passed over the solid support upon or within which the binding reagent is immobilized. One specific chemokine receptor of interest is CCR9, CCR1, CCR3 and/or CCR5. The binding reagent can be any binding reagent capable of specifically binding to the receptor in question. By "specific binding" is meant that the binding reagent has sufficient specificity of binding and appropriate binding affinity/kinetics to permit removal of cells expressing CCR9, CCR1, CCR3 and/or CCR5 from the peripheral blood. Whilst it is not precluded that the binding reagent is capable of binding to other molecules, such as other chemokine receptors, the binding reagent will preferentially bind to cells expressing CCR9, CCR1, CCR3 and/or CCR5 and in particular to cells expressing increased levels of CCR9, CCR1, CCR3 and/or CCR5 (as defined further herein).

The binding reagent capable of specifically binding to CCR9, CCR1, CCR3 and/or CCR5 may be either an agonist or an antagonist of CCR9, CCR1, CCR3 and/or CCR5. As the disease condition relies upon up-regulation of expression of or signaling via CCR9, CCR1, CCR3 and/or CCR5, in certain embodiments the binding reagent capable of specifically binding to CCR9, CCR1, CCR3 and/or CCR5 is an antagonist of CCR9, CCR1, CCR3 and/or CCR5. Chemokines are typically, although not necessarily exclusively (particularly in the case of truncated or modified forms) agonists of their cognate receptor and serve to activate the cells expressing the relevant receptor, as would be appreciated by one skilled in the art. Antibodies against the relevant chemokine receptor are generally considered to be antagonists, as would be appreciated by one skilled in the art. Specific examples of binding reagents include proteins or polypeptides, such as antibodies and receptor ligands, in particular chemokines. The binding reagent may be a nucleic acid molecule in certain embodiments. In some embodiments, the nucleic acid is an aptamer. Nucleic acid aptamers are polynucleotides of approximately 15-40 nucleotides long. Nucleic acid aptamers can be made using the SELEX process (systemic evolution of ligands by exponential enrichment) or any other process known to those of skill in the art.

In other embodiments, the binding reagent may be a peptide, and in certain instances, a peptide aptamer. Peptide aptamers are artificial recognition molecules that consist of a variable peptide sequence inserted into a constant scaffold protein (Baines I C, Colas P. Peptide aptamers as guides for small molecule drug discovery. Drug Discov Today. 2006; 11:334-341, incorporated herein by reference). A number of methodologies, such as phage display, ribosome display and yeast two-hybrid screening systems are available for screening a library of potential peptide-based binding agents. Similarly protein scaffolds based on domains such as fibronectins, ankyrin repeats, protein A, SH3 domains, lipocalins and, ubiquitin can be used as the binding agent. Again a number of technologies such as phage display and, ribosome display are available for screening a library of protein—based binding agents. Similarly, libraries of candidate chemical compounds can be screened for specific binding to the relevant chemokine receptor using suitable screening techniques known in the art, which may be high throughput screens in certain embodiments. The candidate binding agent may be immobilized on a solid support and the ability of the agent to specifically retain cells expressing the chemokine receptor of interest or labelled chemokine receptors determined. A range of cell types may be applied to the solid supports to confirm specificity of binding, or alternatively a mixed sample (such as peripheral blood) may be applied to the solid support. Retention of the cell type of interest (expressing the appropriate chemokine receptor) can be confirmed to identify suitable binding agents. A range of CCR9, CCR1, CCR3 and/or CCR5 antagonists are undergoing clinical studies. One example is the CCR9, CCR1, CCR3 and/or CCR5 antagonist YM-344031, which inhibits eosinophil degranulation release from human eosinophils (Suzuki et al., European Journal of Pharmacology 563 (2007) 224-232). Another example is GW766944, undergoing a phase II clinical trial for asthma.

In the context of the various embodiments of the present invention the term "chemokine" also comprises biotinylated or otherwise labelled chemokines. The term "chemokine" also comprises modified and truncated versions of the chemokine and chemokine fragments with the proviso that the modified or truncated form retains its ability to bind to its cognate receptor (and thus remains functional in the context of the various embodiments of the invention). The chemokine does not necessarily need to retain biological activity as it is specific binding affinity for CCR9, CCR1, CCR3 and/or CCR5 that is required. In certain embodiments, the chemokine lacks biological activity, for example in terms of activation of the (CCR9, CCR1, CCR3 and/or CCR5) receptor. As known to those skilled in the art, exemplary modifications may be made to improve protein synthesis, for example uniformity of product and yield. Modifications may comprise amino acid additions, substitutions, deletions or other modifications to one or more amino acids in the chemokine. Modifications may comprise substitution of the wild type amino acid with non-natural amino acids such as norleucine (NLeu) and derivatized amino acids such as pyroglutamic acid (pyroGlu). Such modifications may be made to minimize side-product formation during storage and use of the columns of the various embodiments of the invention. Modifications may be made to improve labelling, for example inclusion of a polyethylene glycol (PEG) spacer to facilitate biotinylation. The biotinylation and/or conjugation with fluorochromes or other labelling groups of the chemokine is performed in a manner which does not substantially affect the receptor binding capacity. Site specific biotinylation or other labelling is preferred as non-selective labelling of chemokines may compromise receptor binding activity. Bioinylation or other labelling is generally preferred at or towards the C-terminus of the protein as the inventors have found that modifications in this area are generally well tolerated (in terms of a minimal effect on receptor binding capability). Biotinylation may be carried out site-specifically at any suitable amino acid. Examples of suitable amino acids include lysine, diaminopropionic acid and ornithine. Generally, reference may be made to Natarajan S et al, Int. J. Pept. Protein Res., 1992, 40, 567-74; Baumeister B, Int. J. Peptide Res. And Therapeutics, 2005, 11, 139-141; Bioconjugate techniques 2nd edition, Greg T. Hermanson, incorporated by reference herein in its entirety.

Truncations may involve deletion of either N or C terminal amino acids as appropriate, or both. Typically, the truncated version will retain the residues required for the chemokine to fold correctly, for example to retain a chemokine fold structure, consistent with the requirement that a truncated version must retain the ability to bind to the relevant receptor (expressed by (on the surface of) a leukocyte). Chemokine molecules typically include disulphide bonds between the 1st and 3rd and 2nd and 4th cysteine residues respectively, as would be understood by one skilled in the art. Where sequences are presented herein, it is assumed that these disulphide bonds will form in the folded protein (unless otherwise stated). Truncated versions may comprise anywhere between 1 and 100 less amino acids, such as 1, 2, 3, 4, 5 etc amino acids, than the wild type amino acid sequence in certain embodiments. Of course, truncated versions may comprise further modification as detailed herein. The modified or truncated version may have 40%, 45%, 50%, 55%, 60%, 65%, 70%, 75%, 80%, 85%, 90%, 95% or more overall amino acid sequence identity with the full length wild type chemokine (where a deletion is counted as a difference in amino acid sequence) in certain embodiments. Over the common sequence between the molecules (i.e the amino acids that have not been deleted), there may be 80%, 85%, 90%, 91%, 92%, 93%, 94%, 95%, 96%, 97%, 98% or 99% amino acid sequence identity in certain embodiments. Sequence identity may be determined using known algorithms, such as BLAST or GAP analysis (GCG Program) (applying default settings), which are freely available. Chemokines may lack the N-terminal signal peptide which is cleaved off during synthesis in vivo.

Specific chemokines useful in the various embodiments of the present invention include eotaxin, eotaxin-2, eotaxin-3 RANTES, MCP-2, MCP-3, MCP-4, MIP-1alpha, MIP-1beta, MEC, HCC-2, CCK1 and CCL25 (TECK). Eotaxin (CCL11) and eotaxin 2 (CCL24) may bind solely to the chemokine receptor CCR3 and TECK (CCL25) may bind solely to the chemokine receptor CCR9 so these chemokines may be preferred in some embodiments. Each chemokine is able to bind to a chemokine receptor implicated in mental disorders such as schizophrenia, depression and bipolar disorder. More specifically, each of eotaxin (CCL11 binds CCR3 only), eotaxin-2, (aka CCL24 binds CCR3 only), eotaxin-3 (aka CCL26 binds CCR3 only), RANTES (CCL5 is promiscuous binding CCR1, CCR3, CCR4, CCR5), MCP-2, (aka CCL8 is promiscuous binding CCR1, CCR2, CCR3, CCR5) MCP-3 (aka CCL7 is promiscuous binding CCR1, CCR2, CCR3), MCP-4 (aka CCL13 is promiscuous binding CCR2 and CCR3), MIP-1a (aka CCL3 promiscuous CCR1, CCR4, CCR5), MIP-1beta (aka CCL4 binds CCR1, CCR2, CCR5), MEC (aka CCL28 binds CCR3 and CCR10), HCC-2 (CCL15 binds CCR1 and CCR3), may be useful for removing CCR1, CCR3 and/or CCR5 expressing cells from the blood of a patient. CCL25 (TECK) binds to CCR9. The chemokines described in greater detail herein (with reference to the relevant figures and amino acid sequences, as set forth in the SEQ ID NOs) may each be applied according to the various embodiments of the present invention.

CCL11 is the gene symbol approved by the HUGO Gene Nomenclature Committee for chemokine (C—C motif) ligand 11, also known as eotaxin. The HGNC ID for this gene is 10610. The gene is located at chromosome position 17q21.1-q21.2. The previous symbol and name for the gene is SCYA11, "small inducible cytokine subfamily A (Cys-Cys), member 11 (eotaxin)". Synonyms for this gene include MGC22554 and "eotaxin-1". The Genbank reference sequence for CCL11 is AB063614.1 as available on 13 Jun. 2011, which is incorporated herein by reference in its entirety.

CCL24 is the gene symbol approved by the HUGO Gene Nomenclature Committee for chemokine (C—C motif) ligand 24, also known as eotaxin-2 and MPIF-2. The HGNC ID for this gene is 10623. The gene is located at chromosome position 7q11.23. The previous symbol and name for the gene is SCYA24, "small inducible cytokine subfamily A (Cys-Cys), member 24". Synonyms for this gene include "CK-beta-6", Ckb-6, MPIF-2, MPIF2, "eotaxin-2", "myeloid progenitor inhibitory factor 2". The Genbank reference sequence for CCL24 is U85768.1 as available on 13 Jun. 2011, which is incorporated herein by reference in its entirety.

CCL26 is the gene symbol approved by the HUGO Gene Nomenclature Committee for chemokine (C—C motif) ligand 26, also known as eotaxin-3. The HGNC ID for this gene is 10625. The gene is located at chromosome position 7q11.22. The previous symbol and name for the gene is SCYA26, "small inducible cytokine subfamily A (Cys-Cys), member 26". Synonyms for this gene include "CC chemokine IMAC", IMAC, MIP-4-a, MIP-4-alpha, TSC-1, "chemokine N1", "eotaxin-3", "macrophage inflammatory protein 4-alpha", "small inducible cytokine A26", "thymic stroma chemokine-1". The Genbank reference sequence for CCL26 is AF124601.1 as available on 13 Jun. 2011, which is incorporated herein by reference in its entirety.

CCL5 is the gene symbol approved by the HUGO Gene Nomenclature Committee for chemokine (C—C motif) ligand 5, also known as RANTES. The HGNC ID for this gene is 10632. The gene is located at chromosome position 17q11.2-q12. The previous symbol and name for the gene is D17S136E, SCYA5, "small inducible cytokine A5 (RANTES)". Synonyms for this gene include "beta-chemokine RANTES", MGC17164, RANTES, "regulated upon activation, normally T-expressed, and presumably secreted", "SIS-delta", SISd, "small inducible cytokine subfamily A (Cys-Cys), member 5", "T-cell specific protein p288", "T-cell specific RANTES protein", TCP228. The Genbank reference sequence for CCL5 is AF043341.1 as available on 13 Jun. 2011, which is incorporated herein by reference in its entirety.

CCL8 is the gene symbol approved by the HUGO Gene Nomenclature Committee for chemokine (C—C motif) ligand 8, also known as MCP-2. The HGNC ID for this gene is 10635. The gene is located at chromosome position 17q11.2. The previous symbol and name for the gene is SCYA8, "small inducible cytokine subfamily A (Cys-Cys), member 8 (monocyte chemotactic protein 2)". Another synonym for this gene is HC14. The Genbank reference sequence for CCL8 is X99886.1 as available on 13 Jun. 2011, which is incorporated herein by reference in its entirety.

CCL7 is the gene symbol approved by the HUGO Gene Nomenclature Committee for chemokine (C—C motif) ligand 7, also known as MCP-3. The HGNC ID for this gene is 10634. The gene is located at chromosome position 17q11.2-q12. The previous symbol and name for the gene is SCYA6, SCYA7, "small inducible cytokine A7 (monocyte chemotactic protein 3)". Synonyms for this gene include FIC, MARC, MCP-3, MCP3, NC28, "monocyte chemoattractant protein 3", "monocyte chemotactic protein 3". The Genbank reference sequence for CCL7 is AF043338 as available on 13 Jun. 2011, which is incorporated herein by reference in its entirety.

CCL13 is the gene symbol approved by the HUGO Gene Nomenclature Committee for chemokine (C—C motif) ligand 13, also known as MCP-4. The HGNC ID for this gene is 10634. The gene is located at chromosome position 17q11.2-q12. The previous symbol and name for the gene is SCYA6, SCYA7, "small inducible cytokine A7 (monocyte chemotactic protein 3)". Synonyms for this gene include FIC, MARC, MCP-3, MCP3, NC28, "monocyte chemoattractant protein 3", "monocyte chemotactic protein 3". The Genbank reference sequence for CCL13 is AJ001634.

CCL3 is the gene symbol approved by the HUGO Gene Nomenclature Committee for chemokine (C—C motif) ligand 3, also known as MIP-1α. The HGNC ID for this gene is 10632. The gene is located at chromosome position 17q12. The previous symbol and name for the gene is SCYA3, "small inducible cytokine A3 (homologous to mouse Mip-1a)". Synonyms for this gene include G0S19-1, LD78ALPHA, MIP-1-alpha. The Genbank reference sequence for CCL3 is M23178.1 as available on 13 Jun. 2011, which is incorporated herein by reference in its entirety.

CCL28 is the gene symbol approved by the HUGO Gene Nomenclature Committee for chemokine (C—C motif) ligand 28, also known as MEC and CCK1. The HGNC ID for this gene is 17700. The gene is located at chromosome position 5p12. Synonyms for this gene include "CC chemokine CCL28", CCK1, MEC, "mucosae-associated epithelial chemokine", SCYA28, "small inducible cytokine A28", "small inducible cytokine subfamily A (Cys-Cys), member 28". The Genbank reference sequence for CCL28 is AF110384.1 as available on 13 Jun. 2011, which is incorporated herein by reference in its entirety.

CCL15 is the gene symbol approved by the HUGO Gene Nomenclature Committee for chemokine (C—C motif) ligand 15, also known as HCC-2 and Lkn-1. The HGNC ID for this gene is 10613. The gene is located at chromosome position 17q11.2. The previous symbol and name for the gene is SCYA15, "small inducible cytokine subfamily A (Cys-Cys), member 15". Synonyms for this gene include "CC chemokine 3", "chemokine CC-2", HCC-2, HMRP-2B, "leukotactin 1", Lkn-1, "macrophage inflammatory protein 5", "MIP-1 delta", MIP-1d, MIP-5, NCC-3, SCYL3. The Genbank reference sequence for CCL15 is AF031587.1 as available on 13 Jun. 2011, which is incorporated herein by reference in its entirety.

CCL4 is the gene symbol approved by the HUGO Gene Nomenclature Committee for chemokine (C—C motif) ligand 4. The HGNC ID for this gene is 10630. The gene is located at chromosome position 17q12-q23. The previous symbol and name for the gene is LAG1, SCYA4, "small inducible cytokine A4 (homologous to mouse Mip-1b)". Synonyms for this gene include Act-2, AT744.1, MIP-1-beta. The Genbank reference sequence for CCL4 is M23502.1 as available on 13 Jun. 2011, which is incorporated herein by reference in its entirety.

CCL25 is the gene symbol approved by the HUGO Gene Nomenclature Committee for chemokine (C—C motif) ligand 25. The HGNC ID for this gene is 10624. The gene is located at chromosome position 19p13.2. The previous symbol and name for the gene is SCYA25, "small inducible cytokine subfamily A (Cys-Cys), member 25". Synonyms for this gene include "Ck beta-15", Ckb15, TECK, "TECK-var", "thymus expressed chemokine". The Genbank reference sequence for CCL25 is U86358.1 as available on 13 Jun. 2011, which is incorporated herein by reference in its entirety.

Examples of suitable modified chemokines of the various embodiments of the invention containing modifications and/or truncations and specifically adapted for use in the invention are described in detail herein. Eotaxin has been produced with Lys73 as the site of biotinylation on the chemokine (numbering based upon the mature protein having the amino acid sequence of SEQ ID NO: 2). Biotinylation permits immobilization of eotaxin on a solid support (via a biotin-avidin interaction). The basic amino acid sequence of eotaxin, including a 23 amino acid leader sequence is set forth as SEQ ID NO: 77. The amino acid sequence of the mature protein is set forth as SEQ ID NO: 78. The inventors have determined that chemokines may display improved binding properties where the chemokine is biotinylated via a spacer group. The spacer may prevent the biotin group from impacting on the binding affinity of the chemokine. Any suitable spacer group may be employed. Further modifications may provide the molecule with advantageous properties.

Accordingly, the invention also provides a modified eoxtaxin chemokine comprising the amino acid sequence set forth as SEQ ID NO: 77 or SEQ ID NO: 78 in which one or more of the following modifications have been made:

a) the C terminus is produced as an amide derivative c) the C terminal region lysine residue at position 96 of SEQ ID NO: 77 or position 73 of SEQ ID NO: 78 is biotinylated, optionally via a spacer group, in order to permit immobilization of the chemokine on a solid support d) Lysine at position 96 of SEQ ID NO: 77 or position 73 of SEQ ID NO: 78 is replaced with another amino acid that can enable biotinylation such as ornithine e) the methionine residue at position 85 of SEQ ID NO: 77 or position 62 of SEQ ID NO: 2 has been replaced with norleucine The C terminal region lysine residue at position 96 of SEQ ID NO: 77 or position 73 of SEQ ID NO: 78 may be biotinylated via a suitable spacer group, such as a polyethylene glycol (PEG) spacer group, in order to permit immobilization of the chemokine on a solid support. In specific embodiments, the PEG spacer is 3,6-dioxo aminooctanoic acid. The sequence and biotinylation of a modified eotaxin chemokine of the invention is shown in FIG. 71. The modified eoxtaxin chemokines may be agonists or antagonists of CCR1, CCR3 and/or CCR5 activity. They can be tested for activity in a suitable assay, such as cell-based assays. In particular, agonist and antagonist properties may be determined in aequorin functional cell-based assay on human CCR1, CCR3 and/or CCR5 receptor.

A further example of a chemokine of the various embodiments of the invention containing modifications and specifically adapted for use in the invention is described in detail herein (see Examples below). The modified CCL8 (MCP-2) corresponds to residues 1 to 76 of the full length mature protein (and lacks the N-terminal signal peptide of 23 amino acids, which is cleaved off) and thus retains the chemokine fold. The Gln at the N-terminus of the protein is subject to pyroGlu formation under physiological conditions. Thus Gln1 of the sequence is substituted with pyroglutamine to prevent mixed species of N-terminal Gln and pyroGlu being generated (SEQ ID NO: 80). This improves the yield of synthesis and ensures a homogeneous chemokine preparation through column manufacture and use. FmocLys(ivDde)-OH is incorporated as residue 75 to facilitate site-specific labelling at this position of the protein (SEQ ID NO: 81). The naturally occurring lysine at position 75 is modified through biotinylation. A suitable spacer, such as a PEG spacer, may be incorporated between the ε-amino functionality and the biotin (SEQ ID NO: 82):

Thus, in certain embodiments the invention also relates to a modified chemokine comprising, consisting essentially of or consisting of the amino acid sequence of SEQ ID NO: 82:

XPDSVSIPITCCFNVINRKIPIQRLESYTRITNIQCPKEAVIFKTKRGK

EVCADPKERWVRDSMKHLDQIFQNLXP

X1=pyroGlu (but may remain as Gln in some embodiments)

X75=an amino acid residue that can be biotinylated, such as lysine, ornithine or diaminopropionic acid and optionally is biotinylated, optionally via a spacer molecule such as PEG, e.g. K(PEG-Biotin).

A further example of a chemokine of the various embodiments of the invention containing modifications and specifically adapted for use in the invention is described in detail herein (see Examples below). The modified CCL11 (Eotaxin) corresponds to residues 1 to 74 of the full length mature protein (and lacks the N-terminal signal peptide of 23 amino acids, which is cleaved off) and thus retains the chemokine fold (SEQ ID NO: 83). The lysine at position 73 may be modified through biotinylation. FmocLys(ivDde)-OH is incorporated as residue 73 to facilitate site-specific labelling at this position of the protein (SEQ ID NO: 84). A suitable spacer, such as a PEG spacer, may be incorporated between the ε-amino functionality and the biotin. The biotinylated version comprises, consists essentially of or consists of the amino acid sequence of SEQ ID NO: 85.

Thus, in other embodiments the invention also relates to a modified chemokine comprising, consisting essentially of or consisting of the amino acid sequence of SEQ ID NO: 83 or SEQ ID NO: 85:

SEQ ID NO: 83
GPASVPTTCCFNLANRKIPLQRLESYRRITSGKCPQKAVIFKTKLAKDI

CADPKKKWVQDSMKYLDQKSPTPXP

X is an amino acid residue that can be biotinylated, such as lysine, ornithine or diaminopropionic acid and optionally is biotinylated, optionally via a spacer molecule such as PEG, e.g. K(PEG-Biotin).

SEQ ID NO: 85
H-GPASVPTTCCFNLANRKIPLQRLESYRRITSGKCPQKAVIFKTKLAK

DICADPKKKWVQDSMKYLDQKSPTPXP-NH2

X is K(PEG-Biotin)

A further example of a chemokine of the various embodiments of the invention containing modifications and specifically adapted for use in the invention is described in detail herein (see Examples below). The modified CCL5 (RANTES) corresponds to residues 1 to 68 of the full length mature protein (and lacks the N-terminal signal peptide of 23 amino acids, which is cleaved off) and thus retains the chemokine fold. The single methionine (Met67) within the sequence is mutated to lysine, to mitigate against oxidation of this residue during the chain assembly (SEQ ID NO: 86). This Met to Lys substitution provides a lysine at position 67 which can be modified through biotinylation. FmocLys (ivDde)-OH is incorporated as residue 67 to facilitate site-specific labelling at this position of the protein (SEQ ID NO: 87). The biotinylated version comprises, consists essentially of or consists of the amino acid sequence of SEQ ID NO: 88.

Thus, in other embodiments the invention also relates to a modified chemokine comprising, consisting essentially of or consisting of the amino acid sequence of SEQ ID NO: 88:

SPYSSDTTPCCFAYIARPLPRAHIKEYFYTSGKCSNPAVVFVTRKNRQVC

ANPEKKWVREYINSLEXS

X is an amino acid residue that can be biotinylated, such as lysine, ornithine or diaminopropionic acid and optionally is biotinylated, optionally via a spacer molecule such as PEG (e.g. K(Biotin))

An example of a chemokine of the various embodiments of the invention containing both modifications and a truncation and specifically adapted for use in the invention is described in detail herein. The truncated CCL25 corresponds to residues 1 to 74 of the full length mature protein (and thus lacks amino acids 75 to 127 and the N-terminal signal peptide of 23 amino acids) and thus retains the chemokine fold. In addition, a methionine to Norleucine substitution is incorporated, to prevent oxidation of the residue during chain assembly. The N terminal glutamine residue is substituted with pyroglutamine to permit uniformity of product during synthesis. Biotinylation is achieved via a PEG spacer at the ε-functionality of the lysine residue found at position 72. The amino acid sequence of the linear molecule (i.e. without the PEG spacer and biotin molecule at amino acid 72 shown) comprises, consists essentially of or consists of the amino acid sequence presented as SEQ ID NO: 89. The final protein may thus comprise, consist essentially of or consist of the amino acid sequence of SEQ ID NO: 91 (see Examples below).

Chemokines useful in the various embodiments of the invention may be synthesised through any suitable means known in the art. Preferably, the chemokines are chemically synthesised as this facilitates modification and labelling etc. However, recombinant DNA based approaches may also be employed in combination with appropriate labelling and modification technologies as required. Thus, in certain embodiments the invention also provides a nucleic acid molecule encoding the chemokines of the various embodiments of the invention. In certain embodiments the invention also relates to a vector containing such a nucleic acid molecule and a host cell containing the vector. The vector may additionally comprise a suitable promoter operably linked to the nucleic acid molecule, to facilitate transcription of the corresponding mRNA molecule. The host cell may be capable of expressing the protein by transcription and translation of the nucleic acid molecule encoding a chemokine of the various embodiments of the invention.

The chemokines useful in the various embodiments of the invention can be biotinylated by methods known in the art such as described in WO 00/50088 A2, which is incorporated herein by reference in its entirety. As indicated above, site-specific labelling of the chemokines of the various embodiments of the invention is preferable, although any labelling technique which does not significantly affect the receptor-binding capacity of the chemokine may be employed. Various site-specifically biotinylated chemokines and native chemokines are available commercially, for instance from Almac, Craigavon, UK. Thus, in the specific embodiments described above, spacers other than PEG spacers may be employed as appropriate. In specific embodiments the one or more chemokines are biotinylated via a spacer group. The spacer may be employed to prevent the biotin group from impacting on the activity of the chemokine, in particular binding of the chemokine to its cognate receptor. Any suitable spacer that facilitates retention of receptor binding properties of the chemokine may be employed in the various embodiments of the invention. In specific embodiments, the spacer is a polyethylene glycol (PEG) spacer. PEG has been shown to be an effective spacer permitting attachment of biotin to the chemokine (which can then be immobilized on the solid support through interaction with streptavidin) without compromising receptor binding capability.

In the context of the various embodiments of the present invention the term "antibody" includes all immunoglobulins or immunoglobulin-like molecules with specific binding affinity for the relevant chemokine receptor (including by way of example and without limitation, IgA, IgD, IgE, IgG and IgM, combinations thereof, and similar molecules produced during an immune response in any vertebrate, for example, in mammals such as humans, goats, rabbits and mice). Specific immunoglobulins useful in the various embodiments of the invention include IgG isotypes. The antibodies useful in the various embodiments of the invention may be monoclonal or polyclonal in origin, but are typically monoclonal antibodies. Antibodies may be human antibodies, non-human antibodies, or humanized versions of non-human antibodies, or chimeric antibodies. Various techniques for antibody humanization are well established and any suitable technique may be employed. The term "antibody" also refers to a polypeptide ligand comprising at least a light chain or heavy chain immunoglobulin variable region which specifically recognizes and binds an epitope of an antigen, and it extends to all antibody derivatives and fragments that retain the ability to specifically bind to the relevant chemokine receptor. These derivative and fragments may include Fab fragments, F(ab')2 fragments, Fv fragments, single chain antibodies, single domain antibodies, Fc fragments etc. The term antibody encompasses antibodies comprised of both heavy and light chains, but also heavy chain (only) antibodies. In specific embodiments, the antibodies may be engineered so as to be specific for more than one chemokine receptor, for example bi-specific to permit binding to two different chemokine receptors. Suitable commercially available antibodies which bind to the chemokine receptors of interest are listed in table 5. They may or may not be labelled. General reference may be made to "Antibodies a laboratory manual: By E Harlow and D Lane. pp 726. Cold Spring Harbor Laboratory. 1988", which reference is incorporated herein in its entirety.

TABLE 5

Commercially available fluorophore labelled antibodies against specific chemokine receptors

| Antibody | Fluorophore | Supplier |
| --- | --- | --- |
| CCR5 | PE | Biolegend |
| CCR9 | APC | R&D Systems |
| CCR1 | Alexa Fluor 647 | Biolegend |
| CCR3 | PE | Biolegend |

The chemokine receptor expressing cells may thus be targeted using alternative binding agents, such as antibodies or other chemical compounds, as defined herein, rather than the natural chemokine binding partner. This approach is a new approach to treating inflammatory conditions.

Thus, in certain embodiments the invention also provides an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine. The binding reagent capable of specifically binding to the chemokine receptor may be an agonist or an antagonist of the chemokine receptor. In specific embodiments, the binding reagent capable of specifically binding to the chemokine receptor is selected from an antibody and a chemical compound.

In other embodiments the invention thus also provides a method for treating an inflammatory condition comprising applying peripheral blood from a patient/subject to an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine) thus removing chemokine receptor expressing cells from the peripheral blood of the patient/subject. The method may comprise returning the blood depleted of the chemokine receptor expressing cells to the patient/subject.

Similarly, in other embodiments the invention provides a binding reagent capable of specifically binding to a chemokine receptor for use in the treatment of an inflammatory condition, wherein the binding reagent is immobilized on a solid support contained within an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient/subject, wherein the binding reagent is not a chemokine), to which is applied peripheral blood from a patient thus removing chemokine receptor expressing cells from the peripheral blood of the patient.

These aspects of the various embodiments of the invention may be integrated into the more focussed therapeutic aspects of the various embodiments of the invention (i.e. treating mental disorders and various aspects thereof) and thus, the remainder of the disclosure, including all specific embodiments applies mutatis mutandis.

Solid support materials for immobilizing the binding reagents of the various embodiments of the invention are known in the art. "Solid support" refers to, for example, materials having a rigid or semi-rigid surface or surfaces, and may take the form of beads, resins, gels, microspheres, or other geometric configurations. A useful support material is one that does not activate blood cells so as to make them coagulate or adhere to the support as peripheral whole blood is applied to the device. In certain embodiments, a support treated with an agent to provide it with anti-coagulation properties, in particular a heparinized support is employed. Alternatively, the blood of the patient may be treated with an anti-coagulant such as heparin prior to application to the support. Useful support materials comprise high molecular weight carbohydrates, in particular carbohydrates having a molecular weight of 100 kDa or more, such as agarose, in particulate form, optionally cross-linked, and cellulose. Other preferred support materials are polymers, such as carboxylated polystyrene, and glass. The support of the various embodiments of the invention may be provided in the form of particles or fibres. The support particles may have regular form, such as spheres or beads, or irregular form. They may be porous or non-porous. A preferred average particle size of the support is from 50 µm to 2 mm. In certain embodiments Sepharose™, a cross linked, beaded-form of agarose, is used as column matrix. It is chosen for its optimal distribution capacity and can provide a large available area for affinity binding. Solid supports may be provided in the form of magnetic beads, with the specific binding reagent immobilized on the magnetic beads. Following capture of the (CCR9, CCR1, CCR3 and/or CCR5) chemokine receptor expressing cells from the blood, the beads can be removed from the blood with the aid of an appropriate magnetic separator.

Methods for immobilizing binding reagents on a solid support are known in the art. A binding reagent, such as a chemokine, antibody, peptide, nucleic acid or chemical compound, can be immobilized on the support in a direct or indirect manner. Immobilization can be by means of a suitable linker in some embodiments. A preferred method of indirect immobilization of a binding reagent, such as a chemokine, relies upon the interaction between biotin and avidin molecules. "Avidin" or "avidin molecule" refers to any type of protein that specifically binds biotin to the substantial exclusion of other (small) molecules that might be present in a biological sample. Examples of avidin include avidins that are naturally present in egg white, oilseed protein (e.g., soybean meal), and grain (e.g., corn/maize), and streptavidin, which is a protein of bacterial origin. Thus, biotinylation of the binding reagent and use of an avidin molecule such as streptavidin immobilized on the solid support allows reliable attachment of the binding reagent to the solid support according to methods known in the art. Specifically, such a method may comprise providing the binding reagent in biotinylated form, providing a solid support having streptavidin immobilized on its surface, contacting the support with an aqueous solution of the biotinylated binding reagent, and rinsing the support with an aqueous solvent. In addition, binding pair interactions, such as antibody-antigen interactions may also be utilised for indirect immobilisation of binding reagent onto a support. In such embodiments the support may be derivatised with one member of a binding pair, such as an antibody or fragment or derivative thereof, as defined herein, which has known affinity for a particular peptide sequence or small molecule hapten. Incorporating the other member of the binding pair, such as an antigen, peptide sequence or the hapten onto or into the binding reagent facilitates immobilisation onto a solid support coated with the corresponding antibody or fragment or derivative thereof. Thus, the binding reagent may be modified to include the peptide sequence or hapten into the linear molecule or may be added as a side chain or label. Any suitable antibody-antigen pair may be employed. The antibody fragment or derivative may be any fragment or derivative that retains specific binding affinity for the appropriate antigen. Examples include Fab, F(ab')2 fragments, scFV, VH domains, single domain antibodies (such as nanobodies), heavy chain antibodies and humanized version of non-human antibodies etc. Other high affinity interactions can be utilised for immobilisation of binding reagents, as long as the binding reagent can be synthesised or derivatised with one of the interacting partners and the solid support synthesised or derivatised with the other interacting partner without loss of binding activity (i.e. binding of the binding reagent to the appropriate chemokine receptor). Immobilization may occur via essentially the same interaction in reverse in some embodiments. Thus, the binding reagent which may be a chemokine for example, may be attached to an antibody as defined herein, and the solid support derivatised with the antigen. The chemokine may be produced as a fusion protein with the antibody.

Alternatively binding reagents, such as chemokines and antibodies, can be immobilised directly onto a solid support using bioconjugation techniques established in the field. For example direct immobilisation of proteins onto cyanogen bromide activated solid supports via amino functionalities within the primary sequence of the protein. Alternatively, sulphydryl functionalities within proteins can be used to directly immobilise the protein to alkyl halide derivatised supports or supports containing free thiol functionalities. In further embodiments, proteins containing α-thioester functionalities can be directly immobilised on supports containing 1,2 amino thiol moieties (eg N-terminal cysteine) using the native chemical ligation reaction. Alternatively proteins modified with ketones and aldehydes can be immobilised on solid supports derivatised with hydrazinyl, hydrazide and aminoxy functionalities using hydrazone/oxime bond forming ligation reactions (and vice versa). Alternatively 'Click' chemistry can be used to immobilise proteins onto solid supports, whereby the protein and the support are derivatised with the appropriate mutually reactive chemical functionalities (azides and alkynes). In other embodiments Staudinger ligation chemistry can be used to immobilise appropriately derivatised proteins onto the appropriately derivatised solid supports.

The solid support is contained within or carried by the apheresis column. Thus, by "loaded" is meant that the column carries or contains the solid support in a manner such that (peripheral) blood can flow through the column in contact with the solid support. Thus, the solid support provides a matrix within the column through which blood flows, in continuous fashion in certain embodiments. This permits cells expressing the specific chemokine receptor to be removed from the blood passing through the column, such that blood exiting the column is depleted of the specific chemokine receptor-expressing cells. In specific embodiments, the apheresis column is loaded with a support comprising streptavidin immobilized on the support and one or more biotinylated binding reagents, such as chemokines, bound to the streptavidin on the support. The solid support may be comprised of a high-molecular weight carbohydrate, optionally cross-linked, such as agarose.

As discussed above, the binding reagent is coupled to the solid support. The relative amounts of binding reagent may be controlled to ensure that coupling between the solid support and the binding reagent will be immediate, minimising the risk of binding reagent decoupling from the solid support. Thus, it may be ensured that there is a relative excess of immobilization sites for the binding reagent on the solid support. Alternatively, or additionally, following immobilization of the binding reagent on the solid support, the solid support may be washed to remove any unbound binding reagent.

The apheresis column utilised in the various embodiments of the present invention acts as a leukapheresis treatment for mental disorders such as schizophrenia, depression and bipolar disorder. The column acts to specifically remove CCR9, CCR1, CCR3 and/or CCR5-expressing cells such as eosinophils and Th2 lymphocytes by exploiting the interaction between CCR9, CCR1, CCR3 and/or CCR5 expressed on the cell surface and a specific binding reagent immobilized on a solid support contained within or carried by the column. The overall column typically comprises, consists of, or consists essentially of three combined components; 1) a housing which contains or carries 2) the solid support and 3) one or more binding reagents (immobilized thereon) which specifically bind one or more chemokine receptors. The housing may be manufactured from any suitable material for clinical use. In certain embodiments the housing is composed of a plastic material. The housing includes an in flow site for entry of blood and an out flow site for blood (depleted of target cells) to exit the column. The housing may be designed to maintain a continuous blood flow through the solid support matrix. The housing (as shown for example in FIG. 9) may include a top portion which comprises a distribution plate (2) at the inflow site (1) to spread the blood evenly over the entire matrix area. The distribution plate may act as a first safety barrier preventing larger particles flowing through the column and into the patient. However, the distribution plate is not essential and may be removed in some embodiments to decrease the overall resistance in the system. The column may contain one or more safety filter units (3 and 4) placed at the inflow (1) and/or outflow (5) sites of the plastic housing. Such filter units may act to prevent particles larger than blood cells passing in and/or out of the column. The safety filter units may contain a plurality of filters, such as two, three or four filters designed to be a robust barrier and stop all particles larger than blood cells passing through the column. Inclusion of safety filters (3 and 4) at both ends of the column serves to minimize the risk of leakage of particles into the patient, including in the event that the device is incorrectly connected resulting in blood flow in the opposite direction to that intended. The safety filters may comprise of any suitable pore size to prevent particles larger than blood cells from passing through the column, as would be readily understood by one skilled in the art. Suitable filters are commercially available. In specific embodiments, the pore size of the filter(s) is between approximately 60 µm and 100 µm, more specifically approximately 80 µm. The solid support and binding reagent components are discussed in further detail herein.

The volume of the housing may be varied depending upon the blood volumes intended to pass through the column. Typically, the volume of the housing is between approximately 40 ml and 200 ml, more specifically 50 ml to 150 ml or 60 ml to 120 ml.

The column is generally applied in the form of an apheresis circuit. In this context, the overall system includes the apheresis column, tubing and an appropriate pump to pump the blood around the circuit. The system is illustrated in FIG. 10. The patient (1) is connected to the extracorporeal circuit via sterile needles to veins in the right and the left arms. A saline bag (3) is also connected and the saline solution is pumped with a suitable pump (2). Blood is drawn from one arm of the patient through the sterile tubing system by the blood pump (4) and passed through the column (6) and back to the patient. The tubing system may be connected to the column via any suitable coupling, such as standard dialysis luer-lock couplings. The couplings on the column may be colour-coded for correct assembly. For example, red tubing for inflow to the red column top and blue tubing for outflow back to the patient. An air detector (8) may be present in the circuit. Inlet pressure (5) and/or Pven sensors (7) may additionally be employed to monitor the pressure in the circuit.

An apheresis pump, such as the 4008 ADS pump manufactured by Fresenius Medical Care or the Adamonitor pump, may monitor the patient's inflow and outflow. The pump may also monitor the pressure in the extracorporeal circulation. The pump may be able to discriminate air by a bubble catcher and air detector. A clot catcher filter may be positioned inside the bubble catcher. The pump may also incorporate an optical detector to distinguish between light, e.g. saline solution or air present in the tubing system and dark e.g. blood present in the tubing system.

A schematic diagram of a suitable pump, showing the air detector and optical filter is shown in FIG. 11. If the pump system detects air bubbles and optical fluctuations or if extracorporeal pressure values are out of the set range, then the pump may stop immediately. Alternatively or additionally a visual/audible alarm may be emitted.

The treatment methods of the various embodiments of the invention may thus rely upon an extracorporeal circuit. The methods may be considered as ex vivo or in vitro methods and be defined solely with reference to steps performed outside of the patient. In some embodiments, however, the method further comprises, prior to application of the blood to the column, collecting peripheral blood from the patient. In a further embodiment, the method further comprises, following the application of the blood to the column, infusing the blood depleted of (CCR9, CCR1, CCR3 and/or CCR5) chemokine receptor expressing cells to the patient. This is then a complete leukapheresis treatment method. Thus, a leukaphereis method, for treating mental disorders such as schizophrenia, depression and bipolar disorder, comprises collecting peripheral blood from the patient; applying the peripheral blood to an apheresis column loaded with a solid support comprising a binding reagent capable of specifically binding to a chemokine receptor, in particular the chemokine receptor CCR9, CCR1, CCR3 and/or CCR5, immobilized directly or indirectly on the support thus removing CCR9, CCR1, CCR3 and/or CCR5 expressing cells from the peripheral blood of the patient; and infusing the depleted blood (of chemokine receptor expressing cells) to the patient.

The peripheral blood may be continuously collected from the patient. Similarly, the depleted blood may be continuously infused to the patient, through use of an appropriate circuit as described herein. Thus, the support may be disposed in a column through which the blood is made to flow. This may be achieved using a suitable pump for example, as also described herein. Blood flow through the column enables the binding reagent(s) immobilized on the solid support to capture the cells expressing the chemokine receptor, thus depleting them from the blood and preventing their contribution to mental disorders such as schizophrenia, depression and bipolar disorder.

The methods of the various embodiments of the invention and binding reagents for use in the methods of the various embodiments of the invention may require that the patient has been selected for treatment on the basis of detecting an increase in the level of CCR9, CCR1, CCR3 and/or CCR5 expressing cells, levels of expression of CCR9, CCR1, CCR3 and/or CCR5 and/or levels of cells with high expression of CCR9, CCR1, CCR3 and/or CCR5 in a sample obtained from the patient. Such companion diagnostic methods are described in greater detail herein and are based, for example, on the observation that inflammation is an important component of mental disorders such as schizophrenia, depression and bipolar disorder and may involve increased levels of CCR9, CCR1, CCR3 and/or CCR5 intracellular signalling via chemokine, such as CCL11 binding. It is also shown herein that levels of CCR9 expressing leukocytes, in particular monocytes, are highly increased in mental disorder, in particular bipolar disorder, patients (compared with healthy controls).

Thus, (in this context) in certain embodiments the invention also provides a method of diagnosing, monitoring progression of, or monitoring treatment of mental disorders such as schizophrenia, depression and bipolar disorder comprising determining:

a) the levels of the chemokine receptor CCR9, CCR1, CCR3 and/or CCR5 expressing cells b) levels of expression of CCR9, CCR1, CCR3 and/or CCR5; and/or c) levels of cells with high expression of CCR9, CCR1, CCR3 and/or CCR5 in a sample obtained from a subject, wherein high levels of CCR9, CCR1, CCR3 and/or CCR5 expressing cells, high levels of expression of CCR9, CCR1, CCR3 and/or CCR5 or high levels of cells with high expression of CCR9, CCR1, CCR3 and/or CCR5 or increased levels of CCR9, CCR1, CCR3 and/or CCR5 expressing cells compared to control, increased levels of expression of CCR9, CCR1, CCR3 and/or CCR5 compared to a control or increased levels of cells with high expression of CCR9, CCR1, CCR3 and/or CCR5 compared to a control indicate the presence or progression of mental disorders such as schizophrenia, depression and bipolar disorder. Levels of chemokine receptor expression, as opposed to cell numbers, may also be investigated as increased levels of chemokine receptor expression per cell may also be diagnostically relevant. The cells may be monocytes or macrophages, in particular CCR9 expressing monocytes or macrophages.

"Diagnosing" is defined herein to include screening for a disease/condition or pre-indication of a disease/condition, identifying a disease/condition or pre-indication of a disease/condition and checking for recurrence of disease/condition following treatment. The methods of the various embodiments of the invention may also have prognostic value, and this is included within the definition of the term "diagnosis". The prognostic value of the methods of the various embodiments of the invention may be used as a marker of potential susceptibility to mental disorders such as schizophrenia, depression and bipolar disorder by identifying levels of CCR9, CCR1, CCR3 and/or CCR5 expression linked to mental disorders such as schizophrenia, depression and bipolar disorder. Thus patients at risk may be identified before the disease has a chance to manifest itself in terms of symptoms identifiable in the patient. In certain embodiments, diagnosis may be made in conjunction with other objective indicators of mental disorders such as schizophrenia, depression and bipolar disorder. Mental disorders such as schizophrenia, depression and bipolar disorder may be diagnosed based on established criteria, such as those specified by the American Psychiatric Association's Diagnostic and Statistical Manual of Mental Disorders and the World Health Organization's International Statistical Classification of Diseases and Related Health Problems, the ICD-10. In specific embodiments, diagnosis is made in conjunction with one or more of the following indicators:

1. Eosinophilia—an increase in eosinophils, which may be defined as the presence of more than 500 eosinophils/microliter of blood.

2. Positive symptoms, such as hallucinations, delusions, disorganized thinking and disorganized speech 3. Negative symptoms, such as poverty of speech (alogia), inability to experience pleasure (anhedonia), lack of desire to form relationships (asociality), and lack of motivation (avolition).

4. According to DSM-IV Two (or more) of the following, each present for a significant portion of time during a 1-month period (or less if successfully treated): (1) delusions (2) hallucinations (3) disorganized speech (e.g., frequent derailment or incoherence) (4) grossly disorganized or catatonic behaviour (5) negative symptoms, i.e., affective flattening, alogia (poverty of speech), or avolition (lack of motivation).

"Monitoring progression of" includes performing the methods to monitor the stage and/or the state and progression of mental disorders such as schizophrenia, depression and bipolar disorder. Monitoring progression may involve performing the diagnostic methods multiple times on the same patient to determine whether the levels of CCR9, CCR1, CCR3 and/or CCR5 expressing cells are increasing, decreasing or remaining stable over a certain time period. This may be in the context of a treatment regime.

"Monitoring the success of a particular treatment" is defined to include determining the levels of CCR9, CCR1, CCR3 and/or CCR5 expressing cells before and after a treatment. The treatment is generally one aimed at treating mental disorders such as schizophrenia, depression and bipolar disorder and may be a treatment according to one of the methods of the various embodiments of the invention as defined herein. Successful treatment may be determined with reference to a decrease in CCR9, CCR1, CCR3 and/or CCR5 expressing cells as a result of, or following, the treatment. Thus, in such methods a level of CCR9, CCR1, CCR3 and/or CCR5 expressing cells is determined prior to treatment. This level is recorded and a further assessment made at a predetermined time following the treatment. The comparison of levels of CCR9, CCR1, CCR3 and/or CCR5 expressing cells permits the success of the treatment to be monitored. In specific embodiments, a single treatment is sufficient to cause a depletion of around 10%, 20%, 30%, 40%, 50%, 60% or 70%, or higher, up to 80%, 90%, 95% or more, or any range of values between and including these amounts, of the specific chemokine receptor, in particular CCR9, CCR1, CCR3 and/or CCR5, expressing cells from the peripheral blood of the patient. In specific embodiments, at least around 50% depletion is achieved in a single treatment. Treatment may lead to depletion of between approximately 100 and 500 million CCR9, CCR1, CCR3 and/or CCR5 expressing cells in certain embodiments. Thus, successful treatment may be defined with reference to depletion of CCR9, CCR1, CCR3 and/or CCR5 expressing cells. The cells may be monocytes or macrophages, in particular CCR9 expressing monocytes or macrophages. Additional factors may be included to determine successful treatment. For example, a lack of increase in CCR9, CCR1, CCR3 and/or CCR5 expressing cells following treatment may indicate successful treatment in terms of preventing further progression of the condition, optionally combined with an improvement in other markers or staging of the mental disorders such as schizophrenia, depression and bipolar disorder.

The sample in which CCR9, CCR1, CCR3 and/or CCR5 expressing cell levels, levels of expression of CCR9, CCR1, CCR3 and/or CCR5 and/or levels of cells with high expression of CCR9, CCR1, CCR3 and/or CCR5 (defined as CCR9, CCR1, CCR3 and/or CCR5hi) are determined may comprise any suitable tissue sample or body fluid sample. Generally, the test sample is obtained from a human subject. Typically, the sample is a blood sample, in particular a peripheral blood sample. The sample may comprise liquor in certain embodiments. The methods may involve determining levels of CCR9, CCR1, CCR3 and/or CCR5 expressing eosinophils, lymphocytes, in particular T lymphocytes and more particularly Th2 lymphocytes, basophils and/or neutrophils and mast cells, in certain embodiments. The cells may be monocytes or macrophages, in particular CCR9 expressing monocytes or macrophages.

Levels of CCR9, CCR1, CCR3 and/or CCR5 expressing cells, levels of expression of CCR9, CCR1, CCR3 and/or CCR5 and/or levels of cells with high expression of CCR9, CCR1, CCR3 and/or CCR5 (defined as CCR9, CCR1, CCR3 and/or CCR5hi) may be determined according to any suitable method. For example, flow cytometry may be employed in order to determine the number of cells expressing CCR9, CCR1, CCR3 and/or CCR5 in the sample, to determine levels of CCR9, CCR1, CCR3 and/or CCR5 expression and/or to identify levels of CCR9, CCR1, CCR3 and/or CCR5hi cells. Flow cytometric techniques are described herein and examples of commercially available antibodies suitably labelled for use in flow cytometry are set out in Table 5 for example. Alternatively, the method may involve steps of collecting and fixing the cells in the sample, followed by incubation with a suitable binding reagent that binds specifically to the CCR9, CCR1, CCR3 and/or CCR5 chemokine receptor expressing cells in the sample. Any suitable binding reagent, as defined herein, may be employed. For example, a CCR-3, CCR-1 and/or CCR-5 specific antibody may be employed. A wash step may be adopted following an incubation period to remove any unbound reagent. Suitable wash steps and incubation conditions would be well known to one skilled in the art. The binding reagent may be directly labeled in order to permit antibody binding to be directly determined. Alternatively a secondary binding reagent, such as an antibody, may be employed which binds to the first binding reagent and carries a label. Again, suitable incubation conditions and wash steps would be apparent to one skilled in the art. The primary and secondary binding reagents may form two halves of a binding pair. The binding interaction should not prevent the primary binding reagent binding to the CCR9, CCR1, CCR3 and/or CCR5 receptor expressing cells, unless a competition assay is being employed. The two halves of a binding pair may comprise an antigen-antibody, antibody-antibody, receptor-ligand, biotin-streptavidin pair etc. in certain embodiments. Other techniques used to quantify chemokine (CCR9, CCR1, CCR3 and/or CCR5) receptor expressing cell levels, to quantify levels of CCR9, CCR1, CCR3 and/or CCR5 expression and/or to quantify levels of CCR9, CCR1, CCR3 and/or CCR5hi cells include PCR-based techniques such as QT-PCR and protein based methods such as western blot. Quantitation may be achieved with reference to fixed cell lines carrying known numbers of various receptor expressing cells and/or known levels of receptor expression per cell. Such fixed cell lines are available commercially (for example ChemiScreen™ cell lines from Millipore). Methods analogous to the treatment methods of the various embodiments of the invention may also be employed, with binding of CCR9, CCR1, CCR3 and/or CCR5 expressing cells to the solid support being determined following peripheral blood being passed through the column.

The levels of CCR9, CCR1, CCR3 and/or CCR5 expressing cells, levels of expression of CCR9, CCR1, CCR3 and/or CCR5 and/or levels of cells with high expression of CCR9, CCR1, CCR3 and/or CCR5 (defined as CCR9, CCR1, CCR3 and/or CCR5hi) may be determined relative to a suitable control. When diagnosing mental disorders such as schizophrenia, depression and bipolar disorder, a threshold level of cells, level of expression of CCR9, CCR1, CCR3 and/or CCR5 and/or level of cells with high expression of CCR9, CCR1, CCR3 and/or CCR5 (defined as CCR9, CCR1, CCR3 and/or CCR5hi) may be set at or over which a positive diagnosis is made. This threshold may be determined based upon measuring levels of CCR9, CCR1, CCR3 and/or CCR5 expressing cells, levels of expression of CCR9, CCR1, CCR3 and/or CCR5 and/or levels of cells with high expression of CCR9, CCR1, CCR3 and/or CCR5 (defined as CCR9, CCR1, CCR3 and/or CCR5hi) in samples obtained from diseased patients and comparing these levels with levels of CCR9, CCR1, CCR3 and/or CCR5 expressing cells, levels of expression of CCR9, CCR1, CCR3 and/or CCR5 and/or levels of cells with high expression of CCR9, CCR1, CCR3 and/or CCR5 (defined as CCR9, CCR1, CCR3 and/or CCR5hi) in samples obtained from healthy subjects.

In certain embodiments, a mental disorder such as schizophrenia, depression and bipolar disorder is diagnosed on the basis of levels of chemokine receptor expressing cells, such as CCR9, CCR1, CCR3 and/or CCR5 expressing cells. A positive diagnosis may be made in subjects based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, a mental disorder such as schizophrenia, depression and bipolar disorder is diagnosed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to healthy controls.

In specific embodiments, a mental disorder such as schizophrenia, depression and bipolar disorder is diagnosed on the basis of levels of CCR9 expressing cells. A positive diagnosis may be made in subjects based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more CCR9 expressing monocytes in the sample, as a percentage of total cells in the sample. Mental disorders such as schizophrenia, depression and bipolar disorder may also be diagnosed on the basis of the presence of a about a 1.2 fold or greater increase, such as about a 1.5, 2, 2.5, 3, 3.5, 4, 4.5, 5, 10, 20, 50 or 100 or greater fold increase in the specific chemokine receptor expressing cells, relative to healthy controls.

In certain embodiments, progression of mental disorders such as schizophrenia, depression and bipolar disorder, which may be in the context of a treatment regime, is monitored on the basis of levels of chemokine receptor expressing cells at different time points. Progression of mental disorders such as schizophrenia, depression and bipolar disorder may be indicated in subjects based upon an increase of greater than about 10%, such as an increase of greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more chemokine receptor expressing cells in the sample, as a percentage of total cells in the sample, compared to a sample taken from the same subject at an earlier time point. In other embodiments, progression of mental disorders such as schizophrenia, depression and bipolar disorder is confirmed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to a sample taken from the same subject at an earlier time point.

In specific embodiments, a mental disorder such as schizophrenia, depression and bipolar disorder is monitored on the basis of levels of CCR9 expressing cells, in particular monocytes. Progression of the disease, which may be in the context of a treatment regime, may be indicated in subjects based upon the presence of an increase of greater than about 10%, such as greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more chemokine receptor expressing cells in the sample, as a percentage of total cells in the sample, compared to a sample taken from the same subject at an earlier time point.

Regression or successful treatment may be monitored based upon similar decreases over various time points. For example, regression or successful treatment may be indicated in subjects based upon a decrease of about 10%, such as a decrease of about 15%, about 20%, about 25%, about 30%, about 35%, about 40%, about 45%, about 50%, about 55%, about 60%, about 65%, about 70%, about 75% or more chemokine receptor expressing cells in the sample, as a percentage of total cells in the sample, compared to a sample taken from the same subject at an earlier time point. In other embodiments, regression of mental disorders such as schizophrenia, depression and bipolar disorder is confirmed on the basis of the presence of a about a 1.2 fold or greater decrease, such as about a 1.5, 2, 2.5, 3, 3.5, 4, 4.5, 5, 10, 20, 50 or 100 or greater fold decrease in chemokine receptor expressing cells, relative to a sample taken from the same subject at an earlier time point.

In specific embodiments, a mental disorder such as schizophrenia, depression and bipolar disorder is monitored on the basis of levels of CCR9 expressing cells, in particular monocytes. Regression or successful treatment of the disease may be made in subjects based upon a decrease of about 50%, such as such as a decrease of about 55%, about 60%, about 65%, about 70%, about 75%, about 80%, about 85%, about 90%, about 95% or more CCR9 expressing cells in the sample, as a percentage of total cells in the sample or by a decrease of about 10%, such as a decrease of about 15%, about 20%, about 25%, about 30%, about 35%, about 40%, about 45%, about 50%, about 55%, about 60%, about 65%, about 70%, about 75% or more chemokine receptor expressing cells in the sample, as a percentage of total cells in the sample, compared to a sample taken from the same subject at an earlier time point. In other embodiments, regression of mental disorders such as schizophrenia, depression and bipolar disorder is confirmed on the basis of the presence of a about a 1.2 fold or greater decrease, such as about a 1.5, 2, 2.5, 3, 3.5, 4, 4.5, 5, 10, 20, 50 or 100 or greater fold decrease in CCR9 expressing cells, in particular monocytes, relative to a sample taken from the same subject at an earlier time point.

Suitable software is freely available (such as the R project for statistical computing) to perform the necessary statistical analysis of the data obtained to calculate a useful threshold. The threshold may be set to maximize sensitivity and/or specificity of the test. Performance of the test in these respects may be measured by plotting a receiver operating characteristics (ROC) curve (sensitivity versus specificity). The area under the curve provides an indication of the overall performance of the test. Thus, once thresholds have been set for diagnosing the condition, a separate control experiment does not necessarily have to be run each time a sample is tested. Rather reference can simply be made to the pre-existing thresholds to determine the diagnosis. However, in certain embodiments, the sample is tested together with a control sample taken from a healthy subject to provide a comparator based upon essentially identical experimental conditions. The test sample is generally tested in parallel with the control sample. The test sample level of CCR9, CCR1, CCR3 and/or CCR5 expressing cells, levels of expression of CCR9, CCR1, CCR3 and/or CCR5 and/or levels of cells with high expression of CCR9, CCR1, CCR3 and/or CCR5 (defined as CCR9, CCR1, CCR3 and/or CCR5hi) can then be compared with that of the control sample to make the diagnosis. A control sample from a disease patient may also be tested in certain embodiments. Reference to controls permits relative levels ("high", "low" etc.) of CCR9, CCR1, CCR3 and/or CCR5 expressing cells in the test sample to be readily identified and the significance thereof interpreted. Reference to controls also permits relative levels of CCR9, CCR1, CCR3 and/or CCR5 expression ("high", "low" etc.) within the cell population to be determined and the significance thereof interpreted. Such determination may, for example, indicate the average levels of CCR9, CCR1, CCR3 and/or CCR5 expression per cell in the test sample.

Thus, in specific embodiments, high or higher levels of CCR9, CCR1, CCR3 and/or CCR5 expressing cells or high or higher levels of CCR9, CCR1, CCR3 and/or CCR5 expression, for example average CCR9, CCR1, CCR3 and/or CCR5 expression per cell, or high or higher levels of CCR9, CCR1, CCR3 and/or CCR5hi cells correlate with active mental disorders such as schizophrenia, depression and bipolar disorder or more active mental disorders such as schizophrenia, depression and bipolar disorder. Similarly, lower or low levels of CCR9, CCR1, CCR3 and/or CCR5 expressing cells, or low or lower levels of CCR9, CCR1, CCR3 and/or CCR5 expression, for example average CCR9, CCR1, CCR3 and/or CCR5 expression per cell, or low or lower levels of CCR9, CCR1, CCR3 and/or CCR5hi cells may correlate with a lack of active inflammation or mental disorders such as schizophrenia, depression and bipolar disorder. This may be defined as "less active disease". It can readily be envisaged that control samples may be assessed and levels of CCR9, CCR1, CCR3 and/or CCR5 expressing cells, levels of expression of CCR9, CCR1, CCR3 and/or CCR5 and/or levels of cells with high expression of CCR9, CCR1, CCR3 and/or CCR5 (defined as CCR9, CCR1, CCR3 and/or CCR5hi) determined across the range of severities of mental disorders such as schizophrenia, depression and bipolar disorder. This may assist in correlating the levels of CCR9, CCR1, CCR3 and/or CCR5 expressing cells, levels of expression of CCR9, CCR1, CCR3 and/or CCR5 and/or levels of cells with high expression of CCR9, CCR1, CCR3 and/or CCR5 (defined as CCR9, CCR1, CCR3 and/or CCR5hi) in the test sample with the relative severity of the condition.

When monitoring progression of, or monitoring treatment of mental disorders such as schizophrenia, depression and bipolar disorder, the control samples may be taken from the subject at an earlier time point. They may, however, be based upon known reference values as discussed above. Thus, relative levels of CCR9, CCR1, CCR3 and/or CCR5 expressing cells, relative levels of CCR9, CCR1, CCR3 and/or CCR5 expression including relative levels of average CCR9, CCR1, CCR3 and/or CCR5 expression per cell or relative levels of CCR9, CCR1, CCR3 and/or CCR5hi cells may be with reference to samples taken from the same subject at a different point in time. In certain embodiments, decreased levels of CCR9, CCR1, CCR3 and/or CCR5 expressing cells decreased relative levels of CCR9, CCR1, CCR3 and/or CCR5 expression including decreased relative levels of average CCR9, CCR1, CCR3 and/or CCR5 expression per cell or decreased relative levels of CCR9, CCR1, CCR3 and/or CCR5hi cells correlate with successful treatment. The treatment may be any suitable treatment, but in specific embodiments is a treatment according to the various embodiments of the invention.

When monitoring progression of mental disorders such as schizophrenia, depression and bipolar disorder, increased levels of CCR9, CCR1, CCR3 and/or CCR5 expressing cells increased relative levels of CCR9, CCR1, CCR3 and/or CCR5 expression including increased relative levels of average CCR9, CCR1, CCR3 and/or CCR5 expression per cell or increased relative levels of CCR9, CCR1, CCR3 and/or CCR5hi cells may indicate the progression of condition or disease. Thus, if levels of CCR9, CCR1, CCR3 and/or CCR5 expressing cells, levels of expression of CCR9, CCR1, CCR3 and/or CCR5 and/or levels of cells with high expression of CCR9, CCR1, CCR3 and/or CCR5 (defined as CCR9, CCR1, CCR3 and/or CCR5hi) are increased in a sample taken later than a sample from the same patient this may indicate progression of the condition.

Since the levels of CCR9, CCR1, CCR3 and/or CCR5 expressing cells, levels of CCR9, CCR1, CCR3 and/or CCR5 expression or levels of CCR9, CCR1, CCR3 and/or CCR5hi cells are diagnostically relevant, determining such levels in a sample obtained from a subject may influence treatment selection for that subject. Accordingly, in certain embodiments the invention provides a method of selecting a suitable treatment for mental disorders such as schizophrenia, depression and bipolar disorder comprising determining:

a) the levels of the chemokine receptor CCR9, CCR1, CCR3 and/or CCR5 expressing cells b) levels of expression of CCR9, CCR1, CCR3 and/or CCR5; and/or c) levels of cells with high expression of CCR9, CCR1, CCR3 and/or CCR5 in a sample obtained from a subject, wherein high levels of CCR9, CCR1, CCR3 and/or CCR5 expressing cells, high levels of expression of CCR9, CCR1, CCR3 and/or CCR5 or high levels of cells with high expression of CCR9, CCR1, CCR3 and/or CCR5 or increased levels of CCR9, CCR1, CCR3 and/or CCR5 expressing cells compared to control, increased levels of expression of CCR9, CCR1, CCR3 and/or CCR5 compared to a control or increased levels of cells with high expression of CCR9, CCR1, CCR3 and/or CCR5 compared to a control, result in selection of a treatment as defined herein for treatment of the mental disorders such as schizophrenia, depression and bipolar disorder. In certain embodiments, the chemokine receptor expressing cells are high chemokine receptor expressing cells, in particular, high CCR9, CCR1, CCR3 and/or CCR5 expressing cells. The cells may be monocytes, in particular CCR9 expressing monocytes.

In specific embodiments, a mental disorder such as schizophrenia, depression and bipolar disorder is treated on the basis of measuring levels of chemokine receptor expressing cells, such as CCR9, CCR1, CCR3 and/or CCR5 expressing cells. Thus, a treatment according to the various embodiments of the invention may be applied based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, a mental disorder such as schizophrenia, depression and bipolar disorder is treated according to the various embodiments of the invention on the basis of the presence of a about a 1.5 fold or greater increase, such as about a 2, 2.5, 3, 3.5, 4, 4.5, 5, 10, 20, 50 or 100 or greater fold increase in chemokine receptor expressing cells, relative to healthy controls.

In specific embodiments, a mental disorder such as schizophrenia, depression and bipolar disorder is treated on the basis of measuring levels of CCR9 expressing cells, in particular monocytes. Thus, a treatment according to the various embodiments of the invention may be applied based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more CCR9 expressing monocytes in the sample, as a percentage of total cells in the sample or on the basis of the presence of a about a 1.5 fold or greater increase, such as about a 2, 2.5, 3, 3.5, 4, 4.5, 5, 10, 20, 50 or 100 or greater fold increase in chemokine receptor expressing cells, relative to healthy controls.

For the avoidance of doubt, all embodiments described in respect of the methods of the various embodiments of the invention apply to these aspects mutatis mutandis and are not repeated for reasons of conciseness. Specifically, mental disorders such as schizophrenia, depression and bipolar disorder may be indicated in conjunction with one or more of the following indicators:

1. Eosinophilia—an increase in eosinophils, which may be defined as the presence of more than 500 eosinophils/microliter of blood.

2. Positive symptoms, such as hallucinations, delusions, disorganized thinking and disorganized speech 3. Negative symptoms, such as poverty of speech (alogia), inability to experience pleasure (anhedonia), lack of desire to form relationships (asociality), and lack of motivation (avolition).

4. According to DSM-IV Two (or more) of the following, each present for a significant portion of time during a 1-month period (or less if successfully treated): (1) delusions (2) hallucinations (3) disorganized speech (e.g., frequent derailment or incoherence (4) grossly disorganized or catatonic behaviour (5) negative symptoms, i.e., affective flattening, alogia (poverty of speech), or avolition (lack of motivation).

In specific embodiments, the sample is a peripheral blood sample or a liquor sample.

The methods and medical uses of the various embodiments of the invention thus can be tailored to the need of individual patients or groups of patients on the basis of the various diagnostic methods of the various embodiments of the invention. By removing from the circulation CCR9, CCR1, CCR3 and/or CCR5 expressing cells, such as eosinophils, (T) lymphocytes, basophils and neutrophils and monocytes, in particular CCR9 expressing monocytes, upregulated in mental disorders such as schizophrenia, depression and bipolar disorder, an important factor in the inflammatory process of mental disorders such as schizophrenia, depression and bipolar disorder can be controlled. The method of the invention may be effective in treating or reversing mental disorders such as schizophrenia, depression and bipolar disorder.

F. Treating Conditions Associated with Allergy

Chemokines are a class of cytokine molecules involved in cell recruitment and activation in inflammation. Chemokines cause chemotaxis and activation of various subpopulations of cells in the immune system. The activity of chemokines is mediated primarily through tight binding to their receptors on the surface of leukocytes. In certain embodiments the present invention is based on the realisation that the interaction between chemokines and cells expressing their receptors may be exploited for the treatment of specific inflammatory conditions associated with allergies. In particular, various allergic conditions, such as asthma, allergic rhinitis, allergic ocular disease, atopic dermatitis, food allergies and allergic inflammation may include an inflammatory component. Allergies may arise in response to a range of allergens originating from a variety of sources, such as plants/pollen (e.g. trees such as birch, grass etc) and animals (e.g. pets such as cats and dogs etc). The inventors have determined that targeting increased recruitment of specific chemokine receptor-expressing cells to the site of inflammation presents a new therapeutic approach to treat such conditions. Moreover, in such conditions, chemokine receptor expression on each cell may be increased again providing a therapeutic approach to treat such conditions. It is shown herein that subjects or patients suffering from allergies displayed increased frequency of CCR3 expressing monocytes. It is further shown herein that subjects suffering from allergic conditions contain chemokine receptor expressing cells in the peripheral blood. Subjects suffering from allergic conditions contain CXCR1 and CXCR2 expressing neutrophils, CCR2 expressing monocytes and CCR3 expressing eosinophils. The expression of these receptors is not always necessary increased in allergic patients; however, the cells expressing the relevant receptors are increased in number in the inflammatory tract of patients with allergic disease. Moreover, the cells are potentially different in their proinflammatory profile with regards to other mediators. Therefore it may be beneficial for the subjects/patients to remove these cells from the circulation in order to prevent and reduce the influx of cells to the inflammatory tract. It is also shown herein that a potentially therapeutic proportion of the relevant chemokine receptor expressing cells can be removed using a suitable binding reagent. Thus, CXCR1 and CXCR2 expressing cells may be depleted from peripheral blood using IL-8 as binding reagent, in particular biotinylated IL-8 conjugated to a sepharose straptvidin matrix. CCR2 expressing cells may be depleted from peripheral blood using MCP-1 (CCL2) as binding reagent, in particular biotinylated MCP-1 conjugated to a sepharose straptvidin matrix. CCR3 expressing cells may be depleted from peripheral blood using eotaxin (CCL11) as binding reagent, in particular biotinylated eotaxin conjugated to a sepharose straptvidin matrix.

Thus, in certain embodiments the invention serves to reduce the recruitment of inflammatory leukocytes, which express characteristic chemokine receptors, and possibly express characteristic chemokine receptors at increased levels, to sites of inflammation linked to allergic disorders such as asthma, allergic rhinitis, allergic ocular disease, atopic dermatitis, food allergies and allergic inflammation. This is achieved using specific binding reagents to capture specific chemokine receptor-expressing (inflammatory) leukocytes from the patient. Accordingly, in certain embodiments the invention provides in a first aspect a method for treating an allergic condition comprising applying peripheral blood from a patient to an apheresis column loaded with a solid support comprising one or more binding reagents capable of specifically binding to a chemokine receptor, in particular one or more of the chemokine receptors CCR3, CXCR1, CXCR2 and/or CCR2, immobilized directly or indirectly on the support thus removing chemokine receptor, in particular CCR3, CXCR1, CXCR2 and/or CCR2, expressing cells from the peripheral blood of the patient. The peripheral blood from which the chemokine receptor expressing cells have been removed may then be returned to the patient in order to complete the treatment. The invention may thus rely on a continuous extracorporeal circuit in some embodiments. Alternatively, the invention may comprise steps of obtaining peripheral blood from the patient, applying the peripheral blood to the column and subsequently returning the peripheral blood from which the chemokine receptor expressing cells have been removed to the patient.

As shown herein, suitable binding reagents can be immobilized onto a solid support, either directly or indirectly, to generate an apheresis column suitable for capturing relevant chemokine receptor-expressing cells. Where increased levels of chemokine receptor expression are observed, such cells may be preferably removed from the peripheral blood using the columns of the various embodiments of the invention. Thus, the methods of the various embodiments of the invention may preferably target CCR3, CXCR1, CXCR2 and/or CCR2hi cells as defined herein for removal from the peripheral blood. "High" expression may be determined according to standard flow cytometry techniques. The level is measured relative to levels of expression of the chemokine receptor in cells taken from a healthy subject. The attached FIG. 82 provides an example of a gating strategy.

Herein, reference to CCR3, CXCR1, CXCR2 and/or CCR2 is intended to encompass selection of any one or more, up to all, of the chemokine receptors listed. In addition, the combination of CCR3, CXCR1 and/or CXCR2 is explicitly contemplated as a separate grouping, to include any one or more of CCR3, CXCR1 and/or CXCR2.

In other embodiments the invention further provides a binding reagent capable of specifically binding to a chemokine receptor, in particular to a chemokine receptor/ the chemokine receptor CCR3, CXCR1, CXCR2 and/or CCR2, for use in the treatment of an allergic condition, wherein the binding reagent is immobilized, directly or indirectly, on a solid support contained within an apheresis column, to which is applied peripheral blood from a patient thus removing chemokine receptor/CCR3, CXCR1, CXCR2 and/or CCR2 expressing cells from the peripheral blood of the patient. In certain embodiments the invention also provides for use of a binding reagent capable of specifically binding to a chemokine receptor/the chemokine receptor CCR3, CXCR1, CXCR2 and/or CCR2 for use in the manufacture of an apheresis column for treatment of an allergic condition, wherein the binding reagent is immobilized on a solid support contained within the apheresis column, to which is applied peripheral blood from a patient thus removing chemokine receptor/CCR3, CXCR1, CXCR2 and/or CCR2 expressing cells from the peripheral blood of the patient.

All embodiments described in respect of the methods of treatment of the various embodiments of the invention apply to these aspects mutatis mutandis and are not repeated for reasons of conciseness. Thus, the following discussion made with reference to the methods of treatment is also applicable to the medical use aspects of the various embodiments of the invention.

In certain embodiments the invention aims to treat a range of specific allergic conditions. Inflammation is an important component of allergic conditions and may involve eosinophilia causing tissue damage. The invention aims to address the inflammatory component of allergic conditions, specifically eosinophilia in some embodiments. Any relevant condition including an inflammatory component may be treated according to the methods of the invention. Specific conditions including an inflammatory component may be selected from asthma, allergic rhinitis, allergic ocular disease, atopic dermatitis, food allergies and allergic inflammation.

By "treatment" is meant a reduction in the specific chemokine receptor expressing cells in the peripheral blood of the patient. The reduction may comprise a reduction in cells that express chemokine receptors, in particular CCR3, CXCR1, CXCR2 and/or CCR2, at increased levels in diseased patients. The patient is typically a human patient but the term patient may include both human and non-human animal subjects in some embodiments. In the context of the various embodiments of the present invention, this typically involves a reduction in CCR3, CXCR1, CXCR2 and/or CCR2 expressing cells, such as "CCR3, CXCR1, CXCR2 and/or CCR2hi" expressing cells, in the peripheral blood of the patient. The CCR3, CXCR1, CXCR2 and/or CCR2 expressing cells comprise, consist essentially of or consist of eosinophils, lymphocytes, in particular T lymphocytes, basophils, mast cells and neutrophils in certain embodiments. In specific embodiments, the cells removed in order to treat allergic conditions comprise eosinophils, in particular CCR3 expressing eosinophils/granulocytes. In other embodiments, the cells removed in order to treat allergic conditions comprise neutrophils, in particular CXCR1 and CXCR2 expressing neutrophils. In other embodiments, the cells removed in order to treat allergic conditions comprise monocytes, in particular CCR2 expressing monocytes. Monocytes are antigen presenting cells that upon entering a site of inflammation produce cytokines and chemokines to recruit further inflammatory cells, and drive a Th2 activation of T lymphocytes. Th2 T cells provide help for B cells to switch towards IgE production. IgE recognizes the allergen. Eotaxin is a chemokine known to attract eosinophils and monocytes, cells that express CCR3. Therefore CCR3 targeting by Eotaxin may permit removal of monocytes and eosinophils cells that potentiate the allergic disorders.

The claimed methods may, in particular, target eosinophils. Eosinophilia is an important component of allergic conditions and may be defined as the presence of more than 500 eosinophils/microliter of blood. Thus, reducing numbers of circulating eosinophils represents an important therapeutic approach. Eosinophils, or eosinophil granulocytes, are white blood cells and represent an important immune system component. Along with mast cells, they also control mechanisms associated with allergy and asthma. They are granulocytes that develop during haematopoiesis in the bone marrow before migrating into blood.

The name "eosinophil" derives from the eosinophilic "acid-loving" properties of the cell. Normally transparent, it is this affinity that causes them to appear brick-red after staining with eosin, a red dye, using the Romanowsky method. The staining is concentrated in small granules within the cellular cytoplasm, which contain many chemical mediators, such as histamines and proteins such as eosinophil peroxidase, ribonuclease (RNase), deoxyribonucleases, lipase, plasminogen, and major basic protein. These mediators are released by a process called degranulation following activation of the eosinophil, and are toxic to both parasite and host tissues.

Eosinophils develop and mature in bone marrow. They differentiate from myeloid precursor cells in response to the cytokines interleukin 3 (IL-3), interleukin 5 (IL-5), and granulocyte macrophage colony-stimulating factor (GM-CSF). Eosinophils produce and store many secondary granule proteins prior to their exit from the bone marrow. After maturation, eosinophils circulate in blood and migrate to inflammatory sites in tissues in response to chemokines such as CCL11 (eotaxin-1), CCL24 (eotaxin-2), CCL5 (RANTES) and MCP1/4. Eosinophils may be activated by Type 2 cytokines released from a specific subset of helper T cells (Th2); IL-5, GM-CSF, and IL-3 are important for eosinophil activation as well as maturation. CD44 and CD69 have been shown to represent different types of cell-surface activation markers for human eosinophils. CD69 is absent from "fresh" eosinophils but expressed following activation (using cytokines). CD44 on the other hand is constitutively expressed but expression is significantly up-regulated in response to activation (Matsumoto et al., Am. J. Respir. Cell Mol. Biol., Volume 18, Number 6, June, 1998 860-866). Cell specific markers for eosinophils include CD9 and CDw125.

The three major types of lymphocyte are T cells, B cells and natural killer (NK) cells. The term "T-lymphocyte" includes CD4+ T cells such as T helper cells (Th1 cells and Th2 cells), and CD8+ T cells such as cytotoxic T cells. Th1 cells may be characterized by expression of CCR5 and production of IFN-γ. Th2 cells may be characterized by expression of CCR3, CXCR1 and/or CXCR2 and production of IL-4.

Basophils may also be known as basophil granulocyte. In contrast to eosinophils, these leukocytes are basophilic, i.e., they are susceptible to staining by basic dyes. Basophils contain large cytoplasmic granules which obscure the cell nucleus under the microscope. However, when unstained, the nucleus is visible and it usually has 2 lobes. Basophils store histamine, which is secreted by the cells upon stimulation.

Basophils have protein receptors on their cell surface that bind IgE, an immunoglobulin involved in macroparasite defense and allergy. It is the bound IgE antibody that confers a selective response of these cells to environmental substances, for example, pollen proteins or helminth antigens. Recent studies in mice suggest that basophils may also regulate the behavior of T cells and mediate the magnitude of the secondary immune response. Basophils may display an immunophenotype based upon expression (or lack thereof, indicated as "+" or "−" respectively of one or more of the following markers: FcεRI+, CD123, CD49b(DX-5)+, CD69+, Thy-1.2+, 2B4+, CD11bdull, CD117(c-kit)−, CD24−, CD19−, CD80−, CD14−, CD23−, Ly49c−, CD122−, CD11c−, Gr-1−, NK1.1−, B220−, CD3−, γδTCR−, αβTCR−, α4 and β4-integrin negative.

When activated, basophils degranulate to release histamine, proteoglycans (e.g. heparin and chondroitin), and proteolytic enzymes (e.g. elastase and lysophospholipase). They also secrete lipid mediators like leukotrienes, and several cytokines. Histamine and proteoglycans are pre-stored in the cell's granules while the other secreted substances are newly generated. Each of these substances contributes to inflammation. Recent evidence suggests that basophils are an important source of the cytokine, interleukin-4, perhaps more important than T cells. Interleukin-4 is considered one of the critical cytokines in the development of allergies and the production of IgE antibody by the immune system. There are other substances that can activate basophils to secrete which suggests that these cells have other roles in inflammation.

Neutrophils, also known as neutrophil granulocytes, may be subdivided into segmented neutrophils (or segs) and banded neutrophils (or bands). Neutrophils form part of the polymorphonuclear cell family (PMNs) together with basophils and eosinophils. Neutrophils staining a neutral pink on hematoxylin and eosin (H&E) histological or cytological preparations. Normally neutrophils contain a nucleus divided into 2-5 lobes.

Neutrophils are one of the first-responders of inflammatory cells to migrate towards the site of inflammation. Neutrophil granulocytes have an average diameter of 12-15 micrometers (μm) in peripheral blood smears. When analyzing a pure neutrophil suspension on an automated cell counter, neutrophils have an average diameter of 8-9 μm.

In addition to recruiting and activating other cells of the immune system, neutrophils play a key role in the front-line defence against invading pathogens. Neutrophils have three strategies for directly attacking micro-organisms: phagocytosis (ingestion), release of soluble anti-microbials (including granule proteins) and generation of neutrophil extracellular traps (NETs). Kinhult et al., (Clin Exp Allergy. 2003 August; 33 (8):1141-6) investigated the expression of surface activation markers on neutrophils, reflecting activation during their recruitment to the nose, and to see whether the inflammatory process during allergic rhinitis influences this process. A marked increase in the expression of CD11b, CD66b and CD63 on the neutrophil cell surface was noticed following migration from the bloodstream to the surface of the nasal mucosa. The expression of the CDb11b was reduced on neutrophils remaining in the circulation. In addition, the level of L-selectin was reduced on neutrophils derived from the blood during allergic inflammation. Cell specific markers for neutrophils include CD15 and CD16 in combination.

CCR3, CXCR1, CXCR2 and/or CCR2 expressed on these aforementioned cells binds to chemokines such as eotaxin. Eotaxin is a major chemoattractant for eosinophils, lymphocytes, in particular T lymphocytes, basophils and neutrophils by means of their binding to its specific cell-surface receptor, CC-chemokine receptor-3 (CCR3). CCR3 is the gene symbol approved by the HUGO Gene Nomenclature Committee for chemokine (C—C motif) receptor 3. The HGNC ID for this gene is 1604. The gene is located at chromosome position 3p21.3. The previous symbol and name for the gene is CMKBR3. Synonyms for this gene include CC-CKR-3, CD193 and CKR3. The Genbank reference sequence for CCR3 is AF247361.1 as available on 13 Jun. 2011, which is incorporated herein by reference in its entirety.

CCR2 is the gene symbol approved by the HUGO Gene Nomenclature Committee for chemokine (C—C motif) receptor 2. The HGNC ID for this gene is 1603. The gene is located at chromosome position 3p21. The previous symbol and name CMKBR2. Synonyms for this gene include CC-CKR-2, CD192, CKR2, FLJ78302, MCP-1-R. The RefSeq reference sequence for CCR1 is NM_001123041.2, as available on 13 Jun. 2011, which is incorporated herein by reference in its entirety.

CXCR1 is the gene symbol approved by the HUGO Gene Nomenclature Committee for chemokine (C—X—C motif) receptor 1. The HGNC ID for this gene is 6026. The gene is located at chromosome position 2q35. The previous symbol and name for the gene is CMKAR1, IL8RA, "interleukin 8 receptor, alpha". Synonyms for this gene include CD181, CDw128a, CKR-1. The Genbank reference sequence for CXCR1 is U111870.1, as available on 13 Jun. 2011, which is incorporated herein by reference in its entirety.

CXCR2 is the gene symbol approved by the HUGO Gene Nomenclature Committee for chemokine (C—X—C motif) receptor 2. The HGNC ID for this gene is 6027. The gene is located at chromosome position 2q35. The previous symbol and name for the gene is IL8RB, "interleukin 8 receptor, beta". Synonyms for this gene include CD182, CMKAR2. The Genbank reference sequence for CXCR2 is U111869.1, as available on 13 Jun. 2011, which is incorporated herein by reference in its entirety.

The various embodiments of the methods of the invention may involve specific binding interactions with any one or more of the further cell-surface markers, characteristic of the cell types targeted according to the invention, in addition to the removal based upon binding to CCR3, CXCR1, CXCR2 and/or CCR2. Suitable binding reagents can be prepared to specifically bind to these cell-surface markers. The discussion of CCR3, CXCR1, CXCR2 and/or CCR2 specific binding reagents thus applies mutatis mutandis.

Kim et al., (Respiratory Medicine (2010) 104, 1436-1443) show that asthma is characterized by eosinophilic inflammation and Th1 response and that none atopic asthma (NAA) patients showed higher percentage eosinophils and Eotaxin levels than atopic asthma and healthy controls.

Treatment according to the various embodiments of the invention may result in alleviation or amelioration of symptoms, prevention of progression, regression of the condition, or complete recovery. Measurable parameters of successful treatment include one or more, up to all, of a reduction in allergic symptoms and an absence of eosinophilia and/or a measurable decrease in eosinophils. In specific embodiments, a single treatment is sufficient to cause a depletion of around 10%, 20%, 30%, 40%, 50%, 60% or 70%, or higher up to 80%, 90%, 95% or more, or any range of values between and including these amounts, of the specific chemokine receptor, in particular CCR3, CXCR1, CXCR2 and/or CCR2, expressing cells from the peripheral blood of the patient. In specific embodiments, at least around 50% depletion is achieved in a single treatment. Thus, successful treatment may be defined with reference to depletion of CCR3, CXCR1, CXCR2 and/or CCR2 expressing cells. Treatment may lead to depletion of between approximately 100 and 500 million CCR3, CXCR1, CXCR2 and/or CCR2 expressing cells, such as eosinophils, in certain embodiments and more particularly to about 100, 150, 200, 250, 300, 350, 400, 450, or 500 million CCR3, CXCR1, CXCR2 and/or CCR2 expressing cells. In specific embodiments, the cells removed in order to treat allergic conditions comprise eosinophils, in particular CCR3 expressing eosinophils/granulocytes. In other embodiments, the cells removed in order to treat allergic conditions comprise neutrophils, in particular CXCR1 and CXCR2 expressing neutrophils. In other embodiments, the cells removed in order to treat allergic conditions comprise monocytes, in particular CCR2 expressing monocytes.

By binding to the column through the binding reagent-chemokine receptor interaction, chemokine receptor expressing cells are immobilized. These immobilized cells express further unoccupied chemokine receptors, which may be of the same or different type to those used for capture. These additional chemokine receptors may permit circulating chemokines which contribute to the inflammatory condition to be captured from the peripheral blood. Thus, a reduction in circulating (specific) chemokine levels may provide a measure of successful treatment.

The duration of treatment may be readily determined by one skilled in the art and will depend upon factors such as the flow rate of the peripheral blood. Duration of treatment may be tied into monitoring of the treatment itself, with the treatment considered complete once a measurable parameter of treatment has reached a defined threshold. Any suitable parameter may be employed as discussed herein. Thus, for example, treatment may be considered complete when a reduction in CCR3, CXCR1, CXCR2 and/or CCR2 expressing cells, such as a 50% reduction in CCR3, CXCR1, CXCR2 and/or CCR2 expressing cells, has been achieved. The apheresis system may be operated at a flow rate of around 10-80 mL/min, or more specifically between around 20-70 mL/min, or between around 30-60 mL/min. In specific embodiments, the treatment is performed for a period of around 10, 20, 30, 40, 50, 60, 70, 80, 90, 100, 110, 120 etc., or any range of values between and including these amounts, minutes. The treatment is typically not aimed to remove all of the cells expressing the chemokine receptor in the peripheral blood, as a basal level of those cells is required in healthy subjects. However, it has been found that only low blood volumes need to be applied to the columns of the various embodiments of the invention in order to achieve effective levels of depletion of the chemokine receptor-expressing cells. Thus, in certain embodiments, around 10-80% or more specifically around 20, 30, 40 or 50%, or any range of values between and including these amounts, of the patient's blood is applied to the column in a single treatment. The volume of blood circulated through the apheresis column or system may be in the region of around 1000-3000 ml, such as around 1000, 1200, 1400, 1600, 1800 or 2000 ml or any range of values between and including these amounts. The treatment may be considered complete once this volume of blood has been circulated. The patient may be administered anticoagulants prior to each treatment session. A suitable solution, such as a sterile saline solution, optionally including an anticoagulant such as Heparin, may be used for priming the apheresis (extracorporeal) system. An additional volume of anticoagulant may be added to the circuit at the start of each treatment session, for example as a bolus injection.

In certain embodiments the invention relies upon a binding reagent which is capable of specifically binding to a chemokine receptor. This specific binding reaction permits cells expressing the chemokine receptor to be removed from the peripheral blood of the patient when the blood is passed over the solid support upon or within which the binding reagent is immobilized. One specific chemokine receptor of interest is CCR3, CXCR1, CXCR2 and/or CCR2. The binding reagent can be any binding reagent capable of specifically binding to the receptor in question. By "specific binding" is meant that the binding reagent has sufficient specificity of binding and appropriate binding affinity/kinetics to permit removal of cells expressing CCR3, CXCR1, CXCR2 and/or CCR2 from the peripheral blood. Whilst it is not precluded that the binding reagent is capable of binding to other molecules, such as other chemokine receptors, the binding reagent will preferentially bind to cells expressing CCR3, CXCR1, CXCR2 and/or CCR2 and in particular to cells expressing increased levels of CCR3, CXCR1, CXCR2 and/or CCR2 (as defined further herein). The binding reagent capable of specifically binding to CCR3, CXCR1, CXCR2 and/or CCR2 may be either an agonist or an antagonist of CCR3, CXCR1, CXCR2 and/or CCR2. As the disease condition relies upon up-regulation of expression of or signaling via CCR3, CXCR1, CXCR2 and/or CCR2, in certain embodiments the binding reagent capable of specifically binding to CCR3, CXCR1, CXCR2 and/or CCR2 is an antagonist of CCR3, CXCR1, CXCR2 and/or CCR2. Chemokines are typically, although not necessarily exclusively (particularly in the case of truncated or modified forms) agonists of their cognate receptor and serve to activate the cells expressing the relevant receptor, as would be appreciated by one skilled in the art. Antibodies against the relevant chemokine receptor are generally considered to be antagonists, as would be appreciated by one skilled in the art. Specific examples of binding reagents include proteins or polypeptides, such as antibodies and receptor ligands, in particular chemokines. The binding reagent may be a nucleic acid molecule in certain embodiments. In some embodiments, the nucleic acid is an aptamer. Nucleic acid aptamers are polynucleotides of approximately 15-40 nucleotides long. Nucleic acid aptamers can be made using the SELEX process (systemic evolution of ligands by exponential enrichment) or any other process known to those of skill in the art.

In other embodiments, the binding reagent may be a peptide, and in certain instances, a peptide aptamer. Peptide aptamers are artificial recognition molecules that consist of a variable peptide sequence inserted into a constant scaffold protein (Baines I C, Colas P. Peptide aptamers as guides for small molecule drug discovery. Drug Discov Today. 2006; 11:334-341, incorporated herein by reference). A number of methodologies, such as phage display, ribosome display and yeast two-hybrid screening systems are available for screening a library of potential peptide-based binding agents. Similarly protein scaffolds based on domains such as fibronectins, ankyrin repeats, protein A, SH3 domains, lipocalins and ubiquitin can be used as the binding agent. Again a number of technologies such as phage display and ribosome display are available for screening a library of protein—based binding agents. Similarly, libraries of candidate chemical compounds can be screened for specific binding to the relevant chemokine receptor using suitable screening techniques known in the art, which may be high throughput screens in certain embodiments. The candidate binding agent may be immobilized on a solid support and the ability of the agent to specifically retain cells expressing the chemokine receptor of interest or labelled chemokine receptors determined. A range of cell types may be applied to the solid supports to confirm specificity of binding, or alternatively a mixed sample (such as peripheral blood) may be applied to the solid support. Retention of the cell type of interest (expressing the appropriate chemokine receptor) can be confirmed to identify suitable binding agents. A range of CCR3 antagonists are undergoing clinical studies. One example is the CCR3 antagonist YM-344031, which inhibits eosinophil degranulation release from human eosinophils (Suzuki et al., European Journal of Pharmacology 563 (2007) 224-232). Another example is GW766944, undergoing a phase II clinical trial for asthma.

In the context of the various embodiments of the present invention the term "chemokine" also comprises biotinylated or otherwise labelled chemokines. The term "chemokine" also comprises modified and truncated versions of the chemokine and chemokine fragments with the proviso that the modified or truncated form retains its ability to bind to its cognate receptor (and thus remains functional in the context of the various embodiments of the invention). The chemokine does not necessarily need to retain biological activity as it is specific binding affinity for CCR3, CXCR1, CXCR2 and/or CCR2 that is required. In certain embodiments, the chemokine lacks biological activity, for example in terms of activation of the (CCR3, CXCR1, CXCR2 and/or CCR2) receptor. Modifications may be made to improve protein synthesis, for example uniformity of product and yield. As known to those skilled in the art, exemplary modifications may comprise amino acid additions, substitutions, deletions or other modifications to one or more amino acids in the chemokine. Modifications may comprise substitution of the wild type amino acid with non-natural amino acids such as norleucine (NLeu) and derivatized amino acids such as pyroglutamic acid (pyroGlu). Such modifications may be made to minimize side-product formation during storage and use of the columns of the various embodiments of the invention. Modifications may be made to improve labelling, for example inclusion of a polyethylene glycol (PEG) spacer to facilitate biotinylation. The biotinylation and/or conjugation with fluorochromes or other labelling groups of the chemokine is performed in a manner which does not substantially affect the receptor binding capacity. Site specific biotinylation or other labelling is preferred as non-selective labelling of chemokines may compromise receptor binding activity. Bioinylation or other labelling is generally preferred at or towards the C-terminus of the protein as the inventors have found that modifications in this area are generally well tolerated (in terms of a minimal effect on receptor binding capability). Biotinylation may be carried out site-specifically at any suitable amino acid. Examples of suitable amino acids include lysine, diaminopropionic acid and ornithine. Generally, reference may be made to Natarajan S et al, Int. J. Pept. Protein Res., 1992, 40, 567-74; Baumeister B, Int. J. Peptide Res. And Therapeutics, 2005, 11, 139-141; Bioconjugate techniques 2nd edition, Greg T. Hermanson, incorporated by reference herein in its entirety.

Truncations may involve deletion of either N or C terminal amino acids as appropriate, or both. Typically, the truncated version will retain the residues required for the chemokine to fold correctly, for example to retain a chemokine fold structure, consistent with the requirement that a truncated version must retain the ability to bind to the relevant receptor (expressed by (on the surface of) a leukocyte). Chemokine molecules typically include disulphide bonds between the 1st and 3rd and 2nd and 4th cysteine residues respectively, as would be understood by one skilled in the art. Where sequences are presented herein, it is assumed that these disulphide bonds will form in the folded protein (unless otherwise stated). Truncated versions may comprise anywhere between 1 and 100 less amino acids, such as 1, 2, 3, 4, 5 etc amino acids, than the wild type amino acid sequence in certain embodiments. Of course, truncated versions may comprise further modification as detailed herein. The modified or truncated version may have 40%, 45%, 50%, 55%, 60%, 65%, 70%, 75%, 80%, 85%, 90%, 95% or more overall amino acid sequence identity with the full length wild type chemokine (where a deletion is counted as a difference in amino acid sequence) in certain embodiments. Over the common sequence between the molecules (i.e the amino acids that have not been deleted), there may be 80%, 85%, 90%, 91%, 92%, 93%, 94%, 95%, 96%, 97%, 98% or 99% amino acid sequence identity in certain embodiments. Sequence identity may be determined using known algorithms, such as BLAST or GAP analysis (GCG Program) (applying default settings), which are freely available. Chemokines may lack the N-terminal signal peptide which is cleaved off during synthesis in vivo.

Specific chemokines useful in the various embodiments of the present invention include Eotaxin (CCL11), eotaxin-2 (CCL24), eotaxin-3 (CCL26), RANTES (CCL25), MCP-1 (CCL2), MCP-2 (CCL8), MCP-3 (CCL7), MCP-4 (CCL13), MCP5 (CCL12), Lkn-1 (CCL15), MEC (CCL28), CXCL1 (GROalpha), CXCL2 (GRObeta), CXCL3 (GROgamma), CXCL5 (ENA-78), CXCL6 (GCP-2), CXCL7 (NAP-2), CXCL8 (I1-8). Eotaxin and eotaxin-2 may bind solely to the chemokine receptor CCR3 and so these chemokines may be preferred in some embodiments. In some embodiments, MCP-1 (CCL2) binds CCR2 expressing cells, such as monocytes. In other embodiments, IL-8 binds CXCR1 and/or CXCR2 expressing cells, such as neutrophils. Each chemokine is able to bind to a chemokine receptor implicated in allergic conditions. More specifically, each of Eotaxin (CCL11), eotaxin-2 (CCL24), eotaxin-3 (CCL26), RANTES (CCL25), MCP-1 (CCL2), MCP-2 (CCL8), MCP-3 (CCL7), MCP-4 (CCL13), MCP5 (CCL12), Lkn-1 (CCL15), MEC (CCL28), CXCL1 (GROalpha), CXCL2 (GRObeta), CXCL3 (GROgamma), CXCL5 (ENA-78), CXCL6 (GCP-2), CXCL7 (NAP-2), CXCL8 (I1-8) may be useful for removing CCR3, CXCR1, CXCR2 and/or CCR2 expressing cells from the blood of a patient. The chemokines described in greater detail herein (with reference to the relevant figures and amino acid sequences, as set forth in the SEQ ID NOs) may each be applied according to the various embodiments of the present invention.

CCL11 is the gene symbol approved by the HUGO Gene Nomenclature Committee for chemokine (C—C motif) ligand 11, also known as eotaxin. The HGNC ID for this gene is 10610. The gene is located at chromosome position 17q21.1-q21.2. The previous symbol and name for the gene is SCYA11, "small inducible cytokine subfamily A (Cys-Cys), member 11 (eotaxin)". Synonyms for this gene include MGC22554 and "eotaxin-1". The Genbank reference sequence for CCL11 is AB063614.1 as available on 13 Jun. 2011, which is incorporated herein by reference in its entirety.

CCL24 is the gene symbol approved by the HUGO Gene Nomenclature Committee for chemokine (C—C motif) ligand 24, also known as eotaxin-2 and MPIF-2. The HGNC ID for this gene is 10623. The gene is located at chromosome position 7q11.23. The previous symbol and name for the gene is SCYA24, "small inducible cytokine subfamily A (Cys-Cys), member 24". Synonyms for this gene include "CK-beta-6", Ckb-6, MPIF-2, MPIF2, "eotaxin-2", "myeloid progenitor inhibitory factor 2". The Genbank reference sequence for CCL24 is U85768.1 as available on 13 Jun. 2011, which is incorporated herein by reference in its entirety.

CCL26 is the gene symbol approved by the HUGO Gene Nomenclature Committee for chemokine (C—C motif) ligand 26, also known as eotaxin-3. The HGNC ID for this gene is 10625. The gene is located at chromosome position 7q11.22. The previous symbol and name for the gene is SCYA26, "small inducible cytokine subfamily A (Cys-Cys), member 26". Synonyms for this gene include "CC chemokine IMAC", IMAC, MIP-4-a, MIP-4-alpha, TSC-1, "chemokine N1", "eotaxin-3", "macrophage inflammatory protein 4-alpha", "small inducible cytokine A26", "thymic stroma chemokine-1". The Genbank reference sequence for CCL26 is AF124601.1 as available on 13 Jun. 2011, which is incorporated herein by reference in its entirety.

CCL5 is the gene symbol approved by the HUGO Gene Nomenclature Committee for chemokine (C—C motif) ligand 5, also known as RANTES. The HGNC ID for this gene is 10632. The gene is located at chromosome position 17q11.2-q12. The previous symbol and name for the gene is D17S136E, SCYA5, "small inducible cytokine A5 (RANTES)". Synonyms for this gene include "beta-chemokine RANTES", MGC17164, RANTES, "regulated upon activation, normally T-expressed, and presumably secreted", "SIS-delta", SISd, "small inducible cytokine subfamily A (Cys-Cys), member 5", "T-cell specific protein p288", "T-cell specific RANTES protein", TCP228. The Genbank reference sequence for CCL5 is AF043341.1 as available on 13 Jun. 2011, which is incorporated herein by reference in its entirety.

CCL8 is the gene symbol approved by the HUGO Gene Nomenclature Committee for chemokine (C—C motif) ligand 8, also known as MCP-2. The HGNC ID for this gene is 10635. The gene is located at chromosome position 17q11.2. The previous symbol and name for the gene is SCYA8, "small inducible cytokine subfamily A (Cys-Cys), member 8 (monocyte chemotactic protein 2)". Another synonym for this gene is HC14. The Genbank reference sequence for CCL8 is X99886.1 as available on 13 Jun. 2011, which is incorporated herein by reference in its entirety.

CCL7 is the gene symbol approved by the HUGO Gene Nomenclature Committee for chemokine (C—C motif) ligand 7, also known as MCP-3. The HGNC ID for this gene is 10634. The gene is located at chromosome position 17q11.2-q12. The previous symbol and name for the gene is SCYA6, SCYA7, "small inducible cytokine A7 (monocyte chemotactic protein 3)". Synonyms for this gene include FIC, MARC, MCP-3, MCP3, NC28, "monocyte chemoattractant protein 3", "monocyte chemotactic protein 3". The Genbank reference sequence for CCL7 is AF043338 as available on 13 Jun. 2011, which is incorporated herein by reference in its entirety.

CCL13 is the gene symbol approved by the HUGO Gene Nomenclature Committee for chemokine (C—C motif) ligand 13, also known as MCP-4. The HGNC ID for this gene is 10634. The gene is located at chromosome position 17q11.2-q12. The previous symbol and name for the gene is SCYA6, SCYA7, "small inducible cytokine A7 (monocyte chemotactic protein 3)". Synonyms for this gene include FIC, MARC, MCP-3, MCP3, NC28, "monocyte chemoattractant protein 3", "monocyte chemotactic protein 3". The Genbank reference sequence for CCL13 is AJ001634 as available on 13 Jun. 2011, which is incorporated herein by reference in its entirety.

CCL28 is the gene symbol approved by the HUGO Gene Nomenclature Committee for chemokine (C—C motif) ligand 28, also known as MEC and CCK1. The HGNC ID for this gene is 17700. The gene is located at chromosome position 5p12. Synonyms for this gene include "CC chemokine CCL28", CCK1, MEC, "mucosae-associated epithelial chemokine", SCYA28, "small inducible cytokine A28", "small inducible cytokine subfamily A (Cys-Cys), member 28". The Genbank reference sequence for CCL28 is AF110384.1 as available on 13 Jun. 2011, which is incorporated herein by reference in its entirety.

IL8 is the gene symbol approved by the HUGO Gene Nomenclature Committee for interleukin 8, also known as CXCL8. The HGNC ID for this gene is 6025. The gene is located at chromosome position 4q13-q21. Synonyms for this gene include 3-10C, AMCF-I, b-ENAP, "chemokine (C—X—C motif) ligand 8", CXCL8, GCP-1, IL-8, K60, LECT, LUCT, LYNAP, MDNCF, MONAP, NAF, NAP-1, SCYB8, TSG-1. The Genbank reference sequence for CXCL8 is Y00787.1 as available on 13 Jun. 2011, which is incorporated herein by reference in its entirety.

CCL2 is the gene symbol approved by the HUGO Gene Nomenclature Committee for chemokine (C—C motif) ligand 2, also known as MCP-1. The HGNC ID for this gene is 10618. The gene is located at chromosome position 17q111.2-q21.1. The previous symbol and name for the gene is SCYA2 "small inducible cytokine A2 (monocyte chemotatic protein 1, homologus to mouse Sig-je)". Synonyms for this gene include GDCF-2, HC11, MCP1, MGC9434, SMC-CF, "monocyte chemoattractant protein-1", "monocyte chemotactic and activating factor", "monocyte chemotactic protein 1, homologous to mouse Sig-je", "monocyte secretory protein JE", "small inducible cytokine subfamily A (Cys-Cys), member 2". The Genbank reference sequence for CCL2 is BC009716.1 as available on 13 Jun. 2011, which is incorporated herein by reference in its entirety.

Examples of suitable modified chemokines of the various embodiments of the invention containing modifications and/or truncations and specifically adapted for use in the invention are described in detail herein. Eotaxin has been produced with Lys73 as the site of biotinylation on the chemokine (numbering based upon the mature protein having the amino acid sequence of SEQ ID NO: 93). Biotinylation permits immobilization of eotaxin on a solid support (via a biotin-avidin interaction). The basic amino acid sequence of eotaxin, including a 23 amino acid leader sequence is set forth as SEQ ID NO: 92. The amino acid sequence of the mature protein is set forth as SEQ ID NO: 93. The inventors have determined that chemokines may display improved binding properties where the chemokine is biotinylated via a spacer group. The spacer may prevent the biotin group from impacting on the binding affinity of the chemokine. Any suitable spacer group may be employed. Further modifications may provide the molecule with advantageous properties.

Accordingly, in certain embodiments the invention also provides a modified eoxtaxin chemokine comprising the amino acid sequence set forth as SEQ ID NO: 92 or SEQ ID NO: 93 in which one or more of the following modifications have been made:

a) the C terminus is produced as an amide derivative c) the (C terminal region) lysine residue at position 96 of SEQ ID NO: 92 or position 73 of SEQ ID NO: 93 is biotinylated, optionally via a spacer group, in order to permit immobilization of the chemokine on a solid support d) the methionine residue at position 85 of SEQ ID NO: 92 or position 62 of SEQ ID NO: 93 has been replaced with norleucine e) the lysine at position 96 of SEQ ID NO: 92 or position 73 of SEQ ID NO: 93 is replaced with another amino acid that can enable biotinylation such as ornithine or diaminopropanoic acid.

The (C terminal region) lysine residue at position 96 of SEQ ID NO: 92 or position 73 of SEQ ID NO: 93 may be biotinylated via a suitable spacer group, such as a polyethylene glycol (PEG) spacer group, in order to permit immobilization of the chemokine on a solid support. In specific embodiments, the PEG spacer is 3,6-dioxo aminooctanoic acid. The sequence and biotinylation of a modified eotaxin chemokine of the invention is shown in FIG. 79. The modified eoxtaxin chemokines may be agonists or antagonists of CCR3 activity. They can be tested for activity in a suitable assay, such as cell-based assays. In particular, agonist and antagonist properties may be determined in aequorin functional cell-based assay on human CCR3 receptor.

An example of a chemokine of the various embodiments of the invention containing modifications and specifically adapted for use in the invention is described in detail herein (see Examples below). The modified CCL8 (MCP-2) corresponds to residues 1 to 76 of the full length mature protein (and lacks the N-terminal signal peptide of 23 amino acids, which is cleaved off) and thus retains the chemokine fold. The Gln at the N-terminus of the protein is subject to pyroGlu formation under physiological conditions. Thus Gln1 of the sequence may thus be substituted with pyroglutamine to prevent mixed species of N-terminal Gln and pyroGlu being generated (SEQ ID NO: 94). This improves the yield of synthesis and ensures a homogeneous chemokine preparation through column manufacture and use. FmocLys(ivDde)-OH is incorporated as residue 75 to facilitate site-specific labelling at this position of the protein (SEQ ID NO: 95). The naturally occurring lysine at position 75 is modified through biotinylation. A PEG spacer may be incorporated between the ε-amino functionality and the biotin (SEQ ID NO: 96).

Thus, in certain embodiments the invention also relates to a modified chemokine comprising, consisting essentially of or consisting of the amino acid sequence of SEQ ID NO: 94:

XPDSVSIPITCCFNVINRKIPIQRLESYTRITNIQCPKEAVIFKTKRGKE

VCADPKERWVRDSMKHLDQIFQNLXP

X1=pyroGlu (but may remain as Gln in some embodiments)
X75=an amino acid residue that can be biotinylated, such as lysine, ornithine or diaminopropionic acid and optionally is biotinylated, optionally via a spacer molecule such as PEG, e.g. K(PEG-Biotin).
Or SEQ ID NO: 96

XPDSVSIPITCCFNVINRKIPIQRLESYTRITNIQCPKEAVIFKTKRGKE

VCADPKERWVRDSMKHLDQIFQNLXP

X1=pyroGlu (but may remain as Gln in some embodiments)
X75=K(PEG-Biotin).

A further example of a chemokine of the various embodiments of the invention containing modifications and specifically adapted for use in the invention is described in detail herein (see Examples below). The modified CCL5 (RANTES) corresponds to residues 1 to 68 of the full length mature protein (and lacks the N-terminal signal peptide of 23 amino acids, which is cleaved off) and thus retains the chemokine fold. The single methionine (Met67) within the sequence is mutated to lysine, to mitigate against oxidation of this residue during the chain assembly (SEQ ID NO: 97). This Met to Lys substitution provides a lysine at position 67 which can be modified through biotinylation. FmocLys (ivDde)-OH is incorporated as residue 67 to facilitate site-specific labelling at this position of the protein (SEQ ID NO: 98). The biotinylated version comprises, consists essentially of or consists of the amino acid sequence of SEQ ID NO: 99.

Thus, in other embodiments the invention also relates to a modified chemokine comprising, consisting essentially of or consisting of the amino acid sequence of SEQ ID NO: 99:

SPYSSDTTPCCFAYIARPLPRAHIKEYFYTSGKCSNPAVVFVTRKNRQVC

ANPEKKWVREYINSLEXS

X is an amino acid residue that can be biotinylated, such as lysine, ornithine or diaminopropionic acid and optionally is biotinylated, optionally via a spacer molecule such as PEG (e.g. K(Biotin))

A further example of a chemokine of the various embodiments of the invention containing modifications and specifically adapted for use in the invention is described in detail herein (see Examples below). The modified CCL2 (MCP-1) corresponds to residues 1 to 76 of the full length mature protein (and lacks the N-terminal signal peptide of 23 amino acids, which is cleaved off) and thus retains the chemokine fold (SEQ ID NO: 100). The Gln at the N-terminus of the protein (Gln1) is substituted with pyroglutamine to prevent mixed species of N-terminal Gln and pyroGlu being generated. This improves the yield of synthesis and ensures a homogeneous chemokine preparation through column manufacture and use. FmocLys(ivDde)-OH is incorporated as residue 75 to facilitate site-specific labelling at this position of the protein (SEQ ID NO: 101). A suitable spacer, such as a PEG spacer, may be incorporated between the ε-amino functionality and the biotin. The biotinylated version comprises, consists essentially of or consists of the amino acid sequence of SEQ ID NO: 102.

Thus, in other embodiments the invention also relates to a modified chemokine comprising, consisting essentially of or consisting of the amino acid sequence of:

SEQ ID NO: 100:
XPDAINAPVTCCYNFTNRKISVQRLASYRRITSSKCPKEAVIFKTIVAKE

ICADPKQKWVQDSMDHLDKQTQTPKT

X=pyroGlu or Gln

And/or SEQ ID NO: 102:
XPDAINAPVTCCYNFTNRKISVQRLASYRRITSSKCPKEAVIFKTIVAKE

ICADPKQKWVQDSMDHLDKQTQTPXT

X1=pyroGlu or Gln
X75 is an amino acid residue that can be biotinylated, such as lysine, ornithine or diaminopropionic acid and optionally is biotinylated, optionally via a spacer molecule such as PEG, optionally K(PEG-Biotin)

A further example of a chemokine of the various embodiments of the invention containing modifications and specifically adapted for use in the invention is described in detail herein (see Examples below). The modified CXCL8 (IL-8) corresponds to residues 1 to 77 of the full length mature protein (and lacks the N-terminal signal peptide of 22 amino acids, which is cleaved off) and thus retains the chemokine fold. An amino acid residue capable of biotinylation, such as lysine or ornithine, is added as residue 78 (SEQ ID NO: 103). FmocLys(ivDde)-OH may be incorporated as residue 78 to facilitate site-specific labelling at this position of the protein (SEQ ID NO: 104). The additional amino acid, in particular lysine or ornithine, at position 78 is modified through biotinylation. A suitable spacer, such as a PEG spacer, may be incorporated between the ε-amino functionality and the biotin (SEQ ID NO: 105).

Thus, in other embodiments the invention also relates to a modified chemokine comprising, consisting essentially of or consisting of the amino acid sequence of SEQ ID NO: 103 or 105:

SEQ ID NO: 103
AVLPRSAKELRCQCIKTYSKPFHPKFIKELRVIESGPHCANTEIIVKLSD
GRELCLDPKENWVQRVVEKFLKRAENSX

X is an amino acid residue that can be biotinylated, such as lysine, ornithine or diaminopropionic acid and optionally is biotinylated, optionally via a spacer molecule such as PEG SEQ ID NO: 105
AVLPRSAKELRCQCIKTYSKPFHPKFIKELRVIESGPHCANTEIIVKLSD
GRELCLDPKENWVQRVVEKFLKRAENSK(PEG-Biotin)

A further example of a chemokine of the various embodiments of the invention containing truncations and modifications and specifically adapted for use in the invention is described in detail herein (see Examples below). The modified CXCL8 (IL-8) corresponds to residues 6 to 77 of the full length mature protein, with the first 5 N-terminal amino acids removed, (and lacks the N-terminal signal peptide of 22 amino acids, which is cleaved off) and thus retains the chemokine fold. An amino acid residue capable of biotinylation, such as lysine or ornithine, is added as residue 78 (SEQ ID NO: 106). FmocLys(ivDde)-OH may be incorporated as residue 78 to facilitate site-specific labelling at this position of the protein (SEQ ID NO: 107). The additional amino acid, in particular lysine or ornithine, at position 78 is modified through biotinylation. A suitable spacer, such as a PEG spacer, may be incorporated between the ε-amino functionality and the biotin (SEQ ID NO: 108).

Thus, in other embodiments the invention also relates to a modified chemokine comprising, consisting essentially of or consisting of the amino acid sequence of SEQ ID NO: 106 or 108:

SEQ ID NO: 196
SAKELRCQCIKTYSKPFHPKFIKELRVIESGPHCANTEIIVKLSDGRELC
LDPKENWVQRVVEKFLKRAENSX

X is an amino acid residue that can be biotinylated, such as lysine, ornithine or diaminopropionic acid and optionally is biotinylated, optionally via a spacer molecule such as PEG SEQ ID NO: 108
SAKELRCQCIKTYSKPFHPKFIKELRVIESGPHCANTEIIVKLSDGRELC
LDPKENWVQRVVEKFLKRAENSX X is K(PEG-Biotin)

A further example of a chemokine of the various embodiments of the invention containing modifications and specifically adapted for use in the invention is described in detail herein (see Examples below). The modified CCL11 (Eotaxin) corresponds to residues 1 to 74 of the full length mature protein (and lacks the N-terminal signal peptide of 23 amino acids, which is cleaved off) and thus retains the chemokine fold (SEQ ID NO: 109). The lysine at position 73 may be modified through biotinylation. FmocLys(ivDde)-OH is incorporated as residue 73 to facilitate site-specific labelling at this position of the protein (SEQ ID NO: 110). A suitable spacer, such as a PEG spacer, may be incorporated between the ε-amino functionality and the biotin. The biotinylated version comprises, consists essentially of or consists of the amino acid sequence of SEQ ID NO: 111.

Thus, in other embodiments the invention also relates to a modified chemokine comprising, consisting essentially of or consisting of the amino acid sequence of SEQ ID NO: 18 or SEQ ID NO: 111:

SEQ ID NO: 109
GPASVPTTCCFNLANRKIPLQRLESYRRITSGKCPQKAVIFKTKLAKDIC
ADPKKKWVQDSMKYLDQKSPTPXP

X is an amino acid residue that can be biotinylated, such as lysine, ornithine or diaminopropionic acid and optionally is biotinylated, optionally via a spacer molecule such as PEG, e.g. K(PEG-Biotin).

SEQ ID NO: 111
H-GPASVPTTCCFNLANRKIPLQRLESYRRITSGKCPQKAVIFKTKLAKD
ICADPKKKWVQDSMKYLDQKSPTPXP-NH2

X is K(PEG-Biotin)

Chemokines useful in the various embodiments of the invention may be synthesised through any suitable means known in the art. Preferably, the chemokines are chemically synthesised as this facilitates modification and labelling etc. However, recombinant DNA based approaches may also be employed in combination with appropriate labelling and modification technologies as required. Thus, in certain embodiments the invention also provides a nucleic acid molecule encoding the chemokines of the various embodiments of the invention. The invention also relates to a vector containing such a nucleic acid molecule and a host cell containing the vector. The vector may additionally comprise a suitable promoter operably linked to the nucleic acid molecule, to facilitate transcription of the corresponding mRNA molecule. The host cell may be capable of expressing the protein by transcription and translation of the nucleic acid molecule encoding a chemokine of the invention.

The chemokines useful in the various embodiments of the invention can be biotinylated by methods known in the art such as described in WO 00/50088 A2, which is incorporated herein by reference in its entirety. As indicated above, site-specific labelling of the chemokines of the various embodiments of the invention is preferable, although any labelling technique which does not significantly affect the receptor-binding capacity of the chemokine may be employed. Various site-specifically biotinylated chemokines and native chemokines are available commercially, for instance from Almac, Craigavon, UK. In specific embodiments the one or more chemokines are biotinylated via a spacer group. The spacer may be employed to prevent the biotin group from impacting on the activity of the chemokine, in particular binding of the chemokine to its cognate receptor. Any suitable spacer that facilitates retention of receptor binding properties of the chemokine may be employed in the various embodiments of the invention. Thus, in the specific embodiments described above, spacers other than PEG spacers may be employed as appropriate. In specific embodiments, the spacer is a polyethylene glycol (PEG) spacer. PEG has been shown to be an effective spacer permitting attachment of biotin to the chemokine (which can then be immobilized on the solid support through interaction with streptavidin) without compromising receptor binding capability.

In the context of the various embodiments of the present invention the term "antibody" includes all immunoglobulins or immunoglobulin-like molecules with specific binding affinity for the relevant chemokine receptor (including by way of example and without limitation, IgA, IgD, IgE, IgG and IgM, combinations thereof, and similar molecules produced during an immune response in any vertebrate, for example, in mammals such as humans, goats, rabbits and mice). Specific immunoglobulins useful in the various embodiments of the invention include IgG isotypes. The antibodies useful in the various embodiments of the invention may be monoclonal or polyclonal in origin, but are typically monoclonal antibodies. Antibodies may be human antibodies, non-human antibodies, or humanized versions of non-human antibodies, or chimeric antibodies. Various techniques for antibody humanization are well established and any suitable technique may be employed. The term "antibody" also refers to a polypeptide ligand comprising at least a light chain or heavy chain immunoglobulin variable region which specifically recognizes and binds an epitope of an antigen, and it extends to all antibody derivatives and fragments that retain the ability to specifically bind to the relevant chemokine receptor. These derivative and fragments may include Fab fragments, F(ab')2 fragments, Fv fragments, single chain antibodies, single domain antibodies, Fc fragments etc. The term antibody encompasses antibodies comprised of both heavy and light chains, but also heavy chain (only) antibodies. In specific embodiments, the antibodies may be engineered so as to be specific for more than one chemokine receptor, for example bi-specific to permit binding to two different chemokine receptors. Suitable commercially available antibodies which bind to the chemokine receptors of interest are listed in table 6 below. They may or may not be labelled. General reference may be made to "Antibodies a laboratory manual: By E Harlow and D Lane. pp 726. Cold Spring Harbor Laboratory. 1988", which reference is incorporated herein in its entirety.

TABLE 6

Commercially available fluorophore labelled antibodies against specific chemokine receptors

| Antibody | Fluorophore | Supplier |
|---|---|---|
| CXCR2 | PE | Biolegend |
| CXCR1 | APC | Biolegend |
| CCR3 | PE | Biolegend |
| CCR2 | PerCPCy5.5 | Biolegend |

The chemokine receptor expressing cells may thus be targeted using alternative binding agents, such as antibodies or other chemical compounds, as defined herein, rather than the natural chemokine binding partner. This approach is a new approach to treating inflammatory conditions.

Accordingly, in certain embodiments the invention also provides an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine. The binding reagent capable of specifically binding to the chemokine receptor may be an agonist or an antagonist of the chemokine receptor. In specific embodiments, the binding reagent capable of specifically binding to the chemokine receptor is selected from an antibody and a chemical compound.

In other embodiments the invention thus also provides a method for treating an inflammatory condition comprising applying peripheral blood from a patient/subject to an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine) thus removing chemokine receptor expressing cells from the peripheral blood of the patient/subject. The method may comprise returning the blood depleted of the chemokine receptor expressing cells to the patient/subject.

Similarly, in other embodiments the invention provides a binding reagent capable of specifically binding to a chemokine receptor for use in the treatment of an inflammatory condition, wherein the binding reagent is immobilized on a solid support contained within an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient/subject, wherein the binding reagent is not a chemokine), to which is applied peripheral blood from a patient thus removing chemokine receptor expressing cells from the peripheral blood of the patient.

These aspects of the various embodiments of the invention may be integrated into the more focused therapeutic aspects of the various embodiments of the invention (i.e. treating allergy conditions and various aspects thereof) and thus, the remainder of the disclosure, including all specific embodiments applies mutatis mutandis.

Solid support materials for immobilizing the binding reagents of the various embodiments of the invention are known in the art. "Solid support" refers to, for example, materials having a rigid or semi-rigid surface or surfaces, and may take the form of beads, resins, gels, microspheres, or other geometric configurations. A useful support material is one that does not activate blood cells so as to make them coagulate or adhere to the support as peripheral whole blood is applied to the device. In certain embodiments, a support treated with an agent to provide it with anti-coagulation properties, in particular a heparinized support is employed. Alternatively, the blood of the patient may be treated with an anti-coagulant such as heparin prior to application to the support. Useful support materials comprise high molecular weight carbohydrates, in particular carbohydrates having a molecular weight of 100 kDa or more, such as agarose, in particulate form, optionally cross-linked, and cellulose. Other preferred support materials are polymers, such as carboxylated polystyrene, and glass. The support of the various embodiments of the invention may be provided in the form of particles or fibres. The support particles may have regular form, such as spheres or beads, or irregular form. They may be porous or non-porous. A preferred average particle size of the support is from 50 µm to 2 mm. In certain embodiments Sepharose™, a cross linked, beaded-form of agarose, is used as column matrix. It is chosen for its optimal distribution capacity and can provide a large available area for affinity binding. Solid supports may be provided in the form of magnetic beads, with the specific binding reagent immobilized on the magnetic beads. Following capture of the (CCR3, CXCR1, CXCR2 and/or CCR2) chemokine receptor expressing cells from the blood, the beads can be removed from the blood with the aid of an appropriate magnetic separator.

Methods for immobilizing binding reagents on a solid support are known in the art. A binding reagent, such as a chemokine, antibody, peptide, nucleic acid or chemical compound, can be immobilized on the support in a direct or indirect manner. Immobilization can be by means of a suitable linker in some embodiments. A preferred method of indirect immobilization of a binding reagent, such as a chemokine, relies upon the interaction between biotin and avidin molecules. "Avidin" or "avidin molecule" refers to any type of protein that specifically binds biotin to the substantial exclusion of other (small) molecules that might be present in a biological sample. Examples of avidin include avidins that are naturally present in egg white, oilseed protein (e.g., soybean meal), and grain (e.g., corn/maize), and streptavidin, which is a protein of bacterial origin Thus, biotinylation of the binding reagent and use of an avidin molecule such as streptavidin immobilized on the solid support allows reliable attachment of the binding reagent to the solid support according to methods known in the art. Specifically, such a method may comprise providing the binding reagent in biotinylated form, providing a solid support having streptavidin immobilized on its surface, contacting the support with an aqueous solution of the biotinylated binding reagent, and rinsing the support with an aqueous solvent. In addition, binding pair interactions, such as antibody-antigen interactions may also be utilised for indirect immobilisation of binding reagent onto a support. In such embodiments the support may be derivatised with one member of a binding pair, such as an antibody or fragment or derivative thereof, as defined herein, which has known affinity for a particular peptide sequence or small molecule hapten. Incorporating the other member of the binding pair, such as an antigen, peptide sequence or the hapten onto or into the binding reagent facilitates immobilisation onto a solid support coated with the corresponding antibody or fragment or derivative thereof. Thus, the binding reagent may be modified to include the peptide sequence or hapten into the linear molecule or may be added as a side chain or label. Any suitable antibody-antigen pair may be employed. The antibody fragment or derivative may be any fragment or derivative that retains specific binding affinity for the appropriate antigen. Examples include Fab, F(ab')2 fragments, scFV, VH domains, single domain antibodies (such as nanobodies), heavy chain antibodies and humanized version of non-human antibodies etc. Other high affinity interactions can be utilised for immobilisation of binding reagents, as long as the binding reagent can be synthesised or derivatised with one of the interacting partners and the solid support synthesised or derivatised with the other interacting partner without loss of binding activity (i.e. binding of the binding reagent to the appropriate chemokine receptor). Immobilization may occur via essentially the same interaction in reverse in some embodiments. Thus, the binding reagent which may be a chemokine for example, may be attached to an antibody as defined herein, and the solid support derivatised with the antigen. The chemokine may be produced as a fusion protein with the antibody.

Alternatively binding reagents, such as chemokines and antibodies, can be immobilised directly onto a solid support using bioconjugation techniques established in the field. For example direct immobilisation of proteins onto cyanogen bromide activated solid supports via amino functionalities within the primary sequence of the protein. Alternatively, sulphydryl functionalities within proteins can be used to directly immobilise the protein to alkyl halide derivatised supports or supports containing free thiol functionalities. In further embodiments, proteins containing α-thioester functionalities can be directly immobilised on supports containing 1,2 amino thiol moieties (eg N-terminal cysteine) using the native chemical ligation reaction. Alternatively proteins modified with ketones and aldehydes can be immobilised on solid supports derivatised with hydrazinyl, hydrazide and aminoxy functionalities using hydrazone/oxime bond forming ligation reactions (and vice versa). Alternatively 'Click' chemistry can be used to immobilise proteins onto solid supports, whereby the protein and the support are derivatised with the appropriate mutually reactive chemical functionalities (azides and alkynes). In other embodiments Staudinger ligation chemistry can be used to immobilise appropriately derivatised proteins onto the appropriately derivatised solid supports.

The solid support is contained within or carried by the apheresis column. Thus, by "loaded" is meant that the column carries or contains the solid support in a manner such that (peripheral) blood can flow through the column in contact with the solid support. Thus, the solid support provides a matrix within the column through which blood flows, in continuous fashion in certain embodiments. This permits cells expressing the specific chemokine receptor to be removed from the blood passing through the column, such that blood exiting the column is depleted of the specific chemokine receptor-expressing cells. In specific embodiments, the apheresis column is loaded with a support comprising streptavidin immobilized on the support and one or more biotinylated binding reagents, such as chemokines, bound to the streptavidin on the support. The solid support may be comprised of a high-molecular weight carbohydrate, optionally cross-linked, such as agarose.

As discussed above, the binding reagent is coupled to the solid support. The relative amounts of binding reagent may be controlled to ensure that coupling between the solid support and the binding reagent will be immediate, minimising the risk of binding reagent decoupling from the solid support. Thus, it may be ensured that there is a relative excess of immobilization sites for the binding reagent on the solid support. Alternatively, or additionally, following immobilization of the binding reagent on the solid support, the solid support may be washed to remove any unbound binding reagent.

The apheresis column utilised in the various embodiments of the present invention acts as a leukapheresis treatment for allergic conditions. The column acts to specifically remove CCR3, CXCR1, CXCR2 and/or CCR2-expressing cells such as eosinophils by exploiting the interaction between CCR3, CXCR1, CXCR2 and/or CCR2 expressed on the cell surface and a specific binding reagent immobilized on a solid support contained within or carried by the column. The overall column typically comprises, consists of, or consists essentially of three combined components; 1) a housing which contains or carries 2) the solid support and 3) one or more binding reagents (immobilized thereon) which specifically bind one or more chemokine receptors. The housing may be manufactured from any suitable material for clinical use. In certain embodiments the housing is composed of a plastic material. The housing includes an in flow site for entry of blood and an out flow site for blood (depleted of target cells) to exit the column. The housing may be designed to maintain a continuous blood flow through the solid support matrix. The housing (as shown for example in FIG. 9) may include a top portion which comprises a distribution plate (2) at the inflow site (1) to spread the blood evenly over the entire matrix area. The distribution plate may act as a first safety barrier preventing larger particles flowing through the column and into the patient. However, the distribution plate is not essential and may be removed in some embodiments to decrease the overall resistance in the system. The column may contain one or more safety filter units (3 and 4) placed at the inflow (1) and/or outflow (5) sites of the plastic housing. Such filter units may act to prevent particles larger than blood cells passing in and/or out of the column. The safety filter units may contain a plurality of filters, such as two, three or four filters designed to be a robust barrier and stop all particles larger than blood cells passing through the column. Inclusion of safety filters (3 and 4) at both ends of the column serves to minimize the risk of leakage of particles into the patient, including in the event that the device is incorrectly connected resulting in blood flow in the opposite direction to that intended. The safety filters may comprise of any suitable pore size to prevent particles larger than blood cells from passing through the column, as would be readily understood by one skilled in the art. Suitable filters are commercially available. In specific embodiments, the pore size of the filter(s) is between approximately 60 μm and 100 μm, more specifically approximately 80 μm. The solid support and binding reagent components are discussed in further detail herein.

The volume of the housing may be varied depending upon the blood volumes intended to pass through the column. Typically, the volume of the housing is between approximately 40 ml and 200 ml, more specifically 50 ml to 150 ml or 60 ml to 120 ml.

The column is generally applied in the form of an apheresis circuit. In this context, the overall system includes the apheresis column, tubing and an appropriate pump to pump the blood around the circuit. The system is illustrated in FIG. 10. The patient (1) is connected to the extracorporeal circuit via sterile needles to veins in the right and the left arms. A saline bag (3) is also connected and the saline solution is pumped with a suitable pump (2). Blood is drawn from one arm of the patient through the sterile tubing system by the blood pump (4) and passed through the column (6) and back to the patient. The tubing system may be connected to the column via any suitable coupling, such as standard dialysis luer-lock couplings. The couplings on the column may be colour-coded for correct assembly. For example, red tubing for inflow to the red column top and blue tubing for outflow back to the patient. An air detector (8) may be present in the circuit. Inlet pressure (5) and/or Pven sensors (7) may additionally be employed to monitor the pressure in the circuit.

An apheresis pump, such as the 4008 ADS pump manufactured by Fresenius Medical Care or the Adamonitor pump, may monitor the patient's inflow and outflow. The pump may also monitor the pressure in the extracorporeal circulation. The pump may be able to discriminate air by a bubble catcher and air detector. A clot catcher filter may be positioned inside the bubble catcher. The pump may also incorporate an optical detector to distinguish between light, e.g. saline solution or air present in the tubing system and dark e.g. blood present in the tubing system.

A schematic diagram of a suitable pump, showing the air detector and optical filter is shown in FIG. 11. If the pump system detects air bubbles and optical fluctuations or if extracorporeal pressure values are out of the set range, then the pump may stop immediately. Alternatively or additionally a visual/audible alarm may be emitted.

The treatment methods of the various embodiments of the invention may thus rely upon an extracorporeal circuit. The methods may be considered as ex vivo or in vitro methods and be defined solely with reference to steps performed outside of the patient. In some embodiments, however, the method further comprises, prior to application of the blood to the column, collecting peripheral blood from the patient. In a further embodiment, the method further comprises, following the application of the blood to the column, infusing the blood depleted of (CCR3, CXCR1, CXCR2 and/or CCR2) chemokine receptor expressing cells to the patient. This is then a complete leukapheresis treatment method. Thus, a leukaphereis method, for treating an allergic condition, comprises collecting peripheral blood from the patient; applying the peripheral blood to an apheresis column loaded with a solid support comprising a binding reagent capable of specifically binding to a chemokine receptor, in particular the chemokine receptor CCR3, CXCR1, CXCR2 and/or CCR2, immobilized directly or indirectly on the support thus removing CCR3, CXCR1, CXCR2 and/or CCR2 expressing cells from the peripheral blood of the patient; and infusing the depleted blood (of chemokine receptor expressing cells) to the patient.

The peripheral blood may be continuously collected from the patient. Similarly, the depleted blood may be continuously infused to the patient, through use of an appropriate circuit as described herein. Thus, the support may be disposed in a column through which the blood is made to flow. This may be achieved using a suitable pump for example, as also described herein. Blood flow through the column enables the binding reagent(s) immobilized on the solid support to capture the cells expressing the chemokine receptor, thus depleting them from the blood and preventing their contribution to the allergic condition.

The methods of the various embodiments of the invention and binding reagents for use in the methods of the various embodiments of the invention may require that the patient has been selected for treatment on the basis of detecting an increase in the level of CCR3, CXCR1, CXCR2 and/or CCR2 expressing cells, levels of expression of CCR3, CXCR1, CXCR2 and/or CCR2 and/or levels of cells with high expression of CCR3, CXCR1, CXCR2 and/or CCR2 in a sample obtained from the patient. Such companion diagnostic methods are described in greater detail herein and are based, for example, on the observation that a range of allergic conditions involve inflammation caused by eosinophilia.

Thus, (in this context) in certain embodiments the invention also provides a method of diagnosing, monitoring progression of, or monitoring treatment of an allergic condition comprising determining:

a) the levels of the chemokine receptor CCR3, CXCR1, CXCR2 and/or CCR2 expressing cells b) levels of expression of CCR3, CXCR1, CXCR2 and/or CCR2; and/or c) levels of cells with high expression of CCR3, CXCR1, CXCR2 and/or CCR2 in a sample obtained from a subject, wherein high levels of CCR3, CXCR1, CXCR2 and/or CCR2 expressing cells, high levels of expression of CCR3, CXCR1, CXCR2 and/or CCR2 or high levels of cells with high expression of CCR3, CXCR1, CXCR2 and/or CCR2 or increased levels of CCR3, CXCR1, CXCR2 and/or CCR2 expressing cells compared to control, increased levels of expression of CCR3, CXCR1, CXCR2 and/or CCR2 compared to a control or increased levels of cells with high expression of CCR3, CXCR1, CXCR2 and/or CCR2 compared to a control indicate the presence or progression of an allergic condition. Levels of chemokine receptor expression, as opposed to cell numbers, may also be investigated as increased levels of chemokine receptor expression per cell may also be diagnostically relevant. In some embodiments, the cells relevant to allergic conditions comprise neutrophils, in particular CXCR1 and CXCR2 expressing neutrophils or eosinophils, in particular CCR3 expressing eosinophils or monocytes, in particular CCR2 or CCR3 expressing monocytes.

"Diagnosing" is defined herein to include screening for a disease/condition or pre-indication of a disease/condition, identifying a disease/condition or pre-indication of a disease/condition and checking for recurrence of disease/condition following treatment. The methods of the various embodiments of the invention may also have prognostic value, and this is included within the definition of the term "diagnosis". The prognostic value of the methods of the various embodiments of the invention may be used as a marker of potential susceptibility to an allergic condition by identifying levels of CCR3, CXCR1, CXCR2 and/or CCR2 expression linked to allergic conditions. Thus patients at risk may be identified before the disease has a chance to manifest itself in terms of symptoms identifiable in the patient. In certain embodiments, diagnosis may be made in conjunction with other objective indicators of an allergic condition. Thus, in specific embodiments, diagnosis is made in conjunction with one or more of the following indicators:

1. Eosinophilia—an increase in eosinophils, which may be defined as the presence of more than 500 eosinophils/microliter of blood.
2. Standard clinical symptoms as would be readily appreciated by one skilled in the art.

"Monitoring progression of" includes performing the methods to monitor the stage and/or the state and progression of the allergic condition. Monitoring progression may involve performing the diagnostic methods multiple times on the same patient to determine whether the levels of CCR3, CXCR1, CXCR2 and/or CCR2 expressing cells are increasing, decreasing or remaining stable over a certain time period. This may be in the context of a treatment regime.

"Monitoring the success of a particular treatment" is defined to include determining the levels of CCR3, CXCR1, CXCR2 and/or CCR2 expressing cells before and after a treatment. The treatment is generally one aimed at treating an allergic condition and may be a treatment according to one of the methods of the various embodiments of the invention as defined herein. Successful treatment may be determined with reference to a decrease in CCR3, CXCR1, CXCR2 and/or CCR2 expressing cells as a result of, or following, the treatment. Thus, in such methods a level of CCR3, CXCR1, CXCR2 and/or CCR2 expressing cells is determined prior to treatment. This level is recorded and a further assessment made at a predetermined time following the treatment. The comparison of levels of CCR3, CXCR1, CXCR2 and/or CCR2 expressing cells permits the success of the treatment to be monitored. In specific embodiments, a single treatment is sufficient to cause a depletion of around 10%, 20%, 30%, 40%, 50%, 60% or 70%, or higher, up to 80%, 90%, 95% or more, or any range of values between and including these amounts, of the specific chemokine receptor, in particular CCR3, CXCR1, CXCR2 and/or CCR2, expressing cells from the peripheral blood of the patient. In specific embodiments, at least around 50% depletion is achieved in a single treatment. Treatment may lead to depletion of between approximately 100 and 500 million CCR3, CXCR1, CXCR2 and/or CCR2 expressing cells in certain embodiments. Thus, successful treatment may be defined with reference to depletion of CCR3, CXCR1, CXCR2 and/or CCR2 expressing cells. Additional factors may be included to determine successful treatment. For example, a lack of increase in CCR3, CXCR1, CXCR2 and/or CCR2 expressing cells following treatment may indicate successful treatment in terms of preventing further progression of the condition, optionally combined with an improvement in other markers or staging of the allergic condition.

In specific embodiments, the allergic condition is selected from asthma, allergic rhinitis, allergic ocular disease, atopic dermatitis, food allergies and allergic inflammation.

The sample in which CCR3, CXCR1, CXCR2 and/or CCR2 expressing cell levels, levels of expression of CCR3, CXCR1, CXCR2 and/or CCR2 and/or levels of cells with high expression of CCR3, CXCR1, CXCR2 and/or CCR2 (defined as CCR3, CXCR1, CXCR2 and/or CCR2hi) are determined may comprise any suitable tissue sample or body fluid sample. Generally, the test sample is obtained from a human subject. Typically, the sample is a blood sample, in particular a peripheral blood sample. The sample may comprise various biopsies, such as nasal or skin biopsy or BAL. in certain embodiments. The methods may involve determining levels of CCR3, CXCR1, CXCR2 and/or CCR2 expressing eosinophils, (T) lymphocytes, basophils and neutrophils in certain embodiments. In some embodiments, the cells relevant to allergic conditions comprise neutrophils, in particular CXCR1 and CXCR2 expressing neutrophils or eosinophils, in particular CCR3 expressing eosinophils or monocytes, in particular CCR2 or CCR3 expressing monocytes.

Levels of CCR3, CXCR1, CXCR2 and/or CCR2 expressing cells, levels of expression of CCR3, CXCR1, CXCR2 and/or CCR2 and/or levels of cells with high expression of CCR3, CXCR1, CXCR2 and/or CCR2 (defined as CCR3, CXCR1, CXCR2 and/or CCR2hi) may be determined according to any suitable method. For example, flow cytometry may be employed in order to determine the number of cells expressing CCR3, CXCR1, CXCR2 and/or CCR2 in the sample, to determine levels of CCR3, CXCR1, CXCR2 and/or CCR2 expression and/or to identify levels of CCR3, CXCR1, CXCR2 and/or CCR2hi cells. Flow cytometric techniques are described herein and examples of commercially available antibodies suitably labelled for use in flow cytometry are set out in Table 6 for example. Alternatively, the method may involve steps of collecting and fixing the cells in the sample, followed by incubation with a suitable binding reagent that binds specifically to the CCR3, CXCR1, CXCR2 and/or CCR2 chemokine receptor expressing cells in the sample. Any suitable binding reagent, as defined herein, may be employed. For example, a CCR-3 specific antibody may be employed. A wash step may be adopted following an incubation period to remove any unbound reagent. Suitable wash steps and incubation conditions would be well known to one skilled in the art. The binding reagent may be directly labeled in order to permit antibody binding to be directly determined. Alternatively a secondary binding reagent, such as an antibody, may be employed which binds to the first binding reagent and carries a label. Again, suitable incubation conditions and wash steps would be apparent to one skilled in the art. The primary and secondary binding reagents may form two halves of a binding pair. The binding interaction should not prevent the primary binding reagent binding to the CCR3, CXCR1, CXCR2 and/or CCR2 receptor expressing cells, unless a competition assay is being employed. The two halves of a binding pair may comprise an antigen-antibody, antibody-antibody, receptor-ligand, biotin-streptavidin pair etc. in certain embodiments. Other techniques used to quantify chemokine (CCR3, CXCR1, CXCR2 and/or CCR2) receptor expressing cell levels, to quantify levels of CCR3, CXCR1, CXCR2 and/or CCR2 expression and/or to quantify levels of CCR3, CXCR1, CXCR2 and/or CCR2hi cells include PCR-based techniques such as QT-PCR and protein based methods such as western blot. Quantitation may be achieved with reference to fixed cell lines carrying known numbers of various receptor expressing cells and/or known levels of receptor expression per cell. Such fixed cell lines are available commercially (for example ChemiScreen™ cell lines from Millipore). Methods analogous to the treatment methods of the various embodiments of the invention may also be employed, with binding of CCR3, CXCR1, CXCR2 and/or CCR2 expressing cells to the solid support being determined following peripheral blood being passed through the column.

The levels of CCR3, CXCR1, CXCR2 and/or CCR2 expressing cells, levels of expression of CCR3, CXCR1, CXCR2 and/or CCR2 and/or levels of cells with high expression of CCR3, CXCR1, CXCR2 and/or CCR2 (defined as CCR3, CXCR1, CXCR2 and/or CCR2hi) may be determined relative to a suitable control. When diagnosing an allergic condition, a threshold level of cells, level of expression of CCR3, CXCR1, CXCR2 and/or CCR2 and/or level of cells with high expression of CCR3, CXCR1, CXCR2 and/or CCR2 (defined as CCR3, CXCR1, CXCR2 and/or CCR2hi) may be set at or over which a positive diagnosis is made. This threshold may be determined based upon measuring levels of CCR3, CXCR1, CXCR2 and/or CCR2 expressing cells, levels of expression of CCR3, CXCR1, CXCR2 and/or CCR2 and/or levels of cells with high expression of CCR3, CXCR1, CXCR2 and/or CCR2 (defined as CCR3, CXCR1, CXCR2 and/or CCR2hi) in samples obtained from diseased patients and comparing these levels with levels of CCR3, CXCR1, CXCR2 and/or CCR2 expressing cells, levels of expression of CCR3, CXCR1, CXCR2 and/or CCR2 and/or levels of cells with high expression of CCR3, CXCR1, CXCR2 and/or CCR2 (defined as CCR3, CXCR1, CXCR2 and/or CCR2hi) in samples obtained from healthy subjects.

In certain embodiments, an allergic condition is diagnosed on the basis of levels of chemokine receptor expressing cells, such as CCR3, CXCR1, CXCR2 and/or CCR2 expressing cells. A positive diagnosis may be made in subjects based upon the presence of greater than about 5%, greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, an allergic condition is diagnosed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to healthy controls.

In specific embodiments, an allergic condition is diagnosed on the basis of levels of CCR3 expressing cells, in particular CCR3 expressing monocytes. A positive diagnosis may be made in subjects based upon the presence of greater than about 5%, greater than about 10%, greater than about 15% or greater than about 20% or more CCR3 expressing cells, in particular monocytes in the sample, as a percentage of total cells in the sample. An allergic condition may also be diagnosed on the basis of the presence of a about a 1.2 fold or greater increase, such as about a 1.5, 2, 2.5, 3, 3.5, 4, 4.5, 5, 10, 20, 50 or 100 or greater fold increase in the specific chemokine receptor expressing cells, relative to healthy controls.

In certain embodiments, progression of an allergic condition, which may be in the context of a treatment regime, is monitored on the basis of levels of chemokine receptor expressing cells at different time points, such as CCR3, CXCR1, CXCR2 and/or CCR2 expressing cells. Progression of an allergic condition may be indicated in subjects based upon an increase of greater than about 5%, greater than about 10%, such as an increase of greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more chemokine receptor expressing cells in the sample, as a percentage of total cells in the sample, compared to a sample taken from the same subject at an earlier time point. In other embodiments, progression of an allergic condition is confirmed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to a sample taken from the same subject at an earlier time point.

In specific embodiments, an allergic condition is monitored on the basis of levels of CCR3 expressing cells, in particular monocytes. Progression of the disease, which may be in the context of a treatment regime, may be indicated in subjects based upon the presence of an increase of greater than about 5%, greater than about 10%, such as greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more chemokine receptor expressing cells in the sample, as a percentage of total cells in the sample, compared to a sample taken from the same subject at an earlier time point. In other embodiments, progression of an allergic condition is confirmed on the basis of the presence of a about a 1.2 fold or greater increase, such as about a 1.5, 2, 2.5, 3, 3.5, 4, 4.5, 5, 10, 20, 50 or 100 or greater fold increase in CCR3 expressing cells, in particular monocytes relative to a sample taken from the same subject at an earlier time point.

Regression or successful treatment may be monitored based upon similar decreases over various time points. For example, regression or successful treatment may be indicated in subjects based upon a decrease of greater than about 5%, about 10%, such as a decrease of about 15%, about 20%, about 25%, about 30%, about 35%, about 40%, about 45%, about 50%, about 55%, about 60%, about 65%, about 70%, about 75% or more chemokine receptor expressing cells in the sample, as a percentage of total cells in the sample, compared to a sample taken from the same subject at an earlier time point. In other embodiments, regression of an allergic condition is confirmed on the basis of the presence of a about a 1.2 fold or greater decrease, such as about a 1.5, 2, 2.5, 3, 3.5, 4, 4.5, 5, 10, 20, 50 or 100 or greater fold decrease in chemokine receptor expressing cells, relative to a sample taken from the same subject at an earlier time point.

In specific embodiments, an allergic condition is monitored on the basis of levels of CCR3 expressing cells, in particular monocytes. Regression or successful treatment of the disease may be made in subjects based upon a decrease of about 3%, such as such as a decrease of about 5%, about 7%, about 8%, about 9%, about 10%, about 11%, about 12%, about 13%, about 15% or more CCR3 expressing cells in the sample, as a percentage of total cells in the sample or by a decrease of about 3%, such as a decrease of about 5%, about 7%, about 8%, about 9%, about 10%, about 11%, about 12%, about 13%, about 15%, or more chemokine receptor expressing cells in the sample, as a percentage of total cells in the sample, compared to a sample taken from the same subject at an earlier time point. In other embodiments, regression of an allergic condition is confirmed on the basis of the presence of a about a 1.2 fold or greater decrease, such as about a 1.5, 2, 2.5, 3, 3.5, 4, 4.5, 5, 10, 20, 50 or 100 or greater fold decrease in CCR3 expressing cells, in particular monocytes relative to a sample taken from the same subject at an earlier time point.

Suitable software is freely available (such as the R project for statistical computing) to perform the necessary statistical analysis of the data obtained to calculate a useful threshold. The threshold may be set to maximize sensitivity and/or specificity of the test. Performance of the test in these respects may be measured by plotting a receiver operating characteristics (ROC) curve (sensitivity versus specificity). The area under the curve provides an indication of the overall performance of the test. Thus, once thresholds have been set for diagnosing the condition, a separate control experiment does not necessarily have to be run each time a sample is tested. Rather reference can simply be made to the pre-existing thresholds to determine the diagnosis. However, in certain embodiments, the sample is tested together with a control sample taken from a healthy subject to provide a comparator based upon essentially identical experimental conditions. The test sample is generally tested in parallel with the control sample. The test sample level of CCR3, CXCR1, CXCR2 and/or CCR2 expressing cells, levels of expression of CCR3, CXCR1, CXCR2 and/or CCR2 and/or levels of cells with high expression of CCR3, CXCR1, CXCR2 and/or CCR2 (defined as CCR3, CXCR1, CXCR2 and/or CCR2hi) can then be compared with that of the control sample to make the diagnosis. A control sample from a disease patient may also be tested in certain embodiments. Reference to controls permits relative levels ("high", "low" etc.) of CCR3, CXCR1, CXCR2 and/or CCR2 expressing cells in the test sample to be readily identified and the significance thereof interpreted. Reference to controls also permits relative levels of CCR3, CXCR1, CXCR2 and/or CCR2 expression ("high", "low" etc.) within the cell population to be determined and the significance thereof interpreted. Such determination may, for example, indicate the average levels of CCR3, CXCR1, CXCR2 and/or CCR2 expression per cell in the test sample.

Thus, in specific embodiments, high or higher levels of CCR3, CXCR1, CXCR2 and/or CCR2 expressing cells or high or higher levels of CCR3, CXCR1, CXCR2 and/or CCR2 expression, for example average CCR3, CXCR1, CXCR2 and/or CCR2 expression per cell, or high or higher levels of CCR3, CXCR1, CXCR2 and/or CCR2hi cells correlate with active allergic condition or more active allergic condition. Similarly, lower or low levels of CCR3, CXCR1, CXCR2 and/or CCR2 expressing cells, or low or lower levels of CCR3, CXCR1, CXCR2 and/or CCR2 expression, for example average CCR3, CXCR1, CXCR2 and/or CCR2 expression per cell, or low or lower levels of CCR3, CXCR1, CXCR2 and/or CCR2hi cells may correlate with a lack of active inflammation or allergic condition. This may be defined as "less active disease". It can readily be envisaged that control samples may be assessed and levels of CCR3, CXCR1, CXCR2 and/or CCR2 expressing cells, levels of expression of CCR3, CXCR1, CXCR2 and/or CCR2 and/or levels of cells with high expression of CCR3, CXCR1, CXCR2 and/or CCR2 (defined as CCR3, CXCR1, CXCR2 and/or CCR2hi) determined across the range of severities of allergic conditions. This may assist in correlating the levels of CCR3, CXCR1, CXCR2 and/or CCR2 expressing cells, levels of expression of CCR3, CXCR1, CXCR2 and/or CCR2 and/or levels of cells with high expression of CCR3, CXCR1, CXCR2 and/or CCR2 (defined as CCR3, CXCR1, CXCR2 and/or CCR2hi) in the test sample with the relative severity of the condition.

When monitoring progression of, or monitoring treatment of an allergic condition, the control samples may be taken from the subject at an earlier time point. They may, however, be based upon known reference values as discussed above. Thus, relative levels of CCR3, CXCR1, CXCR2 and/or CCR2 expressing cells, relative levels of CCR3, CXCR1, CXCR2 and/or CCR2 expression including relative levels of average CCR3, CXCR1, CXCR2 and/or CCR2 expression per cell or relative levels of CCR3, CXCR1, CXCR2 and/or CCR2hi cells may be with reference to samples taken from the same subject at a different point in time. In certain embodiments, decreased levels of CCR3, CXCR1, CXCR2 and/or CCR2 expressing cells decreased relative levels of CCR3, CXCR1, CXCR2 and/or CCR2 expression including decreased relative levels of average CCR3, CXCR1, CXCR2 and/or CCR2 expression per cell or decreased relative levels of CCR3, CXCR1, CXCR2 and/or CCR2hi cells correlate with successful treatment. The treatment may be any suitable treatment, but in specific embodiments is a treatment according to the various embodiments of the invention.

When monitoring progression of an allergic condition, increased levels of CCR3, CXCR1, CXCR2 and/or CCR2 expressing cells increased relative levels of CCR3, CXCR1, CXCR2 and/or CCR2 expression including increased relative levels of average CCR3, CXCR1, CXCR2 and/or CCR2 expression per cell or increased relative levels of CCR3, CXCR1, CXCR2 and/or CCR2hi cells may indicate the progression of condition or disease. Thus, if levels of CCR3, CXCR1, CXCR2 and/or CCR2 expressing cells, levels of expression of CCR3, CXCR1, CXCR2 and/or CCR2 and/or levels of cells with high expression of CCR3, CXCR1, CXCR2 and/or CCR2 (defined as CCR3, CXCR1, CXCR2 and/or CCR2hi) are increased in a sample taken later than a sample from the same patient this may indicate progression of the condition.

Since the levels of CCR3, CXCR1, CXCR2 and/or CCR2 expressing cells, levels of CCR3, CXCR1, CXCR2 and/or CCR2 expression or levels of CCR3, CXCR1, CXCR2 and/or CCR2hi cells are diagnostically relevant, determining such levels in a sample obtained from a subject may influence treatment selection for that subject. Accordingly, in certain embodiments the invention provides a method of selecting a suitable treatment for an allergic condition comprising determining:

a) the levels of the chemokine receptor CCR3, CXCR1, CXCR2 and/or CCR2 expressing cells b) levels of expression of CCR3, CXCR1, CXCR2 and/or CCR2; and/or c) levels of cells with high expression of CCR3, CXCR1, CXCR2 and/or CCR2 in a sample obtained from a subject, wherein high levels of CCR3, CXCR1, CXCR2 and/or CCR2 expressing cells, high levels of expression of CCR3, CXCR1, CXCR2 and/or CCR2 or high levels of cells with high expression of CCR3, CXCR1, CXCR2 and/or CCR2 or increased levels of CCR3, CXCR1, CXCR2 and/or CCR2 expressing cells compared to control, increased levels of expression of CCR3, CXCR1, CXCR2 and/or CCR2 compared to a control or increased levels of cells with high expression of CCR3, CXCR1, CXCR2 and/or CCR2 compared to a control, result in selection of a treatment as defined herein for treatment of the allergic condition. In certain embodiments, the chemokine receptor expressing cells are high chemokine receptor expressing cells, in particular, high CCR3, CXCR1, CXCR2 and/or CCR2 expressing cells. The cells may be CCR3 expressing monocytes.

In specific embodiments, an allergic condition is treated on the basis of measuring levels of chemokine receptor expressing cells. Thus, a treatment according to the various embodiments of the invention may be applied based upon the presence of greater than about 5%, greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, such as CCR3, CXCR1, CXCR2 and/or CCR2 expressing cells, as a percentage of total cells in the sample. In other embodiments, allergic condition is treated according to the various embodiments of the invention on the basis of the presence of a about a 1.5 fold or greater increase, such as about a 2, 2.5, 3, 3.5, 4, 4.5, 5, 10, 20, 50 or 100 or greater fold increase in chemokine receptor expressing cells, relative to healthy controls.

In specific embodiments, an allergic condition is treated on the basis of measuring levels of CCR3 expressing cells, in particular monocytes. Thus, a treatment according to the various embodiments of the invention may be applied based upon the presence of greater than about 2%, greater than about 3%, greater than about 5%, greater than about 7% or greater than about 10% CCR3 expressing monocytes in the sample, as a percentage of total cells in the sample or on the basis of the presence of a about a 1.5 fold or greater increase, such as about a 2, 2.5, 3, 3.5, 4, 4.5, 5, 10, 20, 50 or 100 or greater fold increase in chemokine receptor expressing cells, relative to healthy controls.

For the avoidance of doubt, all embodiments described in respect of the methods of the various embodiments of the invention apply to these aspects mutatis mutandis and are not repeated for reasons of conciseness. Specifically, allergic conditions may be indicated in conjunction with one or more of the following indicators:

1. Eosinophilia—an increase in eosinophils, which may be defined as the presence of more than 500 eosinophils/microliter of blood.

2. Standard clinical symptoms as would be readily appreciated by one skilled in the art.

The allergic condition may be selected from asthma, allergic rhinitis, allergic ocular disease, atopic dermatitis, food allergies and allergic inflammation. In specific embodiments, the sample is a peripheral blood sample.

The methods and medical uses of the various embodiments of the invention thus can be tailored to the need of individual patients or groups of patients on the basis of the various diagnostic methods of the various embodiments of the invention. By removing from the circulation CCR3, CXCR1, CXCR2 and/or CCR2 expressing cells, such as eosinophils, (T) lymphocytes, basophils and neutrophils, upregulated in various inflammatory allergic conditions, an important factor in the inflammatory process of allergic conditions can be controlled. The method of the invention may be effective in treating or reversing conditions such as asthma, allergic rhinitis, allergic ocular disease, atopic dermatitis, food allergies and allergic inflammation.

G. Treating Inflammatory Skin Diseases

Chemokines are a class of cytokine molecules involved in cell recruitment and activation in inflammation. Chemokines cause chemotaxis and activation of various subpopulations of cells in the immune system. The activity of chemokines is mediated primarily through tight binding to their receptors on the surface of leukocytes. In certain embodiments the present invention is based on the realisation that the interaction between chemokines and cells expressing their receptors may be exploited for the treatment of inflammatory skin diseases. In particular, various inflammatory skin diseases, such as psoriasis and atopic dermatitis include an inflammatory component. The inventors have determined that targeting increased recruitment of specific chemokine receptor-expressing cells to the site of inflammation presents a new therapeutic approach to treat such conditions. Moreover, in such conditions, chemokine receptor expression on each cell may be increased again providing a therapeutic approach to treat such conditions. It is shown herein that subjects suffering from inflammatory skin disorders such as psoriasis exhibit increased frequency of chemokine receptor expressing cells in the peripheral blood, in particular CCR4 expressing cells such as CCR4 expressing T lymphocytes, compared to healthy controls. It is also shown herein that the CCR4 expressing cells can be removed using a suitable binding reagent, in particular MDC (in biotinylated form) immobilized on a suitable matrix. Similarly, it is shown herein that CXCR1 and CXCR2-expressing cells, in particular neutrophils, can be depleted in psoriasis patients using a suitable binding reagent, in particular IL-8, in biotinylated form, immobilized on a suitable matrix.

Thus, in certain embodiments the invention serves to reduce the recruitment of inflammatory leukocytes, which express characteristic chemokine receptors, and possibly express characteristic chemokine receptors at increased levels, to sites of inflammation linked to inflammatory skin diseases such as psoriasis and atopic dermatitis. This is achieved using specific binding reagents to capture specific chemokine receptor-expressing inflammatory leukocytes from the patient. Accordingly, in certain embodiments the invention provides in a first aspect a method for treating inflammatory skin disease comprising applying peripheral blood from a patient to an apheresis column loaded with a solid support comprising one or more binding reagents capable of specifically binding to one or more chemokine receptors, in particular to a chemokine receptor selected from CCR4, CXCR1, CXCR2, CCR2, CCR6, CCR3, CCR5, CCR1, CCR9 and/or ChemR23, immobilized directly or indirectly on the support thus removing one or more chemokine receptor, in particular one or more of CCR4, CXCR1, CXCR2, CCR2, CCR6, CCR3, CCR5, CCR1, CCR9 and ChemR23, expressing cells from the peripheral blood of the patient. The peripheral blood from which the chemokine receptor expressing cells have been removed may then be returned to the patient in order to complete the treatment. The invention may thus rely on a continuous extracorporeal circuit in some embodiments. Alternatively, the invention may comprise steps of obtaining peripheral blood from the patient, applying the peripheral blood to the column and subsequently returning the peripheral blood from which the chemokine receptor expressing cells have been removed to the patient.

As shown herein, suitable binding reagents can be immobilized onto a solid support, either directly or indirectly, to generate an apheresis column suitable for capturing relevant chemokine receptor-expressing cells. Where increased levels of chemokine receptor expression are observed, such cells may be preferably removed from the peripheral blood using the columns of the various embodiments of the invention. Thus, the methods of the various embodiments of the invention may preferably target one or more of CCR4hi, CXCR1hi, CXCR2hi, CCR2hi, CCR6hi, CCR3hi, CCR5hi, CCR1hi and CCR9hi cells as defined herein for removal from the peripheral blood. "High" expression may be determined according to standard flow cytometry techniques. The level may be measured relative to levels of expression of the chemokine receptor in cells taken from a healthy subject. The attached FIG. 100 provides an example of a gating strategy.

Herein, reference to CCR4, CXCR1, CXCR2, CCR2, CCR6, CCR3, CCR5, CCR1, CCR9 and/or ChemR23 is intended to encompass selection of any one or more, up to all, of the chemokine receptors listed. In addition, the combination of CCR2, CCR6, CCR3, CCR5, CCR1, CCR9 and/or ChemR23 is explicitly contemplated as a separate grouping, to include any one or more of CCR2, CCR6, CCR3, CCR5, CCR1, CCR9 and ChemR23.

In other embodiments the invention further provides a binding reagent capable of specifically binding to one or more chemokine receptors, in particular to a chemokine receptor/the chemokine receptor selected from CCR4, CXCR1, CXCR2, CCR2, CCR6, CCR3, CCR5, CCR1, CCR9 and/or ChemR23, for use in the treatment of inflammatory skin disease, wherein the one or more binding reagents is immobilized, directly or indirectly, on a solid support contained within an apheresis column, to which is applied peripheral blood from a patient thus removing one or more chemokine receptor/CCR4, CXCR1, CXCR2, CCR2, CCR6, CCR3, CCR5, CCR1, CCR9 and/or ChemR23, expressing cells from the peripheral blood of the patient. In certain embodiments the invention also provides for use of one or more binding reagents capable of specifically binding to a chemokine receptor/the chemokine receptor CCR4, CXCR1, CXCR2, CCR2, CCR6, CCR3, CCR5, CCR1, CCR9 and/or ChemR23, for use in the manufacture of an apheresis column for treatment of inflammatory skin disease, wherein the one or more binding reagents is immobilized on a solid support contained within the apheresis column, to which is applied peripheral blood from a patient thus removing one or more of chemokine receptor/CCR4, CXCR1, CXCR2, CCR2, CCR6, CCR3, CCR5, CCR1, CCR9 and/or ChemR23, expressing cells from the peripheral blood of the patient.

All embodiments described in respect of the methods of treatment of the various embodiments of the invention apply to these aspects mutatis mutandis and are not repeated for reasons of conciseness. Thus, the following discussion made with reference to the methods of treatment is also applicable to the medical use aspects of the various embodiments of the invention.

In certain embodiments the invention aims to treat a range of inflammatory skin diseases. By treatment is meant a reduction in the specific chemokine receptor expressing cells in the peripheral blood of the patient but the term patient may include both human and non-human animal subjects in some embodiments. The reduction may comprise a reduction in cells that express chemokine receptors, in particular one or more of CCR4, CXCR1, CXCR2, CCR2, CCR6, CCR3, CCR5, CCR1, CCR9 and ChemR23, at increased levels in diseased patients. The patient is typically a human patient. In the context of the various embodiments of the present invention, this typically involves a reduction in one or more of CCR4, CXCR1, CXCR2, CCR2, CCR6, CCR3, CCR5, CCR1, CCR9 and ChemR23 expressing cells, such as one or more of "CCR4hi, CXCR1hi, CXCR2hi, CCR2hi, CCR6hi, CCR3hi, CCR5hi, CCR1hi and CCR9hi" expressing cells, in the peripheral blood of the patient. The CCR4, CXCR1, CXCR2, CCR2, CCR6, CCR3, CCR5, CCR1, CCR9 or ChemR23 expressing cells comprise, consist essentially of or consist of monocytes, lymphocytes, neutrophils, macrophages, eosinophils, basophils and dendritic cells, in particular plasma dendritic cells, in certain embodiments. In specific embodiments, the cells removed in order to treat inflammatory skin disorders including psoriasis comprise T cells, in particular CCR4 expressing T cells. In other embodiments, the cells removed in order to treat inflammatory skin disorders including psoriasis comprise neutrophils, in particular CXCR1 and CXCR2 expressing neutrophils.

Monocytes are produced by the bone marrow from haematopoietic stem cell precursors called monoblasts. Monocytes may differentiate into macrophages or dendritic cells. Monocytes and their macrophage and dendritic cell progeny serve a number of functions in the immune system including phagocytosis, antigen presentation and cytokine production. Monocytes may be characterized with reference to expression of the cell surface marker CD14, optionally together with CD16. Classical monocytes may be characterized by high level expression of the CD14 cell surface receptor (CD14++CD16− monocyte). Non-classical monocytes may be characterized by low level expression of CD14 and with additional co-expression of the CD16 receptor (CD14+CD16++ monocyte). Intermediate monocytes may be characterized by high level expression of CD14 and low level expression of CD16 (CD14++CD16+ monocytes). Macrophages are derived from monocytes and are responsible for protecting tissues from foreign substances. They are cells that possess a large smooth nucleus, a large area of cytoplasm and internal vesicles for processing foreign material. The term "macrophage" may refer to a monocyte-derived cell expressing one or more of the following cell surface markers CD14, CD11b, Lysozyme M, MAC-1/MAC-3 and CD68. The term macrophage includes both activated and un-activated macrophages. Activated macrophages may be characterized by expression of one or more of CD69, ENG, FCER2 and IL2RA, HLA-DR, CD86. Un-activated macrophages have not yet received activating signals through for example TLR receptors and therefore they express less activation markers on the cell surface which correlates with lesser maturation. M1 macrophages may be characterized by expression of one or more of CD16+CD32+CD64+ and secrete mainly IL-23 and IL-1, TNF, IL-6 and high levels of IL-12 and in addition effector molecules such as iNOS and ROI. M1 macrophages have cytotoxic features as opposed to M2 macrophages. M2 macrophages may be characterized by expression of one or more of SRA/B+CD163+MR+CD14+ and express TGFβ, IL-10 and IL-1Ra. Tumour associated macrophages (TAMs) share many characteristics with the M2 macrophages and are considered as M2 polarised macrophages. The M1/M2 paradigm can also be found in monocyte subsets where CD14+CD16–CXC3R1low monocytes are considered the "inflammatory" subset and the CD14lowCD16+CXC3R1high are "resident" monocytes.

The three major types of lymphocyte are T cells, B cells and natural killer (NK) cells. The term "T-lymphocyte" includes CD4+ T cells such as T helper cells (Th1 cells and Th2 cells), and CD8+ T cells such as cytotoxic T cells. Th1 cells may be characterized by expression of CCR5 and/or by production of IFN-γ. Th2 cells may be characterized by expression of CCR3 and/or by production of IL-4.

The claimed methods may, in particular, target eosinophils. Eosinophilia is an important component of allergic conditions and may be defined as the presence of more than 500 eosinophils/microliter of blood. Thus, reducing numbers of circulating eosinophils represents an important therapeutic approach. Eosinophils, or eosinophil granulocytes, are white blood cells and represent an important immune system component. Along with mast cells, they also control mechanisms associated with allergy and asthma. They are granulocytes that develop during haematopoiesis in the bone marrow before migrating into blood.

The name "eosinophil" derives from the eosinophilic "acid-loving" properties of the cell. Normally transparent, it is this affinity that causes them to appear brick-red after staining with eosin, a red dye, using the Romanowsky method. The staining is concentrated in small granules within the cellular cytoplasm, which contain many chemical mediators, such as histamines and proteins such as eosinophil peroxidase, ribonuclease (RNase), deoxyribonucleases, lipase, plasminogen, and major basic protein. These mediators are released by a process called degranulation following activation of the eosinophil, and are toxic to both parasite and host tissues.

Eosinophils develop and mature in bone marrow. They differentiate from myeloid precursor cells in response to the cytokines interleukin 3 (IL-3), interleukin 5 (IL-5), and granulocyte macrophage colony-stimulating factor (GM-CSF). Eosinophils produce and store many secondary granule proteins prior to their exit from the bone marrow. After maturation, eosinophils circulate in blood and migrate to inflammatory sites in tissues in response to chemokines such as CCL11 (eotaxin-1), CCL24 (eotaxin-2), CCL5 (RANTES) and MCP1/4. Eosinophils may be activated by Type 2 cytokines released from a specific subset of helper T cells (Th2); IL-5, GM-CSF, and IL-3 are important for eosinophil activation as well as maturation. CD44 and CD69 have been shown to represent different types of cell-surface activation markers for human eosinophils. CD69 is absent from "fresh" eosinophils but expressed following activation (using cytokines). CD44 on the other hand is constitutively expressed but expression is significantly up-regulated in response to activation (Matsumoto et al., Am. J. Respir. Cell Mol. Biol., Volume 18, Number 6, June, 1998 860-866). Cell specific markers for eosinophils include CD9 and CDw125

Basophils may also be known as basophil granulocyte. In contrast to eosinophils, these leukocytes are basophilic, i.e., they are susceptible to staining by basic dyes. Basophils contain large cytoplasmic granules which obscure the cell nucleus under the microscope. However, when unstained, the nucleus is visible and it usually has 2 lobes. Basophils store histamine, which is secreted by the cells upon stimulation.

Basophils have protein receptors on their cell surface that bind IgE, an immunoglobulin involved in macroparasite defense and allergy. It is the bound IgE antibody that confers a selective response of these cells to environmental substances, for example, pollen proteins or helminth antigens. Recent studies in mice suggest that basophils may also regulate the behavior of T cells and mediate the magnitude of the secondary immune response. Basophils may display an immunophenotype based upon expression (or lack thereof, indicated as "+" or "−" respectively of one or more of the following markers: FcεRI+, CD123, CD49b(DX-5)+, CD69+, Thy-1.2+, 2B4+, CD11bdull, CD117(c-kit)−, CD24−, CD19−, CD80−, CD14−, CD23−, Ly49c−, CD122−, CD11c−, Gr-1−, NK1.1−, B220−, CD3−, γδTCR−, αβTCR−, α4 and β4-integrin negative.

When activated, basophils degranulate to release histamine, proteoglycans (e.g. heparin and chondroitin), and proteolytic enzymes (e.g. elastase and lysophospholipase). They also secrete lipid mediators like leukotrienes, and several cytokines. Histamine and proteoglycans are pre-stored in the cell's granules while the other secreted substances are newly generated. Each of these substances contributes to inflammation. Recent evidence suggests that basophils are an important source of the cytokine, interleukin-4, perhaps more important than T cells. Interleukin-4 is considered one of the critical cytokines in the development of allergies and the production of IgE antibody by the immune system. There are other substances that can activate basophils to secrete which suggests that these cells have other roles in inflammation.

Dendritic cells (DCs) are the most important class of "antigen presenting cells" and as such, play a central role in the activation of the immune response. Immature DCs reside in tissues throughout the body are may become activated in response to a variety of stimuli indicating the presence of antigen. Once activated, DCs can release a plethora of cytokines that activate cells of the innate immune system including eosinophils, macrophages and NK cells. Activated DCs also take up and process antigen and, as a result, actively transport antigen to secondary lymphoid organs. At these sites, antigen is presented on the surface of mature DCs, in the context of MHC class I and class II complexes, to immature T and B cells leading to both cellular and humoral immune responses.

DCs represent a heterogeneous class of cells of which there are two main subtypes: myeloid DCs (mDCs) and plasmacytoid DCs (pDCs). These subtypes can be further divided into different subsets which may be classified according to the differential expression of a variety of cell surface markers. Importantly, the different subsets of DCs appear to drive different immune effector responses; for example, CD14+ mDCs appear to specialize in the generation of humoral immunity whereas BDCA3+ mDCs elicit CD8+ T cell responses. Furthermore, pDCs can be distinguished by the surface expression of CD2, and are typically involved in the generation of anti-viral immune responses as a result of rapid type I interferon production.

The methods of the invention may involve specific binding interactions with any one or more of these further cell-surface (and cell-specific) markers in addition to the removal based upon binding to CCR4, CXCR1, CXCR2, CCR2, CCR6, CCR3, CCR5, CCR1, CCR9 or ChemR23. Suitable binding reagents can be prepared to specifically bind to these cell-surface markers. The discussion of CCR4, CXCR1, CXCR2, CCR2, CCR6, CCR3, CCR5, CCR1, CCR9 or ChemR23 specific binding reagents thus applies mutatis mutandis.

CCR4, CXCR1, CXCR2, CCR2, CCR6, CCR3, CCR5, CCR1, CCR9 or ChemR23 expressed on these aforementioned cells are bound by chemokines such as monocyte chemoattractant protein-1 (MCP-1), MCP-2, MCP-3, MCP-4, MCP-5, MIP-3alpha, CCL25, Chemerin, RANTES, MDC and/or IL-8. MCP-1 is a major chemoattractant for monocytes and memory T cells by means of their binding to its specific cell-surface receptor, CC-chemokine receptor-2 (CCR2). CCR2 is the gene symbol approved by the HUGO Gene Nomenclature Committee for chemokine (C—C motif) receptor 2. The HGNC ID for this gene is 1603. The gene is located at chromosome position 3p21. The previous symbol and name for the gene is CMKBR2. Synonyms for this gene include CC-CKR-2, CD192, CKR2, FLJ78302 and MCP-1-R. The NCBI Reference Sequence is NM_001123041.2.

CCR1 is the gene symbol approved by the HUGO Gene Nomenclature Committee for chemokine (C—C motif) receptor 1. The HGNC ID for this gene is 1602. The gene is located at chromosome position 3p21. The previous symbol and name CMKBR1, SCYAR1. Synonyms for this gene include CD191, CKR-1, MIP1aR. The Entrez Gene reference sequence for CCR1 is 1230 as available on 13 Jun. 2011, which is incorporated herein by reference in its entirety.

CCR3 is the gene symbol approved by the HUGO Gene Nomenclature Committee for chemokine (C—C motif) receptor 3. The HGNC ID for this gene is 1604. The gene is located at chromosome position 3p21.3. The previous symbol and name for the gene is CMKBR3. Synonyms for this gene include CC-CKR-3, CD193 and CKR3. The Genbank reference sequence for CCR3 is AF247361.1 as available on 13 Jun. 2011, which is incorporated herein by reference in its entirety.

CCR5 is the gene symbol approved by the HUGO Gene Nomenclature Committee for chemokine (C—C motif) receptor 5. The HGNC ID for this gene is 1605. The gene is located at chromosome position 3p21. The previous symbol and name for the gene is CMKBR5. Synonyms for this gene include CC-CKR-5, CD195 CKR-5, IDDM22 and CKR5. The Entrez Gene reference sequence for CCR5 is 1234 as available on 13 Jun. 2011, which is incorporated herein by reference in its entirety.

CCR6 is the gene symbol approved by the HUGO Gene Nomenclature Committee for chemokine (C—C motif) receptor 6. The HGNC ID for this gene is 1607. The gene is located at chromosome position 6q27. The previous symbol and name for the gene is STRL22. Synonyms for this gene include BN-1, CD196, CKR-L3, CMKBR6, DCR2, DRY-6, GPR-CY4, GPR29. The Genbank reference sequence for CCR6 is U68030.1 as available on 13 Jun. 2011, which is incorporated herein by reference in its entirety.

CCR9 is the gene symbol approved by the HUGO Gene Nomenclature Committee for chemokine (C—C motif) receptor 9. The HGNC ID for this gene is 1610. The gene is located at chromosome position 3p22. The previous symbol and name for the gene is GPR28. Synonyms for this gene include CDw199, GPR-9-6. The Genbank reference sequence for CCR9 is AJ132337.1 as available on 13 Jun. 2011, which is incorporated herein by reference in its entirety.

CMKLR1 is the gene symbol approved by the HUGO Gene Nomenclature Committee for chemokine receptor-like 1, also known as ChemR23. The HGNC ID for this gene is 2121. The gene is located at chromosome position 12q24.1. The Genbank reference sequence for CMKLR1 is U79526.1 as available on 13 Jun. 2011, which is incorporated herein by reference in its entirety.

CCR4 is the gene symbol approved by the HUGO Gene Nomenclature Committee for chemokine (C—C motif) receptor 4. The HGNC ID for this gene is 1605. The gene is located at chromosome position 3p24-p21.3. Synonyms for this gene include CC-CKR-4, CD194, ChemR13, CKR4, CMKBR4, k5-5. The Genbank reference sequence for CCR4 is X85740.1 as available on 13 Jun. 2011, which is incorporated herein by reference in its entirety.

CXCR1 is the gene symbol approved by the HUGO Gene Nomenclature Committee for chemokine (C—X—C motif) receptor 1. The HGNC ID for this gene is 6026. The gene is located at chromosome position 2q35. The previous symbol and name for the gene is CMKAR1, IL8RA, "interleukin 8 receptor, alpha". Synonyms for this gene include CD181, CDw128a, CKR-1. The Genbank reference sequence for CXCR1 is U111870.1 as available on 13 Jun. 2011, which is incorporated herein by reference in its entirety. CXCR2 is the gene symbol approved by the HUGO Gene Nomenclature Committee for chemokine (C—X—C motif) receptor 2. The HGNC ID for this gene is 6027. The gene is located at chromosome position 2q35. The previous symbol and name for the gene is IL8RB, "interleukin 8 receptor, beta". Synonyms for this gene include CD182, CMKAR2. The Genbank reference sequence for CXCR2 is U111869.1 as available on 13 Jun. 2011, which is incorporated herein by reference in its entirety.

Treatment according to the various embodiments of the invention may result in alleviation or amelioration of symptoms, prevention of progression, regression of the condition, or complete recovery. Measurable parameters of successful treatment may be based upon, inter alia, the measures normally used to assess the severity of psoriasis in dermatological practice. These include the proportion of the body surface area (BSA) affected and the Psoriasis Area and Severity Index (PASI). It is generally accepted that patients with a greater than 5% affected BSA have moderate to severe psoriasis and in most recent clinical trials a PASI above 10 or 12 has been used as an inclusion criteria to define moderate to severe psoriasis. An affected BSA greater than 10% and a PASI score of 12 or higher have been proposed as criteria for severe psoriasis for use in clinical trials. While some authors define moderate psoriasis as a PASI between 7 and 12 and severe psoriasis as a PASI higher than 12, others prefer to use the "rule of tens" criteria, which define severe psoriasis as a PASI higher than 10, an affected BSA of more than 10%, or a Dermatology Life Quality Index (DLQI) score greater than 10.

In specific embodiments, a single treatment is sufficient to cause a depletion of around 10%, 20%, 30%, 40%, 50%, 60% or 70%, or higher up to 80%, 90%, 95% or more, or any range of values between and including these amounts, of one or more of the specific chemokine receptor, in particular CCR4, CXCR1, CXCR2, CCR2, CCR6, CCR3, CCR5, CCR1, CCR9 and ChemR23, expressing cells from the peripheral blood of the patient. In specific embodiments, at least around 50% depletion is achieved in a single treatment. Thus, successful treatment may be defined with reference to depletion of one or more of CCR4, CXCR1, CXCR2, CCR2, CCR6, CCR3, CCR5, CCR1, CCR9 and ChemR23 expressing cells. Treatment may lead to depletion of between approximately 100 and 500 million CCR4, CXCR1, CXCR2, CCR2, CCR6, CCR3, CCR5, CCR1, CCR9 and/or ChemR23, expressing cells, such as monocytes, dendritic cells and T lymphocytes, in certain embodiments and more particularly to about 100, 150, 200, 250, 300, 350, 400, 450, or 500 million CCR4, CXCR1, CXCR2, CCR2, CCR6, CCR3, CCR5, CCR1, CCR9 and/or ChemR23 expressing cells. In specific embodiments, the cells removed in order to treat inflammatory skin disorders including psoriasis comprise T cells, in particular CCR4 expressing T cells. In other embodiments, the cells removed in order to treat inflammatory skin disorders including psoriasis comprise neutrophils, in particular CXCR1 and CXCR2 expressing neutrophils.

By binding to the column through the binding reagent-chemokine receptor interaction, chemokine receptor expressing cells are immobilized. These immobilized cells express further unoccupied chemokine receptors, which may be of the same or different type to those used for capture. These additional chemokine receptors may permit circulating chemokines which contribute to the inflammatory condition to be captured from the peripheral blood. Thus, a reduction in circulating (specific) chemokine levels may provide a measure of successful treatment.

The duration of treatment may be readily determined by one skilled in the art and will depend upon factors such as the flow rate of the peripheral blood. Duration of treatment may be tied into monitoring of the treatment itself, with the treatment considered complete once a measurable parameter of treatment has reached a defined threshold. Any suitable parameter may be employed as discussed herein. Thus, for example, treatment may be considered complete when a reduction in one or more of CCR4, CXCR1, CXCR2, CCR2, CCR6, CCR3, CCR5, CCR1, CCR9 and ChemR23 expressing cells, such as a 50% reduction in one or more of CCR4, CXCR1, CXCR2, CCR2, CCR6, CCR3, CCR5, CCR1, CCR9 and ChemR23 expressing cells, has been achieved. The apheresis system may be operated at a flow rate of around 10-80 mL/min, or more specifically between around 20-70 mL/min, or between around 30-60 mL/min. In specific embodiments, the treatment is performed for a period of around 10, 20, 30, 40, 50, 60, 70, 80, 90, 100, 110, 120 etc., or any range of values between and including these amounts, minutes. The treatment is typically not aimed to remove all of the cells expressing the chemokine receptor in the peripheral blood, as a basal level of those cells is required in healthy subjects. However, it has been found that only low blood volumes need to be applied to the columns of the various embodiments of the invention in order to achieve effective levels of depletion of the chemokine receptor-expressing cells. Thus, in certain embodiments, around 10-80% or more specifically around 20, 30, 40 or 50%, or any range of values between and including these amounts, of the patient's blood is applied to the column in a single treatment. The volume of blood circulated through the apheresis column or system may be in the region of around 1000-3000 ml, such as around 1000, 1200, 1400, 1600, 1800 or 2000 ml or any range of values between and including these amounts. The treatment may be considered complete once this volume of blood has been circulated. The patient may be administered anticoagulants prior to each treatment session. A suitable solution, such as a sterile saline solution, optionally including an anticoagulant such as Heparin, may be used for priming the apheresis (extracorporeal) system. An additional volume of anticoagulant may be added to the circuit at the start of each treatment session, for example as a bolus injection.

In certain embodiments the invention relies upon a binding reagent which is capable of specifically binding to a chemokine receptor. This specific binding reaction permits cells expressing the chemokine receptor to be removed from the peripheral blood of the patient when the blood is passed over the solid support upon or within which the binding reagent is immobilized. Specific chemokine receptors of interest include CCR4, CXCR1, CXCR2, CCR2, CCR6, CCR3, CCR5, CCR1, CCR9 and ChemR23. The binding reagent can be any binding reagent capable of specifically binding to the receptor in question. By "specific binding" is meant that the binding reagent displays sufficient specificity of binding and appropriate binding affinity/kinetics to permit removal of cells expressing one or more of CCR4, CXCR1, CXCR2, CCR2, CCR6, CCR3, CCR5, CCR1, CCR9 and ChemR23 from the peripheral blood. Whilst it is not precluded that the binding reagent is capable of binding to other molecules, such as other chemokine receptors, the binding reagent will preferentially bind to cells expressing one or more of CCR4, CXCR1, CXCR2, CCR2, CCR6, CCR3, CCR5, CCR1, CCR9 and ChemR23 and in particular to cells expressing increased levels of one or more of CCR4, CXCR1, CXCR2, CCR2, CCR6, CCR3, CCR5, CCR1, CCR9 and ChemR23 (as defined further herein). The binding reagent capable of specifically binding to CCR4, CXCR1, CXCR2, CCR2, CCR6, CCR3, CCR5, CCR1, CCR9 or ChemR23 may be either an agonist or an antagonist of CCR4, CXCR1, CXCR2, CCR2, CCR6, CCR3, CCR5, CCR1, CCR9 or ChemR23, respectively. As the disease condition relies upon up-regulation of expression of or signaling via CCR4, CXCR1, CXCR2, CCR2, CCR6, CCR3, CCR5, CCR1, CCR9 or ChemR23, in certain embodiments the binding reagent capable of specifically binding to CCR4, CXCR1, CXCR2, CCR2, CCR6, CCR3, CCR5, CCR1, CCR9 or ChemR23 is an antagonist of CCR4, CXCR1, CXCR2, CCR2, CCR6, CCR3, CCR5, CCR1, CCR9 or ChemR23, respectively. Chemokines are typically, although not necessarily exclusively (particularly in the case of truncated or modified forms) agonists of their cognate receptor and serve to activate the cells expressing the relevant receptor, as would be appreciated by one skilled in the art. Antibodies against the relevant chemokine receptor are generally considered to be antagonists, as would be appreciated by one skilled in the art. Specific examples of binding reagents include proteins or polypeptides, such as antibodies and receptor ligands, in particular chemokines. The binding reagent may be a nucleic acid molecule in certain embodiments. In some embodiments, the nucleic acid is an aptamer. Nucleic acid aptamers are polynucleotides of approximately 15-40 nucleotides long. Nucleic acid aptamers can be made using the SELEX process (systemic evolution of ligands by exponential enrichment) or any other process known to those of skill in the art.

In other embodiments, the binding reagent may be a peptide, and in certain instances, a peptide aptamer. Peptide aptamers are artificial recognition molecules that consist of a variable peptide sequence inserted into a constant scaffold protein (Baines I C, Colas P. Peptide aptamers as guides for small molecule drug discovery. Drug Discov Today. 2006; 11:334-341, incorporated herein by reference). A number of methodologies, such as phage display, ribosome display and yeast two-hybrid screening systems are available for screening a library of potential peptide-based binding agents. Similarly protein scaffolds based on domains such as fibronectins, ankyrin repeats, protein A, SH3 domains, lipocalins and ubiquitin can be used as the binding agent. Again a number of technologies such as phage display and ribosome display are available for screening a library of protein—based binding agents. Similarly, libraries of candidate chemical compounds can be screened for specific binding to the relevant chemokine receptor using suitable screening techniques known in the art, which may be high throughput screens in certain embodiments. The candidate binding agent may be immobilized on a solid support and the ability of the agent to specifically retain cells expressing the chemokine receptor of interest or labelled chemokine receptors determined. A range of cell types may be applied to the solid supports to confirm specificity of binding, or alternatively a mixed sample (such as peripheral blood) may be applied to the solid support. Retention of the cell type of interest (expressing the appropriate chemokine receptor) can be confirmed to identify suitable binding agents. A range of small-molecule antagonists of CCR-2 are discussed by Xia M and Sui Z in Expert Opin Ther Pat. 2009 March; 19 (3):295-303—Recent developments in CCR2 antagonists, and incorporated herein by reference.

In the context of the various embodiments of the present invention the term "chemokine" also comprises biotinylated or otherwise labelled chemokines. The term "chemokine" also comprises modified and truncated versions of the chemokine and chemokine fragments with the proviso that the modified or truncated form retains its ability to bind to its cognate receptor (and thus remains functional in the context of the various embodiments of the invention). The chemokine does not necessarily need to retain biological activity as it is specific binding affinity for CCR4, CXCR1, CXCR2, CCR2, CCR6, CCR3, CCR5, CCR1, CCR9 or ChemR23 that is required. In certain embodiments, the chemokine lacks biological activity, for example in terms of activation of the (CCR4, CXCR1, CXCR2, CCR2, CCR6, CCR3, CCR5, CCR1, CCR9 or ChemR23) receptor. Modifications may be made to improve protein synthesis, for example uniformity of product and yield. As known to those skilled in the art, exemplary modifications may comprise amino acid additions, substitutions, deletions or other modifications to one or more amino acids in the chemokine. Modifications may comprise substitution of the wild type amino acid with non-natural amino acids such as norleucine (NLeu) and derivatized amino acids such as pyroglutamic acid (pyroGlu). Such modifications may be made to minimize side-product formation during storage and use of the columns of the various embodiments of the invention. Modifications may be made to improve labelling, for example inclusion of a polyethylene glycol (PEG) spacer to facilitate biotinylation. The biotinylation and/or conjugation with fluorochromes or other labelling groups of the chemokine is performed in a manner which does not substantially affect the receptor binding capacity. Site specific biotinylation or other labelling is preferred as non-selective labelling of chemokines may compromise receptor binding activity. Bioinylation or other labelling is generally preferred at or towards the C-terminus of the protein as the inventors have found that modifications in this area are generally well tolerated (in terms of a minimal effect on receptor binding capability). Biotinylation may be carried out site-specifically at any suitable amino acid. Examples of suitable amino acids include lysine, diaminopropionic acid and ornithine. Generally, reference may be made to Natarajan S et al, Int. J. Pept. Protein Res., 1992, 40, 567-74; Baumeister B, Int. J. Peptide Res. And Therapeutics, 2005, 11, 139-141; Bioconjugate techniques 2nd edition, Greg T. Hermanson, incorporated by reference herein in its entirety.

Truncations may involve deletion of either N or C terminal amino acids as appropriate, or both. Typically, the truncated version will retain the residues required for the chemokine to fold correctly, for example to retain a chemokine fold structure, consistent with the requirement that a truncated version must retain the ability to bind to the relevant receptor (expressed by (on the surface of) a leukocyte). Chemokine molecules typically include disulphide bonds between the 1st and 3rd and 2nd and 4th cysteine residues respectively, as would be understood by one skilled in the art. Where sequences are presented herein, it is assumed that these disulphide bonds will form in the folded protein (unless otherwise stated). Truncated versions may comprise anywhere between 1 and 100 less amino acids, such as 1, 2, 3, 4, 5 etc amino acids, than the wild type amino acid sequence in certain embodiments. Of course, truncated versions may comprise further modification as detailed herein. The modified or truncated version may have 40%, 45%, 50%, 55%, 60%, 65%, 70%, 75%, 80%, 85%, 90%, 95% or more overall amino acid sequence identity with the full length wild type chemokine (where a deletion is counted as a difference in amino acid sequence) in certain embodiments. Over the common sequence between the molecules (i.e the amino acids that have not been deleted), there may be 80%, 85%, 90%, 91%, 92%, 93%, 94%, 95%, 96%, 97%, 98% or 99% amino acid sequence identity in certain embodiments. Sequence identity may be determined using known algorithms, such as BLAST or GAP analysis (GCG Program) (applying default settings), which are freely available. Chemokines may lack the N-terminal signal peptide which is cleaved off during synthesis in vivo.

Specific chemokines useful in the various embodiments of the present invention include MCP-1, MCP-2, MCP-3, MCP-4, MCP-5, MIP-3alpha, CCL25, Chemerin and/or CCL5 (RANTES). MDC and/or IL-8 may also be useful in the present invention. Both MCP-1 and MCP-5 bind solely to the chemokine receptor CCR2 and so these chemokines may be preferred in some embodiments. Each chemokine is able to bind to a chemokine receptor implicated in inflammatory skin disease. More specifically, each of MCP-1, MCP-2, MCP-3, MCP-4, MCP-5, MIP-3alpha, CCL25, Chemerin, RANTES, MDC and/or IL-8 are useful for removing one or more of CCR4, CXCR1, CXCR2, CCR2, CCR6, CCR3, CCR5, CCR1, CCR9 or ChemR23 expressing cells from the blood of a patient. In specific embodiments, the chemokine is selected from MCP-1, MCP-2, MCP-3, MCP-4 and MCP-5 and the chemokine receptor is CCR2. In other embodiments, the chemokine is MIP-3alpha and the chemokine receptor is CCR6. In still further embodiments, the chemokine is RANTES and the chemokine receptor is selected from CCR3, CCR1, CCR5 or CCR9. In still further embodiments, the chemokine is MDC and the chemokine receptor is CCR4. In yet further embodiments, the chemokine is IL-8 and the chemokine receptor is selected from CXCR1 and CXCR2. The chemokines described in greater detail herein (with reference to the relevant figures and amino acid sequences, as set forth in the SEQ ID NOs) may each be applied according to the various embodiments of the present invention.

CCL2 is the gene symbol approved by the HUGO Gene Nomenclature Committee for chemokine (C—C motif) ligand 2, also known as MCP-1. The HGNC ID for this gene is 10618. The gene is located at chromosome position 17q11.2-q21.1. The previous symbol and name for the gene is SCYA2 "small inducible cytokine A2 (monocyte chemotatic protein 1, homologus to mouse Sig-je)". Synonyms for this gene include GDCF-2, HC11, MCP1, MGC9434, SMC-CF, "monocyte chemoattractant protein-1", "monocyte chemotactic and activating factor", "monocyte chemotactic protein 1, homologous to mouse Sig-je", "monocyte secretory protein JE", "small inducible cytokine subfamily A (Cys-Cys), member 2". The Genbank reference sequence for CCL2 is BC009716.1 as available on 13 Jun. 2011, which is incorporated herein by reference in its entirety.

CCL8 is the gene symbol approved by the HUGO Gene Nomenclature Committee for chemokine (C—C motif)

ligand 8, also known as MCP-2. The HGNC ID for this gene is 10635. The gene is located at chromosome position 17q11.2. The previous symbol and name for the gene is SCYA8, "small inducible cytokine subfamily A (Cys-Cys), member 8 (monocyte chemotactic protein 2)". Another synonym for this gene is HC14. The Genbank reference sequence for CCL8 is X99886.1 as available on 13 Jun. 2011, which is incorporated herein by reference in its entirety.

CCL7 is the gene symbol approved by the HUGO Gene Nomenclature Committee for chemokine (C—C motif) ligand 7, also known as MCP-3. The HGNC ID for this gene is 10634. The gene is located at chromosome position 17q11.2-q12. The previous symbol and name for the gene is SCYA6, SCYA7, "small inducible cytokine A7 (monocyte chemotactic protein 3)". Synonyms for this gene include FIC, MARC, MCP-3, MCP3, NC28, "monocyte chemoattractant protein 3", "monocyte chemotactic protein 3". The Genbank reference sequence for CCL7 is AF043338 as available on 13 Jun. 2011, which is incorporated herein by reference in its entirety CCL13 is the gene symbol approved by the HUGO Gene Nomenclature Committee for chemokine (C—C motif) ligand 13, also known as MCP-4. The HGNC ID for this gene is 10634. The gene is located at chromosome position 17q11.2-q12. The previous symbol and name for the gene is SCYA6, SCYA7, "small inducible cytokine A7 (monocyte chemotactic protein 3)". Synonyms for this gene include FIC, MARC, MCP-3, MCP3, NC28, "monocyte chemoattractant protein 3", "monocyte chemotactic protein 3". The Genbank reference sequence for CCL13 is AJ001634 as available on 13 Jun. 2011, which is incorporated herein by reference in its entirety.

MCP-5 is a mouse chemokine in the CC chemokine family. It is also known as Chemokine (C—C motif) ligand 12 (CCL12) and, due to its similarity with the human chemokine MCP-1, sometimes it is called MCP-1-related chemokine. The gene for MCP-5 is found in a cluster of CC chemokines on mouse chromosome 11. The NCBI reference sequence for CCL12 is NC_000077.5 as available on 13 Jun. 2011, which is incorporated herein by reference in its entirety.

CCL20 is the gene symbol approved by the HUGO Gene Nomenclature Committee for chemokine (C—C motif) ligand 20, also known as MIP-3alpha. The HGNC ID for this gene is 10619. The gene is located at chromosome position 2q33-q37. The previous symbol and name for the gene is SCYA20, "small inducible cytokine subfamily A (Cys-Cys), member 20". Synonyms for this gene include CKb4, exodus-1, LARC, MIP-3a, ST38. The Genbank reference sequence for CCL20 is D86955.1 as available on 13 Jun. 2011, which is incorporated herein by reference in its entirety.

CCL5 is the gene symbol approved by the HUGO Gene Nomenclature Committee for chemokine (C—C motif) ligand 5, also known as RANTES. The HGNC ID for this gene is 10632. The gene is located at chromosome position 17q111.2-q12. The previous symbol and name for the gene is D17S136E, SCYA5, "small inducible cytokine A5 (RANTES)". Synonyms for this gene include "beta-chemokine RANTES", MGC17164, RANTES, "regulated upon activation, normally T-expressed, and presumably secreted", "SIS-delta", SISd, "small inducible cytokine subfamily A (Cys-Cys), member 5", "T-cell specific protein p288", "T-cell specific RANTES protein", TCP228. The Genbank reference sequence for CCL5 is AF043341.1 as available on 13 Jun. 2011, which is incorporated herein by reference in its entirety.

CCL25 is the gene symbol approved by the HUGO Gene Nomenclature Committee for chemokine (C—C motif) ligand 25. The HGNC ID for this gene is 10624. The gene is located at chromosome position 19p13.2. The previous symbol and name for the gene is SCYA25, "small inducible cytokine subfamily A (Cys-Cys), member 25". Synonyms for this gene include "Ck beta-15", Ckb15, TECK, "TECK-var", "thymus expressed chemokine". The Genbank reference sequence for CCL25 is U86358.1 as available on 13 Jun. 2011, which is incorporated herein by reference in its entirety.

RARRES2 is the gene symbol approved by the HUGO Gene Nomenclature Committee for retinoic acid receptor responder (tazarotene induced) 2, also known as Chemerin. The HGNC ID for this gene is 9868. The gene is located at chromosome position 7q36.1. Synonyms for this gene include "chemerin", HP10433, TIG2. The Genbank reference sequence for CXCR7 is U77594.1 as available on 13 Jun. 2011, which is incorporated herein by reference in its entirety.

CCL22 is the gene symbol approved by the HUGO Gene Nomenclature Committee for chemokine (C—C motif) ligand 22. The HGNC ID for this gene is 10621. The gene is located at chromosome position 16q13. The previous symbol and name for the gene is SCYA22, "small inducible cytokine subfamily A (Cys-Cys), member 22". Synonyms for this gene include A-152E5.1, ABCD-1, DC/B-CK, MDC, MGC34554, STCP-1. The Genbank reference sequence for CCL22 is U83171.1 as available on 13 Jun. 2011, which is incorporated herein by reference in its entirety.

IL8 is the gene symbol approved by the HUGO Gene Nomenclature Committee for interleukin 8, also known as CXCL8. The HGNC ID for this gene is 6025. The gene is located at chromosome position 4q13-q21. Synonyms for this gene include 3-10C, AMCF-I, b-ENAP, "chemokine (C—X—C motif) ligand 8", CXCL8, GCP-1, IL-8, K60, LECT, LUCT, LYNAP, MDNCF, MONAP, NAF, NAP-1, SCYB8, TSG-1. The Genbank reference sequence for CXCL8 is Y00787.1 as available on 13 Jun. 2011, which is incorporated herein by reference in its entirety.

An example of a chemokine of the various embodiments of the invention containing both modifications and a truncation and specifically adapted for use in the invention is described in detail herein. The truncated CCL25 corresponds to residues 1 to 74 of the full length mature protein (and thus lacks amino acids 75 to 127 and the N-terminal signal peptide of 23 amino acids) and thus retains the chemokine fold. In addition, a methionine to Norleucine substitution is incorporated, to prevent oxidation of the residue during chain assembly. The N terminal glutamine residue is substituted with pyroglutamine to permit uniformity of product during synthesis. Biotinylation is achieved via a PEG spacer at the r-functionality of the lysine residue found at position 72. The amino acid sequence of the linear molecule (i.e. without the PEG spacer and biotin molecule at amino acid 72 shown) comprises, consists essentially of or consists of the amino acid sequence presented as SEQ ID NO: 120. The final protein may thus comprise, consist essentially of or consist of the amino acid sequence of SEQ ID NO: 122 (see Examples below).

Examples of suitable modified chemokines of the various embodiments of the invention containing modifications and/or truncations and specifically adapted for use in the invention are described in detail herein. MCP-1 has been produced with residue 75, which may be a lysine, as the site of biotinylation on the chemokine (numbering based upon the mature protein having the amino acid sequence of SEQ ID NO: 113). Biotinylation permits immobilization of MCP-1 on a solid support (via a biotin-avidin interaction). The basic amino acid sequence of MCP-1, including a 23 amino acid leader sequence is set forth as SEQ ID NO: 112. The amino acid sequence of the mature protein is set forth as SEQ ID NO: 113. The inventors have determined that chemokines may display improved binding properties where the chemokine is biotinylated via a spacer group. The spacer may prevent the biotin group from impacting on the binding affinity of the chemokine. Any suitable spacer group may be employed. Further modifications may provide the molecule with advantageous properties. The invention also relates to derivatives of truncated MCP-1 chemokines. The amino acid sequence of the truncated version is set forth as SEQ ID NO: 114.

Accordingly, in certain embodiments the invention also provides a modified MCP-1 chemokine comprising, consisting essentially of or consisting of the amino acid sequence set forth as SEQ ID NO: 112, SEQ ID NO: 113 or SEQ ID NO: 114 in which one or more of the following modifications have been made:

a) the glutamine residue 1 of SEQ ID NO: 113 has been replaced with pyroglutamine b) the C terminus is produced as an amide derivative (this may be achieved by synthesis on an amide linker)

c) the (C terminal region) residue at position 98 of SEQ ID NO: 112 or position 75 of SEQ ID NO: 113 or position 67 of SEQ ID NO: 114, which may be a lysine or ornithine residue, is biotinylated, optionally via a spacer group, in order to permit immobilization of the chemokine on a solid support; and/or d) the methionine residue at position 87 of SEQ ID NO: 112 or position 64 of SEQ ID NO: 113 or position 56 of SEQ ID NO: 114 has been replaced with norleucine.

The (C terminal region) amino acid, which may be a lysine residue or a functional equivalent, at position 98 of SEQ ID NO: 112 or position 75 of SEQ ID NO: 113 or position 67 of SEQ ID NO: 114 may be biotinylated via a suitable spacer group, such as a polyethylene glycol (PEG) spacer group, in order to permit immobilization of the chemokine on a solid support. In specific embodiments, the PEG spacer is 3,6-dioxo aminooctanoic acid. The sequence and biotinylation of the modified MCP-1 chemokines of the invention are shown in FIGS. 92 to 94 respectively. The modified MCP-1 chemokines may be agonists or antagonists of CCR2 activity. They can be tested for activity in a suitable assay, such as cell-based assays. In particular, agonist and antagonist properties may be determined in functional cell-based assay on human CCR2 receptor.

MCP-5 only binds CCR2 and should be selective in its removal of CCR2 expressing cells. The full length amino acid sequence, including the signal peptide, is set forth as SEQ ID NO: 115. The amino acid sequence of N-terminal processed MCP-5 chemokine is 82 amino acids long and is set forth as SEQ ID NO: 116. An amino acid sequence alignment suggests that MCP-5 has a C-terminal extension when compared to the amino acid sequence of MCP-1. The results of this alignment are shown in FIG. 95. C-terminal truncated versions of MCP-5 can thus be synthesised. This truncated version will comprise, consist essentially of or consist of MCP-5 residues 1-76, set forth as SEQ ID NO: 117.

Accordingly, the various embodiments of the invention also provide a modified MCP-5 chemokine comprising the amino acid sequence set forth as SEQ ID NO: 115, SEQ ID NO: 116 or SEQ ID NO: 117 in which the isoleucine residue at position 97 of SEQ ID NO: 115 or at position 75 of SEQ ID NO: 116 or SEQ ID NO: 117 has been replaced with lysine. In certain embodiments, the modified MCP-5 chemokine comprises, consists essentially of or consists of the amino acid sequence of SEQ ID NO: 118. The modified MCP-5 chemokine may be biotinylated at the lysine (or a functional equivalent) residue at position 97 of SEQ ID NO: 115 or at position 75 of SEQ ID NO: 116 or SEQ ID NO: 117. Biotinylation may be via a suitable spacer group. Specific examples of the spacer group include a PEG spacer, optionally 3,6-dioxo aminooctanoic acid. In some embodiments, the C terminus is produced as an amide derivative. This may be achieved by synthesis on an amide linker. In certain embodiments, the modified MCP-5 chemokine comprises, consists essentially of or consists of the sequence and biotinylation shown in FIG. 96. The modified MCP-5 chemokine may be an agonist or an antagonist of CCR2 activity. They can be tested for activity in a suitable assay, such as cell-based assays. In particular, agonist and antagonist properties may be determined in a functional cell-based assay on human CCR2 receptor.

An example of a chemokine of the various embodiments of the invention containing modifications and specifically adapted for use in the invention is described in detail herein (see Examples below). The modified CCL8 (MCP-2) corresponds to residues 1 to 76 of the full length mature protein (and lacks the N-terminal signal peptide of 23 amino acids, which is cleaved off) and thus retains the chemokine fold. The Gln at the N-terminus of the protein is subject to pyroGlu formation under physiological conditions. Thus Gln1 of the sequence may thus be substituted with pyroglutamine to prevent mixed species of N-terminal Gln and pyroGlu being generated (SEQ ID NO: 129). This improves the yield of synthesis and ensures a homogeneous chemokine preparation through column manufacture and use. FmocLys(ivDde)-OH is incorporated as residue 75 to facilitate site-specific labelling at this position of the protein (SEQ ID NO: 130). The naturally occurring lysine at position 75 is modified through biotinylation. A PEG spacer may be incorporated between the ϵ-amino functionality and the biotin (SEQ ID NO: 131).

Thus, in certain embodiments the invention also relates to a modified chemokine comprising, consisting essentially of or consisting of the amino acid sequence of SEQ ID NO: 129:

XPDSVSIPITCCFNVINRKIPIQRLESYTRITNIQCPKEAVIFKTKRGKE

VCADPKERWVRDSMKHLDQIFQNLXP

X1=pyroGlu (but may remain as Gln in some embodiments)

X75=an amino acid residue that can be biotinylated, such as lysine, ornithine or diaminopropionic acid and optionally is biotinylated, optionally via a spacer molecule such as PEG, e.g. K(PEG-Biotin).

Or SEQ ID NO: 131

XPDSVSIPITCCFNVINRKIPIQRLESYTRITNIQCPKEAVIFKTKRGKE

VCADPKRWVRDSMKHLDQIFQNLXP

X1=pyroGlu (but may remain as Gln in some embodiments)

X75=K(PEG-Biotin).

A further example of a chemokine of the various embodiments of the invention containing modifications and specifically adapted for use in the invention is described in detail herein (see Examples below). The modified CCL5 (RANTES) corresponds to residues 1 to 68 of the full length mature protein (and lacks the N-terminal signal peptide of 23 amino acids, which is cleaved off) and thus retains the chemokine fold. The single methionine (Met67) within the sequence is mutated to lysine, to mitigate against oxidation of this residue during the chain assembly (SEQ ID NO: 126). This Met to Lys substitution provides a lysine at position 67 which can be modified through biotinylation. FmocLys (ivDde)-OH is incorporated as residue 67 to facilitate site-specific labelling at this position of the protein (SEQ ID NO: 127). The biotinylated version comprises, consists essentially of or consists of the amino acid sequence of SEQ ID NO: 128.

Thus, in other embodiments the invention also relates to a modified chemokine comprising, consisting essentially of or consisting of the amino acid sequence of SEQ ID NO: 128:

SPYSSDTTPCCFAYIARPLPRAHIKEYFYTSGKCSNPAVVFVTRKNRQVC

ANPEKKWVREYINSLEXS

X is an amino acid residue that can be biotinylated, such as lysine, ornithine or diaminopropionic acid and optionally is biotinylated, optionally via a spacer molecule such as PEG (e.g. K(Biotin))

A further example of a chemokine of the various embodiments of the invention containing modifications and specifically adapted for use in the invention is described in detail herein (see Examples below). The modified CCL2 (MCP-1) corresponds to residues 1 to 76 of the full length mature protein (and lacks the N-terminal signal peptide of 23 amino acids, which is cleaved off) and thus retains the chemokine fold (SEQ ID NO: 123). The Gln at the N-terminus of the protein (Gln1) is substituted with pyroglutamine to prevent mixed species of N-terminal Gln and pyroGlu being generated. This improves the yield of synthesis and ensures a homogeneous chemokine preparation through column manufacture and use. FmocLys(ivDde)-OH is incorporated as residue 75 to facilitate site-specific labelling at this position of the protein (SEQ ID NO: 124). A suitable spacer, such as a PEG spacer, may be incorporated between the ε-amino functionality and the biotin. The biotinylated version comprises, consists essentially of or consists of the amino acid sequence of SEQ ID NO: 125.

Thus, in other embodiments the invention also relates to a modified chemokine comprising, consisting essentially of or consisting of the amino acid sequence of:

SEQ ID NO: 123:
XPDAINAPVTCCYNFTNRKISVQRLASYRRITSSKCPKEAVIFKTIVA

KEICADPKQKWVQDSMDHLDKQTQTPKT

X=pyroGlu

And/or SEQ ID NO: 125:
XPDAINAPVTCCYNFTNRKISVQRLASYRRITSSKCPKEAVIFKTIVAK

EICADPKQKWVQDSMDHLDKQTQTPXT

X1=pyroGlu

X75 is an amino acid residue that can be biotinylated, such as lysine, ornithine or diaminopropionic acid and optionally is biotinylated, optionally via a spacer molecule such as PEG, optionally K(PEG-Biotin)

A further example of a chemokine of the various embodiments of the invention containing modifications and specifically adapted for use in the invention is described in detail herein (see Examples below). The modified CCL20 (MIP-3a) corresponds to residues 1 to 70 of the full length mature protein (and lacks the N-terminal signal peptide of 26 amino acids, which is cleaved off) and thus retains the chemokine fold (SEQ ID NO: 138). FmocLys(ivDde)-OH is incorporated as residue 68 to facilitate site-specific labelling at this position of the protein (SEQ ID NO: 139). The naturally occurring lysine at position 68 is modified through biotinylation. A PEG spacer may be incorporated between the ε-amino functionality and the biotin. The final protein may thus comprise, consist essentially of or consist of the amino acid sequence of SEQ ID NO: 140.

Thus, in other embodiments the invention also relates to a modified chemokine comprising, consisting essentially of or consisting of the amino acid sequence of SEQ ID NO: 140:

ASNFDCCLGYTDRILHPKFIVGFTRQLANEGCDINAIIFHTKKKLSV

CANPKQTWVKYIVRLLSKKVXNM

X is an amino acid residue that can be biotinylated, such as lysine, ornithine or diaminopropionic acid and optionally is biotinylated, optionally via a spacer molecule such as PEG, in particular K(PEG-Biotin)

A further example of a chemokine of the various embodiments of the invention containing modifications and specifically adapted for use in the invention is described in detail herein (see Examples below). The modified CCL22 (MDC) corresponds to residues 1 to 69 of the full length mature protein (and lacks the N-terminal signal peptide of 24 amino acids, which is cleaved off) and thus retains the chemokine fold (SEQ ID NO: 141). FmocLys(ivDde)-OH is incorporated as residue 66 to facilitate site-specific labelling at this position of the protein (SEQ ID NO: 142). The naturally occurring lysine at position 66 is modified through biotinylation. A PEG spacer may be incorporated between the ε-amino functionality and the biotin. The final protein may thus comprise, consist essentially of or consist of the amino acid sequence of SEQ ID NO: 143.

Thus, other embodiments the invention also relates to a modified chemokine comprising, consisting essentially of or consisting of the amino acid sequence of SEQ ID NO: 143:

GPYGANMEDSVCCRDYVRYRLPLRVVKHFYWTSDSCPRPGVVLLTF

RDKEICADPRVPWVKMILNXLSQ

X is an amino acid residue that can be biotinylated, such as lysine, ornithine or diaminopropionic acid and optionally is biotinylated, optionally via a spacer molecule such as PEG, especially K(PEG-Biotin)

A further example of a chemokine of the various embodiments of the invention containing modifications and specifically adapted for use in the invention is described in detail herein (see Examples below). The modified CXCL8 (IL-8) corresponds to residues 1 to 77 of the full length mature protein (and lacks the N-terminal signal peptide of 22 amino acids, which is cleaved off) and thus retains the chemokine fold. An amino acid residue capable of biotinylation, such as lysine or ornithine, is added as residue 78 (SEQ ID NO: 21). FmocLys(ivDde)-OH may be incorporated as residue 78 to facilitate site-specific labelling at this position of the protein (SEQ ID NO: 133). The additional amino acid, in particular lysine or ornithine, at position 78 is modified through biotinylation. A suitable spacer, such as a PEG spacer, may be incorporated between the ε-amino functionality and the biotin (SEQ ID NO: 134).

Thus, in other embodiments the invention also relates to a modified chemokine comprising, consisting essentially of or consisting of the amino acid sequence of SEQ ID NO: 132 or 134:

SEQ ID NO: 132
AVLPRSAKELRCQCIKTYSKPFHPKFIKELRVIESGPHCANTEIIVKL

SDGRELCLDPKENWVQRVVEKFLKRAENSX

X is an amino acid residue that can be biotinylated, such as lysine, ornithine or diaminopropionic acid and optionally is biotinylated, optionally via a spacer molecule such as PEG

SEQ ID NO: 134
AVLPRSAKELRCQCIKTYSKPFHPKFIKELRVIESGPHCANTEIIVKL

SDGRELCLDPKENWVQRVVEKFLKRAENSK(PEG-Biotin)

A further example of a chemokine of the various embodiments of the invention containing truncations and modifications and specifically adapted for use in the invention is described in detail herein (see Examples below). The modified CXCL8 (IL-8) corresponds to residues 6 to 77 of the full length mature protein, with the first 5 N-terminal amino acids removed, (and lacks the N-terminal signal peptide of 22 amino acids, which is cleaved off) and thus retains the chemokine fold. An amino acid residue capable of biotinylation, such as lysine or ornithine, is added as residue 78 (SEQ ID NO: 135). FmocLys(ivDde)-OH may be incorporated as residue 78 to facilitate site-specific labelling at this position of the protein (SEQ ID NO: 136). The additional amino acid, in particular lysine or ornithine, at position 78 is modified through biotinylation. A suitable spacer, such as a PEG spacer, may be incorporated between the ε-amino functionality and the biotin (SEQ ID NO: 137).

Thus, in other embodiments the invention also relates to a modified chemokine comprising, consisting essentially of or consisting of the amino acid sequence of SEQ ID NO: 135 or 137:

SEQ ID NO: 135
SAKELRCQCIKTYSKPFHPKFIKELRVIESGPHCANTEIIVKLSDGRE

LCLDPKENWVQRVVEKFLKRAENSX

X is an amino acid residue that can be biotinylated, such as lysine, ornithine or diaminopropionic acid and optionally is biotinylated, optionally via a spacer molecule such as PEG

SEQ ID NO: 137
SAKELRCQCIKTYSKPFHPKFIKELRVIESGPHCANTEIIVKLSDGRE

LCLDPKENWVQRVVEKFLKRAENSX

X is K(PEG-Biotin)

Chemokines useful in the various embodiments of the invention may be synthesised through any suitable means known in the art. Preferably, the chemokines are chemically synthesised as this facilitates modification and labelling etc. However, recombinant DNA based approaches may also be employed in combination with appropriate labelling and modification technologies as required. Thus, in certain embodiments the invention also provides a nucleic acid molecule encoding the chemokines of the various embodiments of the invention. In certain embodiments the invention also relates to a vector containing such a nucleic acid molecule and a host cell containing the vector. The vector may additionally comprise a suitable promoter operably linked to the nucleic acid molecule, to facilitate transcription of the corresponding mRNA molecule. The host cell may be capable of expressing the protein by transcription and translation of the nucleic acid molecule encoding a chemokine of the various embodiments of the invention.

The chemokines useful in the various embodiments of the invention can be biotinylated by methods known in the art such as described in WO 00/50088 A2, which is incorporated herein by reference in its entirety. As indicated above, site-specific labelling of the chemokines of the various embodiments of the invention is preferable, although any labelling technique which does not significantly affect the receptor-binding capacity of the chemokine may be employed. Various site-specifically biotinylated chemokines and native chemokines are available commercially, for instance from Almac, Craigavon, UK. In specific embodiments the one or more chemokines are biotinylated via a spacer group. The spacer may be employed to prevent the biotin group from impacting on the activity of the chemokine, in particular binding of the chemokine to its cognate receptor. Any suitable spacer that facilitates retention of receptor binding properties of the chemokine may be employed in the various embodiments of the invention. Thus, in the specific embodiments described above, spacers other than PEG spacers may be employed as appropriate. In specific embodiments, the spacer is a polyethylene glycol (PEG) spacer. PEG has been shown to be an effective spacer permitting attachment of biotin to the chemokine (which can then be immobilized on the solid support through interaction with streptavidin) without compromising receptor binding capability.

In the context of the present various embodiments of the invention the term "antibody" includes all immunoglobulins or immunoglobulin-like molecules with specific binding affinity for the relevant chemokine receptor (including by way of example and without limitation, IgA, IgD, IgE, IgG and IgM, combinations thereof, and similar molecules produced during an immune response in any vertebrate, for example, in mammals such as humans, goats, rabbits and mice). Specific immunoglobulins useful in the various embodiments of the invention include IgG isotypes. The antibodies useful in the various embodiments of the invention may be monoclonal or polyclonal in origin, but are typically monoclonal antibodies. Antibodies may be human antibodies, non-human antibodies, or humanized versions of non-human antibodies, or chimeric antibodies. Various techniques for antibody humanization are well established and any suitable technique may be employed. The term "antibody" also refers to a polypeptide ligand comprising at least a light chain or heavy chain immunoglobulin variable region which specifically recognizes and binds an epitope of an antigen, and it extends to all antibody derivatives and fragments that retain the ability to specifically bind to the relevant chemokine receptor. These derivative and fragments may include Fab fragments, F(ab')2 fragments, Fv fragments, single chain antibodies, single domain antibodies, Fc fragments etc. The term antibody encompasses antibodies comprised of both heavy and light chains, but also heavy chain (only) antibodies. In specific embodiments, the antibodies may be engineered so as to be specific for more than one chemokine receptor, for example bi-specific to permit binding to two different chemokine receptors. Suitable commercially available antibodies which bind to the chemokine receptors of interest are listed in table 7 below. They may or may not be labelled. General reference may be made to "Antibodies a laboratory manual: By E Harlow and D Lane. pp 726. Cold Spring Harbor Laboratory. 1988", which reference is incorporated herein in its entirety.

TABLE 7

Commercially available fluorophore labelled antibodies against specific chemokine receptors

| Antibody | Fluorophore | Supplier |
|---|---|---|
| CCR5 | PE | Biolegend |
| CXCR1 | APC | Biolegend |
| CCR6 | PerCP Cy5.5 | BD Biosciences |
| CCR4 | PerCP Cy5.5 | BD Biosciences |
| CCR9 | APC | R&D Systems |
| CCR3 | PE | Biolegend |
| CXCR2 | APC | R&D Systems |
| CCR1 | Alexa Fluor 647 | Biolegend |
| CCR2 | PerCP Cy5.5 | Biolegend |
| ChemR23 | APC | R&D Systems |

Anti-CCR2 antibodies are described for example in WO 2010/021697, incorporated herein by reference. Further examples of potentially useful antibodies include MLN-1202, an anti-CCR2 monoclonal antibody currently undergoing clinical trials (Millennium Pharmaceuticals).

The chemokine receptor expressing cells may thus be targeted using alternative binding agents, such as antibodies or other chemical compounds, as defined herein, rather than the natural chemokine binding partner. This approach is a new approach to treating inflammatory conditions.

Thus, in certain embodiments the invention also provides an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine. The binding reagent capable of specifically binding to the chemokine receptor may be an agonist or an antagonist of the chemokine receptor. In specific embodiments, the binding reagent capable of specifically binding to the chemokine receptor is selected from an antibody and a chemical compound.

In other embodiments the invention thus also provides a method for treating an inflammatory condition comprising applying peripheral blood from a patient/subject to an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine) thus removing chemokine receptor expressing cells from the peripheral blood of the patient/subject. The method may comprise returning the blood depleted of the chemokine receptor expressing cells to the patient/subject.

Similarly, in other embodiments the invention provides a binding reagent capable of specifically binding to a chemokine receptor for use in the treatment of an inflammatory condition, wherein the binding reagent is immobilized on a solid support contained within an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient/subject, wherein the binding reagent is not a chemokine), to which is applied peripheral blood from a patient thus removing chemokine receptor expressing cells from the peripheral blood of the patient.

These aspects of the various embodiments of the invention may be integrated into the more focussed therapeutic aspects of the various embodiments of the invention (i.e. treating inflammatory skin diseases and various aspects thereof) and thus, the remainder of the disclosure, including all specific embodiments applies mutatis mutandis.

Solid support materials for immobilizing the binding reagents of the various embodiments of the invention are known in the art. "Solid support" refers to, for example, materials having a rigid or semi-rigid surface or surfaces, and may take the form of beads, resins, gels, microspheres, or other geometric configurations. A useful support material is one that does not activate blood cells so as to make them coagulate or adhere to the support as peripheral whole blood is applied to the device. In certain embodiments, a support treated with an agent to provide it with anti-coagulation properties, in particular a heparinized support is employed. Alternatively, the blood of the patient may be treated with an anti-coagulant such as heparin prior to application to the support. Useful support materials comprise high molecular weight carbohydrates, in particular carbohydrates having a molecular weight of 100 kDa or more, such as agarose, in particulate form, optionally cross-linked, and cellulose. Other preferred support materials are polymers, such as carboxylated polystyrene, and glass. The support of the various embodiments of the invention may be provided in the form of particles or fibres. The support particles may have regular form, such as spheres or beads, or irregular form. They may be porous or non-porous. A preferred average particle size of the support is from 50 µm to 2 mm. In certain embodiments Sepharose™, a cross linked, beaded-form of agarose, is used as column matrix. It is chosen for its optimal distribution capacity and can provide a large available area for affinity binding. Solid supports may be provided in the form of magnetic beads, with the specific binding reagent immobilized on the magnetic beads. Following capture of the (CCR4, CXCR1, CXCR2, CCR2, CCR6, CCR3, CCR5, CCR1, CCR9 or ChemR23) chemokine receptor expressing cells from the blood, the beads can be removed from the blood with the aid of an appropriate magnetic separator.

Methods for immobilizing binding reagents on a solid support are known in the art. A binding reagent, such as a chemokine, antibody, peptide, nucleic acid or chemical compound, can be immobilized on the support in a direct or indirect manner. Immobilization can be by means of a suitable linker in some embodiments. A preferred method of indirect immobilization of a binding reagent, such as a chemokine, relies upon the interaction between biotin and avidin molecules. "Avidin" or "avidin molecule" refers to any type of protein that specifically binds biotin to the substantial exclusion of other (small) molecules that might be present in a biological sample. Examples of avidin include avidins that are naturally present in egg white, oilseed protein (e.g., soybean meal), and grain (e.g., corn/maize), and streptavidin, which is a protein of bacterial origin. Thus, biotinylation of the binding reagent and use of an avidin molecule such as streptavidin immobilized on the solid support allows reliable attachment of the binding reagent to the solid support according to methods known in the art. Specifically, such a method may comprise providing the binding reagent in biotinylated form, providing a solid support having streptavidin immobilized on its surface, contacting the support with an aqueous solution of the biotinylated binding reagent, and rinsing the support with an aqueous solvent. In addition, binding pair interactions, such as antibody-antigen interactions, may also be utilised for indirect immobilisation of binding reagent onto a support. In such embodiments the support may be derivatised with one member of a binding pair, such as an antibody or fragment or derivative thereof, as defined herein, which has known affinity for a particular peptide sequence or small molecule hapten. Incorporating the other member of the binding pair, such as an antigen, peptide sequence or the hapten onto or into the binding reagent facilitates immobilisation onto a solid support coated with the corresponding antibody or fragment or derivative thereof. Thus, the binding reagent may be modified to include the peptide sequence or hapten into the linear molecule or may be added as a side chain or label. Any suitable antibody-antigen pair may be employed. The antibody fragment or derivative may be any fragment or derivative that retains specific binding affinity for the appropriate antigen. Examples include Fab, F(ab')2 fragments, scFV, VH domains, single domain antibodies (such as nanobodies), heavy chain antibodies and humanized version of non-human antibodies etc. Other high affinity interactions can be utilised for immobilisation of binding reagents, as long as the binding reagent can be synthesised or derivatised with one of the interacting partners and the solid support synthesised or derivatised with the other interacting partner without loss of binding activity (i.e. binding of the binding reagent to the appropriate chemokine receptor). Immobilization may occur via essentially the same interaction in reverse in some embodiments. Thus, the binding reagent which may be a chemokine for example, may be attached to an antibody as defined herein, and the solid support derivatised with the antigen. The chemokine may be produced as a fusion protein with the antibody.

Alternatively binding reagents, such as chemokines and antibodies, can be immobilised directly onto a solid support using bioconjugation techniques established in the field. For example direct immobilisation of proteins onto cyanogen bromide activated solid supports via amino functionalities within the primary sequence of the protein. Alternatively, sulphydryl functionalities within proteins can be used to directly immobilise the protein to alkyl halide derivatised supports or supports containing free thiol functionalities. In further embodiments, proteins containing α-thioester functionalities can be directly immobilised on supports containing 1,2 amino thiol moieties (eg N-terminal cysteine) using the native chemical ligation reaction. Alternatively proteins modified with ketones and aldehydes can be immobilised on solid supports derivatised with hydrazinyl, hydrazide and aminoxy functionalities using hydrazone/oxime bond forming ligation reactions (and vice versa). Alternatively 'Click' chemistry can be used to immobilise proteins onto solid supports, whereby the protein and the support are derivatised with the appropriate mutually reactive chemical functionalities (azides and alkynes). In other embodiments Staudinger ligation chemistry can be used to immobilise appropriately derivatised proteins onto the appropriately derivatised solid supports.

The solid support is contained within or carried by the apheresis column. Thus, by "loaded" is meant that the column carries or contains the solid support in a manner such that (peripheral) blood can flow through the column in contact with the solid support. Thus, the solid support provides a matrix within the column through which blood flows, in continuous fashion in certain embodiments. This permits cells expressing the specific chemokine receptor to be removed from the blood passing through the column, such that blood exiting the column is depleted of the specific chemokine receptor-expressing cells. In specific embodiments, the apheresis column is loaded with a support comprising streptavidin immobilized on the support and one or more biotinylated binding reagents, such as chemokines, bound to the streptavidin on the support. The solid support may be comprised of a high-molecular weight carbohydrate, optionally cross-linked, such as agarose.

As discussed above, the binding reagent is coupled to the solid support. The relative amounts of binding reagent may be controlled to ensure that coupling between the solid support and the binding reagent will be immediate, minimising the risk of binding reagent decoupling from the solid support. Thus, it may be ensured that there is a relative excess of immobilization sites for the binding reagent on the solid support. Alternatively, or additionally, following immobilization of the binding reagent on the solid support, the solid support may be washed to remove any unbound binding reagent.

The apheresis column utilised in the various embodiments of the present invention acts as a leukapheresis treatment for conditions associated with inflammatory skin diseases. The column acts to specifically remove one or more of CCR4, CXCR1, CXCR2, CCR2, CCR6, CCR3, CCR5, CCR1, CCR9 and ChemR23-expressing monocytes, dendritic cells or T lymphocytes by exploiting the interaction between CCR4, CXCR1, CXCR2, CCR2, CCR6, CCR3, CCR5, CCR1, CCR9 or ChemR23 expressed on the cell surface and a specific binding reagent immobilized on a solid support contained within or carried by the column. The overall column typically comprises, consists of, or consists essentially of three combined components; 1) a housing which contains or carries 2) the solid support and 3) one or more binding reagents (immobilized thereon) which specifically bind one or more chemokine receptors. The housing may be manufactured from any suitable material for clinical use. In certain embodiments the housing is composed of a plastic material. The housing includes an in flow site for entry of blood and an out flow site for blood (depleted of target cells) to exit the column. The housing may be designed to maintain a continuous blood flow through the solid support matrix. The housing (as shown for example in FIG. 9) may include a top portion which comprises a distribution plate (2) at the inflow site (1) to spread the blood evenly over the entire matrix area. The distribution plate may act as a first safety barrier preventing larger particles flowing through the column and into the patient. However, the distribution plate is not essential and may be removed in some embodiments to decrease the overall resistance in the system. The column may contain one or more safety filter units (3 and 4) placed at the inflow (1) and/or outflow (5) sites of the plastic housing. Such filter units may act to prevent particles larger than blood cells passing in and/or out of the column. The safety filter units may contain a plurality of filters, such as two, three or four filters designed to be a robust barrier and stop all particles larger than blood cells passing through the column. Inclusion of safety filters (3 and 4) at both ends of the column serves to minimize the risk of leakage of particles into the patient, including in the event that the device is incorrectly connected resulting in blood flow in the opposite direction to that intended. The safety filters may comprise of any suitable pore size to prevent particles larger than blood cells from passing through the column, as would be readily understood by one skilled in the art. Suitable filters are commercially available. In specific embodiments, the pore size of the filter(s) is between approximately 60 µm and 100 µm, more specifically approximately 80 µm. The solid support and binding reagent components are discussed in further detail herein.

The volume of the housing may be varied depending upon the blood volumes intended to pass through the column. Typically, the volume of the housing is between approximately 40 ml and 200 ml, more specifically 50 ml to 150 ml or 60 ml to 120 ml.

The column is generally applied in the form of an apheresis circuit. In this context, the overall system includes the apheresis column, tubing and an appropriate pump to pump the blood around the circuit. The system is illustrated in FIG. 10. The patient (1) is connected to the extracorporeal circuit via sterile needles to veins in the right and the left arms. A saline bag (3) is also connected and the saline solution is pumped with a suitable pump (2). Blood is drawn from one arm of the patient through the sterile tubing system by the blood pump (4) and passed through the column (6) and back to the patient. The tubing system may be connected to the column via any suitable coupling, such as standard dialysis luer-lock couplings. The couplings on the column may be colour-coded for correct assembly. For example, red tubing for inflow to the red column top and blue tubing for outflow back to the patient. An air detector (8) may be present in the circuit. Inlet pressure (5) and/or Pven sensors (7) may additionally be employed to monitor the pressure in the circuit.

An apheresis pump, such as the 4008 ADS pump manufactured by Fresenius Medical Care or the Adamonitor pump, may monitor the patient's inflow and outflow. The pump may also monitor the pressure in the extracorporeal circulation. The pump may be able to discriminate air by a bubble catcher and air detector. A clot catcher filter may be positioned inside the bubble catcher. The pump may also incorporate an optical detector to distinguish between light, e.g. saline solution or air present in the tubing system and dark e.g. blood present in the tubing system.

A schematic diagram of a suitable pump, showing the air detector and optical filter is shown in FIG. 11. If the pump system detects air bubbles and optical fluctuations or if extracorporeal pressure values are out of the set range, then the pump may stop immediately. Alternatively or additionally a visual/audible alarm may be emitted.

The treatment methods of the various embodiments of the invention may thus rely upon an extracorporeal circuit. The methods may be considered as ex vivo or in vitro methods and be defined solely with reference to steps performed outside of the patient. In some embodiments, however, the method further comprises, prior to application of the blood to the column, collecting peripheral blood from the patient. In a further embodiment, the method further comprises, following the application of the blood to the column, infusing the blood depleted of (CCR4, CXCR1, CXCR2, CCR2, CCR6, CCR3, CCR5, CCR1, CCR9 and/or ChemR23), chemokine receptor expressing cells to the patient. This is then a complete leukapheresis treatment method. Thus, a leukaphereis method, for treating inflammatory skin disease, comprises collecting peripheral blood from the patient; applying the peripheral blood to an apheresis column loaded with a solid support comprising one or more binding reagents capable of specifically binding to one or more chemokine receptors, in particular the chemokine receptor CCR4, CXCR1, CXCR2, CCR2, CCR6, CCR3, CCR5, CCR1, CCR9 and/or ChemR23 immobilized directly or indirectly on the support thus removing one or more of CCR4, CXCR1, CXCR2, CCR2, CCR6, CCR3, CCR5, CCR1, CCR9 and ChemR23 expressing cells from the peripheral blood of the patient; and infusing the depleted blood (of chemokine receptor expressing cells) to the patient.

The peripheral blood may be continuously collected from the patient. Similarly, the depleted blood may be continuously infused to the patient, through use of an appropriate circuit as described herein. Thus, the support may be disposed in a column through which the blood is made to flow. This may be achieved using a suitable pump for example, as also described herein. Blood flow through the column enables the binding reagent(s) immobilized on the solid support to capture the cells expressing the chemokine receptor, thus depleting them from the blood and preventing their contribution to the inflammatory skin disease.

The methods of the various embodiments of the invention and binding reagents for use in the methods of the various embodiments of the invention may require that the patient has been selected for treatment on the basis of detecting an increase in the level of chemokine receptor, in particular, one or more of CCR4, CXCR1, CXCR2, CCR2, CCR6, CCR3, CCR5, CCR1, CCR9 and ChemR23 expressing cells in a sample obtained from the patient. Such companion diagnostic methods are described in greater detail herein and are based, for example, on the observation that CCR4, CXCR1, CXCR2, CCR2, CCR6, CCR3, CCR5, CCR1, CCR9 and/or ChemR23, expression may be elevated in patients with an inflammatory skin disease. More specifically, it is shown herein that levels of CCR4 expressing leukocytes, in particular T cells, are increased in psoriasis patients (compared with healthy controls).

Thus, (in this context) in certain embodiments the invention also provides a method of diagnosing, monitoring progression of, or monitoring treatment of inflammatory skin disease comprising determining:

a) the levels of one or more of the chemokine receptor CCR4, CXCR1, CXCR2, CCR2, CCR6, CCR3, CCR5, CCR1, CCR9 and ChemR23 expressing cells b) levels of expression of one or more of CCR4, CXCR1, CXCR2, CCR2, CCR6, CCR3, CCR5, CCR1, CCR9 and ChemR23; and/or c) levels of cells with high expression of one or more of CCR4, CXCR1, CXCR2, CCR2, CCR6, CCR3, CCR5, CCR1, CCR9 and ChemR23 in a sample obtained from a subject, wherein high levels of one or more of CCR4, CXCR1, CXCR2, CCR2, CCR6, CCR3, CCR5, CCR1, CCR9 and ChemR23 expressing cells, high levels of expression of one or more of CCR4, CXCR1, CXCR2, CCR2, CCR6, CCR3, CCR5, CCR1, CCR9 and ChemR23 or high levels of cells with high expression of one or more of CCR4, CXCR1, CXCR2, CCR2, CCR6, CCR3, CCR5, CCR1, CCR9 and ChemR23 or increased levels of one or more of CCR4, CXCR1, CXCR2, CCR2, CCR6, CCR3, CCR5, CCR1, CCR9 and ChemR23 expressing cells compared to control, increased levels of expression of one or more of CCR4, CXCR1, CXCR2, CCR2, CCR6, CCR3, CCR5, CCR1, CCR9 and ChemR23 compared to a control or increased levels of cells with high expression of one or more of CCR4, CXCR1, CXCR2, CCR2, CCR6, CCR3, CCR5, CCR1, CCR9 and ChemR23 compared to a control indicate the presence or progression of inflammatory skin disease. Levels of chemokine receptor expression, as opposed to cell numbers, may also be investigated as increased levels of chemokine receptor expression per cell may also be diagnostically relevant. The cells may be lymphocytes such as CCR4 expressing lymphocytes, in particular CCR4 expressing T cells. The cells may be neutrophils such as CXCR1 and/or CXCR2 expressing neutrophils.

"Diagnosing" is defined herein to include screening for a disease/condition or pre-indication of a disease/condition, identifying a disease/condition or pre-indication of a disease/condition and checking for recurrence of disease/condition following treatment. The methods of the various embodiments of the invention may also have prognostic value, and this is included within the definition of the term "diagnosis". The prognostic value of the methods of the various embodiments of the invention may be used as a marker of potential susceptibility to inflammatory skin disease by identifying levels of one or more of CCR4, CXCR1, CXCR2, CCR2, CCR6, CCR3, CCR5, CCR1, CCR9 and ChemR23 expression linked to conditions associated with an inflammatory skin disease. Thus patients at risk may be identified before the disease has a chance to manifest itself in terms of symptoms identifiable in the patient. In certain embodiments, diagnosis may be made in conjunction with other objective indicators of inflammatory skin disease. Thus, in specific embodiments, diagnosis is made in conjunction with one or more of the following indicators: the proportion of the body surface area (BSA) affected and the Psoriasis Area and Severity Index (PASI).

"Monitoring progression of" includes performing the methods to monitor the stage and/or the state and progression of the inflammatory skin disease. Monitoring progression may involve performing the diagnostic methods multiple times on the same patient to determine whether the levels of one or more of CCR4, CXCR1, CXCR2, CCR2, CCR6, CCR3, CCR5, CCR1, CCR9 and ChemR23 expressing cells are increasing, decreasing or remaining stable over a certain time period. This may be in the context of a treatment regime.

"Monitoring the success of a particular treatment" is defined to include determining the levels of one or more of CCR4, CXCR1, CXCR2, CCR2, CCR6, CCR3, CCR5, CCR1, CCR9 and ChemR23 expressing cells before and after a treatment. The treatment is generally one aimed at treating inflammatory skin disease and may be a treatment according to one of the methods of the various embodiments of the invention as defined herein. Successful treatment may be determined with reference to a decrease in one or more of CCR4, CXCR1, CXCR2, CCR2, CCR6, CCR3, CCR5, CCR1, CCR9 and ChemR23 expressing cells as a result of, or following, the treatment. Thus, in such methods a level of one or more of CCR4, CXCR1, CXCR2, CCR2, CCR6, CCR3, CCR5, CCR1, CCR9 and ChemR23 expressing cells is determined prior to treatment. This level is recorded and a further assessment made at a predetermined time following the treatment. The comparison of levels of one or more of CCR4, CXCR1, CXCR2, CCR2, CCR6, CCR3, CCR5, CCR1, CCR9 and ChemR23 expressing cells permits the success of the treatment to be monitored. In specific embodiments, a single treatment is sufficient to cause a depletion of around 10%, 20%, 30%, 40%, 50%, 60% or 70%, or higher, up to 80%, 90%, 95% or more, or any range of values between and including these amounts, of one or more specific chemokine receptors, in particular one or more of CCR4, CXCR1, CXCR2, CCR2, CCR6, CCR3, CCR5, CCR1, CCR9 and ChemR23, expressing cells from the peripheral blood of the patient. In specific embodiments, at least around 50% depletion is achieved in a single treatment. Thus, successful treatment may be defined with reference to depletion of CCR4, CXCR1, CXCR2, CCR2, CCR6, CCR3, CCR5, CCR1, CCR9 and ChemR23 expressing cells. Treatment may lead to depletion of between approximately 100 and 500 million of one or more of CCR4, CXCR1, CXCR2, CCR2, CCR6, CCR3, CCR5, CCR1, CCR9 and ChemR23 expressing cells, such as monocytes, in certain embodiments. Additional factors may be included to determine successful treatment. For example, a lack of increase in CCR4, CXCR1, CXCR2, CCR2, CCR6, CCR3, CCR5, CCR1, CCR9 or ChemR23 expressing cells following treatment may indicate successful treatment in terms of preventing further progression of the condition, optionally combined with an improvement in other markers or staging of the inflammatory skin disease.

In specific embodiments, the inflammatory skin disease is selected from psoriasis and atopic dermatitis.

The sample in which one or more of CCR4, CXCR1, CXCR2, CCR2, CCR6, CCR3, CCR5, CCR1, CCR9 and ChemR23 expressing cell levels, levels of expression of one or more of CCR4, CXCR1, CXCR2, CCR2, CCR6, CCR3, CCR5, CCR1, CCR9 and ChemR23 and/or levels of cells with high expression of one or more of CCR4, CXCR1, CXCR2, CCR2, CCR6, CCR3, CCR5, CCR1, CCR9 and ChemR23 (defined as CCR4hi, CXCR1hi, CXCR2hi, CCR2hi, CCR6hi, CCR3hi, CCR5hi, CCR1hi, CCR9hi or ChemR23hi) are determined may comprise any suitable tissue sample or body fluid sample. Generally, the test sample is obtained from a human subject. Typically, the sample is a blood sample, in particular a peripheral blood sample. The sample may comprise a skin sample, such as a pinch biopsy, in certain embodiments. The methods may involve determining levels of one or more of CCR4, CXCR1, CXCR2, CCR2, CCR6, CCR3, CCR5, CCR1, CCR9 and ChemR23 expressing monocytes, dendritic cells, macrophages or lymphocytes in certain embodiments.

Levels of CCR4, CXCR1, CXCR2, CCR2, CCR6, CCR3, CCR5, CCR1, CCR9 or ChemR23 expressing cells, levels of expression of CCR4, CXCR1, CXCR2, CCR2, CCR6, CCR3, CCR5, CCR1, CCR9 or ChemR23 and/or levels of cells with high expression of CCR4, CXCR1, CXCR2, CCR2, CCR6, CCR3, CCR5, CCR1, CCR9 or ChemR23 (defined as CCR4hi, CXCR1hi, CXCR2hi, CCR2hi, CCR6hi, CCR3hi, CCR5hi, CCR1hi, CCR9hi or ChemR23hi) may be determined according to any suitable method. For example, flow cytometry may be employed in order to determine the number of cells expressing CCR4, CXCR1, CXCR2, CCR2, CCR6, CCR3, CCR5, CCR1, CCR9 or ChemR23 in the sample, to determine levels of CCR4, CXCR1, CXCR2, CCR2, CCR6, CCR3, CCR5, CCR1, CCR9 or ChemR23 expression and/or to identify levels of CCR2hi, CCR6hi, CCR3hi, CCR5hi, CCR1hi, CCR9hi or ChemR23hi cells. Flow cytometric techniques are described herein and examples of commercially available antibodies suitably labelled for use in flow cytometry are set out in Table 7 for example. Alternatively, the method may involve steps of collecting and fixing the cells in the sample, followed by incubation with a suitable binding reagent that binds specifically to the CCR4, CXCR1, CXCR2, CCR2, CCR6, CCR3, CCR5, CCR1, CCR9 or ChemR23 chemokine receptor expressing cells in the sample. Any suitable binding reagent, as defined herein, may be employed. For example, a CCR4, CXCR1, CXCR2, CCR2, CCR6, CCR3, CCR5, CCR1, CCR9 or ChemR23 specific antibody may be employed. A wash step may be adopted following an incubation period to remove any unbound reagent. Suitable wash steps and incubation conditions would be well known to one skilled in the art. The binding reagent may be directly labeled in order to permit antibody binding to be directly determined. Alternatively a secondary binding reagent, such as an antibody, may be employed which binds to the first binding reagent and carries a label. Again, suitable incubation conditions and wash steps would be apparent to one skilled in the art. The primary and secondary binding reagents may form two halves of a binding pair. The binding interaction should not prevent the primary binding reagent binding to the CCR4, CXCR1, CXCR2, CCR2, CCR6, CCR3, CCR5, CCR1, CCR9 or ChemR23 receptor expressing cells, unless a competition assay is being employed. The two halves of a binding pair may comprise an antigen-antibody, antibody-antibody, receptor-ligand, biotin-streptavidin pair etc. in certain embodiments. Other techniques used to quantify chemokine (CCR2) receptor expressing cell levels, to quantify levels of CCR4, CXCR1, CXCR2, CCR2, CCR6, CCR3, CCR5, CCR1, CCR9 or ChemR23 expression and/or to quantify levels of CCR4hi, CXCR1hi, CXCR2hi, CCR2hi, CCR6hi, CCR3hi, CCR5hi, CCR1hi, CCR9hi or ChemR23hi cells include PCR-based techniques such as QT-PCR and protein based methods such as western blot. Quantitation may be achieved with reference to fixed cell lines carrying known numbers of various receptor expressing cells and/or known levels of receptor expression per cell. Such fixed cell lines are available commercially (for example ChemiScreen™ cell lines from Millipore). Methods analogous to the treatment methods of the various embodiments of the invention may also be employed, with binding of CCR4, CXCR1, CXCR2, CCR2, CCR6, CCR3, CCR5, CCR1, CCR9 or ChemR23 expressing cells to the solid support being determined following peripheral blood being passed through the column.

The levels of CCR4, CXCR1, CXCR2, CCR2, CCR6, CCR3, CCR5, CCR1, CCR9 or ChemR23 expressing cells, levels of expression of CCR4, CXCR1, CXCR2, CCR2, CCR6, CCR3, CCR5, CCR1, CCR9 or ChemR23 and/or levels of cells with high expression of CCR4, CXCR1, CXCR2, CCR2, CCR6, CCR3, CCR5, CCR1, CCR9 or ChemR23 (defined as CCR2hi, CCR6hi, CCR3hi, CCR5hi, CCR1hi, CCR9hi or ChemR23hi) may be determined relative to a suitable control. When diagnosing an inflammatory skin disease, a threshold level of cells, level of expression of CCR4, CXCR1, CXCR2, CCR2, CCR6, CCR3, CCR5, CCR1, CCR9 or ChemR23 and/or level of cells with high expression of CCR4, CXCR1, CXCR2, CCR2, CCR6, CCR3, CCR5, CCR1, CCR9 or ChemR23 (defined as CCR2hi, CCR6hi, CCR3hi, CCR5hi, CCR1hi, CCR9hi or ChemR23hi) may be set at or over which a positive diagnosis is made. This threshold may be determined based upon measuring levels of CCR4, CXCR1, CXCR2, CCR2, CCR6, CCR3, CCR5, CCR1, CCR9 or ChemR23 expressing cells, levels of expression of CCR4, CXCR1, CXCR2, CCR2, CCR6, CCR3, CCR5, CCR1, CCR9 or ChemR23 and/or levels of cells with high expression of CCR4, CXCR1, CXCR2, CCR2, CCR6, CCR3, CCR5, CCR1, CCR9 or ChemR23 (defined as CCR4hi, CXCR1hi, CXCR2hi, CCR2hi, CCR6hi, CCR3hi, CCR5hi, CCR1hi, CCR9hi or ChemR23hi) in samples obtained from diseased patients and comparing these levels with levels of CCR4, CXCR1, CXCR2, CCR2, CCR6, CCR3, CCR5, CCR1, CCR9 or ChemR23 expressing cells, levels of expression of CCR4, CXCR1, CXCR2, CCR2, CCR6, CCR3, CCR5, CCR1, CCR9 or ChemR23 and/or levels of cells with high expression of CCR4, CXCR1, CXCR2, CCR2, CCR6, CCR3, CCR5, CCR1, CCR9 or ChemR23 (defined as CCR4hi, CXCR1hi, CXCR2hi, CCR2hi, CCR6hi, CCR3hi, CCR5hi, CCR1hi, CCR9hi or ChemR23hi) in samples obtained from healthy subjects.

In certain embodiments, inflammatory skin disease such as psoriasis or atopic dermatitis is diagnosed on the basis of levels of chemokine receptor expressing cells, such as CCR4, CXCR1, CXCR2, CCR2, CCR6, CCR3, CCR5, CCR1, CCR9 or ChemR23 expressing cells. A positive diagnosis may be made in subjects based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, inflammatory skin disease such as psoriasis or atopic dermatitis is diagnosed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to healthy controls.

In specific embodiments, inflammatory skin disease such as psoriasis or atopic dermatitis is diagnosed on the basis of levels of CCR4 expressing cells, in particular lymphocytes such as T lympohcytes. A positive diagnosis may be made in subjects based upon the presence of greater than about 10%, greater than about 12% or greater than about 15% CCR4 expressing T cells in the sample, as a percentage of total cells in the sample. Inflammatory skin disease such as psoriasis or atopic dermatitis may also be diagnosed on the basis of the presence of a about a 1.2 fold or greater increase, such as about a 1.5, 2, 2.5, 3, 3.5, 4, 4.5, 5, 10, 20, 50 or 100 or greater fold increase in the specific chemokine receptor expressing cells, relative to healthy controls.

In certain embodiments, progression of inflammatory skin disease such as psoriasis or atopic dermatitis, which may be in the context of a treatment regime, is monitored on the basis of levels of chemokine receptor expressing cells at different time points. Progression of inflammatory skin disease such as psoriasis or atopic dermatitis may be indicated in subjects based upon an increase of greater than about 10%, such as an increase of greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more chemokine receptor expressing cells in the sample, as a percentage of total cells in the sample, compared to a sample taken from the same subject at an earlier time point. In other embodiments, progression of inflammatory skin disease such as psoriasis or atopic dermatitis is confirmed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to a sample taken from the same subject at an earlier time point.

In specific embodiments, inflammatory skin disease such as psoriasis or atopic dermatitis is monitored on the basis of levels of CCR4 expressing cells, in particular lymphocytes such as T lymphocytes. Progression of the disease, which may be in the context of a treatment regime, may be indicated in subjects based upon the presence of an increase of greater than about 3%, such as greater than about 4%, greater than about 5%, greater than about 6%, greater than about 7%, greater than about 8%, greater than about 10%, greater than about 15%, greater than about 20%, greater than about 25%, greater than about 30%, greater than about 35%, greater than about 40%, greater than about 45% or more chemokine receptor expressing cells in the sample, as a percentage of total cells in the sample, compared to a sample taken from the same subject at an earlier time point. In other embodiments, progression of inflammatory skin disease such as psoriasis or atopic dermatitis is confirmed on the basis of the presence of a about a 1.2 fold or greater increase, such as about a 1.5, 2, 2.5, 3, 3.5, 4, 4.5, 5, 10, 20, 50 or 100 or greater fold increase in CCR4 expressing cells, in particular lymphocytes such as T lymphocytes, relative to a sample taken from the same subject at an earlier time point.

Regression or successful treatment may be monitored based upon similar decreases over various time points. For example, regression or successful treatment may be indicated in subjects based upon a decrease of about 3%, such as a decrease of about 4%, about 5%, about 6%, about 7%, about 8%, about 9%, about 10%, about 11%, about 15%, about 20%, about 25%, about 30%, about 35% or more chemokine receptor expressing cells in the sample, as a percentage of total cells in the sample, compared to a sample taken from the same subject at an earlier time point. In other embodiments, regression of inflammatory skin disease such as psoriasis or atopic dermatitis is confirmed on the basis of the presence of a about a 1.2 fold or greater decrease, such as about a 1.5, 2, 2.5, 3, 3.5, 4, 4.5, 5, 10, 20, 50 or 100 or greater fold decrease in chemokine receptor expressing cells, relative to a sample taken from the same subject at an earlier time point.

In specific embodiments, inflammatory skin disease such as psoriasis or atopic dermatitis is monitored on the basis of levels of CCR4 expressing cells, in particular lymphocytes such as T lymphocytes. Regression or successful treatment of the disease may be made in subjects based upon a decrease of about 2%, such as such as a decrease of about 3%, about 4%, about 5%, about 6%, about 7%, about 8%, about 9%, about 10%, about 15% or more CCR4 expressing cells, in particular lymphocytes such as T lymphocytes in the sample, as a percentage of total cells in the sample or by a decrease of about 2%, such as such as a decrease of about 3%, about 4%, about 5%, about 6%, about 7%, about 8%, about 9%, about 10%, about 15% or more CCR4 expressing cells, in particular lymphocytes such as T lymphocytes in the sample, as a percentage of total cells in the sample, compared to a sample taken from the same subject at an earlier time point. In other embodiments, regression of inflammatory skin disease such as psoriasis or atopic dermatitis is confirmed on the basis of the presence of a about a 1.2 fold or greater decrease, such as about a 1.5, 2, 2.5, 3, 3.5, 4, 4.5, 5, 10, 20, 50 or 100 or greater fold decrease in CCR4 expressing cells, in particular lymphocytes such as T lymphocytes, relative to a sample taken from the same subject at an earlier time point.

Suitable software is freely available (such as the R project for statistical computing) to perform the necessary statistical analysis of the data obtained to calculate a useful threshold. The threshold may be set to maximize sensitivity and/or specificity of the test. Performance of the test in these respects may be measured by plotting a receiver operating characteristics (ROC) curve (sensitivity versus specificity). The area under the curve provides an indication of the overall performance of the test. Thus, once thresholds have been set for diagnosing the condition, a separate control experiment does not necessarily have to be run each time a sample is tested. Rather reference can simply be made to the pre-existing thresholds to determine the diagnosis. However, in certain embodiments, the sample is tested together with a control sample taken from a healthy subject to provide a comparator based upon essentially identical experimental conditions. The test sample is generally tested in parallel with the control sample. The test sample level of CCR4, CXCR1, CXCR2, CCR2, CCR6, CCR3, CCR5, CCR1, CCR9 or ChemR23 expressing cells, levels of expression of CCR4, CXCR1, CXCR2, CCR2, CCR6, CCR3, CCR5, CCR1, CCR9 or ChemR23 and/or levels of cells with high expression of CCR4, CXCR1, CXCR2, CCR2, CCR6, CCR3, CCR5, CCR1, CCR9 or ChemR23 (defined as CCR2hi, CCR6hi, CCR3hi, CCR5hi, CCR1hi, CCR9hi or ChemR23hi) can then be compared with that of the control sample to make the diagnosis. A control sample from a disease patient may also be tested in certain embodiments. Reference to controls permits relative levels ("high", "low" etc.) of CCR4, CXCR1, CXCR2, CCR2, CCR6, CCR3, CCR5, CCR1, CCR9 or ChemR23 expressing cells in the test sample to be readily identified and the significance thereof interpreted. Reference to controls also permits relative levels of CCR4, CXCR1, CXCR2, CCR2, CCR6, CCR3, CCR5, CCR1, CCR9 or ChemR23 expression ("high", "low" etc.) within the cell population to be determined and the significance thereof interpreted. Such determination may, for example, indicate the average levels of CCR4, CXCR1, CXCR2, CCR2, CCR6, CCR3, CCR5, CCR1, CCR9 or ChemR23 expression per cell in the test sample.

Thus, in specific embodiments, high or higher levels of one or more of CCR4, CXCR1, CXCR2, CCR2, CCR6, CCR3, CCR5, CCR1, CCR9 and ChemR23 expressing cells or high or higher levels of one or more of CCR4, CXCR1, CXCR2, CCR2, CCR6, CCR3, CCR5, CCR1, CCR9 and ChemR23 expression, for example average CCR4, CXCR1, CXCR2, CCR2, CCR6, CCR3, CCR5, CCR1, CCR9 or ChemR23 expression per cell, or high or higher levels of one or more of CCR2hi, CCR6hi, CCR3hi, CCR5hi, CCR1hi, CCR9hi and ChemR23hi cells correlate with active inflammatory skin disease or more active inflammatory skin disease. Similarly, lower or low levels of one or more of CCR4, CXCR1, CXCR2, CCR2, CCR6, CCR3, CCR5, CCR1, CCR9 and ChemR23 expressing cells, or low or lower levels of one or more of CCR4, CXCR1, CXCR2, CCR2, CCR6, CCR3, CCR5, CCR1, CCR9 and ChemR23 expression, for example average CCR4, CXCR1, CXCR2, CCR2, CCR6, CCR3, CCR5, CCR1, CCR9 or ChemR23 expression per cell, or low or lower levels of one or more of CCR2hi, CCR6hi, CCR3hi, CCR5hi, CCR1hi, CCR9hi and ChemR23hi cells may correlate with a lack of active inflammation or inflammatory skin disease. This may be defined as "less active disease". It can readily be envisaged that control samples may be assessed and levels of CCR4, CXCR1, CXCR2, CCR2, CCR6, CCR3, CCR5, CCR1, CCR9 or ChemR23 expressing cells, levels of expression of CCR4, CXCR1, CXCR2, CCR2, CCR6, CCR3, CCR5, CCR1, CCR9 or ChemR23 and/or levels of cells with high expression of CCR4, CXCR1, CXCR2, CCR2, CCR6, CCR3, CCR5, CCR1, CCR9 or ChemR23 (defined as CCR2hi, CCR6hi, CCR3hi, CCR5hi, CCR1hi, CCR9hi or ChemR23hi) determined across the range of severities of conditions associated with inflammatory skin disease. This may assist in correlating the levels of CCR4, CXCR1, CXCR2, CCR2, CCR6, CCR3, CCR5, CCR1, CCR9 or ChemR23 expressing cells, levels of expression of CCR4, CXCR1, CXCR2, CCR2, CCR6, CCR3, CCR5, CCR1, CCR9 or ChemR23 and/or levels of cells with high expression of CCR4, CXCR1, CXCR2, CCR2, CCR6, CCR3, CCR5, CCR1, CCR9 or ChemR23 (defined as CCR2hi, CCR6hi, CCR3hi, CCR5hi, CCR1hi, CCR9hi or ChemR23hi) in the test sample with the relative severity of the condition.

When monitoring progression of, or monitoring treatment of inflammatory skin disease, the control samples may be taken from the subject at an earlier time point. They may, however, be based upon known reference values as discussed above. Thus, relative levels of CCR4, CXCR1, CXCR2, CCR2, CCR6, CCR3, CCR5, CCR1, CCR9 or ChemR23 expressing cells, relative levels of CCR4, CXCR1, CXCR2, CCR2, CCR6, CCR3, CCR5, CCR1, CCR9 or ChemR23 expression including relative levels of average CCR4, CXCR1, CXCR2, CCR2, CCR6, CCR3, CCR5, CCR1, CCR9 or ChemR23 expression per cell or relative levels of CCR2hi, CCR6hi, CCR3hi, CCR5hi, CCR1hi, CCR9hi or ChemR23hi cells may be with reference to samples taken from the same subject at a different point in time. In certain embodiments, decreased levels of one or more of CCR4, CXCR1, CXCR2, CCR2, CCR6, CCR3, CCR5, CCR1, CCR9 and ChemR23 expressing cells, decreased relative levels of one or more of CCR4, CXCR1, CXCR2, CCR2, CCR6, CCR3, CCR5, CCR1, CCR9 and ChemR23 expression including decreased relative levels of average CCR4, CXCR1, CXCR2, CCR2, CCR6, CCR3, CCR5, CCR1, CCR9 or ChemR23 expression per cell, or decreased relative levels of one or more of CCR2hi, CCR6hi, CCR3hi, CCR5hi, CCR1hi, CCR9hi or ChemR23hi cells correlate with successful treatment. The treatment may be any suitable treatment, but in specific embodiments is a treatment according to the various embodiments of the invention.

When monitoring progression of inflammatory skin disease, increased levels of one or more of CCR4, CXCR1, CXCR2, CCR2, CCR6, CCR3, CCR5, CCR1, CCR9 and ChemR23 expressing cells increased relative levels of one or more of CCR4, CXCR1, CXCR2, CCR2, CCR6, CCR3, CCR5, CCR1, CCR9 and ChemR23 expression including increased relative levels of average CCR4, CXCR1, CXCR2, CCR2, CCR6, CCR3, CCR5, CCR1, CCR9 or ChemR23 expression per cell or increased relative levels of one or more of CCR2hi, CCR6hi, CCR3hi, CCR5hi, CCR1hi, CCR9hi and ChemR23hi cells may indicate the progression of condition or disease. Thus, if levels of one or more of CCR4, CXCR1, CXCR2, CCR2, CCR6, CCR3, CCR5, CCR1, CCR9 and ChemR23 expressing cells, levels of expression of one or more of CCR4, CXCR1, CXCR2, CCR2, CCR6, CCR3, CCR5, CCR1, CCR9 and ChemR23 and/or levels of cells with high expression of one or more of CCR4, CXCR1, CXCR2, CCR2, CCR6, CCR3, CCR5, CCR1, CCR9 and ChemR23 (defined as CCR2hi, CCR6hi, CCR3hi, CCR5hi, CCR1hi, CCR9hi or ChemR23hi) are increased in a sample taken later than a sample from the same patient this may indicate progression of the condition.

Since the levels of one or more of CCR4, CXCR1, CXCR2, CCR2, CCR6, CCR3, CCR5, CCR1, CCR9 and ChemR23 expressing cells, levels of one or more of CCR4, CXCR1, CXCR2, CCR2, CCR6, CCR3, CCR5, CCR1, CCR9 and ChemR23 expression or levels of one or more of CCR2hi, CCR6hi, CCR3hi, CCR5hi, CCR1hi, CCR9hi or ChemR23hi cells are diagnostically relevant, determining such levels in a sample obtained from a subject may influence treatment selection for that subject. Accordingly, in a related aspect the various embodiments of the invention provides a method of selecting a suitable treatment for inflammatory skin disease comprising determining:

a) the levels of one or more of the chemokine receptor CCR4, CXCR1, CXCR2, CCR2, CCR6, CCR3, CCR5, CCR1, CCR9 and ChemR23 expressing cells b) levels of expression of one or more of CCR4, CXCR1, CXCR2, CCR2, CCR6, CCR3, CCR5, CCR1, CCR9 and ChemR23; and/or c) levels of cells with high expression of one or more of CCR4, CXCR1, CXCR2, CCR2, CCR6, CCR3, CCR5, CCR1, CCR9 and ChemR23 in a sample obtained from a subject, wherein high levels of one or more of CCR4, CXCR1, CXCR2, CCR2, CCR6, CCR3, CCR5, CCR1, CCR9 and ChemR23 expressing cells, high levels of expression of one or more of CCR4, CXCR1, CXCR2, CCR2, CCR6, CCR3, CCR5, CCR1, CCR9 and ChemR23 or high levels of cells with high expression of CCR4, CXCR1, CXCR2, CCR2, CCR6, CCR3, CCR5, CCR1, CCR9 or ChemR23 or ChemR23 or increased levels of one or more of CCR4, CXCR1, CXCR2, CCR2, CCR6, CCR3, CCR5, CCR1, CCR9 and ChemR23 expressing cells compared to control, increased levels of expression of one or more of CCR4, CXCR1, CXCR2, CCR2, CCR6, CCR3, CCR5, CCR1, CCR9 and ChemR23 compared to a control or increased levels of cells with high expression of one or more of CCR4, CXCR1, CXCR2, CCR2, CCR6, CCR3, CCR5, CCR1, CCR9 and ChemR23 compared to a control, result in selection of a treatment as defined herein for treatment of the inflammatory skin disease. In certain embodiments, the chemokine receptor expressing cells are high chemokine receptor expressing cells, in particular, high CCR4, CXCR1, CXCR2, CCR2, CCR6, CCR3, CCR5, CCR1, CCR9 or ChemR23 expressing cells. The cells may be lymphocytes such as CCR4 expressing lymphocytes, in particular CCR4 expressing T cells. The cells may be neutrophils such as CXCR1 and/or CXCR2 expressing neutrophils.

In specific embodiments, inflammatory skin disease such as psoriasis or atopic dermatitis is treated on the basis of measuring levels of chemokine receptor expressing cells. Thus, a treatment according to the various embodiments of the invention may be applied based upon the presence of greater than about 10%, greater than about 15%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, inflammatory skin disease such as psoriasis or atopic dermatitis is treated according to the various embodiments of the invention on the basis of the presence of a about a 1.5 fold or greater increase, such as about a 2, 2.5, 3, 3.5, 4, 4.5, 5, 10, 20, 50 or 100 or greater fold increase in chemokine receptor expressing cells, relative to healthy controls.

In specific embodiments, inflammatory skin disease such as psoriasis or atopic dermatitis is treated on the basis of measuring levels of CCR4 expressing cells, in particular lymphocytes such as T lympohcytes. Thus, a treatment according to the various embodiments of the invention may be applied based upon the presence of greater than about 10%, greater than about 15% or greater than about 20% CCR4 expressing T cells in the sample, as a percentage of total cells in the sample. In other embodiments, inflammatory skin disease such as psoriasis or atopic dermatitis is treated according to the various embodiments of the invention on the basis of the presence of a about a 1.5 fold or greater increase, such as about a 2, 2.5, 3, 3.5, 4, 4.5, 5, 10, 20, 50 or 100 or greater fold increase in CCR4 expressing cells, in particular lymphocytes such as T lympohcytes, relative to healthy controls.

For the avoidance of doubt, all embodiments described in respect of the methods of the various embodiments of the invention apply to these aspects mutatis mutandis and are not repeated for reasons of conciseness. Specifically, inflammatory skin disorders may be indicated in conjunction with one or more of the following indicators:

the proportion of the body surface area (BSA) affected and the Psoriasis Area and Severity Index (PASI). The inflammatory skin disease may be selected from psoriasis and atopic dermatitis. In specific embodiments, the sample is a peripheral blood sample.

The methods and medical uses of the various embodiments of the invention thus can be tailored to the need of individual patients or groups of patients on the basis of the various diagnostic methods of the various embodiments of the invention. By removing from the circulation one or more of CCR4, CXCR1, CXCR2, CCR2, CCR6, CCR3, CCR5, CCR1, CCR9 and ChemR23 expressing cells, such as monocytes, lymphocytes, neutrophils, macrophages, eosinophils, dendritic cells and basophils upregulated in various inflammatory skin diseases, an important factor in the inflammatory process of inflammatory skin disease can be controlled. The method of the invention may be effective in treating or reversing conditions such as psoriasis and atopic dermatitis.

H. Treating Multiple Sclerosis

Chemokines are a class of cytokine molecules involved in cell recruitment and activation in inflammation. Chemokines cause chemotaxis and activation of various subpopulations of cells in the immune system. The activity of chemokines is mediated primarily through tight binding to their receptors on the surface of leukocytes. In certain embodiments the present invention is based on the realisation that the interaction between chemokines and cells expressing their receptors may be exploited for the treatment of multiple sclerosis. In particular, various types of multiple sclerosis, such as active and stable relapsing-remitting multiple sclerosis include an inflammatory component. The inventors have determined that targeting increased recruitment of specific chemokine receptor-expressing cells to the site of inflammation presents a new therapeutic approach to treat such conditions. Moreover, in such conditions, chemokine receptor expression on each cell may be increased again providing a therapeutic approach to treat such conditions. It is shown herein that subjects suffering from MS exhibit increased frequency of chemokine receptor expressing cells in the peripheral blood, in particular CCR2 and CCR6 expressing T lymphocytes, compared to healthy controls. It is also shown herein that the CCR2 cells can be removed using a suitable binding reagent, in particular MCP-1 (in biotinylated form) immobilized on a suitable matrix. Similarly, it is shown herein that (the additional) CCR6-expressing cells can be depleted using a suitable binding reagent, in particular CCL20 (MIP-31), in biotinylated form, immobilized on a suitable matrix.

Thus, in certain embodiments the invention serves to reduce the recruitment of inflammatory leukocytes, which express characteristic chemokine receptors, and possibly express characteristic chemokine receptors at increased levels, to sites of inflammation linked to multiple sclerosis such as active and stable relapsing-remitting multiple sclerosis, primary progressive, secondary progressive and progressive relapsing multiple sclerosis. This is achieved using specific binding reagents to capture specific chemokine receptor-expressing inflammatory leukocytes from the patient. Accordingly, in certain embodiments the invention provides in a first aspect a method for treating multiple sclerosis comprising applying peripheral blood from a patient to an apheresis column loaded with a solid support comprising one or more binding reagents capable of specifically binding to one or more chemokine receptors, in particular to the chemokine receptors selected from CCR2, CCR6, CCR3, CCR5, CCR1, CXCR3 and/or CCR9, immobilized directly or indirectly on the support thus removing chemokine receptor, in particular one or more of CCR2, CCR6, CCR3, CCR5, CCR1, CXCR3 and/or CCR9, expressing cells from the peripheral blood of the patient. The peripheral blood from which the chemokine receptor expressing cells have been removed may then be returned to the patient in order to complete the treatment. The invention may thus rely on a continuous extracorporeal circuit in some embodiments. Alternatively, in certain embodiments the invention may comprise steps of obtaining peripheral blood from the patient, applying the peripheral blood to the column and subsequently returning the peripheral blood from which the chemokine receptor expressing cells have been removed to the patient.

As shown herein, suitable binding reagents can be immobilized onto a solid support, either directly or indirectly, to generate an apheresis column suitable for capturing relevant chemokine receptor-expressing cells. Where increased levels of chemokine receptor expression are observed, such cells may be preferably removed from the peripheral blood using the columns of the various embodiments of the invention. Thus, the methods of the various embodiments of the invention may preferably target one or more of CCR2hi, CCR6hi, CCR3hi, CCR5hi, CCR1hi, CXCR3hi and/or CCR9hi cells as defined herein for removal from the peripheral blood. "High" expression may be determined according to standard flow cytometry techniques. The level is measured relative to levels of expression of the chemokine receptor in cells taken from a healthy subject. The attached FIG. 116 provides an example of a gating strategy.

In other embodiments the invention further provides a binding reagent capable of specifically binding to one or more chemokine receptors, in particular to a chemokine receptor selected from CCR2, CCR6, CCR3, CCR5, CCR1, CXCR3 and/or CCR9, for use in the treatment of multiple sclerosis, wherein the one or more binding reagents is immobilized, directly or indirectly, on a solid support contained within an apheresis column, to which is applied peripheral blood from a patient thus removing one or more chemokine receptor/CCR2, CCR6, CCR3, CCR5, CCR1, CXCR3 and/or CCR9 expressing cells from the peripheral blood of the patient. In certain embodiments the invention also provides for use of one or more binding reagents capable of specifically binding to a chemokine receptor/the chemokine receptor CCR2, CCR6, CCR3, CCR5, CCR1, CXCR3 and/or CCR9 for use in the manufacture of an apheresis column for treatment of multiple sclerosis, wherein the one or more binding reagents is immobilized on a solid support contained within the apheresis column, to which is applied peripheral blood from a patient thus removing one or more chemokine receptor/CCR2, CCR6, CCR3, CCR5, CCR1, CXCR3 and/or CCR9 expressing cells from the peripheral blood of the patient.

All embodiments described in respect of the methods of treatment of the various embodiments of the invention apply to these aspects mutatis mutandis and are not repeated for reasons of conciseness. Thus, the following discussion made with reference to the methods of treatment is also applicable to the medical use aspects of the various embodiments of the invention.

In certain embodiments the invention aims to treat multiple sclerosis. By treatment is meant a reduction in the specific chemokine receptor expressing cells in the peripheral blood of the patient. The reduction may comprise a reduction in cells that express chemokine receptors, in particular one or more of CCR2, CCR6, CCR3, CCR5, CCR1, CXCR3 and/or CCR9, at increased levels in diseased patients. The patient is typically a human patient but the term patient may include both human and non-human animal subjects in some embodiments. In the context of the various embodiments of the present invention, this typically involves a reduction in one or more of CCR2, CCR6, CCR3, CCR5, CCR1, CXCR3 and/or CCR9 expressing cells, such as one or more of "CCR2hi, CCR6hi, CCR3hi, CCR5hi, CCR1hi, CXCR3hi and/or CCR9hi" expressing cells, in the peripheral blood of the patient. The CCR2, CCR6, CCR3, CCR5, CCR1, CXCR3 and/or CCR9 expressing cells comprise, consist essentially of or consist of monocytes, lymphocytes, neutrophils, macrophages, eosinophils and basophils, in certain embodiments. In specific embodiments the cells removed in order to treat MS comprise T lymphocytes, in particular CCR2 and/or CCR6 expressing T lymphocytes.

Monocytes are produced by the bone marrow from haematopoietic stem cell precursors called monoblasts. Monocytes may differentiate into macrophages or dendritic cells. Monocytes and their macrophage and dendritic cell progeny serve a number of functions in the immune system including phagocytosis, antigen presentation and cytokine production. Monocytes may be characterized with reference to expression of the cell surface marker CD14, optionally together with CD16. Classical monocytes may be characterized by high level expression of the CD14 cell surface receptor (CD14++CD16− monocyte). Non-classical monocytes may be characterized by low level expression of CD14 and with additional co-expression of the CD16 receptor (CD14+ CD16++ monocyte). Intermediate monocytes may be characterized by high level expression of CD14 and low level expression of CD16 (CD14++CD16+ monocytes). Macrophages are derived from monocytes and are responsible for protecting tissues from foreign substances. They are cells that possess a large smooth nucleus, a large area of cytoplasm and internal vesicles for processing foreign material. The term "macrophage" may refer to a monocyte-derived cell expressing one or more of the following cell surface markers CD14, CD11b, Lysozyme M, MAC-1/MAC-3 and CD68. The term macrophage includes both activated and un-activated macrophages. Activated macrophages may be characterized by expression of one or more of CD69, ENG, FCER2 and IL2RA, HLA-DR, CD86. Un-activated macrophages have not yet received activating signals through for example TLR receptors and therefore they express less activation markers on the cell surface which correlates with lesser maturation. M1 macrophages may be characterized by expression of one or more of CD16+CD32+CD64+ and secrete mainly IL-23 and IL-1, TNF, IL-6 and high levels of IL-12 and in addition effector molecules such as iNOS and ROI. M1 macrophages have cytotoxic features as opposed to M2 macrophages. M2 macrophages may be characterized by expression of one or more of SRA/B+CD163+MR+CD14+ and express TGFβ, IL-10 and IL-1Ra. Tumour associated macrophages (TAMs) share many characteristics with the M2 macrophages and are considered as M2 polarised macrophages. The M1/M2 paradigm can also be found in monocyte subsets where CD14+CD16−CXC3R1low monocytes are considered the "inflammatory" subset and the CD14lowCD16+CXC3R1high are "resident" monocytes.

The three major types of lymphocyte are T cells, B cells and natural killer (NK) cells. The term "T-lymphocyte" includes CD4+ T cells such as T helper cells (Th1 cells and Th2 cells), and CD8+ T cells such as cytotoxic T cells. Th1 cells may be characterized by expression of CCR5 and/or by production of IFN-γ. Th2 cells may be characterized by expression of CCR3 and/or by production of IL-4.

The claimed methods may target eosinophils. The name "eosinophil" derives from the eosinophilic "acid-loving" properties of the cell. Normally transparent, it is this affinity that causes them to appear brick-red after staining with eosin, a red dye, using the Romanowsky method. The staining is concentrated in small granules within the cellular cytoplasm, which contain many chemical mediators, such as histamines and proteins such as eosinophil peroxidase, ribonuclease (RNase), deoxyribonucleases, lipase, plasminogen, and major basic protein. These mediators are released by a process called degranulation following activation of the eosinophil, and are toxic to both parasite and host tissues.

Eosinophils develop and mature in bone marrow. They differentiate from myeloid precursor cells in response to the cytokines interleukin 3 (IL-3), interleukin 5 (IL-5), and granulocyte macrophage colony-stimulating factor (GM-CSF). Eosinophils produce and store many secondary granule proteins prior to their exit from the bone marrow. After maturation, eosinophils circulate in blood and migrate to inflammatory sites in tissues in response to chemokines such as CCL11 (eotaxin-1), CCL24 (eotaxin-2), CCL5 (RANTES) and MCP1/4. Eosinophils may be activated by Type 2 cytokines released from a specific subset of helper T cells (Th2); IL-5, GM-CSF, and IL-3 are important for eosinophil activation as well as maturation. CD44 and CD69 have been shown to represent different types of cell-surface activation markers for human eosinophils. CD69 is absent from "fresh" eosinophils but expressed following activation (using cytokines). CD44 on the other hand is constitutively expressed but expression is significantly up-regulated in response to activation (Matsumoto et al., Am. J. Respir. Cell Mol. Biol., Volume 18, Number 6, June, 1998 860-866). Cell specific markers for eosinophils include CD9 and CDw125.

Basophils may also be known as basophil granulocyte. In contrast to eosinophils, these leukocytes are basophilic, i.e., they are susceptible to staining by basic dyes. Basophils contain large cytoplasmic granules which obscure the cell nucleus under the microscope. However, when unstained, the nucleus is visible and it usually has 2 lobes. Basophils store histamine, which is secreted by the cells upon stimulation.

Basophils have protein receptors on their cell surface that bind IgE, an immunoglobulin involved in macroparasite defense and allergy. It is the bound IgE antibody that confers a selective response of these cells to environmental substances, for example, pollen proteins or helminth antigens. Recent studies in mice suggest that basophils may also regulate the behavior of T cells and mediate the magnitude of the secondary immune response. Basophils may display an immunophenotype based upon expression (or lack thereof, indicated as "+" or "−" respectively of one or more of the following markers: FcεRI+, CD123, CD49b(DX-5)+, CD69+, Thy-1.2+, 2B4+, CD11bdull, CD117(c-kit)−, CD24−, CD19−, CD80−, CD14−, CD23−, Ly49c−, CD122−, CD11c−, Gr-1−, NK1.1−, B220−, CD3−, γδTCR−, βTCR−, α4 and β4-integrin negative.

When activated, basophils degranulate to release histamine, proteoglycans (e.g. heparin and chondroitin), and proteolytic enzymes (e.g. elastase and lysophospholipase). They also secrete lipid mediators like leukotrienes, and several cytokines. Histamine and proteoglycans are pre-stored in the cell's granules while the other secreted substances are newly generated. Each of these substances contributes to inflammation. Recent evidence suggests that basophils are an important source of the cytokine, interleukin-4, perhaps more important than T cells. Interleukin-4 is considered one of the critical cytokines in the development of allergies and the production of IgE antibody by the immune system. There are other substances that can activate basophils to secrete which suggests that these cells have other roles in inflammation.

The various embodiments of the methods of the invention may involve specific binding interactions with any one or more of these further cell-surface (and cell-specific) markers in addition to the removal based upon binding to CCR2, CCR6, CCR3, CCR5, CCR1, CXCR3 and/or CCR9. Suitable binding reagents can be prepared to specifically bind to these cell-surface markers. The discussion of CCR2, CCR6, CCR3, CCR5, CCR1, CXCR3 and/or CCR9 specific binding reagents thus applies mutatis mutandis.

CCR2, CCR6, CCR3, CCR5, CCR1, CXCR3 and/or CCR9 expressed on these aforementioned cells are bound by chemokines such as monocyte chemoattractant protein-1 (MCP-1), MCP-2, MCP-3, MCP-4, MCP-5, MIP-3alpha, MIG (CXCL9), IP10 (CXCL10), CXCL11 (I-TAC) and RANTES. Eotaxin (aka CCL11 binds CCR3 only), eotaxin-2 (aka CCL24 binds CCR3 only), eotaxin-3 (aka CCL26 binds CCR3 only), RANTES (CCL5 is promiscuous CCR1, CCR3, CCR5), MCP-2, (aka CCL8 is promiscuous) MCP-3 (aka CCL7 is promiscuous), MCP-4 (aka CCL13 is promiscuous), MIP-1α (aka CCL3 promiscuous CCR1, CCR3, CCR5), MEC (CCL28 binds CCR3 and CCR10), HCC-2 (CCL15 binds CCR1 and CCR3). Chemokines MIP1g (CCL9), MRP-2 (CCL10), Mlp-1d (CCL15) and CCL23 appear to bind CCR1 only, Chemokines Eotaxin, Eotaxin-2 only bind CCR3, Chemokine MIP1b (CCL4) only binds CCR5. MCP-5 binds CCR2 only.

MCP-1 (CCL2) is a major chemoattractant for monocytes and memory T cells by means of their binding to its specific cell-surface receptor, CC-chemokine receptor-2 (CCR2). CCR2 is the gene symbol approved by the HUGO Gene Nomenclature Committee for chemokine (C—C motif) receptor 2. The HGNC ID for this gene is 1603. The gene is located at chromosome position 3p21. The previous symbol and name for the gene is CMKBR2. Synonyms for this gene include CC-CKR-2, CD192, CKR2, FLJ78302 and MCP-1-R. The NCBI Reference Sequence is NM_001123041.2 as available on 13 Jun. 2011, which is incorporated herein by reference in its entirety.

CCR1 is the gene symbol approved by the HUGO Gene Nomenclature Committee for chemokine (C—C motif) receptor 1. The HGNC ID for this gene is 1602. The gene is located at chromosome position 3p21. The previous symbol and name CMKBR1, SCYAR1. Synonyms for this gene include CD191, CKR-1, MIP1aR. The Entrez Gene reference sequence for CCR1 is 1230 as available on 13 Jun. 2011, which is incorporated herein by reference in its entirety.

CCR3 is the gene symbol approved by the HUGO Gene Nomenclature Committee for chemokine (C—C motif) receptor 3. The HGNC ID for this gene is 1604. The gene is located at chromosome position 3p21.3. The previous symbol and name for the gene is CMKBR3. Synonyms for this gene include CC-CKR-3, CD193 and CKR3. The Genbank reference sequence for CCR3 is AF247361.1 as available on 13 Jun. 2011, which is incorporated herein by reference in its entirety.

CCR5 is the gene symbol approved by the HUGO Gene Nomenclature Committee for chemokine (C—C motif) receptor 5. The HGNC ID for this gene is 1605. The gene is located at chromosome position 3p21. The previous symbol and name for the gene is CMKBR5. Synonyms for this gene include CC-CKR-5, CD195 CKR-5, IDDM22 and CKR5. The Entrez Gene reference sequence for CCR5 is 1234 as available on 13 Jun. 2011, which is incorporated herein by reference in its entirety.

CCR6 is the gene symbol approved by the HUGO Gene Nomenclature Committee for chemokine (C—C motif) receptor 6. The HGNC ID for this gene is 1607. The gene is located at chromosome position 6q27. The previous symbol and name for the gene is STRL22. Synonyms for this gene include BN-1, CD196, CKR-L3, CMKBR6, DCR2, DRY-6, GPR-CY4, GPR29. The Genbank reference sequence for CCR6 is U68030.1 as available on 13 Jun. 2011, which is incorporated herein by reference in its entirety.

CCR9 is the gene symbol approved by the HUGO Gene Nomenclature Committee for chemokine (C—C motif) receptor 9. The HGNC ID for this gene is 1610. The gene is located at chromosome position 3p22. The previous symbol and name for the gene is GPR28. Synonyms for this gene include CDw199, GPR-9-6. The Genbank reference sequence for CCR9 is AJ132337.1 as available on 13 Jun. 2011, which is incorporated herein by reference in its entirety.

CXCR3 is the gene symbol approved by the HUGO Gene Nomenclature Committee for chemokine (C—X—C motif) receptor 3. The HGNC ID for this gene is 4540. The gene is located at chromosome position Xq13. The previous symbol and name for the gene is "G protein-coupled receptor 9", GPR9. Synonyms for this gene include CD183, CKR-L2, CMKAR3, IP10-R and MigR. The Genbank reference sequence for CXCR3 is U32674.1 as available on 13 Jun. 2011, which is incorporated herein by reference in its entirety.

Treatment according to the various embodiments of the invention may result in alleviation or amelioration of symptoms, prevention of progression, regression of the condition, or complete recovery. Measurable parameters of successful treatment include one or more, up to all, of Multiple Sclerosis Severity Score or MRI. In specific embodiments, a single treatment is sufficient to cause a depletion of around 10%, 20%, 30%, 40%, 50%, 60% or 70%, or higher up to 80%, 90%, 95% or more, or any range of values between and including these amounts, of one or more of a specific chemokine receptor, in particular one or more of CCR2, CCR6, CCR3, CCR5, CCR1, CXCR3 and/or CCR9, expressing cells from the peripheral blood of the patient. In specific embodiments, at least around 50% depletion is achieved in a single treatment. Thus, successful treatment may be defined with reference to depletion of one or more of CCR2, CCR6, CCR3, CCR5, CCR1, CXCR3 and/or CCR9 expressing cells. Treatment may lead to depletion of between approximately 100 and 500 million CCR2, CCR6, CCR3, CCR5, CCR1 and/or CCR9 expressing cells, such as monocytes, in certain embodiments and more particularly to about 100, 150, 200, 250, 300, 350, 400, 450, or 500 million CCR2, CCR6, CCR3, CCR5, CCR1 and/or CCR9 expressing cells.

By binding to the column through the binding reagent-chemokine receptor interaction, chemokine receptor expressing cells are immobilized. These immobilized cells express further unoccupied chemokine receptors, which may be of the same or different type to those used for capture. These additional chemokine receptors may permit circulating chemokines which contribute to the inflammatory condition to be captured from the peripheral blood. Thus, a reduction in circulating (specific) chemokine levels may provide a measure of successful treatment.

The duration of treatment may be readily determined by one skilled in the art and will depend upon factors such as the flow rate of the peripheral blood. Duration of treatment may be tied into monitoring of the treatment itself, with the treatment considered complete once a measurable parameter of treatment has reached a defined threshold. Any suitable parameter may be employed as discussed herein. Thus, for example, treatment may be considered complete when a reduction in one or more of CCR2, CCR6, CCR3, CCR5, CCR1, CXCR3 and/or CCR9 expressing cells, such as a 50% reduction in one or more of CCR2, CCR6, CCR3, CCR5, CCR1, CXCR3 and/or CCR9 expressing cells, has been achieved. The apheresis system may be operated at a flow rate of around 10-80 mL/min, or more specifically between around 20-70 mL/min, or between around 30-60 mL/min. In specific embodiments, the treatment is performed for a period of around 10, 20, 30, 40, 50, 60, 70, 80, 90, 100, 110, 120 etc., or any range of values between and including these amounts, minutes. The treatment is typically not aimed to remove all of the cells expressing the chemokine receptor in the peripheral blood, as a basal level of those cells is required in healthy subjects. However, it has been found that only low blood volumes need to be applied to the columns of the various embodiments of the invention in order to achieve effective levels of depletion of the chemokine receptor-expressing cells. Thus, in certain embodiments, around 10-80% or more specifically around 20, 30, 40 or 50%, or any range of values between and including these amounts, of the patient's blood is applied to the column in a single treatment. The volume of blood circulated through the apheresis column or system may be in the region of around 1000-3000 ml, such as around 1000, 1200, 1400, 1600, 1800 or 2000 ml or any range of values between and including these amounts. The treatment may be considered complete once this volume of blood has been circulated. The patient may be administered anticoagulants prior to each treatment session. A suitable solution, such as a sterile saline solution, optionally including an anticoagulant such as Heparin, may be used for priming the apheresis (extracorporeal) system. An additional volume of anticoagulant may be added to the circuit at the start of each treatment session, for example as a bolus injection.

In certain embodiments the invention relies upon a binding reagent which is capable of specifically binding to a chemokine receptor. This specific binding reaction permits cells expressing the chemokine receptor to be removed from the peripheral blood of the patient when the blood is passed over the solid support upon or within which the binding reagent is immobilized. Specific chemokine receptors of interest include CCR2, CCR6, CCR3, CCR5, CCR1, CXCR3 and/or CCR9. The binding reagent can be any binding reagent capable of specifically binding to the receptor in question. By "specific binding" is meant that the binding reagent displays sufficient specificity of binding and appropriate binding affinity/kinetics to permit removal of cells expressing one or more of CCR2, CCR6, CCR3, CCR5, CCR1, CXCR3 and/or CCR9 from the peripheral blood. Whilst it is not precluded that the binding reagent is capable of binding to other molecules, such as other chemokine receptors, the binding reagent will preferentially bind to cells expressing one or more of CCR2, CCR6, CCR3, CCR5, CCR1, CXCR3 and/or CCR9 and in particular to cells expressing increased levels of one or more of CCR2, CCR6, CCR3, CCR5, CCR1, CXCR3 and/or CCR9 (as defined further herein). The binding reagent capable of specifically binding to CCR2, CCR6, CCR3, CCR5, CCR1, CXCR3 and/or CCR9 may be either an agonist or an antagonist of CCR2, CCR6, CCR3, CCR5, CCR1, CXCR3 and/or CCR9. As the disease condition relies upon up-regulation of expression of or signaling via CCR2, CCR6, CCR3, CCR5, CCR1, CXCR3 and/or CCR9, in certain embodiments the binding reagent capable of specifically binding to CCR2, CCR6, CCR3, CCR5, CCR1, CXCR3 and/or CCR9 is an antagonist of CCR2, CCR6, CCR3, CCR5, CCR1, CXCR3 and/or CCR9, respectively. Chemokines are typically, although not necessarily exclusively (particularly in the case of truncated or modified forms) agonists of their cognate receptor and serve to activate the cells expressing the relevant receptor, as would be appreciated by one skilled in the art. Antibodies against the relevant chemokine receptor are generally considered to be antagonists, as would be appreciated by one skilled in the art. Specific examples of binding reagents include proteins or polypeptides, such as antibodies and receptor ligands, in particular chemokines. The binding reagent may be a nucleic acid molecule in certain embodiments. In some embodiments, the nucleic acid is an aptamer. Nucleic acid aptamers are polynucleotides of approximately 15-40 nucleotides long. Nucleic acid aptamers can be made using the SELEX process (systemic evolution of ligands by exponential enrichment) or any other process known to those of skill in the art.

In other embodiments, the binding reagent may be a peptide, and in certain instances, a peptide aptamer. Peptide aptamers are artificial recognition molecules that consist of a variable peptide sequence inserted into a constant scaffold protein (Baines I C, Colas P. Peptide aptamers as guides for small molecule drug discovery. Drug Discov Today. 2006; 11:334-341, incorporated herein by reference). A number of methodologies, such as phage display, ribosome display and yeast two-hybrid screening systems are available for screening a library of potential peptide-based binding agents. Similarly protein scaffolds based on domains such as fibronectins, ankyrin repeats, protein A, SH3 domains, lipocalins and ubiquitin can be used as the binding agent. Again a number of technologies such as phage display and ribosome display are available for screening a library of protein-based binding agents. Similarly, libraries of candidate chemical compounds can be screened for specific binding to the relevant chemokine receptor using suitable screening techniques known in the art, which may be high throughput screens in certain embodiments. The candidate binding agent may be immobilized on a solid support and the ability of the agent to specifically retain cells expressing the chemokine receptor of interest or labelled chemokine receptors determined. A range of cell types may be applied to the solid supports to confirm specificity of binding, or alternatively a mixed sample (such as peripheral blood) may be applied to the solid support. Retention of the cell type of interest (expressing the appropriate chemokine receptor) can be confirmed to identify suitable binding agents. A range of small-molecule antagonists of CCR-2 are discussed by Xia M and Sui Z in Expert Opin Ther Pat. 2009 March; 19 (3):295-303—Recent developments in CCR2 antagonists, and incorporated herein by reference.

In the context of the various embodiments of the present invention the term "chemokine" also comprises biotinylated or otherwise labelled chemokines. The term "chemokine" also comprises modified and truncated versions of the chemokine and chemokine fragments with the proviso that the modified or truncated form retains its ability to bind to its cognate receptor (and thus remains functional in the context of various embodiments of the invention). The chemokine does not necessarily need to retain biological activity as it is specific binding affinity for CCR2, CCR6, CCR3, CCR5, CCR1, CXCR3 and/or CCR9 that is required. In certain embodiments, the chemokine lacks biological activity, for example in terms of activation of the (CCR2, CCR6, CCR3, CCR5, CCR1, CXCR3 and/or CCR9) receptor. Modifications may be made to improve protein synthesis, for example uniformity of product and yield. As known to those skilled in the art, exemplary modifications may comprise amino acid additions, substitutions, deletions or other modifications to one or more amino acids in the chemokine. Modifications may comprise substitution of the wild type amino acid with non-natural amino acids such as norleucine (NLeu) and derivatized amino acids such as pyroglutamic acid (pyroGlu). Such modifications may be made to minimize side-product formation during storage and use of the columns of the various embodiments of the invention. Modifications may be made to improve labelling, for example inclusion of a polyethylene glycol (PEG) spacer to facilitate biotinylation. The biotinylation and/or conjugation with fluorochromes or other labelling groups of the chemokine is performed in a manner which does not substantially affect the receptor binding capacity. Site specific biotinylation or other labelling is preferred as non-selective labelling of chemokines may compromise receptor binding activity. Bioinylation or other labelling is generally preferred at or towards the C-terminus of the protein as the inventors have found that modifications in this area are generally well tolerated (in terms of a minimal effect on receptor binding capability). Biotinylation may be carried out site-specifically at any suitable amino acid. Examples of suitable amino acids include lysine, diaminopropionic acid and ornithine. Generally, reference may be made to Natarajan S et al, Int. J. Pept. Protein Res., 1992, 40, 567-74; Baumeister B, Int. J. Peptide Res. And Therapeutics, 2005, 11, 139-141; Bioconjugate techniques 2nd edition, Greg T. Hermanson, incorporated by reference herein in its entirety.

Truncations may involve deletion of either N or C terminal amino acids as appropriate, or both. Typically, the truncated version will retain the residues required for the chemokine to fold correctly, for example to retain a chemokine fold structure, consistent with the requirement that a truncated version must retain the ability to bind to the relevant receptor (expressed by (on the surface of) a leukocyte). Chemokine molecules typically include disulphide bonds between the 1st and 3rd and 2nd and 4th cysteine residues respectively, as would be understood by one skilled in the art. Where sequences are presented herein, it is assumed that these disulphide bonds will form in the folded protein (unless otherwise stated). Truncated versions may comprise anywhere between 1 and 100 less amino acids, such as 1, 2, 3, 4, 5 etc amino acids, than the wild type amino acid sequence in certain embodiments. Of course, truncated versions may comprise further modification as detailed herein. The modified or truncated version may have 40%, 45%, 50%, 55%, 60%, 65%, 70%, 75%, 80%, 85%, 90%, 95% or more overall amino acid sequence identity with the full length wild type chemokine (where a deletion is counted as a difference in amino acid sequence) in certain embodiments. Over the common sequence between the molecules (i.e the amino acids that have not been deleted), there may be 80%, 85%, 90%, 91%, 92%, 93%, 94%, 95%, 96%, 97%, 98% or 99% amino acid sequence identity in certain embodiments. Sequence identity may be determined using known algorithms, such as BLAST or GAP analysis (GCG Program) (applying default settings), which are freely available. Chemokines may lack the N-terminal signal peptide which is cleaved off during synthesis in vivo.

Specific chemokines useful in the various embodiments of the present invention include MCP-1, MCP-2, MCP-3, MCP-4, MCP-5, MIP-3alpha, MIG (CXCL9), IP10 (CXCL10), CXCL11 (I-TAC), CCL25 and RANTES. Both MCP-1 and MCP-5 bind solely to the chemokine receptor CCR2 and so these chemokines may be preferred in some embodiments. Each chemokine is able to bind to a chemokine receptor implicated in multiple sclerosis.

Chemokines MIP1g (CCL9), MRP-2 (CCL10), MIp-1d (CCL15) and CCL23 appear to bind CCR1 only, Chemokines Eotaxin, Eotaxin-2 only bind CCR3, Chemokine MIP1b (CCL4) only binds CCR5, Chemokine MIP3a (CCL20) only binds to CCR6, More specifically, each of MCP-1, MCP-2, MCP-3, MCP-4, MCP-5, MIP-3alpha, MIG (CXCL9), IP10 (CXCL10), CXCL11 (I-TAC) and RANTES are useful for removing one or more of CCR2, CCR6, CCR3, CCR5, CCR1, CXCR3 and/or CCR9 expressing cells from the blood of a patient. In specific embodiments, the chemokine is selected from MCP-1, MCP-2, MCP-3, MCP-4 and MCP-5 and the chemokine receptor is CCR2. In other embodiments, the chemokine is MIP-3a and the chemokine receptor is CCR6. In still further embodiments, the chemokine is RANTES and the chemokine receptor is selected from CCR3, CCR1, CCR5 or CCR9.

The chemokines described in greater detail herein (with reference to the relevant figures and amino acid sequences, as set forth in the SEQ ID NOs and the corresponding experimental examples) may each be applied according to the present invention.

CCL2 is the gene symbol approved by the HUGO Gene Nomenclature Committee for chemokine (C—C motif) ligand 2, also known as MCP-1. The HGNC ID for this gene is 10618. The gene is located at chromosome position 17q11.2-q21.1. The previous symbol and name for the gene is SCYA2 "small inducible cytokine A2 (monocyte chemotatic protein 1, homologus to mouse Sig-je)". Synonyms for this gene include GDCF-2, HC11, MCP1, MGC9434, SMC-CF, "monocyte chemoattractant protein-1", "monocyte chemotactic and activating factor", "monocyte chemotactic protein 1, homologous to mouse Sig-je", "monocyte secretory protein JE", "small inducible cytokine subfamily A (Cys-Cys), member 2". The Genbank reference sequence for CCL2 is BC009716.1 as available on 13 Jun. 2011, which is incorporated herein by reference in its entirety.

CCL8 is the gene symbol approved by the HUGO Gene Nomenclature Committee for chemokine (C—C motif)

ligand 8, also known as MCP-2. The HGNC ID for this gene is 10635. The gene is located at chromosome position 17q11.2. The previous symbol and name for the gene is SCYA8, "small inducible cytokine subfamily A (Cys-Cys), member 8 (monocyte chemotactic protein 2)". Another synonym for this gene is HC14. The Genbank reference sequence for CCL8 is X99886.1 as available on 13 Jun. 2011, which is incorporated herein by reference in its entirety.

CCL7 is the gene symbol approved by the HUGO Gene Nomenclature Committee for chemokine (C—C motif) ligand 7, also known as MCP-3. The HGNC ID for this gene is 10634. The gene is located at chromosome position 17q11.2-q12. The previous symbol and name for the gene is SCYA6, SCYA7, "small inducible cytokine A7 (monocyte chemotactic protein 3)". Synonyms for this gene include FIC, MARC, MCP-3, MCP3, NC28, "monocyte chemoattractant protein 3", "monocyte chemotactic protein 3". The Genbank reference sequence for CCL7 is AF043338 as available on 13 Jun. 2011, which is incorporated herein by reference in its entirety.

CCL13 is the gene symbol approved by the HUGO Gene Nomenclature Committee for chemokine (C—C motif) ligand 13, also known as MCP-4. The HGNC ID for this gene is 10634. The gene is located at chromosome position 17q11.2-q12. The previous symbol and name for the gene is SCYA6, SCYA7, "small inducible cytokine A7 (monocyte chemotactic protein 3)". Synonyms for this gene include FIC, MARC, MCP-3, MCP3, NC28, "monocyte chemoattractant protein 3", "monocyte chemotactic protein 3". The Genbank reference sequence for CCL13 is AJ001634 as available on 13 Jun. 2011, which is incorporated herein by reference in its entirety.

MCP-5 is a mouse chemokine in the CC chemokine family. It is also known as Chemokine (C—C motif) ligand 12 (CCL12) and, due to its similarity with the human chemokine MCP-1, sometimes it is called MCP-1-related chemokine. The gene for MCP-5 is found in a cluster of CC chemokines on mouse chromosome 11. The NCBI reference sequence for CCL12 is NC_000077.5 as available on 13 Jun. 2011, which is incorporated herein by reference in its entirety.

CCL20 is the gene symbol approved by the HUGO Gene Nomenclature Committee for chemokine (C—C motif) ligand 20, also known as MIP-3alpha. The HGNC ID for this gene is 10619. The gene is located at chromosome position 2q33-q37. The previous symbol and name for the gene is SCYA20, "small inducible cytokine subfamily A (Cys-Cys), member 20". Synonyms for this gene include CKb4, exodus-1, LARC, MIP-3a, ST38. The Genbank reference sequence for CCL20 is D86955.1 as available on 13 Jun. 2011, which is incorporated herein by reference in its entirety.

CCL5 is the gene symbol approved by the HUGO Gene Nomenclature Committee for chemokine (C—C motif) ligand 5, also known as RANTES. The HGNC ID for this gene is 10632. The gene is located at chromosome position 17q11.2-q12. The previous symbol and name for the gene is D17S136E, SCYA5, "small inducible cytokine A5 (RANTES)". Synonyms for this gene include "beta-chemokine RANTES", MGC17164, RANTES, "regulated upon activation, normally T-expressed, and presumably secreted", "SIS-delta", SISd, "small inducible cytokine subfamily A (Cys-Cys), member 5", "T-cell specific protein p288", "T-cell specific RANTES protein", TCP228. The Genbank reference sequence for CCL5 is AF043341.1 as available on 13 Jun. 2011, which is incorporated herein by reference in its entirety.

CXCL11 is the gene symbol approved by the HUGO Gene Nomenclature Committee for chemokine (C—X—C motif) ligand 11. The HGNC ID for this gene is 10638. The gene is located at chromosome position 4q21. The previous symbol and name for the gene is SCYB9B, SCYB11, "small inducible cytokine subfamily B (Cys-X-Cys), member 11". Synonyms for this gene include b-R1, H174, I-TAC, IP-9. The Genbank reference sequence for CXCL11 is U66096.1 as available on 13 Jun. 2011, which is incorporated herein by reference in its entirety.

CCL25 is the gene symbol approved by the HUGO Gene Nomenclature Committee for chemokine (C—C motif) ligand 25. The HGNC ID for this gene is 10624. The gene is located at chromosome position 19p13.2. The previous symbol and name for the gene is SCYA25, "small inducible cytokine subfamily A (Cys-Cys), member 25". Synonyms for this gene include "Ck beta-15", Ckb15, TECK, "TECK-var", "thymus expressed chemokine". The Genbank reference sequence for CCL25 is U86358.1 as available on 13 Jun. 2011, which is incorporated herein by reference in its entirety.

CXCL10 is the gene symbol approved by the HUGO Gene Nomenclature Committee for chemokine (C—X—C motif) ligand 10. The HGNC ID for this gene is 10637. The gene is located at chromosome position 4q21. The previous symbol and name for the gene is INP10, SCYB10, "small inducible cytokine subfamily B (Cys-X-Cys), member 10". Synonyms for this gene include C7, crg-2, gIP-10, IFI10, IP-10, mob-1. The Genbank reference sequence for CXCL10 is X02530.1 as available on 13 Jun. 2011, which is incorporated herein by reference in its entirety.

Examples of suitable modified chemokines of the various embodiments of the invention containing modifications and/or truncations and specifically adapted for use in the invention are described in detail herein. MCP-1 has been produced with residue 75, which may be a lysine (or any other amino acid such as ornithine and diaminopropionic acid, that may be biotinylated), as the site of biotinylation on the chemokine (numbering based upon the mature protein having the amino acid sequence of SEQ ID NO: 145). Biotinylation permits immobilization of MCP-1 on a solid support (via a biotin-avidin interaction). The basic amino acid sequence of MCP-1, including a 23 amino acid leader sequence is set forth as SEQ ID NO: 144. The amino acid sequence of the mature protein is set forth as SEQ ID NO: 145. The inventors have determined that chemokines may display improved binding properties where the chemokine is biotinylated via a spacer group. The spacer may prevent the biotin group from impacting on the binding affinity of the chemokine. Any suitable spacer group may be employed. Further modifications may provide the molecule with advantageous properties. The invention also relates to derivatives of truncated MCP-1 chemokines. The amino acid sequence of the truncated version is set forth as SED ID NO: 146.

Accordingly, in certain embodiments the invention also provides a modified MCP-1 chemokine comprising, consisting essentially of or consisting of the amino acid sequence set forth as SEQ ID NO: 144, SEQ ID NO: 145 or SEQ ID NO: 146 in which one or more of the following modifications have been made:

a) the glutamine residue 1 of SEQ ID NO: 145 has been replaced with pyroglutamine b) the C terminus is produced as an amide derivative (this may be achieved by synthesis on an amide linker)

c) the (C terminal region) residue at position 98 of SEQ ID NO: 144 or position 75 of SEQ ID NO: 145 or position 67 of SEQ ID NO: 146, which may be a lysine or ornithine residue, is biotinylated, optionally via a spacer group, in order to permit immobilization of the chemokine on a solid support; and/or d) the methionine residue at position 87 of SEQ ID NO: 144 or position 64 of SEQ ID NO: 145 or position 56 of SEQ ID NO: 146 has been replaced with norleucine.

The (C terminal region) amino acid, which may be a lysine residue or a functional equivalent, at position 98 of SEQ ID NO: 144 or position 75 of SEQ ID NO: 145 or position 67 of SEQ ID NO: 146 may be biotinylated via a suitable spacer group, such as a polyethylene glycol (PEG) spacer group, in order to permit immobilization of the chemokine on a solid support. In specific embodiments, the PEG spacer is 3,6-dioxo aminooctanoic acid. The sequence and biotinylation of the modified MCP-1 chemokines of the invention are shown in FIGS. 110 to 112 respectively. The modified MCP-1 chemokines may be agonists or antagonists of CCR2 activity. They can be tested for activity in a suitable assay, such as cell-based assays. In particular, agonist and antagonist properties may be determined in functional cell-based assay on human CCR2 receptor.

MCP-5 only binds CCR2 and should be selective in its removal of CCR2 expressing cells. The full length amino acid sequence, including the signal peptide, is set forth as SEQ ID NO: 147. The amino acid sequence of N-terminal processed MCP-5 chemokine is 82 amino acids long and is set forth as SEQ ID NO: 148. An amino acid sequence alignment suggests that MCP-5 has a C-terminal extension when compared to the amino acid sequence of MCP-1. The results of this alignment are shown in FIG. 113. C-terminal truncated versions of MCP-5 can thus be synthesised. This truncated version will comprise, consist essentially of or consist of MCP-5 residues 1-76, set forth as SEQ ID NO: 149.

Accordingly, in certain embodiments the invention also provides a modified MCP-5 chemokine comprising the amino acid sequence set forth as SEQ ID NO: 147, SEQ ID NO: 148 or SEQ ID NO: 149 in which the isoleucine residue at position 97 of SEQ ID NO: 147 or at position 75 of SEQ ID NO: 148 or SEQ ID NO: 149 has been replaced with lysine (or a functional equivalent such as ornithine or diaminopropionic acid, which can be biotinylated). In certain embodiments, the modified MCP-5 chemokine comprises, consists essentially of or consists of the amino acid sequence of SEQ ID NO: 150. The modified MCP-5 chemokine may be biotinylated at the lysine (or a functional equivalent) residue at position 97 of SEQ ID NO: 147 or at position 75 of SEQ ID NO: 148 or SEQ ID NO: 149. Biotinylation may be via a suitable spacer group. Specific examples of the spacer group include a PEG spacer, optionally 3,6-dioxo aminooctanoic acid. In some embodiments, the C terminus is produced as an amide derivative. This may be achieved by synthesis on an amide linker. In certain embodiments, the modified MCP-5 chemokine comprises, consists essentially of or consists of the sequence and biotinylation shown in FIG. 114. The modified MCP-5 chemokine may be an agonist or an antagonist of CCR2 activity. They can be tested for activity in a suitable assay, such as cell-based assays. In particular, agonist and antagonist properties may be determined in a functional cell-based assay on human CCR2 receptor.

An example of a CCL25 chemokine of the various embodiments of the invention containing both modifications and a truncation and specifically adapted for use in the invention is described in WO2010/029317, incorporated herein by reference. Reference may also be made to Examples below and SEQ ID NOs 166 to 168.

A further example of a chemokine of the various embodiments of the invention containing modifications and specifically adapted for use in the invention is described in detail herein (see Examples below). The modified CCL2 (MCP-1) corresponds to residues 1 to 76 of the full length mature protein (and lacks the N-terminal signal peptide of 23 amino acids, which is cleaved off) and thus retains the chemokine fold. The Gln at the N-terminus of the protein (Gln1) is substituted with pyroglutamine to prevent mixed species of N-terminal Gln and pyroGlu being generated (SEQ ID NO: 151). This improves the yield of synthesis and ensures a homogeneous chemokine preparation through column manufacture and use. FmocLys(ivDde)-OH is incorporated as residue 75 to facilitate site-specific labelling at this position of the protein (SEQ ID NO: 152). A suitable spacer, such as a PEG spacer, may be incorporated between the ε-amino functionality and the biotin. Thus, the invention relates to a modified chemokine, including a biotinylated version, which comprises, consists essentially of or consists of the amino acid sequence of SEQ ID NO: 153:

H-XPDAINAPVTCCYNFTNRKISVQRLASYRRITSSKCPKEAVIFKTIV

AKEICADPKQKWVQDSMDHLDKQTQTPXT-NH2

X1=pyroGlu (but may remain as Gln in some embodiments)

X75=an amino acid residue that can be biotinylated, such as lysine, ornithine or diaminopropionic acid and optionally is biotinylated, optionally via a spacer molecule such as PEG, e.g. K(PEG-Biotin).

A further example of a chemokine of the various embodiments of the invention containing modifications and specifically adapted for use in the invention is described in detail herein (see Examples below). The modified CCL8 (MCP-2) corresponds to residues 1 to 76 of the full length mature protein (and lacks the N-terminal signal peptide of 23 amino acids, which is cleaved off) and thus retains the chemokine fold. The Gln at the N-terminus of the protein is subject to pyroGlu formation under physiological conditions. Thus Gln1 of the sequence is substituted with pyroglutamine to prevent mixed species of N-terminal Gln and pyroGlu being generated (SEQ ID NO: 154). This improves the yield of synthesis and ensures a homogeneous chemokine preparation through column manufacture and use. FmocLys(ivDde)-OH is incorporated as residue 75 to facilitate site-specific labelling at this position of the protein (SEQ ID NO: 155). The naturally occurring lysine at position 75 is modified through biotinylation. A suitable spacer, such as a PEG spacer, may be incorporated between the ε-amino functionality and the biotin (SEQ ID NO: 156):

Thus, in certain embodiments the invention also relates to a modified chemokine comprising, consisting essentially of or consisting of the amino acid sequence of SEQ ID NO: 156:

XPDSVSIPITCCFNVINRKIPIQRLESYTRITNIQCPKEAVIFKTKRGK

EVCADPKERWVRDSMKHLDQIFQNLXP

X1=pyroGlu (but may remain as Gln in some embodiments)

X75=an amino acid residue that can be biotinylated, such as lysine, ornithine or diaminopropionic acid and optionally is biotinylated, optionally via a spacer molecule such as PEG, e.g. K(PEG-Biotin).

A further example of a chemokine of the various embodiments of the invention containing modifications and specifically adapted for use in the invention is described in detail herein (see Examples below). The modified CCL11 (Eotaxin) corresponds to residues 1 to 74 of the full length mature protein (and lacks the N-terminal signal peptide of 23 amino acids, which is cleaved off) and thus retains the chemokine fold (SEQ ID NO: 157). The lysine at position 73 may be modified through biotinylation. FmocLys(ivDde)-OH is incorporated as residue 73 to facilitate site-specific labelling at this position of the protein (SEQ ID NO: 158). A suitable spacer, such as a PEG spacer, may be incorporated between the ε-amino functionality and the biotin. The biotinylated version comprises, consists essentially of or consists of the amino acid sequence of SEQ ID NO: 159.

Thus, in other embodiments the invention also relates to a modified chemokine comprising, consisting essentially of or consisting of the amino acid sequence of SEQ ID NO: 157 or SEQ ID NO: 159:

SEQ ID NO: 157
GPASVPTTCCFNLANRKIPLQRLESYRRITSGKCPQKAVIFKTKLAKDI

CADPKKKWVQDSMKYLDQKSPTPXP

X is an amino acid residue that can be biotinylated, such as lysine, ornithine or diaminopropionic acid and optionally is biotinylated, optionally via a spacer molecule such as PEG, e.g. K(PEG-Biotin).

SEQ ID NO: 159
H-GPASVPTTCCFNLANRKIPLQRLESYRRITSGKCPQKAVIFKTKLAK

DICADPKKKWVQDSMKYLDQKSPTPXP-NH2

X is K(PEG-Biotin)

A further example of a chemokine of the various embodiments of the invention containing modifications and specifically adapted for use in the invention is described in detail herein (see Examples below). The modified CCL5 (RANTES) corresponds to residues 1 to 68 of the full length mature protein (and lacks the N-terminal signal peptide of 23 amino acids, which is cleaved off) and thus retains the chemokine fold. The single methionine (Met67) within the sequence is mutated to lysine, to mitigate against oxidation of this residue during the chain assembly (SEQ ID NO: 160). This Met to Lys substitution provides a lysine at position 67 which can be modified through biotinylation. FmocLys(ivDde)-OH is incorporated as residue 67 to facilitate site-specific labelling at this position of the protein (SEQ ID NO: 161). The biotinylated version comprises, consists essentially of or consists of the amino acid sequence of SEQ ID NO: 162.

Thus, in other embodiments the invention also relates to a modified chemokine comprising, consisting essentially of or consisting of the amino acid sequence of SEQ ID NO: 162:

SPYSSDTTPCCFAYIARPLPRAHIKEYFYTSGKCSNPAVVFVTRKNRQ

VCANPEKKWVREYINSLEXS

X is an amino acid residue that can be biotinylated, such as lysine, ornithine or diaminopropionic acid and optionally is biotinylated, optionally via a spacer molecule such as PEG (e.g. K(Biotin))

A further example of a chemokine of the various embodiments of the invention containing modifications and specifically adapted for use in the invention is described in detail herein (see Examples below). The modified CCL20 (MIP-3a) corresponds to residues 1 to 70 of the full length mature protein (and lacks the N-terminal signal peptide of 26 amino acids, which is cleaved off) and thus retains the chemokine fold (SEQ ID NO: 163). FmocLys(ivDde)-OH is incorporated as residue 68 to facilitate site-specific labelling at this position of the protein (SEQ ID NO: 164). The naturally occurring lysine at position 68 is modified through biotinylation. A PEG spacer may be incorporated between the ε-amino functionality and the biotin. The final protein may thus comprise, consist essentially of or consist of the amino acid sequence of SEQ ID NO: 165.

Thus, in certain embodiments the invention also relates to a modified chemokine comprising, consisting essentially of or consisting of the amino acid sequence of SEQ ID NO: 165:

ASNFDCCLGYTDRILHPKFIVGFTRQLANEGCDINAIIFHTKKKLSVC

ANPKQTWVKYIVRLLSKKVXNM

X is an amino acid residue that can be biotinylated, such as lysine, ornithine or diaminopropionic acid and optionally is biotinylated, optionally via a spacer molecule such as PEG, in particular K(PEG-Biotin)

A further example of a chemokine of the various embodiments of the invention containing modifications and specifically adapted for use in the invention is described in detail herein (see Examples below). The modified CXCL11 (ITAC) corresponds to residues 1 to 73 of the full length mature protein (and lacks the N-terminal signal peptide of 21 amino acids, which is cleaved off) and thus retains the chemokine fold (SEQ ID NO: 169). An additional lysine is inserted at the C-terminus, optionally via a PEG spacer, at position 74. The chemokine may thus comprise, consist essentially of or consist of the amino acid sequence of SEQ ID NO: 171.

SEQ ID NO: 171:
FPMFKRGRCLCIGPGVKAVKVADIEKASIMYPSNNCDKIEVIITLKENK

GQRCLNPKSKQARLIIKKVERKNFX

X is an amino acid residue that can be biotinylated, such as lysine, ornithine or diaminopropionic acid and optionally is biotinylated, optionally via a spacer molecule such as PEG. The amino acid residue may be added via a spacer molecule such as PEG and may thus be "PEG-K".

FmocLys(ivDde)-OH is incorporated, following Fmoc-12-amino-4,7,10-trioxadodecanoic acid, as residue 74 to facilitate site-specific labelling at this position of the protein (SEQ ID NO: 170). The e-amino side chain functionality of the additional Lys(74) is modified through biotinylation. The final protein may thus comprise, consist essentially of or consist of the amino acid sequence of SEQ ID NO: 171 where residue 74 is PEG-K.

A further example of a chemokine of the various embodiments of the invention containing modifications and specifically adapted for use in the invention is described in detail herein (see Examples below). The modified CXCL10 (IP-10) corresponds to residues 1 to 77 of the full length mature protein (and lacks the N-terminal signal peptide of 21 amino acids, which is cleaved off) and thus retains the chemokine fold. An amino acid which is capable of biotinylation, such as lysine or ornithine for example, may be inserted as residue 78. Insertion may be via a spacer, such as a PEG spacer. The linear amino acid sequence (SEQ ID NO: 172) is shown, prior to attachment of the PEG spacer, additional lysine and biotin molecules:

VPLSRTVRCTCISISNQPVNPRSLEKLEIIPASQFCPRVEIIATMKKKGE

KRCLNPESKAIKNLLKAVSKERSKRSP

Thus, position 78 may be modified through biotinylation. FmocLys(ivDde)-OH may be incorporated as residue 78 to facilitate site-specific labelling at this position of the protein (SEQ ID NO: 173). A suitable spacer, such as a PEG spacer, may be incorporated between the ε-amino functionality and the biotin. The biotinylated version comprises, consists essentially of or consists of the amino acid sequence of SEQ ID NO: 174.

Thus, in certain embodiments the invention also relates to a modified chemokine comprising, consisting essentially of or consisting of the amino acid sequence of SEQ ID NO: 174:

VPLSRTVRCTCISISNQPVNPRSLEKLEIIPASQFCPRVEIIATMKKKGE

KRCLNPESKAIKNLLKAVSKERSKRSPX

X is an amino acid residue that can be biotinylated, such as lysine, ornithine or diaminopropionic acid and optionally is biotinylated, optionally via a spacer molecule such as PEG, e.g. K(PEG-Biotin) and may be attached via a spacer molecule, e.g. PEG-K(Biotin)

The specific chemokines, including derivatives thereof as described herein, newly synthesised for use in the methods of the invention may represent separate aspects of the invention. Biotinylation is positioned so as to permit immobilisation whilst retaining receptor binding capability.

Chemokines useful in the various embodiments of the invention may be synthesised through any suitable means known in the art. Preferably, the chemokines are chemically synthesised as this facilitates modification and labelling etc. However, recombinant DNA based approaches may also be employed in combination with appropriate labelling and modification technologies as required. Thus, in certain embodiments the invention also provides a nucleic acid molecule encoding the chemokines of the various embodiments of the invention. In certain embodiments the invention also relates to a vector containing such a nucleic acid molecule and a host cell containing the vector. The vector may additionally comprise a suitable promoter operably linked to the nucleic acid molecule, to facilitate transcription of the corresponding mRNA molecule. The host cell may be capable of expressing the protein by transcription and translation of the nucleic acid molecule encoding a chemokine of the various embodiments of the invention.

The chemokines useful in the various embodiments of the invention can be biotinylated by methods known in the art such as described in WO 00/50088 A2, which is incorporated herein by reference in its entirety. As indicated above, site-specific labelling of the chemokines of the various embodiments of the invention is preferable, although any labelling technique which does not significantly affect the receptor-binding capacity of the chemokine may be employed. Various site-specifically biotinylated chemokines and native chemokines are available commercially, for instance from Almac, Craigavon, UK. In specific embodiments the one or more chemokines are biotinylated via a spacer group. The spacer may be employed to prevent the biotin group from impacting on the activity of the chemokine, in particular binding of the chemokine to its cognate receptor. Any suitable spacer that facilitates retention of receptor binding properties of the chemokine may be employed in the various embodiments of the invention. Thus, in the specific embodiments described above, spacers other than PEG spacers may be employed as appropriate. In specific embodiments, the spacer is a polyethylene glycol (PEG) spacer. PEG has been shown to be an effective spacer permitting attachment of biotin to the chemokine (which can then be immobilized on the solid support through interaction with streptavidin) without compromising receptor binding capability.

In the context of the various embodiments of the present invention the term "antibody" includes all immunoglobulins or immunoglobulin-like molecules with specific binding affinity for the relevant chemokine receptor (including by way of example and without limitation, IgA, IgD, IgE, IgG and IgM, combinations thereof, and similar molecules produced during an immune response in any vertebrate, for example, in mammals such as humans, goats, rabbits and mice). Specific immunoglobulins useful in the various embodiments of the invention include IgG isotypes. The antibodies useful in the various embodiments of the invention may be monoclonal or polyclonal in origin, but are typically monoclonal antibodies. Antibodies may be human antibodies, non-human antibodies, or humanized versions of non-human antibodies, or chimeric antibodies. Various techniques for antibody humanization are well established and any suitable technique may be employed. The term "antibody" also refers to a polypeptide ligand comprising at least a light chain or heavy chain immunoglobulin variable region which specifically recognizes and binds an epitope of an antigen, and it extends to all antibody derivatives and fragments that retain the ability to specifically bind to the relevant chemokine receptor. These derivative and fragments may include Fab fragments, F(ab')2 fragments, Fv fragments, single chain antibodies, single domain antibodies, Fc fragments etc. The term antibody encompasses antibodies comprised of both heavy and light chains, but also heavy chain (only) antibodies. In specific embodiments, the antibodies may be engineered so as to be specific for more than one chemokine receptor, for example bi-specific to permit binding to two different chemokine receptors. Suitable commercially available antibodies which bind to the chemokine receptors of interest are listed in table 8. They may or may not be labelled. General reference may be made to "Antibodies a laboratory manual: By E Harlow and D Lane. pp 726. Cold Spring Harbor Laboratory. 1988", which reference is incorporated herein in its entirety.

TABLE 8

Commercially available fluorophore labelled antibodies against specific chemokine receptors

| Antibody | Fluorophore | Supplier |
|---|---|---|
| CCR5 | PE | Biolegend |
| CCR2 | PerCP Cy5.5 | Biolegend |
| CCR6 | PerCP Cy5.5 | BD Biosciences |

TABLE 8-continued

Commercially available fluorophore labelled antibodies against specific chemokine receptors

| Antibody | Fluorophore | Supplier |
|---|---|---|
| CCR3 | PE | Biolegend |
| CCR1 | Alexa Fluor 647 | Biolegend |
| CCR9 | APC | R&D Systems |

Anti-CCR2 antibodies are described for example in WO 2010/021697, incorporated herein by reference. Further examples of potentially useful antibodies include MLN-1202, an anti-CCR2 monoclonal antibody currently undergoing clinical trials (Millennium Pharmaceuticals).

The chemokine receptor expressing cells may thus be targeted using alternative binding agents, such as antibodies or other chemical compounds, as defined herein, rather than the natural chemokine binding partner. This approach is a new approach to treating inflammatory conditions and in particular multiple sclerosis.

Thus, in certain embodiments the invention also provides an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine. The binding reagent capable of specifically binding to the chemokine receptor may be an agonist or an antagonist of the chemokine receptor. In specific embodiments, the binding reagent capable of specifically binding to the chemokine receptor is selected from an antibody and a chemical compound.

In other embodiments the invention thus also provides a method for treating an inflammatory condition (in particular MS) comprising applying peripheral blood from a patient/subject to an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine) thus removing chemokine receptor expressing cells from the peripheral blood of the patient/subject. The method may comprise returning the blood depleted of the chemokine receptor expressing cells to the patient/subject.

Similarly, in other embodiments the invention provides a binding reagent capable of specifically binding to a chemokine receptor for use in the treatment of an inflammatory condition, wherein the binding reagent is immobilized on a solid support contained within an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient/subject, wherein the binding reagent is not a chemokine), to which is applied peripheral blood from a patient thus removing chemokine receptor expressing cells from the peripheral blood of the patient.

These aspects of the various embodiments of the invention may be integrated into the more focused therapeutic aspects of the various embodiments of the invention and thus, the remainder of the disclosure, including all specific embodiments applies mutatis mutandis.

Solid support materials for immobilizing the binding reagents of the various embodiments of the invention are known in the art. "Solid support" refers to, for example, materials having a rigid or semi-rigid surface or surfaces, and may take the form of beads, resins, gels, microspheres, or other geometric configurations. A useful support material is one that does not activate blood cells so as to make them coagulate or adhere to the support as peripheral whole blood is applied to the device. In certain embodiments, a support treated with an agent to provide it with anti-coagulation properties, in particular a heparinized support is employed. Alternatively, the blood of the patient may be treated with an anti-coagulant such as heparin prior to application to the support. Useful support materials comprise high molecular weight carbohydrates, in particular carbohydrates having a molecular weight of 100 kDa or more, such as agarose, in particulate form, optionally cross-linked, and cellulose. Other preferred support materials are polymers, such as carboxylated polystyrene, and glass. The support of the various embodiments of the invention may be provided in the form of particles or fibres. The support particles may have regular form, such as spheres or beads, or irregular form. They may be porous or non-porous. A preferred average particle size of the support is from 50 µm to 2 mm. In certain embodiments Sepharose™, a cross linked, beaded-form of agarose, is used as column matrix. It is chosen for its optimal distribution capacity and can provide a large available area for affinity binding. Solid supports may be provided in the form of magnetic beads, with the specific binding reagent immobilized on the magnetic beads. Following capture of the (CCR2, CCR6, CCR3, CCR5, CCR1, CXCR3 and/or CCR9) chemokine receptor expressing cells from the blood, the beads can be removed from the blood with the aid of an appropriate magnetic separator.

Methods for immobilizing binding reagents on a solid support are known in the art. A binding reagent, such as a chemokine, antibody, peptide, nucleic acid or chemical compound, can be immobilized on the support in a direct or indirect manner. Immobilization can be by means of a suitable linker in some embodiments. A preferred method of indirect immobilization of a binding reagent, such as a chemokine, relies upon the interaction between biotin and avidin molecules. "Avidin" or "avidin molecule" refers to any type of protein that specifically binds biotin to the substantial exclusion of other (small) molecules that might be present in a biological sample. Examples of avidin include avidins that are naturally present in egg white, oilseed protein (e.g., soybean meal), and grain (e.g., corn/maize), and streptavidin, which is a protein of bacterial origin. Thus, biotinylation of the binding reagent and use of an avidin molecule such as streptavidin immobilized on the solid support allows reliable attachment of the binding reagent to the solid support according to methods known in the art. Specifically, such a method may comprise providing the binding reagent in biotinylated form, providing a solid support having streptavidin immobilized on its surface, contacting the support with an aqueous solution of the biotinylated binding reagent, and rinsing the support with an aqueous solvent. In addition, binding pair interactions, such as antibody-antigen interactions, may also be utilised for indirect immobilisation of binding reagent onto a support. In such embodiments the support may be derivatised with one member of a binding pair, such as an antibody or fragment or derivative thereof, as defined herein, which has known affinity for a particular peptide sequence or small molecule hapten. Incorporating the other member of the binding pair, such as an antigen, peptide sequence or the hapten onto or into the binding reagent facilitates immobilisation onto a solid support coated with the corresponding antibody or fragment or derivative thereof. Thus, the binding reagent may be modified to include the peptide sequence or hapten into the linear molecule or may be added as a side chain or label. Any suitable antibody-antigen pair may be employed. The antibody fragment or derivative may be any fragment or derivative that retains specific binding affinity for the appropriate antigen. Examples include Fab, F(ab')2 fragments, scFV, VH domains, single domain antibodies (such as nanobodies), heavy chain antibodies and humanized version of non-human antibodies etc. Other high affinity interactions can be utilised for immobilisation of binding reagents, as long as the binding reagent can be synthesised or derivatised with one of the interacting partners and the solid support synthesised or derivatised with the other interacting partner without loss of binding activity (i.e. binding of the binding reagent to the appropriate chemokine receptor). Immobilization may occur via essentially the same interaction in reverse in some embodiments. Thus, the binding reagent which may be a chemokine for example, may be attached to an antibody as defined herein, and the solid support derivatised with the antigen. The chemokine may be produced as a fusion protein with the antibody.

Alternatively binding reagents, such as chemokines and antibodies, can be immobilised directly onto a solid support using bioconjugation techniques established in the field. For example direct immobilisation of proteins onto cyanogen bromide activated solid supports via amino functionalities within the primary sequence of the protein. Alternatively, sulphydryl functionalities within proteins can be used to directly immobilise the protein to alkyl halide derivatised supports or supports containing free thiol functionalities. In further embodiments, proteins containing α-thioester functionalities can be directly immobilised on supports containing 1,2 amino thiol moieties (eg N-terminal cysteine) using the native chemical ligation reaction. Alternatively proteins modified with ketones and aldehydes can be immobilised on solid supports derivatised with hydrazinyl, hydrazide and aminoxy functionalities using hydrazone/oxime bond forming ligation reactions (and vice versa). Alternatively 'Click' chemistry can be used to immobilise proteins onto solid supports, whereby the protein and the support are derivatised with the appropriate mutually reactive chemical functionalities (azides and alkynes). In other embodiments Staudinger ligation chemistry can be used to immobilise appropriately derivatised proteins onto the appropriately derivatised solid supports.

The solid support is contained within or carried by the apheresis column. Thus, by "loaded" is meant that the column carries or contains the solid support in a manner such that (peripheral) blood can flow through the column in contact with the solid support. Thus, the solid support provides a matrix within the column through which blood flows, in continuous fashion in certain embodiments. This permits cells expressing the specific chemokine receptor to be removed from the blood passing through the column, such that blood exiting the column is depleted of the specific chemokine receptor-expressing cells. In specific embodiments, the apheresis column is loaded with a support comprising streptavidin immobilized on the support and one or more biotinylated binding reagents, such as chemokines, bound to the streptavidin on the support. The solid support may be comprised of a high-molecular weight carbohydrate, optionally cross-linked, such as agarose.

As discussed above, the binding reagent is coupled to the solid support. The relative amounts of binding reagent may be controlled to ensure that coupling between the solid support and the binding reagent will be immediate, minimising the risk of binding reagent decoupling from the solid support. Thus, it may be ensured that there is a relative excess of immobilization sites for the binding reagent on the solid support. Alternatively, or additionally, following immobilization of the binding reagent on the solid support, the solid support may be washed to remove any unbound binding reagent.

The apheresis column utilised in the various embodiments of the present invention acts as a leukapheresis treatment for conditions associated with multiple sclerosis. The column acts to specifically remove one or more of CCR2, CCR6, CCR3, CCR5, CCR1, CXCR3 and/or CCR9-expressing monocytes by exploiting the interaction between CCR2, CCR6, CCR3, CCR5, CCR1, CXCR3 and/or CCR9 expressed on the cell surface and a specific binding reagent immobilized on a solid support contained within or carried by the column. The overall column typically comprises, consists of, or consists essentially of three combined components; 1) a housing which contains or carries 2) the solid support and 3) one or more binding reagents (immobilized thereon) which specifically bind one or more chemokine receptors. The housing may be manufactured from any suitable material for clinical use. In certain embodiments the housing is composed of a plastic material. The housing includes an in flow site for entry of blood and an out flow site for blood (depleted of target cells) to exit the column. The housing may be designed to maintain a continuous blood flow through the solid support matrix. The housing (as shown for example in FIG. 9) may include a top portion which comprises a distribution plate (2) at the inflow site (1) to spread the blood evenly over the entire matrix area. The distribution plate may act as a first safety barrier preventing larger particles flowing through the column and into the patient. However, the distribution plate is not essential and may be removed in some embodiments to decrease the overall resistance in the system. The column may contain one or more safety filter units (3 and 4) placed at the inflow (1) and/or outflow (5) sites of the plastic housing. Such filter units may act to prevent particles larger than blood cells passing in and/or out of the column. The safety filter units may contain a plurality of filters, such as two, three or four filters designed to be a robust barrier and stop all particles larger than blood cells passing through the column. Inclusion of safety filters (3 and 4) at both ends of the column serves to minimize the risk of leakage of particles into the patient, including in the event that the device is incorrectly connected resulting in blood flow in the opposite direction to that intended. The safety filters may comprise of any suitable pore size to prevent particles larger than blood cells from passing through the column, as would be readily understood by one skilled in the art. Suitable filters are commercially available. In specific embodiments, the pore size of the filter(s) is between approximately 60 μm and 100 μm, more specifically approximately 80 μm. The solid support and binding reagent components are discussed in further detail herein.

The volume of the housing may be varied depending upon the blood volumes intended to pass through the column. Typically, the volume of the housing is between approximately 40 ml and 200 ml, more specifically 50 ml to 150 ml or 60 ml to 120 ml.

The column is generally applied in the form of an apheresis circuit. In this context, the overall system includes the apheresis column, tubing and an appropriate pump to pump the blood around the circuit. The system is illustrated in FIG. 10. The patient (1) is connected to the extracorporeal circuit via sterile needles to veins in the right and the left arms. A saline bag (3) is also connected and the saline solution is pumped with a suitable pump (2). Blood is drawn from one arm of the patient through the sterile tubing system by the blood pump (4) and passed through the column (6) and back to the patient. The tubing system may be connected to the column via any suitable coupling, such as standard dialysis luer-lock couplings. The couplings on the column may be colour-coded for correct assembly. For example, red tubing for inflow to the red column top and blue tubing for outflow back to the patient. An air detector (8) may be present in the circuit. Inlet pressure (5) and/or Pven sensors (7) may additionally be employed to monitor the pressure in the circuit.

An apheresis pump, such as the 4008 ADS pump manufactured by Fresenius Medical Care or the Adamonitor pump, may monitor the patient's inflow and outflow. The pump may also monitor the pressure in the extracorporeal circulation. The pump may be able to discriminate air by a bubble catcher and air detector. A clot catcher filter may be positioned inside the bubble catcher. The pump may also incorporate an optical detector to distinguish between light, e.g. saline solution or air present in the tubing system and dark e.g. blood present in the tubing system.

A schematic diagram of a suitable pump, showing the air detector and optical filter is shown in FIG. 11. If the pump system detects air bubbles and optical fluctuations or if extracorporeal pressure values are out of the set range, then the pump may stop immediately. Alternatively or additionally a visual/audible alarm may be emitted.

The treatment methods of the various embodiments of the invention may thus rely upon an extracorporeal circuit. The methods may be considered as ex vivo or in vitro methods and be defined solely with reference to steps performed outside of the patient. In some embodiments, however, the method further comprises, prior to application of the blood to the column, collecting peripheral blood from the patient. In a further embodiment, the method further comprises, following the application of the blood to the column, infusing the blood depleted of (CCR2, CCR6, CCR3, CCR5, CCR1, CXCR3 and/or CCR9) chemokine receptor expressing cells to the patient. This is then a complete leukapheresis treatment method. Thus, a leukaphereis method, for treating multiple sclerosis, comprises collecting peripheral blood from the patient; applying the peripheral blood to an apheresis column loaded with a solid support comprising one or more binding reagents capable of specifically binding to one or more chemokine receptors, in particular the chemokine receptor CCR2, CCR6, CCR3, CCR5, CCR1, CXCR3 and/or CCR9, immobilized directly or indirectly on the support thus removing one or more of CCR2, CCR6, CCR3, CCR5, CCR1, CXCR3 and/or CCR9 expressing cells from the peripheral blood of the patient; and infusing the depleted blood (of chemokine receptor expressing cells) to the patient.

The peripheral blood may be continuously collected from the patient. Similarly, the depleted blood may be continuously infused to the patient, through use of an appropriate circuit as described herein. Thus, the support may be disposed in a column through which the blood is made to flow. This may be achieved using a suitable pump for example, as also described herein. Blood flow through the column enables the binding reagent(s) immobilized on the solid support to capture the cells expressing the chemokine receptor, thus depleting them from the blood and preventing their contribution to the (inflammatory) multiple sclerosis.

The methods of the various embodiments of the invention and binding reagents for use in the methods of the various embodiments of the invention may require that the patient has been selected for treatment on the basis of detecting an increase in the level of chemokine receptor, in particular, one or more of CCR2, CCR6, CCR3, CCR5, CCR1, CXCR3 and/or CCR9 expressing cells in a sample obtained from the patient. Such companion diagnostic methods are described in greater detail herein and are based, for example, on the observation that CCR2, CCR6, CCR3, CCR5, CCR1, CXCR3 and/or CCR9 expression may be elevated in patients with multiple sclerosis. More specifically, it is shown herein that levels of CCR2 and CCR6 expressing leukocytes, in particular T lymphocytes, are increased in MS patients (compared with healthy controls).

Thus, (in this context) in certain embodiments the invention also provides a method of diagnosing, monitoring progression of, or monitoring treatment of multiple sclerosis comprising determining:

a) the levels of one or more of the chemokine receptor CCR2, CCR6, CCR3, CCR5, CCR1, CXCR3 and/or CCR9 expressing cells b) levels of expression of one or more of CCR2, CCR6, CCR3, CCR5, CCR1, CXCR3 and/or CCR9; and/or c) levels of cells with high expression of one or more of CCR2, CCR6, CCR3, CCR5, CCR1, CXCR3 and/or CCR9 in a sample obtained from a subject, wherein high levels of one or more of CCR2, CCR6, CCR3, CCR5, CCR1, CXCR3 and/or CCR9 expressing cells, high levels of expression of one or more of CCR2, CCR6, CCR3, CCR5, CCR1, CXCR3 and/or CCR9 or high levels of cells with high expression of one or more of CCR2, CCR6, CCR3, CCR5, CCR1, CXCR3 and/or CCR9 or increased levels of one or more of CCR2, CCR6, CCR3, CCR5, CCR1, CXCR3 and/or CCR9 expressing cells compared to control, increased levels of expression of one or more of CCR2, CCR6, CCR3, CCR5, CCR1, CXCR3 and/or CCR9 compared to a control or increased levels of cells with high expression of one or more of CCR2, CCR6, CCR3, CCR5, CCR1, CXCR3 and/or CCR9 compared to a control indicate the presence or progression of multiple sclerosis. Levels of chemokine receptor expression, as opposed to cell numbers, may also be investigated as increased levels of chemokine receptor expression per cell may also be diagnostically relevant. The cells may be lymphoctes, in particular T cells.

"Diagnosing" is defined herein to include screening for a disease/condition or pre-indication of a disease/condition, identifying a disease/condition or pre-indication of a disease/condition and checking for recurrence of disease/condition following treatment. The methods of the various embodiments of the invention may also have prognostic value, and this is included within the definition of the term "diagnosis". The prognostic value of the methods of the various embodiments of the invention may be used as a marker of potential susceptibility to multiple sclerosis by identifying levels of one or more of CCR2, CCR6, CCR3, CCR5, CCR1, CXCR3 and/or CCR9 expression linked to conditions associated with an multiple sclerosis. Thus patients at risk may be identified before the disease has a chance to manifest itself in terms of symptoms identifiable in the patient. In certain embodiments, diagnosis may be made in conjunction with other objective indicators of multiple sclerosis. Thus, in specific embodiments, diagnosis is made in conjunction with one or more of the following indicators: clinical measures, multiple sclerosis severity score, MRI and ologoclonal immunoglobulin pattern in a suitable sample such as liquor.

"Monitoring progression of" includes performing the methods to monitor the stage and/or the state and progression of the multiple sclerosis. Monitoring progression may involve performing the diagnostic methods multiple times on the same patient to determine whether the levels of one or more of CCR2, CCR6, CCR3, CCR5, CCR1, CXCR3 and/or CCR9 expressing cells are increasing, decreasing or remaining stable over a certain time period. This may be in the context of a treatment regime.

"Monitoring the success of a particular treatment" is defined to include determining the levels of one or more of CCR2, CCR6, CCR3, CCR5, CCR1, CXCR3 and/or CCR9 expressing cells before and after a treatment. The treatment is generally one aimed at treating multiple sclerosis and may be a treatment according to one of the methods of the various embodiments of the invention as defined herein. Successful treatment may be determined with reference to a decrease in one or more of CCR2, CCR6, CCR3, CCR5, CCR1, CXCR3 and/or CCR9 expressing cells as a result of, or following, the treatment. Thus, in such methods a level of one or more of CCR2, CCR6, CCR3, CCR5, CCR1, CXCR3 and/or CCR9 expressing cells is determined prior to treatment. This level is recorded and a further assessment made at a predetermined time following the treatment. The comparison of levels of one or more of CCR2, CCR6, CCR3, CCR5, CCR1, CXCR3 and/or CCR9 expressing cells permits the success of the treatment to be monitored. In specific embodiments, a single treatment is sufficient to cause a depletion of around 10%, 20%, 30%, 40%, 50%, 60% or 70%, or higher, up to 80%, 90%, 95% or more, or any range of values between and including these amounts, of one or more specific chemokine receptors, in particular one or more of CCR2, CCR6, CCR3, CCR5, CCR1, CXCR3 and/or CCR9, expressing cells from the peripheral blood of the patient. In specific embodiments, at least around 50% depletion is achieved in a single treatment. Thus, successful treatment may be defined with reference to depletion of one or more of CCR2, CCR6, CCR3, CCR5, CCR1, CXCR3 and/or CCR9 expressing cells. Treatment may lead to depletion of between approximately 100 and 500 million one or more of CCR2, CCR6, CCR3, CCR5, CCR1, CXCR3 and/or CCR9 expressing cells, such as monocytes or lymphocytes, in particular T-cells, in certain embodiments. Additional factors may be included to determine successful treatment. For example, a lack of increase in one or more of CCR2, CCR6, CCR3, CCR5, CCR1, CXCR3 and/or CCR9 expressing cells following treatment may indicate successful treatment in terms of preventing further progression of the condition, optionally combined with an improvement in other markers or staging of the multiple sclerosis.

In specific embodiments, the multiple sclerosis is selected from active and stable relapsing-remitting multiple sclerosis.

The sample in which one or more of CCR2, CCR6, CCR3, CCR5, CCR1, CXCR3 and/or CCR9 expressing cell levels, levels of expression of one or more of CCR2, CCR6, CCR3, CCR5, CCR1, CXCR3 and/or CCR9 and/or levels of cells with high expression of one or more of CCR2, CCR6, CCR3, CCR5, CCR1, CXCR3 and/or CCR9 (defined as CCR2hi, CCR6hi, CCR3hi, CCR5hi, CCR1hi, CXCR3hi and/or CCR9hi, CCR6hi, CCR3hi, CCR5hi, CCR1hi or CCR9hi) are determined may comprise any suitable tissue sample or body fluid sample. Generally, the test sample is obtained from a human subject. Typically, the sample is a blood sample, in particular a peripheral blood sample. The sample may comprise cerebrospinal fluid (liquor) in certain embodiments. The methods may involve determining levels of one or more of CCR2, CCR6, CCR3, CCR5, CCR1, CXCR3 and/or CCR9 expressing monocytes, macrophages or lymphocytes in certain embodiments, such as CCR2 and/or CCR6 expressing T-cells.

Levels of CCR2, CCR6, CCR3, CCR5, CCR1, CXCR3 and/or CCR9 expressing cells, levels of expression of CCR2, CCR6, CCR3, CCR5, CCR1, CXCR3 and/or CCR9 and/or levels of cells with high expression of CCR2, CCR6, CCR3, CCR5, CCR1, CXCR3 and/or CCR9 (defined as CCR2hi, CCR6hi, CCR3hi, CCR5hi, CCR1hi, CXCR3hi and/or CCR9hi) may be determined according to any suitable method. For example, flow cytometry may be employed in order to determine the number of cells expressing CCR2, CCR6, CCR3, CCR5, CCR1, CXCR3 and/or CCR9 in the sample, to determine levels of CCR2, CCR6, CCR3, CCR5, CCR1, CXCR3 and/or CCR9 expression and/or to identify levels of CCR2hi, CCR6hi, CCR3hi, CCR5hi, CCR1hi, CXCR3hi and/or CCR9hi cells. Flow cytometric techniques are described herein and examples of commercially available antibodies suitably labelled for use in flow cytometry are set out in Table 8 for example. Alternatively, the method may involve steps of collecting and fixing the cells in the sample, followed by incubation with a suitable binding reagent that binds specifically to the CCR2, CCR6, CCR3, CCR5, CCR1, CXCR3 and/or CCR9 chemokine receptor expressing cells in the sample. Any suitable binding reagent, as defined herein, may be employed. For example, a CCR2, CCR6, CCR3, CCR5, CCR1, CXCR3 and/or CCR9 specific antibody may be employed. A wash step may be adopted following an incubation period to remove any unbound reagent. Suitable wash steps and incubation conditions would be well known to one skilled in the art. The binding reagent may be directly labeled in order to permit antibody binding to be directly determined. Alternatively a secondary binding reagent, such as an antibody, may be employed which binds to the first binding reagent and carries a label. Again, suitable incubation conditions and wash steps would be apparent to one skilled in the art. The primary and secondary binding reagents may form two halves of a binding pair. The binding interaction should not prevent the primary binding reagent binding to the CCR2, CCR6, CCR3, CCR5, CCR1, CXCR3 and/or CCR9 receptor expressing cells, unless a competition assay is being employed. The two halves of a binding pair may comprise an antigen-antibody, antibody-antibody, receptor-ligand, biotin-streptavidin pair etc. in certain embodiments. Other techniques used to quantify chemokine (CCR2) receptor expressing cell levels, to quantify levels of CCR2, CCR6, CCR3, CCR5, CCR1, CXCR3 and/or CCR9 expression and/or to quantify levels of CCR2hi, CCR6hi, CCR3hi, CCR5hi, CCR1hi, CXCR3hi and/or CCR9hi cells include PCR-based techniques such as QT-PCR and protein based methods such as western blot. Quantitation may be achieved with reference to fixed cell lines carrying known numbers of various receptor expressing cells and/or known levels of receptor expression per cell. Such fixed cell lines are available commercially (for example ChemiScreen™ cell lines from Millipore). Methods analogous to the treatment methods of the various embodiments of the invention may also be employed, with binding of CCR2, CCR6, CCR3, CCR5, CCR1, CXCR3 and/or CCR9 expressing cells to the solid support being determined following peripheral blood being passed through the column.

The levels of CCR2, CCR6, CCR3, CCR5, CCR1, CXCR3 and/or CCR9 expressing cells, levels of expression of CCR2, CCR6, CCR3, CCR5, CCR1, CXCR3 and/or CCR9 and/or levels of cells with high expression of CCR2, CCR6, CCR3, CCR5, CCR1, CXCR3 and/or CCR9 (defined as CCR2hi, CCR6hi, CCR3hi, CCR5hi, CCR1hi, CXCR3hi and/or CCR9hi) may be determined relative to a suitable control. When diagnosing multiple sclerosis, a threshold level of cells, level of expression of CCR2, CCR6, CCR3, CCR5, CCR1, CXCR3 and/or CCR9 and/or level of cells with high expression of CCR2, CCR6, CCR3, CCR5, CCR1, CXCR3 and/or CCR9 (defined as CCR2hi, CCR6hi, CCR3hi, CCR5hi, CCR1hi, CXCR3hi and/or CCR9hi) may be set at or over which a positive diagnosis is made. This threshold may be determined based upon measuring levels of CCR2, CCR6, CCR3, CCR5, CCR1, CXCR3 and/or CCR9 expressing cells, levels of expression of CCR2, CCR6, CCR3, CCR5, CCR1, CXCR3 and/or CCR9 and/or levels of cells with high expression of CCR2, CCR6, CCR3, CCR5, CCR1, CXCR3 and/or CCR9 (defined as CCR2hi, CCR6hi, CCR3hi, CCR5hi, CCR1hi, CXCR3hi and/or CCR9hi) in samples obtained from diseased patients and comparing these levels with levels of CCR2, CCR6, CCR3, CCR5, CCR1, CXCR3 and/or CCR9 expressing cells, levels of expression of CCR2, CCR6, CCR3, CCR5, CCR1, CXCR3 and/or CCR9 and/or levels of cells with high expression of CCR2, CCR6, CCR3, CCR5, CCR1, CXCR3 and/or CCR9 (defined as CCR2hi, CCR6hi, CCR3hi, CCR5hi, CCR1hi, CXCR3hi and/or CCR9hi) in samples obtained from healthy subjects.

In certain embodiments, multiple sclerosis is diagnosed on the basis of levels of chemokine receptor expressing cells, such as CCR2, CCR6, CCR3, CCR5, CCR1, CXCR3 and/or CCR9 expressing cells. A positive diagnosis may be made in subjects based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, multiple sclerosis is diagnosed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to healthy controls.

In specific embodiments, multiple sclerosis is diagnosed on the basis of levels of CCR2 or CCR6 expressing cells, such as lymphocytes and in particular T lymphocytes. A positive diagnosis may be made in subjects based upon the presence of greater than about 7%, greater than about 10% or greater than about 15% CCR2 expressing T cells in the sample, as a percentage of total cells in the sample. A positive diagnosis may be made in subjects based upon the presence of greater than about 18%, greater than about 20% or greater than about 22% CCR6 expressing T cells in the sample, as a percentage of total cells in the sample. Multiple sclerosis may also be diagnosed on the basis of the presence of a about a 1.2 fold or greater increase, such as about a 1.5, 2, 2.5, 3, 3.5, 4, 4.5, 5, 10, 20, 50 or 100 or greater fold increase in CCR2 or CCR6 expressing cells, such as lymphocytes and in particular T lymphocytes, relative to healthy controls.

In certain embodiments, progression of multiple sclerosis, which may be in the context of a treatment regime, is monitored on the basis of levels of chemokine receptor expressing cells at different time points. Progression of multiple sclerosis may be indicated in subjects based upon an increase of greater than about 3%, greater than about 4%, greater than about 5%, such as an increase of greater than about 6%, greater than about 7%, greater than about 8%, greater than about 9%, greater than about 10%, greater than about 12%, greater than about 15%, greater than about 20%, greater than about 25%, greater than about 30%, greater than about 35%, greater than about 40%, greater than about 45% or more chemokine receptor expressing cells in the sample, as a percentage of total cells in the sample, compared to a sample taken from the same subject at an earlier time point. In other embodiments, progression of multiple sclerosis is confirmed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to a sample taken from the same subject at an earlier time point.

In specific embodiments, multiple sclerosis is monitored on the basis of levels of CCR2 or CCR6 expressing cells, such as lymphocytes and in particular T lymphocytes. Progression of the disease, which may be in the context of a treatment regime, may be indicated in subjects based upon the presence of an increase of greater than about 3%, greater than about 4%, greater than about 5%, such as an increase of greater than about 6%, greater than about 7%, greater than about 8%, greater than about 9%, greater than about 10%, greater than about 12%, greater than about 15%, greater than about 20%, greater than about 25%, greater than about 30%, greater than about 35%, greater than about 40%, greater than about 45% or more chemokine receptor expressing cells in the sample, as a percentage of total cells in the sample, compared to a sample taken from the same subject at an earlier time point. In other embodiments, progression of multiple sclerosis is confirmed on the basis of the presence of a about a 1.2 fold or greater increase, such as about a 1.5, 2, 2.5, 3, 3.5, 4, 4.5, 5, 10, 20, 50 or 100 or greater fold increase in CCR2 or CCR6 expressing cells, such as lymphocytes and in particular T lymphocytes, relative to a sample taken from the same subject at an earlier time point.

Regression or successful treatment may be monitored based upon similar decreases over various time points. For example, regression or successful treatment may be indicated in subjects based upon a decrease of about 3%, such as a decrease of about 4%, about 5%, about 6%, about 7%, about 8%, about 9%, about 10%, about 12%, about 15%, about 20%, about 25%, about 30%, about 35% or more chemokine receptor expressing cells in the sample, as a percentage of total cells in the sample, compared to a sample taken from the same subject at an earlier time point. In other embodiments, regression of multiple sclerosis is confirmed on the basis of the presence of a about a 1.2 fold or greater decrease, such as about a 1.5, 2, 2.5, 3, 3.5, 4, 4.5, 5, 10, 20, 50 or 100 or greater fold decrease in chemokine receptor expressing cells, relative to a sample taken from the same subject at an earlier time point.

In specific embodiments, multiple sclerosis is monitored on the basis of levels of CCR2 or CCR6 expressing cells, such as lymphocytes and in particular T lymphocytes. Regression or successful treatment of the disease may be made in subjects based upon a decrease of about 3%, such as a decrease of about 4%, about 5%, about 6%, about 7%, about 8%, about 9%, about 10%, about 12%, about 15%, about 20%, about 25%, about 30%, about 35% or more CCR2 or CCR6 expressing cells, such as lymphocytes and in particular T lymphocytes in the sample, as a percentage of total cells in the sample or by a decrease of about 3%, such as a decrease of about 4%, about 5%, about 6%, about 7%, about 8%, about 9%, about 10%, about 12%, about 15%, about 20%, about 25%, about 30%, about 35% or more CCR2 or CCR6 expressing cells, such as lymphocytes and in particular T lymphocytes chemokine receptor expressing cells in the sample, as a percentage of total cells in the sample, compared to a sample taken from the same subject at an earlier time point. In other embodiments, regression of multiple sclerosis is confirmed on the basis of the presence of a about a 1.2 fold or greater decrease, such as about a 1.5, 2, 2.5, 3, 3.5, 4, 4.5, 5, 10, 20, 50 or 100 or greater fold decrease in CCR2 or CCR6 expressing cells, such as lymphocytes and in particular T lymphocytes, relative to a sample taken from the same subject at an earlier time point.

Suitable software is freely available (such as the R project for statistical computing) to perform the necessary statistical analysis of the data obtained to calculate a useful threshold. The threshold may be set to maximize sensitivity and/or specificity of the test. Performance of the test in these respects may be measured by plotting a receiver operating characteristics (ROC) curve (sensitivity versus specificity). The area under the curve provides an indication of the overall performance of the test. Thus, once thresholds have been set for diagnosing the condition, a separate control experiment does not necessarily have to be run each time a sample is tested. Rather reference can simply be made to the pre-existing thresholds to determine the diagnosis. However, in certain embodiments, the sample is tested together with a control sample taken from a healthy subject to provide a comparator based upon essentially identical experimental conditions. The test sample is generally tested in parallel with the control sample. The test sample level of CCR2, CCR6, CCR3, CCR5, CCR1, CXCR3 and/or CCR9 expressing cells, levels of expression of CCR2, CCR6, CCR3, CCR5, CCR1, CXCR3 and/or CCR9 and/or levels of cells with high expression of CCR2, CCR6, CCR3, CCR5, CCR1, CXCR3 and/or CCR9 (defined as CCR2hi, CCR6hi, CCR3hi, CCR5hi, CCR1hi, CXCR3hi and/or CCR9hi) can then be compared with that of the control sample to make the diagnosis. A control sample from a disease patient may also be tested in certain embodiments. Reference to controls permits relative levels ("high", "low" etc.) of CCR2, CCR6, CCR3, CCR5, CCR1, CXCR3 and/or CCR9 expressing cells in the test sample to be readily identified and the significance thereof interpreted. Reference to controls also permits relative levels of CCR2, CCR6, CCR3, CCR5, CCR1, CXCR3 and/or CCR9 expression ("high", "low" etc.) within the cell population to be determined and the significance thereof interpreted. Such determination may, for example, indicate the average levels of CCR2, CCR6, CCR3, CCR5, CCR1, CXCR3 and/or CCR9 expression per cell in the test sample.

Thus, in specific embodiments, high or higher levels of one or more of CCR2, CCR6, CCR3, CCR5, CCR1, CXCR3 and/or CCR9 expressing cells or high or higher levels of CCR2, CCR6, CCR3, CCR5, CCR1, CXCR3 and/or CCR9 expression, for example average CCR2, CCR6, CCR3, CCR5, CCR1, CXCR3 and/or CCR9 expression per cell, or high or higher levels of one or more of CCR2hi, CCR6hi, CCR3hi, CCR5hi, CCR1hi, CXCR3hi and/or CCR9hi cells correlate with active disease or more active multiple sclerosis. Similarly, lower or low levels of one or more of CCR2, CCR6, CCR3, CCR5, CCR1 and CCR9 expressing cells, or low or lower levels of CCR2, CCR6, CCR3, CCR5, CCR1, CXCR3 and/or CCR9 expression, for example average CCR2, CCR6, CCR3, CCR5, CCR1, CXCR3 and/or CCR9 expression per cell, or low or lower levels of one or more of CCR2hi, CCR6hi, CCR3hi, CCR5hi, CCR1hi and CCR9hi cells may correlate with a lack of active inflammation or multiple sclerosis. This may be defined as "less active disease". It can readily be envisaged that control samples may be assessed and levels of CCR2, CCR6, CCR3, CCR5, CCR1, CXCR3 and/or CCR9 expressing cells, levels of expression of CCR2, CCR6, CCR3, CCR5, CCR1, CXCR3 and/or CCR9 and/or levels of cells with high expression of CCR2, CCR6, CCR3, CCR5, CCR1, CXCR3 and/or CCR9 (defined as CCR2hi, CCR6hi, CCR3hi, CCR5hi, CCR1hi, CXCR3hi and/or CCR9hi) determined across the range of severities of conditions associated with multiple sclerosis. This may assist in correlating the levels of CCR2, CCR6, CCR3, CCR5, CCR1, CXCR3 and/or CCR9 expressing cells, levels of expression of CCR2, CCR6, CCR3, CCR5, CCR1, CXCR3 and/or CCR9 and/or levels of cells with high expression of CCR2, CCR6, CCR3, CCR5, CCR1, CXCR3 and/or CCR9 (defined as CCR2hi, CCR6hi, CCR3hi, CCR5hi, CCR1hi, CXCR3hi and/or CCR9hi) in the test sample with the relative severity of the condition.

When monitoring progression of, or monitoring treatment of multiple sclerosis, the control samples may be taken from the subject at an earlier time point. They may, however, be based upon known reference values as discussed above. Thus, relative levels of CCR2, CCR6, CCR3, CCR5, CCR1, CXCR3 and/or CCR9 expressing cells, relative levels of CCR2, CCR6, CCR3, CCR5, CCR1, CXCR3 and/or CCR9 expression including relative levels of average CCR2, CCR6, CCR3, CCR5, CCR1, CXCR3 and/or CCR9 expression per cell or relative levels of CCR2hi, CCR6hi, CCR3hi, CCR5hi, CCR1hi, CXCR3hi and/or CCR9hi cells may be with reference to samples taken from the same subject at a different point in time. In certain embodiments, decreased levels of one or more of CCR2, CCR6, CCR3, CCR5, CCR1, CXCR3 and/or CCR9 expressing cells decreased relative levels of one or more of CCR2, CCR6, CCR3, CCR5, CCR1, CXCR3 and/or CCR9 expression including decreased relative levels of average CCR2, CCR6, CCR3, CCR5, CCR1, CXCR3 and/or CCR9 expression per cell, or decreased relative levels of one or more of CCR2hi, CCR6hi, CCR3hi, CCR5hi, CCR1hi, CXCR3hi and/or CCR9hi cells correlate with successful treatment. The treatment may be any suitable treatment, but in specific embodiments is a treatment according to the various embodiments of the invention.

When monitoring progression of multiple sclerosis, increased levels of one or more of CCR2, CCR6, CCR3, CCR5, CCR1, CXCR3 and/or CCR9 expressing cells increased relative levels of one or more of CCR2, CCR6, CCR3, CCR5, CCR1, CXCR3 and/or CCR9 expression including increased relative levels of average CCR2, CCR6, CCR3, CCR5, CCR1, CXCR3 and/or CCR9 expression per cell or increased relative levels of one or more of CCR2hi, CCR6hi, CCR3hi, CCR5hi, CCR1hi and CCR9hi cells may indicate the progression of condition or disease. Thus, if levels of one or more of CCR2, CCR6, CCR3, CCR5, CCR1, CXCR3 and/or CCR9 expressing cells, levels of expression of one or more of CCR2, CCR6, CCR3, CCR5, CCR1, CXCR3 and/or CCR9 and/or levels of cells with high expression of one or more of CCR2, CCR6, CCR3, CCR5, CCR1, CXCR3 and/or CCR9 (defined as CCR2hi, CCR6hi, CCR3hi, CCR5hi, CCR1hi, CXCR3hi and/or CCR9hi) are increased in a sample taken later than a sample from the same patient this may indicate progression of the condition.

Since the levels of one or more of CCR2, CCR6, CCR3, CCR5, CCR1, CXCR3 and/or CCR9 expressing cells, levels of one or more of CCR2, CCR6, CCR3, CCR5, CCR1, CXCR3 and/or CCR9 expression or levels of one or more of CCR2hi, CCR6hi, CCR3hi, CCR5hi, CCR1hi, CXCR3hi and/or CCR9hi cells are diagnostically relevant, determining such levels in a sample obtained from a subject may influence treatment selection for that subject. Accordingly, in certain embodiments the invention provides a method of selecting a suitable treatment for multiple sclerosis comprising determining:

a) the levels of the one or more of chemokine receptor CCR2, CCR6, CCR3, CCR5, CCR1, CXCR3 and/or CCR9 expressing cells b) levels of expression of one or more of CCR2, CCR6, CCR3, CCR5, CCR1, CXCR3 and/or CCR9; and/or c) levels of cells with high expression of one or more of CCR2, CCR6, CCR3, CCR5, CCR1, CXCR3 and/or CCR9 in a sample obtained from a subject, wherein high levels of one or more of CCR2, CCR6, CCR3, CCR5, CCR1, CXCR3 and/or CCR9 expressing cells, high levels of expression of one or more of CCR2, CCR6, CCR3, CCR5, CCR1, CXCR3 and/or CCR9 or high levels of cells with high expression of CCR2, CCR6, CCR3, CCR5, CCR1, CXCR3 and/or CCR9 or increased levels of one or more of CCR2, CCR6, CCR3, CCR5, CCR1, CXCR3 and/or CCR9 expressing cells compared to control, increased levels of expression of one or more of CCR2, CCR6, CCR3, CCR5, CCR1, CXCR3 and/or CCR9 compared to a control or increased levels of cells with high expression of one or more of CCR2, CCR6, CCR3, CCR5, CCR1, CXCR3 and/or CCR9 compared to a control, result in selection of a treatment as defined herein for treatment of the multiple sclerosis. In certain embodiments, the chemokine receptor expressing cells are high chemokine receptor expressing cells, in particular, high CCR2, CCR6, CCR3, CCR5, CCR1, CXCR3 and/or CCR9 expressing cells. The cells may be lymphocytes, in particular T-lymphocytes. The cells may be CCR2 and/or CCR6 expressing cells, such as T-cells, in specific embodiments.

In specific embodiments, multiple sclerosis is treated on the basis of measuring levels of chemokine receptor expressing cells, such as CCR2, CCR6, CCR3, CCR5, CCR1, CXCR3 and/or CCR9 expressing cells. Thus, a treatment according to the various embodiments of the invention may be applied based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, multiple sclerosis is treated according to the various embodiments of the invention on the basis of the presence of a about a 1.5 fold or greater increase, such as about a 2, 2.5, 3, 3.5, 4, 4.5, 5, 10, 20, 50 or 100 or greater fold increase in chemokine receptor expressing cells, relative to healthy controls.

In specific embodiments, multiple sclerosis is treated on the basis of measuring levels of CCR2 or CCR6 expressing cells, such as lymphocytes and in particular T lymphocytes. Thus, a treatment according to the various embodiments of the invention may be applied based upon the presence of greater than about 7%, greater than about 10% or greater than about 15% CCR2 expressing T cells in the sample, as a percentage of total cells in the sample. Thus, a treatment according to the various embodiments of the invention may be applied based upon the presence of greater than about 18%, greater than about 20% or greater than about 22% CCR6 expressing T cells in the sample, as a percentage of total cells in the sample. Alternatively, multiple sclerosis is treated on the basis of the presence of a about a 1.5 fold or greater increase, such as about a 2, 2.5, 3, 3.5, 4, 4.5, 5, 10, 20, 50 or 100 or greater fold increase in CCR2 or CCR6 expressing cells, such as lymphocytes and in particular T lymphocytes, relative to healthy controls.

For the avoidance of doubt, all embodiments described in respect of the methods of the various embodiments of the invention apply to these aspects mutatis mutandis and are not repeated for reasons of conciseness. Specifically, multiple sclerosis may be indicated in conjunction with one or more of the following indicators:

clinical measures, multiple sclerosis severity score, MRI and ologoclonal immunoglobulin pattern in a suitable sample such as liquor.

The multiple sclerosis may be selected from active and stable relapsing-remitting multiple sclerosis. In specific embodiments, the sample is a peripheral blood sample.

The methods and medical uses of the various embodiments of the invention thus can be tailored to the need of individual patients or groups of patients on the basis of the various diagnostic methods of the various embodiments of the invention. By removing from the circulation one or more of CCR2, CCR6, CCR3, CCR5, CCR1, CXCR3 and/or CCR9 expressing cells, such as monocytes, lymphocytes, neutrophils, macrophages, eosinophils and basophils (in particular T-cells, including CCR2 and/or CCR6 expressing T-lymphocytes), upregulated in multiple sclerosis, an important factor in the inflammatory process of multiple sclerosis can be controlled. The method of the invention may be effective in treating or reversing conditions such as active and stable relapsing-remitting multiple sclerosis.

I. Treating Cardiovascular Disease

Chemokines are a class of cytokine molecules involved in cell recruitment and activation in inflammation. Chemokines cause chemotaxis and activation of various subpopulations of cells in the immune system. The activity of chemokines is mediated primarily through tight binding to their receptors on the surface of leukocytes. In certain embodiments the present invention is based on the realisation that the interaction between chemokines and cells expressing their receptors may be exploited for the treatment of specific inflammatory cardiovascular disease. In particular, various cardiovascular diseases, such as arteriosclerosis, in particular atherosclerosis, include an inflammatory component. The inventors have determined that targeting increased recruitment of specific chemokine receptor-expressing cells to the site of inflammation presents a new therapeutic approach to treat such conditions. Moreover, in such conditions, chemokine receptor expression on each cell may be increased again providing a therapeutic approach to treat such conditions. It is shown herein that subjects suffering from atherosclerosis exhibit increased frequency of chemokine receptor expressing cells in the peripheral blood, in particular CCR1 expressing monocytes, compared to healthy controls. It is also shown herein that the CCR1 cells can be removed using a suitable binding reagent, in particular RANTES (in biotinylated form) immobilized on a suitable matrix. Similarly, it is shown herein that CCR2-expressing cells can be depleted in atherosclerosis patients using a suitable binding reagent, in particular MCP-1, in biotinylated form, immobilized on a suitable matrix.

Thus, in certain embodiments the invention serves to reduce the recruitment of inflammatory leukocytes, which express characteristic chemokine receptors, and possibly express characteristic chemokine receptors at increased levels, to sites of inflammation linked to cardiovascular diseases, such as arteriosclerosis, in particular atherosclerosis. This is achieved using specific binding reagents to capture specific chemokine receptor-expressing inflammatory leukocytes from the patient. Accordingly, in certain embodiments the invention provides in a first aspect a method for treating cardiovascular disease comprising applying peripheral blood from a patient to an apheresis column loaded with a solid support comprising one or more binding reagents capable of specifically binding to a chemokine receptor, in particular a chemokine receptor selected from CCR1, CCR2 and CCR7, immobilized directly or indirectly on the support thus removing chemokine receptor, in particular CCR1, CCR2 and CCR7, expressing cells from the peripheral blood of the patient. The peripheral blood from which the chemokine receptor expressing cells have been removed may then be returned to the patient in order to complete the treatment. The invention may thus rely on a continuous extracorporeal circuit in some embodiments. Alternatively, the invention may comprise steps of obtaining peripheral blood from the patient, applying the peripheral blood to the column and subsequently returning the peripheral blood from which the chemokine receptor expressing cells have been removed to the patient.

As shown herein, suitable binding reagents can be immobilized onto a solid support, either directly or indirectly, to generate an apheresis column suitable for capturing relevant chemokine receptor-expressing cells. Where increased levels of chemokine receptor expression are observed, such cells may be preferably removed from the peripheral blood using the columns of the various embodiments of the invention in some embodiments. Thus, the methods of the various embodiments of the invention may preferably target CCR1hi, CCR2hi and/or CCR7hi cells as defined herein for removal from the peripheral blood. "High" expression may be determined according to standard flow cytometry techniques. The level is measured relative to levels of expression of the chemokine receptor in cells taken from a healthy subject. The attached FIG. 128 provides an example of a gating strategy.

Herein, reference to CCR1, CCR2 and/or CCR7 is intended to encompass selection of any one or more, up to all, of the chemokine receptors listed. In addition, the combination of CCR2 and/or CCR7 is explicitly contemplated as a separate grouping, to include any one or more of CCR2 and CCR7.

In other embodiments the invention further provides one or more binding reagents capable of specifically binding to a chemokine receptor, in particular to a chemokine receptor/the chemokine receptor selected from CCR1, CCR2 and CCR7, for use in the treatment of cardiovascular disease, wherein the binding reagent is immobilized, directly or indirectly, on a solid support contained within an apheresis column, to which is applied peripheral blood from a patient thus removing chemokine receptor/CCR1, CCR2 and/or CCR7 expressing cells from the peripheral blood of the patient. In certain embodiments the invention also provides for use of a binding reagent capable of specifically binding to a chemokine receptor/the chemokine receptor CCR1, CCR2 and/or CCR7 for use in the manufacture of an apheresis column for treatment of cardiovascular disease, wherein the binding reagent is immobilized on a solid support contained within the apheresis column, to which is applied peripheral blood from a patient thus removing chemokine receptor/CCR1, CCR2 and/or CCR7 expressing cells from the peripheral blood of the patient.

All embodiments described in respect of the methods of treatment of the various embodiments of the invention apply to these aspects mutatis mutandis and are not repeated for reasons of conciseness. Thus, the following discussion made with reference to the methods of treatment is also applicable to the medical use aspects of the various embodiments of the invention.

In certain embodiments the invention aims to treat cardiovascular disease. MCP-1 is secreted from endothelial cells and smooth muscle cells and plays a critical role in the development of cardiovascular diseases. It has been shown (Niu and Kolattakudy. Clinical Science (2009) 117, 95-109) that MCP-1, by its chemotactic activity, causes diapedesis of monocytes from the lumen to the subendothelial space where they become foam cells, initiating fatty streak formation that leads to atherosclerotic plaque formation. Inflammatory macrophages probably play a role in plaque rupture and the resulting ischaemic episode as well as restenosis after angioplasty. There is strong evidence that MCP-1 plays a major role in myocarditis, ischaemia/reperfusion injury in the heart and in transplant rejection. MCP-1 also plays a role in cardiac repair and manifests protective effects under certain conditions. Such protective effects may be due to the induction of protective ER (endoplasmic reticulum) stress chaperones by MCP-1. Under sustained ER stress caused by chronic exposure to MCP-1, the protection would break down resulting in the development of heart failure. MCP-1 is also involved in ischaemic angiogenesis. In mice, blocking of MCP-1 or CCR2 show beneficial effects against cardiovascular disease. In particular, MCP-1 knockout (KO) mice or CCR2 KO mice have reduced atherosclerosis, whereas MCP-1 overexpression increases foam cell formation and atherosclerosis. Any relevant condition including an inflammatory component may be treated according to the methods of the invention. Specific conditions including an inflammatory component are thus cardiovascular disease, including arteriosclerosis and in particular atherosclerosis.

By "treatment" is meant a reduction in the specific chemokine receptor expressing cells in the peripheral blood of the patient. The reduction may comprise a reduction in cells that express chemokine receptors, in particular CCR1, CCR2 and/or CCR7, at increased levels in diseased patients. The patient is typically a human patient but the term patient may include both human and non-human animal subjects in some embodiments. In the context of the various embodiments of the present invention, this typically involves a reduction in CCR1, CCR2 and/or CCR7 expressing cells, such as "CCR1, CCR2 and/or CCR7hi" expressing cells, in the peripheral blood of the patient. The CCR1, CCR2 and/or CCR7 expressing cells comprise, consist essentially of or consist of monocytes, including differentiated forms thereof such as macrophages and foam cells and/or lymphocytes, in particular T-lymphocytes, and/or dendritic cells, in particular plasma dendritic cells in certain embodiments. In specific embodiments the cells removed in order to treat atherosclerosis comprise monocytes, in particular CCR1 and/or CCR2 expressing monocytes. Monocytes are produced by the bone marrow from haematopoietic stem cell precursors called monoblasts. Monocytes may differentiate into macrophages or dendritic cells. Monocytes and their macrophage and dendritic cell progeny serve a number of functions in the immune system including phagocytosis, antigen presentation and cytokine production. Monocytes may be characterized with reference to expression of the cell surface marker CD14, optionally together with CD16. Classical monocytes may be characterized by high level expression of the CD14 cell surface receptor (CD14++CD16− monocyte). Non-classical monocytes may be characterized by low level expression of CD14 and with additional co-expression of the CD16 receptor (CD14+CD16++ monocyte). Intermediate monocytes may be characterized by high level expression of CD14 and low level expression of CD16 (CD14++CD16+ monocytes). Macrophages are derived from monocytes and are responsible for protecting tissues from foreign substances. They are cells that possess a large smooth nucleus, a large area of cytoplasm and internal vesicles for processing foreign material. The term "macrophage" may refer to a monocyte-derived cell expressing one or more of the following cell surface markers CD14, CD11b, Lysozyme M, MAC-1/MAC-3 and CD68. The term macrophage includes both activated and un-activated macrophages. Activated macrophages may be characterized by expression of one or more of CD69, ENG, FCER2 and IL2RA, HLA-DR, CD86. Un-activated macrophages have not yet received activating signals through for example TLR receptors and therefore they express less activation markers on the cell surface which correlates with lesser maturation. M1 macrophages may be characterized by expression of one or more of CD16+CD32+CD64+ and secrete mainly IL-23 and IL-1, TNF, IL-6 and high levels of IL-12 and in addition effector molecules such as iNOS and ROI. M1 macrophages have cytotoxic features as opposed to M2 macrophages. M2 macrophages may be characterized by expression of one or more of SRA/B+CD163+MR+CD14+ and express TGFβ, IL-10 and IL-1Ra. Tumour associated macrophages (TAMs) share many characteristics with the M2 macrophages and are considered as M2 polarised macrophages. The M1/M2 paradigm can also be found in monocyte subsets where CD14+CD16−CXC3R1low monocytes are considered the "inflammatory" subset and the CD14lowCD16+CXC3R1high are "resident" monocytes. A critical event in atherogenesis is the focal accumulation of lipid-laden foam cells (FC) derived from macrophages (MF), smooth muscle cells, and other vascular cells with subsequent fatty streak formation. Macrophages engulf oxidized low-density lipoproteins (LDLs) by endocytosis. The oxidized LDL accumulates in the phagocytes, forming a foam cell. Characteristic markers of foam cells include CD68 and alphaVbeta3 integrin.

The three major types of lymphocyte are T cells, B cells and natural killer (NK) cells. The term "T-lymphocyte" includes CD4+ T cells such as T helper cells (Th1 cells and Th2 cells), and CD8+ T cells such as cytotoxic T cells. Th1 cells may be characterized by expression of CCR5 and/or by production of IFN-γ. Th2 cells may be characterized by expression of CCR3 and/or by production of IL-4.

Dendritic cells (DCs) are the most important class of "antigen presenting cells" and as such, play an central role in the activation of the immune response. Immature DCs reside in tissues throughout the body are may become activated in response to a variety of stimuli indicating the presence of antigen. Once activated, DCs can release a plethora of cytokines that activate cells of the innate immune system including eosinophils, macrophages and NK cells. Activated DCs also take up and process antigen and, as a result, actively transport antigen to secondary lymphoid organs. At these sites, antigen is presented on the surface of mature DCs, in the context of MHC class I and class II complexes, to immature T and B cells leading to both cellular and humoral immune responses.

DCs represent a heterogeneous class of cells of which there are two main subtypes: myeloid DCs (mDCs) and plasmacytoid DCs (pDCs). These subtypes can be further divided into different subsets which may be classified according to the differential expression of a variety of cell surface markers. Importantly, the different subsets of DCs appear to drive different immune effector responses; for example, CD14+ mDCs appear to specialize in the generation of humoral immunity whereas BDCA3+ mDCs elicit CD8+ T cell responses. Furthermore, pDCs can be distinguished by the surface expression of CD2, and are typically involved in the generation of anti-viral immune responses as a result of rapid type I interferon production.

CCR1, CCR2 and CCR7 expressed on these aforementioned cells binds to chemokines such as monocyte chemoattractant protein-1 (MCP-1). MCP-1 is a major chemoattractant for monocytes and memory T cells by means of their binding to its specific cell-surface receptor, CC-chemokine receptor-2 (CCR2). CCR2 is the gene symbol approved by the HUGO Gene Nomenclature Committee for chemokine (C—C motif) receptor 2. The HGNC ID for this gene is 1603. The gene is located at chromosome position 3p21. The previous symbol and name for the gene is CMKBR2. Synonyms for this gene include CC-CKR-2, CD192, CKR2, FLJ78302, MCP-1-R. The NCBI Reference Sequence is NM_001123041.2 as available on 13 Jun. 2011, which is incorporated herein by reference in its entirety.

CCR7 is the gene symbol approved by the HUGO Gene Nomenclature Committee for chemokine (C—C motif) receptor 7. The HGNC ID for this gene is 1608. The gene is located at chromosome position 17q12-q21.2. The previous symbol and name for the gene is CMKBR7, EBI1. Synonyms for this gene include BLR2, CD197 and CDw197. The RefSeq reference sequence for CCR7 is NM_001838.3 as available on 13 Jun. 2011, which is incorporated herein by reference in its entirety.

CCR1 is the gene symbol approved by the HUGO Gene Nomenclature Committee for chemokine (C—C motif) receptor 1. The HGNC ID for this gene is 1602. The gene is located at chromosome position 3p21. The previous symbol and name CMKBR1, SCYAR1. Synonyms for this gene include CD191, CKR-1, MIP1aR. The RefSeq reference sequence for CCR1 is NM_001295.2 as available on 13 Jun. 2011, which is incorporated herein by reference in its entirety.

The various embodiments of the methods of the invention may involve specific binding interactions with any one or more of these further cell-surface markers in addition to the removal based upon binding to CCR1, CCR2 and/or CCR7. Suitable binding reagents can be prepared to specifically bind to these cell-surface markers. The discussion of CCR1, CCR2 and/or CCR7 specific binding reagents thus applies mutatis mutandis.

Treatment according to the various embodiments of the invention may result in alleviation or amelioration of symptoms, prevention of progression, regression of the condition, or complete recovery. Measurable parameters of successful treatment include one or more, up to all, of ECG, angiography, MRI, Technicium sestamibi scintigraphy (SPECT). In specific embodiments, a single treatment is sufficient to cause a depletion of around 10%, 20%, 30%, 40%, 50%, 60% or 70%, or higher up to 80%, 90%, 95% or more, or any range of values between and including these amounts, of the specific chemokine receptor, in particular CCR1, CCR2 and/or CCR7, expressing cells from the peripheral blood of the patient. In specific embodiments, at least around 50% depletion is achieved in a single treatment. Thus, successful treatment may be defined with reference to depletion of CCR1, CCR2 and/or CCR7 expressing cells. Treatment may lead to depletion of between approximately 100 and 500 million CCR1, CCR2 and/or CCR7 expressing cells, such as monocytes, in certain embodiments and more particularly to about 100, 150, 200, 250, 300, 350, 400, 450, or 500 million CCR1, CCR2 and/or CCR7 expressing cells.

By binding to the column through the binding reagent-chemokine receptor interaction, chemokine receptor expressing cells are immobilized. These immobilized cells express further unoccupied chemokine receptors, which may be of the same or different type to those used for capture. These additional chemokine receptors may permit circulating chemokines which contribute to the inflammatory condition to be captured from the peripheral blood. Thus, a reduction in circulating (specific) chemokine levels may provide a measure of successful treatment.

The duration of treatment may be readily determined by one skilled in the art and will depend upon factors such as the flow rate of the peripheral blood. Duration of treatment may be tied into monitoring of the treatment itself, with the treatment considered complete once a measurable parameter of treatment has reached a defined threshold. Any suitable parameter may be employed as discussed herein. Thus, for example, treatment may be considered complete when a reduction in CCR1, CCR2 and/or CCR7 expressing cells, such as a 50% reduction in CCR1, CCR2 and/or CCR7 expressing cells, has been achieved. The apheresis system may be operated at a flow rate of around 10-80 mL/min, or more specifically between around 20-70 mL/min, or between around 30-60 mL/min. In specific embodiments, the treatment is performed for a period of around 10, 20, 30, 40, 50, 60, 70, 80, 90, 100, 110, 120 etc., or any range of values between and including these amounts, minutes. The treatment is typically not aimed to remove all of the cells expressing the chemokine receptor in the peripheral blood, as a basal level of those cells is required in healthy subjects. However, it has been found that only low blood volumes need to be applied to the columns of the various embodiments of the invention in order to achieve effective levels of depletion of the chemokine receptor-expressing cells. Thus, in certain embodiments, around 10-80% or more specifically around 20, 30, 40 or 50%, or any range of values between and including these amounts, of the patient's blood is applied to the column in a single treatment. The volume of blood circulated through the apheresis column or system may be in the region of around 1000-3000 ml, such as around 1000, 1200, 1400, 1600, 1800 or 2000 ml or any range of values between and including these amounts. The treatment may be considered complete once this volume of blood has been circulated. The patient may be administered anticoagulants prior to each treatment session. A suitable solution, such as a sterile saline solution, optionally including an anticoagulant such as Heparin, may be used for priming the apheresis (extracorporeal) system. An additional volume of anticoagulant may be added to the circuit at the start of each treatment session, for example as a bolus injection.

In certain embodiments the invention relies upon a binding reagent which is capable of specifically binding to a chemokine receptor. This specific binding reaction permits cells expressing the chemokine receptor to be removed from the peripheral blood of the patient when the blood is passed over the solid support upon or within which the binding reagent is immobilized. Specific chemokine receptors of interest include CCR1, CCR2 and CCR7. The binding reagent can be any binding reagent capable of specifically binding to the receptor in question. By "specific binding" is meant that the binding reagent displays sufficient specificity of binding and appropriate binding affinity/kinetics to permit removal of cells expressing CCR1, CCR2 and/or CCR7 from the peripheral blood. Whilst it is not precluded that the binding reagent is capable of binding to other molecules, such as other chemokine receptors, the binding reagent will preferentially bind to cells expressing CCR1, CCR2 and/or CCR7 and in particular to cells expressing increased levels of CCR1, CCR2 and/or CCR7 (as defined further herein). The binding reagent capable of specifically binding to CCR1, CCR2 and/or CCR7 may be either an agonist or an antagonist of CCR1, CCR2 and/or CCR7. As the disease condition relies upon up-regulation of expression of or signaling via CCR1, CCR2 and/or CCR7, in certain embodiments the binding reagent capable of specifically binding to CCR1, CCR2 and/or CCR7 is an antagonist of CCR1, CCR2 and/or CCR7. Chemokines are typically, although not necessarily exclusively (particularly in the case of truncated or modified forms) agonists of their cognate receptor and serve to activate the cells expressing the relevant receptor, as would be appreciated by one skilled in the art. Antibodies against the relevant chemokine receptor are generally considered to be antagonists, as would be appreciated by one skilled in the art. Specific examples of binding reagents include proteins or polypeptides, such as antibodies and receptor ligands, in particular chemokines. The binding reagent may be a nucleic acid molecule in certain embodiments. In some embodiments, the nucleic acid is an aptamer. Nucleic acid aptamers are polynucleotides of approximately 15-40 nucleotides long. Nucleic acid aptamers can be made using the SELEX process (systemic evolution of ligands by exponential enrichment) or any other process known to those of skill in the art.

In other embodiments, the binding reagent may be a peptide, and in certain instances, a peptide aptamer. Peptide aptamers are artificial recognition molecules that consist of a variable peptide sequence inserted into a constant scaffold protein (Baines I C, Colas P. Peptide aptamers as guides for small molecule drug discovery. Drug Discov Today. 2006; 11:334-341, incorporated herein by reference). A number of methodologies, such as phage display, ribosome display and yeast two-hybrid screening systems are available for screening a library of potential peptide-based binding agents. Similarly protein scaffolds based on domains such as fibronectins, ankyrin repeats, protein A, SH3 domains, lipocalins, and ubiquitin can be used as the binding agent. Again a number of technologies such as phage display and ribosome display are available for screening a library of protein-based binding agents. Similarly, libraries of candidate chemical compounds can be screened for specific binding to the relevant chemokine receptor using suitable screening techniques known in the art, which may be high throughput screens in certain embodiments. The candidate binding agent may be immobilized on a solid support and the ability of the agent to specifically retain cells expressing the chemokine receptor of interest or labelled chemokine receptors determined. A range of cell types may be applied to the solid supports to confirm specificity of binding, or alternatively a mixed sample (such as peripheral blood) may be applied to the solid support. Retention of the cell type of interest (expressing the appropriate chemokine receptor) can be confirmed to identify suitable binding agents. A range of small-molecule antagonists of CCR-2 are discussed by Xia M and Sui Z in Expert Opin Ther Pat. 2009 March; 19 (3):295-303—Recent developments in CCR2 antagonists, and incorporated herein by reference.

In the context of the various embodiments of the present invention the term "chemokine" also comprises biotinylated or otherwise labelled chemokines. The term "chemokine" also comprises modified and truncated versions of the chemokine and chemokine fragments with the proviso that the modified or truncated form retains its ability to bind to its cognate receptor (and thus remains functional in the context of the various embodiments of the invention). The chemokine does not necessarily need to retain biological activity as it is specific binding affinity for CCR1, CCR2 and/or CCR7 that is required. In certain embodiments, the chemokine lacks biological activity, for example in terms of activation of the (CCR1, CCR2 and/or CCR7) receptor. Modifications may be made to improve protein synthesis, for example uniformity of product and yield. As known to those skilled in the art, exemplary modifications may comprise amino acid additions, substitutions, deletions or other modifications to one or more amino acids in the chemokine. Modifications may comprise substitution of the wild type amino acid with non-natural amino acids such as norleucine (NLeu) and derivatized amino acids such as pyroglutamic acid (pyroGlu). Such modifications may be made to minimize side-product formation during storage and use of the columns of the various embodiments of the invention. Modifications may be made to improve labelling, for example inclusion of a polyethylene glycol (PEG) spacer to facilitate biotinylation. The biotinylation and/or conjugation with fluorochromes or other labelling groups of the chemokine is performed in a manner which does not substantially affect the receptor binding capacity. Site specific biotinylation or other labelling is preferred as non-selective labelling of chemokines may compromise receptor binding activity. Bioinylation or other labelling is generally preferred at or towards the C-terminus of the protein as the inventors have found that modifications in this area are generally well tolerated (in terms of a minimal effect on receptor binding capability). Biotinylation may be carried out site-specifically at any suitable amino acid. Examples of suitable amino acids include lysine, diaminopropionic acid and ornithine. Truncations may involve deletion of either N or C terminal amino acids as appropriate, or both. Typically, the truncated version will retain the residues required for the chemokine to fold correctly, for example to retain a chemokine fold structure, consistent with the requirement that a truncated version must retain the ability to bind to the relevant receptor (expressed by (on the surface of) a leukocyte). Chemokine molecules typically include disulphide bonds between the 1st and 3rd and 2nd and 4th cysteine residues respectively, as would be understood by one skilled in the art. Where sequences are presented herein, it is assumed that these disulphide bonds will form in the folded protein (unless otherwise stated). Truncated versions may comprise anywhere between 1 and 100 less amino acids, such as 1, 2, 3, 4, 5 etc amino acids, than the wild type amino acid sequence in certain embodiments. Of course, truncated versions may comprise further modification as detailed herein. The modified or truncated version may have 40%, 45%, 50%, 55%, 60%, 65%, 70%, 75%, 80%, 85%, 90%, 95% or more overall amino acid sequence identity with the full length wild type chemokine (where a deletion is counted as a difference in amino acid sequence) in certain embodiments. Over the common sequence between the molecules (i.e the amino acids that have not been deleted), there may be 80%, 85%, 90%, 91%, 92%, 93%, 94%, 95%, 96%, 97%, 98% or 99% amino acid sequence identity in certain embodiments. Sequence identity may be determined using known algorithms, such as BLAST or GAP analysis (GCG Program), (applying default settings), which are freely available. Chemokines may lack the N-terminal signal peptide which is cleaved off during synthesis in vivo. Biotinylation may be carried out site-specifically at any suitable amino acid. Examples of suitable amino acids include lysine, diaminopropionic acid and ornithine. Generally, reference may be made to Natarajan S et al, Int. J. Pept. Protein Res., 1992, 40, 567-74; Baumeister B, Int. J. Peptide Res. And Therapeutics, 2005, 11, 139-141; Bioconjugate techniques 2nd edition, Greg T. Hermanson, incorporated by reference herein in its entirety.

Specific chemokines useful in the present various embodiments of the invention include MCP-1, MCP-2, MCP-3, MCP-4 and MCP-5. Both MCP-1 and MCP-5 bind solely to the chemokine receptor CCR2 and so these chemokines may be preferred in some embodiments. Each chemokine is able to bind to a chemokine receptor implicated in a cardiovascular disease associated disorder or condition. More specifically, each of MCP-1, MCP-2, MCP-3, MCP-4 and MCP-5 are useful for removing CCR2 expressing cells from the blood of a patient. CCL19 (MIP-3beta) and CCL21 (SLC) each bind to the chemokine receptor CCR7 and may be useful in the present invention. CCL5 (RANTES) binds to CCR1 and may be useful in the various embodiments of the present invention.

CCL2 is the gene symbol approved by the HUGO Gene Nomenclature Committee for chemokine (C—C motif) ligand 2, also known as MCP-1. The HGNC ID for this gene is 10618. The gene is located at chromosome position 17q11.2-q21.1. The previous symbol and name for the gene is SCYA2 "small inducible cytokine A2 (monocyte chemotatic protein 1, homologus to mouse Sig-je)". Synonyms for this gene include GDCF-2, HC11, MCP1, MGC9434, SMC-CF, "monocyte chemoattractant protein-1", "monocyte chemotactic and activating factor", "monocyte chemotactic protein 1, homologous to mouse Sig-je", "monocyte secretory protein JE", "small inducible cytokine subfamily A (Cys-Cys), member 2". The Genbank reference sequence for CCL2 is BC009716.1 as available on 13 Jun. 2011, which is incorporated herein by reference in its entirety.

CCL8 is the gene symbol approved by the HUGO Gene Nomenclature Committee for chemokine (C—C motif) ligand 8, also known as MCP-2. The HGNC ID for this gene is 10635. The gene is located at chromosome position 17q11.2. The previous symbol and name for the gene is SCYA8, "small inducible cytokine subfamily A (Cys-Cys), member 8 (monocyte chemotactic protein 2)". Another synonym for this gene is HC14. The Genbank reference sequence for CCL8 is X99886.1 as available on 13 Jun. 2011, which is incorporated herein by reference in its entirety.

CCL7 is the gene symbol approved by the HUGO Gene Nomenclature Committee for chemokine (C—C motif) ligand 7, also known as MCP-3. The HGNC ID for this gene is 10634. The gene is located at chromosome position 17q11.2-q12. The previous symbol and name for the gene is SCYA6, SCYA7, "small inducible cytokine A7 (monocyte chemotactic protein 3)". Synonyms for this gene include FIC, MARC, MCP-3, MCP3, NC28, "monocyte chemoattractant protein 3", "monocyte chemotactic protein 3". The Genbank reference sequence for CCL7 is AF043338 as available on 13 Jun. 2011, which is incorporated herein by reference in its entirety.

CCL13 is the gene symbol approved by the HUGO Gene Nomenclature Committee for chemokine (C—C motif) ligand 13, also known as MCP-4. The HGNC ID for this gene is 10634. The gene is located at chromosome position 17q11.2-q12. The previous symbol and name for the gene is SCYA6, SCYA7, "small inducible cytokine A7 (monocyte chemotactic protein 3)". Synonyms for this gene include FIC, MARC, MCP-3, MCP3, NC28, "monocyte chemoattractant protein 3", "monocyte chemotactic protein 3". The Genbank reference sequence for CCL13 is AJ001634 as available on 13 Jun. 2011, which is incorporated herein by reference in its entirety.

MCP-5 is a mouse chemokine in the CC chemokine family. It is also known as Chemokine (C—C motif) ligand 12 (CCL12) and, due to its similarity with the human chemokine MCP-1, sometimes it is called MCP-1-related chemokine. The gene for MCP-5 is found in a cluster of CC chemokines on mouse chromosome 11. The NCBI reference sequence for CCL12 is NC_000077.5 as available on 13 Jun. 2011, which is incorporated herein by reference in its entirety.

CCL19 is the gene symbol approved by the HUGO Gene Nomenclature Committee for chemokine (C—C motif) ligand 19, also known as MIP-3b. The HGNC ID for this gene is 10617. The gene is located at chromosome position 9p13. The previous symbol and name for the gene is SCYA19, "small inducible cytokine subfamily A (Cys-Cys), member 19". Synonyms for this gene include "beta chemokine exodus-3", "CC chemokine ligand 19", "CK beta-11", CKb11, "EBI1-ligand chemokine", ELC, exodus-3, "macrophage inflammatory protein 3-beta", MIP-3b. The Genbank reference sequence for CCL19 is AB000887.1 as available on 13 Jun. 2011, which is incorporated herein by reference in its entirety.

CCL5 is the gene symbol approved by the HUGO Gene Nomenclature Committee for chemokine (C—C motif) ligand 5, also known as RANTES. The HGNC ID for this gene is 10632. The gene is located at chromosome position 17q11.2-q12. The previous symbol and name for the gene is D17S136E, SCYA5, "small inducible cytokine A5 (RANTES)". Synonyms for this gene include "beta-chemokine RANTES", MGC17164, RANTES, "regulated upon activation, normally T-expressed, and presumably secreted", "SIS-delta", SISd, "small inducible cytokine subfamily A (Cys-Cys), member 5", "T-cell specific protein p288", "T-cell specific RANTES protein", TCP228. The Genbank reference sequence for CCL5 is AF043341.1 as available on 13 Jun. 2011, which is incorporated herein by reference in its entirety.

CCL21 is the gene symbol approved by the HUGO Gene Nomenclature Committee for chemokine (C—C motif) ligand 21. The HGNC ID for this gene is 10620. The gene is located at chromosome position 9p13. The previous symbol and name for the gene is SCYA21, "small inducible cytokine subfamily A (Cys-Cys), member 21". Synonyms for this gene include 6Ckine, "beta chemokine exodus-2", CKb9, ECL, "Efficient Chemoattractant for Lymphocytes", exodus-2, "secondary lymphoid tissue chemokine", SLC, TCA4. The Genbank reference sequence for CCL21 is AB002409.1 as available on 13 Jun. 2011, which is incorporated herein by reference in its entirety.

Examples of suitable modified chemokines of the various embodiments of the invention containing modifications and/or truncations and specifically adapted for use in the invention are described in detail herein. MCP-1 has been produced with residue 75, which may be a lysine, as the site of biotinylation on the chemokine (numbering based upon the mature protein having the amino acid sequence of SEQ ID NO: 176). Biotinylation permits immobilization of MCP-1 on a solid support (via a biotin-avidin interaction). The basic amino acid sequence of MCP-1, including a 23 amino acid leader sequence is set forth as SEQ ID NO: 175. The amino acid sequence of the mature protein is set forth as SEQ ID NO: 176. The inventors have determined that chemokines may display improved binding properties where the chemokine is biotinylated via a spacer group. The spacer may prevent the biotin group from impacting on the binding affinity of the chemokine. Any suitable spacer group may be employed. Further modifications may provide the molecule with advantageous properties. The invention also relates to derivatives of truncated MCP-1 chemokines. The amino acid sequence of the truncated version is set forth as SED ID NO: 177.

Accordingly, the invention also provides a modified MCP-1 chemokine comprising, consisting essentially of or consisting of the amino acid sequence set forth as SEQ ID NO: 1, SEQ ID NO: 176 or SEQ ID NO: 177 in which one or more of the following modifications have been made:

a) the glutamine residue 1 of SEQ ID NO: 176 has been replaced with pyroglutamine b) the C terminus is produced as an amide derivative (this may be achieved by synthesis on an amide linker)

c) the (C terminal region) residue at position 98 of SEQ ID NO: 175 or position 75 of SEQ ID NO: 176 or position 67 of SEQ ID NO: 177, which may be a lysine or ornithine residue, is biotinylated, optionally via a spacer group, in order to permit immobilization of the chemokine on a solid support; and/or d) the methionine residue at position 87 of SEQ ID NO: 175 or position 64 of SEQ ID NO: 176 or position 56 of SEQ ID NO: 177 has been replaced with norleucine.

The (C terminal region) amino acid, which may be a lysine residue or a functional equivalent, at position 98 of SEQ ID NO: 175 or position 75 of SEQ ID NO: 176 or position 67 of SEQ ID NO: 177 may be biotinylated via a suitable spacer group, such as a polyethylene glycol (PEG) spacer group, in order to permit immobilization of the chemokine on a solid support. In specific embodiments, the PEG spacer is 3,6-dioxo aminooctanoic acid. The sequence and biotinylation of the modified MCP-1 chemokines of the invention are shown in FIGS. 123 to 125 respectively. The modified MCP-1 chemokines may be agonists or antagonists of CCR2 activity. They can be tested for activity in a suitable assay, such as cell-based assays. In particular, agonist and antagonist properties may be determined in functional cell-based assay on human CCR2 receptor.

MCP-5 only binds CCR2 and should be selective in its removal of CCR2 expressing cells. The full length amino acid sequence, including the signal peptide, is set forth as SEQ ID NO: 178. The amino acid sequence of N-terminal processed MCP-5 chemokine is 82 amino acids long and is set forth as SEQ ID NO: 179. An amino acid sequence alignment suggests that MCP-5 has a C-terminal extension when compared to the amino acid sequence of MCP-1. The results of this alignment are shown in FIG. 126. C-terminal truncated versions of MCP-5 can thus be synthesised. This truncated version will comprise, consist essentially of or consist of MCP-5 residues 1-76, set forth as SEQ ID NO: 180.

Accordingly, the invention also provides a modified MCP-5 chemokine comprising the amino acid sequence set forth as SEQ ID NO: 178, SEQ ID NO: 179 or SEQ ID NO: 180 in which the isoleucine residue at position 97 of SEQ ID NO: 178 or at position 75 of SEQ ID NO: 179 or SEQ ID NO: 180 has been replaced with lysine. In certain embodiments, the modified MCP-5 chemokine comprises, consists essentially of or consists of the amino acid sequence of SEQ ID NO: 181. The modified MCP-5 chemokine may be biotinylated at the lysine (or a functional equivalent) residue at position 97 of SEQ ID NO: 178 or at position 75 of SEQ ID NO: 179 or SEQ ID NO: 180. Biotinylation may be via a suitable spacer group. Specific examples of the spacer group include a PEG spacer, optionally 3,6-dioxo aminooctanoic acid. In some embodiments, the C terminus is produced as an amide derivative. This may be achieved by synthesis on an amide linker. In certain embodiments, the modified MCP-5 chemokine comprises, consists essentially of or consists of the sequence and biotinylation shown in FIG. 127. The modified MCP-5 chemokine may be an agonist or an antagonist of CCR2 activity. Chemokines and modified chemokines can be tested for activity in a suitable assay, such as cell-based assays. In particular, agonist and antagonist properties may be determined in a functional cell-based assay on human CCR2 receptor.

An example of a chemokine of the various embodiments of the invention containing modifications and specifically adapted for use in the invention is described in detail herein (see Examples below). The modified CCL8 (MCP-2) corresponds to residues 1 to 76 of the full length mature protein (and lacks the N-terminal signal peptide of 23 amino acids, which is cleaved off) and thus retains the chemokine fold. The Gln at the N-terminus of the protein is subject to pyroGlu formation under physiological conditions. Thus Gln1 of the sequence may thus be substituted with pyroglutamine to prevent mixed species of N-terminal Gln and pyroGlu being generated (SEQ ID NO: 188). This improves the yield of synthesis and ensures a homogeneous chemokine preparation through column manufacture and use. FmocLys(ivDde)-OH is incorporated as residue 75 to facilitate site-specific labelling at this position of the protein (SEQ ID NO: 189). The naturally occurring lysine at position 75 is modified through biotinylation. A PEG spacer may be incorporated between the ε-amino functionality and the biotin (SEQ ID NO: 190).

Thus, in certain embodiments the invention also relates to a modified chemokine comprising, consisting essentially of or consisting of the amino acid sequence of SEQ ID NO: 188:

```
XPDSVSIPITCCFNVINRKIPIQRLESYTRITNIQCPKEAVIFKTKRGKE
VCADPKERWVRDSMKHLDQIFQNLXP
```

X1=pyroGlu (but may remain as Gln in some embodiments)

X75=an amino acid residue that can be biotinylated, such as lysine, ornithine or diaminopropionic acid and optionally is biotinylated, optionally via a spacer molecule such as PEG, e.g. K(PEG-Biotin).

Or SEQ ID NO: 190

```
XPDSVSIPITCCFNVINRKIPIQRLESYTRITNIQCPKEAVIFKTKRGKE
VCADPKERWVRDSMKHLDQIFQNLXP
```

X1=pyroGlu (but may remain as Gln in some embodiments)

X75=K(PEG-Biotin).

A further example of a chemokine of the various embodiments of the invention containing modifications and specifically adapted for use in the invention is described in detail herein (see Examples below). The modified CCL5 (RANTES) corresponds to residues 1 to 68 of the full length mature protein (and lacks the N-terminal signal peptide of 23 amino acids, which is cleaved off) and thus retains the chemokine fold. The single methionine (Met67) within the sequence is mutated to lysine, to mitigate against oxidation of this residue during the chain assembly (SEQ ID NO: 185). This Met to Lys substitution provides a lysine at position 67 which can be modified through biotinylation. FmocLys (ivDde)-OH is incorporated as residue 67 to facilitate site-specific labelling at this position of the protein (SEQ ID NO: 186). The biotinylated version comprises, consists essentially of or consists of the amino acid sequence of SEQ ID NO: 187.

Thus, in other embodiments the invention also relates to a modified chemokine comprising, consisting essentially of or consisting of the amino acid sequence of SEQ ID NO: 187:

```
SPYSSDTTPCCFAYIARPLPRAHIKEYFYTSGKCSNPAVVFVTRKNRQVC
ANPEKKWVREYINSLEXS
```

X is an amino acid residue that can be biotinylated, such as lysine, ornithine or diaminopropionic acid and optionally is biotinylated, optionally via a spacer molecule such as PEG (e.g. K(Biotin))

A further example of a chemokine of the various embodiments of the invention containing modifications and specifically adapted for use in the invention is described in detail herein (see Examples below). The modified CCL2 (MCP-1) corresponds to residues 1 to 76 of the full length mature protein (and lacks the N-terminal signal peptide of 23 amino acids, which is cleaved off) and thus retains the chemokine fold. The Gln at the N-terminus of the protein (Gln1) is substituted with pyroglutamine to prevent mixed species of N-terminal Gln and pyroGlu being generated (SEQ ID NO: 182). This improves the yield of synthesis and ensures a homogeneous chemokine preparation through column manufacture and use. FmocLys(ivDde)-OH is incorporated as residue 75 to facilitate site-specific labelling at this position of the protein (SEQ ID NO: 183). A suitable spacer, such as a PEG spacer, may be incorporated between the ε-amino functionality and the biotin. The biotinylated version comprises, consists essentially of or consists of the amino acid sequence of SEQ ID NO: 184.

Thus, in other embodiments the invention also relates to a modified chemokine comprising, consisting essentially of or consisting of the amino acid sequence of:

```
SEQ ID NO: 182:
XPDAINAPVTCCYNFTNRKISVQRLASYRRITSSKCPKEAVIFKTIVAKE
ICADPKQKWVQDSMDHLDKQTQTPKT
```

X=pyroGlu or Gln

And/or SEQ ID NO: 184:
```
XPDAINAPVTCCYNFTNRKISVQRLASYRRITSSKCPKEAVIFKTIVAKE
ICADPKQKWVQDSMDHLDKQTQTPXT
```

X1=pyroGlu or Gln

X75 is an amino acid residue that can be biotinylated, such as lysine, ornithine or diaminopropionic acid and optionally is biotinylated, optionally via a spacer molecule such as PEG, optionally K(PEG-Biotin)

A further example of a chemokine of the various embodiments of the invention containing modifications and specifically adapted for use in the invention is described in detail herein (see Examples below). The modified CCL19 (MIP-3β) corresponds to residues 1 to 77 of the full length mature protein (and lacks the N-terminal signal peptide of 21 amino acids, which is cleaved off) and thus retains the chemokine fold. An additional lysine is inserted at the C-terminus, at position 78. The chemokine may thus comprise, consist essentially of or consist of the amino acid sequence of SEQ ID NO: 191. FmocLys(ivDde)-OH is incorporated as residue 78 to facilitate site-specific labelling at this position of the protein (SEQ ID NO: 192). The e-amino side chain functionality of Lys(78) is modified through biotinylation. The final protein may thus comprise, consist essentially of or consist of the amino acid sequence of SEQ ID NO: 193.

Thus, in other embodiments the invention also relates to a modified chemokine comprising, consisting essentially of or consisting of the amino acid sequence of SEQ ID NO: 191 or 193:

```
                                          SEQ ID NO: 191
GTNDAEDCCLSVTQKPIPGYIVRNFHYLLIKDGCRVPAVVFTTLRGRQLC

APPDQPWVERIIQRLQRTSAKMKRRSSX
```

X is an amino acid residue that can be biotinylated, such as lysine, ornithine or diaminopropionic acid and optionally is biotinylated (e.g. K-biotin), optionally via a spacer molecule such as PEG, in particular K(PEG-Biotin)

```
                                          SEQ ID NO: 193
GTNDAEDCCLSVTQKPIPGYIVRNFHYLLIKDGCRVPAVVFTTLRGRQLC

APPDQPWVERIIQRLQRTSAKMKRRSSX
```

X is K(Biotin)

Chemokines useful in the various embodiments of the invention may be synthesised through any suitable means known in the art. Preferably, the chemokines are chemically synthesised as this facilitates modification and labelling etc. However, recombinant DNA based approaches may also be employed in combination with appropriate labelling and modification technologies as required. Thus, in certain embodiments the invention also provides a nucleic acid molecule encoding the chemokines of the various embodiments of the invention. In certain embodiments the invention also relates to a vector containing such a nucleic acid molecule and a host cell containing the vector. The vector may additionally comprise a suitable promoter operably linked to the nucleic acid molecule, to facilitate transcription of the corresponding mRNA molecule. The host cell may be capable of expressing the protein by transcription and translation of the nucleic acid molecule encoding a chemokine of the various embodiments of the invention.

The chemokines useful in the various embodiments of the invention can be biotinylated by methods known in the art such as described in WO 00/50088 A2, which is incorporated herein by reference in its entirety. As indicated above, site-specific labelling of the chemokines of the various embodiments of the invention is preferable, although any labelling technique which does not significantly affect the receptor-binding capacity of the chemokine may be employed. Various site-specifically biotinylated chemokines and native chemokines are available commercially, for instance from Almac, Craigavon, UK. In specific embodiments the one or more chemokines are biotinylated via a spacer group. The spacer may be employed to prevent the biotin group from impacting on the activity of the chemokine, in particular binding of the chemokine to its cognate receptor. Any suitable spacer that facilitates retention of receptor binding properties of the chemokine may be employed in the various embodiments of the invention. Thus, in the specific embodiments described above, spacers other than PEG spacers may be employed as appropriate. In specific embodiments, the spacer is a polyethylene glycol (PEG) spacer. PEG has been shown to be an effective spacer permitting attachment of biotin to the chemokine (which can then be immobilized on the solid support through interaction with streptavidin) without compromising receptor binding capability.

In the context of the various embodiments of the present invention the term "antibody" includes all immunoglobulins or immunoglobulin-like molecules with specific binding affinity for the relevant chemokine receptor (including by way of example and without limitation, IgA, IgD, IgE, IgG and IgM, combinations thereof, and similar molecules produced during an immune response in any vertebrate, for example, in mammals such as humans, goats, rabbits and mice). Specific immunoglobulins useful in the various embodiments of the invention include IgG isotypes. The antibodies useful in the various embodiments of the invention may be monoclonal or polyclonal in origin, but are typically monoclonal antibodies. Antibodies may be human antibodies, non-human antibodies, or humanized versions of non-human antibodies, or chimeric antibodies. Various techniques for antibody humanization are well established and any suitable technique may be employed. The term "antibody" also refers to a polypeptide ligand comprising at least a light chain or heavy chain immunoglobulin variable region which specifically recognizes and binds an epitope of an antigen, and it extends to all antibody derivatives and fragments that retain the ability to specifically bind to the relevant chemokine receptor. These derivative and fragments may include Fab fragments, F(ab')2 fragments, Fv fragments, single chain antibodies, single domain antibodies, Fc fragments etc. The term antibody encompasses antibodies comprised of both heavy and light chains, but also heavy chain (only) antibodies. In specific embodiments, the antibodies may be engineered so as to be specific for more than one chemokine receptor, for example bi-specific to permit binding to two different chemokine receptors. Suitable commercially available antibodies which bind to the chemokine receptors of interest are listed in table 9. They may or may not be labelled. General reference may be made to "Antibodies a laboratory manual: By E Harlow and D Lane. pp 726. Cold Spring Harbor Laboratory. 1988", which reference is incorporated herein in its entirety.

TABLE 9

Commercially available fluorophore labelled antibodies against specific chemokine receptors

| Antibody | Fluorophore | Supplier |
|---|---|---|
| CCR1 | Alexa Fluor 647 | Biolegend |
| CCR2 | PerCP Cy5.5 | Biolegend |
| CCR7 | PerCP Cy5.5 | Biolegend |

Anti-CCR2 antibodies are described for example in WO 2010/021697, incorporated herein by reference. Further examples of potentially useful antibodies include MLN-1202, an anti-CCR2 monoclonal antibody currently undergoing clinical trials (Millennium Pharmaceuticals).

The chemokine receptor expressing cells may thus be targeted using alternative binding agents, such as antibodies or other chemical compounds, as defined herein, rather than the natural chemokine binding partner. This approach is a new approach to treating inflammatory conditions.

Thus, in certain embodiments the invention also provides an apheresis column loaded with a solid support comprising a binding reagent capable of specifically binding to a chemokine receptor immobilized directly or indirectly on the support to permit removal of a cell expressing the chemokine receptor from the peripheral blood of a patient/subject, wherein the binding reagent is not a chemokine. The binding reagent capable of specifically binding to the chemokine receptor may be an agonist or an antagonist of the chemokine receptor. In specific embodiments, the binding reagent capable of specifically binding to the chemokine receptor is selected from an antibody and a chemical compound.

In other embodiments the invention thus also provides a method for treating an inflammatory condition comprising applying peripheral blood from a patient/subject to an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine) thus removing chemokine receptor expressing cells from the peripheral blood of the patient/subject. The method may comprise returning the blood depleted of the chemokine receptor expressing cells to the patient/subject.

Similarly, in other embodiments the invention provides a binding reagent capable of specifically binding to a chemokine receptor for use in the treatment of an inflammatory condition, wherein the binding reagent is immobilized on a solid support contained within an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient/subject, wherein the binding reagent is not a chemokine), to which is applied peripheral blood from a patient thus removing chemokine receptor expressing cells from the peripheral blood of the patient.

These aspects of the various embodiments of the invention may be integrated into the more focussed therapeutic aspects of the various embodiments of the invention (i.e. treating cardiovascular disease and various aspects thereof) and thus, the remainder of the disclosure, including all specific embodiments applies mutatis mutandis.

Solid support materials for immobilizing the binding reagents of the various embodiments of the invention are known in the art. "Solid support" refers to, for example, materials having a rigid or semi-rigid surface or surfaces, and may take the form of beads, resins, gels, microspheres, or other geometric configurations. A useful support material is one that does not activate blood cells so as to make them coagulate or adhere to the support as peripheral whole blood is applied to the device. In certain embodiments, a support treated with an agent to provide it with anti-coagulation properties, in particular a heparinized support is employed. Alternatively, the blood of the patient may be treated with an anti-coagulant such as heparin prior to application to the support. Useful support materials comprise high molecular weight carbohydrates, in particular carbohydrates having a molecular weight of 100 kDa or more, such as agarose, in particulate form, optionally cross-linked, and cellulose. Other preferred support materials are polymers, such as carboxylated polystyrene, and glass. The support of the various embodiments of the invention may be provided in the form of particles or fibres. The support particles may have regular form, such as spheres or beads, or irregular form. They may be porous or non-porous. A preferred average particle size of the support is from 50 µm to 2 mm. In certain embodiments Sepharose™, a cross linked, beaded-form of agarose, is used as column matrix. It is chosen for its optimal distribution capacity and can provide a large available area for affinity binding. Solid supports may be provided in the form of magnetic beads, with the specific binding reagent immobilized on the magnetic beads. Following capture of the (CCR1, CCR2 and/or CCR7) chemokine receptor expressing cells from the blood, the beads can be removed from the blood with the aid of an appropriate magnetic separator.

Methods for immobilizing binding reagents on a solid support are known in the art. A binding reagent, such as a chemokine, antibody, peptide, nucleic acid or chemical compound, can be immobilized on the support in a direct or indirect manner. Immobilization can be by means of a suitable linker in some embodiments. A preferred method of indirect immobilization of a binding reagent, such as a chemokine, relies upon the interaction between biotin and avidin molecules. "Avidin" or "avidin molecule" refers to any type of protein that specifically binds biotin to the substantial exclusion of other (small) molecules that might be present in a biological sample. Examples of avidin include avidins that are naturally present in egg white, oilseed protein (e.g., soybean meal), and grain (e.g., corn/maize), and streptavidin, which is a protein of bacterial origin. Thus, biotinylation of the binding reagent and use of an avidin molecule such as streptavidin immobilized on the solid support allows reliable attachment of the binding reagent to the solid support according to methods known in the art. Specifically, such a method may comprise providing the binding reagent in biotinylated form, providing a solid support having streptavidin immobilized on its surface, contacting the support with an aqueous solution of the biotinylated binding reagent, and rinsing the support with an aqueous solvent. In addition, binding pair interactions, such as antibody-antigen interactions, may also be utilised for indirect immobilisation of binding reagent onto a support. In such embodiments the support may be derivatised with one member of a binding pair, such as an antibody or fragment or derivative thereof, as defined herein, which has known affinity for a particular peptide sequence or small molecule hapten. Incorporating the other member of the binding pair, such as an antigen, peptide sequence or the hapten onto or into the binding reagent facilitates immobilisation onto a solid support coated with the corresponding antibody or fragment or derivative thereof. Thus, the binding reagent may be modified to include the peptide sequence or hapten into the linear molecule or may be added as a side chain or label. Any suitable antibody-antigen pair may be employed. The antibody fragment or derivative may be any fragment or derivative that retains specific binding affinity for the appropriate antigen. Examples include Fab, F(ab')2 fragments, scFV, VH domains, single domain antibodies (such as nanobodies), heavy chain antibodies and humanized version of non-human antibodies etc. Other high affinity interactions can be utilised for immobilisation of binding reagents, as long as the binding reagent can be synthesised or derivatised with one of the interacting partners and the solid support synthesised or derivatised with the other interacting partner without loss of binding activity (i.e. binding of the binding reagent to the appropriate chemokine receptor). Immobilization may occur via essentially the same interaction in reverse in some embodiments. Thus, the binding reagent which may be a chemokine for example, may be attached to an antibody as defined herein, and the solid support derivatised with the antigen. The chemokine may be produced as a fusion protein with the antibody.

Alternatively binding reagents, such as chemokines and antibodies, can be immobilised directly onto a solid support using bioconjugation techniques established in the field. For example direct immobilisation of proteins onto cyanogen bromide activated solid supports via amino functionalities within the primary sequence of the protein. Alternatively, sulphydryl functionalities within proteins can be used to directly immobilise the protein to alkyl halide derivatised supports or supports containing free thiol functionalities. In further embodiments, proteins containing α-thioester functionalities can be directly immobilised on supports containing 1,2 amino thiol moieties (eg N-terminal cysteine) using the native chemical ligation reaction. Alternatively proteins modified with ketones and aldehydes can be immobilised on solid supports derivatised with hydrazinyl, hydrazide and aminoxy functionalities using hydrazone/oxime bond forming ligation reactions (and vice versa). Alternatively 'Click' chemistry can be used to immobilise proteins onto solid supports, whereby the protein and the support are derivatised with the appropriate mutually reactive chemical functionalities (azides and alkynes). In other embodiments Staudinger ligation chemistry can be used to immobilise appropriately derivatised proteins onto the appropriately derivatised solid supports.

The solid support is contained within or carried by the apheresis column. Thus, by "loaded" is meant that the column carries or contains the solid support in a manner such that (peripheral) blood can flow through the column in contact with the solid support. Thus, the solid support provides a matrix within the column through which blood flows, in continuous fashion in certain embodiments. This permits cells expressing the specific chemokine receptor to be removed from the blood passing through the column, such that blood exiting the column is depleted of the specific chemokine receptor-expressing cells. In specific embodiments, the apheresis column is loaded with a support comprising streptavidin immobilized on the support and one or more biotinylated binding reagents, such as chemokines, bound to the streptavidin on the support. The solid support may be comprised of a high-molecular weight carbohydrate, optionally cross-linked, such as agarose.

As discussed above, the binding reagent is coupled to the solid support. The relative amounts of binding reagent may be controlled to ensure that coupling between the solid support and the binding reagent will be immediate, minimising the risk of binding reagent decoupling from the solid support. Thus, it may be ensured that there is a relative excess of immobilization sites for the binding reagent on the solid support. Alternatively, or additionally, following immobilization of the binding reagent on the solid support, the solid support may be washed to remove any unbound binding reagent.

The apheresis column utilised in the various embodiments of the present invention acts as a leukapheresis treatment for cardiovascular disease. The column acts to specifically remove CCR1, CCR2 and/or CCR7-expressing monocytes by exploiting the interaction between CCR1, CCR2 and/or CCR7 expressed on the cell surface and a specific binding reagent immobilized on a solid support contained within or carried by the column. The overall column typically comprises, consists of, or consists essentially of three combined components; 1) a housing which contains or carries 2) the solid support and 3) one or more binding reagents (immobilized thereon) which specifically bind one or more chemokine receptors. The housing may be manufactured from any suitable material for clinical use. In certain embodiments the housing is composed of a plastic material. The housing includes an in flow site for entry of blood and an out flow site for blood (depleted of target cells) to exit the column. The housing may be designed to maintain a continuous blood flow through the solid support matrix. The housing (as shown for example in FIG. 9) may include a top portion which comprises a distribution plate (2) at the inflow site (1) to spread the blood evenly over the entire matrix area. The distribution plate may act as a first safety barrier preventing larger particles flowing through the column and into the patient. However, the distribution plate is not essential and may be removed in some embodiments to decrease the overall resistance in the system. The column may contain one or more safety filter units (3 and 4) placed at the inflow (1) and/or outflow (5) sites of the plastic housing. Such filter units may act to prevent particles larger than blood cells passing in and/or out of the column. The safety filter units may contain a plurality of filters, such as two, three or four filters designed to be a robust barrier and stop all particles larger than blood cells passing through the column. Inclusion of safety filters (3 and 4) at both ends of the column serves to minimize the risk of leakage of particles into the patient, including in the event that the device is incorrectly connected resulting in blood flow in the opposite direction to that intended. The safety filters may comprise of any suitable pore size to prevent particles larger than blood cells from passing through the column, as would be readily understood by one skilled in the art. Suitable filters are commercially available. In specific embodiments, the pore size of the filter(s) is between approximately 60 μm and 100 μm, more specifically approximately 80 μm. The solid support and binding reagent components are discussed in further detail herein.

The volume of the housing may be varied depending upon the blood volumes intended to pass through the column. Typically, the volume of the housing is between approximately 40 ml and 200 ml, more specifically 50 ml to 150 ml or 60 ml to 120 ml.

The column is generally applied in the form of an apheresis circuit. In this context, the overall system includes the apheresis column, tubing and an appropriate pump to pump the blood around the circuit. The system is illustrated in FIG. 10. The patient (1) is connected to the extracorporeal circuit via sterile needles to veins in the right and the left arms. A saline bag (3) is also connected and the saline solution is pumped with a suitable pump (2). Blood is drawn from one arm of the patient through the sterile tubing system by the blood pump (4) and passed through the column (6) and back to the patient. The tubing system may be connected to the column via any suitable coupling, such as standard dialysis luer-lock couplings. The couplings on the column may be colour-coded for correct assembly. For example, red tubing for inflow to the red column top and blue tubing for outflow back to the patient. An air detector (8) may be present in the circuit. Inlet pressure (5) and/or Pven sensors (7) may additionally be employed to monitor the pressure in the circuit.

An apheresis pump, such as the 4008 ADS pump manufactured by Fresenius Medical Care or the Adamonitor pump, may monitor the patient's inflow and outflow. The pump may also monitor the pressure in the extracorporeal circulation. The pump may be able to discriminate air by a bubble catcher and air detector. A clot catcher filter may be positioned inside the bubble catcher. The pump may also incorporate an optical detector to distinguish between light, e.g. saline solution or air present in the tubing system and dark e.g. blood present in the tubing system.

A schematic diagram of a suitable pump, showing the air detector and optical filter is shown in FIG. 11. If the pump system detects air bubbles and optical fluctuations or if extracorporeal pressure values are out of the set range, then the pump may stop immediately. Alternatively or additionally a visual/audible alarm may be emitted.

The treatment methods of the various embodiments of the invention may thus rely upon an extracorporeal circuit. The methods may be considered as ex vivo or in vitro methods and be defined solely with reference to steps performed outside of the patient. In some embodiments, however, the method further comprises, prior to application of the blood to the column, collecting peripheral blood from the patient. In a further embodiment, the method further comprises, following the application of the blood to the column, infusing the blood depleted of (CCR1, CCR2 and/or CCR7) chemokine receptor expressing cells to the patient. This is then a complete leukapheresis treatment method. Thus, a leukaphereis method, for treating a cardiovascular disease, comprises collecting peripheral blood from the patient; applying the peripheral blood to an apheresis column loaded with a solid support comprising a binding reagent capable of specifically binding to a chemokine receptor, in particular the chemokine receptor CCR1, CCR2 and/or CCR7, immobilized directly or indirectly on the support thus removing CCR1, CCR2 and/or CCR7 expressing cells from the peripheral blood of the patient; and infusing the depleted blood (of chemokine receptor expressing cells) to the patient.

The peripheral blood may be continuously collected from the patient. Similarly, the depleted blood may be continuously infused to the patient, through use of an appropriate circuit as described herein. Thus, the support may be disposed in a column through which the blood is made to flow. This may be achieved using a suitable pump for example, as also described herein. Blood flow through the column enables the binding reagent(s) immobilized on the solid support to capture the cells expressing the chemokine receptor, thus depleting them from the blood and preventing their contribution to the inflammatory cardiovascular disease.

The methods of the various embodiments of the invention and binding reagents for use in the methods of the various embodiments of the invention may require that the patient has been selected for treatment on the basis of detecting an increase in the level of chemokine receptor, in particular, CCR1, CCR2 and/or CCR7 expressing cells in a sample obtained from the patient. Such companion diagnostic methods are described in greater detail herein and are based, for example, on the observation that CCR1, CCR2 and/or CCR7 expression on specific cells may be elevated in patients with cardiovascular disease. More specifically, it is shown herein that levels of CCR1 expressing leukocytes, in particular monocytes, are increased in atherosclerosis patients (compared with healthy controls).

Thus, (in this context) in certain embodiments the invention also provides a method of diagnosing, monitoring progression of, or monitoring treatment of cardiovascular disease comprising determining:
 a) the levels of the chemokine receptor CCR1, CCR2 and/or CCR7 expressing cells
 b) levels of expression of CCR1, CCR2 and/or CCR7; and/or
 c) levels of cells with high expression of CCR1, CCR2 and/or CCR7 in a sample obtained from a subject, wherein high levels of CCR1, CCR2 and/or CCR7 expressing cells, high levels of expression of CCR1, CCR2 and/or CCR7 or high levels of cells with high expression of CCR1, CCR2 and/or CCR7 or increased levels of CCR1, CCR2 and/or CCR7 expressing cells compared to control, increased levels of expression of CCR1, CCR2 and/or CCR7 compared to a control or increased levels of cells with high expression of CCR1, CCR2 and/or CCR7 compared to a control indicate the presence or progression of cardiovascular disease. Levels of chemokine receptor expression, as opposed to cell numbers, may also be investigated as increased levels of chemokine receptor expression per cell may also be diagnostically relevant. The cells may be monocytes such as CCR1 expressing, and possibly also CCR2 expressing, monocytes.

"Diagnosing" is defined herein to include screening for a disease/condition or pre-indication of a disease/condition, identifying a disease/condition or pre-indication of a disease/condition and checking for recurrence of disease/condition following treatment. The methods of the various embodiments of the invention may also have prognostic value, and this is included within the definition of the term "diagnosis". The prognostic value of the methods of the various embodiments of the invention may be used as a marker of potential susceptibility to cardiovascular disease by identifying levels of CCR1, CCR2 and/or CCR7 expression linked to conditions associated with that syndrome. Thus patients at risk may be identified before the disease has a chance to manifest itself in terms of symptoms identifiable in the patient. In certain embodiments, diagnosis may be made in conjunction with other objective indicators of cardiovascular disease. Thus, in specific embodiments, diagnosis is made in conjunction with one or more of the following indicators:

Clinical indicators may be employed, as would be understood by one skilled in the art. The diagnosis of cardiovascular disease is made on patients history with exercise induced chest pain, shortness of breath. Physical examination including ECG, exercise ECG (stress test) and cardiac catheterization. Lab test include cardiac enzymes. These findings can be combined with the determination of circulating proinflammatory cells expressing coronary vessel homing cells.

"Monitoring progression of" includes performing the methods to monitor the stage and/or the state and progression of the cardiovascular disease. Monitoring progression may involve performing the diagnostic methods multiple times on the same patient to determine whether the levels of CCR1, CCR2 and/or CCR7 expressing cells are increasing, decreasing or remaining stable over a certain time period. This may be in the context of a treatment regime.

"Monitoring the success of a particular treatment" is defined to include determining the levels of CCR1, CCR2 and/or CCR7 expressing cells before and after a treatment. The treatment is generally one aimed at treating cardiovascular disease and may be a treatment according to one of the methods of the various embodiments of the invention as defined herein. Successful treatment may be determined with reference to a decrease in CCR1, CCR2 and/or CCR7 expressing cells as a result of, or following, the treatment. Thus, in such methods a level of CCR1, CCR2 and/or CCR7 expressing cells is determined prior to treatment. This level is recorded and a further assessment made at a predetermined time following the treatment. The comparison of levels of CCR1, CCR2 and/or CCR7 expressing cells permits the success of the treatment to be monitored. In specific embodiments, a single treatment is sufficient to cause a depletion of around 10%, 20%, 30%, 40%, 50%, 60% or 70%, or higher, up to 80%, 90%, 95% or more, or any range of values between and including these amounts, of the specific chemokine receptor, in particular CCR1, CCR2 and/or CCR7, expressing cells from the peripheral blood of the patient. In specific embodiments, at least around 50% depletion is achieved in a single treatment. Thus, successful treatment may be defined with reference to depletion of CCR1, CCR2 and/or CCR7 expressing cells. Treatment may lead to depletion of between approximately 100 and 500 million CCR1, CCR2 and/or CCR7 expressing cells, such as monocytes, in certain embodiments. Additional factors may be included to determine successful treatment. For example, a lack of increase in CCR1, CCR2 and/or CCR7 expressing cells following treatment may indicate successful treatment in terms of preventing further progression of the condition, optionally combined with an improvement in other markers or staging of the cardiovascular disease.

In specific embodiments, the cardiovascular disease is atherosclerosis.

The sample in which CCR1, CCR2 and/or CCR7 expressing cell levels, levels of expression of CCR1, CCR2 and/or CCR7 and/or levels of cells with high expression of CCR1, CCR2 and/or CCR7 (defined as CCR1hi, CCR2hi and/or CCR7hi) are determined may comprise any suitable tissue sample or body fluid sample. Generally, the test sample is obtained from a human subject. Typically, the sample is a blood sample, in particular a peripheral blood sample. The sample may comprise an adipose tissue biopsy in certain embodiments. The methods may involve determining levels of CCR1, CCR2 and/or CCR7 expressing monocytes, macrophages, dendritic cells or lymphocytes in certain embodiments.

Levels of CCR1, CCR2 and/or CCR7 expressing cells, levels of expression of CCR1, CCR2 and/or CCR7 and/or levels of cells with high expression of CCR1, CCR2 and/or CCR7 (defined as CCR1hi, CCR2hi and/or CCR7hi) may be determined according to any suitable method. For example, flow cytometry may be employed in order to determine the number of cells expressing CCR1, CCR2 and/or CCR7 in the sample, to determine levels of CCR1, CCR2 and/or CCR7 expression and/or to identify levels of CCR1hi, CCR2hi and/or CCR7hi cells. Flow cytometric techniques are described herein and examples of commercially available antibodies suitably labelled for use in flow cytometry are set out in Table 9 for example. Alternatively, the method may involve steps of collecting and fixing the cells in the sample, followed by incubation with a suitable binding reagent that binds specifically to the CCR1, CCR2 and/or CCR7 chemokine receptor expressing cells in the sample. Any suitable binding reagent, as defined herein, may be employed. For example, a CCR-2 specific antibody may be employed. A wash step may be adopted following an incubation period to remove any unbound reagent. Suitable wash steps and incubation conditions would be well known to one skilled in the art. The binding reagent may be directly labeled in order to permit antibody binding to be directly determined. Alternatively a secondary binding reagent, such as an antibody, may be employed which binds to the first binding reagent and carries a label. Again, suitable incubation conditions and wash steps would be apparent to one skilled in the art. The primary and secondary binding reagents may form two halves of a binding pair. The binding interaction should not prevent the primary binding reagent binding to the CCR1, CCR2 and/or CCR7 receptor expressing cells, unless a competition assay is being employed. The two halves of a binding pair may comprise an antigen-antibody, antibody-antibody, receptor-ligand, biotin-streptavidin pair etc. in certain embodiments. Other techniques used to quantify chemokine (CCR1, CCR2 and/or CCR7) receptor expressing cell levels, to quantify levels of CCR1, CCR2 and/or CCR7 expression and/or to quantify levels of CCR1hi, CCR2hi and/or CCR7hi cells include PCR-based techniques such as QT-PCR and protein based methods such as western blot. Quantitation may be achieved with reference to fixed cell lines carrying known numbers of various receptor expressing cells and/or known levels of receptor expression per cell. Such fixed cell lines are available commercially (for example ChemiScreen™ cell lines from Millipore). Methods analogous to the treatment methods of the invention may also be employed, with binding of CCR1, CCR2 and/or CCR7 expressing cells to the solid support being determined following peripheral blood being passed through the column.

The levels of CCR1, CCR2 and/or CCR7 expressing cells, levels of expression of CCR1, CCR2 and/or CCR7 and/or levels of cells with high expression of CCR1, CCR2 and/or CCR7 (defined as CCR1hi, CCR2hi and/or CCR7hi) may be determined relative to a suitable control. When diagnosing a cardiovascular disease, a threshold level of cells, level of expression of CCR1, CCR2 and/or CCR7 and/or level of cells with high expression of CCR1, CCR2 and/or CCR7 (defined as CCR1hi, CCR2hi and/or CCR7hi) may be set at or over which a positive diagnosis is made. This threshold may be determined based upon measuring levels of CCR1, CCR2 and/or CCR7 expressing cells, levels of expression of CCR1, CCR2 and/or CCR7 and/or levels of cells with high expression of CCR1, CCR2 and/or CCR7 (defined as CCR1hi, CCR2hi and/or CCR7hi) in samples obtained from diseased patients and comparing these levels with levels of CCR1, CCR2 and/or CCR7 expressing cells, levels of expression of CCR1, CCR2 and/or CCR7 and/or levels of cells with high expression of CCR1, CCR2 and/or CCR7 (defined as CCR1hi, CCR2hi and/or CCR7hi) in samples obtained from healthy subjects.

In certain embodiments, a cardiovascular disease such as atherosclerosis is diagnosed on the basis of levels of chemokine receptor expressing cells, such as CCR1, CCR2 and/or CCR7 expressing cells. A positive diagnosis may be made in subjects based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, a cardiovascular disease such as atherosclerosis is diagnosed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to healthy controls.

In specific embodiments, a cardiovascular disease such as atherosclerosis is diagnosed on the basis of levels of CCR1 expressing cells, in particular monocytes. A positive diagnosis may be made in subjects based upon the presence of greater than about 70%, greater than about 75%, greater than about 80%, greater than about 85% or greater than about 90% CCR1 expressing monocytes in the sample, as a percentage of total cells in the sample. Cardiovascular disease such as atherosclerosis may also be diagnosed on the basis of the presence of a about a 1.2 fold or greater increase, such as about a 1.5, 2, 2.5, 3, 3.5, 4, 4.5, 5, 10, 20, 50 or 100 or greater fold increase in CCR1 expressing cells, in particular monocytes, relative to healthy controls.

In certain embodiments, progression of cardiovascular disease such as atherosclerosis, which may be in the context of a treatment regime, is monitored on the basis of levels of chemokine receptor expressing cells at different time points, such as CCR1, CCR2 and/or CCR7 expressing cells. Progression of cardiovascular disease such as atherosclerosis may be indicated in subjects based upon an increase of greater than about 10%, such as an increase of greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more chemokine receptor expressing cells in the sample, as a percentage of total cells in the sample, compared to a sample taken from the same subject at an earlier time point. In other embodiments, progression of cardiovascular disease such as atherosclerosis is confirmed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to a sample taken from the same subject at an earlier time point.

In specific embodiments, cardiovascular disease such as atherosclerosis is monitored on the basis of levels of CCR1 expressing cells, in particular monocytes. Progression of the disease, which may be in the context of a treatment regime, may be indicated in subjects based upon the presence of an increase of greater than about 10%, such as greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more chemokine receptor expressing cells in the sample, as a percentage of total cells in the sample, compared to a sample taken from the same subject at an earlier time point. In other embodiments, progression of cardiovascular disease such as atherosclerosis is confirmed on the basis of the presence of a about a 1.2 fold or greater increase, such as about a 1.5, 2, 2.5, 3, 3.5, 4, 4.5, 5, 10, 20, 50 or 100 or greater fold increase in CCR1 expressing cells, in particular monocytes, relative to a sample taken from the same subject at an earlier time point.

Regression or successful treatment may be monitored based upon similar decreases over various time points. For example, regression or successful treatment may be indicated in subjects based upon a decrease of about 10%, such as a decrease of about 15%, about 20%, about 25%, about 30%, about 35%, about 40%, about 45%, about 50%, about 55%, about 60%, about 65%, about 70%, about 75% or more chemokine receptor expressing cells in the sample, as a percentage of total cells in the sample, compared to a sample taken from the same subject at an earlier time point. In other embodiments, regression of cardiovascular disease such as atherosclerosis is confirmed on the basis of the presence of a about a 1.2 fold or greater decrease, such as about a 1.5, 2, 2.5, 3, 3.5, 4, 4.5, 5, 10, 20, 50 or 100 or greater fold decrease in chemokine receptor expressing cells, relative to a sample taken from the same subject at an earlier time point.

In specific embodiments, cardiovascular disease such as atherosclerosis is monitored on the basis of levels of CCR1 expressing cells, in particular monocytes. Regression or successful treatment of the disease may be made in subjects based upon a decrease of about 10%, such as such as a decrease of about 15%, about 20%, about 25%, about 30%, about 35%, about 40%, about 45%, about 50%, about 55% or more CCR1 expressing cells, in particular monocytes in the sample, as a percentage of total cells in the sample or by a decrease of about 10%, such as a decrease of about 15%, about 20%, about 25%, about 30%, about 35%, about 40%, about 45%, about 50%, about 55%, about 60%, about 65%, about 70%, about 75% or more CCR1 expressing cells, in particular monocytes in the sample, as a percentage of total cells in the sample, compared to a sample taken from the same subject at an earlier time point. In other embodiments, regression of cardiovascular disease such as atherosclerosis is confirmed on the basis of the presence of a about a 1.2 fold or greater decrease, such as about a 1.5, 2, 2.5, 3, 3.5, 4, 4.5, 5, 10, 20, 50 or 100 or greater fold decrease in CCR1 expressing cells, in particular monocytes, relative to a sample taken from the same subject at an earlier time point.

Suitable software is freely available (such as the R project for statistical computing) to perform the necessary statistical analysis of the data obtained to calculate a useful threshold. The threshold may be set to maximize sensitivity and/or specificity of the test. Performance of the test in these respects may be measured by plotting a receiver operating characteristics (ROC) curve (sensitivity versus specificity). The area under the curve provides an indication of the overall performance of the test. Thus, once thresholds have been set for diagnosing the condition, a separate control experiment does not necessarily have to be run each time a sample is tested. Rather reference can simply be made to the pre-existing thresholds to determine the diagnosis. However, in certain embodiments, the sample is tested together with a control sample taken from a healthy subject to provide a comparator based upon essentially identical experimental conditions. The test sample is generally tested in parallel with the control sample. The test sample level of CCR1, CCR2 and/or CCR7 expressing cells, levels of expression of CCR1, CCR2 and/or CCR7 and/or levels of cells with high expression of CCR1, CCR2 and/or CCR7 (defined as CCR1hi, CCR2hi and/or CCR7hi) can then be compared with that of the control sample to make the diagnosis. A control sample from a disease patient may also be tested in certain embodiments. Reference to controls permits relative levels ("high", "low" etc.) of CCR1, CCR2 and/or CCR7 expressing cells in the test sample to be readily identified and the significance thereof interpreted. Reference to controls also permits relative levels of CCR1, CCR2 and/or CCR7 expression ("high", "low" etc.) within the cell population to be determined and the significance thereof interpreted. Such determination may, for example, indicate the average levels of CCR1, CCR2 and/or CCR7 expression per cell in the test sample.

Thus, in specific embodiments, high or higher levels of CCR1, CCR2 and/or CCR7 expressing cells or high or higher levels of CCR1, CCR2 and/or CCR7 expression, for example average CCR1, CCR2 and/or CCR7 expression per cell, or high or higher levels of CCR1hi, CCR2hi and/or CCR7hi cells correlate with active disease or more active disease associated with cardiovascular disease. Similarly, lower or low levels of CCR1, CCR2 and/or CCR7 expressing cells, or low or lower levels of CCR1, CCR2 and/or CCR7 expression, for example average CCR1, CCR2 and/or CCR7 expression per cell, or low or lower levels of CCR1hi, CCR2hi and/or CCR7hi cells may correlate with a lack of active inflammation or disease associated with cardiovascular disease. This may be defined as "less active disease". It can readily be envisaged that control samples may be assessed and levels of CCR1, CCR2 and/or CCR7 expressing cells, levels of expression of CCR1, CCR2 and/or CCR7 and/or levels of cells with high expression of CCR1, CCR2 and/or CCR7 (defined as CCR1hi, CCR2hi and/or CCR7hi) determined across the range of severities of cardiovascular disease. This may assist in correlating the levels of CCR1, CCR2 and/or CCR7 expressing cells, levels of expression of CCR1, CCR2 and/or CCR7 and/or levels of cells with high expression of CCR1, CCR2 and/or CCR7 (defined as CCR1hi, CCR2hi and/or CCR7hi) in the test sample with the relative severity of the condition.

When monitoring progression of, or monitoring treatment of a cardiovascular disease, the control samples may be taken from the subject at an earlier time point. They may, however, be based upon known reference values as discussed above. Thus, relative levels of CCR1, CCR2 and/or CCR7 expressing cells, relative levels of CCR1, CCR2 and/or CCR7 expression including relative levels of average CCR1, CCR2 and/or CCR7 expression per cell or relative levels of CCR1hi, CCR2hi and/or CCR7hi cells may be with reference to samples taken from the same subject at a different point in time. In certain embodiments, decreased levels of CCR1, CCR2 and/or CCR7 expressing cells decreased relative levels of CCR1, CCR2 and/or CCR7 expression including decreased relative levels of average CCR1, CCR2 and/or CCR7 expression per cell or decreased relative levels of CCR1hi, CCR2hi and/or CCR7hi cells correlate with successful treatment. The treatment may be any suitable treatment, but in specific embodiments is a treatment according to the various embodiments of the invention. When monitoring progression of a cardiovascular disease, increased levels of CCR1, CCR2 and/or CCR7 expressing cells increased relative levels of CCR1, CCR2 and/or CCR7 expression including increased relative levels of average CCR1, CCR2 and/or CCR7 expression per cell or increased relative levels of CCR1hi, CCR2hi and/or CCR7hi cells may indicate the progression of condition or disease. Thus, if levels of CCR1, CCR2 and/or CCR7 expressing cells, levels of expression of CCR1, CCR2 and/or CCR7 and/or levels of cells with high expression of CCR1, CCR2 and/or CCR7 (defined as CCR1hi, CCR2hi and/or CCR7hi) are increased in a sample taken later than a sample from the same patient this may indicate progression of the condition.

Since the levels of CCR1, CCR2 and/or CCR7 expressing cells, levels of CCR1, CCR2 and/or CCR7 expression or levels of CCR1hi, CCR2hi and/or CCR7hi cells are diagnostically relevant, determining such levels in a sample obtained from a subject may influence treatment selection for that subject. Accordingly, in certain embodiments the invention provides a method of selecting a suitable treatment for cardiovascular disease comprising determining:

a) the levels of the chemokine receptor CCR1, CCR2 and/or CCR7 expressing cells b) levels of expression of CCR1, CCR2 and/or CCR7; and/or c) levels of cells with high expression of CCR1, CCR2 and/or CCR7 in a sample obtained from a subject, wherein high levels of CCR1, CCR2 and/or CCR7 expressing cells, high levels of expression of CCR1, CCR2 and/or CCR7 or high levels of cells with high expression of CCR1, CCR2 and/or CCR7 or increased levels of CCR1, CCR2 and/or CCR7 expressing cells compared to control, increased levels of expression of CCR1, CCR2 and/or CCR7 compared to a control or increased levels of cells with high expression of CCR1, CCR2 and/or CCR7 compared to a control, result in selection of a treatment as defined herein for treatment of the cardiovascular disease. In certain embodiments, the chemokine receptor expressing cells are high chemokine receptor expressing cells, in particular, high CCR1, CCR2 and/or CCR7 expressing cells. The cells may be monocytes such as CCR1 expressing, and possibly also CCR2 expressing, monocytes.

In specific embodiments, cardiovascular disease such as atherosclerosis is treated on the basis of measuring levels of chemokine receptor expressing cells, such as CCR1, CCR2 and/or CCR7 expressing cells. Thus, a treatment according to the various embodiments of the invention may be applied based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, cardiovascular disease such as atherosclerosis is treated according to the various embodiments of the invention on the basis of the presence of a about a 1.5 fold or greater increase, such as about a 2, 2.5, 3, 3.5, 4, 4.5, 5, 10, 20, 50 or 100 or greater fold increase in chemokine receptor expressing cells, relative to healthy controls.

In specific embodiments, cardiovascular disease such as atherosclerosis is treated on the basis of measuring levels of CCR1 expressing cells, in particular monocytes. Thus, a treatment according to the various embodiments of the invention may be applied based upon the presence of greater than about 70%, greater than about 75%, greater than about 80%, greater than about 85% or greater than about 90% CCR1 expressing monocytes in the sample, as a percentage of total cells in the sample or on the basis of the presence of a about a 1.5 fold or greater increase, such as about a 2, 2.5, 3, 3.5, 4, 4.5, 5, 10, 20, 50 or 100 or greater fold increase in CCR1 expressing cells, in particular monocytes, relative to healthy controls.

For the avoidance of doubt, all embodiments described in respect of the methods of the various embodiments of the invention apply to these aspects mutatis mutandis and are not repeated for reasons of conciseness. Specifically, cardiovascular disease may be indicated in conjunction with one or more of the following indicators: Clinical indicators may be employed, as would be understood by one skilled in the art. The diagnosis of cardiovascular disease is made on patients history with exercise induced chest pain, shortness of breath. Physical examination including ECG, exercise ECG (stress test) and cardiac catheterization. Lab test include cardiac enzymes. These findings can be combined with the determination of circulating proinflammatory cells expressing coronary vessel homing cells.

The cardiovascular disease may be atherosclerosis. In specific embodiments, the sample is a peripheral blood sample.

The methods and medical uses of the various embodiments of the invention thus can be tailored to the need of individual patients or groups of patients on the basis of the various diagnostic methods of the various embodiments of the invention. By removing from the circulation CCR1, CCR2 and/or CCR7 expressing cells, such as monocytes, macrophages and lymphocytes, in particular monocytes, upregulated in various inflammatory cardiovascular disease, an important factor in the inflammatory process of cardiovascular disease can be controlled. The method of the invention may be effective in treating or reversing conditions such as atherosclerosis.

J. Treating Primary Sclerosing Cholangitis

Chemokines are a class of cytokine molecules involved in cell recruitment and activation in inflammation. Chemokines cause chemotaxis and activation of various subpopulations of cells in the immune system. The activity of chemokines is mediated primarily through tight binding to their receptors on the surface of leukocytes. In certain embodiments the present invention is based on the realisation that the interaction between chemokines and cells expressing their receptors may be exploited for the treatment of primary sclerosing cholangitis (PSC). The inventors have determined that targeting increased recruitment of specific chemokine receptor-expressing cells to the site of inflammation presents a new therapeutic approach to treat such conditions. Moreover, in such conditions, chemokine receptor expression on each cell may be increased again providing a therapeutic approach to treat such conditions. The inventors have also determined that PSC patients include higher levels of CCR9 expressing monocytes in the blood. The disease relevant monocytes may also have high expression of HLA-DR (referred to herein as HLA-DRhi). The treatments and diagnostic methods herein may accordingly be applicable in particular to monocytes and to HLA-DRhi monocytes. HLA-DR is a MHC class II cell surface receptor encoded by the human leukocyte antigen complex on chromosome 6 region 6p21.31.

Thus, in certain embodiments the invention serves to reduce the recruitment of inflammatory leukocytes, which express characteristic chemokine receptors, and possibly express characteristic chemokine receptors at increased levels, to sites of inflammation linked to disorders such as primary sclerosing cholangitis. This is achieved using specific binding reagents to capture specific chemokine receptor-expressing inflammatory leukocytes from the patient. Accordingly, in certain embodiments the invention provides in a first aspect a method for treating primary sclerosing cholangitis comprising applying peripheral blood from a patient to an apheresis column loaded with a solid support comprising one or more binding reagents capable of specifically binding to one or more chemokine receptors, in particular the chemokine receptor CCR9, CXCR4, CCR7 and/or CCR5, immobilized directly or indirectly on the support thus removing one or more chemokine receptors, in particular CCR9, CXCR4, CCR7 and/or CCR5, expressing cells from the peripheral blood of the patient. The peripheral blood from which the chemokine receptor expressing cells have been removed may then be returned to the patient in order to complete the treatment. The invention may thus rely on a continuous extracorporeal circuit in some embodiments. Alternatively, in certain embodiments the invention may comprise steps of obtaining peripheral blood from the patient, applying the peripheral blood to the column and subsequently returning the peripheral blood from which the chemokine receptor expressing cells have been removed to the patient.

As shown herein, suitable binding reagents can be immobilized onto a solid support, either directly or indirectly, to generate an apheresis column suitable for capturing relevant chemokine receptor-expressing cells. Where increased levels of chemokine receptor expression are observed, such cells may be preferably removed from the peripheral blood using the columns of the various embodiments of the invention. Thus, the methods of the various embodiments of the invention may preferably target one or more of CCR9hi, CXCR4hi, CCR7hi and CCR5hi cells as defined herein for removal from the peripheral blood. "High" expression may be determined according to standard flow cytometry techniques. The level is measured relative to levels of expression of the chemokine receptor in cells taken from a healthy subject. The attached FIG. 143 provides an example of a gating strategy. The CCR9hi cells may be monocytes and may also be HLA-DRhi.

In other embodiments the invention further provides a binding reagent capable of specifically binding to one or more chemokine receptors, in particular to a chemokine receptor/the chemokine receptor CCR9, CXCR4, CCR7 and/or CCR5, for use in the treatment of primary sclerosing cholangitis, wherein the one or more binding reagents is immobilized, directly or indirectly on a solid support contained within an apheresis column, to which is applied peripheral blood from a patient thus removing one or more chemokine receptor/CCR9, CXCR4, CCR7 and CCR5 expressing cells from the peripheral blood of the patient. In certain embodiments the invention also provides for use of one or more binding reagents capable of specifically binding to a chemokine receptor/the chemokine receptor CCR9, CXCR4, CCR7 and/or CCR5 for use in the manufacture of an apheresis column for treatment of primary sclerosing cholangitis, wherein the one or more binding reagents is immobilized on a solid support contained within the apheresis column, to which is applied peripheral blood from a patient thus removing chemokine receptor/CCR9, CXCR4, CCR7 and/or CCR5 expressing cells from the peripheral blood of the patient.

All embodiments described in respect of the methods of treatment of the various embodiments of the invention apply to these aspects mutatis mutandis and are not repeated for reasons of conciseness. Thus, the following discussion made with reference to the methods of treatment is also applicable to the medical use aspects of the various embodiments of the invention.

In certain embodiments the invention aims to treat primary sclerosing cholangitis. By treatment is meant a reduction in the specific chemokine receptor expressing cells in the peripheral blood of the patient. The reduction may comprise a reduction in cells that express chemokine receptors, in particular one or more of CCR9, CXCR4, CCR7 and CCR5, at increased levels in diseased patients. The patient is typically a human patient but the term patient may include both human and non-human animal subjects in some embodiments. In the context of the various embodiments of the present invention, this typically involves a reduction in one or more of CCR9, CXCR4, CCR7 and CCR5 expressing cells, such as "CCR9 hi, CXCR4 hi, CCR7 and/or CCR5 hi expressing cells, in the peripheral blood of the patient. The CCR9, CXCR4, CCR7 and/or CCR5 expressing cells comprise, consist essentially of or consist of monocytes, macrophages and/or lymphocytes, in particular T-lymphocytes, in certain embodiments. The cells may be monocytes and in particular may comprise HLA-DRhi monocytes. Monocytes are produced by the bone marrow from haematopoietic stem cell precursors called monoblasts. Monocytes may differentiate into macrophages or dendritic cells. Monocytes and their macrophage and dendritic cell progeny serve a number of functions in the immune system including phagocytosis, antigen presentation and cytokine production. Monocytes may be characterized with reference to expression of the cell surface marker CD14, optionally together with CD16. Classical monocytes may be characterized by high level expression of the CD14 cell surface receptor (CD14++CD16− monocyte). Non-classical monocytes may be characterized by low level expression of CD14 and with additional co-expression of the CD16 receptor (CD14+CD16++ monocyte). Intermediate monocytes may be characterized by high level expression of CD14 and low level expression of CD16 (CD14++CD16+ monocytes). Macrophages are derived from monocytes and are responsible for protecting tissues from foreign substances. They are cells that possess a large smooth nucleus, a large area of cytoplasm and internal vesicles for processing foreign material. The term "macrophage" may refer to a monocyte-derived cell expressing one or more of the following cell surface markers CD14, CD11b, Lysozyme M, MAC-1/MAC-3 and CD68. The term macrophage includes both activated and un-activated macrophages. Activated macrophages may be characterized by expression of CD69, ENG, FCER2 and IL2RA, HLA-DR, CD86. Un-activated macrophages have not yet received activating signals through for example TLR receptors and therefore they express less activation markers on the cell surface which correlates with lesser maturation. M1 macrophages may be characterized by expression of one or more of CD16+CD32+CD64+ and secrete mainly IL-23 and IL-1, TNF, IL-6 and high levels of IL-12 and in addition effector molecules such as iNOS and ROI. M1 macrophages have cytotoxic features as opposed to M2 macrophages. M2 macrophages may be characterized by expression of one or more of SRA/B+CD163+MR+CD14+ and express TGFβ, IL-10 and IL-1Ra. Tumour associated macrophages (TAMs) share many characteristics with the M2 macrophages and are considered as M2 polarised macrophages. The M1/M2 paradigm can also be found in monocyte subsets where CD14+ CD16−CXC3R1low monocytes are considered the "inflammatory" subset and the CD14lowCD16+CXC3R1high are "resident" monocytes.

The three major types of lymphocyte are T cells, B cells and natural killer (NK) cells. The term "T-lymphocyte" includes CD4+ T cells such as T helper cells (Th1 cells and Th2 cells), and CD8+ T cells such as cytotoxic T cells. Th1 cells may be characterized by expression of CCR5 and/or by production of IFN-γ. Th2 cells may be characterized by expression of CCR3 and/or by production of IL-4.

CCR9, CXCR4, CCR7 and/or CCR5 expressed on these aforementioned cells binds to chemokines such as CCL25 (TECK), CXCL12, CCL19, CCL21 or CCL5 (RANTES). CCR9 is the gene symbol approved by the HUGO Gene Nomenclature Committee for chemokine (C—C motif) receptor 9. The HGNC ID for this gene is 1610. The gene is located at chromosome position 3p22. The previous symbol and name for the gene is GPR28. Synonyms for this gene include CDw199, GPR-9-6. The Genbank reference sequence for CCR9 is AJ132337.1 as available on 13 Jun. 2011, which is incorporated herein by reference in its entirety.

CXCR4 is the gene symbol approved by the HUGO Gene Nomenclature Committee for chemokine (C—X—C motif) receptor 4. The HGNC ID for this gene is 2561. The gene is located at chromosome position 2q21. The previous symbol and name for the gene is "chemokine (C—X—C motif), receptor 4 (fusin)". Synonyms for this gene include CD184, D2S201E, fusin, HM89, HSY3RR, LESTR, NPY3R, NPYR, NPYY3R. The Genbank reference sequence for CXCR4 is AF005058.1 as available on 13 Jun. 2011, which is incorporated herein by reference in its entirety.

CCR7 is the gene symbol approved by the HUGO Gene Nomenclature Committee for chemokine (C—C motif) receptor 7. The HGNC ID for this gene is 1608. The gene is located at chromosome position 17q112-q21.2. The previous symbol and name for the gene is CMKBR7, EBI1. Synonyms for this gene include BLR2, CD197 and CDw197. The RefSeq reference sequence for CCR7 is NM_001838.3 as available on 13 Jun. 2011, which is incorporated herein by reference in its entirety.

CCR5 is the gene symbol approved by the HUGO Gene Nomenclature Committee for chemokine (C—C motif) receptor 5. The HGNC ID for this gene is 1606. The gene is located at chromosome position 3p21. The previous symbol and name for the gene is CMKBR5. Synonyms for this gene include CC-CKR-5, CD195 CKR-5, IDDM22 and CKR5. The RefSeq reference sequence for CCR1 is NM_000579.3 as available on 13 Jun. 2011, which is incorporated herein by reference in its entirety.

The various embodiments of the methods of the invention may involve specific binding interactions with any these further cell-surface markers in addition to the removal based upon binding to CCR9, CXCR4, CCR7 and/or CCR5. Suitable binding reagents can be prepared to specifically bind to these cell-surface markers. The discussion of CCR9, CXCR4, CCR7 and/or CCR5 specific binding reagents thus applies mutatis mutandis.

Treatment according to the various embodiments of the invention may result in alleviation or amelioration of symptoms, prevention of progression, regression of the condition, or complete recovery. Measurable parameters of successful treatment include one or more, up to all, of a liver values AST, ALT, ALP, bilirubin, PK and ERCP, MRI. In specific embodiments, a single treatment is sufficient to cause a depletion of around 10%, 20%, 30%, 40%, 50%, 60% or 70%, or higher up to 80%, 90%, 95% or more, or any range of values between and including these amounts, of a specific chemokine receptor, in particular one or more of CCR9, CXCR4, CCR7 and CCR5, expressing cells from the peripheral blood of the patient. In specific embodiments, at least around 50% depletion is achieved in a single treatment. Thus, successful treatment may be defined with reference to depletion of one or more of CCR9, CXCR4, CCR7 and CCR5 expressing cells. Treatment may lead to depletion of between approximately 100 and 500 million CCR9, CXCR4, CCR7 and/or CCR5 expressing cells, such as monocytes, in certain embodiments, and more particularly to about 100, 150, 200, 250, 300, 350, 400, 450, or 500 million CCR9, CXCR4, CCR7 and/or CCR5 expressing cells.

By binding to the column through the binding reagent-chemokine receptor interaction, chemokine receptor expressing cells are immobilized. These immobilized cells express further unoccupied chemokine receptors, which may be of the same or different type to those used for capture. These additional chemokine receptors may permit circulating chemokines which contribute to the inflammatory condition to be captured from the peripheral blood. Thus, a reduction in circulating (specific) chemokine levels may provide a measure of successful treatment.

The duration of treatment may be readily determined by one skilled in the art and will depend upon factors such as the flow rate of the peripheral blood. Duration of treatment may be tied into monitoring of the treatment itself, with the treatment considered complete once a measurable parameter of treatment has reached a defined threshold. Any suitable parameter may be employed as discussed herein. Thus, for example, treatment may be considered complete when a reduction in one or more of CCR9, CXCR4, CCR7 and CCR5 expressing cells, such as a 50% reduction in one or more of CCR9, CXCR4, CCR7 and CCR5 expressing cells, has been achieved. The apheresis system may be operated at a flow rate of around 10-80 mL/min, or more specifically between around 20-70 mL/min, or between around 30-60 mL/min. In specific embodiments, the treatment is performed for a period of around 10, 20, 30, 40, 50, 60, 70, 80, 90, 100, 110, 120 etc., or any range of values between and including these amounts, minutes. The treatment is typically not aimed to remove all of the cells expressing the chemokine receptor in the peripheral blood, as a basal level of those cells is required in healthy subjects. However, it has been found that only low blood volumes need to be applied to the columns of the various embodiments of the invention in order to achieve effective levels of depletion of the chemokine receptor-expressing cells. Thus, in certain embodiments, around 10-80% or more specifically around 20, 30, 40 or 50%, or any range of values between and including these amounts, of the patient's blood is applied to the column in a single treatment. The volume of blood circulated through the apheresis column or system may be in the region of around 1000-3000 ml, such as around 1000, 1200, 1400, 1600, 1800 or 2000 ml or any range of values between and including these amounts. The treatment may be considered complete once this volume of blood has been circulated. The patient may be administered anticoagulants prior to each treatment session. A suitable solution, such as a sterile saline solution, optionally including an anticoagulant such as Heparin, may be used for priming the apheresis (extracorporeal) system. An additional volume of anticoagulant may be added to the circuit at the start of each treatment session, for example as a bolus injection.

In certain embodiments the invention relies upon a binding reagent which is capable of specifically binding to a chemokine receptor. This specific binding reaction permits cells expressing the chemokine receptor to be removed from the peripheral blood of the patient when the blood is passed over the solid support upon or within which the binding reagent is immobilized. Specific chemokine receptors of interest include CCR9, CXCR4, CCR7 and CCR5, particularly CCR9. The binding reagent can be any binding reagent capable of specifically binding to the receptor in question. By "specific binding" is meant that the binding reagent displays sufficient specificity of binding and appropriate binding affinity/kinetics to permit removal of cells expressing one or more of CCR9, CXCR4, CCR7 and/or CCR5 from the peripheral blood. Whilst it is not precluded that the binding reagent is capable of binding to other molecules, such as other chemokine receptors, the binding reagent will preferentially bind to cells expressing one or more of CCR9, CXCR4, CCR7 and CCR5 and in particular to cells expressing increased levels of CCR9, CXCR4, CCR7 and/or CCR5 (as defined further herein). The binding reagent capable of specifically binding to CCR9, CXCR4, CCR7 and/or CCR5 may be either an agonist or an antagonist of CCR9, CXCR4, CCR7 and/or CCR5, respectively. As the disease condition relies upon up-regulation of expression of or signaling via CCR9, CXCR4, CCR7 and/or CCR5, in certain embodiments the binding reagent capable of specifically binding to CCR9, CXCR4, CCR7 and/or CCR5 is an antagonist of CCR9, CXCR4, CCR7 and/or CCR5, respectively. Chemokines are typically, although not necessarily exclusively (particularly in the case of truncated or modified forms) agonists of their cognate receptor and serve to activate the cells expressing the relevant receptor, as would be appreciated by one skilled in the art. Antibodies against the relevant chemokine receptor are generally considered to be antagonists, as would be appreciated by one skilled in the art. Specific examples of binding reagents include proteins or polypeptides, such as antibodies and receptor ligands, in particular chemokines. The binding reagent may be a nucleic acid molecule in certain embodiments. In some embodiments, the nucleic acid is an aptamer. Nucleic acid aptamers are polynucleotides of approximately 15-40 nucleotides long. Nucleic acid aptamers can be made using the SELEX process (systemic evolution of ligands by exponential enrichment) or any other process known to those of skill in the art.

In other embodiments, the binding reagent may be a peptide, and in certain instances, a peptide aptamer. Peptide aptamers are artificial recognition molecules that consist of a variable peptide sequence inserted into a constant scaffold protein (Baines I C, Colas P. Peptide aptamers as guides for small molecule drug discovery. Drug Discov Today. 2006; 11:334-341, incorporated herein by reference). A number of methodologies, such as phage display, ribosome display and yeast two-hybrid screening systems are available for screening a library of potential peptide-based binding agents. Similarly protein scaffolds based on domains such as fibronectins, ankyrin repeats, protein A, SH3 domains, lipocalins and ubiquitin can be used as the binding agent. Again a number of technologies such as phage display and ribosome display are available for screening a library of protein—based binding agents. Similarly, libraries of candidate chemical compounds can be screened for specific binding to the relevant chemokine receptor using suitable screening techniques known in the art, which may be high throughput screens in certain embodiments. The candidate binding agent may be immobilized on a solid support and the ability of the agent to specifically retain cells expressing the chemokine receptor of interest or labelled chemokine receptors determined. A range of cell types may be applied to the solid supports to confirm specificity of binding, or alternatively a mixed sample (such as peripheral blood) may be applied to the solid support. Retention of the cell type of interest (expressing the appropriate chemokine receptor) can be confirmed to identify suitable binding agents.

In the context of the various embodiments of the present invention the term "chemokine" also comprises biotinylated or otherwise labelled chemokines. The term "chemokine" also comprises modified and truncated versions of the chemokine and chemokine fragments with the proviso that the modified or truncated form retains its ability to bind to its cognate receptor (and thus remains functional in the context of the various embodiments of the invention). The chemokine does not necessarily need to retain biological activity as it is specific binding affinity for CCR9, CXCR4, CCR7 and/or CCR5 that is required. In certain embodiments, the chemokine lacks biological activity, for example in terms of activation of the (CCR9, CXCR4, CCR7 and/or CCR5) receptor. Modifications may be made to improve protein synthesis, for example uniformity of product and yield. As known to those skilled in the art, exemplary modifications may comprise amino acid additions, substitutions, deletions or other modifications to one or more amino acids in the chemokine. Modifications may comprise substitution of the wild type amino acid with non-natural amino acids such as norleucine (NLeu) and derivatized amino acids such as pyroglutamic acid (pyroGlu). Such modifications may be made to minimize side-product formation during storage and use of the columns of the various embodiments of the invention. Modifications may be made to improve labelling, for example inclusion of a polyethylene glycol (PEG) spacer to facilitate biotinylation. The biotinylation and/or conjugation with fluorochromes or other labelling groups of the chemokine is performed in a manner which does not substantially affect the receptor binding capacity. Site specific biotinylation or other labelling is preferred as non-selective labelling of chemokines may compromise receptor binding activity. Biotinylation or other labelling is generally preferred at or towards the C-terminus of the protein as the inventors have found that modifications in this area are generally well tolerated (in terms of a minimal effect on receptor binding capability). Biotinylation may be carried out site-specifically at any suitable amino acid. Examples of suitable amino acids include lysine, diaminopropionic acid and ornithine. Generally, reference may be made to Natarajan S et al, Int. J. Pept. Protein Res., 1992, 40, 567-74; Baumeister B, Int. J. Peptide Res. And Therapeutics, 2005, 11, 139-141; Bioconjugate techniques 2nd edition, Greg T. Hermanson, incorporated by reference herein in its entirety.

Truncations may involve deletion of either N or C terminal amino acids as appropriate, or both. Typically, the truncated version will retain the residues required for the chemokine to fold correctly, for example to retain a chemokine fold structure, consistent with the requirement that a truncated version must retain the ability to bind to the relevant receptor (expressed by (on the surface of) a leukocyte). Chemokine molecules typically include disulphide bonds between the 1st and 3rd and 2nd and 4th cysteine residues respectively, as would be understood by one skilled in the art. Where sequences are presented herein, it is assumed that these disulphide bonds will form in the folded protein (unless otherwise stated). Truncated versions may comprise anywhere between 1 and 100 less amino acids, such as 1, 2, 3, 4, 5 etc amino acids, than the wild type amino acid sequence in certain embodiments. Of course, truncated versions may comprise further modification as detailed herein. The modified or truncated version may have 40%, 45%, 50%, 55%, 60%, 65%, 70%, 75%, 80%, 85%, 90%, 95% or more overall amino acid sequence identity with the full length wild type chemokine (where a deletion is counted as a difference in amino acid sequence) in certain embodiments. Over the common sequence between the molecules (i.e the amino acids that have not been deleted), there may be 80%, 85%, 90%, 91%, 92%, 93%, 94%, 95%, 96%, 97%, 98% or 99% amino acid sequence identity in certain embodiments. Sequence identity may be determined using known algorithms, such as BLAST or GAP analysis (GCG Program) (applying default settings), which are freely available. Chemokines may lack the N-terminal signal peptide which is cleaved off during synthesis in vivo.

Specific chemokines useful in the various embodiments of the present invention for binding to CCR9, CXCR4, CCR7 and/or CCR5 include CCL25 (TECK), CXCL12, CCL19, CCL21 or CCL5 (RANTES). CCL25, CXCL12, CCL21 or CCL5 are able to bind to chemokine receptors implicated in primary sclerosing cholangitis. More specifically, CCL25, CXCL12, CCL19, CCL21 or CCL5 are useful for removing CCR9, CXCR4, CCR7 and/or CCR5 expressing cells from the blood of a patient. The chemokines described in greater detail herein (with reference to the relevant figures and amino acid sequences, as set forth in the SEQ ID NOs) may each be applied according to the various embodiments of the present invention.

CCL3, CCL5, CCL8 all bind to CCR5 and may thus be useful in the invention. CCL25 is the gene symbol approved by the HUGO Gene Nomenclature Committee for chemokine (C—C motif) ligand 25. The HGNC ID for this gene is 10624. The gene is located at chromosome position 19p13.2. The previous symbol and name for the gene is SCYA25, "small inducible cytokine subfamily A (Cys-Cys), member 25". Synonyms for this gene include "Ck beta-15", Ckb15, TECK, "TECKvar", "thymus expressed chemokine". The Genbank reference sequence for CCL25 is U86358.1 as available on 13 Jun. 2011, which is incorporated herein by reference in its entirety.

CXCL12 is the gene symbol approved by the HUGO Gene Nomenclature Committee for chemokine (C—X—C motif) ligand 12. The HGNC ID for this gene is 10672. The gene is located at chromosome position 10q11.1. The previous symbol and name for the gene is SDF1, SDF1A, SDF1B, "stromal cell-derived factor 1". Synonyms for this gene include PBSF, SCYB12, SDF-1a, SDF-1b, TLSF-a, TLSF-b, TPAR1. The Genbank reference sequence for CXCL12 is L36033.1 as available on 13 Jun. 2011, which is incorporated herein by reference in its entirety.

CCL21 is the gene symbol approved by the HUGO Gene Nomenclature Committee for chemokine (C—C motif) ligand 21. The HGNC ID for this gene is 10620. The gene is located at chromosome position 9p13. The previous symbol and name for the gene is SCYA21, "small inducible cytokine subfamily A (Cys-Cys), member 21". Synonyms for this gene include 6Ckine, "beta chemokine exodus-2", CKb9, ECL, "Efficient Chemoattractant for Lymphocytes", exodus-2, "secondary lymphoid tissue chemokine", SLC, TCA4. The Genbank reference sequence for CCL21 is AB002409.1 as available on 13 Jun. 2011, which is incorporated herein by reference in its entirety.

CCL5 is the gene symbol approved by the HUGO Gene Nomenclature Committee for chemokine (C—C motif) ligand 5, also known as RANTES. The HGNC ID for this gene is 10632. The gene is located at chromosome position 17q11.2-q12. The previous symbol and name for the gene is D17S136E, SCYA5, "small inducible cytokine A5 (RANTES)". Synonyms for this gene include "beta-chemokine RANTES", MGC17164, RANTES, "regulated upon activation, normally T-expressed, and presumably secreted", "SIS-delta", SISd, "small inducible cytokine subfamily A (Cys-Cys), member 5", "T-cell specific protein p288", "T-cell specific RANTES protein", TCP228. The Genbank reference sequence for CCL5 is AF043341.1 as available on 13 Jun. 2011, which is incorporated herein by reference in its entirety.

CCL19 is the gene symbol approved by the HUGO Gene Nomenclature Committee for chemokine (C—C motif) ligand 19, also known as MIP-3b. The HGNC ID for this gene is 10617. The gene is located at chromosome position 9p13. The previous symbol and name for the gene is SCYA19, "small inducible cytokine subfamily A (Cys-Cys), member 19". Synonyms for this gene include "beta chemokine exodus-3", "CC chemokine ligand 19", "CK beta-11", CKb11, "EBI1-ligand chemokine", ELC, exodus-3, "macrophage inflammatory protein 3-beta", MIP-3b. The Genbank reference sequence for CCL19 is AB000887.1 as available on 13 Jun. 2011, which is incorporated herein by reference in its entirety.

CCL8 is the gene symbol approved by the HUGO Gene Nomenclature Committee for chemokine (C—C motif) ligand 8, also known as MCP-2. The HGNC ID for this gene is 10635. The gene is located at chromosome position 17q11.2. The previous symbol and name for the gene is SCYA8, "small inducible cytokine subfamily A (Cys-Cys), member 8 (monocyte chemotactic protein 2)". Another synonym for this gene is HC14. The Genbank reference sequence for CCL8 is X99886.1 as available on 13 Jun. 2011, which is incorporated herein by reference in its entirety.

CCL3 is the gene symbol approved by the HUGO Gene Nomenclature Committee for chemokine (C—C motif) ligand 3, also known as MIP-1a. The HGNC ID for this gene is 10627. The gene is located at chromosome position 17q12. The previous symbol and name for the gene is SCYA3, "small inducible cytokine A3 (homologous to mouse Mip-1a)". Synonyms for this gene include G0S19-1, LD78ALPHA, MIP-1-alpha. The Genbank reference sequence for CCL3 is M23178.1 as available on 13 Jun. 2011, which is incorporated herein by reference in its entirety.

An example of a chemokine of the various embodiments of the invention containing both modifications and a truncation and specifically adapted for use in the invention is described in detail herein. The truncated CCL25 corresponds to residues 1 to 74 of the full length mature protein (and thus lacks amino acids 75 to 127 and the N-terminal signal peptide of 23 amino acids) and thus retains the chemokine fold. In addition, a methionine to Norleucine substitution is incorporated, to prevent oxidation of the residue during chain assembly. The N terminal glutamine residue is substituted with pyroglutamine to permit uniformity of product during synthesis. Biotinylation is achieved via a PEG spacer at the ε-functionality of the lysine residue found at position 72. The amino acid sequence of the linear molecule (i.e. without the PEG spacer and biotin molecule at amino acid 72 shown) comprises, consists essentially of or consists of the amino acid sequence presented as SEQ ID NO: 194. Chemokines of the invention may be synthesised through any suitable means. The final protein may thus comprise, consist essentially of or consist of the amino acid sequence of SEQ ID NO: 197 (see Examples below).

A further example of a chemokine of the various embodiments of the invention containing modifications and specifically adapted for use in the invention is described in detail herein (see Example 3 below). The modified CCL8 (MCP-2) corresponds to residues 1 to 76 of the full length mature protein (and lacks the N-terminal signal peptide of 23 amino acids, which is cleaved off) and thus retains the chemokine fold. The Gln at the N-terminus of the protein is subject to pyroGlu formation under physiological conditions. Thus Gln1 of the sequence is substituted with pyroglutamine to prevent mixed species of N-terminal Gln and pyroGlu being generated (SEQ ID NO: 198). This improves the yield of synthesis and ensures a homogeneous chemokine preparation through column manufacture and use. FmocLys(ivDde)-OH is incorporated as residue 75 to facilitate site-specific labelling at this position of the protein (SEQ ID NO: 199). The naturally occurring lysine at position 75 is modified through biotinylation. A suitable spacer, such as a PEG spacer, may be incorporated between the ε-amino functionality and the biotin (SEQ ID NO: 200):

Thus, in certain embodiments the invention also relates to a modified chemokine comprising, consisting essentially of or consisting of the amino acid sequence of SEQ ID NO: 198 or SEQ ID NO: 200:

```
                                            SEQ ID NO: 198
XPDSVSIPITCCFNVINRKIPIQRLESYTRITNIQCPKEAVIFKTKRGKE

VCADPKERWVRDSMKHLDQIFQNLKP
```

X=pyroGlu or Gln

```
                                            SEQ ID NO: 200
XPDSVSIPITCCFNVINRKIPIQRLESYTRITNIQCPKEAVIFKTKRGKE

VCADPKERWVRDSMKHLDQIFQNLXP
```

X1=pyroGlu (but may remain as Gln in some embodiments)

X75=an amino acid residue that can be biotinylated, such as lysine, ornithine or diaminopropionic acid and optionally is biotinylated, optionally via a spacer molecule such as PEG, e.g. K(PEG-Biotin).

A further example of a chemokine of the various embodiments of the invention containing modifications and specifically adapted for use in the invention is described in detail herein (see Examples below). The modified CCL5 (RANTES) corresponds to residues 1 to 68 of the full length mature protein (and lacks the N-terminal signal peptide of 23 amino acids, which is cleaved off) and thus retains the chemokine fold. The single methionine (Met67) within the sequence is mutated to lysine, to mitigate against oxidation of this residue during the chain assembly. SEQ ID NO: 201 presents the amino acid sequence prior to mutation. This Met to Lys substitution provides a lysine at position 67 which can be modified through biotinylation. FmocLys (ivDde)-OH is incorporated as residue 67 to facilitate site-specific labelling at this position of the protein (SEQ ID NO: 202). The biotinylated version comprises, consists essentially of or consists of the amino acid sequence of SEQ ID NO: 203.

Thus, in other embodiments the invention also relates to a modified chemokine comprising, consisting essentially of or consisting of the amino acid sequence of SEQ ID NO: 203:

```
SPYSSDTTPCCFAYIARPLPRAHIKEYFYTSGKCSNPAVVFVTRKNRQVC

ANPEKKWVREYINSLEXS
```

X is an amino acid residue that can be biotinylated, such as lysine, ornithine or diaminopropionic acid and optionally is biotinylated, optionally via a spacer molecule such as PEG (e.g. K(Biotin))

A further example of a chemokine of the various embodiments of the invention containing truncation and modifications and specifically adapted for use in the invention is described in detail herein (see Examples below). The truncated CXCL12 (SDF-1α) corresponds to residues 1 to 67 of the full length mature protein (and lacks the N-terminal signal peptide of 21 amino acids, which is cleaved off from an immature protein of total length 93 amino acids) and thus retains the chemokine fold (SEQ ID NO: 204). FmocLys (ivDde)-OH is incorporated as residue 64 to facilitate site-specific labelling at this position of the protein (SEQ ID NO: 205). The naturally occurring lysine at position 64 is modified through biotinylation. The final protein may thus comprise, consist essentially of or consist of the amino acid sequence of SEQ ID NO: 206.

Thus, the invention also relates to a modified chemokine comprising, consisting essentially of or consisting of the amino acid sequence of SEQ ID NO: 206:

```
KPVSLSYRCPCRFFESHVARANVKHLKILNTPNCALQIVARLKNNNRQVC

IDPKLKWIQEYLEXALN
```

X is an amino acid residue that can be biotinylated, such as lysine, ornithine or diaminopropionic acid and optionally is biotinylated, optionally via a spacer molecule such as PEG, e.g. K(PEG-Biotin)

A further example of a chemokine of the various embodiments of the invention containing modifications and specifically adapted for use in the invention is described in detail herein (see Examples below). The modified CCL19 (MIP-3β) corresponds to residues 1 to 77 of the full length mature protein (and lacks the N-terminal signal peptide of 21 amino acids, which is cleaved off) and thus retains the chemokine fold. An additional lysine is inserted at the C-terminus, at position 78. The chemokine may thus comprise, consist essentially of or consist of the amino acid sequence of SEQ ID NO: 207. FmocLys(ivDde)-OH is incorporated as residue 78 to facilitate site-specific labelling at this position of the protein (SEQ ID NO: 208). The ε-amino side chain functionality of Lys(78) is modified through biotinylation. The final protein may thus comprise, consist essentially of or consist of the amino acid sequence of SEQ ID NO: 209.

Thus, in other embodiments the invention also relates to a modified chemokine comprising, consisting essentially of or consisting of the amino acid sequence of SEQ ID NO: 209:

GTNDAEDCCLSVTQKPIPGYIVRNFHYLLIKDGCRVPAVVFTTLRGRQLC

APPDQPWVERIIQRLQRTSAKMKRRSSX

X is an amino acid residue that can be biotinylated, such as lysine, ornithine or diaminopropionic acid and optionally is biotinylated, optionally via a spacer molecule such as PEG, e.g. K(PEG-Biotin)

Chemokines useful in the various embodiments of the invention may be synthesised through any suitable means known in the art. Preferably, the chemokines are chemically synthesised as this facilitates modification and labelling etc. However, recombinant DNA based approaches may also be employed in combination with appropriate labelling and modification technologies as required. Thus, in certain embodiments the invention also provides a nucleic acid molecule encoding the chemokines of the various embodiments of the invention. In certain embodiments the invention also relates to a vector containing such a nucleic acid molecule and a host cell containing the vector. The vector may additionally comprise a suitable promoter operably linked to the nucleic acid molecule, to facilitate transcription of the corresponding mRNA molecule. The host cell may be capable of expressing the protein by transcription and translation of the nucleic acid molecule encoding a chemokine of the various embodiments of the invention.

The chemokines useful in the various embodiments of the invention can be biotinylated by methods known in the art such as described in WO 00/50088 A2, which is incorporated herein by reference. As indicated above, site-specific labelling of the chemokines of the various embodiments of the invention is preferable, although any labelling technique which does not significantly affect the receptor-binding capacity of the chemokine may be employed. Various site-specifically biotinylated chemokines and native chemokines are available commercially, for instance from Almac, Craigavon, UK. In specific embodiments the one or more chemokines are biotinylated via a spacer group. The spacer may be employed to prevent the biotin group from impacting on the activity of the chemokine, in particular binding of the chemokine to its cognate receptor. Any suitable spacer that facilitates retention of receptor binding properties of the chemokine may be employed in the various embodiments of the invention. Thus, in the specific embodiments described above, spacers other than PEG spacers may be employed as appropriate. In specific embodiments, the spacer is a polyethylene glycol (PEG) spacer. PEG has been shown to be an effective spacer permitting attachment of biotin to the chemokine (which can then be immobilized on the solid support through interaction with streptavidin) without compromising receptor binding capability.

In the context of the various embodiments of the present invention the term "antibody" includes all immunoglobulins or immunoglobulin-like molecules with specific binding affinity for the relevant chemokine receptor (including by way of example and without limitation, IgA, IgD, IgE, IgG and IgM, combinations thereof, and similar molecules produced during an immune response in any vertebrate, for example, in mammals such as humans, goats, rabbits and mice). Specific immunoglobulins useful in the various embodiments of the invention include IgG isotypes. The antibodies useful in the various embodiments of the invention may be monoclonal or polyclonal in origin, but are typically monoclonal antibodies. Antibodies may be human antibodies, non-human antibodies, or humanized versions of non-human antibodies, or chimeric antibodies. Various techniques for antibody humanization are well established and any suitable technique may be employed. The term "antibody" also refers to a polypeptide ligand comprising at least a light chain or heavy chain immunoglobulin variable region which specifically recognizes and binds an epitope of an antigen, and it extends to all antibody derivatives and fragments that retain the ability to specifically bind to the relevant chemokine receptor. These derivative and fragments may include Fab fragments, F(ab')2 fragments, Fv fragments, single chain antibodies, single domain antibodies, Fc fragments etc. The term antibody encompasses antibodies comprised of both heavy and light chains, but also heavy chain (only) antibodies. In specific embodiments, the antibodies may be engineered so as to be specific for more than one chemokine receptor, for example bi-specific to permit binding to two different chemokine receptors. Suitable commercially available antibodies which bind to the chemokine receptors of interest are listed in table 10 below. They may or may not be labelled. General reference may be made to "Antibodies a laboratory manual: By E Harlow and D Lane. pp 726. Cold Spring Harbor Laboratory. 1988", which reference is incorporated herein in its entirety. Anti-CCR2 antibodies are described for example in WO 2010/021697, incorporated herein by reference. Further examples of potentially useful antibodies include MLN-1202, an anti-CCR2 monoclonal antibody currently undergoing clinical trials (Millennium Pharmaceuticals).

TABLE 10

Commercially available fluorophore labelled antibodies against specific chemokine receptors

| Antibody | Fluorophore | Supplier |
| --- | --- | --- |
| CCR5 | PE | Biolegend |
| CCR9 | APC | R&D Systems |
| CCR7 | PerCP Cy5.5 | Biolegend |
| CXCR4 | APC | R&D Systems |

The chemokine receptor expressing cells may thus be targeted using alternative binding agents, such as antibodies or other chemical compounds, as defined herein, rather than the natural chemokine binding partner. This approach is a new approach to treating inflammatory conditions.

Accordingly, the various embodiments of the invention also provide an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine. The binding reagent capable of specifically binding to the chemokine receptor may be an agonist or an antagonist of the chemokine receptor. In specific embodiments, the binding reagent capable of specifically binding to the chemokine receptor is selected from an antibody and a chemical compound.

In other embodiments the invention thus also provides a method for treating an inflammatory condition comprising applying peripheral blood from a patient/subject to an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine) thus removing chemokine receptor expressing cells from the peripheral blood of the patient/subject. The method may comprise returning the blood depleted of the chemokine receptor expressing cells to the patient/subject.

Similarly, in other embodiments the invention provides a binding reagent capable of specifically binding to a chemokine receptor for use in the treatment of an inflammatory condition, wherein the binding reagent is immobilized on a solid support contained within an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient/subject, wherein the binding reagent is not a chemokine), to which is applied peripheral blood from a patient thus removing chemokine receptor expressing cells from the peripheral blood of the patient.

These aspects of the various embodiments of the invention may be integrated into the more focused therapeutic aspects of the various embodiments of the invention (i.e. treating PSC and various aspects thereof) and thus, the remainder of the disclosure, including all specific embodiments applies mutatis mutandis.

Solid support materials for immobilizing the binding reagents of the various embodiments of the invention are known in the art. "Solid support" refers to, for example, materials having a rigid or semi-rigid surface or surfaces, and may take the form of beads, resins, gels, microspheres, or other geometric configurations. A useful support material is one that does not activate blood cells so as to make them coagulate or adhere to the support as peripheral whole blood is applied to the device. In certain embodiments, a support treated with an agent to provide it with anti-coagulation properties, in particular a heparinized support is employed. Alternatively, the blood of the patient may be treated with an anti-coagulant such as heparin prior to application to the support. Useful support materials comprise high molecular weight carbohydrates, in particular carbohydrates having a molecular weight of 100 kDa or more, such as agarose, in particulate form, optionally cross-linked, and cellulose. Other preferred support materials are polymers, such as carboxylated polystyrene, and glass. The support of the various embodiments of the invention may be provided in the form of particles or fibres. The support particles may have regular form, such as spheres or beads, or irregular form. They may be porous or non-porous. A preferred average particle size of the support is from 50 µm to 2 mm. In certain embodiments Sepharose™, a cross linked, beaded-form of agarose, is used as column matrix. It is chosen for its optimal distribution capacity and can provide a large available area for affinity binding. Solid supports may be provided in the form of magnetic beads, with the specific binding reagent immobilized on the magnetic beads. Following capture of the (CCR9, CXCR4, CCR7 and/or CCR5) chemokine receptor expressing cells from the blood, the beads can be removed from the blood with the aid of an appropriate magnetic separator.

Methods for immobilizing binding reagents on a solid support are known in the art. A binding reagent, such as a chemokine, antibody, peptide, nucleic acid or chemical compound, can be immobilized on the support in a direct or indirect manner. Immobilization can be by means of a suitable linker in some embodiments. A preferred method of indirect immobilization of a binding reagent, such as a chemokine, relies upon the interaction between biotin and avidin molecules. "Avidin" or "avidin molecule" refers to any type of protein that specifically binds biotin to the substantial exclusion of other (small) molecules that might be present in a biological sample. Examples of avidin include avidins that are naturally present in egg white, oilseed protein (e.g., soybean meal), and grain (e.g., corn/maize), and streptavidin, which is a protein of bacterial origin. Thus, biotinylation of the binding reagent and use of an avidin molecule such as streptavidin immobilized on the solid support allows reliable attachment of the binding reagent to the solid support according to methods known in the art. Specifically, such a method may comprise providing the binding reagent in biotinylated form, providing a solid support having streptavidin immobilized on its surface, contacting the support with an aqueous solution of the biotinylated binding reagent, and rinsing the support with an aqueous solvent. In addition, binding pair interactions, such as antibody-antigen interactions, may also be utilised for indirect immobilisation of binding reagent onto a support. In such embodiments the support may be derivatised with one member of a binding pair, such as an antibody or fragment or derivative thereof, as defined herein, which has known affinity for a particular peptide sequence or small molecule hapten. Incorporating the other member of the binding pair, such as an antigen, peptide sequence or the hapten onto or into the binding reagent facilitates immobilisation onto a solid support coated with the corresponding antibody or fragment or derivative thereof. Thus, the binding reagent may be modified to include the peptide sequence or hapten into the linear molecule or may be added as a side chain or label. Any suitable antibody-antigen pair may be employed. The antibody fragment or derivative may be any fragment or derivative that retains specific binding affinity for the appropriate antigen. Examples include Fab, F(ab')2 fragments, scFV, VH domains, single domain antibodies (such as nanobodies), heavy chain antibodies and humanized version of non-human antibodies etc. Other high affinity interactions can be utilised for immobilisation of binding reagents, as long as the binding reagent can be synthesised or derivatised with one of the interacting partners and the solid support synthesised or derivatised with the other interacting partner without loss of binding activity (i.e. binding of the binding reagent to the appropriate chemokine receptor). Immobilization may occur via essentially the same interaction in reverse in some embodiments. Thus, the binding reagent which may be a chemokine for example, may be attached to an antibody as defined herein, and the solid support derivatised with the antigen. The chemokine may be produced as a fusion protein with the antibody.

Alternatively binding reagents, such as chemokines and antibodies, can be immobilised directly onto a solid support using bioconjugation techniques established in the field. For example direct immobilisation of proteins onto cyanogen bromide activated solid supports via amino functionalities within the primary sequence of the protein. Alternatively, sulphydryl functionalities within proteins can be used to directly immobilise the protein to alkyl halide derivatised supports or supports containing free thiol functionalities. In further embodiments, proteins containing α-thioester functionalities can be directly immobilised on supports containing 1,2 amino thiol moieties (eg N-terminal cysteine) using the native chemical ligation reaction. Alternatively proteins modified with ketones and aldehydes can be immobilised on solid supports derivatised with hydrazinyl, hydrazide and aminoxy functionalities using hydrazone/oxime bond forming ligation reactions (and vice versa). Alternatively 'Click' chemistry can be used to immobilise proteins onto solid supports, whereby the protein and the support are derivatised with the appropriate mutually reactive chemical functionalities (azides and alkynes). In other embodiments Staudinger ligation chemistry can be used to immobilise appropriately derivatised proteins onto the appropriately derivatised solid supports.

The solid support is contained within or carried by the apheresis column. Thus, by "loaded" is meant that the column carries or contains the solid support in a manner such that (peripheral) blood can flow through the column in contact with the solid support. Thus, the solid support provides a matrix within the column through which blood flows, in continuous fashion in certain embodiments. This permits cells expressing the specific chemokine receptor to be removed from the blood passing through the column, such that blood exiting the column is depleted of the specific chemokine receptor-expressing cells. In specific embodiments, the apheresis column is loaded with a support comprising streptavidin immobilized on the support and one or more biotinylated binding reagents, such as chemokines, bound to the streptavidin on the support. The solid support may be comprised of a high-molecular weight carbohydrate, optionally cross-linked, such as agarose.

As discussed above, the binding reagent is coupled to the solid support. The relative amounts of binding reagent may be controlled to ensure that coupling between the solid support and the binding reagent will be immediate, minimising the risk of binding reagent decoupling from the solid support. Thus, it may be ensured that there is a relative excess of immobilization sites for the binding reagent on the solid support. Alternatively, or additionally, following immobilization of the binding reagent on the solid support, the solid support may be washed to remove any unbound binding reagent.

The apheresis column utilised in the various embodiments of the present invention acts as a leukapheresis treatment for primary sclerosing cholangitis. The column acts to specifically remove one or more of CCR9, CXCR4, CCR7 and CCR5-expressing monocytes or leukocytes by exploiting the interaction between CCR9, CXCR4, CCR7 and/or CCR5 expressed on the cell surface and a specific binding reagent immobilized on a solid support contained within or carried by the column. The overall column typically comprises, consists of, or consists essentially of three combined components; 1) a housing which contains or carries 2) the solid support and 3) one or more binding reagents (immobilized thereon) which specifically bind one or more chemokine receptors. The housing may be manufactured from any suitable material for clinical use. In certain embodiments the housing is composed of a plastic material. The housing includes an in flow site for entry of blood and an out flow site for blood (depleted of target cells) to exit the column. The housing may be designed to maintain a continuous blood flow through the solid support matrix. The housing (as shown for example in FIG. 9) may include a top portion which comprises a distribution plate (2) at the inflow site (1) to spread the blood evenly over the entire matrix area. The distribution plate may act as a first safety barrier preventing larger particles flowing through the column and into the patient. However, the distribution plate is not essential and may be removed in some embodiments to decrease the overall resistance in the system. The column may contain one or more safety filter units (3 and 4) placed at the inflow (1) and/or outflow (5) sites of the plastic housing. Such filter units may act to prevent particles larger than blood cells passing in and/or out of the column. The safety filter units may contain a plurality of filters, such as two, three or four filters designed to be a robust barrier and stop all particles larger than blood cells passing through the column. Inclusion of safety filters (3 and 4) at both ends of the column serves to minimize the risk of leakage of particles into the patient, including in the event that the device is incorrectly connected resulting in blood flow in the opposite direction to that intended. The safety filters may comprise of any suitable pore size to prevent particles larger than blood cells from passing through the column, as would be readily understood by one skilled in the art. Suitable filters are commercially available. In specific embodiments, the pore size of the filter(s) is between approximately 60 μm and 100 μm, more specifically approximately 80 μm. The solid support and binding reagent components are discussed in further detail herein.

The volume of the housing may be varied depending upon the blood volumes intended to pass through the column. Typically, the volume of the housing is between approximately 40 ml and 200 ml, more specifically 50 ml to 150 ml or 60 ml to 120 ml.

The column is generally applied in the form of an apheresis circuit. In this context, the overall system includes the apheresis column, tubing and an appropriate pump to pump the blood around the circuit. The system is illustrated in FIG. 10. The patient (1) is connected to the extracorporeal circuit via sterile needles to veins in the right and the left arms. A saline bag (3) is also connected and the saline solution is pumped with a suitable pump (2). Blood is drawn from one arm of the patient through the sterile tubing system by the blood pump (4) and passed through the column (6) and back to the patient. The tubing system may be connected to the column via any suitable coupling, such as standard dialysis luer-lock couplings. The couplings on the column may be colour-coded for correct assembly. For example, red tubing for inflow to the red column top and blue tubing for outflow back to the patient. An air detector (8) may be present in the circuit. Inlet pressure (5) and/or Pven sensors (7) may additionally be employed to monitor the pressure in the circuit.

An apheresis pump, such as the 4008 ADS pump manufactured by Fresenius Medical Care or the Adamonitor pump, may monitor the patient's inflow and outflow. The pump may also monitor the pressure in the extracorporeal circulation. The pump may be able to discriminate air by a bubble catcher and air detector. A clot catcher filter may be positioned inside the bubble catcher. The pump may also incorporate an optical detector to distinguish between light, e.g. saline solution or air present in the tubing system and dark e.g. blood present in the tubing system.

A schematic diagram of a suitable pump, showing the air detector and optical filter is shown in FIG. 11. If the pump system detects air bubbles and optical fluctuations or if extracorporeal pressure values are out of the set range, then the pump may stop immediately. Alternatively or additionally a visual/audible alarm may be emitted.

The treatment methods of the various embodiments of the invention may thus rely upon an extracorporeal circuit. The methods may be considered as ex vivo or in vitro methods and be defined solely with reference to steps performed outside of the patient. In some embodiments, however, the method further comprises, prior to application of the blood to the column, collecting peripheral blood from the patient. In a further embodiment, the method further comprises, following the application of the blood to the column, infusing the blood depleted of (CCR9, CXCR4, CCR7 and/or CCR5) chemokine receptor expressing cells to the patient. This is then a complete leukapheresis treatment method. Thus, a leukaphereis method, for treating primary sclerosing cholangitis, comprises collecting peripheral blood from the patient; applying the peripheral blood to an apheresis column loaded with a solid support comprising one or more binding reagents capable of specifically binding to one or more chemokine receptors, in particular the chemokine receptor CCR9, CXCR4, CCR7 and/or CCR5, immobilized directly or indirectly on the support thus removing one or more of CCR9, CXCR4, CCR7 and CCR5 expressing cells from the peripheral blood of the patient; and infusing the depleted blood (of chemokine receptor expressing cells) to the patient.

The peripheral blood may be continuously collected from the patient. Similarly, the depleted blood may be continuously infused to the patient, through use of an appropriate circuit as described herein. Thus, the support may be disposed in a column through which the blood is made to flow. This may be achieved using a suitable pump for example, as also described herein. Blood flow through the column enables the binding reagent(s) immobilized on the solid support to capture the cells expressing the chemokine receptor, thus depleting them from the blood and preventing their contribution to the inflammatory primary sclerosing cholangitis.

The methods of the various embodiments of the invention and binding reagents for use in the methods of the various embodiments of the invention may require that the patient has been selected for treatment on the basis of detecting an increase in the level of chemokine receptor, in particular, one or more of CCR9, CXCR4, CCR7 and CCR5 expressing cells in a sample obtained from the patient. Such companion diagnostic methods are described in greater detail herein and are based, for example, on the observation that CCR9, CXCR4, CCR7 and/or CCR5 expression on monocytes is elevated in patients with primary sclerosing cholangitis.

Thus, (in this context) in certain embodiments the invention also provides a method of diagnosing, monitoring progression of, or monitoring treatment of primary sclerosing cholangitis comprising determining:

a) the levels of one or more of the chemokine receptor CCR9, CXCR4, CCR7 and CCR5 expressing cells b) levels of expression of one or more of CCR9, CXCR4, CCR7 and CCR5; and/or c) levels of cells with high expression of one or more of CCR9, CXCR4, CCR7 and CCR5 in a sample obtained from a subject, wherein high levels of one or more of CCR9, CXCR4, CCR7 and CCR5 expressing cells, high levels of expression of one or more of CCR9, CXCR4, CCR7 and CCR5 or high levels of cells with high expression of CCR9, CXCR4, CCR7 or CCR5 or increased levels of one or more of CCR9, CXCR4, CCR7 and CCR5 expressing cells compared to control, increased levels of expression of one or more of CCR9, CXCR4, CCR7 and CCR5 compared to a control or increased levels of cells with high expression of one or more of CCR9, CXCR4, CCR7 and CCR5 compared to a control indicate the presence or progression of primary sclerosing cholangitis. Levels of chemokine receptor expression, as opposed to cell numbers, may also be investigated as increased levels of chemokine receptor expression per cell may also be diagnostically relevant. The cells may be monocytes, in particular CCR9 expressing and HLA-DRhi monocytes as described herein.

"Diagnosing" is defined herein to include screening for a disease/condition or pre-indication of a disease/condition, identifying a disease/condition or pre-indication of a disease/condition and checking for recurrence of disease/condition following treatment. The methods of the various embodiments of the invention may also have prognostic value, and this is included within the definition of the term "diagnosis". The prognostic value of the methods of the various embodiments of the invention may be used as a marker of potential susceptibility to primary sclerosing cholangitis by identifying levels of CCR9, CXCR4, CCR7 and/or CCR5 expression linked to conditions associated with that syndrome. Thus patients at risk may be identified before the disease has a chance to manifest itself in terms of symptoms identifiable in the patient. In certain embodiments, diagnosis may be made in conjunction with other objective indicators of PSC. Thus, in specific embodiments, diagnosis is made in conjunction with the following indicators:

Diagnosis is made clinically with associated ALT, AST, ALP, bilirubin and patognomonic ERCP picture. In addition the identification of circulating biliary tract homing proinflammatory cells cam be monitored for chemokine receptor expression.

"Monitoring progression of" includes performing the methods to monitor the stage and/or the state and progression of the primary sclerosing cholangitis. Monitoring progression may involve performing the diagnostic methods multiple times on the same patient to determine whether the levels of one or more of CCR9, CXCR4, CCR7 and CCR5 expressing cells are increasing, decreasing or remaining stable over a certain time period. This may be in the context of a treatment regime.

"Monitoring the success of a particular treatment" is defined to include determining the levels of one or more of CCR9, CXCR4, CCR7 and CCR5 expressing cells before and after a treatment. The cells may be monocytes, in particular CCR9 expressing and HLA-DRhi monocytes as described herein. The treatment is generally one aimed at treating primary sclerosing cholangitis and may be a treatment according to one of the methods of the various embodiments of the invention as defined herein. Successful treatment may be determined with reference to a decrease in one or more of CCR9, CXCR4, CCR7 and CCR5 expressing cells as a result of, or following, the treatment. Thus, in such methods a level of one or more of CCR9, CXCR4, CCR7 and CCR5 expressing cells is determined prior to treatment. This level is recorded and a further assessment made at a predetermined time following the treatment. The comparison of levels of one or more of CCR9, CXCR4, CCR7 and CCR5 expressing cells permits the success of the treatment to be monitored. In specific embodiments, a single treatment is sufficient to cause a depletion of around 10%, 20%, 30%, 40%, 50%, 60% or 70%, or higher, up to 80%, 90%, 95% or more, or any range of values between and including these amounts, of one or more specific chemokine receptors, in particular CCR9, CXCR4, CCR7 and/or CCR5, expressing cells from the peripheral blood of the patient. In specific embodiments, at least around 50% depletion is achieved in a single treatment. Thus, successful treatment may be defined with reference to depletion of one or more of CCR9, CXCR4, CCR7 and CCR5 expressing cells. Treatment may lead to depletion of between approximately 100 and 500 million of one of more of CCR9, CXCR4, CCR7 and CCR5 expressing cells, such as monocytes, in certain embodiments. Additional factors may be included to determine successful treatment. For example, a lack of increase in one or more of CCR9, CXCR4, CCR7 and CCR5 expressing cells following treatment may indicate successful treatment in terms of preventing further progression of the condition, optionally combined with an improvement in other markers or staging of the primary sclerosing cholangitis.

By binding to the column through the binding reagent-chemokine receptor interaction, chemokine receptor expressing cells are immobilized. These immobilized cells express further unoccupied chemokine receptors, which may be of the same or different type to those used for capture. These additional chemokine receptors may permit circulating chemokines which contribute to the inflammatory condition to be captured from the peripheral blood. Thus, a reduction in circulating (specific) chemokine levels may provide a measure of successful treatment.

The sample in which one or more of CCR9, CXCR4, CCR7 and CCR5 expressing cell levels, levels of expression of one or more of CCR9, CXCR4, CCR7 and CCR5 and/or levels of cells with high expression of one or more of CCR9, CXCR4, CCR7 and CCR5 (defined as CCR9 hi, CXCR4 hi, CCR7 hi and/or CCR5hi) are determined may comprise any suitable tissue sample or body fluid sample. Generally, the test sample is obtained from a human subject. Typically, the sample is a blood sample, in particular a peripheral blood sample. The sample may comprise a liver sample, such as a liver biopsy in certain embodiments. The methods may involve determining levels of one or more of CCR9, CXCR4, CCR7 and CCR5 expressing monocytes, macrophages or lymphocytes in certain embodiments.

Levels of CCR9, CXCR4, CCR7 and/or CCR5 expressing cells, levels of expression of CCR9, CXCR4, CCR7 and/or CCR5 and/or levels of cells with high expression of CCR9, CXCR4, CCR7 and/or CCR5 (defined as CCR9 hi, CXCR4 hi, CCR7 hi and/or CCR5hi) may be determined according to any suitable method. For example, flow cytometry may be employed in order to determine the number of cells expressing CCR9, CXCR4, CCR7 and/or CCR5 in the sample, to determine levels of CCR9, CXCR4, CCR7 and/or CCR5 expression and/or to identify levels of CCR9 hi, CXCR4 hi, CCR7 hi and/or CCR5hi cells. Flow cytometric techniques are described herein and examples of commercially available antibodies suitably labelled for use in flow cytometry are set out in Table 10 for example. Alternatively, the method may involve steps of collecting and fixing the cells in the sample, followed by incubation with a suitable binding reagent that binds specifically to the CCR9, CXCR4, CCR7 and/or CCR5 chemokine receptor expressing cells in the sample. Any suitable binding reagent, as defined herein, may be employed. For example, a CCR9, CXCR4, CCR7 and/or CCR5 specific antibody may be employed. A wash step may be adopted following an incubation period to remove any unbound reagent. Suitable wash steps and incubation conditions would be well known to one skilled in the art. The binding reagent may be directly labeled in order to permit antibody binding to be directly determined. Alternatively a secondary binding reagent, such as an antibody, may be employed which binds to the first binding reagent and carries a label. Again, suitable incubation conditions and wash steps would be apparent to one skilled in the art. The primary and secondary binding reagents may form two halves of a binding pair. The binding interaction should not prevent the primary binding reagent binding to the CCR9, CXCR4, CCR7 and/or CCR5 receptor expressing cells, unless a competition assay is being employed. The two halves of a binding pair may comprise an antigen-antibody, antibody-antibody, receptor-ligand, biotin-streptavidin pair etc. in certain embodiments. Other techniques used to quantify chemokine (CCR9, CXCR4, CCR7 and/or CCR5) receptor expressing cell levels, to quantify levels of CCR9, CXCR4, CCR7 and/or CCR5 expression and/or to quantify levels of CCR9 hi, CXCR4 hi, CCR7 hi and/or CCR5hi cells include PCR-based techniques such as QT-PCR and protein based methods such as western blot. Quantitation may be achieved with reference to fixed cell lines carrying known numbers of various receptor expressing cells and/or known levels of receptor expression per cell. Such fixed cell lines are available commercially (for example ChemiScreen™ cell lines from Millipore). Methods analogous to the treatment methods of the various embodiments of the invention may also be employed, with binding of CCR expressing cells to the solid support being determined following peripheral blood being passed through the column.

The levels of CCR9, CXCR4, CCR7 and/or CCR5 expressing cells, levels of expression of CCR9, CXCR4, CCR7 and/or CCR5 and/or levels of cells with high expression of CCR9, CXCR4, CCR7 and/or CCR5 (defined as CCR9hi, CXCR4hi, CCR7hi and/or CCR5hi) may be determined relative to a suitable control. When diagnosing primary sclerosing cholangitis, a threshold level of cells, level of expression of CCR9, CXCR4, CCR7 and/or CCR5 and/or level of cells with high expression of CCR9, CXCR4, CCR7 and/or CCR5 (defined as CCR9, CXCR4, CCR7 and/or CCR5hi) may be set at or over which a positive diagnosis is made. This threshold may be determined based upon measuring levels of CCR9, CXCR4, CCR7 and/or CCR5 expressing cells, levels of expression of CCR9, CXCR4, CCR7 and/or CCR5 and/or levels of cells with high expression of CCR9, CXCR4, CCR7 and/or CCR5 (defined as CCR9hi, CXCR4hi, CCR7hi and/or CCR5hi) in samples obtained from diseased patients and comparing these levels with levels of CCR9, CXCR4, CCR7 and/or CCR5 expressing cells, levels of expression of CCR9, CXCR4, CCR7 and/or CCR5 and/or levels of cells with high expression of CCR9, CXCR4, CCR7 and/or CCR5 (defined as CCR9hi, CXCR4hi, CCR7hi and/or CCR5hi) in samples obtained from healthy subjects.

In certain embodiments, primary sclerosing cholangitis is diagnosed on the basis of levels of chemokine receptor expressing cells, such as CCR9, CXCR4, CCR7 and/or CCR5 expressing cells. A positive diagnosis may be made in subjects based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, primary sclerosing cholangitis is diagnosed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, such as CCR9, CXCR4, CCR7 and/or CCR5 expressing cells, relative to healthy controls.

In specific embodiments, primary sclerosing cholangitis is diagnosed on the basis of levels of CCR9 expressing cells, in particular monocytes. A positive diagnosis may be made in subjects based upon the presence of greater than about 8%, greater than about 9%, greater than about 10%, greater than about 12% or greater than about 15% CCR9 expressing cells, in particular monocytes in the sample, as a percentage of total cells in the sample. Primary sclerosing cholangitis may also be diagnosed on the basis of the presence of a about a 1.2 fold or greater increase, such as about a 1.5, 2, 2.5, 3, 3.5, 4, 4.5, 5, 10, 20, 50 or 100 or greater fold increase in the CCR9 expressing cells, in particular monocytes, relative to healthy controls.

In certain embodiments, progression of primary sclerosing cholangitis, which may be in the context of a treatment regime, is monitored on the basis of levels of chemokine receptor expressing cells, such as CCR9, CXCR4, CCR7 and/or CCR5 expressing cells at different time points. Progression of primary sclerosing cholangitis may be indicated in subjects based upon an increase of greater than about 2%, greater than about 3%, greater than about 4%, greater than about 5%, greater than about 6%, greater than about 7%, or greater than about 10%, such as an increase of greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more chemokine receptor expressing cells in the sample, as a percentage of total cells in the sample, compared to a sample taken from the same subject at an earlier time point. In other embodiments, progression of primary sclerosing cholangitis is confirmed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, such as CCR9, CXCR4, CCR7 and/or CCR5 expressing cells, relative to a sample taken from the same subject at an earlier time point.

In specific embodiments, primary sclerosing cholangitis is monitored on the basis of levels of CCR9 expressing cells, in particular monocytes. Progression of the disease, which may be in the context of a treatment regime, may be indicated in subjects based upon the presence of an increase of greater than about 2%, greater than about 3%, greater than about 4%, greater than about 5%, greater than about 6%, greater than about 7%, or greater than about 10% or more chemokine receptor expressing cells in the sample, as a percentage of total cells in the sample, compared to a sample taken from the same subject at an earlier time point. In other embodiments, progression of primary sclerosing cholangitis is confirmed on the basis of the presence of a about a 1.2 fold or greater increase, such as about a 1.5, 2, 2.5, 3, 3.5, 4, 4.5, 5, 10, 20, 50 or 100 or greater fold increase in CCR9 expressing cells, in particular monocytes, relative to a sample taken from the same subject at an earlier time point.

Regression or successful treatment may be monitored based upon similar decreases over various time points. For example, regression or successful treatment may be indicated in subjects based upon a decrease of greater than about 2%, greater than about 3%, greater than about 4%, greater than about 5%, greater than about 6%, greater than about 7%, or about 10%, such as a decrease of about 15%, about 20%, about 25%, about 30%, about 35%, about 40%, about 45%, about 50%, about 55%, about 60%, about 65%, about 70%, about 75% or more chemokine receptor expressing cells in the sample, as a percentage of total cells in the sample, compared to a sample taken from the same subject at an earlier time point. In other embodiments, regression of primary sclerosing cholangitis is confirmed on the basis of the presence of a about a 1.2 fold or greater decrease, such as about a 1.5, 2, 2.5, 3, 3.5, 4, 4.5, 5, 10, 20, 50 or 100 or greater fold decrease in chemokine receptor expressing cells, such as CCR9, CXCR4, CCR7 and/or CCR5 expressing cells, relative to a sample taken from the same subject at an earlier time point.

In specific embodiments, primary sclerosing cholangitis is monitored on the basis of levels of CCR9 expressing cells, in particular monocytes. Regression or successful treatment of the disease may be made in subjects based upon a decrease of greater than about 2%, greater than about 3%, greater than about 4%, greater than about 5%, greater than about 6%, greater than about 7%, or about 10%, such as a decrease of about 15%, about 20%, about 25%, about 30%, about 35%, about 40%, about 45%, about 50%, about 55%, about 60%, about 65%, about 70%, about 75% or more CCR9 expressing cells, in particular monocytes in the sample, as a percentage of total cells in the sample or by a decrease of about 2%, such as a decrease of about 3%, about 4%, about 5%, about 6%, about 7%, about 8%, about 9%, about 10%, about 15%, about 20%, about 25%, about 30%, about 35% or more CCR9 expressing cells, in particular monocytes in the sample, as a percentage of total cells in the sample, compared to a sample taken from the same subject at an earlier time point.

Suitable software is freely available (such as the R project for statistical computing) to perform the necessary statistical analysis of the data obtained to calculate a useful threshold. The threshold may be set to maximize sensitivity and/or specificity of the test. Performance of the test in these respects may be measured by plotting a receiver operating characteristics (ROC) curve (sensitivity versus specificity). The area under the curve provides an indication of the overall performance of the test. Thus, once thresholds have been set for diagnosing the condition, a separate control experiment does not necessarily have to be run each time a sample is tested. Rather reference can simply be made to the pre-existing thresholds to determine the diagnosis. However, in certain embodiments, the sample is tested together with a control sample taken from a healthy subject to provide a comparator based upon essentially identical experimental conditions. The test sample is generally tested in parallel with the control sample. The test sample level of CCR9, CXCR4, CCR7 and/or CCR5 expressing cells, levels of expression of CCR9, CXCR4, CCR7 and/or CCR5 and/or levels of cells with high expression of CCR9, CXCR4, CCR7 and/or CCR5 (defined as CCR9 hi, CXCR4 hi, CCR7 hi and/or CCR5hi) can then be compared with that of the control sample to make the diagnosis. A control sample from a disease patient may also be tested in certain embodiments. Reference to controls permits relative levels ("high", "low" etc.) of CCR9, CXCR4, CCR7 and/or CCR5 expressing cells in the test sample to be readily identified and the significance thereof interpreted. Reference to controls also permits relative levels of CCR9, CXCR4, CCR7 and/or CCR5 expression ("high", "low" etc.) within the cell population to be determined and the significance thereof interpreted. Such determination may, for example, indicate the average levels of CCR9, CXCR4, CCR7 and/or CCR5 expression per cell in the test sample.

Thus, in specific embodiments, high or higher levels of one or more of CCR9, CXCR4, CCR7 and CCR5 expressing cells or high or higher levels of one or more of CCR9, CXCR4, CCR7 and CCR5 expression, for example average CCR9, CXCR4, CCR7 and/or CCR5 expression per cell, or high or higher levels of one or more of CCR9hi, CXCR4hi, CCR7hi and CCR5hi cells correlate with active disease or more active primary sclerosing cholangitis. Similarly, lower or low levels of one or more of CCR9, CXCR4, CCR7 and CCR5 expressing cells, or low or lower levels of one or more of CCR9, CXCR4, CCR7 and CCR5 expression, for example average CCR9, CXCR4, CCR7 and/or CCR5 expression per cell, or low or lower levels of one or more of CCR9 hi, CXCR4 hi, CCR7 hi and hiCCR5hi cells may correlate with a lack of active inflammation or primary sclerosing cholangitis. This may be defined as "less active disease". It can readily be envisaged that control samples may be assessed and levels of CCR9, CXCR4, CCR7 and/or CCR5 expressing cells, levels of expression of CCR9, CXCR4, CCR7 and/or CCR5 and/or levels of cells with high expression of CCR9, CXCR4, CCR7 and/or CCR5 (defined as CCR9 hi, CXCR4 hi, CCR7hi and/or CCR5hi) determined across the range of severities of primary sclerosing cholangitis. This may assist in correlating the levels of CCR9, CXCR4, CCR7 and/or CCR5 expressing cells, levels of expression of CCR9, CXCR4, CCR7 and/or CCR5 and/or levels of cells with high expression of CCR9, CXCR4, CCR7 and/or CCR5 (defined as CCR9hi, CXCR4hi, CCR7hi and/or CCR5hi) in the test sample with the relative severity of the condition.

When monitoring progression of, or monitoring treatment of primary sclerosing cholangitis, the control samples may be taken from the subject at an earlier time point. They may, however, be based upon known reference values as discussed above. Thus, relative levels of CCR9, CXCR4, CCR7 and/or CCR5 expressing cells, relative levels of CCR9, CXCR4, CCR7 and/or CCR5 expression including relative levels of average CCR9, CXCR4, CCR7 and/or CCR5 expression per cell or relative levels of CCR9 hi, CXCR4 hi, CCR7 hi and/or CCR5hi cells may be with reference to samples taken from the same subject at a different point in time. In certain embodiments, decreased levels of CCR9, CXCR4, CCR7 and/or CCR5 expressing cells, decreased relative levels of CCR9, CXCR4, CCR7 and/or CCR5 expression including decreased relative levels of average CCR9, CXCR4, CCR7 and/or CCR5 expression per cell, or decreased relative levels of CCR9 hi, CXCR4 hi, CCR7 hi and/or hiCCR5hi cells correlate with successful treatment. The treatment may be any suitable treatment, but in specific embodiments is a treatment according to the various embodiments of the invention.

When monitoring progression of primary sclerosing cholangitis, increased levels of CCR9, CXCR4, CCR7 and/or CCR5 expressing cells increased relative levels of CCR9, CXCR4, CCR7 and/or CCR5 expression including increased relative levels of average CCR9, CXCR4, CCR7 and/or CCR5 expression per cell or increased relative levels of CCR9, CXCR4, CCR7 and/or CCR5hi cells may indicate the progression of condition or disease. Thus, if levels of CCR9, CXCR4, CCR7 and/or CCR5 expressing cells, levels of expression of CCR9, CXCR4, CCR7 and/or CCR5 and/or levels of cells with high expression of CCR9, CXCR4, CCR7 and/or CCR5 (defined as CCR9 hi, CXCR4 hi, CCR7 hi and/or CCR5hi) are increased in a sample taken later than a sample from the same patient this may indicate progression of the condition.

Since the levels of one or more of CCR9, CXCR4, CCR7 and CCR5 expressing cells, levels of one or more of CCR9, CXCR4, CCR7 and CCR5 expression or levels of one or more of CCR9 hi, CXCR4 hi, CCR7 hi and/or CCR5hi cells are diagnostically relevant, determining such levels in a sample obtained from a subject may influence treatment selection for that subject. Accordingly, in certain embodiments the invention provides a method of selecting a suitable treatment for primary sclerosing cholangitis comprising determining:

a) the levels of one or more of the chemokine receptor CCR9, CXCR4, CCR7 and CCR5 expressing cells b) levels of expression of one or more of CCR9, CXCR4, CCR7 and CCR5; and/or c) levels of cells with high expression of one or more of CCR9, CXCR4, CCR7 and CCR5 in a sample obtained from a subject, wherein high levels of one or more of CCR9, CXCR4, CCR7 and CCR5 expressing cells, high levels of expression of one or more of CCR9, CXCR4, CCR7 and CCR5 or high levels of cells with high expression of CCR9, CXCR4, CCR7 and/or CCR5 or increased levels of one or more of CCR9, CXCR4, CCR7 and CCR5 expressing cells compared to control, increased levels of expression of one or more of CCR9, CXCR4, CCR7 and CCR5 compared to a control or increased levels of cells with high expression of one or more of CCR9, CXCR4, CCR7 and CCR5 compared to a control, result in selection of a treatment as defined herein for treatment of the primary sclerosing cholangitis. In certain embodiments, the chemokine receptor expressing cells are high chemokine receptor expressing cells, in particular, high CCR9, CXCR4, CCR7 and/or CCR5 expressing cells.

In specific embodiments, primary sclerosing cholangitis is treated on the basis of measuring levels of chemokine receptor expressing cells, such as CCR9, CXCR4, CCR7 and/or CCR5 expressing cells. Thus, a treatment according to the various embodiments of the invention may be applied based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, primary sclerosing cholangitis is treated according to the various embodiments of the invention on the basis of the presence of a about a 1.5 fold or greater increase, such as about a 2, 2.5, 3, 3.5, 4, 4.5, 5, 10, 20, 50 or 100 or greater fold increase in chemokine receptor expressing cells, such as CCR9, CXCR4, CCR7 and/or CCR5 expressing cells, relative to healthy controls.

In specific embodiments, primary sclerosing cholangitis is treated on the basis of measuring levels of CCR9 expressing cells, in particular monocytes. Thus, a treatment according to the various embodiments of the invention may be applied based upon the presence of greater than about 2%, greater than about 3%, greater than about 4%, greater than about 5%, greater than about 6%, greater than about 7%, greater than about 10%, greater than about 12% or greater than about 15% or more CCR9 expressing cells, in particular monocytes in the sample, as a percentage of total cells in the sample or on the basis of the presence of a about a 1.5 fold or greater increase, such as about a 2, 2.5, 3, 3.5, 4, 4.5, 5, 10, 20, 50 or 100 or greater fold increase in CCR9 expressing cells, in particular monocytes, relative to healthy controls.

For the avoidance of doubt, all embodiments described in respect of the methods of the various embodiments of the invention apply to these aspects mutatis mutandis and are not repeated for reasons of conciseness. Specifically, primary sclerosing cholangitis may be indicated in conjunction with the following indicators:

Diagnosis is made clinically with associated ALT, AST, ALP, bilirubin and patognomonic ERCP picture. In addition the identification of circulating biliary tract homing proinflammatory cells cam be monitored for chemokine receptor expression The methods and medical uses of the various embodiments of the invention thus can be tailored to the need of individual patients or groups of patients on the basis of the various diagnostic methods of the various embodiments of the invention. By removing from the circulation one or more of CCR9, CXCR4, CCR7 and CCR5 expressing cells, such as monocytes, macrophages and lymphocytes, in particular monocytes, upregulated in various inflammatory conditions associated with primary sclerosing cholangitis, an important factor in the inflammatory process of primary sclerosing cholangitis can be controlled.

K. Treating Respiratory Conditions

Chemokines are a class of cytokine molecules involved in cell recruitment and activation in inflammation. Chemokines cause chemotaxis and activation of various subpopulations of cells in the immune system. The activity of chemokines is mediated primarily through tight binding to their receptors on the surface of leukocytes. In certain embodiments the present invention is based on the realisation that the interaction between chemokines and cells expressing their receptors may be exploited for the treatment of respiratory conditions, in particular sarcoidosis and Chronic Obstructive Pulmonary Disease (COPD). In particular, various respiratory conditions, in particular sarcoidosis and Chronic Obstructive Pulmonary Disease (COPD) include an inflammatory component. Whilst sarcoidosis is predominantly considered a respiratory condition, general treatment of sarcoidosis affecting any organ of the body may be possible within the scope of the various embodiments of the present invention. The inventors have determined that targeting increased recruitment of specific chemokine receptor-expressing cells to the site of inflammation presents a new therapeutic approach to treat such conditions. Moreover, in such conditions, chemokine receptor expression on each cell may be increased again providing a therapeutic approach to treat such conditions. It is shown herein that subjects suffering from respiratory conditions such as sarcoidosis exhibit increased frequency of chemokine receptor expressing cells in the peripheral blood. Subjects with sarcoidosis exhibit increased frequency of CCR1 expressing cells such as CCR1 expressing monocytes, compared to healthy controls. It is also shown herein that the CCR1 expressing cells can be removed using a suitable binding reagent, in particular RANTES (in biotinylated form) immobilized on a suitable matrix. Similarly, it is shown herein that the monocytes also express CCR2. The CCR2 expressing monocytes can be depleted in sarcoidosis patients using a suitable binding reagent, in particular MCP-1, in biotinylated form, immobilized on a suitable matrix. It is also shown herein that subjects suffering from respiratory conditions such as sarcoidosis exhibit increased frequency of CCR7 expressing cells such as CCR7 expressing lymphocytes, and also central memory T cells, compared to healthy controls. It is also shown herein that the CCR7 expressing cells can be removed using a suitable binding reagent, in particular MIP3b (in biotinylated form) immobilized on a suitable matrix.

Thus, in certain embodiments the invention serves to reduce the recruitment of inflammatory leukocytes, which express characteristic chemokine receptors, and possibly express characteristic chemokine receptors at increased levels, to sites of inflammation linked to respiratory conditions, in particular sarcoidosis and Chronic Obstructive Pulmonary Disease (COPD). This is achieved using specific binding reagents to capture specific chemokine receptor-expressing inflammatory leukocytes from the patient. Accordingly, in certain embodiments the invention provides in a first aspect a method for treating respiratory conditions, in particular sarcoidosis and Chronic Obstructive Pulmonary Disease (COPD) comprising applying peripheral blood from a patient to an apheresis column loaded with a solid support comprising one or more binding reagents capable of specifically binding to one or more chemokine receptors, in particular the chemokine receptors CCR2, CCR1, CCR3, CCR5, CXCR1, CXCR2 and/or CCR7, immobilized directly or indirectly on the support thus removing one or more chemokine receptor, in particular one or more of CCR2, CCR1, CCR3, CCR5, CXCR1, CXCR2 and/or CCR7, expressing cells from the peripheral blood of the patient. The peripheral blood from which the chemokine receptor expressing cells have been removed may then be returned to the patient in order to complete the treatment. The invention may thus rely on a continuous extracorporeal circuit in some embodiments. Alternatively, in certain embodiments the invention may comprise steps of obtaining peripheral blood from the patient, applying the peripheral blood to the column and subsequently returning the peripheral blood from which the chemokine receptor expressing cells have been removed to the patient.

As shown herein, suitable binding reagents can be immobilized onto a solid support, either directly or indirectly, to generate an apheresis column suitable for capturing relevant chemokine receptor-expressing cells. Where increased levels of chemokine receptor expression are observed, such cells may be preferably removed from the peripheral blood using the columns of the various embodiments of the invention. Thus, the methods of the various embodiments of the invention may preferably target one or more of CCR2hi, CCR1hi, CCR3hi, CCR5hi, CXCR1hi, CXCR2hi and/or CCR7hi cells as defined herein for removal from the peripheral blood. "High" expression may be determined according to standard flow cytometry techniques. The level is measured relative to levels of expression of the chemokine receptor in cells taken from a healthy subject. The attached FIG. 160 provides an example of a gating strategy.

Herein, reference to CCR2, CCR1, CCR3, CCR5, CXCR1, CXCR2 and/or CCR7 is intended to encompass selection of any one or more, up to all, of the chemokine receptors listed. In addition, the combination of CCR2, CCR1, CCR3, CCR5, CXCR1 and/or CXCR2 is explicitly contemplated as a separate grouping, to include any one or more of CCR2, CCR1, CCR3, CCR5, CXCR1 and CXCR2.

In other embodiments the invention further provides a binding reagent capable of specifically binding to one or more chemokine receptors, in particular to a chemokine receptor/the chemokine receptor CCR2, CCR1, CCR3, CCR5, CXCR1, CXCR2 and/or CCR7, for use in the treatment of respiratory conditions, in particular sarcoidosis and Chronic Obstructive Pulmonary Disease (COPD), wherein the one or more binding reagents is immobilized, directly or indirectly, on a solid support contained within an apheresis column, to which is applied peripheral blood from a patient thus removing one or more chemokine receptor/ CCR2, CCR1, CCR3, CCR5, CXCR1, CXCR2 and/or CCR7 expressing cells from the peripheral blood of the patient. In certain embodiments the invention also provides for use of one or more binding reagents capable of specifically binding to a chemokine receptor/the chemokine receptor CCR2, CCR1, CCR3, CCR5, CXCR1, CXCR2 and/or CCR7 for use in the manufacture of an apheresis column for treatment of respiratory conditions, in particular sarcoidosis and Chronic Obstructive Pulmonary Disease (COPD), wherein the one or more binding reagents is immobilized on a solid support contained within the apheresis column, to which is applied peripheral blood from a patient thus removing one or more of chemokine receptor/CCR2, CCR1, CCR3, CCR5, CXCR1, CXCR2 and/or CCR7 expressing cells from the peripheral blood of the patient.

All embodiments described in respect of the methods of treatment of the various embodiments of the invention apply to these aspects mutatis mutandis and are not repeated for reasons of conciseness. Thus, the following discussion made with reference to the various embodiments of the methods of treatment is also applicable to the medical use aspects of the invention.

In certain embodiments the invention aims to treat a range of respiratory conditions, in particular sarcoidosis and Chronic Obstructive Pulmonary Disease (COPD). By treatment is meant a reduction in the specific chemokine receptor expressing cells in the peripheral blood of the patient. The reduction may comprise a reduction in cells that express chemokine receptors, in particular one or more of CCR2, CCR1, CCR3, CCR5, CXCR1, CXCR2 and/or CCR7, at increased levels in diseased patients. The patient is typically a human patient but the term patient may include both human and non-human animal subjects in some embodiments. In the context of the various embodiments of the present invention, this typically involves a reduction in one or more of CCR2, CCR1, CCR3, CCR5, CXCR1, CXCR2 and/or CCR7 expressing cells, such as one or more of CCR2hi, CCR1hi, CCR3hi, CCR5hi, CXCR1hi, CXCR2hi and/or CCR7hi expressing cells, in the peripheral blood of the patient. The CCR2, CCR1, CCR3, CCR5, CXCR1, CXCR2 and/or CCR7 expressing cells comprise, consist essentially of or consist of monocytes, macrophages, lymphocytes, in particular T-lymphocytes, and/or eosinophils in certain embodiments. In specific embodiments, the cells removed in order to treat respiratory conditions such as sarcoidosis comprise monocytes, in particular CCR1 and/or CCR2 expressing monocytes. In other embodiments cells removed in order to treat respiratory conditions such as sarcoidosis comprise lymphocytes, specifically T lymphocytes such as central memory T cells, in particular CCR7 expressing T cells.

Monocytes are produced by the bone marrow from haematopoietic stem cell precursors called monoblasts. Monocytes may differentiate into macrophages or dendritic cells. Monocytes and their macrophage and dendritic cell progeny serve a number of functions in the immune system including phagocytosis, antigen presentation and cytokine production. Monocytes may be characterized with reference to expression of the cell surface marker CD14, optionally together with CD16. Classical monocytes may be characterized by high level expression of the CD14 cell surface receptor (CD14++CD16− monocyte). Non-classical monocytes may be characterized by low level expression of CD14 and with additional co-expression of the CD16 receptor (CD14+CD16++ monocyte). Intermediate monocytes may be characterized by high level expression of CD14 and low level expression of CD16 (CD14++CD16+ monocytes). Macrophages are derived from monocytes and are responsible for protecting tissues from foreign substances. They are cells that possess a large smooth nucleus, a large area of cytoplasm and internal vesicles for processing foreign material. The term "macrophage" may refer to a monocyte-derived cell expressing one or more of the following cell surface markers CD14, CD11b, Lysozyme M, MAC-1/MAC-3 and CD68. The term macrophage includes both activated and un-activated macrophages. Activated macrophages may be characterized by expression of one or more of CD69, ENG, FCER2 and IL2RA, HLA-DR, CD86. Un-activated macrophages have not yet received activating signals through for example TLR receptors and therefore they express less activation markers on the cell surface which correlates with lesser maturation. M1 macrophages may be characterized by expression of one or more of CD16+CD32+CD64+ and secrete mainly IL-23 and IL-1, TNF, IL-6 and high levels of IL-12 and in addition effector molecules such as iNOS and ROI. M1 macrophages have cytotoxic features as opposed to M2 macrophages. M2 macrophages may be characterized by expression of one or more of SRA/B+CD163+MR+CD14+ and express TGFβ, IL-10 and IL-1Ra. Tumour associated macrophages (TAMs) share many characteristics with the M2 macrophages and are considered as M2 polarised macrophages. The M1/M2 paradigm can also be found in monocyte subsets where CD14+CD16−CXC3R1low monocytes are considered the "inflammatory" subset and the CD14lowCD16+CXC3R1high are "resident" monocytes.

The three major types of lymphocyte are T cells, B cells and natural killer (NK) cells. The term "T-lymphocyte" includes CD4+ T cells such as T helper cells (Th1 cells and Th2 cells), and CD8+ T cells such as cytotoxic T cells. Th1 cells may be characterized by expression of CCR5 and/or by production of IFN-γ. Th2 cells may be characterized by expression of CCR3 and/or by production of IL-4.

The claimed methods may, in particular, target eosinophils. Eosinophilia is an important component of certain respiratory conditions and may be defined as the presence of more than 500 eosinophils/microliter of blood. Thus, reducing numbers of circulating eosinophils represents an important therapeutic approach. Eosinophils, or eosinophil granulocytes, are white blood cells and represent an important immune system component. Along with mast cells, they also control mechanisms associated with allergy and asthma. They are granulocytes that develop during haematopoiesis in the bone marrow before migrating into blood.

The name "eosinophil" derives from the eosinophilic "acid-loving" properties of the cell. Normally transparent, it is this affinity that causes them to appear brick-red after staining with eosin, a red dye, using the Romanowsky method. The staining is concentrated in small granules within the cellular cytoplasm, which contain many chemical mediators, such as histamines and proteins such as eosinophil peroxidase, ribonuclease (RNase), deoxyribonucleases, lipase, plasminogen, and major basic protein. These mediators are released by a process called degranulation following activation of the eosinophil, and are toxic to both parasite and host tissues.

Eosinophils develop and mature in bone marrow. They differentiate from myeloid precursor cells in response to the cytokines interleukin 3 (IL-3), interleukin 5 (IL-5), and granulocyte macrophage colony-stimulating factor (GM-CSF). Eosinophils produce and store many secondary granule proteins prior to their exit from the bone marrow. After maturation, eosinophils circulate in blood and migrate to inflammatory sites in tissues in response to chemokines such as CCL11 (eotaxin-1), CCL24 (eotaxin-2), CCL5 (RANTES) and MCP1/4. Eosinophils may be activated by Type 2 cytokines released from a specific subset of helper T cells (Th2); IL-5, GM-CSF, and IL-3 are important for eosinophil activation as well as maturation. CD44 and CD69 have been shown to represent different types of cell-surface activation markers for human eosinophils. CD69 is absent from "fresh" eosinophils but expressed following activation (using cytokines). CD44 on the other hand is constitutively expressed but expression is significantly up-regulated in response to activation (Matsumoto et al., Am. J. Respir. Cell Mol. Biol., Volume 18, Number 6, June, 1998 860-866). Cell specific markers for eosinophils include CD9 and CDw125.

CCR2, CCR1, CCR3, CCR5, CXCR1, CXCR2 and/or CCR7 expressed on these aforementioned cells bind to chemokines such as CCL2 (binds CCR2), CCL3, CCL5, CCL9 (binds CCR1), CCL11 (binds CCR3), CCL12 (binds CCR2), CCL-14 (binds CCR1), CCL16 (binds CCR1), CCL28 (binds CCR3), CCL24 (binds CCR3), CCL26 (binds CCR3) and/or CXCL8 (binds CXCR1 and CXCR2). Chemokines MIP1g (CCL9), MRP-2 (CCL10), MIp-Id (CCL15) and CCL23 appear to bind CCR1 only.

Chemokines Eotaxin (CCL11) and CCL24 (Eotaxin-2) only bind CCR3.

Chemokine MIP1b (CCL4) only binds CCR5.

CXCR1 binds CXCL6, CXCL7, CXCL8.

CXCR2 binds CXCL1, 2, 3, 5, 6, 7, 8.

CCR1 is the gene symbol approved by the HUGO Gene Nomenclature Committee for chemokine (C—C motif) receptor 1. The HGNC ID for this gene is 1602. The gene is located at chromosome position 3p21. The previous symbol and name CMKBR1, SCYAR1. Synonyms for this gene include CD191, CKR-1, MIP1αR. The Entrez Gene reference sequence for CCR1 is 1230 as available on 13 Jun. 2011, which is incorporated herein by reference in its entirety.

CCR2 is the gene symbol approved by the HUGO Gene Nomenclature Committee for chemokine (C—C motif) receptor 2. The HGNC ID for this gene is 1603. The gene is located at chromosome position 3p21. The previous symbol and name for the gene is CMKBR2. Synonyms for this gene include CC-CKR-2, CD192, CKR2, FLJ78302, MCP-1-R. The NCBI Reference Sequence is NM_001123041.2 as available on 13 Jun. 2011, which is incorporated herein by reference in its entirety.

CCR3 is the gene symbol approved by the HUGO Gene Nomenclature Committee for chemokine (C—C motif) receptor 3. The HGNC ID for this gene is 1604. The gene is located at chromosome position 3p21.3. The previous symbol and name for the gene is CMKBR3. Synonyms for this gene include CC-CKR-3, CD193 and CKR3. The Genbank reference sequence for CCR3 is AF247361.1 as available on 13 Jun. 2011, which is incorporated herein by reference in its entirety.

CCR5 is the gene symbol approved by the HUGO Gene Nomenclature Committee for chemokine (C—C motif) receptor 5. The HGNC ID for this gene is 1605. The gene is located at chromosome position 3p21. The previous symbol and name for the gene is CMKBR5. Synonyms for this gene include CC-CKR-5, CD195 CKR-5, IDDM22 and CKR5. The Entrez Gene reference sequence for CCR5 is 1234 as available on 13 Jun. 2011, which is incorporated herein by reference in its entirety.

CXCR1 is the gene symbol approved by the HUGO Gene Nomenclature Committee for chemokine (C—X—C motif) receptor 1. The HGNC ID for this gene is 6026. The gene is located at chromosome position 2q35. The previous symbol and name for the gene is CMKAR1, IL8RA, "interleukin 8 receptor, alpha". Synonyms for this gene include CD181, CDw128a, CKR-1. The Genbank reference sequence for CXCR1 is U111870.1 as available on 13 Jun. 2011, which is incorporated herein by reference in its entirety.

CXCR2 is the gene symbol approved by the HUGO Gene Nomenclature Committee for chemokine (C—X—C motif) receptor 2. The HGNC ID for this gene is 6027. The gene is located at chromosome position 2q35. The previous symbol and name for the gene is IL8RB, "interleukin 8 receptor, beta". Synonyms for this gene include CD182, CMKAR2. The Genbank reference sequence for CXCR2 is U111869.1 as available on 13 Jun. 2011, which is incorporated herein by reference in its entirety.

CCR7 is the gene symbol approved by the HUGO Gene Nomenclature Committee for chemokine (C—C motif) receptor 7. The HGNC ID for this gene is 1608. The gene is located at chromosome position 17q112-q21.2. The previous symbol and name for the gene is CMKBR7, EBI1. Synonyms for this gene include BLR2, CD197 and CDw197. The RefSeq reference sequence for CCR7 is NM_001838.3 as available on 13 Jun. 2011, which is incorporated herein by reference in its entirety.

The various embodiments of the methods of the invention may involve specific binding interactions with any one or more of these further cell-surface markers in addition to the removal based upon binding to CCR2, CCR1, CCR3, CCR5, CXCR1, CXCR2 and/or CCR7. Suitable binding reagents can be prepared to specifically bind to these cell-surface markers. The discussion of CCR2, CCR1, CCR3, CCR5, CXCR1, CXCR2 and/or CCR7 specific binding reagents thus applies mutatis mutandis.

Treatment according to the various embodiments of the invention may result in alleviation or amelioration of symptoms, prevention of progression, regression of the condition, or complete recovery. Measurable parameters of successful treatment include one or more, up to all, of lung function with spirometry, PEF, lung biopsy. Pulsoxymeter. paO2, paCO2. In specific embodiments, a single treatment is sufficient to cause a depletion of around 10%, 20%, 30%, 40%, 50%, 60% or 70%, or higher up to 80%, 90%, 95% or more, or any range of values between and including these amounts, of one or more of a specific chemokine receptor, in particular one or more of CCR2, CCR1, CCR3, CCR5, CXCR1, CXCR2 and/or CCR7, expressing cells from the peripheral blood of the patient. In specific embodiments, at least around 50% depletion is achieved in a single treatment. Thus, successful treatment may be defined with reference to depletion of one or more of CCR2, CCR1, CCR3, CCR5, CXCR1, CXCR2 and/or CCR7 expressing cells. Treatment may lead to depletion of between approximately 100 and 500 million CCR2, CCR1, CCR3, CCR5, CXCR1, CXCR2 and/or CCR7 expressing cells, such as monocytes, in certain embodiments and more particularly to about 100, 150, 200, 250, 300, 350, 400, 450, or 500 million CCR2, CCR1, CCR3, CCR5, CXCR1, CXCR2 and/or CCR7 expressing cells.

By binding to the column through the binding reagent-chemokine receptor interaction, chemokine receptor expressing cells are immobilized. These immobilized cells express further unoccupied chemokine receptors, which may be of the same or different type to those used for capture. These additional chemokine receptors may permit circulating chemokines which contribute to the inflammatory condition to be captured from the peripheral blood. Thus, a reduction in circulating (specific) chemokine levels may provide a measure of successful treatment.

The duration of treatment may be readily determined by one skilled in the art and will depend upon factors such as the flow rate of the peripheral blood. Duration of treatment may be tied into monitoring of the treatment itself, with the treatment considered complete once a measurable parameter of treatment has reached a defined threshold. Any suitable parameter may be employed as discussed herein. Thus, for example, treatment may be considered complete when a reduction in one or more of CCR2, CCR1, CCR3, CCR5, CXCR1, CXCR2 and/or CCR7 expressing cells, such as a 50% reduction in one or more of CCR2, CCR1, CCR3, CCR5, CXCR1, CXCR2 and/or CCR7 expressing cells, has been achieved. The apheresis system may be operated at a flow rate of around 10-80 mL/min, or more specifically between around 20-70 mL/min, or between around 30-60 mL/min. In specific embodiments, the treatment is performed for a period of around 10, 20, 30, 40, 50, 60, 70, 80, 90, 100, 110, 120 etc., or any range of values between and including these amounts, minutes. The treatment is typically not aimed to remove all of the cells expressing the chemokine receptor in the peripheral blood, as a basal level of those cells is required in healthy subjects. However, it has been found that only low blood volumes need to be applied to the columns of the various embodiments of the invention in order to achieve effective levels of depletion of the chemokine receptor-expressing cells. Thus, in certain embodiments, around 10-80% or more specifically around 20, 30, 40 or 50%, or any range of values between and including these amounts, of the patient's blood is applied to the column in a single treatment. The volume of blood circulated through the apheresis column or system may be in the region of around 1000-3000 ml, such as around 1000, 1200, 1400, 1600, 1800 or 2000 ml or any range of values between and including these amounts. The treatment may be considered complete once this volume of blood has been circulated. The patient may be administered anticoagulants prior to each treatment session. A suitable solution, such as a sterile saline solution, optionally including an anticoagulant such as Heparin, may be used for priming the apheresis (extracorporeal) system. An additional volume of anticoagulant may be added to the circuit at the start of each treatment session, for example as a bolus injection.

In certain embodiments the invention relies upon a binding reagent which is capable of specifically binding to a chemokine receptor. This specific binding reaction permits cells expressing the chemokine receptor to be removed from the peripheral blood of the patient when the blood is passed over the solid support upon or within which the binding reagent is immobilized. Specific chemokine receptors of interest include CCR2, CCR1, CCR3, CCR5, CXCR1, CXCR2 and/or CCR7. The binding reagent can be any binding reagent capable of specifically binding to the receptor in question. By "specific binding" is meant that the binding reagent displays sufficient specificity of binding and appropriate binding affinity/kinetics to permit removal of cells expressing one or more of CCR2, CCR1, CCR3, CCR5, CXCR1, CXCR2 and/or CCR7 from the peripheral blood. Whilst it is not precluded that the binding reagent is capable of binding to other molecules, such as other chemokine receptors, the binding reagent will preferentially bind to cells expressing one or more of CCR2, CCR1, CCR3, CCR5, CXCR1, CXCR2 and/or CCR7 and in particular to cells expressing increased levels of one or more of CCR2, CCR1, CCR3, CCR5, CXCR1, CXCR2 and/or CCR7 (as defined further herein). The binding reagent capable of specifically binding to CCR2, CCR1, CCR3, CCR5, CXCR1, CXCR2 and/or CCR7 may be either an agonist or an antagonist of CCR2, CCR1, CCR3, CCR5, CXCR1, CXCR2 and/or CCR7, respectively. As the disease condition relies upon up-regulation of expression of or signaling via CCR2, CCR1, CCR3, CCR5, CXCR1, CXCR2 and/or CCR7, in certain embodiments the binding reagent capable of specifically binding to CCR2, CCR1, CCR3, CCR5, CXCR1, CXCR2 and/or CCR7 is an antagonist of CCR2, CCR1, CCR3, CCR5, CXCR1, CXCR2 and/or CCR7, respectively. Chemokines are typically, although not necessarily exclusively (particularly in the case of truncated or modified forms) agonists of their cognate receptor and serve to activate the cells expressing the relevant receptor, as would be appreciated by one skilled in the art. Antibodies against the relevant chemokine receptor are generally considered to be antagonists, as would be appreciated by one skilled in the art. Specific examples of binding reagents include proteins or polypeptides, such as antibodies and receptor ligands, in particular chemokines. The binding reagent may be a nucleic acid molecule in certain embodiments. In some embodiments, the nucleic acid is an aptamer. Nucleic acid aptamers are polynucleotides of approximately 15-40 nucleotides long. Nucleic acid aptamers can be made using the SELEX process (systemic evolution of ligands by exponential enrichment) or any other process known to those of skill in the art.

In other embodiments, the binding reagent may be a peptide, and in certain instances, a peptide aptamer. Peptide aptamers are artificial recognition molecules that consist of a variable peptide sequence inserted into a constant scaffold protein (Baines I C, Colas P. Peptide aptamers as guides for small molecule drug discovery. Drug Discov Today. 2006; 11:334-341, incorporated herein by reference). A number of methodologies, such as phage display, ribosome display and yeast two-hybrid screening systems are available for screening a library of potential peptide-based binding agents. Similarly protein scaffolds based on domains such as fibronectins, ankyrin repeats, protein A, SH3 domains, lipocalins and ubiquitin can be used as the binding agent. Again a number of technologies such as phage display and ribosome display are available for screening a library of protein—based binding agents. Similarly, libraries of candidate chemical compounds can be screened for specific binding to the relevant chemokine receptor using suitable screening techniques known in the art, which may be high throughput screens in certain embodiments. The candidate binding agent may be immobilized on a solid support and the ability of the agent to specifically retain cells expressing the chemokine receptor of interest or labelled chemokine receptors determined. A range of cell types may be applied to the solid supports to confirm specificity of binding, or alternatively a mixed sample (such as peripheral blood) may be applied to the solid support. Retention of the cell type of interest (expressing the appropriate chemokine receptor) can be confirmed to identify suitable binding agents. A range of small-molecule antagonists of CCR-2 are discussed by Xia M and Sui Z in Expert Opin Ther Pat. 2009 March; 19 (3):295-303—Recent developments in CCR2 antagonists, and incorporated herein by reference.

In the context of the various embodiments of the present invention the term "chemokine" also comprises biotinylated or otherwise labelled chemokines. The term "chemokine" also comprises modified and truncated versions of the chemokine and chemokine fragments with the proviso that the modified or truncated form retains its ability to bind to its cognate receptor (and thus remains functional in the context of the various embodiments of the invention). The chemokine does not necessarily need to retain biological activity as it is specific binding affinity for CCR2, CCR1, CCR3, CCR5, CXCR1, CXCR2 and/or CCR7 that is required. In certain embodiments, the chemokine lacks biological activity, for example in terms of activation of the (CCR2, CCR1, CCR3, CCR5, CXCR1, CXCR2 and/or CCR7) receptor. Modifications may be made to improve protein synthesis, for example uniformity of product and yield. As known to those skilled in the art, exemplary modifications may comprise amino acid additions, substitutions, deletions or other modifications to one or more amino acids in the chemokine. Modifications may comprise substitution of the wild type amino acid with non-natural amino acids such as norleucine (NLeu) and derivatized amino acids such as pyroglutamic acid (pyroGlu). Such modifications may be made to minimize side-product formation during storage and use of the columns of the various embodiments of the invention. Modifications may be made to improve labelling, for example inclusion of a polyethylene glycol (PEG) spacer to facilitate biotinylation. The biotinylation and/or conjugation with fluorochromes or other labelling groups of the chemokine is performed in a manner which does not substantially affect the receptor binding capacity. Site specific biotinylation or other labelling is preferred as non-selective labelling of chemokines may compromise receptor binding activity. Biotinylation or other labelling is generally preferred at or towards the C-terminus of the protein as the inventors have found that modifications in this area are generally well tolerated (in terms of a minimal effect on receptor binding capability). Biotinylation may be carried out site-specifically at any suitable amino acid. Examples of suitable amino acids include lysine, diaminopropionic acid and ornithine. Generally, reference may be made to Natarajan S et al, Int. J. Pept. Protein Res., 1992, 40, 567-74; Baumeister B, Int. J. Peptide Res. And Therapeutics, 2005, 11, 139-141; Bioconjugate techniques 2nd edition, Greg T. Hermanson, incorporated by reference herein in its entirety.

Truncations may involve deletion of either N or C terminal amino acids as appropriate, or both. Typically, the truncated version will retain the residues required for the chemokine to fold correctly, for example to retain a chemokine fold structure, consistent with the requirement that a truncated version must retain the ability to bind to the relevant receptor (expressed by (on the surface of) a leukocyte). Chemokine molecules typically include disulphide bonds between the 1st and 3rd and 2nd and 4th cysteine residues respectively, as would be understood by one skilled in the art. Where sequences are presented herein, it is assumed that these disulphide bonds will form in the folded protein (unless otherwise stated). Truncated versions may comprise anywhere between 1 and 100 less amino acids, such as 1, 2, 3, 4, 5 etc amino acids, than the wild type amino acid sequence in certain embodiments. Of course, truncated versions may comprise further modification as detailed herein. The modified or truncated version may have 40%, 45%, 50%, 55%, 60%, 65%, 70%, 75%, 80%, 85%, 90%, 95% or more overall amino acid sequence identity with the full length wild type chemokine (where a deletion is counted as a difference in amino acid sequence) in certain embodiments. Over the common sequence between the molecules (i.e the amino acids that have not been deleted), there may be 80%, 85%, 90%, 91%, 92%, 93%, 94%, 95%, 96%, 97%, 98% or 99% amino acid sequence identity in certain embodiments. Sequence identity may be determined using known algorithms, such as BLAST or GAP analysis (GCG Program) (applying default settings), which are freely available. Chemokines may lack the N-terminal signal peptide which is cleaved off during synthesis in vivo.

Specific chemokines useful in the various embodiments of the present invention for binding to CCR2 include CCL2 (MCP-1), MCP-2, MCP-3, MCP-4 (CCL12) and MCP-5. Both MCP-1 and MCP-5 bind solely to the chemokine receptor CCR2 and so these chemokines may be preferred in some embodiments. Each chemokine is able to bind to a chemokine receptor implicated in respiratory conditions, in particular sarcoidosis and Chronic Obstructive Pulmonary Disease (COPD). More specifically, each of MCP-1, MCP-2, MCP-3, MCP-4 and MCP-5 are useful for removing CCR2 expressing cells from the blood of a patient. Specific chemokines useful in the various embodiments of the present invention for binding to CCR1, CCR3 and/or CCR5 include CCL5 (RANTES). RANTES is able to bind to chemokine receptors implicated in respiratory conditions, in particular sarcoidosis and Chronic Obstructive Pulmonary Disease (COPD). More specifically, RANTES is useful for removing CCR1, CCR3 and/or CCR5 expressing cells from the blood of a patient.

Specific chemokines useful for binding to CCR1 include CCL9, MRP-2 (CCL10), CCL14, CCL15, CCL16 and CCL23 Specific chemokines useful for binding to CCR3 include CCL11 (Eotaxin), CCL28, CCL24 (Eotaxin 2) and CCL26. Specific chemokines useful for binding to CCR5 include CCL3, CCL4, CCL5, CCL8 with CCL4 binding only to CCR5. Specific chemokines useful in the various embodiments of the present invention for binding to CXCR1 and/or CXCR2 include CXCL8 (IL-8). IL-8 is able to bind to chemokine receptors implicated in respiratory conditions, in particular sarcoidosis and Chronic Obstructive Pulmonary Disease (COPD). Specific chemokines useful in the various embodiments of the present invention for binding to CXCR1 include CXCL6, CXCL7, CXCL8. Specific chemokines useful in the various embodiments of the present invention for binding to CXCR2 include CXCL1, 2, 3, 5, 6, 7, 8. CCL19 is useful for the removal of CCR7 expressing cells.

The chemokines described in greater detail herein (with reference to the relevant figures and amino acid sequences, as set forth in the SEQ ID NOs) may each be applied according to the present invention.

CCL2 is the gene symbol approved by the HUGO Gene Nomenclature Committee for chemokine (C—C motif) ligand 2, also known as MCP-1. The HGNC ID for this gene is 10618. The gene is located at chromosome position 17q11.2-q21.1. The previous symbol and name for the gene is SCYA2 "small inducible cytokine A2 (monocyte chemotatic protein 1, homologus to mouse Sig-je)". Synonyms for this gene include GDCF-2, HC11, MCP1, MGC9434, SMC-CF, "monocyte chemoattractant protein-1", "monocyte chemotactic and activating factor", "monocyte chemotactic protein 1, homologous to mouse Sig-je", "monocyte secretory protein JE", "small inducible cytokine subfamily A (Cys-Cys), member 2". The Genbank reference sequence for CCL2 is BC009716.1 as available on 13 Jun. 2011, which is incorporated herein by reference in its entirety.

CCL4 is the gene symbol approved by the HUGO Gene Nomenclature Committee for chemokine (C—C motif) ligand 4. The HGNC ID for this gene is 10630. The gene is located at chromosome position 17q12-q23. The previous symbol and name for the gene is LAG1, SCYA4, "small inducible cytokine A4 (homologous to mouse Mip-1b)". Synonyms for this gene include Act-2, AT744.1, MIP-1-beta. The Genbank reference sequence for CCL4 is M23502.1 as available on 13 Jun. 2011, which is incorporated herein by reference in its entirety.

CCL8 is the gene symbol approved by the HUGO Gene Nomenclature Committee for chemokine (C—C motif) ligand 8, also known as MCP-2. The HGNC ID for this gene is 10635. The gene is located at chromosome position 17q11.2. The previous symbol and name for the gene is SCYA8, "small inducible cytokine subfamily A (Cys-Cys), member 8 (monocyte chemotactic protein 2)". Another synonym for this gene is HC14. The Genbank reference sequence for CCL8 is X99886.1 as available on 13 Jun. 2011, which is incorporated herein by reference in its entirety.

CCL7 is the gene symbol approved by the HUGO Gene Nomenclature Committee for chemokine (C—C motif) ligand 7, also known as MCP-3. The HGNC ID for this gene is 10634. The gene is located at chromosome position 17q11.2-q12. The previous symbol and name for the gene is SCYA6, SCYA7, "small inducible cytokine A7 (monocyte chemotactic protein 3)". Synonyms for this gene include FIC, MARC, MCP-3, MCP3, NC28, "monocyte chemoattractant protein 3", "monocyte chemotactic protein 3". The Genbank reference sequence for CCL7 is AF043338 as available on 13 Jun. 2011, which is incorporated herein by reference in its entirety.

CCL13 is the gene symbol approved by the HUGO Gene Nomenclature Committee for chemokine (C—C motif) ligand 13, also known as MCP-4. The HGNC ID for this gene is 10611. The gene is located at chromosome position 17q11.2. The previous symbol and name for the gene is SCYA13, "small inducible cytokine subfamily A (Cys-Cys), member 13". Synonyms for this gene include CKb10, MCP-4, MGC17134, NCC-1, SCYL1. The Genbank reference sequence for CCL13 is AJ001634 as available on 13 Jun. 2011, which is incorporated herein by reference in its entirety.

MCP-5 is a mouse chemokine in the CC chemokine family. It is also known as Chemokine (C—C motif) ligand 12 (CCL12) and, due to its similarity with the human chemokine MCP-1, sometimes it is called MCP-1-related chemokine. The gene for MCP-5 is found in a cluster of CC chemokines on mouse chromosome 11. The NCBI reference sequence for CCL12 is NC_000077.5. Previous symbol SCYA12 as available on 13 Jun. 2011, which is incorporated herein by reference in its entirety.

CCL3 is the gene symbol approved by the HUGO Gene Nomenclature Committee for chemokine (C—C motif) ligand 3, also known as MIP-1α. The HGNC ID for this gene is 10627. The gene is located at chromosome position 17q12. The previous symbol and name for the gene is SCYA3, "small inducible cytokine A3 (homologous to mouse Mip-1a)". Synonyms for this gene include G0S19-1, LD78ALPHA, MIP-1-alpha. The Genbank reference sequence for CCL3 is M23178.1 as available on 13 Jun. 2011, which is incorporated herein by reference in its entirety.

CCL5 is the gene symbol approved by the HUGO Gene Nomenclature Committee for chemokine (C—C motif) ligand 5, also known as RANTES. The HGNC ID for this gene is 10632. The gene is located at chromosome position 17q11.2-q12. The previous symbol and name for the gene is D17S136E, SCYA5, "small inducible cytokine A5 (RANTES)". Synonyms for this gene include "beta-chemokine RANTES", MGC17164, RANTES, "regulated upon activation, normally T-expressed, and presumably secreted", "SIS-delta", SISd, "small inducible cytokine subfamily A (Cys-Cys), member 5", "T-cell specific protein p288", "T-cell specific RANTES protein", TCP228. The Genbank reference sequence for CCL5 is AF043341.1 as available on 13 Jun. 2011, which is incorporated herein by reference in its entirety.

IL8 is the gene symbol approved by the HUGO Gene Nomenclature Committee for interleukin 8, also known as CXCL8. The HGNC ID for this gene is 6025. The gene is located at chromosome position 4q13-q21. Synonyms for this gene include 3-10C, AMCF-I, b-ENAP, "chemokine (C—X—C motif) ligand 8", CXCL8, GCP-1, IL-8, K60, LECT, LUCT, LYNAP, MDNCF, MONAP, NAF, NAP-1, SCYB8, TSG-1. The Genbank reference sequence for CXCL8 is Y00787.1 as available on 13 Jun. 2011, which is incorporated herein by reference in its entirety.

CCL11 is the gene symbol approved by the HUGO Gene Nomenclature Committee for chemokine (C—C motif) ligand 11, also known as eotaxin. The HGNC ID for this gene is 10610. The gene is located at chromosome position 17q21.1-q21.2. The previous symbol and name for the gene is SCYA11, "small inducible cytokine subfamily A (Cys-Cys), member 11 (eotaxin)". Synonyms for this gene include MGC22554 and "eotaxin-1". The Genbank reference sequence for CCL11 is AB063614.1 as available on 13 Jun. 2011, which is incorporated herein by reference in its entirety.

CCL15 is the gene symbol approved by the HUGO Gene Nomenclature Committee for chemokine (C—C motif) ligand 15, also known as HCC-2 and Lkn-1. The HGNC ID for this gene is 10613. The gene is located at chromosome position 17q11.2. The previous symbol and name for the gene is SCYA15, "small inducible cytokine subfamily A (Cys-Cys), member 15". Synonyms for this gene include "CC chemokine 3", "chemokine CC-2", HCC-2, HMRP-2B, "leukotactin 1", Lkn-1, "macrophage inflammatory protein 5", "MIP-1 delta", MIP-1d, MIP-5, NCC-3, SCYL3. The Genbank reference sequence for CCL15 is AF031587.1 as available on 13 Jun. 2011, which is incorporated herein by reference in its entirety.

CCL14 is the gene symbol approved by the HUGO Gene Nomenclature Committee for chemokine (C—C motif) ligand 14. The HGNC ID for this gene is 10612. The gene is located at chromosome position 17q11.2. The previous symbol and name for the gene is SCYA14, "small inducible cytokine subfamily A (Cys-Cys), member 14". Synonyms for this gene include CKb1, HCC-1, HCC-3, MCIF, NCC-2, SCYL2. The Genbank reference sequence for CCL14 is Z49270.1 as available on 13 Jun. 2011, which is incorporated herein by reference in its entirety.

CCL16 is the gene symbol approved by the HUGO Gene Nomenclature Committee for chemokine (C—C motif) ligand 16. The HGNC ID for this gene is 10614. The gene is located at chromosome position 17q11.2. The previous symbol and name for the gene is SCYA16, "small inducible cytokine subfamily A (Cys-Cys), member 16". Synonyms for this gene include CKb12, HCC-4, LCC-1, LEC, LMC, Mtn-1, NCC-4, SCYL4. The Genbank reference sequence for CCL16 is AB007454.1 as available on 13 Jun. 2011, which is incorporated herein by reference in its entirety.

CCL18 is the gene symbol approved by the HUGO Gene Nomenclature Committee for chemokine (C—C motif) ligand 18 (pulmonary and activation-regulated). The HGNC ID for this gene is 10616. The gene is located at chromosome position 17q11.2. The previous symbol and name for the gene is SCYA18, "small inducible cytokine subfamily A (Cys-Cys), member 18, pulmonary and activation-regulated". Synonyms for this gene include AMAC-1, CKb7, DC-CK1, DCCK1, MIP-4, PARC. The Genbank reference sequence for CCL18 is Y13710.1 as available on 13 Jun. 2011, which is incorporated herein by reference in its entirety.

CCL23 is the gene symbol approved by the HUGO Gene Nomenclature Committee for chemokine (C—C motif) ligand 23. The HGNC ID for this gene is 10622. The gene is located at chromosome position 17q11.2. The previous symbol and name for the gene is SCYA23, "small inducible cytokine subfamily A (Cys-Cys), member 23". Synonyms for this gene include Ckb-8, CKb8, MIP-3, MPIF-1. The Genbank reference sequence for CCL23 is U58913.1 as available on 13 Jun. 2011, which is incorporated herein by reference in its entirety.

CCL24 is the gene symbol approved by the HUGO Gene Nomenclature Committee for chemokine (C—C motif) ligand 24, also known as eotaxin-2 and MPIF-2. The HGNC ID for this gene is 10623. The gene is located at chromosome position 7q11.23. The previous symbol and name for the gene is SCYA24, "small inducible cytokine subfamily A (Cys-Cys), member 24". Synonyms for this gene include "CK-beta-6", Ckb-6, MPIF-2, MPIF2, "eotaxin-2", "myeloid progenitor inhibitory factor 2". The Genbank reference sequence for CCL24 is U85768.1 as available on 13 Jun. 2011, which is incorporated herein by reference in its entirety.

CCL26 is the gene symbol approved by the HUGO Gene Nomenclature Committee for chemokine (C—C motif) ligand 26, also known as eotaxin-3. The HGNC ID for this gene is 10625. The gene is located at chromosome position 7q11.22. The previous symbol and name for the gene is SCYA26, "small inducible cytokine subfamily A (Cys-Cys), member 26". Synonyms for this gene include "CC chemokine IMAC", IMAC, MIP-4-a, MIP-4-alpha, TSC-1, "chemokine N1", "eotaxin-3", "macrophage inflammatory protein 4-alpha", "small inducible cytokine A26", "thymic stroma chemokine-1". The Genbank reference sequence for CCL26 is AF124601.1 as available on 13 Jun. 2011, which is incorporated herein by reference in its entirety.

CXCL1 is the gene symbol approved by the HUGO Gene Nomenclature Committee for chemokine (C—X—C motif) ligand 1 (melanoma growth stimulating activity, alpha). The HGNC ID for this gene is 4602. The gene is located at chromosome position 4q13.3. The previous symbol and name for the gene is "fibroblast secretory protein", FSP, GRO1, "GRO1 oncogene (melanoma growth stimulating activity, alpha)", MGSA. Synonyms for this gene include GROa, MGSA-a, NAP-3, SCYB1. The Genbank reference sequence for CXCL1 is J03561.1 as available on 13 Jun. 2011, which is incorporated herein by reference in its entirety.

CXCL2 is the gene symbol approved by the HUGO Gene Nomenclature Committee for chemokine (C—X—C motif) ligand 2. The HGNC ID for this gene is 4603. The gene is located at chromosome position 4q113.3. The previous symbol and name for the gene is GRO2, "GRO2 oncogene". Synonyms for this gene include CINC-2a, GROb, MGSA-b, MIP-2a, SCYB2. The Genbank reference sequence for CXCL2 is M36820.1 as available on 13 Jun. 2011, which is incorporated herein by reference in its entirety.

CXCL3 is the gene symbol approved by the HUGO Gene Nomenclature Committee for chemokine (C—X—C motif) ligand 3. The HGNC ID for this gene is 4604. The gene is located at chromosome position 4q21. The previous symbol and name for the gene is GRO3, "GRO3 oncogene". Synonyms for this gene include CINC-2b, GROg, MIP-2b, SCYB3. The Genbank reference sequence for CXCL3 is M36821.1 as available on 13 Jun. 2011, which is incorporated herein by reference in its entirety.

CXCL5 is the gene symbol approved by the HUGO Gene Nomenclature Committee for chemokine (C—X—C motif) ligand 5. The HGNC ID for this gene is 10642. The gene is located at chromosome position 4q13.3. The previous symbol and name for the gene is SCYB5, "small inducible cytokine subfamily B (Cys-X-Cys), member 5 (epithelial-derived neutrophil-activating peptide 78)". A synonym for this gene is ENA-78. The Genbank reference sequence for CXCL5 is X78686.1 as available on 13 Jun. 2011, which is incorporated herein by reference in its entirety.

CXCL6 is the gene symbol approved by the HUGO Gene Nomenclature Committee for chemokine (C—X—C motif) ligand 6. The HGNC ID for this gene is 10643. The gene is located at chromosome position 4q113.3. The previous symbol and name for the gene is chemokine (C—X—C motif) ligand 6 (granulocyte chemotactic protein 2). Synonyms for this gene include CKA-3, GCP-2. The Genbank reference sequence for CXCL6 is U83303.1 as available on 13 Jun. 2011, which is incorporated herein by reference in its entirety.

PPBP is the gene symbol approved by the HUGO Gene Nomenclature Committee for pro-platelet basic protein (chemokine (C—X—C motif) ligand 7), also known as CXCL7. The HGNC ID for this gene is 9240. The gene is located at chromosome position 412-q13. The previous symbol and name for the gene is THBGB1. Synonyms for this gene include b-TG1, Beta-TG, "beta-thromboglobulin", "connective tissue-activating peptide III", CTAP3, CTAPIII, CXCL7, LA-PF4, LDGF, MDGF, NAP-2, NAP-2-L1, "neutrophil-activating peptide-2", PBP, "platelet basic protein", SCYB7, TGB, TGB1. The Genbank reference sequence for PPBP is M54995.1 as available on 13 Jun. 2011, which is incorporated herein by reference in its entirety.

CXCL11 is the gene symbol approved by the HUGO Gene Nomenclature Committee for chemokine (C—X—C motif) ligand 11. The HGNC ID for this gene is 10638. The gene is located at chromosome position 4q21. The previous symbol and name for the gene is SCYB9B, SCYB11, "small inducible cytokine subfamily B (Cys-X-Cys), member 11". Synonyms for this gene include b-R1, H174, I-TAC, IP-9. The Genbank reference sequence for CXCL11 is U66096.1 as available on 13 Jun. 2011, which is incorporated herein by reference in its entirety.

CCL19 is the gene symbol approved by the HUGO Gene Nomenclature Committee for chemokine (C—C motif) ligand 19, also known as MIP-3b. The HGNC ID for this gene is 10617. The gene is located at chromosome position 9p13. The previous symbol and name for the gene is SCYA19, "small inducible cytokine subfamily A (Cys-Cys), member 19". Synonyms for this gene include "beta chemokine exodus-3", "CC chemokine ligand 19", "CK beta-11", CKb11, "EBI1-ligand chemokine", ELC, exodus-3, "macrophage inflammatory protein 3-beta", MIP-3b. The Genbank reference sequence for CCL19 is AB000887.1 as available on 13 Jun. 2011, which is incorporated herein by reference in its entirety.

Examples of suitable modified chemokines of the various embodiments of the invention containing modifications and/or truncations and specifically adapted for use in the invention are described in detail herein. MCP-1 has been produced with residue 75, which may be a lysine, as the site of biotinylation on the chemokine (numbering based upon the mature protein having the amino acid sequence of SEQ ID NO: 211). Biotinylation permits immobilization of MCP-1 on a solid support (via a biotin-avidin interaction). The basic amino acid sequence of MCP-1, including a 23 amino acid leader sequence is set forth as SEQ ID NO: 210. The amino acid sequence of the mature protein is set forth as SEQ ID NO: 211. The inventors have determined that chemokines may display improved binding properties where the chemokine is biotinylated via a spacer group. The spacer may prevent the biotin group from impacting on the binding affinity of the chemokine. Any suitable spacer group may be employed. Further modifications may provide the molecule with advantageous properties. The invention also relates to derivatives of truncated MCP-1 chemokines. The amino acid sequence of the truncated version is set forth as SED ID NO: 212.

Accordingly, in certain embodiments the invention also provides a modified MCP-1 chemokine comprising, consisting essentially of or consisting of the amino acid sequence set forth as SEQ ID NO: 210, SEQ ID NO: 211 or SEQ ID NO: 212 in which one or more of the following modifications have been made:

a) the glutamine residue 1 of SEQ ID NO: 211 has been replaced with pyroglutamine b) the C terminus is produced as an amide derivative (this may be achieved by synthesis on an amide linker)

c) the (C terminal region) residue at position 98 of SEQ ID NO: 210 or position 75 of SEQ ID NO: 211 or position 67 of SEQ ID NO: 212, which may be a lysine or ornithine residue or other residue suitable for labelling, is biotinylated, optionally via a spacer group, in order to permit immobilization of the chemokine on a solid support; and/or d) the methionine residue at position 87 of SEQ ID NO: 210 or position 64 of SEQ ID NO: 211 or position 56 of SEQ ID NO: 212 has been replaced with norleucine.

The (C terminal region) amino acid, which may be a lysine residue or a functional equivalent, at position 98 of SEQ ID NO: 210 or position 75 of SEQ ID NO: 211 or position 67 of SEQ ID NO: 212 may be biotinylated via a suitable spacer group, such as a polyethylene glycol (PEG) spacer group, in order to permit immobilization of the chemokine on a solid support. In specific embodiments, the PEG spacer is 3,6-dioxo aminooctanoic acid. The sequence and biotinylation of the modified MCP-1 chemokines of the invention are shown in FIGS. 153 to 155 respectively. The modified MCP-1 chemokines may be agonists or antagonists of CCR2 activity. They can be tested for activity in a suitable assay, such as cell-based assays. In particular, agonist and antagonist properties may be determined in functional cell-based assay on human CCR2 receptor.

MCP-5 only binds CCR2 and should be selective in its removal of CCR2 expressing cells. The full length amino acid sequence, including the signal peptide, is set forth as SEQ ID NO: 213. The amino acid sequence of N-terminal processed MCP-5 chemokine is 82 amino acids long and is set forth as SEQ ID NO: 214. An amino acid sequence alignment suggests that MCP-5 has a C-terminal extension when compared to the amino acid sequence of MCP-1. The results of this alignment are shown in FIG. 156. C-terminal truncated versions of MCP-5 can thus be synthesised. This truncated version will comprise, consist essentially of or consist of MCP-5 residues 1-76, set forth as SEQ ID NO: 215.

Accordingly, in certain embodiments the invention also provides a modified MCP-5 chemokine comprising the amino acid sequence set forth as SEQ ID NO: 213, SEQ ID NO: 214 or SEQ ID NO: 215 in which the isoleucine residue at position 97 of SEQ ID NO: 213 or at position 75 of SEQ ID NO: 214 or SEQ ID NO: 215 has been replaced with lysine. In certain embodiments, the modified MCP-5 chemokine comprises, consists essentially of or consists of the amino acid sequence of SEQ ID NO: 216. The modified MCP-5 chemokine may be biotinylated at the lysine (or a functional equivalent) residue at position 97 of SEQ ID NO: 213 or at position 75 of SEQ ID NO: 214 or SEQ ID NO: 215. Biotinylation may be via a suitable spacer group. Specific examples of the spacer group include a PEG spacer, optionally 3,6-dioxo aminooctanoic acid. In some embodiments, the C terminus is produced as an amide derivative. This may be achieved by synthesis on an amide linker. In certain embodiments, the modified MCP-5 chemokine comprises, consists essentially of or consists of the sequence and biotinylation shown in FIG. 157. The modified MCP-5 chemokine may be an agonist or an antagonist of CCR2 activity. They can be tested for activity in a suitable assay, such as cell-based assays. In particular, agonist and antagonist properties may be determined in a functional cell-based assay on human CCR2 receptor.

Eotaxin has been produced with Lys73 as the site of biotinylation on the chemokine (numbering based upon the mature protein having the amino acid sequence of SEQ ID NO: 218). Biotinylation permits immobilization of eotaxin on a solid support (via a biotin-avidin interaction). The basic amino acid sequence of eotaxin, including a 23 amino acid leader sequence is set forth as SEQ ID NO: 217. The amino acid sequence of the mature protein is set forth as SEQ ID NO: 218. The inventors have determined that chemokines may display improved binding properties where the chemokine is biotinylated via a spacer group. The spacer may prevent the biotin group from impacting on the binding affinity of the chemokine. Any suitable spacer group may be employed. Further modifications may provide the molecule with advantageous properties.

Accordingly, in certain embodiments the invention also provides a modified eoxtaxin chemokine comprising the amino acid sequence set forth as SEQ ID NO: 217 or SEQ ID NO: 218 in which one or more of the following modifications have been made:

a) the C terminus is produced as an amide derivative c) the (C terminal region) lysine residue at position 96 of SEQ ID NO: 217 or position 73 of SEQ ID NO: 218 is biotinylated, optionally via a spacer group, in order to permit immobilization of the chemokine on a solid support d) the methionine residue at position 85 of SEQ ID NO: 217 or position 62 of SEQ ID NO: 218 has been replaced with norleucine e) the Lysine at position 96 of SEQ ID NO: 217 or position 73 of SEQ ID NO: 218 s replaced with another amino acid that can enable biotinylation such as ornithine The (C terminal region) lysine residue at position 96 of SEQ ID NO: 217 or position 73 of SEQ ID NO: 218 may be biotinylated via a suitable spacer group, such as a polyethylene glycol (PEG) spacer group, in order to permit immobilization of the chemokine on a solid support. In specific embodiments, the PEG spacer is 3,6-dioxo aminooctanoic acid. The sequence and biotinylation of a modified eotaxin chemokine of the invention is shown in FIG. 153. The modified eoxtaxin chemokines may be agonists or antagonists of CCR3 activity. They can be tested for activity in a suitable assay, such as cell-based assays. In particular, agonist and antagonist properties may be determined in aequorin functional cell-based assay on human CCR3 receptor.

An example of a chemokine of the various embodiments of the invention containing modifications and specifically adapted for use in the invention is described in detail herein (see Examples below). The modified CCL8 (MCP-2) corresponds to residues 1 to 76 of the full length mature protein (and lacks the N-terminal signal peptide of 23 amino acids, which is cleaved off) and thus retains the chemokine fold. The Gln at the N-terminus of the protein is subject to pyroGlu formation under physiological conditions. Thus Gln1 of the sequence may thus be substituted with pyroglutamine to prevent mixed species of N-terminal Gln and pyroGlu being generated (SEQ ID NO: 222). This improves the yield of synthesis and ensures a homogeneous chemokine preparation through column manufacture and use. FmocLys(ivDde)-OH is incorporated as residue 75 to facilitate site-specific labelling at this position of the protein (SEQ ID NO: 223). The naturally occurring lysine at position 75 is modified through biotinylation. A PEG spacer may be incorporated between the ε-amino functionality and the biotin (SEQ ID NO: 224).

Thus, in other embodiments the invention also relates to a modified chemokine comprising, consisting essentially of or consisting of the amino acid sequence of SEQ ID NO: 222:

XPDSVSIPITCCFNVINRKIPIQRLESYTRITNIQCPKEAVIFKTKRGKE

VCADPKERWVRDSMKHLDQIFQNLXP

X1=pyroGlu (but may remain as Gln in some embodiments)

X75=an amino acid residue that can be biotinylated, such as lysine, ornithine or diaminopropionic acid and optionally is biotinylated, optionally via a spacer molecule such as PEG, e.g. K(PEG-Biotin).

Or SEQ ID NO: 224
XPDSVSIPITCCFNVINRKIPIQRLESYTRITNIQCPKEAVIFKTKRGKE

VCADPKERWVRDSMKHLDQIFQNLXP

X1=pyroGlu (but may remain as Gln in some embodiments)

X75=K(PEG-Biotin).

A further example of a chemokine of the various embodiments of the invention containing modifications and specifically adapted for use in the invention is described in detail herein (see Examples below). The modified CCL5 (RANTES) corresponds to residues 1 to 68 of the full length mature protein (and lacks the N-terminal signal peptide of 23 amino acids, which is cleaved off) and thus retains the chemokine fold. The single methionine (Met67) within the sequence is mutated to lysine, to mitigate against oxidation of this residue during the chain assembly (SEQ ID NO: 225). This Met to Lys substitution provides a lysine at position 67 which can be modified through biotinylation. FmocLys (ivDde)-OH is incorporated as residue 67 to facilitate site-specific labelling at this position of the protein (SEQ ID NO: 226). The biotinylated version comprises, consists essentially of or consists of the amino acid sequence of SEQ ID NO: 227.

Thus, in other embodiments the invention also relates to a modified chemokine comprising, consisting essentially of or consisting of the amino acid sequence of SEQ ID NO: 227:

SPYSSDTTPCCFAYIARPLPRAHIKEYFYTSGKCSNPAVVFVTRKNRQVC

ANPEKKWVREYINSLEXS

X is an amino acid residue that can be biotinylated, such as lysine, ornithine or diaminopropionic acid and optionally is biotinylated, optionally via a spacer molecule such as PEG (e.g. K(Biotin))

A further example of a chemokine of the various embodiments of the invention containing modifications and specifically adapted for use in the invention is described in detail herein (see Examples below). The modified CCL2 (MCP-1) corresponds to residues 1 to 76 of the full length mature protein (and lacks the N-terminal signal peptide of 23 amino acids, which is cleaved off) and thus retains the chemokine fold (SEQ ID NO: 219). The Gln at the N-terminus of the protein (Gln1) is substituted with pyroglutamine to prevent mixed species of N-terminal Gln and pyroGlu being generated. This improves the yield of synthesis and ensures a homogeneous chemokine preparation through column manufacture and use. FmocLys(ivDde)-OH is incorporated as residue 75 to facilitate site-specific labelling at this position of the protein (SEQ ID NO: 220). A suitable spacer, such as a PEG spacer, may be incorporated between the ε-amino functionality and the biotin. The biotinylated version comprises, consists essentially of or consists of the amino acid sequence of SEQ ID NO: 221.

Thus, in other embodiments the invention also relates to a modified chemokine comprising, consisting essentially of or consisting of the amino acid sequence of:

SEQ ID NO: 219:
XPDAINAPVTCCYNFTNRKISVQRLASYRRITSSKCPKEAVIFKTIVAKE

ICADPKQKWVQDSMDHLDKQTQTPKT

X=pyroGlu or Gln

And/or SEQ ID NO: 221:
XPDAINAPVTCCYNFTNRKISVQRLASYRRITSSKCPKEAVIFKTIVAKE

ICADPKQKWVQDSMDHLDKQTQTPXT

X1=pyroGlu or Gln

X75 is an amino acid residue that can be biotinylated, such as lysine, ornithine or diaminopropionic acid and optionally is biotinylated, optionally via a spacer molecule such as PEG, optionally K(PEG-Biotin)

A further example of a chemokine of the various embodiments of the invention containing modifications and specifically adapted for use in the invention is described in detail herein (see Examples below). The modified CCL19 (MIP-3β) corresponds to residues 1 to 77 of the full length mature protein (and lacks the N-terminal signal peptide of 21 amino acids, which is cleaved off) and thus retains the chemokine fold. An additional lysine is inserted at the C-terminus, at position 78. The chemokine may thus comprise, consist essentially of or consist of the amino acid sequence of SEQ ID NO: 228. FmocLys(ivDde)-OH is incorporated as residue 78 to facilitate site-specific labelling at this position of the protein (SEQ ID NO: 229). The e-amino side chain functionality of Lys(78) is modified through biotinylation. The final protein may thus comprise, consist essentially of or consist of the amino acid sequence of SEQ ID NO: 230.

Thus, in other embodiments the invention also relates to a modified chemokine comprising, consisting essentially of or consisting of the amino acid sequence of SEQ ID NO: 228 or 230:

SEQ ID NO: 228
GTNDAEDCCLSVTQKPIPGYIVRNFHYLLIKDGCRVPAVVFTTLRGRQLC

APPDQPWVERIIQRLQRTSAKMKRRSSX

X is an amino acid residue that can be biotinylated, such as lysine, ornithine or diaminopropionic acid and optionally is biotinylated (e.g. K-biotin), optionally via a spacer molecule such as PEG, in particular K(PEG-Biotin)

SEQ ID NO: 230
GTNDAEDCCLSVTQKPIPGYIVRNFHYLLIKDGCRVPAVVFTTLRGRQLC

APPDQPWVERIIQRLQRTSAKMKRRSSX

X is K(Biotin)

A further example of a chemokine of the various embodiments of the invention containing modifications and specifically adapted for use in the invention is described in detail herein (see Examples below). The modified CXCL8 (IL-8) corresponds to residues 1 to 77 of the full length mature protein (and lacks the N-terminal signal peptide of 22 amino acids, which is cleaved off) and thus retains the chemokine fold. An amino acid residue capable of biotinylation, such as lysine or ornithine, is added as residue 78 (SEQ ID NO: 231). FmocLys(ivDde)-OH may be incorporated as residue 78 to facilitate site-specific labelling at this position of the protein (SEQ ID NO: 232). The additional amino acid, in particular lysine or ornithine, at position 78 is modified through biotinylation. A suitable spacer, such as a PEG spacer, may be incorporated between the ε-amino functionality and the biotin (SEQ ID NO: 233).

Thus, in other embodiments the invention also relates to a modified chemokine comprising, consisting essentially of or consisting of the amino acid sequence of SEQ ID NO: 231 or 233:

SEQ ID NO: 231
AVLPRSAKELRCQCIKTYSKPFHPKFIKELRVIESGPHCANTEIIVKL

SDGRELCLDPKENWVQRVVEKFLKRAENSX

X is an amino acid residue that can be biotinylated, such as lysine, ornithine or diaminopropionic acid and optionally is biotinylated, optionally via a spacer molecule such as PEG

SEQ ID NO: 233
AVLPRSAKELRCQCIKTYSKPFHPKFIKELRVIESGPHCANTEIIVKL

SDGRELCLDPKENWVQRVVEKFLKRAENSK(PEG-Biotin)

A further example of a chemokine of the various embodiments of the invention containing truncations and modifications and specifically adapted for use in the invention is described in detail herein (see Examples below). The modified CXCL8 (IL-8) corresponds to residues 6 to 77 of the full length mature protein, with the first 5 N-terminal amino acids removed, (and lacks the N-terminal signal peptide of 22 amino acids, which is cleaved off) and thus retains the chemokine fold. An amino acid residue capable of biotinylation, such as lysine or ornithine, is added as residue 78 (SEQ ID NO: 234). FmocLys(ivDde)-OH may be incorporated as residue 78 to facilitate site-specific labelling at this position of the protein (SEQ ID NO: 235). The additional amino acid, in particular lysine or ornithine, at position 78 is modified through biotinylation. A suitable spacer, such as a PEG spacer, may be incorporated between the ε-amino functionality and the biotin (SEQ ID NO: 236).

Thus, in other embodiments the invention also relates to a modified chemokine comprising, consisting essentially of or consisting of the amino acid sequence of SEQ ID NO: 234 or 236:

SEQ ID NO: 234
SAKELRCQCIKTYSKPFHPKFIKELRVIESGPHCANTEIIVKLSDGREL

CLDPKENWVQRVVEKFLKRAENSX

X is an amino acid residue that can be biotinylated, such as lysine, ornithine or diaminopropionic acid and optionally is biotinylated, optionally via a spacer molecule such as PEG

SEQ ID NO: 236
SAKELRCQCIKTYSKPFHPKFIKELRVIESGPHCANTEIIVKLSDGREL

CLDPKENWVQRVVEKFLKRAENSX

X is K(PEG-Biotin)

A further example of a chemokine of the various embodiments of the invention containing modifications and specifically adapted for use in the invention is described in detail herein (see Examples below). The modified CCL11 (Eotaxin) corresponds to residues 1 to 74 of the full length mature protein (and lacks the N-terminal signal peptide of 23 amino acids, which is cleaved off) and thus retains the chemokine fold (SEQ ID NO: 237). The lysine at position 73 may be modified through biotinylation. FmocLys(ivDde)-OH is incorporated as residue 73 to facilitate site-specific labelling at this position of the protein (SEQ ID NO: 238). A suitable spacer, such as a PEG spacer, may be incorporated between the ε-amino functionality and the biotin. The biotinylated version comprises, consists essentially of or consists of the amino acid sequence of SEQ ID NO: 239.

Thus, in other embodiments the invention also relates to a modified chemokine comprising, consisting essentially of or consisting of the amino acid sequence of SEQ ID NO: 237 or SEQ ID NO: 239:

SEQ ID NO: 237
GPASVPTTCCFNLANRKIPLQRLESYRRITSGKCPQKAVIFKTKLAKDIC

ADPKKKWVQDSMKYLDQKSPTPXP

X is an amino acid residue that can be biotinylated, such as lysine, ornithine or diaminopropionic acid and optionally is biotinylated, optionally via a spacer molecule such as PEG, e.g. K(PEG-Biotin).

SEQ ID NO: 239
H-GPASVPTTCCFNLANRKIPLQRLESYRRITSGKCPQKAVIFKTKLAKD

ICADPKKKWVQDSMKYLDQKSPTPXP-NH2

X is K(PEG-Biotin)

Chemokines useful in the various embodiments of the invention may be synthesised through any suitable means known in the art. Preferably, the chemokines are chemically synthesised as this facilitates modification and labelling etc. However, recombinant DNA based approaches may also be employed in combination with appropriate labelling and modification technologies as required. Thus, in certain embodiments the invention also provides a nucleic acid molecule encoding the chemokines of the various embodiments of the invention. In certain embodiments the invention also relates to a vector containing such a nucleic acid molecule and a host cell containing the vector. The vector may additionally comprise a suitable promoter operably linked to the nucleic acid molecule, to facilitate transcription of the corresponding mRNA molecule. The host cell may be capable of expressing the protein by transcription and translation of the nucleic acid molecule encoding a chemokine of the various embodiments of the invention.

The chemokines useful in the various embodiments of the invention can be biotinylated by methods known in the art such as described in WO 00/50088 A2, which is incorporated herein by reference in its entirety. As indicated above, site-specific labelling of the chemokines of the various embodiments of the invention is preferable, although any labelling technique which does not significantly affect the receptor-binding capacity of the chemokine may be employed. Various site-specifically biotinylated chemokines and native chemokines are available commercially, for instance from Almac, Craigavon, UK. In specific embodiments the one or more chemokines are biotinylated via a spacer group. The spacer may be employed to prevent the biotin group from impacting on the activity of the chemokine, in particular binding of the chemokine to its cognate receptor. Any suitable spacer that facilitates retention of receptor binding properties of the chemokine may be employed in the various embodiments of the invention. Thus, in the specific embodiments described above, spacers other than PEG spacers may be employed as appropriate. In specific embodiments, the spacer is a polyethylene glycol (PEG) spacer. PEG has been shown to be an effective spacer permitting attachment of biotin to the chemokine (which can then be immobilized on the solid support through interaction with streptavidin) without compromising receptor binding capability.

In the context of the various embodiments of the present invention the term "antibody" includes all immunoglobulins or immunoglobulin-like molecules with specific binding affinity for the relevant chemokine receptor (including by way of example and without limitation, IgA, IgD, IgE, IgG and IgM, combinations thereof, and similar molecules produced during an immune response in any vertebrate, for example, in mammals such as humans, goats, rabbits and mice). Specific immunoglobulins useful in the various embodiments of the invention include IgG isotypes. The antibodies useful in the various embodiments of the invention may be monoclonal or polyclonal in origin, but are typically monoclonal antibodies. Antibodies may be human antibodies, non-human antibodies, or humanized versions of non-human antibodies, or chimeric antibodies. Various techniques for antibody humanization are well established and any suitable technique may be employed. The term "antibody" also refers to a polypeptide ligand comprising at least a light chain or heavy chain immunoglobulin variable region which specifically recognizes and binds an epitope of an antigen, and it extends to all antibody derivatives and fragments that retain the ability to specifically bind to the relevant chemokine receptor. These derivative and fragments may include Fab fragments, F(ab')2 fragments, Fv fragments, single chain antibodies, single domain antibodies, Fc fragments etc. The term antibody encompasses antibodies comprised of both heavy and light chains, but also heavy chain (only) antibodies. In specific embodiments, the antibodies may be engineered so as to be specific for more than one chemokine receptor, for example bi-specific to permit binding to two different chemokine receptors. Suitable commercially available antibodies which bind to the chemokine receptors of interest are listed in table 11. They may or may not be labelled. General reference may be made to "Antibodies a laboratory manual: By E Harlow and D Lane. pp 726. Cold Spring Harbor Laboratory. 1988", which reference is incorporated herein by reference in its entirety.

TABLE 11

Commercially available fluorophore labelled antibodies against specific chemokine receptors

| Antibody | Fluorophore | Supplier |
| --- | --- | --- |
| CCR2 | PerCP Cy5.5 | Biolegend |
| CCR1 | Alexa Fluor 647 | Biolegend |
| CCR3 | PE | Biolegend |
| CCR5 | PE | Biolegend |
| CXCR1 | APC | Biolegend |
| CXCR2 | PE | Biolegend |
| CCR7 | PerCP Cy5.5 | Biolegend |

Anti-CCR2 antibodies are described for example in WO 2010/021697, incorporated herein by reference. Further examples of potentially useful antibodies include MLN-1202, an anti-CCR2 monoclonal antibody currently undergoing clinical trials (Millennium Pharmaceuticals).

The chemokine receptor expressing cells may thus be targeted using alternative binding agents, such as antibodies or other chemical compounds, as defined herein, rather than the natural chemokine binding partner. This approach is a new approach to treating inflammatory conditions.

Accordingly, in certain embodiments the invention also provides an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine. The binding reagent capable of specifically binding to the chemokine receptor may be an agonist or an antagonist of the chemokine receptor. In specific embodiments, the binding reagent capable of specifically binding to the chemokine receptor is selected from an antibody and a chemical compound.

In other embodiments the invention thus also provides a method for treating an inflammatory condition comprising applying peripheral blood from a patient/subject to an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine) thus removing chemokine receptor expressing cells from the peripheral blood of the patient/subject. The method may comprise returning the blood depleted of the chemokine receptor expressing cells to the patient/subject.

Similarly, in other embodiments the invention provides a binding reagent capable of specifically binding to a chemokine receptor for use in the treatment of an inflammatory condition, wherein the binding reagent is immobilized on a solid support contained within an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient/subject, wherein the binding reagent is not a chemokine), to which is applied peripheral blood from a patient thus removing chemokine receptor expressing cells from the peripheral blood of the patient.

These aspects of the various embodiments of the invention may be integrated into the more focused therapeutic aspects of the various embodiments of the invention (i.e. treating respiratory conditions such as sarcoidosis and COPD and various aspects thereof) and thus, the remainder of the disclosure, including all specific embodiments applies mutatis mutandis.

Solid support materials for immobilizing the binding reagents of the various embodiments of the invention are known in the art. "Solid support" refers to, for example, materials having a rigid or semi-rigid surface or surfaces, and may take the form of beads, resins, gels, microspheres, or other geometric configurations. A useful support material is one that does not activate blood cells so as to make them coagulate or adhere to the support as peripheral whole blood is applied to the device. In certain embodiments, a support treated with an agent to provide it with anti-coagulation properties, in particular a heparinized support is employed. Alternatively, the blood of the patient may be treated with an anti-coagulant such as heparin prior to application to the support. Useful support materials comprise high molecular weight carbohydrates, in particular carbohydrates having a molecular weight of 100 kDa or more, such as agarose, in particulate form, optionally cross-linked, and cellulose. Other preferred support materials are polymers, such as carboxylated polystyrene, and glass. The support of the various embodiments of the invention may be provided in the form of particles or fibres. The support particles may have regular form, such as spheres or beads, or irregular form. They may be porous or non-porous. A preferred average particle size of the support is from 50 μm to 2 mm. In certain embodiments Sepharose™, a cross linked, beaded-form of agarose, is used as column matrix. It is chosen for its optimal distribution capacity and can provide a large available area for affinity binding. Solid supports may be provided in the form of magnetic beads, with the specific binding reagent immobilized on the magnetic beads. Following capture of the (CCR2, CCR1, CCR3, CCR5, CXCR1, CXCR2 and/or CCR7) chemokine receptor expressing cells from the blood, the beads can be removed from the blood with the aid of an appropriate magnetic separator.

Methods for immobilizing binding reagents on a solid support are known in the art. A binding reagent, such as a chemokine, antibody, peptide, nucleic acid or chemical compound, can be immobilized on the support in a direct or indirect manner. Immobilization can be by means of a suitable linker in some embodiments. A preferred method of indirect immobilization of a binding reagent, such as a chemokine, relies upon the interaction between biotin and avidin molecules. "Avidin" or "avidin molecule" refers to any type of protein that specifically binds biotin to the substantial exclusion of other (small) molecules that might be present in a biological sample. Examples of avidin include avidins that are naturally present in egg white, oilseed protein (e.g., soybean meal), and grain (e.g., corn/maize), and streptavidin, which is a protein of bacterial origin Thus, biotinylation of the binding reagent and use of an avidin molecule such as streptavidin immobilized on the solid support allows reliable attachment of the binding reagent to the solid support according to methods known in the art. Specifically, such a method may comprise providing the binding reagent in biotinylated form, providing a solid support having streptavidin immobilized on its surface, contacting the support with an aqueous solution of the biotinylated binding reagent, and rinsing the support with an aqueous solvent. In addition, binding pair interactions, such as antibody-antigen interactions, may also be utilised for indirect immobilisation of binding reagent onto a support. In such embodiments the support may be derivatised with one member of a binding pair, such as an antibody or fragment or derivative thereof, as defined herein, which has known affinity for a particular peptide sequence or small molecule hapten. Incorporating the other member of the binding pair, such as an antigen, peptide sequence or the hapten onto or into the binding reagent facilitates immobilisation onto a solid support coated with the corresponding antibody or fragment or derivative thereof. Thus, the binding reagent may be modified to include the peptide sequence or hapten into the linear molecule or may be added as a side chain or label. Any suitable antibody-antigen pair may be employed. The antibody fragment or derivative may be any fragment or derivative that retains specific binding affinity for the appropriate antigen. Examples include Fab, F(ab')2 fragments, scFV, VH domains, single domain antibodies (such as nanobodies), heavy chain antibodies and humanized version of non-human antibodies etc. Other high affinity interactions can be utilised for immobilisation of binding reagents, as long as the binding reagent can be synthesised or derivatised with one of the interacting partners and the solid support synthesised or derivatised with the other interacting partner without loss of binding activity (i.e. binding of the binding reagent to the appropriate chemokine receptor). Immobilization may occur via essentially the same interaction in reverse in some embodiments. Thus, the binding reagent which may be a chemokine for example, may be attached to an antibody as defined herein, and the solid support derivatised with the antigen. The chemokine may be produced as a fusion protein with the antibody.

Alternatively binding reagents, such as chemokines and antibodies, can be immobilised directly onto a solid support using bioconjugation techniques established in the field. For example direct immobilisation of proteins onto cyanogen bromide activated solid supports via amino functionalities within the primary sequence of the protein. Alternatively, sulphydryl functionalities within proteins can be used to directly immobilise the protein to alkyl halide derivatised supports or supports containing free thiol functionalities. In further embodiments, proteins containing α-thioester functionalities can be directly immobilised on supports containing 1,2 amino thiol moieties (eg N-terminal cysteine) using the native chemical ligation reaction. Alternatively proteins modified with ketones and aldehydes can be immobilised on solid supports derivatised with hydrazinyl, hydrazide and aminoxy functionalities using hydrazone/oxime bond forming ligation reactions (and vice versa). Alternatively 'Click' chemistry can be used to immobilise proteins onto solid supports, whereby the protein and the support are derivatised with the appropriate mutually reactive chemical functionalities (azides and alkynes). In other embodiments Staudinger ligation chemistry can be used to immobilise appropriately derivatised proteins onto the appropriately derivatised solid supports.

The solid support is contained within or carried by the apheresis column. Thus, by "loaded" is meant that the column carries or contains the solid support in a manner such that (peripheral) blood can flow through the column in contact with the solid support. Thus, the solid support provides a matrix within the column through which blood flows, in continuous fashion in certain embodiments. This permits cells expressing the specific chemokine receptor to be removed from the blood passing through the column, such that blood exiting the column is depleted of the specific chemokine receptor-expressing cells. In specific embodiments, the apheresis column is loaded with a support comprising streptavidin immobilized on the support and one or more biotinylated binding reagents, such as chemokines, bound to the streptavidin on the support. The solid support may be comprised of a high-molecular weight carbohydrate, optionally cross-linked, such as agarose.

As discussed above, the binding reagent is coupled to the solid support. The relative amounts of binding reagent may be controlled to ensure that coupling between the solid support and the binding reagent will be immediate, minimising the risk of binding reagent decoupling from the solid support. Thus, it may be ensured that there is a relative excess of immobilization sites for the binding reagent on the solid support. Alternatively, or additionally, following immobilization of the binding reagent on the solid support, the solid support may be washed to remove any unbound binding reagent.

The apheresis column utilised in the various embodiments of the present invention acts as a leukapheresis treatment for respiratory conditions, in particular sarcoidosis and Chronic Obstructive Pulmonary Disease (COPD). The column acts to specifically remove one or more of CCR2, CCR1, CCR3, CCR5, CXCR1, CXCR2 and/or CCR7-expressing monocytes or leukocytes by exploiting the interaction between CCR2, CCR1, CCR3, CCR5, CXCR1, CXCR2 and/or CCR7 expressed on the cell surface and a specific binding reagent immobilized on a solid support contained within or carried by the column. The overall column typically comprises, consists of, or consists essentially of three combined components; 1) a housing which contains or carries 2) the solid support and 3) one or more binding reagents (immobilized thereon) which specifically bind one or more chemokine receptors. The housing may be manufactured from any suitable material for clinical use. In certain embodiments the housing is composed of a plastic material. The housing includes an in flow site for entry of blood and an out flow site for blood (depleted of target cells) to exit the column. The housing may be designed to maintain a continuous blood flow through the solid support matrix. The housing (as shown for example in FIG. 9) may include a top portion which comprises a distribution plate (2) at the inflow site (1) to spread the blood evenly over the entire matrix area. The distribution plate may act as a first safety barrier preventing larger particles flowing through the column and into the patient. However, the distribution plate is not essential and may be removed in some embodiments to decrease the overall resistance in the system. The column may contain one or more safety filter units (3 and 4) placed at the inflow (1) and/or outflow (5) sites of the plastic housing. Such filter units may act to prevent particles larger than blood cells passing in and/or out of the column. The safety filter units may contain a plurality of filters, such as two, three or four filters designed to be a robust barrier and stop all particles larger than blood cells passing through the column. Inclusion of safety filters (3 and 4) at both ends of the column serves to minimize the risk of leakage of particles into the patient, including in the event that the device is incorrectly connected resulting in blood flow in the opposite direction to that intended. The safety filters may comprise of any suitable pore size to prevent particles larger than blood cells from passing through the column, as would be readily understood by one skilled in the art. Suitable filters are commercially available. In specific embodiments, the pore size of the filter(s) is between approximately 60 μm and 100 μm, more specifically approximately 80 μm. The solid support and binding reagent components are discussed in further detail herein.

The volume of the housing may be varied depending upon the blood volumes intended to pass through the column. Typically, the volume of the housing is between approximately 40 ml and 200 ml, more specifically 50 ml to 150 ml or 60 ml to 120 ml.

The column is generally applied in the form of an apheresis circuit. In this context, the overall system includes the apheresis column, tubing and an appropriate pump to pump the blood around the circuit. The system is illustrated in FIG. 10. The patient (1) is connected to the extracorporeal circuit via sterile needles to veins in the right and the left arms. A saline bag (3) is also connected and the saline solution is pumped with a suitable pump (2). Blood is drawn from one arm of the patient through the sterile tubing system by the blood pump (4) and passed through the column (6) and back to the patient. The tubing system may be connected to the column via any suitable coupling, such as standard dialysis luer-lock couplings. The couplings on the column may be colour-coded for correct assembly. For example, red tubing for inflow to the red column top and blue tubing for outflow back to the patient. An air detector (8) may be present in the circuit. Inlet pressure (5) and/or Pven sensors (7) may additionally be employed to monitor the pressure in the circuit.

An apheresis pump, such as the 4008 ADS pump manufactured by Fresenius Medical Care or the Adamonitor pump, may monitor the patient's inflow and outflow. The pump may also monitor the pressure in the extracorporeal circulation. The pump may be able to discriminate air by a bubble catcher and air detector. A clot catcher filter may be positioned inside the bubble catcher. The pump may also incorporate an optical detector to distinguish between light, e.g. saline solution or air present in the tubing system and dark e.g. blood present in the tubing system.

A schematic diagram of a suitable pump, showing the air detector and optical filter is shown in FIG. 11. If the pump system detects air bubbles and optical fluctuations or if extracorporeal pressure values are out of the set range, then the pump may stop immediately. Alternatively or additionally a visual/audible alarm may be emitted.

The treatment methods of the various embodiments of the invention may thus rely upon an extracorporeal circuit. The methods may be considered as ex vivo or in vitro methods and be defined solely with reference to steps performed outside of the patient. In some embodiments, however, the method further comprises, prior to application of the blood to the column, collecting peripheral blood from the patient. In a further embodiment, the method further comprises, following the application of the blood to the column, infusing the blood depleted of (CCR2, CCR1, CCR3, CCR5, CXCR1, CXCR2 and/or CCR7) chemokine receptor expressing cells to the patient. This is then a complete leukapheresis treatment method. Thus, a leukaphereis method, for treating respiratory conditions, in particular sarcoidosis and Chronic Obstructive Pulmonary Disease (COPD), comprises collecting peripheral blood from the patient; applying the peripheral blood to an apheresis column loaded with a solid support comprising one or more binding reagents capable of specifically binding to one or more chemokine receptors, in particular the chemokine receptor CCR2, CCR1, CCR3, CCR5, CXCR1, CXCR2 and/or CCR7, immobilized directly or indirectly on the support thus removing one or more of CCR2, CCR1, CCR3, CCR5, CXCR1, CXCR2 and/or CCR7 expressing cells from the peripheral blood of the patient; and infusing the depleted blood (of chemokine receptor expressing cells) to the patient.

The peripheral blood may be continuously collected from the patient. Similarly, the depleted blood may be continuously infused to the patient, through use of an appropriate circuit as described herein. Thus, the support may be disposed in a column through which the blood is made to flow. This may be achieved using a suitable pump for example, as also described herein. Blood flow through the column enables the binding reagent(s) immobilized on the solid support to capture the cells expressing the chemokine receptor, thus depleting them from the blood and preventing their contribution to the inflammatory respiratory conditions, in particular sarcoidosis and Chronic Obstructive Pulmonary Disease (COPD).

The methods of the various embodiments of the invention and binding reagents for use in the methods of the various embodiments of the invention may require that the patient has been selected for treatment on the basis of detecting an increase in the level of chemokine receptor, in particular, one or more of CCR2, CCR1, CCR3, CCR5, CXCR1, CXCR2 and/or CCR7 expressing cells in a sample obtained from the patient. Such companion diagnostic methods are described in greater detail herein and are based, for example, on the observation that CCR2, CCR1, CCR3, CCR5, CXCR1, CXCR2 and/or CCR7 expression may be elevated in patients with respiratory conditions, in particular sarcoidosis and Chronic Obstructive Pulmonary Disease (COPD). It is shown herein that subjects suffering from respiratory conditions such as sarcoidosis exhibit increased frequency of chemokine receptor expressing cells in the peripheral blood. Subjects with sarcoidosis exhibit increased frequency of CCR1 expressing cells such as CCR1 expressing monocytes, compared to healthy controls. Similarly, it is shown herein that the monocytes also express CCR2. It is also shown herein that subjects suffering from respiratory conditions such as sarcoidosis exhibit increased frequency of CCR7 expressing cells such as CCR7 expressing lymphocytes, and also central memory T cells, compared to healthy controls.

Thus, (in this context) in certain embodiments the invention also provides a method of diagnosing, monitoring progression of, or monitoring treatment of respiratory conditions, in particular sarcoidosis and Chronic Obstructive Pulmonary Disease (COPD) comprising determining:

a) the levels of one or more of the chemokine receptor CCR2, CCR1, CCR3, CCR5, CXCR1, CXCR2 and/or CCR7 expressing cells b) levels of expression of one or more of CCR2, CCR1, CCR3, CCR5, CXCR1, CXCR2 and/or CCR7; and/or c) levels of cells with high expression of one or more of CCR2, CCR1, CCR3, CCR5, CXCR1, CXCR2 and/or CCR7 in a sample obtained from a subject, wherein high levels of one or more of CCR2, CCR1, CCR3, CCR5, CXCR1, CXCR2 and/or CCR7 expressing cells, high levels of expression of one or more of CCR2, CCR1, CCR3, CCR5, CXCR1, CXCR2 and/or CCR7 or high levels of cells with high expression of one or more of CCR2, CCR1, CCR3, CCR5, CXCR1, CXCR2 and/or CCR7 or increased levels of one or more of CCR2, CCR1, CCR3, CCR5, CXCR1, CXCR2 and/or CCR7 expressing cells compared to control, increased levels of expression of one or more of CCR2, CCR1, CCR3, CCR5, CXCR1, CXCR2 and/or CCR7 compared to a control or increased levels of cells with high expression of one or more of CCR2, CCR1, CCR3, CCR5, CXCR1, CXCR2 and/or CCR7 compared to a control indicate the presence or progression of respiratory conditions, in particular sarcoidosis and Chronic Obstructive Pulmonary Disease (COPD). Levels of chemokine receptor expression, as opposed to cell numbers, may also be investigated as increased levels of chemokine receptor expression per cell may also be diagnostically relevant. In specific embodiments, the cells relevant to diagnosis etc. of respiratory conditions such as sarcoidosis comprise monocytes, in particular CCR1 and/or CCR2 expressing monocytes. In other embodiments cells relevant to diagnosis etc. of respiratory conditions such as sarcoidosis comprise lymphocytes, specifically T lymphocytes such as central memory T cells, in particular CCR7 expressing T cells.

"Diagnosing" is defined herein to include screening for a disease/condition or pre-indication of a disease/condition, identifying a disease/condition or pre-indication of a disease/condition and checking for recurrence of disease/condition following treatment. The methods of the various embodiments of the invention may also have prognostic value, and this is included within the definition of the term "diagnosis". The prognostic value of the methods of the various embodiments of the invention may be used as a marker of potential susceptibility to respiratory conditions, in particular sarcoidosis and Chronic Obstructive Pulmonary Disease (COPD) by identifying levels of one or more of CCR2, CCR1, CCR3, CCR5, CXCR1, CXCR2 and/or CCR7 expression linked to the respiratory condition. Thus patients at risk may be identified before the disease has a chance to manifest itself in terms of symptoms identifiable in the patient. In certain embodiments, diagnosis may be made in conjunction with other objective indicators of respiratory conditions, in particular sarcoidosis and Chronic Obstructive Pulmonary Disease (COPD): The diagnosis of sarcoidosis may be made based upon clionical findings; x-ray, biopsy, s-Ca, ACE activity. COPD diagnosis may also be made by clinical findings; X-ray spirometry and blood gas analysis.

"Monitoring progression of" includes performing the methods to monitor the stage and/or the state and progression of the respiratory conditions, in particular sarcoidosis and Chronic Obstructive Pulmonary Disease (COPD). Monitoring progression may involve performing the diagnostic methods multiple times on the same patient to determine whether the levels of one or more of CCR2, CCR1, CCR3, CCR5, CXCR1, CXCR2 and/or CCR7 expressing cells are increasing, decreasing or remaining stable over a certain time period. This may be in the context of a treatment regime.

"Monitoring the success of a particular treatment" is defined to include determining the levels of one or more of CCR2, CCR1, CCR3, CCR5, CXCR1, CXCR2 and/or CCR7 expressing cells before and after a treatment. The treatment is generally one aimed at treating respiratory conditions, in particular sarcoidosis and Chronic Obstructive Pulmonary Disease (COPD) and may be a treatment according to one of the methods of the various embodiments of the invention as defined herein. Successful treatment may be determined with reference to a decrease in one or more of CCR2, CCR1, CCR3, CCR5, CXCR1, CXCR2 and/or CCR7 expressing cells as a result of, or following, the treatment. Thus, in such methods a level of one or more of CCR2, CCR1, CCR3, CCR5, CXCR1, CXCR2 and/or CCR7 expressing cells is determined prior to treatment. This level is recorded and a further assessment made at a predetermined time following the treatment. The comparison of levels of one or more of CCR2, CCR1, CCR3, CCR5, CXCR1, CXCR2 and/or CCR7 expressing cells permits the success of the treatment to be monitored. In specific embodiments, a single treatment is sufficient to cause a depletion of around 10%, 20%, 30%, 40%, 50%, 60% or 70%, or higher, up to 80%, 90%, 95% or more, or any range of values between and including these amounts, of one or more specific chemokine receptors, in particular one or more of CCR2, CCR1, CCR3, CCR5, CXCR1, CXCR2 and/or CCR7, expressing cells from the peripheral blood of the patient. In specific embodiments, at least around 50% depletion is achieved in a single treatment. Thus, successful treatment may be defined with reference to depletion of one or more of CCR2, CCR1, CCR3, CCR5, CXCR1, CXCR2 and/or CCR7 expressing cells. Treatment may lead to depletion of between approximately 100 and 500 million of one or more of CCR2, CCR1, CCR3, CCR5, CXCR1, CXCR2 and/or CCR7 expressing cells, such as monocytes, in certain embodiments. Additional factors may be included to determine successful treatment. For example, a lack of increase in one or more of CCR2, CCR1, CCR3, CCR5, CXCR1, CXCR2 and/or CCR7 expressing cells following treatment may indicate successful treatment in terms of preventing further progression of the condition, optionally combined with an improvement in other markers or staging of the respiratory conditions, in particular sarcoidosis and Chronic Obstructive Pulmonary Disease (COPD).

By binding to the column through the binding reagent-chemokine receptor interaction, chemokine receptor expressing cells are immobilized. These immobilized cells express further unoccupied chemokine receptors, which may be of the same or different type to those used for capture. These additional chemokine receptors may permit circulating chemokines which contribute to the inflammatory condition to be captured from the peripheral blood. Thus, a reduction in circulating (specific) chemokine levels may provide a measure of successful treatment. In specific embodiments, the cells relevant to diagnosis etc. of respiratory conditions such as sarcoidosis comprise monocytes, in particular CCR1 and/or CCR2 expressing monocytes. In other embodiments cells relevant to diagnosis etc. of respiratory conditions such as sarcoidosis comprise lymphocytes, specifically T lymphocytes such as central memory T cells, in particular CCR7 expressing T cells.

In specific embodiments, the respiratory conditions are selected from sarcoidosis and Chronic Obstructive Pulmonary Disease (COPD).

The sample in which one or more of CCR2, CCR1, CCR3, CCR5, CXCR1, CXCR2 and/or CCR7 expressing cell levels, levels of expression of one or more of CCR2, CCR1, CCR3, CCR5, CXCR1, CXCR2 and/or CCR7 and/or levels of cells with high expression of one or more of CCR2, CCR1, CCR3, CCR5, CXCR1, CXCR2 and/or CCR7 (defined as CCR2hi, CCR1hi, CCR3hi, CCR5hi, CXCR1hi, CXCR2hi or CCR7hi) are determined may comprise any suitable tissue sample or body fluid sample. Generally, the test sample is obtained from a human subject. Typically, the sample is a blood sample, in particular a peripheral blood sample. The sample may comprise an adipose tissue biopsy in certain embodiments. The methods may involve determining levels of one or more of CCR2, CCR1, CCR3, CCR5, CXCR1, CXCR2 and/or CCR7 expressing monocytes, macrophages or lymphocytes in certain embodiments. In specific embodiments, the cells relevant to diagnosis etc. of respiratory conditions such as sarcoidosis comprise monocytes, in particular CCR1 and/or CCR2 expressing monocytes. In other embodiments cells relevant to diagnosis etc. of respiratory conditions such as sarcoidosis comprise lymphocytes, specifically T lymphocytes such as central memory T cells, in particular CCR7 expressing T cells.

Levels of CCR2, CCR1, CCR3 or CCR5 expressing cells, levels of expression of CCR2, CCR1, CCR3, CCR5, CXCR1, CXCR2 and/or CCR7 and/or levels of cells with high expression of CCR2, CCR1, CCR3, CCR5, CXCR1, CXCR2 and/or CCR7 (defined as CCR2hi, CCR1hi, CCR3hi, CCR5hi, CXCR1hi, CXCR2hi and/or CCR7hi) may be determined according to any suitable method. For example, flow cytometry may be employed in order to determine the number of cells expressing CCR2, CCR1, CCR3, CCR5, CXCR1, CXCR2 and/or CCR7 in the sample, to determine levels of CCR2, CCR1, CCR3, CCR5, CXCR1, CXCR2 and/or CCR7 expression and/or to identify levels of CCR2hi, CCR1hi, CCR3hi, CCR5hi, CXCR1hi, CXCR2hi and/or CCR7hi cells. Flow cytometric techniques are described herein and examples of commercially available antibodies suitably labelled for use in flow cytometry are set out in Table 11 for example. Alternatively, the method may involve steps of collecting and fixing the cells in the sample, followed by incubation with a suitable binding reagent that binds specifically to the CCR2, CCR1, CCR3, CCR5, CXCR1, CXCR2 and/or CCR7 chemokine receptor expressing cells in the sample. Any suitable binding reagent, as defined herein, may be employed. For example, a CCR2, CCR1, CCR3, CCR5, CXCR1 or CXCR2 specific antibody may be employed. A wash step may be adopted following an incubation period to remove any unbound reagent. Suitable wash steps and incubation conditions would be well known to one skilled in the art. The binding reagent may be directly labeled in order to permit antibody binding to be directly determined. Alternatively a secondary binding reagent, such as an antibody, may be employed which binds to the first binding reagent and carries a label. Again, suitable incubation conditions and wash steps would be apparent to one skilled in the art. The primary and secondary binding reagents may form two halves of a binding pair. The binding interaction should not prevent the primary binding reagent binding to the CCR2, CCR1, CCR3, CCR5, CXCR1, CXCR2 and/or CCR7 receptor expressing cells, unless a competition assay is being employed. The two halves of a binding pair may comprise an antigen-antibody, antibody-antibody, receptor-ligand, biotin-streptavidin pair etc. in certain embodiments. Other techniques used to quantify chemokine (CCR2, CCR1, CCR3, CCR5, CXCR1, CXCR2 and/or CCR7) receptor expressing cell levels, to quantify levels of CCR2, CCR1, CCR3, CCR5, CXCR1, CXCR2 and/or CCR7 expression and/or to quantify levels of CCR2hi, CCR1hi, CCR3hi, CCR5hi, CXCR1hi, CXCR2hi and/or CCR7hi cells include PCR-based techniques such as QT-PCR and protein based methods such as western blot. Quantitation may be achieved with reference to fixed cell lines carrying known numbers of various receptor expressing cells and/or known levels of receptor expression per cell. Such fixed cell lines are available commercially (for example ChemiScreen™ cell lines from Millipore). Methods analogous to the treatment methods of the various embodiments of the invention may also be employed, with binding of CCR2, CCR1, CCR3, CCR5, CXCR1, CXCR2 and/or CCR7 expressing cells to the solid support being determined following peripheral blood being passed through the column.

The levels of CCR2, CCR1, CCR3, CCR5, CXCR1, CXCR2 and/or CCR7 expressing cells, levels of expression of CCR2, CCR1, CCR3, CCR5, CXCR1, CXCR2 and/or CCR7 and/or levels of cells with high expression of CCR2, CCR1, CCR3, CCR5, CXCR1, CXCR2 and/or CCR7 (defined as CCR2hi, CCR1hi, CCR3hi, CCR5hi, CXCR1hi, CXCR2hi or CCR7hi) may be determined relative to a suitable control. When diagnosing a respiratory condition, a threshold level of cells, level of expression of CCR2, CCR1, CCR3, CCR5, CXCR1, CXCR2 and/or CCR7 and/or level of cells with high expression of CCR2, CCR1, CCR3, CCR5, CXCR1, CXCR2 and/or CCR7 (defined as CCR2hi, CCR1hi, CCR3hi, CCR5hi, CXCR1hi, CXCR2hi or CCR7hi) may be set at or over which a positive diagnosis is made. This threshold may be determined based upon measuring levels of CCR2, CCR1, CCR3, CCR5, CXCR1, CXCR2 and/or CCR7 expressing cells, levels of expression of CCR2, CCR1, CCR3, CCR5, CXCR1, CXCR2 and/or CCR7 and/or levels of cells with high expression of CCR2, CCR1, CCR3, CCR5, CXCR1, CXCR2 and/or CCR7 (defined as CCR2hi, CCR1hi, CCR3hi, CCR5hi, CXCR1hi, CXCR2hi or CCR7hi) in samples obtained from diseased patients and comparing these levels with levels of CCR2, CCR1, CCR3, CCR5, CXCR1, CXCR2 and/or CCR7 expressing cells, levels of expression of CCR2, CCR1, CCR3, CCR5, CXCR1, CXCR2 and/or CCR7 and/or levels of cells with high expression of CCR2, CCR1, CCR3, CCR5, CXCR1, CXCR2 and/or CCR7 (defined as CCR2hi, CCR1hi, CCR3hi, CCR5hi, CXCR1hi, CXCR2hi or CCR7hi) in samples obtained from healthy subjects.

In certain embodiments, a respiratory disorder is diagnosed on the basis of levels of chemokine receptor expressing cells. A positive diagnosis may be made in subjects based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, a respiratory disorder is diagnosed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to healthy controls.

In specific embodiments, sarcoidosis is diagnosed on the basis of levels of CCR1 or CCR7 expressing cells. A positive diagnosis may be made in subjects based upon the presence of greater than about 10%, greater than about 15% or greater than about 20% CCR7 expressing central memory T cells in the sample, as a percentage of total cells in the sample. A positive diagnosis may be made in subjects based upon the presence of greater than about 40%, greater than about 45%, greater than about 50%, greater than about 55%, greater than about 60%, greater than about 65%, greater than about 70%, greater than about 75%, greater than about 80% or greater than about 85% or more CCR7 expressing T cells in the sample, as a percentage of total cells in the sample. A positive diagnosis may be made in subjects based upon the presence of greater than about 60%, greater than about 65%, greater than about 70%, greater than about 75%, greater than about 80%, greater than about 85% or greater than about 90% CCR1 expressing monocytes in the sample, as a percentage of total cells in the sample. Sarcoidosis may also be diagnosed on the basis of the presence of a about a 1.2 fold or greater increase, such as about a 1.5, 2, 2.5, 3, 3.5, 4, 4.5, 5, 10, 20, 50 or 100 or greater fold increase in the specific chemokine receptor expressing cells, relative to healthy controls.

In certain embodiments, progression of a respiratory disorder, which may be in the context of a treatment regime, is monitored on the basis of levels of chemokine receptor expressing cells at different time points. Progression of a respiratory disorder may be indicated in subjects based upon an increase of greater than about 10%, such as an increase of greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more chemokine receptor expressing cells in the sample, as a percentage of total cells in the sample, compared to a sample taken from the same subject at an earlier time point. In other embodiments, progression of a respiratory disorder is confirmed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to a sample taken from the same subject at an earlier time point.

In specific embodiments, sarcoidosis is monitored on the basis of levels of CCR1 or CCR7 expressing cells such as CCR7 expressing central memory T, CCR7 expressing T cells or CCR1 expressing monocytes. Progression of the disease, which may be in the context of a treatment regime, may be indicated in subjects based upon the presence of an increase of greater than about 10%, such as greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more chemokine receptor expressing cells in the sample, as a percentage of total cells in the sample, compared to a sample taken from the same subject at an earlier time point.

Regression or successful treatment may be monitored based upon similar decreases over various time points. For example, regression or successful treatment may be indicated in subjects based upon a decrease of about 10%, such as a decrease of about 15%, about 20%, about 25%, about 30%, about 35%, about 40%, about 45%, about 50%, about 55%, about 60%, about 65%, about 70%, about 75% or more chemokine receptor expressing cells in the sample, as a percentage of total cells in the sample, compared to a sample taken from the same subject at an earlier time point. In other embodiments, regression of respiratory disorders is confirmed on the basis of the presence of a about a 1.2 fold or greater decrease, such as about a 1.5, 2, 2.5, 3, 3.5, 4, 4.5, 5, 10, 20, 50 or 100 or greater fold decrease in chemokine receptor expressing cells, relative to a sample taken from the same subject at an earlier time point.

In specific embodiments, sarcoidosis is monitored on the basis of levels of CCR1 or CCR7 expressing cells such as CCR7 expressing central memory T, CCR7 expressing T cells or CCR1 expressing monocytes. Regression or successful treatment of the disease may be made in subjects based upon a decrease of about 50%, such as such as a decrease of about 55%, about 60%, about 65%, about 70%, about 75%, about 80%, about 85%, about 90%, about 95% or more CCR1 or CCR7 expressing cells in the sample, as a percentage of total cells in the sample or by a decrease of about 10%, such as a decrease of about 15%, about 20%, about 25%, about 30%, about 35%, about 40%, about 45%, about 50%, about 55%, about 60%, about 65%, about 70%, about 75% or more chemokine receptor expressing cells in the sample, as a percentage of total cells in the sample, compared to a sample taken from the same subject at an earlier time point.

Suitable software is freely available (such as the R project for statistical computing) to perform the necessary statistical analysis of the data obtained to calculate a useful threshold. The threshold may be set to maximize sensitivity and/or specificity of the test. Performance of the test in these respects may be measured by plotting a receiver operating characteristics (ROC) curve (sensitivity versus specificity). The area under the curve provides an indication of the overall performance of the test. Thus, once thresholds have been set for diagnosing the condition, a separate control experiment does not necessarily have to be run each time a sample is tested. Rather reference can simply be made to the pre-existing thresholds to determine the diagnosis. However, in certain embodiments, the sample is tested together with a control sample taken from a healthy subject to provide a comparator based upon essentially identical experimental conditions. The test sample is generally tested in parallel with the control sample. The test sample level of CCR2, CCR1, CCR3, CCR5, CXCR1, CXCR2 and/or CCR7 expressing cells, levels of expression of CCR2, CCR1, CCR3, CCR5, CXCR1, CXCR2 and/or CCR7 and/or levels of cells with high expression of CCR2, CCR1, CCR3, CCR5, CXCR1, CXCR2 and/or CCR7 (defined as CCR2hi, CCR1hi, CCR3hi, CCR5hi, CXCR1hi, CXCR2hi or CCR7hi) can then be compared with that of the control sample to make the diagnosis. A control sample from a disease patient may also be tested in certain embodiments. Reference to controls permits relative levels ("high", "low" etc.) of CCR2, CCR1, CCR3, CCR5, CXCR1, CXCR2 and/or CCR7 expressing cells in the test sample to be readily identified and the significance thereof interpreted. Reference to controls also permits relative levels of CCR2, CCR1, CCR3, CCR5, CXCR1, CXCR2 and/or CCR7 expression ("high", "low" etc.) within the cell population to be determined and the significance thereof interpreted. Such determination may, for example, indicate the average levels of CCR2, CCR1, CCR3, CCR5, CXCR1, CXCR2 and/or CCR7 expression per cell in the test sample.

Thus, in specific embodiments, high or higher levels of one or more of CCR2, CCR1, CCR3, CCR5, CXCR1, CXCR2 and/or CCR7 expressing cells or high or higher levels of one or more of CCR2, CCR1, CCR3, CCR5, CXCR1, CXCR2 and/or CCR7 expression, for example average CCR2, CCR1, CCR3, CCR5, CXCR1, CXCR2 and/or CCR7 expression per cell, or high or higher levels of one or more of CCR2hi, CCR1hi, CCR3hi, CCR5hi, CXCR1hi, CXCR2hi and/or CCR7hi cells correlate with active disease or more active disease. Similarly, lower or low levels of one or more of CCR2, CCR1, CCR3, CCR5, CXCR1, CXCR2 and/or CCR7 expressing cells, or low or lower levels of one or more of CCR2, CCR1, CCR3, CCR5, CXCR1, CXCR2 and/or CCR7 expression, for example average CCR2, CCR1, CCR3, CCR5, CXCR1, CXCR2 and/or CCR7 expression per cell, or low or lower levels of one or more of CCR2hi, CCR1hi, CCR3hi, CCR5hi, CXCR1hi, CXCR2hi and/or CCR7hi cells may correlate with a lack of active inflammation or disease. This may be defined as "less active disease". It can readily be envisaged that control samples may be assessed and levels of CCR2, CCR1, CCR3, CCR5, CXCR1, CXCR2 and/or CCR7 expressing cells, levels of expression of CCR2, CCR1, CCR3, CCR5, CXCR1, CXCR2 and/or CCR7 and/or levels of cells with high expression of CCR2, CCR1, CCR3, CCR5, CXCR1, CXCR2 and/or CCR7 (defined as CCR2hi, CCR1hi, CCR3hi, CCR5hi, CXCR1hi, CXCR2hi or CCR7hi) determined across the range of severities of respiratory conditions. This may assist in correlating the levels of CCR2, CCR1, CCR3, CCR5, CXCR1, CXCR2 and/or CCR7 expressing cells, levels of expression of CCR2, CCR1, CCR3, CCR5, CXCR1, CXCR2 and/or CCR7 and/or levels of cells with high expression of CCR2, CCR1, CCR3, CCR5, CXCR1, CXCR2 and/or CCR7 (defined as CCR2hi, CCR1hi, CCR3hi, CCR5hi, CXCR1hi, CXCR2hi or CCR7hi) in the test sample with the relative severity of the condition.

When monitoring progression of, or monitoring treatment of respiratory conditions, in particular sarcoidosis and Chronic Obstructive Pulmonary Disease (COPD), the control samples may be taken from the subject at an earlier time point. They may, however, be based upon known reference values as discussed above. Thus, relative levels of CCR2, CCR1, CCR3, CCR5, CXCR1, CXCR2 and/or CCR7 expressing cells, relative levels of CCR2, CCR1, CCR3, CCR5, CXCR1, CXCR2 and/or CCR7 expression including relative levels of average CCR2, CCR1, CCR3, CCR5, CXCR1, CXCR2 and/or CCR7 expression per cell or relative levels of CCR2hi, CCR1hi, CCR3hi, CCR5hi, CXCR1hi, CXCR2hi and/or CCR7hi cells may be with reference to samples taken from the same subject at a different point in time. In certain embodiments, decreased levels of one or more of CCR2, CCR1, CCR3, CCR5, CXCR1, CXCR2 and/or CCR7 expressing cells, decreased relative levels of one or more of CCR2, CCR1, CCR3, CCR5, CXCR1, CXCR2 and/or CCR7 expression including decreased relative levels of average CCR2, CCR1, CCR3, CCR5, CXCR1, CXCR2 and/or CCR7 expression per cell, or decreased relative levels of one or more of CCR2hi, CCR1hi, CCR3hi, CCR5hi, CXCR1hi, CXCR2hi and/or CCR7hi cells correlate with successful treatment. The treatment may be any suitable treatment, but in specific embodiments is a treatment according to the various embodiments of the invention.

When monitoring progression of respiratory conditions, in particular sarcoidosis and Chronic Obstructive Pulmonary Disease (COPD), increased levels of one or more of CCR2, CCR1, CCR3, CCR5, CXCR1, CXCR2 and/or CCR7 expressing cells increased relative levels of one or more of CCR2, CCR1, CCR3, CCR5, CXCR1, CXCR2 and/or CCR7 expression including increased relative levels of average CCR2, CCR1, CCR3, CCR5, CXCR1, CXCR2 and/or CCR7 expression per cell or increased relative levels of one or more of CCR2hi, CCR1hi, CCR3hi, CCR5hi, CXCR1hi, CXCR2hi and/or CCR7hi cells may indicate the progression of condition or disease. Thus, if levels of one or more of CCR2, CCR1, CCR3, CCR5, CXCR1, CXCR2 and/or CCR7 expressing cells, levels of expression of one or more of CCR2, CCR1, CCR3, CCR5, CXCR1, CXCR2 and/or CCR7 and/or levels of cells with high expression of one or more of CCR2, CCR1, CCR3, CCR5, CXCR1, CXCR2 and/or CCR7 (defined as CCR2hi, CCR1hi, CCR3hi, CCR5hi, CXCR1hi, CXCR2hi or CCR7hi) are increased in a sample taken later than a sample from the same patient this may indicate progression of the condition.

Since the levels of one or more of CCR2, CCR1, CCR3, CCR5, CXCR1, CXCR2 and/or CCR7 expressing cells, levels of one or more of CCR2, CCR1, CCR3, CCR5, CXCR1, CXCR2 and/or CCR7 expression or levels of one or more of CCR2hi, CCR1hi, CCR3hi, CCR5hi, CXCR1hi, CXCR2hi and/or CCR7hi cells are diagnostically relevant, determining such levels in a sample obtained from a subject may influence treatment selection for that subject. Accordingly, in certain embodiments the invention provides a method of selecting a suitable treatment for respiratory conditions, in particular sarcoidosis and Chronic Obstructive Pulmonary Disease (COPD) comprising determining:

a) the levels of one or more of the chemokine receptor CCR2, CCR1, CCR3, CCR5, CXCR1, CXCR2 and/or CCR7 expressing cells b) levels of expression of one or more of CCR2, CCR1, CCR3, CCR5, CXCR1, CXCR2 and/or CCR7; and/or c) levels of cells with high expression of one or more of CCR2, CCR1, CCR3, CCR5, CXCR1, CXCR2 and/or CCR7 in a sample obtained from a subject, wherein high levels of one or more of CCR2, CCR1, CCR3, CCR5, CXCR1, CXCR2 and/or CCR7 expressing cells, high levels of expression of one or more of CCR2, CCR1, CCR3, CCR5, CXCR1, CXCR2 and/or CCR7 or high levels of cells with high expression of CCR2, CCR1, CCR3, CCR5, CXCR1, CXCR2 and/or CCR7 or increased levels of one or more of CCR2, CCR1, CCR3, CCR5, CXCR1, CXCR2 and/or CCR7 expressing cells compared to control, increased levels of expression of one or more of CCR2, CCR1, CCR3, CCR5, CXCR1, CXCR2 and/or CCR7 compared to a control or increased levels of cells with high expression of one or more of CCR2, CCR1, CCR3, CCR5, CXCR1, CXCR2 and/or CCR7 compared to a control, result in selection of a treatment as defined herein for treatment of the respiratory conditions, in particular sarcoidosis and Chronic Obstructive Pulmonary Disease (COPD). In certain embodiments, the chemokine receptor expressing cells are high chemokine receptor expressing cells, in particular, high CCR2, CCR1, CCR3, CCR5, CXCR1, CXCR2 and/or CCR7 expressing cells. In specific embodiments, the cells comprise monocytes, in particular CCR1 and/or CCR2 expressing monocytes. In other embodiments the cells comprise lymphocytes, specifically T lymphocytes such as central memory T cells, in particular CCR7 expressing T cells.

In specific embodiments, a respiratory disorder is treated on the basis of measuring levels of chemokine receptor expressing cells. Thus, a treatment according to the various embodiments of the invention may be applied based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, a respiratory disorder is treated according to the various embodiments of the invention on the basis of the presence of a about a 1.5 fold or greater increase, such as about a 2, 2.5, 3, 3.5, 4, 4.5, 5, 10, 20, 50 or 100 or greater fold increase in chemokine receptor expressing cells, relative to healthy controls.

In specific embodiments, sarcoidosis is treated on the basis of levels of CCR1 or CCR7 expressing cells. Thus, a treatment according to the various embodiments of the invention may be applied based upon the presence of greater than about 10%, greater than about 15% or greater than about 20% CCR7 expressing central memory T cells in the sample, as a percentage of total cells in the sample. Thus, a treatment according to the various embodiments of the invention may be applied based upon the presence of greater than about 40%, greater than about 45%, greater than about 50%, greater than about 55%, greater than about 60%, greater than about 65%, greater than about 70%, greater than about 75%, greater than about 80% or greater than about 85% or more CCR7 expressing T cells in the sample, as a percentage of total cells in the sample. Thus, a treatment according to the various embodiments of the invention may be applied based upon the presence of greater than about 60%, greater than about 65%, greater than about 70%, greater than about 75%, greater than about 80%, greater than about 85% or greater than about 90% CCR1 expressing monocytes in the sample, as a percentage of total cells in the sample. Sarcoidosis may also be treated on the basis of the presence of a about a 1.2 fold or greater increase, such as about a 1.5, 2, 2.5, 3, 3.5, 4, 4.5, 5, 10, 20, 50 or 100 or greater fold increase in the specific chemokine receptor expressing cells, relative to healthy controls.

For the avoidance of doubt, all embodiments described in respect of the methods of the various embodiments of the invention apply to these aspects mutatis mutandis and are not repeated for reasons of conciseness. Specifically, respiratory conditions, in particular sarcoidosis and Chronic Obstructive Pulmonary Disease (COPD) may be indicated in conjunction with one or more of the following indicators: The diagnosis of sarcoidosis may be made based upon clionical findings; x-ray, biopsy, s-Ca, ACE activity. COPD diagnosis may also be made by clinical findings; X-ray spirometry and blood gas analysis.

In specific embodiments, the sample is a peripheral blood sample.

The methods and medical uses of the various embodiments of the invention thus can be tailored to the need of individual patients or groups of patients on the basis of the various diagnostic methods of the various embodiments of the invention. By removing from the circulation one or more of CCR2, CCR1, CCR3, CCR5, CXCR1, CXCR2 and/or CCR7 expressing cells, such as monocytes, macrophages and lymphocytes, in particular monocytes, upregulated in various inflammatory conditions associated with respiratory conditions, in particular sarcoidosis and Chronic Obstructive Pulmonary Disease (COPD), an important factor in the inflammatory process of such conditions can be controlled.

L. Treating Conditions Associated With Sepsis

Chemokines are a class of cytokine molecules involved in cell recruitment and activation in inflammation. Chemokines cause chemotaxis and activation of various subpopulations of cells in the immune system. The activity of chemokines is mediated primarily through tight binding to their receptors on the surface of leukocytes. In certain embodiments the present invention is based on the realisation that the interaction between chemokines and cells expressing their receptors may be exploited for the treatment of specific inflammatory conditions associated with sepsis. The inventors have determined that targeting increased recruitment of specific chemokine receptor-expressing cells to the site of inflammation presents a new therapeutic approach to treat such conditions. Moreover, in such conditions, chemokine receptor expression on each cell may be increased again providing a therapeutic approach to treat such conditions. It is shown herein that patients suffering from respiratory distress syndrome (RDS) exhibit an increase in circulating neutrophils compared to healthy controls. The neutrophils express characteristic chemokine receptors including CXCR1, CXCR2 and CCR5. This provides a therapeutic approach to treat this condition, by removal of CXCR1, CXCR2 and/or CCR5 expressing cells using a suitable binding reagent. Moreover, it is also shown herein that CCR5 expressing neutrophils are highly increased in bronchoalveolar lavage fluid (BALF) in patients suffering from RDS. Thus, the invention may be applied to treat sepsis and/or RDS, including but not limited to sepsis-associated RDS and Acute RDS (ARDS).

Thus, in certain embodiments the invention serves to reduce the recruitment of inflammatory leukocytes, which express characteristic chemokine receptors, and possibly express characteristic chemokine receptors at increased levels, to sites of inflammation linked to sepsis. This is achieved using specific binding reagents to capture specific chemokine receptor-expressing inflammatory leukocytes from the patient. Accordingly, in certain embodiments the invention provides in a first aspect a method for treating sepsis comprising applying peripheral blood from a patient to an apheresis column loaded with a solid support comprising one or more binding reagents capable of specifically binding to one or more chemokine receptors, in particular the chemokine receptors CCR2, CXCR1, CXCR2 and/or CCR5, immobilized directly or indirectly on the support thus removing one or more chemokine receptor, in particular one or more of CCR2, CXCR1, CXCR2 and/or CCR5, expressing cells from the peripheral blood of the patient. The peripheral blood from which the chemokine receptor expressing cells have been removed may then be returned to the patient in order to complete the treatment. The invention may thus rely on a continuous extracorporeal circuit in some embodiments. Alternatively, in certain embodiments the invention may comprise steps of obtaining peripheral blood from the patient, applying the peripheral blood to the column and subsequently returning the peripheral blood from which the chemokine receptor expressing cells have been removed to the patient.

In certain embodiments the invention also provides a method for treating respiratory distress syndrome (RDS), in particular acute respiratory distress syndrome (ARDS) comprising applying peripheral blood from a patient to an apheresis column loaded with a solid support comprising one or more binding reagents capable of specifically binding to one or more chemokine receptors, in particular the chemokine receptors CCR2, CXCR1, CXCR2 and/or CCR5 immobilized directly or indirectly on the support thus removing one or more chemokine receptor, in particular one or more of CCR2, CXCR1, CXCR2 and/or CCR5 expressing cells from the peripheral blood of the patient. With regard to RDS treatment and diagnosis, CXCR1, CXCR2 and/or CCR5 chemokine receptor expressing cells (such as neutrophils) may be of particular relevance. The peripheral blood from which the relevant chemokine receptor expressing cells have been removed may then be returned to the patient in order to complete the treatment. The invention may thus rely on a continuous extracorporeal circuit in some embodiments. Alternatively, the invention may comprise steps of obtaining peripheral blood from the patient, applying the peripheral blood to the column and subsequently returning the peripheral blood from which the relevant chemokine receptor expressing cells have been removed to the patient.

Herein, reference to "CCR2, CXCR1, CXCR2, and/or CCR5" is intended to encompass selection of any one or more of the chemokine receptors listed. In addition, the combination of CCR2, CXCR1 and/or CXCR2 is explicitly contemplated as a separate grouping, to include any one or more of CCR2, CXCR1 and CXCR2. The grouping of CCR2, CXCR1, CXCR2, and/or CCR5 includes any one or more, up to all, of CCR2, CXCR1, CXCR2 and CCR5.

As shown herein, suitable binding reagents can be immobilized onto a solid support either directly or indirectly, to generate an apheresis column suitable for capturing relevant chemokine receptor-expressing cells. Where increased levels of chemokine receptor expression are observed, such cells may be preferably removed from the peripheral blood using the columns of the various embodiments of the invention. Thus, the methods of the various embodiments of the invention may preferably target one or more of CCR2hi, CXCR1hi, CXCR2hi and/or CCR5hi cells as defined herein for removal from the peripheral blood. "High" expression may be determined according to standard flow cytometry techniques. The level is measured relative to levels of expression of the chemokine receptor in cells taken from a healthy subject. The attached FIG. 177 provides an example of a gating strategy.

In other embodiments the invention further provides a binding reagent capable of specifically binding to one or more chemokine receptors, in particular to a chemokine receptor/the chemokine receptor CCR2, CXCR1, CXCR2 and/or CCR5, for use in the treatment of sepsis, wherein the one or more binding reagents is immobilized, directly or indirectly, on a solid support contained within an apheresis column, to which is applied peripheral blood from a patient thus removing one or more chemokine receptor/CCR2, CXCR1, CXCR2 and/or CCR5 expressing cells from the peripheral blood of the patient. In certain embodiments the invention also provides for use of one or more binding reagents capable of specifically binding to a chemokine receptor/the chemokine receptor CCR2, CXCR1, CXCR2 and/or CCR5 for use in the manufacture of an apheresis column for treatment of sepsis, wherein the one or more binding reagents is immobilized on a solid support contained within the apheresis column, to which is applied peripheral blood from a patient thus removing one or more of chemokine receptor/CCR2, CXCR1, CXCR2 and/or CCR5 expressing cells from the peripheral blood of the patient.

In certain embodiments the invention further provides a binding reagent capable of specifically binding to one or more chemokine receptors, in particular to a/the chemokine receptor CCR2, CXCR1, CXCR2 and/or CCR5, for use in the treatment of RDS, optionally ARDS, wherein the one or more binding reagents is immobilized on a solid support contained within an apheresis column, to which is applied peripheral blood from a patient thus removing one or more chemokine receptor/CCR2, CXCR1, CXCR2 and/or CCR5 expressing cells from the peripheral blood of the patient. The invention also provides for use of one or more binding reagents capable of specifically binding to a chemokine receptor/the chemokine receptor CCR2, CXCR1, CXCR2 and/or CCR5 for use in the manufacture of an apheresis column for treatment of RDS, optionally ARDS, wherein the one or more binding reagents is immobilized on a solid support contained within the apheresis column, to which is applied peripheral blood from a patient thus removing one or more of chemokine receptor/CCR2, CXCR1, CXCR2 and/or CCR5 expressing cells from the peripheral blood of the patient.

All embodiments described in respect of the methods of treatment of the various embodiments of the invention apply to these aspects mutatis mutandis and are not repeated for reasons of conciseness. Thus, the following discussion made with reference to the methods of treatment is also applicable to the medical use aspects of the invention various embodiments of the.

In certain embodiments the invention aims to treat sepsis and/or RDS (including but not limited to sepsis-associated RDS). By treatment is meant a reduction in the specific chemokine receptor expressing cells in the peripheral blood of the patient. The reduction may comprise a reduction in cells that express chemokine receptors, in particular one or more of CCR2, CXCR1, CXCR2 and/or CCR5, at increased levels in diseased patients. The patient is typically a human patient but the term patient may include both human and non-human animal subjects in some embodiments. In the context of the various embodiments of the present invention, this typically involves a reduction in one or more of CCR2, CXCR1, CXCR2 and/or CCR5 expressing cells, such as one or more of CCR2hi, CXCR1hi, CXCR2hi and/or CCR5hi expressing cells, in the peripheral blood of the patient. The CCR2, CXCR1, CXCR2 and/or CCR5 expressing cells comprise, consist essentially of or consist of monocytes, macrophages and/or lymphocytes, in particular T-lymphocytes, or neutrophils in certain embodiments. Monocytes are produced by the bone marrow from haematopoietic stem cell precursors called monoblasts. Monocytes may differentiate into macrophages or dendritic cells. Monocytes and their macrophage and dendritic cell progeny serve a number of functions in the immune system including phagocytosis, antigen presentation and cytokine production. Monocytes may be characterized with reference to expression of the cell surface marker CD14, optionally together with CD16. Classical monocytes may be characterized by high level expression of the CD14 cell surface receptor (CD14++CD16– monocyte). Non-classical monocytes may be characterized by low level expression of CD14 and with additional co-expression of the CD16 receptor (CD14+CD16++ monocyte). Intermediate monocytes may be characterized by high level expression of CD14 and low level expression of CD16 (CD14++CD16+ monocytes). Macrophages are derived from monocytes and are responsible for protecting tissues from foreign substances. They are cells that possess a large smooth nucleus, a large area of cytoplasm and internal vesicles for processing foreign material. The term "macrophage" may refer to a monocyte-derived cell expressing one or more of the following cell surface markers CD14, CD11b, Lysozyme M, MAC-1/MAC-3 and CD68. The term macrophage includes both activated and un-activated macrophages. Activated macrophages may be characterized by expression of one or more of CD69, ENG, FCER2 and IL2RA, HLA-DR, CD86. Un-activated macrophages have not yet received activating signals through for example TLR receptors and therefore they express less activation markers on the cell surface which correlates with lesser maturation. M1 macrophages may be characterized by expression of one or more of CD16+CD32+CD64+ and secrete mainly IL-23 and IL-1, TNF, IL-6 and high levels of IL-12 and in addition effector molecules such as iNOS and ROI. M1 macrophages have cytotoxic features as opposed to M2 macrophages. M2 macrophages may be characterized by expression of one or more of SRA/B+CD163+MR+CD14+ and express TGFβ, IL-10 and IL-1Ra. Tumour associated macrophages (TAMs) share many characteristics with the M2 macrophages and are considered as M2 polarised macrophages. The M1/M2 paradigm can also be found in monocyte subsets where CD14+CD16–CXC3R1low monocytes are considered the "inflammatory" subset and the CD14lowCD16+CXC3R1high are "resident" monocytes.

The three major types of lymphocyte are T cells, B cells and natural killer (NK) cells. The term "T-lymphocyte" includes CD4+ T cells such as T helper cells (Th1 cells and Th2 cells), and CD8+ T cells such as cytotoxic T cells. Th1 cells may be characterized by expression of CCR5 and/or by production of IFN-γ. Th2 cells may be characterized by expression of CCR3 and/or by production of IL-4.

Neutrophils, also known as neutrophil granulocytes, may be subdivided into segmented neutrophils (or segs) and banded neutrophils (or bands). Neutrophils form part of the polymorphonuclear cell family (PMNs) together with basophils and eosinophils. Neutrophils staining a neutral pink on hematoxylin and eosin (H&E) histological or cytological preparations. Normally neutrophils contain a nucleus divided into 2-5 lobes.

Neutrophils are one of the first-responders of inflammatory cells to migrate towards the site of inflammation. Neutrophil granulocytes have an average diameter of 12-15 micrometers (μm) in peripheral blood smears. When analyzing a pure neutrophil suspension on an automated cell counter, neutrophils have an average diameter of 8-9 μm.

In addition to recruiting and activating other cells of the immune system, neutrophils play a key role in the front-line defence against invading pathogens. Neutrophils have three strategies for directly attacking micro-organisms: phagocytosis (ingestion), release of soluble anti-microbials (including granule proteins) and generation of neutrophil extracellular traps (NETs). Kinhult et al., (Clin Exp Allergy. 2003 August; 33 (8):1141-6) investigated the expression of surface activation markers on neutrophils, reflecting activation during their recruitment to the nose, and to see whether the inflammatory process during allergic rhinitis influences this process. A marked increase in the expression of CD11b, CD66b and CD63 on the neutrophil cell surface was noticed following migration from the bloodstream to the surface of the nasal mucosa. The expression of the CDb11b was reduced on neutrophils remaining in the circulation. In addition, the level of L-selectin was reduced on neutrophils derived from the blood during allergic inflammation.

CCR2, CXCR1, CXCR2 and/or CCR5 expressed on these aforementioned cells binds to chemokines such as monocyte chemoattractant protein-1 (MCP-1) or CXCL8. MCP-1 is a major chemoattractant for monocytes and memory T cells by means of their binding to its specific cell-surface receptor, CC-chemokine receptor-2. CXCL8 binds to CXCR1 and/or CXCR2. CXCR1 binds to IL-8 (CXCL8) and CXCR2 may bind any one or more of CXCL1, CXCL2, CXCL3, CXCL5, CXCL6, CXCL7 and CXCL8. CCL3, CCL5 (RANTES) and CCL8 each bind to CCR5.

CCR2 is the gene symbol approved by the HUGO Gene Nomenclature Committee for chemokine (C—C motif) receptor 2. The HGNC ID for this gene is 1603. The gene is located at chromosome position 3p21. The previous symbol and name for the gene is CMKBR2. Synonyms for this gene include CC-CKR-2, CD192, CKR2, FLJ78302, MCP-1-R. The NCBI Reference Sequence is NM_001123041.2 as available on 13 Jun. 2011, which is incorporated herein by reference in its entirety.

CXCR1 is the gene symbol approved by the HUGO Gene Nomenclature Committee for chemokine (C—X—C motif) receptor 1. The HGNC ID for this gene is 6026. The gene is located at chromosome position 2q35. The previous symbol and name for the gene is CMKAR1, IL8RA, "interleukin 8 receptor, alpha". Synonyms for this gene include CD181, CDw128a, CKR-1. The Genbank reference sequence for CXCR1 is U111870.1 as available on 13 Jun. 2011, which is incorporated herein by reference in its entirety.

CXCR2 is the gene symbol approved by the HUGO Gene Nomenclature Committee for chemokine (C—X—C motif) receptor 2. The HGNC ID for this gene is 6027. The gene is located at chromosome position 2q35. The previous symbol and name for the gene is IL8RB, "interleukin 8 receptor, beta". Synonyms for this gene include CD182, CMKAR2. The Genbank reference sequence for CXCR2 is U111869.1 as available on 13 Jun. 2011, which is incorporated herein by reference in its entirety.

CCR5 is the gene symbol approved by the HUGO Gene Nomenclature Committee for chemokine (C—C motif) receptor 5. The HGNC ID for this gene is 1606. The gene is located at chromosome position 3p21. The previous symbol and name for the gene is CMKBR5. Synonyms for this gene include CC-CKR-5, CD195 CKR-5, IDDM22 and CKR5.

The RefSeq reference sequence for CCR1 is NM_000579.3 as available on 13 Jun. 2011, which is incorporated herein by reference in its entirety.

The various embodiments of the methods of the invention may involve specific binding interactions with any one or more of these further cell-surface markers in addition to the removal based upon binding to CCR2, CXCR1, CXCR2 and/or CCR5. Suitable binding reagents can be prepared to specifically bind to these cell-surface markers. The discussion of CCR2, CXCR1, CXCR2 and/or CCR5 specific binding reagents thus applies mutatis mutandis.

Treatment according to the various embodiments of the invention may result in alleviation or amelioration of symptoms, prevention of progression, regression of the condition, or complete recovery. Measurable parameters of successful treatment include one or more, up to all, of improvement in vital signs including pO2, respiration, Xray findings, CRP, ESR levels and decreased temperature and evidence of clearance of bacteria in blood cultures. In specific embodiments, a single treatment is sufficient to cause a depletion of around 10%, 20%, 30%, 40%, 50%, 60% or 70%, or higher up to 80%, 90%, 95% or more, or any range of values between and including these amounts, of one or more of a specific chemokine receptor, in particular one or more of CCR2, CXCR1, CXCR2 and/or CCR5, expressing cells from the peripheral blood of the patient. In specific embodiments, at least around 50% depletion is achieved in a single treatment. Thus, successful treatment may be defined with reference to depletion of one or more of CCR2, CXCR1, CXCR2 and/or CCR5 expressing cells. Treatment may lead to depletion of between approximately 100 and 500 million CCR2, CXCR1, CXCR2 and/or CCR5 expressing cells, such as monocytes or neutrophils, in certain embodiments and more particularly to about 100, 150, 200, 250, 300, 350, 400, 450, or 500 million CCR2, CXCR1, CXCR2 and/or CCR5 expressing cells. Treatment may lead to depletion of CCR2, CXCR1, CXCR2 and/or CCR5 expressing neutrophils in some embodiments.

By binding to the column through the binding reagent-chemokine receptor interaction, chemokine receptor expressing cells are immobilized. These immobilized cells express further unoccupied chemokine receptors, which may be of the same or different type to those used for capture. These additional chemokine receptors may permit circulating chemokines which contribute to the inflammatory condition to be captured from the peripheral blood. Thus, a reduction in circulating (specific) chemokine levels may provide a measure of successful treatment.

The duration of treatment may be readily determined by one skilled in the art and will depend upon factors such as the flow rate of the peripheral blood. Duration of treatment may be tied into monitoring of the treatment itself, with the treatment considered complete once a measurable parameter of treatment has reached a defined threshold. Any suitable parameter may be employed as discussed herein. Thus, for example, treatment may be considered complete when a reduction in one or more of CCR2, CXCR1, CXCR2 and/or CCR5 expressing cells, such as a 50% reduction in one or more of CCR2, CXCR1, CXCR2 and/or CCR5 expressing cells, has been achieved. The apheresis system may be operated at a flow rate of around 10-80 mL/min, or more specifically between around 20-70 mL/min, or between around 30-60 mL/min. In specific embodiments, the treatment is performed for a period of around 10, 20, 30, 40, 50, 60, 70, 80, 90, 100, 110, 120 etc., or any range of values between and including these amounts, minutes. The treatment is typically not aimed to remove all of the cells expressing the chemokine receptor in the peripheral blood, as a basal level of those cells is required in healthy subjects. However, it has been found that only low blood volumes need to be applied to the columns of the various embodiments of the invention in order to achieve effective levels of depletion of the chemokine receptor-expressing cells. Thus, in certain embodiments, around 10-80% or more specifically around 20, 30, 40 or 50%, or any range of values between and including these amounts, of the patient's blood is applied to the column in a single treatment. The volume of blood circulated through the apheresis column or system may be in the region of around 1000-3000 ml, such as around 1000, 1200, 1400, 1600, 1800 or 2000 ml or any range of values between and including these amounts. The treatment may be considered complete once this volume of blood has been circulated. The patient may be administered anticoagulants prior to each treatment session. A suitable solution, such as a sterile saline solution, optionally including an anticoagulant such as Heparin, may be used for priming the apheresis (extracorporeal) system. An additional volume of anticoagulant may be added to the circuit at the start of each treatment session, for example as a bolus injection.

In certain embodiments the invention relies upon a binding reagent which is capable of specifically binding to a chemokine receptor. This specific binding reaction permits cells expressing the chemokine receptor to be removed from the peripheral blood of the patient when the blood is passed over the solid support upon or within which the binding reagent is immobilized. Specific chemokine receptors of interest include CCR2, CXCR1, CXCR2 and/or CCR5, particularly CCR2. The binding reagent can be any binding reagent capable of specifically binding to the receptor in question. By "specific binding" is meant that the binding reagent displays sufficient specificity of binding and appropriate binding affinity/kinetics to permit removal of cells expressing one or more of CCR2, CXCR1, CXCR2 and/or CCR5 from the peripheral blood. Whilst it is not precluded that the binding reagent is capable of binding to other molecules, such as other chemokine receptors, the binding reagent will preferentially bind to cells expressing one or more of CCR2, CXCR1, CXCR2 and/or CCR5 and in particular to cells expressing increased levels of one or more of CCR2, CXCR1, CXCR2 and/or CCR5 (as defined further herein). The binding reagent capable of specifically binding to CCR2, CXCR1, CXCR2 and/or CCR5 may be either an agonist or an antagonist of CCR2, CXCR1, CXCR2 and/or CCR5, respectively. As the disease condition relies upon up-regulation of expression of or signaling via CCR2, CXCR1, CXCR2 and/or CCR5, in certain embodiments the binding reagent capable of specifically binding to CCR2, CXCR1, CXCR2 and/or CCR5 is an antagonist of CCR2, CXCR1, CXCR2 and/or CCR5, respectively. Chemokines are typically, although not necessarily exclusively (particularly in the case of truncated or modified forms) agonists of their cognate receptor and serve to activate the cells expressing the relevant receptor, as would be appreciated by one skilled in the art. Antibodies against the relevant chemokine receptor are generally considered to be antagonists, as would be appreciated by one skilled in the art. Specific examples of binding reagents include proteins or polypeptides, such as antibodies and receptor ligands, in particular chemokines. The binding reagent may be a nucleic acid molecule in certain embodiments. In some embodiments, the nucleic acid is an aptamer. Nucleic acid aptamers are polynucleotides of approximately 15-40 nucleotides long. Nucleic acid aptamers can be made using the SELEX process (systemic evolution of ligands by exponential enrichment) or any other process known to those of skill in the art.

In other embodiments, the binding reagent may be a peptide, and in certain instances, a peptide aptamer. Peptide aptamers are artificial recognition molecules that consist of a variable peptide sequence inserted into a constant scaffold protein (Baines I C, Colas P. Peptide aptamers as guides for small molecule drug discovery. Drug Discov Today. 2006; 11:334-341, incorporated herein by reference). A number of methodologies, such as phage display, ribosome display and yeast two-hybrid screening systems are available for screening a library of potential peptide-based binding agents. Similarly protein scaffolds based on domains such as fibronectins, ankyrin repeats, protein A, SH3 domains, lipocalins and ubiquitin can be used as the binding agent. Again a number of technologies such as phage display and ribosome display are available for screening a library of protein—based binding agents. Similarly, libraries of candidate chemical compounds can be screened for specific binding to the relevant chemokine receptor using suitable screening techniques known in the art, which may be high throughput screens in certain embodiments. The candidate binding agent may be immobilized on a solid support and the ability of the agent to specifically retain cells expressing the chemokine receptor of interest or labelled chemokine receptors determined. A range of cell types may be applied to the solid supports to confirm specificity of binding, or alternatively a mixed sample (such as peripheral blood) may be applied to the solid support. Retention of the cell type of interest (expressing the appropriate chemokine receptor) can be confirmed to identify suitable binding agents. A range of small-molecule antagonists of CCR-2 are discussed by Xia M and Sui Z in Expert Opin Ther Pat. 2009 March; 19 (3):295-303—Recent developments in CCR2 antagonists, and incorporated herein by reference.

In the context of the various embodiments of the present invention the term "chemokine" also comprises biotinylated or otherwise labelled chemokines. The term "chemokine" also comprises modified and truncated versions of the chemokine and chemokine fragments with the proviso that the modified or truncated form retains its ability to bind to its cognate receptor (and thus remains functional in the context of the various embodiments of the invention). The chemokine does not necessarily need to retain biological activity as it is specific binding affinity for CCR2, CXCR1, CXCR2 and/or CCR5 that is required. In certain embodiments, the chemokine lacks biological activity, for example in terms of activation of the (CCR2, CXCR1, CXCR2 and/or CCR5) receptor. Modifications may be made to improve protein synthesis, for example uniformity of product and yield. As known to those skilled in the art, exemplary modifications may comprise amino acid additions, substitutions, deletions or other modifications to one or more amino acids in the chemokine. Modifications may comprise substitution of the wild type amino acid with non-natural amino acids such as norleucine (NLeu) and derivatized amino acids such as pyroglutamic acid (pyroGlu). Such modifications may be made to minimize side-product formation during storage and use of the columns of the various embodiments of the invention. Modifications may be made to improve labelling, for example inclusion of a polyethylene glycol (PEG) spacer to facilitate biotinylation. The biotinylation and/or conjugation with fluorochromes or other labelling groups of the chemokine is performed in a manner which does not substantially affect the receptor binding capacity. Site specific biotinylation or other labelling is preferred as non-selective labelling of chemokines may compromise receptor binding activity. Biotinylation or other labelling is generally preferred at or towards the C-terminus of the protein as the inventors have found that modifications in this area are generally well tolerated (in terms of a minimal effect on receptor binding capability). Biotinylation may be carried out site-specifically at any suitable amino acid. Examples of suitable amino acids include lysine, diaminopropionic acid and ornithine. Generally, reference may be made to Natarajan S et al, Int. J. Pept. Protein Res., 1992, 40, 567-74; Baumeister B, Int. J. Peptide Res. And Therapeutics, 2005, 11, 139-141; Bioconjugate techniques 2nd edition, Greg T. Hermanson, incorporated by reference herein in its entirety.

Truncations may involve deletion of either N or C terminal amino acids as appropriate, or both. Typically, the truncated version will retain the residues required for the chemokine to fold correctly, for example to retain a chemokine fold structure, consistent with the requirement that a truncated version must retain the ability to bind to the relevant receptor (expressed by (on the surface of) a leukocyte). Chemokine molecules typically include disulphide bonds between the 1st and 3rd and 2nd and 4th cysteine residues respectively, as would be understood by one skilled in the art. Where sequences are presented herein, it is assumed that these disulphide bonds will form in the folded protein (unless otherwise stated). Truncated versions may comprise anywhere between 1 and 100 less amino acids, such as 1, 2, 3, 4, 5 etc amino acids, than the wild type amino acid sequence in certain embodiments. Of course, truncated versions may comprise further modification as detailed herein. The modified or truncated version may have 40%, 45%, 50%, 55%, 60%, 65%, 70%, 75%, 80%, 85%, 90%, 95% or more overall amino acid sequence identity with the full length wild type chemokine (where a deletion is counted as a difference in amino acid sequence) in certain embodiments. Over the common sequence between the molecules (i.e the amino acids that have not been deleted), there may be 80%, 85%, 90%, 91%, 92%, 93%, 94%, 95%, 96%, 97%, 98% or 99% amino acid sequence identity in certain embodiments. Sequence identity may be determined using known algorithms, such as BLAST or GAP analysis (GCG Program) (applying default settings), which are freely available. Chemokines may lack the N-terminal signal peptide which is cleaved off during synthesis in vivo.

Specific chemokines useful in the various embodiments of the present invention for binding to CCR2 include MCP-1, MCP-2, MCP-3, MCP-4 and MCP-5. Both MCP-1 and MCP-5 bind solely to the chemokine receptor CCR2 and so these chemokines may be preferred in some embodiments. Each chemokine is able to bind to a chemokine receptor implicated in a sepsis associated disorder or condition. More specifically, each of MCP-1, MCP-2, MCP-3, MCP-4 and MCP-5 are useful for removing CCR2 expressing cells from the blood of a patient. Specific chemokines useful in the present invention for binding to CXCR1 and/or CXCR2 include CXCL8. CXCL8 is able to bind to chemokine receptors implicated in sepsis and RDS. More specifically, CXCL8 is useful for removing CXCR1 and/or CXCR2 expressing cells from the blood of a patient. For CXCR2 binding chemokines useful may include CXCL1, CXCL2, CXCL3, CXCL5, CXCL6, CXCL7 and CXCL8. The chemokines described in greater detail herein (with reference to the relevant figures and amino acid sequences, as set forth in the SEQ ID NOs) may each be applied according to the various embodiments of the present invention. CCL5 (RANTES), CCL3 and CCL8 may each bind to CCR5, and thus may be useful for removal of CCR5 expressing cells.

CCL2 is the gene symbol approved by the HUGO Gene Nomenclature Committee for chemokine (C—C motif) ligand 2, also known as MCP-1. The HGNC ID for this gene is 10618. The gene is located at chromosome position 17q11.2-q21.1. The previous symbol and name for the gene is SCYA2 "small inducible cytokine A2 (monocyte chemotatic protein 1, homologus to mouse Sig-je)". Synonyms for this gene include GDCF-2, HC11, MCP1, MGC9434, SMC-CF, "monocyte chemoattractant protein-1", "monocyte chemotactic and activating factor", "monocyte chemotactic protein 1, homologous to mouse Sig-je", "monocyte secretory protein JE", "small inducible cytokine subfamily A (Cys-Cys), member 2". The Genbank reference sequence for CCL2 is BC009716.1 as available on 13 Jun. 2011, which is incorporated herein by reference in its entirety.

CCL8 is the gene symbol approved by the HUGO Gene Nomenclature Committee for chemokine (C—C motif) ligand 8, also known as MCP-2. The HGNC ID for this gene is 10635. The gene is located at chromosome position 17q11.2. The previous symbol and name for the gene is SCYA8, "small inducible cytokine subfamily A (Cys-Cys), member 8 (monocyte chemotactic protein 2)". Another synonym for this gene is HC14. The Genbank reference sequence for CCL8 is X99886.1 as available on 13 Jun. 2011, which is incorporated herein by reference in its entirety.

CCL7 is the gene symbol approved by the HUGO Gene Nomenclature Committee for chemokine (C—C motif) ligand 7, also known as MCP-3. The HGNC ID for this gene is 10634. The gene is located at chromosome position 17q11.2-q12. The previous symbol and name for the gene is SCYA6, SCYA7, "small inducible cytokine A7 (monocyte chemotactic protein 3)". Synonyms for this gene include FIC, MARC, MCP-3, MCP3, NC28, "monocyte chemoattractant protein 3", "monocyte chemotactic protein 3". The Genbank reference sequence for CCL7 is AF043338 as available on 13 Jun. 2011, which is incorporated herein by reference in its entirety.

CCL13 is the gene symbol approved by the HUGO Gene Nomenclature Committee for chemokine (C—C motif) ligand 13, also known as MCP-4. The HGNC ID for this gene is 10611. The gene is located at chromosome position 17q11.2. The previous symbol and name for the gene is SCYA13, "small inducible cytokine subfamily A (Cys-Cys), member 13". Synonyms for this gene include CKb10, MCP-4, MGC17134, NCC-1, SCYL1. The Genbank reference sequence for CCL13 is AJ001634 as available on 13 Jun. 2011, which is incorporated herein by reference in its entirety.

MCP-5 is a mouse chemokine in the CC chemokine family. It is also known as Chemokine (C—C motif) ligand 12 (CCL12) and, due to its similarity with the human chemokine MCP-1, sometimes it is called MCP-1-related chemokine. The gene for MCP-5 is found in a cluster of CC chemokines on mouse chromosome 11. The previous symbol for MCP-5 is SCYA12. The NCBI reference sequence for CCL12 is NC_000077.5 as available on 13 Jun. 2011, which is incorporated herein by reference in its entirety.

CXCL1 is the gene symbol approved by the HUGO Gene Nomenclature Committee for chemokine (C—X—C motif) ligand 1 (melanoma growth stimulating activity, alpha). The HGNC ID for this gene is 4602. The gene is located at chromosome position 4q13.3. The previous symbol and name for the gene is "fibroblast secretory protein", FSP, GRO1, "GRO1 oncogene (melanoma growth stimulating activity, alpha)", MGSA. Synonyms for this gene include GROa, MGSA-a, NAP-3, SCYB1. The Genbank reference sequence for CXCL1 is J03561.1 as available on 13 Jun. 2011, which is incorporated herein by reference in its entirety.

CXCL2 is the gene symbol approved by the HUGO Gene Nomenclature Committee for chemokine (C—X—C motif) ligand 2. The HGNC ID for this gene is 4603. The gene is located at chromosome position 4q113.3. The previous symbol and name for the gene is GRO2, "GRO2 oncogene". Synonyms for this gene include CINC-2a, GROb, MGSA-b, MIP-2a, SCYB2. The Genbank reference sequence for CXCL2 is M36820.1 as available on 13 Jun. 2011, which is incorporated herein by reference in its entirety CXCL3 is the gene symbol approved by the HUGO Gene Nomenclature Committee for chemokine (C—X—C motif) ligand 3. The HGNC ID for this gene is 4604. The gene is located at chromosome position 4q21. The previous symbol and name for the gene is GRO3, "GRO3 oncogene". Synonyms for this gene include CINC-2b, GROg, MIP-2b, SCYB3. The Genbank reference sequence for CXCL3 is M36821.1 as available on 13 Jun. 2011, which is incorporated herein by reference in its entirety CXCL5 is the gene symbol approved by the HUGO Gene Nomenclature Committee for chemokine (C—X—C motif) ligand 5. The HGNC ID for this gene is 10642. The gene is located at chromosome position 4q113.3. The previous symbol and name for the gene is SCYB5, "small inducible cytokine subfamily B (Cys-X-Cys), member 5 (epithelial-derived neutrophil-activating peptide 78)". A synonym for this gene is ENA-78. The Genbank reference sequence for CXCL5 is X78686.1 as available on 13 Jun. 2011, which is incorporated herein by reference in its entirety CXCL6 is the gene symbol approved by the HUGO Gene Nomenclature Committee for chemokine (C—X—C motif) ligand 6. The HGNC ID for this gene is 10643. The gene is located at chromosome position 4q113.3. The previous symbol and name for the gene is chemokine (C—X—C motif) ligand 6 (granulocyte chemotactic protein 2). Synonyms for this gene include CKA-3, GCP-2. The Genbank reference sequence for CXCL6 is U83303.1 as available on 13 Jun. 2011, which is incorporated herein by reference in its entirety PPBP is the gene symbol approved by the HUGO Gene Nomenclature Committee for pro-platelet basic protein (chemokine (C—X—C motif) ligand 7), also known as CXCL7. The HGNC ID for this gene is 9240. The gene is located at chromosome position 412-q13. The previous symbol and name for the gene is THBGB1. Synonyms for this gene include b-TG1, Beta-TG, "beta-thromboglobulin", "connective tissue-activating peptide III", CTAP3, CTAPIII, CXCL7, LA-PF4, LDGF, MDGF, NAP-2, NAP-2-L1, "neutrophil-activating peptide-2", PBP, "platelet basic protein", SCYB7, TGB, TGB1. The Genbank reference sequence for PPBP is M54995.1 as available on 13 Jun. 2011, which is incorporated herein by reference in its entirety IL8 is the gene symbol approved by the HUGO Gene Nomenclature Committee for interleukin 8, also known as CXCL8. The HGNC ID for this gene is 6025. The gene is located at chromosome position 4q13-q21. Synonyms for this gene include 3-10C, AMCF-I, b-ENAP, "chemokine (C—X—C motif) ligand 8", CXCL8, GCP-1, IL-8, K60, LECT, LUCT, LYNAP, MDNCF, MONAP, NAF, NAP-1, SCYB8, TSG-1. The Genbank reference sequence for CXCL8 is Y00787.1 as available on 13 Jun. 2011, which is incorporated herein by reference in its entirety CCL5 is the gene symbol approved by the HUGO Gene Nomenclature Committee for chemokine (C—C motif) ligand 5, also known as RANTES. The HGNC ID for this gene is 10632. The gene is located at chromosome position 17q11.2-q12. The previous symbol and name for the gene is D17S136E, SCYA5, "small inducible cytokine A5 (RANTES)". Synonyms for this gene include "beta-chemokine RANTES", MGC17164, RANTES, "regulated upon activation, normally T-expressed, and presumably secreted", "SIS-delta", SISd, "small inducible cytokine subfamily A (Cys-Cys), member 5", "T-cell specific protein p288", "T-cell specific RANTES protein", TCP228. The Genbank reference sequence for CCL5 is AF043341.1 as available on 13 Jun. 2011, which is incorporated herein by reference in its entirety.

CCL3 is the gene symbol approved by the HUGO Gene Nomenclature Committee for chemokine (C—C motif) ligand 3, also known as MIP-1α. The HGNC ID for this gene is 10627. The gene is located at chromosome position 17q12. The previous symbol and name for the gene is SCYA3, "small inducible cytokine A3 (homologous to mouse Mip-1a)". Synonyms for this gene include G0S19-1, LD78ALPHA, MIP-1-alpha. The Genbank reference sequence for CCL3 is M23178.1 as available on 13 Jun. 2011, which is incorporated herein by reference in its entirety.

Examples of suitable modified chemokines of the various embodiments of the invention containing modifications and/or truncations and specifically adapted for use in the invention are described in detail herein. MCP-1 has been produced with residue 75, which may be a lysine, as the site of biotinylation on the chemokine (numbering based upon the mature protein having the amino acid sequence of SEQ ID NO: 241). Biotinylation permits immobilization of MCP-1 on a solid support (via a biotin-avidin interaction). The basic amino acid sequence of MCP-1, including a 23 amino acid leader sequence is set forth as SEQ ID NO: 240. The amino acid sequence of the mature protein is set forth as SEQ ID NO: 241. The inventors have determined that chemokines may display improved binding properties where the chemokine is biotinylated via a spacer group. The spacer may prevent the biotin group from impacting on the binding affinity of the chemokine. Any suitable spacer group may be employed. Further modifications may provide the molecule with advantageous properties. The invention also relates to derivatives of truncated MCP-1 chemokines. The amino acid sequence of the truncated version is set forth as SED ID NO: 242.

Accordingly, in certain embodiments the invention also provides a modified MCP-1 chemokine comprising, consisting essentially of or consisting of the amino acid sequence set forth as SEQ ID NO: 240, SEQ ID NO: 241 or SEQ ID NO: 242 in which one or more of the following modifications have been made:

a) the glutamine residue 240 of SEQ ID NO: 241 has been replaced with pyroglutamine b) the C terminus is produced as an amide derivative (this may be achieved by synthesis on an amide linker)

c) the (C terminal region) residue at position 98 of SEQ ID NO: 240 or position 75 of SEQ ID NO: 241 or position 67 of SEQ ID NO: 142, which may be a lysine or ornithine residue or other suitable alternative (such as diaminopropanoic acid), is biotinylated, optionally via a spacer group, in order to permit immobilization of the chemokine on a solid support; and/or d) the methionine residue at position 87 of SEQ ID NO: 240 or position 64 of SEQ ID NO: 241 or position 56 of SEQ ID NO: 242 has been replaced with norleucine.

The (C terminal region) amino acid, which may be a lysine residue or a functional equivalent, at position 98 of SEQ ID NO: 240 or position 75 of SEQ ID NO: 241 or position 67 of SEQ ID NO: 242 may be biotinylated via a suitable spacer group, such as a polyethylene glycol (PEG) spacer group, in order to permit immobilization of the chemokine on a solid support. In specific embodiments, the PEG spacer is 3,6-dioxo aminooctanoic acid. The sequence and biotinylation of the modified MCP-1 chemokines of the invention are shown in FIGS. 172 to 173 respectively. The modified MCP-1 chemokines may be agonists or antagonists of CCR2 activity. They can be tested for activity in a suitable assay, such as cell-based assays. In particular, agonist and antagonist properties may be determined in functional cell-based assay on human CCR2 receptor.

A further example of a chemokine of the various embodiments of the invention containing modifications and specifically adapted for use in the invention is described in detail herein (see Examples below). The modified CCL2 (MCP-1) corresponds to residues 1 to 76 of the full length mature protein (and lacks the N-terminal signal peptide of 23 amino acids, which is cleaved off) and thus retains the chemokine fold. The Gln at the N-terminus of the protein (Gln1) is substituted with pyroglutamine to prevent mixed species of N-terminal Gln and pyroGlu being generated (SEQ ID NO: 247). This improves the yield of synthesis and ensures a homogeneous chemokine preparation through column manufacture and use. FmocLys(ivDde)-OH is incorporated as residue 75 to facilitate site-specific labelling at this position of the protein (SEQ ID NO: 248). A suitable spacer, such as a PEG spacer, may be incorporated between the ε-amino functionality and the biotin. Thus, the invention relates to a modified chemokine, including a biotinylated version, which comprises, consists essentially of or consists of the amino acid sequence of SEQ ID NO: 249:

H-XPDAINAPVTCCYNFTNRKISVQRLASYRRITSSKCPKEAVIFKTIVA

KEICADPKQKWVQDSMDHLDKQTQTPXT-NH2

X1=pyroGlu (but may remain as Gln in some embodiments)

X75=an amino acid residue that can be biotinylated, such as lysine, ornithine or diaminopropionic acid and optionally is biotinylated, optionally via a spacer molecule such as PEG, e.g. K(PEG-Biotin).

MCP-5 only binds CCR2 and should be selective in its removal of CCR2 expressing cells. The full length amino acid sequence, including the signal peptide, is set forth as SEQ ID NO: 243. The amino acid sequence of N-terminal processed MCP-5 chemokine is 82 amino acids long and is set forth as SEQ ID NO: 244. An amino acid sequence alignment suggests that MCP-5 has a C-terminal extension when compared to the amino acid sequence of MCP-1. The results of this alignment are shown in FIG. 175. C-terminal truncated versions of MCP-5 can thus be synthesised. This truncated version will comprise, consist essentially of or consist of MCP-5 residues 1-76, set forth as SEQ ID NO: 245.

Accordingly, in certain embodiments the invention also provides a modified MCP-5 chemokine comprising the amino acid sequence set forth as SEQ ID NO: 243, SEQ ID NO: 244 or SEQ ID NO: 245 in which the isoleucine residue at position 97 of SEQ ID NO: 243 or at position 75 of SEQ ID NO: 244 or SEQ ID NO: 245 has been replaced with lysine (or a functional equivalent as defined herein). In certain embodiments, the modified MCP-5 chemokine comprises, consists essentially of or consists of the amino acid sequence of SEQ ID NO: 246. The modified MCP-5 chemokine may be biotinylated at the lysine (or a functional equivalent) residue at position 97 of SEQ ID NO: 243 or at position 75 of SEQ ID NO: 244 or SEQ ID NO: 245. Biotinylation may be via a suitable spacer group. Specific examples of the spacer group include a PEG spacer, optionally 3,6-dioxo aminooctanoic acid. In some embodiments, the C terminus is produced as an amide derivative. This may be achieved by synthesis on an amide linker. In certain embodiments, the modified MCP-5 chemokine comprises, consists essentially of or consists of the sequence and biotinylation shown in FIG. 176. The modified MCP-5 chemokine may be an agonist or an antagonist of CCR2 activity. They can be tested for activity in a suitable assay, such as cell-based assays. In particular, agonist and antagonist properties may be determined in a functional cell-based assay on human CCR2 receptor.

A further example of a chemokine of the various embodiments of the invention containing modifications and specifically adapted for use in the invention is described in detail herein (see Examples below). The modified CCL8 (MCP-2) corresponds to residues 1 to 76 of the full length mature protein (and lacks the N-terminal signal peptide of 23 amino acids, which is cleaved off) and thus retains the chemokine fold. The Gln at the N-terminus of the protein is subject to pyroGlu formation under physiological conditions. Thus Gln1 of the sequence is substituted with pyroglutamine to prevent mixed species of N-terminal Gln and pyroGlu being generated (SEQ ID NO: 250). This improves the yield of synthesis and ensures a homogeneous chemokine preparation through column manufacture and use. FmocLys(ivDde)-OH is incorporated as residue 75 to facilitate site-specific labelling at this position of the protein (SEQ ID NO: 251). The naturally occurring lysine at position 75 is modified through biotinylation. A suitable spacer, such as a PEG spacer, may be incorporated between the ε-amino functionality and the biotin (SEQ ID NO: 252):

Thus, in certain embodiments the invention also relates to a modified chemokine comprising, consisting essentially of or consisting of the amino acid sequence of SEQ ID NO: 252:

XPDSVSIPITCCFNVINRKIPIQRLESYTRITNIQCPKEAVIFKTKRGKE

VCADPKERWVRDSMKHLDQIFQNLXP

X1=pyroGlu (but may remain as Gln in some embodiments)

X75=an amino acid residue that can be biotinylated, such as lysine, ornithine or diaminopropionic acid and optionally is biotinylated, optionally via a spacer molecule such as PEG, e.g. K(PEG-Biotin).

A further example of a chemokine of the various embodiments of the invention containing modifications and specifically adapted for use in the invention is described in detail herein (see Examples below). The modified CCL5 (RANTES) corresponds to residues 1 to 68 of the full length mature protein (and lacks the N-terminal signal peptide of 23 amino acids, which is cleaved off) and thus retains the chemokine fold. The single methionine (Met67) within the sequence is mutated to lysine, to mitigate against oxidation of this residue during the chain assembly (SEQ ID NO: 253). This Met to Lys substitution provides a lysine at position 67 which can be modified through biotinylation. FmocLys(ivDde)-OH is incorporated as residue 67 to facilitate site-specific labelling at this position of the protein (SEQ ID NO: 254). The biotinylated version comprises, consists essentially of or consists of the amino acid sequence of SEQ ID NO: 255.

Thus, in other embodiments the invention also relates to a modified chemokine comprising, consisting essentially of or consisting of the amino acid sequence of SEQ ID NO: 255:

SPYSSDTTPCCFAYIARPLPRAHIKEYFYTSGKCSNPAVVFVTRKNRQVC

ANPEKKWVREYINSLEXS

X is an amino acid residue that can be biotinylated, such as lysine, ornithine or diaminopropionic acid and optionally is biotinylated, optionally via a spacer molecule such as PEG (e.g. K(Biotin))

A further example of a chemokine of the various embodiments of the invention containing modifications and specifically adapted for use in the invention is described in detail herein (see Examples below). The modified CXCL8 (IL-8) corresponds to residues 1 to 77 of the full length mature protein (and lacks the N-terminal signal peptide of 22 amino acids, which is cleaved off) and thus retains the chemokine fold. An amino acid residue capable of biotinylation, such as lysine or ornithine, is added as residue 78 (SEQ ID NO: 256). FmocLys(ivDde)-OH may be incorporated as residue 78 to facilitate site-specific labelling at this position of the protein (SEQ ID NO: 257). The additional amino acid, in particular lysine or ornithine, at position 78 is modified through biotinylation. A suitable spacer, such as a PEG spacer, may be incorporated between the ε-amino functionality and the biotin (SEQ ID NO: 258).

Thus, in other embodiments the invention also relates to a modified chemokine comprising, consisting essentially of or consisting of the amino acid sequence of SEQ ID NO: 256 or 258:

SEQ ID NO: 256
AVLPRSAKELRCQCIKTYSKPFHPKFIKELRVIESGPHCANTEIIVKL

SDGRELCLDPKENWVQRVVEKFLKRAENSX

X is an amino acid residue that can be biotinylated, such as lysine, ornithine or diaminopropionic acid and optionally is biotinylated, optionally via a spacer molecule such as PEG

SEQ ID NO: 258
AVLPRSAKELRCQCIKTYSKPFHPKFIKELRVIESGPHCANTEIIVKL

SDGRELCLDPKENWVQRVVEKFLKRAENSK(PEG-Biotin)

A further example of a chemokine of the various embodiments of the invention containing truncations and modifications and specifically adapted for use in the invention is described in detail herein (see Examples below). The modified CXCL8 (IL-8) corresponds to residues 6 to 77 of the full length mature protein, with the first 5 N-terminal amino acids removed, (and lacks the N-terminal signal peptide of 22 amino acids, which is cleaved off) and thus retains the chemokine fold. An amino acid residue capable of biotinylation, such as lysine or ornithine, is added as residue 78 (SEQ ID NO: 259). FmocLys(ivDde)-OH may be incorporated as residue 78 to facilitate site-specific labelling at this position of the protein (SEQ ID NO: 260). The additional amino acid, in particular lysine or ornithine, at position 78 is modified through biotinylation. A suitable spacer, such as a PEG spacer, may be incorporated between the ϵ-amino functionality and the biotin (SEQ ID NO: 261).

Thus, in other embodiments the invention also relates to a modified chemokine comprising, consisting essentially of or consisting of the amino acid sequence of SEQ ID NO: 259 or 260:

SEQ ID NO: 259
SAKELRCQCIKTYSKPFHPKFIKELRVIESGPHCANTEIIVKLSDGREL

CLDPKENWVQRVVEKFLKRAENSX

X is an amino acid residue that can be biotinylated, such as lysine, ornithine or diaminopropionic acid and optionally is biotinylated, optionally via a spacer molecule such as PEG

SEQ ID NO: 261
SAKELRCQCIKTYSKPFHPKFIKELRVIESGPHCANTEIIVKLSDGREL

CLDPKENWVQRVVEKFLKRAENSX

X is K(PEG-Biotin)

Chemokines useful in the various embodiments of the invention may be synthesised through any suitable means known in the art. Preferably, the chemokines are chemically synthesised as this facilitates modification and labelling etc. However, recombinant DNA based approaches may also be employed in combination with appropriate labelling and modification technologies as required. Thus, in certain embodiments the invention also provides a nucleic acid molecule encoding the chemokines of the various embodiments of the invention. In certain embodiments the invention also relates to a vector containing such a nucleic acid molecule and a host cell containing the vector. The vector may additionally comprise a suitable promoter operably linked to the nucleic acid molecule, to facilitate transcription of the corresponding mRNA molecule. The host cell may be capable of expressing the protein by transcription and translation of the nucleic acid molecule encoding a chemokine of the various embodiments of the invention.

The chemokines useful in the various embodiments of the invention can be biotinylated by methods known in the art such as described in WO 00/50088 A2, which is incorporated herein by reference in its entirety. As indicated above, site-specific labelling of the chemokines of the various embodiments of the invention is preferable, although any labelling technique which does not significantly affect the receptor-binding capacity of the chemokine may be employed. Various site-specifically biotinylated chemokines and native chemokines are available commercially, for instance from Almac, Craigavon, UK. In specific embodiments the one or more chemokines are biotinylated via a spacer group. The spacer may be employed to prevent the biotin group from impacting on the activity of the chemokine, in particular binding of the chemokine to its cognate receptor. Any suitable spacer that facilitates retention of receptor binding properties of the chemokine may be employed in the various embodiments of the invention. Thus, in the specific embodiments described above, spacers other than PEG spacers may be employed as appropriate. In specific embodiments, the spacer is a polyethylene glycol (PEG) spacer. PEG has been shown to be an effective spacer permitting attachment of biotin to the chemokine (which can then be immobilized on the solid support through interaction with streptavidin) without compromising receptor binding capability.

In the context of the various embodiments of the present invention the term "antibody" includes all immunoglobulins or immunoglobulin-like molecules with specific binding affinity for the relevant chemokine receptor (including by way of example and without limitation, IgA, IgD, IgE, IgG and IgM, combinations thereof, and similar molecules produced during an immune response in any vertebrate, for example, in mammals such as humans, goats, rabbits and mice). Specific immunoglobulins useful in the various embodiments of the invention include IgG isotypes. The antibodies useful in the various embodiments of the invention may be monoclonal or polyclonal in origin, but are typically monoclonal antibodies. Antibodies may be human antibodies, non-human antibodies, or humanized versions of non-human antibodies, or chimeric antibodies. Various techniques for antibody humanization are well established and any suitable technique may be employed. The term "antibody" also refers to a polypeptide ligand comprising at least a light chain or heavy chain immunoglobulin variable region which specifically recognizes and binds an epitope of an antigen, and it extends to all antibody derivatives and fragments that retain the ability to specifically bind to the relevant chemokine receptor. These derivative and fragments may include Fab fragments, F(ab')2 fragments, Fv fragments, single chain antibodies, single domain antibodies, Fc fragments etc. The term antibody encompasses antibodies comprised of both heavy and light chains, but also heavy chain (only) antibodies. In specific embodiments, the antibodies may be engineered so as to be specific for more than one chemokine receptor, for example bi-specific to permit binding to two different chemokine receptors. Anti-CCR2 antibodies are described for example in WO 2010/021697, incorporated herein by reference. Further examples of potentially useful antibodies include MLN-1202, an anti-CCR2 monoclonal antibody currently undergoing clinical trials (Millennium Pharmaceuticals). Suitable commercially available antibodies which bind to the chemokine receptors of interest are listed in table 12 below. They may or may not be labelled. General reference may be made to "Antibodies a laboratory manual: By E Harlow and D Lane. pp 726. Cold Spring Harbor Laboratory. 1988", which reference is incorporated herein in its entirety.

TABLE 12

Commercially available fluorophore labelled antibodies against specific chemokine receptors

| Antibody | Fluorophore | Supplier |
|---|---|---|
| CCR5 | PE | Biolegend |
| CXCR1 | APC | Biolegend |
| CXCR2 | PE | BD Biosciences |
| CCR2 | PerCP Cy5.5 | BD Biosciences |

The chemokine receptor expressing cells may thus be targeted using alternative binding agents, such as antibodies or other chemical compounds, as defined herein, rather than the natural chemokine binding partner. This approach is a new approach to treating inflammatory conditions.

Accordingly, in certain embodiments the invention also provides an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine. The binding reagent capable of specifically binding to the chemokine receptor may be an agonist or an antagonist of the chemokine receptor. In specific embodiments, the binding reagent capable of specifically binding to the chemokine receptor is selected from an antibody and a chemical compound.

In other embodiments the invention thus also provides a method for treating an inflammatory condition comprising applying peripheral blood from a patient/subject to an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient, wherein the binding reagent is not a chemokine) thus removing chemokine receptor expressing cells from the peripheral blood of the patient/subject. The method may comprise returning the blood depleted of the chemokine receptor expressing cells to the patient/subject.

Similarly, in other embodiments the invention provides a binding reagent capable of specifically binding to a chemokine receptor for use in the treatment of an inflammatory condition, wherein the binding reagent is immobilized on a solid support contained within an apheresis column as defined above (an apheresis column loaded with a solid support comprising a binding reagent capable of specifically binding to a chemokine receptor immobilized directly or indirectly on the support to permit removal of a cell expressing the chemokine receptor from the peripheral blood of a patient/subject, wherein the binding reagent is not a chemokine), to which is applied peripheral blood from a patient thus removing chemokine receptor expressing cells from the peripheral blood of the patient.

These aspects of the various embodiments of the invention may be integrated into the more focused therapeutic aspects of the various embodiments of the invention (i.e. treating sepsis and RDS in particular ARDS, including but not limited to sepsis-associated RDS) and thus, the remainder of the disclosure, including all specific embodiments applies mutatis mutandis.

Solid support materials for immobilizing the binding reagents of the various embodiments of the invention are known in the art. "Solid support" refers to, for example, materials having a rigid or semi-rigid surface or surfaces, and may take the form of beads, resins, gels, microspheres, or other geometric configurations. A useful support material is one that does not activate blood cells so as to make them coagulate or adhere to the support as peripheral whole blood is applied to the device. In certain embodiments, a support treated with an agent to provide it with anti-coagulation properties, in particular a heparinized support is employed. Alternatively, the blood of the patient may be treated with an anti-coagulant such as heparin prior to application to the support. Useful support materials comprise high molecular weight carbohydrates, in particular carbohydrates having a molecular weight of 100 kDa or more, such as agarose, in particulate form, optionally cross-linked, and cellulose. Other preferred support materials are polymers, such as carboxylated polystyrene, and glass. The support of the various embodiments of the invention may be provided in the form of particles or fibres. The support particles may have regular form, such as spheres or beads, or irregular form. They may be porous or non-porous. A preferred average particle size of the support is from 50 µm to 2 mm. In certain embodiments Sepharose™, a cross linked, beaded-form of agarose, is used as column matrix. It is chosen for its optimal distribution capacity and can provide a large available area for affinity binding. Solid supports may be provided in the form of magnetic beads, with the specific binding reagent immobilized on the magnetic beads. Following capture of the (CCR2, CXCR1, CXCR2 and/or CCR5) chemokine receptor expressing cells from the blood, the beads can be removed from the blood with the aid of an appropriate magnetic separator.

Methods for immobilizing binding reagents on a solid support are known in the art. A binding reagent, such as a chemokine, antibody, peptide, nucleic acid or chemical compound, can be immobilized on the support in a direct or indirect manner. Immobilization can be by means of a suitable linker in some embodiments. A preferred method of indirect immobilization of a binding reagent, such as a chemokine, relies upon the interaction between biotin and avidin molecules. "Avidin" or "avidin molecule" refers to any type of protein that specifically binds biotin to the substantial exclusion of other (small) molecules that might be present in a biological sample. Examples of avidin include avidins that are naturally present in egg white, oilseed protein (e.g., soybean meal), and grain (e.g., corn/maize), and streptavidin, which is a protein of bacterial origin. Thus, biotinylation of the binding reagent and use of an avidin molecule such as streptavidin immobilized on the solid support allows reliable attachment of the binding reagent to the solid support according to methods known in the art. Specifically, such a method may comprise providing the binding reagent in biotinylated form, providing a solid support having streptavidin immobilized on its surface, contacting the support with an aqueous solution of the biotinylated binding reagent, and rinsing the support with an aqueous solvent. In addition, binding pair interactions, such as antibody-antigen interactions, may also be utilised for indirect immobilisation of binding reagent onto a support. In such embodiments the support may be derivatised with one member of a binding pair, such as an antibody or fragment or derivative thereof, as defined herein, which has known affinity for a particular peptide sequence or small molecule hapten. Incorporating the other member of the binding pair, such as an antigen, peptide sequence or the hapten onto or into the binding reagent facilitates immobilisation onto a solid support coated with the corresponding antibody or fragment or derivative thereof. Thus, the binding reagent may be modified to include the peptide sequence or hapten into the linear molecule or may be added as a side chain or label. Any suitable antibody-antigen pair may be employed. The antibody fragment or derivative may be any fragment or derivative that retains specific binding affinity for the appropriate antigen. Examples include Fab, F(ab')2 fragments, scFV, VH domains, single domain antibodies (such as nanobodies), heavy chain antibodies and humanized version of non-human antibodies etc. Other high affinity interactions can be utilised for immobilisation of binding reagents, as long as the binding reagent can be synthesised or derivatised with one of the interacting partners and the solid support synthesised or derivatised with the other interacting partner without loss of binding activity (i.e. binding of the binding reagent to the appropriate chemokine receptor). Immobilization may occur via essentially the same interaction in reverse in some embodiments. Thus, the binding reagent which may be a chemokine for example, may be attached to an antibody as defined herein, and the solid support derivatised with the antigen. The chemokine may be produced as a fusion protein with the antibody.

Alternatively binding reagents, such as chemokines and antibodies, can be immobilised directly onto a solid support using bioconjugation techniques established in the field. For example direct immobilisation of proteins onto cyanogen bromide activated solid supports via amino functionalities within the primary sequence of the protein. Alternatively, sulphydryl functionalities within proteins can be used to directly immobilise the protein to alkyl halide derivatised supports or supports containing free thiol functionalities. In further embodiments, proteins containing α-thioester functionalities can be directly immobilised on supports containing 1,2 amino thiol moieties (eg N-terminal cysteine) using the native chemical ligation reaction. Alternatively proteins modified with ketones and aldehydes can be immobilised on solid supports derivatised with hydrazinyl, hydrazide and aminoxy functionalities using hydrazone/oxime bond forming ligation reactions (and vice versa). Alternatively 'Click' chemistry can be used to immobilise proteins onto solid supports, whereby the protein and the support are derivatised with the appropriate mutually reactive chemical functionalities (azides and alkynes). In other embodiments Staudinger ligation chemistry can be used to immobilise appropriately derivatised proteins onto the appropriately derivatised solid supports.

The solid support is contained within or carried by the apheresis column. Thus, by "loaded" is meant that the column carries or contains the solid support in a manner such that (peripheral) blood can flow through the column in contact with the solid support. Thus, the solid support provides a matrix within the column through which blood flows, in continuous fashion in certain embodiments. This permits cells expressing the specific chemokine receptor to be removed from the blood passing through the column, such that blood exiting the column is depleted of the specific chemokine receptor-expressing cells. In specific embodiments, the apheresis column is loaded with a support comprising streptavidin immobilized on the support and one or more biotinylated binding reagents, such as chemokines, bound to the streptavidin on the support. The solid support may be comprised of a high-molecular weight carbohydrate, optionally cross-linked, such as agarose.

As discussed above, the binding reagent is coupled to the solid support. The relative amounts of binding reagent may be controlled to ensure that coupling between the solid support and the binding reagent will be immediate, minimising the risk of binding reagent decoupling from the solid support. Thus, it may be ensured that there is a relative excess of immobilization sites for the binding reagent on the solid support. Alternatively, or additionally, following immobilization of the binding reagent on the solid support, the solid support may be washed to remove any unbound binding reagent.

The apheresis column utilised in the various embodiments of the present invention acts as a leukapheresis treatment for conditions associated with sepsis and/or for the treatment of RDS (including but not limited to sepsis-associated RDS). The column acts to specifically remove one or more of CCR2, CXCR1, CXCR2 and/or CCR5-expressing monocytes, neutrophils or leukocytes by exploiting the interaction between CCR2, CXCR1, CXCR2 and/or CCR5 expressed on the cell surface and a specific binding reagent immobilized on a solid support contained within or carried by the column. The overall column typically comprises, consists of, or consists essentially of three combined components; 1) a housing which contains or carries 2) the solid support and 3) one or more binding reagents (immobilized thereon) which specifically bind one or more chemokine receptors. The housing may be manufactured from any suitable material for clinical use. In certain embodiments the housing is composed of a plastic material. The housing includes an in flow site for entry of blood and an out flow site for blood (depleted of target cells) to exit the column. The housing may be designed to maintain a continuous blood flow through the solid support matrix. The housing (as shown for example in FIG. 9) may include a top portion which comprises a distribution plate (2) at the inflow site (1) to spread the blood evenly over the entire matrix area. The distribution plate may act as a first safety barrier preventing larger particles flowing through the column and into the patient. However, the distribution plate is not essential and may be removed in some embodiments to decrease the overall resistance in the system. The column may contain one or more safety filter units (3 and 4) placed at the inflow (1) and/or outflow (5) sites of the plastic housing. Such filter units may act to prevent particles larger than blood cells passing in and/or out of the column. The safety filter units may contain a plurality of filters, such as two, three or four filters designed to be a robust barrier and stop all particles larger than blood cells passing through the column. Inclusion of safety filters (3 and 4) at both ends of the column serves to minimize the risk of leakage of particles into the patient, including in the event that the device is incorrectly connected resulting in blood flow in the opposite direction to that intended. The safety filters may comprise of any suitable pore size to prevent particles larger than blood cells from passing through the column, as would be readily understood by one skilled in the art. Suitable filters are commercially available. In specific embodiments, the pore size of the filter(s) is between approximately 60 μm and 100 μm, more specifically approximately 80 μm. The solid support and binding reagent components are discussed in further detail herein.

The volume of the housing may be varied depending upon the blood volumes intended to pass through the column. Typically, the volume of the housing is between approximately 40 ml and 200 ml, more specifically 50 ml to 150 ml or 60 ml to 120 ml. The column is generally applied in the form of an apheresis circuit. In this context, the overall system includes the apheresis column, tubing and an appropriate pump to pump the blood around the circuit. The system is illustrated in FIG. 10. The patient (1) is connected to the extracorporeal circuit via sterile needles to veins in the right and the left arms. A saline bag (3) is also connected and the saline solution is pumped with a suitable pump (2). Blood is drawn from one arm of the patient through the sterile tubing system by the blood pump (4) and passed through the column (6) and back to the patient. The tubing system may be connected to the column via any suitable coupling, such as standard dialysis luer-lock couplings. The couplings on the column may be colour-coded for correct assembly. For example, red tubing for inflow to the red column top and blue tubing for outflow back to the patient. An air detector (8) may be present in the circuit. Inlet pressure (5) and/or Pven sensors (7) may additionally be employed to monitor the pressure in the circuit.

An apheresis pump, such as the 4008 ADS pump manufactured by Fresenius Medical Care or the Adamonitor pump, may monitor the patient's inflow and outflow. The pump may also monitor the pressure in the extracorporeal circulation. The pump may be able to discriminate air by a bubble catcher and air detector. A clot catcher filter may be positioned inside the bubble catcher. The pump may also incorporate an optical detector to distinguish between light, e.g. saline solution or air present in the tubing system and dark e.g. blood present in the tubing system.

A schematic diagram of a suitable pump, showing the air detector and optical filter is shown in FIG. 11. If the pump system detects air bubbles and optical fluctuations or if extracorporeal pressure values are out of the set range, then the pump may stop immediately. Alternatively or additionally a visual/audible alarm may be emitted.

The treatment methods of the various embodiments of the invention may thus rely upon an extracorporeal circuit. The methods may be considered as ex vivo or in vitro methods and be defined solely with reference to steps performed outside of the patient. In some embodiments, however, the method further comprises, prior to application of the blood to the column, collecting peripheral blood from the patient. In a further embodiment, the method further comprises, following the application of the blood to the column, infusing the blood depleted of (CCR2, CXCR1, CXCR2 and/or CCR5) chemokine receptor expressing cells to the patient. This is then a complete leukapheresis treatment method. Thus, a leukaphereis method, for treating sepsis, comprises collecting peripheral blood from the patient; applying the peripheral blood to an apheresis column loaded with a solid support comprising one or more binding reagents capable of specifically binding to one or more chemokine receptors, in particular the chemokine receptor CCR2, CXCR1, CXCR2 and/or CCR5, immobilized directly or indirectly on the support thus removing one or more of CCR2, CXCR1, CXCR2 and/or CCR5 expressing cells from the peripheral blood of the patient; and infusing the depleted blood (of chemokine receptor expressing cells) to the patient.

The peripheral blood may be continuously collected from the patient. Similarly, the depleted blood may be continuously infused to the patient, through use of an appropriate circuit as described herein. Thus, the support may be disposed in a column through which the blood is made to flow. This may be achieved using a suitable pump for example, as also described herein. Blood flow through the column enables the binding reagent(s) immobilized on the solid support to capture the cells expressing the chemokine receptor, thus depleting them from the blood and preventing their contribution to the inflammatory condition associated with sepsis.

The methods of the various embodiments of the invention and binding reagents for use in the methods of the various embodiments of the invention may require that the patient has been selected for treatment on the basis of detecting an increase in the level of chemokine receptor, in particular, one or more of CCR2, CXCR1, CXCR2 and/or CCR5 expressing cells in a sample obtained from the patient. Such companion diagnostic methods are described in greater detail herein and are based, for example, on the observation that CCR2, CXCR1, CXCR2 and/or CCR5 expression may be elevated in patients with sepsis. As is shown herein, RDS patients have an increased frequency of CXCR1, CXCR2 and CCR5 expressing neutrophils compared to healthy controls.

Thus, (in this context) in certain embodiments the invention also provides a method of diagnosing, monitoring progression of, or monitoring treatment of sepsis (including sepsis-associated RDS) comprising determining:

a) the levels of one or more of the chemokine receptor CCR2, CXCR1, CXCR2 and/or CCR5 expressing cells b) levels of expression of one or more of CCR2, CXCR1, CXCR2 and/or CCR5; and/or c) levels of cells with high expression of one or more of CCR2, CXCR1, CXCR2 and/or CCR5 in a sample obtained from a subject, wherein high levels of one or more of CCR2, CXCR1, CXCR2 and/or CCR5 expressing cells, high levels of expression of one or more of CCR2, CXCR1, CXCR2 and/or CCR5 or high levels of cells with high expression of one or more of CCR2, CXCR1, CXCR2 and/or CCR5 or increased levels of one or more of CCR2, CXCR1, CXCR2 and/or CCR5 expressing cells compared to control, increased levels of expression of one or more of CCR2, CXCR1, CXCR2 and/or CCR5 compared to a control or increased levels of cells with high expression of one or more of CCR2, CXCR1, CXCR2 and/or CCR5 compared to a control indicate the presence or progression of sepsis. Levels of chemokine receptor expression, as opposed to cell numbers, may also be investigated as increased levels of chemokine receptor expression per cell may also be diagnostically relevant.

The invention also provides a method of diagnosing, monitoring progression of, or monitoring treatment of RDS (including ARDS) comprising determining:

a) the levels of one or more of the chemokine receptor CCR2, CXCR1, CXCR2 and/or CCR5 expressing cells b) levels of expression of one or more of CCR2, CXCR1, CXCR2 and/or CCR5; and/or c) levels of cells with high expression of one or more of CCR2, CXCR1, CXCR2 and/or CCR5 in a sample obtained from a subject, wherein high levels of one or more of CCR2, CXCR1, CXCR2 and/or CCR5 expressing cells, high levels of expression of one or more of CCR2, CXCR1, CXCR2 and/or CCR5 or high levels of cells with high expression of one or more of CCR2, CXCR1, CXCR2 and/or CCR5 or increased levels of one or more of CCR2, CXCR1, CXCR2 and/or CCR5 expressing cells compared to control, increased levels of expression of one or more of CCR2, CXCR1, CXCR2 and/or CCR5 compared to a control or increased levels of cells with high expression of one or more of CCR2, CXCR1, CXCR2 and/or CCR5 compared to a control indicate the presence or progression of RDS. Levels of chemokine receptor expression, as opposed to cell numbers, may also be investigated as increased levels of chemokine receptor expression per cell may also be diagnostically relevant.

"Diagnosing" is defined herein to include screening for a disease/condition or pre-indication of a disease/condition, identifying a disease/condition or pre-indication of a disease/condition and checking for recurrence of disease/condition following treatment. The methods of the various embodiments of the invention may also have prognostic value, and this is included within the definition of the term "diagnosis". The prognostic value of the methods of the various embodiments of the invention may be used as a marker of potential susceptibility to sepsis and/or RDS (including but not limited to sepsis-associated RDS) by identifying levels of one or more of CCR2, CXCR1, CXCR2 and/or CCR5 expression linked to conditions associated with that syndrome. Thus patients at risk may be identified before the disease has a chance to manifest itself in terms of symptoms identifiable in the patient. In certain embodiments, diagnosis may be made in conjunction with other objective indicators of sepsis and/or RDS (including but not limited to sepsis-associated RDS). Thus, in specific embodiments, diagnosis is made in conjunction with one or more of the following indicators:

Defined as Body temperature <36° C. (97° F.) or >38° C. (100° F.) (hypothermia or fever).

Heart rate >90 beats per minute.

Respiratory rate >20 breaths per minute or, on blood gas, a PaCO2 less than 32 mm Hg (4.3 kPa) (tachypnea or hypocapnia due to hyperventilation).

White blood cell count <4,000 cells/mm3 or >12,000 cells/mm3 (<4×109 or >12×109 cells/L).

Clinical indicators, as understood by one skilled in the art, including in vital signs such as pO2, respiration, Xray findings, CRP, ESR levels and patient temperature and evidence/quantitation of bacteria in blood cultures "Monitoring progression of" includes performing the methods to monitor the stage and/or the state and progression of the condition associated with sepsis and/or RDS (including but not limited to sepsis-associated RDS). Monitoring progression may involve performing the diagnostic methods multiple times on the same patient to determine whether the levels of one or more of CCR2, CXCR1, CXCR2 and/or CCR5 expressing cells are increasing, decreasing or remaining stable over a certain time period. This may be in the context of a treatment regime.

"Monitoring the success of a particular treatment" is defined to include determining the levels of one or more of CCR2, CXCR1, CXCR2 and/or CCR5 expressing cells before and after a treatment. The treatment is generally one aimed at treating sepsis and/or RDS (including but not limited to sepsis-associated RDS) and may be a treatment according to one of the methods of the various embodiments of the invention as defined herein. Successful treatment may be determined with reference to a decrease in one or more of CCR2, CXCR1, CXCR2 and/or CCR5 expressing cells as a result of, or following, the treatment. Thus, in such methods a level of one or more of CCR2, CXCR1, CXCR2 and/or CCR5 expressing cells is determined prior to treatment. This level is recorded and a further assessment made at a predetermined time following the treatment. The comparison of levels of one or more of CCR2, CXCR1, CXCR2 and/or CCR5 expressing cells permits the success of the treatment to be monitored. In specific embodiments, a single treatment is sufficient to cause a depletion of around 10%, 20%, 30%, 40%, 50%, 60% or 70%, or higher, up to 80%, 90%, 95% or more, or any range of values between and including these amounts, of one or more specific chemokine receptors, in particular one or more of CCR2, CXCR1, CXCR2 and/or CCR5, expressing cells from the peripheral blood of the patient. In specific embodiments, at least around 50% depletion is achieved in a single treatment. Thus, successful treatment may be defined with reference to depletion of one or more of CCR2, CXCR1, CXCR2 and/or CCR5 expressing cells. Treatment may lead to depletion of between approximately 100 and 500 million of one of more of CCR2, CXCR1, CXCR2 and/or CCR5 expressing cells, such as monocytes or neutrophils, in certain embodiments. Additional factors may be included to determine successful treatment. For example, a lack of increase in one or more of CCR2, CXCR1, CXCR2 and/or CCR5 expressing cells following treatment may indicate successful treatment in terms of preventing further progression of the condition, optionally combined with an improvement in other markers or staging of the condition associated with sepsis and/or RDS (including but not limited to sepsis-associated RDS). By binding to the column through the binding reagent-chemokine receptor interaction, chemokine receptor expressing cells are immobilized. These immobilized cells express further unoccupied chemokine receptors, which may be of the same or different type to those used for capture. These additional chemokine receptors may permit circulating chemokines which contribute to the inflammatory condition to be captured from the peripheral blood. Thus, a reduction in circulating (specific) chemokine levels may provide a measure of successful treatment.

The sample in which one or more of CCR2, CXCR1, CXCR2 and/or CCR5 expressing cell levels, levels of expression of one or more of CCR2, CXCR1, CXCR2 and/or CCR5 and/or levels of cells with high expression of one or more of CCR2, CXCR1, CXCR2 and/or CCR5 (defined as CCR2hi, CXCR1hi, CXCR2hi and/or CCR5hi) are determined may comprise any suitable tissue sample or body fluid sample. Generally, the test sample is obtained from a human subject. Typically, the sample is a blood sample, in particular a peripheral blood sample. The sample may comprise bronchoalveolar lavage fluid in certain embodiments (BALF). The methods may involve determining levels of one or more of CCR2, CXCR1, CXCR2 and/or CCR5 expressing neutrophils in blood or in BALF in certain embodiments. The methods may involve determining levels of one or more of CCR2, CXCR1, CXCR2 and/or CCR5 expressing monocytes, macrophages or lymphocytes in certain embodiments.

Levels of CCR2, CXCR1 and/or CXCR2 expressing cells, levels of expression of CCR2, CXCR1, CXCR2 and/or CCR5 and/or levels of cells with high expression of CCR2, CXCR1, CXCR2 and/or CCR5 (defined as CCR2hi, CXCR1hi and/or CXCR2hi) may be determined according to any suitable method. For example, flow cytometry may be employed in order to determine the number of cells expressing CCR2, CXCR1, CXCR2 and/or CCR5 in the sample, to determine levels of CCR2, CXCR1, CXCR2 and/or CCR5 expression and/or to identify levels of CCR2hi, CXCR1hi, CXCR2hi and/or CCR5hi cells. Flow cytometric techniques are described herein and examples of commercially available antibodies suitably labelled for use in flow cytometry are set out in Table 12 for example. Alternatively, the methods may involve steps of collecting and fixing the cells in the sample, followed by incubation with a suitable binding reagent that binds specifically to the CCR2, CXCR1, CXCR2 and/or CCR5 chemokine receptor expressing cells in the sample. Any suitable binding reagent, as defined herein, may be employed. For example, a CCR2, CXCR1, CXCR2 and/or CCR5 specific antibody may be employed. A wash step may be adopted following an incubation period to remove any unbound reagent. Suitable wash steps and incubation conditions would be well known to one skilled in the art. The binding reagent may be directly labeled in order to permit antibody binding to be directly determined. Alternatively a secondary binding reagent, such as an antibody, may be employed which binds to the first binding reagent and carries a label. Again, suitable incubation conditions and wash steps would be apparent to one skilled in the art. The primary and secondary binding reagents may form two halves of a binding pair. The binding interaction should not prevent the primary binding reagent binding to the CCR2, CXCR1, CXCR2 and/or CCR5 receptor expressing cells, unless a competition assay is being employed. The two halves of a binding pair may comprise an antigen-antibody, antibody-antibody, receptor-ligand, biotin-streptavidin pair etc. in certain embodiments. Other techniques used to quantify chemokine (CCR2, CXCR1, CXCR2 and/or CCR5) receptor expressing cell levels, to quantify levels of CCR2, CXCR1, CXCR2 and/or CCR5 expression and/or to quantify levels of CCR2hi, CXCR1hi, CXCR2hi and/or CCR5hi cells include PCR-based techniques such as QT-PCR and protein based methods such as western blot. Quantitation may be achieved with reference to fixed cell lines carrying known numbers of various receptor expressing cells and/or known levels of receptor expression per cell. Such fixed cell lines are available commercially (for example ChemiScreen™ cell lines from Millipore). Methods analogous to the treatment methods of the various embodiments of the invention may also be employed, with binding of CCR expressing cells to the solid support being determined following peripheral blood being passed through the column.

The levels of CCR2, CXCR1, CXCR2 and/or CCR5 expressing cells, levels of expression of CCR2, CXCR1, CXCR2 and/or CCR5 and/or levels of cells with high expression of CCR2, CXCR1, CXCR2 and/or CCR5 (defined as CCR2, CXCR1, CXCR2 and/or CCR5hi) may be determined relative to a suitable control. When diagnosing a condition associated with a sepsis and/or RDS (including but not limited to sepsis-associated RDS), a threshold level of cells, level of expression of CCR2, CXCR1, CXCR2 and/or CCR5 and/or level of cells with high expression of CCR2, CXCR1, CXCR2 and/or CCR5 (defined as CCR2hi, CXCR1hi, CXCR2hi and/or CCR5hi) may be set at or over which a positive diagnosis is made. This threshold may be determined based upon measuring levels of CCR2, CXCR1, CXCR2 and/or CCR5 expressing cells, levels of expression of CCR2, CXCR1, CXCR2 and/or CCR5 and/or levels of cells with high expression of CCR2, CXCR1, CXCR2 and/or CCR5 (defined as CCR2hi, CXCR1hi, CXCR2hi and/or CCR5hi) in samples obtained from diseased patients and comparing these levels with levels of CCR2, CXCR1, CXCR2 and/or CCR5 expressing cells, levels of expression of CCR2, CXCR1, CXCR2 and/or CCR5 and/or levels of cells with high expression of CCR2, CXCR1, CXCR2 and/or CCR5 (defined as CCR2hi, CXCR1hi, CXCR2hi and/or CCR5hi) in samples obtained from healthy subjects.

In certain embodiments, sepsis and/or respiratory distress syndrome (RDS) is diagnosed on the basis of levels of chemokine receptor expressing cells, such as CCR2, CXCR1, CXCR2 and/or CCR5 expressing cells. A positive diagnosis may be made in subjects based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, sepsis and/or respiratory distress syndrome (RDS) is diagnosed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, such as CCR2, CXCR1, CXCR2 and/or CCR5 expressing cells, relative to healthy controls.

In specific embodiments, RDS is diagnosed on the basis of levels of CXCR1, CXCR2 or CCR5 expressing cells, in particular neutrophils. A positive diagnosis may be made in subjects based upon the presence of greater than about 2%, greater than about 3%, greater than about 4%, greater than about 5%, greater than about 10%, greater than about 15% or greater than about 20% CCR5 expressing cells, in particular neutrophils in the sample, as a percentage of total cells in the sample. A positive diagnosis may be made in subjects based upon the presence of greater than about 40%, greater than about 45%, greater than about 50%, greater than about 55%, greater than about 60%, greater than about 65%, greater than about 70%, greater than about 75%, greater than about 80%, greater than about 85% or more CXCR1 or CXCR2 expressing cells, in particular neutrophils in the sample, as a percentage of total cells in the sample. A positive diagnosis may be made in subjects based upon the presence of about a 1.2 fold or greater increase, such as about a 1.5, 2, 2.5, 3, 3.5, 4, 4.5, 5, 10, 20, 50 or 100 or greater fold increase in the specific chemokine receptor expressing cells, relative to healthy controls.

In certain embodiments, progression of sepsis and/or respiratory distress syndrome (RDS), which may be in the context of a treatment regime, is monitored on the basis of levels of chemokine receptor expressing cells, such as CCR2, CXCR1, CXCR2 and/or CCR5 expressing cells at different time points. Progression of sepsis and/or respiratory distress syndrome (RDS) may be indicated in subjects based upon an increase of greater than about 1%, greater than about 2%, greater than about 3%, greater than about 4%, greater than about 5%, greater than about 10%, such as an increase of greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75% or more chemokine receptor expressing cells in the sample, as a percentage of total cells in the sample, compared to a sample taken from the same subject at an earlier time point. In other embodiments, progression of sepsis and/or respiratory distress syndrome (RDS) is confirmed on the basis of the presence of a about a 1.2 fold or greater increase, such as about a 1.5, 2, 2.5, 3, 3.5, 4, 4.5, 5, 10, 20, 50 or 100 or greater fold increase in chemokine receptor expressing cells, relative to a sample taken from the same subject at an earlier time point.

In specific embodiments, sepsis and/or RDS is monitored on the basis of levels of CXCR1, CXCR2 or CCR5 expressing cells, in particular neutrophils. Progression of the disease, which may be in the context of a treatment regime, may be indicated in subjects based upon the presence of an increase of greater than about 2%, greater than about 3%, greater than about 4%, greater than about 5%, greater than about 10%, greater than about 15% or greater than about 20% CCR5 expressing cells, in particular neutrophils in the sample, as a percentage of total cells in the sample, compared to a sample taken from the same subject at an earlier time point. In other embodiments, progression of the disease, which may be in the context of a treatment regime, may be indicated in subjects based upon the presence of an increase of greater than about 40%, greater than about 45%, greater than about 50%, greater than about 55%, greater than about 60%, greater than about 65%, greater than about 70%, greater than about 75%, greater than about 80%, greater than about 85% or more CXCR1 or CXCR2 expressing cells, in particular neutrophils in the sample, as a percentage of total cells in the sample, compared to a sample taken from the same subject at an earlier time point.

In other embodiments, progression of sepsis and/or respiratory distress syndrome (RDS) is confirmed on the basis of the presence of a about a 1.2 fold or greater increase, such as about a 1.5, 2, 2.5, 3, 3.5, 4, 4.5, 5, 10, 20, 50 or 100 or greater fold increase in CXCR1, CXCR2 or CCR5 expressing cells, in particular neutrophils, relative to a sample taken from the same subject at an earlier time point.

Regression or successful treatment may be monitored based upon similar decreases over various time points. For example, regression or successful treatment may be indicated in subjects based upon a decrease of greater than about 1%, greater than about 2%, greater than about 3%, greater than about 4%, greater than about 5%, about 10%, such as a decrease of about 15%, about 20%, about 25%, about 30%, about 35%, about 40%, about 45%, about 50%, about 55%, about 60%, about 65%, about 70%, about 75% or more chemokine receptor expressing cells, such as CCR2, CXCR1, CXCR2 and/or CCR5 expressing cells in the sample, as a percentage of total cells in the sample, compared to a sample taken from the same subject at an earlier time point. In other embodiments, regression of sepsis and/or respiratory distress syndrome (RDS) is confirmed on the basis of the presence of a about a 1.2 fold or greater decrease, such as about a 1.5, 2, 2.5, 3, 3.5, 4, 4.5, 5, 10, 20, 50 or 100 or greater fold decrease in chemokine receptor expressing cells, relative to a sample taken from the same subject at an earlier time point.

In specific embodiments, sepsis and/or respiratory distress syndrome (RDS) is monitored on the basis of levels of CXCR1, CXCR2 or CCR5 expressing cells, in particular neutrophils. Regression or successful treatment of the disease may be made in subjects based upon a decrease of greater than about 2%, greater than about 3%, greater than about 4%, greater than about 5%, greater than about 10%, greater than about 15% or greater than about 20% CCR5 expressing cells, in particular neutrophils in the sample, as a percentage of total cells in the sample or by a decrease of about greater than about 2%, greater than about 3%, greater than about 4%, greater than about 5%, greater than about 10%, greater than about 15% or greater than about 20% CCR5 expressing cells, in particular neutrophils in the sample, as a percentage of total cells in the sample, compared to a sample taken from the same subject at an earlier time point.

In other embodiments, regression or successful treatment of the disease may be made in subjects based upon a decrease of greater than about 40%, greater than about 45%, greater than about 50%, greater than about 55%, greater than about 60%, greater than about 65%, greater than about 70%, greater than about 75%, greater than about 80%, greater than about 85% or more CXCR1 or CXCR2 expressing cells, in particular neutrophils in the sample, as a percentage of total cells in the sample or by a decrease of greater than about 40%, greater than about 45%, greater than about 50%, greater than about 55%, greater than about 60%, greater than about 65%, greater than about 70%, greater than about 75%, greater than about 80%, greater than about 85% or more CXCR1 or CXCR2 expressing cells, in particular neutrophils in the sample, as a percentage of total cells in the sample, compared to a sample taken from the same subject at an earlier time point.

In still further embodiments, regression of sepsis and/or respiratory distress syndrome (RDS) is confirmed on the basis of the presence of a about a 1.2 fold or greater decrease, such as about a 1.5, 2, 2.5, 3, 3.5, 4, 4.5, 5, 10, 20, 50 or 100 or greater fold decrease in CXCR1, CXCR2 or CCR5 expressing cells, in particular neutrophils, relative to a sample taken from the same subject at an earlier time point.

Suitable software is freely available (such as the R project for statistical computing) to perform the necessary statistical analysis of the data obtained to calculate a useful threshold. The threshold may be set to maximize sensitivity and/or specificity of the test. Performance of the test in these respects may be measured by plotting a receiver operating characteristics (ROC) curve (sensitivity versus specificity). The area under the curve provides an indication of the overall performance of the test. Thus, once thresholds have been set for diagnosing the condition, a separate control experiment does not necessarily have to be run each time a sample is tested. Rather reference can simply be made to the pre-existing thresholds to determine the diagnosis. However, in certain embodiments, the sample is tested together with a control sample taken from a healthy subject to provide a comparator based upon essentially identical experimental conditions. The test sample is generally tested in parallel with the control sample. The test sample level of CCR2, CXCR1, CXCR2 and/or CCR5 expressing cells, levels of expression of CCR2, CXCR1, CXCR2 and/or CCR5 and/or levels of cells with high expression of CCR2, CXCR1, CXCR2 and/or CCR5 (defined as CCR2hi, CXCR1hi, CXCR2hi and/or CCR5hi) can then be compared with that of the control sample to make the diagnosis. A control sample from a disease patient may also be tested in certain embodiments. Reference to controls permits relative levels ("high", "low" etc.) of CCR2, CXCR1, CXCR2 and/or CCR5 expressing cells in the test sample to be readily identified and the significance thereof interpreted. Reference to controls also permits relative levels of CCR2, CXCR1, CXCR2 and/or CCR5 expression ("high", "low" etc.) within the cell population to be determined and the significance thereof interpreted. Such determination may, for example, indicate the average levels of CCR2, CXCR1, CXCR2 and/or CCR5 expression per cell in the test sample.

Thus, in specific embodiments, high or higher levels of one or more of CCR2, CXCR1, CXCR2 and/or CCR5 expressing cells or high or higher levels of one or more of CCR2, CXCR1, CXCR2 and/or CCR5 expression, for example average CCR2, CXCR1, CXCR2 and/or CCR5 expression per cell, or high or higher levels of one or more of CCR2hi, CXCR1hi, CXCR2hi and/or CCR5hi cells correlate with active disease or more active disease associated with sepsis and/or RDS. Similarly, lower or low levels of one or more of CCR2, CXCR1, CXCR2 and/or CCR5 expressing cells, or low or lower levels of one or more of CCR2, CXCR1, CXCR2 and/or CCR5 expression, for example average CCR2, CXCR1, CXCR2 and/or CCR5 expression per cell, or low or lower levels of one or more of CCR2hi, CXCR1hi, CXCR2hi and/or CCR5hi cells may correlate with a lack of active inflammation or disease associated with sepsis and/or RDS (including but not limited to sepsis-associated RDS). This may be defined as "less active disease". It can readily be envisaged that control samples may be assessed and levels of CCR2, CXCR1, CXCR2 and/or CCR5 expressing cells, levels of expression of CCR2, CXCR1, CXCR2 and/or CCR5 and/or levels of cells with high expression of CCR2, CXCR1, CXCR2 and/or CCR5 (defined as CCR2hi, CXCR1hi, CXCR2hi and/or CCR5hi) determined across the range of severities of conditions associated with sepsis and/or RDS (including but not limited to sepsis-associated RDS). This may assist in correlating the levels of CCR2, CXCR1, CXCR2 and/or CCR5 expressing cells, levels of expression of CCR2, CXCR1, CXCR2 and/or CCR5 and/or levels of cells with high expression of CCR2, CXCR1, CXCR2 and/or CCR5 (defined as CCR2hi, CXCR1hi, CXCR2hi and/or CCR5hi) in the test sample with the relative severity of the condition.

When monitoring progression of, or monitoring treatment of sepsis and/or RDS (including but not limited to sepsis-associated RDS), the control samples may be taken from the subject at an earlier time point. They may, however, be based upon known reference values as discussed above. Thus, relative levels of CCR2, CXCR1, CXCR2 and/or CCR5 expressing cells, relative levels of CCR2, CXCR1, CXCR2 and/or CCR5 expression including relative levels of average CCR2, CXCR1, CXCR2 and/or CCR5 expression per cell or relative levels of CCR2hi, CXCR1hi, CXCR2hi and/or CCR5hi cells may be with reference to samples taken from the same subject at a different point in time. In certain embodiments, decreased levels of one or more of CCR2, CXCR1, CXCR2 and/or CCR5 expressing cells, decreased relative levels of one or more of CCR2, CXCR1, CXCR2 and/or CCR5 expression including decreased relative levels of average CCR2, CXCR1, CXCR2 and/or CCR5 expression per cell, or decreased relative levels of one or more of CCR2hi, CXCR1hi, CXCR2hi and/or CCR5hi cells correlate with successful treatment. The treatment may be any suitable treatment, but in specific embodiments is a treatment according to the various embodiments of the invention.

When monitoring progression of sepsis and/or RDS (including but not limited to sepsis-associated RDS), increased levels of one or more of CCR2, CXCR1, CXCR2 and/or CCR5 expressing cells increased relative levels of one or more of CCR2, CXCR1, CXCR2 and/or CCR5 expression including increased relative levels of average CCR2, CXCR1, CXCR2 and/or CCR5 expression per cell or increased relative levels of one or more of CCR2hi, CXCR1hi, CXCR2hi and/or CCR5hi cells may indicate the progression of condition or disease. Thus, if levels of one or more of CCR2, CXCR1, CXCR2 and/or CCR5 expressing cells, levels of expression of one or more of CCR2, CXCR1, CXCR2 and/or CCR5 and/or levels of cells with high expression of one or more of CCR2, CXCR1, CXCR2 and/or CCR5 (defined as CCR2hi, CXCR1hi, CXCR2hi and/or CCR5hi) are increased in a sample taken later than a sample from the same patient this may indicate progression of the condition.

Since the levels of one or more of CCR2, CXCR1, CXCR2 and/or CCR5 expressing cells, levels of one or more of CCR2, CXCR1, CXCR2 and/or CCR5 expression or levels of one or more of CCR2hi, CXCR1hi, CXCR2hi and/or CCR5hi cells are diagnostically relevant, determining such levels in a sample obtained from a subject may influence treatment selection for that subject. Accordingly, in certain embodiments the invention provides a method of selecting a suitable treatment for sepsis (including sepsis-associated RDS) comprising determining:
a) the levels of one or more of the chemokine receptor CCR2, CXCR1, CXCR2 and/or CCR5 expressing cells
b) levels of expression of one or more of CCR2, CXCR1, CXCR2 and/or CCR5; and/or
c) levels of cells with high expression of one or more of CCR2, CXCR1, CXCR2 and/or CCR5
in a sample obtained from a subject, wherein high levels of one or more of CCR2, CXCR1, CXCR2 and/or CCR5 expressing cells, high levels of expression of one or more of CCR2, CXCR1, CXCR2 and/or CCR5 or high levels of cells with high expression of CCR2, CXCR1, CXCR2 and/or CCR5 or increased levels of one or more of CCR2, CXCR1, CXCR2 and/or CCR5 expressing cells compared to control, increased levels of expression of one or more of CCR2, CXCR1, CXCR2 and/or CCR5 compared to a control or increased levels of cells with high expression of one or more of CCR2, CXCR1, CXCR2 and/or CCR5 compared to a control, result in selection of a treatment as defined herein for treatment of the condition associated with sepsis. In certain embodiments, the chemokine receptor expressing cells are high chemokine receptor expressing cells, in particular, high CCR2, CXCR1, CXCR2 and/or CCR5 expressing cells.

Similarly, the invention provides a method of selecting a suitable treatment for RDS, in particular ARDS, comprising determining:
a) the levels of one or more of the chemokine receptor CCR2, CXCR1, CXCR2 and/or CCR5 expressing cells
b) levels of expression of one or more of CCR2, CXCR1, CXCR2 and/or CCR5; and/or
c) levels of cells with high expression of one or more of CCR2, CXCR1, CXCR2 and/or CCR5
in a sample obtained from a subject, wherein high levels of one or more of CCR2, CXCR1, CXCR2 and/or CCR5 expressing cells, high levels of expression of one or more of CCR2, CXCR1, CXCR2 and/or CCR5 or high levels of cells with high expression of CCR2, CXCR1, CXCR2 and/or CCR5 or increased levels of one or more of CCR2, CXCR1, CXCR2 and/or CCR5 expressing cells compared to control, increased levels of expression of one or more of CCR2, CXCR1, CXCR2 and/or CCR5 compared to a control or increased levels of cells with high expression of one or more of CCR2, CXCR1, CXCR2 and/or CCR5 compared to a control, result in selection of a treatment as defined herein for treatment of the RDS, in particular ARDS. In certain embodiments, the chemokine receptor expressing cells are high chemokine receptor expressing cells, in particular, high CCR2, CXCR1, CXCR2 and/or CCR5 expressing cells.

In specific embodiments, sepsis and/or respiratory distress syndrome (RDS) is treated on the basis of measuring levels of chemokine receptor expressing cells, such as CCR2, CXCR1, CXCR2 and/or CCR5 expressing cells. Thus, a treatment according to the various embodiments of the invention may be applied based upon the presence of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, or more chemokine receptor expressing cells in the sample, as a percentage of total cells in the sample. In other embodiments, sepsis and/or respiratory distress syndrome (RDS) is treated according to the various embodiments of the invention on the basis of the presence of a about a 1.5 fold or greater increase, such as about a 2, 2.5, 3, 3.5, 4, 4.5, 5, 10, 20, 50 or 100 or greater fold increase in chemokine receptor expressing cells, such as CCR2, CXCR1, CXCR2 and/or CCR5 expressing cells, relative to healthy controls.

In specific embodiments, sepsis and/or respiratory distress syndrome (RDS) is treated on the basis of measuring levels of CCR2CXCR1, CXCR2 or CCR5 expressing cells, in particular neutrophils. Thus, a treatment according to the various embodiments of the invention may be applied based upon the presence of greater than about 2%, greater than about 3%, greater than about 4%, greater than about 5%, greater than about 10%, greater than about 15% or greater than about 20% CCR5 expressing cells, in particular neutrophils in the sample, as a percentage of total cells in the sample or on the basis of the presence of a about a 1.5 fold or greater increase, such as about a 2, 2.5, 3, 3.5, 4, 4.5, 5, 10, 20, 50 or 100 or greater fold increase in CCR5 expressing cells, relative to healthy controls.

Thus, a treatment according to the various embodiments of the invention may be applied based upon the presence of greater than greater than about 40%, greater than about 45%, greater than about 50%, greater than about 55%, greater than about 60%, greater than about 65%, greater than about 70%, greater than about 75%, greater than about 80%, greater than about 85% or more CXCR1 or CXCR2 expressing cells, in particular neutrophils in the sample, as a percentage of total cells in the sample or on the basis of the presence of a about a 1.5 fold or greater increase, such as about a 2, 2.5, 3, 3.5, 4, 4.5, 5, 10, 20, 50 or 100 or greater fold increase in CXCR1 or CXCR2 receptor expressing cells, relative to healthy controls.

For the avoidance of doubt, all embodiments described in respect of the methods of the various embodiments of the invention apply to these aspects mutatis mutandis and are not repeated for reasons of conciseness. Specifically, sepsis may be indicated in conjunction with one or more of the following indicators:

Defined as Body temperature <36° C. (97° F.) or >38° C. (100° F.) (hypothermia or fever).

Heart rate >90 beats per minute.

Respiratory rate >20 breaths per minute or, on blood gas, a PaCO2 less than 32 mm Hg (4.3 kPa) (tachypnea or hypocapnia due to hyperventilation).

White blood cell count <4,000 cells/mm3 or >12,000 cells/mm3 (<4×109 or >12×109 cells/L).

Clinical indicators, as understood by one skilled in the art, including in vital signs such as pO2, respiration, Xray findings, CRP, ESR levels and patient temperature and evidence/quantitation of bacteria in blood cultures In specific embodiments, the sample is a peripheral blood sample or may be a BALF.

The methods and medical uses of the various embodiments of the invention thus can be tailored to the need of individual patients or groups of patients on the basis of the various diagnostic methods of the various embodiments of the invention. By removing from the circulation one or more of CCR2, CXCR1, CXCR2 and/or CCR5 expressing cells, such as monocytes, macrophages, neutrophils and lymphocytes, in particular monocytes, upregulated in various inflammatory conditions associated with sepsis, an important factor in the inflammatory process of sepsis associated conditions can be controlled. By removing from the circulation one or more of CCR5, CXCR1 and/or CXCR2 and/or CCR2 expressing cells, in particular neutrophils, upregulated in RDS and in particular ARDS (including but not limited to sepsis-associated RDS), an important factor in the inflammatory process of RDS (including but not limited to sepsis-associated RDS) can be controlled.

M. Modified and Truncated Chemokines

The modified and truncated chemokines described in greater detail herein (with reference to the relevant amino acid sequences, as set forth in the SEQ ID NOs and accompanying experimental examples) may each be applied according to the various embodiments of the present invention. Such modified forms may instruct the skilled person regarding additional modified forms of the same and other chemokines which may be suitable for use in the various embodiments of the invention. Chemokines show variable sequence homology varying forrom less than 20% to over 90% but all share very similar tertiary structures consisting of a disordered N-terminus, followed by a long loop (the N-loop) that ends in a 310 helix, a 3-stranded β-sheet and a C-terminal helix. The overall topology is stabilsed by disulphide bonds. This common tertiary structure is a common feature of the chemokine protein family (Fernandez E J and Lolis E, Annu. Rev. Pharmacol. Toxicol., 202, 42, 469-99; Allen S J et al, Annu. Rev. Immunol., 2007, 25, 787-820, incorporated herein by reference).

Truncations within this N-terminal region can maintain binding to the receptor but can lead to a change or loss of function (for examples Zhang Y J et al, J. Biol. Chem., 1994, 269, 15918; Gong J-H and Clark-Lewis I., J. Exp. Med., 1995, 181, 631-640; Fernandez E J and Lolis E., Annu. Rev. Pharmacol. Toxicol., 202, 42, 469-99; Allen S J et al, Annu. Rev. Immunol., 2007, 25, 787-820, each of which is incorporated herein by reference).

Truncations forat the C-terminus of the chemokine can also be made and maintain receptor binding activity (Treating Inflammatory Disorders, Ola Winqvist and Graham Cotton, WO2010/029317, incorporated herein by reference in its entirety).

In other embodiments, fragments and variants of chemokines are used in the devices and methods as disclosed herein. More particularly, such fragments and variants retain the ability to specifically bind to their cognate chemokine receptor. Chemokines are known by those skilled in the art to share specific receptor binding domains, including a similar monomeric fold, characterized, for example, by a disordered amino-terminal domain, followed by a conserved core region, consisting of the so called "N-loop," three anti-parallel β-strands, and a carboxyl-terminal α-helix. While not being bound by theory, it is believed that the chemokine-chemokine receptor interaction is a two-step mechanism, in which the core of the chemokine interacts first with a binding site formed by the extracellular domains of the receptor, while another interaction is formed between the chemokine N terminus and a second binding site on the receptor in order to trigger receptor activation. Thus, a "fragment," such as a functional fragment of a chemokine is intended to mean a portion of the amino acid sequence of the protein that retains binding for its cognate receptor. The fragment may include, for example, the monomeric fold region, or portions thereof such as the amino-terminal domain, the conserved core region and/or the "N-loop," the anti-parallel β-strands, and/or the carboxyl-terminal α-helix or combinations and portions thereof.

Further, it is recognized that a polypeptide can be considerably mutated without materially altering one or more of the polypeptide's functions, for example, without altering specific binding and/or the folding of the protein. The genetic code is well known to be degenerate, and thus different codons encode the same amino acids. Even where an amino acid substitution is introduced, the mutation can be conservative and have no material impact on the essential functions of a protein (see for example, Stryer, Biochemistry 4th Ed., W. Freeman & Co., New York, N.Y., 1995). This includes, for example, the ability of the protein to bind and interact with other proteins, such as a truncated chemokine binding to its cognate receptor.

In some examples, part of a polypeptide chain can be deleted without impairing or eliminating all of its functions. For example, the deletion of between about 1 and about 20 amino acids on the C- and/or N-terminus, such as deletions of about 1, 2, 3, 4, 5, 6, 7, 8, 9, 10, 11, 12, 13, 14, 15, 16, 17, 18, 19, or 20 amino acids at the C- and/or N-terminus, can result in a chemokine that retains function, such as specific binding of its cognate receptor. Such truncations can retain the full function of an entire protein, and/or can allow for retained functions such as protein-protein interactions as in the case of ligand-receptor interactions. Chemokines having deletions of a small number of amino acids, for example, less than about 20% (such as less than about 18%, less than about 15%, less than about 10%, less than about 8%, less than about 5%, less than about 2%, or less than about 1%) of the total number of amino acids in the wild type chemokine can also be used in the methods and devices disclosed herein. Moreover, insertions or additions can be made in the polypeptide chain for example, adding epitope tags, without impairing or eliminating its functions (Ausubel et al., Current Protocols in Molecular Biology, Greene Publ. Assoc. and Wiley-Intersciences, 1998). Other modifications that can be made without materially impairing one or more functions of a polypeptide include, for example, in vivo or in vitro chemical and biochemical modifications or the incorporation of unusual amino acids. In some examples, a functional fragment of a chemokine may consist of about 10 or more, about 25 or more, about 50 or more, about 75 or more, about 100 or more, about 125 or more, about 150, about 175 or more, or about more or 200 or more amino acid residues of a chemokine amino acid sequence.

In some examples, the chemokine or a functional fragment thereof has an amino acid that has at least about 60% or 65% sequence identity, about 70% or 75% sequence identity, about 80% or 85% sequence identity, about 90%, 91%, 92%, 93%, 94%, 95%, 96%, 97%, 98% or 99% sequence identity over its full length as compared to a reference sequence, such as those detailed herein, for example using the NCBI Blast 2.0 gapped BLAST set to default parameters. Alignment may also be performed manually by inspection. One or more conservative amino acid modifications can also be made in the chemokine amino acid sequence, whether an addition, deletion or modification, that does not substantially alter the 3-dimensional structure of the polypeptide or its ability to bind to the cognate receptor. For example, a conservative amino acid substitution does not affect the ability of the chemokine to specifically bind its cognate receptor. Conservative substitution tables providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

Peptides, such as chemokines and fragments thereof, can be modified by a variety of chemical techniques to produce derivatives having essentially the same activity or function—such as binding to a cognate receptor—as the unmodified peptides, and optionally having other desirable properties. For example, carboxylic acid groups of the protein, whether carboxyl-terminal or side chain, may be provided in the form of a salt of a pharmaceutically-acceptable cation or esterified to form a C1-C16 ester, or converted to an amide of formula NR1R2 wherein R1 and R2 are each independently H or C1-C16 alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to C1-C16 alkyl or dialkyl amino or further converted to an amide.

Hydroxyl groups of the peptide side chains can be converted to C1-C16 alkoxy or to a C1-C16 ester using well-recognized techniques. Phenyl and phenolic rings of the peptide side chains can be substituted with one or more halogen atoms, such as F, Cl, Br or I, or with C1-C16 alkyl, C1-C16 alkoxy, carboxylic acids and esters thereof, or amides of such carboxylic acids. Methylene groups of the peptide side chains can be extended to homologous C2-C4 alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclizing methods include the formation of thioethers and carboxyl- and amino-terminal amides and esters.

Peptidomimetic and organomimetic embodiments are also within the scope of the present disclosure, whereby the three-dimensional arrangement of the chemical constituents of such peptido- and organomimetics mimic the three-dimensional arrangement of the peptide backbone and component amino acid side chains, resulting in such peptido- and organomimetics of the proteins of this disclosure. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, Pharmaceutical Biotechnology, Interpharm Press: Buffalo Grove, Ill., pp. 165 174 and Principles of Pharmacology Munson (ed.) 1995, Ch. 102, for descriptions of techniques used in CADD. Also included within the scope of the disclosure are mimetics prepared using such techniques.

Amino acids in a peptide, polypeptide, or protein generally are chemically bound together via amide linkages (CONH). Additionally, amino acids may be bound together by other chemical bonds. For example, linkages for amino acids or amino acid analogs can include CH2NH—, —CH2S—, —CH2-CH2-, —CH=CH— (cis and trans), —COCH2-, —CH(OH)CH2-, and —CHH2SO— (These and others can be found in Spatola, in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci pp. 463-468, 1980; Hudson, et al., Int J Pept Prot Res 14:177-185, 1979; Spatola et al. Life Sci 38:1243-1249, 1986; Harm J. Chem. Soc Perkin Trans. 1307-314, 1982; Almquist et al. J. Med. Chem. 23:1392-1398, 1980; Jennings-White et al. Tetrahedron Lett 23:2533, 1982; Holladay et al. Tetrahedron. Lett 24:4401-4404, 1983; and Hruby Life Sci 31:189-199, 1982. Fragments and variants of the chemokines used in the disclosed devices and method as disclosed herein are fragments and variants that retain the ability to specifically bind to their chemokine receptor. Chemokines share a similar monomeric fold, characterized by a disordered amino-terminal domain, followed by a conserved core region, consisting of the so called "N-loop," three anti-parallel β-strands, and a carboxyl-terminal α-helix. While not being bound by theory, it is believed that the chemokine-chemokine receptor interaction is a two-step mechanism, in which the core of the chemokine interacts first with a binding site formed by the extracellular domains of the receptor, while another interaction is formed between the chemokine N terminus and a second binding site on the receptor in order to trigger receptor activation. Thus, a "fragment," such as a functional fragment of a chemokine is intended to mean a portion of the amino acid sequence of the protein that retains binding for its cognate receptor. The fragment may include, for example, the monomeric fold region, or portions thereof such as the amino-terminal domain, the conserved core region and/or the "N-loop," the anti-parallel β-strands, and/or the carboxyl-terminal α-helix or combinations thereof. Further, it is recognized that a polypeptide can be considerably mutated without materially altering one or more of the polypeptide's functions, for example, without altering specific binding and/or the folding of the protein. The genetic code is well known to be degenerate, and thus different codons encode the same amino acids. Even where an amino acid substitution is introduced, the mutation can be conservative and have no material impact on the essential functions of a protein (see for example, Stryer, Biochemistry 4th Ed., W. Freeman & Co., New York, N.Y., 1995).

In some examples, part of a polypeptide chain can be deleted without impairing or eliminating all of its functions, for example, the deletion of between about 1 and about 20 amino acids on the C- and/or N-terminus, such as deletions of about 1, 2, 3, 4, 5, 6, 7, 8, 9, 10, 11, 12, 13, 14, 15, 16, 17, 18, 19, or 20 amino acids at the C- and/or N-terminus, can result in a chemokine that retains function, such as specific binding of its cognate receptor. Such truncations can retain the full function of an entire protein. Chemokines having deletions of a small number of amino acids, for example, less than about 20% (such as less than about 18%, less than about 15%, less than about 10%, less than about 8%, less than about 5%, less than about 2%, or less than about 1%) of the total number of amino acids in the wild type chemokine can also be used in the methods and devices disclosed herein. Moreover, insertions or additions can be made in the polypeptide chain for example, adding epitope tags, without impairing or eliminating its functions (Ausubel et al., Current Protocols in Molecular Biology, Greene Publ. Assoc. and Wiley-Intersciences, 1998). Other modifications that can be made without materially impairing one or more functions of a polypeptide include, for example, in vivo or in vitro chemical and biochemical modifications or the incorporation of unusual amino acids. In some examples, a functional fragment of a chemokine may consist of 10 or more, 25 or more, 50 or more, 75 or more, 100 or more, or 200 or more amino acid residues of a chemokine amino acid sequence.

In some examples, chemokine or a functional fragment thereof has an amino acid that has at least about 60% or 65% sequence identity, about 70% or 75% sequence identity, about 80% or 85% sequence identity, about 90%, 91%, 92%, 93%, 94%, 95%, 96%, 97%, 98% or 99% sequence identity over its full length as compared to a reference sequence, such as those detailed herein, for example using the NCBI Blast 2.0 gapped BLAST set to default parameters. Alignment may also be performed manually by inspection. One or more conservative amino acid modifications can also be made in the chemokine amino acid sequence, whether an addition, deletion or modification, that does not substantially alter the 3-dimensional structure of the polypeptide. For example, a conservative amino acid substitution does not affect the ability of the chemokine to specifically bind its cognate receptor. Conservative substitution tables providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

Peptides, such as chemokines, can be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a C1-C16 ester, or converted to an amide of formula NR1R2 wherein R1 and R2 are each independently H or C1-C16 alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to C1-C16 alkyl or dialkyl amino or further converted to an amide.

Hydroxyl groups of the peptide side chains can be converted to C1-C16 alkoxy or to a C1-C16 ester using well-recognized techniques. Phenyl and phenolic rings of the peptide side chains can be substituted with one or more halogen atoms, such as F, Cl, Br or I, or with C1-C16 alkyl, C1-C16 alkoxy, carboxylic acids and esters thereof, or amides of such carboxylic acids. Methylene groups of the peptide side chains can be extended to homologous C2-C4 alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclizing methods include the formation of thioethers and carboxyl- and amino-terminal amides and esters.

Peptidomimetic and organomimetic embodiments are also within the scope of the present disclosure, whereby the three-dimensional arrangement of the chemical constituents of such peptido- and organomimetics mimic the three-dimensional arrangement of the peptide backbone and component amino acid side chains, resulting in such peptido- and organomimetics of the proteins of this disclosure. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, Pharmaceutical Biotechnology, Interpharm Press: Buffalo Grove, Ill., pp. 165 174 and Principles of Pharmacology Munson (ed.) 1995, Ch. 102, for descriptions of techniques used in CADD. Also included within the scope of the disclosure are mimetics prepared using such techniques.

Amino acids in a peptide, polypeptide or protein generally are chemically bound together via amide linkages (CONH). Additionally, amino acids may be bound together by other chemical bonds. For example, linkages for amino acids or amino acid analogs can include $CH_2NH$—, —$CH_2S$—, —$CH_2$-$CH_2$-, —CH=CH— (cis and trans), —$COCH_2$-, —CH(OH)$CH_2$-, and —CH$H_2$SO— (These and others can be found in Spatola, in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci pp. 463-468, 1980; Hudson, et al., Int J Pept Prot Res 14:177-185, 1979; Spatola et al. Life Sci 38:1243-1249, 1986; Harm J. Chem. Soc Perkin Trans. 1307-314, 1982; Almquist et al. J. Med. Chem. 23:1392-1398, 1980; Jennings-White et al. Tetrahedron Lett 23:2533, 1982; Holladay et al. Tetrahedron. Lett 24:4401-4404, 1983; and Hruby Life Sci 31:189-199, 1982.

DESCRIPTION OF THE FIGURES

A. Diagnosing and Treating Inflammatory Bowel Disease and Irritable Bowel Syndrome FIG. 1. Representative flow cytometry plots showing the gating strategies used throughout the study for the CD14+ HLA-DRhi (lower left), CD14loCD16+ (lower middle) and CD14+CD16− (lower right) monocyte populations.

(A) Frequency of CD14+HLA-DRhi monocytes in peripheral blood of IBD patients compared to controls, as determined with flow cytometry. Bars represent mean values ±SEM from controls (n=11) and patients (n=31) with active ulcerative colitis (n=20; UC-DAI 6-12) or Crohn's disease (n=11; HBI 8-16) (p=0.006).

(B) Regression analysis of CD14+HLA-DRhi monocytes and clinical disease activity in patients with ulcerative colitis (p=0.024; r2=0.072). Data represents measurements (n=84) from 28 unique patients at different time points during treatment.

(C) Regression analysis of CD14+HLA-DRhi monocytes and clinical disease activity in patients with Crohn's disease (p=0.016; r2=0.190). Data represents measurements (n=29) from 11 unique patients at different time points during treatment FIG. 3. CD14+HLA-DRhi monocytes are targets for therapy in IBD.

CD14+HLA-DRhi monocyte levels in IBD patients during treatment with (A) GMA apheresis (n=18), (B) corticosteroids (n=16) or (C) anti-TNF-α biological therapy (n=14). Control patient reference levels (n=11) are included in all graphs. (D) IBD patients receiving GMA or corticosteroid therapy, divided into remission (n=12) and non-remission (n=7) patients as well as healthy controls (n=11). Error bars represent group mean values ±SEM.

FIG. 4. CD14+HLA-DRhi monocytes produce high levels of inflammatory mediators.

(A) Representative flow cytometry plots depicting CD14+HLA-DRhi and CD14+HLADR lo purity after flow cytometry sorting.

(B) PCR analysis of TNF-α in CD14+HLA-DRhi monocytes after LPS activation for 2 hrs (n=4, p=0.0047).

(C) Functional grouping of target transcripts from PCR array analysis of CD14+HLADR hi and CD14+HLA-DRlo monocytes from three independent healthy donors after LPS activation for 6 hrs.

(D) The 20 target transcripts that represented the strongest up- and down-regulation in PCR array analyses of CD14+HLA-DRhi monocytes as compared to the CD14+HLADR lo population after LPS activation for 6 hrs. Fold changes range between 347.3-10.9 and −10.3-232.3, respectively.

FIG. 5. The relative chemokine receptor expression in CD14+HLA-DRhi monocytes.

(A) The CD14+HLA-DRhi subset is distinguished from CD14loCD16+ and CD14+CD16− monocytes by their expression of CCR7 and CCR9. (B) Chemokine receptors whose expression levels do not differentiate the CD14+HLA-DRhi population. (C) Control staining showing the difference in expression of CD16 and HLA-DR as well as morphology defined by side-scatter (SSC) and forward-scatter (FSC) appearance between the monocyte populations discussed in this study. Data presented are from one representative IBD patient.

Figure 6:
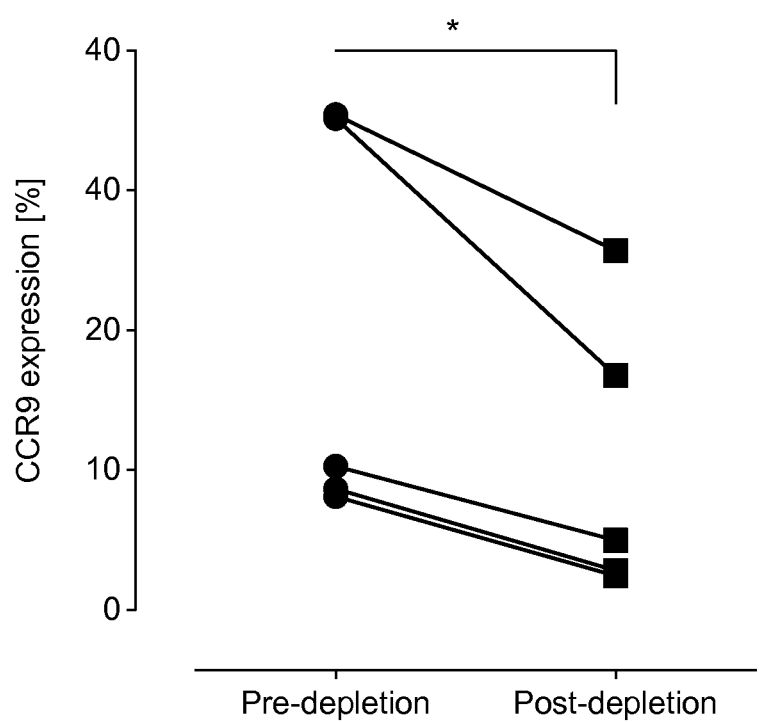

FIG. 6. CCR9-CCL25 functional interaction assay in CD14+HLA-DRhi monocytes

Depletion of CCR9-expressing CD14+HLA-DRhi monocytes from IBD patients using

CCL25-coated microbeads (n=5; p=0.0112).

Figure 7A:
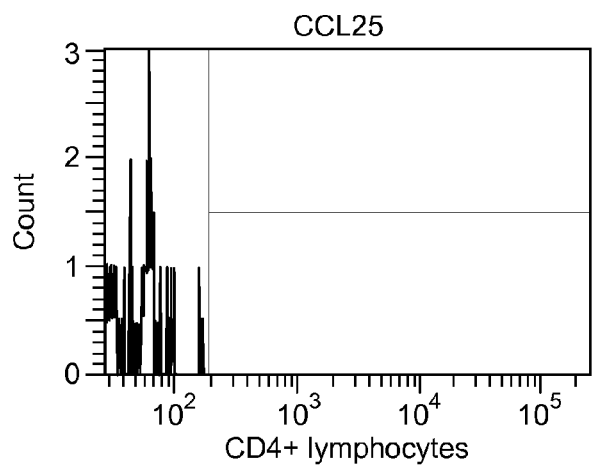
Figure 7B:
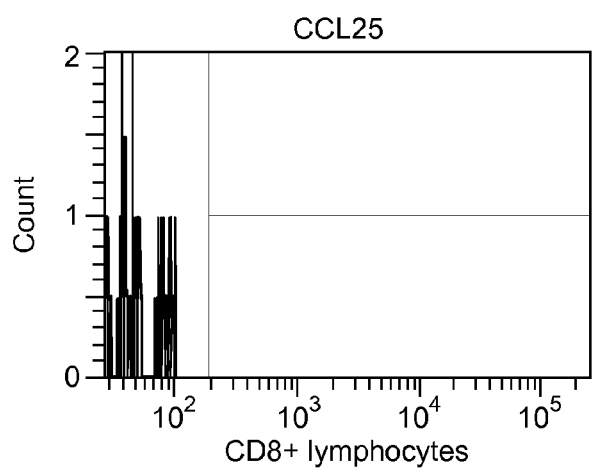
Figure 7C:
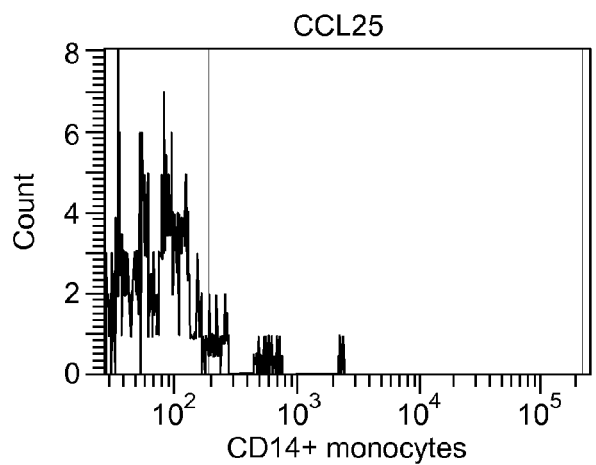
Figure 8A:
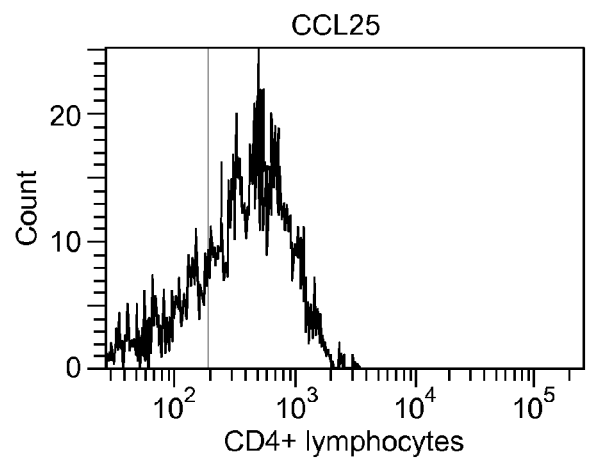
Figure 8B:
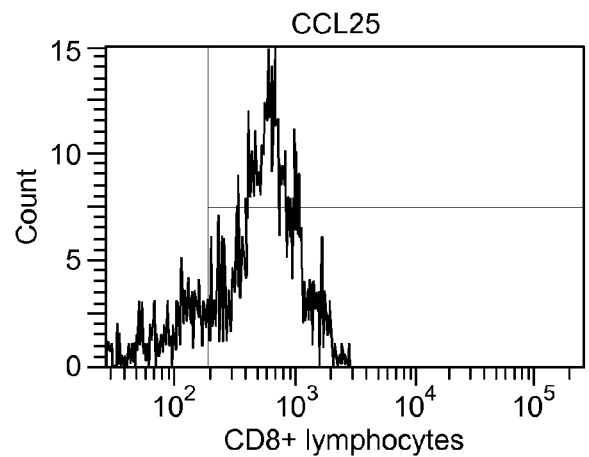
Figure 8C:
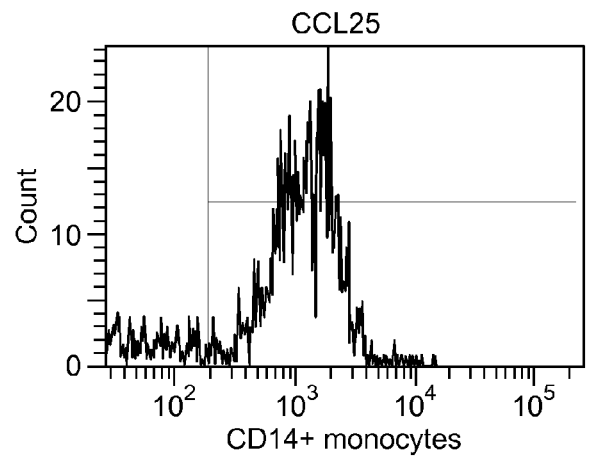
Figure 9:
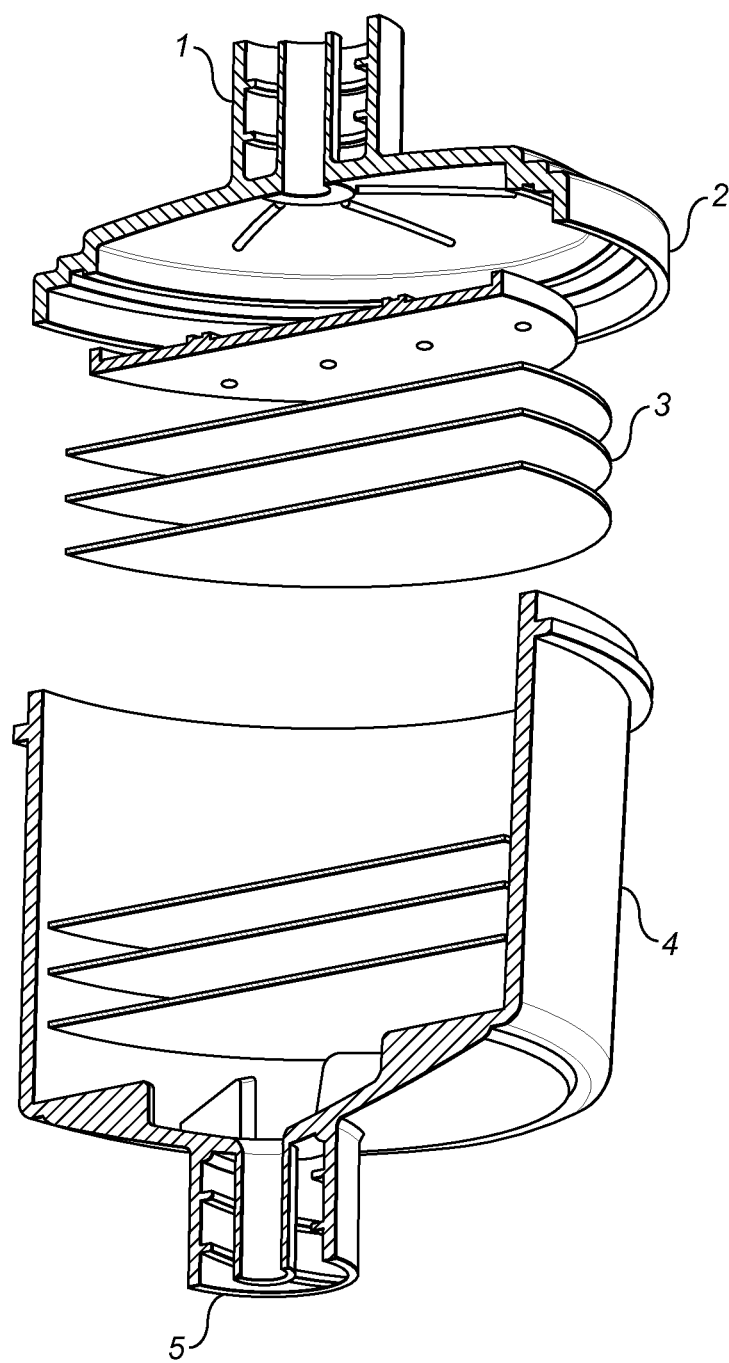

FIGS. 7a, 7b & 7c—the binding of biotinylated CCL25 by CD4+, CD8+ T-cells and CD14+ monocytes respectively, obtained from peripheral blood of a healthy donor;

FIGS. 8a, 8b & 8c—the binding of biotinylized CCL25 by CD4+, CD8+ T-cells and CD14+ monocytes respectively, obtained from peripheral blood of a patient with CD;

FIG. 9—The plastic house and top showing the distribution plate (2) and safety filter units (3 and 4).

Figure 10:
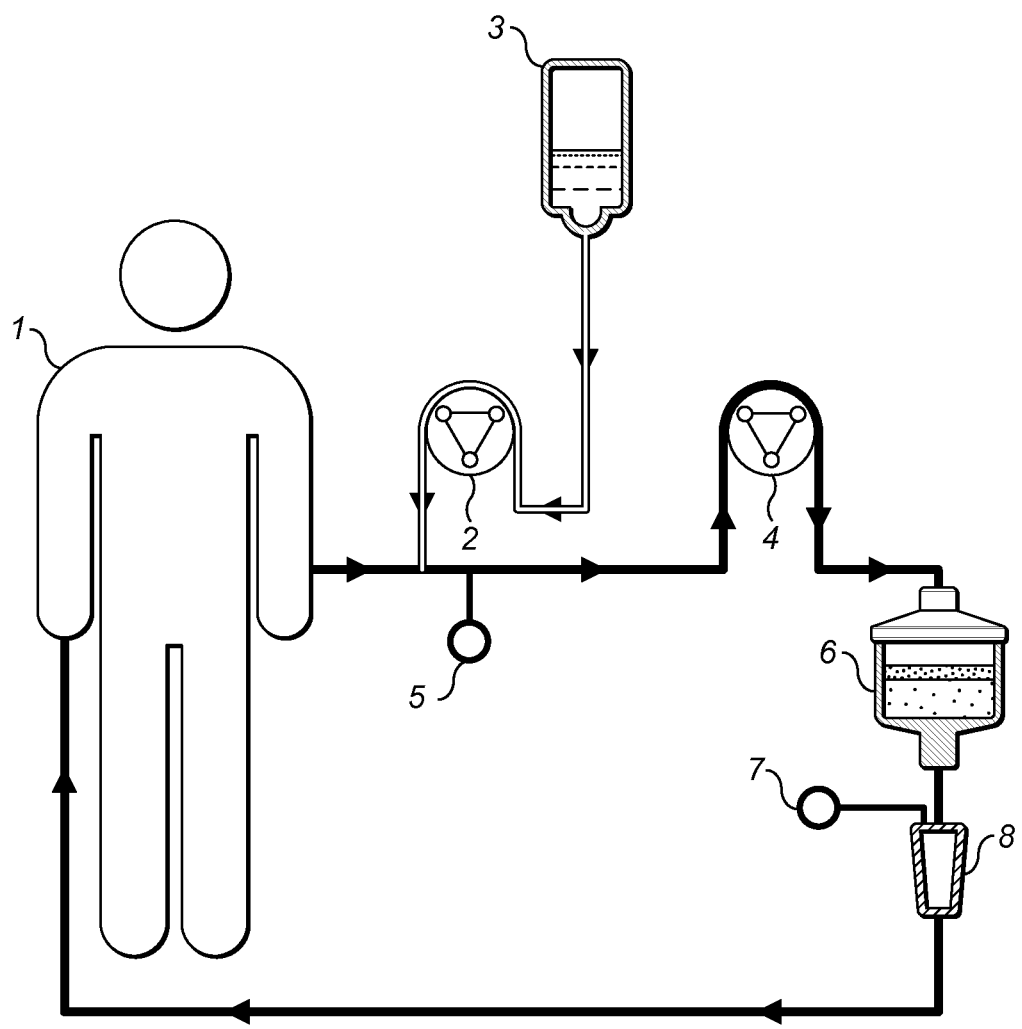

FIG. 10—The overall leukapheresis system.

Figure 11:
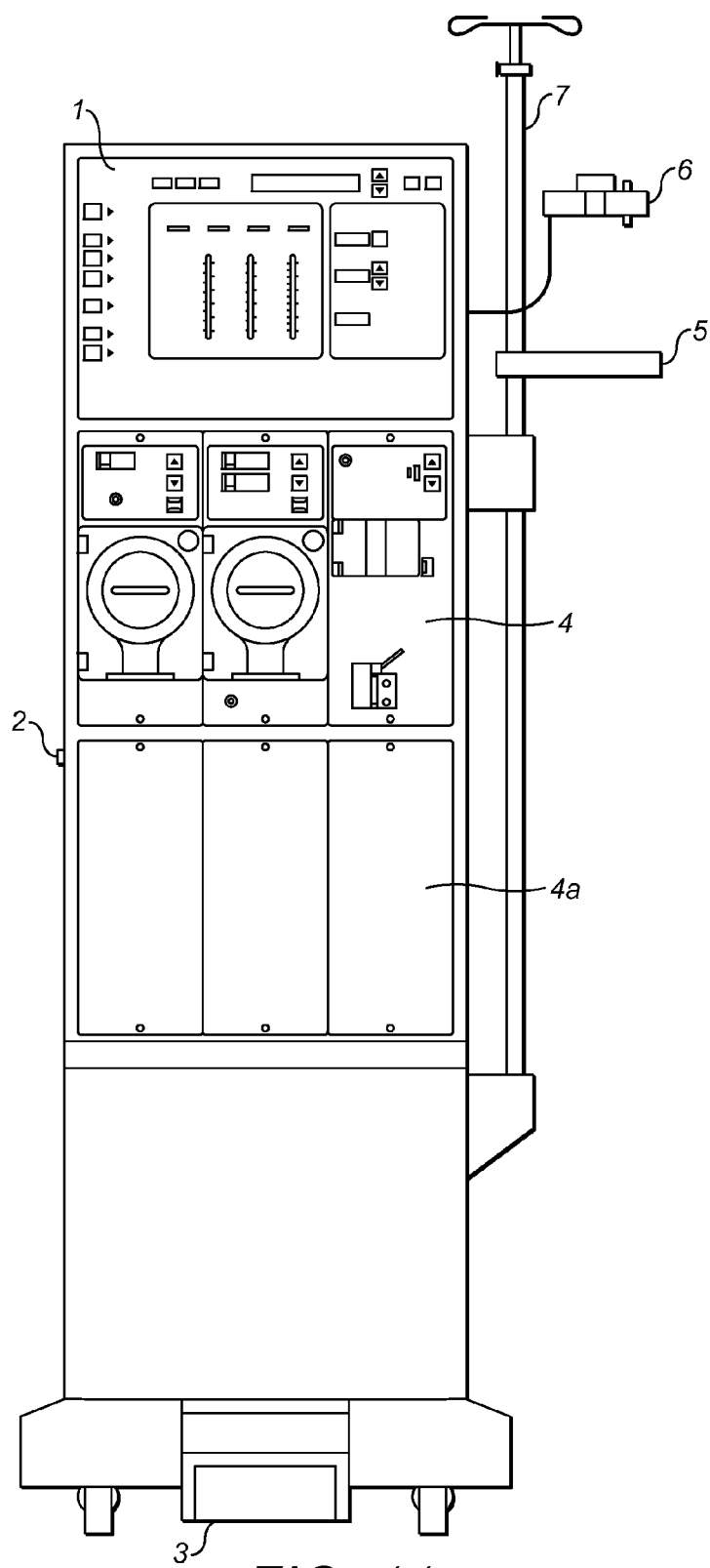

FIG. 11—The pump with air detector and optical detector (4).

Figure 12:
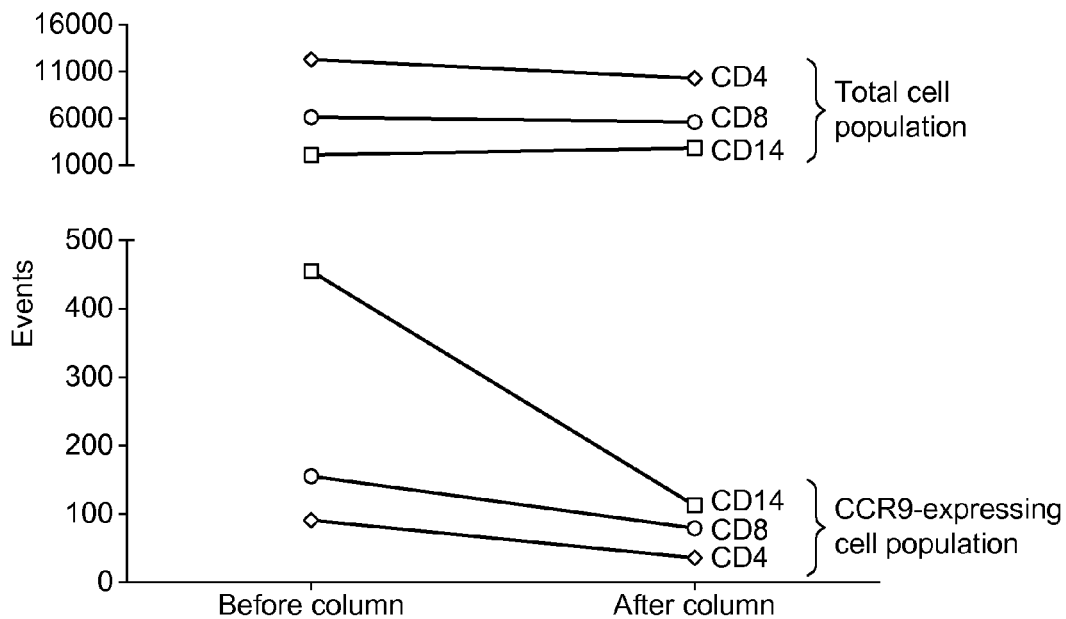

FIG. 12—Depletion of CCR9-expressing cell populations in one blood donor. Total cell populations are unaffected after the column passage.

Figure 13:
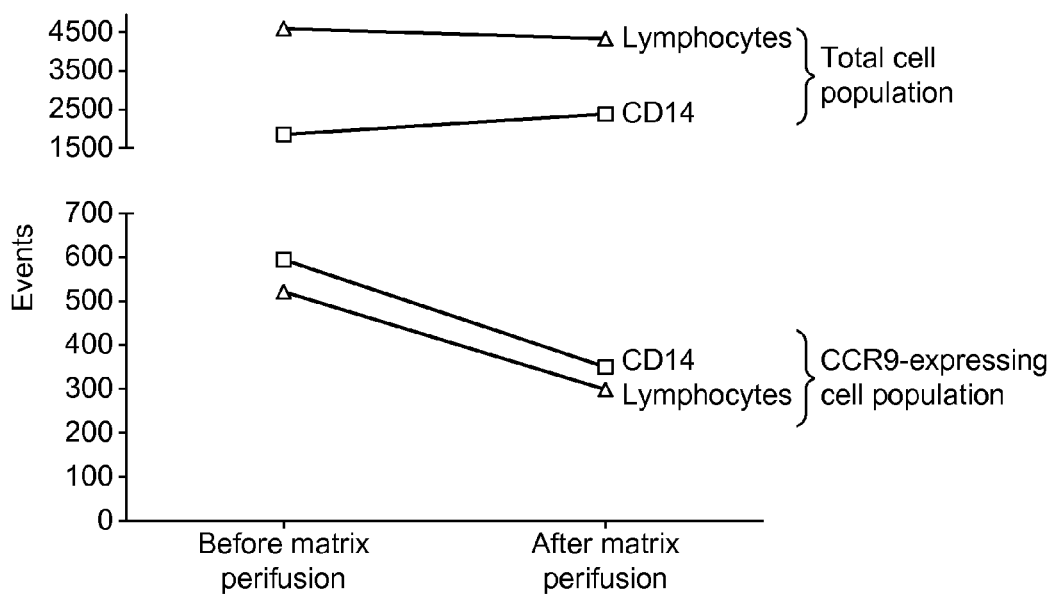

FIG. 13—Depletion of CCR9-expressing cell populations in one IBD patient. Total cell populations are unaffected after the column passage.

Figure 14:
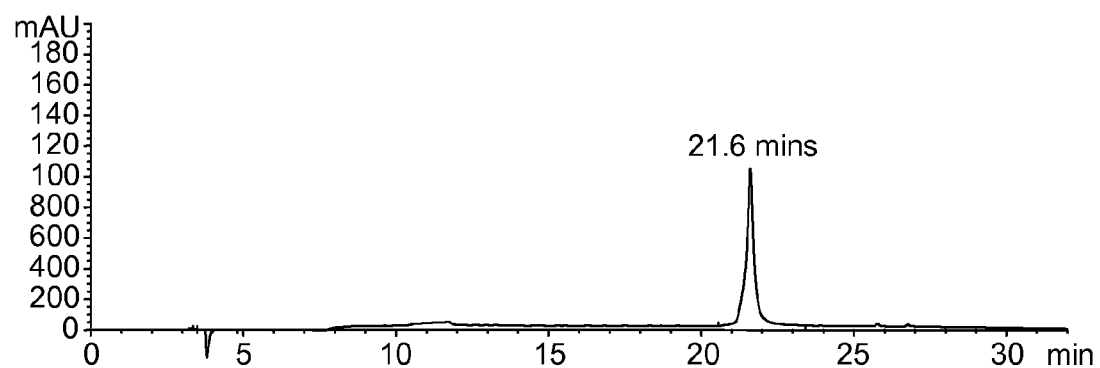

FIG. 14—HPLC of purified folded Biotin-TECK(Nleu).

Figure 15:
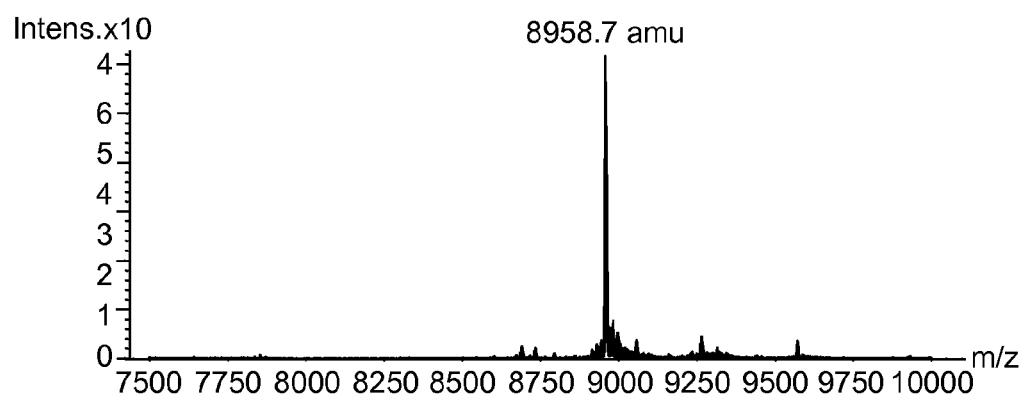

FIG. 15—Electrospray ionisation with tandem mass spectrometry (ES/MS) data of purified folded Biotin-TECK (Nleu).

Figure 16:
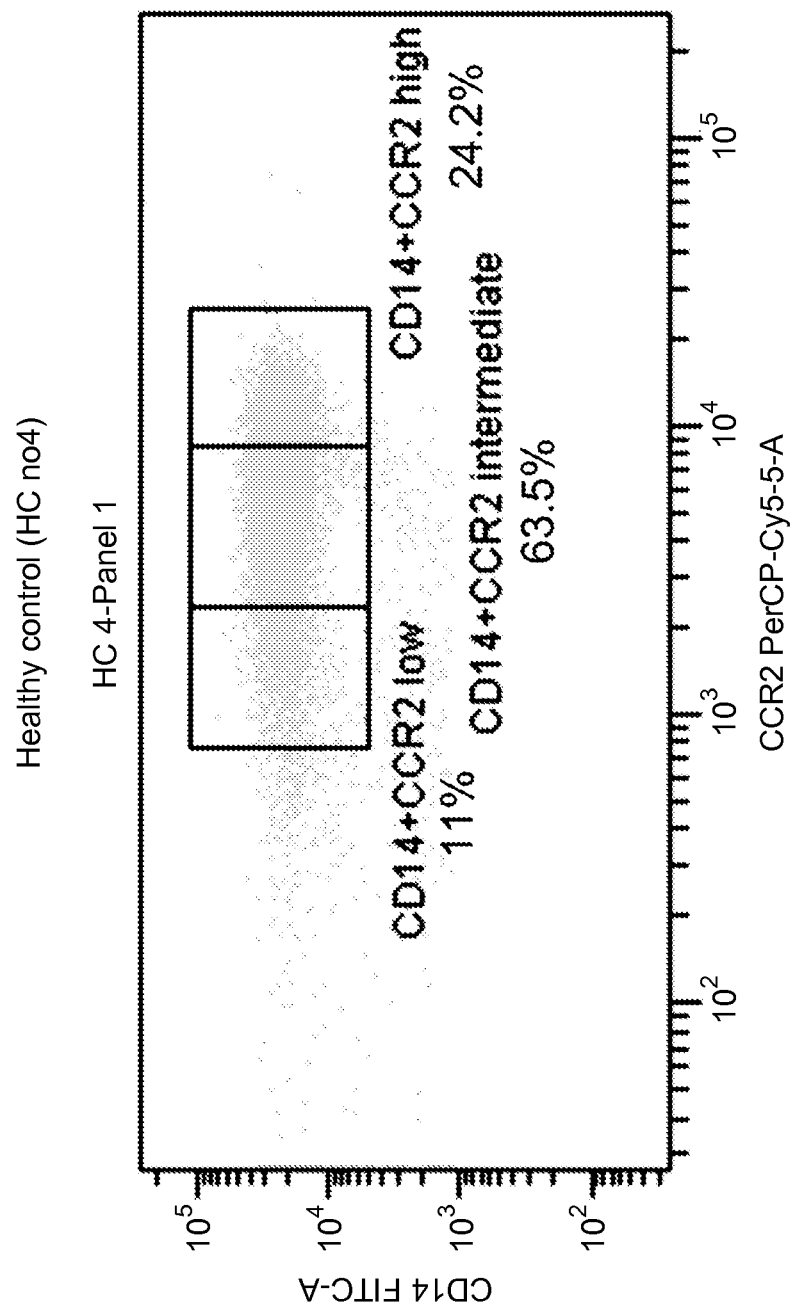

FIG. 16—example of gating criteria for CCR2 expressing monocytes

Figure 17:
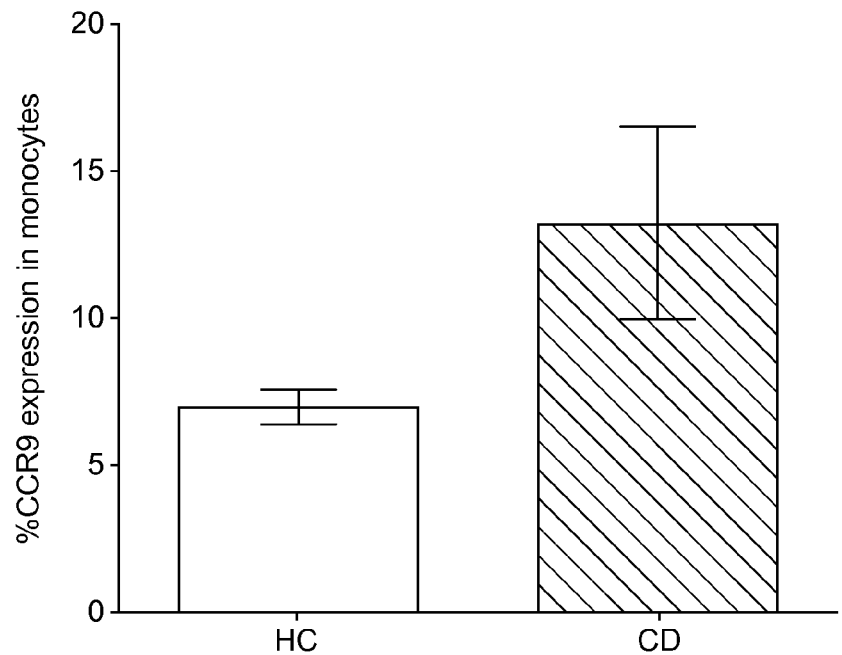

FIG. 17—Expression of CCR9 expressing monocytes in seven patients with Crohn's disease (CD) and in 20 healthy controls (HC). Blood from patients with CD and healthy controls was analysed for the expression of various chemokine receptors by flow cytometry. The monocytes were characterized as CD14 positive cells.

Figure 18:
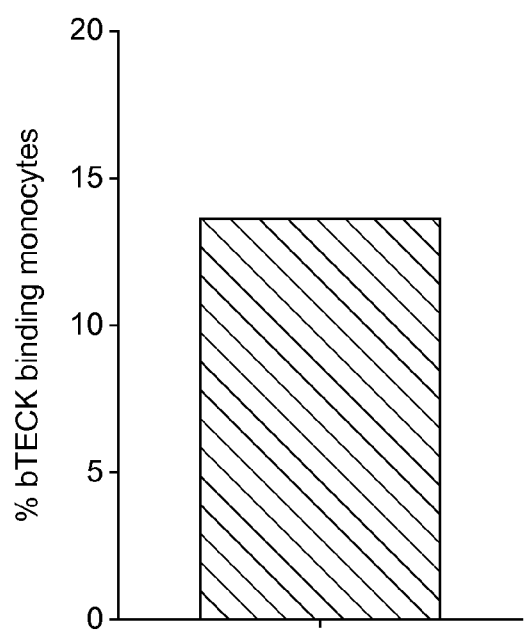

FIG. 18—Binding of the chemokine bTECK (CCL25) to monocytes from a patient with Crohn's disease. Blood from a patient with CD was incubated with bTECK and analysed with flow cytometry. The monocytes were characterized as CD14 positive cells.

Figure 19:
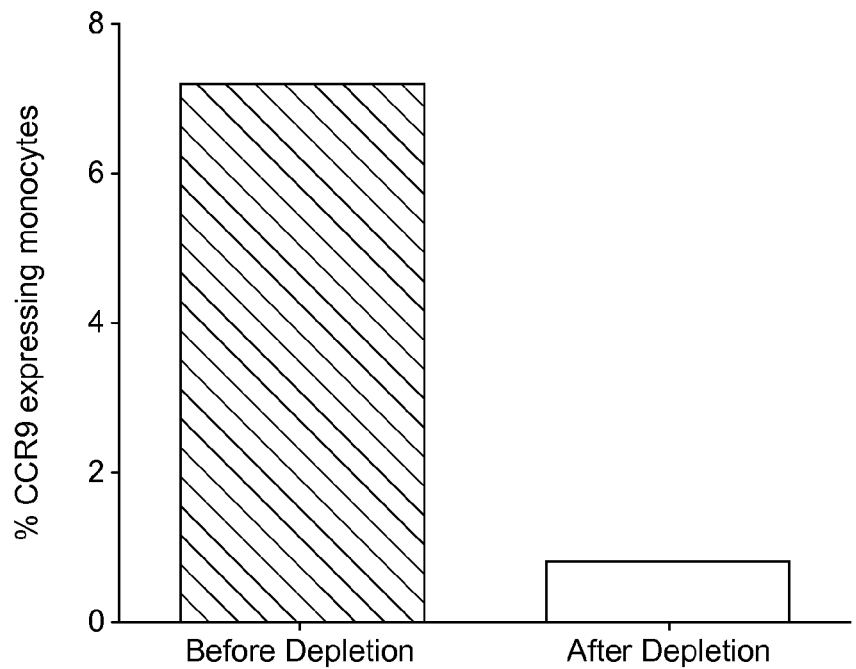

FIG. 19—Depletion of CCR9 expressing monocytes with Sepharose Streptavidin-matrix conjugated with bTECK. Blood cells from a patient with CD were incubated with bTECK—Sepharose Streptavidin-matrix. Unbound cells were retrieved by washing the matrix with Phosphate Buffer Saline. The cells (After Depletion) were then analysed with flow cytometry and compared with cells that had not been incubated with bTECK-matrix (Before Depletion).

Figure 20:
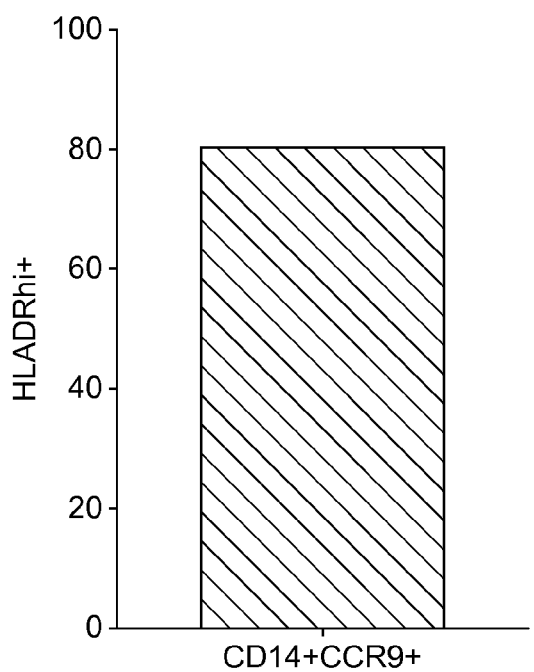

FIG. 20—The CCR9 expressing monocytes show a 80% expression of HLADRhi. The monocytes were characterized as CD14 positive cells.

Figure 21:
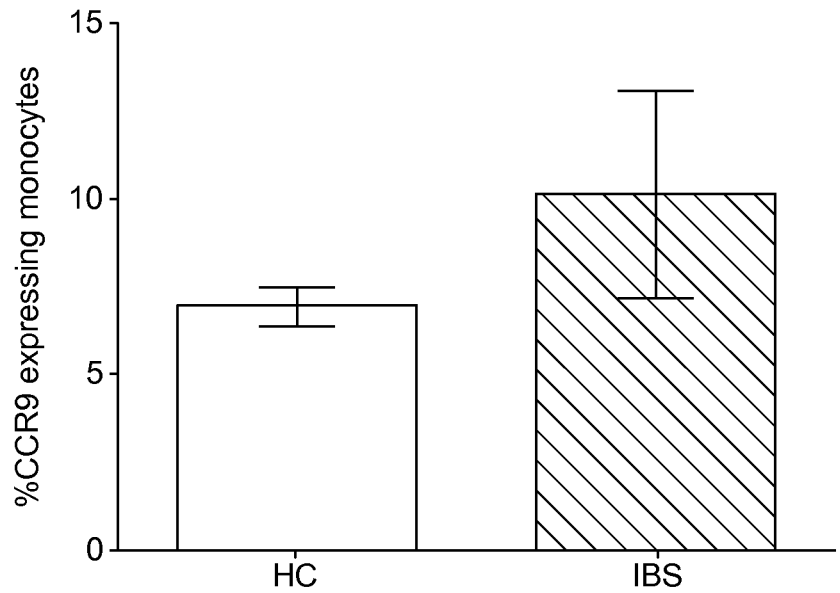

FIG. 21—Expression of CCR9 expressing monocytes in 2 patients with Irritable bowel syndrome (IBS) and in 20 healthy controls (HC). Blood from patients with IBS and healthy controls was analysed for the expression of various chemokine receptors by flow cytometry. The monocytes were characterized as CD14 positive cells.

Figure 22:
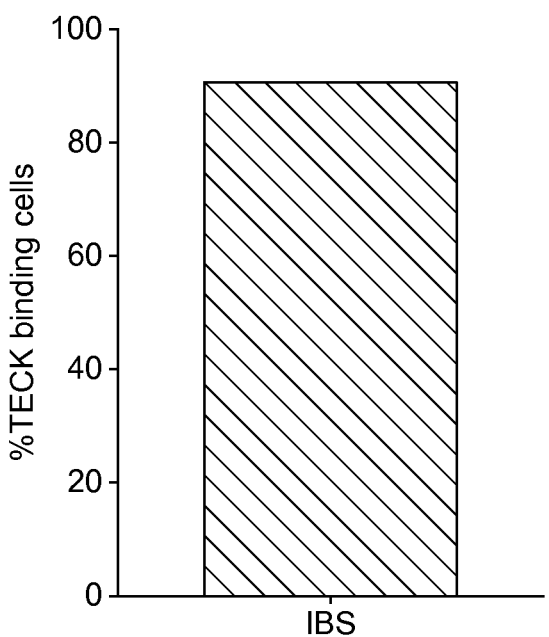

FIG. 22—Binding of the chemokine bTECK (CCL25) to monocytes from a patient with IBS. Blood from a patient with IBS was incubated with bTECK and analysed with flow cytometry. The monocytes were characterized as CD14 positive cells.

Figure 23:
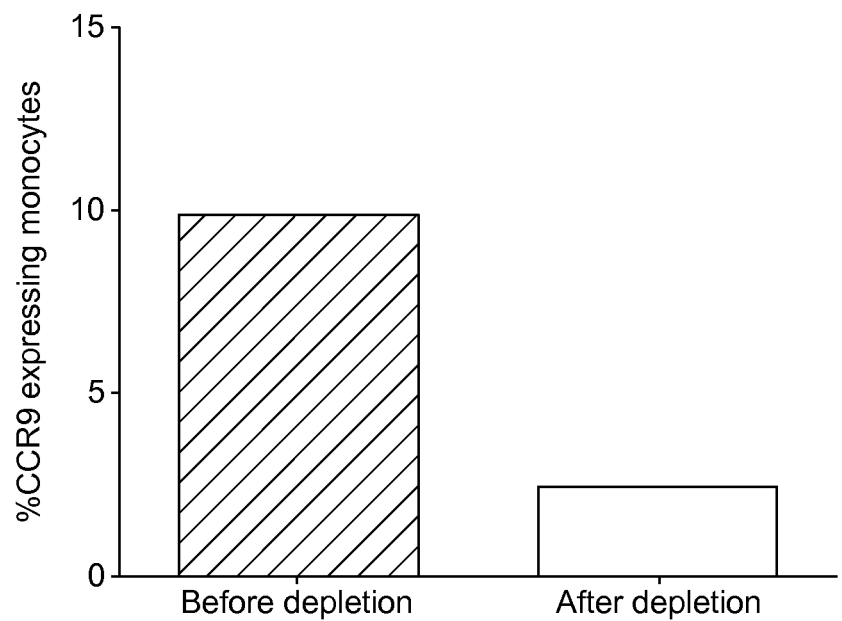

FIG. 23—Depletion of CCR9 expressing monocytes with Sepharose Streptavidin-matrix conjugated with bTECK. Blood cells from a patient with IBS were incubated with bTECK—Sepharose Streptavidin-matrix. Unbound cells were retrieved by washing the matrix with Phosphate Buffer Saline. The cells (After Depletion) were then analysed with flow cytometry and compared with cells that had not been incubated with bTECK-matrix (Before Depletion).

Figure 24:
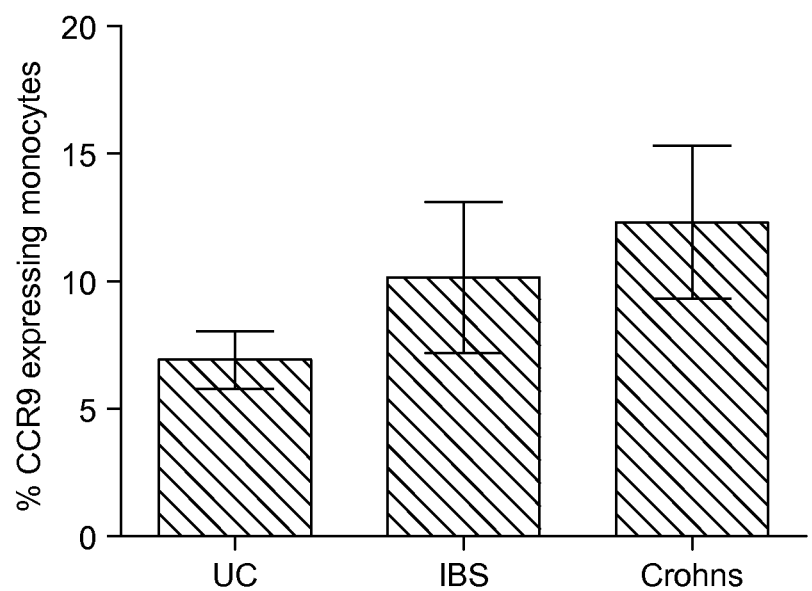

FIG. 24—Expression of CCR9 expressing monocytes in 4 patients with Ulcerative Colitis (UC), 2 patients with Irritable bowel syndrome (IBS) and 8 patients with Crohns Disease (Crohns). Blood from patients was analysed for the expression of various chemokine receptors by flow cytometry. The monocytes were characterized as CD14 positive cells.

Figure 25A:
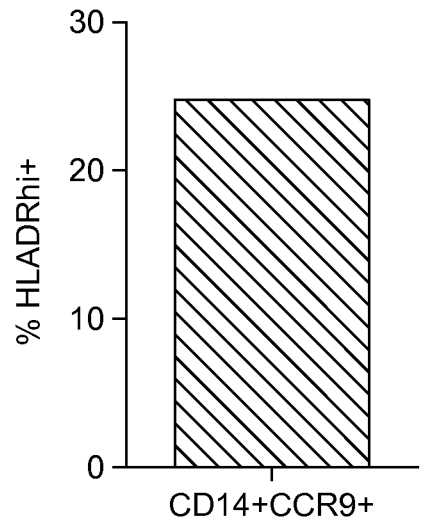

FIG. 25a—The CCR9 expressing monocytes show a 25% expression of HLADRhi.

Figure 25B:
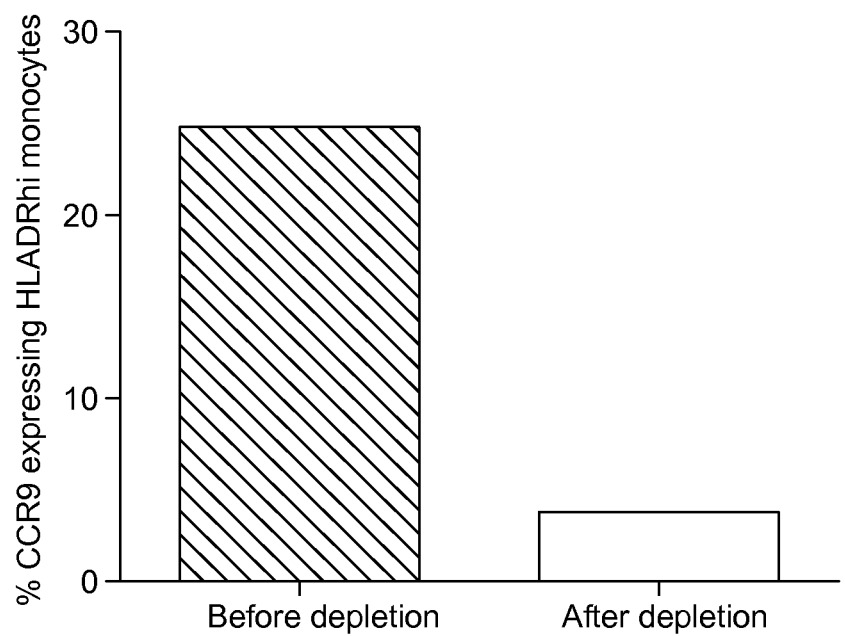

FIG. 25b—The CCR9 expressing monocytes which also have a high expression of HLADR can be depleted with bTECK conjugated sepharose matrix. The monocytes were characterized as CD14 positive cells.

B. Treating Conditions Associated with Metabolic Syndrome

Figure 26A:
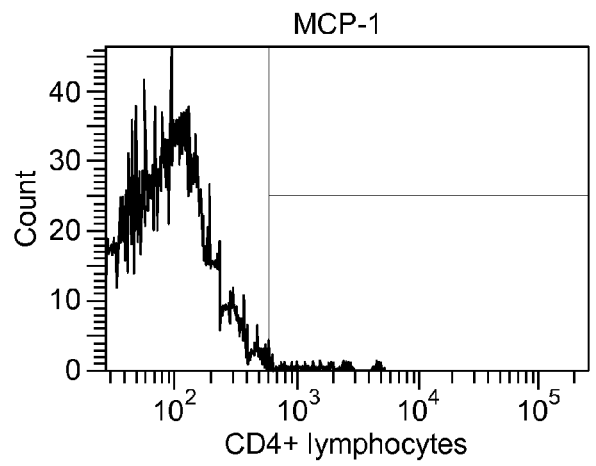
Figure 26B:
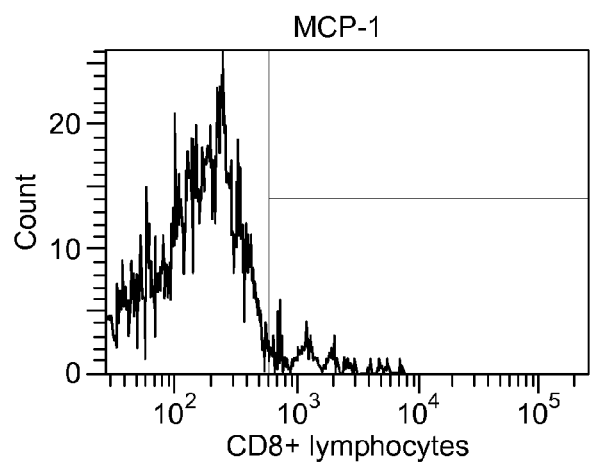
Figure 26C:
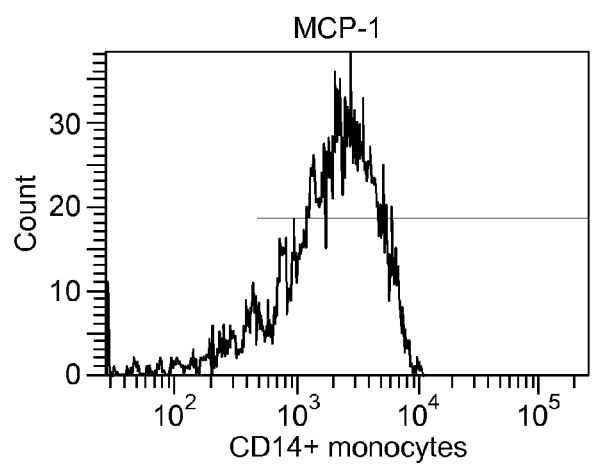

FIGS. 26a, 226b & 26c—the binding of biotinylized MCP-1 by CD4+, CD8+ T-cells and CD14+ monocytes respectively, obtained from peripheral blood of a healthy donor.

Figure 27A:
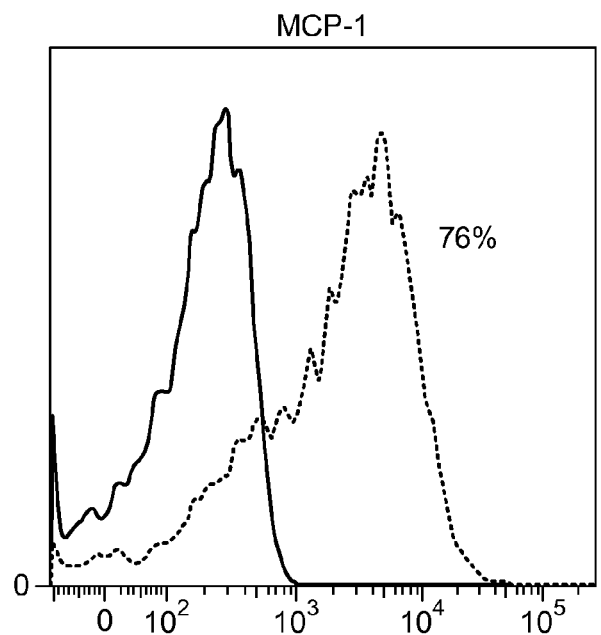

FIG. 27a—binding of MCP-1 to monocytes (dashed line) in peripheral blood taken from IBD patients. The graph represents a summary of four tests.

Figure 27B:
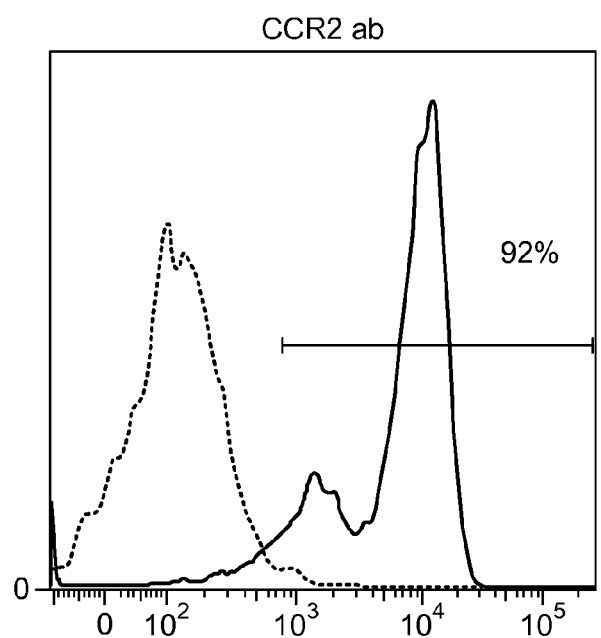

FIG. 27b—binding of CCR2-antibody to monocytes (line) in peripheral blood taken from IBD patients. The graph represents a summary of four tests.

Figure 28A:
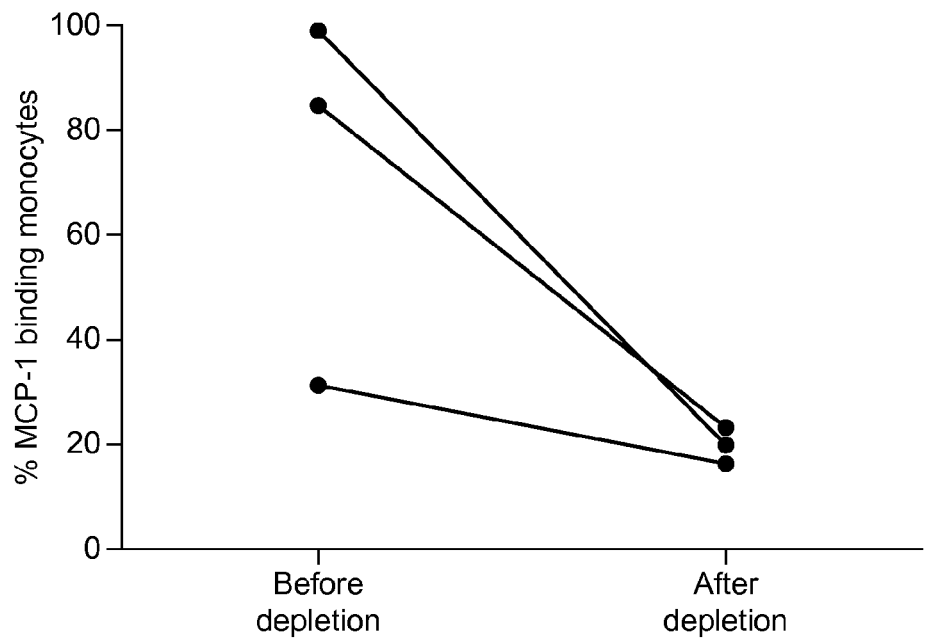

FIG. 28a—Results of in vitro depletion tests performed on the bMCP-1 coupled matrix showing ability to eliminate CCR2-expressing cells from blood from three healthy donors.

Figure 28B:
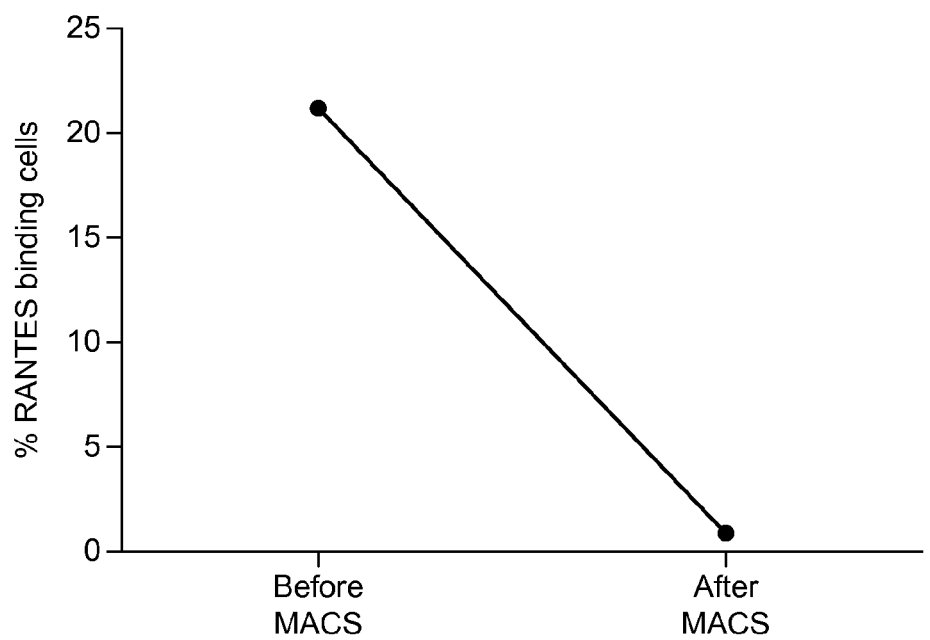

FIG. 28b—Results of in vitro depletion tests performed on the biotinylated RANTES coupled matrix showing ability to eliminate chemokine receptor-expressing cells from peripheral blood taken from a healthy donor.

Figure 29:
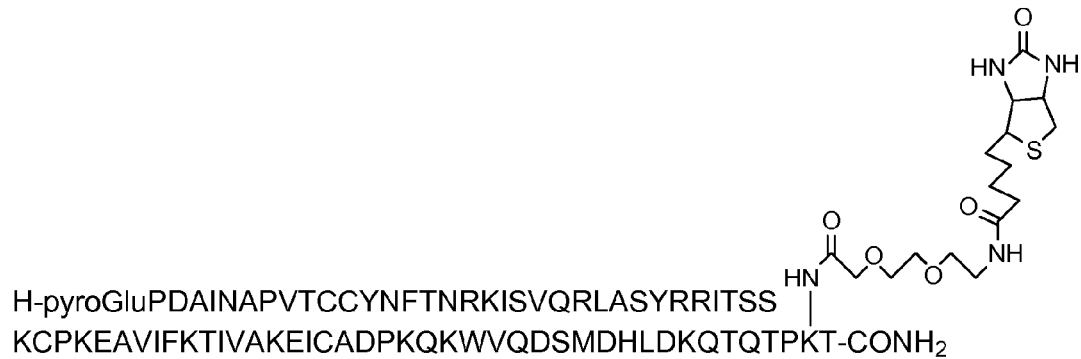

FIG. 29—Sequence (SED ID NO: 8) and biotinylation, via a spacer group, of mature protein MCP-1 derivative containing Gln to pyroGlu modification.

Figure 30:
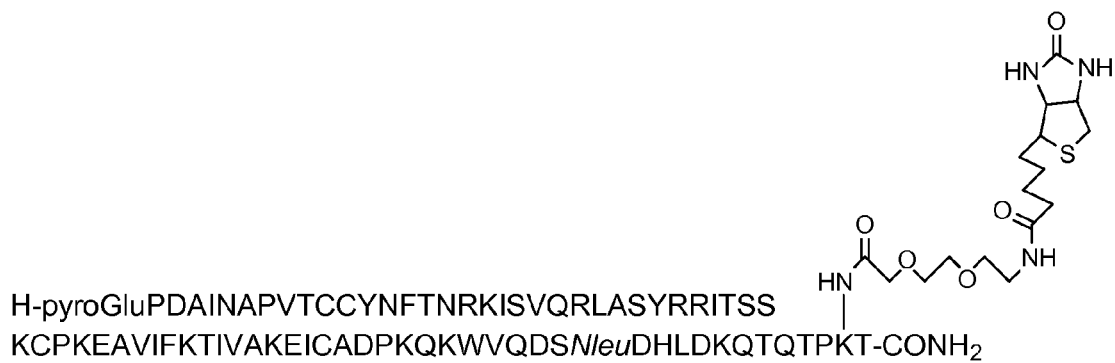

FIG. 30—Sequence (SED ID NO: 8) and biotinylation, via a spacer group, of mature protein MCP-1 derivative containing Gln to pyroGlu modification and Met to Norleu substitution.

Figure 31:
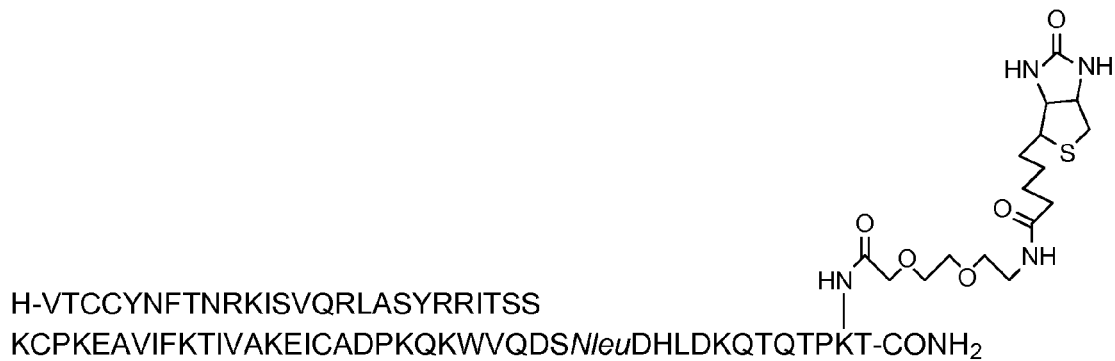

FIG. 31—Sequence (SED ID NO: 8) and biotinylation, via a spacer group, of truncated MCP-1 derivative containing Met to Norleu substitution.

FIG. 32—Alignment of MCP-1 (residues 25-99 of SEQ ID NO: 11) and MCP-5 (residues 24-104 of SEQ ID NO: 10) amino acid sequences.

Figure 33:
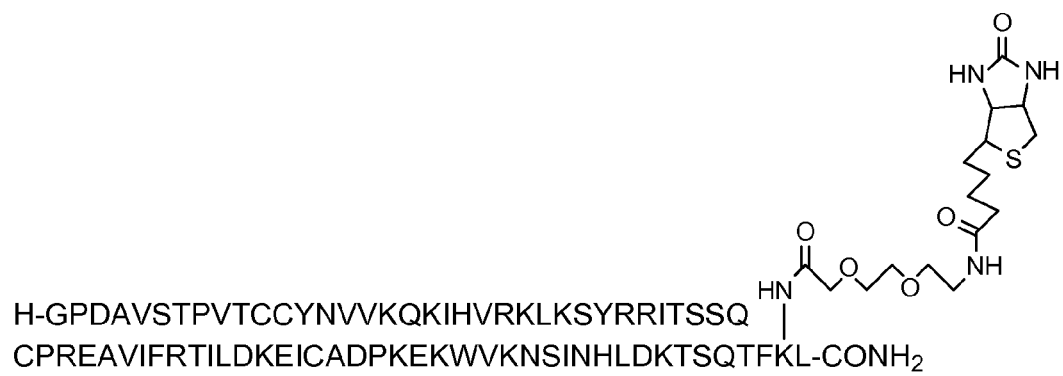

FIG. 33—Sequence (SED ID NO: 13) and biotinylation, via a spacer group, of (C-terminal) truncated MCP-5 derivative containing Ile to Lys modification.

Figure 34:
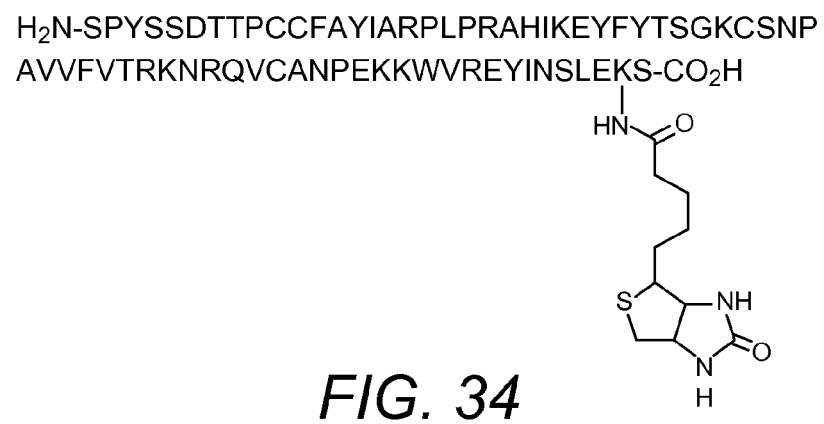

FIG. 34—Sequence (SED ID NO: 14) and biotinylation, of RANTES derivative

Figure 35:
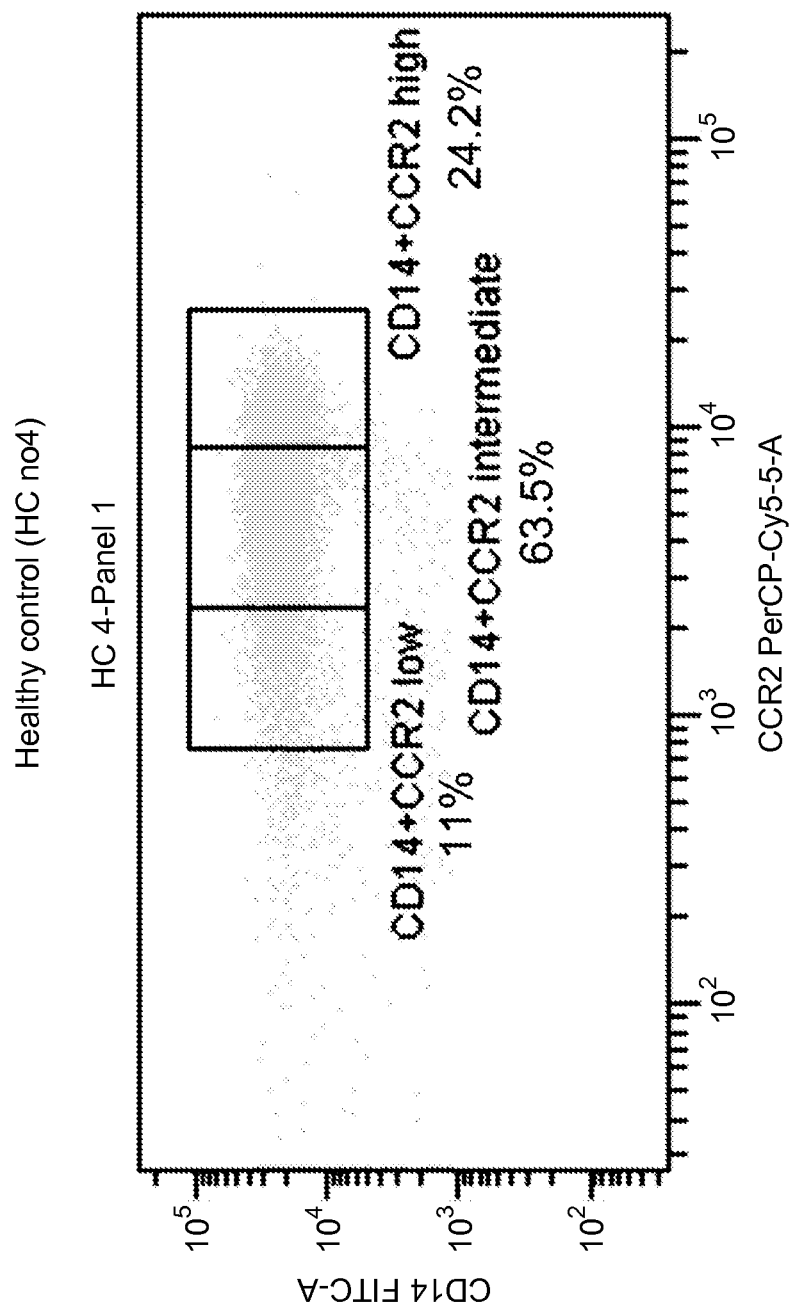

FIG. 35—Example of gating criteria for CCR2-expressing monocytes.

Figure 36:
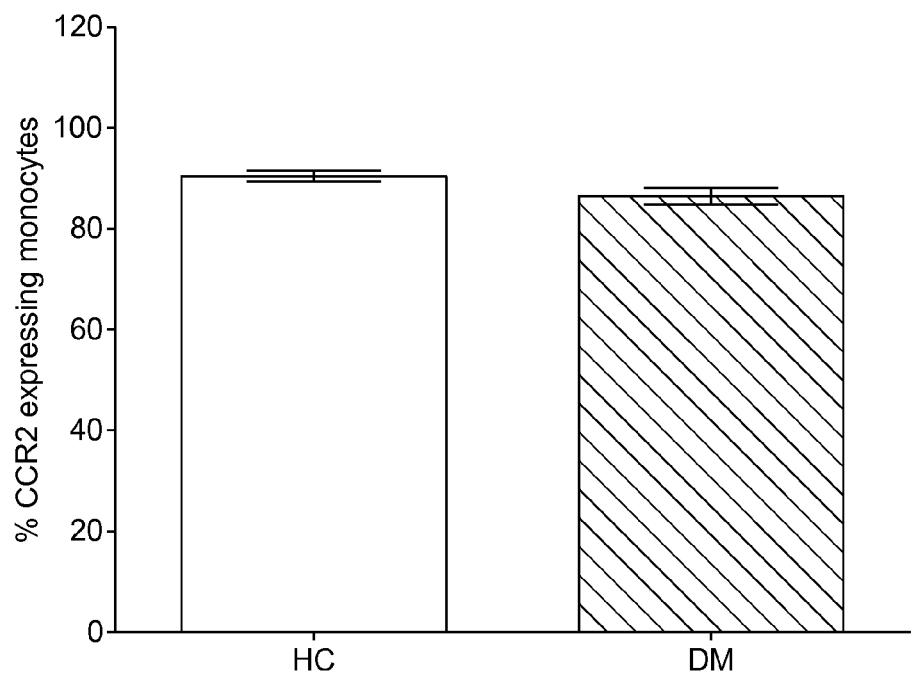

FIG. 36—Expression of CCR2 expressing monocytes in 9 patients with diabetes mellitus (DM) and in 20 healthy controls (HC). Blood from patients with DM and healthy controls was analysed for the expression of various chemokine receptors by flow cytometry. The monocytes were characterized as CD14 positive cells.

Figure 37:
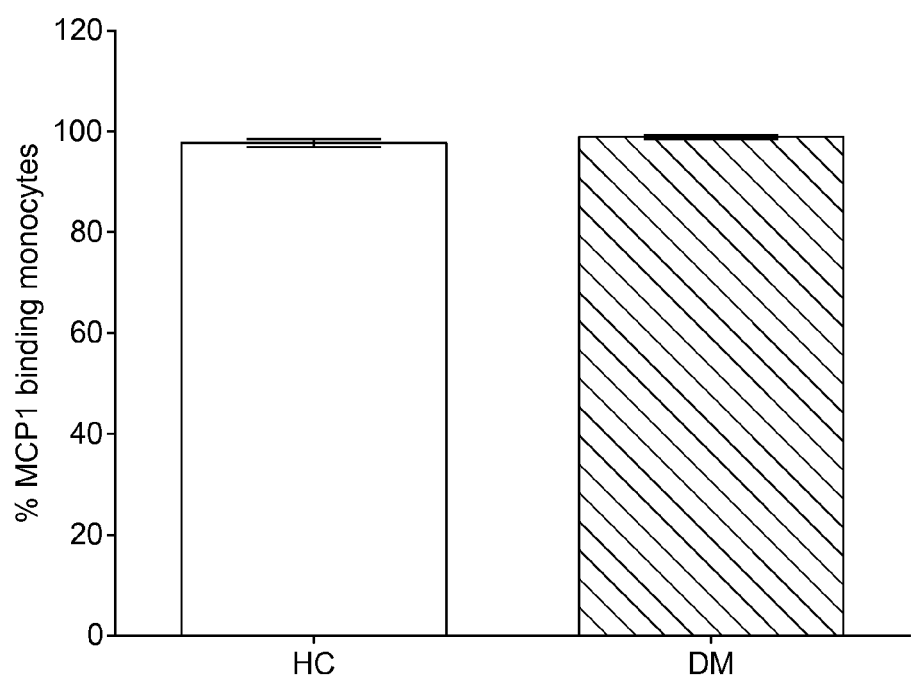

FIG. 37—Binding of the chemokine bMCP1 (CCL2) to monocytes from 3 patients with Diabetes Mellitus and in 20 healthy controls (HC). Blood from 3 patient with DM was incubated with bMCP1 and analysed with flow cytometry. The monocytes were characterized as CD14 positive cells.

Figure 38:
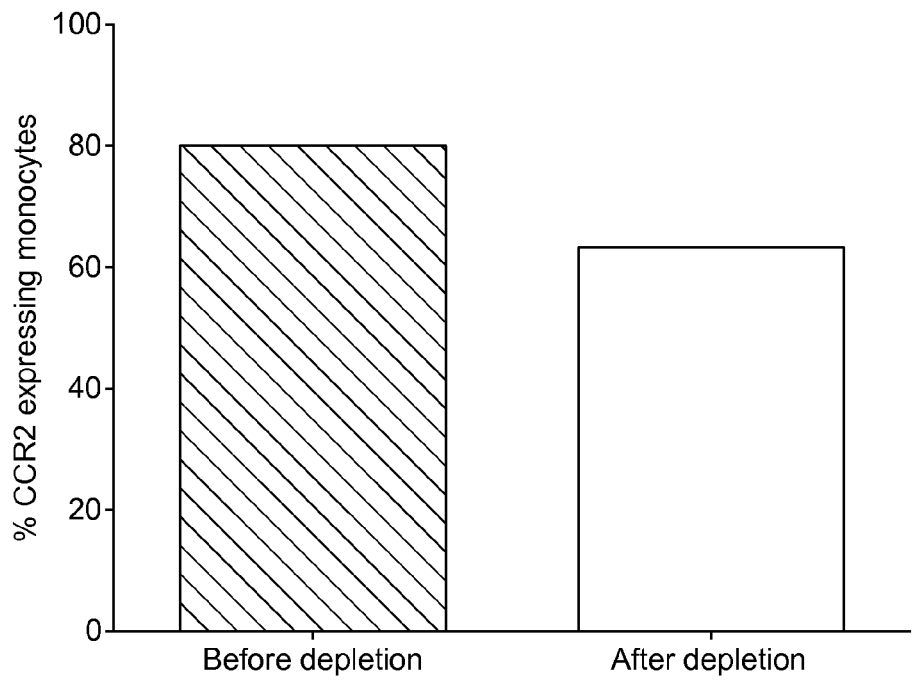

FIG. 38—Depletion of CCR2 expressing monocytes with Sepharose Streptavidin-matrix conjugated with bMCP1. Blood cells from a patient with DM were incubated with bMCP1—Sepharose Streptavidin-matrix. Unbound cells were retrieved by washing the matrix with Phosphate Buffer Saline. The cells (After Depletion) were then analysed with flow cytometry and compared with cells that had not been incubated with bMCP1-matrix (Before Depletion).

Figure 39:
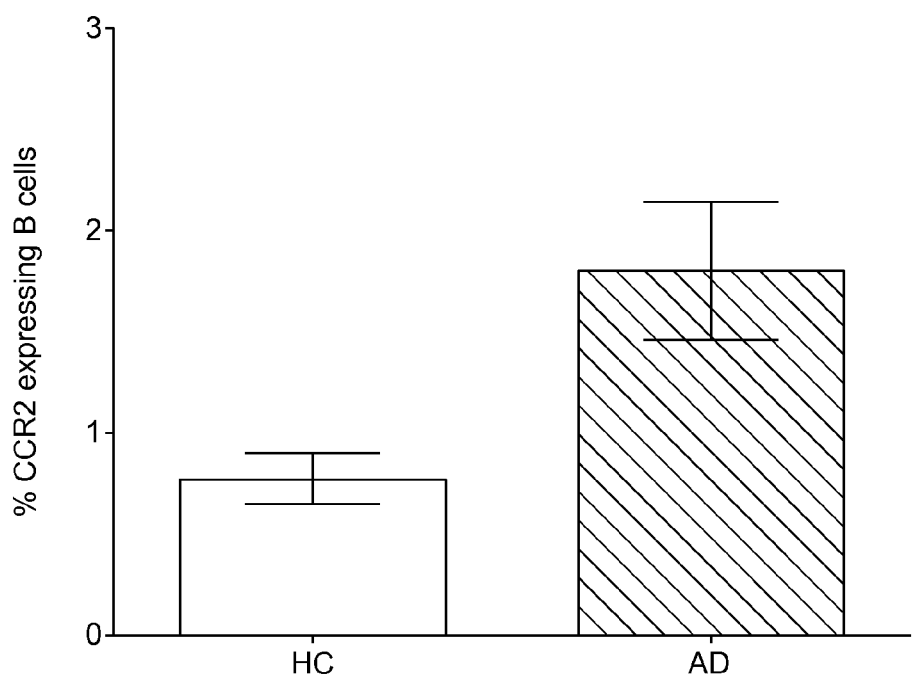

FIG. 39—Expression of CCR2 expressing B cells in seven patients with adiposis dolorosa (AD) and in 20 healthy controls (HC). Blood from patients with AD and healthy controls was analysed for the expression of various chemokine receptors by flow cytometry. The B cells were characterized as CD19 positive cells.

Figure 40:
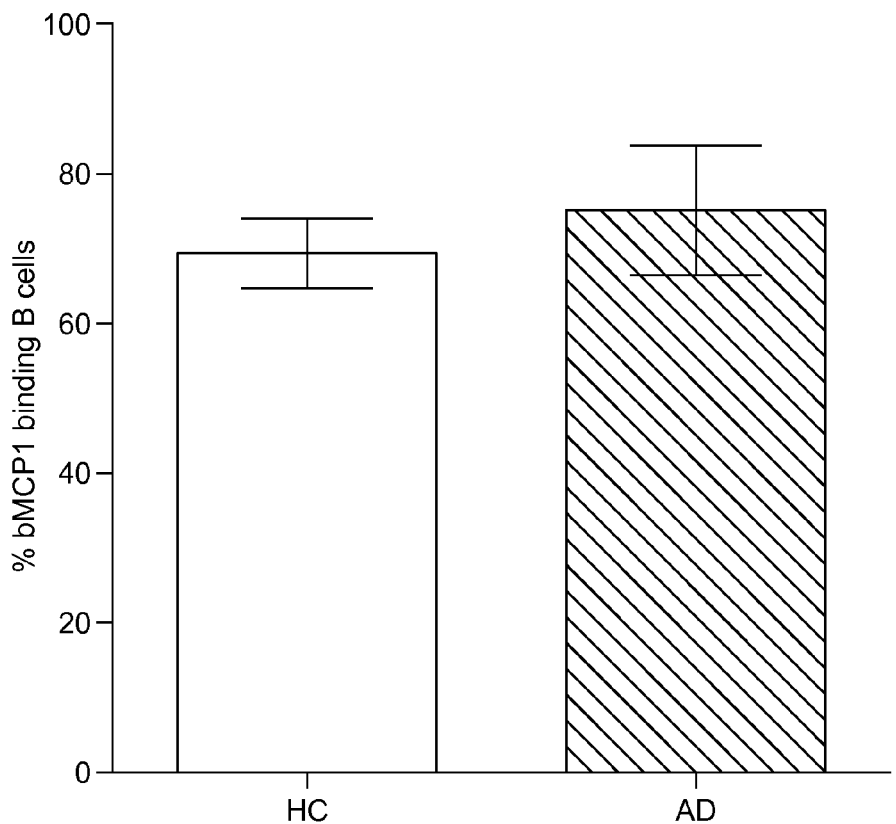

FIG. 40—Binding of the chemokine bMCP1 (CCL2) to B cells from seven patient with Adiposis Dolorosa. Blood from a patient with AD was incubated with bMCP1 and analysed with flow cytometry. The B cells were characterized as CD19 positive cells.

Figure 41:
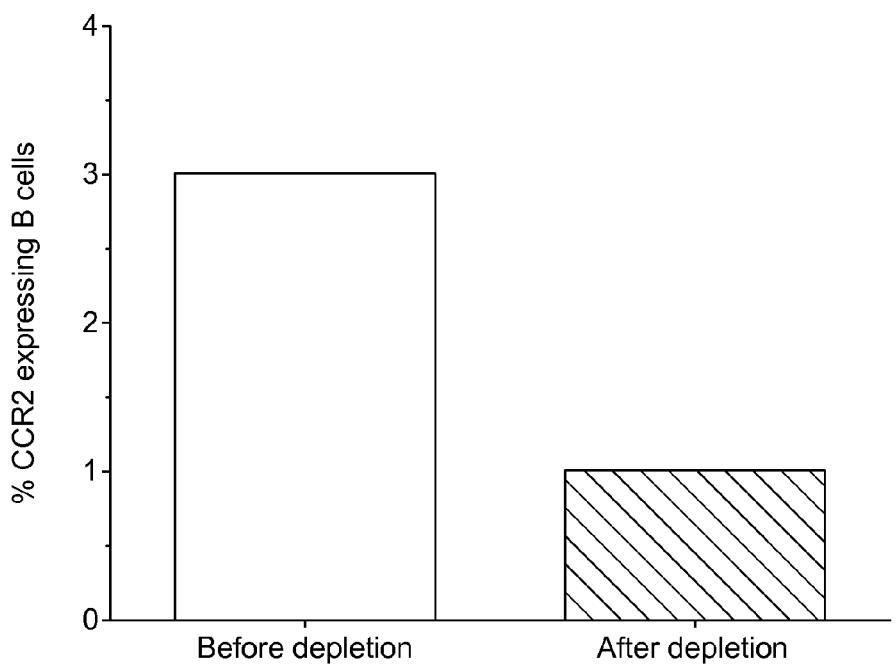

FIG. 41—Depletion of CCR2 expressing B cells with Sepharose Streptavidin-matrix conjugated with bMCP1. Blood cells from a patient with AD were incubated with bMCP1-Sepharose Streptavidin-matrix. Unbound cells were retrieved by washing the matrix with Phosphate Buffer Saline. The cells (After Depletion) were then analysed with flow cytometry and compared with cells that had not been incubated with bMCP1-matrix (Before Depletion).

Figure 42:
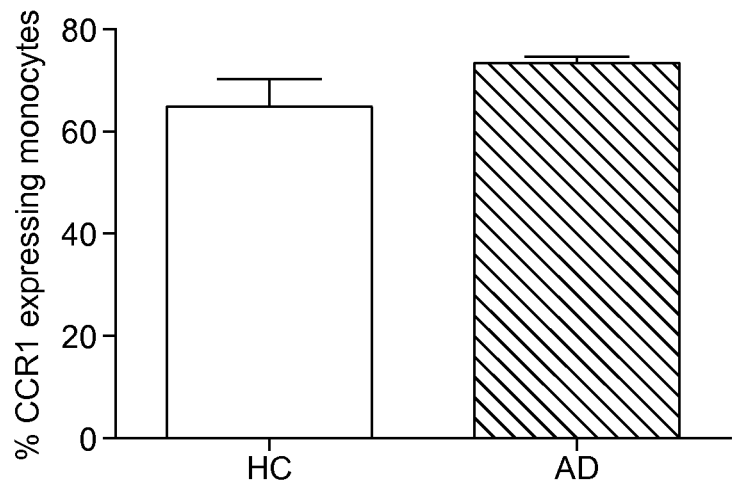

FIG. 42—Increased frequency of CCR1 expressing monocytes in 4 patients with Adiposis dolorosa compared to healthy controls.

Figure 43:
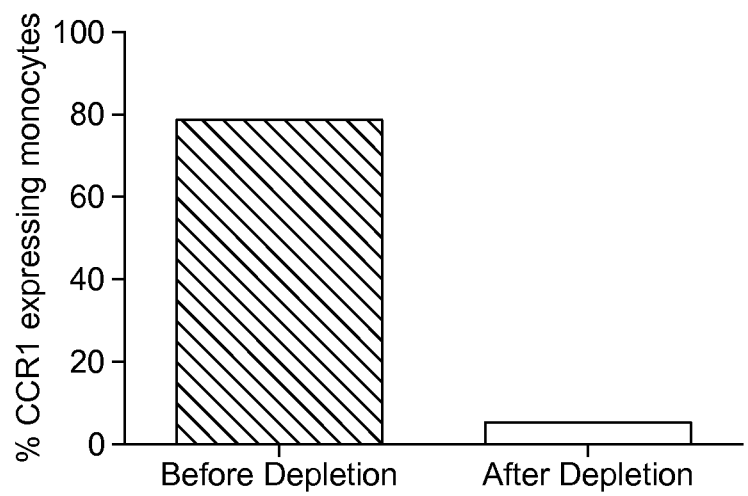

FIG. 43—Depletion of CCR1 expressing moncoytes with SepharoseStrepavidin-matrix-bRANTES. Blood cells from a healthy control were incubated with biotinylated chemokine-Sepharose Streptavidin-matrix. Unbound cells were retrieved by washing the matrix. The cells (After Depletion) were then analysed with flow cytometry and compared with cells that had not been incubated with bchemokine-matrix (Before Depletion).

Figure 44:
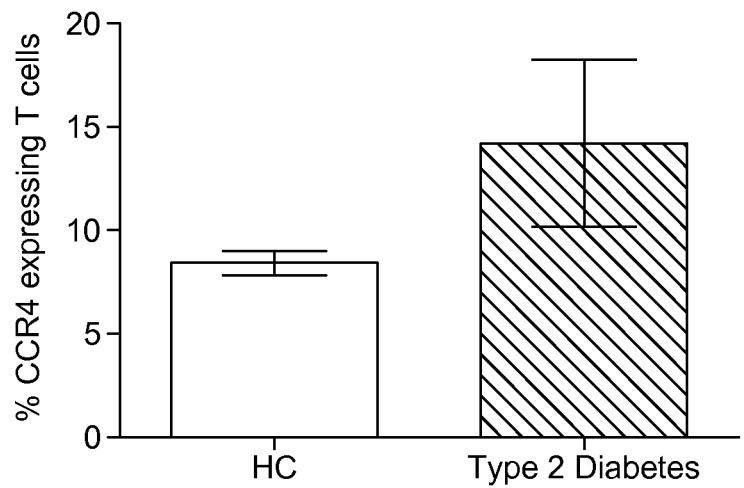

FIG. 44—Increased frequency of CCR4 expressing T cells in four patients with type 2 Diabetes.

Figure 45:
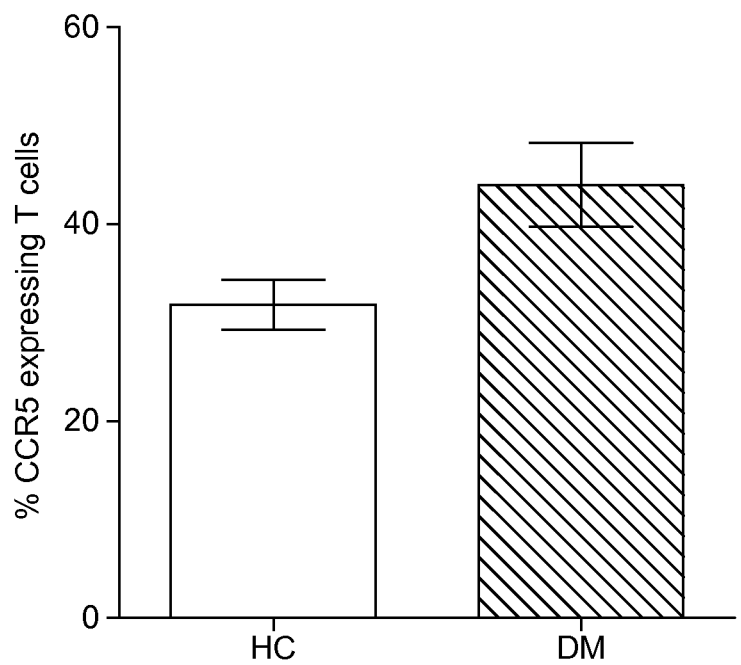

FIG. 45—Increased frequency of CCR5 expressing T cells in four patients with type 2 Diabetes.

C. Treating Inflammatory Arthritis

Figure 46A:
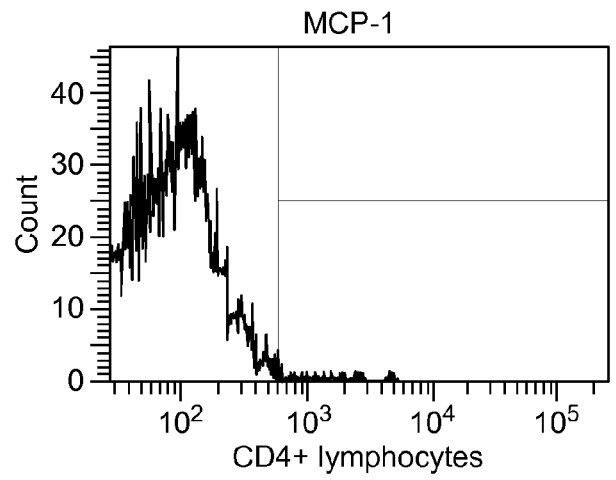
Figure 46B:
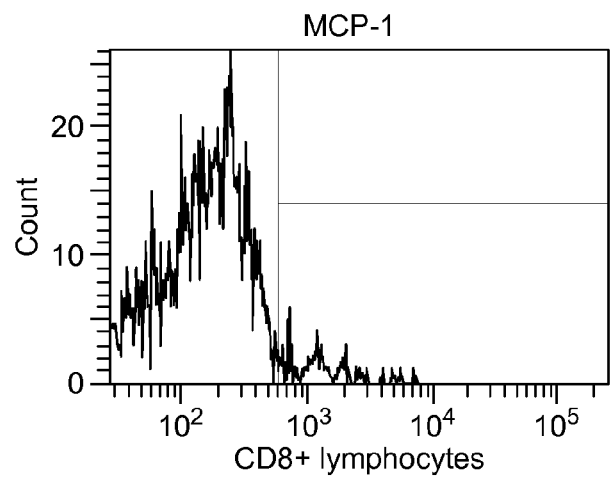
Figure 46C:
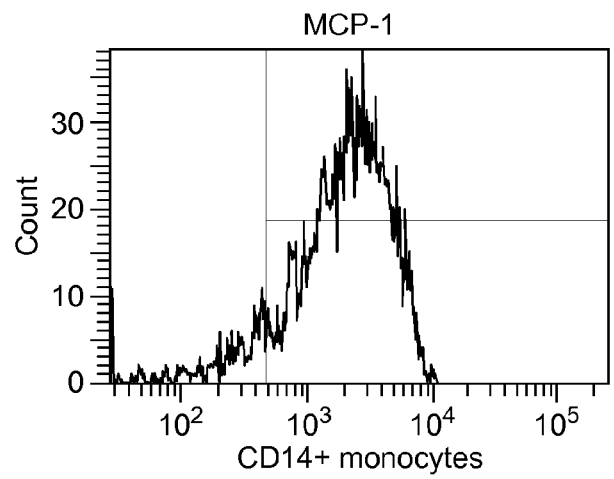

FIGS. 46a, 46b & 46c—the binding of biotinylized MCP-1 by CD4+, CD8+ T-cells and CD14+ monocytes respectively, obtained from peripheral blood of a healthy donor.

Figure 47A:
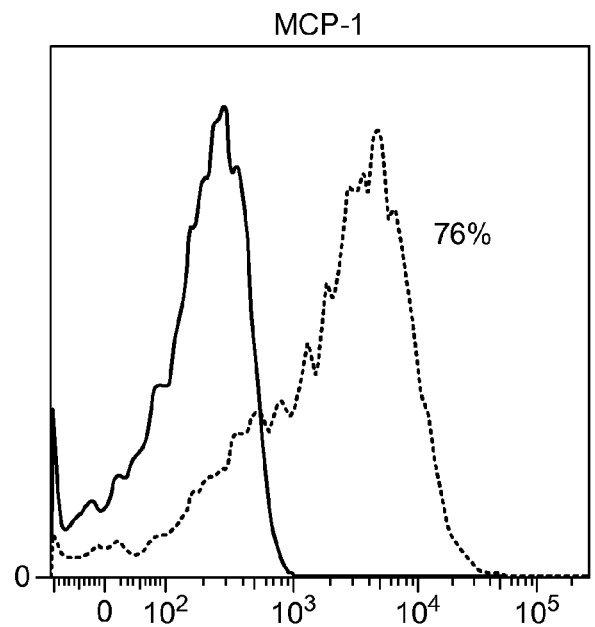

FIG. 47a—binding of MCP-1 to monocytes (dashed line) in peripheral blood taken from IBD patients. The graph represents a summary of four tests.

Figure 47B:
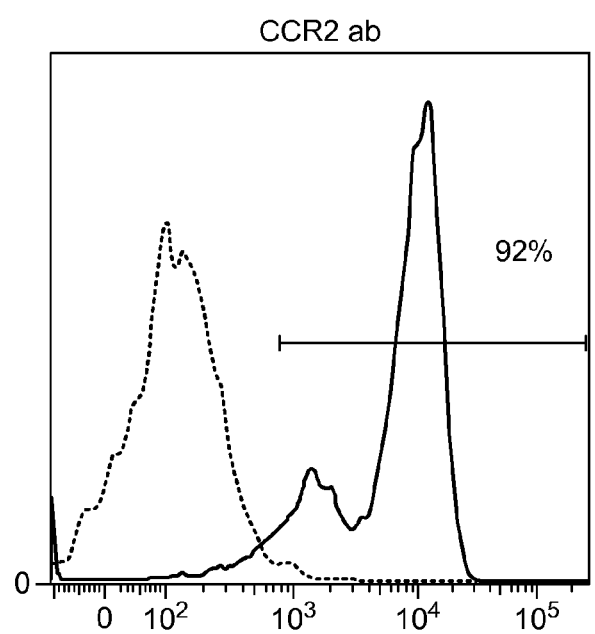

FIG. 47b—binding of CCR2-antibody to monocytes (line) in peripheral blood taken from IBD patients. The graph represents a summary of four tests.

Figure 48A:
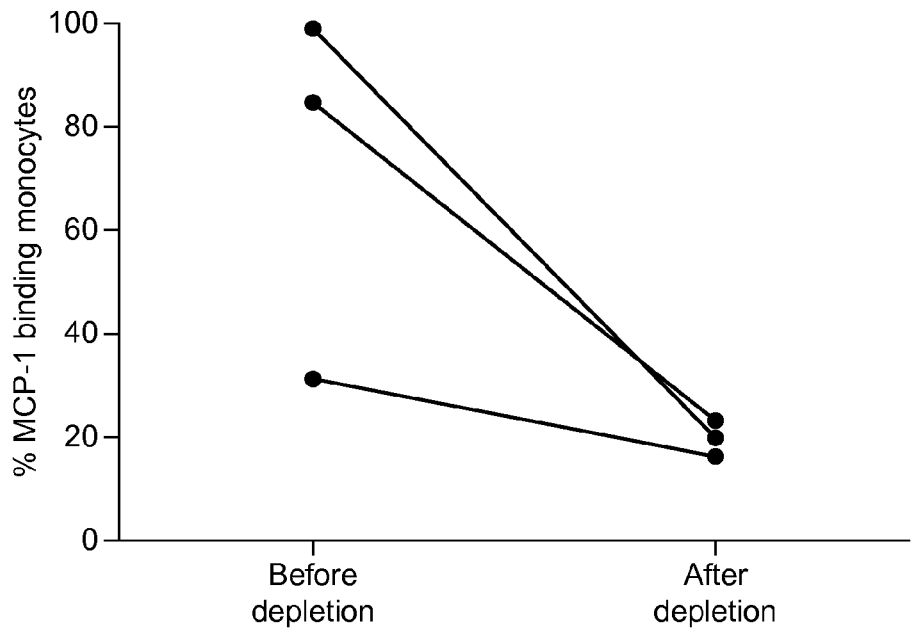

FIG. 48a—Results of in vitro depletion tests performed on the bMCP-1 coupled matrix showing ability to eliminate CCR2-expressing cells from blood from three healthy donors.

Figure 48B:
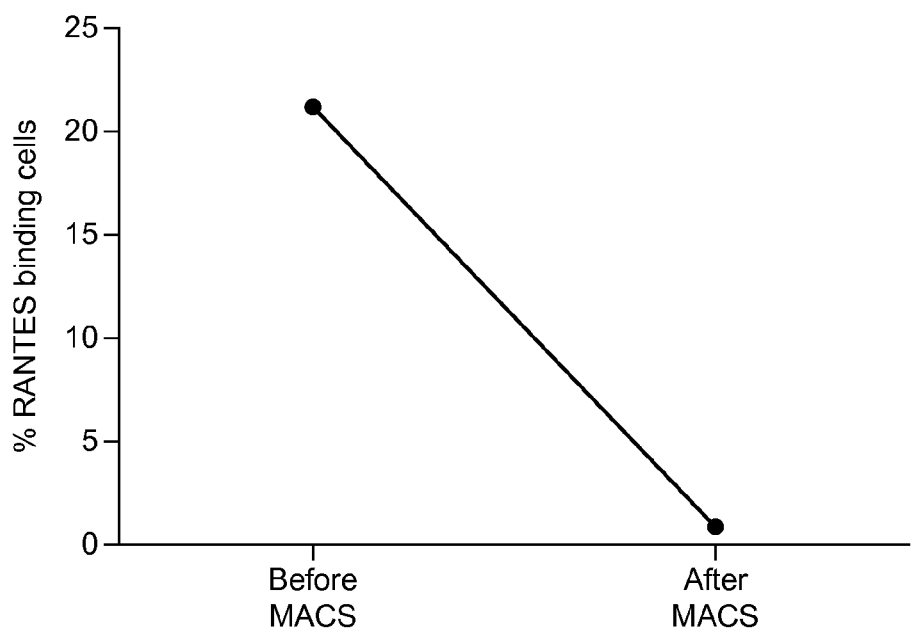

FIG. 48b—Results of in vitro depletion tests performed on the biotinylated RANTES coupled matrix showing ability to eliminate chemokine receptor-expressing cells (CCR1, 3 or 5) from peripheral blood taken from a healthy donor.

Figure 49:
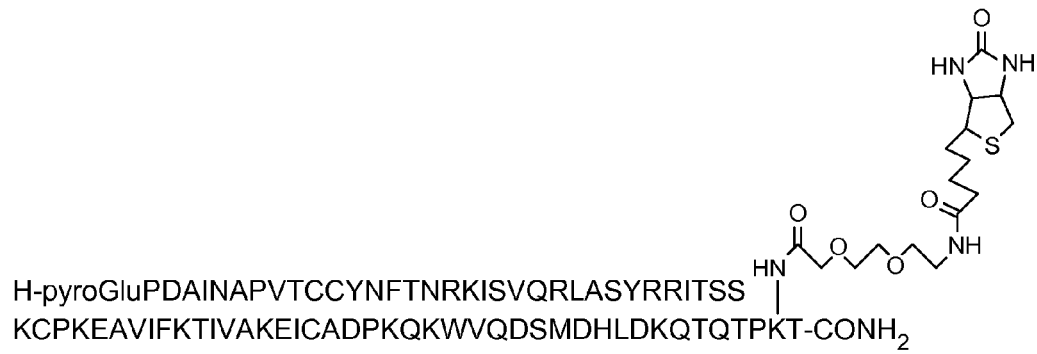

FIG. 49—Sequence (SED ID NO: 24) and biotinylation, via a spacer group, of mature protein MCP-1 derivative containing Gln to pyroGlu modification.

Figure 50:
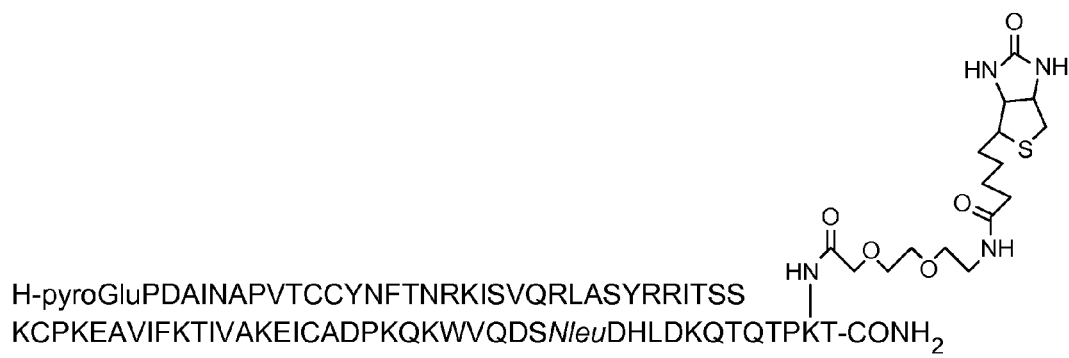

FIG. 50—Sequence (SED ID NO: 24) and biotinylation, via a spacer group, of mature protein MCP-1 derivative containing Gln to pyroGlu modification and Met to Norleu substitution.

Figure 51:
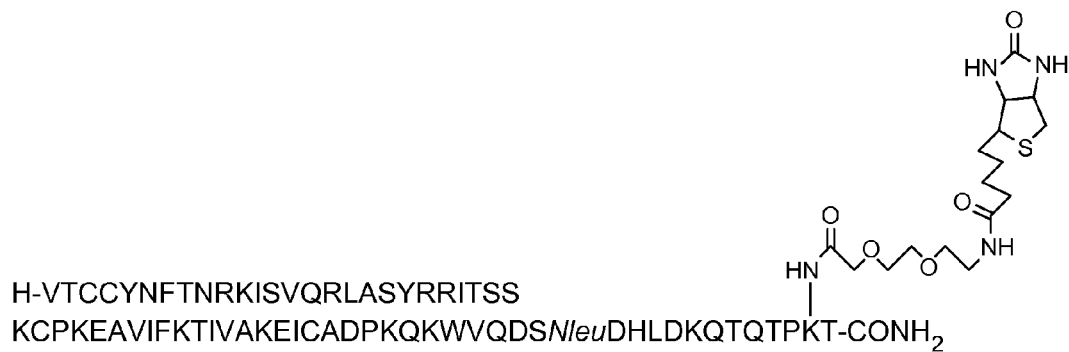

FIG. 51—Sequence (SED ID NO: 25) and biotinylation, via a spacer group, of truncated MCP-1 derivative containing Met to Norleu substitution.

FIG. 52—Alignment of MCP-1 (residues 25-99 of SEQ ID NO: 11) and MCP-5 (residues 24-104 of SEQ ID NO: 10) amino acid sequences.

Figure 53:
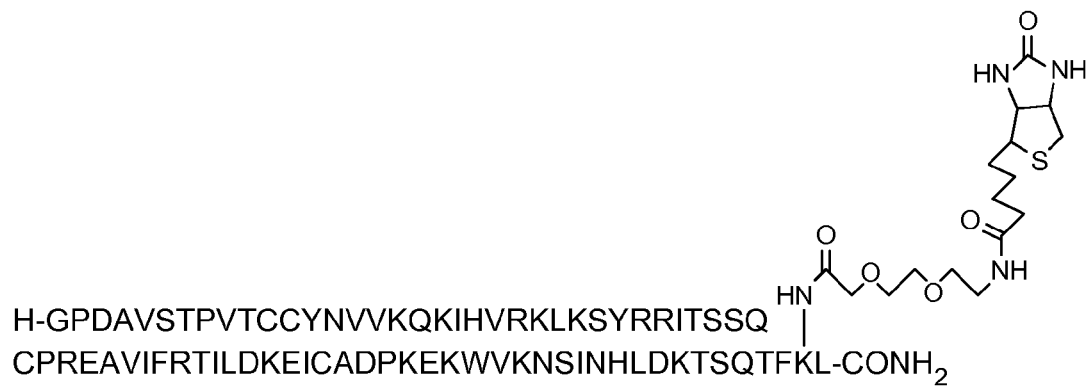

FIG. 53—Sequence (SED ID NO: 27) and biotinylation, via a spacer group, of (C-terminal) truncated MCP-5 derivative containing Ile to Lys modification.

Figure 54:
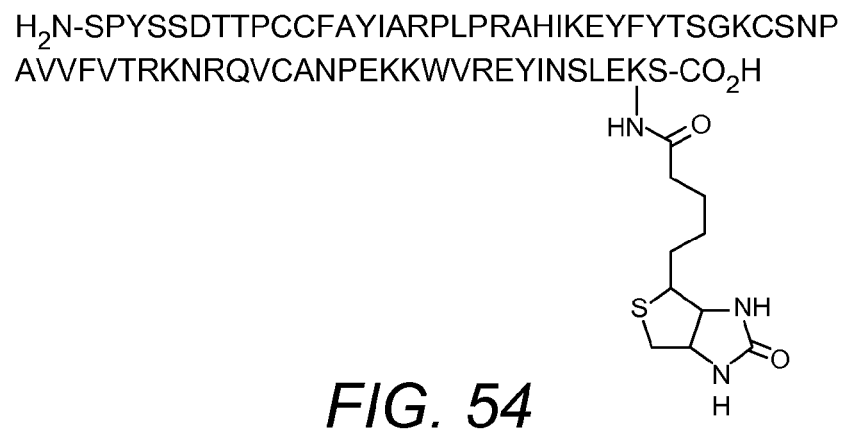

FIG. 54—Sequence and (SED ID NO: 34) biotinylation, of RANTES derivative

Figure 55:
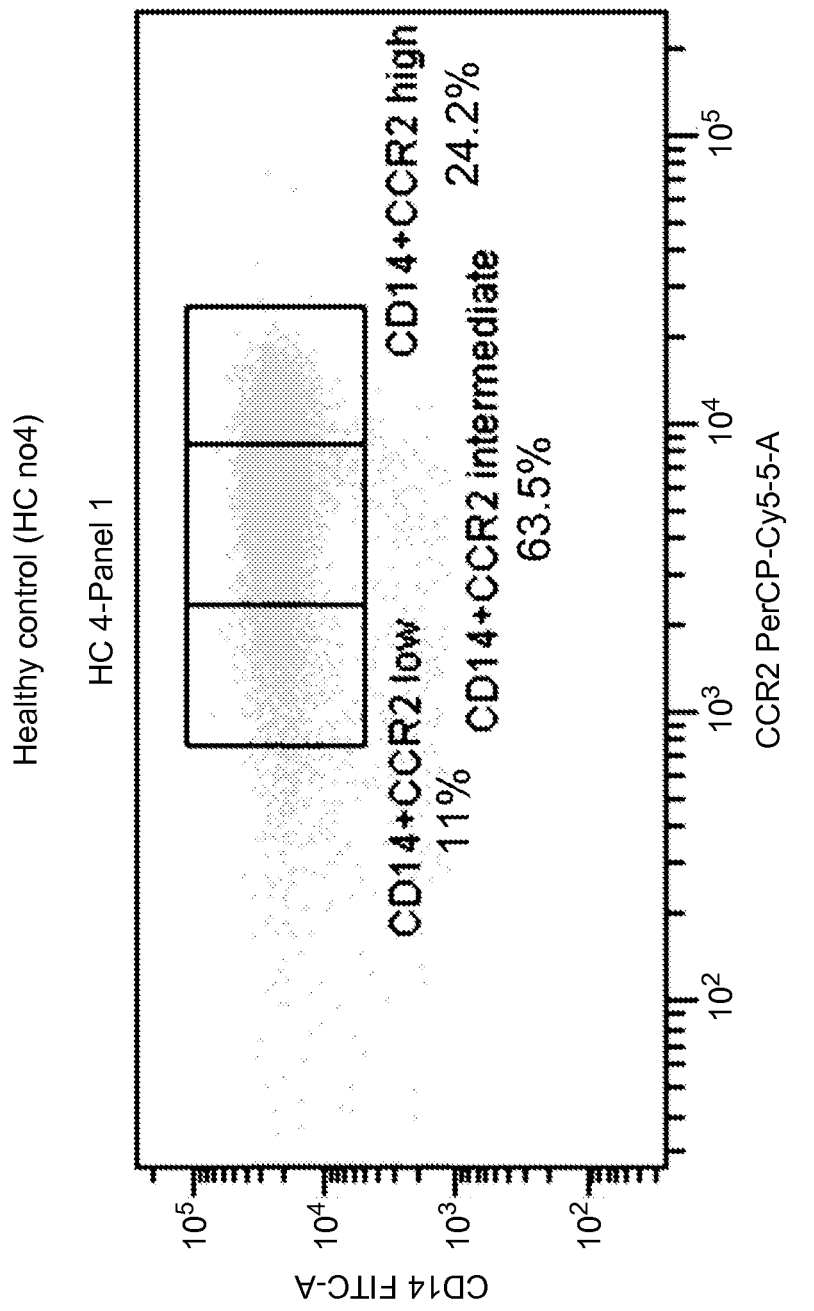

FIG. 55—example of gating criteria for CCR2 expressing monocytes.

Figure 56A:
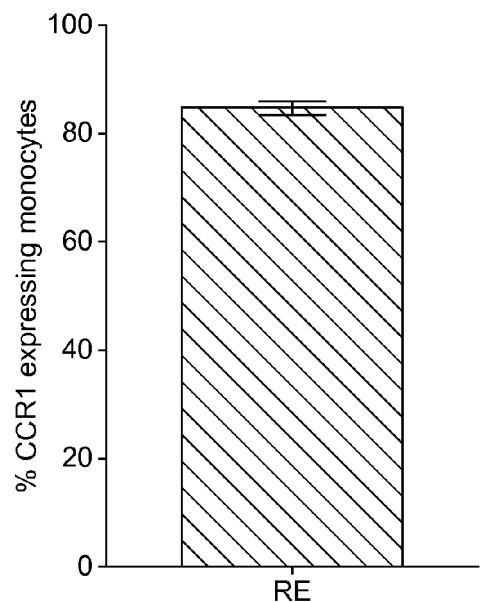

FIG. 56a—Expression of CCR1 receptor on monocytes in 2 patients with Rheumatoid arthritis (RE).

Figure 56B:
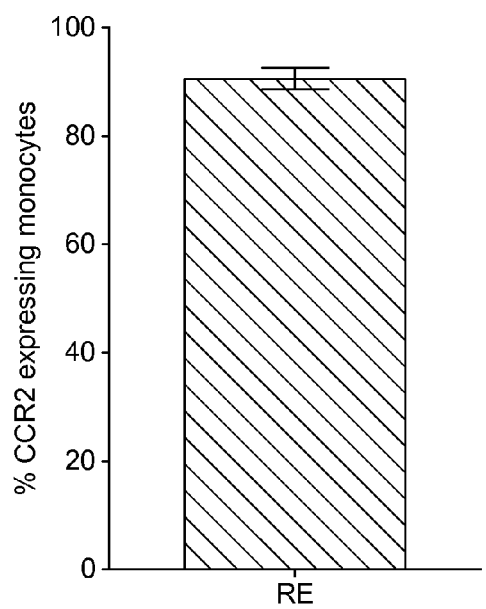

FIG. 56b—Expression of CCR2 receptor on monocytes in 2 patients with Rheumatoid arthritis (RE).

Figure 56C:
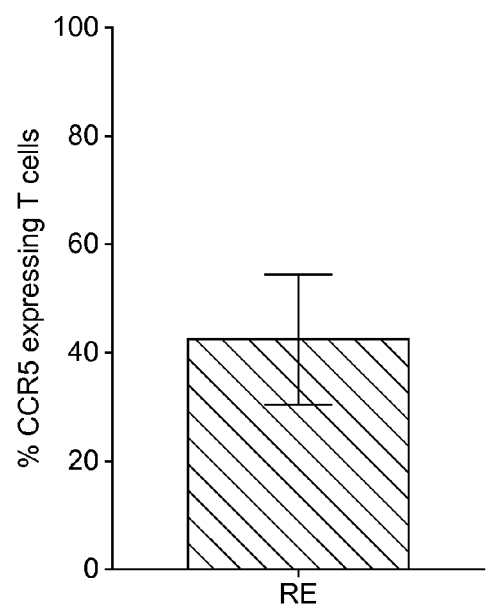

FIG. 56c—Expression of CCR5 receptor on T cells in 2 patients with Rheumatoid arthritis (RE). Blood from patients with RE was analysed for the expression of various chemokine receptors by flow cytometry. The monocytes were characterized as CD14 positive cells and T cells were characterized as CD3 positive cells.

Figure 57A:
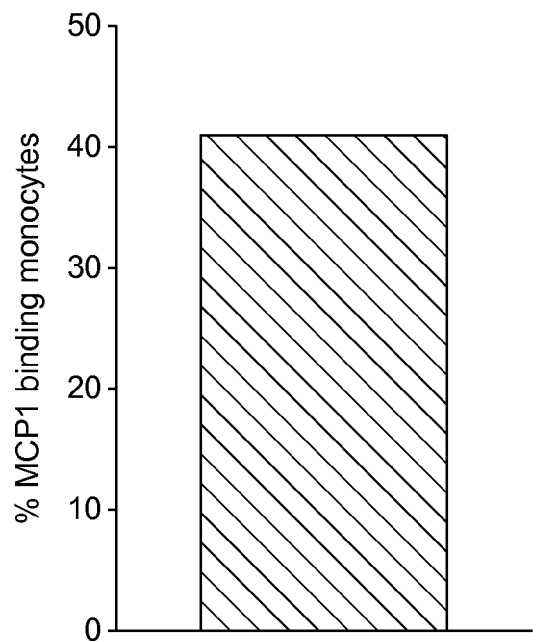

FIG. 57a—Binding of the chemokine bMCP1 (CCL2) to monocytes from a patient with Rheumatoid arthritis. Blood from a patient with RE was incubated with bMCP1 and analysed with flow cytometry. The monocytes were characterized as CD14 positive cells.

Figure 57B:
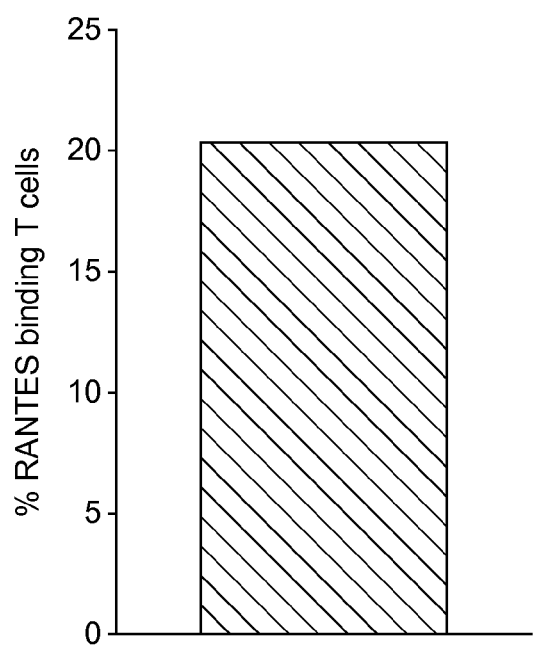

FIG. 57b—Binding of the chemokine bRANTES (CCL5) to T cells from a patient with Rheumatoid arthritis. Blood from a patient with RE was incubated with bRANTES and analysed with flow cytometry. The T cells were characterized as CD3 positive cells.

Figure 58A:
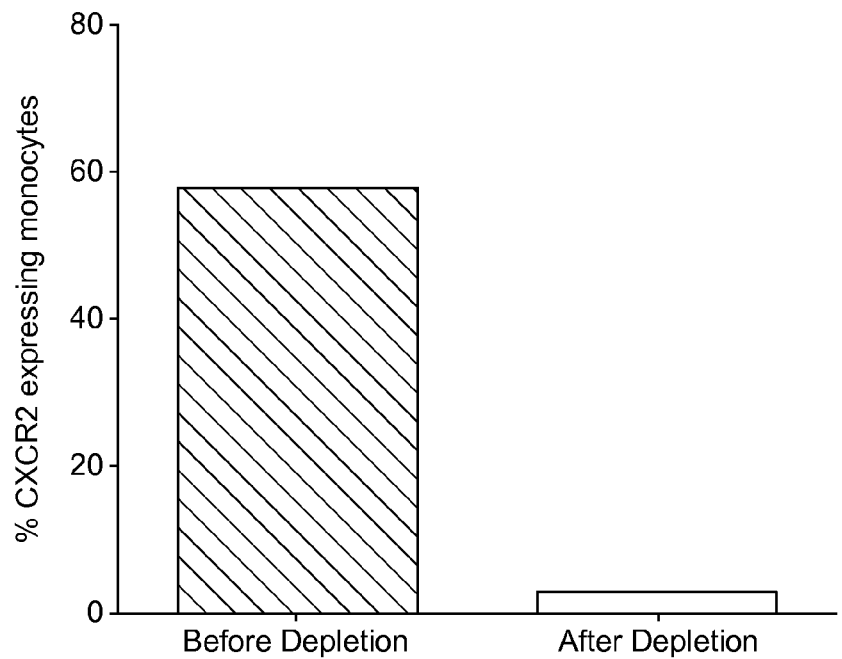

FIG. 58a—Depletion of CCR2 expressing monocytes with Sepharose Streptavidin-matrix conjugated with bMCP1.

Figure 58B:
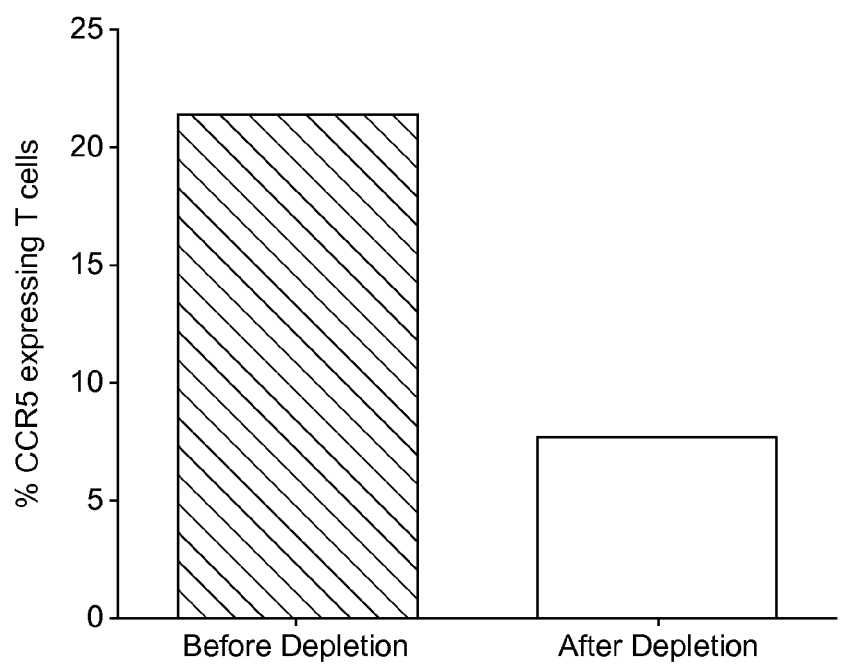

FIG. 58b—Depletion of CCR5 expressing T cells with Sepharose Streptavidin-matrix conjugated with bRANTES. Blood cells from a patient with Rheumatoid arthritis were incubated with b chemokine-Sepharose Streptavidin-matrix. Unbound cells were retrieved by washing the matrix with Phosphate Buffer Saline. The cells (After Depletion) were then analysed with flow cytometry and compared with cells that had not been incubated with b-chemokine-matrix (Before Depletion).

D. Treating Cancer

Figure 59:
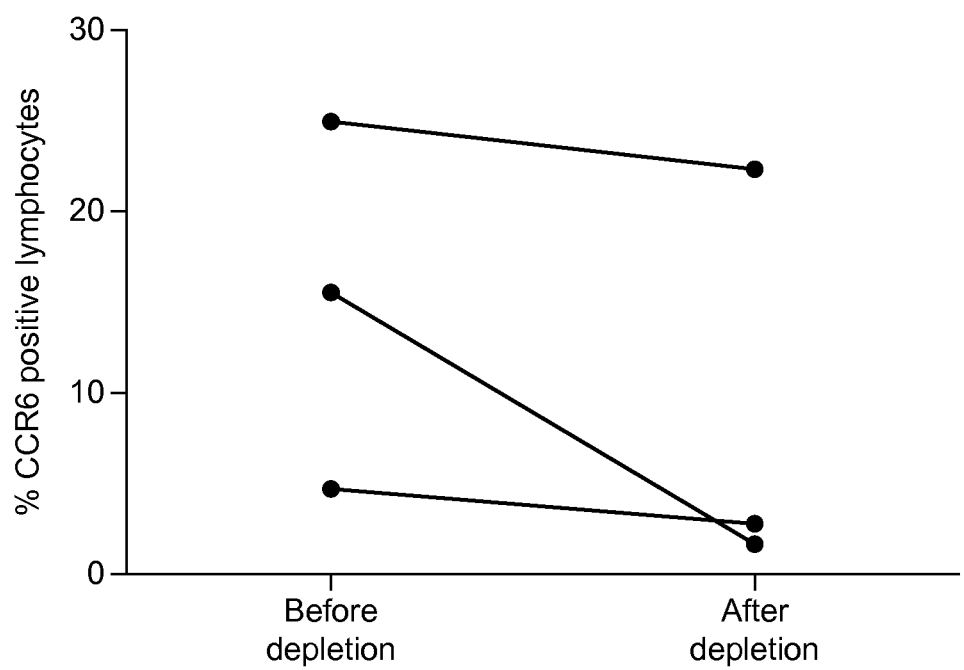

FIG. 59—Results of in vitro depletion tests performed on the biotinylated MIP-3alpha coupled matrix showing ability to eliminate CCR6-expressing lymphocytes from blood from three healthy donors.

Figure 60:
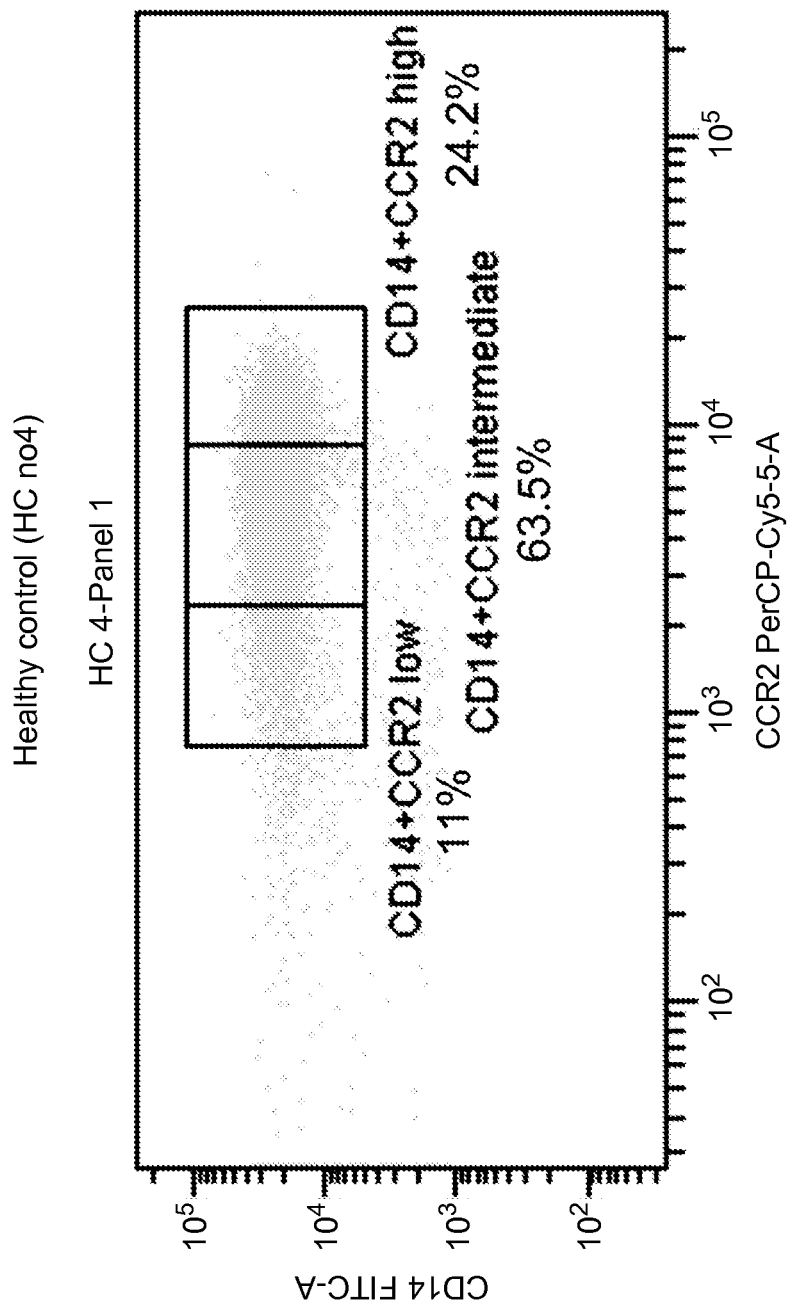

FIG. 60—Example of gating criteria for CCR2 expressing monocytes

Figure 61:
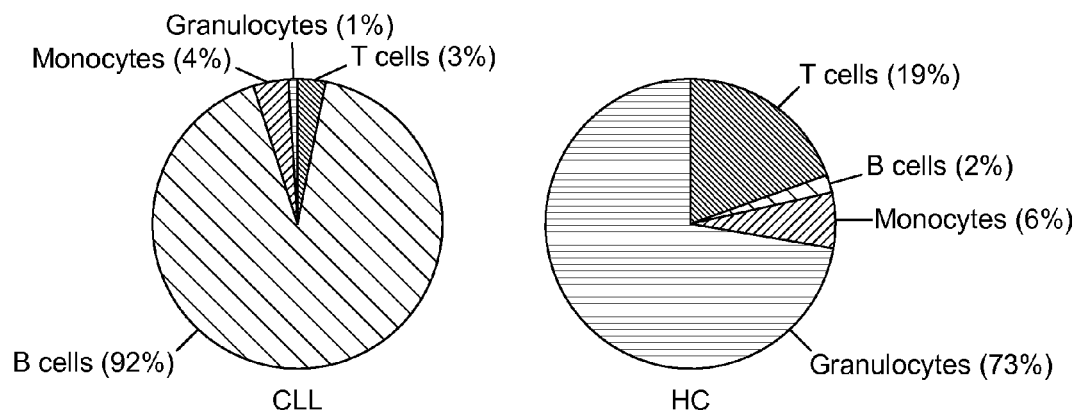

FIG. 61—Percentage of different leukocyte populations in a patient with Chronic Lymphatic Leukemia and in a healthy control (HC). Blood from a patient with CLL and a healthy control were analysed for the expression of cell specific markers with flow cytometry. The B cells were characterized as CD19 positive, the T cells as CD3 positive, granulocytes as CD16 positive and monocytes as CD14 positive.

Figure 62:
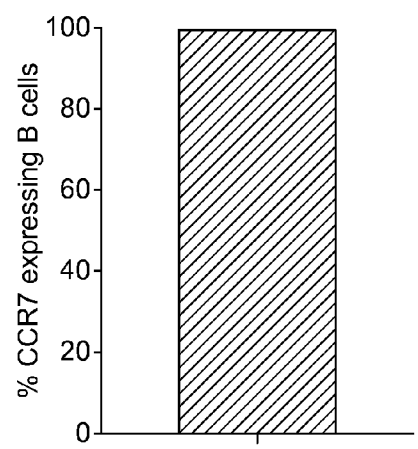

FIG. 62—Expression of CCR7 on B cells from a patient with Chronic Lymphatic Leukemia. Blood from a patient with CCL was analysed for the expression of various chemokine receptors by flow cytometry. The B cells were characterized as CD19+ lymphocytes.

Figure 63:
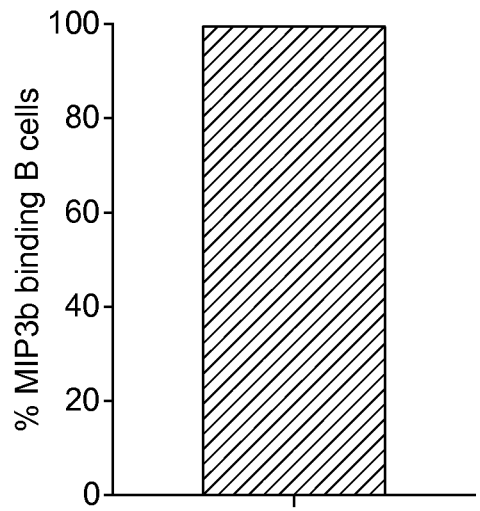

FIG. 63—Binding of the biotinylated chemokine MIP3b (CCL19) to B cells from a patient with Chronic Lymphatic Leukemia. Blood from a patient with CLL was incubated with bMIP3b and analysed by flow cytometry. The B cells were characterized as CD19+ lymphocytes.

Figure 64:
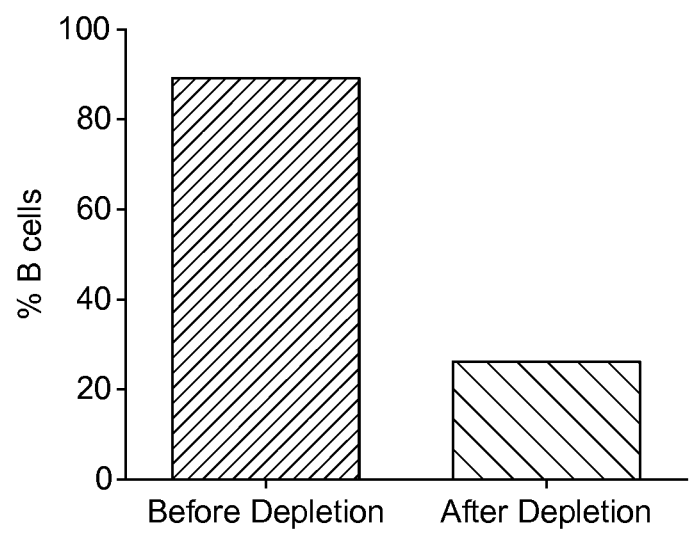

FIG. 64—Depletion of B cells with Sepharose Streptavidin matrix conjugated with bMIP3b. Blood cells from a patient with CLL were incubated with bMIP3b-SepharoseStreptavidin matrix. Unbound cells were retrieved by washing the matrix with Phosphate Buffer Saline. The cells (After Depletion) were then analysed by flow cytometry and compared with cells that had not been incubated with the MIP3b-matrix (Before Depletion).

Figure 65:
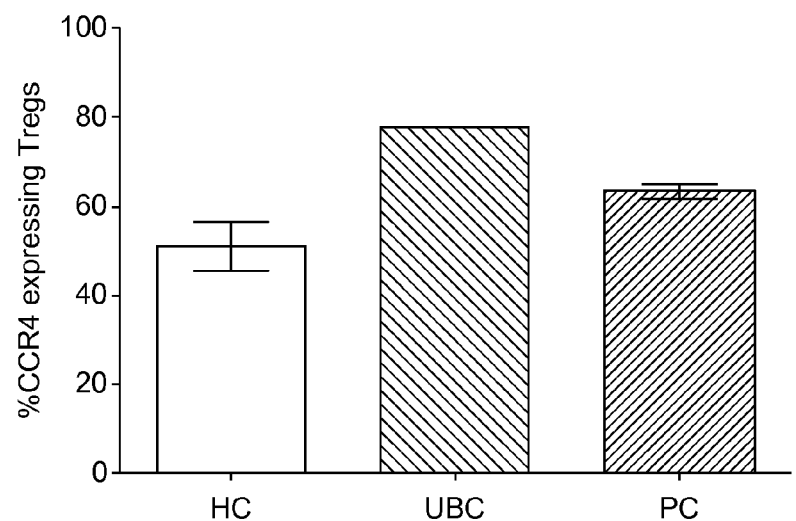

FIG. 65—Frequency of CCR4 positive Tregs in eight healthy controls (HC), two patients with Pancreatic Cancer (PC) and one patient with Urinay Bladder Cancer (UBC). The expression of chemokine receptors and specific cell markers was analyzed with flow cytometry. The Tregs were defined as CD4 positive, CD25 positive (hi), CD127 negative cells.

Figure 66:
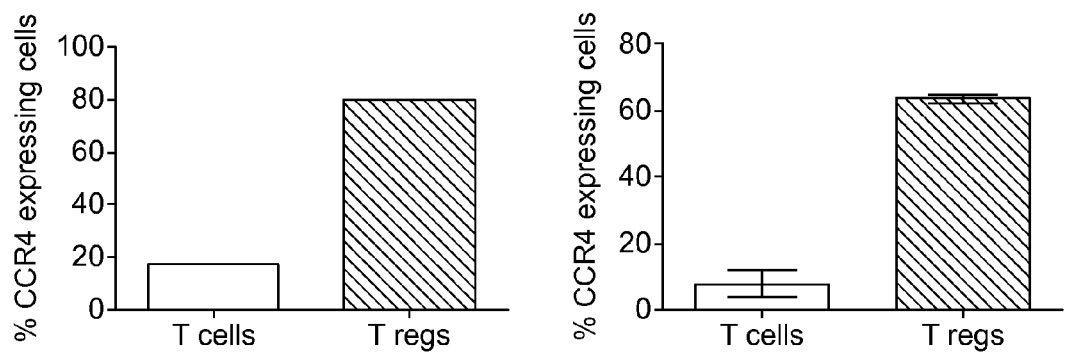

FIG. 66—CCR4 expression on Tregs compared to T cells in UBC (left) and PC (right). The expression of chemokine receptors and specific cell markers was analysed with flow cytometry in two patients with PC and one patient with UBC.

Figure 67:
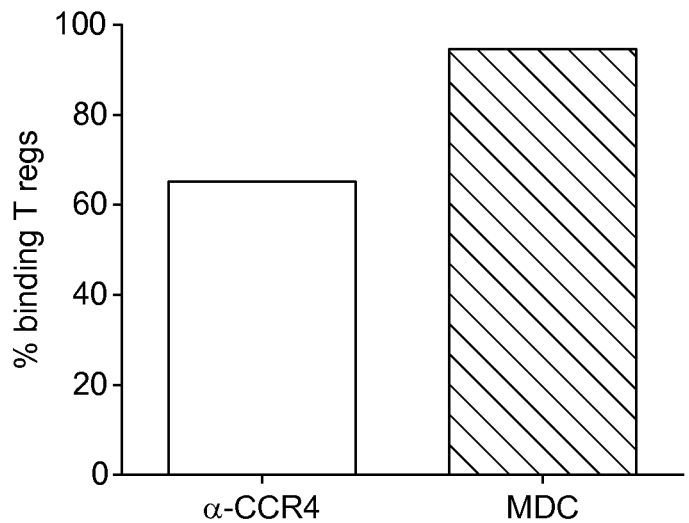

FIG. 67—Binding of the chemokine bMDC to Tregs. Blood cells from a patient with PC were incubated with biotinylated chemokine or an anti-CCR4 antibody and analyzed with flow cytometry.

Figure 68:
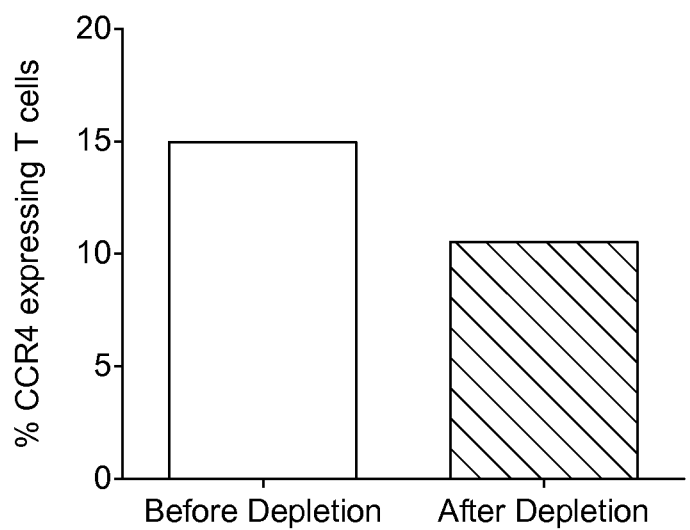

FIG. 68—Depletion of CCR4 expressing T cells with Sepharose Streptavidin-matrix conjugated with biotinylated MDC (bMDC). Blood cells from a patient with UBC were incubated with biotinylated chemokine-Sepharose Streptavidin-matrix. Unbound cells were retrieved by washing the matrix. The unbound cells (After Depletion) were then analysed with flow cytometry and compared with cells that had not been incubated with bchemokine-matrix (Before Depletion).

E. Treating Mental Disorders

Figure 69A:
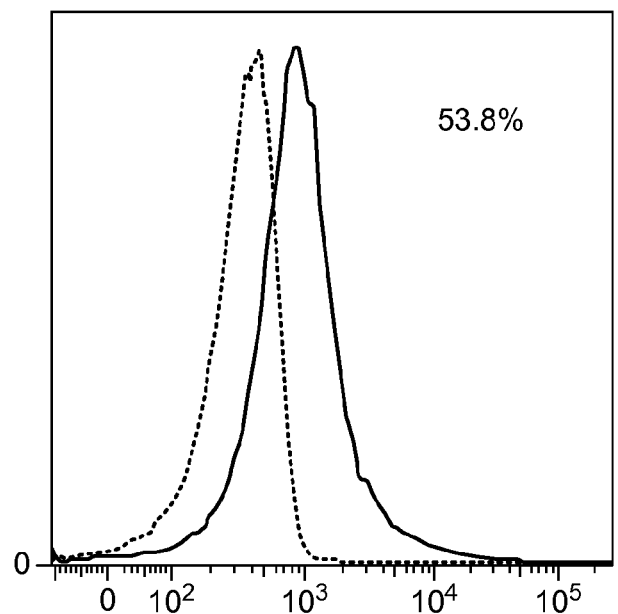

FIG. 69a—binding of eotaxin to neutrophils/eosinophils (line) in peripheral blood. The graph represents a summary of four tests.

Figure 69B:
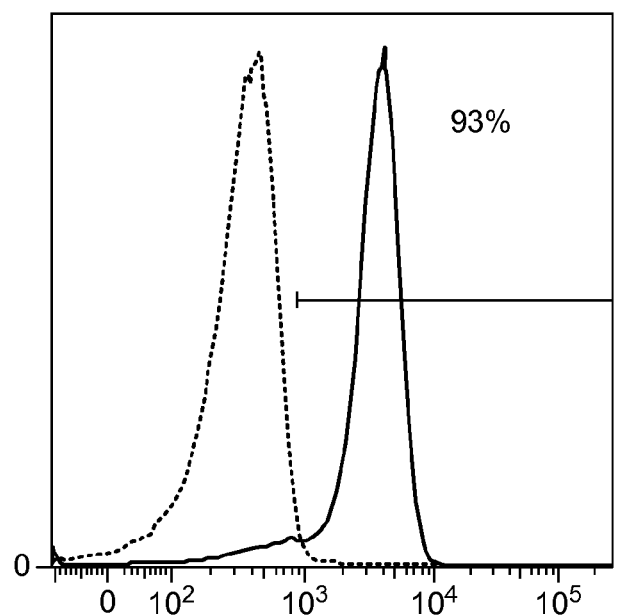

FIG. 69b—binding of CCR3-antibody to neutrophils/eosinophils (line) in peripheral blood. The graph represents a summary of four tests.

Figure 70A:
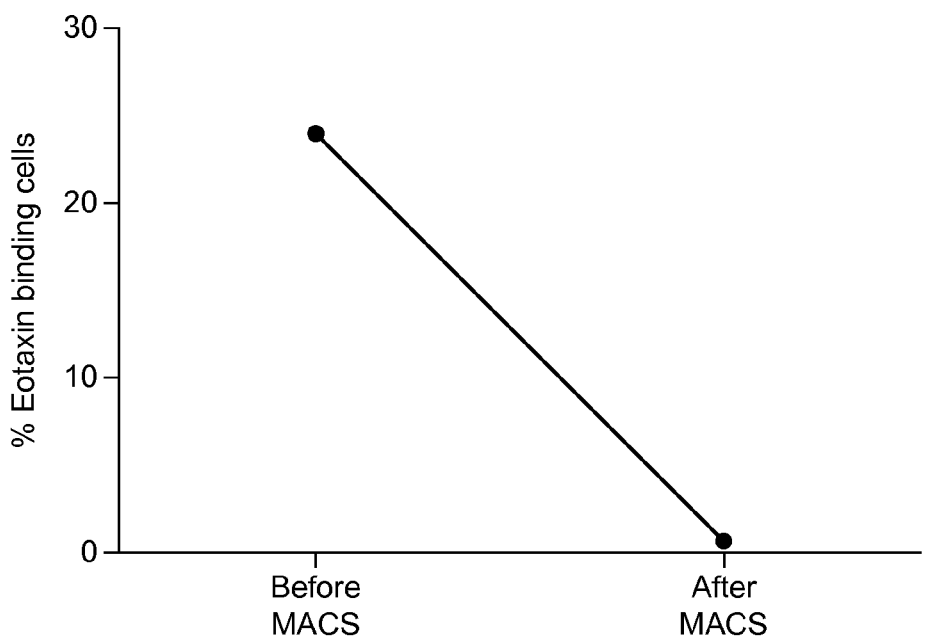

FIG. 70a—Results of in vitro depletion tests performed on the biotinylated eotaxin coupled matrix showing ability to eliminate CCR3-expressing cells from blood from a healthy donor.

Figure 70B:
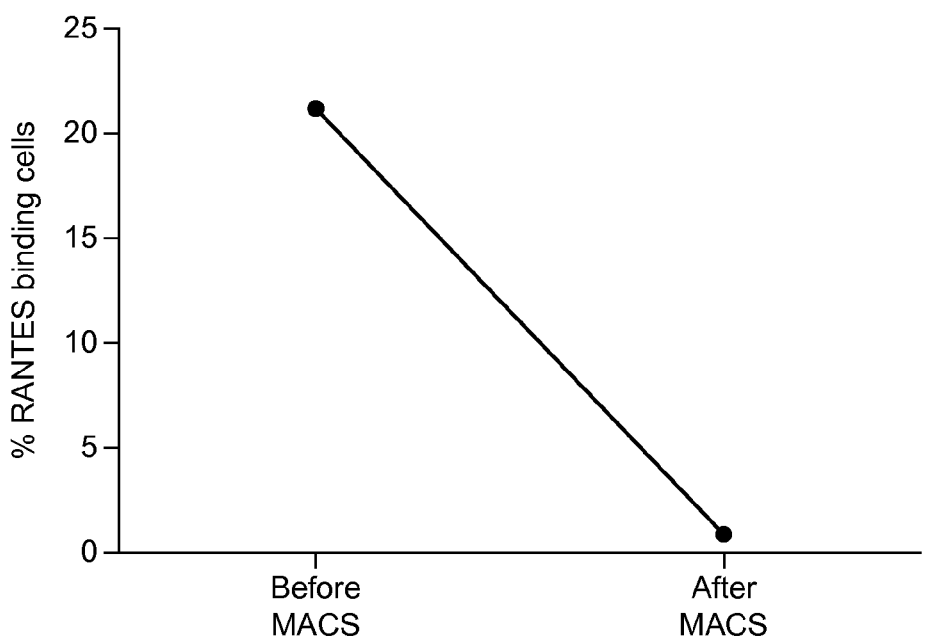

FIG. 70b—Results of in vitro depletion tests performed on the biotinylated RANTES coupled matrix showing ability to eliminate chemokine receptor-expressing cells from peripheral blood taken from a healthy donor.

Figure 71:

FIG. 71—Sequence (SED ID NO: 78) and biotinylation, via a spacer group, of mature protein eotaxin derivative containing C-terminal amide.

Figure 72:
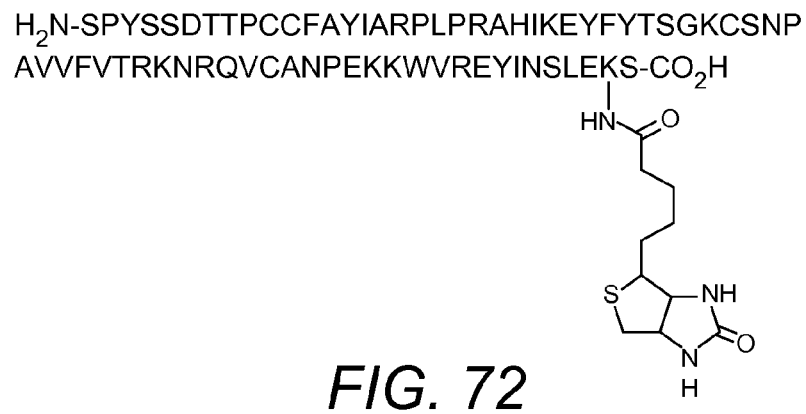

FIG. 72—Sequence (SED ID NO: 86) and biotinylation, of RANTES derivative.

Figure 73:
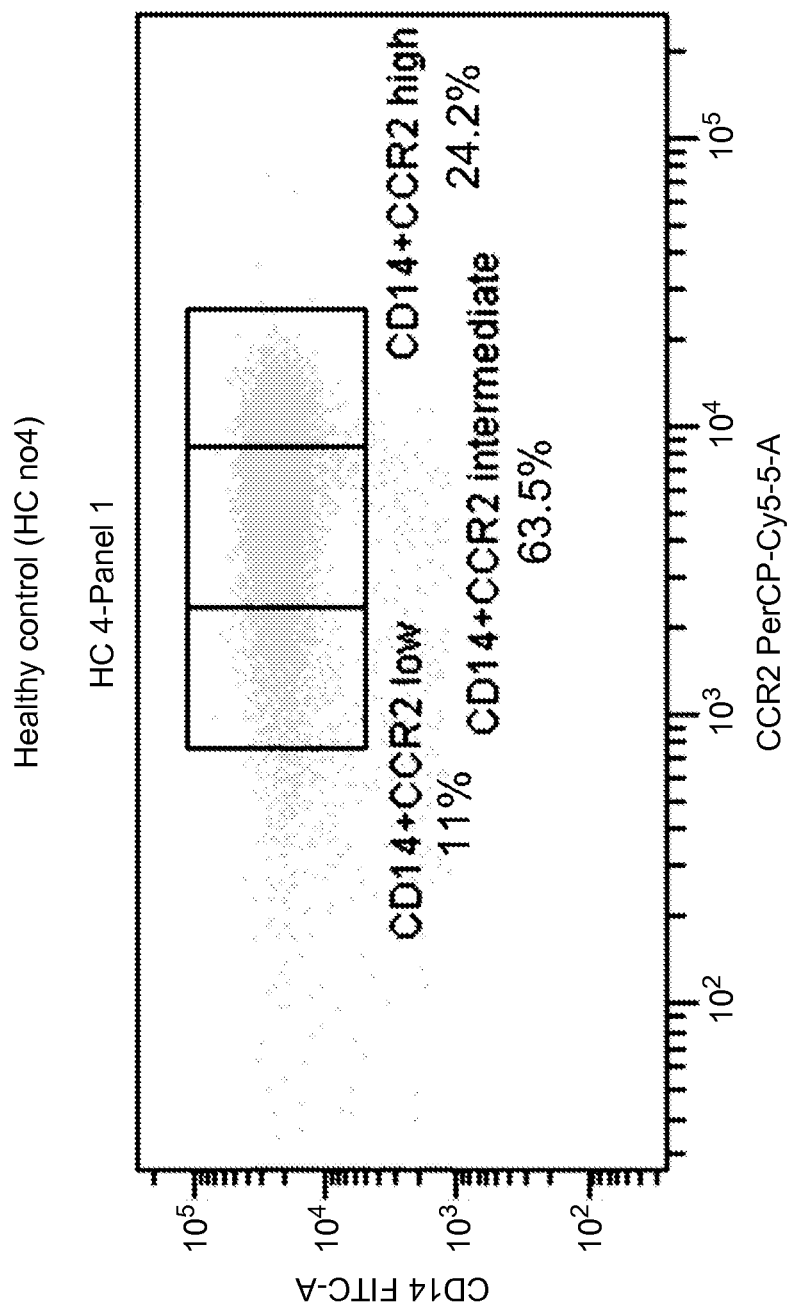

FIG. 73—Example of gating criteria for CCR2 expressing monocytes.

Figure 74:
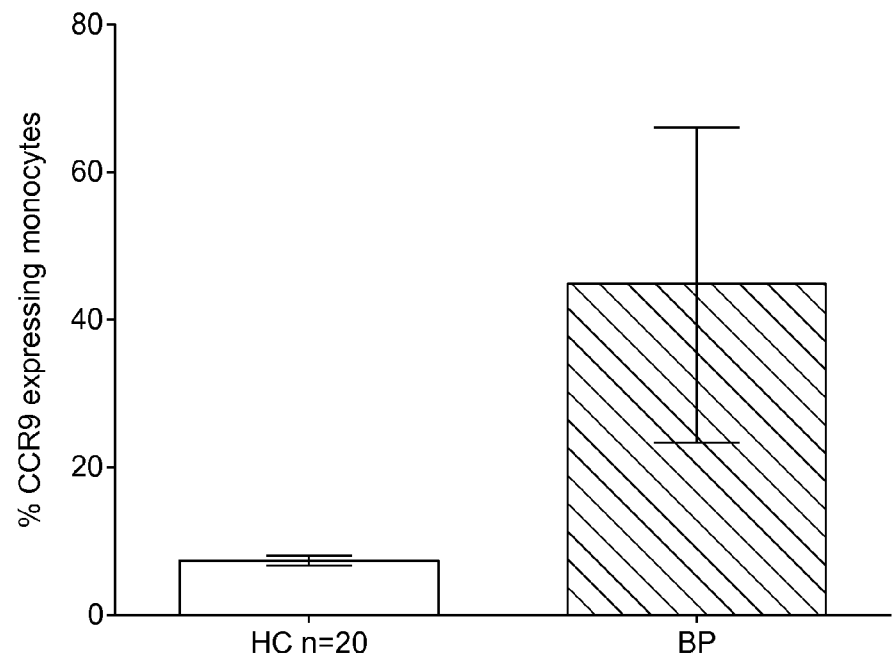

FIG. 74—Frequency of CCR9 expressing monocytes in two patients with bipolar disorder (BP) and in 20 healthy controls (HC). Blood was analysed for the expression of various chemokine receptors by flow cytometry. The monocytes were characterized as CD14 positive cells.

Figure 75:
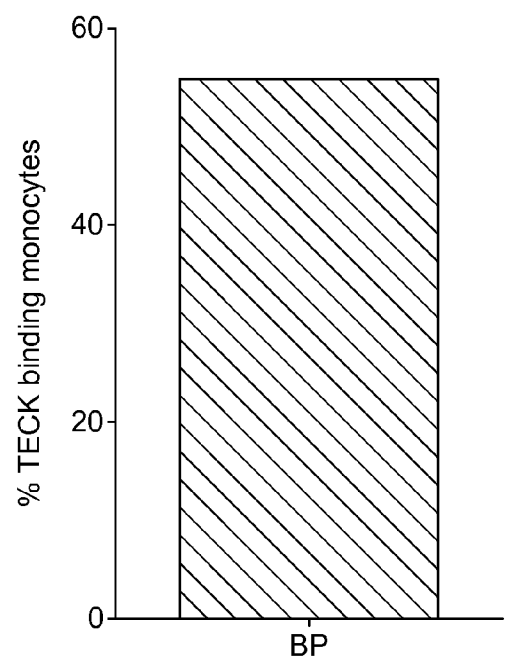

FIG. 75—Binding of the chemokine bTECK (CCL25) to blood monocytes from a patient with BP. Blood was incubated with bTECK and analysed with flow cytometry. The monocytes were characterized as CD14 positive cells.

Figure 76:
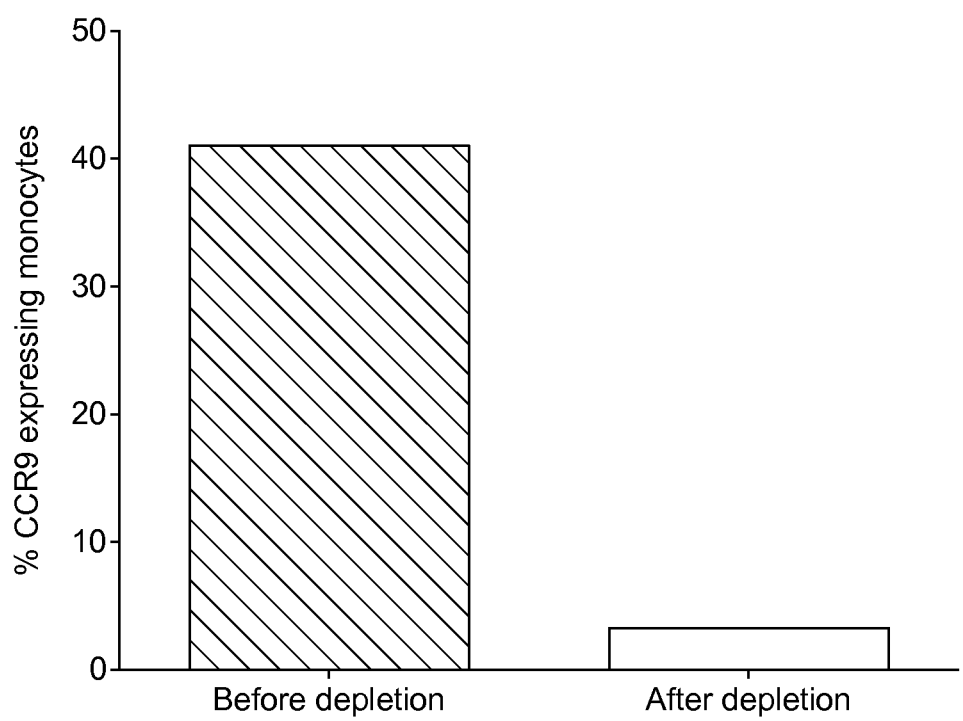

FIG. 76—Depletion of CCR9 expressing monocytes and with Sepharose Streptavidin-matrix conjugated with bTECK. Blood cells from a patient with bipolar disorder were incubated with bTECK-Sepharose Streptavidin-matrix. Unbound cells were retrieved by washing the matrix with Phosphate Buffer Saline. The cells (After Depletion) were then analysed with flow cytometry and compared with cells that had not been incubated with bTECK-matrix (Before Depletion).

F. Treating Conditions Associated with Allergy

Figure 77A:
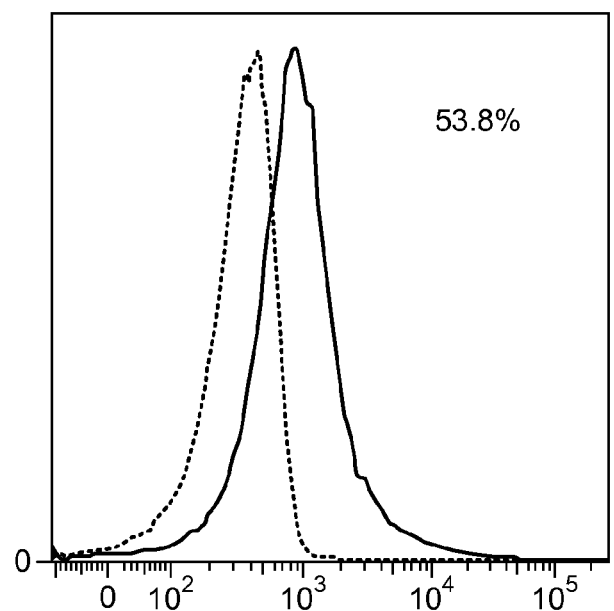

FIG. 77a—binding of eotaxin to neutrophils/eosinophils (line) in peripheral blood. The graph represents a summary of four tests.

Figure 77B:
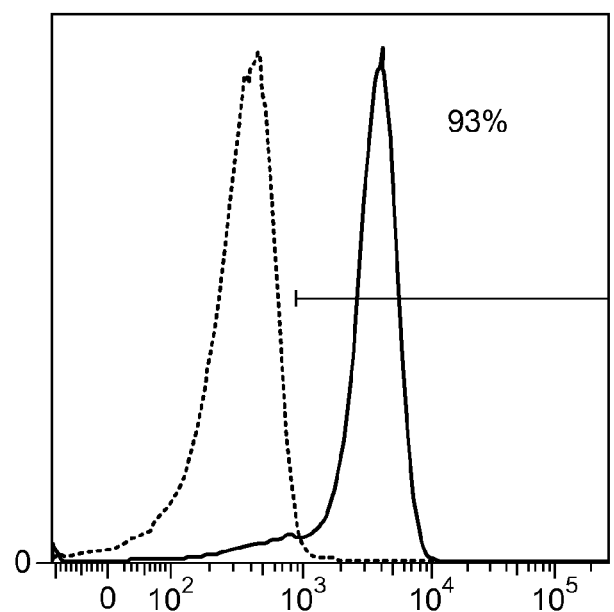

FIG. 77b—binding of CCR3-antibody to neutrophils/eosinophils (line) in peripheral blood. The graph represents a summary of four tests.

Figure 78A:
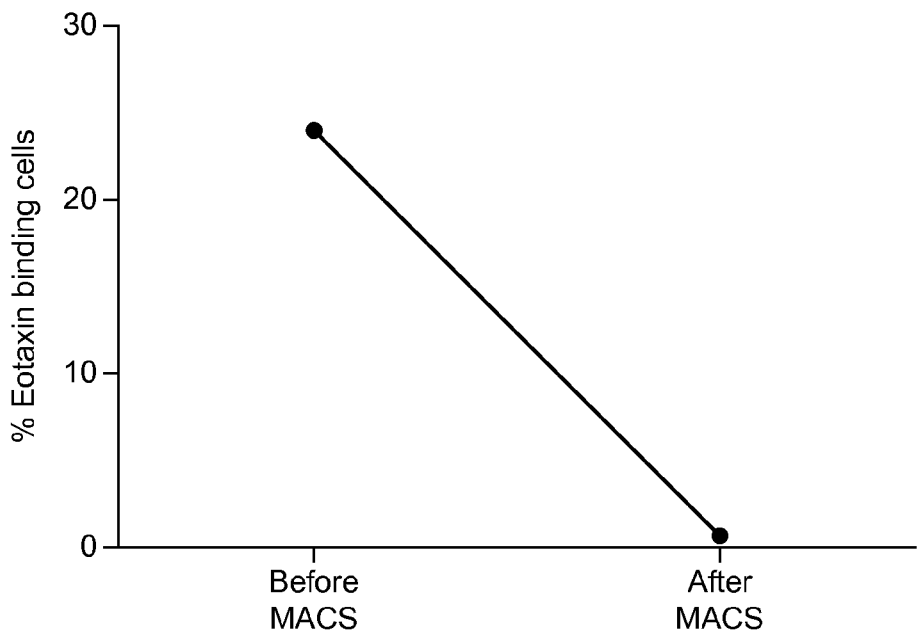

FIG. 78a—Results of in vitro depletion tests performed on the biotinylated eotaxin coupled matrix showing ability to eliminate CCR3-expressing cells from blood from a healthy donor.

Figure 78B:
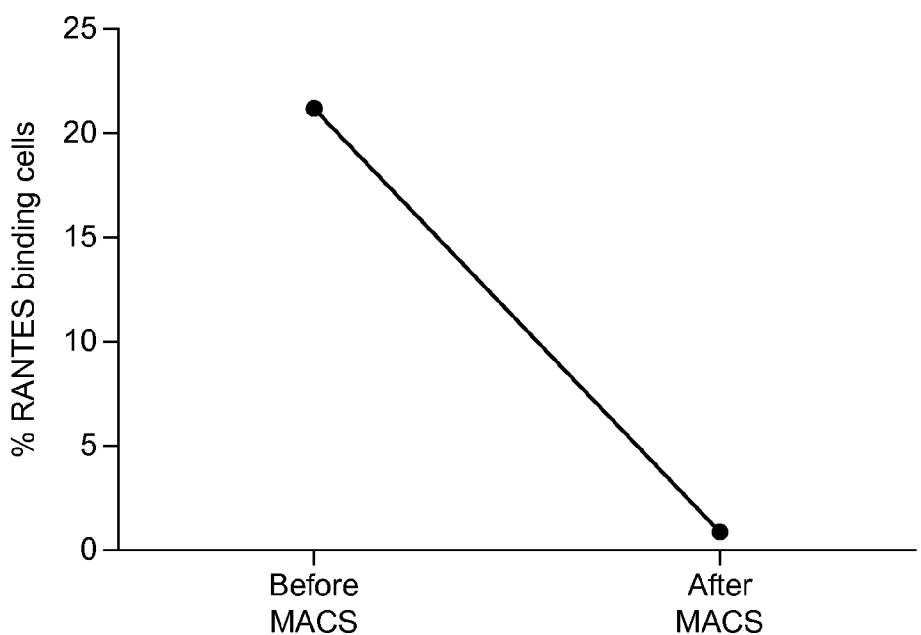

FIG. 78b—Results of in vitro depletion tests performed on the biotinylated RANTES coupled matrix showing ability to eliminate chemokine receptor-expressing cells from peripheral blood taken from a healthy donor.

Figure 79:

FIG. 79—Sequence (SED ID NO: 93) and biotinylation, via a spacer group, of mature protein eotaxin derivative containing C-terminal amide.

Figure 80:
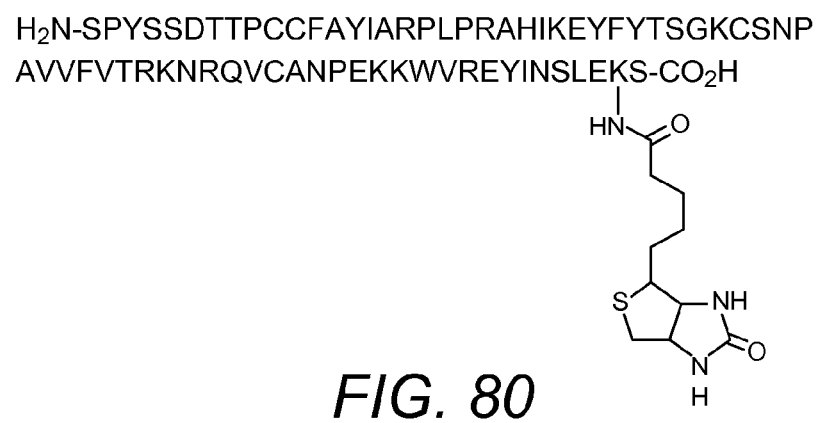

FIG. 80—Sequence (SED ID NO: 97) and biotinylation, of RANTES derivative

Figure 81A:
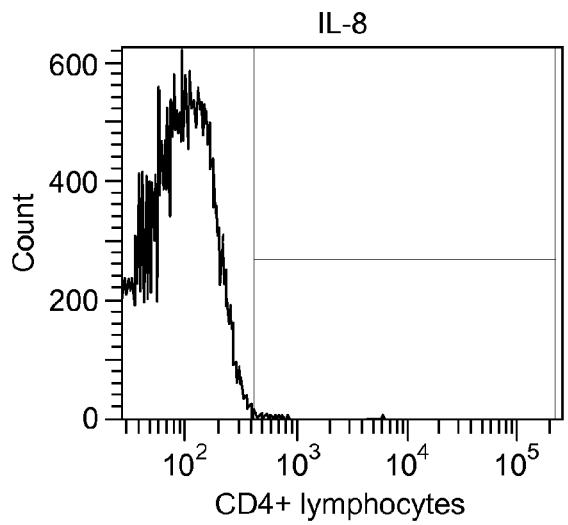
Figure 81B:
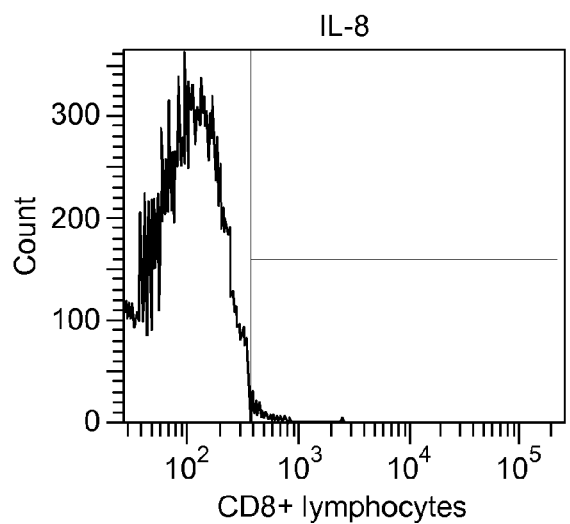
Figure 81C:
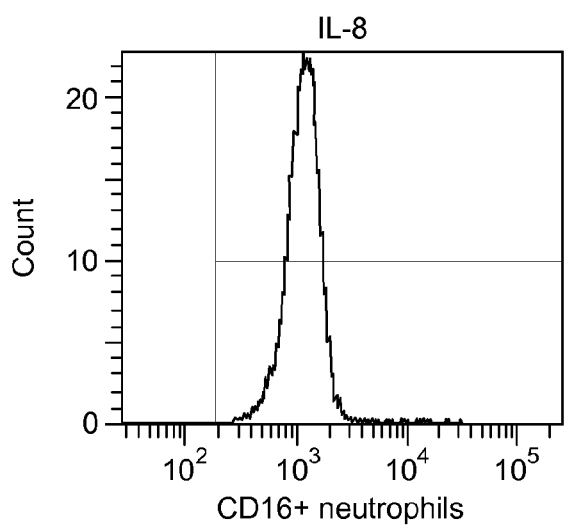
Figure 82:
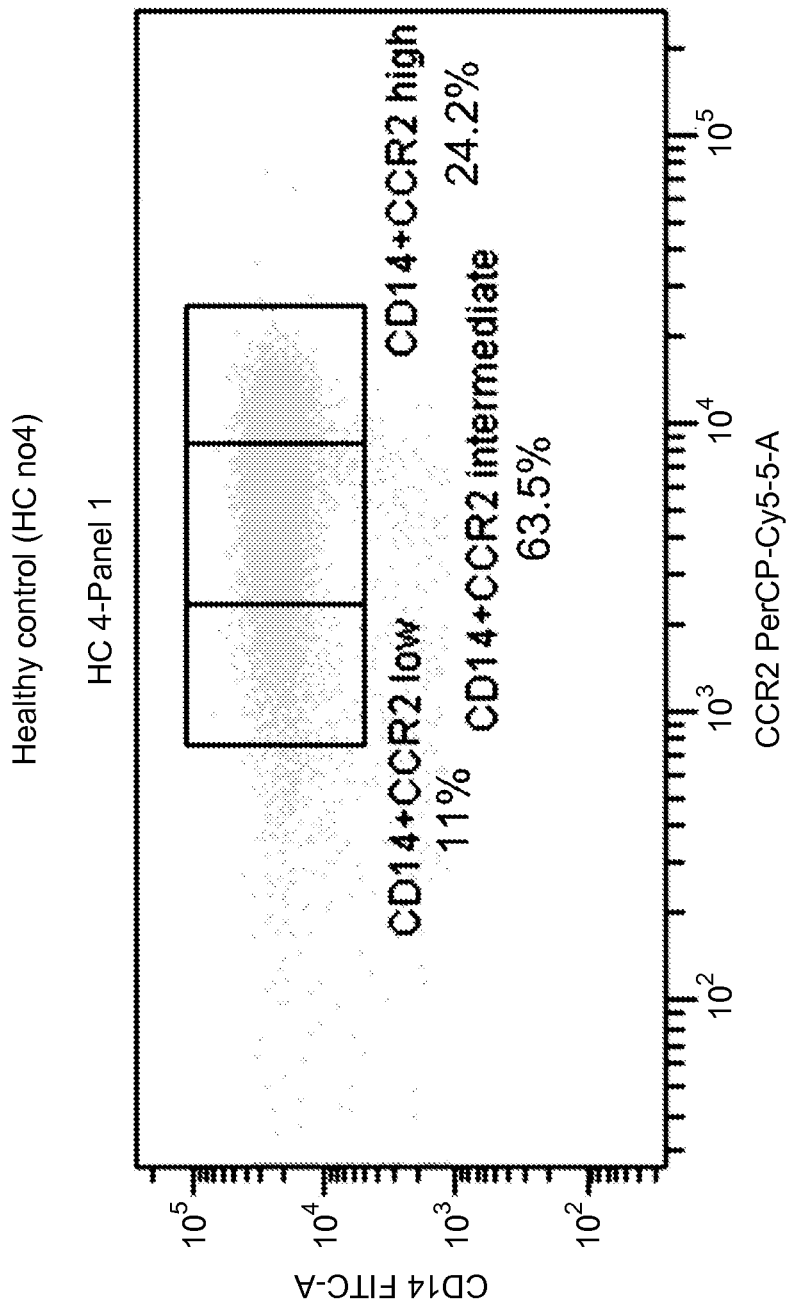

FIGS. 81a, 81b & 81c—the binding of IL-8 by CD4+, CD8+ T-cells and CD16+ neutrophils respectively, obtained from peripheral blood of a healthy donor;

FIG. 82—example of gating criteria for CCR2 expressing monocytes.

Figure 83A:
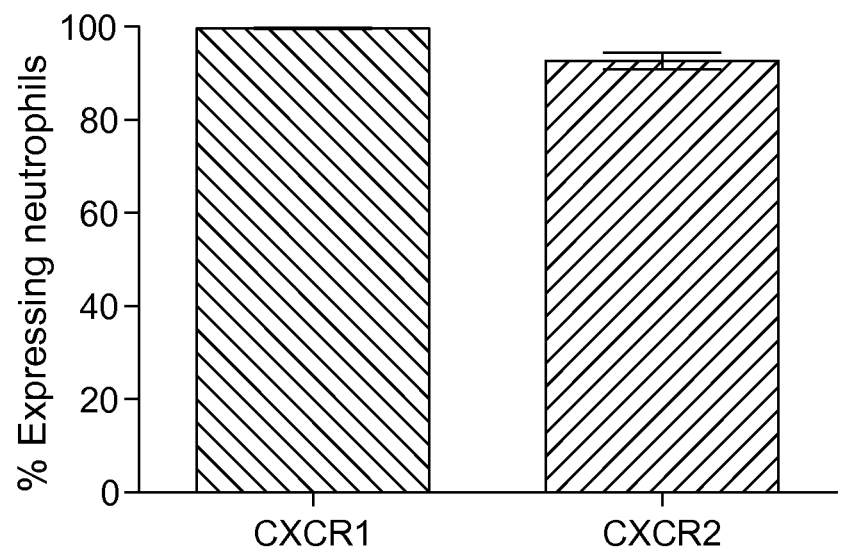

FIG. 83a—Frequency of neutrophils that express CXCR1 and CXCR2.

Figure 83B:
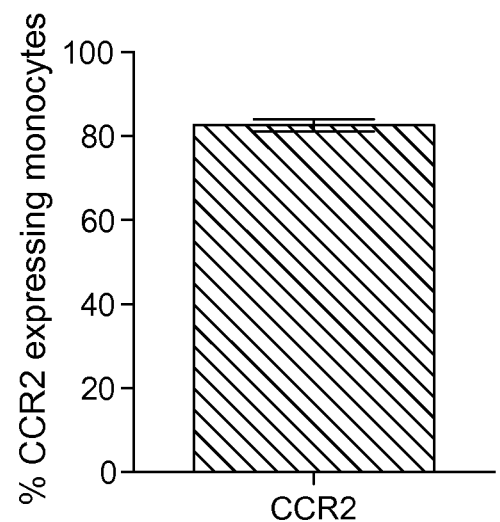

FIG. 83b—Frequency of monocytes that express CCR2.

Figure 83C:
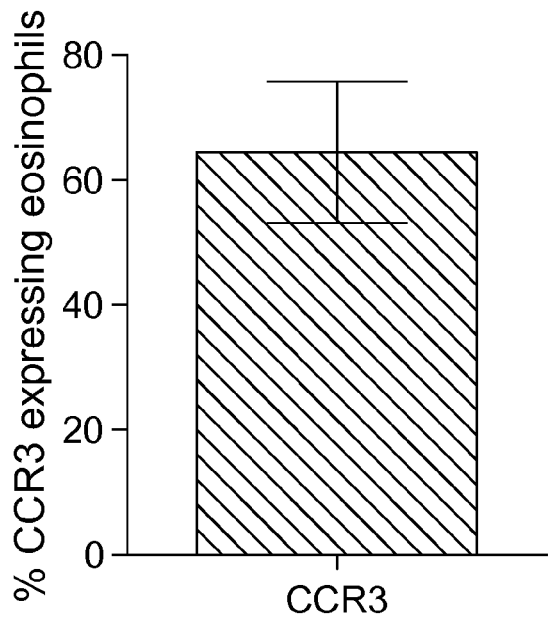

FIG. 83c—Frequency of eosinophils that express CCR3.

Figure 84A:
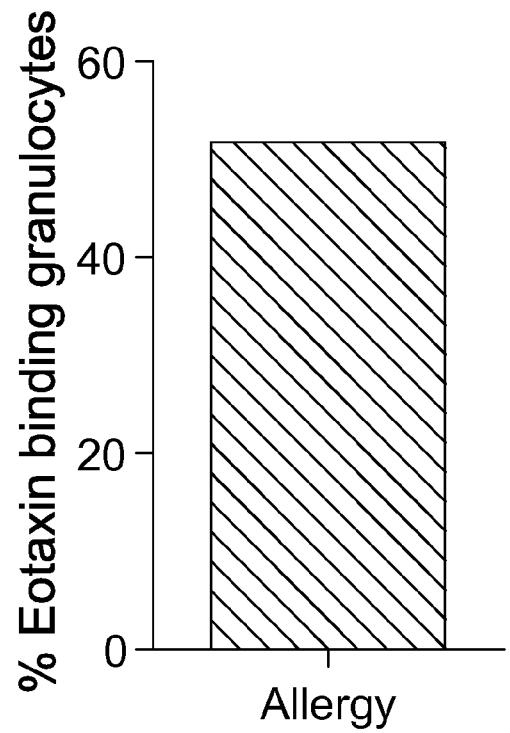

FIG. 84a—Binding of the chemokine bEotaxin (CCL11) to granulocytes from patient with allergy. Blood from a patient with allergy was incubated with bEotaxin and analysed with flow cytometry. Granuocytes were characterized based on size and granularity.

Figure 84B:
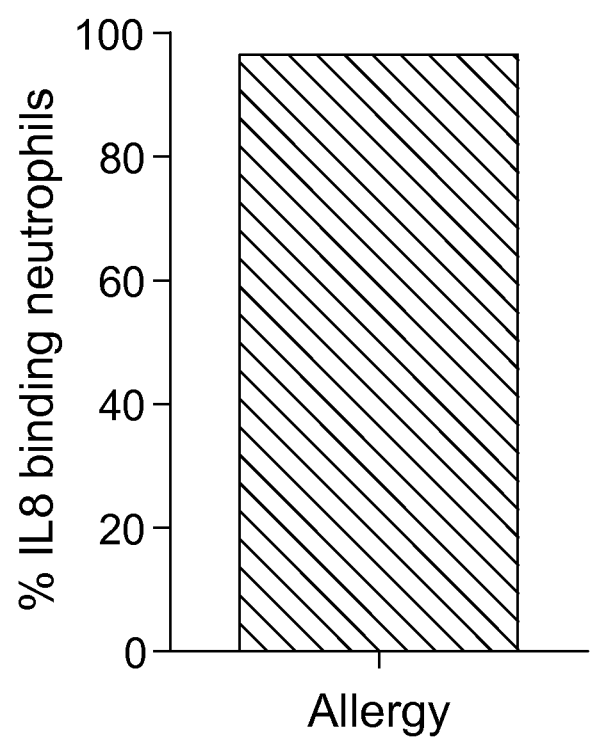

FIG. 84b—Binding of the chemokine bIL8 to neutrophils from a patient with allergy. Blood from a patient with allergy was incubated with bIL8 and analysed with flow cytometry. The neutrophils were characterized as CD16 positive cells.

Figure 85A:
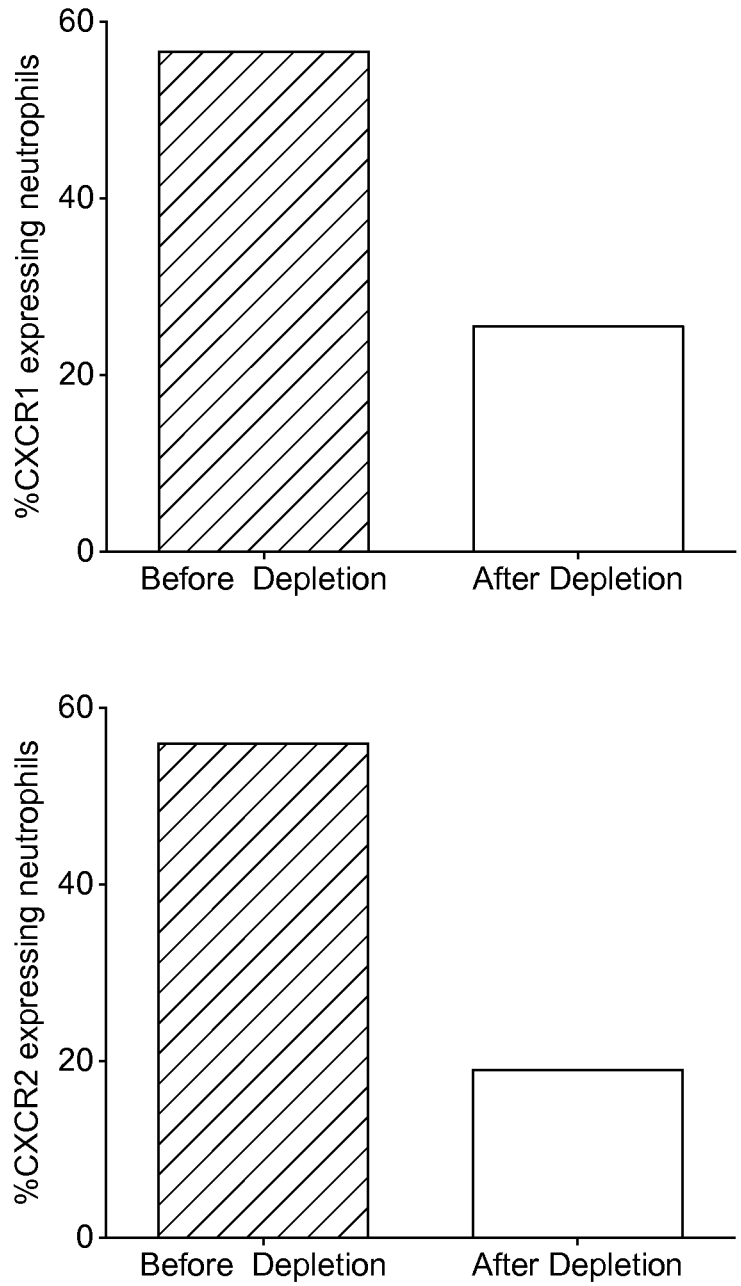

FIG. 85a—Depletion of CXCR1 and CXCR2 expressing neutrophils with Sepharose Streptavidin-matrix conjugated with bIL8.

Figure 85B:
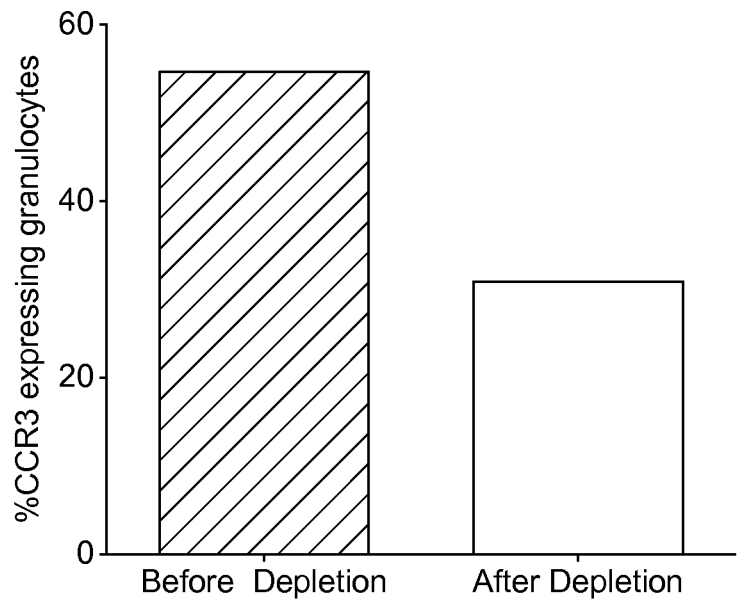

FIG. 85b—Depletion of CCR3 expressing granulocytes with Sepharose Streptavidin-matrix conjugated with bEotaxin.

Figure 85C:
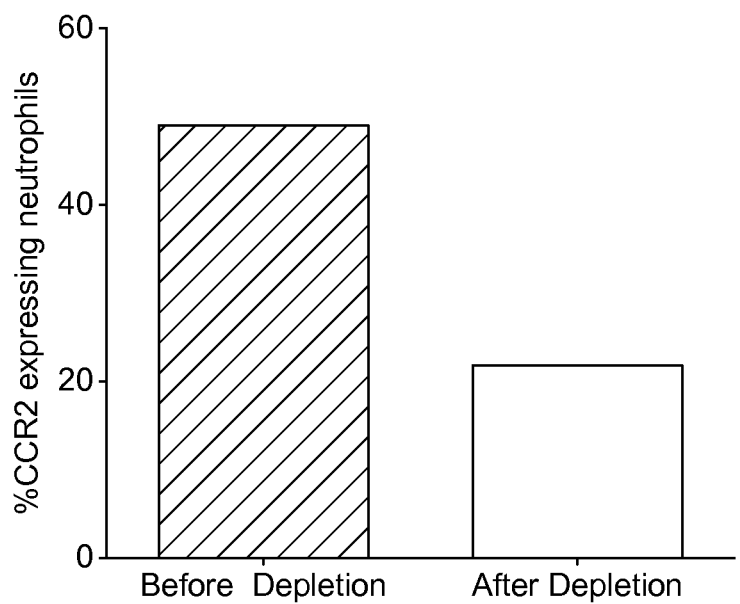

FIG. 85c—Depletion of CCR2 expressing monocytes with Sepharose Streptavidin-matrix conjugated with bMCP1. Blood cells from a patient with allergy were incubated with biotinylated-Chemokine-SepharoseStreptavidin-matrix. Unbound cells were retrieved by washing the matrix with Phosphate Buffer Saline. The cells (After Depletion) were then analysed with flow cytometry and compared with cells that had not been incubated with bMCP1-matrix (Before Depletion).

Figure 86:
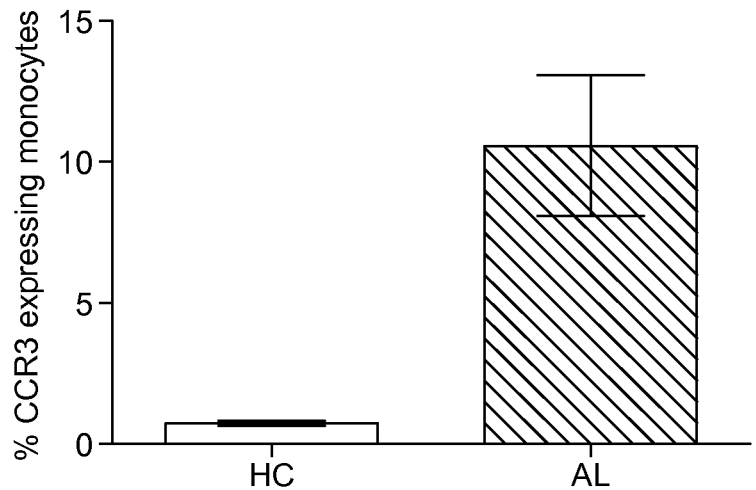

FIG. 86—Increased frequency of CCR3 expressing monocytes in blood from 4 allergic patients compared to 20 healthy controls. Analysed with flow cytometry.

Figure 87:
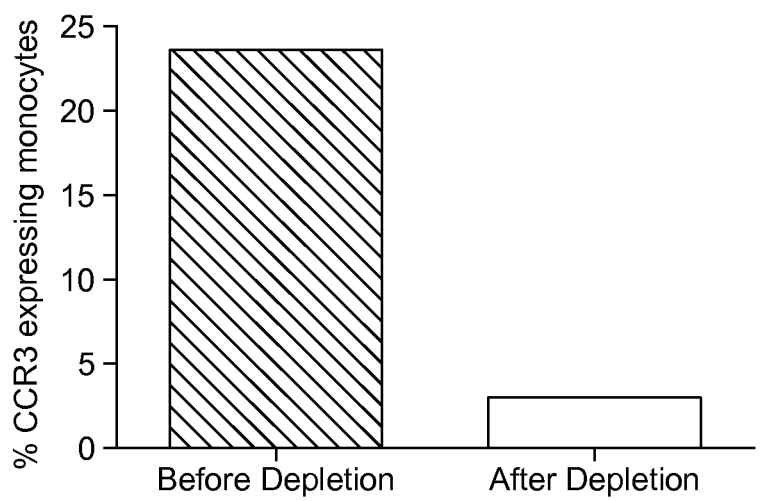

FIG. 87—Depletion of CCR3 expressing monocytes in one allergic patient with Sepharose StreptavidinMatrix-bEotaxin.

Figure 88:
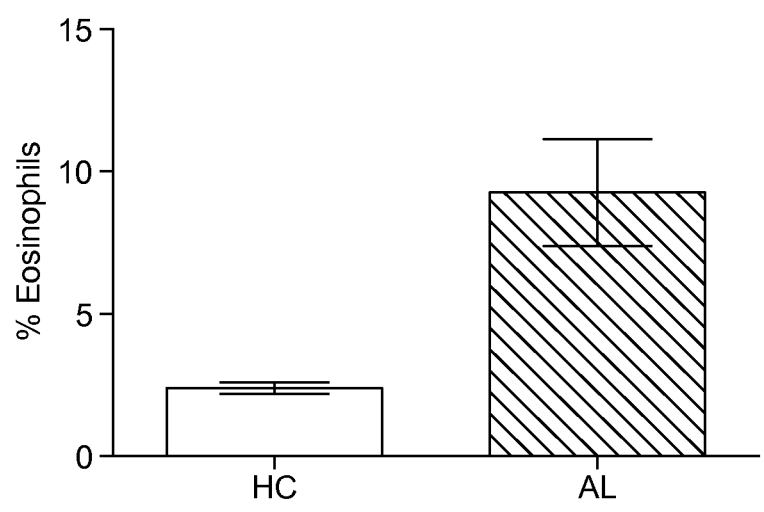

FIG. 88—Increased frequency of eosinophils in blood from four allergic patients compared to twenty healthy controls. Analysed with flow cytometry. Eosinophils were characterized as CD16 negative granulocytes.

G. Treating Inflammatory Skin Diseases

Figure 89A:
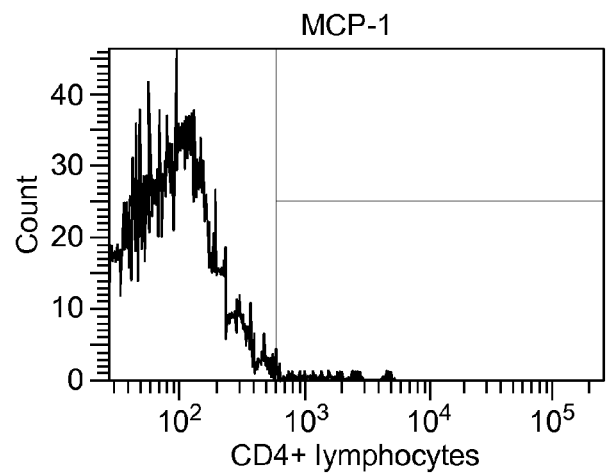
Figure 89B:
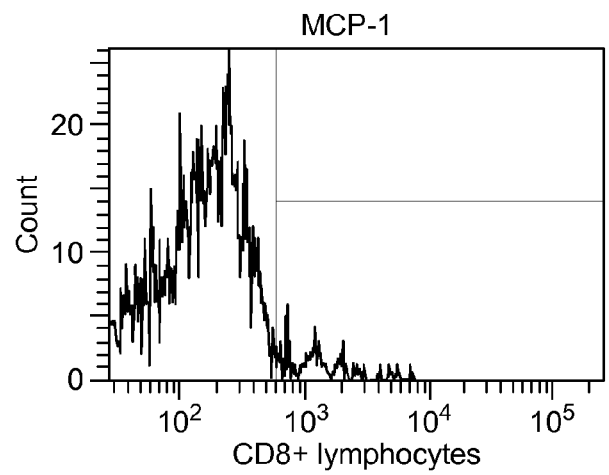
Figure 89C:
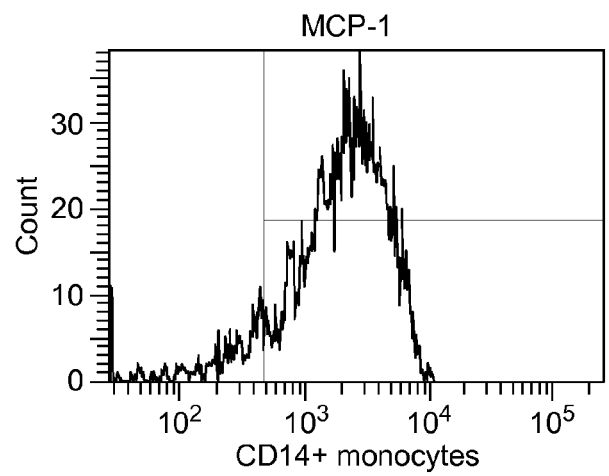

FIGS. 89a, 89b & 89c—the binding of biotinylized MCP-1 by CD4+, CD8+ T-cells and CD14+ monocytes respectively, obtained from peripheral blood of a healthy donor.

Figure 89D:
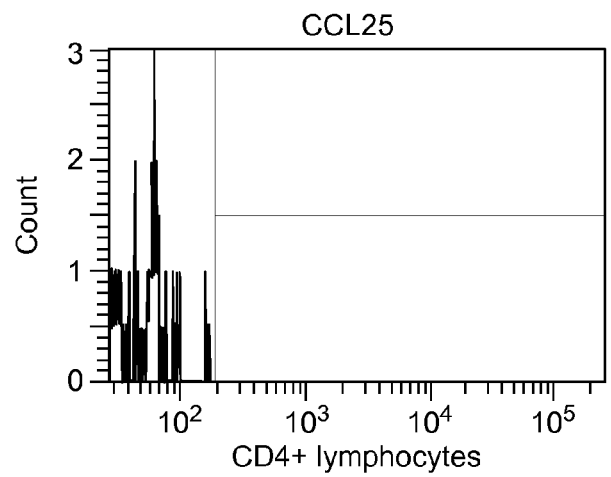
Figure 89E:
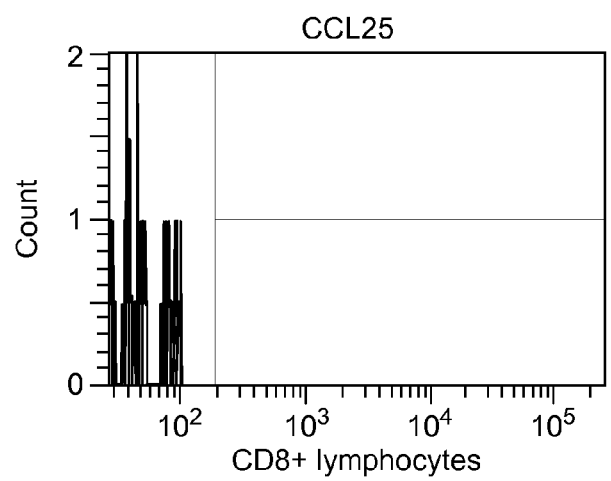
Figure 89F:
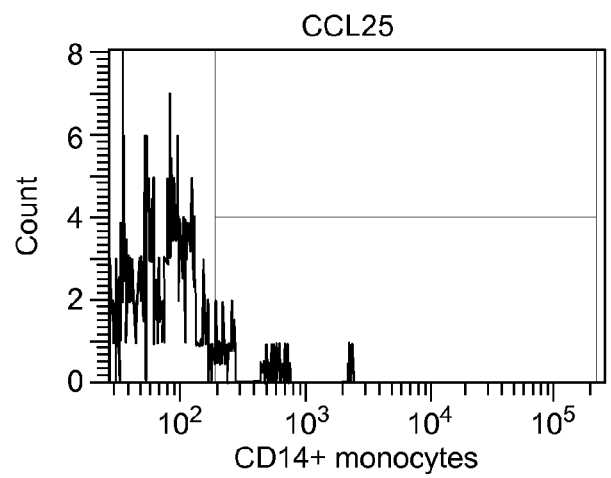
Figure 89G:
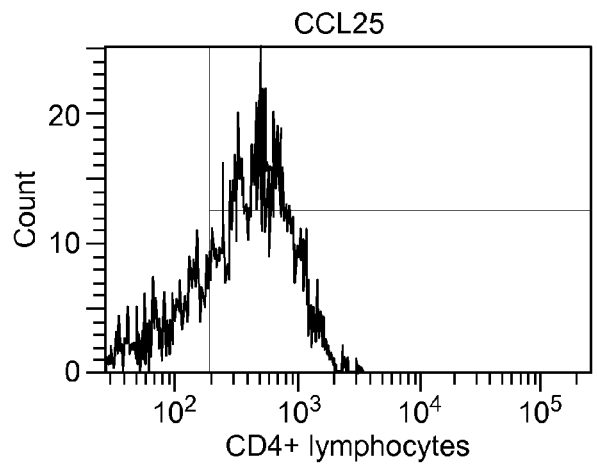
Figure 89H:
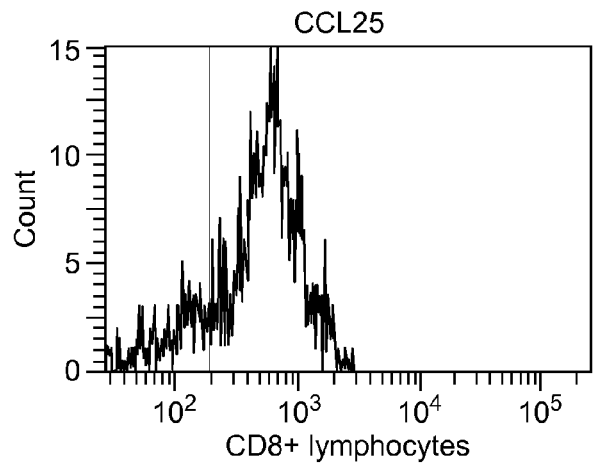
Figure 89I:
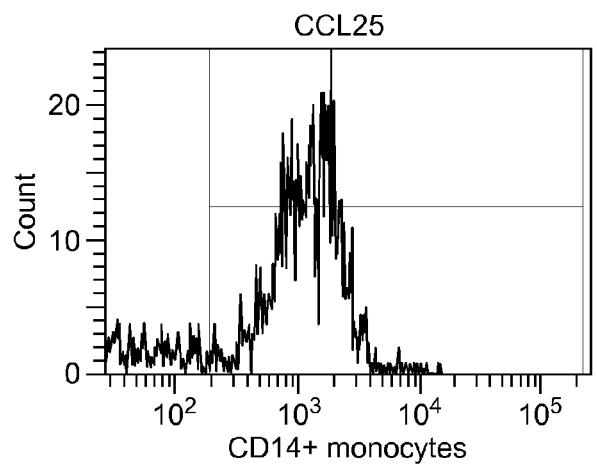
Figure 90A:
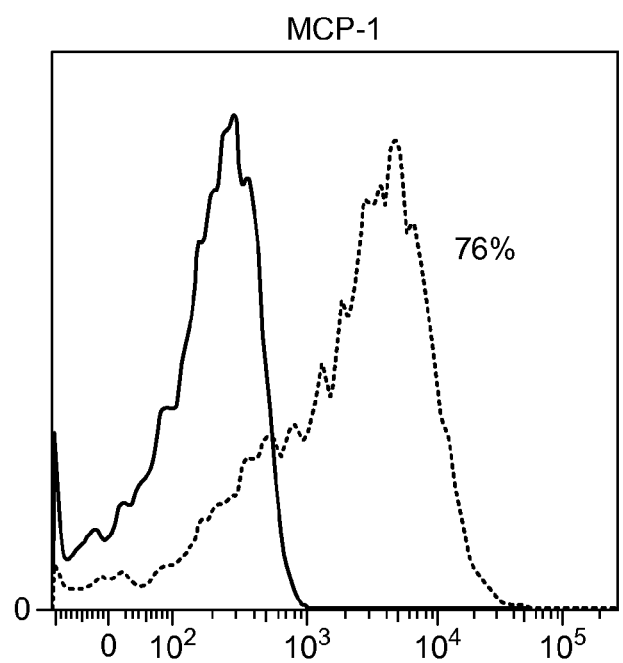

FIGS. 89d, 89e & 89f—the binding of biotinylized CCL25 by CD4+, CD8+ T-cells and CD14+ monocytes respectively, obtained from peripheral blood of a healthy donor;

FIGS. 89g, 89h & 89i—the binding of biotinylized CCL25 by CD4+, CD8+ T-cells and CD14+ monocytes respectively, obtained from peripheral blood of a patient with CD;

FIG. 90a—binding of MCP-1 to monocytes (dashed line) in peripheral blood taken from IBD patients. The graph represents a summary of four tests.

Figure 90B:
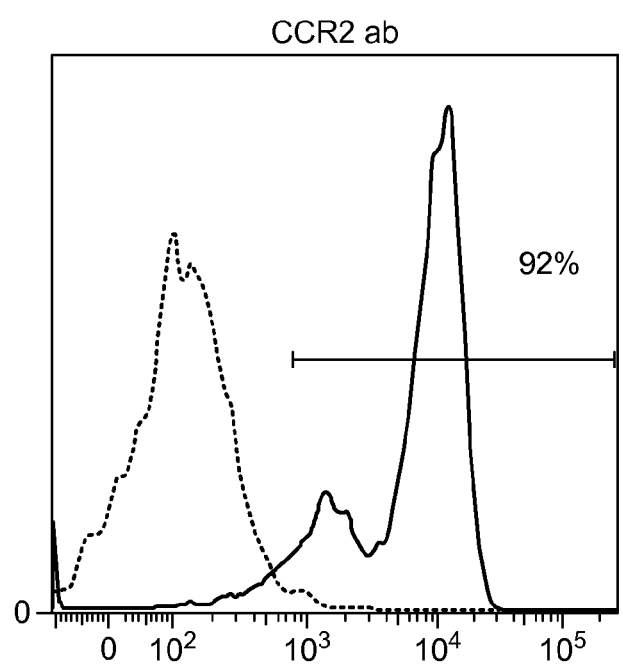

FIG. 90b—binding of CCR2-antibody to monocytes (line) in peripheral blood taken from IBD patients. The graph represents a summary of four tests.

Figure 91A:
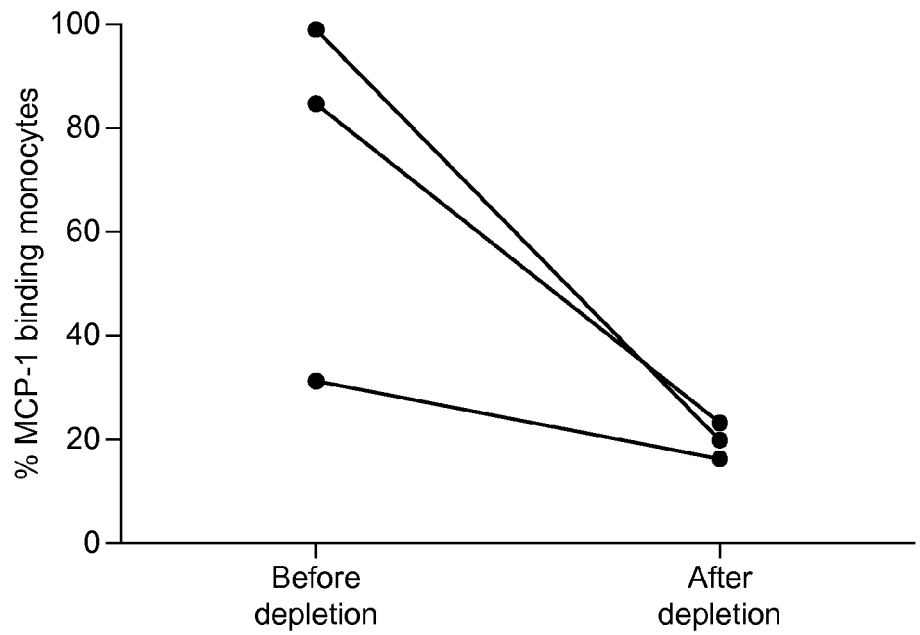

FIG. 91a—Results of in vitro depletion tests performed on the bMCP-1 coupled matrix showing ability to eliminate CCR2-expressing cells from blood from three healthy donors.

Figure 91B:
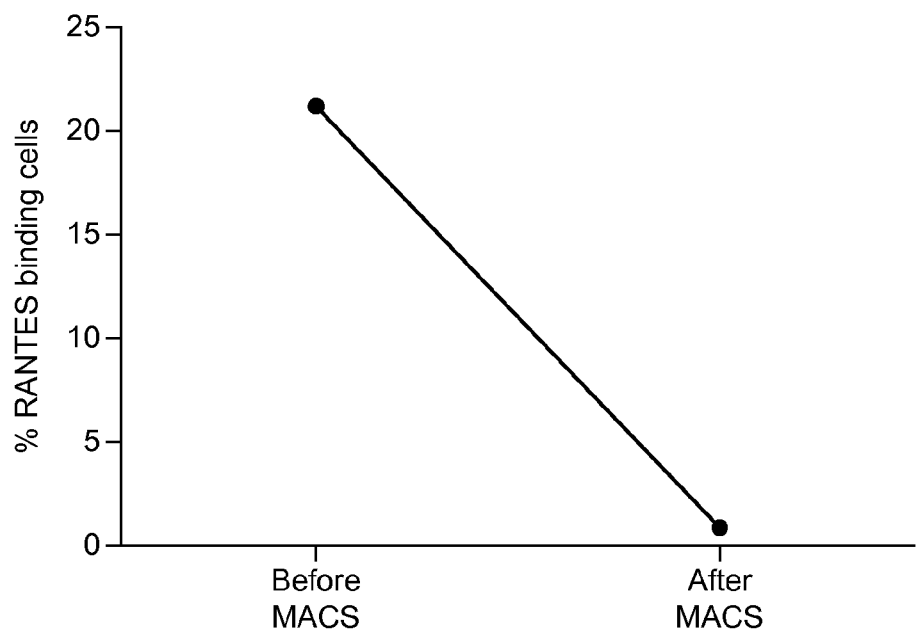

FIG. 91b—Results of in vitro depletion tests performed on the biotinylated RANTES coupled matrix showing ability to eliminate chemokine receptor-expressing cells from peripheral blood of a healthy donor.

Figure 91C:
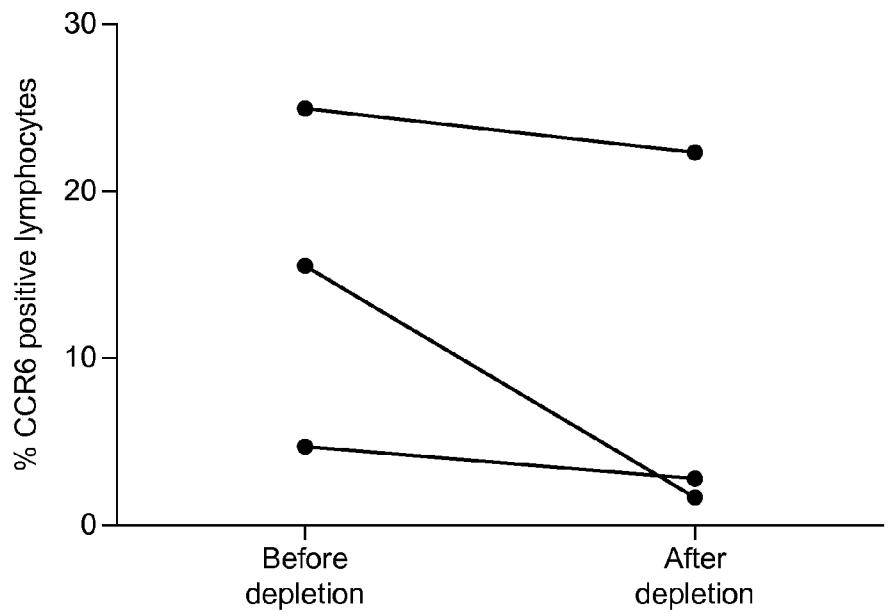

FIG. 91c—Results of in vitro depletion tests performed on the biotinylated MIP-3a coupled matrix showing ability to eliminate CCR6-expressing lymphocytes from blood from three healthy donors.

Figure 91D:
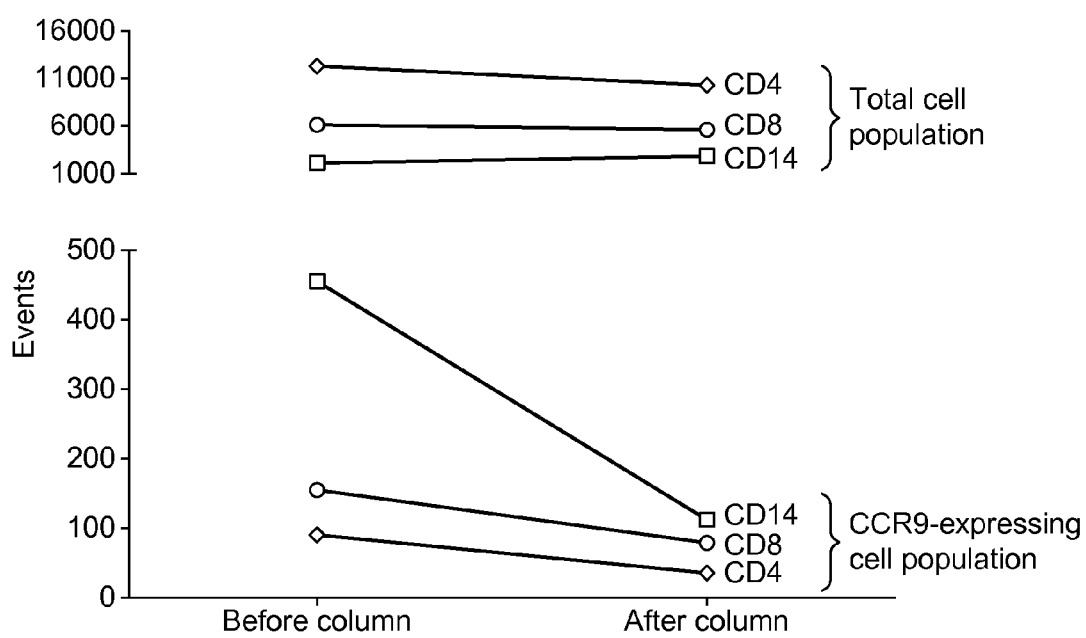

FIG. 91d—Depletion of CCR9-expressing cell populations in one blood donor. Total cell populations are unaffected after the column passage.

Figure 91E:
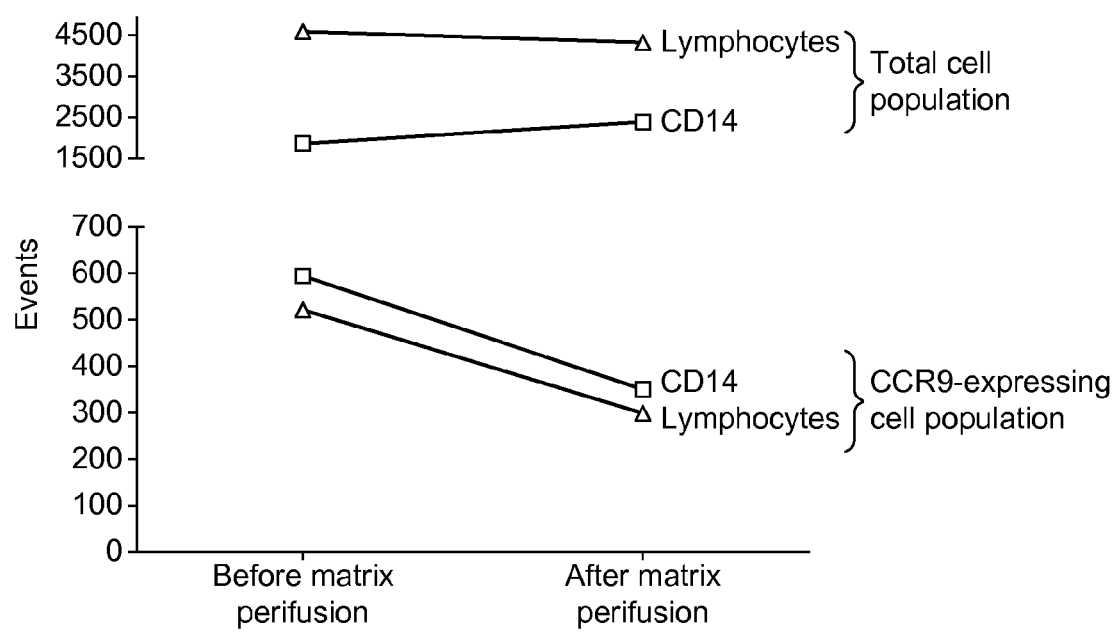

FIG. 91e—Depletion of CCR9-expressing cell populations in one IBD patient. Total cell populations are unaffected after the column passage.

Figure 92:
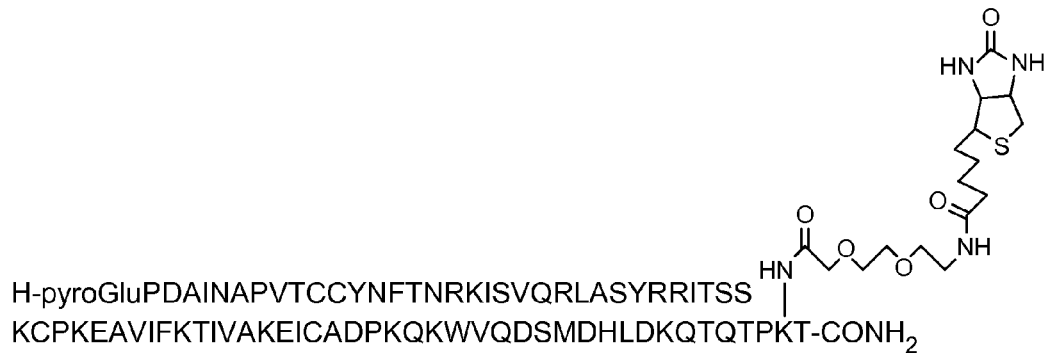

FIG. 92—Sequence (SED ID NO: 113) and biotinylation, via a spacer group, of mature protein MCP-1 derivative containing Gln to pyroGlu modification.

Figure 93:
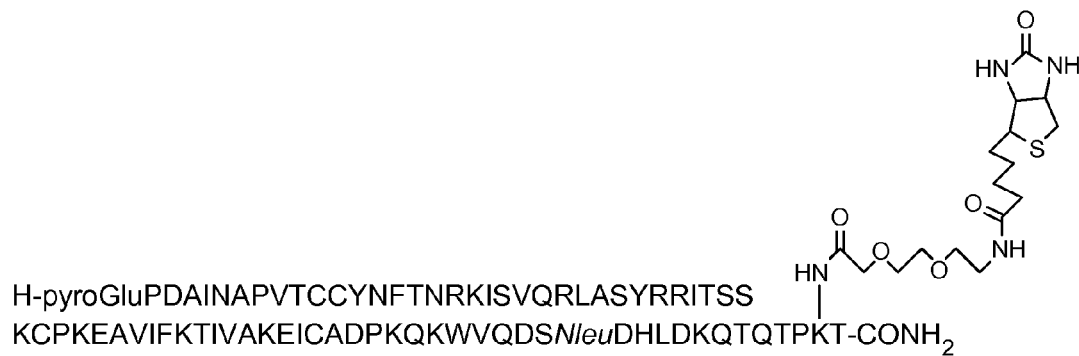

FIG. 93—Sequence (SED ID NO: 113) and biotinylation, via a spacer group, of mature protein MCP-1 derivative containing Gln to pyroGlu modification and Met to Norleu substitution.

Figure 94:
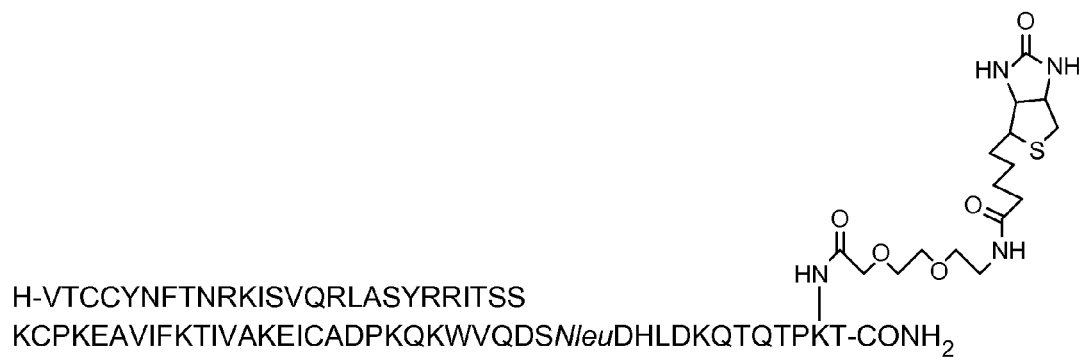

FIG. 94—Sequence (SED ID NO: 114) and biotinylation, via a spacer group, of truncated MCP-1 derivative containing Met to Norleu substitution.

FIG. 95—Alignment of MCP-1 (residues 25-99 of SEQ ID NO: 11) and MCP-5 (residues 24-104 of SEQ ID NO: 10) amino acid sequences.

Figure 96:
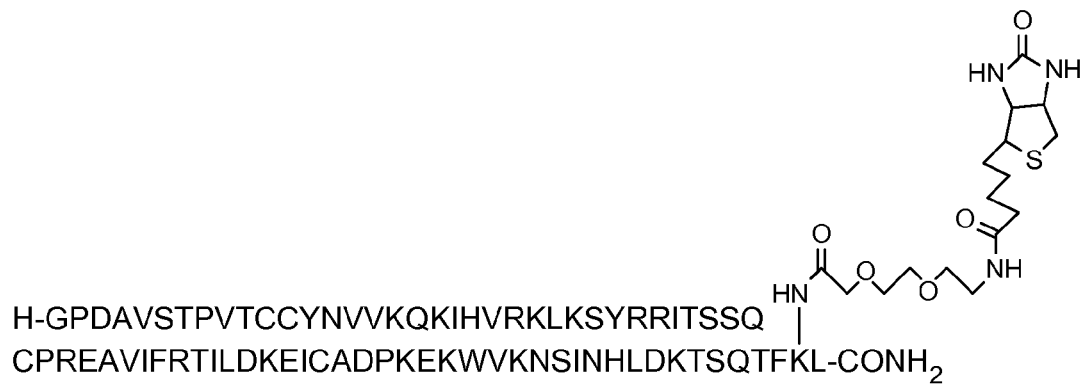

FIG. 96—Sequence (SED ID NO: 118) and biotinylation, via a spacer group, of (C-terminal) truncated MCP-5 derivative containing Ile to Lys modification.

Figure 97:
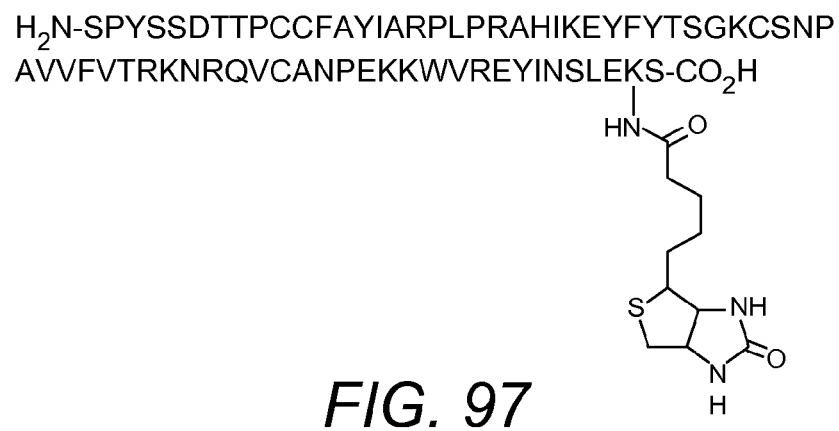

FIG. 97—Sequence (SED ID NO: 126) and biotinylation, of RANTES derivative

Figure 98:
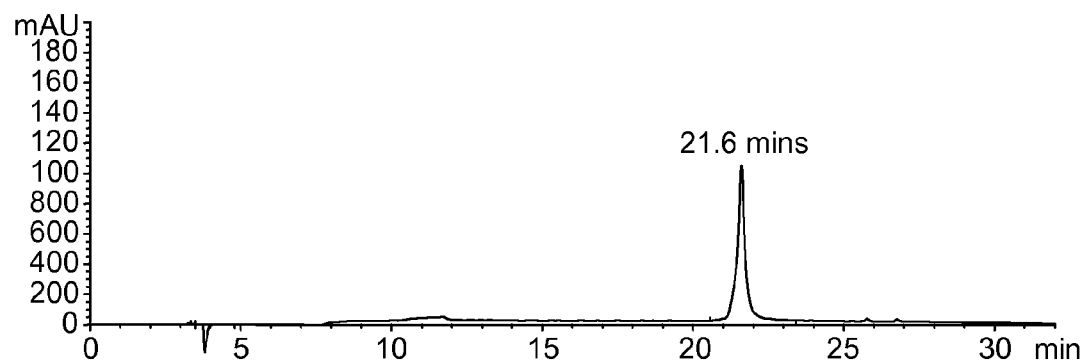

FIG. 98—HPLC of purified folded Biotin-TECK(Nleu).

Figure 99:
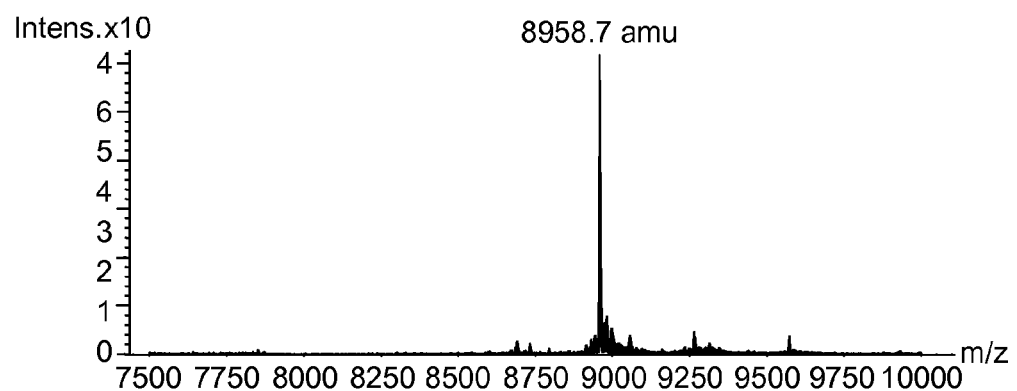

FIG. 99—Electrospray ionisation with tandem mass spectrometry (ES/MS) data of purified folded Biotin-TECK (Nleu).

Figure 100:
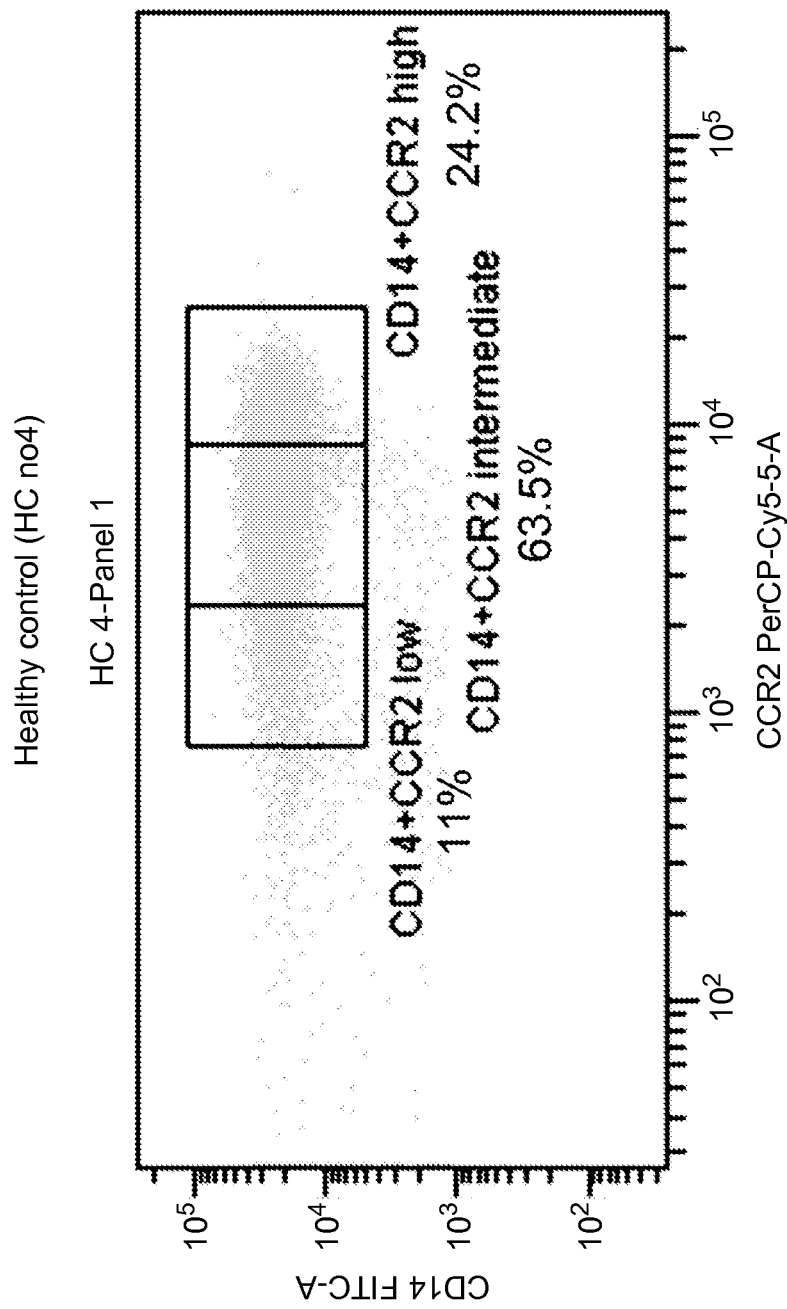

FIG. 100—example of gating criteria for CCR2 expressing monocytes.

Figure 101:
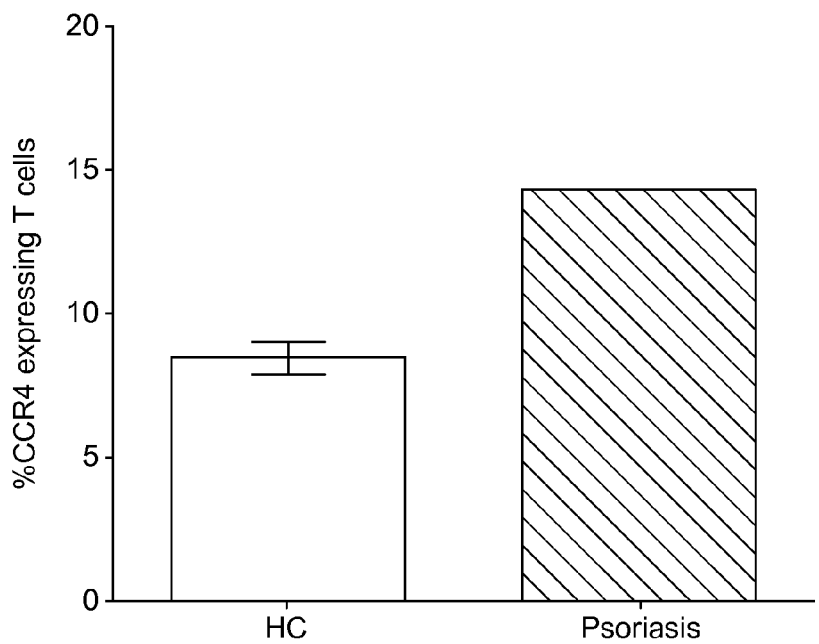

FIG. 101—Frequency of CCR4 expressing T cells in one patient with psoriasis. The expression of chemokine receptors and specific cell markers were analysed with flow cytometry.

Figure 102:
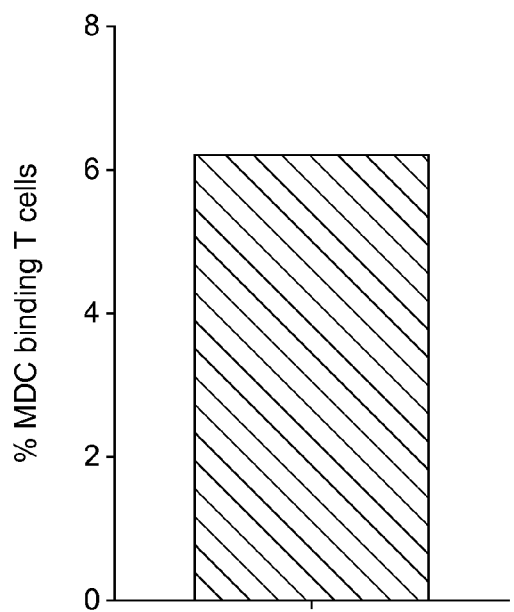

FIG. 102—Expression of CCR4 compared to binding of bMDC to blood T cells from a patient with psoriasis. The expression of chemokine receptors, binding of chemokine, and specific cell markers were analysed with flow cytometry.

Figure 103:
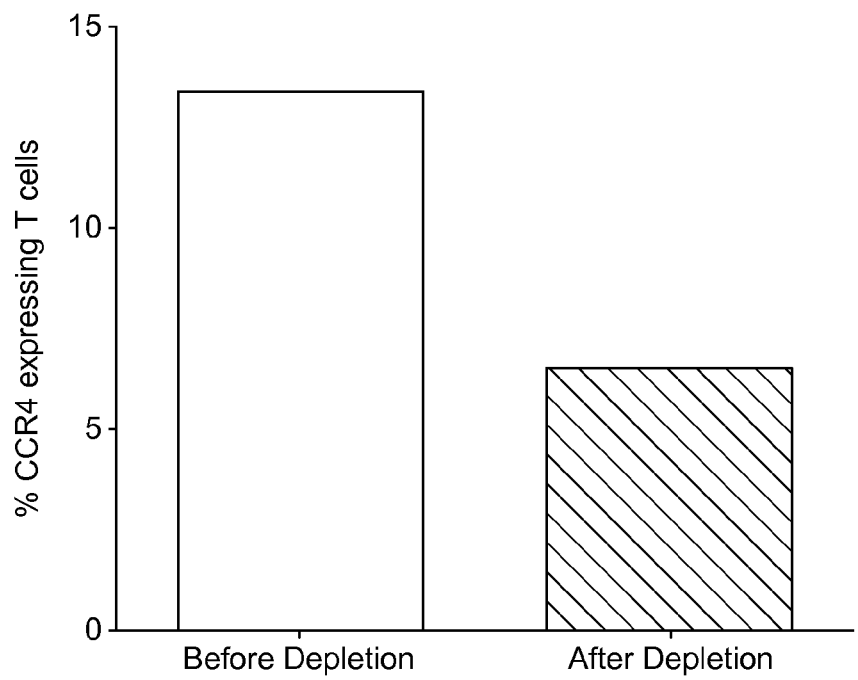

FIG. 103—Depletion of CCR4 expressing T cells with Sepharose Streptavidin-matrix conjugated with bMDC. Blood cells from a healthy control were incubated with biotinylated MDC-Sepharose Streptavidin-matrix. Unbound cells were retrieved by washing the matrix. The cells (After Depletion) were then analysed with flow cytometry and compared with cells that had not been incubated with bMDC-matrix (Before Depletion).

Figure 104:
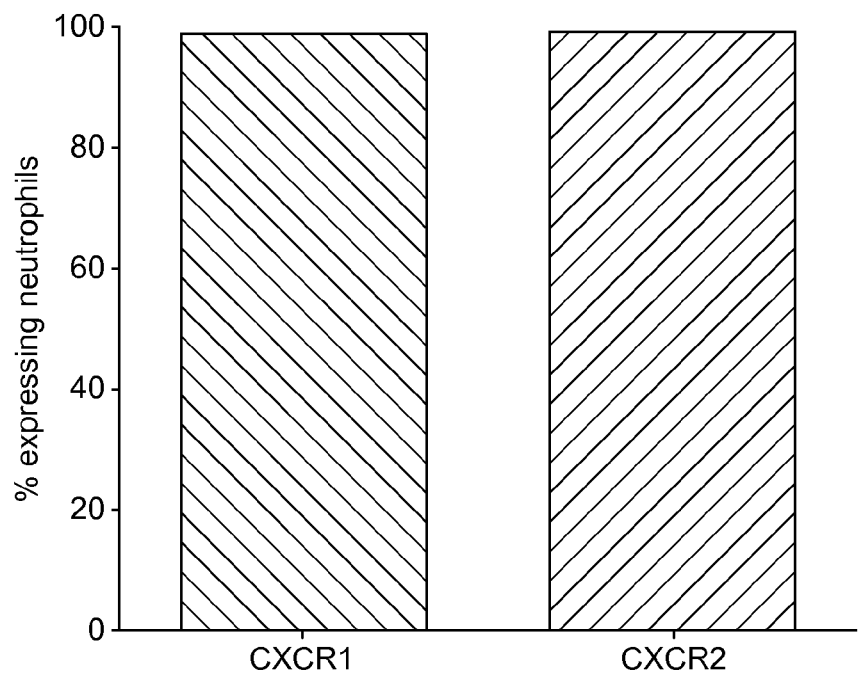

FIG. 104—Expression of CXCR1 and CXCR2 on neutrophils from a patient with psoriasis. The expression of chemokine receptors, binding of chemokine and specific cell markers were analysed with flow cytometry.

Figure 105:
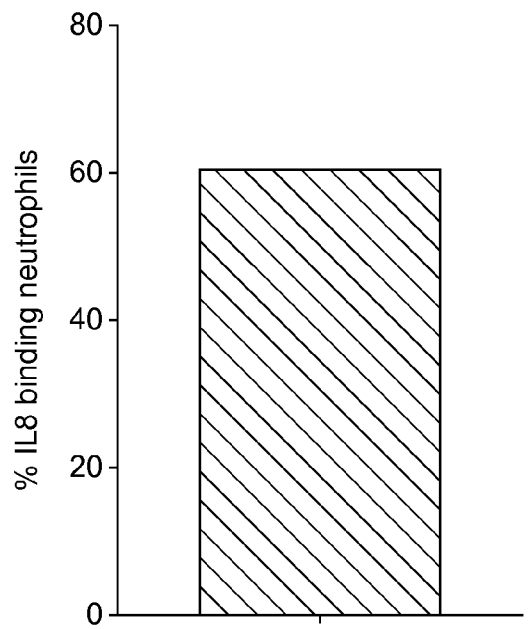

FIG. 105—Binding of the chemokine bIL-8 to neutrophils in blood from a psoriasis patient. Blood from a psoriasis patient was incubated with bIL-8 and analysed with flow cytometry. The neutrophils were characterized as CD16 positive cells.

Figure 106:
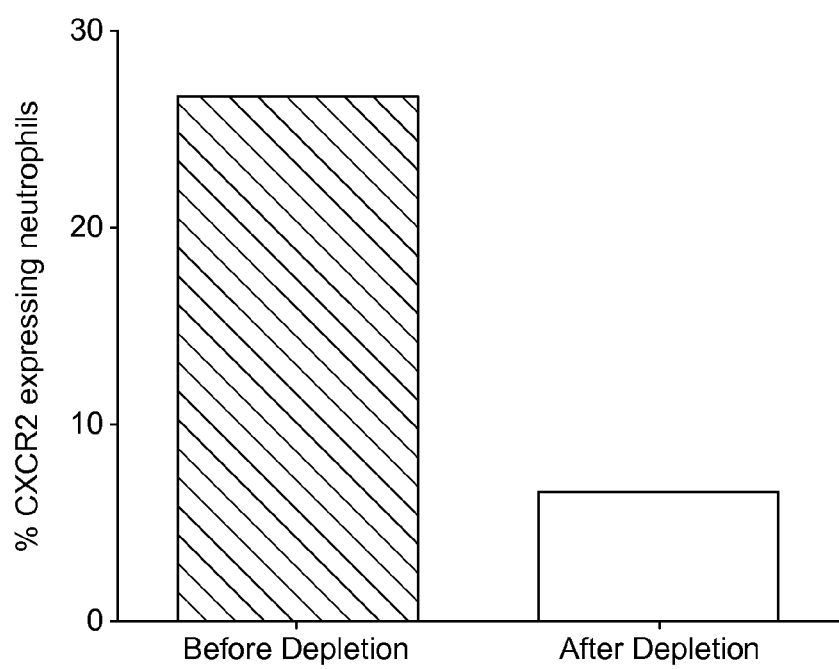

FIG. 106—Depletion of CXCR2 expressing neutrophils with Sepharose Streptavidin-matrix conjugated with bIL-8. Blood cells from a psoriasis patient were incubated with bIL-8 Sepharose Streptavidin-matrix. Unbound cells were retrieved by washing the matrix with Phosphate Buffer Saline. The cells (After Depletion) were then analysed with flow cytometry and compared with cells that had not been incubated with bIL-8-matrix (Before Depletion).

H. Treating Multiple Sclerosis

Figure 107A:
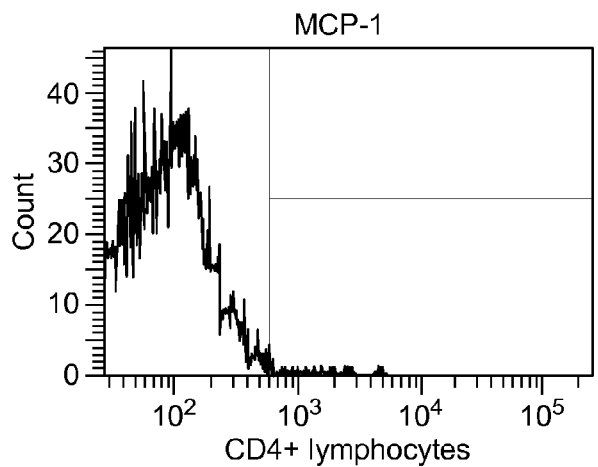
Figure 107B:
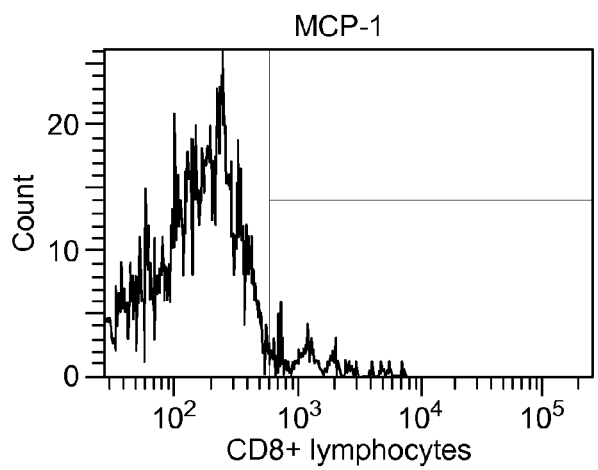
Figure 107C:
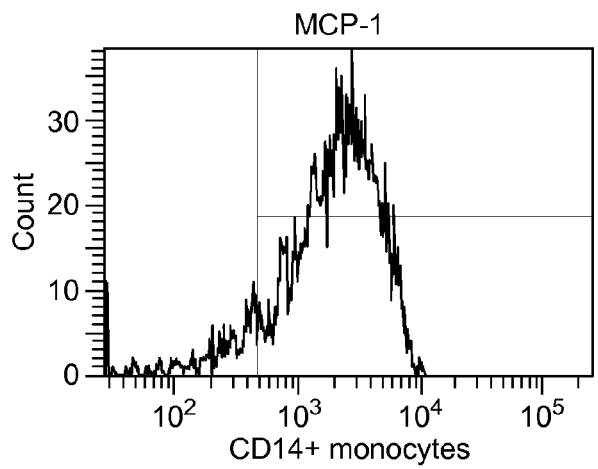

FIGS. 107a, 107b & 107c—the binding of biotinylized MCP-1 by CD4+, CD8+ T-cells and CD14+ monocytes respectively, obtained from peripheral blood of a healthy donor.

Figure 108A:
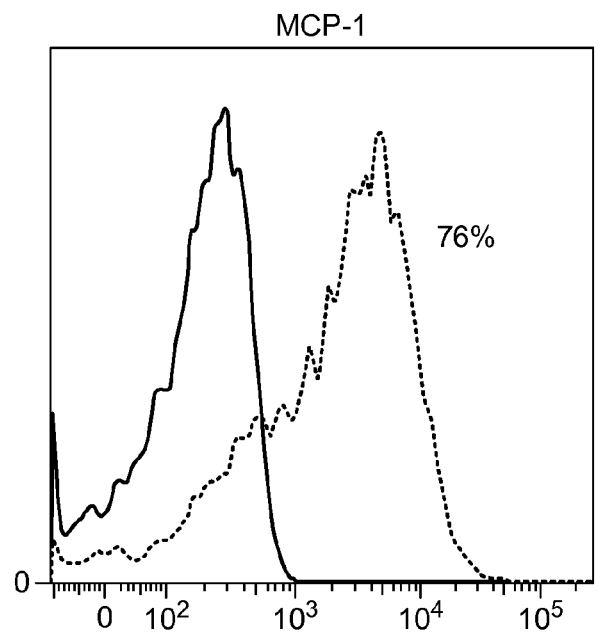

FIG. 108a—binding of MCP-1 to monocytes (dashed line) in peripheral blood taken from IBD patients. The graph represents a summary of four tests.

Figure 108B:
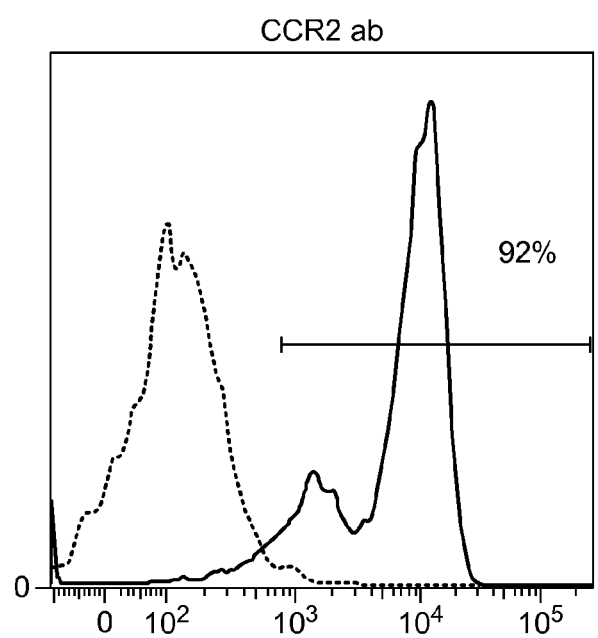

FIG. 108b—binding of CCR2-antibody to monocytes (line) in peripheral blood taken from IBD patients. The graph represents a summary of four tests.

Figure 109A:
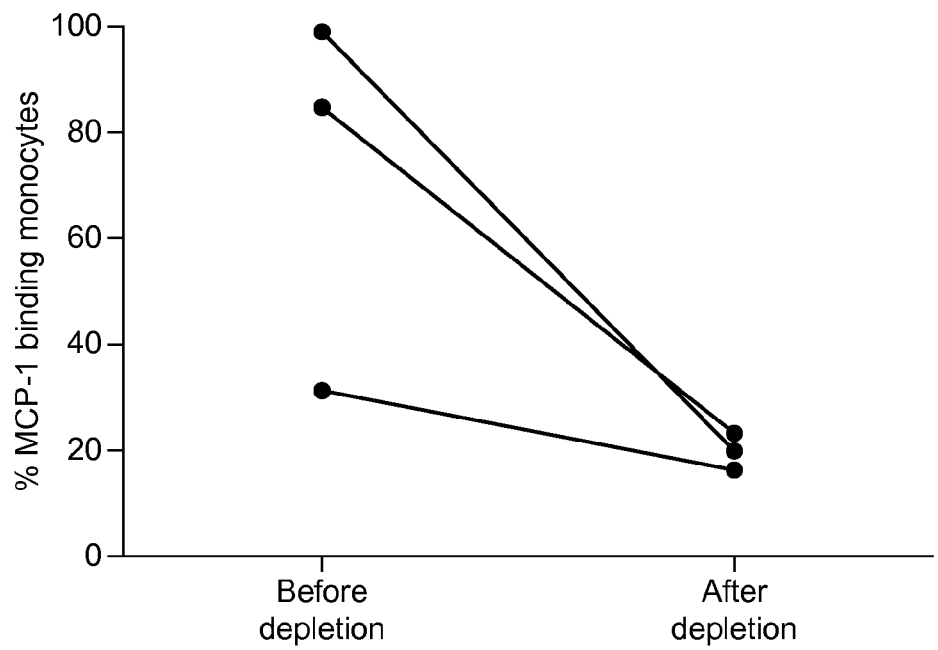

FIG. 109a—Results of in vitro depletion tests performed on the bMCP-1 coupled matrix showing ability to eliminate CCR2-expressing cells from blood from three healthy donors.

Figure 109B:
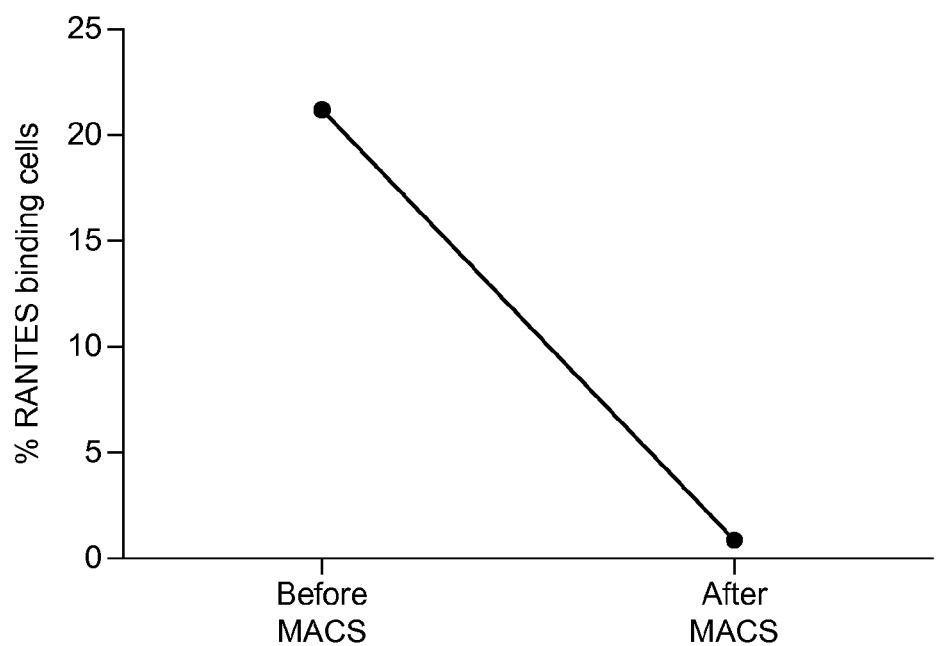

FIG. 109b—Results of in vitro depletion tests performed on the biotinylated RANTES coupled matrix showing ability to eliminate chemokine receptor-expressing cells from peripheral blood of a healthy donor.

Figure 109C:
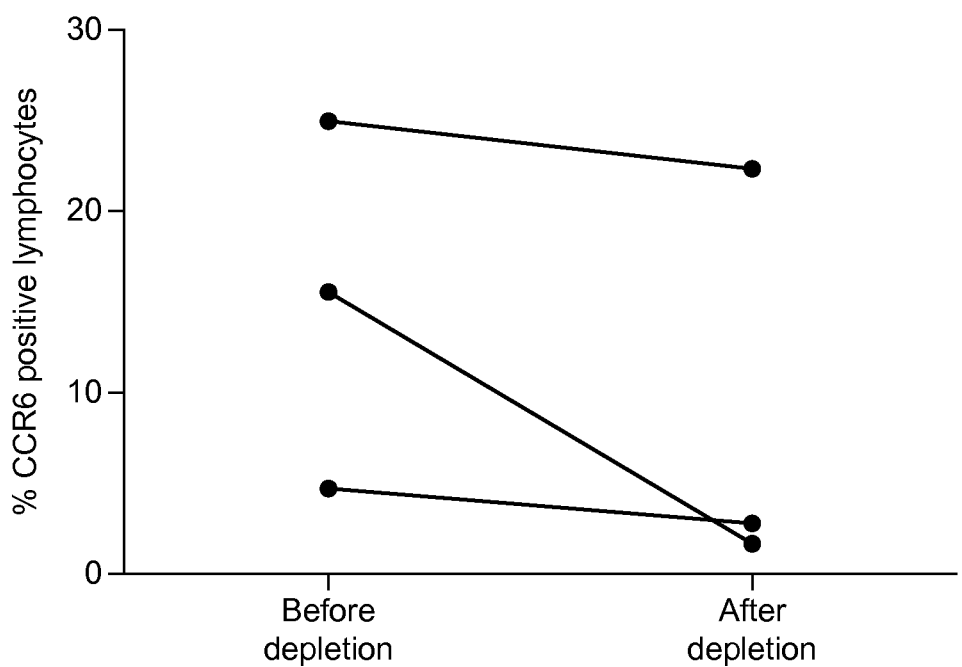

FIG. 109c—Results of in vitro depletion tests performed on the biotinylated MIP-3a coupled matrix showing ability to eliminate CCR6-expressing lymphocytes from blood from three healthy donors.

Figure 110:
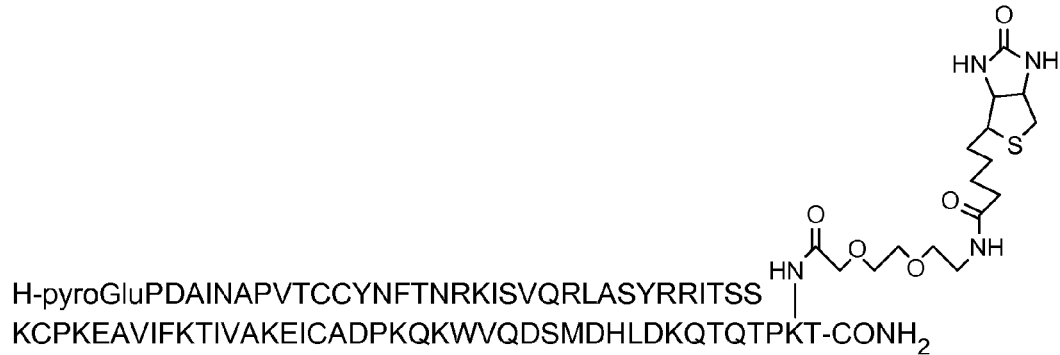

FIG. 110—Sequence (SED ID NO: 145) and biotinylation, via a spacer group, of mature protein MCP-1 derivative containing Gln to pyroGlu modification.

Figure 111:
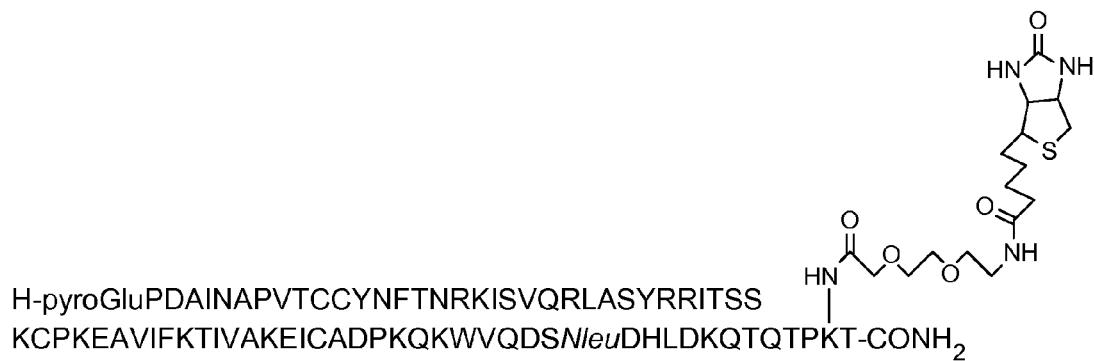

FIG. 111—Sequence (SED ID NO: 145) and biotinylation, via a spacer group, of mature protein MCP-1 derivative containing Gln to pyroGlu modification and Met to Norleu substitution.

Figure 112:
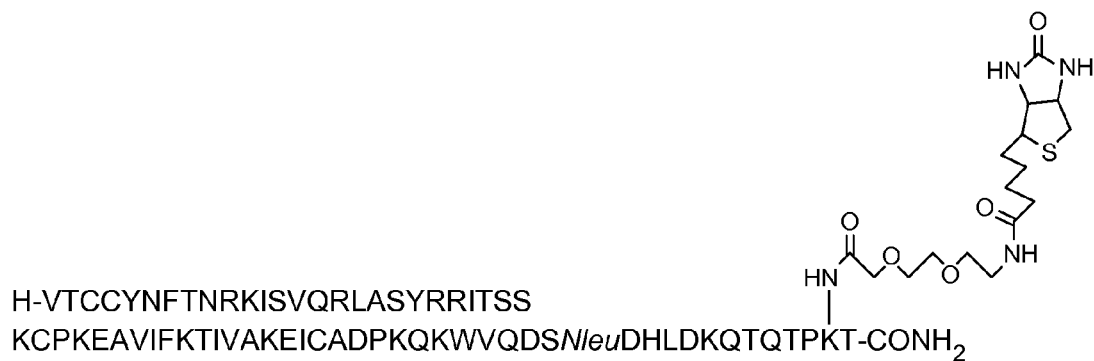

FIG. 112—Sequence (SED ID NO: 146) and biotinylation, via a spacer group, of truncated MCP-1 derivative containing Met to Norleu substitution.

FIG. 113—Alignment of MCP-1 (residues 25-99 of SEQ ID NO: 11) and MCP-5 (residues 24-104 of SEQ ID NO: 10) amino acid sequences.

Figure 114:
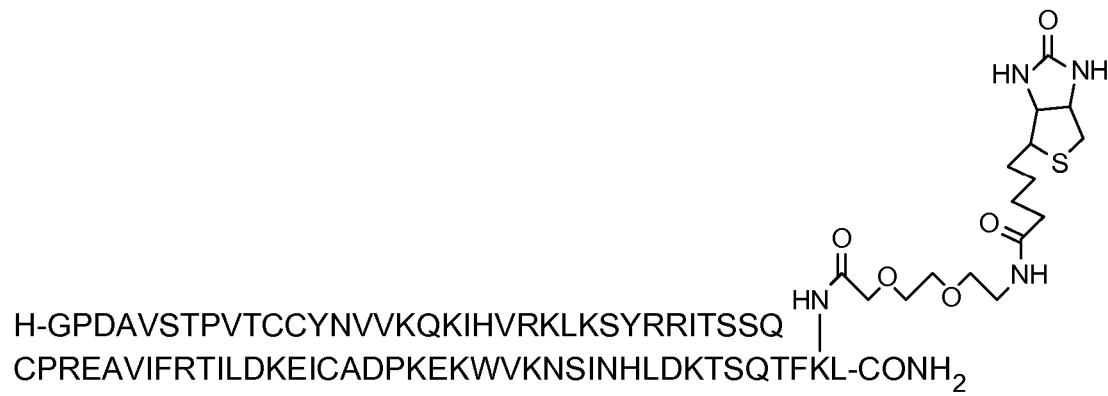

FIG. 114—Sequence (SED ID NO: 150) and biotinylation, via a spacer group, of (C-terminal) truncated MCP-5 derivative containing Ile to Lys modification.

Figure 115:
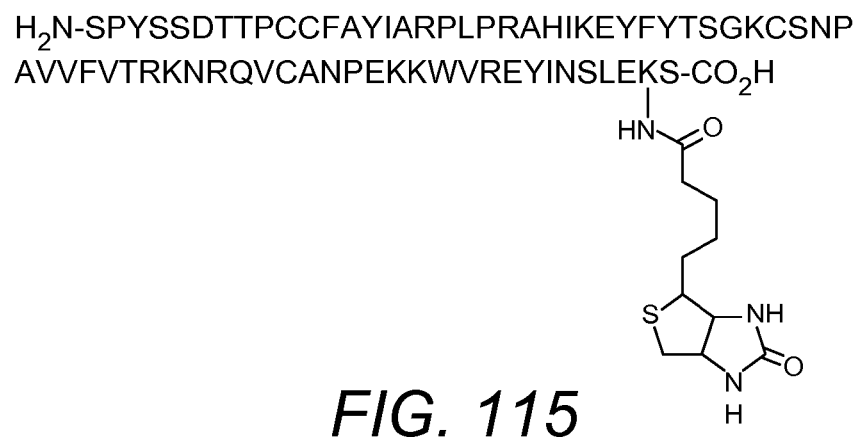

FIG. 115—Sequence (SED ID NO: 160) and biotinylation, of RANTES derivative

Figure 116:
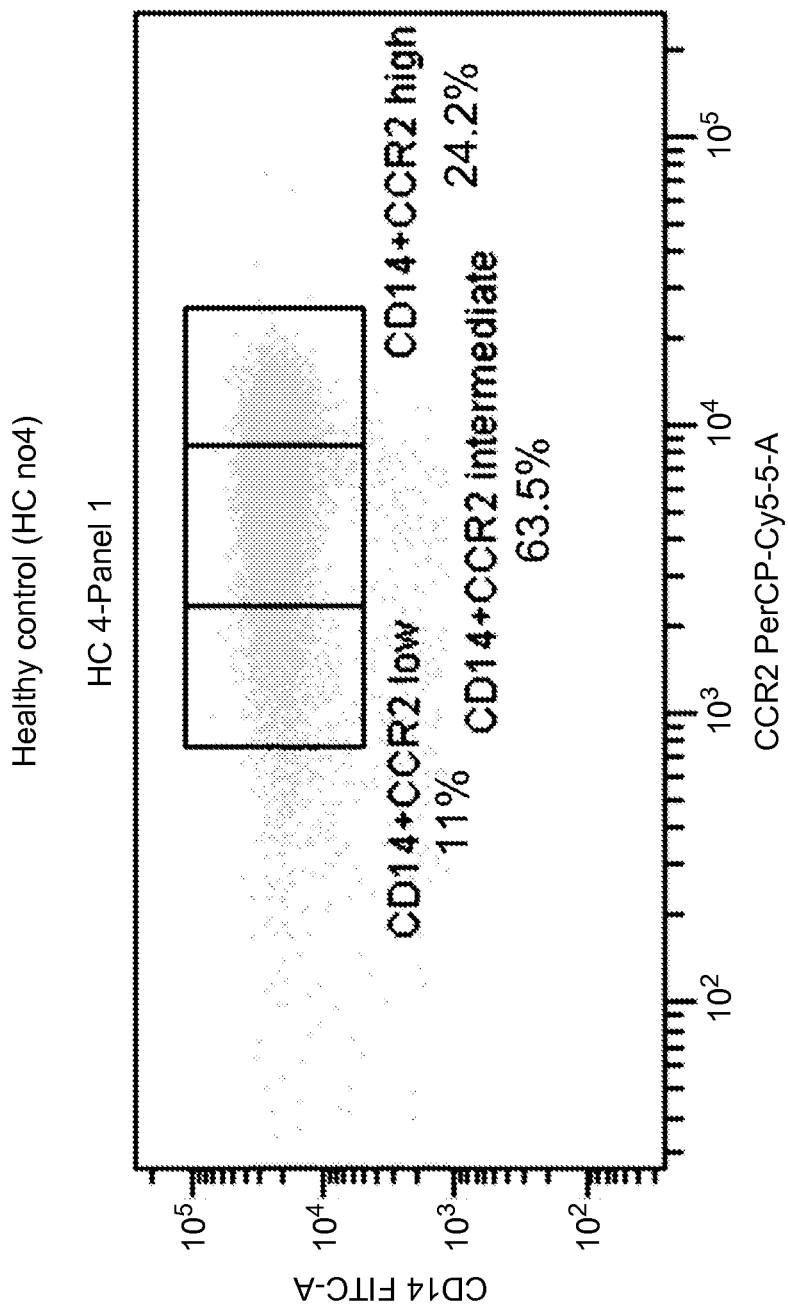

FIG. 116—example of gating criteria for CCR2 expressing monocytes.

Figure 117A:
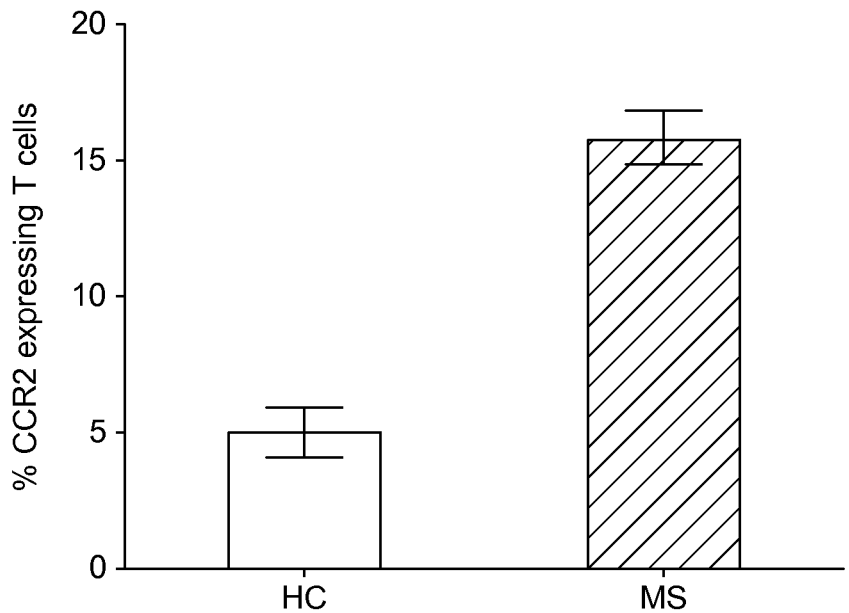

FIG. 117a—Frequency of CCR2 positive T cells. Bars represent mean and SEM of T cells that express CCR2 in 2 patients and 20 healthy controls.

Figure 117B:
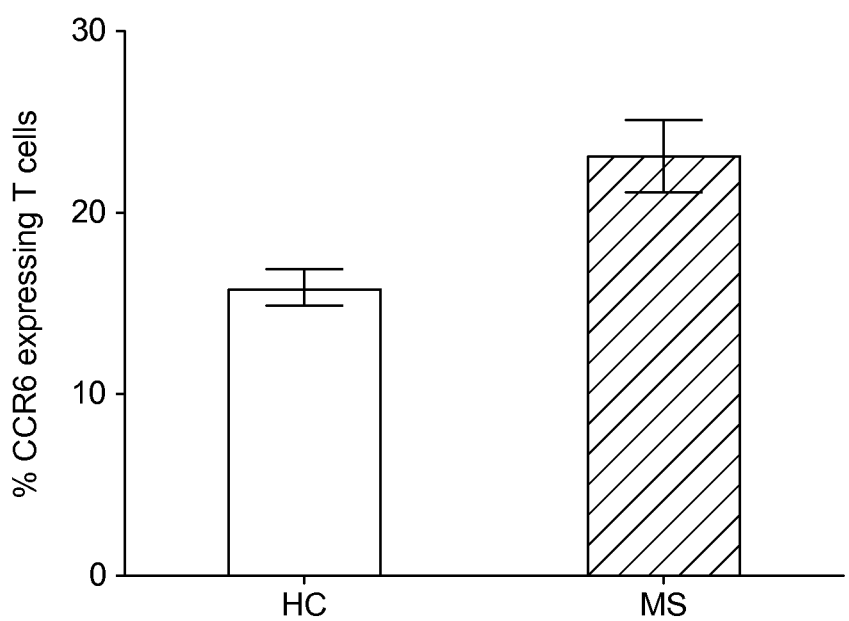

FIG. 117b—Frequency of CCR6 positive T cells. Bars represent mean and SEM of T cells that express CCR6 in 5 patients and 20 healthy controls. The expression of chemokine receptors and specific cell markers were analysed with flow cytometry. The T cells were characterized as CD3 positive.

Figure 118A:
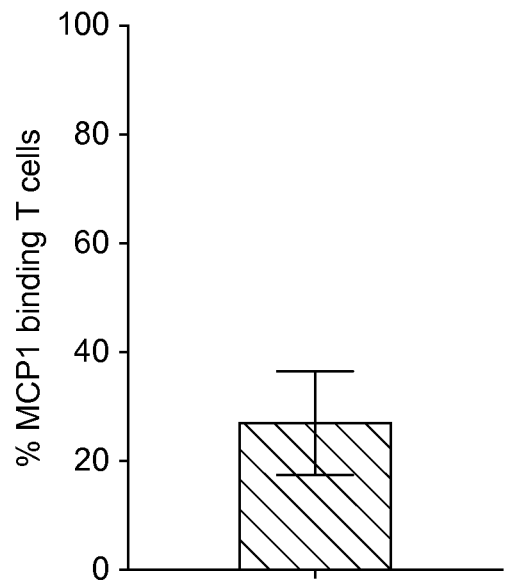

FIG. 118a—Binding of the chemokine bMCP-1 to T cells. Bar represents mean frequency and SEM of MCP-1 binding T cells in 5 patients with MS.

Figure 118B:
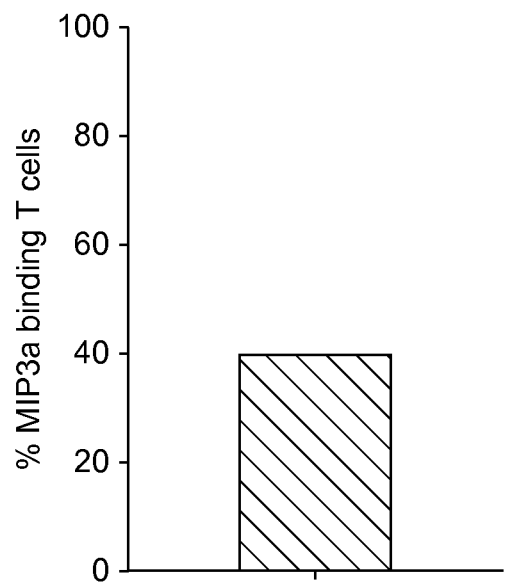

FIG. 118b—Binding of the chemokine bMIP3a to T cells. Bar represents frequency of MIP3a-binding T cells in 1 patient with MS. Blood was incubated with biotinylated chemokine and analysed with flow cytometry. The T cells were characterized as CD3 positive.

Figure 119A:
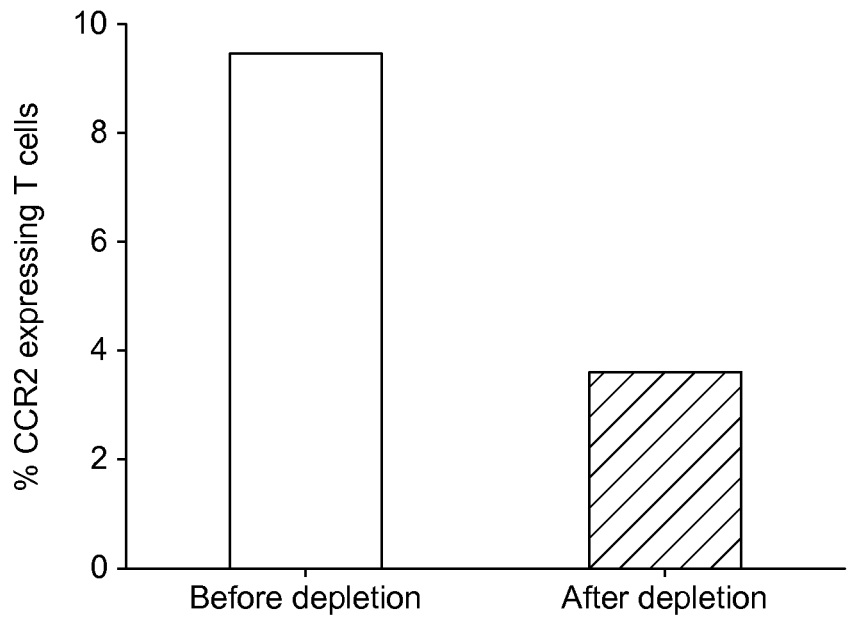

FIG. 119a—Depletion of CCR2 expressing T cells with Sepharose Streptavidin-matrix conjugated with bMCP-1.

Figure 119B:
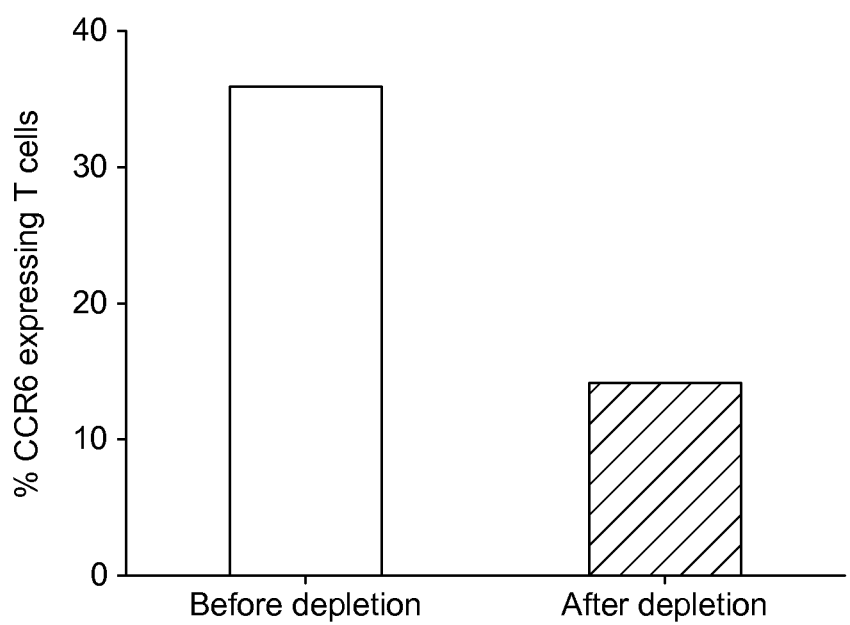

FIG. 119b—Depletion of CCR6 expressing T cells with Sepharose Streptavidin-matrix conjugated with bMIP3a. Blood cells from a patient with MS were incubated with biotinylated chemokine-Sepharose Streptavidin-matrix. Unbound cells were retrieved by washing the matrix. The cells (After Depletion) were then analysed with flow cytometry and compared with cells that had not been incubated with bchemokine-matrix (Before Depletion).

I. Treating Cardiovascular Disease

Figure 120A:
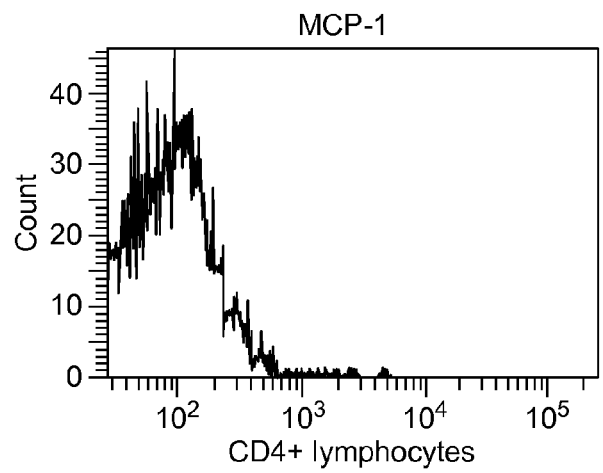
Figure 120B:
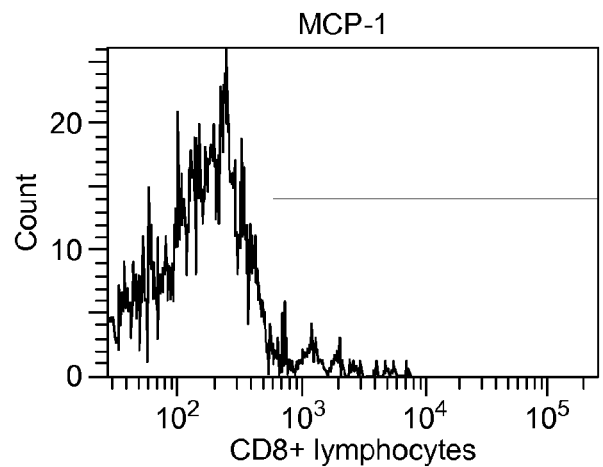
Figure 120C:
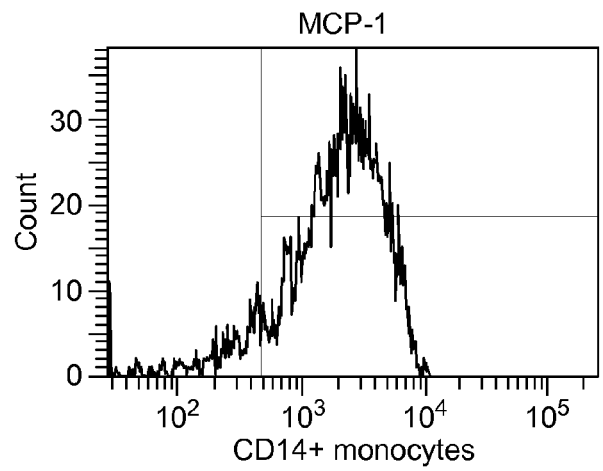

FIGS. 120a, 120b & 120c—the binding of biotinylized MCP-1 by CD4+, CD8+ T-cells and CD14+ monocytes respectively, obtained from peripheral blood of a healthy donor.

Figure 121A:
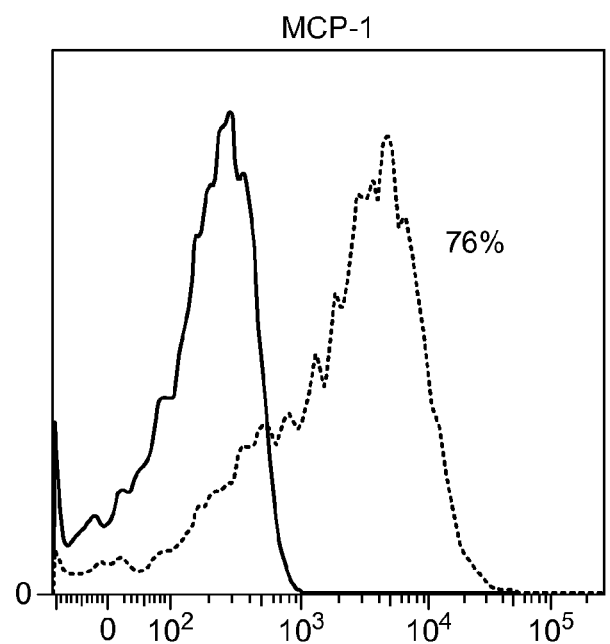

FIG. 121a—binding of MCP-1 to monocytes (dashed line) in peripheral blood taken from IBD patients. The graph represents a summary of four tests.

Figure 121B:
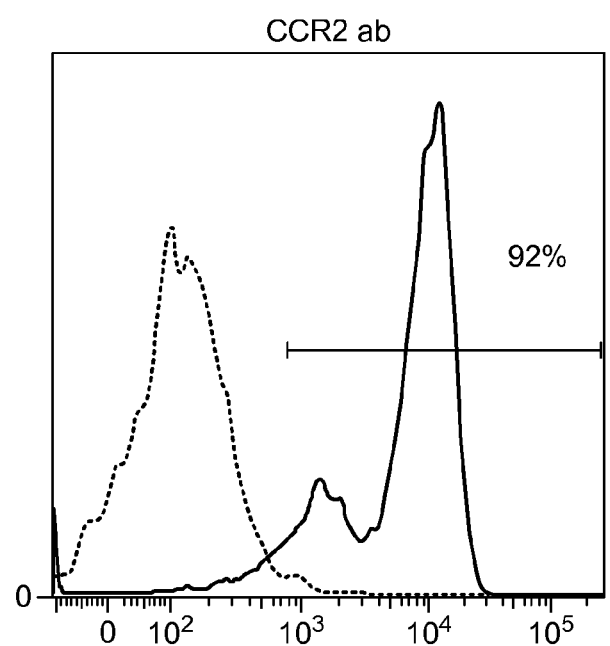

FIG. 121b—binding of CCR2-antibody to monocytes (line) in peripheral blood taken from IBD patients. The graph represents a summary of four tests.

Figure 122:
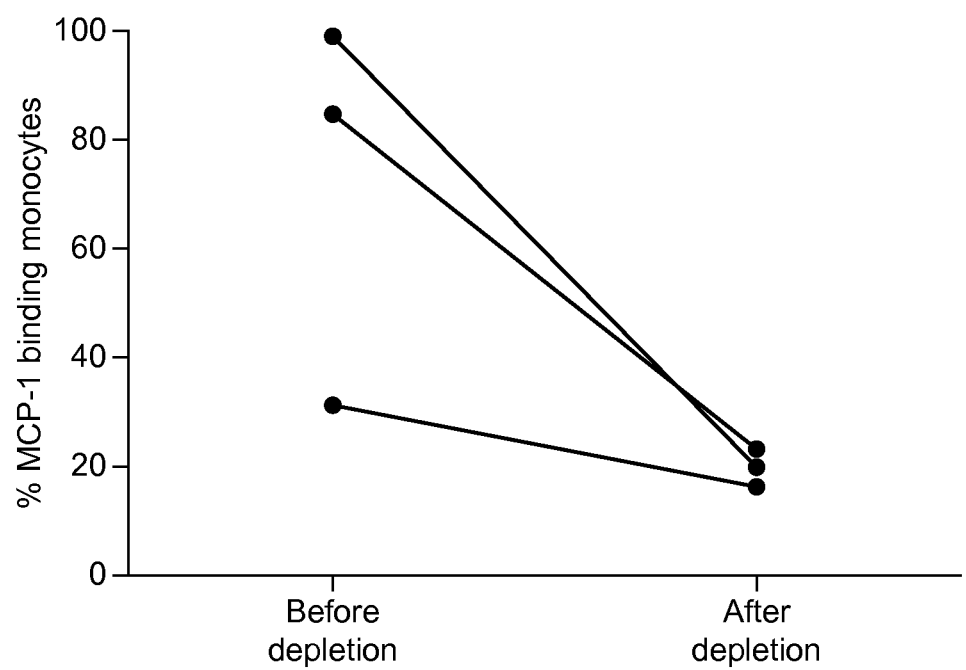

FIG. 122—Results of in vitro depletion tests performed on the bMCP-1 coupled matrix showing ability to eliminate CCR2-expressing cells from blood from three healthy donors.

Figure 123:
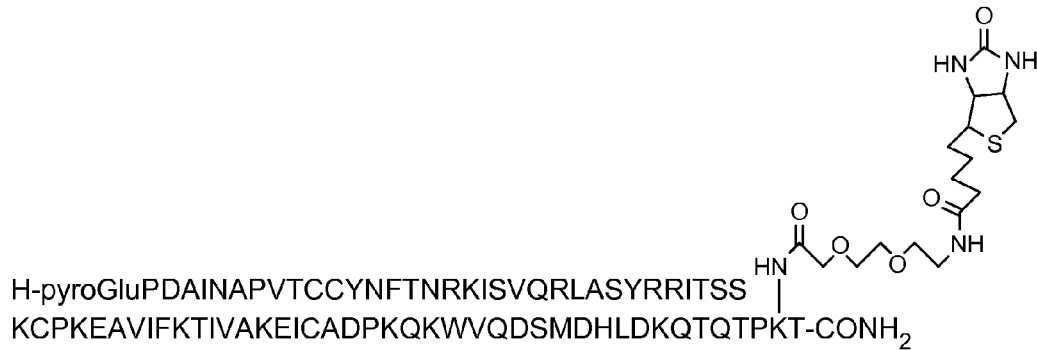

FIG. 123—Sequence (SED ID NO: 176) and biotinylation, via a spacer group, of mature protein MCP-1 derivative containing Gln to pyroGlu modification.

Figure 124:
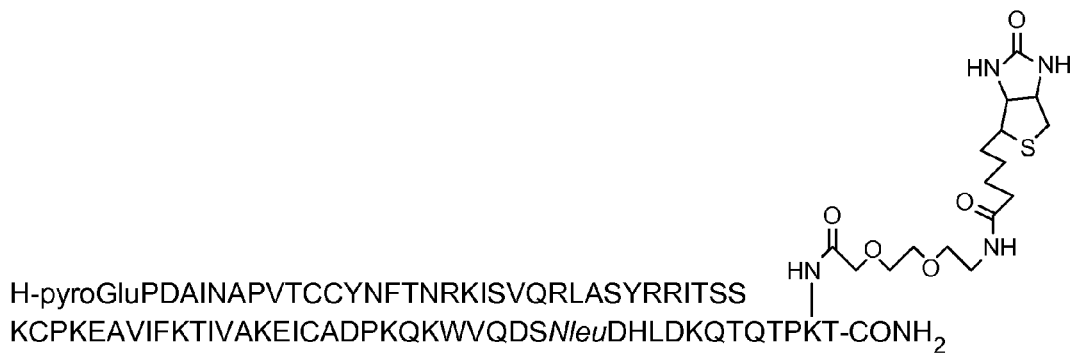

FIG. 124—Sequence (SED ID NO: 176) and biotinylation, via a spacer group, of mature protein MCP-1 derivative containing Gln to pyroGlu modification and Met to Norleu substitution.

Figure 125:
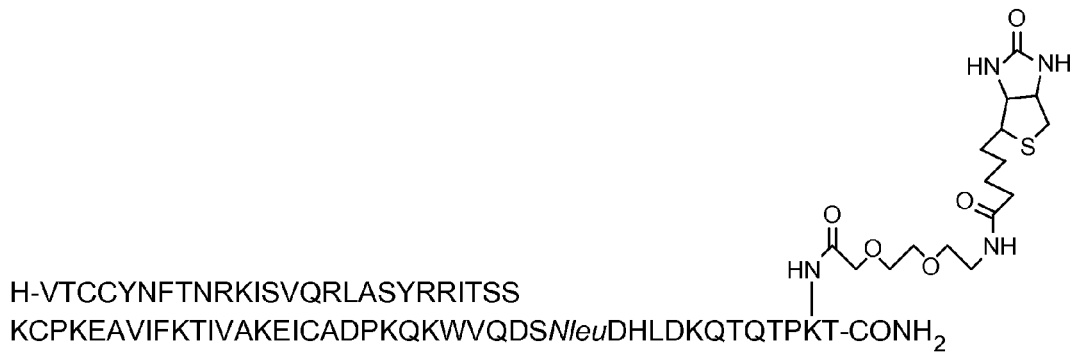

FIG. 125—Sequence (SED ID NO: 177) and biotinylation, via a spacer group, of truncated MCP-1 derivative containing Met to Norleu substitution.

FIG. 126—Alignment of MCP-1 (residues 25-99 of SEQ ID NO: 11) and MCP-5 (residues 24-104 of SEQ ID NO: 10) amino acid sequences.

FIG. 127—Sequence (SED ID NO: 181) and biotinylation, via a spacer group, of (C-terminal) truncated MCP-5 derivative containing Ile to Lys modification.

Figure 128:
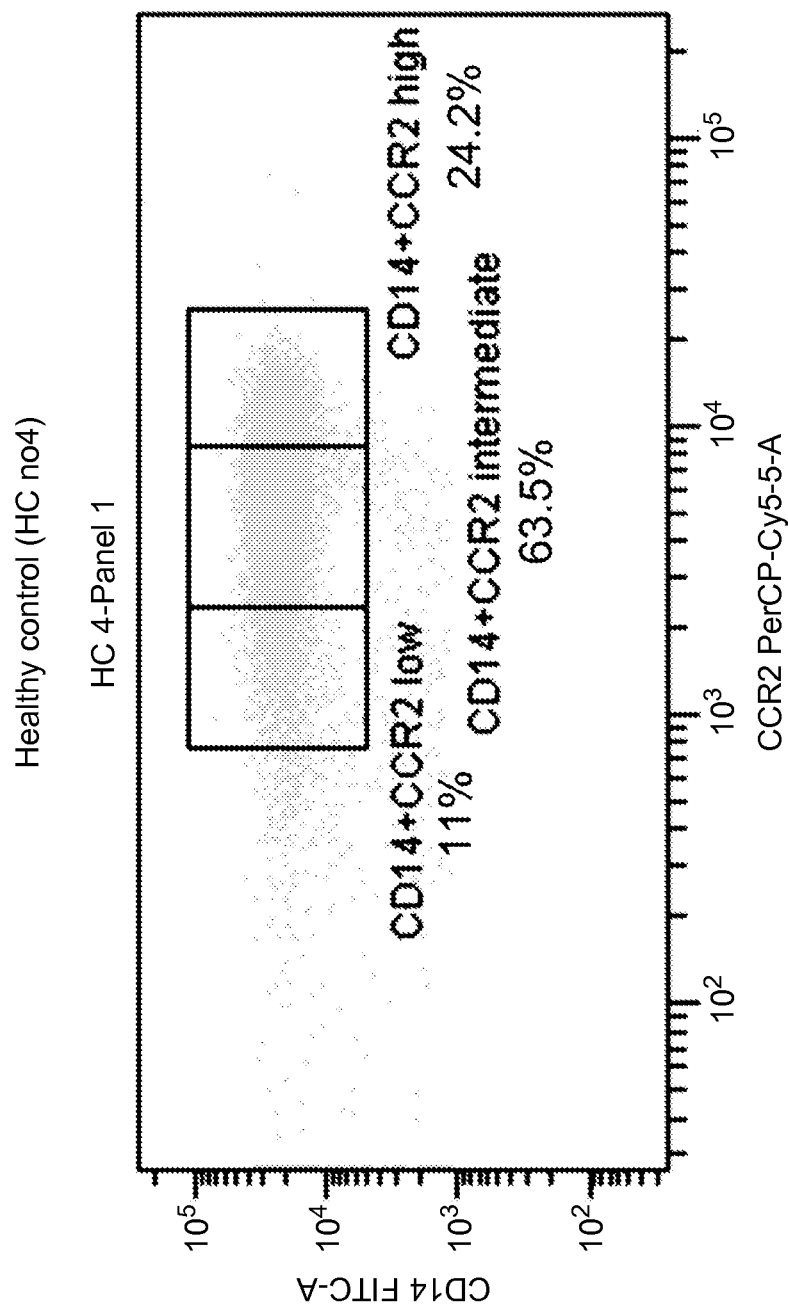

FIG. 128—example of gating criteria for CCR2 expressing monocytes.

Figure 129:
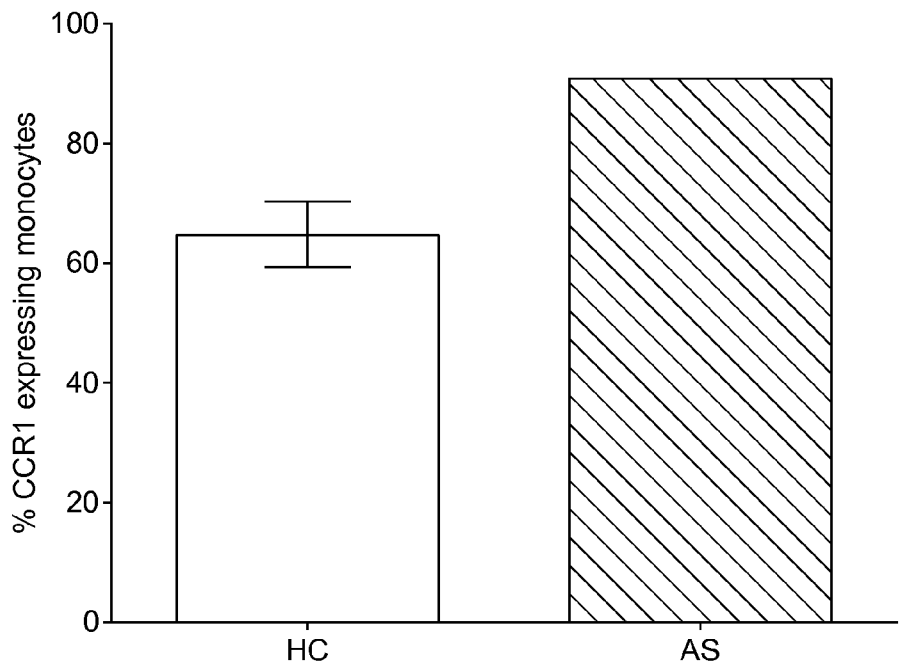

FIG. 129—Frequency of CCR1 expressing monocytes in 20 healthy controls and one patient with atherosclerosis (AS). The expression of chemokine receptors and specific cell markers were analysed with flow cytometry.

Figure 130:
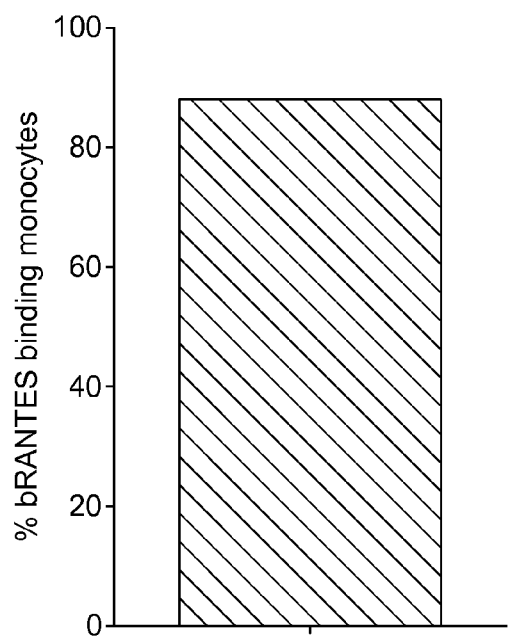

FIG. 130—Binding of bRANTES to blood monocytes from a patient with atherosclerosis. The binding of chemokine and expression of specific cell markers were analysed with flow cytometry.

Figure 131:
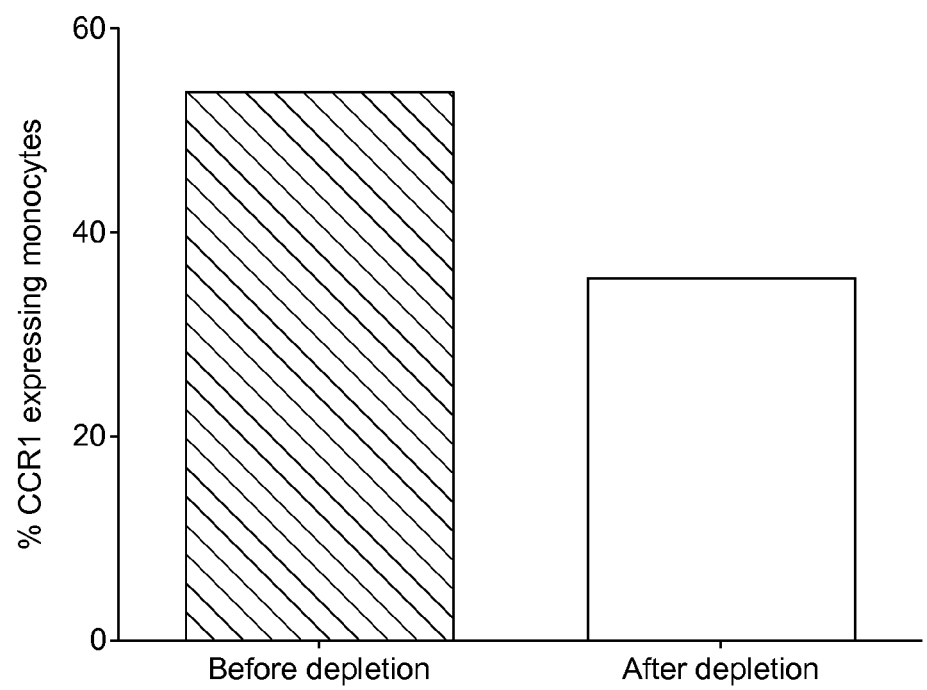

FIG. 131—Depletion of CCR1 expressing monocytes with Sepharose Streptavidin-matrix conjugated with bRANTES. Blood cells from an atherosclerosis patient were incubated with biotinylated chemokine-Sepharose Streptavidin-matrix. Unbound cells were retrieved by washing the matrix. The cells (After Depletion) were then analysed with flow cytometry and compared with cells that had not been incubated with biotinylated-chemokine-matrix (Before Depletion).

Figure 132:
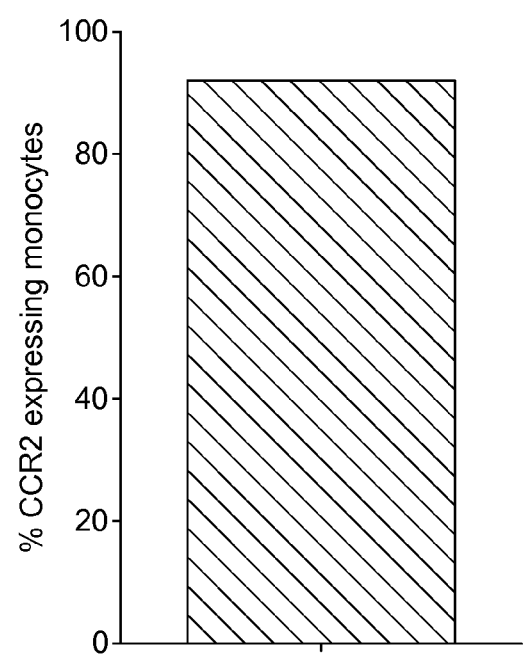

FIG. 132—Expression of CCR2 on monocytes from one patient with atherosclerosis. The expression of chemokine receptors, binding of chemokine and specific cell markers were analysed with flow cytometry.

Figure 133:
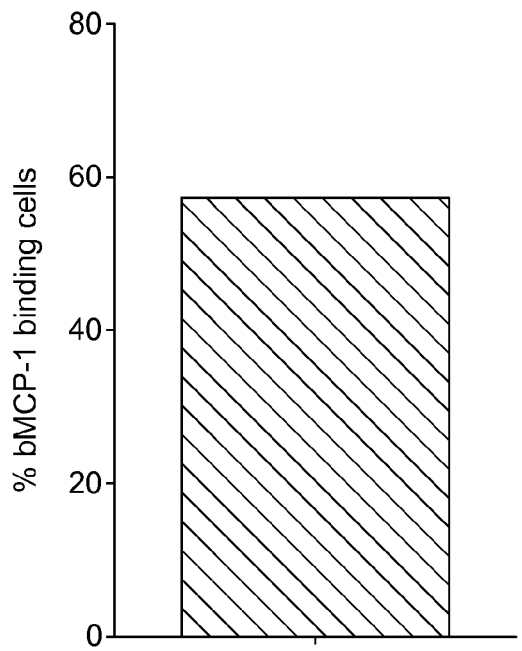

FIG. 133—Binding of the chemokine bMCP-1 to monocytes. Bars represent frequency of bMCP-1 binding monocytes and CCR2 expressing monocytes in blood from a patient with atherosclerosis. Blood was incubated with biotinylated chemokine and analysed with flow cytometry.

Figure 134:
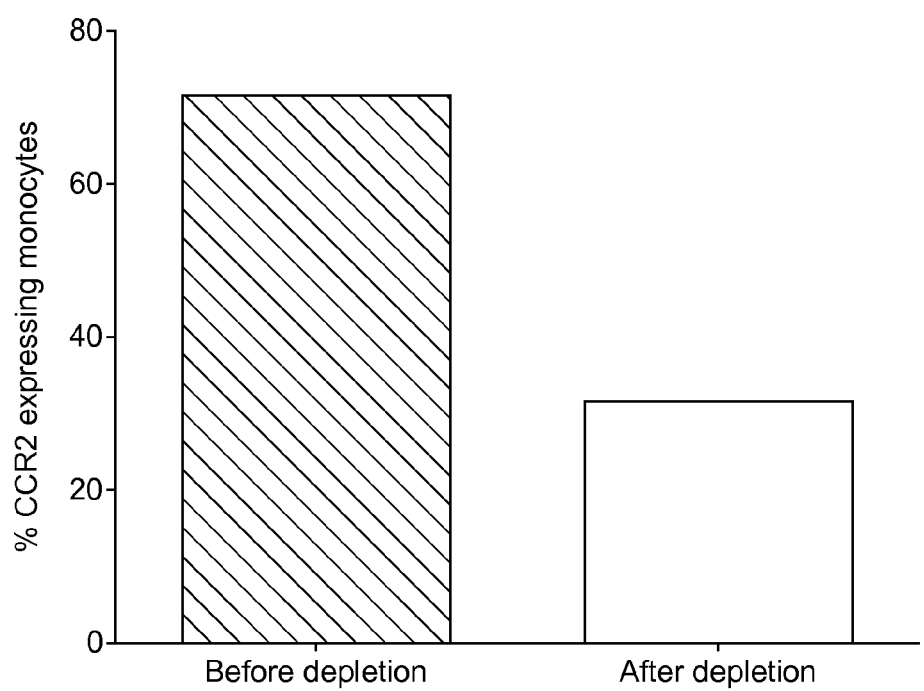

FIG. 134—Depletion of CCR2 expressing monocytes with Sepharose Streptavidin-matrix conjugated with bMCP-1. Blood cells from a patient with atherosclerosis were incubated with biotinylated chemokine-Sepharose Streptavidin-matrix. Unbound cells were retrieved by washing the matrix. The cells (After Depletion) were then analysed with flow cytometry and compared with cells that had not been incubated with b-chemokine-matrix (Before Depletion).

J. Treating Primary Sclerosing Cholangitis

Figure 135A:
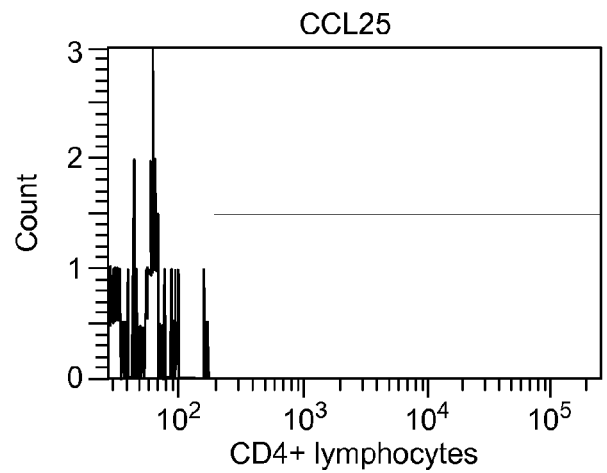
Figure 135B:
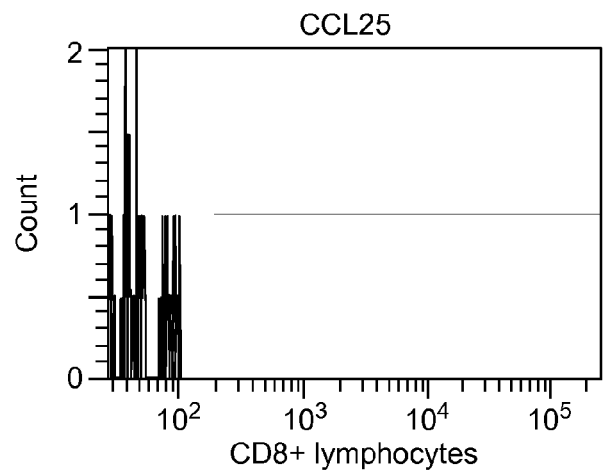
Figure 135C:
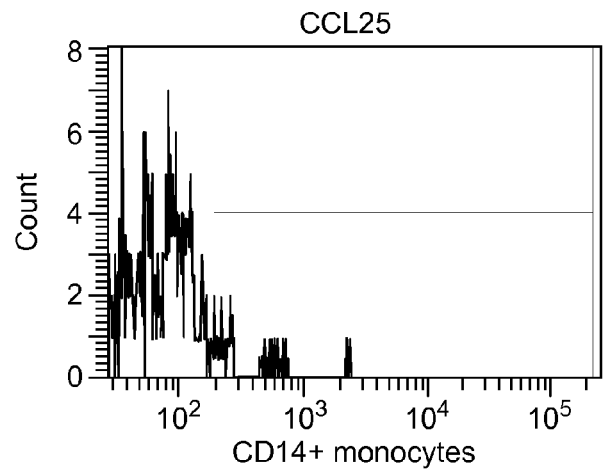
Figure 136A:
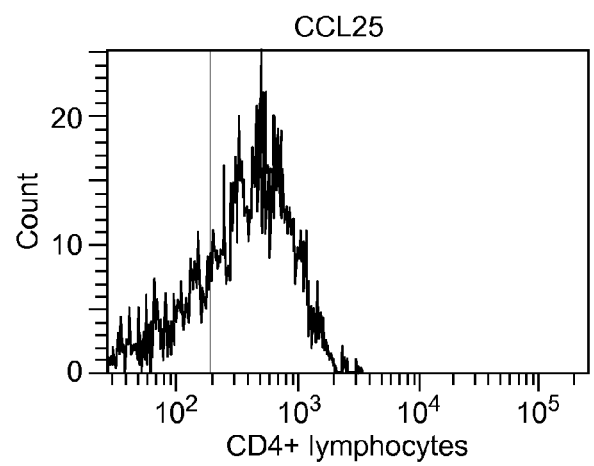
Figure 136B:
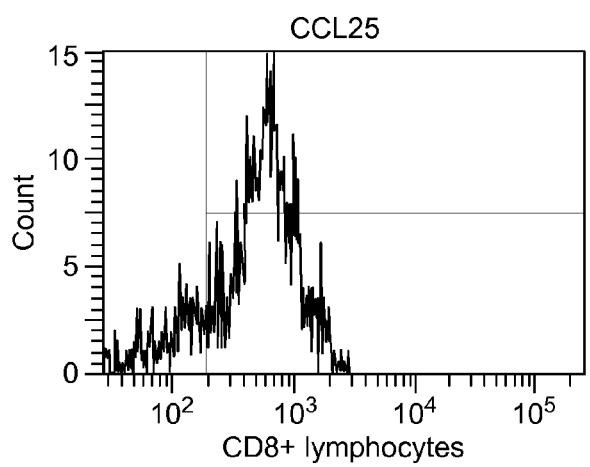
Figure 136C:
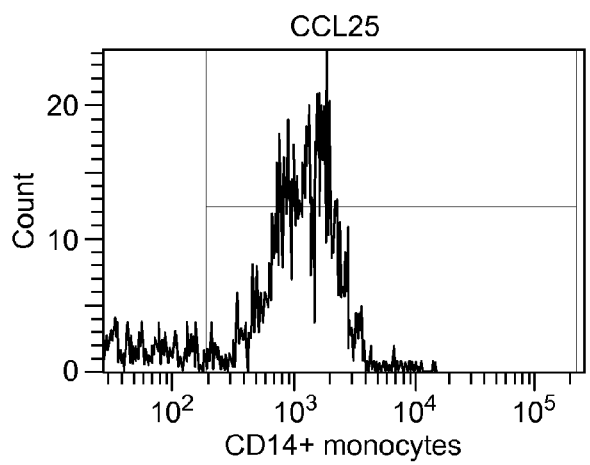
Figure 137:
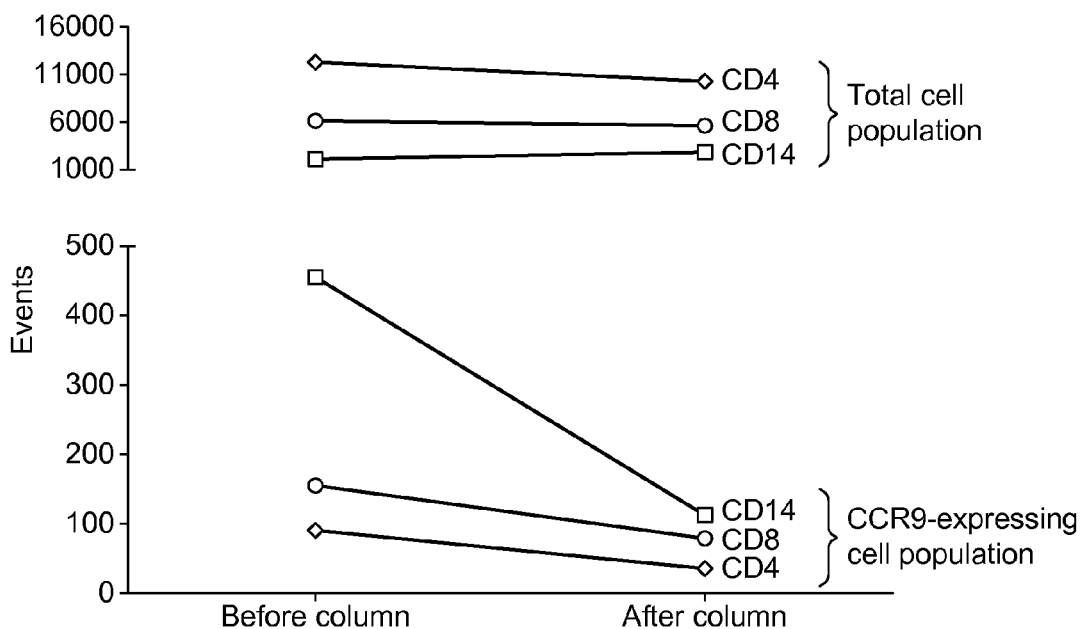

FIGS. 135a, 135b & 135c—the binding of biotinylated CCL25 by CD4+, CD8+ T-cells and CD14+ monocytes respectively, obtained from peripheral blood of a healthy donor;

FIGS. 136a, 136b & 136c—the binding of biotinylized CCL25 by CD4+, CD8+ T-cells and CD14+ monocytes respectively, obtained from peripheral blood of a patient with CD;

FIG. 137—Depletion of CCR9-expressing cell populations in one blood donor. Total cell populations are unaffected after the column passage.

Figure 138:
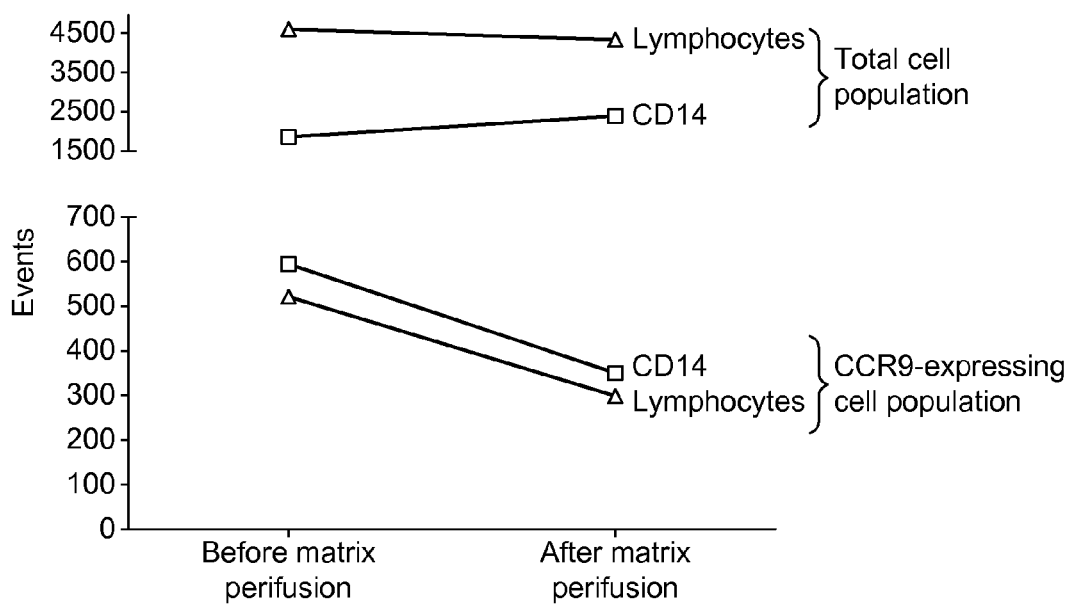

FIG. 138—Depletion of CCR9-expressing cell populations in one IBD patient. Total cell populations are unaffected after the column passage FIG. 139—Sequence (SEQ ID NO: 195) and biotinylation of RANTES derivative FIG. 140—Results of in vitro depletion tests performed on the biotinylated RANTES coupled matrix showing ability to eliminate chemokine receptor-expressing cells from peripheral blood taken from a healthy donor.

Figure 141:
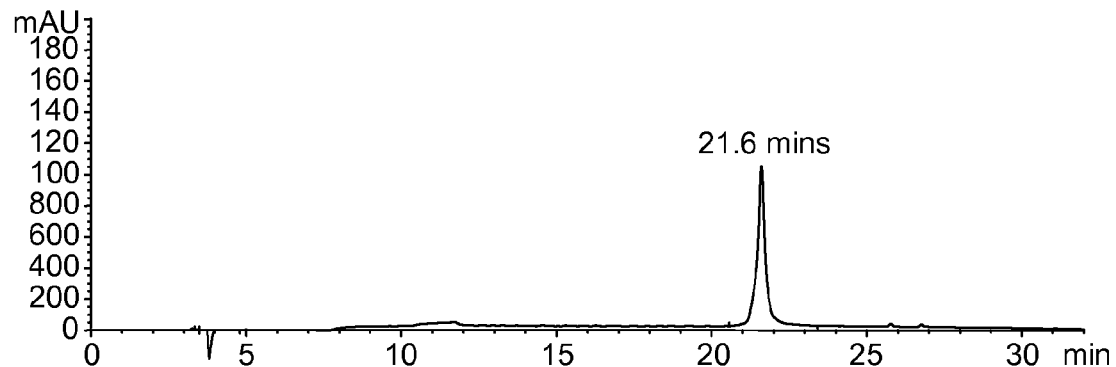

FIG. 141—HPLC of purified folded Biotin-TECK (Nleu)

Figure 142:
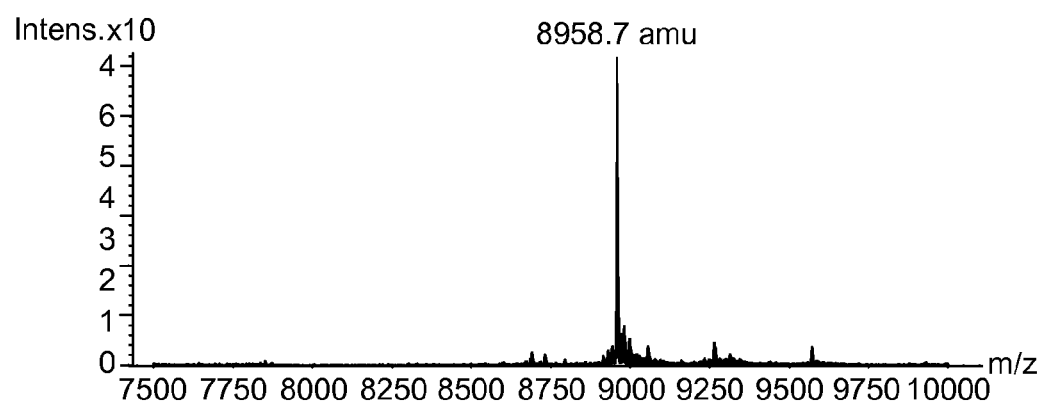

FIG. 142—Electrospray ionisation with tandem mass spectrometry (ES/MS) data of purified folded Biotin-TECK (Nleu).

Figure 143:
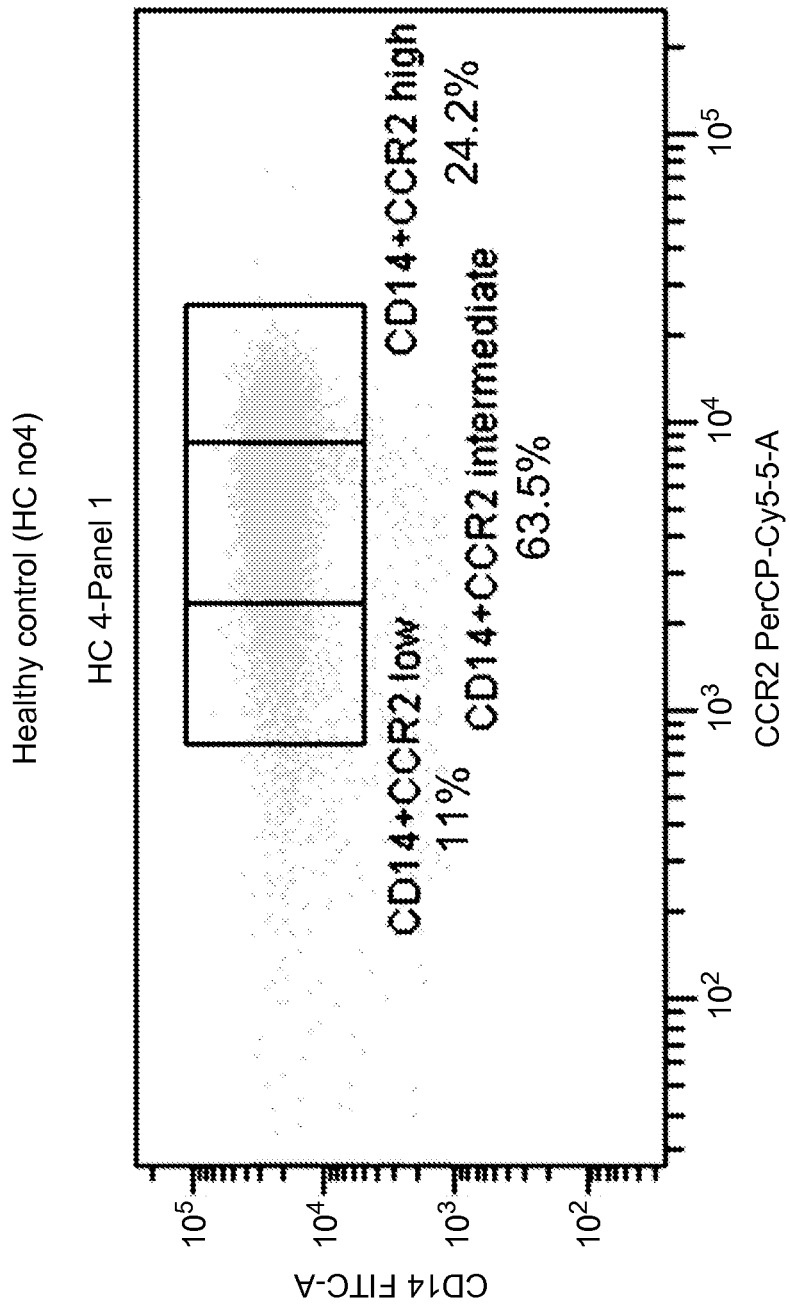

FIG. 143—Example of gating criteria for CCR2 expressing monocytes

Figure 144A:
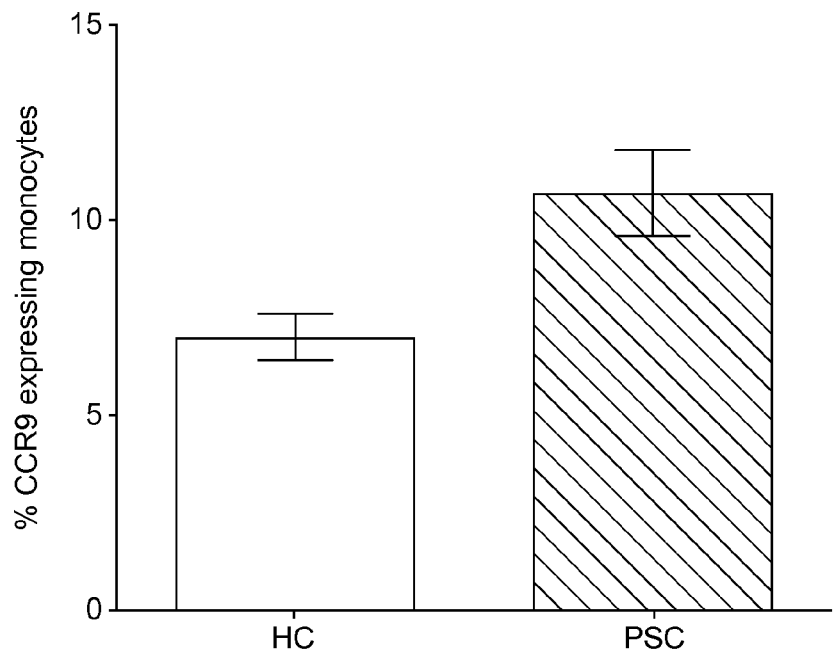

FIG. 144a—Expression of CCR9 expressing monocytes in 4 patients with Primary sclerosing cholangitis (PSC) and in 20 healthy controls (HC).

Figure 144B:
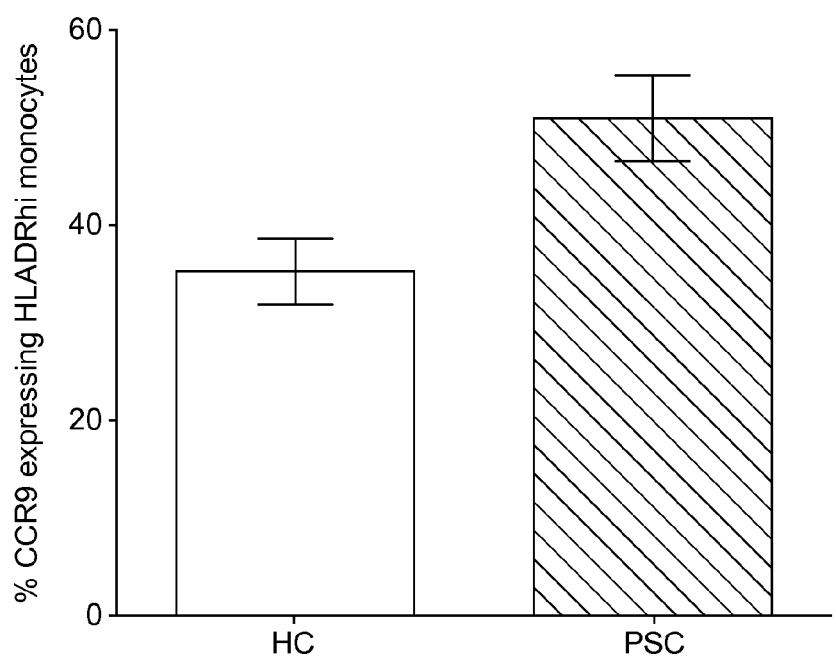

FIG. 144b—Expression of CCR9 in activated (HLADRhi) monocytes in 4 patients with Primary sclerosing cholangitis (PSC) and in 20 healthy controls (HC). Blood from patients with PSC and healthy controls was analysed for the expression of various chemokine receptors by flow cytometry. The monocytes were characterized as CD14 positive cells, and the activated monocytes are characterized as highly expressed HLADR CD14 positive cells.

Figure 145:
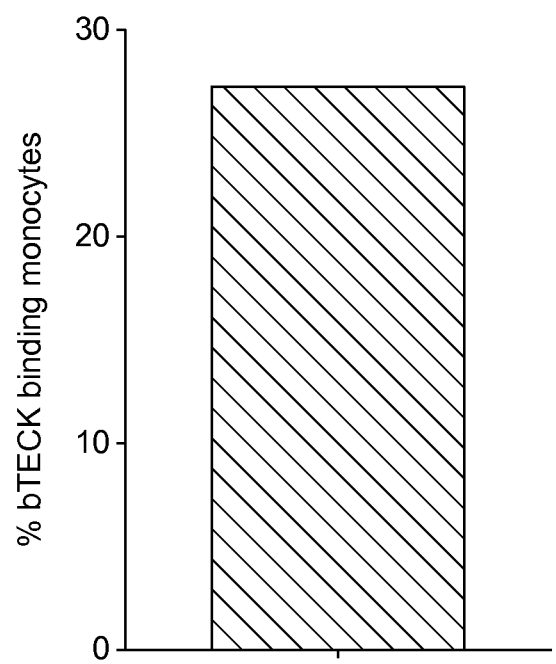

FIG. 145—Binding of the chemokine bTECK (CCL25) to monocytes from a patient with Primary sclerosing cholangitis. Blood from a patient with PSC was incubated with bTECK and analysed with flow cytometry. The monocytes were characterized as CD14 positive cells.

Figure 146A:
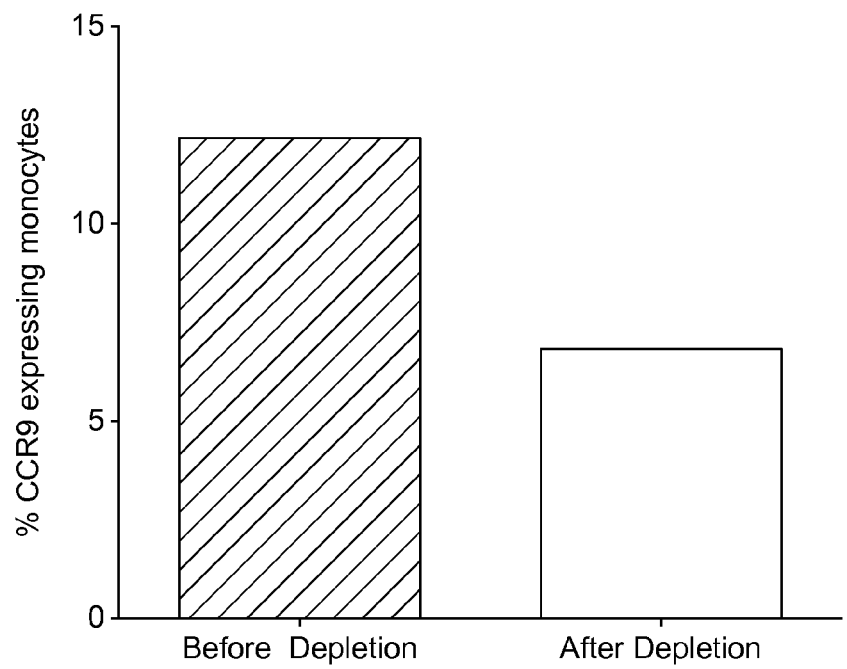

FIG. 146a—Depletion of CCR9 expressing monocytes with Sepharose Streptavidin-matrix conjugated with bTECK.

Figure 146B:
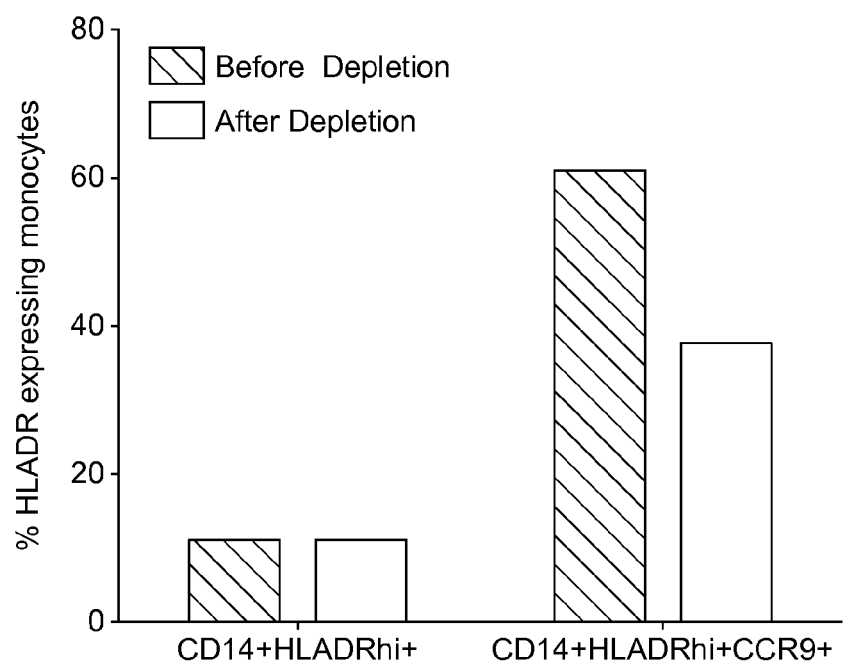

FIG. 146b—Depletion of activated CCR9 expressing monocytes with Sepharose Streptavidin-matrix conjugated with bTECK. Blood cells from a patient with PSC were incubated with bTECK-Sepharose Streptavidin-matrix. Unbound cells were retrieved by washing the matrix with Phosphate Buffer Saline. The cells (After Depletion) were then analysed with flow cytometry and compared with cells that had not been incubated with bTECK-matrix (Before Depletion).

K. Treating Respiratory Conditions

Figure 147A:
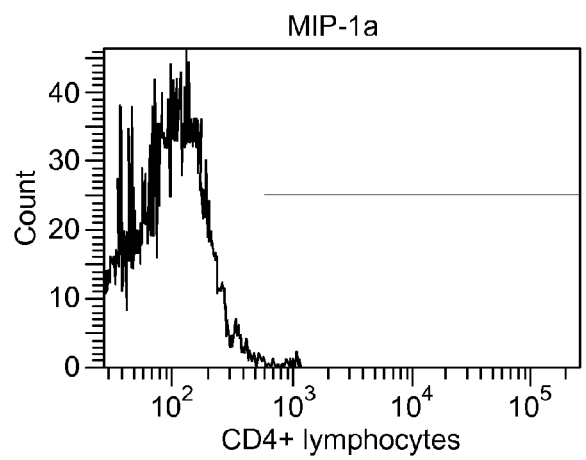
Figure 147B:
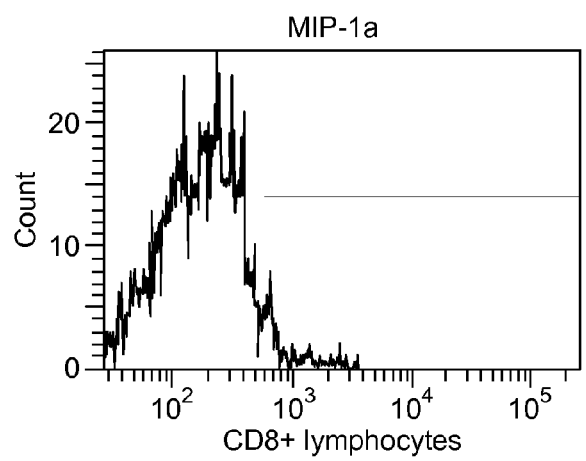
Figure 147C:
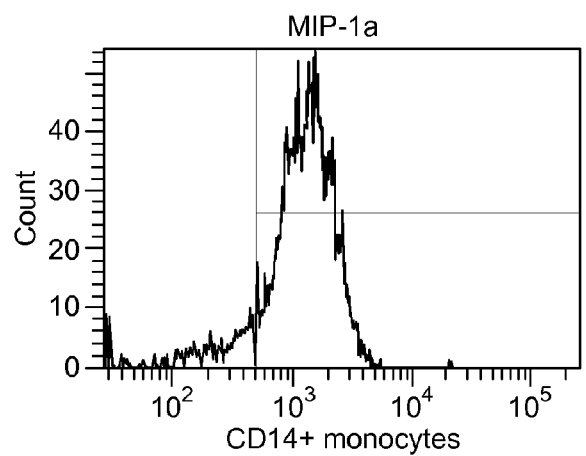
Figure 148A:
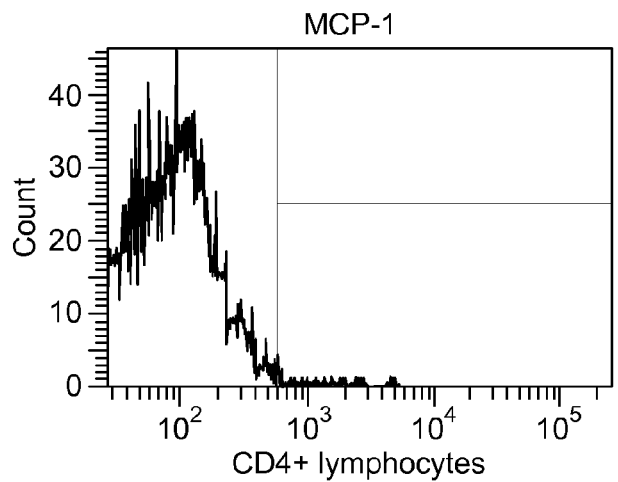
Figure 148B:
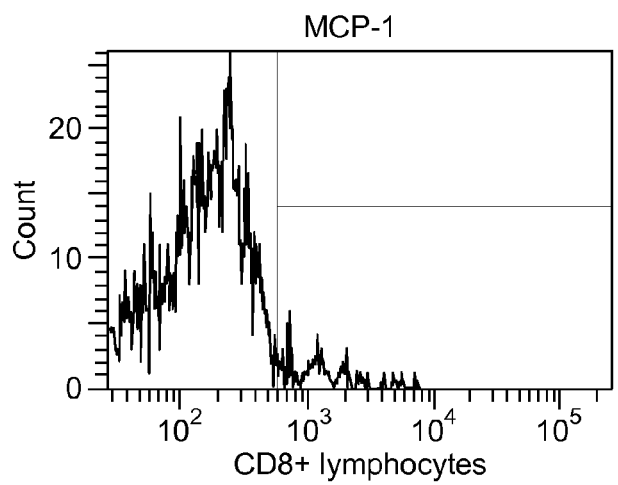
Figure 148C:
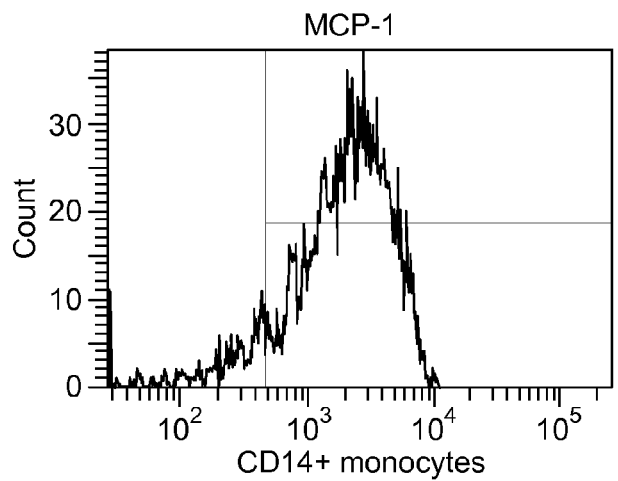
Figure 149A:
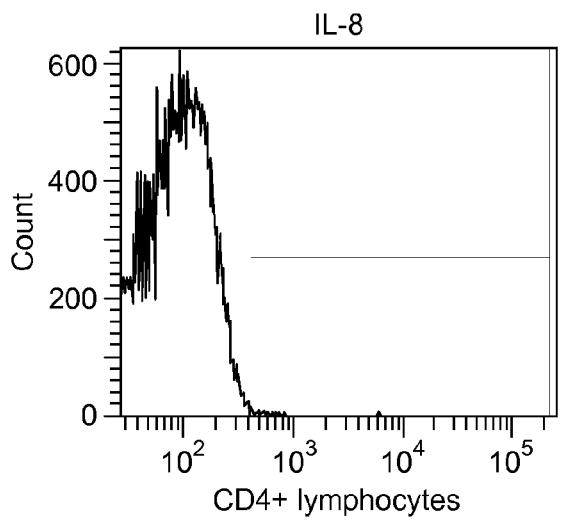
Figure 149B:
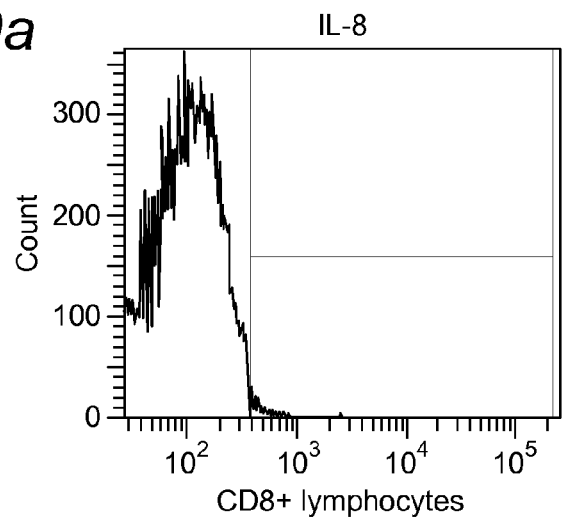
Figure 149C:
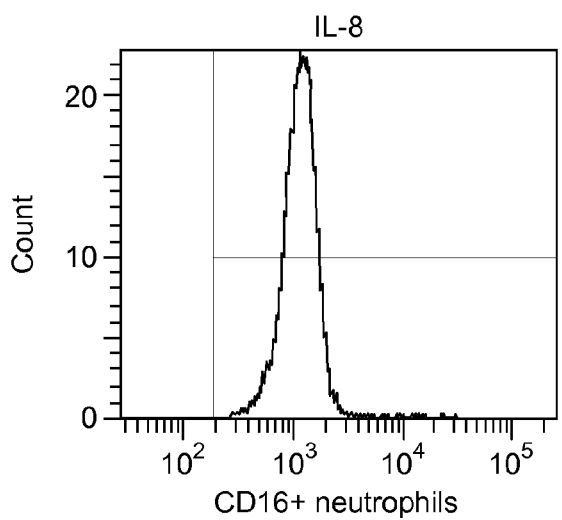
Figure 150A:
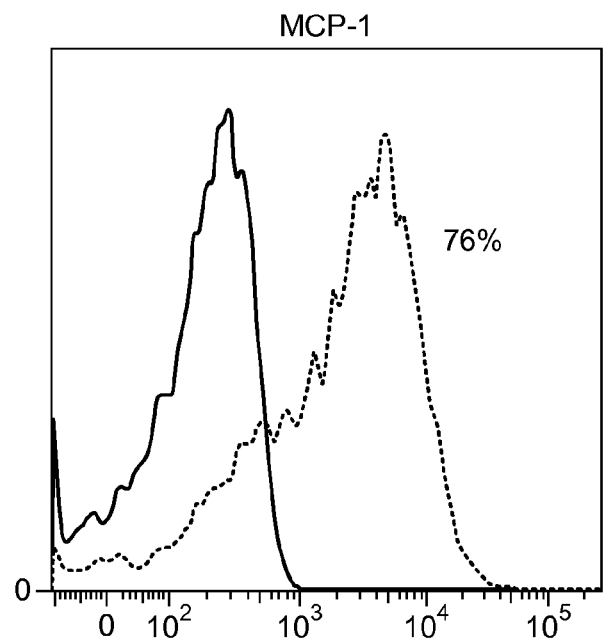

FIGS. 147a, 147b & 147c—the binding of biotinylized MIP-1α by CD4+, CD8+ T-cells and CD14+ monocytes respectively, obtained from peripheral blood of a healthy donor;

FIGS. 148a, 148b & 148c—the binding of biotinylized MCP-1 by CD4+, CD8+ T-cells and CD14+ monocytes respectively, obtained from peripheral blood of a healthy donor;

FIGS. 149a, 149b & 149c—the binding of IL-8 by CD4+, CD8+ T-cells and CD16+ monocytes respectively, obtained from peripheral blood of a healthy donor FIG. 150a—binding of MCP-1 to monocytes (dashed line) in peripheral blood taken from IBD patients. The graph represents a summary of four tests.

Figure 150B:
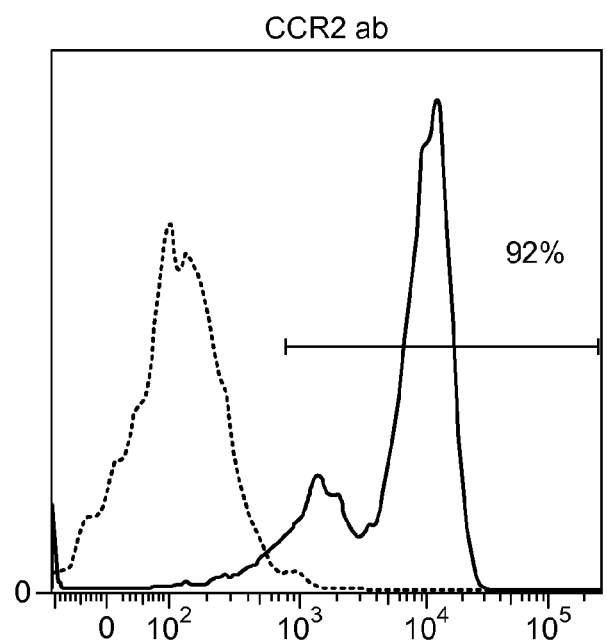

FIG. 150b—binding of CCR2-antibody to monocytes (line) in peripheral blood taken from IBD patients. The graph represents a summary of four tests.

Figure 151A:
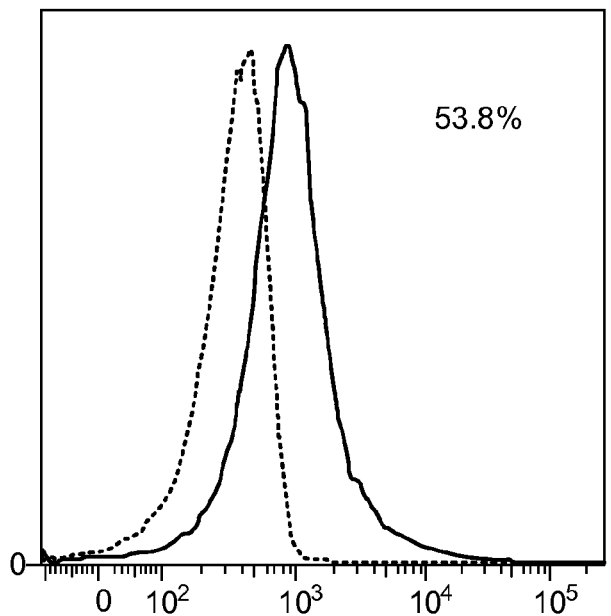

FIG. 151a—binding of eotaxin to neutrophils/eosinophils (dashed line) in peripheral blood. The graph represents a summary of four tests.

Figure 151B:
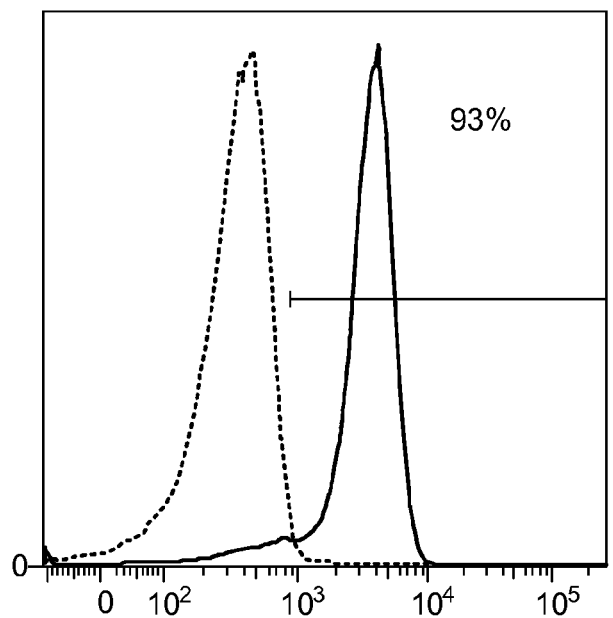

FIG. 151b—binding of CCR3-antibody to neutrophils/eosinophils (line) in peripheral blood. The graph represents a summary of four tests.

Figure 152A:
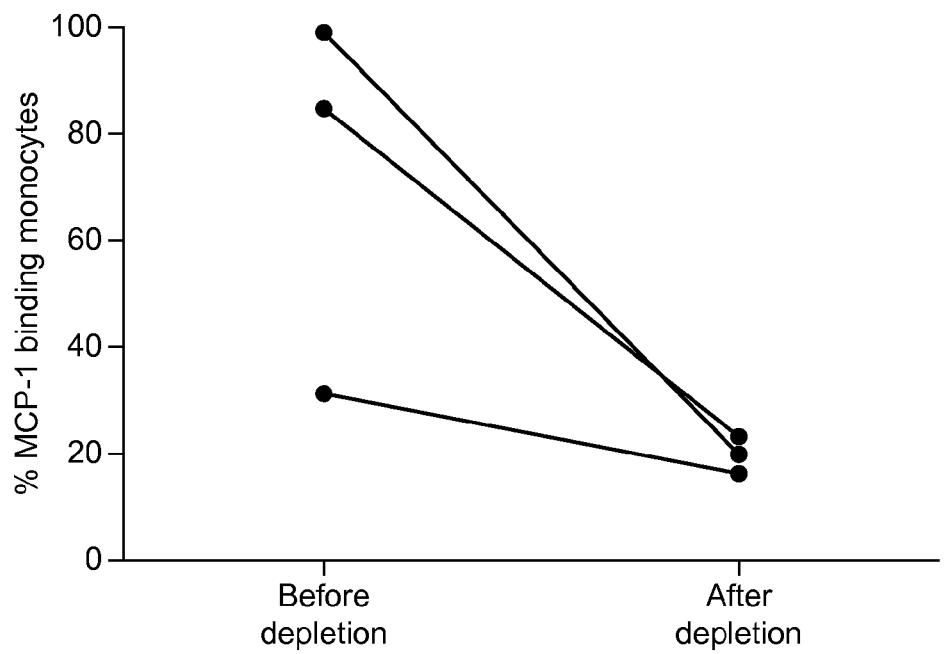

FIG. 152a—Results of in vitro depletion tests performed on the bMCP-1 coupled matrix showing ability to eliminate CCR2-expressing cells from blood from three healthy donors.

Figure 152B:
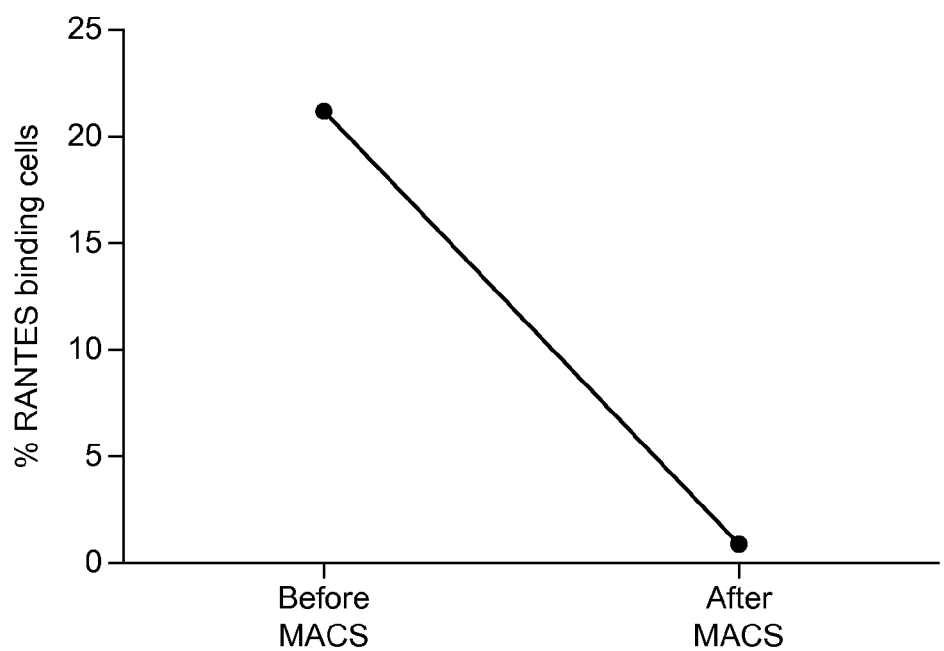

FIG. 152b—Results of in vitro depletion tests performed on the biotinylated RANTES coupled matrix showing ability to eliminate chemokine receptor-expressing cells from peripheral blood taken from a healthy donor.

Figure 152C:
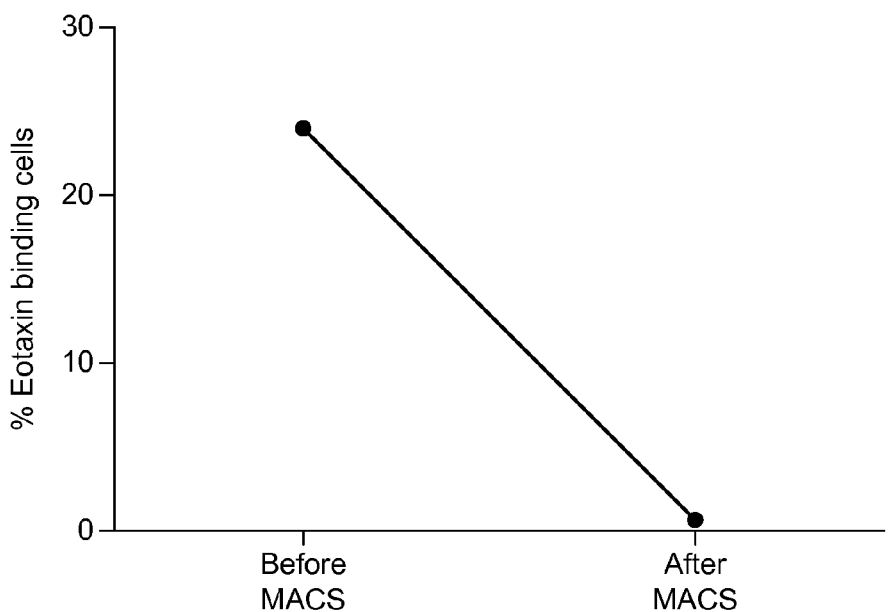

FIG. 152c—Results of in vitro depletion tests performed on the biotinylated eotaxin coupled matrix showing ability to eliminate CCR3-expressing cells from blood from a healthy donor.

Figure 153:
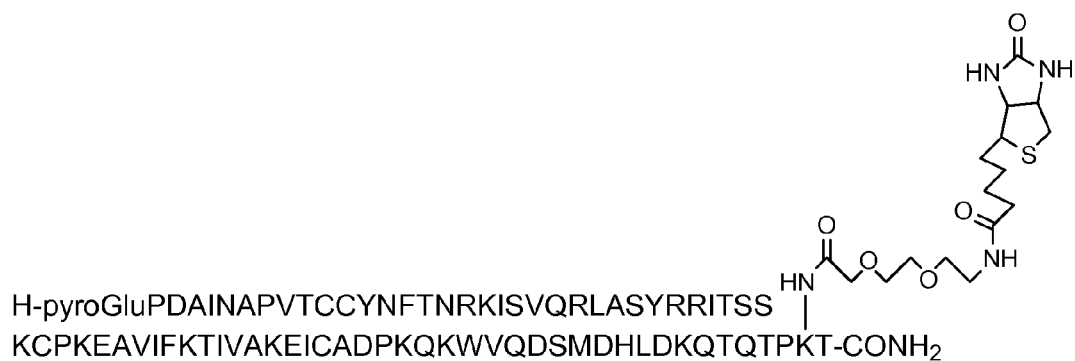

FIG. 153—Sequence (SEQ ID NO: 211) and biotinylation, via a spacer group, of mature protein MCP-1 derivative containing Gln to pyroGlu modification.

Figure 154:
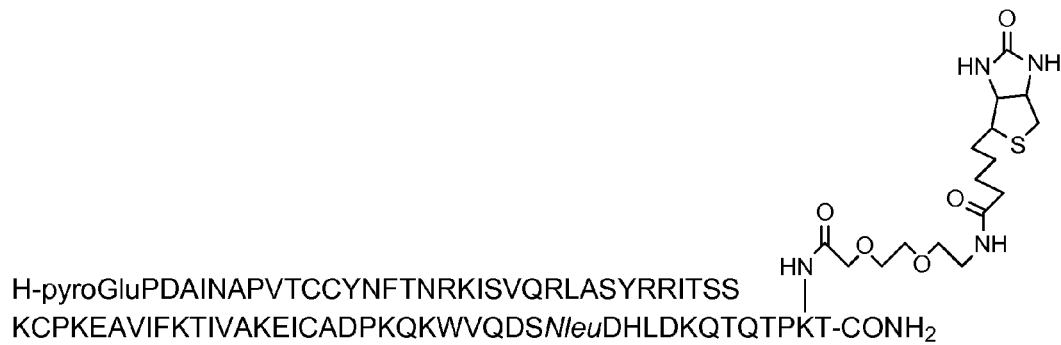

FIG. 154—Sequence (SEQ ID NO: 211) and biotinylation, via a spacer group, of mature protein MCP-1 derivative containing Gln to pyroGlu modification and Met to Norleu substitution.

Figure 155:
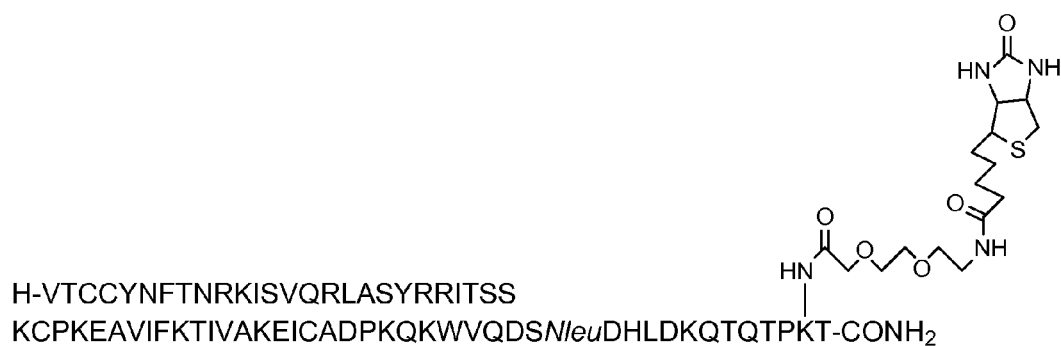

FIG. 155—Sequence (SEQ ID NO: 212) and biotinylation, via a spacer group, of truncated MCP-1 derivative containing Met to Norleu substitution.

FIG. 156—Alignment of MCP-1 (residues 25-99 of SEQ ID NO: 11) and MCP-5 (residues 24-104 of SEQ ID NO: 10) amino acid sequences.

Figure 157:
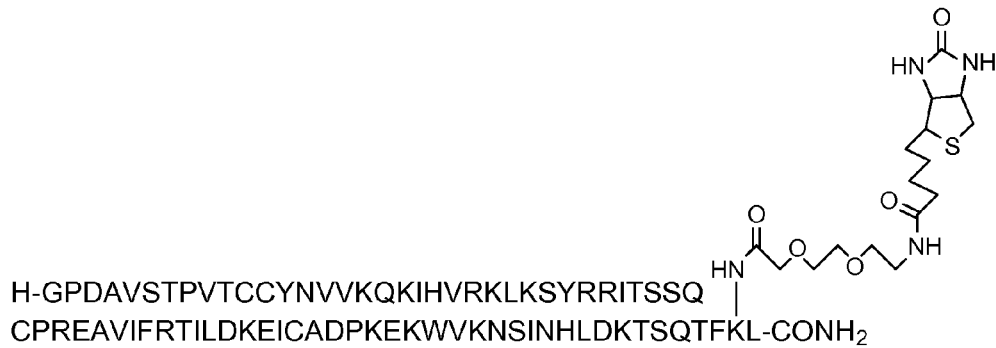

FIG. 157—Sequence (SEQ ID NO: 216) and biotinylation, via a spacer group, of (C-terminal) truncated MCP-5 derivative containing Ile to Lys modification.

Figure 158:
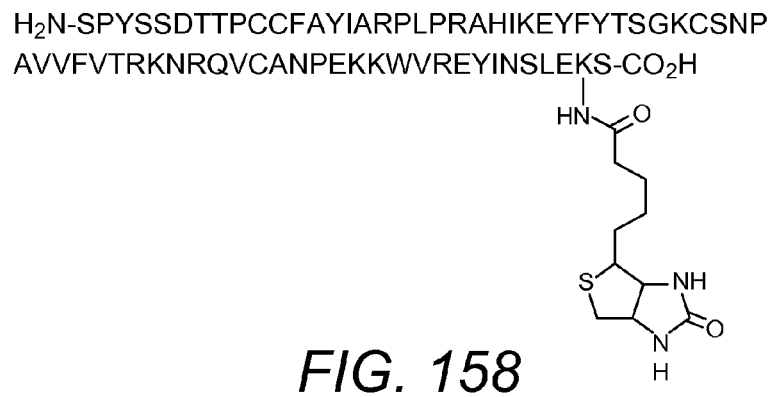

FIG. 158—Sequence (SEQ ID NO: 225) and biotinylation, of RANTES derivative.

Figure 159:

FIG. 159—Sequence (SEQ ID NO: 218) and biotinylation, via a spacer group, of mature protein eotaxin derivative containing C-terminal amide.

Figure 160:
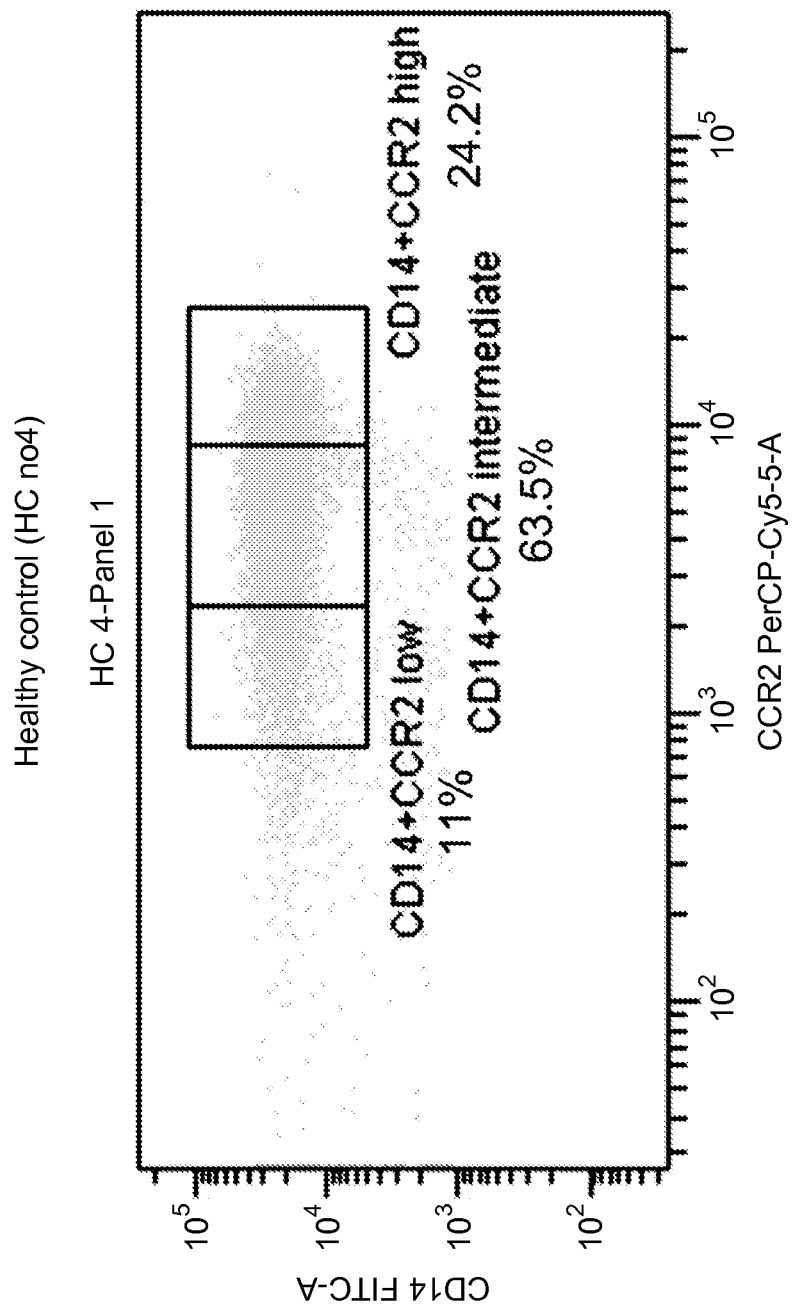

FIG. 160—Example of gating criteria for CCR2 expressing monocytes

Figure 161:
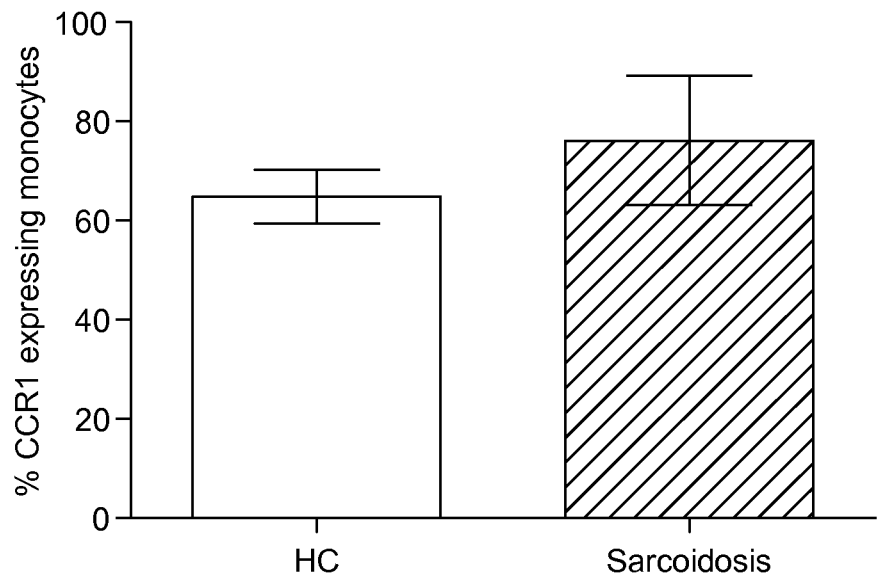

FIG. 161—Frequency of CCR1 expressing monocytes in 20 healthy controls and 2 patients with sarcoidosis. The expression of chemokine receptors and specific cell markers were analysed with flow cytometry.

Figure 162:
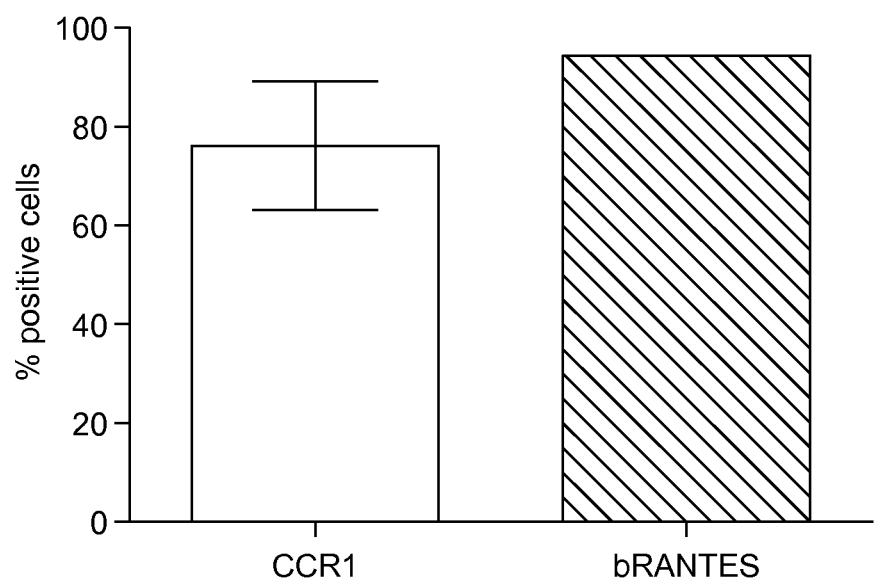

FIG. 162—Expression of CCR1 compared to binding of bRANTES to blood monocytes from a patient with sarcoidosis. The expression of chemokine receptors, binding of chemokine, and specific cell markers were analysed with flow cytometry.

Figure 163:
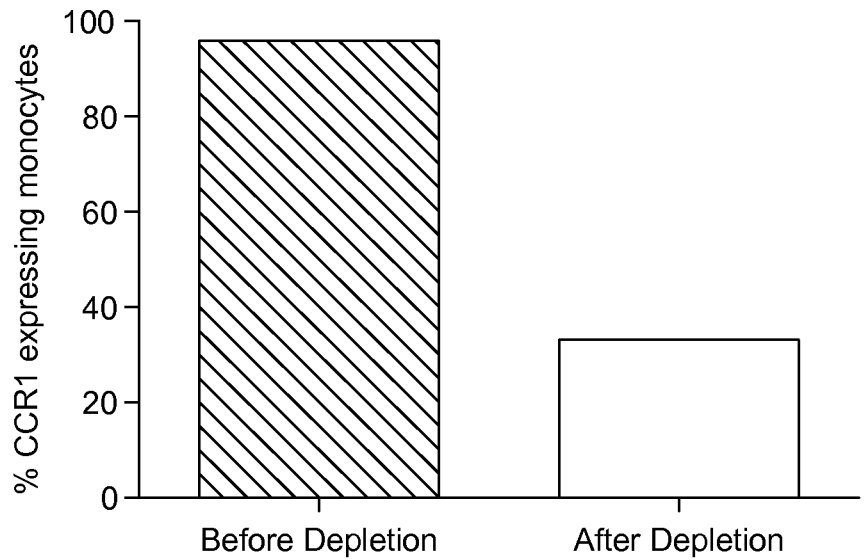

FIG. 163—Depletion of CCR1 expressing monocytes with Sepharose Streptavidin-matrix conjugated with bRANTES. Blood cells from a healthy control were incubated with biotinylated chemokine-Sepharose Streptavidin-matrix. Unbound cells were retrieved by washing the matrix. The cells (After Depletion) were then analysed with flow cytometry and compared with cells that had not been incubated with biotinylated-chemokine-matrix (Before Depletion).

Figure 164:
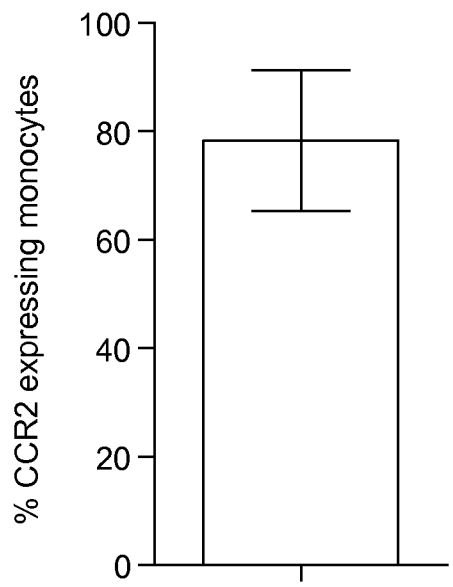

FIG. 164—Expression of CCR2 on monocytes from two patients with sarcoidosis. The expression of chemokine receptors, binding of chemokine and specific cell markers were analysed with flow cytometry.

Figure 165:
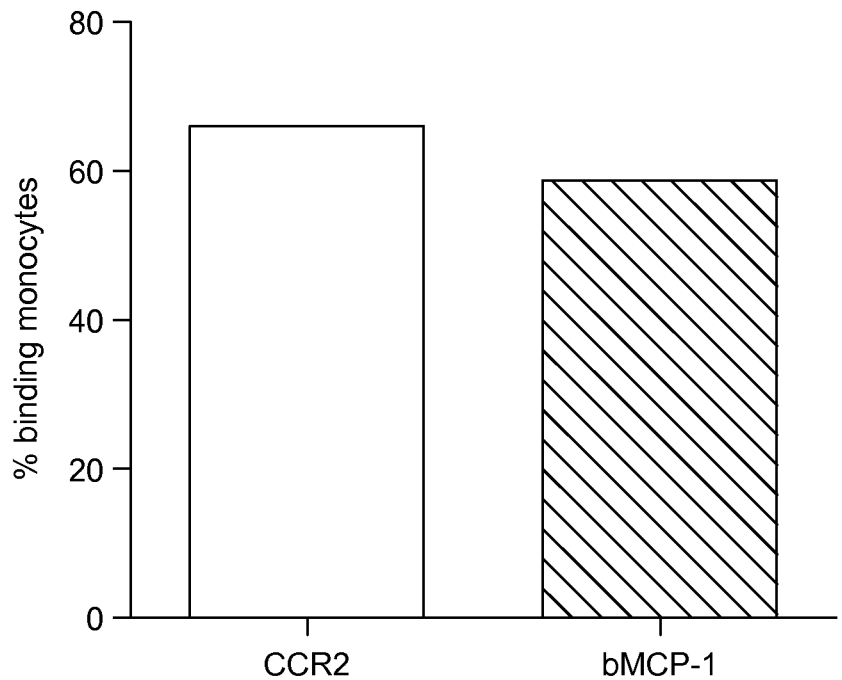

FIG. 165—Binding of the chemokine bMCP-1 to monocytes. Bars represent frequency of MCP-1 binding monocytes and CCR2 expressing monocytes in blood from a patient with sarcoidosis. Blood was incubated with biotinylated chemokine and analysed with flow cytometry.

Figure 166:
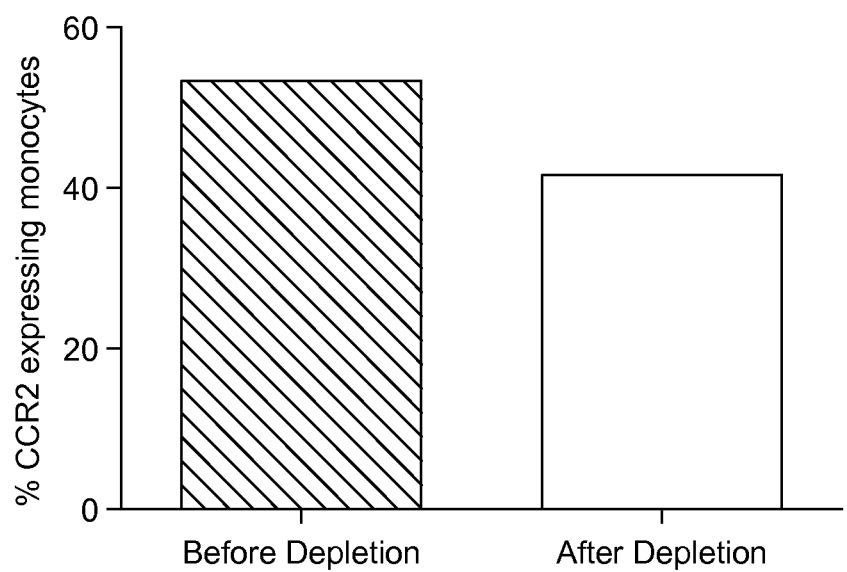

FIG. 166—Depletion of CCR2 expressing monocytes with Sepharose Streptavidin-matrix conjugated with bMCP-1. Blood cells from a healthy control were incubated with biotinylated chemokine-Sepharose Streptavidin-matrix. Unbound cells were retrieved by washing the matrix. The cells (After Depletion) were then analysed with flow cytometry and compared with cells that had not been incubated with bchemokine-matrix (Before Depletion).

Figure 167A:
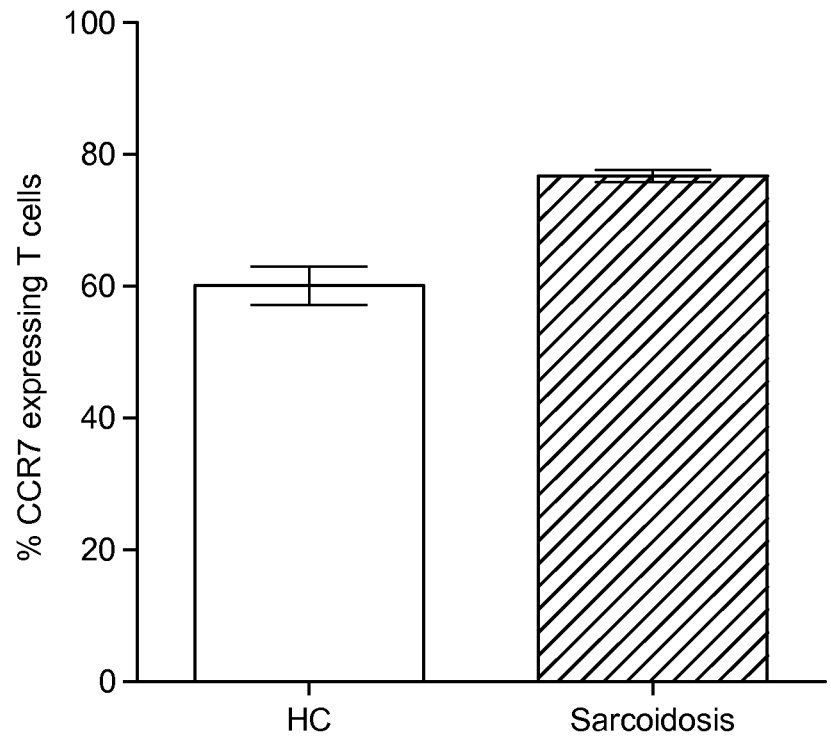

FIG. 167a—Frequency of CCR7 expressing T cells. Bars represent frequency of T cells that express CCR7 in 2 patients and 20 healthy controls. The expression of chemokine receptors and specific cell markers were analysed with flow cytometry. The T cells were characterized as CD3 positive.

Figure 167B:
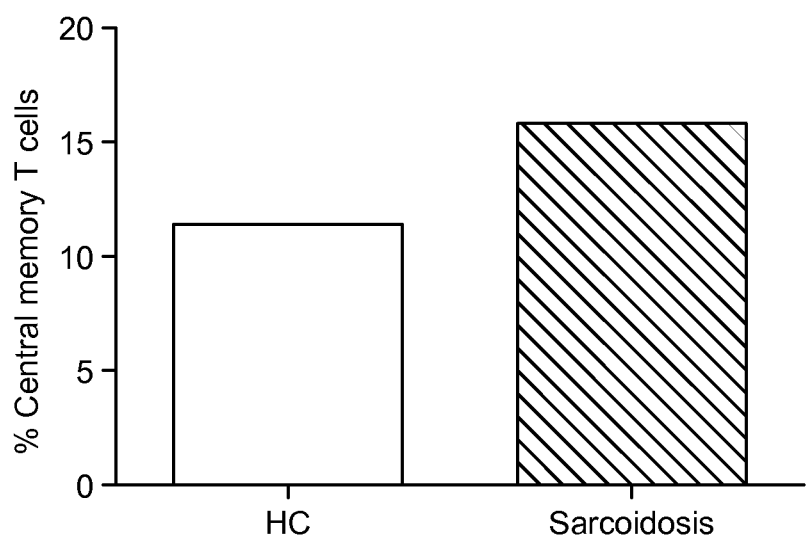

FIG. 167b—Frequency of central memory T cells in one patient with sarcoidosis. The central memory T cells were characterized as CD3 positive, CD4 positive, CD45RA negative, CCR7 positive cells.

Figure 168:
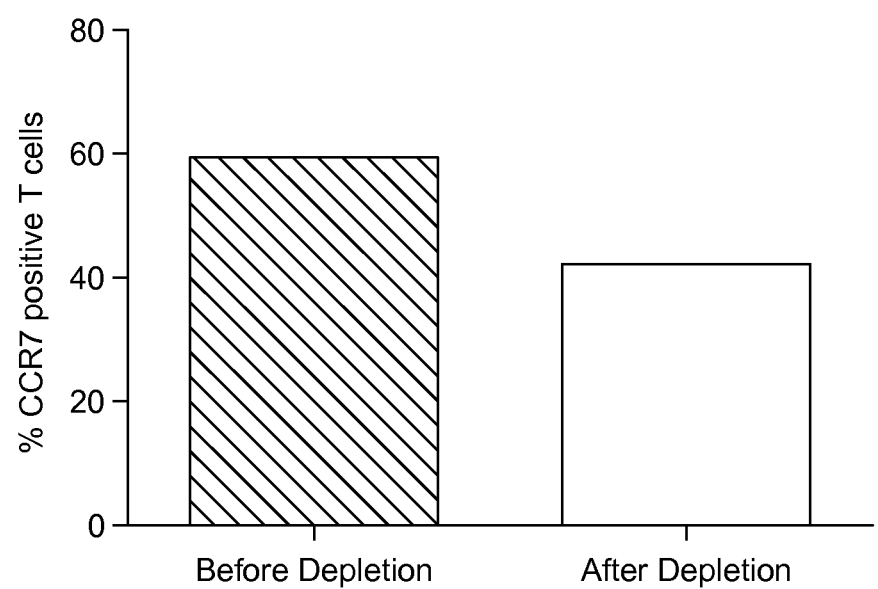

FIG. 168—Depletion of CCR7 expressing T cells with Sepharose Streptavidin-matrix conjugated with bMIP3b. Blood cells from a patient with Sarciodosis were incubated with biotinylated chemokine-Sepharose Streptavidin-matrix. Unbound cells were retrieved by washing the matrix. The cells (After Depletion) were then analysed with flow cytometry and compared with cells that had not been incubated with bchemokine-matrix (Before Depletion).

L. Treating Conditions Associated with Sepsis

Figure 169A:
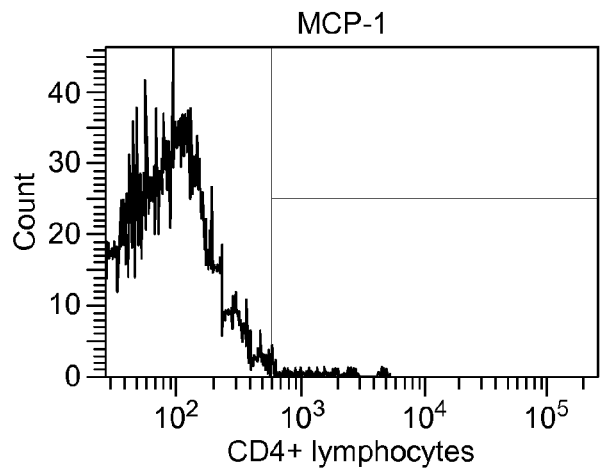
Figure 169B:
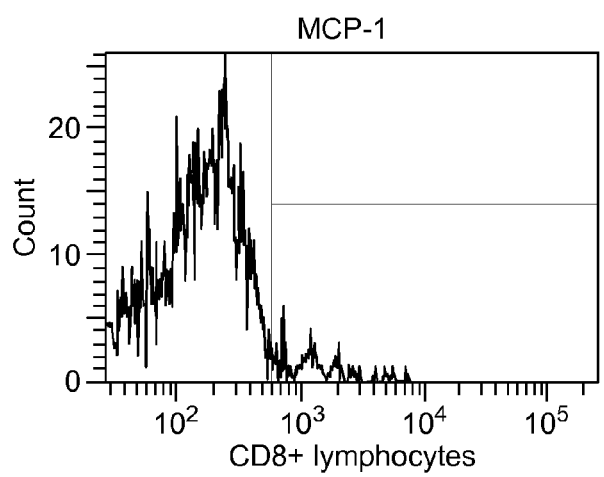
Figure 169C:
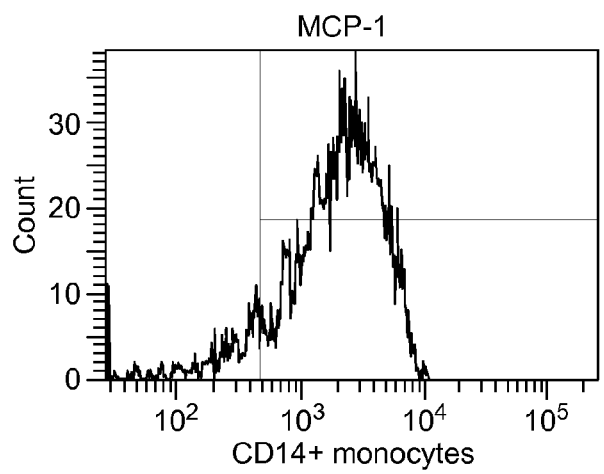

FIGS. 169a, 169b & 169c—the binding of biotinylized MCP-1 by CD4+, CD8+ T-cells and CD14+ monocytes respectively, obtained from peripheral blood of a healthy donor.

Figure 169D:
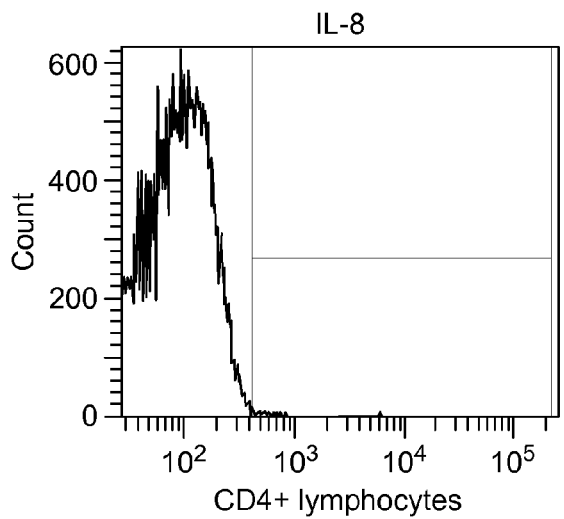
Figure 169E:
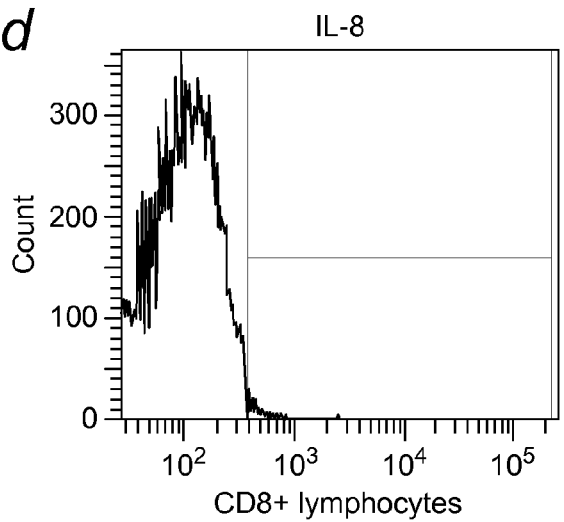
Figure 169F:
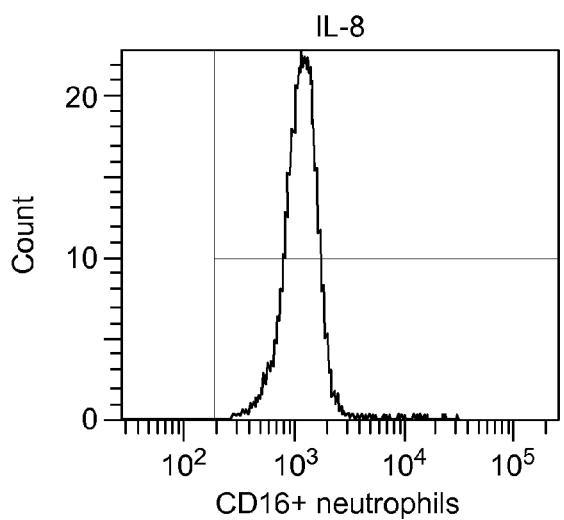
Figure 170A:
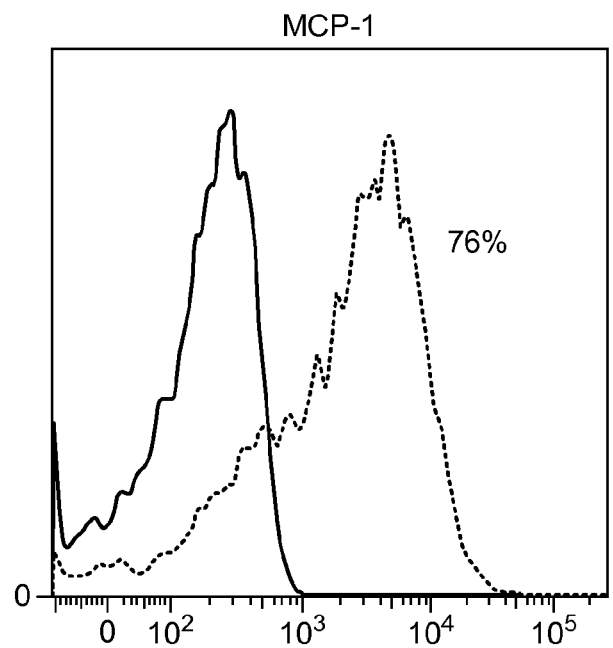

FIGS. 169d, 169e & 169f—the binding of IL-8 by CD4+, CD8+ T-cells and CD16+ neutrophils respectively, obtained from peripheral blood of a healthy donor FIG. 170a—binding of MCP-1 to monocytes (dashed line) in peripheral blood taken from IBD patients. The graph represents a summary of four tests.

Figure 170B:
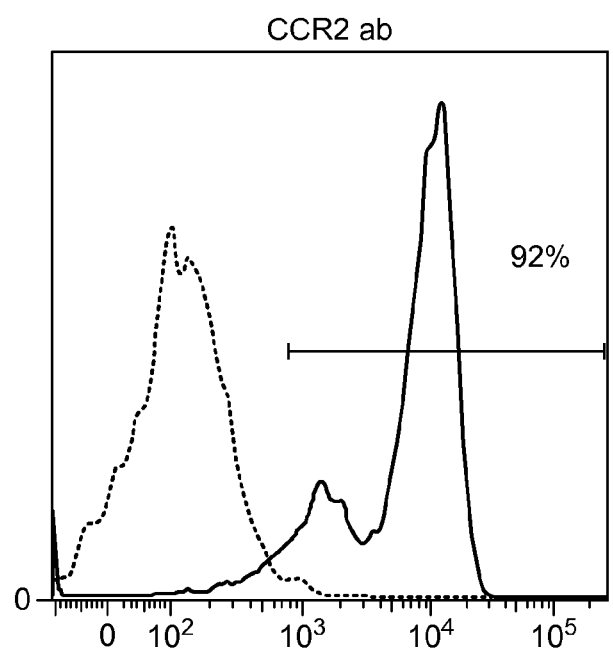

FIG. 170b—binding of CCR2-antibody to monocytes (line) in peripheral blood taken from IBD patients. The graph represents a summary of four tests.

Figure 171:
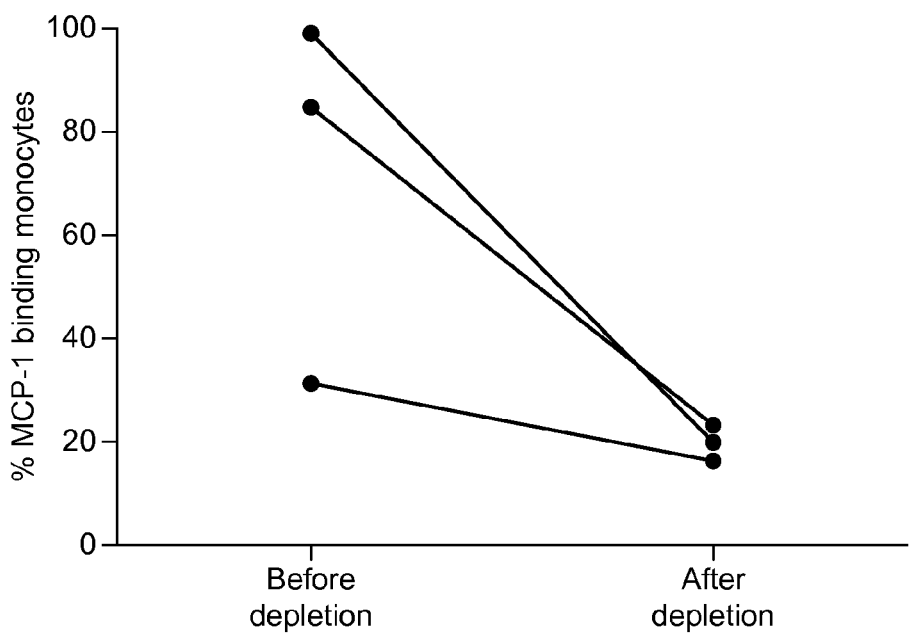

FIG. 171—Results of in vitro depletion tests performed on the bMCP-1 coupled matrix showing ability to eliminate CCR2-expressing cells from blood from three healthy donors.

Figure 172:
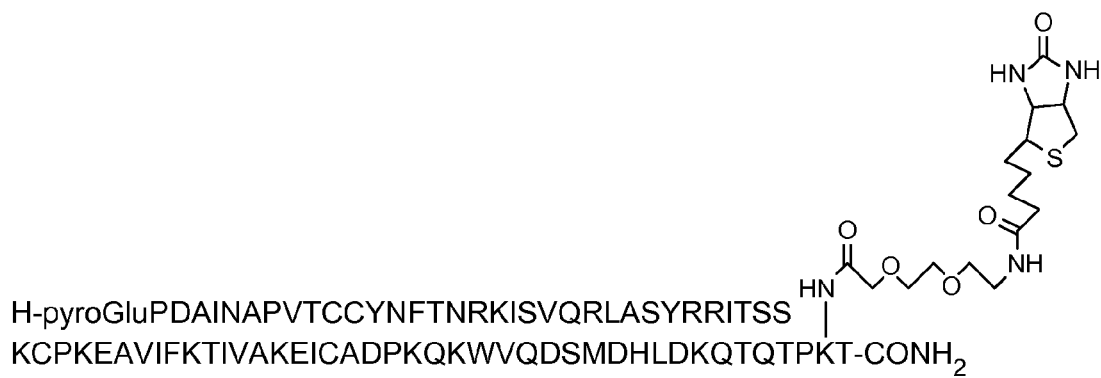

FIG. 172—Sequence (SEQ ID NO: 241) and biotinylation, via a spacer group, of mature protein MCP-1 derivative containing Gln to pyroGlu modification.

Figure 173:
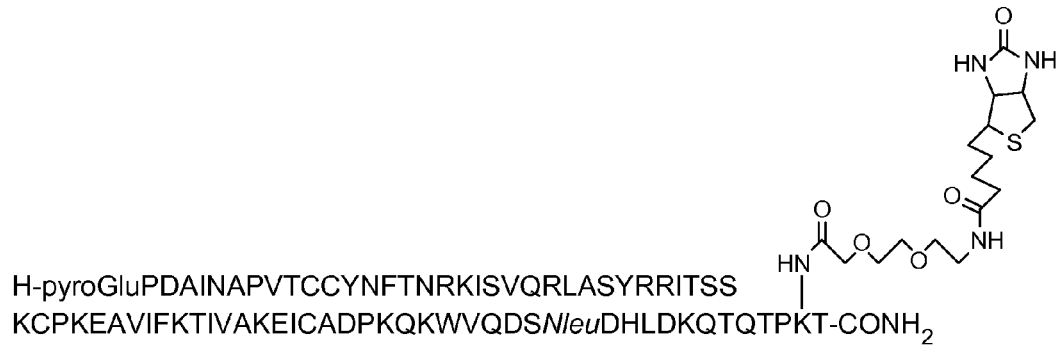

FIG. 173—Sequence (SEQ ID NO: 241) and biotinylation, via a spacer group, of mature protein MCP-1 derivative containing Gln to pyroGlu modification and Met to Norleu substitution.

Figure 174:
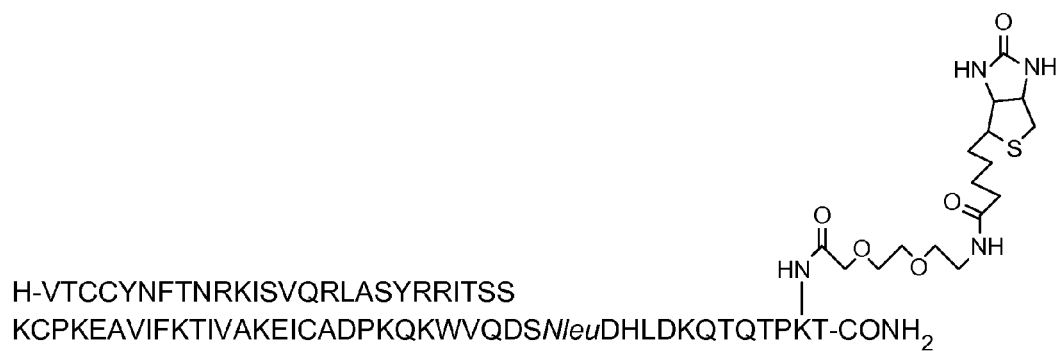

FIG. 174—Sequence (SEQ ID NO: 242) and biotinylation, via a spacer group, of truncated MCP-1 derivative containing Met to Norleu substitution.

FIG. 175—Alignment of MCP-1 (residues 25-99 of SEQ ID NO: 11) and MCP-5 (residues 24-104 of SEQ ID NO: 10) amino acid sequences.

FIG. 176—Sequence (SEQ ID NO: 246) and biotinylation, via a spacer group, of (C-terminal) truncated MCP-5 derivative containing Ile to Lys modification.

Figure 177:
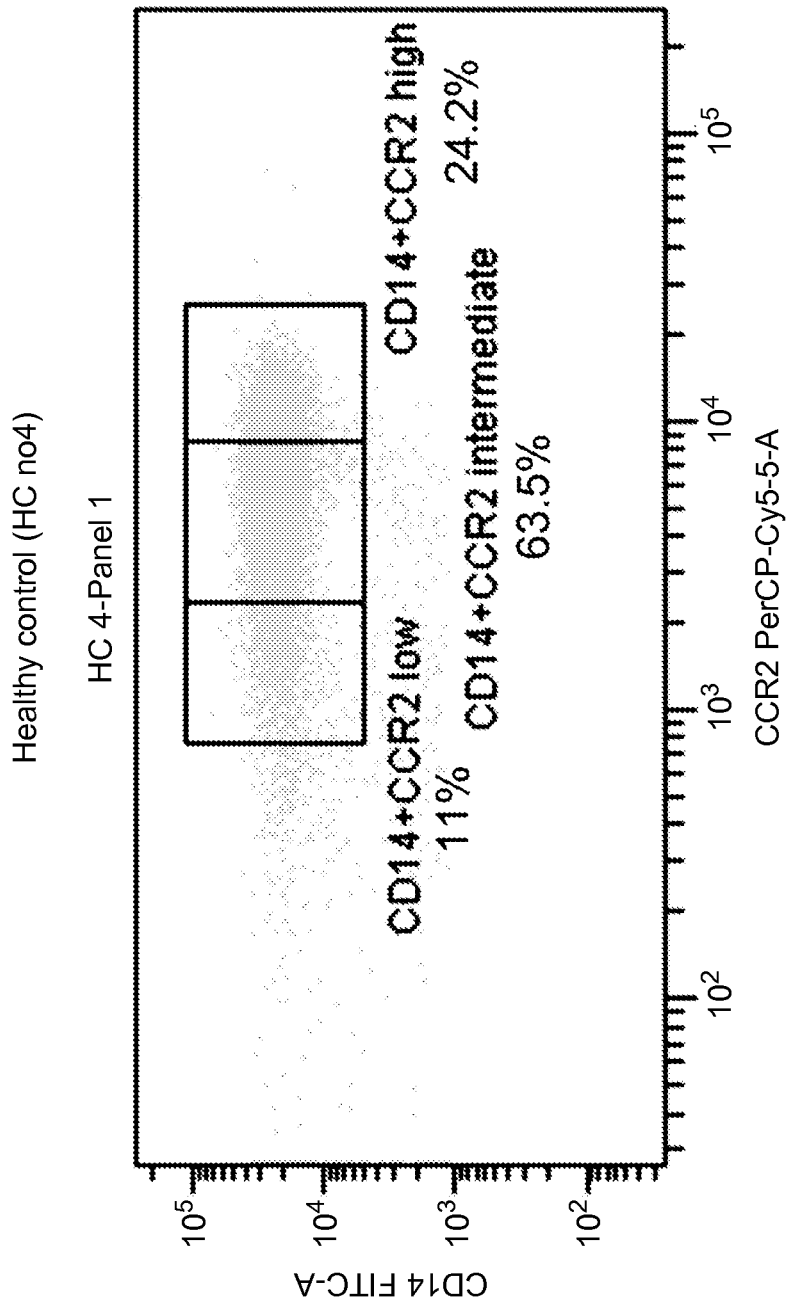

FIG. 177—example of gating criteria for CCR2 expressing monocytes.

Figure 178:
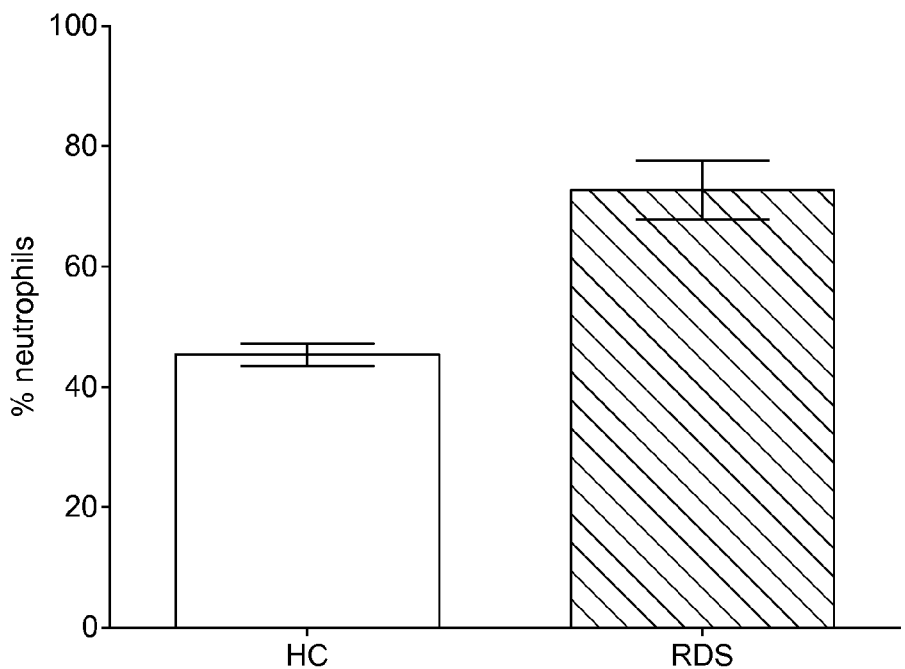

FIG. 178—Frequency of neutrophils in peripheral blood of RDS patents and healthy controls (HC). Bars represent mean and SEM of CD16 positive granulocytes in blood from 8 RDS patients and 20 HC. Blood was analysed for the expression of cell specific markers with flow cytometry.

Figure 179:
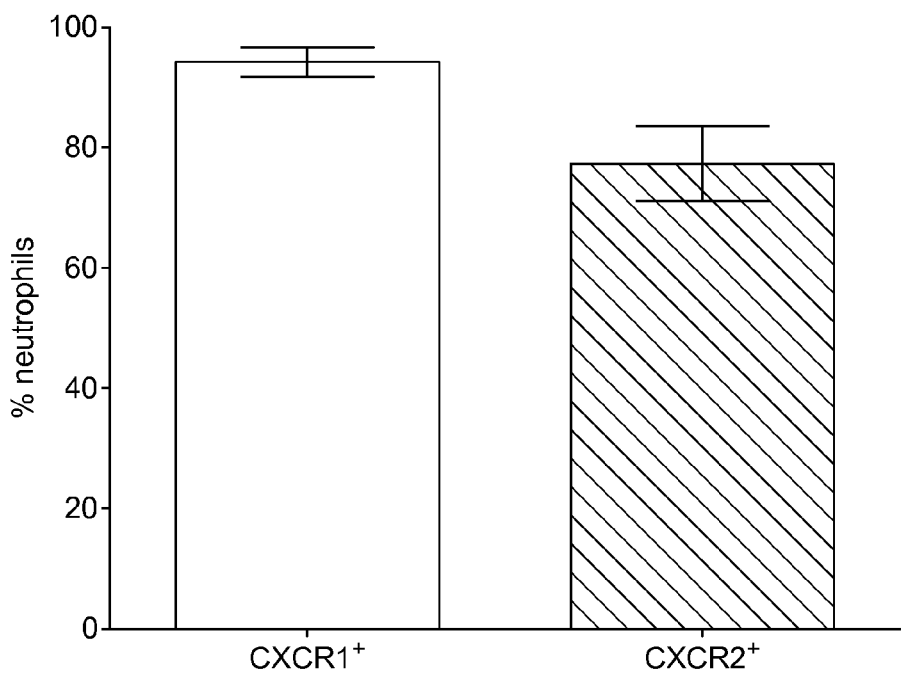

FIG. 179—Expression of CXCR1 and CXCR2 on neutrophils from patients with RDS. Blood was analysed for the expression of chemokine receptors by flow cytometry. Bars represent mean and SEM of CXCR1 positive and CXCR2 positive neutrophils in 6 RDS patients. Blood was analysed for the expression of cell specific markers by flow cytometry and neutrophils were characterized as CD16 expressing granulocytes.

Figure 180:
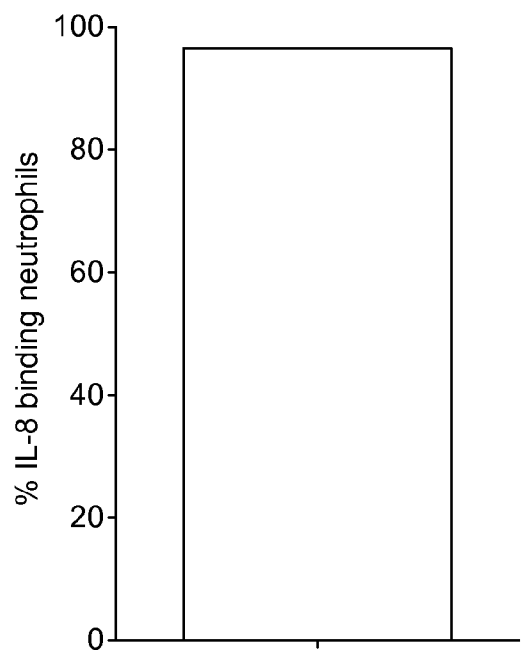

FIG. 180—Binding of biotinylated IL-8 (bIL-8) to neutrophils from a healthy control. Bar represent percentage of neutrophils that bind biotinylated IL-8, analysed with flow cytometry.

Figure 181:
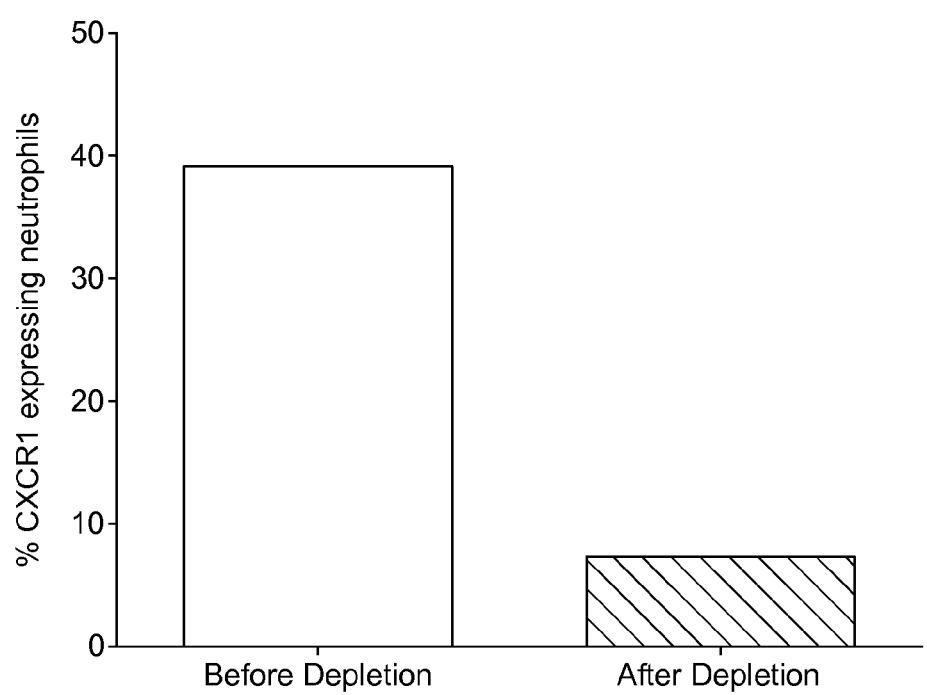

FIG. 181—Depletion of neutrophils with a CXCR1-antibody and MACS. Bars represent percentage of CXCR1 positive neutrophils before and after MACS. Peripheral blood from a RDS patient was used for the experiment.

Figure 182A:
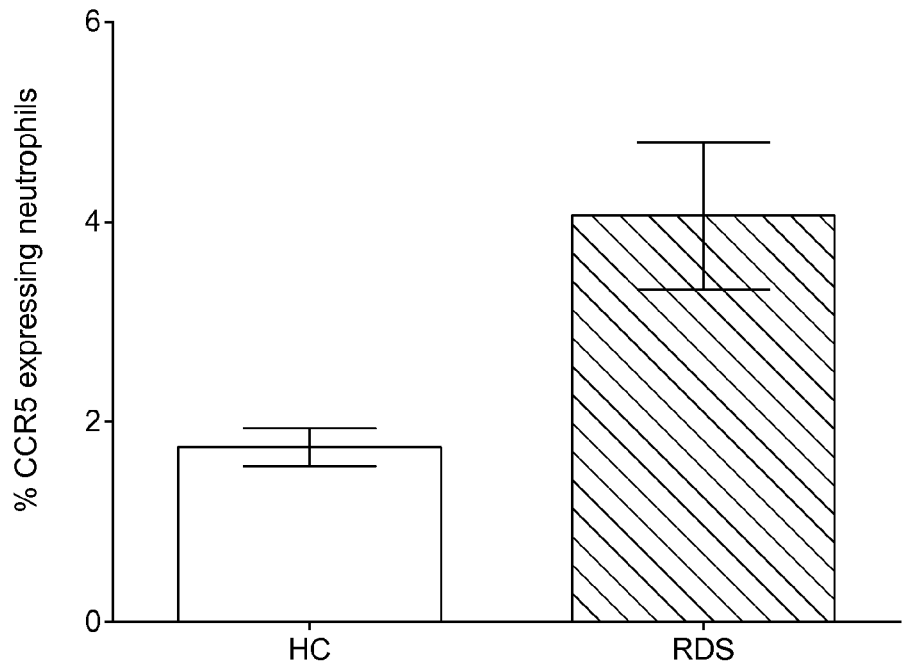

FIG. 182a—Frequency of CCR5 expressing neutrophils in patients with RDS (n=6) and healthy controls (n=20) Bars represent mean and SEM of CCR5 expressing neutrophils, analysed with flow cytometry.

Figure 182B:
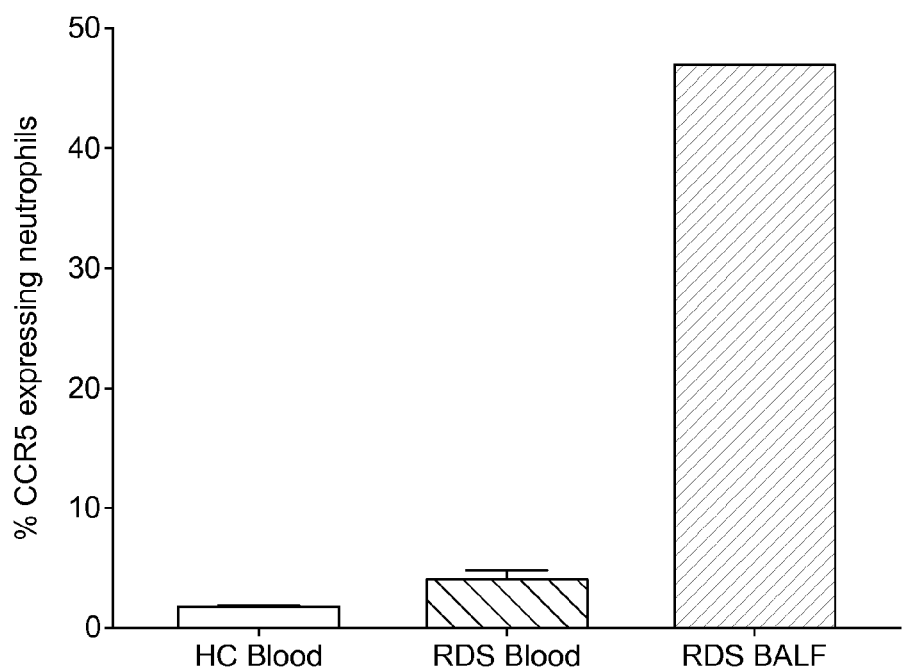

FIG. 182b—Frequency of CCR5 expressing cells in blood from healthy controls and RDS patients and in BALF from RDS patient. Bars represent mean and SEM of CCR5 expressing neutrophils, analysed with flow cytometry.

Figure 183:
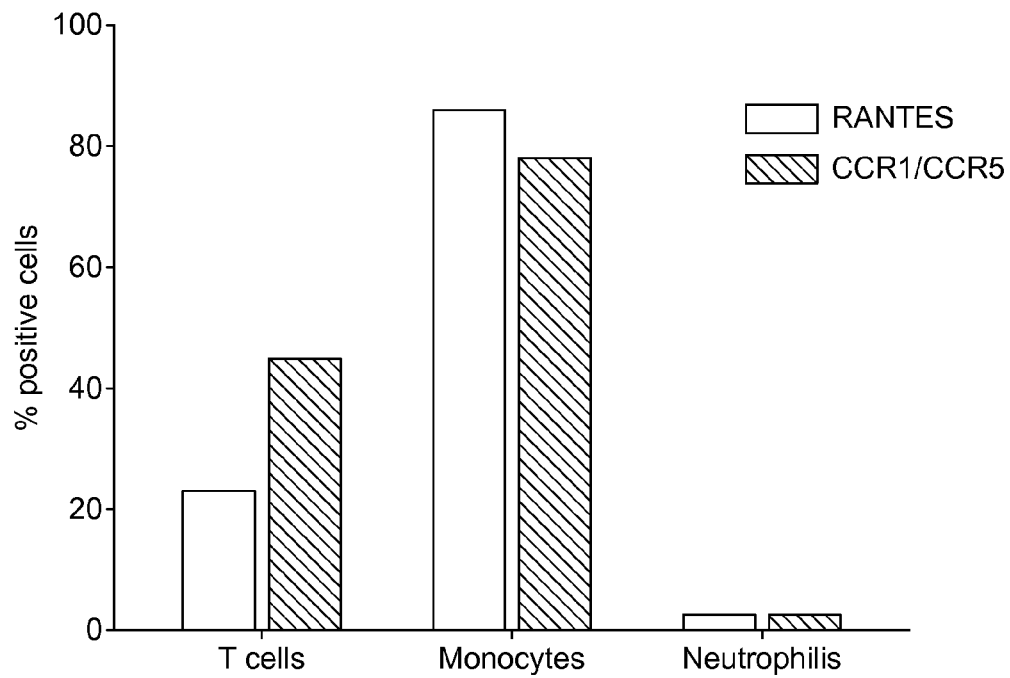

FIG. 183—Binding of RANTES and CCR5 (T cells and neutrophils) or RANTES and CCR1 (monocytes). Bars represent percentage of positive cells in blood from healthy control.

Figure 184:
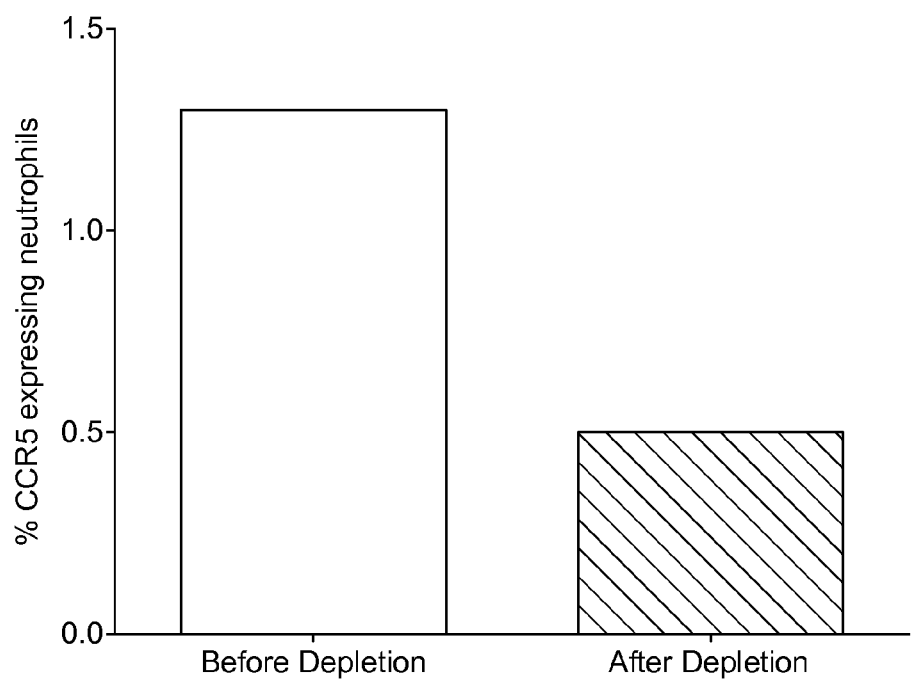

FIG. 184—Depletion of CCR5 expressing neutrophils with an anti-CCR5 antibody and MACS.

Figure 185:
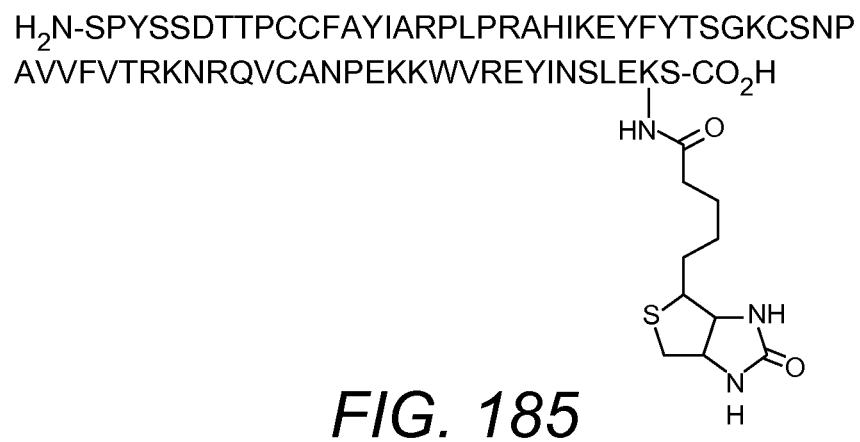

FIG. 185—Sequence (SEQ ID NO: 253) and biotinylation of RANTES derivative

Figure 186:
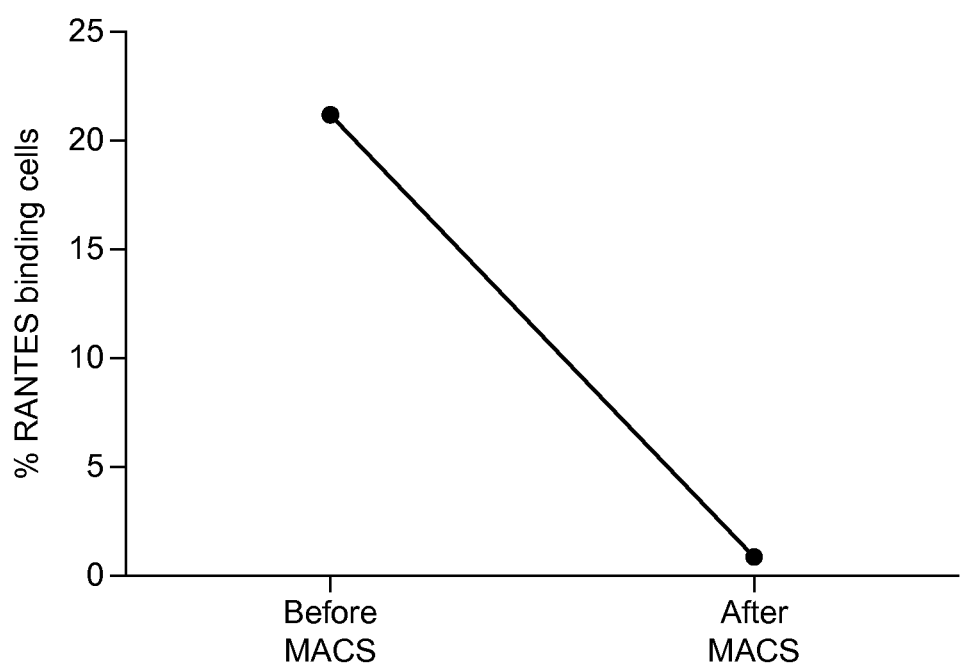

FIG. 186—Results of in vitro depletion tests performed on the biotinylated RANTES coupled matrix showing ability to eliminate chemokine receptor-expressing cells from peripheral blood taken from a healthy donor.

The various embodiments of the invention will now be described in more detail by reference to the following non-limiting embodiments and examples:

DESCRIPTION OF PREFERRED EMBODIMENTS

A. Diagnosing and Treating Inflammatory Bowel Disease and Irritable Bowel Syndrome

Example 1

CCR9-Expressing CD14+HLA-DRhi Blood Monocytes Promote Intestinal Inflammation in IBD Introduction Crohn's disease (CD) and ulcerative colitis (UC) (Inflammatory bowel diseases; IBD) are chronic, inflammatory disorders of the gastrointestinal tract resulting from a disrupted balance between the mucosal immune system and commensal flora. To date, the immunological pathophysiology behind IBD remains poorly understood. Traditionally, adaptive immunity was believed to play an important role in the onset of IBD. Studies in patients and animal models have shown that CD is driven by T helper 1-signaling with IL-12 and IFN-γ production, whereas UC is characterized by T helper 2-responses and IL-13. (1) However, the Th1/Th2 paradigm has been questioned over the last decade.[2] Since the discovery of the NOD2/CARD15 susceptibility locus that encodes a pattern recognition receptor mainly expressed on dendritic cells and monocytes, the focus of IBD research has shifted towards innate immunity.[3,4] Currently, innate mechanisms are believed to be responsible for the onset of acute mucosal inflammation in genetically susceptible individuals, whereas the chronic state might be maintained by adaptive elements.[5]

Monocytes are bone marrow-derived leukocytes of the myeloid lineage that migrate to the tissue and differentiate into macrophages or dendritic cells (DCs). Increased turnover rates and elevated levels of circulating monocytes have been demonstrated in IBD.[6,7] Furthermore, monocytes have the ability to migrate to the inflamed mucosa and mediate inflammation, but the phenotype of these monocytes as well as the mechanisms underlying this relocation remains to be elucidated.[8-10] Currently, two main human monocyte subpopulations have been characterized. The CD14+CD16− cells have been shown to produce the regulatory cytokine IL-10 and are most commonly referred to as classical monocytes. The CD14loCD16+ subset is characterized by production of pro-inflammatory cytokines as well as high surface expression of inflammatory markers such as CD43.[11-13] However, a larger degree of heterogeneity among human monocyte populations with regards to their surface antigen expression has lately been observed.[14] Monocyte HLA-DR expression has been demonstrated to play an important role in conditions characterized by immune responses against bacterial agents.[15,16] Although the CD14+CD16− subset has been reported to express HLA-DR, the specific contribution of CD14+HLA-DRhi monocytes to intestinal inflammation has not been studied. Since it is well established that induction of colitis in human as well as in animal models requires the presence of bacteria, we set out to study CD14+HLA-DRhi monocytes in patients with chronic intestinal inflammation.[17]

Materials and Methods

Patients

In total, 51 IBD patients (UC=31; CD=20) were included in this study (Table 13). The patients were monitored during treatment with corticosteroids (n=16), the anti-TNF-α antibodies infliximab or adalimumab (Remicade® or Humira®; n=17), or Granulocyte/Monocyte apheresis (GMA; Adacolumn®; n=18). Four to six biopsies from affected rectum and sigmoideum were collected together with blood samples before the start of treatment, followed by weekly sampling for four consecutive weeks. Patients were assessed using the UC-DAI (UC) and Harvey-Bradshaw (HBI; CD) indices. Clinical remission was reviewed at week 11 post-treatment and defined as <3 for UC-DAI and <5 for HBI.[8,41] Fourteen controls without IBD were included in the study. All patients were enrolled through formal consent and the study was approved by the regional ethics committee.

Leukocyte Isolation and Activation

For flow cytometry studies, peripheral blood mononuclear cells (PBMC) were obtained from heparinised whole blood by incubation in hypotonic buffer (160 mM NH4Cl, mM Tris-HCl, pH=7.4). For PCR and CCL25 depletion experiments, PBMC were obtained from anti-coagulated healthy donor buffy coats by density gradient centrifugation using Ficoll-Paque (GE Healthcare). For PCR experiments, CD14+ monocytes were negatively isolated using Monocyte Isolation Kit II (Miltenyi Biotec). Monocytes were subsequently activated with LPS (lipopolysaccharide; Sigma) (200 ng/mL/106 cells) for 2 hrs (TNF-α PCR) or 6 hrs (PCR array) in RPMI medium (Hyclone) supplemented with 1% L-glutamine and 1% PEST (penicillin-streptomycin).

Flow Cytometry

PBMC were stained for flow cytometry analysis or sorting using combinations of the antibody conjugates described in Table 14. All stainings were carried out according to the instructions of the manufacturer for the respective antibody conjugate. An IgG2a-FITC (BD Biosciences) isotype control was used to define CCR9 positivity. Flow cytometry analyses and sorting experiments were carried out using a FACSAria cytometer and data was analysed using FACSDiva software (BD Biosciences).

PCR Experiments

Figure 4A:
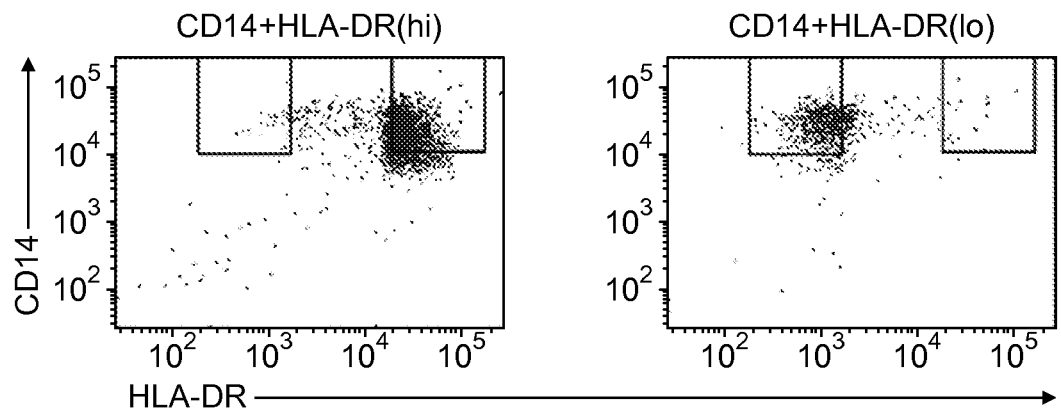
Figure 4B:
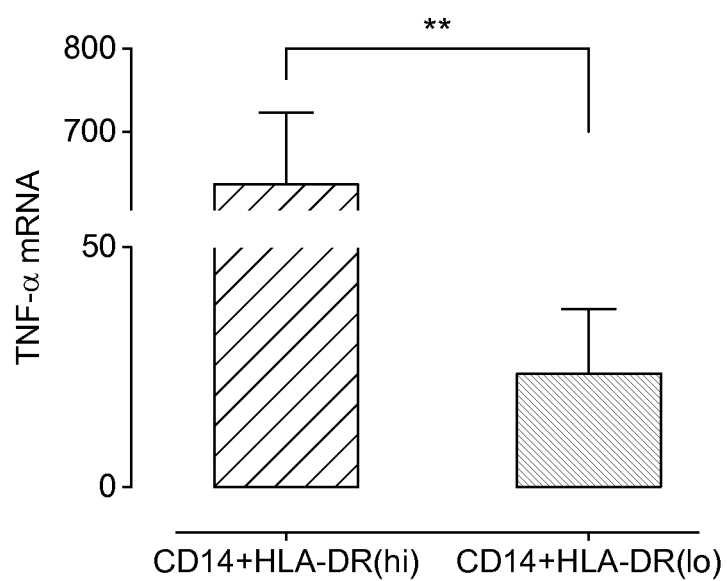

For TNF-α PCR experiments, RNA isolation was performed using TRIZOL reagent (Invitrogen). For the CCL25 experiment, intestinal biopsies were collected through flexible sigmoidoscopy from UC patients and immediately submerged in RNAlater (Ambion). RNA was subsequently isolated using RNeasy Mini Kit (Qiagen) according to the manufacturer's protocol. For the TNF-α and CCL25 experiments, 100 ng RNA per sample was included in a reverse transcriptase reaction using iScript cDNA synthesis kit (Bio-Rad). For PCR array analyses, RNA was isolated from sorted CD14+HLA-DRhi and CD14+HLA-DRlo populations using RNeasy Mini Kit (Qiagen). For each of the analyzed populations, equal amounts of RNA from three independent donors were pooled and cDNA was synthesized using RT2 First Strand Kit (SABiosciences) from 150 ng of RNA. Subsequently, cDNA was put into a RT2 qPCR Master Mix (SABiosciences) reaction and loaded onto a Human Inflammatory Response and Autoimmunity 96-well PCR array plate according to the instructions of the manufacturer (SABiosciences). In all PCR experiments, quantitative PCR was performed on an iCyclerIQ Optical System using 2×IQ SYBR Green supermix and iCycler IQ Optical System Software v3.1 (Bio-Rad) for data retrieval. In the TNF-α and CCL25 experiments, expression levels were normalized to RNA polymerase II using either the 2-ΔCt (TNF-α; FIG. 4B) or 2-ΔCt (CCL25) methods. Primers used were TNF-α forward (5'-CTCTCTCCCCTGGAAAGGAC-3', SEQ ID NO: 262); TNF-α reverse (5'-GCCAGAGGGCTGATTA-GAGA-3', SEQ ID NO: 263); CCL25 forward (5'-AAGGTTTTTGCAAAGCTCCA-3', SEQ ID NO: 264); CCL25 reverse (5'-TACTGCTGCTGATGGGATTG-3', SEQ ID NO: 265); RPII forward (5'-GCACCACGTC-CAATGACAT-3', SEQ ID NO: 266); RPII reverse (5'-GTGCGGCTGCTTCCATAA-3', SEQ ID NO: 267). For PCR array analyses, expression levels were normalized to the arithmetic mean expression of the B2M, HPRT1, RPL13A, GAPDH and ACTB housekeeping genes using the 2-ΔCt method.

CCL25 Depletion Assay

Biotinylated CCL25 (Almac Sciences) was bound to a solid support consisting of a streptavidin-sepharose matrix (GE Healthcare). PBMC from six healthy donors was perfused through the device and CCR9 expression was analysed before and after using flow cytometry.

Statistical Analyses

Figure 2A:
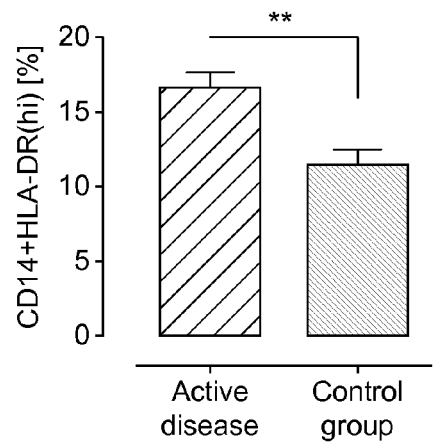
FIG. 2. CD14+HLA-DRhi monocytes are increased and correlate to disease activity in patients with ulcerative colitis and Crohn's disease.
Figure 2B:
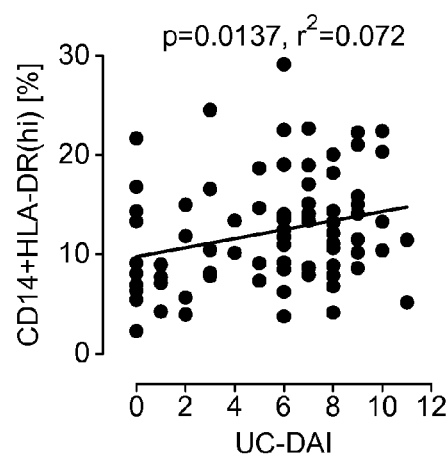
Figure 2C:
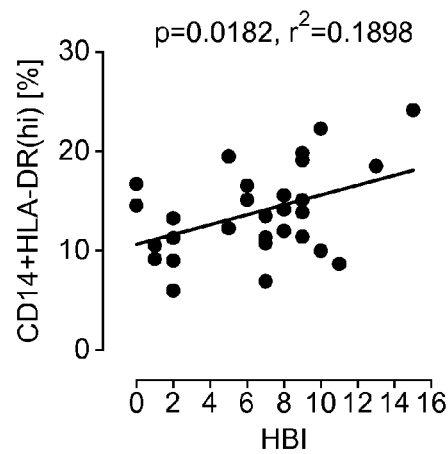

All group analyses were carried out using two-tailed dependent Student's t-test (FIGS. 2-4 and 6) or two-tailed independent Student's t-test (FIG. 3). Regression analyses were performed using ordinal regression test for non-parametric data (FIG. 2B-C). All calculations were carried out in GraphPad Prism v5 software (GraphPad Software, Inc.). Values of p≤0.05 were regarded as significant and depicted as follows: p≤0.05=*, p<0.01=, p≤0.001=*. In all figures, error bars represent ±SEM.

Ethical Considerations

The study was approved by the Stockholm Regional Ethical Review Board in Stockholm, Sweden. The ethical approval applies to all central from which patients were recruited (South Hospital, Stockholm, Sweden; Karolinska Hospital, Stockholm, Sweden; Danderyd Hospital, Stockholm, Sweden). All patients were enrolled through formal written consent.

Results

Figure 1:
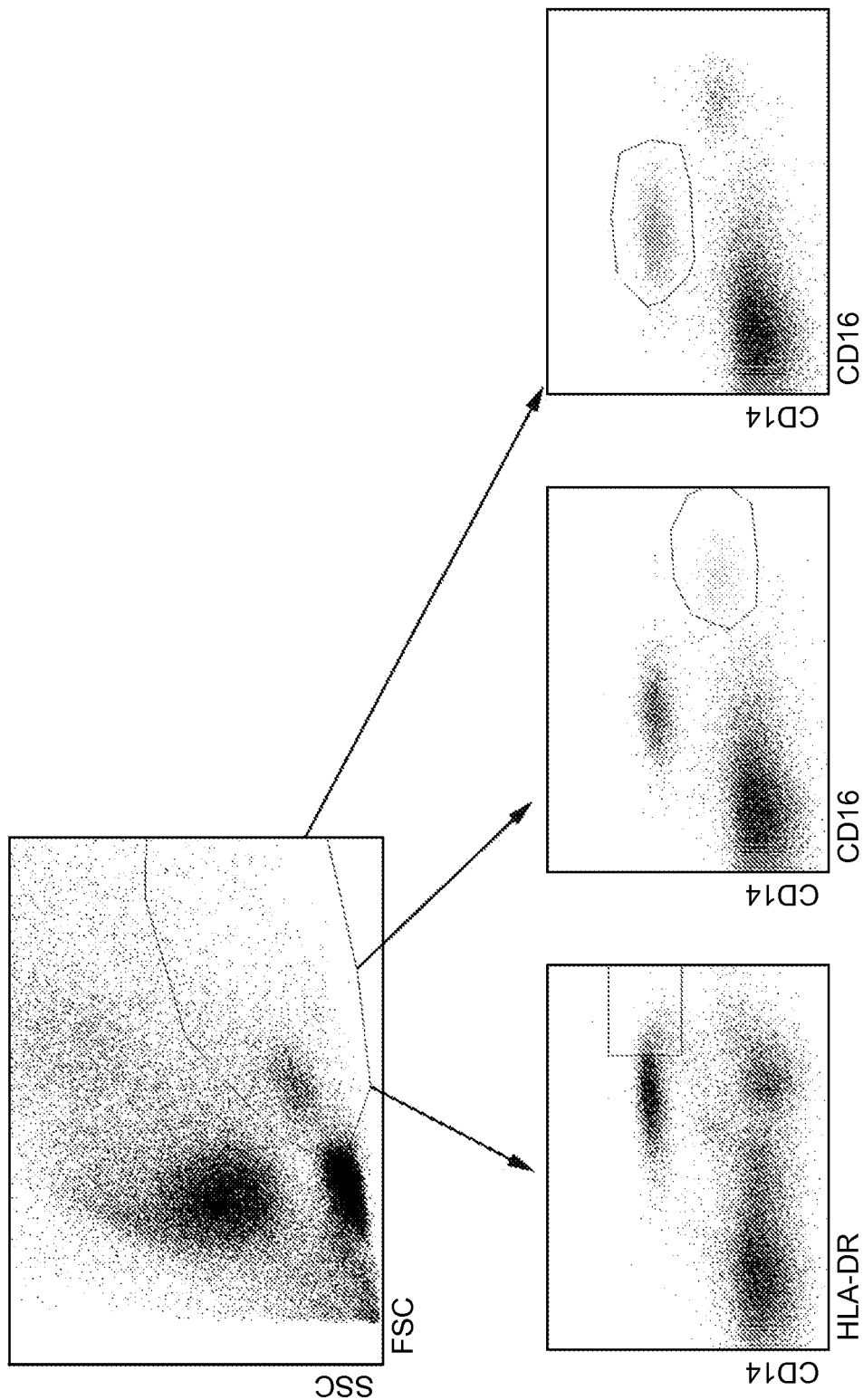

The Frequency of CD14+HLA-DRhi Monocytes Correlates to Clinical Disease Activity in Ulcerative Colitis and Crohn's Disease To investigate the role of CD14+HLA-DRhi monocytes in the IBD patients, we used flow cytometry to identify the population in peripheral blood (FIG. 1). When analyzing blood from patients and controls we found that active inflammation in the colon correlated to a significantly higher frequency of these monocytes compared with the control group (FIG. 2A, p=0.006).

In order to assess the correlation between monocyte levels and disease activity, we carried out regression analyses of CD14+HLA-DRhi frequency against two commonly used disease activity indices for the assessment of ulcerative colitis and Crohn's disease, respectively. We could observe a significant correlation with disease activity in both UC (UCDAI) (FIG. 2B; p=0.0137, r2=0.072) and CD (Harvey-Bradshaw) (FIG. 2C; p=0.0182, r2=0.1898). Thus, the frequency of circulating pro-inflammatory CD14+HLA-DRhi monocytes correlates with established disease activity indices of IBD.

Figure 3A:
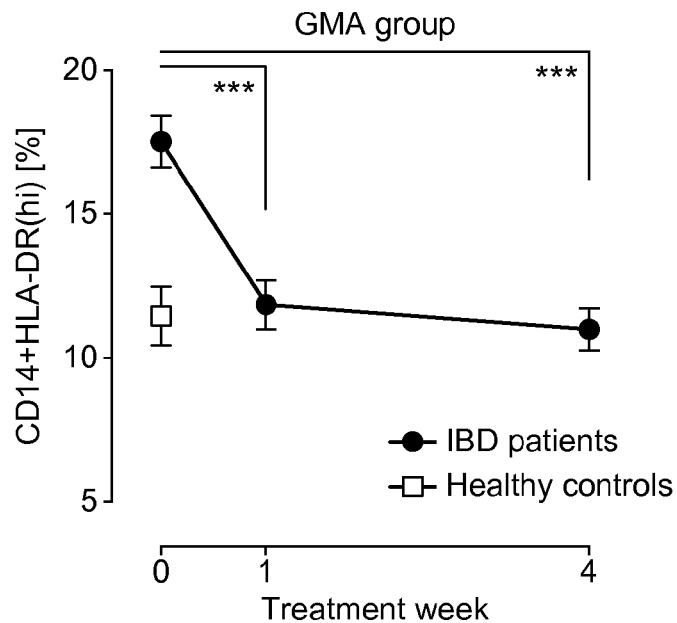
Figure 3B:
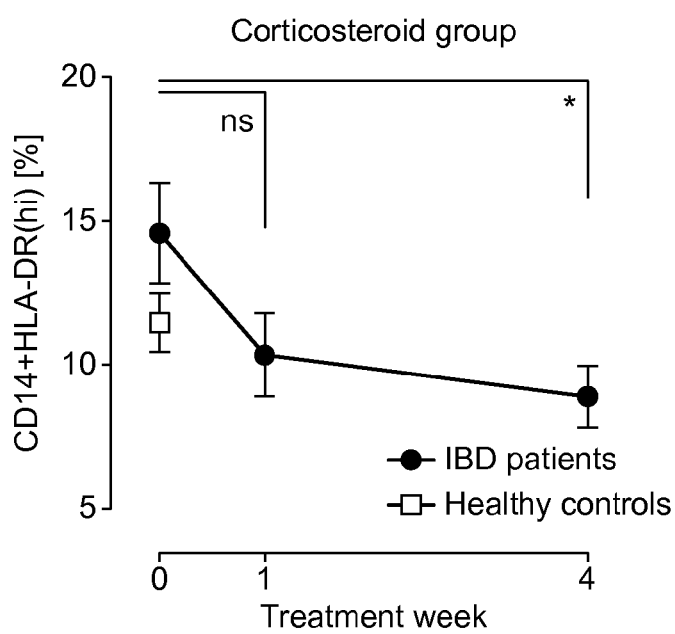
Figure 3C:
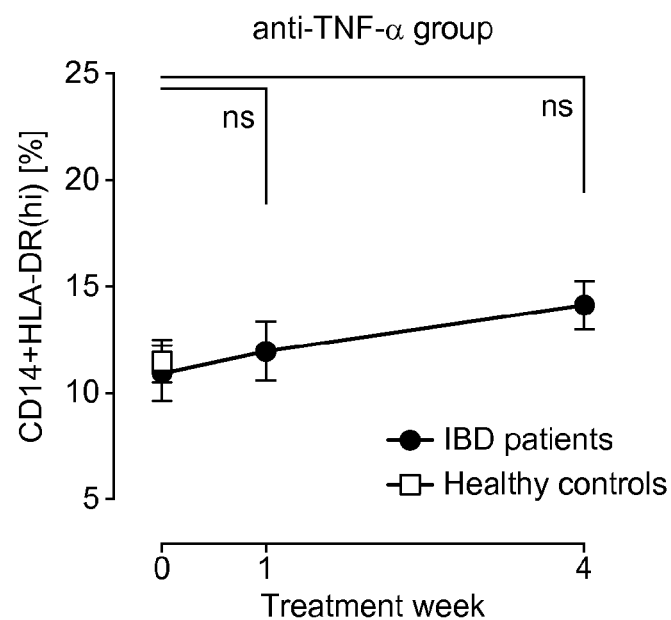

CD14+HLA-DRhi Monocytes are Potential Therapeutic Targets and Markers of Inflammation in Colitis Next, we investigated whether the CD14+HLA-DRhi population was affected by conventional IBD therapy. Patients with active intestinal inflammation who received either corticosteroids or anti-TNF-α antibodies (infliximab or adalimumab) were monitored for five consecutive weeks. A patient group treated with Granulocyte/Monocyte apheresis was included for comparison considering the selective removal of monocytes associated with Adacolumn®. (18) When plotting these treatment regimes separately, the patient group receiving GMA therapy accounted for the most prominent decrease (FIG. 3A). The monocyte population was also attenuated already after one week of therapy among corticosteroid patients. The suppression was maintained, reaching levels well below those of healthy control patients at week 4 (FIG. 3B, p<0.05). The decreased population of CD14+HLA-DRhi during treatment was not influenced by the diagnosis UC or CD, extension of the disease in the colon, concomitant azathioprine treatment or gender (data not shown). Interestingly, biological therapy with antibodies against TNF-α did not significantly affect the proportion of CD14+HLA-DRhi monocytes (FIG. 3C). Among these patients, CD14+HLADRhi never reached the reference level observed in the controls.

Figure 3D:
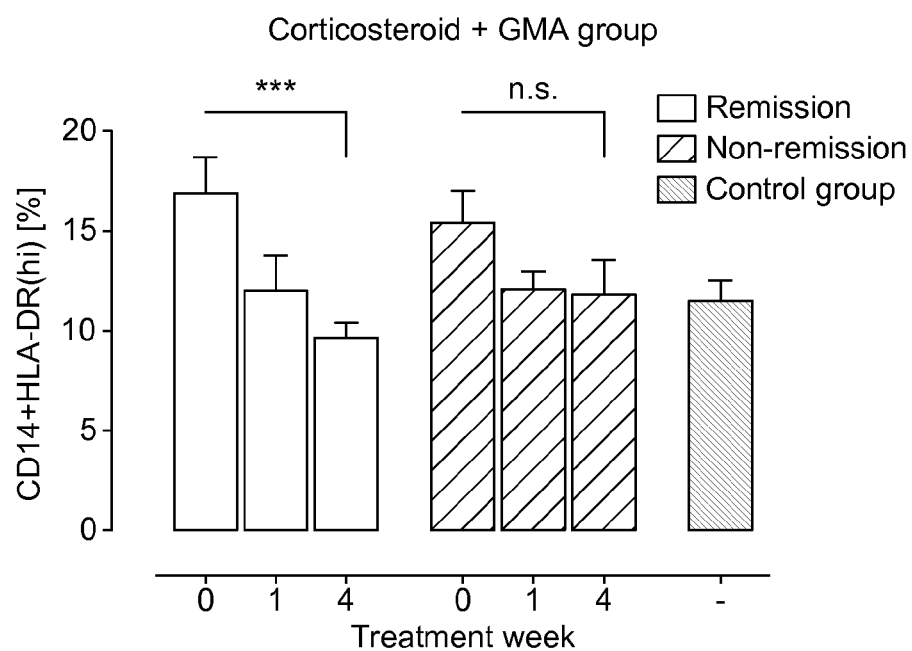

Lastly, we investigated whether the CD14+HLA-DRhi population was selectively affected in patients achieving long-term remission at week 11 post-treatment. Among patients receiving corticosteroids or GMA apheresis, the monocyte population was significantly decreased in those who later achieved or maintained remission. This was not observed among the non-remission patients (FIG. 3D).

CD14+HLA-DRhi Monocytes Produce High Levels of Inflammatory Mediators

Figure 4C:
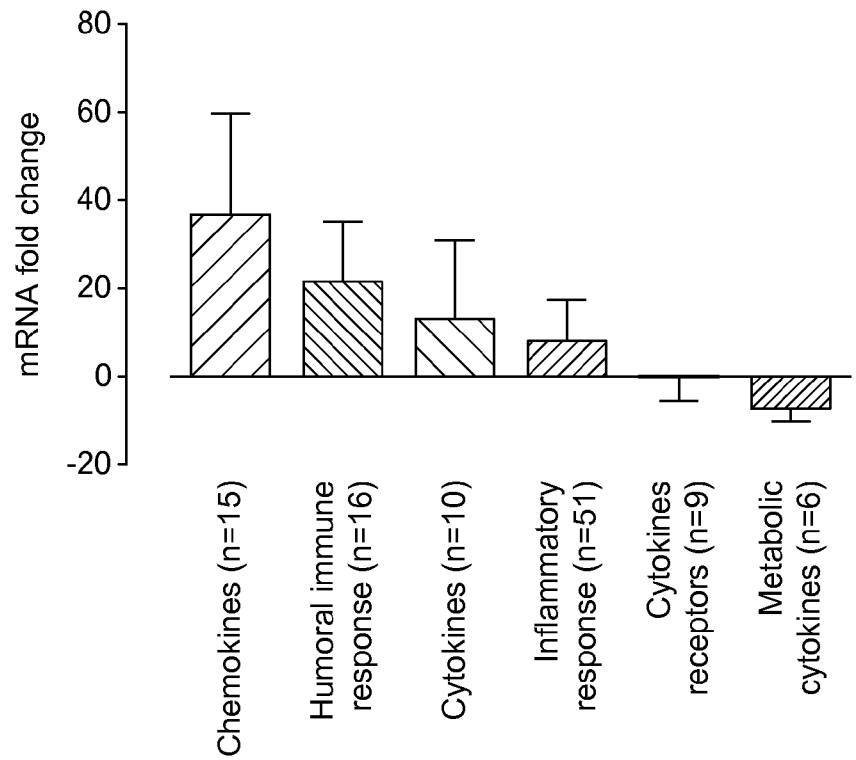
Figure 4D:
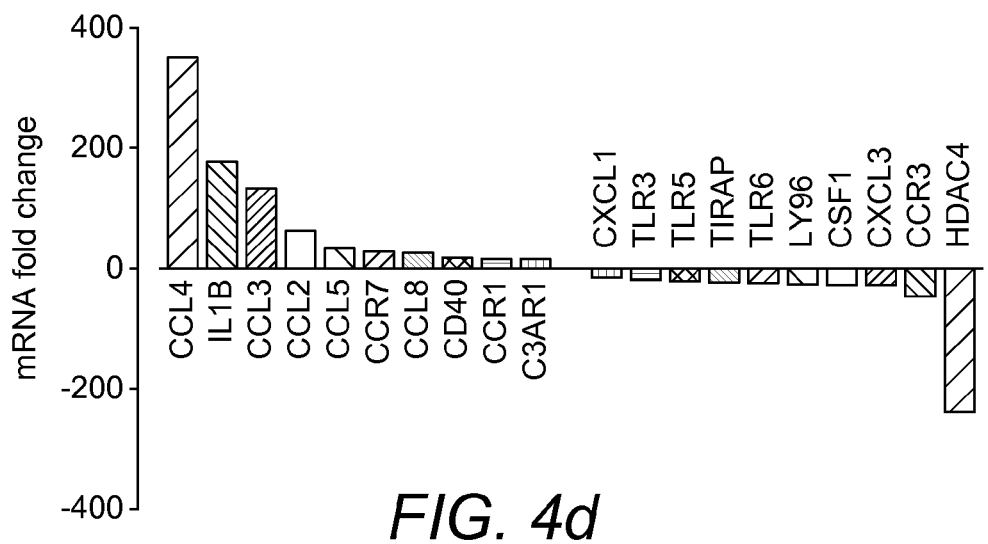

With the purpose of investigating the capacity of CD14+HLA-DRhi monocytes to produce inflammatory mediators, monocytes from healthy blood donors were cultured in the presence of lipopolysaccharide (LPS). The HLA-DRhi population and its CD14+HLA-DRlo counterpart were subsequently sorted with flow cytometry (FIG. 4A). The two cell populations were investigated with regards to the production of the proinflammatory cytokine TNF-α. Interestingly, the CD14+HLA-DRhi population produced 500-fold increased levels of TNF-α transcripts upon LPS-stimulation compared to the CD14+HLA-DRlo cells (FIG. 4B). Furthermore, PCR array analyses were carried out on sorted CD14+HLA-DRhi monocytes from three independent donors after activation with LPS in order to establish the distinctive phenotype of the population. In accordance with our hypothesis several gene transcripts described as being involved in monocyte-mediated immune responses were up-regulated in the CD14+HLA-DRhi monocytes. Increased gene expression was mainly found among chemotactic cytokines and genes involved in the humoral immune response (FIG. 4C). The most prominent fold change difference between the CD14+HLADR hi and the CD14+HLA-DRlo monocytes was observed for the chemotactic cytokine CCL4. The transcript with the most apparent down-regulation among HLA-DRhi monocytes was the HDAC4 gene that encodes a histone deacetylase that functions as a transcriptional repressor.[19] Together, this data shows that CD14+HLA-DR$^{hi}$ monocytes have strong proinflammatory potential.

CD14+HLA-DRhi Monocytes Express the Gut-Homing Chemokine Receptor CCR9

Figure 5A:
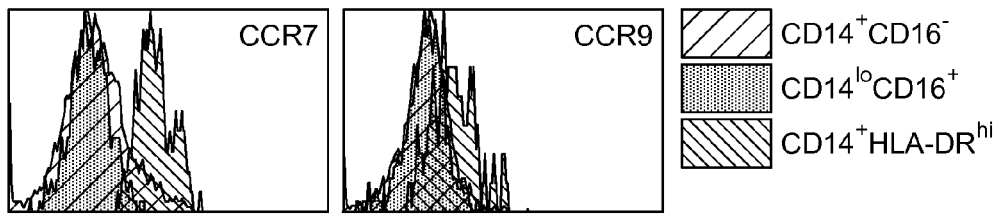
Figure 5B:
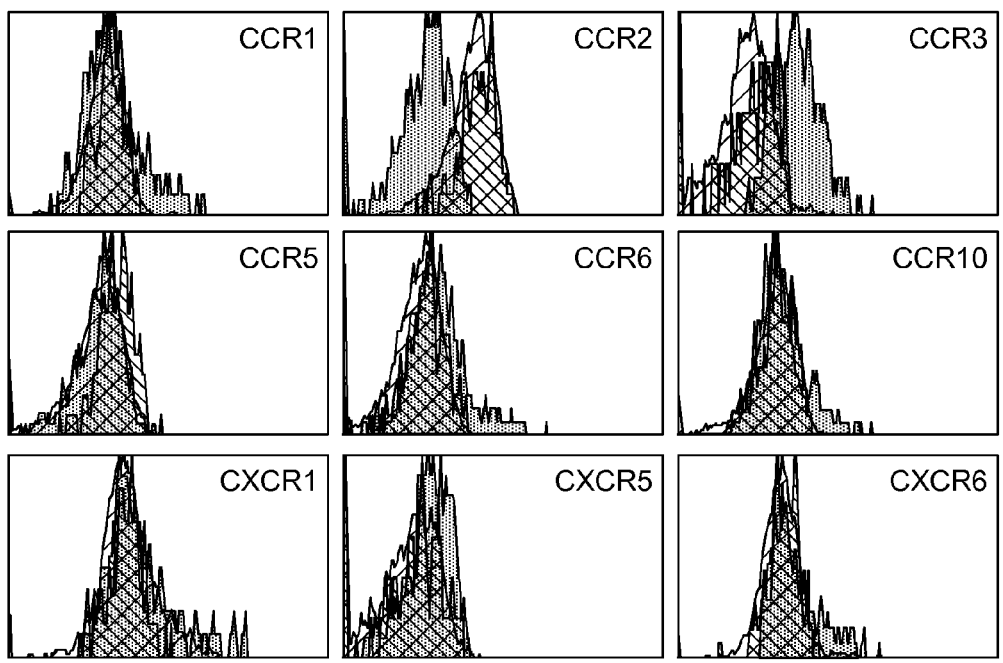

Next, we studied the surface expression of various chemokine receptors on CD14+HLA-DRhi monocytes in relation to the CD14+CD16− and CD14loCD16+ subsets. Although we could observe significant overlap between many of these markers in terms of their expression in the respective subsets, the CD14+HLA-DRhi population was clearly distinguished by its expression of CCR7 and CCR9 (FIG. 5A). CCR7 is mainly described as a lymph-node homing receptor for dendritic cells and T helper cells, and has previously not been reported to be expressed on circulating monocytes.[20] CCR9 has been shown to be important in lymphocyte homing to the gut through interactions with its ligand CCL25, expressed in the intestinal mucosa.[21, 22] Although CCR9-CCL25 interactions have been well characterized in T helper cells, their role in monocytes is unclear. The general CD14+ monocyte population exhibited significantly higher CCR9 expression compared to CD4+ T lymphocytes, which together with CD8+ T lymphocytes have been described as the main CCR9 expressing cell types ($p<0.05$).[23] When comparing CCR9 expression in CD14+HLA-DRhi with CD14loCD16+ and CD14+CD16− monocytes, the HLA-DRhi subset displayed significantly increased levels (FIG. 5A). In contrast, the expression of CCR2, a chemokine receptor responsible for general monocyte migration, was not increased on the HLA-DRhi monocytes indicating that gut-homing phenotype constitutes a specific feature of the monocytes rather than reflecting general immunological activation (FIG. 5B).[24] We also analyzed colonic mucosal tissue biopsies with real-time PCR and found that the CCR9 ligand, CCL25/TECK, was expressed in the colon. To establish a functional interaction between CCL25 and CCR9, we carried out depletion experiments by perfusing peripheral blood cells through a solid support containing CCL25-coated sepharose beads. The frequency of CCR9-positive CD14+HLA-DRhi monocytes was significantly reduced after encounter with the CCL25-coated sepharose beads, showing that CCR9 on CD14+HLA-DRhi monocytes could bind CCL25 and be removed from the blood ($p<0.05$; FIG. 6). In conclusion, pro-inflammatory CD14+HLA-DRhi monocytes express high levels of the gut-homing chemokine receptor CCR9 which directs them to the site of mucosal inflammation.

Discussion

In this study, we identify CCR9-expressing CD14+HLA-DRhi blood monocytes as an important player in intestinal inflammation. The expression of HLA-DR on monocytes is vital to the inflammatory response and has been shown to determine the efficacy of antigen presentation to T helper cells. (25, 26) Monocytes with high expression of HLA-DR have also been shown to infiltrate the joints of patients with rheumatoid arthritis, an inflammatory disease successfully treated with TNF-α antibodies.[27] In addition, carrying the class II HLA-DRB1*0103 allele correlates with an increased risk for developing ulcerative colitis.[28] Several studies have suggested that monocytes per se are targeted by conventional IBD therapy.[6, 29, 30] Our results suggest that specific down-regulation of the HLA-DRhi subpopulation may be an important mechanism behind resolution of the inflammation. In this study, patients treated with Granulocyte/Monocyte apheresis were added for comparison since Adacolumn® is the only treatment specifically targeting circulating monocytes. These cells are removed through Fcγ receptor binding to the cellulose acetate beads in the column, leaving circulating T-cells unaffected.[18] Corticosteroid therapy mediates a decrease in the number of circulating CD14+HLA-DRhi monocytes that is comparable to GMA (FIG. 3B). This suppression seems to be important for the induction of remission, since significant decrease of CD14+HLA-DRhi monocytes is only observed in the patients achieving long-term remission (FIG. 3D). Interestingly, patients subjected to biological treatment did not display a decrease of pro-inflammatory monocytes (FIG. 3C). We speculate that by removing TNF-α, one of the main products of these monocytes, autocrine feed-back mechanisms leading to cellular activation might be induced. The observation underscores the difference in mode of action between anti-TNF-α antibodies and corticosteroids and should be further investigated since anti-TNF-α failure may partly depend on the monocytes' production of additional pro-inflammatory chemokines, cytokines and integrin receptors counterbalancing TNF-α suppression.

Classically, leukocyte populations have been defined through their capability to produce inflammatory mediators such as cytokines and chemokines. In order to gain a functional understanding of how CD14+HLA-DRhi monocytes mediate inflammation, we investigated their pro-inflammatory potential at the mRNA level compared to their HLA-DRlo-expressing counterpart. In this context, the HLA-DRhi subset produced markedly elevated levels of gene transcripts associated with activation and pro-inflammatory phenotype. The population displayed a 500-fold increase of TNF-α transcript levels, which establishes the HLA-DRhi subset as one of the most important producers of this cytokine. Other genes were also investigated by PCR array analysis, revealing the highest up-regulation in CCL4, CCL3 and IL-1β, all cytokines previously described to be involved in the recruitment of inflammatory cells to the intestinal mucosa in IBD (FIG. 4D).[31-35] The most prominent difference was observed in the CCL4/MIP-1 gene, with up-regulated transcript levels of more than 300-fold. The inflammatory role of CCL4 was reported by Bystry and colleagues; activated T helper cells were demonstrated to efficiently migrate towards a CCL4 tissue gradient through CCR5 interaction.[31] Thus, our finding that CCL4 transcripts were produced in high levels by CD14+HLA-DR$^{hi}$ monocytes supports their inflammatory potential.[36] The transcript with the most apparent down-regulation in HLA-DRhi monocytes was the HDAC4 gene that encodes a histone deacetylase that functions as a transcriptional repressor.[19] Together, these data indicate that CD14+HLA-DRhi is a transcriptionally active subset that readily expresses genes important for mediating mucosal immune responses.

Figure 5C:
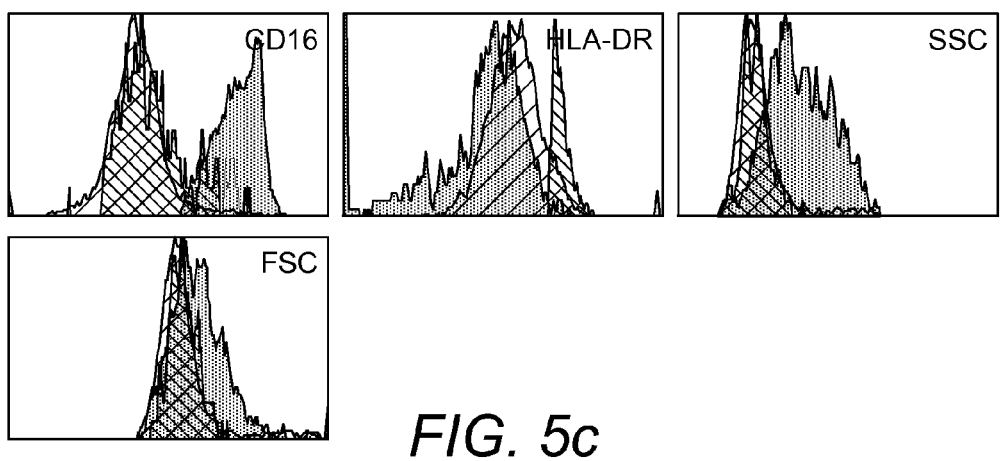

On the surface level, CD14+HLA-DRhi monocytes only partially express CD16, suggesting that the population constitutes a separate subset that is not included in its entirety when defining pro-inflammatory monocytes through their expression of CD14lo CD16+ (FIG. 5C). The population is further defined by its expression of CCR7 and the gut-homing receptor CCR9, which clearly distinguishes HLA-DRhi monocytes from the CD14+CD16− and CD14loCD16+ subsets (FIG. 5).

In the context of intestinal inflammation, interactions between CCR9-expressing T cells and CCL25 (TECK) expressed in the gut epithelium have been implicated as an important mechanism for recruiting circulating lymphocytes to the intestinal mucosa.[21] However, whether this mechanism also applies for the extensive infiltration of blood monocytes to the intestinal mucosa observed during inflammation has never been studied.[37] It was recently shown that CCR9-expressing monocytes are increased in peripheral blood of patients with rheumatoid arthritis. However, the role of these cells in IBD remains unclear. In accordance with the results from this study, we show that the CD14+ CD16– and CD14loCD16+ subsets express similar levels of CCR9.[38] Those levels were notably superseded by the CCR9 expression on CD14+HLA-DRhi monocytes (FIG. 5A). Surprisingly, this expression was considerably higher than that observed on T cells, which is considered to be the main CCR9– carrying cell type.[23] In contrast, the expression of CCR2, another chemokine receptor important for monocyte relocation in several disease groups, was not increased on HLA-DRhi monocytes (FIG. 5B).[24] This suggests that the specific increase in CCR9 expression among CD14+HLA-DRhi may reflect a gut-specific phenotype, rather than a generally activated subset. The ligand for CCR9, CCL25, was found to be expressed in mucosal tissue by QT-PCR analysis, which is supported by other reports identifying CCL25 in the colon.[22, 39] In conclusion, these data suggest that monocytes in general and CD14+HLA-DRhi in particular possess the ability to relocate to the intestinal mucosa through CCR9-CCL25 interactions.

T cells have been shown to acquire their CCR9 expression through retinoic-acid dependent imprinting by mesenterial lymph node dendritic cells.[40] The issue of whether CCR9 expression on monocytes is acquired through similar mechanisms seems controversial, especially since blood monocytes are not known to traffic lymph nodes to the same extent as T cells. Here, we show that CD14+HLA-DRhi monocytes are defined by their high expression of CCR7, a marker mainly described as a lymph-node homing receptor for dendritic cells and T helper cells (FIG. 5A).[20] Therefore, it is tempting to speculate that CCR7-expressing CD14+HLA-DRhi monocytes traffic the lymph nodes to a higher extent than has previously been known, and that CCR9 imprinting in these monocytes may occur through mechanisms similar to those reported in T cells. Being beyond the scope of this study, the mechanisms behind CCR9 induction in monocytes, as well as the functional role of their CCR7 expression, need to be addressed in the future.

In this study, we have shown that CD14+HLA-DRhi blood monocytes are increased in patients with active intestinal inflammation, and correlate with disease severity as defined by the UC-DAI and HBI disease activity indices. Furthermore, these monocytes produce major amounts of inflammatory mediators and express high levels of the gut-homing receptor CCR9. In summary, these findings indicate that CD14+HLA-DRhi blood monocytes play an important role in IBD and that future studies evaluating these monocytes as specific targets for IBD therapy are highly motivated.

REFERENCES

1. Bouma G, Strober W. The immunological and genetic basis of inflammatory bowel disease. Nat Rev Immunol. 2003; 3:521-533
2. Desreumaux P, Brandt E, Gambiez L, et al. Distinct cytokine patterns in early and chronic ileal lesions of Crohn's disease. Gastroenterology. 1997; 113:118-126
3. Hugot J P, Laurent-Puig P, Gower-Rousseau C, et al. Mapping of a susceptibility locus for Crohn's disease on chromosome 16. Nature. 1996; 379:821-823
4. Hugot J P, Chamaillard M, Zouali H, et al. Association of NOD2 leucine-rich repeat variants with susceptibility to Crohn's disease. Nature. 2001; 411:599-603
5. Arseneau K O, Tamagawa H, Pizarro T T, et al. Innate and adaptive immune responses related to IBD pathogenesis. Curr Gastroenterol Rep. 2007; 9:508-512
6. Hanai H, Iida T, Takeuchi K, et al. Adsorptive depletion of elevated proinflammatory CD14+CD16+DR++ monocytes in patients with inflammatory bowel disease. Am J Gastroenterol. 2008; 103:1210-1216
7. Mahida Y R, Wu K C, Jewell D P. Respiratory burst activity of intestinal macrophages in normal and inflammatory bowel disease. Gut. 1989; 30:1362-1370
8. D'Haens G, Sandborn W J, Feagan B G, et al. A review of activity indices and efficacy end points for clinical trials of medical therapy in adults with ulcerative colitis. Gastroenterology. 2007; 132:763-786
9. Rugtveit J, Brandtzaeg P, Halstensen T S, et al. Increased macrophage subset in inflammatory bowel disease: apparent recruitment from peripheral blood monocytes. Gut. 1994; 35:669-674
10. Smythies L E, Maheshwari A, Clements R, et al. Mucosal IL-8 and TGF-beta recruit blood monocytes: evidence for cross-talk between the lamina propria stroma and myeloid cells. J Leukoc Biol. 2006; 80:492-499
11. Feng G, Lu J, Gross J. Generation of transgenic mice. Methods Mol. Med. 2004; 99:255-267
12. Frankenberger M, Sternsdorf T, Pechumer H, et al. Differential cytokine expression in human blood monocyte subpopulations: a polymerase chain reaction analysis. Blood. 1996; 87:373-377
13. Belge K U, Dayyani F, Horelt A, et al. The proinflammatory CD14+CD16+DR++ monocytes are a major source of TNF. J. Immunol. 2002; 168:3536-3542
14. Tallone T, Turconi G, Soldati G, et al. Heterogeneity of human monocytes: an optimized four-color flow cytometry protocol for analysis of monocyte subsets. J Cardiovasc Transl Res. 2011; 4:211-219
15. Genel F, Atlihan F, Ozsu E, et al. Monocyte HLA-DR expression as predictor of poor outcome in neonates with late onset neonatal sepsis. J. Infect. 2010; 60:224-228
16. Fu Q, Cui N, Yu W, et al. Percentages of CD4+ T regulatory cells and HLA-DR expressing monocytes in severe intra-abdominal infections. Scand J Infect Dis. 2010; 42:475-478
17. Blumberg R S, Saubermann L J, Strober W. Animal models of mucosal inflammation and their relation to human inflammatory bowel disease. Curr Opin Immunol. 1999; 11:648-656
18. Saniabadi A R, Hanai H, Takeuchi K, et al. Adacolumn, an adsorptive carrier based granulocyte and monocyte apheresis device for the treatment of inflammatory and refractory diseases associated with leukocytes. Ther Apher Dial. 2003; 7:48-59
19. Bertos N R, Wang A H, Yang X J. Class II histone deacetylases: structure, function, and regulation. Biochem Cell Biol. 2001; 79:243-252
20. Forster R, Davalos-Misslitz A C, Rot A. CCR7 and its ligands: balancing immunity and tolerance. Nat Rev Immunol. 2008; 8:362-371
21. Johansson-Lindbom B, Agace W W. Generation of gut-homing T cells and their localization to the small intestinal mucosa. Immunol Rev. 2007; 215:226-242
22. Wurbel M A, Philippe J M, Nguyen C, et al. The chemokine TECK is expressed by thymic and intestinal epithelial cells and attracts double- and single-positive thymocytes expressing the TECK receptor CCR9. Eur J. Immunol. 2000; 30:262-271
23. Zabel B A, Agace W W, Campbell J J, et al. Human G protein-coupled receptor GPR-9-6/CC chemokine receptor 9 is selectively expressed on intestinal homing T lymphocytes, mucosal lymphocytes, and thymocytes and 23. is required for thymus-expressed chemokine-mediated chemotaxis. J Exp Med. 1999; 190:1241-1256
24. Deshmane S L, Kremlev S, Amini S, et al. Monocyte chemoattractant protein-1 (MCP-1): an overview. J Interferon Cytokine Res. 2009; 29:313-326
25. Don Porto Carero A, Hoet P H, Nemery B, et al. Increased HLA-DR expression after exposure of human monocytic cells to air particulates. Clin Exp Allergy. 2002; 32:296-300
26. Portillo G, Turner M, Chantry D, et al. Effect of cytokines on HLA-DR and IL-1 production by a monocytic tumour, THP-1. Immunology. 1989; 66:170-175
27. Ridley M G, Kingsley G, Pitzalis C, et al. Monocyte activation in rheumatoid arthritis: evidence for in situ activation and differentiation in joints. Br J Rheumatol. 1990; 29:84-88
28. Anderson C A, Massey D C, Barrett J C, et al. Investigation of Crohn's disease risk loci in ulcerative colitis further defines their molecular relationship. Gastroenterology. 2009; 136:523-529 e523
29. Fingerle-Rowson G, Angstwurm M, Andreesen R, et al. Selective depletion of CD14+CD16+ monocytes by glucocorticoid therapy. Clin Exp Immunol. 1998; 112:501-506
30. Koch S, Kucharzik T, Heidemann J, et al. Investigating the role of proinflammatory CD16+ monocytes in the pathogenesis of inflammatory bowel disease. Clin Exp Immunol. 161:332-341
31. Bystry R S, Aluvihare V, Welch K A, et al. B cells and professional APCs recruit regulatory T cells via CCL4. Nat. Immunol. 2001; 2:1126-1132
32. Ottonello L, Montecucco F, Bertolotto M, et al. CCL3 (MIP-1alpha) induces in vitro migration of GM-CSF-primed human neutrophils via CCR5-dependent activation of ERK 1/2. Cell Signal. 2005; 17:355-363
33. Ramos C D, Canetti C, Souto J T, et al. MIP-1alpha [CCL3] acting on the CCR1 receptor mediates neutrophil migration in immune inflammation via sequential release of TNF-alpha and LTB4. J Leukoc Biol. 2005; 78:167-177
34. Uguccioni M, Gionchetti P, Robbiani D F, et al. Increased expression of IP-10, IL-8, MCP-1, and MCP-3 in ulcerative colitis. Am J Pathol. 1999; 155:331-336
35. Grimm M C, Elsbury S K, Pavli P, et al. Enhanced expression and production of monocyte chemoattractant protein-1 in inflammatory bowel disease mucosa. J Leukoc Biol. 1996; 59:804-812
36. Zhou L, Braat H, Faber K N, et al. Monocytes and their pathophysiological role in Crohn's disease. Cell Mol Life Sci. 2009; 66:192-202
37. Grimm M C, Pullman W E, Bennett G M, et al. Direct evidence of monocyte recruitment to inflammatory bowel disease mucosa. J Gastroenterol Hepatol. 1995; 10:387-395
38. Schmutz C, Cartwright A, Williams H, et al. Monocytes/macrophages express chemokine receptor CCR9 in rheumatoid arthritis and CCL25 stimulates their differentiation. Arthritis Res Ther. 2010; 12:R161
39. Walters M, Berahovich R, Wang Y, et al. Presence of CCR9 and its ligand CCL25/TECK in the colon: Scientific rationale for the use of CCR9 small molecule antagonist CCX282-B in colonic disorders [abstract]. Gut2008: OP184
40. Iwata M, Hirakiyama A, Eshima Y, et al. Retinoic acid imprints gut-homing specificity on T cells. Immunity. 2004; 21:527-538
41. Vermeire S, Schreiber S, Sandborn W J, et al. Correlation between the Crohn's Disease Activity and Harvey-Bradshaw Indices in Assessing Crohn's Disease Severity. Clin Gastroenterol Hepatol.

Tables

TABLE 13

Patient demography.

| | | |
|---|---|---|
| Gender | Male | 32 |
| | Female | 19 |
| Age mean | | 37.9 |
| Diagnosis | Ulcerative colitis | 31 |
| | Crohn's disease | 20 |
| Extension | Extensive | 25 |
| | Left-sided | 19 |
| | Proctitis | 5 |
| | Ileocekal | 2 |
| Intervention | Corticosteroids[1,2] | 16 |
| | Anti-TNF-$\alpha$[3,5] | 17 |
| | GMA apheresis[4,5] | 18 |
| Azathioprine | Yes | 21 |
| | No | 30 |

[1]Fifteen patients were introduced to 20-45 mg prednisone followed by tapering of 5 mg weekly.
[2]One patient received topical corticosteroids for ulcerative proctosigmoiditis.
[3]Anti-TNF-$\alpha$ treatment was administered either as infusions of 5 mg/kg infliximab week 0, 2 and 6 or subcutaneous injections of 80 mg Adalimumab week 0 followed by 40 mg every other week.
[4]In the GMA apheresis group, each patient received a total of 5-8 Adacolumn® leukocytapheresis session 1-2 times weekly.
[5]Some patients were receiving baseline corticosteroid medication

TABLE 14

Flow cytometry antibodies used in the study

| Marker | Conjugate | Clone | Manufacturer |
|---|---|---|---|
| CD4 | Pacific Blue | RPA-T4 | BD |
| CD14 | APC | M5E2 | BD |
| CD16 | PE-Cy7 | 3G8 | BD |
| HLA-DR | PerCP | L243 | BD |
| CCR1 | Alexa Fluor 647 | TG4 | Biolegend |
| CCR2 | PerCP-Cy5.5 | TG5 | Biolegend |
| CCR3 | PE | 5E8 | Biolegend |
| CCR5 | PE | HM-CCR5 | Biolegend |
| CCR6 | PerCP-Cy5.5 | 11A9 | BD |
| CCR7 | PerCP-Cy5.5 | TG8 | Biolegend |
| CCR9 | APC | 112509 | R&D Systems |
| CCR10 | PE | 314305 | R&D Systems |
| CXCR1 | APC | 8F1 | Biolegend |
| CXCR5 | PerCP-Cy5.5 | TG2 | Biolegend |
| CXCR6 | PE | 56811 | R&D Systems |

Example 2

Affinity of Blood Cells to CCL25

Materials and Methods

Isolation of peripheral blood leukocytes. Heparinized peripheral blood from healthy blood donors or IBD patients was fixed with 4% paraformaldehyde for 4 minutes, hemolyzed for 15 minutes with a 0.83% ammonium chloride solution and washed twice in FACS buffer to obtain a suspension of blood leukocytes.

Chemokines. The leukocytes were incubated for 30 min in the dark at 4° C. with the following biotinylated and Alexa647 Fluor® labeled chemokines: CCL25 (in concentrations of 0.1 ng/µL, 0.5 ng/µL and 5 ng/µL). The cells were then washed with FACS-buffer and analyzed by flow cytometry. All chemokines used in the Examples were provided by Almac Sciences Scotland Ltd, Edinburgh, Scotland.

Flow cytometry assay. The flow cytometry assay was performed on a two laser FACS Calibur cytometer (BD Immunocytometry systems, San José, Ca, USA). Ten thousand cells were counted and analysed in each sample. For data analyses, Cell Quest Pro software from Becton Dickinson was used.

In the experiment with biotinylated CCL25 it was found that neither T-cells (CD4+ lymphocytes; CD8+ lymphocytes) nor monocytes (CD14+ monocytes) from the peripheral blood of a healthy donor (FIGS. 7a, 7b and 7c) bound to the biotinylated chemokine. In contrast, about 80% of the CD8+ lymphocytes and about 90% of the CD4+ lymphocytes and the monocytes from a patient with Crohn's disease bound to CCL25 (FIGS. 8a, 8b and 8c).

Example 3

Preparation of a Chemokine Column for Blood Cell Apheresis

To streptavidin cross-linked agarose (ProZyme, San Leandro, Calif., U.S.A.) beads in the range from 75 µm to 300 g suspended (200 ml, ~50%, v/v) in an aqueous solution of 25 mM sodium phosphate (pH 7.0) and 150 mM NaCl was added a solution of 75 µg biotinylated CCL25 (Almac Sciences) in the same buffer at 22° C. and slowly stirred by hand for 3 min. After standing for another 20 min, the support was filtered off, washed thrice with neutral aqueous sodium phosphate/sodium chloride and filled into a glass column (i.d. 25 mm, length 12 cm).

Example 4

Separation of Monocytes from Peripheral Blood of a Healthy Donor with the Chemokine Column of Example 3

Heparinized peripheral blood from a healthy male donor was analyzed by flow cytometry for CD4+ lymphocytes, CD8+ lymphocytes and CD14 monocytes. 100 ml of the blood was filtered through the column at a rate of about 8 ml per min and washed with FACS buffer. The filtered blood was analyzed for the same cells. It was found that about 95% of the monocytes had been retained by the column whereas more than 90% each of CD4+ and CD8+ lymphocytes had been recovered.

Example 5

Tailored Leukapheresis

Column Design and Properties
Introduction
Apheresis is an established treatment used for depletion of blood components, such as antibodies, low-density lipoproteins (LDL) and blood cells. Leukapheresis is the apheresis treatment used for removal of white blood cells, leukocytes. The patient is connected to an extracorporeal blood circulating system; the blood is drawn from a vein in one arm, passed through a column device and returned into the other arm of the patient. Side effects of leukapheresis treatments are varying from mild events like headache, dizziness, hypotension, palpitation and flush seen in 0.1 to 5% of treated patients.
The Column
The column is intended to be used as a leukapheresis treatment for inflammatory bowel disease, including Crohn's disease (CD) and ulcerative cholitis (UC). It will specifically remove CD14, HLA-DR, CCR9 and/or CCR7-expressing gut-homing leukocytes through the use of suitable binding reagents contained on a resin, exploiting the CD14, HLA-DR, CCR9 and/or CCR7-binding reagent interaction. The column consists of three combined components, the plastic house, the streptavidin (SA) Sepharose™ BigBeads matrix and binding reagent bound to the matrix. The treatment is conducted using the same techniques as a standard apheresis procedure.
The Plastic House (FIG. 9)
The plastic house, designed to keep a continuous blood flow through the matrix, consists of a transparent body and red-coloured top. The top has a distribution plate (2) at the inflow site (1) to spread the blood evenly over the entire matrix area. The plate is the first safety barrier preventing larger particles flowing through the column and into the patient. Safety filter units (3 and 4) are placed at the inflow (1) and outflow (5) sites of the plastic housing. The safety filter unit contains three filters designed to be a robust barrier and stop all particles larger than blood cells passing through the column. The plastic housing design is shown in FIG. 9. The design with safety filters (3 and 4) at both ends of the column device will minimize the risk of leakage of particles into the patient, including in the event that the device is placed up side down with the blood flow in the opposite direction to that anticipated.
Streptavidin Sepharose™ BigBeads
The second component in the device is the affinity matrix called streptavidin Sepharose™ BigBeads (Sepharose™ GE Healthcare, Sweden). Sepharose™ is a cross linked, beaded-form of agarose, which is a polysaccharide extracted from seaweed. Sepharose™ and agarose are commonly used as column matrices in biomedical affinity techniques. It is chosen for its optimal distribution capacity and can provide a large available area for affinity binding.
bTECK
Coupled to the matrix is the third component of the device, in this example the bTECK. This bTECK peptide is a synthetic, engineered version of the human chemokine TECK, which is truncated and biotinylated, but retains its binding activity to the TECK receptor CCR9. By biotinylating the engineered TECK, it is able to bind to the streptavidin molecules in the Sepharose™ matrix. The biotin-streptavidin binding is known be one of the strongest biological interactions with a Kd in the order of 4×10-14 M. The calculated ratio of streptavidin:biotin binding sites in the column is 10:1. Therefore, the coupling between the matrix and bTECK will be immediate, minimising the risk of bTECK decoupling from the matrix.
The Apheresis System
To conduct the leukapheresis the following components are needed; the column, tubing system, and a 4008 ADS pump (Fresenius Medical Care).
The Circuit
The system is illustrated in FIG. 10. The patient (1) is connected to the extracorporeal circuit via sterile Venflon needles to veins in the right and the left arms. A saline bag (3) is also connected and the saline solution is pumped with an ACD pump (2). Blood is drawn from one arm of the patient through the sterile tubing system by the blood pump (4) and passed through the column (6) and back to the patient. The tubing system is connected to the column via standard dialysis luer-lock couplings. The couplings on the column are colour-coded for correct assembly; red tubing for inflow to the red column top and blue tubing for outflow back to the patient. An air detector (8) is present. Inlet pressure (5) and Pven sensors (7) are employed to monitor the pressure in the circuit.

The 4008 ADS Pump

An apheresis pump, from Fresenius Medical Care, monitors the patient's inflow and outflow, the pressure in the extracorporeal circulation and can discriminate air by a bubble catcher and air detector. A clot catcher filter is placed inside the bubble catcher. The pump also has an optical detector to distinguish between light, e.g. saline solution or air present in the tubing system and dark e.g. blood present in the tubing system.

A schematic diagram of the pump, showing the air detector and optical filter is shown in FIG. 11. If the pump system detects air bubbles and optical fluctuations or if extracorporeal pressure values are out of the set range, then the pump stops immediately and a visual/audible alarm are emitted.

LEGEND FOR FIG. 11

1. Monitor
2. Holder for waste bag
3. Modules (left to right—Blood pump, ACD pump, Air detector)
4. Reserve places for further modules
5. Absorber holder
6. Drip detector
7. IV pole Preparation of the Patient The patient will be administered anticoagulants prior to each treatment session. A sterile saline solution with 5000 IE Heparin will be used for priming the extracorporeal system, thereafter a bolus injection with 4000 IE Heparin will be added into the circuit at the start of each treatment session.

Leukapheresis Time and Flow Rate

The apheresis system should be operated at a flow rate of 30-60 mL/min. A treatment is finalised after 1800 mL of blood has been circulated.

Storage Conditions

The column devices should be stored between 1 and 25° C. avoiding freezing and more elevated temperatures. Stability data >3 months indicate no difference in functionality over time or by temperature (room temperature and refrigerated). The columns will be kept in refrigerated conditions until use. Mechanical damage as those resulting from violent vibrations and trauma should be avoided. Column stored outside of these recommendations should not be used.

Transport Conditions

The column devices will be transported under refrigerated condition, avoiding freezing and more elevated temperatures. Mechanical damage such as those resulting from violent vibrations and trauma should be avoided.

Example 6

Non-Clinical Studies

In-Vitro Depletion of Target Cell Populations

To investigate the ability to eliminate CCR9-expressing cells, in vitro tests have been performed on the bTECK coupled matrix. Blood was collected from blood donors and inflammatory bowel disease patients and passed through the column device containing bTECK coupled matrix. Blood samples were taken before and after column passage and analyzed by flow cytometry (FACS) for the depletion of CCR9-expressing cells.

The results demonstrate significant depletion of the target population CD14− positive CCR9-expressing cells post matrix perfusion; while total CD14-positive cells remain unchanged. Depletion tests were performed on blood from healthy donors and IBD patients confirming similar effects. The results are shown in FIGS. 12 and 13 respectively. In conclusion, the in-vitro results demonstrate a specific reduction of 50-75% of the CCR9-expressing cells by the column. Non-CCR9-expressing cells remained unaffected.

Example 7

TECK-PEG-Biotin Synthesis Summary

Target Molecule:

TECK (Met to Nleu substitution) derivatised at the ε-amino side chain functionality of Lys72 with PEG-Biotin (TFA salt)

Modifications:

Truncated form of human TECK corresponding to residues 1-74 of the mature protein, which encompasses the sequence corresponding to the chemokine fold. The full length mature protein is 127 amino acids (the signal peptide is 23 amino acids in a 150 amino acid immature protein). The single methionine within the sequence was altered to Norleucine, to mitigate against oxidation of this residue during the chain assembly, which was observed during the synthesis of the natural sequence derivative. The Gln at the N-terminus of the proteins is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 72 was modified through biotinylation on the resin. A PEG spacer was incorporated between the ε-amino functionality and the biotin.

The linear amino acid sequence (SEQ ID NO: 1) is shown, prior to attachment of the PEG spacer and biotin molecules at amino acid 72 (K):

HXGVFEDCCLAYHYPIGWAVLRRAWTYRIQEVSGSCNLPAAIFYLPKRH

RKVCGNPKSREVQRAXKLLDARNKVF-OH

X1=pyroGlu or Gln
X64=Norleucine

The engineered TECK sequence was assembled on a solid support, using Fmoc protocols for solid-phase peptide synthesis (SEQ ID NO: 2):

HXGVFEDCCLAYHYPIGWAVLRRAWTYRIQEVSGSCNLPAAIFYLPKRH

RKVCGNPKSREVQRAXKLLDARNXVF-RESIN

X1=pyroGlu or Gln
X64=Norleucine
X72=K(Dde)

FmocLys(Dde)-OH was incorporated as residue 72 to facilitate site-specific labelling at this position of the protein.

Met to Nle substitution.

N-terminal Gln to pyroglutamic acid substitution.

Removal of Dde Protection:

The Dde protecting group was removed by treatment of all resin (2.5 g) with a solution of 2% hydrazine in DMF (100 ml) over 1 hour period to afford 2.0 g resin.

Labelling Steps:
1. Couple Fmoc-8-Amino-3,6-Dioctanoic Acid
Resin (1.5 g) was swollen in DMF (2 ml) and then a solution of Fmoc-8-amino-3,6-dioctanoic acid (0.38 g, 1 mmol), DIC solution (2 ml, 0.5M in DMF) and HOCt solution (2 ml, 0.5M in DMF) was added. The mixture was sonicated for 2 hours and then washed with DMF.
2. Cap
The resin was capped with 0.5M acetic anhydride/DMF solution (20 ml) for 5 minutes and then washed with DMF.
3. Fmoc Deprotection
Fmoc deprotection was carried out by treatment with 20% piperidine in DMF solution (2×50 ml) for 15 minutes each. The resin was washed with DMF.
4. Couple Biotin-OSu
A solution of Biotin-NHS ester (341 mg, 1 mmol) and DIPEA (348 ul, 2 mmol) in DMF (10 ml) was added to the resin and the mixture was sonicated for 3 hours. The resin was washed thoroughly with DMF and DCM then dried in vacuo. Dry resin obtained=1.5 g.
Cleavage:
Dry peptide resin (1.5 g) and the mixture was cleaved with TFA (30 ml) containing a scavenger cocktail consisting of TIS, thioanisole, water, EDT and phenol and the mixture was stirred at room temperature for 6 hours. The solution was filtered into cold ether and the resin rinsed with TFA. The peptide was centrifuged, washed with ether, centrifuged and lyophilised to give 1.0 g crude peptide.
Folding Protocol:
Crude peptide (100 mg) was dissolved into 6M GnHCl (233 ml) and then rapidly diluted to 2M GnHCl concentration by the addition of 50 mM TRIS pH8 (467 ml) containing 0.5 mM GSSG and 5 mM GSH. The mixture was stirred at room temperature for 2.5 days and then analysed by HPLC (Jupiter C18, 250×4.6 mm column, 10-60% B over 30 minutes. HPLC analysis confirmed the formation of desired product as well as mis-folded by-products.
Purification:
The folded protein was purified by reverse phase HPLC using a Jupiter C18, 250×21 mm column, 9 ml/min, 10-60% B over 50 minutes. 11.1 mg of pure folded Nle-TECK-Biotin was afforded.

FIG. 14 shows HPLC of purified folded Biotin-TECK (Nleu). The protein eluted in a single peak at 21.6 mins.

FIG. 15 shows Electrospray ionisation with tandem mass spectrometry (ES/MS) data of purified folded Biotin-TECK (Nleu). The expected mass was 8959.4 Da.
Functional Assay Data:
TECK-Biotin-Nle was tested for agonist activity in an Aequorin assay against hCCR9, (Euroscreen) and an EC50 value of 63.6 nM was reported. c.f. EC50 for native TECK is 67.87 nM.

The final active chemokine thus has the following sequence (SEQ ID NO: 3):

H-XGVFEDCCLAYHYPIGWAVLRRAWTYRIQEVSGSCNLPAAIFYLPKR

HRKVCGNPKSREVQRAXKLLDARNXVF-OH

X1=pyroGlu
X64=norleucine
X72=an amino acid residue that can be biotinylated, such as lysine, ornithine or diaminopropionic acid and optionally is biotinylated, optionally via a spacer molecule such as PEG, such as K(PEG-Biotin).

Example 8

Synthesis of BiotinMIP-3b (CCL19)

Assembly:
Chemical synthesis of chemokines was performed using standard Fmoc solid phase peptides synthesis (SPPS) techniques on an ABI 433 peptide synthesiser. DIC (0.5 M in DMF) and OxymaPure (0.5 M in DMF) were used for activation, acetic anhydride (0.5 M in DMF) for capping, and 20% piperidine in DMF for Fmoc deprotection. Rink Amide resin was utilised for the generation of C-terminal amide chemokines and Wang resin for C-terminal acid chemokines. After assembly, the resin was washed with DMF and DCM and then dried in vacuo.
Removal of Dde Protection:
The Dde protecting group was removed by treatment of resin with a solution of 2.5% hydrazine in DMF (200 ml) over a 2 hour period. The resin was then washed with DMF.
Labelling Steps:
1. Couple Fmoc-8-Amino-3,6-Dioctanoic Acid (PEG)
Resin was swollen in DMF and then a solution of Fmoc-8-amino-3,6-dioctanoic acid (0.38 g, 1 mmol), DIC solution (2 ml, 0.5 M in DMF) and OxymaPure solution (2 ml, 0.5 M in DMF) was added. The mixture was sonicated for 3 hours and then washed with DMF.
2. Capping
The resin was capped with acetic anhydride solution (0.5 M in DMF, 10 ml) for 5 minutes and then washed with DMF.
3. Fmoc deprotection
Fmoc deprotection was carried out by treatment with 20% piperidine in DMF solution (2×50 ml) for 15 minutes each. The resin was washed with DMF.
4. Couple Biotin-OSu
A solution of Biotin-OSu (341 mg, 1 mmol) and DIPEA (348 ml 2 mmol) in DMF (10 ml) was added to the resin and the mixture was sonicated for 3 hours. The resin was washed thoroughly with DMF and DCM then dried in vacuo.
Cleavage:
Dry resin was treated with TFA (10 ml) containing a scavenger cocktail consisting of TIS (500 ml), thioanisole (500 ml), water (500 ml), DMS (500 ml), EDT (250 ml), NH$_4$I (500 mg) and phenol (500 mg) and the mixture was stirred at room temperature for 5 hours. The solution was filtered into cold ether and the resin rinsed with TFA. The precipitated peptide was centrifuged, washed with ether, centrifuged and lyophilised.
Purification Protocol:
The crude peptide was purified by reverse phase HPLC (RP-HPLC) using a Jupiter C18, 250×21 mm column, 9 ml/min, eluting with an optimised gradient [Buffer A: water containing 0.1% TFA, Buffer B: acetonitrile containing 0.1% TFA].
Folding Protocol:
Pure peptide (10 mg) was dissolved into 6M GnHCl (16 ml) and then rapidly diluted to 2M GnHCl concentration by the addition of 50 mM TRIS pH 8.5 (84 ml) containing 0.3 mM GSSG and 3 mM GSH. The mixture was stirred at room temperature for 24 hours and then analysed by RP-HPLC (Jupiter C18, 250×4.6 mm column, 10-60% B over 30 minutes. Purification by RP-HPLC using an optimised gradient afforded the desired product.
Target Molecule:
MIP-3b derivatised at the e-amino side chain functionality of Lys(78) with Biotin (TFA salt)

Modifications:

Human MIP-3b corresponding to residues 1-77, is initially expressed as 98 amino acids comprising the chemokine fold, and a 21 amino acid signal peptide which is cleaved off. An additional lysine was inserted at the C-terminus, at position 78, and modified through biotinylation on the resin.

The linear amino acid sequence (SEQ ID NO: 4) is shown, prior to attachment of the biotin molecule at amino acid 78 (K):

H-GTNDAEDCCLSVTQKPIPGYIVRNFHYLLIKDGCRVPAVVFTTLRGR

QLCAPPDQPWVERIIQRLQRTSAKMKRRSSX-NH₂

X is an amino acid residue that can be biotinylated, such as lysine, ornithine or diaminopropionic acid and optionally is biotinylated, optionally via a spacer molecule such as PEG, e.g. K(PEG-Biotin)

The engineered MIP-3b sequence was assembled on a solid support (Rink Amide resin), using Fmoc protocols for solid-phase peptide synthesis as described in the general protocols section:

H-GTNDAEDCCLSVTQKPIPGYIVRNFHYLLIKDGCRVPAVVFTTLRGR

QLCAPPDQPWVERIIQRLQRTSAKMKRRSSX-RESIN

X is FmocLys(ivDde)

FmocLys(ivDde)-OH was incorporated as residue 78 to facilitate site-specific labelling at this position of the protein (SEQ ID NO: 5). Subsequent removal of the ivDde protecting group, followed by coupling of the Biotin, was carried out as described in the general protocol section. Cleavage, purification and folding protocols were carried out as described to furnish the desired active chemokine (SEQ ID NO: 6).

H-GTNDAEDCCLSVTQKPIPGYIVRNFHYLLIKDGCRVPAVVFTTLRGR

QLCAPPDQPWVERIIQRLQRTSAKMKRRSSX-NH₂

X is K(Biotin)

Electrospray ionisation with tandem mass spectrometry (ESI-TOF-MS) data of purified folded biotinMIP-3b: obtained=9148.8 Da; expected 9149.7 Da.

Functional Assay Data:

biotinMip-3b was tested for agonist activity in an Aequorin assay against hCCR7, (Euroscreen) and an EC50 value of 11.0 nM was reported. c.f. EC50 for recombinant native MIP-3b is 1.6 nM.

Example 9

Treatment of Crohn's Disease (CD)

Materials and Methods

1. Flow Cytometric Analysis of Peripheral Blood

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH₄Cl, pH 7.5) for 15 min at 37° C. The cells were washed in PBS with 2% Bovine Growth Serum, incubated with 10% human serum for 15 min at room temperature (RT) and stained with antibodies (Table 15) at 4° C. for 30 min. The cells were analysed by flow cytometry on a FACS Canto flow cytometer with the FACSDiva software (BD Biosciences).

TABLE 15

List of antibodies for flow cytometric analysis.

| Antibody | Fluorophore | Supplier |
| --- | --- | --- |
| CD14 | FITC | Beckman Coulter |
| Streptavidin | PE, APC | Biolegend |
| CD16 | PE Cy7 | BD Biosciences |
| CCR9 | APC | R&D Systems |
| HLADR | APC Cy7 | Biolegend |
| CD3 | V450 | BD Biosciences |
| CD19 | V500 | BD Biosciences |

2. Chemokine Binding Test

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH₄Cl, pH 7.5) for 15 min at 37° C. The cells were washed in PBS with 2% Bovine Growth Serum, incubated with 10% human serum 15 min at room temperature (RT) and stained with cell specific antibodies together with biotinylated chemokine (1 μM) or the corresponding chemokine receptor antibody at 4° C. for 30 min (Table 15). The biotinylated chemokine was detected via the interaction between biotin and a fluorophore conjugated Streptavidin. The samples were analysed by flow cytometry on a FACS Canto flow cytometer with the FACSDiva software (BD Biosciences).

3. Cell Depletion by Matrix Conjugated with Biotinylated Chemokine

Cells were prepared from peripheral blood (section 1). 1 mL Sepharose BigBeads matrix conjugated with 0.4 mg/mL Streptavidin (GE Healthcare) was washed in 50 mL PBS and added to a 5 mL polystyrene tube (BD Falcon™). Biotinylated chemokine (1 μM) was added to the tube and incubated for 20 min at RT to enable immobilization of the chemokine on the matrix via the biotin-streptavidin interaction. Next, the cells were added to the chemokine-matrix and incubated for 20 min at RT. The cells that did not bind to the matrix were removed by washing the matrix with PBS in a sterile 40 um nylon filter (BD Falcon™ Cell Strainer). The flow through cells were stained with antibodies (Table 15), analysed by flow cytometry and compared with cells from peripheral blood that had not been incubated with the chemokine-matrix.

Results and Discussion

Crohn's Disease (CD)

1. Flow Cytometric Analysis of Peripheral Blood

White blood cells from CD patients was analysed with flow cytometry. The patients exhibited increased numbers of circulating CCR9 expressing monocytes, a mean of 13% compared to approximately 7% in healthy blood (FIG. 17).

2. Chemokine Binding Test

CCR9 binds to the gut homing chemokine TECK (CCL25) and is important for cell migration to the small intestine. In accordance with the CCR9 expression, 14% of the monocytes bind to the biotinylated TECK (bTECK) (FIG. 18).

3. Cell Depletion by Matrix Conjugated with Biotinylated Chemokine

89% of the CCR9 expressing monocytes were efficiently depleted with bTECK-conjugated Sepharose Streptavidin Matrix. Before depletion there were 7.2% CCR9 expressing monocytes and after depletion 0.8% (FIG. 19).

80% of the CCR9 expressing monocytes also have a high expression of HLADR suggesting a proinflammatory phenotype (FIG. 20).

We conclude that monocytes in CD (CD14$^+$HLA-DR$^{hi}$ monocytes) express CCR9 and bind the ligand bTECK. Furthermore, the majority of the CCR9 expressing monocytes can be removed with Sepharose Streptavidin matrix conjugated with bTECK.

Example 10

Diagnosis and Treatment of IBS

The inventors have surprisingly found that Irritable Bowel Syndrome (IBS) patients, or subject suffering from IBS, display an increased frequency (or level) of chemokine receptor expressing cells, in particular monocytes, more specifically CCR9 expressing monocytes. Thus, IBS patients may display inflammation that is comparable to that shown by patients suffering from IBD. Irritable bowel syndrome (IBS) is a condition characterized by chronic abdominal pain, discomfort, bloating, and alteration of bowel habits. It is currently diagnosed on the basis of symptoms only. Accordingly, identification of a pro-inflammatory component provides new avenues for treatment and diagnosis of this debilitating condition.

Materials and Methods
1. Flow Cytometric Analysis of Peripheral Blood

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5) for 15 min at 37° C. The cells were washed in PBS with 2% Bovine Growth Serum, incubated with 10% human serum for 15 min at room temperature (RT) and stained with antibodies (Table 16) at 4° C. for 30 min. The cells were analysed by flow cytometry on a FACS Canto flow cytometer with the FACSDiva software (BD Biosciences).

TABLE 16

List of antibodies for flow cytometric analysis.

| Antibody | Fluorophore | Supplier |
| --- | --- | --- |
| CD14 | FITC | Beckman Coulter |
| Streptavidin | PE, APC | Biolegend |
| CD16 | PE Cy7 | BD Biosciences |
| CCR9 | APC | R&D Systems |
| HLADR | APC Cy7 | Biolegend |
| CD3 | V450 | BD Biosciences |
| CD19 | V500 | BD Biosciences |

2. Chemokine Binding Test

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5) for 15 min at 37° C. The cells were washed in PBS with 2% Bovine Growth Serum, incubated with 10% human serum 15 min at room temperature (RT) and stained with cell specific antibodies together with biotinylated chemokine (1 µM) or the corresponding chemokine receptor antibody at 4° C. for 30 min (Table 16). The biotinylated chemokine was detected via the interaction between biotin and a fluorophore conjugated Streptavidin. The samples were analysed by flow cytometry on a FACS Canto flow cytometer with the FACSDiva software (BD Biosciences).

3. Cell Depletion by Matrix Conjugated with Biotinylated Chemokine

Cells were prepared from peripheral blood (section 1). 1 mL Sepharose BigBeads matrix conjugated with 0.4 mg/mL Streptavidin (GE Healthcare) was washed in 50 mL PBS and added to a 5 mL polystyrene tube (BD Falcon™). Biotinylated chemokine (1 µM) was added to the tube and incubated for 20 min at RT to enable immobilization of the chemokine on the matrix via the biotin-streptavidin interaction. Next, the cells were added to the chemokine-matrix and incubated for 20 min at RT. The cells that did not bind to the matrix were removed by washing the matrix with PBS in a sterile 40 um nylon filter (BD Falcon™ Cell Strainer). The flow through cells were stained with antibodies (Table 16), analysed by flow cytometry and compared with cells from peripheral blood that had not been incubated with the chemokine-matrix.

Results and Discussion
Irritable Bowel Syndrome (IBS)

White blood cells from IBS patients was analysed with flow cytometry. The patients exhibited increased numbers of circulating CCR9 expressing monocytes compared to healthy blood (FIG. 21).

Irritable bowel syndrome is a condition characterized by chronic abdominal pain, discomfort, bloating, and alteration of bowel habits. It is currently diagnosed on the basis of symptoms only. The symptoms of IBS are very similar to IBD, Crohns disease (CD) and Ulcerative Colitis (UC), which also show an increase in CCR9 expressing monocytes (FIG. 24).

CCR9 binds to the gut homing chemokine TECK (CCL25) and is important for cell migration to the small intestine. The monocytes in IBS patient blood bind to the biotinylated TECK (bTECK) (FIG. 22).

Depletion of CCR9 expressing monocytes in IBS patient using bTECK conjugated sepharose streptavidin matrix is shown in FIG. 23.

About 25% of the CCR9 expressing monocytes also have a high expression of HLADR suggesting a proinflammatory phenotype (FIG. 25a). These cells can be depleted using bTECK conjugated sepharose streptavidin matrix (FIG. 25b).

We conclude that monocytes in IBS express CCR9 and bind the ligand bTECK. Furthermore, the majority of the CCR9 expressing monocytes can be removed with Sepharose Streptavidin matrix conjugated with bTECK.

B. Treating Conditions Associated with Metabolic Syndrome

It has been shown (Jianli Niu and Pappachan E. Kolattakudy. Clinical Science (2009) 117, 95-109) that CCR2 expression on monocytes is elevated in diabetic patients. Transgenic mice with an adipose-tissue-specific expression of MCP-1 have macrophage infiltration into adipose tissue, increased hepatic triacylglycerol content and insulin resistance. MCP-1-knockout mice fed a high-fat diet have a drastically reduced macrophage accumulation into adipose tissue and hepatic steatosis when compared with high-fat-fed wild-type mice. Inhibition of MCP-1 function by the acute expression of a dominant negative mutant of MCP-1 ameliorated insulin resistance in db/db mice and in high-fat-fed wild-type mice. Moreover, increased level of serum MCP-1 correlates with markers of the metabolic syndrome, including obesity, insulin resistance, Type 2 diabetes, hypertension and increased serum triacylglyerol concentrations. Monocyte chemoattractant protein-1 (MCP-1) is a major chemoattractant for monocytes and memory T cells by means of their binding to its specific cell-surface receptor, CC-chemokine receptor-2 (CCR2). On this basis, the inventors have selected CCR2 expressing cells as a target for treatment of conditions associated with metabolic syndrome. Serum levels of RANTES are increased in patients with obesity, impaired oral glucose tolerance test and in patients with Type 2 diabetes. RANTES is produced by adipocytes and it recruits and activates T cells, monocytes, basophils, eosinophils and mast cells by binding to CCR1, CCR3 and CCR5 chemokine receptors, which causes an inflammation leading to increased insulin resistance. Polymorphisms of the RANTES gene are associated with the Type 2 diabetes, again linking RANTES to diabetes development. In a diabetes prevention study with lifestyle intervention of owerweight patients with impaired oral glucose tolerance test the patients with the highest serum levels of RANTES were more prone to developType 2 diabetes as compared to controls, implying RANTES in the disease development of Type 2 diabetes.

It is shown herein that MCP-1 can be used to reduce CCR2-expressing monocyte levels in diabetic subjects. It is also shown herein that MCP-1 can be used to reduce CCR2-expressing B cell levels in subjects suffering from AD. It is also shown herein that levels of CCR2 expressing leukocytes in particular B lymphocytes are increased in AD patients. This provides a target for leukapheresis treatment and diagnosis according to the invention.

Materials and Methods

Isolation of Peripheral Blood Leukocytes.

Heparinized peripheral blood from healthy blood donors or inflammatory bowel disease (IBD) patients was fixed with 4% paraformaldehyde for 4 minutes, hemolyzed for 15 minutes with a 0.83% ammonium chloride solution and washed twice in FACS buffer to obtain a suspension of blood leukocytes.

Chemokines.

The leukocytes were incubated for 30 min in the dark at 4° C. with biotinylated and Alexa647 Fluor® labeled MCP-1 (in concentrations 10 ng/µL and 50 ng/µL). The cells were then washed with FACS-buffer and analyzed by flow cytometry. All chemokines used in the Examples were provided by Almac Sciences Scotland Ltd, Edinburgh, Scotland.

Flow Cytometry Assay.

The flow cytometry assay was performed on a two laser FACS Calibur cytometer (BD Immunocytometry systems, San José, Ca, USA). Ten thousand cells were counted and analysed in each sample. For data analyses, Cell Quest Pro software from Becton Dickinson was used.

Example 11

Binding of Monocytes to MCP-1

In the experiment with biotinylated MCP-1 it was found that about 90% of the monocytes obtained from peripheral blood of healthy donors had bound to the cytokine after 30 min of incubation (FIG. 26a), whereas CD4+ and CD8+ lymphocytes had not bound (FIGS. 26b and 26c).

Example 12

Monocytes were investigated for their expression of CCR2 (FIG. 27b) and their ability to bind MCP-1 (FIG. 27a). CCR2 expression was noted an all monocytes with the majority of monocytes expressing high levels, using an anti-CCR2 antibody (FIG. 27b). The MCP-1 binding to monocytes shown in FIG. 27a corresponds to the $CCR2^{hi}$ expressing population shown in FIG. 27b. Thus, MCP-1 binds favourably to $CCR2^{hi}$ expressing cells.

Example 13

Tailored Leukapheresis

Column Design and Properties
Introduction

Apheresis is an established treatment used for depletion of blood components, such as antibodies, low-density lipoproteins (LDL) and blood cells. Leukapheresis is the apheresis treatment used for removal of white blood cells, leukocytes. The patient is connected to an extracorporeal blood circulating system; the blood is drawn from a vein in one arm, passed through a column device and returned into the other arm of the patient. Side effects of leukapheresis treatments are varying from mild events like headache, dizziness, hypotension, palpitation and flush seen in 0.1 to 5% of treated patients.

The Column

The column is intended to be used as a leukapheresis treatment for a condition associated with metabolic syndrome. It will specifically remove CCR2, CCR1, CCR3, CCR4 or CCR5-expressing leukocytes, in particular monocytes, through the use of a binding reagent, more specifically an MCP-1, MCP-2, MCP-3, MCP-4, MCP-5 and/or RANTES containing resin, exploiting the CCR2, CCR1, CCR3, CCR4 or CCR5-chemokine interaction. The column consists of three combined components, the plastic house, the streptavidin (SA) Sepharose™ BigBeads matrix and one or more of biotinylated MCP-1, MCP-2, MCP-3, MCP-4, MCP-5 and RANTES bound to the matrix. The treatment is conducted using the same techniques as a standard apheresis procedure.

The Plastic House (FIG. 9)

The plastic house, designed to keep a continuous blood flow through the matrix, consists of a transparent body and red-coloured top. The top has a distribution plate (2) at the inflow site (1) to spread the blood evenly over the entire matrix area. The plate is the first safety barrier preventing larger particles flowing through the column and into the patient. Safety filter units (3 and 4) are placed at the inflow (1) and outflow (5) sites of the plastic housing. The safety filter unit contains three filters designed to be a robust barrier and stop all particles larger than blood cells passing through the column. The plastic housing design is shown in FIG. 9. The design with safety filters (3 and 4) at both ends of the column device will minimize the risk of leakage of particles into the patient, including in the event that the device is placed up side down with the blood flow in the opposite direction to that anticipated.

Streptavidin Sepharose™ BigBeads

The second component in the device is the affinity matrix called streptavidin Sepharose™ BigBeads (Sepharose™ GE Healthcare, Sweden). Sepharose™ is a cross linked, beaded-form of agarose, which is a polysaccharide extracted from seaweed. Sepharose™ and agarose are commonly used as column matrices in biomedical affinity techniques. It is chosen for its optimal distribution capacity and can provide a large available area for affinity binding.

Binding Reagent

Coupled to the matrix is the third component of the device, one or more binding reagents that bind specifically to CCR2, CCR1, CCR3, CCR4 or CCR5. One or more hemokines selected from the group consisting of: MCP-1, MCP-2, MCP-3, MCP-4, MCP-5, RANTES, CCL17 (TARC) and CCL22 (MDC) may be employed. These peptides may be synthetic, engineered versions of the human chemokine, which are truncated and biotinylated, but retain binding activity to the CCR2, CCR1, CCR3, CCR4 or CCR5 receptor. By biotinylating the engineered chemokine, it is able to bind to the streptavidin molecules in the Sepharose™ matrix. The biotin-streptavidin binding is known be one of the strongest biological interactions with a Kd in the order of $4\times10^{-14}$ M. The calculated ratio of streptavidin:biotin binding sites in the column is 10:1. Therefore, the coupling between the matrix and chemokine will be immediate, minimising the risk of chemokine decoupling from the matrix.

The Apheresis System

To conduct the leukapheresis the following components are needed; the column, tubing system, and a 4008 ADS pump (Fresenius Medical Care).

The Circuit

The system is illustrated in FIG. 10. The patient (1) is connected to the extracorporeal circuit via sterile Venflon needles to veins in the right and the left arms. A saline bag (3) is also connected and the saline solution is pumped with an ACD pump (2). Blood is drawn from one arm of the patient through the sterile tubing system by the blood pump (4) and passed through the column (6) and back to the patient. The tubing system is connected to the column via standard dialysis luer-lock couplings. The couplings on the column are colour-coded for correct assembly; red tubing for inflow to the red column top and blue tubing for outflow back to the patient. An air detector (8) is present. Inlet pressure (5) and Pven sensors (7) are employed to monitor the pressure in the circuit.

The 4008 ADS Pump

An apheresis pump, from Fresenius Medical Care, monitors the patient's inflow and outflow, the pressure in the extracorporeal circulation and can discriminate air by a bubble catcher and air detector. A clot catcher filter is placed inside the bubble catcher. The pump also has an optical detector to distinguish between light, e.g. saline solution or air present in the tubing system and dark e.g. blood present in the tubing system.

A schematic diagram of the pump, showing the air detector and optical filter is shown in FIG. 11. If the pump system detects air bubbles and optical fluctuations or if extracorporeal pressure values are out of the set range, then the pump stops immediately and a visual/audible alarm are emitted.

LEGEND FOR FIG. 11

1. Monitor
2. Holder for waste bag
3. Modules (left to right—Blood pump, ACD pump, Air detector)
4. Reserve places for further modules
5. Absorber holder
6. Drip detector
7. IV pole Preparation of the Patient The patient will be administered anticoagulants prior to each treatment session. A sterile saline solution with 5000 IE Heparin will be used for priming the extracorporeal system, thereafter a bolus injection with 4000 IE Heparin will be added into the circuit at the start of each treatment session.

Leukapheresis Time and Flow Rate

The apheresis system should be operated at a flow rate of 30-60 mL/min. A treatment is finalised after 1800 mL of blood has been circulated.

Storage Conditions

The column devices should be stored between 1 and 25° C. avoiding freezing and more elevated temperatures. Stability data >3 months indicate no difference in functionality over time or by temperature (room temperature and refrigerated). The columns will be kept in refrigerated conditions until use. Mechanical damage as those resulting from violent vibrations and trauma should be avoided. Column stored outside of these recommendations should not be used.

Transport Conditions

The column devices will be transported under refrigerated condition, avoiding freezing and more elevated temperatures. Mechanical damage such as those resulting from violent vibrations and trauma should be avoided.

In-Vitro Depletion of Target Cell Populations

To investigate the ability to eliminate CCR2-expressing cells, in vitro tests have been performed on the bMCP-1 coupled matrix. Blood was collected from blood donors and passed through the column device containing bMCP-1 coupled matrix. Blood samples were taken before and after column passage and analyzed by flow cytometry (FACS) for the depletion of CCR2-expressing cells.

The results demonstrate significant depletion of the target population CCR2-expressing monocytes post matrix perfusion. Depletion tests were performed on blood from three healthy donors. The results are shown in FIG. 28a.

The in-vitro results demonstrate a specific reduction of up to 80% of the CCR2-expressing cells by the column. Notably, individuals with fewer CCR2 expressing cells initially achieved lower depletion. The remaining levels of monocytes were around 20-30% in each case, irrespective of the starting point. Non-CCR2-expressing cells remained unaffected (data not shown).

To investigate the ability to eliminate CCR1, 3 and 5-expressing cells, in vitro tests have been performed on the biotinylated RANTES coupled matrix. Blood was collected from blood donors and passed through the column device containing biotinylated RANTES coupled matrix. Blood samples were taken before and after column passage and analyzed by flow cytometry (FACS) for the depletion of CCR1, 3 or 5-expressing cells.

The RANTES molecule was synthesized by Almac. The amino acid sequence of the biotinylated RANTES molecule is set forth as SEQ ID NO: 14:

H2N-SPYSSDTTPCCFAYIARPLPRAHIKEYFYTSGKCSNPAVVFVTRK

NRQVCANPEKKWVREYINSLEKS-CO2H

This molecule has the naturally occurring methionine at position 67 replaced with lysine to facilitate biotinylation at position 67.

The side-chain of Lys 67 was directly biotinylated to given the protein primary structure shown in FIG. 34. The protein was folded and disulphide bonds formed between the first and third cysteine in the sequence and between the 2nd and 4th cysteines. The results demonstrate significant depletion of the target population chemokine receptor-expressing cells post matrix perfusion. Depletion tests were performed on blood from a healthy donor. The results are shown in FIG. 28b.

The in-vitro results demonstrate a specific reduction of around 20% of the chemokine receptor-expressing cells by the column. Non-CCR1, 3 and 5-expressing cells remained unaffected (data not shown).

Example 14

MCP1 Derivatives

MCP-1 has been produced with residue 75 as the site of biotinylation on the chemokine (numbering based upon the mature protein having the amino acid sequence of SEQ ID NO: 2). Biotinylation permits immobilization of MCP-1 on a solid support (via a biotin-avidin interaction). The basic amino acid sequence of MCP-1, including a 23 amino acid leader sequence is set forth as SEQ ID NO: 7,

```
MKVSAALLCLLLIAATFIPQGLAQPDAINAPVTCCYNFTN

RKISVQRLAS YRRITSSKCP KEAVIFKTIVAKEICADPKQ

KWVQDSMDHLDKQTQTPKT
```

The amino acid sequence of the mature protein is set forth as SEQ ID NO: 8,

```
QPDAINA PVTCCYNFTN RKISVQRLAS YRRITSSKCP

KEAVIFKTIV AKEICADPKQ KWVQDSXDHL DKQTQTPKT
```

X=Met or Norleucine
The inventors have determined that chemokines may display improved binding properties where the chemokine is biotinylated via a spacer group. The spacer may prevent the biotin group from impacting on the binding affinity of the chemokine.

Thus, MCP-1 derivatised at the ϵ-amino side chain functionality of Lys75 with PEG-Biotin (TFA salt) will be synthesised. The PEG spacer will be 3,6,-dioxoaminooctanoic acid. The Gln at the N-terminus of the proteins is subject to pyroGlu formation under physiological conditions. Thus the first glutamine (Gln1) of the sequence will be substituted with pyroglutamine. The molecule will be synthesised as a C-terminal amide (via synthesis on an amide linker). The molecule is shown schematically in FIG. 29.

A biotinMCP-1 Met to Nleu analogue will also be synthesised. The single methionine within the sequence will be altered to Norleucine, to mitigate against oxidation of this residue during the chain assembly and improve stability of the final product. This molecule is shown schematically in FIG. 30, see also SEQ ID NO: 8.

Once synthesised, the activity of the various biotinMCP-1 derivatives will be determined in cell-based assays. In particular, agonist and antagonist properties will be determined in aequorin functional cell-based assay on human CCR2 receptor. The relevant molecules have been synthesised, see Example below.

Example 15

Synthesis of a Ccr2 Antagonist Biotinmcp-1 which Binds to the Receptor without Activation Antagonist Activity (J-H Gong and I. Clark-Lewis, J. Exp. Med., 1995, 181, 63) has been shown for an MCP-1 derivative truncated at the N-terminus. In particular, deletion of residues 1-8, results in binding to CCR2 with Kd 8.3 nM. This protein was unable to cause chemotaxis of CCR2 positive cells. (inhibition of chemotaxis IC50 20 nM)

The amino acid sequence of the truncated version is set forth as SEQ ID NO: 9:

```
VTCCYNFTN RKISVQRLAS YRRITSSKCP KEAVIFKTIV

AKEICADPKQ KWVQDSMDHL DKQTQTPKT
```

A derivative of this truncated version will be synthesised comprising residues 9 to 76 of the mature protein (MCP-1 9-76) with Met64 to Nleu substitution and derivatised at the ϵ-amino side chain functionality of Lys75 with PEG-Biotin (TFA salt). This molecule is shown schematically in FIG. 31. The PEG spacer will be 3,6,-dioxoaminooctanoic acid.

Once synthesised, the activity of the various biotinMCP-1 derivatives will be determined in cell-based assays. In particular, agonist and antagonist properties will be determined in aequorin functional cell-based assay on human CCR2 receptor.

Example 16

Demonstrate Removal of Ccr2 Expressing Cells Using an Alternative Chemokine Ligand to mcp-1

CCR2 also binds chemokines MCP-2, MCP-3, MCP-4, MCP-5, and HCC-4 in addition to MCP-1. MCP-5 only binds CCR2 and should be selective in its removal of CCR2 expressing cells. MCP5 is a mouse chemokine shown to chemotact human CCR2 cells with EC50<3 nM.

The full length amino acid sequence, including the signal peptide, is set forth as SEQ ID NO: 4

MKISTLLCLL LIATTISPQV LAGPDAVSTP VTCCYNVVKQ

KIHVRKLKSY RRITSSQCPR EAVIFRTILD KEICADPKEK

WVKNSINHLD KTSQTFILEP SCLG

The amino acid sequence of N-terminal processed MCP-5 chemokine is 82 amino acids long and is set forth as SEQ ID NO: 11

GPDAVSTP VTCCYNVVKQ KIHVRKLKSY RRITSSQCPR

EAVIFRTILD KEICADPKEK WVKNSINHLD KTSQTFILEP

SCLG

An amino acid sequence alignment suggests that MCP-5 has a C-terminal extension when compared to the amino acid sequence of MCP-1. The results of this alignment are shown in FIG. 32. On this basis a C-terminal truncated version of MCP-5 will be synthesised. This truncated version will comprise MCP-5 residues 1-76, set forth as SEQ ID NO: 12:

GPDAVSTP VTCCYNVVKQ KIHVRKLKSY RRITSSQCPR

EAVIFRTILD KEICADPKEK WVKNSINHLD KTSQTFIL

In the truncated version, Ile75 to be substituted with Lys, set forth as SEQ ID NO: 13:

GPDAVSTP VTCCYNVVKQ KIHVRKLKSY RRITSSQCPR

EAVIFRTILD KEICADPKEK WVKNSINHLD KTSQTFKL

Following substitution, the substituted version will be biotinylated at position 75, a lysine or other suitable residue such as ornithine or diaminopropanoic acid via A PEG spacer (3,6,-dioxoaminooctanoic acid). The protein will be synthesised on an amide linker to yield a C-terminal amide derivative. This molecule is shown schematically in FIG. 33.

Once synthesised, the activity of the various biotinMCP-5 derivatives will be determined in cell-based assays. In particular, agonist and antagonist properties will be determined in aequorin functional cell-based assay on human CCR2 receptor.

Examples 17 to 19

Synthesis of Additional Chemokines

General Protocols
Assembly:
Chemical synthesis of chemokines was performed using standard Fmoc solid phase peptides synthesis (SPPS) techniques on an ABI 433 peptide synthesiser. DIC (0.5 M in DMF) and OxymaPure (0.5 M in DMF) were used for activation, acetic anhydride (0.5 M in DMF) for capping, and 20% piperidine in DMF for Fmoc deprotection. Rink Amide resin was utilised for the generation of C-terminal amide chemokines and Wang resin for C-terminal acid chemokines. After assembly, the resin was washed with DMF and DCM and then dried in vacuo.
Removal of Dde Protection:
The Dde protecting group was removed by treatment of resin with a solution of 2.5% hydrazine in DMF (200 ml) over a 2 hour period. The resin was then washed with DMF.
Labelling Steps:
1. Couple Fmoc-8-Amino-3,6-Dioctanoic Acid (PEG) Resin was swollen in DMF and then a solution of Fmoc-8-amino-3,6-dioctanoic acid (0.38 g, 1 mmol), DIC solution (2 ml, 0.5 M in DMF) and OxymaPure solution (2 ml, 0.5 M in DMF) was added. The mixture was sonicated for 3 hours and then washed with DMF.
2. Capping
The resin was capped with acetic anhydride solution (0.5 M in DMF, 10 ml) for 5 minutes and then washed with DMF.
3. Fmoc Deprotection
Fmoc deprotection was carried out by treatment with 20% piperidine in DMF solution (2×50 ml) for 15 minutes each. The resin was washed with DMF.
4. Couple Biotin-OSu
A solution of Biotin-OSu (341 mg, 1 mmol) and DIPEA (348 ml) in DMF (10 ml) was added to the resin and the mixture was sonicated for 3 hours. The resin was washed thoroughly with DMF and DCM then dried in vacuo.
Cleavage:
Dry resin was treated with TFA (10 ml) containing a scavenger cocktail consisting of TIS (500 ml), thioanisole (500 ml), water (500 ml), DMS (500 ml), EDT (250 ml), $NH_4I$ (500 mg) and phenol (500 mg) and the mixture was stirred at room temperature for 5 hours. The solution was filtered into cold ether and the resin rinsed with TFA. The precipitated peptide was centrifuged, washed with ether, centrifuged and lyophilised.
Purification Protocol:
The crude peptide was purified by reverse phase HPLC (RP-HPLC) using a Jupiter C18, 250×21 mm column, 9 ml/min, eluting with an optimised gradient [Buffer A: water containing 0.1% TFA, Buffer B: acetonitrile containing 0.1% TFA].

Folding Protocol:
Pure peptide (10 mg) was dissolved into 6M GnHCl (16 ml) and then rapidly diluted to 2M GnHCl concentration by the addition of 50 mM TRIS pH 8.5 (84 ml) containing 0.3 mM GSSG and 3 mM GSH. The mixture was stirred at room temperature for 24 hours and then analysed by RP-HPLC (Jupiter C18, 250×4.6 mm column, 10-60% B over 30 minutes. Purification by RP-HPLC using an optimised gradient afforded the desired product.

Example 17

BiotinMCP-1 (CCL2)

Target Molecule: MCP-1 derivatised at the ε-amino side chain functionality of Lys(75) with PEG-Biotin (TFA salt)
Modifications:
Human MCP-1 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the ε-amino functionality and the biotin.

The linear amino acid sequence (SEQ ID NO: 15) is shown, prior to attachment of the PEG spacer and biotin molecules at amino acid 75 (K):

H-XPDAINAPVTCCYNFTNRKISVQRLASYRRITSSKCPKEAVIFKTIVA

KEICADPKQKWVQDSMDHLDKQTQTPKT-$NH_2$

X=pyroGlu or Gln
The engineered MCP-1 sequence was assembled on a solid support (Rink Amide resin), using Fmoc protocols for solid-phase peptide synthesis as described in the general protocols section:

SEQ ID NO: 16
H-XPDAINAPVTCCYNFTNRKISVQRLASYRRITSSKCPKEAVIFKTIVA

KEICADPKQKWVQDSMDHLDKQTQTPXT-RESIN

X1=pyroGlu or Gln
X75=K(ivDde)
FmocLys(ivDde)-OH was incorporated as residue 75 to facilitate site-specific labelling at this position of the protein. Subsequent removal of the ivDde protecting group, followed by coupling of the PEG spacer and Biotin, was carried out as described in the general protocol section. Cleavage, purification and folding protocols were carried out as described to furnish the desired active chemokine.

SEQ ID NO: 17
H-XPDAINAPVTCCYNFTNRKISVQRLASYRRITSSKCPKEAVIFKTIVA

KEICADPKQKWVQDSMDHLDKQTQTPXT-$NH_2$

X1=pyroGlu or Gln
X75 is an amino acid residue that can be biotinylated, such as lysine, ornithine or diaminopropionic acid and optionally is biotinylated, optionally via a spacer molecule such as PEG, optionally K(PEG-Biotin)

Electrospray ionisation with tandem mass spectrometry (ESI-TOF-MS) data of purified folded biotinMCP-1: obtained=9032.8 Da; expected 9034.4 Da.

Functional Assay Data:
biotinMCP-1 was tested for agonist activity in an Aequorin assay against hCCR2b, (Euroscreen) and an EC50 value of 9.6 nM was reported. c.f. EC50 for recombinant native MCP-1 is 3.1 nM.

Example 18

BiotinRANTES (CCL5)

Target Molecule:
RANTES derivatised at the ε-amino side chain functionality of Lys(67) with Biotin (TFA salt)
Modifications:
Human RANTES corresponding to residues 1-68, is initially expressed as 91 amino acids comprising the chemokine fold, and a 23 amino acid signal peptide which is cleaved off. The single methionine (Met67) within the sequence was mutated to lysine, to mitigate against oxidation of this residue during the chain assembly, which was observed during the synthesis of the natural sequence derivative. This Met to Lys substitution provided a lysine at position 67 which was modified through biotinylation on the resin.

The linear amino acid sequence (SEQ ID NO: 18) is shown, prior to attachment of the biotin molecule at amino acid 67 (K):

H-SPYSSDTTPCCFAYIARPLPRAHIKEYFYTSGKCSNPAVVFVTRKNRQ

VCANPEKKWVREYINSLEKS-OH

The engineered RANTES sequence was assembled on a solid support (Wang resin), using Fmoc protocols for solid-phase peptide synthesis as described in the general protocols section:

H-SPYSSDTTPCCFAYIARPLPRAHIKEYFYTSGKCSNPAVVFVTRKNRQ

VCANPEKKWVREYINSLEXS-RESIN

X is K(ivDde)
FmocLys(ivDde)-OH was incorporated as residue 67 to facilitate site-specific labelling at this position of the protein (SEQ ID NO: 19). Subsequent removal of the ivDde protecting group, followed by coupling of the Biotin, was carried out as described in the general protocol section. Cleavage, purification and folding protocols were carried out as described to furnish the desired active chemokine (SEQ ID NO: 20).

H-SPYSSDTTPCCFAYIARPLPRAHIKEYFYTSGKCSNPAVVFVTRKNRQ

VCANPEKKWVREYINSLEXS-OH

X is an amino acid residue that can be biotinylated, such as lysine, ornithine or diaminopropionic acid and optionally is biotinylated, optionally via a spacer molecule such as PEG (e.g. K(Biotin))

Electrospray ionisation with tandem mass spectrometry (ESI-TOF-MS) data of purified folded biotinRANTES: obtained=8068.9 Da; expected 8070.2 Da.

Functional Assay Data:
BiotinRANTES was tested for agonist activity in an Aequorin assay against hCCR5, (Euroscreen) and an EC50 value of 0.5 nM was reported.

Example 19

BiotinMCP-2 (CCL8)

Target Molecule:
MCP-2 derivatised at the ε-amino side chain functionality of Lys(75) with PEG-Biotin (TFA salt)
Modifications:
Human MCP-2 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the ε-amino functionality and the biotin.

The linear amino acid sequence (SEQ ID NO: 21) is shown, prior to attachment of the PEG spacer and biotin molecules at amino acid 75 (K):

H-XPDSVSIPITCCFNVINRKIPIQRLESYTRITNIQCPKEAVIFKTKRG

KEVCADPKERWVRDSMKHLDQIFQNLKP-NH$_2$

X=pyroGlu or Gln
The engineered MCP-2 sequence was assembled on a solid support (Rink Amide resin), using Fmoc protocols for solid-phase peptide synthesis as described in the general protocols section:

H-XPDSVSIPITCCFNVINRKIPIQRLESYTRITNIQCPKEAVIFKTKRG

KEVCADPKERWVRDSMKHLDQIFQNLXP-NH$_2$

X1=pyroGlu or Gln
X75=K(ivDde)
FmocLys(ivDde)-OH was incorporated as residue 75 to facilitate site-specific labelling at this position of the protein (SEQ ID NO: 22). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 23):

H-XPDSVSIPITCCFNVINRKIPIQRLESYTRITNIQCPKEAVIFKTKRG

KEVCADPKERWVRDSMKHLDQIFQNLXP-NH$_2$

X1=pyroGlu or Gln
X75=an amino acid residue that can be biotinylated, such as lysine, ornithine or diaminopropionic acid and optionally is biotinylated, optionally via a spacer molecule such as PEG, e.g. K(PEG-Biotin).

Electrospray ionisation with tandem mass spectrometry (ESI-TOF-MS) data of purified folded biotinMCP-2: obtained=9263.6 Da; expected 9263.8 Da.

Functional Assay Data:

biotinMCP-2 was tested for activity in an Aequorin assay against hCCR2b, (Euroscreen) and was shown to be a partial agonist with an EC50 value of 50.9 nM. c.f. EC50 for recombinant native MCP-2 is 23.5 nM (partial agonist).

Example 20

Diagnosis and Treatment of Diabetes Mellitus (DM)

Materials and Methods
1. Flow Cytometric Analysis of Peripheral Blood

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM $NH_4Cl$, pH 7.5) for 15 min at 37° C. The cells were washed in PBS with 2% Bovine Growth Serum, incubated with 10% human serum for 15 min at room temperature (RT) and stained with antibodies (Table 17) at 4° C. for 30 min. The cells were analysed by flow cytometry on a FACS Canto flow cytometer with the FACSDiva software (BD Biosciences).

TABLE 17

List of antibodies for flow cytometric analysis.

| Antibody | Fluorophore | Supplier |
| --- | --- | --- |
| CD14 | FITC | Beckman Coulter |
| CCR5 | PE | Biolegend |
| CCR3 | PE | Biolegend |
| Streptavidin | PE, APC | Biolegend |
| CCR2 | PerCP Cy5.5 | Biolegend |
| CD3 | V450 | BD Biosciences |
| CD19 | V500 | BD Biosciences |
| CD16 | PE Cy7 | BD Biosciences |
| CCR4 | PerCP Cy5.5 | BD Biosciences |

2. Chemokine Binding Test

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM $NH_4Cl$, pH 7.5) for 15 min at 37° C. The cells were washed in PBS with 2% Bovine Growth Serum, incubated with 10% human serum 15 min at room temperature (RT) and stained with cell specific antibodies together with biotinylated chemokine (1 µM) or the corresponding chemokine receptor antibody at 4° C. for 30 min (Table 17). The biotinylated chemokine was detected via the interaction between biotin and a fluorophore conjugated Streptavidin. The samples were analysed by flow cytometry on a FACS Canto flow cytometer with the FACSDiva software (BD Biosciences).

3. Cell Depletion by Matrix Conjugated with Biotinylated Chemokine

Cells were prepared from peripheral blood (section 1). 1 mL Sepharose BigBeads matrix conjugated with 0.4 mg/mL Streptavidin (GE Healthcare) was washed in 50 mL PBS and added to a 5 mL polystyrene tube (BD Falcon™). Biotinylated chemokine (1 µM) was added to the tube and incubated for 20 min at RT to enable immobilization of the chemokine on the matrix via the biotin-streptavidin interaction. Next, the cells were added to the chemokine-matrix and incubated for 20 min at RT. The cells that did not bind to the matrix were removed by washing the matrix with PBS in a sterile 40 um nylon filter (BD Falcon™ Cell Strainer). The flow through cells were stained with antibodies (Table 17), analysed by flow cytometry and compared with cells from peripheral blood that had not been incubated with the chemokine-matrix.

Results and Discussion
Diabetes Mellitus (DM)
1. Flow Cytometric Analysis of Peripheral Blood White blood cells from DM patients were analysed with flow cytometry. About 80% of the monocytes are shown to express the chemokine receptor CCR2 (FIG. 36) based upon flow cytometry data and binding by an anti-CCR2 antibody. CCR2 and its ligand MCP1 (CCL2) are important for monocyte migration and infiltration into the inflamed tissue. CCR2 is expressed on the majority of the monocytes in both diabetes patients and healthy controls. The expression of the CCR2 receptor on monocytes is not increased in diabetes patients; however, the monocytes in diabetes are potentially different in their pro-inflammatory profile with regards to other mediators. Furthermore, the ligand MCP-1 is secreted by inflamed and damaged tissue, such as the pancreas in diabetes, and will attract CCR2 expressing monocytes. In healthy individuals, this signal is absent and the monocytes will not migrate into the tissue even though they express CCR2. Thus, migration of pro-inflammatory CCR2 expressing monocytes is rather regulated by the level of the ligand MCP-1 than the level of CCR2 expression.

FIG. 44 shows an increased frequency of CCR4 expressing T cells in four patients with type 2 Diabetes compared to healthy controls. FIG. 23 shows an increased frequency of CCR5 expressing T cells in four patients with type 2 Diabetes compared to healthy controls. These cells may be depleted using suitable chemokines such as CCL17 (TARC) and CCL22 (MDC), which bind CCR4 only and CCL5 (RANTES) which binds CCR5.

2. Chemokine Binding Test

In accordance with the CCR2 expression, all the monocytes binds to biotinylated MCP1 (bMCP1) (FIG. 37).

3. Cell Depletion by Matrix Conjugated with Biotinylated Chemokine

21% of the CCR2 expressing monocytes were efficiently depleted with bMCP1-conjugated Sepharose Streptavidin Matrix. Before depletion there were 80% CCR2 expressing monocytes and after depletion 63% (FIG. 38).

We conclude that monocytes in DM express CCR2 and bind the ligand bMCP1. Furthermore, 20% of the CCR2 expressing monocytes can be removed with Sepharose Streptavidin matrix conjugated with bMCP1.

Example 21

Diagnosis and Treatment of Adiposis Dolorosa

Materials and Methods
1. Flow Cytometric Analysis of Peripheral Blood

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM $NH_4Cl$, pH 7.5) for 15 min at 37° C. The cells were washed in PBS with 2% Bovine Growth Serum, incubated with 10% human serum for 15 min at room temperature (RT) and stained with antibodies (Table 18) at 4° C. for 30 min. The cells were analysed by flow cytometry on a FACS Canto flow cytometer with the FACSDiva software (BD Biosciences).

TABLE 18

List of antibodies for flow cytometric analysis.

| Antibody | Fluorophore | Supplier |
| --- | --- | --- |
| CD14 | FITC | Beckman Coulter |
| Streptavidin | PE, APC | Biolegend |
| CCR2 | PerCP Cy5.5 | Biolegend |
| CD16 | PE Cy7 | BD Biosciences |
| HLADR | APC Cy7 | Biolegend |
| CD3 | V450 | BD Biosciences |
| CD19 | V500 | BD Biosciences |

2. Chemokine Binding Test

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5) for 15 min at 37° C. The cells were washed in PBS with 2% Bovine Growth Serum, incubated with 10% human serum 15 min at room temperature (RT) and stained with cell specific antibodies together with biotinylated chemokine (1 µM) or the corresponding chemokine receptor antibody at 4° C. for 30 min (Table 18). The biotinylated chemokine was detected via the interaction between biotin and a fluorophore conjugated Streptavidin. The samples were analysed by flow cytometry on a FACS Canto flow cytometer with the FACSDiva software (BD Biosciences).

3. Cell Depletion by Matrix Conjugated with Biotinylated Chemokine

Cells were prepared from peripheral blood (section 1). 1 mL Sepharose BigBeads matrix conjugated with 0.4 mg/mL Streptavidin (GE Healthcare) was washed in 50 mL PBS and added to a 5 mL polystyrene tube (BD Falcon™). Biotinylated chemokine (1 µM) was added to the tube and incubated for 20 min at RT to enable immobilization of the chemokine on the matrix via the biotin-streptavidin interaction. Next, the cells were added to the chemokine-matrix and incubated for 20 min at RT. The cells that did not bind to the matrix were removed by washing the matrix with PBS in a sterile 40 um nylon filter (BD Falcon™ Cell Strainer). The flow through cells were stained with antibodies (Table 18), analysed by flow cytometry and compared with cells from peripheral blood that had not been incubated with the chemokine-matrix.

Results and Discussion

1. Flow Cytometric Analysis of Peripheral Blood

White blood cells from AD patients was analysed with flow cytometry. The patients exhibited two fold increased numbers of circulating CCR2 expressing B cells (mean of 1.8% compared to approximately 0.7% in healthy blood) (FIG. 39).

FIG. 20 shows an increased frequency of CCR1 expressing monocytes in 4 patients with Addipois dolorosa compared to healthy controls.

2. Chemokine Binding Test

CCR2 binds to the chemokine MCP1 (CCL2) and is important for cell recruitment to inflammation sites. 65% of the B cells bind to the biotinylated MCP1 (bMCP1) (FIG. 40).

3. Cell Depletion by Matrix Conjugated with Biotinylated Chemokine

67% of the CCR2 expressing B cells were efficiently depleted with bMCP1-conjugated Sepharose Streptavidin Matrix. Before depletion there were 3% CCR2 expressing B cells and after depletion 1% (FIG. 41).

We conclude that B cells in AD express CCR2 and bind the ligand bMCP1. Furthermore, 67% of the CCR2 expressing B cells can be removed with Sepharose Streptavidin matrix conjugated with bMCP1.

FIG. 43 shows depletion of CCR1 expressing moncoytes with SepharoseStrepavidin-matrix-bRANTES. Blood cells from a healthy control were incubated with biotinylated chemokine-Sepharose Streptavidin-matrix. Unbound cells were retrieved by washing the matrix. The cells (After Depletion) were then analysed with flow cytometry and compared with cells that had not been incubated with bchemokine-matrix (Before Depletion). Thus, monocytes expressing CCR1 are upregulated in AD. These cells can be effectively depleted using a suitable chemokine, in this case biotinylated CCL5 (RANTES).

C. Treating Inflammatory Arthritis

The expression of MCP-1 precedes the development of MA. RA in patients with autoantibodies against citrullinated peptides and the MCP-1 levels remain higher during active disease.

This implies as an important inflammatory mediator of disease and that MCP-1 levels is a marker of disease activity for RA and in patients with juvenile RA. The increased levels of MCP-1 in the inflammatory joint will recruit proinflammatory monocytes, machropages to the joint to further increase the inflammation. Thus, removing MCP-1 recruitable cells by tailored leukapheresis is a promising treatment.

In animal models of RA (adjuvant-induced arthritis model) local and systemic elevated levels of the chemokine RANTES has been observed. This implies that proinflammatory cells recruited by the increased expression of RANTES in the joint is a contributing mechanism to the arthritis disease.

Thus, in some phases of the disease MCP-1 or RANTES may be the dominant chemokine recruiting different sets of proinflammatory cells to the joint indicating different stages of the inflammatory disease. By investigating chemokines, and the expression of chemokine receptors on circulating proinflammatory cells the inflammatory stage and direction can be determined, supporting a personalized choice for removing a particular disease creating cell population from the circulation by tailored chemokine leukapheresis. RA is a systemic autoimmune disease and can affect any area of the body, including the nervous system, the lungs, the vasculature and the heart. The joints become inflamed and infiltration of inflammatory cells lead to cartilage destruction. The infiltration of cells is regulated by chemokine secretion in the synovial ("Molecular aspects of rheumatoid arthritis: chemokines in the joints of patients": Iwamoto T et al, Minireview FEBS Journal 275 (2008) 4448-4455).

Chemocentryx have ongoing clinical studies on a CCR1 antagonist, CCX354, to target the chemokine-infiltration mechanism in RA. Results indicate problems with dose-finding. ("Pharmacokinetic and pharmacodynamic evaluation of novel CCR1 antagonist CCX354 in healthy human subjects: implications for selection of clinical dose": Dairaghi D J et al, Nature Volume 89 number 5, May 2011).

It is shown herein that subjects suffering from rheumatoid arthritis contain chemokine receptor expressing cells in the peripheral blood, in particular CCR1 and CCR2 expressing monocytes. It is also shown herein that the CCR2 and CCR1 cells can be removed using a suitable binding reagent, in particular CCL2 to remove CCR2 expressing cells and CCL5 (RANTES) (in biotinylated form) immobilized on a suitable matrix to remove CCR1 expressing cells. Similarly, it is shown herein that CCR5-expressing lymphocytes, in particular T-lymphocytes can be depleted in subjects suffering from rheumatoid arthritis using a suitable binding reagent, in particular CCL5 (RANTES), in biotinylated form, immobilized on a suitable matrix. Leukocytes with pro inflammatory functions are in the circulation and are recruited to the site of inflammation, i.e, the joint, by the expression of local chemokines allowing transmigration of effector leukocytes into the joint. Thus, normal expression levels in the presence of local production of chemokines will promote inflammation. In a healthy subject where there is no production of local chemokines there is no extravasation of leukocytes to the joint. Therefore, subjects may have an increased expression level of chemokine receptor, increased number of chemokine receptor expressing cells or the chemokine receptor expression may be normal but the patient has an increased level of local chemokine production.

Chemokines can be measured using immunological techniques such as ELISA. Such approaches may be multiplexed as needed. The chemokine levels are increased in the joint, attracting a particular chemokine receptor expressing cell. Although the number of cells may not be increased in the circulation, that transmigration into the joint will worsen the joint inflammation. In blood the decrease in the chemokine receptor expressing population targeted by the column will be used for monitoring treatment as discussed herein.

Examples 22 and 23

Materials and Methods

Isolation of Peripheral Blood Leukocytes.

Heparinized peripheral blood from healthy blood donors or inflammatory bowel disease (IBD) patients was fixed with 4% paraformaldehyde for 4 minutes, hemolyzed for 15 minutes with a 0.83% ammonium chloride solution and washed twice in FACS buffer to obtain a suspension of blood leukocytes.

Chemokines.

The leukocytes were incubated for 30 min in the dark at 4° C. with biotinylated and Alexa647 Fluor® labelled MCP-1 (in concentrations 10 ng/μL and 50 ng/μL). The cells were then washed with FACS-buffer and analyzed by flow cytometry. All chemokines used in the Examples were provided by Almac Sciences Scotland Ltd, Edinburgh, Scotland.

Flow Cytometry Assay.

The flow cytometry assay was performed on a two laser FACS Calibur cytometer (BD Immunocytometry systems, San José, Ca, USA). Ten thousand cells were counted and analysed in each sample. For data analyses, Cell Quest Pro software from Becton Dickinson was used.

Example 22

Binding of Monocytes to MCP-1

In the experiment with biotinylated MCP-1 it was found that about 90% of the monocytes obtained from peripheral blood of healthy donors had bound to the cytokine after 30 min of incubation (FIG. 46a), whereas CD4+ and CD8+ lymphocytes had not bound (FIGS. 46b and 46c).

Example 23

Monocytes were investigated for their expression of CCR2 (FIG. 47b) and their ability to bind MCP-1 (FIG. 47a). CCR2 expression was noted an all monocytes with the majority of monocytes expressing high levels, using an anti-CCR2 antibody (FIG. 47b). The MCP-1 binding to monocytes shown in FIG. 47a corresponds to the CCR2$^{hi}$ expressing population shown in FIG. 47b. Thus, MCP-1 binds favourably to CCR2$^{hi}$ expressing cells.

Example 24

Tailored Leukapheresis

Column Design and Properties
Introduction

Apheresis is an established treatment used for depletion of blood components, such as antibodies, low-density lipoproteins (LDL) and blood cells. Leukapheresis is the apheresis treatment used for removal of white blood cells, leukocytes. The patient is connected to an extracorporeal blood circulating system; the blood is drawn from a vein in one arm, passed through a column device and returned into the other arm of the patient. Side effects of leukapheresis treatments are varying from mild events like headache, dizziness, hypotension, palpitation and flush seen in 0.1 to 5% of treated patients.

The Column

The column is intended to be used as a leukapheresis treatment for inflammatory arthritis. It will specifically remove CCR2, CCR1, CCR3 or CCR5-expressing leukocytes, in particular monocytes, through the use of a binding reagent, more specifically an MCP-1, MCP-2, MCP-3, MCP-4, MCP-5 and/or RANTES containing resin, exploiting the CCR2, CCR1, CCR3 or CCR5-chemokine interaction. The column consists of three combined components, the plastic house, the streptavidin (SA) Sepharose™ BigBeads matrix and one or more of biotinylated MCP-1, MCP-2, MCP-3, MCP-4, MCP-5 and RANTES bound to the matrix. The treatment is conducted using the same techniques as a standard apheresis procedure.

The Plastic House (FIG. 9)

The plastic house, designed to keep a continuous blood flow through the matrix, consists of a transparent body and red-coloured top. The top has a distribution plate (2) at the inflow site (1) to spread the blood evenly over the entire matrix area. The plate is the first safety barrier preventing larger particles flowing through the column and into the patient. Safety filter units (3 and 4) are placed at the inflow (1) and outflow (5) sites of the plastic housing. The safety filter unit contains three filters designed to be a robust barrier and stop all particles larger than blood cells passing through the column. The plastic housing design is shown in FIG. 9. The design with safety filters (3 and 4) at both ends of the column device will minimize the risk of leakage of particles into the patient, including in the event that the device is placed up side down with the blood flow in the opposite direction to that anticipated.

Streptavidin Sepharose™ BigBeads

The second component in the device is the affinity matrix called streptavidin Sepharose™ BigBeads (Sepharose™ GE Healthcare, Sweden). Sepharose™ is a cross linked, beaded-form of agarose, which is a polysaccharide extracted from seaweed. Sepharose™ and agarose are commonly used as column matrices in biomedical affinity techniques. It is chosen for its optimal distribution capacity and can provide a large available area for affinity binding.

Binding Reagent

Coupled to the matrix is the third component of the device, one or more binding reagents that bind specifically to CCR2, CCR1, CCR3 or CCR5. One or more chemokines selected from the group consisting of: MCP-1, MCP-2, MCP-3, MCP-4, MCP-5 and RANTES may be employed. These peptides may be synthetic, engineered versions of the human chemokine, which are truncated and biotinylated, but retain binding activity to the CCR2, CCR1, CCR3 or CCR5 receptor. By biotinylating the engineered chemokine, it is able to bind to the streptavidin molecules in the Sepharose™ matrix. The biotin-streptavidin binding is known be one of the strongest biological interactions with a Kd in the order of $4 \times 10^{-14}$ M. The calculated ratio of streptavidin:biotin binding sites in the column is 10:1. Therefore, the coupling between the matrix and chemokine will be immediate, minimising the risk of chemokine decoupling from the matrix.

The Apheresis System

To conduct the leukapheresis the following components are needed; the column, tubing system, and a 4008 ADS pump (Fresenius Medical Care).

The Circuit

The system is illustrated in FIG. 10. The patient (1) is connected to the extracorporeal circuit via sterile Venflon needles to veins in the right and the left arms. A saline bag (3) is also connected and the saline solution is pumped with an ACD pump (2). Blood is drawn from one arm of the patient through the sterile tubing system by the blood pump (4) and passed through the column (6) and back to the patient. The tubing system is connected to the column via standard dialysis luer-lock couplings. The couplings on the column are colour-coded for correct assembly; red tubing for inflow to the red column top and blue tubing for outflow back to the patient. An air detector (8) is present. Inlet pressure (5) and Pven sensors (7) are employed to monitor the pressure in the circuit.

The 4008 ADS Pump

An apheresis pump, from Fresenius Medical Care, monitors the patient's inflow and outflow, the pressure in the extracorporeal circulation and can discriminate air by a bubble catcher and air detector. A clot catcher filter is placed inside the bubble catcher. The pump also has an optical detector to distinguish between light, e.g. saline solution or air present in the tubing system and dark e.g. blood present in the tubing system.

A schematic diagram of the pump, showing the air detector and optical filter is shown in FIG. 11. If the pump system detects air bubbles and optical fluctuations or if extracorporeal pressure values are out of the set range, then the pump stops immediately and a visual/audible alarm are emitted.

Legend for FIG. 11:
1. Monitor
2. Holder for waste bag
3. Modules (left to right—Blood pump, ACD pump, Air detector)
4. Reserve places for further modules
5. Absorber holder
6. Drip detector
7. IV pole Preparation of the Patient The patient will be administered anticoagulants prior to each treatment session. A sterile saline solution with 5000 IE Heparin will be used for priming the extracorporeal system, thereafter a bolus injection with 4000 IE Heparin will be added into the circuit at the start of each treatment session.

Leukapheresis Time and Flow Rate

The apheresis system should be operated at a flow rate of 30-60 mL/min. A treatment is finalised after 1800 mL of blood has been circulated.

Storage Conditions

The column devices should be stored between 1 and 25° C. avoiding freezing and more elevated temperatures. Stability data >3 months indicate no difference in functionality over time or by temperature (room temperature and refrigerated). The columns will be kept in refrigerated conditions until use. Mechanical damage as those resulting from violent vibrations and trauma should be avoided. Column stored outside of these recommendations should not be used.

Transport Conditions

The column devices will be transported under refrigerated condition, avoiding freezing and more elevated temperatures. Mechanical damage such as those resulting from violent vibrations and trauma should be avoided.

In-Vitro Depletion of Target Cell Populations

To investigate the ability to eliminate CCR2-expressing cells, in vitro tests have been performed on the bMCP-1 coupled matrix. Blood was collected from blood donors and passed through the column device containing bMCP-1 coupled matrix. Blood samples were taken before and after column passage and analyzed by flow cytometry (FACS) for the depletion of CCR2-expressing cells.

The results demonstrate significant depletion of the target population CCR2-expressing monocytes post matrix perfusion. Depletion tests were performed on blood from three healthy donors. The results are shown in FIG. 48a.

The in-vitro results demonstrate a specific reduction of up to 80% of the CCR2-expressing cells by the column. Notably, individuals with fewer CCR2 expressing cells initially achieved lower depletion. The remaining levels of monocytes were around 20-30% in each case, irrespective of the starting point. Non-CCR2-expressing cells remained unaffected (data not shown).

To investigate the ability to eliminate CCR1, 3 and 5-expressing cells, in vitro tests have been performed on the biotinylated RANTES coupled matrix. Blood was collected from blood donors and passed through the magnetic column device containing biotinylated RANTES coupled MACS beads. Blood samples were taken before and after column passage and analyzed by flow cytometry (FACS) for the depletion of CCR1, 3 or 5-expressing cells. The results demonstrate significant depletion of the target population chemokine receptor-expressing cells post matrix perfusion. Depletion tests were performed on blood from a healthy donor. The results are shown in FIG. 48b.

The in-vitro results demonstrate a specific reduction of around 20% of the chemokine receptor-expressing cells by the column. Non-CCR1, 3 and 5-expressing cells remained unaffected (data not shown).

The RANTES molecule was synthesized by Almac. The amino acid sequence of the biotinylated RANTES molecule is set forth as SEQ ID NO: 34:

H2N-SPYSSDTTPCCFAYIARPLPRAHIKEYFYTSGKCSNPAVVFVTRKN

RQVCANPEKKWVREYINSLEKS-CO2H

This molecule has the naturally occurring methionine at position 67 replaced with lysine to facilitate biotinylation at position 67.

The side-chain of Lys 67 was directly biotinylated to given the protein primary structure shown in FIG. 54. The protein was folded and disulphide bonds formed between the first and third cysteine in the sequence and between the 2nd and 4th cysteines.

Example 25

MCP1 Derivatives

MCP-1 has been produced with residue 75 as the site of biotinylation on the chemokine (numbering based upon the mature protein having the amino acid sequence of SEQ ID NO: 25). Biotinylation permits immobilization of MCP-1 on a solid support (via a biotin-avidin interaction). The basic amino acid sequence of MCP-1, including a 23 amino acid leader sequence is set forth as SEQ ID NO: 24,

```
MKVSAALLCL LLIAATFIPQ GLAQPDAINA PVTCCYNFTN

RKISVQRLAS YRRITSSKCP KEAVIFKTIV AKEICADPKQ

KWVQDSMDHL DKQTQTPKT
```

The amino acid sequence of the mature protein is set forth as SEQ ID NO: 25,

```
QPDAINA PVTCCYNFTN RKISVQRLAS YRRITSSKCP

KEAVIFKTIV AKEICADPKQ KWVQDSMDHL DKQTQTPKT
```

The inventors have determined that chemokines may display improved binding properties where the chemokine is biotinylated via a spacer group. The spacer may prevent the biotin group from impacting on the binding affinity of the chemokine.

Thus, MCP-1 derivatised at the ε-amino side chain functionality of Lys75 with PEG-Biotin (TFA salt) will be synthesised. The PEG spacer will be 3,6,-dioxoaminooctanoic acid. The Gln at the N-terminus of the proteins is subject to pyroGlu formation under physiological conditions. Thus the first glutamine (Gln1) of the sequence will be substituted with pyroglutamine. The molecule will be synthesised as a C-terminal amide (via synthesis on an amide linker). The molecule is shown schematically in FIG. 49.

A biotinMCP-1 Met to Nleu analogue will also be synthesised. The single methionine within the sequence will be altered to Norleucine, to mitigate against oxidation of this residue during the chain assembly and improve stability of the final product. This molecule is shown schematically in FIG. 50.

Once synthesised, the activity of the various biotinMCP-1 derivatives will be determined in cell-based assays. In particular, agonist and antagonist properties will be determined in aequorin functional cell-based assay on human CCR2 receptor.

Example 26

Synthesis of a Ccr2 Antagonist Biotinmcp-1 which Binds to the Receptor without Activation Antagonist Activity (J-H Gong and I. Clark-Lewis, J. Exp. Med., 1995, 181, 63) has been shown for an MCP-1 derivative truncated at the N-terminus. In particular, deletion of residues 1-8, results in binding to CCR2 with Kd 8.3 nM. This protein was unable to cause chemotaxis of CCR2 positive cells. (inhibition of chemotaxis IC50 20 nM)

The amino acid sequence of the truncated version is set forth as SED ID NO: 26:

```
VTCCYNFTN RKISVQRLAS YRRITSSKCP KEAVIFKTIV

AKEICADPKQ KWVQDSMDHL DKQTQTPKT
```

A derivative of this truncated version will be synthesised comprising residues 9 to 76 of the mature protein (MCP-1 9-76) with Met64 to Nleu substitution and derivatised at the ε-amino side chain functionality of Lys75 with PEG-Biotin (TFA salt). This molecule is shown schematically in FIG. 51. The PEG spacer will be 3,6,-dioxoaminooctanoic acid.

Once synthesised, the activity of the various biotinMCP-1 derivatives will be determined in cell-based assays. In particular, agonist and antagonist properties will be determined in aequorin functional cell-based assay on human CCR2 receptor.

Example 27

Demonstrate Removal of Ccr2 Expressing Cells Using an Alternative Chemokine Ligand to mcp-1

CCR2 also binds chemokines MCP-2, MCP-3, MCP-4, MCP-5, and HCC-4 in addition to MCP-1. MCP-5 only binds CCR2 and should be selective in its removal of CCR2 expressing cells. MCP5 is a mouse chemokine shown to chemotact human CCR2 cells with EC50<3 nM.

The full length amino acid sequence, including the signal peptide, is set forth as SEQ ID NO: 27

```
MKISTLLCLL LIATTISPQV LAGPDAVSTP VTCCYNVVKQ

KIHVRKLKSY RRITSSQCPR EAVIFRTILD KEICADPKEK

WVKNSINHLD KTSQTFILEP SCLG
```

The amino acid sequence of N-terminal processed MCP-5 chemokine is 82 amino acids long and is set forth as SEQ ID NO: 28

```
GPDAVSTP VTCCYNVVKQ KIHVRKLKSY RRITSSQCPR

EAVIFRTILD KEICADPKEK WVKNSINHLD KTSQTFILEP SCLG
```

An amino acid sequence alignment suggests that MCP-5 has a C-terminal extension when compared to the amino acid sequence of MCP-1. The results of this alignment are shown in FIG. 52. On this basis a C-terminal truncated version of MCP-5 will be synthesised. This truncated version will comprise MCP-5 residues 1-76, set forth as SEQ ID NO: 29:

```
GPDAVSTP VTCCYNVVKQ KIHVRKLKSY RRITSSQCPR

EAVIFRTILD KEICADPKEK WVKNSINHLD KTSQTFIL
```

In the truncated version, Ile75 to be substituted with Lys, set forth as SEQ ID NO: 27:

```
GPDAVSTP VTCCYNVVKQ KIHVRKLKSY RRITSSQCPR

EAVIFRTILD KEICADPKEK WVKNSINHLD KTSQTFKL
```

Following substitution, the substituted version will be biotinylated at position 75, a lysine or other suitable residue such as ornithine or diaminopropanoic acid via A PEG spacer (3,6,-dioxoaminooctanoic acid). The protein will be synthesised on an amide linker to yield a C-terminal amide derivative. This molecule is shown schematically in FIG. 53.

Once synthesised, the activity of the various biotinMCP-5 derivatives will be determined in cell-based assays. In particular, agonist and antagonist properties will be determined in aequorin functional cell-based assay on human CCR2 receptor.

Once synthesised, the activity of the various biotinMCP-5 derivatives will be determined in cell-based assays. In particular, agonist and antagonist properties will be determined in aequorin functional cell-based assay on human CCR2 receptor.

Examples 28 to 31

Chemokine Synthesis

General Protocols
Assembly:

Chemical synthesis of chemokines was performed using standard Fmoc solid phase peptides synthesis (SPPS) techniques on an ABI 433 peptide synthesiser. DIC (0.5 M in DMF) and OxymaPure (0.5 M in DMF) were used for activation, acetic anhydride (0.5 M in DMF) for capping, and 20% piperidine in DMF for Fmoc deprotection. Rink Amide resin was utilised for the generation of C-terminal amide chemokines and Wang resin for C-terminal acid chemokines. After assembly, the resin was washed with DMF and DCM and then dried in vacuo.

Removal of Dde Protection:

The Dde protecting group was removed by treatment of resin with a solution of 2.5% hydrazine in DMF (200 ml) over a 2 hour period. The resin was then washed with DMF.

Labelling Steps:
1. Couple Fmoc-8-Amino-3,6-Dioctanoic Acid (PEG)

Resin was swollen in DMF and then a solution of Fmoc-8-amino-3,6-dioctanoic acid (0.38 g, 1 mmol), DIC solution (2 ml, 0.5 M in DMF) and OxymaPure solution (2 ml, 0.5 M in DMF) was added. The mixture was sonicated for 3 hours and then washed with DMF.

2. Capping

The resin was capped with acetic anhydride solution (0.5 M in DMF, 10 ml) for 5 minutes and then washed with DMF.

3. Fmoc Deprotection

Fmoc deprotection was carried out by treatment with 20% piperidine in DMF solution (2×50 ml) for 15 minutes each. The resin was washed with DMF.

4. Couple Biotin-OSu

A solution of Biotin-OSu (341 mg, 1 mmol) and DIPEA (348 ml) in DMF (10 ml) was added to the resin and the mixture was sonicated for 3 hours. The resin was washed thoroughly with DMF and DCM then dried in vacuo.

Cleavage:

Dry resin was treated with TFA (10 ml) containing a scavenger cocktail consisting of TIS (500 ml), thioanisole (500 ml), water (500 ml), DMS (500 ml), EDT (250 ml), $NH_4I$ (500 mg) and phenol (500 mg) and the mixture was stirred at room temperature for 5 hours. The solution was filtered into cold ether and the resin rinsed with TFA. The precipitated peptide was centrifuged, washed with ether, centrifuged and lyophilised.

Purification Protocol:

The crude peptide was purified by reverse phase HPLC (RP-HPLC) using a Jupiter C18, 250×21 mm column, 9 ml/min, eluting with an optimised gradient [Buffer A: water containing 0.1% TFA, Buffer B: acetonitrile containing 0.1% TFA].

Folding Protocol:

Pure peptide (10 mg) was dissolved into 6M GnHCl (16 ml) and then rapidly diluted to 2M GnHCl concentration by the addition of 50 mM TRIS pH 8.5 (84 ml) containing 0.3 mM GSSG and 3 mM GSH. The mixture was stirred at room temperature for 24 hours and then analysed by RP-HPLC (Jupiter C18, 250×4.6 mm column, 10-60% B over 30 minutes. Purification by RP-HPLC using an optimised gradient afforded the desired product.

Example 28

BiotinMCP-1 (CCL2)

Target Molecule:

MCP-1 derivatised at the ε-amino side chain functionality of Lys(75) with PEG-Biotin (TFA salt)

Modifications:

Human MCP-1 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the ε-amino functionality and the biotin.

The linear amino acid sequence (SEQ ID NO: 31) is shown, prior to attachment of the PEG spacer and biotin molecules at amino acid 75 (K):

H-XPDAINAPVTCCYNFTNRKISVQRLASYRRITSSKCPKEAVIFKTIVA

KEICADPKQKWVQDSMDHLDKQTQTPKT-NH$_2$

X=pyroGlu or Gln

The engineered MCP-1 sequence was assembled on a solid support (Rink Amide resin), using Fmoc protocols for solid-phase peptide synthesis as described in the general protocols section:

SEQ ID NO: 32
H-XPDAINAPVTCCYNFTNRKISVQRLASYRRITSSKCPKEAVIFKTIVA

KEICADPKQKWVQDSMDHLDKQTQTPXT-RESIN

X1=pyroGlu or Gln
X75=K(ivDde)

FmocLys(ivDde)-OH was incorporated as residue 75 to facilitate site-specific labelling at this position of the protein. Subsequent removal of the ivDde protecting group, followed by coupling of the PEG spacer and Biotin, was carried out as described in the general protocol section. Cleavage, purification and folding protocols were carried out as described to furnish the desired active chemokine.

SEQ ID NO: 33
H-XPDAINAPVTCCYNFTNRKISVQRLASYRRITSSKCPKEAVIFKTIVA

KEICADPKQKWVQDSMDHLDKQTQTPXT-NH$_2$

X1=pyroGlu or Gln
X75 is an amino acid residue that can be biotinylated, such as lysine, ornithine or diaminopropionic acid and optionally is biotinylated, optionally via a spacer molecule such as PEG, optionally K(PEG-Biotin)

Electrospray ionisation with tandem mass spectrometry (ESI-TOF-MS) data of purified folded biotinMCP-1: obtained=9032.8 Da; expected 9034.4 Da.

Functional Assay Data:

biotinMCP-1 was tested for agonist activity in an Aequorin assay against hCCR2b, (Euroscreen) and an EC50 value of 9.6 nM was reported. c.f. EC50 for recombinant native MCP-1 is 3.1 nM.

Example 29

BiotinRANTES (CCL5)

Target Molecule:

RANTES derivatised at the ε-amino side chain functionality of Lys(67) with Biotin (TFA salt)

Modifications:

Human RANTES corresponding to residues 1-68, is initially expressed as 91 amino acids comprising the chemokine fold, and a 23 amino acid signal peptide which is cleaved off. The single methionine (Met67) within the sequence was mutated to lysine, to mitigate against oxidation of this residue during the chain assembly, which was observed during the synthesis of the natural sequence derivative. This Met to Lys substitution provided a lysine at position 67 which was modified through biotinylation on the resin.

The linear amino acid sequence (SEQ ID NO: 34) is shown, prior to attachment of the biotin molecule at amino acid 67 (K):

H-SPYSSDTTPCCFAYIARPLPRAHIKEYFYTSGKCSNPAVVFVTRKNRQ

VCANPEKKWVREYINSLEKS-OH

The engineered RANTES sequence was assembled on a solid support (Wang resin), using Fmoc protocols for solid-phase peptide synthesis as described in the general protocols section:

H-SPYSSDTTPCCFAYIARPLPRAHIKEYFYTSGKCSNPAVVFVTRKNRQ

VCANPEKKWVREYINSLEXS-RESIN

X is K(ivDde)

FmocLys(ivDde)-OH was incorporated as residue 67 to facilitate site-specific labelling at this position of the protein (SEQ ID NO: 35). Subsequent removal of the ivDde protecting group, followed by coupling of the Biotin, was carried out as described in the general protocol section. Cleavage, purification and folding protocols were carried out as described to furnish the desired active chemokine (SEQ ID NO: 36).

H-SPYSSDTTPCCFAYIARPLPRAHIKEYFYTSGKCSNPAVVFVTRKNRQ

VCANPEKKWVREYINSLEXS-OH

X is an amino acid residue that can be biotinylated, such as lysine, ornithine or diaminopropionic acid and optionally is biotinylated, optionally via a spacer molecule such as PEG (e.g. K(Biotin))

Electrospray ionisation with tandem mass spectrometry (ESI-TOF-MS) data of purified folded biotinRANTES: obtained=8068.9 Da; expected 8070.2 Da.

Functional Assay Data:

BiotinRANTES was tested for agonist activity in an Aequorin assay against hCCR5, (Euroscreen) and an EC50 value of 0.5 nM was reported.

Example 30

BiotinMCP-2 (CCL8)

Target Molecule: MCP-2 derivatised at the e-amino side chain functionality of Lys(75) with PEG-Biotin (TFA salt)

Modifications:

Human MCP-2 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the ε-amino functionality and the biotin.

The linear amino acid sequence (SEQ ID NO: 37) is shown, prior to attachment of the PEG spacer and biotin molecules at amino acid 75 (K):

H-XPDSVSIPITCCFNVINRKIPIQRLESYTRITNIQCPKEAVIFKTKR

GKEVCADPKERWVRDSMKHLDQIFQNLKP-NH$_2$

X=pyroGlu or Gln

The engineered MCP-2 sequence was assembled on a solid support (Rink Amide resin), using Fmoc protocols for solid-phase peptide synthesis as described in the general protocols section:

H-XPDSVSIPITCCFNVINRKIPIQRLESYTRITNIQCPKEAVIFKTKR

GKEVCADPKERWVRDSMKHLDQIFQNLXP-NH$_2$

X1=pyroGlu or Gln X75=K(ivDde)

FmocLys(ivDde)-OH was incorporated as residue 75 to facilitate site-specific labelling at this position of the protein (SEQ ID NO: 38). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 39):

H-XPDSVSIPITCCFNVINRKIPIQRLESYTRITNIQCPKEAVIFKTKR

GKEVCADPKERWVRDSMKHLDQIFQNLXP-NH$_2$

X1=pyroGlu or Gln

X75=an amino acid residue that can be biotinylated, such as lysine, ornithine or diaminopropionic acid and optionally is biotinylated, optionally via a spacer molecule such as PEG, e.g. K(PEG-Biotin).

Electrospray ionisation with tandem mass spectrometry (ESI-TOF-MS) data of purified folded biotinMCP-2: obtained=9263.6 Da; expected 9263.8 Da.

Functional Assay Data:

biotinMCP-2 was tested for activity in an Aequorin assay against hCCR2b, (Euroscreen) and was shown to be a partial agonist with an EC50 value of 50.9 nM. c.f. EC50 for recombinant native MCP-2 is 23.5 nM (partial agonist).

Example 31

BiotinEotaxin (CCL11)

Target Molecule Eotaxin derivatised at the ε-amino side chain functionality of Lys(73) with PEG-Biotin (TFA salt)

Modifications:

Human eotaxin corresponding to residues 1-74, is initially expressed as 97 amino acids comprising the chemokine fold, and a 23 amino acid signal peptide which is cleaved off. The naturally occurring lysine at position 73 was modified through biotinylation on the resin. A PEG spacer was incorporated between the ε-amino functionality and the biotin.

The linear amino acid sequence (SEQ ID NO: 40) is shown, prior to attachment of the PEG spacer and biotin molecules at amino acid 73 (K):

H-GPASVPTTCCFNLANRKIPLQRLESYRRITSGKCPQKAVIFKTKLA

KDICADPKKKWVQDSMKYLDQKSPTPXP-NH$_2$

X is an amino acid residue that can be biotinylated, such as lysine, ornithine or diaminopropionic acid and optionally is biotinylated, optionally via a spacer molecule such as PEG, e.g. K(PEG-Biotin).

The engineered eotaxin sequence was assembled on a solid support (Rink Amide resin), using Fmoc protocols for solid-phase peptide synthesis as described in the general protocols section:

H-GPASVPTTCCFNLANRKIPLQRLESYRRITSGKCPQKAVIFKTKLAKD

ICADPKKKWVQDSMKYLDQKSPTPXP-NH$_2$

X is K(ivDde)

FmocLys(ivDde)-OH was incorporated as residue 73 to facilitate site-specific labelling at this position of the protein (SEQ ID NO: 41). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 42):

H-GPASVPTTCCFNLANRKIPLQRLESYRRITSGKCPQKAVIFKTKLAKD

ICADPKKKWVQDSMKYLDQKSPTPXP-NH$_2$

X is K(PEG-Biotin)

Electrospray ionisation with tandem mass spectrometry (ESi-TOF-MS) data of purified folded biotinEotaxin: obtained=8731.3 Da; expected 8731.3 Da.

Functional Assay Data:

biotinEotaxin was tested for activity in an Aequorin assay against hCCR3, (Euroscreen) and was shown to be an antagonist with an EC50 value of 211.8 nM. c.f. EC50 for recombinant native eotaxin is 10.7 nM (agonist).

Example 32

Diagnosis and Treatment of Inflammatory Arthritis

Materials and Methods
1. Flow Cytometric Analysis of Peripheral Blood

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH$_4$Cl, pH 7.5) for 15 min at 37° C. The cells were washed in PBS with 2% Bovine Growth Serum, incubated with 10% human serum for 15 min at room temperature (RT) and stained with antibodies (Table 19) at 4° C. for 30 min. The cells were analysed by flow cytometry on a FACS Canto flow cytometer with the FACSDiva software (BD Biosciences).

TABLE 19

List of antibodies for flow cytometric analysis.

| Antibody | Fluorophore | Supplier |
|---|---|---|
| CD14 | FITC | Beckman Coulter |
| CCR5 | PE | Biolegend |
| Streptavidin | PE, APC | Biolegend |
| CCR2 | PerCP Cy5.5 | Biolegend |
| CD16 | PE Cy7 | BD Biosciences |
| CCR1 | Alexa Fluor 647 | Biolegend |
| CD3 | V450 | BD Biosciences |
| CD19 | V500 | BD Biosciences |

2. Chemokine Binding Test

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5) for 15 min at 37° C. The cells were washed in PBS with 2% Bovine Growth Serum, incubated with 10% human serum 15 min at room temperature (RT) and stained with cell specific antibodies together with biotinylated chemokine (1 μM) or the corresponding chemokine receptor antibody at 4° C. for 30 min (Table 19). The biotinylated chemokine was detected via the interaction between biotin and a fluorophore conjugated Streptavidin. The samples were analysed by flow cytometry on a FACS Canto flow cytometer with the FACSDiva software (BD Biosciences).

3. Cell Depletion by Matrix Conjugated with Biotinylated Chemokine

Cells were prepared from peripheral blood (section 1). 1 mL Sepharose BigBeads matrix conjugated with 0.4 mg/mL Streptavidin (GE Healthcare) was washed in 50 mL PBS and added to a 5 mL polystyrene tube (BD Falcon™). Biotinylated chemokine (1 μM) was added to the tube and incubated for 20 min at RT to enable immobilization of the chemokine on the matrix via the biotin-streptavidin interaction. Next, the cells were added to the chemokine-matrix and incubated for 20 min at RT. The cells that did not bind to the matrix were removed by washing the matrix with PBS in a sterile 40 um nylon filter (BD Falcon™ Cell Strainer). The flow through cells were stained with antibodies (Table 19), analysed by flow cytometry and compared with cells from peripheral blood that had not been incubated with the chemokine-matrix.

Results and Discussion
1. Flow Cytometric Analysis of Peripheral Blood
White blood cells from patients with RE were analysed for the expression of chemokine receptors with flow cytometry. The majority of the monocytes express the chemokine receptors CCR1 (FIG. 56a) and CCR2 (FIG. 56b) and 40% of the T cells express CCR5 (FIG. 56b), based upon flow cytometry data and binding by anti-CCR1, anti-CCR2 and anti-CCR5 antibodies.
2. Chemokine Binding Test The ligand for CCR2 is MCP-1 (CCL2) and the ligand for CCR1 and CCR5 is RANTES (CCL5). Both MCP1 and RANTES are expressed in the synovial fluid of patients with rheumatoid arthritis and are associated with migration of inflammatory immune cells into the joint.

Circulating blood cells from RE patient bound to biotinylated MCP1 (bMCP1) and biotinylated RANTES (bRANTES) (FIGS. 57a and 57b).

3. Cell Depletion by Matrix Conjugated with Biotinylated Chemokine

A majority of the CCR2 expressing monocytes were efficiently depleted with bMCP1-conjugated Sepharose Streptavidin Matrix. (FIG. 58a). 64% of the CCR5 expressing T cells were efficiently depleted with bRANTES-conjugated Sepharose Streptavidin Matrix. (FIG. 58b).

We conclude that circulating immune cells in rheumatoid arthritis patients express CCR1, CCR2 and CCR5 and bind the ligands bMCP1 and bRANTES. Furthermore, 94% of the CCR2 and 64% CCR5 expressing cells can be removed with Sepharose Streptavidin matrix conjugated with the corresponding biotinylated chemokine.

D. Treating Cancer

The mechanism behind seeding of metastatic cells in to particular organs is by the expression of chemokines in the organ recruiting chemokine receptor expressing tumor cells. For example metastatic colon cancer cells express CCR6 and they home to liver because CCL20 is expressed in the liver allowing entrance of CCR6 expressing cancer cells.

In non Hodgkin lymphomas (T-NHL) the expression of CCR7 indicates a higher lymphatic dissemination which was demonstrated to migrate towards CCL21, the preferred chemokine for entrance of cells in to lymphoid organs.

Lung cancer metastases seem to be dependent on the expression of CXCR4 on tumour cells and the local expression of the corresponding chemokine CXCL12 (SDF-1) for the successful metastasis. In line with these findings development of small molecules for inhibition of CXCR4 mediated metastasis is under development.

Regulatory T cells (Tregs) are upregulated in many cancers as an immune escape mechanism induced by the tumor. In order to avoid immune recognition and elimination tumors activate and recruit Tregs. The production of chemokines by the tumor results in recruitment of circulating Tregs and therefore protection against immune recognition and elimination. Tregs may be recruited to the tumour by CCL17 and CCL22 binding to CCR4 expressed on the Treg. In addition CCR8 mediated recruitment by CCL1 may occur. Since many treatment regimes with chemotherapy involve activation of the immune system, eliminating Tregs in the circulation by leukapheresis may thus favour immune recognition and elimination of tumor cells, thereby enhancing cancer therapy.

In chronic leukemic disorders the number of circulating tumor cells inhibit normal hematopoeis and therefore cause symptoms. The increased production of chemokines such as CCL3 correlates with poor prognosis (Blood. 2011 Feb. 3; 117(5):1662-9. Epub 2010 Nov. 29). Thus elimination of chemokine receptor expressing leukemic cells will favorably affect the disease in terms of symptoms and disease progression.

It is shown herein that cancer patients, in particular subjects suffering from UBC and PC, exhibit an increased frequency of CCR4 expressing circulating Tregs and that this response is specific to Tregs (and does not apply to other T lymphocytes). CCR4 expressing cells may be thus be targeted in order to treat cancer. Treatment may rely upon suitable binding reagents such as CCL22 (MDC) and derivatives thereof, as described herein in further detail. It is also shown herein that subject suffering from leukemias, such as CLL, have a highly increased number of circulating B cells. The B cells express characteristic chemokine receptors, such as CCR7. It is also shown herein that CCR7 expressing B cells may be efficiently depleted using MIP3b as a specific binding reagent in a leukapheresis method.

Example 33

Tailored Leukapheresis

Column Design and Properties
Introduction

Apheresis is an established treatment used for depletion of blood components, such as antibodies, low-density lipoproteins (LDL) and blood cells. Leukapheresis is the apheresis treatment used for removal of white blood cells, leukocytes. The patient is connected to an extracorporeal blood circulating system; the blood is drawn from a vein in one arm, passed through a column device and returned into the other arm of the patient. Side effects of leukapheresis treatments are varying from mild events like headache, dizziness, hypotension, palpitation and flush seen in 0.1 to 5% of treated patients.

The Column

The column is intended to be used as a leukapheresis treatment for cancer. It will specifically remove CCR5, CCR6, CCR7, CCR8, CXCR4, CXCR7, CCR4, CCR9, CCR10, CXCR3 and/or CXCR5-expressing cells, such as tumour cells and leukocytes, such as regulatory T lymphocytes, through the use of a binding reagent, more specifically an MIP-3alpha (CCL20), CCL19, CCL21, CCL1, CXCL11, CXCL12, CCL25 (TECK), CCL27 (CTACK), CCL28 (MEC), CXCL9 (MIG), CXCL10 (IP10), CXCL13 (BCA-1), CCL17 (TARC) and CCL22 (MDC) containing resin, exploiting the CCR5, CCR6, CCR7, CCR8, CXCR4, CXCR7, CCR4, CCR9, CCR10, CXCR3 and/or CXCR5-chemokine interaction. Treg receptor expressing cells, such as CLA receptor, CCR4 or CCR8 expressing cells may be specifically removed through the use of an appropriate binding reagent, more specifically an SELE, CCL17, CCL22 and/or CCL1 containing resin. The column consists of three combined components, the plastic house, the streptavidin (SA) Sepharose™ BigBeads matrix and one or more of biotinylated MIP-3alpha (CCL20), CCL19, CCL21, CCL1, CXCL11, CXCL12, CCL25 (TECK), CCL27 (CTACK), CCL28 (MEC), CXCL9 (MIG), CXCL10 (IP10), CXCL13 (BCA-1), CCL17 (TARC) and CCL22 (MDC) and/or SELE, CCL17, CCL22 and/or CCL1 bound to the matrix. The treatment is conducted using the same techniques as a standard apheresis procedure.

The Plastic House (FIG. 9)

The plastic house, designed to keep a continuous blood flow through the matrix, consists of a transparent body and red-coloured top. The top has a distribution plate (2) at the inflow site (1) to spread the blood evenly over the entire matrix area. The plate is the first safety barrier preventing larger particles flowing through the column and into the patient. Safety filter units (3 and 4) are placed at the inflow (1) and outflow (5) sites of the plastic housing. The safety filter unit contains three filters designed to be a robust barrier and stop all particles larger than blood cells passing through the column. The plastic housing design is shown in FIG. 1. The design with safety filters (3 and 4) at both ends of the column device will minimize the risk of leakage of particles into the patient, including in the event that the device is placed up side down with the blood flow in the opposite direction to that anticipated.

Streptavidin Sepharose™ BigBeads

The second component in the device is the affinity matrix called streptavidin Sepharose™ BigBeads (Sepharose™ GE Healthcare, Sweden). Sepharose™ is a cross linked, beaded-form of agarose, which is a polysaccharide extracted from seaweed. Sepharose™ and agarose are commonly used as column matrices in biomedical affinity techniques. It is chosen for its optimal distribution capacity and can provide a large available area for affinity binding.

Binding Reagent

Coupled to the matrix is the third component of the device, one or more binding reagents that bind specifically to CCR5, CCR6, CCR7, CCR8, CXCR4, CXCR7, CCR4, CCR9, CCR10, CXCR3 and/or CXCR5 and/or to CLA receptor, CCR4 and/or CCR8 where Tregs are specifically targeted. One or more chemokines selected from the group consisting of: MIP-3alpha (CCL20), CCL19, CCL21, CCL1, CXCL11, CXCL12, CCL25 (TECK), CCL27 (CTACK), CCL28 (MEC), CXCL9 (MIG), CXCL10 (IP10), CXCL13 (BCA-1), CCL17 (TARC) and CCL22 (MDC) may be employed. Alternatively, SELE, CCL17, CCL22 and/or CCL1 may be employed to target Tregs. These peptides may be synthetic, engineered versions of the human chemokine, which are truncated and biotinylated, but retain binding activity to the CCR5, CCR6, CCR7, CCR8, CXCR4, CXCR7, CCR4, CCR9, CCR10, CXCR3 and/or CXCR5 receptor (or CLA receptor, CCR4 and/or CCR8 where Tregs are targeted). By biotinylating the engineered chemokine, it is able to bind to the streptavidin molecules in the Sepharose™ matrix. The biotin-streptavidin binding is known be one of the strongest biological interactions with a Kd in the order of $4 \times 10^{-14}$ M. The calculated ratio of streptavidin:biotin binding sites in the column is 10:1. Therefore, the coupling between the matrix and chemokine will be immediate, minimising the risk of chemokine decoupling from the matrix.

The Apheresis System

To conduct the leukapheresis the following components are needed; the column, tubing system, and a 4008 ADS pump (Fresenius Medical Care).

The Circuit

The system is illustrated in FIG. 10. The patient (1) is connected to the extracorporeal circuit via sterile Venflon needles to veins in the right and the left arms. A saline bag (3) is also connected and the saline solution is pumped with an ACD pump (2). Blood is drawn from one arm of the patient through the sterile tubing system by the blood pump (4) and passed through the column (6) and back to the patient. The tubing system is connected to the column via standard dialysis luer-lock couplings. The couplings on the column are colour-coded for correct assembly; red tubing for inflow to the red column top and blue tubing for outflow back to the patient. An air detector (8) is present. Inlet pressure (5) and Pven sensors (7) are employed to monitor the pressure in the circuit.

The 4008 ADS Pump

An apheresis pump, from Fresenius Medical Care, monitors the patient's inflow and outflow, the pressure in the extracorporeal circulation and can discriminate air by a bubble catcher and air detector. A clot catcher filter is placed inside the bubble catcher. The pump also has an optical detector to distinguish between light, e.g. saline solution or air present in the tubing system and dark e.g. blood present in the tubing system.

A schematic diagram of the pump, showing the air detector and optical filter is shown in FIG. 11. If the pump system detects air bubbles and optical fluctuations or if extracorporeal pressure values are out of the set range, then the pump stops immediately and a visual/audible alarm are emitted.

LEGEND FOR FIG. 11

1. Monitor
2. Holder for waste bag
3. Modules (left to right—Blood pump, ACD pump, Air detector)
4. Reserve places for further modules
5. Absorber holder
6. Drip detector
7. IV pole Preparation of the Patient The patient will be administered anticoagulants prior to each treatment session. A sterile saline solution with 5000 IE Heparin will be used for priming the extracorporeal system, thereafter a bolus injection with 4000 IE Heparin will be added into the circuit at the start of each treatment session.

Leukapheresis Time and Flow Rate

The apheresis system should be operated at a flow rate of 30-60 mL/min. A treatment is finalised after 1800 mL of blood has been circulated.

Storage Conditions

The column devices should be stored between 1 and 25° C. avoiding freezing and more elevated temperatures. Stability data >3 months indicate no difference in functionality over time or by temperature (room temperature and refrigerated). The columns will be kept in refrigerated conditions until use. Mechanical damage as those resulting from violent vibrations and trauma should be avoided. Column stored outside of these recommendations should not be used.

Transport Conditions

The column devices will be transported under refrigerated condition, avoiding freezing and more elevated temperatures. Mechanical damage such as those resulting from violent vibrations and trauma should be avoided.

In-Vitro Depletion of Target Cell Populations

To investigate the ability to eliminate CCR6-expressing cells, in vitro tests have been performed on the biotinylated MIP-3alpha coupled matrix. Blood was collected from blood donors and passed through the column device containing biotinylated MIP-3alpha coupled matrix. Blood samples were taken before and after column passage and analyzed by flow cytometry (FACS) for the depletion of CCR6-expressing cells.

The results demonstrate significant depletion of the target population CCR6-expressing lymphocytes post matrix perfusion. Depletion tests were performed on blood from three healthy donors. The results are shown in FIG. 59.

The in-vitro results demonstrate a specific reduction of up to around 15% of the CCR6-expressing cells by the column. Non-CCR6-expressing cells remained unaffected (data not shown).

Example 34A

Treatment of Chronic Lymphatic Leukemia (CLL) Patient

Materials and Methods

1. Flow Cytometric Analysis of Peripheral Blood

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5) for 15 min at 37° C. The cells were washed in PBS with 2% Bovine Growth Serum, incubated with 10% human serum for 15 min at room temperature (RT) and stained with antibodies (Table 20) at 4° C. for 30 min. The cells were analysed by flow cytometry on a FACS Canto flow cytometer with the FACSDiva software (BD Biosciences).

TABLE 20

List of antibodies for flow cytometric analysis.

| Antibody | Fluorophore | Supplier |
|---|---|---|
| CD14 | FITC | Beckman Coulter |
| Streptavidin | PE, APC | Biolegend |
| CCR7 | PerCP Cy5.5 | Biolegend |
| CD16 | PE Cy7 | BD Biosciences |
| CD3 | V450 | BD Biosciences |
| CD19 | V500 | BD Biosciences |

2. Chemokine Binding Test

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5) for 15 min at 37° C. The cells were washed in PBS with 2% Bovine Growth Serum, incubated with 10% human serum for 15 min at room temperature (RT) and stained with cell specific antibodies together with biotinylated chemokine (1 µM) or the corresponding chemokine receptor antibody at 4° C. for 30 min (Table 20). The biotinylated chemokine was detected via the interaction between biotin and a fluorophore conjugated Streptavidin. The samples were analysed by flow cytometry on a FACS Canto flow cytometer with the FACSDiva software (BD Biosciences).

3. Cell Depletion by Matrix Conjugated with Biotinylated Chemokine

Cells were prepared from peripheral blood (section 1). 1 mL Sepharose BigBeads matrix conjugated with 0.4 mg/mL Streptavidin (GE Healthcare) was washed in 50 mL PBS and added to a 5 mL polystyrene tube (BD Falcon™). Biotinylated chemokine (1 µM) was added to the tube and incubated for 20 min at RT to enable immobilization of the chemokine on the matrix via the biotin-streptavidin interaction. Next, the cells were added to the chemokine-matrix and incubated for 20 min at RT. The cells that did not bind to the matrix were removed by washing the matrix with PBS in a sterile 40 µm nylon filter (BD Falcon™ Cell Strainer). The flow through cells were stained with antibodies (Table 20), analysed by flow cytometry and compared with cells from peripheral blood that had not been incubated with the chemokine-matrix.

Results and Discussion

1. Flow Cytometric Analysis of Peripheral Blood

White blood cells from a CLL patient were analysed by flow cytometry. The patient had a highly increased number of circulating B cells; 92% compared to approximately 2% in healthy blood (FIG. 61). This finding is common in CLL where malignant B cells undergo extensive proliferation, accumulate in the bone marrow and blood and crowd out healthy blood cells.

2. Chemokine Binding Test

All the B cells were shown to express the chemokine receptor CCR7 (FIG. 62) based upon flow cytometry data and binding by an anti-CCR7 antibody. CCR7 is important for lymph node homing which is mediated by binding to chemokines such as MIP3b (CCL19) and SLC (CCL21) that are expressed in lymphoid tissue. In accordance with the CCR7 expression, all the B cells bound to a biotinylated MIP3b (bMIP3b) (FIG. 63).

3. Cell Depletion by Matrix Conjugated with Biotinylated Chemokine

The B cells were efficiently depleted using bMIP3b-conjugated Sepharose Streptavidin Matrix. Before depletion the B cells constituted 89.1% of the cells and after depletion 26.4% (FIG. 64).

We conclude that B cells in CLL express CCR7 and bind the ligand bMIP3b. Furthermore the majority (62.7%) of the CCR7 expressing B cells can be removed using a Sepharose Streptavidin matrix conjugated with bMIP3b.

Example 34B

Treatment of Cancers Via Removal of CCR4 Expressing Tregs Using Biotinylated-MDC (CCL22)

Materials and Methods

1. Flow Cytometric Analysis of Peripheral Blood

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH$_4$Cl, pH 7.5) for 15 min at 37° C. The cells were washed in PBS with 2% Bovine Growth Serum, incubated with 10% human serum for 15 min at room temperature (RT) and stained with antibodies (Table 21) at 4° C. for 30 min. The cells were analysed by flow cytometry on a FACS Canto flow cytometer with the FACSDiva software (BD Biosciences).

TABLE 21

List of antibodies for flow cytometric analysis.

| Antibody | Fluorophore | Supplier |
|---|---|---|
| CCR4 | PerCP Cy5.5 | BD Biosciences |
| CD127 | PE Cy7 | Biolegend |
| CD4 | V500 | Biolegend |
| CD25 | APCCy7 | Biolegend |
| CD3 | Pacific blue | BD Biosciences |
| Streptavdin | PerCpCy5.5 | BD Biosciences |
| CD25 | FITC | BD Biosciences |

2. Chemokine Binding Test

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5)

for 15 min at 37° C. The cells were washed in PBS with 2% Bovine Growth Serum, incubated with 10% human serum 15 min at room temperature (RT) and stained with cell specific antibodies together with biotinylated chemokine (1 µM) or the corresponding chemokine receptor antibody at 4° C. for 30 min (Table 21). The biotinylated chemokine was detected via the interaction between biotin and a fluorophore conjugated Streptavidin. The samples were analysed by flow cytometry on a FACS Canto flow cytometer with the FACSDiva software (BD Biosciences).

3. Cell Depletion by Matrix Conjugated with Biotinylated Chemokine

Cells were prepared from peripheral blood (section 1). 1 mL Sepharose BigBeads matrix conjugated with 0.4 mg/mL Streptavidin (GE Healthcare) was washed in 50 mL PBS and added to a 5 mL polystyrene tube (BD Falcon™). Biotinylated chemokine (1 µM) was added to the tube and incubated for 20 min at RT to enable immobilization of the chemokine on the matrix via the biotin-streptavidin interaction. Next, the cells were added to the chemokine-matrix and incubated for 20 min at RT. The cells that did not bind to the matrix were removed by washing the matrix with PBS in a sterile 40 um nylon filter (BD Falcon™ Cell Strainer). The flow through cells were stained with antibodies (Table 21), analysed by flow cytometry and compared with cells from peripheral blood that had not been incubated with the chemokine-matrix.

Results and Discussion

T regulatory cells (Tregs) are a subpopulation of T cells that suppress the immune system in order to maintain immune homeostasis. In cancer, the Tregs can inhibit an effective immune response against the tumor and thus removal of the Tregs could lead to a better immune activation against the cancer cells. White blood cells from patients with Urinary Bladder Cancer (UBC) and Pancreas Cancer (PC) were analyzed for the expression of chemokine receptors with flow cytometry. The cancer patients exhibited an increased frequency of circulating T regulatory cells (Tregs) that expressed the chemokine receptor CCR4, based upon flow cytometry data and binding by an anti-CCR4 antibody (FIG. 65). In both UBC and PC patients, CCR4 was highly upregulated on Tregs compared with the total T cell population (FIG. 66).

The ligand for CCR4 is the chemokine MDC (CCL22). In accordance with the CCR4 expression, the Tregs bound to biotinylated MDC (bMDC) (FIG. 67).

The CCR4 expressing T cells could be depleted with bMDC-conjugated Sepharose Streptavidin Matrix (FIG. 68).

We conclude that the frequency of Tregs that express CCR4 is enhanced in PC and UBC. These cells can bind the ligand bMDC. The Tregs express significantly more CCR4 than conventional T cells and can thus be specifically deleted with Sepharose Streptavidin matrix conjugated with bMDC.

Examples 35 to 42

General Protocols

Synthesis of Chemokines
Assembly:

Chemical synthesis of chemokines was performed using standard Fmoc solid phase peptides synthesis (SPPS) techniques on an ABI 433 peptide synthesiser. DIC (0.5 M in DMF) and OxymaPure (0.5 M in DMF) were used for activation, acetic anhydride (0.5 M in DMF) for capping, and 20% piperidine in DMF for Fmoc deprotection. Rink Amide resin was utilised for the generation of C-terminal amide chemokines and Wang resin for C-terminal acid chemokines. After assembly, the resin was washed with DMF and DCM and then dried in vacuo.

Removal of Dde Protection:

The Dde protecting group was removed by treatment of resin with a solution of 2.5% hydrazine in DMF (200 ml) over a 2 hour period. The resin was then washed with DMF.

Labelling Steps:

1. Couple Fmoc-8-Amino-3,6-Dioctanoic Acid (PEG)

Resin was swollen in DMF and then a solution of Fmoc-8-amino-3,6-dioctanoic acid (0.38 g, 1 mmol), DIC solution (2 ml, 0.5 M in DMF) and OxymaPure solution (2 ml, 0.5 M in DMF) was added. The mixture was sonicated for 3 hours and then washed with DMF.

2. Capping

The resin was capped with acetic anhydride solution (0.5 M in DMF, 10 ml) for 5 minutes and then washed with DMF.

3. Fmoc deprotection

Fmoc deprotection was carried out by treatment with 20% piperidine in DMF solution (2×50 ml) for 15 minutes each. The resin was washed with DMF.

4. Couple Biotin-OSu

A solution of Biotin-OSu (341 mg, 1 mmol) and DIPEA (348 ml) in DMF (10 ml) was added to the resin and the mixture was sonicated for 3 hours. The resin was washed thoroughly with DMF and DCM then dried in vacuo.

Cleavage:

Dry resin was treated with TFA (10 ml) containing a scavenger cocktail consisting of TIS (500 ml), thioanisole (500 ml), water (500 ml), DMS (500 ml), EDT (250 ml), $NH_4I$ (500 mg) and phenol (500 mg) and the mixture was stirred at room temperature for 5 hours. The solution was filtered into cold ether and the resin rinsed with TFA. The precipitated peptide was centrifuged, washed with ether, centrifuged and lyophilised.

Purification Protocol:

The crude peptide was purified by reverse phase HPLC (RP-HPLC) using a Jupiter C18, 250×21 mm column, 9 ml/min, eluting with an optimised gradient [Buffer A: water containing 0.1% TFA, Buffer B: acetonitrile containing 0.1% TFA].

Folding Protocol:

Pure peptide (10 mg) was dissolved into 6M GnHCl (16 ml) and then rapidly diluted to 2M GnHCl concentration by the addition of 50 mM TRIS pH 8.5 (84 ml) containing 0.3 mM GSSG and 3 mM GSH. The mixture was stirred at room temperature for 24 hours and then analysed by RP-HPLC (Jupiter C18, 250×4.6 mm column, 10-60% B over 30 minutes). Purification by RP-HPLC using an optimised gradient afforded the desired product.

Example 35

BiotinMCP-2 (CCL8)

Target Molecule:

MCP-2 derivatised at the e-amino side chain functionality of Lys(75) with PEG-Biotin (TFA salt)

Modifications:

Human MCP-2 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the ε-amino functionality and the biotin.

The linear amino acid sequence (SEQ ID NO: 43) is shown, prior to attachment of the PEG spacer and biotin molecules at amino acid 75 (K):

H-XPDSVSIPITCCFNVINRKIPIQRLESYTRITNIQCPKEAVIFKTKR

GKEVCADPKE RWVRDSMKHLDQIFQNLXP-NH$_2$

X1=pyroGlu or Gln
X75=an amino acid residue that can be biotinylated, such as lysine, ornithine or diaminopropionic acid and optionally is biotinylated, optionally via a spacer molecule such as PEG, in particular K(PEG-Biotin)

The engineered MCP-2 sequence was assembled on a solid support (Rink Amide resin), using Fmoc protocols for solid-phase peptide synthesis as described in the general protocols section:

H-XPDSVSIPITCCFNVINRKIPIQRLESYTRITNIQCPKEAVIFKTKRG

KEVCADPKERWVRDSMKHLDQIFQNLXP-NH$_2$

X1=pyroGlu or Gln
X75=K(ivDde)

FmocLys(ivDde)-OH was incorporated as residue 75 to facilitate site-specific labelling at this position of the protein (SEQ ID NO: 44). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 45).

H-XPDSVSIPITCCFNVINRKIPIQRLESYTRITNIQCPKEAVIFKTKRG

KEVCADPKERWVRDSMKHLDQIFQNLXP-NH$_2$

X1=pyroGlu or Gln
X75=K(PEG-Biotin)

Electrospray ionisation with tandem mass spectrometry (ESI-TOF-MS) data of purified folded biotinMCP-2: obtained=9263.6 Da; expected 9263.8 Da.
Functional Assay Data:

biotinMCP-2 was tested for activity in an Aequorin assay against hCCR2b, (Euroscreen) and was shown to be a partial agonist with an EC50 value of 50.9 nM. c.f. EC50 for recombinant native MCP-2 is 23.5 nM (partial agonist).

Example 36

BiotinRANTES (CCL5)

Target Molecule:
RANTES derivatised at the ε-amino side chain functionality of Lys(67) with Biotin (TFA salt)
Modifications:
Human RANTES corresponding to residues 1-68, is initially expressed as 91 amino acids comprising the chemokine fold, and a 23 amino acid signal peptide which is cleaved off. The single methionine (Met67) within the sequence was mutated to lysine, to mitigate against oxidation of this residue during the chain assembly, which was observed during the synthesis of the natural sequence derivative. This Met to Lys substitution provided a lysine at position 67 which was modified through biotinylation on the resin.

The linear amino acid sequence (SEQ ID NO: 46) is shown, prior to attachment of the biotin molecule at amino acid 67 (K):

H-SPYSSDTTPCCFAYIARPLPRAHIKEYFYTSGKCSNPAVVFVTRKNRQ

VCANPEKKWVREYINSLEKS-OH

The engineered RANTES sequence was assembled on a solid support (Wang resin), using Fmoc protocols for solid-phase peptide synthesis as described in the general protocols section:

H-SPYSSDTTPCCFAYIARPLPRAHIKEYFYTSGKCSNPAVVFVTRKNRQ

VCANPEKKWVREYINSLEXS-RESIN

X=K(ivDde)

FmocLys(ivDde)-OH was incorporated as residue 67 to facilitate site-specific labelling at this position of the protein (SEQ ID NO: 47). Subsequent removal of the ivDde protecting group, followed by coupling of the Biotin, was carried out as described in the general protocol section. Cleavage, purification and folding protocols were carried out as described to furnish the desired active chemokine (SEQ ID NO: 48).

H-SPYSSDTTPCCFAYIARPLPRAHIKEYFYTSGKCSNPAVVFVTRKNRQ

VCANPEKKWVREYINSLEXS-OH

X is an amino acid residue that can be biotinylated, such as lysine, ornithine or diaminopropionic acid and optionally is biotinylated (e.g. K-biotin), optionally via a spacer molecule such as PEG, in particular K(PEG-Biotin)

Electrospray ionisation with tandem mass spectrometry (ESI-TOF-MS) data of purified folded biotinRANTES: obtained=8068.9 Da; expected 8070.2 Da.
Functional Assay Data:

BiotinRANTES was tested for agonist activity in an Aequorin assay against hCCR5, (Euroscreen) and an EC50 value of 0.5 nM was reported.

Example 37

BiotinMIP-3a (CCL20)

Target Molecule:
MIP-3a derivatised at the ε-amino side chain functionality of Lys(68) with PEG-Biotin (TFA salt)
Modifications:
Human MIP-3a corresponding to residues 1-70, is initially expressed as 96 amino acids comprising the chemokine fold, and a 26 amino acid signal peptide which is cleaved off. The naturally occurring lysine at position 68 was modified through biotinylation on the resin. A PEG spacer was incorporated between the ε-amino functionality and the biotin.

The linear amino acid sequence (SEQ ID NO: 49) is shown, prior to attachment of the PEG spacer and biotin molecules at amino acid 68 (K):

H-ASNFDCCLGYTDRILHPKFIVGFTRQLANEGCDINAIIFHTKKKLSVC

ANPKQTWVKYIVRLLSKKVKNM-OH

The engineered MIP-3a sequence was assembled on a solid support (Wang resin), using Fmoc protocols for solid-phase peptide synthesis as described in the general protocols section:

H-ASNFDCCLGYTDRILHPKFIVGFTRQLANEGCDINAIIFHTKKKLSVC

ANPKQTWVKYIVRLLSKKVXNM-RESIN

X=K(ivDde)
FmocLys(ivDde)-OH was incorporated as residue 68 to facilitate site-specific labelling at this position of the protein (SEQ ID NO: 50). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 51).

H-ASNFDCCLGYTDRILHPKFIVGFTRQLANEGCDINAIIFHTKKKLSVC

ANPKQTWVKYIVRLLSKKVXNM-OH

X is an amino acid residue that can be biotinylated, such as lysine, ornithine or diaminopropionic acid and optionally is biotinylated, optionally via a spacer molecule such as PEG, in particular K(PEG-Biotin)
Electrospray ionisation with tandem mass spectrometry (ESI-TOF-MS) data of purified folded biotinMip-3a: obtained=8396.4 Da; expected 8397.0 Da.
Functional Assay Data:
BiotinMIP-3a was tested for agonist activity in an Aequorin assay against hCCR6, (Euroscreen) and an EC50 value of 1.6 nM was reported. c.f. EC50 for recombinant native MIP-3a is 1.0 nM.

Example 38

BiotinSDF-1a (CXCL12)

Target Molecule:
SDF-1a derivatised at the e-amino side chain functionality of Lys(64) with Biotin (TFA salt)
Modifications:
Truncated form of human SDF-1a corresponding to residues 1-67 of the mature protein, which encompasses the sequence corresponding to the chemokine fold. The full length mature protein is 72 amino acids (the signal peptide is 21 amino acids in a 93 amino acid immature protein). The naturally occurring lysine at position 64 was modified through biotinylation on the resin.
The linear amino acid sequence (SEQ ID NO: 52) is shown, prior to attachment of the biotin molecule at amino acid 64 (K):

H-KPVSLSYRCPCRFFESHVARANVKHLKILNTPNCALQIVARLKNNNR

QVCIDPKLKWIQEYLEKALN-OH

The engineered SDF-1a sequence was assembled on a solid support (Wang resin), using Fmoc protocols for solid-phase peptide synthesis as described in the general protocols section:

H-KPVSLSYRCPCRFFESHVARANVKHLKILNTPNCALQIVARLKNNNRQ

VCIDPKLKWIQEYLEKXALN-RESIN

X=K(ivDde)
FmocLys(ivDde)-OH was incorporated as residue 64 to facilitate site-specific labelling at this position of the protein (SEQ ID NO: 53). Subsequent removal of the ivDde protecting group, followed by coupling of the Biotin, was carried out as described in the general protocol section. Cleavage, purification and folding protocols were carried out as described to furnish the desired active chemokine (SEQ ID NO: 54).

H-KPVSLSYRCPCRFFESHVARANVKHLKILNTPNCALQIVARLKNNNRQ

VCIDPKLKWIQEYLEXALN-OH

X is an amino acid residue that can be biotinylated, such as lysine, ornithine or diaminopropionic acid and optionally is biotinylated, optionally via a spacer molecule such as PEG, especially K(Biotin)
Electrospray ionisation with tandem mass spectrometry (ESI-TOF-MS) data of purified folded biotinSDF-1a: obtained=8055.5 Da; expected 8057.5 Da.
Functional Assay Data:
biotinSDF-1a was tested for agonist activity in an Aequorin assay against hCXCR4, (Euroscreen) and an EC50 value of 17.3 nM was reported. c.f. EC50 for recombinant native SDF-1a is 12.0 nM.

Example 39

BiotinMDC (CCL22)

Target Molecule:
MDC derivatised at the e-amino side chain functionality of Lys(66) with PEG-Biotin (TFA salt)
Modifications:
Human MDC corresponding to residues 1-69, is initially expressed as 93 amino acids comprising the chemokine fold, and a 24 amino acid signal peptide which is cleaved off. The naturally occurring lysine at position 66 was modified through biotinylation on the resin. A PEG spacer was incorporated between the ϵ-amino functionality and the biotin.
The linear amino acid sequence (SEQ ID NO: 55) is shown, prior to attachment of the PEG spacer and biotin molecules at amino acid 66 (K):

H-GPYGANMEDSVCCRDYVRYRLPLRVVKHFYWTSDSCPRPGVVLLTF

RDKEICADPRVPWVKMILNKLSQ-NH$_2$

The engineered MDC sequence was assembled on a solid support (Rink Amide resin), using Fmoc protocols for solid-phase peptide synthesis as described in the general protocols section:

H-GPYGANMEDSVCCRDYVRYRLPLRVVKHFYWTSDSCPRPGVVLLTFRD

KEICADPRVPWVKMILNXLSQ-RESIN

X=K(ivDde)
FmocLys(ivDde)-OH was incorporated as residue 66 to facilitate site-specific labelling at this position of the protein (SEQ ID NO: 56). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 57).

H-GPYGANMEDSVCCRDYVRYRLPLRVVKHFYWTSDSCPRPGVVLLTFR

DKEICADPRVPWVKMILNXLSQ-NH$_2$

X is an amino acid residue that can be biotinylated, such as lysine, ornithine or diaminopropionic acid and optionally is biotinylated, optionally via a spacer molecule such as PEG, especially K(PEG-Biotin)

Electrospray ionisation with tandem mass spectrometry (ESI-TOF-MS) data of purified folded biotinMDC: obtained=8456.1 Da; expected 8456.9 Da.

Functional Assay Data:

BiotinMDC was tested for agonist activity in an Aequorin assay against hCCR4, (Euroscreen) and an EC50 value of 4.5 nM was reported. c.f. EC50 for recombinant native MDC is 3.6 nM.

Example 40

BiotinTARC (CCL17)

Target Molecule:

TARC derivatised at the e-amino side chain functionality of Lys(72) with PEG-Biotin (TFA salt)

Modifications:

Human TARC corresponding to residues 1-71, is initially expressed as 94 amino acids comprising the chemokine fold, and a 23 amino acid signal peptide which is cleaved off. An additional lysine was inserted at the C-terminus, at position 72, and modified through biotinylation on the resin. A PEG spacer was incorporated between the ε-amino functionality and the biotin.

The linear amino acid sequence (SEQ ID NO: 58) is shown, prior to attachment of the PEG spacer and biotin molecules at amino acid 72 (K):

H-ARGTNVGRECCLEYFKGAIPLRKLKTWYQTSEDCSRDAIVFVTVQGRA

ICSDPNNKRVKNAVKYLQSLERSX-NH$_2$

X is an amino acid residue that can be biotinylated, such as lysine, ornithine or diaminopropionic acid and optionally is biotinylated (e.g. K-biotin), optionally via a spacer molecule such as PEG, in particular K(PEG-Biotin)

The engineered TARC sequence was assembled on a solid support (Rink Amide resin), using Fmoc protocols for solid-phase peptide synthesis as described in the general protocols section:

H-ARGTNVGRECCLEYFKGAIPLRKLKTWYQTSEDCSRDAIVFVTVQG

RAICSDPNNKRVKNAVKYLQSLERSX-RESIN

X=K(ivDde)

FmocLys(ivDde)-OH was incorporated as residue 72 to facilitate site-specific labelling at this position of the protein (SEQ ID NO: 59). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 60).

H-ARGTNVGRECCLEYFKGAIPLRKLKTWYQTSEDCSRDAIVFVTVQG

RAICSDPNNKRVKNAVKYLQSLERSX-NH$_2$

X=K(PEG-Biotin)

Electrospray ionisation with tandem mass spectrometry (ESI-TOF-MS) data of purified folded biotinTARC: obtained=8577.2 Da; expected 8577.8 Da.

Functional Assay Data:

BiotinTARC was tested for agonist activity in an Aequorin assay against hCCR4, (Euroscreen) and an EC50 value of 3.1 nM was reported. c.f. EC50 for recombinant native TARC is 2.6 nM.

Example 41

BiotinMIP-3b (CCL19)

Target Molecule:

MIP-3b derivatised at the e-amino side chain functionality of Lys(78) with Biotin (TFA salt)

Modifications:

Human MIP-3b corresponding to residues 1-77, is initially expressed as 98 amino acids comprising the chemokine fold, and a 21 amino acid signal peptide which is cleaved off. An additional lysine was inserted at the C-terminus, at position 78, and modified through biotinylation on the resin.

The linear amino acid sequence (SEQ ID NO: 61) is shown, prior to attachment of the biotin molecule at amino acid 78 (K):

H-GTNDAEDCCLSVTQKPIPGYIVRNFHYLLIKDGCRVPAVVFTTLRGRQ

LCAPPDQPWVERIIQRLQRTSAKMKRRSSX-NH$_2$

X is an amino acid residue that can be biotinylated, such as lysine, ornithine or diaminopropionic acid and optionally is biotinylated (e.g. K-biotin), optionally via a spacer molecule such as PEG, in particular K(PEG-Biotin)

The engineered MIP-3b sequence was assembled on a solid support (Rink Amide resin), using Fmoc protocols for solid-phase peptide synthesis as described in the general protocols section:

H-GTNDAEDCCLSVTQKPIPGYIVRNFHYLLIKDGCRVPAVVFTTLRGRQ

LCAPPDQPWVERIIQRLQRTSAKMKRRSSX-RESIN

X is FmocLys(ivDde)

FmocLys(ivDde)-OH was incorporated as residue 78 to facilitate site-specific labelling at this position of the protein (SEQ ID NO: 62). Subsequent removal of the ivDde protecting group, followed by coupling of the Biotin, was carried out as described in the general protocol section. Cleavage, purification and folding protocols were carried out as described to furnish the desired active chemokine (SEQ ID NO: 63).

H-GTNDAEDCCLSVTQKPIPGYIVRNFHYLLIKDGCRVPAVVFTTLRGRQ

LCAPPDQPWVERIIQRLQRTSAKMKRRSSX-NH$_2$

X is K(Biotin)

Electrospray ionisation with tandem mass spectrometry (ESI-TOF-MS) data of purified folded biotinMIP-3b: obtained=9148.8 Da; expected 9149.7 Da.

Functional Assay Data:

biotinMip-3b was tested for agonist activity in an Aequorin assay against hCCR7, (Euroscreen) and an EC50 value of 11.0 nM was reported. c.f. EC50 for recombinant native MIP-3b is 1.6 nM.

Example 42

BiotinITAC (CXCL11)

Target Molecule:

ITAC derivatised with Biotin at the e-amino side chain functionality of an additional Lysine inserted at the C-terminus after a PEG spacer (TFA salt)

Modifications:

Human ITAC corresponding to residues 1-73, is initially expressed as 94 amino acids comprising the chemokine fold, and a 21 amino acid signal peptide which is cleaved off. A PEG spacer and an additional lysine were inserted at the C-terminus, and modified through biotinylation on the resin. The PEG spacer was incorporated at the C-terminus between the protein and the additional lysine.

The linear amino acid sequence (SEQ ID NO: 64) is shown, prior to attachment of the PEG spacer, additional lysine and biotin molecules:

H-FPMFKRGRCLCIGPGVKAVKVADIEKASIMYPSNNCDKIEVIITLKEN

KGQRCLNPKSKQARLIIKKVERKNF-OH

The engineered ITAC sequence was assembled on a solid support (Wang resin), using Fmoc protocols for solid-phase peptide synthesis as described in the general protocols section:

H-FPMFKRGRCLCIGPGVKAVKVADIEKASIMYPSNNCDKIEVIITLKEN

KGQRCLNPKSKQARLIIKKVERKNFX-RESIN

X is PEG-K(ivDde)

Fmoc-12-amino-4,7,10-trioxadodecanoic acid followed by FmocLys(ivDde)-OH were incorporated at the C-terminus to facilitate site-specific labelling with biotin at the ε-amino side chain functionality of the additional Lys (SEQ ID NO: 66). Subsequent removal of the ivDde protecting group, followed by coupling of the Biotin, was carried out as described in the general protocol section. Cleavage, purification and folding protocols were carried out as described to furnish the desired active chemokine (SEQ ID NO: 67).

H-FPMFKRGRCLCIGPGVKAVKVADIEKASIMYPSNNCDKIEVIITLKEN

KGQRCLNPKSKQARLIIKKVERKNFX-OH

X is PEG-K(Biotin)

Electrospray ionisation with tandem mass spectrometry (ESI-TOF-MS) data of purified folded biotinITAC: obtained=8866.5 Da; expected 8860.6 Da.

Functional Assay Data:

biotinITAC was tested for agonist activity in an Aequorin assay against hCXCR3, (Euroscreen) and an EC50 value of 15.7 nM was reported. c.f. EC50 for recombinant native ITAC is 0.7 nM.

Example 43

BiotinTECK (CCL25)

Target Molecule:

TECK (Met to Nleu substitution) derivatised at the ε-amino side chain functionality of Lys72 with PEG-Biotin (TFA salt)

Modifications:

Truncated form of human TECK corresponding to residues 1-74 of the mature protein, which encompasses the sequence corresponding to the chemokine fold. The full length mature protein is 127 amino acids (the signal peptide is 23 amino acids in a 150 amino acid immature protein). The single methionine within the sequence was altered to Norleucine, to mitigate against oxidation of this residue during the chain assembly, which was observed during the synthesis of the natural sequence derivative. The Gln at the N-terminus of the proteins is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 72 was modified through biotinylation on the resin. A PEG spacer was incorporated between the ε-amino functionality and the biotin.

The linear amino acid sequence (SEQ ID NO: 68) is shown, prior to attachment of the PEG spacer and biotin molecules at amino acid 72 (K):

H-XGVFEDCCLAYHYPIGWAVLRRAWTYRIQEVSGSCNLPAAIFYLPKR

HRKVCGNPKSREVQRAXKLLDARNXVF-OH

X1=pyroGlu or Gln
X64=Norleucine
X72=an amino acid residue that can be biotinylated, such as lysine, ornithine or diaminopropionic acid and optionally is biotinylated, optionally via a spacer molecule such as PEG, e.g. K(PEG-Biotin)

The engineered TECK sequence was assembled on a solid support (Wang resin), using Fmoc protocols for solid-phase peptide synthesis as described in the general protocols section:

H-XGVFEDCCLAYHYPIGWAVLRRAWTYRIQEVSGSCNLPAAIFYLPKRH

RKVCGNPKSREVQRAXKLLDARNXVF-RESIN

X1=pyroGlu or Gln
X64=Norleucine
X72=K(ivDde)

FmocLys(ivDde)-OH was incorporated as residue 72 to facilitate site-specific labelling at this position of the protein (SEQ ID NO: 69). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 70).

H-XGVFEDCCLAYHYPIGWAVLRRAWTYRIQEVSGSCNLPAAIFYLPKRH

RKVCGNPKSREVQRAXKLLDARNXVF-OH

X1=pyroGlu or Gln
X64=Norleucine
X72 is K(PEG-Biotin)

Electrospray ionisation with tandem mass spectrometry (ESI-TOF-MS) data of purified folded biotinTECK(Met to Nleu substitution): obtained=8958.5 Da; expected 8959.6 Da.

Functional Assay Data:

biotinTECK(Met to Nleu substitution) was tested for agonist activity in an Aequorin assay against hCCR9, (Euroscreen) and an EC50 value of 63.6 nM was reported. c.f. EC50 for recombinant native TECK is 67.9 nM.

Example 44

BiotinCTAC (CCL27)

Target Molecule:

CTAC derivatised at the ε-amino side chain functionality of Lys(87) with PEG-Biotin (TFA salt)

Modifications:

Human CTAC corresponding to residues 1-88, is initially expressed as 112 amino acids comprising the chemokine fold, and a 24 amino acid signal peptide which is cleaved off. The Met(87) within the sequence was mutated to lysine to provide a lysine at position 87 which was modified through biotinylation on the resin. A PEG spacer was incorporated between the ε-amino functionality and the biotin.

The linear amino acid sequence (SEQ ID NO: 71) is shown, prior to attachment of the PEG spacer and biotin molecules:

FLLPPSTACCTQLYRKPLSDKLLRKVIQVELQEADGDCHLQAFVLHLAQR

SICIHPQNPSLSQWFEHQERKLHGTLPKLNFGMLRKXG

X is an amino acid residue that can be biotinylated, such as lysine, ornithine or diaminopropionic acid and optionally is biotinylated, optionally via a spacer molecule such as PEG, e.g. K(PEG-Biotin)

The engineered CTAC sequence was assembled on a solid support (Wang resin), using Fmoc protocols for solid-phase peptide synthesis as described in the general protocols section:

H-FLLPPSTACCTQLYRKPLSDKLLRKVIQVELQEADGDCHLQAFVLHLA

QRSICIHPQNPSLSQWFEHQERKLHGTLPKLNFGMLRKXG-RESIN

X=K(ivDde)

FmocLys(ivDde)-OH was incorporated as residue 87 to facilitate site-specific labelling at this position of the protein (SEQ ID NO: 72). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 73).

H-FLLPPSTACCTQLYRKPLSDKLLRKVIQVELQEADGDCHLQAFVLHLA

QRSICIHPQNPSLSQWFEHQERKLHGTLPKLNFGMLRKXG-OH

X=K(PEG-Biotin)

Electrospray ionisation with tandem mass spectrometry (ESI-TOF-MS) data of purified folded biotinCTAC: obtained=10513.4 Da; expected 10514.2 Da.

Functional Assay Data:

BiotinCTAC was tested for agonist activity in an Aequorin assay against hCCR10, (Euroscreen) and an EC50 value of 49.4 nM was reported. c.f. EC50 for recombinant native CTAC is 33.5 nM.

Example 45

BiotinIP-10 (CXCL10)

Target Molecule:

IP-10 derivatised with Biotin at the ε-amino side chain functionality of an additional Lysine inserted at the C-terminus after a PEG spacer (TFA salt)

Modifications:

Human IP-10 corresponding to residues 1-77, is initially expressed as 98 amino acids comprising the chemokine fold, and a 21 amino acid signal peptide which is cleaved off. A PEG spacer and an additional lysine were inserted at the C-terminus, and modified through biotinylation on the resin. The PEG spacer was incorporated at the C-terminus between the protein and the additional lysine.

The linear amino acid sequence (SEQ ID NO: 74) is shown, prior to attachment of the PEG spacer, additional lysine and biotin molecules:

H-VPLSRTVRCTCISISNQPVNPRSLEKLEIIPASQFCPRVEIIATMKKK

GEKRCLNPESKAIKNLLKAVSKERSKRSP-OH

The engineered IP-10 sequence was assembled on a solid support (Wang resin), using Fmoc protocols for solid-phase peptide synthesis as described in the general protocols section:

H-VPLSRTVRCTCISISNQPVNPRSLEKLEIIPASQFCPRVEIIATMKKK

GEKRCLNPESKAIKNLLKAVSKERSKRSPX-RESIN

X is K(ivDde), optionally attached via a spacer such as PEG, e.g.—PEG-K(ivDde)

Fmoc-8-amino-3,6-dioctanoic acid followed by FmocLys (ivDde)-OH were incorporated at the C-terminus to facilitate site-specific labelling with biotin at the ε-amino side chain functionality of the additional Lys (SEQ ID NO: 75). Subsequent removal of the ivDde protecting group, followed by coupling of the Biotin, was carried out as described in the general protocol section. Cleavage, purification and folding protocols were carried out as described to furnish the desired active chemokine. The final active chemokine thus has the following sequence (SEQ ID NO: 76):

H-VPLSRTVRCTCISISNQPVNPRSLEKLEIIPASQFCPRVEIIATMKKK

GEKRCLNPESKAIKNLLKAVSKERSKRSPX-OH

X is an amino acid residue that can be biotinylated, such as lysine, ornithine or diaminopropionic acid and optionally is biotinylated, optionally via a spacer molecule such as PEG, e.g. K(PEG-Biotin) and may be attached via a spacer molecule, e.g. PEG-K(Biotin)

Electrospray ionisation with tandem mass spectrometry (ESI-TOF-MS) data of purified folded biotinIP-110: obtained=9141.0 Da; expected 9141.9 Da.

Functional Assay Data:

BiotinIP-10 was tested for agonist activity in an Aequorin assay against hCXCR3, (Euroscreen) and an EC50 value of 8.7 nM was reported. c.f. EC50 for recombinant native IP-10 is 4.4 nM.

E. Treating Mental Disorders

Inflammation is an important component of mental disorders such as schizophrenia, depression and bipolar disorder and may involve increased levels of CCR1, CCR3 and/or CCR5 intracellular signalling via CCL11 binding. CCL11 is a ligand for CCR1, CCR3 and/or CCR5, a receptor expressed preferentially on Th2 lymphocytes, mast cells and eosinophils. Higher serum levels of CCL11 in mental disorders such as schizophrenia, depression and bipolar disorder suggest that this disease may be associated with a Th1/Th2 imbalance with a shift toward a Th2 immune response.

In mental disorders, such as Schizophrenia, depression and bipolar disorder, research has focused on finding diagnostic biomarkers to improve classification of disease and treatment of patients. It has been shown in patient plasma samples that high pro-inflammatory cytokine and chemokine expression correlate with depression and fatigue ("Plasma Protein Biomarkers for Depression and Schizophrenia by Multi Analyte Profiling of Case-Control Collections": Domenici E et al, PLoS ONE 5 (2): e9166, 2010).

Clozapine, the first atypical antipsychotic, is indicated for the treatment of therapyresistant schizophrenia. It needs to be monitored closely because of its well-known potential side-effects, especially agranulocytosis. Agranulocytosis, also known as Agranulosis or Granulopenia, is an acute condition involving a severe and dangerous leukopenia (lowered white blood cell count) in the circulating blood. This indicates that granulocytes; neutrophils, basophils and eosinophils are of major importance for the schizophrenic disease.

It is shown herein that subjects suffering from mental disorders such as bipolar disorder exhibit highly increased frequency of chemokine receptor expressing cells in the peripheral blood, in particular CCR9 expressing monocytes, compared to healthy controls. It is also shown herein that the CCR9 cells can be removed using a suitable binding reagent, in particular CCL25 (in biotinylated form) immobilized on a suitable matrix.

Example 46

Materials and Methods

Isolation of Peripheral Blood Leukocytes.

Heparinized peripheral blood from healthy blood donors patients was fixed with 4% paraformaldehyde for 4 minutes, hemolyzed for 15 minutes with a 0.83% ammonium chloride solution and washed twice in FACS buffer to obtain a suspension of blood leukocytes.

Chemokines.

The leukocytes were incubated for 30 min in the dark at 4° C. with biotinylated and Alexa647 Fluor® labeled eotaxin (in concentrations 10 ng/µL and 50 ng/µL). The cells were then washed with FACS-buffer and analyzed by flow cytometry. All chemokines used in the Examples were provided by Almac Sciences Scotland Ltd, Edinburgh, Scotland.

Flow Cytometry Assay.

The flow cytometry assay was performed on a two laser FACS Calibur cytometer (BD Immunocytometry systems, San José, Ca, USA). Ten thousand cells were counted and analysed in each sample. For data analyses, Cell Quest Pro software from Becton Dickinson was used.

Neutrophils/eosinophils were investigated for their expression of CCR3 (FIG. 69b) and their ability to bind eotaxin (FIG. 69a). CCR3 expression was noted on all neutrophils/eosinophils with the majority of neutrophils/eosinophils expressing high levels, using an anti-CCR3 antibody (FIG. 69b). The eotaxin binding to neutrophils/eosinophils shown in FIG. 1a corresponds to the $CCR3^{hi}$ expressing population shown in FIG. 69b. Thus, eotaxin binds favourably to $CCR3^{hi}$ expressing cells.

Example 47

Tailored Leukapheresis

Column Design and Properties
Introduction

Apheresis is an established treatment used for depletion of blood components, such as antibodies, low-density lipoproteins (LDL) and blood cells. Leukapheresis is the apheresis treatment used for removal of white blood cells, leukocytes. The patient is connected to an extracorporeal blood circulating system; the blood is drawn from a vein in one arm, passed through a column device and returned into the other arm of the patient. Side effects of leukapheresis treatments are varying from mild events like headache, dizziness, hypotension, palpitation and flush seen in 0.1 to 5% of treated patients.

The Column

The column is intended to be used as a leukapheresis treatment for mental disorders such as schizophrenia, depression and bipolar disorder. It will specifically remove CCR9, CCR1, CCR3 and/or CCR5-expressing leukocytes, in particular eosinophils, through the use of a binding reagent, more specifically a biotinylated eotaxin containing resin, exploiting the CCR9, CCR1, CCR3 and/or CCR5-chemokine interaction. The column consists of three combined components, the plastic house, the streptavidin (SA) Sepharose™ BigBeads matrix and biotinylated eotaxin bound to the matrix. The treatment is conducted using the same techniques as a standard apheresis procedure.

The Plastic House (FIG. 9)

The plastic house, designed to keep a continuous blood flow through the matrix, consists of a transparent body and red-coloured top. The top has a distribution plate (2) at the inflow site (1) to spread the blood evenly over the entire matrix area. The plate is the first safety barrier preventing larger particles flowing through the column and into the patient. Safety filter units (3 and 4) are placed at the inflow (1) and outflow (5) sites of the plastic housing. The safety filter unit contains three filters designed to be a robust barrier and stop all particles larger than blood cells passing through the column. The plastic housing design is shown in FIG. 9. The design with safety filters (3 and 4) at both ends of the column device will minimize the risk of leakage of particles into the patient, including in the event that the device is placed up side down with the blood flow in the opposite direction to that anticipated.

Streptavidin Sepharose™ BigBeads

The second component in the device is the affinity matrix called streptavidin Sepharose™ BigBeads (Sepharose™ GE Healthcare, Sweden). Sepharose™ is a cross linked, beaded-form of agarose, which is a polysaccharide extracted from seaweed. Sepharose™ and agarose are commonly used as column matrices in biomedical affinity techniques. It is chosen for its optimal distribution capacity and can provide a large available area for affinity binding.

Binding Reagent

Coupled to the matrix is the third component of the device, the binding reagent that binds specifically to CCR9, CCR1, CCR3 and/or CCR5. Chemokines such as eotaxin may be employed. These peptides may be synthetic, engineered versions of the human chemokine, which are truncated and biotinylated, but retain binding activity to the CCR9, CCR1, CCR3 and/or CCR5 receptor. By biotinylating the engineered chemokine, it is able to bind to the streptavidin molecules in the Sepharose™ matrix. The biotin-streptavidin binding is known be one of the strongest biological interactions with a Kd in the order of $4 \times 10^{-14}$ M. The calculated ratio of streptavidin:biotin binding sites in the column is 10:1. Therefore, the coupling between the matrix and chemokine will be immediate, minimising the risk of chemokine decoupling from the matrix.

The Apheresis System

To conduct the leukapheresis the following components are needed; the column, tubing system, and a 4008 ADS pump (Fresenius Medical Care).

The Circuit

The system is illustrated in FIG. 10. The patient (1) is connected to the extracorporeal circuit via sterile Venflon needles to veins in the right and the left arms. A saline bag (3) is also connected and the saline solution is pumped with an ACD pump (2). Blood is drawn from one arm of the patient through the sterile tubing system by the blood pump (4) and passed through the column (6) and back to the patient. The tubing system is connected to the column via standard dialysis luer-lock couplings. The couplings on the column are colour-coded for correct assembly; red tubing for inflow to the red column top and blue tubing for outflow back to the patient. An air detector (8) is present. Inlet pressure (5) and Pven sensors (7) are employed to monitor the pressure in the circuit.

The 4008 ADS Pump

An apheresis pump, from Fresenius Medical Care, monitors the patient's inflow and outflow, the pressure in the extracorporeal circulation and can discriminate air by a bubble catcher and air detector. A clot catcher filter is placed inside the bubble catcher. The pump also has an optical detector to distinguish between light, e.g. saline solution or air present in the tubing system and dark e.g. blood present in the tubing system.

1A schematic diagram of the pump, showing the air detector and optical filter is shown in FIG. 11. If the pump system detects air bubbles and optical fluctuations or if extracorporeal pressure values are out of the set range, then the pump stops immediately and a visual/audible alarm are emitted.

LEGEND FOR FIG. 11

1. Monitor
2. Holder for waste bag
3. Modules (left to right—Blood pump, ACD pump, Air detector)
4. Reserve places for further modules
5. Absorber holder
6. Drip detector
7. IV pole Preparation of the Patient The patient will be administered anticoagulants prior to each treatment session. A sterile saline solution with 5000 IE Heparin will be used for priming the extracorporeal system, thereafter a bolus injection with 4000 IE Heparin will be added into the circuit at the start of each treatment session.

Leukapheresis Time and Flow Rate

The apheresis system should be operated at a flow rate of 30-60 mL/min. A treatment is finalised after 1800 mL of blood has been circulated.

Storage Conditions

The column devices should be stored between 1 and 25° C. avoiding freezing and more elevated temperatures. Stability data >3 months indicate no difference in functionality over time or by temperature (room temperature and refrigerated). The columns will be kept in refrigerated conditions until use. Mechanical damage as those resulting from violent vibrations and trauma should be avoided. Column stored outside of these recommendations should not be used.

Transport Conditions

The column devices will be transported under refrigerated condition, avoiding freezing and more elevated temperatures. Mechanical damage such as those resulting from violent vibrations and trauma should be avoided.

In-Vitro Depletion of Target Cell Populations—Eotaxin

To investigate the ability to eliminate CCR3-expressing cells, in vitro tests have been performed on the eotaxin coupled matrix. Blood was collected from blood donors and passed through the magnetic column device containing eotaxin coupled MACS beads. Blood samples were taken before and after column passage and analyzed by flow cytometry (FACS) for the depletion of CCR3-expressing cells.

The results demonstrate significant depletion of the target population CCR3-expressing neutrophils/eosinophils post matrix perfusion. Depletion tests were performed on blood from a healthy donor. The results are shown in FIG. 70a.

In conclusion, the in-vitro results demonstrate a specific reduction of around 25% of the CCR9, CCR1, CCR3 and/or CCR5-expressing cells by the column. Non-CCR9, CCR1, CCR3 and/or CCR5-expressing cells remained unaffected (data not shown).

In-Vitro Depletion of Target Cell Populations—RANTES

To investigate the ability to eliminate CCR1, 3 and 5-expressing cells, in vitro tests have been performed on the biotinylated RANTES coupled matrix. Blood was collected from blood donors and passed through the column device containing biotinylated RANTES coupled matrix. Blood samples were taken before and after column passage and analyzed by flow cytometry (FACS) for the depletion of CCR1, 3 or 5-expressing cells.

The RANTES molecule was synthesized by Almac. The amino acid sequence of the biotinylated RANTES molecule is set forth as SEQ ID NO: 79:

H2N-SPYSSDTTPCCFAYIARPLPRAHIKEYFYTSGKCSNPAVVFVTRKN

RQVCANPEKKWVREYINSLEKS-CO2H

This molecule has the naturally occurring methionine at position 67 replaced with lysine to facilitate biotinylation at position 67.

The side-chain of Lys 67 was directly biotinylated to given the protein primary structure shown in FIG. 72. The protein was folded and disulphide bonds formed between the first and third cysteine in the sequence and between the 2nd and 4th cysteines. The results demonstrate significant depletion of the target population chemokine receptor-expressing cells post matrix perfusion. Depletion tests were performed on blood from a healthy donor. The results are shown in FIG. 70b.

The in-vitro results demonstrate a specific reduction of around 20% of the chemokine receptor-expressing cells by the column. Non-CCR1, 3 and 5-expressing cells remained unaffected (data not shown).

Example 48

Eotaxin Derivatives

Eotaxin has been produced with Lys73 as the site of biotinylation on the chemokine (numbering based upon the mature protein having the amino acid sequence of SEQ ID NO: 2). Biotinylation permits immobilization of eotaxin on a solid support (via a biotin-avidin interaction). The basic amino acid sequence of eoxtaxin, including a 23 amino acid leader sequence (signal peptide) is set forth as SEQ ID NO: 77,

```
MKVSAALLWL LLIAAAFSPQ GLAGPASVPT TCCFNLANRK IPLQRL

ESYRRITSGKCPQK AVIFKTKLAK DICADPKKKW VQDSMKYLDQ

KSPTPKP
```

The amino acid sequence of the mature protein is set forth as SEQ ID NO: 78,

```
GPASVPT TCCFNLANRK IPLQRLESYR RITSGKCPQK AVIFKTKLA

KDICADPKKKW VQDSMKYLDQ KSPTPKP
```

The inventors have determined that chemokines may display improved binding properties where the chemokine is biotinylated via a spacer group. The spacer may prevent the biotin group from impacting on the binding affinity of the chemokine.

Thus, eoxtaxin derivatised at the ε-amino side chain functionality of Lys73 with PEG-Biotin (TFA salt) will be synthesised. The PEG spacer will be 3,6,-dioxoaminooc-tanoic acid. The molecule will be synthesised as a C-terminal amide (via synthesis on an amide linker) to avoid diketopiperazine formation during the synthesis. The molecule is shown schematically in FIG. 71.

A biotin eotaxin Met to Nleu analogue will also be synthesised. The single methionine within the sequence will be altered to Norleucine, to mitigate against oxidation of this residue during the chain assembly and improve stability of the final product. Once synthesised, the activity of the various eoxtaxin derivatives will be determined in cell-based assays. In particular, agonist and antagonist properties will be determined in aequorin functional cell-based assay on human CCR3 receptor.

Examples 49 to 52

General Protocols for Chemokine Synthesis

Assembly:
Chemical synthesis of chemokines was performed using standard Fmoc solid phase peptides synthesis (SPPS) techniques on an ABI 433 peptide synthesiser. DIC (0.5 M in DMF) and OxymaPure (0.5 M in DMF) were used for activation, acetic anhydride (0.5 M in DMF) for capping, and 20% piperidine in DMF for Fmoc deprotection. Rink Amide resin was utilised for the generation of C-terminal amide chemokines and Wang resin for C-terminal acid chemokines. After assembly, the resin was washed with DMF and DCM and then dried in vacuo.

Removal of Dde Protection:
The Dde protecting group was removed by treatment of resin with a solution of 2.5% hydrazine in DMF (200 ml) over a 2 hour period. The resin was then washed with DMF.

Labelling Steps:
1. Couple Fmoc-8-Amino-3,6-Dioctanoic Acid (PEG)
Resin was swollen in DMF and then a solution of Fmoc-8-amino-3,6-dioctanoic acid (0.38 g, 1 mmol), DIC solution (2 ml, 0.5 M in DMF) and OxymaPure solution (2 ml, 0.5 M in DMF) was added. The mixture was sonicated for 3 hours and then washed with DMF.

2. Capping
The resin was capped with acetic anhydride solution (0.5 M in DMF, 10 ml) for 5 minutes and then washed with DMF.

3. Fmoc Deprotection
Fmoc deprotection was carried out by treatment with 20% piperidine in DMF solution (2×50 ml) for 15 minutes each. The resin was washed with DMF.

4. Couple Biotin-OSu
A solution of Biotin-OSu (341 mg, 1 mmol) and DIPEA (348 ml) in DMF (10 ml) was added to the resin and the mixture was sonicated for 3 hours. The resin was washed thoroughly with DMF and DCM then dried in vacuo.

Cleavage:
Dry resin was treated with TFA (10 ml) containing a scavenger cocktail consisting of TIS (500 ml), thioanisole (500 ml), water (500 ml), DMS (500 ml), EDT (250 ml), $NH_4I$ (500 mg) and phenol (500 mg) and the mixture was stirred at room temperature for 5 hours. The solution was filtered into cold ether and the resin rinsed with TFA. The precipitated peptide was centrifuged, washed with ether, centrifuged and lyophilised.

Purification Protocol:
The crude peptide was purified by reverse phase HPLC (RP-HPLC) using a Jupiter C18, 250×21 mm column, 9 ml/min, eluting with an optimised gradient [Buffer A: water containing 0.1% TFA, Buffer B: acetonitrile containing 0.1% TFA].

Folding Protocol:
Pure peptide (10 mg) was dissolved into 6M GnHCl (16 ml) and then rapidly diluted to 2M GnHCl concentration by the addition of 50 mM TRIS pH 8.5 (84 ml) containing 0.3 mM GSSG and 3 mM GSH. The mixture was stirred at room temperature for 24 hours and then analysed by RP-HPLC (Jupiter C18, 250×4.6 mm column, 10-60% B over 30 minutes. Purification by RP-HPLC using an optimised gradient afforded the desired product.

Example 49

BiotinMCP-2 (CCL8)

Target Molecule:
MCP-2 derivatised at the e-amino side chain functionality of Lys(75) with PEG-Biotin (TFA salt)

Modifications:
Human MCP-2 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the ε-amino functionality and the biotin.

The linear amino acid sequence (SEQ ID NO: 80) is shown, prior to attachment of the PEG spacer and biotin molecules at amino acid 75 (K):

H-XPDSVSIPITCCFNVINRKIPIQRLESYTRITNIQCPKEAVIFKTKRG
KEVCADPKERWVRDSMKHLDQIFQNLKP-NH$_2$

X=pyroGlu or Gln

The engineered MCP-2 sequence was assembled on a solid support (Rink Amide resin), using Fmoc protocols for solid-phase peptide synthesis as described in the general protocols section:

H-XPDSVSIPITCCFNVINRKIPIQRLESYTRITNIQCPKEAVIFKTKRG
KEVCADPKERWVRDSMKHLDQIFQNLXP-NH$_2$

X1=pyroGlu or Gln
X75=K(ivDde)

FmocLys(ivDde)-OH was incorporated as residue 75 to facilitate site-specific labelling at this position of the protein (SEQ ID NO: 81). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 82):

H-XPDSVSIPITCCFNVINRKIPIQRLESYTRITNIQCPKEAVIFKTKRG
KEVCADPKERWVRDSMKHLDQIFQNLXP-NH$_2$

X1=pyroGlu or Gln
X75=an amino acid residue that can be biotinylated, such as lysine, ornithine or diaminopropionic acid and optionally is biotinylated, optionally via a spacer molecule such as PEG, e.g. K(PEG-Biotin).

Electrospray ionisation with tandem mass spectrometry (ESI-TOF-MS) data of purified folded biotinMCP-2: obtained=9263.6 Da; expected 9263.8 Da.

Functional Assay Data:

biotinMCP-2 was tested for activity in an Aequorin assay against hCCR2b, (Euroscreen) and was shown to be a partial agonist with an EC50 value of 50.9 nM. c.f. EC50 for recombinant native MCP-2 is 23.5 nM (partial agonist).

Example 50

BiotinEotaxin (CCL11)

Target Molecule:
Eotaxin derivatised at the ε-amino side chain functionality of Lys(73) with PEG-Biotin (TFA salt)
Modifications:
Human eotaxin corresponding to residues 1-74, is initially expressed as 97 amino acids comprising the chemokine fold, and a 23 amino acid signal peptide which is cleaved off. The naturally occurring lysine at position 73 was modified through biotinylation on the resin. A PEG spacer was incorporated between the ε-amino functionality and the biotin.

The linear amino acid sequence (SEQ ID NO: 83) is shown, prior to attachment of the PEG spacer and biotin molecules at amino acid 73 (K):

H-GPASVPTTCCFNLANRKIPLQRLESYRRITSGKCPQKAVIFKTKLAKD
ICADPKKKWVQDSMKYLDQKSPTPXP-NH$_2$

X is an amino acid residue that can be biotinylated, such as lysine, ornithine or diaminopropionic acid and optionally is biotinylated, optionally via a spacer molecule such as PEG, e.g. K(PEG-Biotin).

The engineered eotaxin sequence was assembled on a solid support (Rink Amide resin), using Fmoc protocols for solid-phase peptide synthesis as described in the general protocols section:

H-GPASVPTTCCFNLANRKIPLQRLESYRRITSGKCPQKAVIFKTKLAKD
ICADPKKKWVQDSMKYLDQKSPTPXP-NH$_2$

X is K(ivDde)

FmocLys(ivDde)-OH was incorporated as residue 73 to facilitate site-specific labelling at this position of the protein (SEQ ID NO: 84). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 85):

H-GPASVPTTCCFNLANRKIPLQRLESYRRITSGKCPQKAVIFKTKLAKD
ICADPKKKWVQDSMKYLDQKSPTPXP-NH$_2$

X is K(PEG-Biotin)

Electrospray ionisation with tandem mass spectrometry (ESi-TOF-MS) data of purified folded biotinEotaxin: obtained=8731.3 Da; expected 8731.3 Da.

Functional Assay Data:

biotinEotaxin was tested for activity in an Aequorin assay against hCCR3, (Euroscreen) and was shown to be an antagonist with an EC50 value of 211.8 nM. c.f. EC50 for recombinant native eotaxin is 10.7 nM (agonist).

Example 51

BiotinRANTES (CCL5)

Target Molecule:
RANTES derivatised at the ε-amino side chain functionality of Lys(67) with Biotin (TFA salt)
Modifications:
Human RANTES corresponding to residues 1-68, is initially expressed as 91 amino acids comprising the chemokine fold, and a 23 amino acid signal peptide which is cleaved off. The single methionine (Met67) within the sequence was mutated to lysine, to mitigate against oxidation of this residue during the chain assembly, which was observed during the synthesis of the natural sequence derivative. This Met to Lys substitution provided a lysine at position 67 which was modified through biotinylation on the resin. The linear amino acid sequence (SEQ ID NO: 86) is shown, prior to attachment of the biotin molecule at amino acid 67 (K):

H-SPYSSDTTPCCFAYIARPLPRAHIKEYFYTSGKCSNPAVVFVTRKNRQ

VCANPEKKWVREYINSLEKS-OH

The engineered RANTES sequence was assembled on a solid support (Wang resin), using Fmoc protocols for solid-phase peptide synthesis as described in the general protocols section:

H-SPYSSDTTPCCFAYIARPLPRAHIKEYFYTSGKCSNPAVVFVTRKNRQ

VCANPEKKWVREYINSLEXS-RESIN

X is K(ivDde)

FmocLys(ivDde)-OH was incorporated as residue 67 to facilitate site-specific labelling at this position of the protein (SEQ ID NO: 87). Subsequent removal of the ivDde protecting group, followed by coupling of the Biotin, was carried out as described in the general protocol section. Cleavage, purification and folding protocols were carried out as described to furnish the desired active chemokine (SEQ ID NO: 88).

H-SPYSSDTTPCCFAYIARPLPRAHIKEYFYTSGKCSNPAVVFVTRKNRQ

VCANPEKKWVREYINSLEXS-OH

X is an amino acid residue that can be biotinylated, such as lysine, ornithine or diaminopropionic acid and optionally is biotinylated, optionally via a spacer molecule such as PEG (e.g. K(Biotin))

Electrospray ionisation with tandem mass spectrometry (ESI-TOF-MS) data of purified folded biotinRANTES: obtained=8068.9 Da; expected 8070.2 Da.

Functional Assay Data:

BiotinRANTES was tested for agonist activity in an Aequorin assay against hCCR5, (Euroscreen) and an EC50 value of 0.5 nM was reported.

Example 52

BiotinTECK (CCL25)

Target Molecule:

TECK (Met to Nleu substitution) derivatised at the ε-amino side chain functionality of Lys72 with PEG-Biotin (TFA salt)

Modifications:

Truncated form of human TECK corresponding to residues 1-74 of the mature protein, which encompasses the sequence corresponding to the chemokine fold. The full length mature protein is 127 amino acids (the signal peptide is 23 amino acids in a 150 amino acid immature protein). The single methionine within the sequence was altered to Norleucine, to mitigate against oxidation of this residue during the chain assembly, which was observed during the synthesis of the natural sequence derivative. The Gln at the N-terminus of the proteins is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 72 was modified through biotinylation on the resin. A PEG spacer was incorporated between the ε-amino functionality and the biotin.

The linear amino acid sequence (SEQ ID NO: 89) is shown, prior to attachment of the PEG spacer and biotin molecules at amino acid 72 (K):

H-XGVFEDCCLAYHYPIGWAVLRRAWTYRIQEVSGSCNLPAAIFYLPKRH

RKVCGNPKSREVQRAXKLLDARNKVF-OH

X1=pyroGlu or Gln
X64=Norleucine

The engineered TECK sequence was assembled on a solid support (Wang resin), using Fmoc protocols for solid-phase peptide synthesis as described in the general protocols section (SEQ ID NO: 90):

H-XGVFEDCCLAYHYPIGWAVLRRAWTYRIQEVSGSCNLPAAIFYLPKRH

RKVCGNPKSREVQRAXKLLDARNXVF-RESIN

X1=pyroGlu or Gln
X64=Norleucine
X72=K(Dde)

FmocLys(ivDde)-OH was incorporated as residue 72 to facilitate site-specific labelling at this position of the protein. Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 91).

H-XGVFEDCCLAYHYPIGWAVLRRAWTYRIQEVSGSCNLPAAIFYLPKRH

RKVCGNPKSREVQRAXKLLDARNXVF-OH

X1=pyroGlu or Gln
X64=norleucine
X72=an amino acid residue that can be biotinylated, such as lysine, ornithine or diaminopropionic acid and optionally is biotinylated, optionally via a spacer molecule such as PEG, such as K(PEG-Biotin)

Electrospray ionisation with tandem mass spectrometry (ESI-TOF-MS) data of purified folded biotinTECK(Met to Nleu substitution): obtained=8958.5 Da; expected 8959.6 Da.

Functional Assay Data:

biotinTECK(Met to Nleu substitution) was tested for agonist activity in an Aequorin assay against hCCR9, (Euroscreen) and an EC50 value of 63.6 nM was reported. c.f. EC50 for recombinant native TECK is 67.9 nM.

Example 53

Diagnosis and Treatment of Bipolar Disorder (BP)

Materials and Methods
1. Flow Cytometric Analysis of Peripheral Blood

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM $NH_4Cl$, pH 7.5) for 15 min at 37° C. The cells were washed in PBS with 2%

Bovine Growth Serum, incubated with 10% human serum for 15 min at room temperature (RT) and stained with antibodies (Table 22) at 4° C. for 30 min. The cells were analysed by flow cytometry on a FACS Canto flow cytometer with the FACSDiva software (BD Biosciences).

TABLE 22

List of antibodies for flow cytometric analysis.

| Antibody | Fluorophore | Supplier |
| --- | --- | --- |
| CD14 | FITC | Beckman Coulter |
| Streptavidin | PE, APC | Biolegend |
| CD16 | PE Cy7 | BD Biosciences |
| CCR9 | APC | R&D Systems |
| HLADR | APC Cy7 | Biolegend |
| CD3 | V450 | BD Biosciences |
| CD19 | V500 | BD Biosciences |

2. Chemokine Binding Test

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5) for 15 min at 37° C. The cells were washed in PBS with 2% Bovine Growth Serum, incubated with 10% human serum 15 min at room temperature (RT) and stained with cell specific antibodies together with biotinylated chemokine (1 µM) or the corresponding chemokine receptor antibody at 4° C. for 30 min (Table 22). The biotinylated chemokine was detected via the interaction between biotin and a fluorophore conjugated Streptavidin. The samples were analysed by flow cytometry on a FACS Canto flow cytometer with the FACSDiva software (BD Biosciences).

3. Cell Depletion by Matrix Conjugated with Biotinylated Chemokine

Cells were prepared from peripheral blood (section 1). 1 mL Sepharose BigBeads matrix conjugated with 0.4 mg/mL Streptavidin (GE Healthcare) was washed in 50 mL PBS and added to a 5 mL polystyrene tube (BD Falcon™). Biotinylated chemokine (1 µM) was added to the tube and incubated for 20 min at RT to enable immobilization of the chemokine on the matrix via the biotin-streptavidin interaction. Next, the cells were added to the chemokine-matrix and incubated for 20 min at RT. The cells that did not bind to the matrix were removed by washing the matrix with PBS in a sterile 40 um nylon filter (BD Falcon™ Cell Strainer). The flow through cells were stained with antibodies (Table 22), analysed by flow cytometry and compared with cells from peripheral blood that had not been incubated with the chemokine-matrix.

Results and Discussion

1. Flow Cytometric Analysis of Peripheral Blood

White blood cells from two patients with bipolar disorder (BP) were analysed with flow cytometry. Both patients exhibited a highly increased frequency of CCR9 expressing monocytes (FIG. 74).

2. Chemokine Binding Test

The CCR9 receptor binds to the chemokine TECK (CCL25) which is mainly expressed in the gut but potentially also in the central nervous system (CNS). Migration of immune cells towards TECK mediates inflammation.

The monocytes from a patient with BP bound biotinylated TECK (bTECK) (FIG. 75).

3. Cell Depletion

The majority of the CCR9 expressing monocytes were depleted with bTECK-conjugated Sepharose Streptavidin Matrix (FIG. 76).

We conclude that the frequency of monocytes that express the chemokine receptor CCR9 is highly increased in bipolar disorder. These monocytes bind the ligand bTECK, and can be removed with Sepharose Streptavidin matrix conjugated with bTECK.

F. Treating Conditions Associated with Allergy

A range of allergic conditions include an inflammatory component. Eosinophilia appears to be central to allergy related conditions. For example, Kim et al., (Respiratory Medicine (2010) 104, 1436-1443) show that asthma is characterized by eosinophilic inflammation and Th1 response and that none atopic asthma (NAA) patients showed higher percentage eosinophils and Eotaxin levels than atopic asthma and healthy controls. The inventors have identified removal of CCR-3 expressing cells, up-regulated in allergic inflammation, as a suitable therapeutic target. The inventors show, see FIG. 88 that eosinophils are increased in frequency in (peripheral blood of) allergic subjects compared to healthy subjects.

It is shown herein (see FIG. 86) that subjects or patients suffering from allergies displayed increased frequency of CCR3 expressing monocytes and that these cells can be depleted using a suitable reagent (FIG. 87) such as eotaxin (CCL11). It is further shown herein that subjects suffering from allergic conditions contain chemokine receptor expressing cells in the peripheral blood. Subjects suffering from allergic conditions contain CXCR1 and CXCR2 expressing neutrophils, CCR2 expressing monocytes and CCR3 expressing eosinophils. The expression of these receptors was not increased in allergic patients; however, the cells expressing the relevant receptors are increased in number in the inflammatory tract of patients with allergic disease. Moreover, the cells are potentially different in their pro-inflammatory profile with regards to other mediators. Therefore it may be beneficial for the subjects/patients to remove these cells from the circulation in order to prevent and reduce the influx of cells to the inflammatory tract. It is also shown herein that a potentially therapeutic proportion of the relevant chemokine receptor expressing cells can be removed using a suitable binding reagent. Thus, CXCR1 and CXCR2 expressing cells may be depleted from peripheral blood using IL-8 as binding reagent, in particular biotinylated IL-8 conjugated to a sepharose straptvidin matrix. CCR2 expressing cells may be depleted from peripheral blood using MCP-1 (CCL2) as binding reagent, in particular biotinylated MCP-1 conjugated to a sepharose straptvidin matrix. CCR3 expressing cells may be depleted from peripheral blood using eotaxin (CCL11) as binding reagent, in particular biotinylated eotaxin conjugated to a sepharose straptvidin matrix.

Example 54

Materials and Methods

Isolation of Peripheral Blood Leukocytes.

Heparinized peripheral blood from healthy blood donors patients was fixed with 4% paraformaldehyde for 4 minutes, hemolyzed for 15 minutes with a 0.83% ammonium chloride solution and washed twice in FACS buffer to obtain a suspension of blood leukocytes.

Chemokines.

The leukocytes were incubated for 30 min in the dark at 4° C. with biotinylated and Alexa647 Fluor® labeled eotaxin (in concentrations 10 ng/µL and 50 ng/µL). The cells were then washed with FACS-buffer and analyzed by flow cytometry. All chemokines used in the Examples were provided by Almac Sciences Scotland Ltd, Edinburgh, Scotland.

Flow Cytometry Assay.

The flow cytometry assay was performed on a two laser FACS Calibur cytometer (BD Immunocytometry systems, San José, Ca, USA). Ten thousand cells were counted and analysed in each sample. For data analyses, Cell Quest Pro software from Becton Dickinson was used.

Neutrophils/eosinophils were investigated for their expression of CCR3, (FIG. 77b) and their ability to bind eotaxin (FIG. 77a). CCR3, expression was noted in all neutrophils/eosinophils with the majority of neutrophils/eosinophils expressing high levels, using an anti-CCR3, antibody (FIG. 77b). The eotaxin binding to neutrophils/eosinophils shown in FIG. 77a corresponds to the $CCR3^{hi}$ expressing population shown in FIG. 77b. Thus, eotaxin binds favourably to $CCR3^{hi}$ expressing cells.

Example 55

Tailored Leukapheresis

Column Design and Properties
Introduction

Apheresis is an established treatment used for depletion of blood components, such as antibodies, low-density lipoproteins (LDL) and blood cells. Leukapheresis is the apheresis treatment used for removal of white blood cells, leukocytes. The patient is connected to an extracorporeal blood circulating system; the blood is drawn from a vein in one arm, passed through a column device and returned into the other arm of the patient. Side effects of leukapheresis treatments are varying from mild events like headache, dizziness, hypotension, palpitation and flush seen in 0.1 to 5% of treated patients.

The Column

The column is intended to be used as a leukapheresis treatment for an allergic condition. It will specifically remove CCR3, CXCR1, CXCR2 and/or CCR2-expressing leukocytes, in particular eosinophils, through the use of a binding reagent, more specifically a biotinylabeted eotaxin containing resin, exploiting the CCR3, CXCR1, CXCR2 and/or CCR2-chemokine interaction. The column consists of three combined components, the plastic house, the streptavidin (SA) Sepharose™ BigBeads matrix and biotinylated eotaxin bound to the matrix. The treatment is conducted using the same techniques as a standard apheresis procedure.

The Plastic House (FIG. 9)

The plastic house, designed to keep a continuous blood flow through the matrix, consists of a transparent body and red-coloured top. The top has a distribution plate (2) at the inflow site (1) to spread the blood evenly over the entire matrix area. The plate is the first safety barrier preventing larger particles flowing through the column and into the patient. Safety filter units (3 and 4) are placed at the inflow (1) and outflow (5) sites of the plastic housing. The safety filter unit contains three filters designed to be a robust barrier and stop all particles larger than blood cells passing through the column. The plastic housing design is shown in FIG. 9. The design with safety filters (3 and 4) at both ends of the column device will minimize the risk of leakage of particles into the patient, including in the event that the device is placed up side down with the blood flow in the opposite direction to that anticipated.

Streptavidin Sepharose™ BigBeads

The second component in the device is the affinity matrix called streptavidin Sepharose™ BigBeads (Sepharose™ GE Healthcare, Sweden). Sepharose™ is a cross linked, beaded-form of agarose, which is a polysaccharide extracted from seaweed. Sepharose™ and agarose are commonly used as column matrices in biomedical affinity techniques. It is chosen for its optimal distribution capacity and can provide a large available area for affinity binding.

Binding Reagent

Coupled to the matrix is the third component of the device, the binding reagent that binds specifically to CCR3, CXCR1, CXCR2 and/or CCR2. Chemokines such as eotaxin may be employed. These peptides may be synthetic, engineered versions of the human chemokine, which are truncated and biotinylated, but retain binding activity to the CCR3, CXCR1, CXCR2 and/or CCR2 receptor. By biotinylating the engineered chemokine, it is able to bind to the streptavidin molecules in the Sepharose™ matrix. The biotin-streptavidin binding is known be one of the strongest biological interactions with a Kd in the order of $4 \times 10^{-14}$ M. The calculated ratio of streptavidin:biotin binding sites in the column is 10:1. Therefore, the coupling between the matrix and chemokine will be immediate, minimising the risk of chemokine decoupling from the matrix.

The Apheresis System

To conduct the leukapheresis the following components are needed; the column, tubing system, and a 4008 ADS pump (Fresenius Medical Care).

The Circuit

The system is illustrated in FIG. 10. The patient (1) is connected to the extracorporeal circuit via sterile Venflon needles to veins in the right and the left arms. A saline bag (3) is also connected and the saline solution is pumped with an ACD pump (2). Blood is drawn from one arm of the patient through the sterile tubing system by the blood pump (4) and passed through the column (6) and back to the patient. The tubing system is connected to the column via standard dialysis luer-lock couplings. The couplings on the column are colour-coded for correct assembly; red tubing for inflow to the red column top and blue tubing for outflow back to the patient. An air detector (8) is present. Inlet pressure (5) and Pven sensors (7) are employed to monitor the pressure in the circuit.

The 4008 ADS Pump

An apheresis pump, from Fresenius Medical Care, monitors the patient's inflow and outflow, the pressure in the extracorporeal circulation and can discriminate air by a bubble catcher and air detector. A clot catcher filter is placed inside the bubble catcher. The pump also has an optical detector to distinguish between light, e.g. saline solution or air present in the tubing system and dark e.g. blood present in the tubing system.

A schematic diagram of the pump, showing the air detector and optical filter is shown in FIG. 11. If the pump system detects air bubbles and optical fluctuations or if extracorporeal pressure values are out of the set range, then the pump stops immediately and a visual/audible alarm are emitted.

LEGEND FOR FIG. 11

1. Monitor
2. Holder for waste bag

3. Modules (left to right—Blood pump, ACD pump, Air detector)
4. Reserve places for further modules
5. Absorber holder
6. Drip detector
7. IV pole Preparation of the Patient The patient will be administered anticoagulants prior to each treatment session. A sterile saline solution with 5000 IE Heparin will be used for priming the extracorporeal system, thereafter a bolus injection with 4000 IE Heparin will be added into the circuit at the start of each treatment session.

Leukapheresis Time and Flow Rate

The apheresis system should be operated at a flow rate of 30-60 mL/min. A treatment is finalised after 1800 mL of blood has been circulated.

Storage Conditions

The column devices should be stored between 1 and 25° C. avoiding freezing and more elevated temperatures. Stability data >3 months indicate no difference in functionality over time or by temperature (room temperature and refrigerated). The columns will be kept in refrigerated conditions until use. Mechanical damage as those resulting from violent vibrations and trauma should be avoided. Column stored outside of these recommendations should not be used.

Transport Conditions

The column devices will be transported under refrigerated condition, avoiding freezing and more elevated temperatures. Mechanical damage such as those resulting from violent vibrations and trauma should be avoided.

In-Vitro Depletion of Target Cell Populations—Eotaxin

To investigate the ability to eliminate CCR3-expressing cells, in vitro tests have been performed on the eotaxin coupled matrix. Blood was collected from blood donors and passed through a magnetic column device containing eotaxin coupled MACS beads. Blood samples were taken before and after column passage and analyzed by flow cytometry (FACS) for the depletion of CCR3-expressing cells.

The results demonstrate significant depletion of the target population CCR3-expressing neutrophils/eosinophils post matrix perfusion. Depletion tests were performed on blood from a healthy donor. The results are shown in FIG. 78a.

In conclusion, the in-vitro results demonstrate a specific reduction of around 25% of the CCR3-expressing cells by the column. Non-CCR3-expressing cells remained unaffected (data not shown).

In-Vitro Depletion of Target Cell Populations—RANTES

To investigate the ability to eliminate CCR1, 3 or 5-expressing cells, in vitro tests have been performed on the biotinylated RANTES coupled matrix. Blood was collected from blood donors and passed through the column device containing biotinylated RANTES coupled matrix. Blood samples were taken before and after column passage and analyzed by flow cytometry (FACS) for the depletion of CCR1, 3 or 5-expressing cells.

The results demonstrate significant depletion of the target population chemokine receptor-expressing cells post matrix perfusion. Depletion tests were performed on blood from a healthy donor. The results are shown in FIG. 78b.

The in-vitro results demonstrate a specific reduction of the majority of the chemokine receptor 1, 3 or 5-expressing cells by the column.

The RANTES molecule was synthesized by Almac. The amino acid sequence of the biotinylated RANTES molecule is set forth as SEQ ID NO: 97:

H2N-SPYSSDTTPCCFAYIARPLPRAHIKEYFYTSGKCSNPAVVFVTRKN

RQVCANPEKKWVREYINSLEKS-CO2H

This molecule has the naturally occurring methionine at position 67 replaced with lysine to facilitate biotinylation at position 67.

The side-chain of Lys 67 was directly biotinylated to given the protein primary structure shown in FIG. 80. The protein was folded and disulphide bonds formed between the first and third cysteine residues in the sequence and between the 2nd and 4th cysteines.

Example 56

Eotaxin Derivatives

Eotaxin has been produced with position 73, thought to be a lysine residue, as the site of biotinylation on the chemokine (numbering based upon the mature protein having the amino acid sequence of SEQ ID NO: 2). Biotinylation permits immobilization of eotaxin on a solid support (via a biotin-avidin interaction). The basic amino acid sequence of eoxtaxin, including a 23 amino acid leader sequence (signal peptide) is set forth as SEQ ID NO: 92,

MKVSAALLWL LLIAAAFSPQ GLAGPASVPT TCCFNLANRK

IPLQRLESYR RITSGKCPQK AVIFKTKLAK DICADPKKKW

VQDSMKYLDQ KSPTPKP

The amino acid sequence of the mature protein is set forth as SEQ ID NO: 93,

GPASVPT TCCFNLANRK IPLQRLESYR RITSGKCPQK

AVIFKTKLAK DICADPKKKW VQDSMKYLDQ KSPTPKP

The inventors have determined that chemokines may display improved binding properties where the chemokine is biotinylated via a spacer group. The spacer may prevent the biotin group from impacting on the binding affinity of the chemokine.

Thus, eoxtaxin derivatised at the ϵ-amino side chain functionality of Lys73 with PEG-Biotin (TFA salt) will be synthesised. The PEG spacer will be 3,6,-dioxoaminooctanoic acid. The molecule will be synthesised as a C-terminal amide (via synthesis on an amide linker) to avoid diketopiperazine formation during the synthesis. The molecule is shown schematically in FIG. 79.

A biotin eotaxin Met to Nleu analogue will also be synthesised. The single methionine within the sequence will be altered to Norleucine, to mitigate against oxidation of this residue during the chain assembly and improve stability of the final product.

Once synthesised, the activity of the various eoxtaxin derivatives will be determined in cell-based assays. In particular, agonist and antagonist properties will be determined in functional cell-based assay on human CCR3 receptor.

Example 57

Affinity of Blood Cells to Biotinylated IL-8

Materials and Methods

Isolation of Peripheral Blood Leukocytes.

Heparinized peripheral blood from healthy blood donors or IBD patients was fixed with 4% paraformaldehyde for 4 minutes, hemolyzed for 15 minutes with a 0.83% ammonium chloride solution and washed twice in FACS buffer to obtain a suspension of blood leukocytes.

Chemokines.

The leukocytes were incubated for 30 min in the dark at 4° C. with the following biotinylated and Alexa647 Fluor® labeled chemokines: CCL25 (in concentrations of 0.1 ng/µL, 0.5 ng/µL and 5 ng/µL), MIP-1α or MCP-1 (in concentrations 10 ng/µL and 50 ng/µL). The cells were then washed with FACS-buffer and analyzed by flow cytometry. All chemokines used in the Examples were provided by Almac Sciences Scotland Ltd, Edinburgh, Scotland.

Flow Cytometry Assay.

The flow cytometry assay was performed on a two laser FACS Calibur cytometer (BD Immunocytometry systems, San José, Ca, USA). Ten thousand cells were counted and analysed in each sample. For data analyses, Cell Quest Pro software from Becton Dickinson was used.

In FIG. 81 the binding to biotinylated IL-8 (CXCL8) of CD4+ lymphocytes (FIG. 81a), CD8+ lymphocytes (FIG. 81a) and CD16+ neutrophils (FIG. 81c) obtained from healthy donors is shown. After 30 min of incubation all CD16+ neutrophils bound to IL-8. In contrast no binding was observed with CD4+ lymphocytes and CD8+ lymphocytes.

Examples 58 to 63

Chemokine Synthesis

General Protocols
Assembly:

Chemical synthesis of chemokines was performed using standard Fmoc solid phase peptides synthesis (SPPS) techniques on an ABI 433 peptide synthesiser. DIC (0.5 M in DMF) and OxymaPure (0.5 M in DMF) were used for activation, acetic anhydride (0.5 M in DMF) for capping, and 20% piperidine in DMF for Fmoc deprotection. Rink Amide resin was utilised for the generation of C-terminal amide chemokines and Wang resin for C-terminal acid chemokines. After assembly, the resin was washed with DMF and DCM and then dried in vacuo.

Removal of Dde Protection:

The Dde protecting group was removed by treatment of resin with a solution of 2.5% hydrazine in DMF (200 ml) over a 2 hour period. The resin was then washed with DMF.

Labelling Steps:
1. Couple Fmoc-8-Amino-3,6-Dioctanoic Acid (PEG)

Resin was swollen in DMF and then a solution of Fmoc-8-amino-3,6-dioctanoic acid (0.38 g, 1 mmol), DIC solution (2 ml, 0.5 M in DMF) and OxymaPure solution (2 ml, 0.5 M in DMF) was added. The mixture was sonicated for 3 hours and then washed with DMF.

2. Capping

The resin was capped with acetic anhydride solution (0.5 M in DMF, 10 ml) for 5 minutes and then washed with DMF.

3. Fmoc Deprotection

Fmoc deprotection was carried out by treatment with 20% piperidine in DMF solution (2×50 ml) for 15 minutes each. The resin was washed with DMF.

4. Couple Biotin-OSu

A solution of Biotin-OSu (341 mg, 1 mmol) and DIPEA (348 ml) in DMF (10 ml) was added to the resin and the mixture was sonicated for 3 hours. The resin was washed thoroughly with DMF and DCM then dried in vacuo.

Cleavage:

Dry resin was treated with TFA (10 ml) containing a scavenger cocktail consisting of TIS (500 ml), thioanisole (500 ml), water (500 ml), DMS (500 ml), EDT (250 ml), $NH_4I$ (500 mg) and phenol (500 mg) and the mixture was stirred at room temperature for 5 hours. The solution was filtered into cold ether and the resin rinsed with TFA. The precipitated peptide was centrifuged, washed with ether, centrifuged and lyophilised.

Purification Protocol:

The crude peptide was purified by reverse phase HPLC (RP-HPLC) using a Jupiter C18, 250×21 mm column, 9 ml/min, eluting with an optimised gradient [Buffer A: water containing 0.1% TFA, Buffer B: acetonitrile containing 0.1% TFA].

Folding Protocol:

Pure peptide (10 mg) was dissolved into 6M GnHCl (16 ml) and then rapidly diluted to 2M GnHCl concentration by the addition of 50 mM TRIS pH 8.5 (84 ml) containing 0.3 mM GSSG and 3 mM GSH. The mixture was stirred at room temperature for 24 hours and then analysed by RP-HPLC (Jupiter C18, 250×4.6 mm column, 10-60% B over 30 minutes. Purification by RP-HPLC using an optimised gradient afforded the desired product.

Example 58

BiotinMCP-1 (CCL2)

Target Molecule:

MCP-1 derivatised at the ε-amino side chain functionality of Lys(75) with PEG-Biotin (TFA salt)

Modifications:

Human MCP-1 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the ε-amino functionality and the biotin.

The linear amino acid sequence (SEQ ID NO: 100) is shown, prior to attachment of the PEG spacer and biotin molecules at amino acid 75 (K):

H-XPDAINAPVTCCYNFTNRKISVQRLASYRRITSSKCPKEAVIFKTIVA

KEICADPKQKWVQDSMDHLDKQTQTPKT-NH₂

X=pyroGlu or Gln

The engineered MCP-1 sequence was assembled on a solid support (Rink Amide resin), using Fmoc protocols for solid-phase peptide synthesis as described in the general protocols section:

SEQ ID NO: 101
H-XPDAINAPVTCCYNFTNRKISVQRLASYRRITSSKCPKEAVIFKTIVA

KEICADPKQKWVQDSMDHLDKQTQTPXT-RESIN

X1=pyroGlu or Gln
X75=K(ivDde)

FmocLys(ivDde)-OH was incorporated as residue 75 to facilitate site-specific labelling at this position of the protein. Subsequent removal of the ivDde protecting group, followed by coupling of the PEG spacer and Biotin, was carried out as described in the general protocol section. Cleavage, purification and folding protocols were carried out as described to furnish the desired active chemokine.

SEQ ID NO: 102
H-XPDAINAPVTCCYNFTNRKISVQRLASYRRITSSKCPKEAVIFKTIVA

KEICADPKQKWVQDSMDHLDKQTQTPXT-NH$_2$

X1=pyroGlu or Gln
X75 is an amino acid residue that can be biotinylated, such as lysine, ornithine or diaminopropionic acid and optionally is biotinylated, optionally via a spacer molecule such as PEG, optionally K(PEG-Biotin)

Electrospray ionisation with tandem mass spectrometry (ESI-TOF-MS) data of purified folded biotinMCP-1: obtained=9032.8 Da; expected 9034.4 Da.
Functional Assay Data:
biotinMCP-1 was tested for agonist activity in an Aequorin assay against hCCR2b, (Euroscreen) and an EC50 value of 9.6 nM was reported. c.f. EC50 for recombinant native MCP-1 is 3.1 nM.

Example 59

BiotinRANTES (CCL5)

Target Molecule:
RANTES derivatised at the ε-amino side chain functionality of Lys(67) with Biotin (TFA salt)
Modifications:
Human RANTES corresponding to residues 1-68, is initially expressed as 91 amino acids comprising the chemokine fold, and a 23 amino acid signal peptide which is cleaved off. The single methionine (Met67) within the sequence was mutated to lysine, to mitigate against oxidation of this residue during the chain assembly, which was observed during the synthesis of the natural sequence derivative. This Met to Lys substitution provided a lysine at position 67 which was modified through biotinylation on the resin.

The linear amino acid sequence (SEQ ID NO: 97) is shown, prior to attachment of the biotin molecule at amino acid 67 (K):

H-SPYSSDTTPCCFAYIARPLPRAHIKEYFYTSGKCSNPAVVFVTRKNRQ

VCANPEKKWVREYINSLEKS-OH

The engineered RANTES sequence was assembled on a solid support (Wang resin), using Fmoc protocols for solid-phase peptide synthesis as described in the general protocols section:

H-SPYSSDTTPCCFAYIARPLPRAHIKEYFYTSGKCSNPAVVFVTRKNRQ

VCANPEKKWVREYINSLEXS-RESIN

X is K(ivDde)
FmocLys(ivDde)-OH was incorporated as residue 67 to facilitate site-specific labelling at this position of the protein (SEQ ID NO: 98). Subsequent removal of the ivDde protecting group, followed by coupling of the Biotin, was carried out as described in the general protocol section. Cleavage, purification and folding protocols were carried out as described to furnish the desired active chemokine (SEQ ID NO: 99).

H-SPYSSDTTPCCFAYIARPLPRAHIKEYFYTSGKCSNPAVVFVTRKNRQ

VCANPEKKWVREYINSLEXS-OH

X is an amino acid residue that can be biotinylated, such as lysine, ornithine or diaminopropionic acid and optionally is biotinylated, optionally via a spacer molecule such as PEG (e.g. K(Biotin))

Electrospray ionisation with tandem mass spectrometry (ESI-TOF-MS) data of purified folded biotinRANTES: obtained=8068.9 Da; expected 8070.2 Da.
Functional Assay Data:
BiotinRANTES was tested for agonist activity in an Aequorin assay against hCCR5, (Euroscreen) and an EC50 value of 0.5 nM was reported.

Example 60

BiotinMCP-2 (CCL8)

Target Molecule:
MCP-2 derivatised at the ε-amino side chain functionality of Lys(75) with PEG-Biotin (TFA salt)
Modifications:
Human MCP-2 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the ε-amino functionality and the biotin.

The linear amino acid sequence (SEQ ID NO: 94) is shown, prior to attachment of the PEG spacer and biotin molecules at amino acid 75 (K):

H-XPDSVSIPITCCFNVINRKIPIQRLESYTRITNIQCPKEAVIFKTKRG

KEVCADPKERWVRDSMKHLDQIFQNLKP-NH$_2$

X=pyroGlu or Gln
The engineered MCP-2 sequence was assembled on a solid support (Rink Amide resin), using Fmoc protocols for solid-phase peptide synthesis as described in the general protocols section:

H-XPDSVSIPITCCFNVINRKIPIQRLESYTRITNIQCPKEAVIFKTKR

GKEVCADPKERWVRDSMKHLDQIFQNLXP-NH$_2$

X1=pyroGlu or Gln
X75=K(ivDde)
FmocLys(ivDde)-OH was incorporated as residue 75 to facilitate site-specific labelling at this position of the protein (SEQ ID NO: 95). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 96):

H-XPDSVSIPITCCFNVINRKIPIQRLESYTRITNIQCPKEAVIFKTKR

GKEVCADPKERWVRDSMKHLDQIFQNLXP-NH$_2$

X1=pyroGlu or Gln
X75=an amino acid residue that can be biotinylated, such as lysine, ornithine or diaminopropionic acid and optionally is biotinylated, optionally via a spacer molecule such as PEG, e.g. K(PEG-Biotin).

Electrospray ionisation with tandem mass spectrometry (ESI-TOF-MS) data of purified folded biotinMCP-2: obtained=9263.6 Da; expected 9263.8 Da.
Functional Assay Data:

biotinMCP-2 was tested for activity in an Aequorin assay against hCCR2b, (Euroscreen) and was shown to be a partial agonist with an EC50 value of 50.9 nM. c.f. EC50 for recombinant native MCP-2 is 23.5 nM (partial agonist).

Example 61

BiotinIL-8 (CXCL8)

Target Molecule:
IL-8 derivatised at the e-amino side chain functionality of Lys(78) with PEG-Biotin (TFA salt)
Modifications:
Human IL-8 corresponding to residues 1-77, is initially expressed as 99 amino acids comprising the chemokine fold, and a 22 amino acid signal peptide which is cleaved off. An additional lysine was inserted at the C-terminus at position 78, and modified through biotinylation on the resin. A PEG spacer was incorporated between the e-amino functionality and the biotin.
The linear amino acid sequence (SEQ ID NO: 103) is shown, prior to attachment of the PEG spacer and biotin molecules:

H-AVLPRSAKELRCQCIKTYSKPFHPKFIKELRVIESGPHCANTEIIV

KLSDGRELCLDPKENWVQRVVEKFLKRAENSX-NH$_2$

X is an amino acid residue that can be biotinylated, such as lysine, ornithine or diaminopropionic acid and optionally is biotinylated, optionally via a spacer molecule such as PEG, e.g. K(PEG-Biotin)

The engineered IL-8 sequence was assembled on a solid support (Rink Amide resin), using Fmoc protocols for solid-phase peptide synthesis as described in the general protocols section:

H-AVLPRSAKELRCQCIKTYSKPFHPKFIKELRVIESGPHCANTEIIV

KLSDGRELCLDPKENWVQRVVEKFLKRAENSX-RESIN

X is K(ivDde)
FmocLys(ivDde)-OH was incorporated as residue 78 to facilitate site-specific labelling at this position of the protein (SEQ ID NO: 104). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 105):

H-AVLPRSAKELRCQCIKTYSKPFHPKFIKELRVIESGPHCANTEIIV

KLSDGRELCLDPKENWVQRVVEKFLKRAENSX-NH$_2$

X is K(PEG-Biotin)
Electrospray ionisation with tandem mass spectrometry (ESI-TOF-MS) data of purified folded biotinIL-8: obtained=9416.9 Da; expected 9417.0 Da.
Functional Assay Data:
BiotinIL-8 was tested for agonist activity in an Aequorin assay against hCXCR1, (Euroscreen) and an EC50 value of 18.9 nM was reported. c.f. EC50 for recombinant native IL-8 is 4.2 nM.

Example 62

BiotinIL-8 (6-78)

Target Molecule:
IL-8 (6-78) derivatised at the e-amino side chain functionality of Lys(78) with PEG-Biotin (TFA salt)
Modifications:
Truncated form of IL-8 corresponding to residues 6-77, the first five N-terminal residues have been removed and an additional lysine was inserted at the C-terminus at position 78, and modified through biotinylation on the resin. A PEG spacer was incorporated between the e-amino functionality and the biotin.
The linear amino acid sequence (SEQ ID NO: 106) is shown, prior to attachment of the PEG spacer and biotin molecules:

H-SAKELRCQCIKTYSKPFHPKFIKELRVIESGPHCANTEIIVKLSD

GRELCLDPKENWVQRVVEKFLKRAENSX-NH$_2$

X is an amino acid residue that can be biotinylated, such as lysine, ornithine or diaminopropionic acid and optionally is biotinylated, optionally via a spacer molecule such as PEG The engineered IL-8 sequence was assembled on a solid support (Rink Amide resin), using Fmoc protocols for solid-phase peptide synthesis as described in the general protocols section:

H-SAKELRCQCIKTYSKPFHPKFIKELRVIESGPHCANTEIIVKLSDG

RELCLDPKENWVQRVVEKFLKRAENSX-RESIN

X is K(ivDde)
FmocLys(ivDde)-OH was incorporated as residue 78 to facilitate site-specific labelling at this position of the protein (SEQ ID NO: 107). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 108):

H-SAKELRCQCIKTYSKPFHPKFIKELRVIESGPHCANTEIIVKLSDG

RELCLDPKENWVQRVVEKFLKRAENSX-NH$_2$

X is K(PEG-Biotin)
Electrospray ionisation with tandem mass spectrometry (ESI-TOF-MS) data of purified folded biotinIL-8 (6-78): obtained=8880.50 Da; expected 8880.4 Da.

Functional Assay Data:

BiotinIL-8 (6-78) was tested for agonist activity in an Aequorin assay against hCXCR1, (Euroscreen) and an EC50 value of 6.1 nM was reported. c.f. EC50 for recombinant native IL-8 is 4.2 nM.

Example 63

BiotinEotaxin (CCL11)

Target Molecule:

Eotaxin derivatised at the e-amino side chain functionality of Lys(73) with PEG-Biotin (TFA salt)

Modifications:

Human eotaxin corresponding to residues 1-74, is initially expressed as 97 amino acids comprising the chemokine fold, and a 23 amino acid signal peptide which is cleaved off. The naturally occurring lysine at position 73 was modified through biotinylation on the resin. A PEG spacer was incorporated between the ε-amino functionality and the biotin.

The linear amino acid sequence (SEQ ID NO: 109) is shown, prior to attachment of the PEG spacer and biotin molecules at amino acid 73 (K):

H-GPASVPTTCCFNLANRKIPLQRLESYRRITSGKCPQKAVIFKTKLA

KDICADPKKKWVQDSMKYLDQKSPTPXP-NH$_2$

X is an amino acid residue that can be biotinylated, such as lysine, ornithine or diaminopropionic acid and optionally is biotinylated, optionally via a spacer molecule such as PEG, e.g. K(PEG-Biotin).

The engineered eotaxin sequence was assembled on a solid support (Rink Amide resin), using Fmoc protocols for solid-phase peptide synthesis as described in the general protocols section:

H-GPASVPTTCCFNLANRKIPLQRLESYRRITSGKCPQKAVIFKTKLA

KDICADPKKKWVQDSMKYLDQKSPTPXP-NH$_2$

X is K(ivDde)

FmocLys(ivDde)-OH was incorporated as residue 73 to facilitate site-specific labelling at this position of the protein (SEQ ID NO: 110). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 111):

H-GPASVPTTCCFNLANRKIPLQRLESYRRITSGKCPQKAVIFKTKLA

KDICADPKKKWVQDSMKYLDQKSPTPXP-NH$_2$

X is K(PEG-Biotin)

Electrospray ionisation with tandem mass spectrometry (ESi-TOF-MS) data of purified folded biotinEotaxin: obtained=8731.3 Da; expected 8731.3 Da.

Functional Assay Data:

biotinEotaxin was tested for activity in an Aequorin assay against hCCR3, (Euroscreen) and was shown to be an antagonist with an EC50 value of 211.8 nM. c.f. EC50 for recombinant native eotaxin is 10.7 nM (agonist).

Example 64

Treatment of Allergy Using CXCR1, CXCR2, CCR2 and CCR3 and Biotinylated IL8, Eotaxin and MCP1

Materials and Methods

1. Flow Cytometric Analysis of Peripheral Blood

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5) for 15 min at 37° C. The cells were washed in PBS with 2% Bovine Growth Serum, incubated with 10% human serum for 15 min at room temperature (RT) and stained with antibodies (Table 23) at 4° C. for 30 min. The cells were analysed by flow cytometry on a FACS Canto flow cytometer with the FACSDiva software (BD Biosciences).

TABLE 23

List of antibodies for flow cytometric analysis.

| Antibody | Fluorophore | Supplier |
|---|---|---|
| CCR3 | PE | Biolegend |
| CCR2 | PerCPCy5.5 | Biolegend |
| CXCR1 | APC | Biolegend |
| CXCR2 | PE | Biolegend |
| CD16 | PECy7 | BD |
| Streptavdin | APC | BD |
| CD14 | FITC | Beckman Coulter |

2. Chemokine Binding Test

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5) for 15 min at 37° C. The cells were washed in PBS with 2% Bovine Growth Serum, incubated with 10% human serum 15 min at room temperature (RT) and stained with cell specific antibodies together with biotinylated chemokine (1 μM) or the corresponding chemokine receptor antibody at 4° C. for 30 min (Table 23). The biotinylated chemokine was detected via the interaction between biotin and a fluorophore conjugated Streptavidin. The samples were analysed by flow cytometry on a FACS Canto flow cytometer with the FACSDiva software (BD Biosciences).

3. Cell Depletion by Matrix Conjugated with Biotinylated Chemokine

Cells were prepared from peripheral blood (section 1). 1 mL Sepharose BigBeads matrix conjugated with 0.4 mg/mL Streptavidin (GE Healthcare) was washed in 50 mL PBS and added to a 5 mL polystyrene tube (BD Falcon™). Biotinylated chemokine was added to the tube and incubated for 20 min at RT to enable immobilization of the chemokine on the matrix via the biotin-streptavidin interaction. Next, the cells were added to the chemokine-matrix and incubated for 20 min at RT. The cells that did not bind to the matrix were removed by washing the matrix with PBS in a sterile 40 um nylon filter (BD Falcon™ Cell Strainer). The flow through cells were stained with antibodies (Table 23), analysed by flow cytometry and compared with cells from peripheral blood that had not been incubated with the chemokine-matrix.

Results and Discussion
1. Flow Cytometric Analysis of Peripheral Blood

White blood cells from patients with allergy (three of the patients were allergic to birch and one patient was allergic to cats, dogs and grass) were analysed for cell surface markers with flow cytometry. The neutrophils expressed the chemokine receptors CXCR1 and CXCR2, the monocytes expressed CCR2 and the eosinophils expressed CCR3, based upon flow cytometry data (FIG. 83a-c).

The expression of these receptors was not increased in allergic patients; however, the cells are increased in the inflammatory tract of patients with allergic disease. Moreover, the cells are potentially different in their pro-inflammatory profile with regards to other mediators. Therefore it could be beneficial for the patients to remove these cells from the circulation in order to prevent and reduce the influx of cells to the inflammatory tract. CCR3 expressing monocyte levels are increased in allergic patients (FIG. 86).

2. Chemokine Binding Test

The ligand for CXCR1 and CXCR2 is IL-8, the ligand for CCR3 is eotaxin, and the ligand for CCR2 is MCP-1. Circulating blood cells from patients with allergy bind to biotinylated IL8 (bIL8) and biotinylated Eotaxin (bEotaxin) (FIGS. 85a and b).

3. Cell Depletion by Matrix Conjugated with Biotinylated Chemokine

About 50 percent of the CXCR1 and CXCR2 expressing neutrophils were efficiently depleted with bIL8-conjugated Sepharose Streptavidin Matrix (FIG. 85a). 44% of the CCR3 expressing granulocytes were efficiently depleted with bEotaxin-conjugated Sepharose Streptavidin Matrix (FIG. 85b). 50 percent of the CCR2 expressing monocytes were efficiently depleted with bMCP-conjugated Sepharose Streptavidin Matrix (FIG. 85c).

CCR3 expressing monocytes can be depleted using biotinylated eotaxin (FIG. 87. We conclude that the immune cells from allergic patients express the CXCR1, CXCR2, CCR2 and CCR3 receptors. The cells can bind their respective ligand and can be removed with Sepharose Streptavidin matrix conjugated with the corresponding biotinylated chemokine.

G. Treating Inflammatory Skin Diseases

Patients with psoriasis and AD have an increased number of circulating CCR2 expressing monocytes or increased proinflammtory properties of CCR2 expressing monocytes compared to healthy controls. When investigating the skin from patients with psoriasis and AD there is a selective infiltration of CCR2 expressing monocytes in affected skin areas. To support this notion keratinocytes produce high amounts of MCP-1 thus recruiting CCR2 expressing cells.

The expression of RANTES is increased in psoriatic lesions, produced by the keratinocytes. Skin infiltrating T cell infiltrates are an important cell population involved in disease development. Supporting these ideas is that CCR6 deficient mice fail to develop IL-23 induced, IL-22 dependent psoriasis-like inflammation demonstrating the importance recruitment of CCR6 expressing T cells for the development of the disease. Moreover animal models of contact dermatitis can be abolished using RANTES antagonists.

It is shown herein that subjects suffering from inflammatory skin disorders such as psoriasis exhibit increased frequency of chemokine receptor expressing cells in the peripheral blood, in particular CCR4 expressing cells such as CCR4 expressing T lymphocytes, compared to healthy controls. It is also shown herein that the CCR4 expressing cells can be removed using a suitable binding reagent, in particular MDC (in biotinylated form) immobilized on a suitable matrix. Similarly, it is shown herein that CXCR1 and CXCR2-expressing cells, in particular neutrophils, can be depleted in psoriasis patients using a suitable binding reagent, in particular IL-8, in biotinylated form, immobilized on a suitable matrix.

Examples 65 and 66

Materials and Methods

Isolation of Peripheral Blood Leukocytes.

Heparinized peripheral blood from healthy blood donors or inflammatory bowel disease (IBD) patients was fixed with 4% paraformaldehyde for 4 minutes, hemolyzed for 15 minutes with a 0.83% ammonium chloride solution and washed twice in FACS buffer to obtain a suspension of blood leukocytes.

Chemokines.

The leukocytes were incubated for 30 min in the dark at 4° C. with biotinylated and Alexa647 Fluor® labeled chemokine (e.g. MCP-1) (in concentrations 10 ng/μL and 50 ng/μL). The cells were then washed with FACS-buffer and analyzed by flow cytometry. All chemokines used in the Examples were provided by Almac Sciences Scotland Ltd, Edinburgh, Scotland.

Flow Cytometry Assay.

The flow cytometry assay was performed on a two laser FACS Calibur cytometer (BD Immunocytometry systems, San José, Ca, USA). Ten thousand cells were counted and analysed in each sample. For data analyses, Cell Quest Pro software from Becton Dickinson was used.

Example 65

Binding of Monocytes to MCP-1

In the experiment with biotinylated MCP-1 it was found that about 90% of the monocytes obtained from peripheral blood of healthy donors had bound to the cytokine after 30 min of incubation (FIG. 89a), whereas CD4+ and CD8+ lymphocytes had not bound (FIGS. 89b and 89c).

Example 66

Monocytes were investigated for their expression of CCR2 (FIG. 90b) and their ability to bind MCP-1 (FIG. 90a). CCR2 expression was noted an all monocytes with the majority of monocytes expressing high levels, using an anti-CCR2 antibody (FIG. 90b). The MCP-1 binding to monocytes shown in FIG. 90a corresponds to the CCR2$^{hi}$ expressing population shown in FIG. 90b. Thus, MCP-1 binds favourably to CCR2$^{hi}$ expressing cells.

Example 67

Affinity of Blood Cells to CCL25

In the experiment with biotinylated CCL25 it was found that neither T-cells (CD4+ lymphocytes; CD8+ lymphocytes) nor monocytes (CD14+ monocytes) from the peripheral blood of a healthy donor (FIGS. 89d, 89e and 89f) bound to the biotinylated chemokine. In contrast, about 80% of the CD8+ lymphocytes and about 90% of the CD4+ lymphocytes and the monocytes from a patient with Crohn's disease bound to CCL25 (FIGS. 89g, 89h and 89i).

Example 68

Tailored Leukapheresis

Column Design and Properties
Introduction

Apheresis is an established treatment used for depletion of blood components, such as antibodies, low-density lipoproteins (LDL) and blood cells. Leukapheresis is the apheresis treatment used for removal of white blood cells, leukocytes. The patient is connected to an extracorporeal blood circulating system; the blood is drawn from a vein in one arm, passed through a column device and returned into the other arm of the patient. Side effects of leukapheresis treatments are varying from mild events like headache, dizziness, hypotension, palpitation and flush seen in 0.1 to 5% of treated patients.

The Column

The column is intended to be used as a leukapheresis treatment for inflammatory skin disease. It will specifically remove CCR2-expressing leukocytes, in particular monocytes, through the use of a binding reagent, more specifically an MCP-1, MCP-2, MCP-3, MCP-4 and/or MCP-5 containing resin, exploiting the CCR2-chemokine interaction. The column consists of three combined components, the plastic house, the streptavidin (SA) Sepharose™ BigBeads matrix and one or more of bMCP-1 bound to the matrix. The treatment is conducted using the same techniques as a standard apheresis procedure.

The Plastic House (FIG. 9)

The plastic house, designed to keep a continuous blood flow through the matrix, consists of a transparent body and red-coloured top. The top has a distribution plate (2) at the inflow site (1) to spread the blood evenly over the entire matrix area. The plate is the first safety barrier preventing larger particles flowing through the column and into the patient. Safety filter units (3 and 4) are placed at the inflow (1) and outflow (5) sites of the plastic housing. The safety filter unit contains three filters designed to be a robust barrier and stop all particles larger than blood cells passing through the column. The plastic housing design is shown in FIG. 9. The design with safety filters (3 and 4) at both ends of the column device will minimize the risk of leakage of particles into the patient, including in the event that the device is placed up side down with the blood flow in the opposite direction to that anticipated.

Streptavidin Sepharose™ BigBeads

The second component in the device is the affinity matrix called streptavidin Sepharose™ BigBeads (Sepharose™ GE Healthcare, Sweden). Sepharose™ is a cross linked, beaded-form of agarose, which is a polysaccharide extracted from seaweed. Sepharose™ and agarose are commonly used as column matrices in biomedical affinity techniques. It is chosen for its optimal distribution capacity and can provide a large available area for affinity binding.

Binding Reagent

Coupled to the matrix is the third component of the device, one or more binding reagents that bind specifically to CCR4, CXCR1, CXCR2, CCR2, CCR6, CCR3, CCR5, CCR1, CCR9 or ChemR23. One or more chemokines selected from the group consisting of: MCP-1. MCP-2, MCP-3, MCP-4, MCP-5, MIP-3alpha, RANTES, CCL25 and/or Chemerin may be employed. These peptides may be synthetic, engineered versions of the human chemokine, which are truncated and biotinylated, but retain binding activity to the CCR4, CXCR1, CXCR2, CCR2, CCR6, CCR3, CCR5, CCR1, CCR9 or ChemR23 receptor. By biotinylating the engineered chemokine, it is able to bind to the streptavidin molecules in the Sepharose™ matrix. The biotin-streptavidin binding is known be one of the strongest biological interactions with a Kd in the order of $4 \times 10^{-14}$ M. The calculated ratio of streptavidin:biotin binding sites in the column is 10:1. Therefore, the coupling between the matrix and chemokine will be immediate, minimising the risk of chemokine decoupling from the matrix.

The Apheresis System

To conduct the leukapheresis the following components are needed; the column, tubing system, and a 4008 ADS pump (Fresenius Medical Care).

The Circuit

The system is illustrated in FIG. 10. The patient (1) is connected to the extracorporeal circuit via sterile Venflon needles to veins in the right and the left arms. A saline bag (3) is also connected and the saline solution is pumped with an ACD pump (2). Blood is drawn from one arm of the patient through the sterile tubing system by the blood pump (4) and passed through the column (6) and back to the patient. The tubing system is connected to the column via standard dialysis luer-lock couplings. The couplings on the column are colour-coded for correct assembly; red tubing for inflow to the red column top and blue tubing for outflow back to the patient. An air detector (8) is present. Inlet pressure (5) and Pven sensors (7) are employed to monitor the pressure in the circuit.

The 4008 ADS Pump

An apheresis pump, from Fresenius Medical Care, monitors the patient's inflow and outflow, the pressure in the extracorporeal circulation and can discriminate air by a bubble catcher and air detector. A clot catcher filter is placed inside the bubble catcher. The pump also has an optical detector to distinguish between light, e.g. saline solution or air present in the tubing system and dark e.g. blood present in the tubing system.

A schematic diagram of the pump, showing the air detector and optical filter is shown in FIG. 11. If the pump system detects air bubbles and optical fluctuations or if extracorporeal pressure values are out of the set range, then the pump stops immediately and a visual/audible alarm are emitted.

LEGEND FOR FIG. 22

1. Monitor
2. Holder for waste bag
3. Modules (left to right—Blood pump, ACD pump, Air detector)
4. Reserve places for further modules
5. Absorber holder
6. Drip detector
7. IV pole Preparation of the Patient The patient will be administered anticoagulants prior to each treatment session. A sterile saline solution with 5000 IE Heparin will be used for priming the extracorporeal system, thereafter a bolus injection with 4000 IE Heparin will be added into the circuit at the start of each treatment session.

Leukapheresis Time and Flow Rate

The apheresis system should be operated at a flow rate of 30-60 mL/min. A treatment is finalised after 1800 mL of blood has been circulated.

Storage Conditions

The column devices should be stored between 1 and 25° C. avoiding freezing and more elevated temperatures. Stability data >3 months indicate no difference in functionality over time or by temperature (room temperature and refrigerated). The columns will be kept in refrigerated conditions until use. Mechanical damage as those resulting from violent vibrations and trauma should be avoided. Column stored outside of these recommendations should not be used.

Transport Conditions

The column devices will be transported under refrigerated condition, avoiding freezing and more elevated temperatures. Mechanical damage such as those resulting from violent vibrations and trauma should be avoided.

In-Vitro Depletion of Target Cell Populations—MCP-1

To investigate the ability to eliminate CCR2-expressing cells, in vitro tests have been performed on the bMCP-1 coupled matrix. Blood was collected from blood donors and passed through the column device containing bMCP-1 coupled matrix. Blood samples were taken before and after column passage and analyzed by flow cytometry (FACS) for the depletion of CCR2-expressing cells.

The results demonstrate significant depletion of the target population CCR2-expressing monocytes post matrix perfusion. Depletion tests were performed on blood from three healthy donors. The results are shown in FIG. 91a.

In conclusion, the in-vitro results demonstrate a specific reduction of up to 80% of the CCR2-expressing cells by the column. Notably, individuals with fewer CCR2 expressing cells initially achieved lower depletion. The remaining levels of monocytes were around 20-30% in each case, irrespective of the starting point. Non-CCR2-expressing cells remained unaffected (data not shown).

In-Vitro Depletion of Target Cell Populations—RANTES

To investigate the ability to eliminate CCR1, 3 and 5-expressing cells, in vitro tests have been performed on the biotinylated RANTES coupled matrix. Blood was collected from blood donors and passed through a magnetic column device containing biotinylated RANTES coupled to MACs beads. Blood samples were taken before and after column passage and analyzed by flow cytometry (FACS) for the depletion of CCR1, 3 and 5-expressing cells.

The results demonstrate significant depletion of the target population chemokine receptor-expressing cells post matrix perfusion. Depletion tests were performed on blood from a healthy donor. The results are shown in FIG. 91b.

The in-vitro results demonstrate a specific reduction of around 20% of the chemokine receptor-expressing cells by the column. Non-CCR1, 3 or 5-expressing cells remained unaffected (data not shown).

In-Vitro Depletion of Target Cell Populations—MIP-3a

To investigate the ability to eliminate CCR6-expressing cells, in vitro tests have been performed on the biotinylated MIP-3a coupled matrix. Blood was collected from blood donors and passed through the column device containing biotinylated MIP-3a coupled matrix. Blood samples were taken before and after column passage and analyzed by flow cytometry (FACS) for the depletion of CCR6-expressing cells.

The results demonstrate significant depletion of the target population CCR6-expressing lymphocytes post matrix perfusion. Depletion tests were performed on blood from three healthy donors. The results are shown in FIG. 91c.

The in-vitro results demonstrate a specific reduction of up to around 15% of the CCR6-expressing cells by the column. Non-CCR6-expressing cells remained unaffected (data not shown).

The RANTES molecule was synthesized by Almac. The amino acid sequence of the biotinylated RANTES molecule is set forth as SEQ ID NO: 119:

H2N-SPYSSDTTPCCFAYIARPLPRAHIKEYFYTSGKCSNPAVVFVTRK

NRQVCANPEKKWVREYINSLEKS-CO2H

This molecule has the naturally occurring methionine at position 67 replaced with lysine to facilitate biotinylation at position 67.

The side-chain of Lys 67 was directly biotinylated to given the protein primary structure shown in FIG. 12. The protein was folded and disulphide bonds formed between the first and third cysteine in the sequence and between the 2nd and 4th cysteines.

In-Vitro Depletion of Target Cell Populations—TECK

To investigate the ability to eliminate CCR9-expressing cells, in vitro tests have been performed on the bTECK coupled matrix. Blood was collected from blood donors and IBD patients and passed through the column device containing bTECK coupled matrix. Blood samples were taken before and after column passage and analyzed by flow cytometry (FACS) for the depletion of CCR9-expressing cells.

The results demonstrate significant depletion of the target population CD14− positive CCR9-expressing cells post matrix perfusion; while total CD14-positive cells remain unchanged. Depletion tests were performed on blood from healthy donors and IBD patients confirming similar effects. The results are shown in FIGS. 91d and 6e respectively.

In conclusion, the in-vitro results demonstrate a specific reduction of 50-75% of the CCR9-expressing cells by the column. Non-CCR9-expressing cells remained unaffected.

Example 69

Mcp1 Derivatives

MCP-1 has been produced with residue 75 as the site of biotinylation on the chemokine (numbering based upon the mature protein having the amino acid sequence of SEQ ID NO: 2). Biotinylation permits immobilization of MCP-1 on a solid support (via a biotin-avidin interaction). The basic amino acid sequence of MCP-1, including a 23 amino acid leader sequence is set forth as SEQ ID NO: 112,

MKVSAALLCL LLIAATFIPQ GLAQPDAINA PVTCCYNFTN

RKISVQRLAS YRRITSSKCP KEAVIFKTIV AKEICADPKQ

KWVQDSMDHL DKQTQTPKT

The amino acid sequence of the mature protein is set forth as SEQ ID NO: 113,

QPDAINA PVTCCYNFTN RKISVQRLAS YRRITSSKCP

KEAVIFKTIV AKEICADPKQ KWVQDSMDHL DKQTQTPKT

The inventors have determined that chemokines may display improved binding properties where the chemokine is biotinylated via a spacer group. The spacer may prevent the biotin group from impacting on the binding affinity of the chemokine.

Thus, MCP-1 derivatised at the ε-amino side chain functionality of Lys75 with PEG-Biotin (TFA salt) will be synthesised. The PEG spacer will be 3,6,-dioxoaminooctanoic acid. The Gln at the N-terminus of the proteins is subject to pyroGlu formation under physiological conditions. Thus the first glutamine (Gln1) of the sequence will be substituted with pyroglutamine. The molecule will be synthesised as a C-terminal amide (via synthesis on an amide linker). The molecule is shown schematically in FIG. 92.

A biotinMCP-1 Met to Nleu analogue will also be synthesised. The single methionine within the sequence will be altered to Norleucine, to mitigate against oxidation of this residue during the chain assembly and improve stability of the final product. This molecule is shown schematically in FIG. 93.

Once synthesised, the activity of the various biotinMCP-1 derivatives will be determined in cell-based assays. In particular, agonist and antagonist properties will be determined in aequorin functional cell-based assay on human CCR2 receptor.

Example 70

Synthesis of a Ccr2 Antagonist Biotinmcp-1 which Binds to the Receptor without Activation Antagonist Activity (J-H Gong and I. Clark-Lewis, J. Exp. Med., 1995, 181, 63) has been shown for an MCP-1 derivative truncated at the N-terminus. In particular, deletion of residues 1-8, results in binding to CCR2 with Kd 8.3 nM. This protein was unable to cause chemotaxis of CCR2 positive cells. (inhibition of chemotaxis IC50 20 nM)
The amino acid sequence of the truncated version is set forth as SEQ ID NO: 114:

```
VTCCYNFTN RKISVQRLAS YRRITSSKCP KEAVIFKTIV

AKEICADPKQ KWVQDSMDHL DKQTQTPKT
```

A derivative of this truncated version will be synthesised comprising residues 9 to 76 of the mature protein (MCP-1 9-76) with Met64 to Nleu substitution and derivatised at the ε-amino side chain functionality of Lys75 with PEG-Biotin (TFA salt). This molecule is shown schematically in FIG. 94. The PEG spacer will be 3,6,-dioxoaminooctanoic acid. Once synthesised, the activity of the various biotinMCP-1 derivatives will be determined in cell-based assays. In particular, agonist and antagonist properties will be determined in aequorin functional cell-based assay on human CCR2 receptor.

Example 71

Demonstrate Removal of Ccr2 Expressing Cells Using an Alternative Chemokine Ligand to Mcp-1

CCR2 also binds chemokines MCP-2, MCP-3, MCP-4, MCP-5, and HCC-4 in addition to MCP-1. MCP-5 only binds CCR2 and should be selective in its removal of CCR2 expressing cells. MCP5 is a mouse chemokine shown to chemotact human CCR2 cells with EC50<3 nM.

The full length amino acid sequence, including the signal peptide, is set forth as SEQ ID NO: 115

```
MKISTLLCLL LIATTISPQV LAGPDAVSTP VTCCYNVVKQ

KIHVRKLKSY RRITSSQCPR EAVIFRTILD KEICADPKEK

WVKNSINHLD KTSQTFILEP SCLG
```

The amino acid sequence of N-terminal processed MCP-5 chemokine is 82 amino acids long and is set forth as SEQ ID NO: 116

```
GPDAVSTP VTCCYNVVKQ KIHVRKLKSY RRITSSQCPR

EAVIFRTILD KEICADPKEK WVKNSINHLD KTSQTFILEP

SCLG
```

An amino acid sequence alignment suggests that MCP-5 has a C-terminal extension when compared to the amino acid sequence of MCP-1. The results of this alignment are shown in FIG. 95. On this basis a C-terminal truncated version of MCP-5 will be synthesised. This truncated version will comprise MCP-5 residues 1-76, set forth as SEQ ID NO: 117:

```
GPDAVSTP VTCCYNVVKQ KIHVRKLKSY RRITSSQCPR

EAVIFRTILD KEICADPKEK WVKNSINHLD KTSQTFIL
```

In the truncated version, Ile75 to be substituted with Lys, set forth as SEQ ID NO: 118:

```
GPDAVSTP VTCCYNVVKQ KIHVRKLKSY RRITSSQCPR

EAVIFRTILD KEICADPKEK WVKNSINHLD KTSQTFKL
```

Following substitution, the substituted version will be biotinylated at position 75, a lysine or other suitable residue such as ornithine or diaminopropanoic acid via A PEG spacer (3,6,-dioxoaminooctanoic acid). The protein will be synthesised on an amide linker to yield a C-terminal amide derivative. This molecule is shown schematically in FIG. 96.

Once synthesised, the activity of the various biotinMCP-5 derivatives will be determined in cell-based assays. In particular, agonist and antagonist properties will be determined in aequorin functional cell-based assay on human CCR2 receptor.

Example 72

TECK-PEG-Biotin Synthesis Summary

Target Molecule:
TECK (Met to Nleu substitution) derivatised at the ε-amino side chain functionality of Lys72 with PEG-Biotin (TFA salt)
Modifications:
Truncated form of human TECK corresponding to residues 1-74 of the mature protein, which encompasses the sequence corresponding to the chemokine fold. The full length mature protein is 127 amino acids (the signal peptide is 23 amino acids in a 150 amino acid immature protein). The single methionine within the sequence was altered to Norleucine, to mitigate against oxidation of this residue during the chain assembly, which was observed during the synthesis of the natural sequence derivative. The Gln at the N-terminus of the proteins is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 72 was modified through biotinylation on the resin. A PEG spacer was incorporated between the ε-amino functionality and the biotin.

The linear amino acid sequence (SEQ ID NO: 120) is shown, prior to attachment of the PEG spacer and biotin molecules at amino acid 72 (K):

H-XGVFEDCCLAYHYPIGWAVLRRAWTYRIQEVSGSCNLPAAIFYLPKR

HRKVCGNPKSREVQRAXKLLDARNXVF-OH

X=pyroGlu
X64=Norleucine
X72=an amino acid residue that can be biotinylated, such as lysine, ornithine or diaminopropionic acid and optionally is biotinylated, optionally via a spacer molecule such as PEG, e.g. K(PEG-Biotin)

The engineered TECK sequence was assembled on a solid support, using Fmoc protocols for solid-phase peptide synthesis:

H-XGVFEDCCLAYHYPIGWAVLRRAWTYRIQEVSGSCNLPAAIFYLPKR

HRKVCGNPKSREVQRAXKLLDARNXVF-RESIN

X1=pyroGlu
X64=Norleucine
X72=K(ivDde)

FmocLys(ivDde)-OH was incorporated as residue 72 to facilitate site-specific labelling at this position of the protein (SEQ ID NO: 121).
Met to Nle substitution.
N-terminal Gln to pyroglutamic acid substitution.
Removal of Dde Protection:

The Dde protecting group was removed by treatment of all resin (2.5 g) with a solution of 2% hydrazine in DMF (100 ml) over 1 hour period to afford 2.0 g resin.
Labelling Steps:
1. Couple Fmoc-8-Amino-3,6-Dioctanoic Acid Resin (1.5 g) was swollen in DMF (2 ml) and then a solution of Fmoc-8-amino-3,6-dioctanoic acid (0.38 g, 1 mmol), DIC solution (2 ml, 0.5M in DMF) and HOCt solution (2 ml, 0.5M in DMF) was added. The mixture was sonicated for 2 hours and then washed with DMF.
2. Cap The resin was capped with 0.5M acetic anhydride/DMF solution (20 ml) for 5 minutes and then washed with DMF.
3. Fmoc Deprotection Fmoc deprotection was carried out by treatment with 20% piperidine in DMF solution (2×50 ml) for 15 minutes each. The resin was washed with DMF.
4. Couple Biotin-OSu A solution of Biotin-NHS ester (341 mg, 1 mmol) and DIPEA (348 ul) in DMF (10 ml) was added to the resin and the mixture was sonicated for 3 hours. The resin was washed thoroughly with DMF and DCM then dried in vacuo. Dry resin obtained=1.5 g.
Cleavage:

Dry peptide resin (1.5 g) and the mixture was cleaved with TFA (30 ml) containing a scavenger cocktail consisting of TIS, thioanisole, water, EDT and phenol and the mixture was stirred at room temperature for 6 hours. The solution was filtered into cold ether and the resin rinsed with TFA. The peptide was centrifuged, washed with ether, centrifuged and lyophilised to give 1.0 g crude peptide.
Folding Protocol:

Crude peptide (100 mg) was dissolved into 6M GnHCl (233 ml) and then rapidly diluted to 2M GnHCl concentration by the addition of 50 mM TRIS pH8 (467 ml) containing 0.5 mM GSSG and 5 mM GSH. The mixture was stirred at room temperature for 2.5 days and then analysed by HPLC (Jupiter C18, 250×4.6 mm column, 10-60% B over 30 minutes. HPLC analysis confirmed the formation of desired product as well as mis-folded by-products.
Purification:

The folded protein was purified by reverse phase HPLC using a Jupiter C18, 250×21 mm column, 9 ml/min, 10-60% B over 50 minutes. 11.1 mg of pure folded Nle-TECK-Biotin was afforded.

FIG. 98 shows HPLC of purified folded Biotin-TECK (Nleu). The protein eluted in a single peak at 21.6 mins.

FIG. 99 shows Electrospray ionisation with tandem mass spectrometry (ES/MS) data of purified folded Biotin-TECK (Nleu). The expected mass was 8959.4 Da.
Functional Assay Data:

TECK-Biotin-Nle was tested for agonist activity in an Aequorin assay against hCCR9 (Euroscreen) and an EC50 value of 63.6 nM was reported. c.f. EC50 for native TECK is 67.87 nM.

The desired active chemokine comprises the amino acid sequence of SEQ ID NO: 122:

H-XGVFEDCCLAYHYPIGWAVLRRAWTYRIQEVSGSCNLPAAIFYLPKR

HRKVCGNPKSREVQRAXKLLDARNXVF-OH

X1=pyroGlu
X64=Norleucine
X72 is K(PEG-Biotin)

Examples 73 to 79

Chemokine Synthesis

General Protocols
Assembly:

Chemical synthesis of chemokines was performed using standard Fmoc solid phase peptides synthesis (SPPS) techniques on an ABI 433 peptide synthesiser. DIC (0.5 M in DMF) and OxymaPure (0.5 M in DMF) were used for activation, acetic anhydride (0.5 M in DMF) for capping, and 20% piperidine in DMF for Fmoc deprotection. Rink Amide resin was utilised for the generation of C-terminal amide chemokines and Wang resin for C-terminal acid chemokines. After assembly, the resin was washed with DMF and DCM and then dried in vacuo.
Removal of Dde Protection:

The Dde protecting group was removed by treatment of resin with a solution of 2.5% hydrazine in DMF (200 ml) over a 2 hour period. The resin was then washed with DMF.
Labelling Steps:
1. Couple Fmoc-8-Amino-3,6-Dioctanoic Acid (PEG)

Resin was swollen in DMF and then a solution of Fmoc-8-amino-3,6-dioctanoic acid (0.38 g, 1 mmol), DIC solution (2 ml, 0.5 M in DMF) and OxymaPure solution (2 ml, 0.5 M in DMF) was added. The mixture was sonicated for 3 hours and then washed with DMF.
2. Capping The resin was capped with acetic anhydride solution (0.5 M in DMF, 10 ml) for 5 minutes and then washed with DMF.
3. Fmoc deprotection Fmoc deprotection was carried out by treatment with 20% piperidine in DMF solution (2×50 ml) for 15 minutes each. The resin was washed with DMF.
4. Couple Biotin-OSu A solution of Biotin-OSu (341 mg, 1 mmol) and DIPEA (348 ml) in DMF (10 ml) was added to the resin and the mixture was sonicated for 3 hours. The resin was washed thoroughly with DMF and DCM then dried in vacuo.

Cleavage:

Dry resin was treated with TFA (10 ml) containing a scavenger cocktail consisting of TIS (500 ml), thioanisole (500 ml), water (500 ml), DMS (500 ml), EDT (250 ml), NH$_4$I (500 mg) and phenol (500 mg) and the mixture was stirred at room temperature for 5 hours. The solution was filtered into cold ether and the resin rinsed with TFA. The precipitated peptide was centrifuged, washed with ether, centrifuged and lyophilised.

Purification Protocol:

The crude peptide was purified by reverse phase HPLC (RP-HPLC) using a Jupiter C18, 250×21 mm column, 9 ml/min, eluting with an optimised gradient [Buffer A: water containing 0.1% TFA, Buffer B: acetonitrile containing 0.1% TFA].

Folding Protocol:

Pure peptide (10 mg) was dissolved into 6M GnHCl (16 ml) and then rapidly diluted to 2M GnHCl concentration by the addition of 50 mM TRIS pH 8.5 (84 ml) containing 0.3 mM GSSG and 3 mM GSH. The mixture was stirred at room temperature for 24 hours and then analysed by RP-HPLC (Jupiter C18, 250×4.6 mm column, 10-60% B over 30 minutes. Purification by RP-HPLC using an optimised gradient afforded the desired product.

Example 73

BiotinMCP-1 (CCL2)

Target Molecule:

MCP-1 derivatised at the ε-amino side chain functionality of Lys(75) with PEG-Biotin (TFA salt)

Modifications:

Human MCP-1 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the ε-amino functionality and the biotin.

The linear amino acid sequence (SEQ ID NO: 123) is shown, prior to attachment of the PEG spacer and biotin molecules at amino acid 75 (K):

H-XPDAINAPVTCCYNFTNRKISVQRLASYRRITSSKCPKEAVIFKTIVA

KEICADPKQKWVQDSMDHLDKQTQTPKT-NH$_2$

X=pyroGlu or Gln

The engineered MCP-1 sequence was assembled on a solid support (Rink Amide resin), using Fmoc protocols for solid-phase peptide synthesis as described in the general protocols section:

SEQ ID NO: 124
H-XPDAINAPVTCCYNFTNRKISVQRLASYRRITSSKCPKEAVIFKTIVA

KEICADPKQKWVQDSMDHLDKQTQTPXT-RESIN

X1=pyroGlu or Gln
X75=K(ivDde)

FmocLys(ivDde)-OH was incorporated as residue 75 to facilitate site-specific labelling at this position of the protein. Subsequent removal of the ivDde protecting group, followed by coupling of the PEG spacer and Biotin, was carried out as described in the general protocol section. Cleavage, purification and folding protocols were carried out as described to furnish the desired active chemokine.

SEQ ID NO: 125
H-XPDAINAPVTCCYNFTNRKISVQRLASYRRITSSKCPKEAVIFKTIVA

KEICADPKQKWVQDSMDHLDKQTQTPXT-NH$_2$

X1=pyroGlu or Gln
X75 is an amino acid residue that can be biotinylated, such as lysine, ornithine or diaminopropionic acid and optionally is biotinylated, optionally via a spacer molecule such as PEG, optionally K(PEG-Biotin)

Electrospray ionisation with tandem mass spectrometry (ESI-TOF-MS) data of purified folded biotinMCP-1: obtained=9032.8 Da; expected 9034.4 Da.

Functional Assay Data:

biotinMCP-1 was tested for agonist activity in an Aequorin assay against hCCR2b, (Euroscreen) and an EC50 value of 9.6 nM was reported. c.f. EC50 for recombinant native MCP-1 is 3.1 nM.

Example 74

BiotinRANTES (CCL5)

Target Molecule:

RANTES derivatised at the ε-amino side chain functionality of Lys(67) with Biotin (TFA salt)

Modifications:

Human RANTES corresponding to residues 1-68, is initially expressed as 91 amino acids comprising the chemokine fold, and a 23 amino acid signal peptide which is cleaved off. The single methionine (Met67) within the sequence was mutated to lysine, to mitigate against oxidation of this residue during the chain assembly, which was observed during the synthesis of the natural sequence derivative. This Met to Lys substitution provided a lysine at position 67 which was modified through biotinylation on the resin.

The linear amino acid sequence (SEQ ID NO: 126) is shown, prior to attachment of the biotin molecule at amino acid 67 (K):

H-SPYSSDTTPCCFAYIARPLPRAHIKEYFYTSGKCSNPAVVFVTRKNRQ

VCANPEKKWVREYINSLEKS-OH

The engineered RANTES sequence was assembled on a solid support (Wang resin), using Fmoc protocols for solid-phase peptide synthesis as described in the general protocols section:

H-SPYSSDTTPCCFAYIARPLPRAHIKEYFYTSGKCSNPAVVFVTRKNRQ

VCANPEKKWVREYINSLEXS-RESIN

X is K(ivDde)

FmocLys(ivDde)-OH was incorporated as residue 67 to facilitate site-specific labelling at this position of the protein (SEQ ID NO: 127). Subsequent removal of the ivDde protecting group, followed by coupling of the Biotin, was carried out as described in the general protocol section. Cleavage, purification and folding protocols were carried out as described to furnish the desired active chemokine (SEQ ID NO: 128).

H-SPYSSDTTPCCFAYIARPLPRAHIKEYFYTSGKCSNPAVVFVTRKNRQ

VCANPEKKWVREYINSLEXS-OH

X is an amino acid residue that can be biotinylated, such as lysine, ornithine or diaminopropionic acid and optionally is biotinylated, optionally via a spacer molecule such as PEG (e.g. K(Biotin))

Electrospray ionisation with tandem mass spectrometry (ESI-TOF-MS) data of purified folded biotinRANTES: obtained=8068.9 Da; expected 8070.2 Da.

Functional Assay Data:

BiotinRANTES was tested for agonist activity in an Aequorin assay against hCCR5, (Euroscreen) and an EC50 value of 0.5 nM was reported.

Example 75

BiotinMCP-2 (CCL8)

Target Molecule:

MCP-2 derivatised at the e-amino side chain functionality of Lys(75) with PEG-Biotin (TFA salt)

Modifications:

Human MCP-2 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the ε-amino functionality and the biotin.

The linear amino acid sequence (SEQ ID NO: 129) is shown, prior to attachment of the PEG spacer and biotin molecules at amino acid 75 (K):

H-XPDSVSIPITCCFNVINRKIPIQRLESYTRITNIQCPKEAVIFKTKR

GKEVCADPKERWVRDSMKHLDQIFQNLKP-NH$_2$

X=pyroGlu or Gln

The engineered MCP-2 sequence was assembled on a solid support (Rink Amide resin), using Fmoc protocols for solid-phase peptide synthesis as described in the general protocols section:

H-XPDSVSIPITCCFNVINRKIPIQRLESYTRITNIQCPKEAVIFKTKR

GKEVCADPKERWVRDSMKHLDQIFQNLXP-NH$_2$

X1=pyroGlu or Gln
X75=K(ivDde)

FmocLys(ivDde)-OH was incorporated as residue 75 to facilitate site-specific labelling at this position of the protein (SEQ ID NO: 130). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 131):

H-XPDSVSIPITCCFNVINRKIPIQRLESYTRITNIQCPKEAVIFKTKRG

KEVCADPKERWVRDSMKHLDQIFQNLXP-NH$_2$

X1=pyroGlu or Gln
X75=an amino acid residue that can be biotinylated, such as lysine, ornithine or diaminopropionic acid and optionally is biotinylated, optionally via a spacer molecule such as PEG, e.g. K(PEG-Biotin).

Electrospray ionisation with tandem mass spectrometry (ESI-TOF-MS) data of purified folded biotinMCP-2: obtained=9263.6 Da; expected 9263.8 Da.

Functional Assay Data:

biotinMCP-2 was tested for activity in an Aequorin assay against hCCR2b, (Euroscreen) and was shown to be a partial agonist with an EC50 value of 50.9 nM. c.f. EC50 for recombinant native MCP-2 is 23.5 nM (partial agonist).

Example 76

BiotinIL-8 (CXCL8)

Target Molecule:

IL-8 derivatised at the e-amino side chain functionality of Lys(78) with PEG-Biotin (TFA salt)

Modifications:

Human IL-8 corresponding to residues 1-77, is initially expressed as 99 amino acids comprising the chemokine fold, and a 22 amino acid signal peptide which is cleaved off. An additional lysine was inserted at the C-terminus at position 78, and modified through biotinylation on the resin. A PEG spacer was incorporated between the e-amino functionality and the biotin.

The linear amino acid sequence (SEQ ID NO: 132) is shown, prior to attachment of the PEG spacer and biotin molecules:

H-AVLPRSAKELRCQCIKTYSKPFHPKFIKELRVIESGPHCANTEIIVKL

SDGRELCLDPKENWVQRVVEKFLKRAENSX-NH$_2$

X is an amino acid residue that can be biotinylated, such as lysine, ornithine or diaminopropionic acid and optionally is biotinylated, optionally via a spacer molecule such as PEG, e.g. K(PEG-Biotin)

The engineered IL-8 sequence was assembled on a solid support (Rink Amide resin), using Fmoc protocols for solid-phase peptide synthesis as described in the general protocols section:

H-AVLPRSAKELRCQCIKTYSKPFHPKFIKELRVIESGPHCANTEIIVKL

SDGRELCLDPKENWVQRVVEKFLKRAENSX-RESIN

X is K(ivDde)

FmocLys(ivDde)-OH was incorporated as residue 78 to facilitate site-specific labelling at this position of the protein (SEQ ID NO: 133). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 134):

H-AVLPRSAKELRCQCIKTYSKPFHPKFIKELRVIESGPHCANTEIIVKL

SDGRELCLDPKENWVQRVVEKFLKRAENSX-NH$_2$

X is K(PEG-Biotin)
Electrospray ionisation with tandem mass spectrometry (ESI-TOF-MS) data of purified folded biotinIL-8: obtained=9416.9 Da; expected 9417.0 Da.
Functional Assay Data:
BiotinIL-8 was tested for agonist activity in an Aequorin assay against hCXCR1, (Euroscreen) and an EC50 value of 18.9 nM was reported. c.f. EC50 for recombinant native IL-8 is 4.1 nM.

Example 77

BiotinIL-8 (6-78)

Target Molecule:
IL-8 (6-78) derivatised at the e-amino side chain functionality of Lys(78) with PEG-Biotin (TFA salt)
Modifications:
Truncated form of IL-8 corresponding to residues 6-77, the first five N-terminal residues have been removed and an additional lysine was inserted at the C-terminus at position 78, and modified through biotinylation on the resin. A PEG spacer was incorporated between the e-amino functionality and the biotin.
The linear amino acid sequence (SEQ ID NO: 135) is shown, prior to attachment of the PEG spacer and biotin molecules:

H-SAKELRCQCIKTYSKPFHPKFIKELRVIESGPHCANTEIIVKLSDGRE

LCLDPKENWVQRVVEKFLKRAENSX-NH$_2$

X is an amino acid residue that can be biotinylated, such as lysine, ornithine or diaminopropionic acid and optionally is biotinylated, optionally via a spacer molecule such as PEG
The engineered IL-8 sequence was assembled on a solid support (Rink Amide resin), using Fmoc protocols for solid-phase peptide synthesis as described in the general protocols section:

H-SAKELRCQCIKTYSKPFHPKFIKELRVIESGPHCANTEIIVKLSDGRE

LCLDPKENWVQRVVEKFLKRAENSX-RESIN

X is K(ivDde)
FmocLys(ivDde)-OH was incorporated as residue 78 to facilitate site-specific labelling at this position of the protein (SEQ ID NO: 136). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 137):

H-SAKELRCQCIKTYSKPFHPKFIKELRVIESGPHCANTEIIVKLSDGRE

LCLDPKENWVQRVVEKFLKRAENSX-NH$_2$

X is K(PEG-Biotin)
Electrospray ionisation with tandem mass spectrometry (ESI-TOF-MS) data of purified folded biotinIL-8 (6-78): obtained=8880.50 Da; expected 8880.4 Da.
Functional Assay Data:
BiotinIL-8 (6-78) was tested for agonist activity in an Aequorin assay against hCXCR1, (Euroscreen) and an EC50 value of 6.1 nM was reported. c.f. EC50 for recombinant native IL-8 is 4.1 nM.

Example 78

BiotinMIP-3a (CCL20)

Target Molecule:
MIP-3a derivatised at the e-amino side chain functionality of Lys(68) with PEG-Biotin (TFA salt)
Modifications:
Human MIP-3a corresponding to residues 1-70, is initially expressed as 96 amino acids comprising the chemokine fold, and a 26 amino acid signal peptide which is cleaved off. The naturally occurring lysine at position 68 was modified through biotinylation on the resin. A PEG spacer was incorporated between the $\epsilon$-amino functionality and the biotin.
The linear amino acid sequence (SEQ ID NO: 138) is shown, prior to attachment of the PEG spacer and biotin molecules at amino acid 68 (K):

H-ASNFDCCLGYTDRILHPKFIVGFTRQLANEGCDINAIIFHTKKKLSVC

ANPKQTWVKYIVRLLSKKVKNM-OH

The engineered MIP-3a sequence was assembled on a solid support (Wang resin), using Fmoc protocols for solid-phase peptide synthesis as described in the general protocols section:

H-ASNFDCCLGYTDRILHPKFIVGFTRQLANEGCDINAIIFHTKKKLSVC

ANPKQTWVKYIVRLLSKKVXNM-RESIN

X=K(ivDde)
FmocLys(ivDde)-OH was incorporated as residue 68 to facilitate site-specific labelling at this position of the protein (SEQ ID NO: 139). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 140).

H-ASNFDCCLGYTDRILHPKFIVGFTRQLANEGCDINAIIFHTKKKLSVC

ANPKQTWVKYIVRLLSKKVXNM-OH

X is an amino acid residue that can be biotinylated, such as lysine, ornithine or diaminopropionic acid and optionally is biotinylated, optionally via a spacer molecule such as PEG, in particular K(PEG-Biotin)

Electrospray ionisation with tandem mass spectrometry (ESI-TOF-MS) data of purified folded biotinMip-3a: obtained=8396.4 Da; expected 8397.0 Da.

Functional Assay Data:

BiotinMIP-3a was tested for agonist activity in an Aequorin assay against hCCR6, (Euroscreen) and an EC50 value of 1.6 nM was reported. c.f. EC50 for recombinant native MIP-3a is 1.0 nM.

Example 79

BiotinMDC (CCL22)

Target Molecule:

MDC derivatised at the e-amino side chain functionality of Lys(66) with PEG-Biotin (TFA salt)

Modifications:

Human MDC corresponding to residues 1-69, is initially expressed as 93 amino acids comprising the chemokine fold, and a 24 amino acid signal peptide which is cleaved off. The naturally occurring lysine at position 66 was modified through biotinylation on the resin. A PEG spacer was incorporated between the ε-amino functionality and the biotin.

The linear amino acid sequence (SEQ ID NO: 141) is shown, prior to attachment of the PEG spacer and biotin molecules at amino acid 66 (K):

H-GPYGANMEDSVCCRDYVRYRLPLRVVKHFYWTSDSCPRPGVVLLTFRD

KEICADPRVPWVKMILNKLSQ-NH$_2$

The engineered MDC sequence was assembled on a solid support (Rink Amide resin), using Fmoc protocols for solid-phase peptide synthesis as described in the general protocols section:

H-GPYGANMEDSVCCRDYVRYRLPLRVVKHFYWTSDSCPRPGVVLLTFRD

KEICADPRVPWVKMILNXLSQ-RESIN

X=K(ivDde)

FmocLys(ivDde)-OH was incorporated as residue 66 to facilitate site-specific labelling at this position of the protein (SEQ ID NO: 142). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 143).

H-GPYGANMEDSVCCRDYVRYRLPLRVVKHFYWTSDSCPRPGVVLLTFR

DKEICADPRVPWVKMILNXLSQ-NH$_2$

X is an amino acid residue that can be biotinylated, such as lysine, ornithine or diaminopropionic acid and optionally is biotinylated, optionally via a spacer molecule such as PEG, especially K(PEG-Biotin)

Electrospray ionisation with tandem mass spectrometry (ESI-TOF-MS) data of purified folded biotinMDC: obtained=8456.1 Da; expected 8456.9 Da.

Functional Assay Data:

BiotinMDC was tested for agonist activity in an Aequorin assay against hCCR4, (Euroscreen) and an EC50 value of 4.5 nM was reported. c.f. EC50 for recombinant native MDC is 3.6 nM.

Example 80

Diagnosis and Treatment of Inflammatory Skin Disease

Materials and Methods

1. Flow Cytometric Analysis of Peripheral Blood

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH$_4$Cl, pH 7.5) for 15 min at 37° C. The cells were washed in PBS with 2% Bovine Growth Serum, incubated with 10% human serum for 15 min at room temperature (RT) and stained with antibodies (Table 24) at 4° C. for 30 min. The cells were analysed by flow cytometry on a FACS Canto flow cytometer with the FACSDiva software (BD Biosciences).

TABLE 24

List of antibodies for flow cytometric analysis.

| Antibody | Fluorophore | Supplier |
|---|---|---|
| CCR4 | PerCpCy5.5 | BD |
| CXCR1 | APC | Biolegend |
| CXCR2 | PE | Biolegend |
| CD16 | PECy7 | BD |
| CD3 | Horizon V450 | BD |
| Streptavdin | APC | BD |

2. Chemokine Binding Test

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5) for 15 min at 37° C. The cells were washed in PBS with 2% Bovine Growth Serum, incubated with 10% human serum 15 min at room temperature (RT) and stained with cell specific antibodies together with biotinylated chemokine (1 µM) or the corresponding chemokine receptor antibody at 4° C. for 30 min (Table 24). The biotinylated chemokine was detected via the interaction between biotin and a fluorophore conjugated Streptavidin. The samples were analysed by flow cytometry on a FACS Canto flow cytometer with the FACSDiva software (BD Biosciences).

3. Cell Depletion by Matrix Conjugated with Biotinylated Chemokine

Cells were prepared from peripheral blood (section 1). 1 mL Sepharose BigBeads matrix conjugated with 0.4 mg/mL Streptavidin (GE Healthcare) was washed in 50 mL PBS and added to a 5 mL polystyrene tube (BD Falcon™). Biotinylated chemokine was added to the tube and incubated for 20 min at RT to enable immobilization of the chemokine on the matrix via the biotin-streptavidin interaction. Next, the cells were added to the chemokine-matrix and incubated for 20 min at RT. The cells that did not bind to the matrix were removed by washing the matrix with PBS in a sterile 40 um nylon filter (BD Falcon™ Cell Strainer). The flow through cells were stained with antibodies (Table 24), analysed by flow cytometry and compared with cells from peripheral blood that had not been incubated with the chemokine-matrix.

Results and Discussion

1. Flow Cytometric Analysis of Peripheral Blood—CCR4

White blood cells from one patient with psoriasis were analysed for the expression of chemokine receptors with flow cytometry. The patient exhibited an increased frequency of CCR4 expressing T cells compared to healthy controls, based upon flow cytometry data and binding by an anti-CCR4 antibody (FIG. 101).

2. Chemokine Binding Test—CCR4

The chemokine receptor CCR4 is necessary for T cell migration to the skin, which leads to inflammation. The ligand for CCR4 is the chemokine MDC (CCL22) which is expressed in inflamed skin lesions.

The T cells could bind biotinylated MDC (bMDC) to a similar extent as the chemokine receptor expression (FIG. 102).

3. Cell Depletion by Matrix Conjugated with Biotinylated Chemokine—CCR4

The CCR4 expressing T cells could be efficiently depleted with biotinylated MDC conjugated Sepharose Streptavidin Matrix (FIG. 103).

1. Flow Cytometric Analysis of Peripheral Blood—CXCR1 and CXCR2

The chemokine receptors CXCR1 and CXCR2 were expressed on neutrophils (FIG. 104), based upon flow cytometry data and binding of an anti-CXCR1 and anti-CXCR2 antibody. Th17 cells produce IL-17 causing IL-8 release and attract neutrophils to sites of skin inflammation. Therefore eliminating neutrophils is predicted to be beneficial for treatment of inflammatory skin conditions such as psoriasis.

2. Chemokine Binding Test—CXCR1 and CXCR2

The ligand for CXCR1 and CXCR2 is IL-8 that mediate migration of neutrophils in inflammation. In accordance with the receptor expression, biotinylated IL-8 (bIL-8) could bind to blood neutrophils from a psoriasis patient (FIG. 105).

3. Cell Depletion by Matrix Conjugated with Biotinylated Chemokine—CXCR1 and CXCR2

The CXCR2 expressing neutrophils could be efficiently depleted with bIL-8 conjugated Sepharose Streptavidin Matrix (FIG. 106).

Conclusions

We conclude that the frequency of CCR4 expressing T cells is enhanced in psoriasis. The CCR4 expressing T cells and CXCR1 and CXCR2 expressing neutrophils could bind their respective chemokines, and could be efficiently depleted with biotinylated chemokine-Sepharose Streptavidin-matrix.

H. Treating Multiple Sclerosis

In secondary progressive MS microglia/MØ present at border of plaques produce chemokines MCP-1 and CXCL10 responsible for attracting CCR2 and CXCR3 expressing cells including macrophages and astrocytes.

It is shown herein that subjects suffering from MS exhibit increased frequency of chemokine receptor expressing cells in the peripheral blood, in particular CCR2 and CCR6 expressing T lymphocytes, compared to healthy controls. It is also shown herein that the CCR2 cells can be removed using a suitable binding reagent, in particular MCP-1 (in biotinylated form) immobilized on a suitable matrix. Similarly, it is shown herein that (the additional) CCR6-expressing cells can be depleted using a suitable binding reagent, in particular CCL20 (MIP-3ı), in biotinylated form, immobilized on a suitable matrix. The CCL5 levels are significantly elevated in cerebrospinal fluid of MS patients with relapsing disease demonstrating that circulating CCL5 is involved in recruiting CCL5 binding cells to the brain. These findings are supported by the enrichment of T cells in cerebrospinal fluid expressing CCR5 and CCR6 suggesting an active accumulation due to a chemokine gradient of CCL5. Therefore eliminating cells normally attracted to the brain by providing an extracorpeal source of CCL5 attached to a column will be useful for the treatment of MS.

Examples 81 and 82

Materials and Methods

Isolation of Peripheral Blood Leukocytes.

Heparinized peripheral blood from healthy blood donors or inflammatory bowel disease (IBD) patients was fixed with 4% paraformaldehyde for 4 minutes, hemolyzed for 15 minutes with a 0.83% ammonium chloride solution and washed twice in FACS buffer to obtain a suspension of blood leukocytes.

Chemokines.

The leukocytes were incubated for 30 min in the dark at 4° C. with biotinylated and Alexa647 Fluor® labeled MCP-1 (in concentrations 10 ng/µL and 50 ng/µL). The cells were then washed with FACS-buffer and analyzed by flow cytometry. All chemokines used in the Examples were provided by Almac Sciences Scotland Ltd, Edinburgh, Scotland.

Flow Cytometry Assay.

The flow cytometry assay was performed on a two laser FACS Calibur cytometer (BD Immunocytometry systems, San José, Ca, USA). Ten thousand cells were counted and analysed in each sample. For data analyses, Cell Quest Pro software from Becton Dickinson was used.

Example 81

Binding of Monocytes to MCP-1

In the experiment with biotinylated MCP-1 it was found that about 90% of the monocytes obtained from peripheral blood of healthy donors had bound to the cytokine after 30 min of incubation (FIG. 107a), whereas CD4+ and CD8+ lymphocytes had not bound (FIGS. 107b and 107c).

Example 82

Monocytes were investigated for their expression of CCR2 (FIG. 108b) and their ability to bind MCP-1 (FIG. 108a). CCR2 expression was noted an all monocytes with the majority of monocytes expressing high levels, using an anti-CCR2 antibody (FIG. 108b). The MCP-1 binding to monocytes shown in FIG. 108a corresponds to the CCR2hi expressing population shown in FIG. 108b. Thus, MCP-1 binds favourably to CCR2hi expressing cells.

Example 83

Tailored Leukapheresis

Column Design and Properties
Introduction

Apheresis is an established treatment used for depletion of blood components, such as antibodies, low-density lipoproteins (LDL) and blood cells. Leukapheresis is the apheresis treatment used for removal of white blood cells, leukocytes. The patient is connected to an extracorporeal blood circulating system; the blood is drawn from a vein in one arm, passed through a column device and returned into the other arm of the patient. Side effects of leukapheresis treatments are varying from mild events like headache, dizziness, hypotension, palpitation and flush seen in 0.1 to 5% of treated patients.

The Column

The column is intended to be used as a leukapheresis treatment for multiple sclerosis. It will specifically remove CCR2, CCR6, CCR3, CCR5, CCR1, CXCR3 and/or CCR9-expressing leukocytes, in particular monocytes, through the use of a binding reagent, more specifically an MCP-1, MCP-2, MCP-3, MCP-4, MCP-5, MIP-3alpha, MIG (CXCL9), IP10 (CXCL10), CXCL11 (I-TAC), CCL25 and RANTES containing resin, exploiting the CCR2, CCR6, CCR3, CCR5, CCR1, CXCR3 and/or CCR9-chemokine interaction. The column consists of three combined components, the plastic house, the streptavidin (SA) Sepharose™ BigBeads matrix and one or more of biotinylated MCP-1, MCP-2, MCP-3, MCP-4, MCP-5, MIP-3alpha, MIG (CXCL9), IP10 (CXCL10), CXCL11 (I-TAC), CCL25 and RANTES bound to the matrix. The treatment is conducted using the same techniques as a standard apheresis procedure.

The Plastic House (FIG. 9)

The plastic house, designed to keep a continuous blood flow through the matrix, consists of a transparent body and red-coloured top. The top has a distribution plate (2) at the inflow site (1) to spread the blood evenly over the entire matrix area. The plate is the first safety barrier preventing larger particles flowing through the column and into the patient. Safety filter units (3 and 4) are placed at the inflow (1) and outflow (5) sites of the plastic housing. The safety filter unit contains three filters designed to be a robust barrier and stop all particles larger than blood cells passing through the column. The plastic housing design is shown in FIG. 9. The design with safety filters (3 and 4) at both ends of the column device will minimize the risk of leakage of particles into the patient, including in the event that the device is placed up side down with the blood flow in the opposite direction to that anticipated.

Streptavidin Sepharose™ BigBeads

The second component in the device is the affinity matrix called streptavidin Sepharose™ BigBeads (Sepharose™ GE Healthcare, Sweden). Sepharose™ is a cross linked, beaded-form of agarose, which is a polysaccharide extracted from seaweed. Sepharose™ and agarose are commonly used as column matrices in biomedical affinity techniques. It is chosen for its optimal distribution capacity and can provide a large available area for affinity binding.

Binding Reagent

Coupled to the matrix is the third component of the device, the one or more binding reagents that bind specifically to CCR2, CCR6, CCR3, CCR5, CCR1, CXCR3 and/or CCR9. One or more chemokines such as those selected from the group consisting of MCP-1, MCP-2, MCP-3, MCP-4, MCP-5, MIP-3alpha, MIG (CXCL9), IP10 (CXCL10), CXCL11 (I-TAC), CCL25 and RANTES may be employed. These peptides may be synthetic, engineered versions of the human chemokine, which are truncated and biotinylated, but retain binding activity to the CCR2, CCR6, CCR3, CCR5, CCR1, CXCR3 and/or CCR9 receptor. By biotinylating the engineered chemokine, it is able to bind to the streptavidin molecules in the Sepharose™ matrix. The biotin-streptavidin binding is known be one of the strongest biological interactions with a Kd in the order of $4 \times 10^{-14}$ M. The calculated ratio of streptavidin:biotin binding sites in the column is 10:1. Therefore, the coupling between the matrix and chemokine will be immediate, minimising the risk of chemokine decoupling from the matrix.

The Apheresis System

To conduct the leukapheresis the following components are needed; the column, tubing system, and a 4008 ADS pump (Fresenius Medical Care).

The Circuit

The system is illustrated in FIG. 10. The patient (1) is connected to the extracorporeal circuit via sterile Venflon needles to veins in the right and the left arms. A saline bag (3) is also connected and the saline solution is pumped with an ACD pump (2). Blood is drawn from one arm of the patient through the sterile tubing system by the blood pump (4) and passed through the column (6) and back to the patient. The tubing system is connected to the column via standard dialysis luer-lock couplings. The couplings on the column are colour-coded for correct assembly; red tubing for inflow to the red column top and blue tubing for outflow back to the patient. An air detector (8) is present. Inlet pressure (5) and Pven sensors (7) are employed to monitor the pressure in the circuit.

The 4008 ADS Pump

An apheresis pump, from Fresenius Medical Care, monitors the patient's inflow and outflow, the pressure in the extracorporeal circulation and can discriminate air by a bubble catcher and air detector. A clot catcher filter is placed inside the bubble catcher. The pump also has an optical detector to distinguish between light, e.g. saline solution or air present in the tubing system and dark e.g. blood present in the tubing system.

A schematic diagram of the pump, showing the air detector and optical filter is shown in FIG. 11. If the pump system detects air bubbles and optical fluctuations or if extracorporeal pressure values are out of the set range, then the pump stops immediately and a visual/audible alarm are emitted.

LEGEND FOR FIG. 11

1. Monitor
2. Holder for waste bag
3. Modules (left to right—Blood pump, ACD pump, Air detector)
4. Reserve places for further modules
5. Absorber holder
6. Drip detector
7. IV pole Preparation of the Patient The patient will be administered anticoagulants prior to each treatment session. A sterile saline solution with 5000 IE Heparin will be used for priming the extracorporeal system, thereafter a bolus injection with 4000 IE Heparin will be added into the circuit at the start of each treatment session.

Leukapheresis Time and Flow Rate

The apheresis system should be operated at a flow rate of 30-60 mL/min. A treatment is finalised after 1800 mL of blood has been circulated.

Storage Conditions

The column devices should be stored between 1 and 25° C. avoiding freezing and more elevated temperatures. Stability data >3 months indicate no difference in functionality over time or by temperature (room temperature and refrigerated). The columns will be kept in refrigerated conditions until use. Mechanical damage as those resulting from violent vibrations and trauma should be avoided. Column stored outside of these recommendations should not be used.

Transport Conditions

The column devices will be transported under refrigerated condition, avoiding freezing and more elevated temperatures. Mechanical damage such as those resulting from violent vibrations and trauma should be avoided.

In-Vitro Depletion of Target Cell Populations—MCP-1

To investigate the ability to eliminate CCR2-expressing cells, in vitro tests have been performed on the bMCP-1 coupled matrix. Blood was collected from blood donors and passed through the column device containing bMCP-1 coupled matrix. Blood samples were taken before and after column passage and analyzed by flow cytometry (FACS) for the depletion of CCR2-expressing cells.

The results demonstrate significant depletion of the target population CCR2-expressing monocytes post matrix perfusion. Depletion tests were performed on blood from three healthy donors. The results are shown in FIG. 109a.

In conclusion, the in-vitro results demonstrate a specific reduction of up to 80% of the CCR2-expressing cells by the column. Notably, individuals with fewer CCR2 expressing cells initially achieved lower depletion. The remaining levels of monocytes were around 20-30% in each case, irrespective of the starting point. Non-CCR2-expressing cells remained unaffected (data not shown).

In-Vitro Depletion of Target Cell Populations—RANTES

To investigate the ability to eliminate CCR1, 3 and 5-expressing cells, in vitro tests have been performed on the biotinylated RANTES coupled matrix. Blood was collected from blood donors and passed through the column device containing biotinylated RANTES coupled matrix. Blood samples were taken before and after column passage and analyzed by flow cytometry (FACS) for the depletion of CCR1, 3 and 5-expressing cells.

The results demonstrate significant depletion of the target population chemokine receptor-expressing cells post matrix perfusion. Depletion tests were performed on blood from a healthy donor. The results are shown in FIG. 109b.

The in-vitro results demonstrate a specific reduction of around 20% of the chemokine receptor-expressing cells by the column. Non-CCR1, 3 or 5-expressing cells remained unaffected (data not shown).

In-Vitro Depletion of Target Cell Populations—MIP-3Alpha

To investigate the ability to eliminate CCR6-expressing cells, in vitro tests have been performed on the biotinylated MIP-3a coupled matrix. Blood was collected from blood donors and passed through the column device containing biotinylated MIP-3a coupled matrix. Blood samples were taken before and after column passage and analyzed by flow cytometry (FACS) for the depletion of CCR6-expressing cells.

The results demonstrate significant depletion of the target population CCR6-expressing lymphocytes post matrix perfusion. Depletion tests were performed on blood from three healthy donors. The results are shown in FIG. 109c.

The in-vitro results demonstrate a specific reduction of up to around 15% of the CCR6-expressing cells by the column. Non-CCR6-expressing cells remained unaffected (data not shown).

The RANTES molecule was synthesized by Almac. The amino acid sequence of the biotinylated RANTES molecule is set forth as SEQ ID NO: 160:

H2N-SPYSSDTTPCCFAYIARPLPRAHIKEYFYTSGKCSNPAVVFVTRKN
RQVCANPEKKWVREYINSLEKS-CO2H

This molecule has the naturally occurring methionine at position 67 replaced with lysine to facilitate biotinylation at position 67.

The side-chain of Lys 67 was directly biotinylated to given the protein primary structure shown in FIG. 115. The protein was folded and disulphide bonds formed between the first and third cysteine in the sequence and between the 2nd and 4th cysteines.

Example 84

MCP1 Derivatives

MCP-1 has been produced with residue 75 as the site of biotinylation on the chemokine (numbering based upon the mature protein having the amino acid sequence of SEQ ID NO: 144). Biotinylation permits immobilization of MCP-1 on a solid support (via a biotin-avidin interaction). The basic amino acid sequence of MCP-1, including a 23 amino acid leader sequence is set forth as SEQ ID NO: 144,

MKVSAALLCL LLIAATFIPQ GLAQPDAINA PVTCCYNFTN

RKISVQRLAS YRRITSSKCP KEAVIFKTIV AKEICADPKQ

KWVQDSMDHL DKQTQTPKT

The amino acid sequence of the mature protein is set forth as SEQ ID NO: 145,

QPDAINA PVTCCYNFTN RKISVQRLAS YRRITSSKCP

KEAVIFKTIV AKEICADPKQ KWVQDSXDHL DKQTQTPKT

X=Met or Nleu

The inventors have determined that chemokines may display improved binding properties where the chemokine is biotinylated via a spacer group. The spacer may prevent the biotin group from impacting on the binding affinity of the chemokine.

Thus, MCP-1 derivatised at the ε-amino side chain functionality of Lys75 with PEG-Biotin (TFA salt) will be synthesised. The PEG spacer will be 3,6,-dioxoaminooctanoic acid. The Gln at the N-terminus of the proteins is subject to pyroGlu formation under physiological conditions. Thus the first glutamine (Gln1) of the sequence will be substituted with pyroglutamine. The molecule will be synthesised as a C-terminal amide (via synthesis on an amide linker). The molecule is shown schematically in FIG. 110.

A biotinMCP-1 Met to Nleu analogue will also be synthesised. The single methionine within the sequence will be altered to Norleucine, to mitigate against oxidation of this residue during the chain assembly and improve stability of the final product. This molecule is shown schematically in FIG. 111 and in SEQ ID NO: 145.

Once synthesised, the activity of the various biotinMCP-1 derivatives will be determined in cell-based assays. In particular, agonist and antagonist properties will be determined in aequorin functional cell-based assay on human CCR2 receptor.

Example 85

Synthesis of a Ccr2 Antagonist Biotinmcp-1 which Binds to the Receptor without Activation Antagonist Activity (J-H Gong and I. Clark-Lewis, J. Exp. Med., 1995, 181, 63) has been shown for an MCP-1 derivative truncated at the N-terminus. In particular, deletion of residues 1-8, results in binding to CCR2 with Kd 8.3 nM. This protein was unable to cause chemotaxis of CCR2 positive cells (inhibition of chemotaxis IC50 20 nM)

The amino acid sequence of the truncated version is set forth as SED ID NO: 146:

```
VTCCYNFTN RKISVQRLAS YRRITSSKCP KEAVIFKTIV

AKEICADPKQ KWVQDSMDHL DKQTQTPKT
```

A derivative of this truncated version will be synthesised comprising residues 9 to 76 of the mature protein (MCP-1 9-76) with Met64 to Nleu substitution and derivatised at the ϵ-amino side chain functionality of Lys75 with PEG-Biotin (TFA salt). This molecule is shown schematically in FIG. 112. The PEG spacer will be 3,6,-dioxoaminooctanoic acid. Once synthesised, the activity of the various biotinMCP-1 derivatives will be determined in cell-based assays. In particular, agonist and antagonist properties will be determined in aequorin functional cell-based assay on human CCR2 receptor.

Example 86

Demonstrate Removal of CCR2 Expressing Cells Using an Alternative Chemokine Ligand to MCP-1

CCR2 also binds chemokines MCP-2, MCP-3, MCP-4, MCP-5, and HCC-4 in addition to MCP-1. MCP-5 only binds CCR2 and should be selective in its removal of CCR2 expressing cells. MCP5 is a mouse chemokine shown to chemotact human CCR2 cells with EC50<3 nM.

The full length amino acid sequence, including the signal peptide, is set forth as SEQ ID NO: 147

```
MKISTLLCLL LIATTISPQV LAGPDAVSTP VTCCYNVVKQ

KIHVRKLKSY RRITSSQCPR EAVIFRTILD KEICADPKEK

WVKNSINHLD KTSQTFILEP SCLG
```

The amino acid sequence of N-terminal processed MCP-5 chemokine is 82 amino acids long and is set forth as SEQ ID NO: 148

```
GPDAVSTP VTCCYNVVKQ KIHVRKLKSY RRITSSQCPR

EAVIFRTILD KEICADPKEK WVKNSINHLD KTSQTFILEP SCLG
```

An amino acid sequence alignment suggests that MCP-5 has a C-terminal extension when compared to the amino acid sequence of MCP-1. The results of this alignment are shown in FIG. 113. On this basis a C-terminal truncated version of MCP-5 will be synthesised. This truncated version will comprise MCP-5 residues 1-76, set forth as SEQ ID NO: 149:

```
GPDAVSTP VTCCYNVVKQ KIHVRKLKSY RRITSSQCPR

EAVIFRTILD KEICADPKEK WVKNSINHLD KTSQTFIL
```

In the truncated version, Ile75 to be substituted with Lys, set forth as SEQ ID NO: 150:

```
GPDAVSTP VTCCYNVVKQ KIHVRKLKSY RRITSSQCPR

EAVIFRTILD KEICADPKEK WVKNSINHLD KTSQTFKL
```

Following substitution, the substituted version will be biotinylated at position 75, a lysine or other suitable residue such as ornithine or diaminopropanoic acid via A PEG spacer (3,6,-dioxoaminooctanoic acid). The protein will be synthesised on an amide linker to yield a C-terminal amide derivative. This molecule is shown schematically in FIG. 114.

Once synthesised, the activity of the various biotinMCP-5 derivatives will be determined in cell-based assays. In particular, agonist and antagonist properties will be determined in aequorin functional cell-based assay on human CCR2 receptor.

Examples 87 to 94

General Protocols for Chemokine Synthesis

Assembly:

Chemical synthesis of chemokines was performed using standard Fmoc solid phase peptides synthesis (SPPS) techniques on an ABI 433 peptide synthesiser. DIC (0.5 M in DMF) and OxymaPure (0.5 M in DMF) were used for activation, acetic anhydride (0.5 M in DMF) for capping, and 20% piperidine in DMF for Fmoc deprotection. Rink Amide resin was utilised for the generation of C-terminal amide chemokines and Wang resin for C-terminal acid chemokines. After assembly, the resin was washed with DMF and DCM and then dried in vacuo.

Removal of Dde Protection:

The Dde protecting group was removed by treatment of resin with a solution of 2.5% hydrazine in DMF (200 ml) over a 2 hour period. The resin was then washed with DMF.

Labelling Steps:

1. Couple Fmoc-8-Amino-3,6-Dioctanoic Acid (PEG)

Resin was swollen in DMF and then a solution of Fmoc-8-amino-3,6-dioctanoic acid (0.38 g, 1 mmol), DIC solution (2 ml, 0.5 M in DMF) and OxymaPure solution (2 ml, 0.5 M in DMF) was added. The mixture was sonicated for 3 hours and then washed with DMF.

2. Capping

The resin was capped with acetic anhydride solution (0.5 M in DMF, 10 ml) for 5 minutes and then washed with DMF.

3. Fmoc Deprotection

Fmoc deprotection was carried out by treatment with 20% piperidine in DMF solution (2×50 ml) for 15 minutes each. The resin was washed with DMF.

4. Couple Biotin-OSu

A solution of Biotin-OSu (341 mg, 1 mmol) and DIPEA (348 ml) in DMF (10 ml) was added to the resin and the mixture was sonicated for 3 hours. The resin was washed thoroughly with DMF and DCM then dried in vacuo.

Cleavage:

Dry resin was treated with TFA (10 ml) containing a scavenger cocktail consisting of TIS (500 ml), thioanisole (500 ml), water (500 ml), DMS (500 ml), EDT (250 ml), $NH_4I$ (500 mg) and phenol (500 mg) and the mixture was stirred at room temperature for 5 hours. The solution was filtered into cold ether and the resin rinsed with TFA. The precipitated peptide was centrifuged, washed with ether, centrifuged and lyophilised.

Purification Protocol:

The crude peptide was purified by reverse phase HPLC (RP-HPLC) using a Jupiter C18, 250×21 mm column, 9 ml/min, eluting with an optimised gradient [Buffer A: water containing 0.1% TFA, Buffer B: acetonitrile containing 0.1% TFA].

Folding Protocol:

Pure peptide (10 mg) was dissolved into 6M GnHCl (16 ml) and then rapidly diluted to 2M GnHCl concentration by the addition of 50 mM TRIS pH 8.5 (84 ml) containing 0.3 mM GSSG and 3 mM GSH. The mixture was stirred at room temperature for 24 hours and then analysed by RP-HPLC (Jupiter C18, 250×4.6 mm column, 10-60% B over 30 minutes. Purification by RP-HPLC using an optimised gradient afforded the desired product.

Example 87

BiotinMCP-1 (CCL2)

Target Molecule:

MCP-1 derivatised at the e-amino side chain functionality of Lys(75) with PEG-Biotin (TFA salt)

Modifications:

Human MCP-1 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the ε-amino functionality and the biotin.

The linear amino acid sequence (SEQ ID NO: 151) is shown, prior to attachment of the PEG spacer and biotin molecules at amino acid 75 (K):

H-XPDAINAPVTCCYNFTNRKISVQRLASYRRITSSKCPKEAVIFKTIVA

KEICADPKQKWVQDSMDHLDKQTQTPKT-NH$_2$

X=pyroGlu

The engineered MCP-1 sequence was assembled on a solid support (Rink Amide resin), using Fmoc protocols for solid-phase peptide synthesis as described in the general protocols section:

H-XPDAINAPVTCCYNFTNRKISVQRLASYRRITSSKCPKEAVIFKTIVA

KEICADPKQKWVQDSMDHLDKQTQTPXT-RESIN

X1=pyroGlu
X75=K(ivDde)

FmocLys(ivDde)-OH was incorporated as residue 75 to facilitate site-specific labelling at this position of the protein (SEQ ID NO: 152). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 153):

H-XPDAINAPVTCCYNFTNRKISVQRLASYRRITSSKCPKEAVIFKTIVA

KEICADPKQKWVQDSMDHLDKQTQTPXT-NH$_2$

X1=pyroGlu

X75=an amino acid residue that can be biotinylated, such as lysine, ornithine or diaminopropionic acid and optionally is biotinylated, optionally via a spacer molecule such as PEG, e.g. K(PEG-Biotin).

Electrospray ionisation with tandem mass spectrometry (ESI-TOF-MS) data of purified folded biotinMCP-1: obtained=9032.8 Da; expected 9034.4 Da.

Functional Assay Data:

biotinMCP-1 was tested for agonist activity in an Aequorin assay against hCCR2b, (Euroscreen) and an EC50 value of 9.6 nM was reported. c.f. EC50 for recombinant native MCP-1 is 3.1 nM.

Example 88

BiotinMCP-2 (CCL8)

Target Molecule:

MCP-2 derivatised at the e-amino side chain functionality of Lys(75) with PEG-Biotin (TFA salt)

Modifications:

Human MCP-2 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the ε-amino functionality and the biotin.

The linear amino acid sequence (SEQ ID NO: 154) is shown, prior to attachment of the PEG spacer and biotin molecules at amino acid 75 (K):

H-XPDSVSIPITCCFNVINRKIPIQRLESYTRITNIQCPKEAVIFKTKRG

KEVCADPKERWVRDSMKHLDQIFQNLKP-NH$_2$

X=pyroGlu

The engineered MCP-2 sequence was assembled on a solid support (Rink Amide resin), using Fmoc protocols for solid-phase peptide synthesis as described in the general protocols section:

H-XPDSVSIPITCCFNVINRKIPIQRLESYTRITNIQCPKEAVIFKTKRG

KEVCADPKERWVRDSMKHLDQIFQNLXP-NH$_2$

X1=pyroGlu
X75=K(ivDde)

FmocLys(ivDde)-OH was incorporated as residue 75 to facilitate site-specific labelling at this position of the protein (SEQ ID NO: 155). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 156):

H-XPDSVSIPITCCFNVINRKIPIQRLESYTRITNIQCPKEAVIFKTKRG

KEVCADPKERWVRDSMKHLDQIFQNLXP-NH$_2$

X1=pyroGlu
X75=an amino acid residue that can be biotinylated, such as lysine, ornithine or diaminopropionic acid and optionally is biotinylated, optionally via a spacer molecule such as PEG, e.g. K(PEG-Biotin).

Electrospray ionisation with tandem mass spectrometry (ESI-TOF-MS) data of purified folded biotinMCP-2: obtained=9263.6 Da; expected 9263.8 Da.
Functional Assay Data:
biotinMCP-2 was tested for activity in an Aequorin assay against hCCR2b, (Euroscreen) and was shown to be a partial agonist with an EC50 value of 50.9 nM. c.f. EC50 for recombinant native MCP-2 is 23.5 nM (partial agonist).

Example 89

BiotinEotaxin (CCL11)

Target Molecule:
Eotaxin derivatised at the e-amino side chain functionality of Lys(73) with PEG-Biotin (TFA salt)
Modifications:
Human eotaxin corresponding to residues 1-74, is initially expressed as 97 amino acids comprising the chemokine fold, and a 23 amino acid signal peptide which is cleaved off. The naturally occurring lysine at position 73 was modified through biotinylation on the resin. A PEG spacer was incorporated between the ε-amino functionality and the biotin.

The linear amino acid sequence (SEQ ID NO: 157) is shown, prior to attachment of the PEG spacer and biotin molecules at amino acid 73 (K):

H-GPASVPTTCCFNLANRKIPLQRLESYRRITSGKCPQKAVIFKTKLAKD

ICADPKKKWVQDSMKYLDQKSPTPXP-NH$_2$

X is an amino acid residue that can be biotinylated, such as lysine, ornithine or diaminopropionic acid and optionally is biotinylated, optionally via a spacer molecule such as PEG, e.g. K(PEG-Biotin).

The engineered eotaxin sequence was assembled on a solid support (Rink Amide resin), using Fmoc protocols for solid-phase peptide synthesis as described in the general protocols section:

H-GPASVPTTCCFNLANRKIPLQRLESYRRITSGKCPQKAVIFKTKLAKD

ICADPKKKWVQDSMKYLDQKSPTPXP-NH$_2$

X is K(ivDde)

FmocLys(ivDde)-OH was incorporated as residue 73 to facilitate site-specific labelling at this position of the protein (SEQ ID NO: 158). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 159):

H-GPASVPTTCCFNLANRKIPLQRLESYRRITSGKCPQKAVIFKTKLAKD

ICADPKKKWVQDSMKYLDQKSPTPXP-NH$_2$

X is K(PEG-Biotin)
Electrospray ionisation with tandem mass spectrometry (ESi-TOF-MS) data of purified folded biotinEotaxin: obtained=8731.3 Da; expected 8731.3 Da.
Functional Assay Data:
biotinEotaxin was tested for activity in an Aequorin assay against hCCR3, (Euroscreen) and was shown to be an antagonist with an EC50 value of 211.8 nM. c.f. EC50 for recombinant native eotaxin is 10.7 nM (agonist).

Example 90

BiotinRANTES (CCL5)

Target Molecule:
RANTES derivatised at the e-amino side chain functionality of Lys(67) with Biotin (TFA salt)
Modifications:
Human RANTES corresponding to residues 1-68, is initially expressed as 91 amino acids comprising the chemokine fold, and a 23 amino acid signal peptide which is cleaved off. The single methionine (Met67) within the sequence was mutated to lysine, to mitigate against oxidation of this residue during the chain assembly, which was observed during the synthesis of the natural sequence derivative. This Met to Lys substitution provided a lysine at position 67 which was modified through biotinylation on the resin.

The linear amino acid sequence (SEQ ID NO: 160) is shown, prior to attachment of the biotin molecule at amino acid 67 (K):

H-SPYSSDTTPCCFAYIARPLPRAHIKEYFYTSGKCSNPAVVFVTRK

NRQVCANPEKKWVREYINSLEKS-OH

The engineered RANTES sequence was assembled on a solid support (Wang resin), using Fmoc protocols for solid-phase peptide synthesis as described in the general protocols section:

H-SPYSSDTTPCCFAYIARPLPRAHIKEYFYTSGKCSNPAVVFVTRKN

RQVCANPEKKWVREYINSLEXS-RESIN

X is K(ivDde)
FmocLys(ivDde)-OH was incorporated as residue 67 to facilitate site-specific labelling at this position of the protein (SEQ ID NO: 161). Subsequent removal of the ivDde protecting group, followed by coupling of the Biotin, was carried out as described in the general protocol section. Cleavage, purification and folding protocols were carried out as described to furnish the desired active chemokine (SEQ ID NO: 162).

H-SPYSSDTTPCCFAYIARPLPRAHIKEYFYTSGKCSNPAVVFVTRKN

RQVCANPEKKWVREYINSLEXS-OH

X is an amino acid residue that can be biotinylated, such as lysine, ornithine or diaminopropionic acid and optionally is biotinylated, optionally via a spacer molecule such as PEG (e.g. K(Biotin))

Electrospray ionisation with tandem mass spectrometry (ESI-TOF-MS) data of purified folded biotinRANTES: obtained=8068.9 Da; expected 8070.2 Da.
Functional Assay Data:
BiotinRANTES was tested for agonist activity in an Aequorin assay against hCCR5, (Euroscreen) and an EC50 value of 0.5 nM was reported.

Example 91

BiotinMIP-3a (CCL20)

Target Molecule:
MIP-3a derivatised at the e-amino side chain functionality of Lys(68) with PEG-Biotin (TFA salt)
Modifications:
Human MIP-3a corresponding to residues 1-70, is initially expressed as 96 amino acids comprising the chemokine fold, and a 26 amino acid signal peptide which is cleaved off. The naturally occurring lysine at position 68 was modified through biotinylation on the resin. A PEG spacer was incorporated between the ε-amino functionality and the biotin.
The linear amino acid sequence (SEQ ID NO: 163) is shown, prior to attachment of the PEG spacer and biotin molecules at amino acid 68 (K):

H-ASNFDCCLGYTDRILHPKFIVGFTRQLANEGCDINAIIFHTKKKLSV

CANPKQTWVKYIVRLLSKKVKNM-OH

The engineered MIP-3a sequence was assembled on a solid support (Wang resin), using Fmoc protocols for solid-phase peptide synthesis as described in the general protocols section:

H-ASNFDCCLGYTDRILHPKFIVGFTRQLANEGCDINAIIFHTKKKLSV

CANPKQTWVKYIVRLLSKKVXNM-RESIN

X=K(ivDde)
FmocLys(ivDde)-OH was incorporated as residue 68 to facilitate site-specific labelling at this position of the protein (SEQ ID NO: 164). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 165).

H-ASNFDCCLGYTDRILHPKFIVGFTRQLANEGCDINAIIFHTKKKLSV

CANPKQTWVKYIVRLLSKKVXNM-OH

X is an amino acid residue that can be biotinylated, such as lysine, ornithine or diaminopropionic acid and optionally is biotinylated, optionally via a spacer molecule such as PEG, in particular K(PEG-Biotin)
Electrospray ionisation with tandem mass spectrometry (ESI-TOF-MS) data of purified folded biotinMip-3a: obtained=8396.4 Da; expected 8397.0 Da.
Functional Assay Data:
BiotinMIP-3a was tested for agonist activity in an Aequorin assay against hCCR6, (Euroscreen) and an EC50 value of 1.6 nM was reported. c.f. EC50 for recombinant native MIP-3a is 1.0 nM.

Example 92

BiotinTECK (CCL25)

Target Molecule:
TECK (Met to Nleu substitution) derivatised at the ε-amino side chain functionality of Lys72 with PEG-Biotin (TFA salt)
Modifications:
Truncated form of human TECK corresponding to residues 1-74 of the mature protein, which encompasses the sequence corresponding to the chemokine fold. The full length mature protein is 127 amino acids (the signal peptide is 23 amino acids in a 150 amino acid immature protein). The single methionine within the sequence was altered to Norleucine, to mitigate against oxidation of this residue during the chain assembly, which was observed during the synthesis of the natural sequence derivative. The Gln at the N-terminus of the proteins is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 72 was modified through biotinylation on the resin. A PEG spacer was incorporated between the ε-amino functionality and the biotin.
The linear amino acid sequence (SEQ ID NO: 166) is shown, prior to attachment of the PEG spacer and biotin molecules at amino acid 72 (K):

H-XGVFEDCCLAYHYPIGWAVLRRAWTYRIQEVSGSCNLPAAIFYLPKR

HRKVCGNPKSREVQRAXKLLDARNKVF-OH

X1=pyroGlu or Gln
X64=Norleucine
The engineered TECK sequence was assembled on a solid support (Wang resin), using Fmoc protocols for solid-phase peptide synthesis as described in the general protocols section:

H-XGVFEDCCLAYHYPIGWAVLRRAWTYRIQEVSGSCNLPAAIFYLPK

RHRKVCGNPKSREVQRAXKLLDARNXVF-RESIN

X1=pyroGlu or Gln
X64=Norleucine
X72=K(Dde)

NPKSREVQRANleKLLDARNK(ivDde)VF-RESIN

FmocLys(ivDde)-OH was incorporated as residue 72 to facilitate site-specific labelling at this position of the protein (SEQ ID NO: 167). Subsequent removal of the ivDde protecting group, followed by coupling of the PEG spacer and Biotin, was carried out as described in the general protocol section. Cleavage, purification and folding protocols were carried out as described to furnish the desired active chemokine.

The final active chemokine thus has the following sequence (SEQ ID NO: 168):

H-XGVFEDCCLAYHYPIGWAVLRRAWTYRIQEVSGSCNLPAAIFYLP
KRHRKVCGNPKSREVQRAXKLLDARNXVF-OH

X1=pyroGlu or Gln
X64=norleucine
X72=an amino acid residue that can be biotinylated, such as lysine, ornithine or diaminopropionic acid and optionally is biotinylated, optionally via a spacer molecule such as PEG, such as K(PEG-Biotin)

Electrospray ionisation with tandem mass spectrometry (ESI-TOF-MS) data of purified folded biotinTECK(Met to Nleu substitution): obtained=8958.5 Da; expected 8959.6 Da.

Functional Assay Data:
biotinTECK(Met to Nleu substitution) was tested for agonist activity in an Aequorin assay against hCCR9, (Euroscreen) and an EC50 value of 63.6 nM was reported. c.f. EC50 for recombinant native TECK is 67.9 nM.

Example 93

BiotinITAC (CXCL11)

Target Molecule:
ITAC derivatised with Biotin at the e-amino side chain functionality of an additional Lysine inserted at the C-terminus after a PEG spacer (TFA salt)

Modifications:
Human ITAC corresponding to residues 1-73, is initially expressed as 94 amino acids comprising the chemokine fold, and a 21 amino acid signal peptide which is cleaved off. A PEG spacer and an additional lysine were inserted at the C-terminus, and modified through biotinylation on the resin. The PEG spacer was incorporated at the C-terminus between the protein and the additional lysine.

The linear amino acid sequence (SEQ ID NO: 169) is shown, prior to attachment of the PEG spacer, additional lysine and biotin molecules:

H-FPMFKRGRCLCIGPGVKAVKVADIEKASIMYPSNNCDKIEVIITLK
ENKGQRCLNPKSKQARLIIKKVERKNF-OH

The engineered ITAC sequence was assembled on a solid support (Wang resin), using Fmoc protocols for solid-phase peptide synthesis as described in the general protocols section:

H-FPMFKRGRCLCIGPGVKAVKVADIEKASIMYPSNNCDKIEVIITLK
ENKGQRCLNPKSKQARLIIKKVERKNFX-RESIN

X is PEG-K(ivDde)

Fmoc-12-amino-4,7,10-trioxadodecanoic acid followed by FmocLys(ivDde)-OH were incorporated at the C-terminus to facilitate site-specific labelling with biotin at the ε-amino side chain functionality of the additional Lys (SEQ ID NO: 170). Subsequent removal of the ivDde protecting group, followed by coupling of the Biotin, was carried out as described in the general protocol section. Cleavage, purification and folding protocols were carried out as described to furnish the desired active chemokine (SEQ ID NO: 171).

H-FPMFKRGRCLCIGPGVKAVKVADIEKASIMYPSNNCDKIEVIITLK
ENKGQRCLNPKSKQARLIIKKVERKNFX-OH

X is an amino acid residue that can be biotinylated, such as lysine, ornithine or diaminopropionic acid and optionally is biotinylated, optionally via a spacer molecule such as PEG, e.g. K(PEG-Biotin) and may be attached via a spacer molecule, e.g. PEG-K(Biotin)

Electrospray ionisation with tandem mass spectrometry (ESI-TOF-MS) data of purified folded biotinITAC: obtained=8866.5 Da; expected 8860.6 Da.

Functional Assay Data:
biotinITAC was tested for agonist activity in an Aequorin assay against hCXCR3, (Euroscreen) and an EC50 value of 15.7 nM was reported. c.f. EC50 for recombinant native ITAC is 0.7 nM.

Example 94

BiotinIP-10 (CXCL10)

Target Molecule:
IP-10 derivatised with Biotin at the e-amino side chain functionality of an additional Lysine inserted at the C-terminus after a PEG spacer (TFA salt)

Modifications: Human IP-10 corresponding to residues 1-77, is initially expressed as 98 amino acids comprising the chemokine fold, and a 21 amino acid signal peptide which is cleaved off. A PEG spacer and an additional lysine were inserted at the C-terminus, and modified through biotinylation on the resin. The PEG spacer was incorporated at the C-terminus between the protein and the additional lysine.

The linear amino acid sequence (SEQ ID NO: 172) is shown, prior to attachment of the PEG spacer, additional lysine and biotin molecules:

H-VPLSRTVRCTCISISNQPVNPRSLEKLEIIPASQFCPRVEIIATMK
KKGEKRCLNPESKAIKNLLKAVSKERSKRSP-OH

The engineered IP-10 sequence was assembled on a solid support (Wang resin), using Fmoc protocols for solid-phase peptide synthesis as described in the general protocols section:

H-VPLSRTVRCTCISISNQPVNPRSLEKLEIIPASQFCPRVEIIATMKK
KGEKRCLNPESKAIKNLLKAVSKERSKRSPX-RESIN

X is K(ivDde), optionally attached via a spacer such as PEG, e.g. -PEG-K(ivDde)

Fmoc-8-amino-3,6-dioctanoic acid followed by FmocLys(ivDde)-OH were incorporated at the C-terminus to facilitate site-specific labelling with biotin at the ε-amino side chain functionality of the additional Lys (SEQ ID NO: 173). Subsequent removal of the ivDde protecting group, followed by coupling of the Biotin, was carried out as described in the general protocol section. Cleavage, purification and folding protocols were carried out as described to furnish the desired active chemokine. The final active chemokine thus has the following sequence (SEQ ID NO: 174):

H-VPLSRTVRCTCISISNQPVNPRSLEKLEIIPASQFCPRVEIIATMKK
KGEKRCLNPESKAIKNLLKAVSKERSKRSPX-OH

X is an amino acid residue that can be biotinylated, such as lysine, ornithine or diaminopropionic acid and optionally is biotinylated, optionally via a spacer molecule such as PEG, e.g. K(PEG-Biotin) and may be attached via a spacer molecule, e.g. PEG-K(Biotin)

Electrospray ionisation with tandem mass spectrometry (ESI-TOF-MS) data of purified folded biotinIP-110: obtained=9141.0 Da; expected 9141.9 Da.

Functional Assay Data:

BiotinIP-10 was tested for agonist activity in an Aequorin assay against hCXCR3, (Euroscreen) and an EC50 value of 8.7 nM was reported. c.f. EC50 for recombinant native IP-10 is 4.4 nM.

Example 95

MS Diagnosis and Treatment Based Upon CCR2 and CCR6 Expressing T-Cells

Materials and Methods

1. Flow Cytometric Analysis of Peripheral Blood

Peripheral blood from patients with Multiple Sclerosis and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM $NH_4Cl$, pH 7.5) for 15 min at 37° C. The cells were washed in PBS with 2% Bovine Growth Serum, incubated with 10% human serum for 15 min at room temperature (RT) and stained with antibodies (Table 25) at 4° C. for 30 min. The cells were analysed with flow cytometry on a FACS Canto flow cytometer with the FACSDiva software (BD Biosciences).

TABLE 25

List of antibodies for flow cytometric analysis.

| Antibody | Fluorophore | Supplier |
| --- | --- | --- |
| CD3 | V450 | BD Biosciences |
| CCR6 | PE | BD Biosciences |
| Streptavidin | PE, APC | Biolegend |
| CCR2 | PerCP Cy5.5 | Biolegend |

2. Chemokine Binding Test

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5) for 15 min at 37° C. The cells were washed in PBS with 2% Bovine Growth Serum, incubated with 10% human serum 15 min at room temperature (RT) and stained with cell specific antibodies together with biotinylated chemokine (1 µM) or the corresponding chemokine receptor antibody at 4° C. for 30 min (Table 25). The biotinylated chemokine was detected via the interaction between biotin and a fluorophore conjugated Streptavidin. The samples were analysed by flow cytometry on a FACS Canto flow cytometer with the FACSDiva software (BD Biosciences).

3. Cell Depletion by Matrix Conjugated with Biotinylated Chemokine

Cells were prepared from peripheral blood (section 1). 1 mL Sepharose BigBeads matrix conjugated with 0.4 mg/mL Streptavidin (GE Healthcare) was washed in 50 mL PBS and added to a 5 mL polystyrene tube (BD Falcon™). Biotinylated chemokine (1 µM) was added to the tube and incubated for 20 min at RT to enable immobilization of the chemokine on the matrix via the biotin-streptavidin interaction. Next, the cells were added to the chemokine-matrix and incubated for 20 min at RT. The cells that did not bind to the matrix were removed by washing the matrix with PBS in a sterile 40 um nylon filter (BD Falcon™ Cell Strainer). The flow through cells were stained with antibodies (Table 25), analysed with flow cytometry and compared with cells from peripheral blood that had not been incubated with the chemokine-matrix.

Results and Discussion

1. Flow Cytometric Analysis of Peripheral Blood

White blood cells from patients with Multiple Sclerosis (MS) were analysed for the expression of chemokine receptors with flow cytometry. The MS patients exhibited an increased frequency of circulating T cells that expressed the chemokine receptor CCR2, 15% compared to approximately 5% in healthy blood (FIG. 117a), based upon flow cytometry data and binding by an anti-CCR2 antibody. Furthermore, the patients had an increased frequency of T cells that expressed CCR6 (FIG. 117b).

2. Chemokine Binding Test

CCR2 binds to the chemokine MCP-1 that mediate migration and infiltration of inflammatory cells to various tissues. The ligand for CCR6 is MIP3a (CCL20) that can mediate migration of T cells into the CNS. Both these receptors are important in the inflammatory process. In accordance with the CCR2 and CCR6 expression, the T cells bound the biotinylated MCP-1 (bMCP-1) (FIG. 118a) and bMIP3a (FIG. 118b).

3. Cell Depletion by Matrix Conjugated with Biotinylated Chemokine

The CCR2 expressing T cells could be efficiently depleted with bMCP-1-conjugated Sepharose Streptavidin Matrix (FIG. 119a), and the CCR6 expressing T cells could be depleted with bMIP3a-conjugated Sepharose Streptavidin Matrix (FIG. 119b)

We conclude that the frequency of T cells that express CCR2 and CCR6 is enhanced in MS. These T cells can bind the ligands MCP-1 and MIP3a. Furthermore, the majority of the CCR2 and CCR6 expressing T cells can be removed with Sepharose Streptavidin matrix conjugated with the corresponding biotinylated chemokine.

I. Treating Cardiovascular Disease

MCP-1 is secreted from endothelial cells and smooth muscle cells and plays a critical role in the development of cardiovascular diseases. It has been shown (Niu and Kolattakudy. Clinical Science (2009) 117, 95-109) that MCP-1, by its chemotactic activity, causes diapedesis of monocytes from the lumen to the subendothelial space where they become foam cells, initiating fatty streak formation that leads to atherosclerotic plaque formation. Inflammatory macrophages probably play a role in plaque rupture and the resulting ischaemic episode as well as restenosis after angioplasty. There is strong evidence that MCP-1 plays a major role in myocarditis, ischaemia/reperfusion injury in the heart and in transplant rejection. MCP-1 also plays a role in cardiac repair and manifests protective effects under certain conditions. Such protective effects may be due to the induction of protective ER (endoplasmic reticulum) stress chaperones by MCP-1. Under sustained ER stress caused by chronic exposure to MCP-1, the protection would break down resulting in the development of heart failure. MCP-1 is also involved in ischaemic angiogenesis. In mice, blocking of MCP-1 or CCR2 show beneficial effects against cardiovascular disease. In particular, MCP-1 knockout (KO) mice or CCR2 KO mice have reduced atherosclerosis, whereas MCP-1 overexpression increases foam cell formation and atherosclerosis. On this basis, the inventors have selected CCR2 expressing cells as a target for treatment of cardiovascular disease using specific binding interactions with CCR2 expressing cells.

It is shown herein that subjects suffering from atherosclerosis exhibit increased frequency of chemokine receptor expressing cells in the peripheral blood, in particular CCR1 expressing monocytes, compared to healthy controls. It is also shown herein that the CCR1 cells can be removed using a suitable binding reagent, in particular RANTES (in biotinylated form) immobilized on or in a suitable matrix. Similarly, it is shown herein that CCR2-expressing cells can be depleted in atherosclerosis patients using a suitable binding reagent, in particular MCP-1, in biotinylated form, immobilized on or in a suitable matrix.

Examples 96 and 97

Materials and Methods

Isolation of Peripheral Blood Leukocytes.

Heparinized peripheral blood from healthy blood donors was fixed with 4% paraformaldehyde for 4 minutes, hemolyzed for 15 minutes with a 0.83% ammonium chloride solution and washed twice in FACS buffer to obtain a suspension of blood leukocytes.

Chemokines.

The leukocytes were incubated for 30 min in the dark at 4° C. with biotinylated and Alexa647 Fluor® labeled MCP-1 (in concentrations 10 ng/µL and 50 ng/µL). The cells were then washed with FACS-buffer and analyzed by flow cytometry. All chemokines used in the Examples were provided by Almac Sciences Scotland Ltd, Edinburgh, Scotland.

Flow Cytometry Assay.

The flow cytometry assay was performed on a two laser FACS Calibur cytometer (BD Immunocytometry systems, San José, Ca, USA). Ten thousand cells were counted and analysed in each sample. For data analyses, Cell Quest Pro software from Becton Dickinson was used.

Example 96

Binding of Monocytes to MCP-1

In the experiment with biotinylated MCP-1 it was found that about 90% of the monocytes obtained from peripheral blood of healthy donors had bound to the cytokine after 30 min of incubation (FIG. 120a), whereas CD4+ and CD8+ lymphocytes had not bound (FIGS. 120b and 120c).

Example 97

Monocytes were investigated for their expression of CCR2 (FIG. 121b) and their ability to bind MCP-1 (FIG. 121a). CCR2 expression was noted an all monocytes with the majority of monocytes expressing high levels, using an anti-CCR2 antibody (FIG. 121b). The MCP-1 binding to monocytes shown in FIG. 121a corresponds to the CCR2$^{hi}$ expressing population shown in FIG. 121b. Thus, MCP-1 binds favourably to CCR2$^{hi}$ expressing cells.

Example 98

Tailored Leukapheresis

Column Design and Properties
Introduction

Apheresis is an established treatment used for depletion of blood components, such as antibodies, low-density lipoproteins (LDL) and blood cells. Leukapheresis is the apheresis treatment used for removal of white blood cells, leukocytes. The patient is connected to an extracorporeal blood circulating system; the blood is drawn from a vein in one arm, passed through a column device and returned into the other arm of the patient. Side effects of leukapheresis treatments are varying from mild events like headache, dizziness, hypotension, palpitation and flush seen in 0.1 to 5% of treated patients.

The Column

The column is intended to be used as a leukapheresis treatment for a cardiovascular disease. It will specifically remove CCR1, CCR2 and/or CCR7-expressing leukocytes, in particular monocytes, through the use of a binding reagent, more specifically an MCP-1, MCP-2, MCP-3, MCP-4 and/or MCP-5 containing resin, or a CCL19 containing resin, exploiting the CCR1, CCR2 and/or CCR7-chemokine interaction. The column consists of three combined components, the plastic house, the streptavidin (SA) Sepharose™ BigBeads matrix and the binding reagent bound to the matrix. The treatment is conducted using the same techniques as a standard apheresis procedure.

The Plastic House (FIG. 9)

The plastic house, designed to keep a continuous blood flow through the matrix, consists of a transparent body and red-coloured top. The top has a distribution plate (2) at the inflow site (1) to spread the blood evenly over the entire matrix area. The plate is the first safety barrier preventing larger particles flowing through the column and into the patient. Safety filter units (3 and 4) are placed at the inflow (1) and outflow (5) sites of the plastic housing. The safety filter unit contains three filters designed to be a robust barrier and stop all particles larger than blood cells passing through the column. The plastic housing design is shown in FIG. 9. The design with safety filters (3 and 4) at both ends of the column device will minimize the risk of leakage of particles into the patient, including in the event that the device is placed up side down with the blood flow in the opposite direction to that anticipated.

Streptavidin Sepharose™ BigBeads

The second component in the device is the affinity matrix called streptavidin Sepharose™ BigBeads (Sepharose™ GE Healthcare, Sweden). Sepharose™ is a cross linked, beaded-form of agarose, which is a polysaccharide extracted from seaweed. Sepharose™ and agarose are commonly used as column matrices in biomedical affinity techniques. It is chosen for its optimal distribution capacity and can provide a large available area for affinity binding.

Binding Reagent

Coupled to the matrix is the third component of the device, the binding reagent that binds specifically to CCR1, CCR2 and/or CCR7. Chemokines such as MCP-1. MCP-2, MCP-3, MCP-4, MCP-5, CCL19 and/or CCL5 may be employed. These peptides may be synthetic, engineered versions of the human chemokine, which are truncated and biotinylated, but retain binding activity to the CCR1, CCR2 and/or CCR7 receptor. By biotinylating the engineered chemokine, it is able to bind to the streptavidin molecules in the Sepharose™ matrix. The biotin-streptavidin binding is known be one of the strongest biological interactions with a Kd in the order of $4 \times 10^{-14}$ M. The calculated ratio of streptavidin:biotin binding sites in the column is 10:1. Therefore, the coupling between the matrix and chemokine will be immediate, minimising the risk of chemokine decoupling from the matrix.

The Apheresis System

To conduct the leukapheresis the following components are needed; the column, tubing system, and a 4008 ADS pump (Fresenius Medical Care).

The Circuit

The system is illustrated in FIG. 10. The patient (1) is connected to the extracorporeal circuit via sterile Venflon needles to veins in the right and the left arms. A saline bag (3) is also connected and the saline solution is pumped with an ACD pump (2). Blood is drawn from one arm of the patient through the sterile tubing system by the blood pump (4) and passed through the column (6) and back to the patient. The tubing system is connected to the column via standard dialysis luer-lock couplings. The couplings on the column are colour-coded for correct assembly; red tubing for inflow to the red column top and blue tubing for outflow back to the patient. An air detector (8) is present. Inlet pressure (5) and Pven sensors (7) are employed to monitor the pressure in the circuit.

The 4008 ADS Pump

An apheresis pump, from Fresenius Medical Care, monitors the patient's inflow and outflow, the pressure in the extracorporeal circulation and can discriminate air by a bubble catcher and air detector. A clot catcher filter is placed inside the bubble catcher. The pump also has an optical detector to distinguish between light, e.g. saline solution or air present in the tubing system and dark e.g. blood present in the tubing system.

A schematic diagram of the pump, showing the air detector and optical filter is shown in FIG. 11. If the pump system detects air bubbles and optical fluctuations or if extracorporeal pressure values are out of the set range, then the pump stops immediately and a visual/audible alarm are emitted.

LEGEND FOR FIG. 11

1. Monitor
2. Holder for waste bag
3. Modules (left to right—Blood pump, ACD pump, Air detector)
4. Reserve places for further modules
5. Absorber holder
6. Drip detector
7. IV pole Preparation of the Patient The patient will be administered anticoagulants prior to each treatment session. A sterile saline solution with 5000 IE Heparin will be used for priming the extracorporeal system, thereafter a bolus injection with 4000 IE Heparin will be added into the circuit at the start of each treatment session.

Leukapheresis Time and Flow Rate

The apheresis system should be operated at a flow rate of 30-60 mL/min. A treatment is finalised after 1800 mL of blood has been circulated.

Storage Conditions

The column devices should be stored between 1 and 25° C. avoiding freezing and more elevated temperatures. Stability data >3 months indicate no difference in functionality over time or by temperature (room temperature and refrigerated). The columns will be kept in refrigerated conditions until use. Mechanical damage as those resulting from violent vibrations and trauma should be avoided. Column stored outside of these recommendations should not be used.

Transport Conditions

The column devices will be transported under refrigerated condition, avoiding freezing and more elevated temperatures. Mechanical damage such as those resulting from violent vibrations and trauma should be avoided.

In-Vitro Depletion of Target Cell Populations

To investigate the ability to eliminate CCR2-expressing cells, in vitro tests have been performed on the bMCP-1 coupled matrix. Blood was collected from blood donors and passed through the column device containing bMCP-1 coupled matrix. Blood samples were taken before and after column passage and analyzed by flow cytometry (FACS) for the depletion of CCR2-expressing cells.

The results demonstrate significant depletion of the target population CCR2-expressing monocytes post matrix perfusion. Depletion tests were performed on blood from three healthy donors. The results are shown in FIG. 122.

In conclusion, the in-vitro results demonstrate a specific reduction of up to 80% of the CCR2-expressing cells by the column. Notably, individuals with fewer CCR2 expressing cells initially achieved lower depletion. The remaining levels of monocytes were around 20-30% in each case, irrespective of the starting point. Non-CCR2-expressing cells remained unaffected (data not shown).

Example 99

MCP1 Derivatives

MCP-1 has been produced with residue 75 as the site of biotinylation on the chemokine (numbering based upon the mature protein having the amino acid sequence of SEQ ID NO: 2). Biotinylation permits immobilization of MCP-1 on a solid support (via a biotin-avidin interaction). The basic amino acid sequence of MCP-1, including a 23 amino acid leader sequence is set forth as SEQ ID NO: 175,

```
MKVSAALLCL LLIAATFIPQ GLAQPDAINA PVTCCYNFTN

RKISVQRLAS YRRITSSKCP KEAVIFKTIV AKEICADPKQ

KWVQDSMDHL DKQTQTPKT
```

The amino acid sequence of the mature protein is set forth as SEQ ID NO: 176,

```
QPDAINA PVTCCYNFTN RKISVQRLAS YRRITSSKCP

KEAVIFKTIV AKEICADPKQ KWVQDSMDHL DKQTQTPKT
```

The inventors have determined that chemokines may display improved binding properties where the chemokine is biotinylated via a spacer group. The spacer may prevent the biotin group from impacting on the binding affinity of the chemokine.

Thus, MCP-1 derivatised at the e-amino side chain functionality of Lys75 with PEG-Biotin (TFA salt) will be synthesised. The PEG spacer will be 3,6,-dioxoaminoocctanoic acid. The Gln at the N-terminus of the proteins is subject to pyroGlu formation under physiological conditions. Thus the first glutamine (Gln1) of the sequence will be substituted with pyroglutamine. The molecule will be synthesised as a C-terminal amide (via synthesis on an amide linker). The molecule is shown schematically in FIG. 123.

A biotinMCP-1 Met to Nleu analogue will also be synthesised. The single methionine within the sequence will be altered to Norleucine, to mitigate against oxidation of this residue during the chain assembly and improve stability of the final product. This molecule is shown schematically in FIG. 124.

Once synthesised, the activity of the various biotinMCP-1 derivatives will be determined in cell-based assays. In particular, agonist and antagonist properties will be determined in aequorin functional cell-based assay on human CCR2 receptor.

Example 100

Synthesis of a Ccr2 Antagonist Biotinmcp-1 which Binds to the Receptor without Activation Antagonist Activity (J-H Gong and I. Clark-Lewis, J. Exp. Med., 1995, 181, 63) has been shown for an MCP-1 derivative truncated at the N-terminus. In particular, deletion of residues 1-8, results in binding to CCR2 with Kd 8.3 nM. This protein was unable to cause chemotaxis of CCR2 positive cells. (inhibition of chemotaxis IC50 20 nM) The amino acid sequence of the truncated version is set forth as SED ID NO: 177:

```
VTCCYNFTN RKISVQRLAS YRRITSSKCP KEAVIFKTIV
AKEICADPKQ KWVQDSMDHL DKQTQTPKT
```

A derivative of this truncated version will be synthesised comprising residues 9 to 76 of the mature protein (MCP-1 9-76) with Met64 to Nleu substitution and derivatised at the ε-amino side chain functionality of Lys75 with PEG-Biotin (TFA salt). This molecule is shown schematically in FIG. 125. The PEG spacer will be 3,6,-dioxoaminooctanoic acid. Once synthesised, the activity of the various biotinMCP-1 derivatives will be determined in cell-based assays. In particular, agonist and antagonist properties will be determined in aequorin functional cell-based assay on human CCR2 receptor.

Example 101

Demonstrate Removal of CCR2 Expressing Cells Using an Alternative Chemokine Ligand to MCP-1

CCR2 also binds chemokines MCP-2, MCP-3, MCP-4, MCP-5, and HCC-4 in addition to MCP-1. MCP-5 only binds CCR2 and should be selective in its removal of CCR2 expressing cells. MCP5 is a mouse chemokine shown to chemotact human CCR2 cells with EC50<3 nM.

The full length amino acid sequence, including the signal peptide, is set forth as SEQ ID NO: 178

```
MKISTLLCLL LIATTISPQV LAGPDAVSTP VTCCYNVVKQ
KIHVRKLKSY RRITSSQCPR EAVIFRTILD KEICADPKEK
WVKNSINHLD KTSQTFILEP SCLG
```

The amino acid sequence of N-terminal processed MCP-5 chemokine is 82 amino acids long and is set forth as SEQ ID NO: 179

```
GPDAVSTP VTCCYNVVKQ KIHVRKLKSY RRITSSQCPR
EAVIFRTILD KEICADPKEK WVKNSINHLD KTSQTFILEP SCLG
```

An amino acid sequence alignment suggests that MCP-5 has a C-terminal extension when compared to the amino acid sequence of MCP-1. The results of this alignment are shown in FIG. 126. On this basis a C-terminal truncated version of MCP-5 will be synthesised. This truncated version will comprise MCP-5 residues 1-76, set forth as SEQ ID NO: 180:

```
GPDAVSTP VTCCYNVVKQ KIHVRKLKSY RRITSSQCPR
EAVIFRTILD KEICADPKEK WVKNSINHLD KTSQTFIL
```

In the truncated version, Ile75 to be substituted with Lys, set forth as SEQ ID NO: 181:

```
GPDAVSTP VTCCYNVVKQ KIHVRKLKSY RRITSSQCPR
EAVIFRTILD KEICADPKEK WVKNSINHLD KTSQTFKL
```

Following substitution, the substituted version will be biotinylated at position 75, a lysine or other suitable residue such as ornithine or diaminopropanoic acid via A PEG spacer (3,6,-dioxoaminooctanoic acid). The protein will be synthesised on an amide linker to yield a C-terminal amide derivative. This molecule is shown schematically in FIG. 127. Once synthesised, the activity of the various biotin-MCP-5 derivatives will be determined in cell-based assays. In particular, agonist and antagonist properties will be determined in (aequorin) functional cell-based assay on human CCR2 receptor.

Examples 102 to 105

Chemokine Synthesis

General Protocols
Assembly:
Chemical synthesis of chemokines was performed using standard Fmoc solid phase peptides synthesis (SPPS) techniques on an ABI 433 peptide synthesiser. DIC (0.5 M in DMF) and OxymaPure (0.5 M in DMF) were used for activation, acetic anhydride (0.5 M in DMF) for capping, and 20% piperidine in DMF for Fmoc deprotection. Rink Amide resin was utilised for the generation of C-terminal amide chemokines and Wang resin for C-terminal acid chemokines. After assembly, the resin was washed with DMF and DCM and then dried in vacuo.
Removal of Dde Protection:
The Dde protecting group was removed by treatment of resin with a solution of 2.5% hydrazine in DMF (200 ml) over a 2 hour period. The resin was then washed with DMF.
Labelling Steps:
1. Couple Fmoc-8-Amino-3,6-Dioctanoic Acid (PEG)
Resin was swollen in DMF and then a solution of Fmoc-8-amino-3,6-dioctanoic acid (0.38 g, 1 mmol), DIC solution (2 ml, 0.5 M in DMF) and OxymaPure solution (2 ml, 0.5 M in DMF) was added. The mixture was sonicated for 3 hours and then washed with DMF.
2. Capping
The resin was capped with acetic anhydride solution (0.5 M in DMF, 10 ml) for 5 minutes and then washed with DMF.

3. Fmoc Deprotection

Fmoc deprotection was carried out by treatment with 20% piperidine in DMF solution (2×50 ml) for 15 minutes each. The resin was washed with DMF.

4. Couple Biotin-OSu

A solution of Biotin-OSu (341 mg, 1 mmol) and DIPEA (348 ml) in DMF (10 ml) was added to the resin and the mixture was sonicated for 3 hours. The resin was washed thoroughly with DMF and DCM then dried in vacuo.

Cleavage:

Dry resin was treated with TFA (10 ml) containing a scavenger cocktail consisting of TIS (500 ml), thioanisole (500 ml), water (500 ml), DMS (500 ml), EDT (250 ml), NH$_4$I (500 mg) and phenol (500 mg) and the mixture was stirred at room temperature for 5 hours. The solution was filtered into cold ether and the resin rinsed with TFA. The precipitated peptide was centrifuged, washed with ether, centrifuged and lyophilised.

Purification Protocol:

The crude peptide was purified by reverse phase HPLC (RP-HPLC) using a Jupiter C18, 250×21 mm column, 9 ml/min, eluting with an optimised gradient [Buffer A: water containing 0.1% TFA, Buffer B: acetonitrile containing 0.1% TFA].

Folding Protocol:

Pure peptide (10 mg) was dissolved into 6M GnHCl (16 ml) and then rapidly diluted to 2M GnHCl concentration by the addition of 50 mM TRIS pH 8.5 (84 ml) containing 0.3 mM GSSG and 3 mM GSH. The mixture was stirred at room temperature for 24 hours and then analysed by RP-HPLC (Jupiter C18, 250×4.6 mm column, 10-60% B over 30 minutes. Purification by RP-HPLC using an optimised gradient afforded the desired product.

Example 102

BiotinMCP-1 (CCL2)

Target Molecule:

MCP-1 derivatised at the ε-amino side chain functionality of Lys(75) with PEG-Biotin (TFA salt)

Modifications:

Human MCP-1 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the ε-amino functionality and the biotin.

The linear amino acid sequence (SEQ ID NO: 182) is shown, prior to attachment of the PEG spacer and biotin molecules at amino acid 75 (K):

H-XPDAINAPVTCCYNFTNRKISVQRLASYRRITSSKCPKEAVIFKTIV

AKEICADPKQKWVQDSMDHLDKQTQTPKT-NH$_2$

X=pyroGlu or Gln

The engineered MCP-1 sequence was assembled on a solid support (Rink Amide resin), using Fmoc protocols for solid-phase peptide synthesis as described in the general protocols section:

SEQ ID NO: 183

H-XPDAINAPVTCCYNFTNRKISVQRLASYRRITSSKCPKEAVIFKTIV

AKEICADPKQKWVQDSMDHLDKQTQTPXT-RESIN

X1=pyroGlu or Gln
X75=K(ivDde)

FmocLys(ivDde)-OH was incorporated as residue 75 to facilitate site-specific labelling at this position of the protein. Subsequent removal of the ivDde protecting group, followed by coupling of the PEG spacer and Biotin, was carried out as described in the general protocol section. Cleavage, purification and folding protocols were carried out as described to furnish the desired active chemokine.

SEQ ID NO: 184

H-XPDAINAPVTCCYNFTNRKISVQRLASYRRITSSKCPKEAVIFKTIV

AKEICADPKQKWVQDSMDHLDKQTQTPXT-NH$_2$

X1=pyroGlu or Gln
X75 is an amino acid residue that can be biotinylated, such as lysine, ornithine or diaminopropionic acid and optionally is biotinylated, optionally via a spacer molecule such as PEG, optionally K(PEG-Biotin)

Electrospray ionisation with tandem mass spectrometry (ESI-TOF-MS) data of purified folded biotinMCP-1: obtained=9032.8 Da; expected 9034.4 Da.

Functional Assay Data:

biotinMCP-1 was tested for agonist activity in an Aequorin assay against hCCR2b, (Euroscreen) and an EC50 value of 9.6 nM was reported. c.f. EC50 for recombinant native MCP-1 is 3.1 nM.

Example 103

BiotinRANTES (CCL5)

Target Molecule:

RANTES derivatised at the ε-amino side chain functionality of Lys(67) with Biotin (TFA salt)

Modifications:

Human RANTES corresponding to residues 1-68, is initially expressed as 91 amino acids comprising the chemokine fold, and a 23 amino acid signal peptide which is cleaved off. The single methionine (Met67) within the sequence was mutated to lysine, to mitigate against oxidation of this residue during the chain assembly, which was observed during the synthesis of the natural sequence derivative. This Met to Lys substitution provided a lysine at position 67 which was modified through biotinylation on the resin.

The linear amino acid sequence (SEQ ID NO: 185) is shown, prior to attachment of the biotin molecule at amino acid 67 (K):

H-SPYSSDTTPCCFAYIARPLPRAHIKEYFYTSGKCSNPAVVFVTRK

RQVCANPEKKWVREYINSLEKS-OH

The engineered RANTES sequence was assembled on a solid support (Wang resin), using Fmoc protocols for solid-phase peptide synthesis as described in the general protocols section:

H-SPYSSDTTPCCFAYIARPLPRAHIKEYFYTSGKCSNPAVVFVTRK

NRQVCANPEKKWVREYINSLEXS-RESIN

X is K(ivDde)

FmocLys(ivDde)-OH was incorporated as residue 67 to facilitate site-specific labelling at this position of the protein (SEQ ID NO: 186). Subsequent removal of the ivDde protecting group, followed by coupling of the Biotin, was carried out as described in the general protocol section. Cleavage, purification and folding protocols were carried out as described to furnish the desired active chemokine (SEQ ID NO: 187).

H-SPYSSDTTPCCFAYIARPLPRAHIKEYFYTSGKCSNPAVVFVTRK

NRQVCANPEKKWVREYINSLEXS-OH

X is an amino acid residue that can be biotinylated, such as lysine, ornithine or diaminopropionic acid and optionally is biotinylated, optionally via a spacer molecule such as PEG (e.g. K(Biotin))

Electrospray ionisation with tandem mass spectrometry (ESI-TOF-MS) data of purified folded biotinRANTES: obtained=8068.9 Da; expected 8070.2 Da.

Functional Assay Data:

BiotinRANTES was tested for agonist activity in an Aequorin assay against hCCR5, (Euroscreen) and an EC50 value of 0.5 nM was reported.

Example 104

BiotinMCP-2 (CCL8)

Target Molecule:

MCP-2 derivatised at the e-amino side chain functionality of Lys(75) with PEG-Biotin (TFA salt)

Modifications:

Human MCP-2 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the $\epsilon$-amino functionality and the biotin.

The linear amino acid sequence (SEQ ID NO: 188) is shown, prior to attachment of the PEG spacer and biotin molecules at amino acid 75 (K):

H-XPDSVSIPITCCFNVINRKIPIQRLESYTRITNIQCPKEAVIFKTKRG

KEVCADPKERWVRDSMKHLDQIFQNLKP-NH$_2$

X=pyroGlu or Gln

The engineered MCP-2 sequence was assembled on a solid support (Rink Amide resin), using Fmoc protocols for solid-phase peptide synthesis as described in the general protocols section:

H-XPDSVSIPITCCFNVINRKIPIQRLESYTRITNIQCPKEAVIFKTKR

GKEVCADPKERWVRDSMKHLDQIFQNLXP-NH$_2$

X1=pyroGlu or Gln
X75=K(ivDde)

FmocLys(ivDde)-OH was incorporated as residue 75 to facilitate site-specific labelling at this position of the protein (SEQ ID NO: 189). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 190):

H-XPDSVSIPITCCFNVINRKIPIQRLESYTRITNIQCPKEAVIFKTKR

GKEVCADPKERWVRDSMKHLDQIFQNLXP-NH$_2$

X1=pyroGlu or Gln
X75=an amino acid residue that can be biotinylated, such as lysine, ornithine or diaminopropionic acid and optionally is biotinylated, optionally via a spacer molecule such as PEG, e.g. K(PEG-Biotin).

Electrospray ionisation with tandem mass spectrometry (ESI-TOF-MS) data of purified folded biotinMCP-2: obtained=9263.6 Da; expected 9263.8 Da.

Functional Assay Data:

biotinMCP-2 was tested for activity in an Aequorin assay against hCCR2b, (Euroscreen) and was shown to be a partial agonist with an EC50 value of 50.9 nM. c.f. EC50 for recombinant native MCP-2 is 23.5 nM (partial agonist).

Example 105

BiotinMIP-3b (CCL19)

Target Molecule:

MIP-3b derivatised at the e-amino side chain functionality of Lys(78) with Biotin (TFA salt)

Modifications:

Human MIP-3b corresponding to residues 1-77, is initially expressed as 98 amino acids comprising the chemokine fold, and a 21 amino acid signal peptide which is cleaved off. An additional lysine was inserted at the C-terminus, at position 78, and modified through biotinylation on the resin.

The linear amino acid sequence (SEQ ID NO: 191) is shown, prior to attachment of the biotin molecule at amino acid 78 (K):

H-GTNDAEDCCLSVTQKPIPGYIVRNFHYLLIKDGCRVPAVVFTTLRG

RQLCAPPDQPWVERIIQRLQRTSAKMKRRSSX-NH$_2$

X is an amino acid residue that can be biotinylated, such as lysine, ornithine or diaminopropionic acid and optionally is biotinylated (e.g. K-biotin), optionally via a spacer molecule such as PEG, in particular K(PEG-Biotin)

The engineered MIP-3b sequence was assembled on a solid support (Rink Amide resin), using Fmoc protocols for solid-phase peptide synthesis as described in the general protocols section:

H-GTNDAEDCCLSVTQKPIPGYIVRNFHYLLIKDGCRVPAVVFTTLRG

RQLCAPPDQPWVERIIQRLQRTSAKMKRRSSX-RESIN

X is FmocLys(ivDde)

FmocLys(ivDde)-OH was incorporated as residue 78 to facilitate site-specific labelling at this position of the protein (SEQ ID NO: 192). Subsequent removal of the ivDde protecting group, followed by coupling of the Biotin, was carried out as described in the general protocol section. Cleavage, purification and folding protocols were carried out as described to furnish the desired active chemokine (SEQ ID NO: 193).

H-GTNDAEDCCLSVTQKPIPGYIVRNFHYLLIKDGCRVPAVVFTTLRG

RQLCAPPDQPWVERIIQRLQRTSAKMKRRSSX-NH$_2$

X is K(Biotin)

Electrospray ionisation with tandem mass spectrometry (ESI-TOF-MS) data of purified folded biotinMIP-3b: obtained=9148.8 Da; expected 9149.7 Da.

Functional Assay Data:

biotinMip-3b was tested for agonist activity in an Aequorin assay against hCCR7, (Euroscreen) and an EC50 value of 11.0 nM was reported. c.f. EC50 for recombinant native MIP-3b is 1.6 nM.

Example 106

Diagnosis and Treatment of Cardiovascular Disease (P117760US00) Using CCR1, CCR2 and Biotinylated MCP-1, and RANTES Materials and Methods 1. Flow Cytometric Analysis of Peripheral Blood Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH$_4$Cl, pH 7.5) for 15 min at 37° C. The cells were washed in PBS with 2% Bovine Growth Serum, incubated with 10% human serum for 15 min at room temperature (RT) and stained with antibodies (Table 26) at 4° C. for 30 min. The cells were analysed by flow cytometry on a FACS Canto flow cytometer with the FACSDiva software (BD Biosciences).

TABLE 26

List of antibodies for flow cytometric analysis.

| Antibody | Fluorophore | Supplier |
| --- | --- | --- |
| CCR1 | Alexa flour 647 | Biolegend |
| CCR2 | PerCPCy5.5 | Biolegend |
| Streptavdin | APC | BD |
| CD14 | FITC | Beckman Coulter |

2. Chemokine Binding Test

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5) for 15 min at 37° C. The cells were washed in PBS with 2% Bovine Growth Serum, incubated with 10% human serum 15 min at room temperature (RT) and stained with cell specific antibodies together with biotinylated chemokine (1 µM) or the corresponding chemokine receptor antibody at 4° C. for 30 min (Table 26). The biotinylated chemokine was detected via the interaction between biotin and a fluorophore conjugated Streptavidin. The samples were analysed by flow cytometry on a FACS Canto flow cytometer with the FACSDiva software (BD Biosciences).

3. Cell Depletion by Matrix Conjugated with Biotinylated Chemokine

Cells were prepared from peripheral blood (section 1). 1 mL Sepharose BigBeads matrix conjugated with 0.4 mg/mL Streptavidin (GE Healthcare) was washed in 50 mL PBS and added to a 5 mL polystyrene tube (BD Falcon™). Biotinylated chemokine was added to the tube and incubated for 20 min at RT to enable immobilization of the chemokine on the matrix via the biotin-streptavidin interaction. Next, the cells were added to the chemokine-matrix and incubated for 20 min at RT. The cells that did not bind to the matrix were removed by washing the matrix with PBS in a sterile 40 um nylon filter (BD Falcon™ Cell Strainer). The flow through cells were stained with antibodies (Table 26), analysed by flow cytometry and compared with cells from peripheral blood that had not been incubated with the chemokine-matrix.

Results and Discussion

1. Flow Cytometric Analysis of Peripheral Blood

White blood cells from one patient with atherosclerosis were analysed for the expression of chemokine receptors with flow cytometry. The patients exhibited increased frequency of monocytes that expressed the receptor CCR1 based upon flow cytometry data and binding of an anti-CCR1 antibody (FIG. 13).

In addition to CCR1, the monocytes express the chemokine receptor CCR2 (FIG. 16), based upon flow cytometry data and binding of an anti-CCR2 antibody.

2. Chemokine Binding Test

The ligand for CCR1 is the chemokine RANTES. RANTES is involved in the recruitment of monocytes to atherosclerotic lesions. The monocytes from a patient with atherosclerosis bound biotinylated RANTES (bRANTES) to the same extent as the chemokine receptor expression (FIG. 14).

The ligand for CCR2 is MCP-1 that is increased in atherosclerotic inflammation. In accordance with the CCR2 expression, biotinylated MCP-1 (bMCP-1) could bind to blood monocytes from an atherosclerosis patient (FIG. 17).

3. Cell Depletion by Matrix Conjugated with Biotinylated Chemokine

The CCR1 expressing monocytes could be efficiently depleted with bRANTES-conjugated Sepharose Streptavidin Matrix (FIG. 15).

The CCR2 expressing monocytes could be depleted with bMCP1-conjugated Sepharose Streptavidin Matrix (FIG. 18).

We conclude that the frequency of CCR1 expressing monocytes is enhanced in atherosclerosis. The CCR2 receptor is expressed on monocytes from atherosclerosis patients to the same extent as in the healthy controls, but the CCR2 expressing cells could differ in their pro-inflammatory profile in the patients compared to healthy controls. The CCR1 and CCR2 expressing monocytes bind the chemokines that corresponded with the chemokine receptor expression, and could be efficiently depleted with the biotinylated chemokine-Sepharose Streptavidin-matrix.

J. Treating Primary Sclerosing Cholangitis

In patients with PSC it has been shown that expression of CCL25, CXCL12, CCL21 or CCL5 in hepatic endothelium mediates recruitment of CCR9, CXCR4, CCR7 and/or CCR5+ lymphocytes to the liver. CCR9, CXCR4, CCR7 and/or CCR5+ lymphocytes have been activated in the gut and homing to the liver might contribute to the strong correlation between IBD and PSC. (Eksteen B 2004)

In several inflammatory liver diseases, including PSC, an upregulation of CXCL12 (SDF-1) was seen in biliary epithelial cells when compared to healthy controls. Increased levels of CXCL12 were also seen in the plasma and the CXCL12 receptor CXCR4 was present on most liver infiltrating lymphocytes. (Terada R 2003) Neolymphoid tissue develops in the liver in patients with PSC, contributing to the chronic inflammation. Expression of the chemokine CCL21 recruits CCR7+ lymphocytes to this lymphoid tissue. (Grant A 2002).

Polymorphisms in the promoter region of the gene coding for RANTES (CCL5) can lead to increased expression of this chemokine. A significant difference in the presence of the −28 G allele was seen when 124 patients with PSC were compared to 362 healthy controls. (Henckaerts 2006)

Thus, the invention focuses on the following Chemokine receptor-Chemokine pairs of interest:
CCR9-CCL25
CXCR4-CXCL12
CCR7-CCL21, CCL19
CCR5-CCL5

The inventors have also determined that PSC patients include higher levels of CCR9 expressing monocytes in the blood. The disease relevant monocytes may also have high expression of HLA-DR (referred to herein as HLA-DR$^{hi}$). The treatments and diagnostic methods herein may accordingly be applicable in particular to monocytes and to HLA-DR$^{hi}$ monocytes.

Materials and Methods

Isolation of Peripheral Blood Leukocytes.

Heparinized peripheral blood from healthy blood donors or IBD patients was fixed with 4% paraformaldehyde for 4 minutes, hemolyzed for 15 minutes with a 0.83% ammonium chloride solution and washed twice in FACS buffer to obtain a suspension of blood leukocytes.

Chemokines.

The leukocytes were incubated for 30 min in the dark at 4° C. with the following biotinylated and Alexa647 Fluor® labeled chemokines: CCL25 (in concentrations of 0.1 ng/μL, 0.5 ng/μL and 5 ng/μL). The cells were then washed with FACS-buffer and analyzed by flow cytometry. All chemokines used in the Examples were provided by Almac Sciences Scotland Ltd, Edinburgh, Scotland.

Flow Cytometry Assay.

The flow cytometry assay was performed on a two laser FACS Calibur cytometer (BD Immunocytometry systems, San José, Ca, USA). Ten thousand cells were counted and analysed in each sample. For data analyses, Cell Quest Pro software from Becton Dickinson was used.

Example 107

Affinity of Blood Cells to CCL25

In the experiment with biotinylated CCL25 it was found that neither T-cells (CD4+ lymphocytes; CD8+ lymphocytes) nor monocytes (CD14+ monocytes) from the peripheral blood of a healthy donor (FIGS. 135a, 135b and 135c) bound to the biotinylated chemokine. In contrast, about 80% of the CD8+ lymphocytes and about 90% of the CD4+ lymphocytes and the monocytes from a patient with Crohn's disease bound to CCL25 (FIGS. 136a, 136b and 136c).

Example 108

Preparation of a Chemokine Column for Blood Cell Apheresis

To streptavidin cross-linked agarose (ProZyme, San Leandro, Calif., U.S.A.) beads in the range from 75 μm to 300μ suspended (200 ml, ~50%, v/v) in an aqueous solution of 25 mM sodium phosphate (pH 7.0) and 150 mM NaCl was added a solution of 75 μg biotinylated MIP-1α (Almac Sciences) in the same buffer at 22° C. and slowly stirred by hand for 3 min. After standing for another 20 min, the support was filtered off, washed thrice with neutral aqueous sodium phosphate/sodium chloride and filled into a glass column (i.d. 25 mm, length 12 cm).

Example 109

Separation of Monocytes from Peripheral Blood of a Healthy Donor with the Chemokine Column of Example 108

Heparinized peripheral blood from a healthy male donor was analyzed by flow cytometry for CD4+ lymphocytes, CD8+ lymphocytes and CD14 monocytes. 100 ml of the blood was filtered through the column at a rate of about 8 ml per min and washed with FACS buffer. The filtered blood was analyzed for the same cells. It was found that about 95% of the monocytes had been retained by the column whereas more than 90% each of CD4+ and CD8+ lymphocytes had been recovered.

Example 110

Tailored Leukapheresis

Column Design and Properties

Introduction

Apheresis is an established treatment used for depletion of blood components, such as antibodies, low-density lipoproteins (LDL) and blood cells. Leukapheresis is the apheresis treatment used for removal of white blood cells, leukocytes. The patient is connected to an extracorporeal blood circulating system; the blood is drawn from a vein in one arm, passed through a column device and returned into the other arm of the patient. Side effects of leukapheresis treatments are varying from mild events like headache, dizziness, hypotension, palpitation and flush seen in 0.1 to 5% of treated patients.

The Column

The column is intended to be used as a leukapheresis treatment for primary sclerosing cholangitis. It will specifically remove CCR9-expressing gut-homing leukocytes through the use of a bTECK containing resin, exploiting the CCR9-TECK interaction. The column consists of three combined components, the plastic house, the streptavidin (SA) Sepharose™ BigBeads matrix and bTECK bound to the matrix. The treatment is conducted using the same techniques as a standard apheresis procedure.

The Plastic House (FIG. 9)

The plastic house, designed to keep a continuous blood flow through the matrix, consists of a transparent body and red-coloured top. The top has a distribution plate (2) at the inflow site (1) to spread the blood evenly over the entire matrix area. The plate is the first safety barrier preventing larger particles flowing through the column and into the patient. Safety filter units (3 and 4) are placed at the inflow (1) and outflow (5) sites of the plastic housing. The safety filter unit contains three filters designed to be a robust barrier and stop all particles larger than blood cells passing through the column. The plastic housing design is shown in FIG. 9. The design with safety filters (3 and 4) at both ends of the column device will minimize the risk of leakage of particles into the patient, including in the event that the device is placed up side down with the blood flow in the opposite direction to that anticipated.

Streptavidin Sepharose™ BigBeads

The second component in the device is the affinity matrix called streptavidin Sepharose™ BigBeads (Sepharose™ GE Healthcare, Sweden). Sepharose™ is a cross linked, beaded-form of agarose, which is a polysaccharide extracted from seaweed. Sepharose™ and agarose are commonly used as column matrices in biomedical affinity techniques. It is chosen for its optimal distribution capacity and can provide a large available area for affinity binding.

bTECK

Coupled to the matrix is the third component of the device, the bTECK. This bTECK peptide is a synthetic, engineered version of the human chemokine TECK, which is truncated and biotinylated, but retains its binding activity to the TECK receptor CCR9. By biotinylating the engineered TECK, it is able to bind to the streptavidin molecules in the Sepharose™ matrix. The biotin-streptavidin binding is known be one of the strongest biological interactions with a Kd in the order of $4 \times 10^{-14}$ M. The calculated ratio of streptavidin:biotin binding sites in the column is 10:1. Therefore, the coupling between the matrix and bTECK will be immediate, minimising the risk of bTECK decoupling from the matrix.

The Apheresis System

To conduct the leukapheresis the following components are needed; the column, tubing system, and a 4008 ADS pump (Fresenius Medical Care).

The Circuit

The system is illustrated in FIG. 10. The patient (1) is connected to the extracorporeal circuit via sterile Venflon needles to veins in the right and the left arms. A saline bag (3) is also connected and the saline solution is pumped with an ACD pump (2). Blood is drawn from one arm of the patient through the sterile tubing system by the blood pump (4) and passed through the column (6) and back to the patient. The tubing system is connected to the column via standard dialysis luer-lock couplings. The couplings on the column are colour-coded for correct assembly; red tubing for inflow to the red column top and blue tubing for outflow back to the patient. An air detector (8) is present. Inlet pressure (5) and Pven sensors (7) are employed to monitor the pressure in the circuit.

The 4008 ADS Pump

An apheresis pump, from Fresenius Medical Care, monitors the patient's inflow and outflow, the pressure in the extracorporeal circulation and can discriminate air by a bubble catcher and air detector. A clot catcher filter is placed inside the bubble catcher. The pump also has an optical detector to distinguish between light, e.g. saline solution or air present in the tubing system and dark e.g. blood present in the tubing system.

A schematic diagram of the pump, showing the air detector and optical filter is shown in FIG. 11. If the pump system detects air bubbles and optical fluctuations or if extracorporeal pressure values are out of the set range, then the pump stops immediately and a visual/audible alarm are emitted.

LEGEND FOR FIG. 11

1. Monitor
2. Holder for waste bag
3. Modules (left to right—Blood pump, ACD pump, Air detector)
4. Reserve places for further modules
5. Absorber holder
6. Drip detector
7. IV pole Preparation of the Patient The patient will be administered anticoagulants prior to each treatment session. A sterile saline solution with 5000 IE Heparin will be used for priming the extracorporeal system, thereafter a bolus injection with 4000 IE Heparin will be added into the circuit at the start of each treatment session.

Leukapheresis Time and Flow Rate

The apheresis system should be operated at a flow rate of 30-60 mL/min. A treatment is finalised after 1800 mL of blood has been circulated.

Storage Conditions

The column devices should be stored between 1 and 25° C. avoiding freezing and more elevated temperatures. Stability data >3 months indicate no difference in functionality over time or by temperature (room temperature and refrigerated). The columns will be kept in refrigerated conditions until use. Mechanical damage as those resulting from violent vibrations and trauma should be avoided. Column stored outside of these recommendations should not be used.

Transport Conditions

The column devices will be transported under refrigerated condition, avoiding freezing and more elevated temperatures. Mechanical damage such as those resulting from violent vibrations and trauma should be avoided.

Example 111

Non-Clinical Studies

In-Vitro Depletion of Target Cell Populations

To investigate the ability to eliminate CCR9-expressing cells, in vitro tests have been performed on the bTECK coupled matrix. Blood was collected from blood donors and primary sclerosing cholangitis patients and passed through the column device containing bTECK coupled matrix. Blood samples were taken before and after column passage and analyzed by flow cytometry (FACS) for the depletion of CCR9-expressing cells. The results demonstrate significant depletion of the target population CD14− positive CCR9-expressing cells post matrix perfusion; while total CD14-positive cells remain unchanged. Depletion tests were performed on blood from healthy donors and IBD patients confirming similar effects. The results are shown in FIGS. 137 and 138 respectively.

In conclusion, the in-vitro results demonstrate a specific reduction of 50-75% of the CCR9-expressing cells by the column. Non-CCR9-expressing cells remained unaffected. To investigate the ability to eliminate CCR5-expressing cells, in vitro tests have been performed on the biotinylated RANTES coupled matrix. Blood was collected from blood donors and passed through the column device containing biotinylated RANTES coupled matrix. Blood samples were taken before and after column passage and analyzed by flow cytometry (FACS) for the depletion of CCR5-expressing cells.

The RANTES molecule was synthesized by Almac. The amino acid sequence of the biotinylated RANTES molecule is set forth as SEQ ID NO: 195:

H2N-SPYSSDTTPCCFAYIARPLPRAHIKEYFYTSGKCSNPAVVFVT
RKNRQVCANPEKKWVREYINSLEKS-CO2H

This molecule has the naturally occurring methionine at position 67 replaced with lysine to facilitate biotinylation at position 67.

Figure 139:
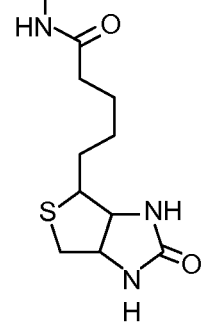

The side-chain of Lys 67 was directly biotinylated to given the protein primary structure shown in FIG. 139. The protein was folded and disulphide bonds formed between the first and third cysteine in the sequence and between the 2nd and 4th cysteines.

Figure 140:
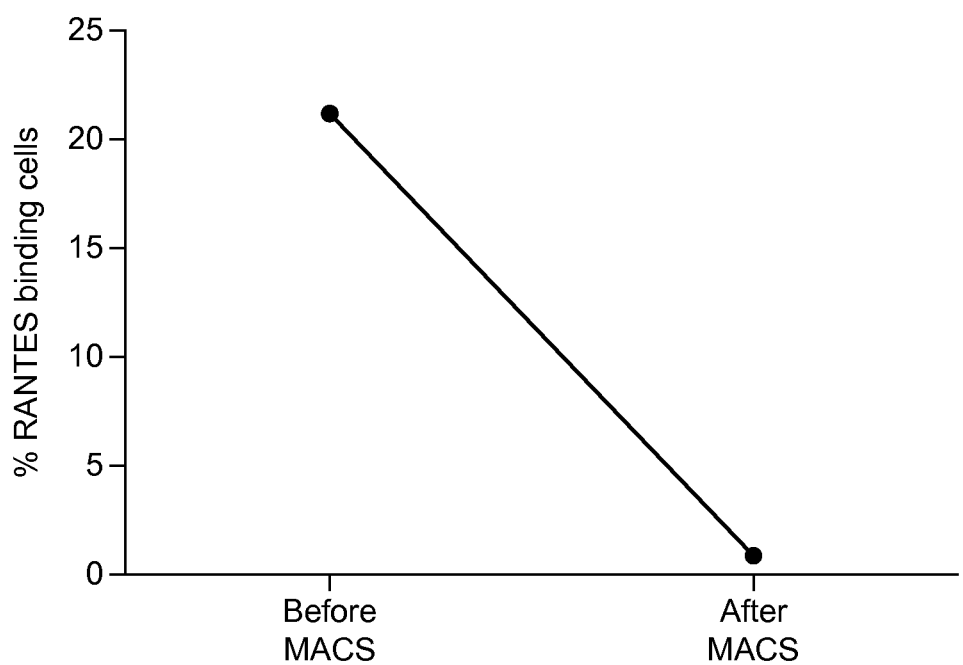

The results demonstrate significant depletion of the target population chemokine receptor-expressing cells post matrix perfusion. Depletion tests were performed on blood from a healthy donor. The results are shown in FIG. 140.

The in-vitro results demonstrate a specific reduction of around 20% of the chemokine receptor-expressing cells by the column. Non-CCR5-expressing cells remained unaffected (data not shown).

Example 112

TECK-PEG-Biotin Synthesis Summary

Target Molecule:
TECK (Met to Nleu substitution) derivatised at the ε-amino side chain functionality of Lys72 with PEG-Biotin (TFA salt)
Modifications:
Truncated form of human TECK corresponding to residues 1-74 of the mature protein, which encompasses the sequence corresponding to the chemokine fold. The full length mature protein is 127 amino acids (the signal peptide is 23 amino acids in a 150 amino acid immature protein). The single methionine within the sequence was altered to Norleucine, to mitigate against oxidation of this residue during the chain assembly, which was observed during the synthesis of the natural sequence derivative. The Gln at the N-terminus of the proteins is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 72 was modified through biotinylation on the resin. A PEG spacer was incorporated between the ε-amino functionality and the biotin.

The linear amino acid sequence (SEQ ID NO: 194) is shown, prior to attachment of the PEG spacer and biotin molecules at amino acid 72 (K):

H-XGVFEDCCLAYHYPIGWAVLRRAWTYRIQEVSGSCNLPAAIFYLPK
RHRKVCGNPKSREVQRAXKLLDARNKVF-OH

X1=pyroGlu or Gln
X64=Norleucine

The engineered TECK sequence was assembled on a solid support, using Fmoc protocols for solid-phase peptide synthesis (SEQ ID NO: 196):

H-XGVFEDCCLAYHYPIGWAVLRRAWTYRIQEVSGSCNLPAAIFYLPK
RHRKVCGNPKSREVQRAXKLLDARNXVF-RESIN

X1=pyroGlu or Gln
X64=Norleucine
X72=K(Dde)
FmocLys(Dde)-OH was incorporated as residue 72 to facilitate site-specific labelling at this position of the protein.
Met to Nle substitution.
N-terminal Gln to pyroglutamic acid substitution.
Removal of Dde Protection:
The Dde protecting group was removed by treatment of all resin (2.5 g) with a solution of 2% hydrazine in DMF (100 ml) over 1 hour period to afford 2.0 g resin.
Labelling Steps:
1. Couple Fmoc-8-Amino-3,6-Dioctanoic Acid
Resin (1.5 g) was swollen in DMF (2 ml) and then a solution of Fmoc-8-amino-3,6-dioctanoic acid (0.38 g, 1 mmol), DIC solution (2 ml, 0.5M in DMF) and HOCt solution (2 ml, 0.5M in DMF) was added. The mixture was sonicated for 2 hours and then washed with DMF.
2. Cap
The resin was capped with 0.5M acetic anhydride/DMF solution (20 ml) for 5 minutes and then washed with DMF.
3. Fmoc Deprotection
Fmoc deprotection was carried out by treatment with 20% piperidine in DMF solution (2×50 ml) for 15 minutes each. The resin was washed with DMF.
4. Couple Biotin-OSu
A solution of Biotin-NHS ester (341 mg, 1 mmol) and DIPEA (348 ul, 2 mmol) in DMF (10 ml) was added to the resin and the mixture was sonicated for 3 hours. The resin was washed thoroughly with DMF and DCM then dried in vacuo. Dry resin obtained=1.5 g.
Cleavage:
Dry peptide resin (1.5 g) and the mixture was cleaved with TFA (30 ml) containing a scavenger cocktail consisting of TIS, thioanisole, water, EDT and phenol and the mixture was stirred at room temperature for 6 hours. The solution was filtered into cold ether and the resin rinsed with TFA. The peptide was centrifuged, washed with ether, centrifuged and lyophilised to give 1.0 g crude peptide.
Folding Protocol:
Crude peptide (100 mg) was dissolved into 6M GnHCl (233 ml) and then rapidly diluted to 2M GnHCl concentration by the addition of 50 mM TRIS pH8 (467 ml) containing 0.5 mM GSSG and 5 mM GSH. The mixture was stirred at room temperature for 2.5 days and then analysed by HPLC (Jupiter C18, 250×4.6 mm column, 10-60% B over 30 minutes. HPLC analysis confirmed the formation of desired product as well as mis-folded by-products.
Purification:
The folded protein was purified by reverse phase HPLC using a Jupiter C18, 250×21 mm column, 9 ml/min, 10-60% B over 50 minutes. 11.1 mg of pure folded Nle-TECK-Biotin was afforded.

FIG. 141 shows HPLC of purified folded Biotin-TECK (Nleu). The protein eluted in a single peak at 21.6 mins.

FIG. 142 shows Electrospray ionisation with tandem mass spectrometry (ES/MS) data of purified folded Biotin-TECK (Nleu). The expected mass was 8959.4 Da.

Functional Assay Data:

TECK-Biotin-Nle was tested for agonist activity in an Aequorin assay against hCCR9, (Euroscreen) and an EC50 value of 63.6 nM was reported. c.f. EC50 for native TECK is 67.87 nM.

The final active chemokine thus has the following sequence (SEQ ID NO: 197):

H-XGVFEDCCLAYHYPIGWAVLRRAWTYRIQEVSGSCNLPAAIFYLPK

RHRKVCGNPKSREVQRAXKLLDARNXVF-OH

X1=pyroGlu or Gln
X64=norleucine
X72=an amino acid residue that can be biotinylated, such as lysine, ornithine or diaminopropionic acid and optionally is biotinylated, optionally via a spacer molecule such as PEG, such as K(PEG-Biotin)

Examples 112 to 115

Further Embodiments

General Protocols
Assembly:

Chemical synthesis of chemokines was performed using standard Fmoc solid phase peptides synthesis (SPPS) techniques on an ABI 433 peptide synthesiser. DIC (0.5 M in DMF) and OxymaPure (0.5 M in DMF) were used for activation, acetic anhydride (0.5 M in DMF) for capping, and 20% piperidine in DMF for Fmoc deprotection. Rink Amide resin was utilised for the generation of C-terminal amide chemokines and Wang resin for C-terminal acid chemokines. After assembly, the resin was washed with DMF and DCM and then dried in vacuo.

Removal of Dde Protection:

The Dde protecting group was removed by treatment of resin with a solution of 2.5% hydrazine in DMF (200 ml) over a 2 hour period. The resin was then washed with DMF.

Labelling Steps:

1. Couple Fmoc-8-Amino-3,6-Dioctanoic Acid (PEG)

Resin was swollen in DMF and then a solution of Fmoc-8-amino-3,6-dioctanoic acid (0.38 g, 1 mmol), DIC solution (2 ml, 0.5 M in DMF) and OxymaPure solution (2 ml, 0.5 M in DMF) was added. The mixture was sonicated for 3 hours and then washed with DMF.

2. Capping

The resin was capped with acetic anhydride solution (0.5 M in DMF, 10 ml) for 5 minutes and then washed with DMF.

3. Fmoc Deprotection

Fmoc deprotection was carried out by treatment with 20% piperidine in DMF solution (2×50 ml) for 15 minutes each. The resin was washed with DMF.

4. Couple Biotin-OSu

A solution of Biotin-OSu (341 mg, 1 mmol) and DIPEA (348 ml, 2 mmol) in DMF (10 ml) was added to the resin and the mixture was sonicated for 3 hours. The resin was washed thoroughly with DMF and DCM then dried in vacuo.

Cleavage:

Dry resin was treated with TFA (10 ml) containing a scavenger cocktail consisting of TIS (500 ml), thioanisole (500 ml), water (500 ml), DMS (500 ml), EDT (250 ml), $NH_4I$ (500 mg) and phenol (500 mg) and the mixture was stirred at room temperature for 5 hours. The solution was filtered into cold ether and the resin rinsed with TFA. The precipitated peptide was centrifuged, washed with ether, centrifuged and lyophilised.

Purification Protocol:

The crude peptide was purified by reverse phase HPLC (RP-HPLC) using a Jupiter C18, 250×21 mm column, 9 ml/min, eluting with an optimised gradient [Buffer A: water containing 0.1% TFA, Buffer B: acetonitrile containing 0.1% TFA].

Folding Protocol:

Pure peptide (10 mg) was dissolved into 6M GnHCl (16 ml) and then rapidly diluted to 2M GnHCl concentration by the addition of 50 mM TRIS pH 8.5 (84 ml) containing 0.3 mM GSSG and 3 mM GSH. The mixture was stirred at room temperature for 24 hours and then analysed by RP-HPLC (Jupiter C18, 250×4.6 mm column, 10-60% B over 30 minutes. Purification by RP-HPLC using an optimised gradient afforded the desired product.

Example 112

BiotinMCP-2 (CCL8)

Target Molecule:

MCP-2 derivatised at the e-amino side chain functionality of Lys(75) with PEG-Biotin (TFA salt)

Modifications:

Human MCP-2 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the ε-amino functionality and the biotin.

The linear amino acid sequence (SEQ ID NO: 198) is shown, prior to attachment of the PEG spacer and biotin molecules at amino acid 75 (K):

H-XPDSVSIPITCCFNVINRKIPIQRLESYTRITNIQCPKEAVIFKTK

RGKEVCADPKERWVRDSMKHLDQIFQNLKP-NH₂

X=pyroGlu or Gln

The engineered MCP-2 sequence was assembled on a solid support (Rink Amide resin), using Fmoc protocols for solid-phase peptide synthesis as described in the general protocols section:

H-XPDSVSIPITCCFNVINRKIPIQRLESYTRITNIQCPKEAVIFKTK

RGKEVCADPKERWVRDSMKHLDQIFQNLXP-NH₂

X1=pyroGlu or Gln
X75=K(ivDde)

FmocLys(ivDde)-OH was incorporated as residue 75 to facilitate site-specific labelling at this position of the protein (SEQ ID NO: 199). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 200):

H-XPDSVSIPITCCFNVINRKIPIQRLESYTRITNIQCPKEAVIPKTK

RGKEVCADPKERWVRDSMKHLDQIFQNLXP-NH₂

X1=pyroGlu or Gln
X75=an amino acid residue that can be biotinylated, such as lysine, ornithine or diaminopropionic acid and optionally is biotinylated, optionally via a spacer molecule such as PEG, e.g. K(PEG-Biotin).

Electrospray ionisation with tandem mass spectrometry (ESI-TOF-MS) data of purified folded biotinMCP-2: obtained=9263.6 Da; expected 9263.8 Da.

Functional Assay Data:

biotinMCP-2 was tested for activity in an Aequorin assay against hCCR2b, (Euroscreen) and was shown to be a partial agonist with an EC50 value of 50.9 nM. c.f. EC50 for recombinant native MCP-2 is 23.5 nM (partial agonist).

Example 113

BiotinRANTES (CCL5)

Target Molecule:

RANTES derivatised at the e-amino side chain functionality of Lys(67) with Biotin (TFA salt)

Modifications:

Human RANTES corresponding to residues 1-68, is initially expressed as 91 amino acids comprising the chemokine fold, and a 23 amino acid signal peptide which is cleaved off. The single methionine (Met67) within the sequence was mutated to lysine, to mitigate against oxidation of this residue during the chain assembly, which was observed during the synthesis of the natural sequence derivative. This Met to Lys substitution provided a lysine at position 67 which was modified through biotinylation on the resin.

The linear amino acid sequence (SEQ ID NO: 201) is shown, prior to attachment of the biotin molecule at amino acid 67 (K):

H-SPYSSDTTPCCFAYIARPLPRAHIKEYFYTSGKCSNPAVVFVTRKN

RQVCANPEKKWVREYINSLEMS-OH

The engineered RANTES sequence was assembled on a solid support (Wang resin), using Fmoc protocols for solid-phase peptide synthesis as described in the general protocols section:

H-SPYSSDTTPCCFAYIARPLPRAHIKEYFYTSGKCSNPAVVFVTRKN

RQVCANPEKKWVREYINSLEXS-RESIN

X is K(ivDde)

FmocLys(ivDde)-OH was incorporated as residue 67 to facilitate site-specific labelling at this position of the protein (SEQ ID NO: 202). Subsequent removal of the ivDde protecting group, followed by coupling of the Biotin, was carried out as described in the general protocol section. Cleavage, purification and folding protocols were carried out as described to furnish the desired active chemokine (SEQ ID NO: 203):

H-SPYSSDTTPCCFAYIARPLPRAHIKEYFYTSGKCSNPAVVFVTRKN

RQVCANPEKKWVREYINSLEXS-OH

X is an amino acid residue that can be biotinylated, such as lysine, ornithine or diaminopropionic acid and optionally is biotinylated, optionally via a spacer molecule such as PEG (e.g. K(Biotin))

Electrospray ionisation with tandem mass spectrometry (ESI-TOF-MS) data of purified folded biotinRANTES: obtained=8068.9 Da; expected 8070.2 Da.

Functional Assay Data:

BiotinRANTES was tested for agonist activity in an Aequorin assay against hCCR5, (Euroscreen) and an EC50 value of 0.5 nM was reported.

Example 114

BiotinSDF-1a (CXCL12)

Target Molecule:

SDF-1a derivatised at the e-amino side chain functionality of Lys(64) with Biotin (TFA salt)

Modifications:

Truncated form of human SDF-1a corresponding to residues 1-67 of the mature protein, which encompasses the sequence corresponding to the chemokine fold. The full length mature protein is 72 amino acids (the signal peptide is 21 amino acids in a 93 amino acid immature protein). The naturally occurring lysine at position 64 was modified through biotinylation on the resin.

The linear amino acid sequence (SEQ ID NO: 204) is shown, prior to attachment of the biotin molecule at amino acid 64 (K):

H-KPVSLSYRCPCRFFESHVARANVKHLKILNTPNCALQIVARLKNNNRQ

VCIDPKLKWIQEYLEKALN-OH

The engineered SDF-1a sequence was assembled on a solid support (Wang resin), using Fmoc protocols for solid-phase peptide synthesis as described in the general protocols section:

H-KPVSLSYRCPCRFFESHVARANVKHLKILNTPNCALQIVARLKNNNRQ

VCIDPKLKWIQEYLEXALN-RESIN

X=K(ivDde)

FmocLys(ivDde)-OH was incorporated as residue 64 to facilitate site-specific labelling at this position of the protein (SEQ ID NO: 205). Subsequent removal of the ivDde protecting group, followed by coupling of the Biotin, was carried out as described in the general protocol section. Cleavage, purification and folding protocols were carried out as described to furnish the desired active chemokine (SEQ ID NO: 206):

H-KPVSLSYRCPCRFFESHVARANVKHLKILNTPNCALQIVARLKNNNRQ

VCIDPKLKWIQEYLEXALN-OH

X is an amino acid residue that can be biotinylated, such as lysine, ornithine or diaminopropionic acid and optionally is biotinylated, optionally via a spacer molecule such as PEG, e.g. K(PEG-Biotin)

Electrospray ionisation with tandem mass spectrometry (ESI-TOF-MS) data of purified folded biotinSDF-1a: obtained=8055.5 Da; expected 8057.5 Da.
Functional Assay Data:
biotinSDF-1a was tested for agonist activity in an Aequorin assay against hCXCR4, (Euroscreen) and an EC50 value of 17.3 nM was reported. c.f. EC50 for recombinant native SDF-1a is 12.0 nM.

Example 115

BiotinMIP-3b (CCL19)

Target Molecule:
MIP-3b derivatised at the e-amino side chain functionality of Lys(78) with Biotin (TFA salt)
Modifications:
Human MIP-3b corresponding to residues 1-77, is initially expressed as 98 amino acids comprising the chemokine fold, and a 21 amino acid signal peptide which is cleaved off. An additional lysine was inserted at the C-terminus, at position 78, and modified through biotinylation on the resin.
The linear amino acid sequence (SEQ ID NO: 207) is shown, prior to attachment of the biotin molecule at amino acid 78 (K):

H-GTNDAEDCCLSVTQKPIPGYIVRNFHYLLIKDGCRVPAVVFTTLRGRQ

LCAPPDQPWVERIIQRLQRTSAKMKRRSSK-NH₂

The engineered MIP-3b sequence was assembled on a solid support (Rink Amide resin), using Fmoc protocols for solid-phase peptide synthesis as described in the general protocols section:

H-GTNDAEDCCLSVTQKPIPGYIVRNFHYLLIKDGCRVPAVVFTTLRGRQ

LCAPPDQPWVERIIQRLQRTSAKMKRRSSX-RESIN

X is K(ivDde)
FmocLys(ivDde)-OH was incorporated as residue 78 to facilitate site-specific labelling at this position of the protein (SEQ ID NO: 208). Subsequent removal of the ivDde protecting group, followed by coupling of the Biotin, was carried out as described in the general protocol section. Cleavage, purification and folding protocols were carried out as described to furnish the desired active chemokine (SEQ ID NO: 209):

H-GTNDAEDCCLSVTQKPIPGYIVRNFHYLLIKDGCRVPAVVFTTLRGRQ

LCAPPDQPWVERIIQRLQRTSAKMKRRSSX-NH₂

X is an amino acid residue that can be biotinylated, such as lysine, ornithine or diaminopropionic acid and optionally is biotinylated, optionally via a spacer molecule such as PEG, e.g. K(PEG-Biotin)
Electrospray ionisation with tandem mass spectrometry (ESI-TOF-MS) data of purified folded biotinMIP-3b: obtained=9148.8 Da; expected 9149.7 Da.
Functional Assay Data:
biotinMip-3b was tested for agonist activity in an Aequorin assay against hCCR7, (Euroscreen) and an EC50 value of 11.0 nM was reported. c.f. EC50 for recombinant native MIP-3b is 1.6 nM.

Example 116

Treatment and Diagnosis of Primary Sclerosing Cholangitis (PSC)

Materials and Methods
1. Flow Cytometric Analysis of Peripheral Blood

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH₄Cl, pH 7.5) for 15 min at 37° C. The cells were washed in PBS with 2% Bovine Growth Serum, incubated with 10% human serum for 15 min at room temperature (RT) and stained with antibodies (Table 27) at 4° C. for 30 min. The cells were analysed by flow cytometry on a FACS Canto flow cytometer with the FACSDiva software (BD Biosciences).

TABLE 27

List of antibodies for flow cytometric analysis.

| Antibody | Fluorophore | Supplier |
| --- | --- | --- |
| CD14 | FITC | Beckman Coulter |
| Streptavidin | PE, APC | Biolegend |
| CD16 | PE Cy7 | BD Biosciences |
| CCR9 | APC | R&D Systems |
| HLADR | APC Cy7 | Biolegend |
| CD3 | V450 | BD Biosciences |
| CD19 | V500 | BD Biosciences |

2. Chemokine Binding Test

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5) for 15 min at 37° C. The cells were washed in PBS with 2% Bovine Growth Serum, incubated with 10% human serum 15 min at room temperature (RT) and stained with cell specific antibodies together with biotinylated chemokine (1 µM) or the corresponding chemokine receptor antibody at 4° C. for 30 min (Table 27). The biotinylated chemokine was detected via the interaction between biotin and a fluorophore conjugated Streptavidin. The samples were analysed by flow cytometry on a FACS Canto flow cytometer with the FACSDiva software (BD Biosciences).

3. Cell Depletion by Matrix Conjugated with Biotinylated Chemokine

Cells were prepared from peripheral blood (section 1). 1 mL Sepharose BigBeads matrix conjugated with 0.4 mg/mL Streptavidin (GE Healthcare) was washed in 50 mL PBS and added to a 5 mL polystyrene tube (BD Falcon™). Biotinylated chemokine (1 µM) was added to the tube and incubated for 20 min at RT to enable immobilization of the chemokine on the matrix via the biotin-streptavidin interaction. Next, the cells were added to the chemokine-matrix and incubated for 20 min at RT. The cells that did not bind to the matrix were removed by washing the matrix with PBS in a sterile 40 um nylon filter (BD Falcon™ Cell Strainer). The flow through cells were stained with antibodies (Table 27), analysed by flow cytometry and compared with cells from peripheral blood that had not been incubated with the chemokine-matrix.

Results and Discussion
Primary Sclerosing Cholangitis (PSC)
1. Flow Cytometric Analysis of Peripheral Blood White blood cells from PSC patients was analysed with flow cytometry. The patients exhibited increased numbers of CCR9 expressing monocytes, a mean of 11% compared to approximately 7% in healthy blood (FIG. 144*a*). 51% of the CCR9 expressing monocytes in PSC have a high expression of HLADR compared to 35% in healthy blood. (FIG. 144*b*)

2. Chemokine Binding Test

CCR9 binds to the chemokine TECK (CCL25) which is mainly expressed in the gut but is also reported to be upregulated in PSC liver. 27% of the monocytes bind to the biotinylated TECK (bTECK) (FIG. 145).

3. Cell Depletion by Matrix Conjugated with Biotinylated Chemokine

44% of the CCR9 expressing monocytes (FIG. 146*a*.) and 39% of the CCR9 expressing HLADRhi monocytes (FIG. 146*b*.) were specifically depleted with bTECK-conjugated Sepharose Streptavidin Matrix.

We conclude that monocytes in PSC express CCR9 and bind the ligand bTECK. Furthermore, the CCR9 expressing monocytes can be removed with Sepharose Streptavidin matrix conjugated with bTECK.

K. Treating Respiratory Conditions

Plasma levels of MCP-1 and MIP-1α were monitored in 26 patients with active pulmonary sarcoidosis over a two year period. During this period, the authors show that levels of these cytokines were closely related to the clinical course of the disease. The authors conclude that plasma MCP-1 and MIP-1a levels are useful indicators of clinical severity of sarcoidosis, and that levels "may reflect subclinical evidence of extrathoracic sarcoidosis and may play a role in initiating monocyte migration into the tissue". Hashimoto S et al, Clin Exp Immunol, 1998 Serum MCP-1 levels were measured in 47 sarcoidosis patients and 10 healthy controls. Chemokine levels were significantly higher in the patient group, and more specifically, correlated positively with patients in early disease stages. Furthermore, MCP-1 was shown to be specifically expressed by macrophages associated with sarcoid lymph nodes. Iyonaga K et al, Sarcoidosis Vasc Diffuse Lung Dis, 1998 The inflammatory cytokines TNF-a, IL-8, MCP-1, MMP9 and GRO-a were measured in 100 COPD patients and 50 matched healthy smokers. These values were subsequently correlated to the BODE index of COPD disease severity. The largest difference in these biomarkers what observed in serum levels of MCP-1 which were significantly increased in the COPD group. The authors conclude that serum MCP-1 levels may be a clinical candidate for distinguishing between healthy smokers and patients with stable COPD. Liu S F et al, Respirology, 2009 TNF-alpha, IL-8, MMP-9, MCP-1, TIMP-1 and TIMP-2 were measured in 20 COPD patients, 10 asymptomatic smokers and 10 non-smoker healthy controls. The authors found highly reproducible and statistically significant elevations of plasma IL-8 among the COPD patients compared to the other groups. No other correlations were observed. Shaker S B et al, Clin Respir J, 2008.

It is shown herein that subjects suffering from respiratory conditions such as sarcoidosis exhibit increased frequency of chemokine receptor expressing cells in the peripheral blood. Subjects with sarcoidosis exhibit increased frequency of CCR1 expressing cells such as CCR1 expressing monocytes, compared to healthy controls. It is also shown herein that the CCR1 expressing cells can be removed using a suitable binding reagent, in particular RANTES (in biotinylated form) immobilized on a suitable matrix. Similarly, it is shown herein that the monocytes also express CCR2. The CCR2 expressing monocytes can be depleted in sarcoidosis patients using a suitable binding reagent, in particular MCP-1, in biotinylated form, immobilized on a suitable matrix. It is also shown herein that subjects suffering from respiratory conditions such as sarcoidosis exhibit increased frequency of CCR7 expressing cells such as CCR7 expressing lymphocytes, and also central memory T cells, compared to healthy controls. It is also shown herein that the CCR7 expressing cells can be removed using a suitable binding reagent, in particular MIP3b (in biotinylated form) immobilized on a suitable matrix.

On this basis the inventors have selected a range of chemokine receptors to use as targets for treatment according to the methods of the invention.

Examples 117 to 125

Materials and Methods

Isolation of Peripheral Blood Leukocytes.

Heparinized peripheral blood from healthy blood donors or inflammatory bowel disease (IBD) patients was fixed with 4% paraformaldehyde for 4 minutes, hemolyzed for 15 minutes with a 0.83% ammonium chloride solution and washed twice in FACS buffer to obtain a suspension of blood leukocytes.

Chemokines.

The leukocytes were incubated for 30 min in the dark at 4° C. with biotinylated and Alexa647 Fluor® labelled chemokine (CCL5, CCL2, CXCL8) (in concentrations 10 ng/μL and 50 ng/L). The cells were then washed with FACS-buffer and analyzed by flow cytometry. All chemokines used in the Examples were provided by Almac Sciences Scotland Ltd, Edinburgh, Scotland.

Flow Cytometry Assay.

The flow cytometry assay was performed on a two laser FACS Calibur cytometer (BD Immunocytometry systems, San José, Ca, USA). Ten thousand cells were counted and analysed in each sample. For data analyses, Cell Quest Pro software from Becton Dickinson was used.

Example 117

Binding of Monocytes to MIP-1α

In the experiment with biotinylated MIP-1α it was found that about 90% of the monocytes obtained from peripheral blood of healthy donors had bound to the cytokine after 30 min of incubation (FIG. 147*c*), whereas CD4+ and CD8+ lymphocytes had not bound (FIGS. 147*a* and 147*b*).

Example 118

Binding of Monocytes to MCP-1

In the experiment with biotinylated MCP-1 it was found that about 90% of the monocytes obtained from peripheral blood of healthy donors had bound to the cytokine after 30 min of incubation (FIG. 148*a*), whereas CD4+ and CD8+ lymphocytes had not bound (FIGS. 148*b* and 148*c*).

Example 119

Affinity of Blood Cells to Biotinylated IL-8

In FIG. 149 the binding to biotinylated IL-8 (CXCL8) of CD4+ lymphocytes (FIG. 149*a*), CD8+ lymphocytes (FIG.

149b) and CD16+ neutrophils (FIG. 149c) obtained from healthy donors is shown. After 30 min of incubation all CD16+ neutrophils bound to IL-8. In contrast no binding was observed with CD4+ lymphocytes and CD8+ lymphocytes.

Example 120

Monocytes were investigated for their expression of CCR2 (FIG. 150b) and their ability to bind MCP-1 (FIG. 150a). CCR2 expression was noted an all monocytes with the majority of monocytes expressing high levels, using an anti-CCR2 antibody (FIG. 150b). The MCP-1 binding to monocytes shown in FIG. 148a corresponds to the CCR2$^{hi}$ expressing population shown in FIG. 150b. Thus, MCP-1 binds favourably to CCR2$^{hi}$ expressing cells.

Example 121

Neutrophils/eosinophils were investigated for their expression of CCR3, (FIG. 147b) and their ability to bind eotaxin (FIG. 151a). CCR3, expression was noted in all neutrophils/eosinophils with the majority of neutrophils/eosinophils expressing high levels, using an anti-CCR3, antibody (FIG. 15b). The eotaxin binding to neutrophils/eosinophils shown in FIG. 151a corresponds to the CCR3$^{hi}$ expressing population shown in FIG. 151b. Thus, eotaxin binds favourably to CCR3$^{hi}$ expressing cells.

Example 122

Preparation of a Chemokine Column for Blood Cell Apheresis

To streptavidin cross-linked agarose (ProZyme, San Leandro, Calif., U.S.A.) beads in the range from 75 µm to 300µ suspended (200 ml, ~50%, v/v) in an aqueous solution of 25 mM sodium phosphate (pH 7.0) and 150 mM NaCl was added a solution of 75 µg biotinylated MIP-1α (Almac Sciences) in the same buffer at 22° C. and slowly stirred by hand for 3 min. After standing for another 20 min, the support was filtered off, washed thrice with neutral aqueous sodium phosphate/sodium chloride and filled into a glass column (i.d. 25 mm, length 12 cm).

Example 123

Separation of Monocytes from Peripheral Blood of a Healthy Donor with the Chemokine Column of Example 122

Heparinized peripheral blood from a healthy male donor was analyzed by flow cytometry for CD4+ lymphocytes, CD8+ lymphocytes and CD14 monocytes. 100 ml of the blood was filtered through the column at a rate of about 8 ml per min and washed with FACS buffer. The filtered blood was analyzed for the same cells. It was found that about 95% of the monocytes had been retained by the column whereas more than 90% each of CD4+ and CD8+ lymphocytes had been recovered.

Example 124

Preparation of Streptavidin Conjugated Magnetic Beads Complexed with Biotinylated MIP-1α

An aqueous suspension of streptavidin conjugated magnetic beads (MagCellect Streptavidin Ferrofluid, 1 ml; R&D Systems, Minneapolis, Minn., U.S.A.) was mixed with 30 µg of MIP-1α (Almac Sciences) in 50 ml of 25 mM sodium phosphate (pH 7.0) and 150 mM NaCl and slowly stirred for 1 hour. The particles were washed thrice with 20 ml portions the same solvent and stored in suspension at 4° C.

Example 125

Separation of CD14+ Monocytes from Peripheral Blood of a Healthy Donor with the Streptavidin Magnetic Beads of Example 124

100 ml of heparinized blood from the healthy donor of Example 124 was mixed with the streptavidin conjugated magnetic beads complexed with biotinylated MIP-1α and slowly stirred for 40 min. The particles were separated from the blood by a magnetic separator, and the blood analyzed for CD14+ monocytes and CD4+ and CD8+ lymphocytes. While essentially no CD14+ monocytes could be detected, CD4+ and CD8+ lymphocytes were present in roughly the original amounts.

Example 126

Tailored Leukapheresis

Column Design and Properties
Introduction
Apheresis is an established treatment used for depletion of blood components, such as antibodies, low-density lipoproteins (LDL) and blood cells. Leukapheresis is the apheresis treatment used for removal of white blood cells, leukocytes. The patient is connected to an extracorporeal blood circulating system; the blood is drawn from a vein in one arm, passed through a column device and returned into the other arm of the patient. Side effects of leukapheresis treatments are varying from mild events like headache, dizziness, hypotension, palpitation and flush seen in 0.1 to 5% of treated patients.
The Column
The column is intended to be used as a leukapheresis treatment for respiratory conditions, in particular sarcoidosis and Chronic Obstructive Pulmonary Disease (COPD). It will specifically remove CCR2, CCR1, CCR3, CCR5, CXCR1, CXCR2 and/or CCR7-expressing leukocytes, in particular monocytes, through the use of a binding reagent containing resin, exploiting the CCR2, CCR1, CCR3, CCR5, CXCR1, CXCR2 and/or CCR7-chemokine interaction. The column consists of three combined components, the plastic house, the streptavidin (SA) Sepharose™ BigBeads matrix and one or more biotinylated chemokine bound to the matrix. The treatment is conducted using the same techniques as a standard apheresis procedure.
The Plastic House (FIG. 9)
The plastic house, designed to keep a continuous blood flow through the matrix, consists of a transparent body and red-coloured top. The top has a distribution plate (2) at the inflow site (1) to spread the blood evenly over the entire matrix area. The plate is the first safety barrier preventing larger particles flowing through the column and into the patient. Safety filter units (3 and 4) are placed at the inflow (1) and outflow (5) sites of the plastic housing. The safety filter unit contains three filters designed to be a robust barrier and stop all particles larger than blood cells passing through the column. The plastic housing design is shown in FIG. 9. The design with safety filters (3 and 4) at both ends of the column device will minimize the risk of leakage of particles into the patient, including in the event that the device is placed up side down with the blood flow in the opposite direction to that anticipated.

Streptavidin Sepharose™ BigBeads

The second component in the device is the affinity matrix called streptavidin Sepharose™ BigBeads (Sepharose™ GE Healthcare, Sweden). Sepharose™ is a cross linked, beaded-form of agarose, which is a polysaccharide extracted from seaweed. Sepharose™ and agarose are commonly used as column matrices in biomedical affinity techniques. It is chosen for its optimal distribution capacity and can provide a large available area for affinity binding.

Binding Reagent

Coupled to the matrix is the third component of the device, one or more binding reagents that bind specifically to CCR2, CCR1, CCR3, CCR5, CXCR1, CXCR2 and/or CCR7. One or more chemokines may be employed. These peptides may be synthetic, engineered versions of the human chemokine, which are truncated and biotinylated, but retain binding activity to the CCR2, CCR1, CCR3, CCR5, CXCR1, CXCR2 and/or CCR7 receptor. By biotinylating the engineered chemokine, it is able to bind to the streptavidin molecules in the Sepharose™ matrix. The biotin-streptavidin binding is known be one of the strongest biological interactions with a Kd in the order of $4 \times 10^{-14}$ M. The calculated ratio of streptavidin:biotin binding sites in the column is 10:1. Therefore, the coupling between the matrix and chemokine will be immediate, minimising the risk of chemokine decoupling from the matrix.

The Apheresis System

To conduct the leukapheresis the following components are needed; the column, tubing system, and a 4008 ADS pump (Fresenius Medical Care).

The Circuit

The system is illustrated in FIG. 10. The patient (1) is connected to the extracorporeal circuit via sterile Venflon needles to veins in the right and the left arms. A saline bag (3) is also connected and the saline solution is pumped with an ACD pump (2). Blood is drawn from one arm of the patient through the sterile tubing system by the blood pump (4) and passed through the column (6) and back to the patient. The tubing system is connected to the column via standard dialysis luer-lock couplings. The couplings on the column are colour-coded for correct assembly; red tubing for inflow to the red column top and blue tubing for outflow back to the patient. An air detector (8) is present. Inlet pressure (5) and Pven sensors (7) are employed to monitor the pressure in the circuit.

The 4008 ADS Pump

An apheresis pump, from Fresenius Medical Care, monitors the patient's inflow and outflow, the pressure in the extracorporeal circulation and can discriminate air by a bubble catcher and air detector. A clot catcher filter is placed inside the bubble catcher. The pump also has an optical detector to distinguish between light, e.g. saline solution or air present in the tubing system and dark e.g. blood present in the tubing system.

A schematic diagram of the pump, showing the air detector and optical filter is shown in FIG. 11. If the pump system detects air bubbles and optical fluctuations or if extracorporeal pressure values are out of the set range, then the pump stops immediately and a visual/audible alarm are emitted.

LEGEND FOR FIG. 11

1. Monitor
2. Holder for waste bag
3. Modules (left to right—Blood pump, ACD pump, Air detector)
4. Reserve places for further modules
5. Absorber holder
6. Drip detector
7. IV pole Preparation of the Patient The patient will be administered anticoagulants prior to each treatment session. A sterile saline solution with 5000 IE Heparin will be used for priming the extracorporeal system, thereafter a bolus injection with 4000 IE Heparin will be added into the circuit at the start of each treatment session.

Leukapheresis Time and Flow Rate

The apheresis system should be operated at a flow rate of 30-60 mL/min. A treatment is finalised after 1800 mL of blood has been circulated.

Storage Conditions

The column devices should be stored between 1 and 25° C. avoiding freezing and more elevated temperatures. Stability data >3 months indicate no difference in functionality over time or by temperature (room temperature and refrigerated). The columns will be kept in refrigerated conditions until use. Mechanical damage as those resulting from violent vibrations and trauma should be avoided. Column stored outside of these recommendations should not be used.

Transport Conditions

The column devices will be transported under refrigerated condition, avoiding freezing and more elevated temperatures. Mechanical damage such as those resulting from violent vibrations and trauma should be avoided.

In-Vitro Depletion of Target Cell Populations

To investigate the ability to eliminate CCR2-expressing cells, in vitro tests have been performed on the bMCP-1 coupled matrix. Blood was collected from blood donors and passed through the column device containing bMCP-1 coupled matrix. Blood samples were taken before and after column passage and analyzed by flow cytometry (FACS) for the depletion of CCR2-expressing cells.

The results demonstrate significant depletion of the target population CCR2-expressing monocytes post matrix perfusion. Depletion tests were performed on blood from three healthy donors. The results are shown in FIG. 152a.

The in-vitro results demonstrate a specific reduction of up to 80% of the CCR2-expressing cells by the column. Notably, individuals with fewer CCR2 expressing cells initially achieved lower depletion. The remaining levels of monocytes were around 20-30% in each case, irrespective of the starting point. Non-CCR2-expressing cells remained unaffected (data not shown).

To investigate the ability to eliminate CCR1, 3 and 5-expressing cells, in vitro tests have been performed on the biotinylated RANTES coupled matrix. Blood was collected from blood donors and passed through the column device containing biotinylated RANTES coupled matrix. Blood samples were taken before and after column passage and analyzed by flow cytometry (FACS) for the depletion of CCR1, 3 or 5-expressing cells.

The RANTES molecule was synthesized by Almac. The amino acid sequence of the biotinylated RANTES molecule is set forth as SEQ ID NO: 225:

H2N-

SPYSSDTTPCCFAYIARPLPRAHIKEYFYTSGKCSNPAVVFVTRKNRQVC

ANPEKKWVREYINSLEKS-CO2H

This molecule has the naturally occurring methionine at position 67 replaced with lysine to facilitate biotinylation at position 67.

The side-chain of Lys 67 was directly biotinylated to given the protein primary structure shown in FIG. 158. The protein was folded and disulphide bonds formed between the first and third cysteine in the sequence and between the 2nd and 4th cysteines.

The results demonstrate significant depletion of the target population chemokine receptor-expressing cells post matrix perfusion. Depletion tests were performed on blood from a healthy donor. The results are shown in FIG. 152*b*.

The in-vitro results demonstrate a specific reduction of around 20% of the chemokine receptor-expressing cells by the column. Non-CCR1, 3 and 5-expressing cells remained unaffected (data not shown).

In-Vitro Depletion of Target Cell Populations

To investigate the ability to eliminate CCR3-expressing cells, in vitro tests have been performed on the eotaxin coupled matrix. Blood was collected from blood donors and passed through the column device (including a magnetic separator) containing eotaxin coupled matrix (MACS beads). Blood samples were taken before and after column passage and analyzed by flow cytometry (FACS) for the depletion of CCR3-expressing cells. The results demonstrate significant depletion of the target population CCR3-expressing neutrophils/eosinophils post matrix perfusion. Depletion tests were performed on blood from a healthy donor. The results are shown in FIG. 152*a*.

In conclusion, the in-vitro results demonstrate a specific reduction of around 25% of the CCR3-expressing cells by the column. Non-CCR3-expressing cells remained unaffected (data not shown).

Example 127

MCP1 Derivatives

MCP-1 has been produced with residue 75 as the site of biotinylation on the chemokine (numbering based upon the mature protein having the amino acid sequence of SEQ ID NO: 2). Biotinylation permits immobilization of MCP-1 on a solid support (via a biotin-avidin interaction). The basic amino acid sequence of MCP-1, including a 23 amino acid leader sequence is set forth as SEQ ID NO: 210,

```
MKVSAALLCL LLIAATFIPQ GLAQPDAINA PVTCCYNFTN

RKISVQRLAS YRRITSSKCP KEAVIFKTIV AKEICADPKQ

KWVQDSMDHL DKQTQTPKT
```

The amino acid sequence of the mature protein is set forth as SEQ ID NO: 211,

```
QPDAINA PVTCCYNFTN RKISVQRLAS YRRITSSKCP

KEAVIFKTIV AKEICADPKQ KWVQDSMDHL DKQTQTPKT
```

The inventors have determined that chemokines may display improved binding properties where the chemokine is biotinylated via a spacer group. The spacer may prevent the biotin group from impacting on the binding affinity of the chemokine.

Thus, MCP-1 derivatised at the ε-amino side chain functionality of Lys75 with PEG-Biotin (TFA salt) will be synthesised. The PEG spacer will be 3,6,-dioxoaminooctanoic acid. The Gln at the N-terminus of the proteins is subject to pyroGlu formation under physiological conditions. Thus the first glutamine (Gln1) of the sequence will be substituted with pyroglutamine. The molecule will be synthesised as a C-terminal amide (via synthesis on an amide linker). The molecule is shown schematically in FIG. 153.

A biotinMCP-1 Met to Nleu analogue will also be synthesised. The single methionine within the sequence will be altered to Norleucine, to mitigate against oxidation of this residue during the chain assembly and improve stability of the final product. This molecule is shown schematically in FIG. 154.

Once synthesised, the activity of the various biotinMCP-1 derivatives will be determined in cell-based assays. In particular, agonist and antagonist properties will be determined in aequorin functional cell-based assay on human CCR2 receptor.

Example 128

Synthesis of a CCR2 Antagonist Biotin MCP-1 which Binds to the Receptor without Activation Antagonist Activity (J-H Gong and I. Clark-Lewis, J. Exp. Med., 1995, 181, 63) has been shown for an MCP-1 derivative truncated at the N-terminus. In particular, deletion of residues 1-8, results in binding to CCR2 with Kd 8.3 nM. This protein was unable to cause chemotaxis of CCR2 positive cells. (inhibition of chemotaxis IC50 20 nM)

The amino acid sequence of the truncated version is set forth as SED ID NO: 212:

```
VTCCYNFTN RKISVQRLAS YRRITSSKCP KEAVIFKTIV

AKEICADPKQ KWVQDSMDHL DKQTQTPKT
```

A derivative of this truncated version will be synthesised comprising residues 9 to 76 of the mature protein (MCP-1 9-76) with Met64 to Nleu substitution and derivatised at the ε-amino side chain functionality of Lys75 with PEG-Biotin (TFA salt). This molecule is shown schematically in FIG. 155. The PEG spacer will be 3,6,-dioxoaminooctanoic acid. Once synthesised, the activity of the various biotinMCP-1 derivatives will be determined in cell-based assays. In particular, agonist and antagonist properties will be determined in aequorin functional cell-based assay on human CCR2 receptor.

Example 129

Demonstrate Removal of CCR2 Expressing Cells Using an Alternative Chemokine Ligand to MCP-1

CCR2 also binds chemokines MCP-2, MCP-3, MCP-4, MCP-5, and HCC-4 in addition to MCP-1. MCP-5 only binds CCR2 and should be selective in its removal of CCR2 expressing cells. MCP5 is a mouse chemokine shown to chemotact human CCR2 cells with EC50<3 nM.

The full length amino acid sequence, including the signal peptide, is set forth as SEQ ID NO: 213

```
MKISTLLCLL LIATTISPQV LAGPDAVSTP VTCCYNVVKQ

KIHVRKLKSY RRITSSQCPR EAVIFRTILD KEICADPKEK

WVKNSINHLD KTSQTFILEP SCLG
```

The amino acid sequence of N-terminal processed MCP-5 chemokine is 82 amino acids long and is set forth as SEQ ID NO: 214

```
GPDAVSTP VTCCYNVVKQ KIHVRKLKSY RRITSSQCPR

EAVIFRTILD KEICADPKEK WVKNSINHLD KTSQTFILEP SCLG
```

An amino acid sequence alignment suggests that MCP-5 has a C-terminal extension when compared to the amino acid sequence of MCP-1. The results of this alignment are shown in FIG. 156. On this basis a C-terminal truncated version of MCP-5 will be synthesised. This truncated version will comprise MCP-5 residues 1-76, set forth as SEQ ID NO: 215:

```
GPDAVSTP VTCCYNVVKQ KIHVRKLKSY RRITSSQCPR

EAVIFRTILD KEICADPKEK WVKNSINHLD KTSQTFIL
```

In the truncated version, Ile75 to be substituted with Lys, set forth as SEQ ID NO: 216:

```
GPDAVSTP VTCCYNVVKQ KIHVRKLKSY RRITSSQCPR

EAVIFRTILD KEICADPKEK WVKNSINHLD KTSQTFKL
```

Following substitution, the substituted version will be biotinylated at position 75, a lysine or other suitable residue such as ornithine or diaminopropanoic acid via A PEG spacer (3,6,-dioxoaminooctanoic acid). The protein will be synthesised on an amide linker to yield a C-terminal amide derivative. This molecule is shown schematically in FIG. 157.

Example 130

Eotaxin Derivatives

Eotaxin has been produced with residue 73 (thought to be a lysine) as the site of biotinylation on the chemokine (numbering based upon the mature protein having the amino acid sequence of SEQ ID NO: 9). Biotinylation permits immobilization of eotaxin on a solid support (via a biotin-avidin interaction). The basic amino acid sequence of eoxtaxin, including a 23 amino acid leader sequence (signal peptide) is set forth as SEQ ID NO: 217,

```
MKVSAALLWL LLIAAAFSPQ GLAGPASVPT TCCFNLANRK

IPLQRLESYR RITSGKCPQK AVIFKTKLAK DICADPKKKW

VQDSMKYLDQ KSPTPKP
```

The amino acid sequence of the mature protein is set forth as SEQ ID NO: 218,

```
GPASVPT TCCFNLANRK IPLQRLESYR RITSGKCPQK

AVIFKTKLAK DICADPKKKW VQDSMKYLDQ KSPTPKP
```

The inventors have determined that chemokines may display improved binding properties where the chemokine is biotinylated via a spacer group. The spacer may prevent the biotin group from impacting on the binding affinity of the chemokine.

Thus, eotaxin derivatised at the ε-amino side chain functionality of Lys73 with PEG-Biotin (TFA salt) will be synthesised. The PEG spacer will be 3,6,-dioxoaminooctanoic acid. The molecule will be synthesised as a C-terminal amide (via synthesis on an amide linker) to avoid diketopiperazine formation during the synthesis. The molecule is shown schematically in FIG. 159.

A biotin eotaxin Met to Nleu analogue will also be synthesised. The single methionine within the sequence will be altered to Norleucine, to mitigate against oxidation of this residue during the chain assembly and improve stability of the final product. Once synthesised, the activity of the various eoxtaxin derivatives will be determined in cell-based assays. In particular, agonist and antagonist properties will be determined in functional cell-based assay on human CCR3 receptor.

Once synthesised, the activity of the various biotinMCP-5 derivatives will be determined in cell-based assays. In particular, agonist and antagonist properties will be determined in functional cell-based assay on human CCR2 receptor.

Examples 131 to 137

Chemokine Synthesis

General Protocols
Assembly:
Chemical synthesis of chemokines was performed using standard Fmoc solid phase peptides synthesis (SPPS) techniques on an ABI 433 peptide synthesiser. DIC (0.5 M in DMF) and OxymaPure (0.5 M in DMF) were used for activation, acetic anhydride (0.5 M in DMF) for capping, and 20% piperidine in DMF for Fmoc deprotection. Rink Amide resin was utilised for the generation of C-terminal amide chemokines and Wang resin for C-terminal acid chemokines. After assembly, the resin was washed with DMF and DCM and then dried in vacuo.
Removal of Dde Protection:
The Dde protecting group was removed by treatment of resin with a solution of 2.5% hydrazine in DMF (200 ml) over a 2 hour period. The resin was then washed with DMF.
Labelling Steps:
1. Couple Fmoc-8-Amino-3,6-Dioctanoic Acid (PEG)
Resin was swollen in DMF and then a solution of Fmoc-8-amino-3,6-dioctanoic acid (0.38 g, 1 mmol), DIC solution (2 ml, 0.5 M in DMF) and OxymaPure solution (2 ml, 0.5 M in DMF) was added. The mixture was sonicated for 3 hours and then washed with DMF.
2. Capping
The resin was capped with acetic anhydride solution (0.5 M in DMF, 10 ml) for 5 minutes and then washed with DMF.
3. Fmoc Deprotection
Fmoc deprotection was carried out by treatment with 20% piperidine in DMF solution (2×50 ml) for 15 minutes each. The resin was washed with DMF.
4. Couple Biotin-OSu
A solution of Biotin-OSu (341 mg, 1 mmol) and DIPEA (348 ml) in DMF (10 ml) was added to the resin and the mixture was sonicated for 3 hours. The resin was washed thoroughly with DMF and DCM then dried in vacuo.
Cleavage:
Dry resin was treated with TFA (10 ml) containing a scavenger cocktail consisting of TIS (500 ml), thioanisole (500 ml), water (500 ml), DMS (500 ml), EDT (250 ml), NH$_4$I (500 mg) and phenol (500 mg) and the mixture was stirred at room temperature for 5 hours. The solution was filtered into cold ether and the resin rinsed with TFA. The precipitated peptide was centrifuged, washed with ether, centrifuged and lyophilised.

Purification Protocol:

The crude peptide was purified by reverse phase HPLC (RP-HPLC) using a Jupiter C18, 250×21 mm column, 9 ml/min, eluting with an optimised gradient [Buffer A: water containing 0.1% TFA, Buffer B: acetonitrile containing 0.1% TFA].

Folding Protocol:

Pure peptide (10 mg) was dissolved into 6M GnHCl (16 ml) and then rapidly diluted to 2M GnHCl concentration by the addition of 50 mM TRIS pH 8.5 (84 ml) containing 0.3 mM GSSG and 3 mM GSH. The mixture was stirred at room temperature for 24 hours and then analysed by RP-HPLC (Jupiter C18, 250×4.6 mm column, 10-60% B over 30 minutes. Purification by RP-HPLC using an optimised gradient afforded the desired product.

Example 131

BiotinMCP-1 (CCL2)

Target Molecule:

MCP-1 derivatised at the ε-amino side chain functionality of Lys(75) with PEG-Biotin (TFA salt)

Modifications:

Human MCP-1 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the ε-amino functionality and the biotin.

The linear amino acid sequence (SEQ ID NO: 219) is shown, prior to attachment of the PEG spacer and biotin molecules at amino acid 75 (K):

H-XPDAINAPVTCCYNFTNRKISVQRLASYRRITSSKCPKEAVIFKTI

VAKEICADPKQKWVQDSMDHLDKQTQTPKT-NH$_2$

X=pyroGlu or Gln

The engineered MCP-1 sequence was assembled on a solid support (Rink Amide resin), using Fmoc protocols for solid-phase peptide synthesis as described in the general protocols section:

SEQ ID NO: 220
H-XPDAINAPVTCCYNFTNRKISVQRLASYRRITSSKCPKEAVIFKTI

VAKEICADPKQKWVQDSMDHLDKQTQTPXT-RESIN

X1=pyroGlu or Gln
X75=K(ivDde)

FmocLys(ivDde)-OH was incorporated as residue 75 to facilitate site-specific labelling at this position of the protein. Subsequent removal of the ivDde protecting group, followed by coupling of the PEG spacer and Biotin, was carried out as described in the general protocol section. Cleavage, purification and folding protocols were carried out as described to furnish the desired active chemokine.

SEQ ID NO: 221
H-XPDAINAPVTCCYNFTNRKISVQRLASYRRITSSKCPKEAVIFKTI

VAKEICADPKQKWVQDSMDHLDKQTQTPXT-NH$_2$

X1=pyroGlu or Gln
X75 is an amino acid residue that can be biotinylated, such as lysine, ornithine or diaminopropionic acid and optionally is biotinylated, optionally via a spacer molecule such as PEG, optionally K(PEG-Biotin)

Electrospray ionisation with tandem mass spectrometry (ESI-TOF-MS) data of purified folded biotinMCP-1: obtained=9032.8 Da; expected 9034.4 Da.

Functional Assay Data:

biotinMCP-1 was tested for agonist activity in an Aequorin assay against hCCR2b, (Euroscreen) and an EC50 value of 9.6 nM was reported. c.f. EC50 for recombinant native MCP-1 is 3.1 nM.

Example 132

BiotinRANTES (CCL5)

Target Molecule:

RANTES derivatised at the ε-amino side chain functionality of Lys(67) with Biotin (TFA salt)

Modifications:

Human RANTES corresponding to residues 1-68, is initially expressed as 91 amino acids comprising the chemokine fold, and a 23 amino acid signal peptide which is cleaved off. The single methionine (Met67) within the sequence was mutated to lysine, to mitigate against oxidation of this residue during the chain assembly, which was observed during the synthesis of the natural sequence derivative. This Met to Lys substitution provided a lysine at position 67 which was modified through biotinylation on the resin.

The linear amino acid sequence (SEQ ID NO: 225) is shown, prior to attachment of the biotin molecule at amino acid 67 (K):

H-SPYSSDTTPCCFAYIARPLPRAHIKEYFYTSGKCSNPAVVFVTRKN

RQVCANPEKKWVREYINSLEKS-OH

The engineered RANTES sequence was assembled on a solid support (Wang resin), using Fmoc protocols for solid-phase peptide synthesis as described in the general protocols section:

H-SPYSSDTTPCCFAYIARPLPRAHIKEYFYTSGKCSNPAVVFVTRKN

RQVCANPEKKWVREYINSLEXS-RESIN

X is K(ivDde)

FmocLys(ivDde)-OH was incorporated as residue 67 to facilitate site-specific labelling at this position of the protein (SEQ ID NO: 226). Subsequent removal of the ivDde protecting group, followed by coupling of the Biotin, was carried out as described in the general protocol section. Cleavage, purification and folding protocols were carried out as described to furnish the desired active chemokine (SEQ ID NO: 227).

H-SPYSSDTTPCCFAYIARPLPRAHIKEYFYTSGKCSNPAVVFVTRKN

RQVCANPEKKWVREYINSLEXS-OH

X is an amino acid residue that can be biotinylated, such as lysine, ornithine or diaminopropionic acid and optionally is biotinylated, optionally via a spacer molecule such as PEG (e.g. K(Biotin))

Electrospray ionisation with tandem mass spectrometry (ESI-TOF-MS) data of purified folded biotinRANTES: obtained=8068.9 Da; expected 8070.2 Da.

Functional Assay Data:

BiotinRANTES was tested for agonist activity in an Aequorin assay against hCCR5, (Euroscreen) and an EC50 value of 0.5 nM was reported.

Example 133

BiotinMCP-2 (CCL8)

Target Molecule:

MCP-2 derivatised at the e-amino side chain functionality of Lys(75) with PEG-Biotin (TFA salt)

Modifications:

Human MCP-2 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the ε-amino functionality and the biotin.

The linear amino acid sequence (SEQ ID NO: 222) is shown, prior to attachment of the PEG spacer and biotin molecules at amino acid 75 (K):

H-XPDSVSIPITCCFNVINRKIPIQRLESYTRITNIQCPKEAVIFKTK

RGKEVCADPKERWVRDSMKHLDQIFQNLKP-NH$_2$

X=pyroGlu or Gln

The engineered MCP-2 sequence was assembled on a solid support (Rink Amide resin), using Fmoc protocols for solid-phase peptide synthesis as described in the general protocols section:

H-XPDSVSIPITCCFNVINRKIPIQRLESYTRITNIQCPKEAVIFKTK

RGKEVCADPKERWVRDSMKHLDQIFQNLXP-NH$_2$

X1=pyroGlu or Gln
X75=K(ivDde)

FmocLys(ivDde)-OH was incorporated as residue 75 to facilitate site-specific labelling at this position of the protein (SEQ ID NO: 223). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 224):

H-XPDSVSIPITCCFNVINRKIPIQRLESYTRITNIQCPKEAVIFKTK

RGKEVCADPKERWVRDSMKHLDQIFQNLXP-NH$_2$

X1=pyroGlu or Gln

X75=an amino acid residue that can be biotinylated, such as lysine, ornithine or diaminopropionic acid and optionally is biotinylated, optionally via a spacer molecule such as PEG, e.g. K(PEG-Biotin).

Electrospray ionisation with tandem mass spectrometry (ESI-TOF-MS) data of purified folded biotinMCP-2: obtained=9263.6 Da; expected 9263.8 Da.

Functional Assay Data:

biotinMCP-2 was tested for activity in an Aequorin assay against hCCR2b, (Euroscreen) and was shown to be a partial agonist with an EC50 value of 50.9 nM. c.f. EC50 for recombinant native MCP-2 is 23.5 nM (partial agonist).

Example 134

BiotinMIP-3b (CCL19)

Target Molecule:

MIP-3b derivatised at the e-amino side chain functionality of Lys(78) with Biotin (TFA salt)

Modifications:

Human MIP-3b corresponding to residues 1-77, is initially expressed as 98 amino acids comprising the chemokine fold, and a 21 amino acid signal peptide which is cleaved off. An additional lysine was inserted at the C-terminus, at position 78, and modified through biotinylation on the resin.

The linear amino acid sequence (SEQ ID NO: 228) is shown, prior to attachment of the biotin molecule at amino acid 78 (K):

H-GTNDAEDCCLSVTQKPIPGYIVRNFHYLLIKDGCRVPAVVFTTLRG

RQLCAPPDQPWVERIIQRLQRTSAKMKRRSSX-NH$_2$

X is an amino acid residue that can be biotinylated, such as lysine, ornithine or diaminopropionic acid and optionally is biotinylated (e.g. K-biotin), optionally via a spacer molecule such as PEG, in particular K(PEG-Biotin)

The engineered MIP-3b sequence was assembled on a solid support (Rink Amide resin), using Fmoc protocols for solid-phase peptide synthesis as described in the general protocols section:

H-GTNDAEDCCLSVTQKPIPGYIVRNFHYLLIKDGCRVPAVVFTTLRG

RQLCAPPDQPWVERIIQRLQRTSAKMKRRSSX-RESIN

X is FmocLys(ivDde)

FmocLys(ivDde)-OH was incorporated as residue 78 to facilitate site-specific labelling at this position of the protein (SEQ ID NO: 229). Subsequent removal of the ivDde protecting group, followed by coupling of the Biotin, was carried out as described in the general protocol section. Cleavage, purification and folding protocols were carried out as described to furnish the desired active chemokine (SEQ ID NO: 230).

H-GTNDAEDCCLSVTQKPIPGYIVRNFHYLLIKDGCRVPAVVFTTLRG

RQLCAPPDQPWVERIIQRLQRTSAKMKRRSSX-NH$_2$

X is K(Biotin)

Electrospray ionisation with tandem mass spectrometry (ESI-TOF-MS) data of purified folded biotinMIP-3b: obtained=9148.8 Da; expected 9149.7 Da.

Functional Assay Data:

biotinMip-3b was tested for agonist activity in an Aequorin assay against hCCR7, (Euroscreen) and an EC50 value of 11.0 nM was reported. c.f. EC50 for recombinant native MIP-3b is 1.6 nM.

Example 135

BiotinIL-8 (CXCL8)

Target Molecule:

IL-8 derivatised at the e-amino side chain functionality of Lys(78) with PEG-Biotin (TFA salt)

Modifications:

Human IL-8 corresponding to residues 1-77, is initially expressed as 99 amino acids comprising the chemokine fold, and a 22 amino acid signal peptide which is cleaved off. An additional lysine was inserted at the C-terminus at position 78, and modified through biotinylation on the resin. A PEG spacer was incorporated between the e-amino functionality and the biotin.

The linear amino acid sequence (SEQ ID NO: 231) is shown, prior to attachment of the PEG spacer and biotin molecules:

H-AVLPRSAKELRCQCIKTYSKPFHPKFIKELRVIESGPHCANTEIIV

KLSDGRELCLDPKENWVQRVVEKFLKRAENSX-NH$_2$

X is an amino acid residue that can be biotinylated, such as lysine, ornithine or diaminopropionic acid and optionally is biotinylated, optionally via a spacer molecule such as PEG, e.g. K(PEG-Biotin)

The engineered IL-8 sequence was assembled on a solid support (Rink Amide resin), using Fmoc protocols for solid-phase peptide synthesis as described in the general protocols section:

H-AVLPRSAKELRCQCIKTYSKPFHPKFIKELRVIESGPHCANTEIIV

KLSDGRELCLDPKENWVQRVVEKFLKRAENSX-RESIN

X is K(ivDde)

FmocLys(ivDde)-OH was incorporated as residue 78 to facilitate site-specific labelling at this position of the protein (SEQ ID NO: 232). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 233):

H-AVLPRSAKELRCQCIKTYSKPFHPKFIKELRVIESGPHCANTEIIVKL

SDGRELCLDPKENWVQRVVEKFLKRAENSX-NH$_2$

X is K(PEG-Biotin)

Electrospray ionisation with tandem mass spectrometry (ESI-TOF-MS) data of purified folded biotinIL-8: obtained=9416.9 Da; expected 9417.0 Da.

Functional Assay Data:

BiotinIL-8 was tested for agonist activity in an Aequorin assay against hCXCR1, (Euroscreen) and an EC50 value of 18.9 nM was reported. c.f. EC50 for recombinant native IL-8 is 4.2 nM.

Example 136

BiotinIL-8 (6-78)

Target Molecule:

IL-8 (6-78) derivatised at the e-amino side chain functionality of Lys(78) with PEG-Biotin (TFA salt)

Modifications:

Truncated form of IL-8 corresponding to residues 6-77, the first five N-terminal residues have been removed and an additional lysine was inserted at the C-terminus at position 78, and modified through biotinylation on the resin. A PEG spacer was incorporated between the e-amino functionality and the biotin.

The linear amino acid sequence (SEQ ID NO: 234) is shown, prior to attachment of the PEG spacer and biotin molecules:

H-SAKELRCQCIKTYSKPFHPKFIKELRVIESGPHCANTEIIVKLSDGRE

LCLDPKENWVQRVVEKFLKRAENSX-NH$_2$

X is an amino acid residue that can be biotinylated, such as lysine, ornithine or diaminopropionic acid and optionally is biotinylated, optionally via a spacer molecule such as PEG The engineered IL-8 sequence was assembled on a solid support (Rink Amide resin), using Fmoc protocols for solid-phase peptide synthesis as described in the general protocols section:

H-SAKELRCQCIKTYSKPFHPKFIKELRVIESGPHCANTEIIVKLSDGRE

LCLDPKENWVQRVVEKFLKRAENSX-RESIN

X is K(ivDde)

FmocLys(ivDde)-OH was incorporated as residue 78 to facilitate site-specific labelling at this position of the protein (SEQ ID NO: 235). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 236):

H-SAKELRCQCIKTYSKPFHPKFIKELRVIESGPHCANTEIIVKLSDGRE

LCLDPKENWVQRVVEKFLKRAENSX-NH$_2$

X is K(PEG-Biotin)

Electrospray ionisation with tandem mass spectrometry (ESI-TOF-MS) data of purified folded biotinIL-8 (6-78): obtained=8880.50 Da; expected 8880.4 Da.

Functional Assay Data:

BiotinIL-8 (6-78) was tested for agonist activity in an Aequorin assay against hCXCR1, (Euroscreen) and an EC50 value of 6.1 nM was reported. c.f. EC50 for recombinant native IL-8 is 4.2 nM.

Example 137

BiotinEotaxin (CCL11)

Target Molecule:

Eotaxin derivatised at the ε-amino side chain functionality of Lys(73) with PEG-Biotin (TFA salt)

Modifications:

Human eotaxin corresponding to residues 1-74, is initially expressed as 97 amino acids comprising the chemokine fold, and a 23 amino acid signal peptide which is cleaved off. The naturally occurring lysine at position 73 was modified through biotinylation on the resin. A PEG spacer was incorporated between the ε-amino functionality and the biotin.

The linear amino acid sequence (SEQ ID NO: 237) is shown, prior to attachment of the PEG spacer and biotin molecules at amino acid 73 (K):

H-GPASVPTTCCFNLANRKIPLQRLESYRRITSGKCPQKAVIFKTKLAKD

ICADPKKKWVQDSMKYLDQKSPTPXP-NH₂

X is an amino acid residue that can be biotinylated, such as lysine, ornithine or diaminopropionic acid and optionally is biotinylated, optionally via a spacer molecule such as PEG, e.g. K(PEG-Biotin).

The engineered eotaxin sequence was assembled on a solid support (Rink Amide resin), using Fmoc protocols for solid-phase peptide synthesis as described in the general protocols section:

H-GPASVPTTCCFNLANRKIPLQRLESYRRITSGKCPQKAVIFKTKLAKD

ICADPKKKWVQDSMKYLDQKSPTPXP-NH₂

X is K(ivDde)

FmocLys(ivDde)-OH was incorporated as residue 73 to facilitate site-specific labelling at this position of the protein (SEQ ID NO: 238). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 239):

H-GPASVPTTCCFNLANRKIPLQRLESYRRITSGKCPQKAVIFKTKLAKD

ICADPKKKWVQDSMKYLDQKSPTPXP-NH₂

X is K(PEG-Biotin)

Electrospray ionisation with tandem mass spectrometry (ESi-TOF-MS) data of purified folded biotinEotaxin: obtained=8731.3 Da; expected 8731.3 Da.

Functional Assay Data:

biotinEotaxin was tested for activity in an Aequorin assay against hCCR3, (Euroscreen) and was shown to be an antagonist with an EC50 value of 211.8 nM. c.f. EC50 for recombinant native eotaxin is 10.7 nM (agonist).

Example 138

Diagnosis and Treatment of Sarcoidosis

Materials and Methods

1. Flow Cytometric Analysis of Peripheral Blood

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5) for 15 min at 37° C. The cells were washed in PBS with 2% Bovine Growth Serum, incubated with 10% human serum for 15 min at room temperature (RT) and stained with antibodies (Table 28) at 4° C. for 30 min. The cells were analysed by flow cytometry on a FACS Canto flow cytometer with the FACSDiva software (BD Biosciences).

TABLE 29

List of antibodies for flow cytometric analysis.

| Antibody | Fluorophore | Supplier |
|---|---|---|
| CCR1 | Alexa flour 647 | Biolegend |
| CCR2 | PerCPCy5.5 | Biolegend |
| CCR7 | PerCpCy5.5 | Biolegend |
| CD4 | V500 | BD |
| CD3 | Horizon V450 | BD |
| Streptavdin | APC | BD |
| CD14 | FITC | Beckman Coulter |
| CD45RA | PECy7 | BD |

2. Chemokine Binding Test

Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5) for 15 min at 37° C. The cells were washed in PBS with 2% Bovine Growth Serum, incubated with 10% human serum 15 min at room temperature (RT) and stained with cell specific antibodies together with biotinylated chemokine (1 μM) or the corresponding chemokine receptor antibody at 4° C. for 30 min (Table 29). The biotinylated chemokine was detected via the interaction between biotin and a fluorophore conjugated Streptavidin. The samples were analysed by flow cytometry on a FACS Canto flow cytometer with the FACSDiva software (BD Biosciences).

3. Cell Depletion by Matrix Conjugated with Biotinylated Chemokine

Cells were prepared from peripheral blood (section 1). 1 mL Sepharose BigBeads matrix conjugated with 0.4 mg/mL Streptavidin (GE Healthcare) was washed in 50 mL PBS and added to a 5 mL polystyrene tube (BD Falcon™). Biotinylated chemokine was added to the tube and incubated for 20 min at RT to enable immobilization of the chemokine on the matrix via the biotin-streptavidin interaction. Next, the cells were added to the chemokine-matrix and incubated for 20 min at RT. The cells that did not bind to the matrix were removed by washing the matrix with PBS in a sterile 40 um nylon filter (BD Falcon™ Cell Strainer). The flow through cells were stained with antibodies (Table 29), analysed by flow cytometry and compared with cells from peripheral blood that had not been incubated with the chemokine-matrix.

Results and Discussion

White blood cells from 2 patients with sarcoidosis were analysed for the expression of chemokine receptors with flow cytometry. The patients exhibited increased frequency of monocytes that expressed the receptor CCR1 based upon flow cytometry data and binding of an anti-CCR1 antibody (FIG. 161).

The ligand for CCR1 is the chemokine RANTES that also binds to CCR5 expressed on T cells. RANTES is expressed in the lungs where it mediates migration of inflammatory cells. The monocytes bind biotinylated RANTES to the same extent as the chemokine receptor expression (FIG. 162).

The CCR1 expressing monocytes could be efficiently depleted with bRANTES-conjugated Sepharose Streptavidin Matrix (FIG. 163).

In addition to CCR1, the monocytes express the chemokine receptor CCR2 (FIG. 164), based upon flow cytometry data and binding of an anti-CCR2 antibody.

The ligand for CCR2 is MCP-1 that mediate migration of monocytes in inflammation. In accordance with the CCR2 expression, biotinylated MCP-1 (bMCP-1) could bind to blood monocytes from a sarcoidosis patient (FIG. 165).

The CCR2 expressing monocytes could be depleted with bMCP1-conjugated Sepharose Streptavidin Matrix (FIG. 166).

The sarcoidosis patients exhibit an increased frequency of circulating T cells that express the chemokine receptor CCR7 (FIG. 167a), based upon flow cytometry data and binding by an anti-CCR7 antibody. Furthermore, the frequency of central memory T cells, which are characterized as CCR7 positive, is increased in sarcoidosis. (FIG. 167b). Central memory T cells contribute to inflammation by mounting a fast and strong immune response the second time the inflammation is triggered, and may be responsible for relapsing sarcoidosis.

The ligand for CCR7 is MIP3b. The CCR7 expressing T cells could be efficiently depleted with bMIP3b-conjugated Sepharose Streptavidin Matrix (FIG. 168)

We conclude that the frequency of CCR1 expressing monocytes and T cells that express CCR7 is enhanced in Sarcoidosis. The CCR2 receptor is expressed on monocytes from sarcoidosis patients to the same extent as in the healthy controls, but the CCR2 expressing cells could differ in their pro-inflammatory profile in the patients compared to healthy controls. Both monocytes and T cells bind the chemokines that corresponded with the expression of the chemokine receptor, and could be efficiently depleted with the corresponding biotinylated chemokine-Sepharose Streptavidin-matrix.

L. Treating Conditions Associated with Sepsis

Sepsis is defined as a systemic inflammation syndrome (SIRS) in response to an infection. If not successfully treated, it may lead to the potentially lethal Multiple Organ Dysfunction Syndrome. Thus, the invention may be aimed at treating SIRS and/or Multiple Organ Dysfunction Syndrome. In short, increased vascular permeability due to released inflammatory cytokines leads to decreased blood pressure. As a consequence, there is insufficient circulation in important organs such as kidneys and lungs, which may lead to organ dysfunction.

The exact cellular mechanism of the progress of SIRS is still unknown, but it has been shown that neutrophils show impaired migrational capacity into infected tissue in patients suffering from sepsis. The neutrophils act as the first line of defense against invading pathogens. If neutrophils cannot efficiently migrate into infected tissue the infection will persists which contributes to the systemic inflammation response.

In addition, in a later stage of SIRS, activated neutrophils migrate in to healthy tissue in remote organs (not affected by the infection) causing tissue destruction. The combination of organ dysfunction and tissue destruction may be fatal for the patient. Factors causing increased vascular permeability:

Proinflammatory molecules such interleukin1-beta, interleukin 6 and tumor necrosing factor-alpha, released by macrophages in the liver and the spleen and granulas released by mast cells.

Role of MCP-1/CCL2 and the CCR2 receptor in sepsis-Neutrophils stimulated by bacterial antigen lipopolysaccharide through Toll-Like Receptors upregulate MCP-1 receptor CCR2. Neutrophils do not normally express CCR2. Interestingly, migration of neutrophils into healthy tissue is mediated through CCR2.

It has been shown that CCR2 plays an important role in the recruitment of neutrophils in a variety of models of inflammation in addition it has been shown that a CCR2 antagonist reduces the severity of acute lung injury.

It may be possible to protect the patient from tissue destruction in remote organs by removing activated neutrophils through the MCP-1/CCR2 interaction.

Chemokine receptor-Chemokine pairs of relevance to the present invention thus include:
CCR2-MCP-1
CXCL1, CXCL2, CXCL3, CXCL5, CXCL6, CXCL7 and CXCL8-CXCR2
CXCL8-CXCR1
CCR5-CCL5, CCL3, CCL8

The invention may also be directed to treating RDS, including but not limited to sepsis-associated RDS. The RDS treated according to the invention is typically acute respiratory distress syndrome (ARDS). Three clinical settings account for 75% of ARDS cases: sepsis, severe multiple trauma and aspiration of saliva/gastric contents. Sepsis is the most common cause of ARDS (referred to herein as sepsis-associated RDS). Some cases of ARDS are linked to large volumes of fluid used during resuscitation post trauma. Other causes include shock, near-drowning, multiple transfusions and inhalation of irritants or toxic fumes that damage the alveolar epithelium. It is shown herein that patients suffering from respiratory distress syndrome (RDS) exhibit an increase in circulating neutrophils compared to healthy controls. The neutrophils express characteristic chemokine receptors including CXCR1, CXCR2 and CCR5. This provides a therapeutic approach to treat this condition, by removal of CXCR1, CXCR2 and/or CCR5 expressing cells using a suitable binding reagent. Moreover, it is also shown herein that CCR5 expressing neutrophils are highly increased in bronchoalveolar lavage fluid (BALF) in patients suffering from RDS. Thus, the invention may be applied to treat sepsis and/or RDS, including but not limited to sepsis-associated RDS.

Materials and Methods

Isolation of Peripheral Blood Leukocytes.

Heparinized peripheral blood from healthy blood donors or inflammatory bowel disease (IBD) patients was fixed with 4% paraformaldehyde for 4 minutes, hemolyzed for 15 minutes with a 0.83% ammonium chloride solution and washed twice in FACS buffer to obtain a suspension of blood leukocytes.

Chemokines.

The leukocytes were incubated for 30 min in the dark at 4° C. with biotinylated and Alexa647 Fluor® labelled MCP-1 or IL-8 (in concentrations 10 ng/μL and 50 ng/μL). The cells were then washed with FACS-buffer and analyzed by flow cytometry. All chemokines used in the Examples were provided by Almac Sciences Scotland Ltd, Edinburgh, Scotland.

Flow Cytometry Assay.

The flow cytometry assay was performed on a two laser FACS Calibur cytometer (BD Immunocytometry systems, San José, Ca, USA). Ten thousand cells were counted and analysed in each sample. For data analyses, Cell Quest Pro software from Becton Dickinson was used.

Example 139

Binding of Monocytes to MCP-1

In the experiment with biotinylated MCP-1 it was found that about 90% of the monocytes obtained from peripheral blood of healthy donors had bound to the cytokine after 30 min of incubation (FIG. 169a), whereas CD4+ and CD8+ lymphocytes had not bound (FIGS. 169b and 169c).

Example 140

Affinity of Blood Cells to Biotinylated IL-8

In FIG. 169 the binding to biotinylated IL-8 (CXCL8) of CD4+ lymphocytes (FIG. 1d), CD8+ lymphocytes (FIG. 169e) and CD16+ neutrophils (FIG. 169f) obtained from healthy donors is shown. After 30 min of incubation all CD16+ neutrophils bound to IL-8. In contrast no binding was observed with CD4+ lymphocytes and CD8+ lymphocytes.

Example 141

Monocytes were investigated for their expression of CCR2 (FIG. 170b) and their ability to bind MCP-1 (FIG. 170a). CCR2 expression was noted an all monocytes with the majority of monocytes expressing high levels, using an anti-CCR2 antibody (FIG. 170b). The MCP-1 binding to monocytes shown in FIG. 170a corresponds to the CCR2$^{hi}$ expressing population shown in FIG. 170b. Thus, MCP-1 binds favourably to CCR2$^{hi}$ expressing cells.

Example 142

Tailored Leukapheresis

Column Design and Properties
Introduction

Apheresis is an established treatment used for depletion of blood components, such as antibodies, low-density lipoproteins (LDL) and blood cells. Leukapheresis is the apheresis treatment used for removal of white blood cells, leukocytes. The patient is connected to an extracorporeal blood circulating system; the blood is drawn from a vein in one arm, passed through a column device and returned into the other arm of the patient. Side effects of leukapheresis treatments are varying from mild events like headache, dizziness, hypotension, palpitation and flush seen in 0.1 to 5% of treated patients.

The Column

The column is intended to be used as a leukapheresis treatment for sepsis. It will specifically remove CCR2, CXCR1, CXCR2 and/or CCR5-expressing leukocytes, in particular monocytes, through the use of a binding reagent, more specifically an MCP-1, MCP-2, MCP-3, MCP-4, MCP-5 and/or CXCL8 containing resin or a CCL5, CCL3 or CCL8 containing resin, exploiting the CCR2, CXCR1, CXCR2 and/or CCR5-chemokine interaction. The column consists of three combined components, the plastic house, the streptavidin (SA) Sepharose™ BigBeads matrix and one or more of biotinylated MCP-1, MCP-2, MCP-3, MCP-4, MCP-5, CXCL8, CCL5, CCL3 or CCL8 bound to the matrix. The treatment is conducted using the same techniques as a standard apheresis procedure.

The Plastic House (FIG. 9)

The plastic house, designed to keep a continuous blood flow through the matrix, consists of a transparent body and red-coloured top. The top has a distribution plate (2) at the inflow site (1) to spread the blood evenly over the entire matrix area. The plate is the first safety barrier preventing larger particles flowing through the column and into the patient. Safety filter units (3 and 4) are placed at the inflow (1) and outflow (5) sites of the plastic housing. The safety filter unit contains three filters designed to be a robust barrier and stop all particles larger than blood cells passing through the column. The plastic housing design is shown in FIG. 9. The design with safety filters (3 and 4) at both ends of the column device will minimize the risk of leakage of particles into the patient, including in the event that the device is placed up side down with the blood flow in the opposite direction to that anticipated.

Streptavidin Sepharose™ BigBeads

The second component in the device is the affinity matrix called streptavidin Sepharose™ BigBeads (Sepharose™ GE Healthcare, Sweden). Sepharose™ is a cross linked, beaded-form of agarose, which is a polysaccharide extracted from seaweed. Sepharose™ and agarose are commonly used as column matrices in biomedical affinity techniques. It is chosen for its optimal distribution capacity and can provide a large available area for affinity binding.

Binding Reagent

Coupled to the matrix is the third component of the device, one or more binding reagents that bind specifically to CCR2, CXCR1, CXCR2 and/or CCR5. One or more chemokines selected from the group consisting of: MCP-1, MCP-2, MCP-3, MCP-4, MCP-5 and CXCL8 may be employed and/or CXCL1, CXCL2, CXCL3, CXCL5, CXCL6, CXCL7 and CXCL8 or CCL5, CCL3 or CCL8 (bind CCR5). These peptides may be synthetic, engineered versions of the human chemokine, which are truncated and biotinylated, but retain binding activity to the CCR2, CXCR1, CXCR2 and/or CCR5 receptor. By biotinylating the engineered chemokine, it is able to bind to the streptavidin molecules in the Sepharose™ matrix. The biotin-streptavidin binding is known be one of the strongest biological interactions with a Kd in the order of $4 \times 10^{-14}$ M. The calculated ratio of streptavidin:biotin binding sites in the column is 10:1. Therefore, the coupling between the matrix and chemokine will be immediate, minimising the risk of chemokine decoupling from the matrix.

The Apheresis System

To conduct the leukapheresis the following components are needed; the column, tubing system, and a 4008 ADS pump (Fresenius Medical Care).

The Circuit

The system is illustrated in FIG. 10. The patient (1) is connected to the extracorporeal circuit via sterile Venflon needles to veins in the right and the left arms. A saline bag (3) is also connected and the saline solution is pumped with an ACD pump (2). Blood is drawn from one arm of the patient through the sterile tubing system by the blood pump (4) and passed through the column (6) and back to the patient. The tubing system is connected to the column via standard dialysis luer-lock couplings. The couplings on the column are colour-coded for correct assembly; red tubing for inflow to the red column top and blue tubing for outflow back to the patient. An air detector (8) is present. Inlet pressure (5) and Pven sensors (7) are employed to monitor the pressure in the circuit.

The 4008 ADS Pump

An apheresis pump, from Fresenius Medical Care, monitors the patient's inflow and outflow, the pressure in the extracorporeal circulation and can discriminate air by a bubble catcher and air detector. A clot catcher filter is placed inside the bubble catcher. The pump also has an optical detector to distinguish between light, e.g. saline solution or air present in the tubing system and dark e.g. blood present in the tubing system.

A schematic diagram of the pump, showing the air detector and optical filter is shown in FIG. 11. If the pump system detects air bubbles and optical fluctuations or if extracorporeal pressure values are out of the set range, then the pump stops immediately and a visual/audible alarm are emitted.

LEGEND FOR FIG. 11

1. Monitor
2. Holder for waste bag
3. Modules (left to right—Blood pump, ACD pump, Air detector)
4. Reserve places for further modules
5. Absorber holder
6. Drip detector
7. IV pole Preparation of the Patient The patient will be administered anticoagulants prior to each treatment session. A sterile saline solution with 5000 IE Heparin will be used for priming the extracorporeal system, thereafter a bolus injection with 4000 IE Heparin will be added into the circuit at the start of each treatment session.

Leukapheresis Time and Flow Rate

The apheresis system should be operated at a flow rate of 30-60 mL/min. A treatment is finalised after 1800 mL of blood has been circulated.

Storage Conditions

The column devices should be stored between 1 and 25° C. avoiding freezing and more elevated temperatures. Stability data >3 months indicate no difference in functionality over time or by temperature (room temperature and refrigerated). The columns will be kept in refrigerated conditions until use. Mechanical damage as those resulting from violent vibrations and trauma should be avoided. Column stored outside of these recommendations should not be used.

Transport Conditions

The column devices will be transported under refrigerated condition, avoiding freezing and more elevated temperatures. Mechanical damage such as those resulting from violent vibrations and trauma should be avoided.

In-Vitro Depletion of Target Cell Populations

To investigate the ability to eliminate CCR2-expressing cells, in vitro tests have been performed on the bMCP-1 coupled matrix. Blood was collected from blood donors and passed through the column device containing bMCP-1 coupled matrix. Blood samples were taken before and after column passage and analyzed by flow cytometry (FACS) for the depletion of CCR2-expressing cells.

The results demonstrate significant depletion of the target population CCR2-expressing monocytes post matrix perfusion. Depletion tests were performed on blood from three healthy donors. The results are shown in FIG. 171.

The in-vitro results demonstrate a specific reduction of up to 80% of the CCR2-expressing cells by the column. Notably, individuals with fewer CCR2 expressing cells initially achieved lower depletion. The remaining levels of monocytes were around 20-30% in each case, irrespective of the starting point. Non-CCR2-expressing cells remained unaffected (data not shown).

Example 143

MCP1 Derivatives

MCP-1 has been produced with residue 75 as the site of biotinylation on the chemokine (numbering based upon the mature protein having the amino acid sequence of SEQ ID NO: 2). Biotinylation permits immobilization of MCP-1 on a solid support (via a biotin-avidin interaction). The basic amino acid sequence of MCP-1, including a 23 amino acid leader sequence is set forth as SEQ ID NO: 240,

```
MKVSAALLCL LLIAATFIPQ GLAQPDAINA PVTCCYNFTN

RKISVQRLAS YRRITSSKCP KEAVIFKTIV AKEICADPKQ

KWVQDSMDHL DKQTQTPKT
```

The amino acid sequence of the mature protein is set forth as SEQ ID NO: 241,

```
QPDAINA PVTCCYNFTN RKISVQRLAS YRRITSSKCP

KEAVIFKTIV AKEICADPKQ KWVQDSXDHL DKQTQTPKT
```

X=Met or Nleu

The inventors have determined that chemokines may display improved binding properties where the chemokine is biotinylated via a spacer group. The spacer may prevent the biotin group from impacting on the binding affinity of the chemokine.

Thus, MCP-1 derivatised at the ε-amino side chain functionality of Lys75 with PEG-Biotin (TFA salt) will be synthesised. The PEG spacer will be 3,6,-dioxoaminooctanoic acid. The Gln at the N-terminus of the proteins is subject to pyroGlu formation under physiological conditions. Thus the first glutamine (Gln1) of the sequence will be substituted with pyroglutamine. The molecule will be synthesised as a C-terminal amide (via synthesis on an amide linker). The molecule is shown schematically in FIG. 172.

A biotinMCP-1 Met to Nleu analogue will also be synthesised. The single methionine within the sequence will be altered to Norleucine, to mitigate against oxidation of this residue during the chain assembly and improve stability of the final product. This molecule is shown schematically in FIG. 173 and in SEQ ID NO: 241.

Once synthesised, the activity of the various biotinMCP-1 derivatives will be determined in cell-based assays. In particular, agonist and antagonist properties will be determined in aequorin functional cell-based assay on human CCR2 receptor.

Example 144

Synthesis of a CCR2 Antagonist biotinMCP-1 which Binds to the Receptor without Activation Antagonist Activity (J-H Gong and I. Clark-Lewis, J. Exp. Med., 1995, 181, 63) has been shown for an MCP-1 derivative truncated at the N-terminus. In particular, deletion of residues 1-8, results in binding to CCR2 with Kd 8.3 nM. This protein was unable to cause chemotaxis of CCR2 positive cells. (inhibition of chemotaxis IC50 20 nM)

The amino acid sequence of the truncated version is set forth as SED ID NO: 242:

```
VTCCYNFTN RKISVQRLAS YRRITSSKCP KEAVIFKTIV

AKEICADPKQ KWVQDSMDHL DKQTQTPKT
```

A derivative of this truncated version will be synthesised comprising residues 9 to 76 of the mature protein (MCP-1 9-76) with Met64 to Nleu substitution and derivatised at the ε-amino side chain functionality of Lys75 with PEG-Biotin (TFA salt). This molecule is shown schematically in FIG. 174. The PEG spacer will be 3,6,-dioxoaminooctanoic acid. Once synthesised, the activity of the various biotinMCP-1 derivatives will be determined in cell-based assays. In particular, agonist and antagonist properties will be determined in aequorin functional cell-based assay on human CCR2 receptor.

Example 145

Demonstrate Removal of CCR2 Expressing Cells Using an Alternative Chemokine Ligand to MCP-1

CCR2 also binds chemokines MCP-2, MCP-3, MCP-4 and MCP-5 in addition to MCP-1. MCP-5 only binds CCR2 and should be selective in its removal of CCR2 expressing cells. MCP5 is a mouse chemokine shown to chemotact human CCR2 cells with EC50<3 nM.

The full length amino acid sequence, including the signal peptide, is set forth as SEQ ID NO: 243

```
MKISTLLCLL LIATTISPQV LAGPDAVSTP VTCCYNVVKQ

KIHVRKLKSY RRITSSQCPR EAVIFRTILD KEICADPKEK

WVKNSINHLD KTSQTFILEP SCLG
```

The amino acid sequence of N-terminal processed MCP-5 chemokine is 82 amino acids long and is set forth as SEQ ID NO: 244

```
GPDAVSTP VTCCYNVVKQ KIHVRKLKSY RRITSSQCPR

EAVIFRTILD KEICADPKEK WVKNSINHLD KTSQTFILEP SCLG
```

An amino acid sequence alignment suggests that MCP-5 has a C-terminal extension when compared to the amino acid sequence of MCP-1. The results of this alignment are shown in FIG. 175. On this basis a C-terminal truncated version of MCP-5 will be synthesised. This truncated version will comprise MCP-5 residues 1-76, set forth as SEQ ID NO: 245:

```
GPDAVSTP VTCCYNVVKQ KIHVRKLKSY RRITSSQCPR

EAVIFRTILD KEICADPKEK WVKNSINHLD KTSQTFIL
```

In the truncated version, Ile75 to be substituted with Lys, set forth as SEQ ID NO: 246:

```
GPDAVSTP VTCCYNVVKQ KIHVRKLKSY RRITSSQCPR

EAVIFRTILD KEICADPKEK WVKNSINHLD KTSQTFXL
```

X is an amino acid residue that can be biotinylated, such as lysine, ornithine or diaminopropionic acid and optionally is biotinylated, optionally via a spacer molecule such as PEG, e.g. K(PEG-Biotin)

Following substitution, the substituted version will be biotinylated at position 75, a lysine or other suitable residue such as ornithine or diaminopropanoic acid via A PEG spacer (3,6,-dioxoaminooctanoic acid). The protein will be synthesised on an amide linker to yield a C-terminal amide derivative. This molecule is shown schematically in FIG. 11. Once synthesised, the activity of the various biotinMCP-5 derivatives will be determined in cell-based assays. In particular, agonist and antagonist properties will be determined in aequorin functional cell-based assay on human CCR2 receptor.

Further Chemokine Examples

General Protocols

Assembly:
Chemical synthesis of chemokines was performed using standard Fmoc solid phase peptides synthesis (SPPS) techniques on an ABI 433 peptide synthesiser. DIC (0.5 M in DMF) and OxymaPure (0.5 M in DMF) were used for activation, acetic anhydride (0.5 M in DMF) for capping, and 20% piperidine in DMF for Fmoc deprotection. Rink Amide resin was utilised for the generation of C-terminal amide chemokines and Wang resin for C-terminal acid chemokines. After assembly, the resin was washed with DMF and DCM and then dried in vacuo.

Removal of Dde Protection:
The Dde protecting group was removed by treatment of resin with a solution of 2.5% hydrazine in DMF (200 ml) over a 2 hour period. The resin was then washed with DMF.

Labelling Steps:
1. Couple Fmoc-8-Amino-3,6-Dioctanoic Acid (PEG)
Resin was swollen in DMF and then a solution of Fmoc-8-amino-3,6-dioctanoic acid (0.38 g, 1 mmol), DIC solution (2 ml, 0.5 M in DMF) and OxymaPure solution (2 ml, 0.5 M in DMF) was added. The mixture was sonicated for 3 hours and then washed with DMF.

2. Capping
The resin was capped with acetic anhydride solution (0.5 M in DMF, 10 ml) for 5 minutes and then washed with DMF.

3. Fmoc Deprotection
Fmoc deprotection was carried out by treatment with 20% piperidine in DMF solution (2×50 ml) for 15 minutes each. The resin was washed with DMF.

4. Couple Biotin-OSu
A solution of Biotin-OSu (341 mg, 1 mmol) and DIPEA (348 ml) in DMF (10 ml) was added to the resin and the mixture was sonicated for 3 hours. The resin was washed thoroughly with DMF and DCM then dried in vacuo.

Cleavage:
Dry resin was treated with TFA (10 ml) containing a scavenger cocktail consisting of TIS (500 ml), thioanisole (500 ml), water (500 ml), DMS (500 ml), EDT (250 ml), NH₄I (500 mg) and phenol (500 mg) and the mixture was stirred at room temperature for 5 hours. The solution was filtered into cold ether and the resin rinsed with TFA. The precipitated peptide was centrifuged, washed with ether, centrifuged and lyophilised.

Purification Protocol:
The crude peptide was purified by reverse phase HPLC (RP-HPLC) using a Jupiter C18, 250×21 mm column, 9 ml/min, eluting with an optimised gradient [Buffer A: water containing 0.1% TFA, Buffer B: acetonitrile containing 0.1% TFA].

Folding Protocol:

Pure peptide (10 mg) was dissolved into 6M GnHCl (16 ml) and then rapidly diluted to 2M GnHCl concentration by the addition of 50 mM TRIS pH 8.5 (84 ml) containing 0.3 mM GSSG and 3 mM GSH. The mixture was stirred at room temperature for 24 hours and then analysed by RP-HPLC (Jupiter C18, 250×4.6 mm column, 10-60% B over 30 minutes. Purification by RP-HPLC using an optimised gradient afforded the desired product.

Example 146

BiotinMCP-1 (CCL2)

Target Molecule:

MCP-1 derivatised at the e-amino side chain functionality of Lys(75) with PEG-Biotin (TFA salt)

Modifications:

Human MCP-1 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the ε-amino functionality and the biotin.

The linear amino acid sequence (SEQ ID NO: 247) is shown, prior to attachment of the PEG spacer and biotin molecules at amino acid 75 (K):

H-XPDAINAPVTCCYNFTNRKISVQRLASYRRITSSKCPKEAVIFKTIVA

KEICADPKQKWVQDSMDHLDKQTQTPKT-NH$_2$

X=pyroGlu or Gln

The engineered MCP-1 sequence was assembled on a solid support (Rink Amide resin), using Fmoc protocols for solid-phase peptide synthesis as described in the general protocols section:

H-XPDAINAPVTCCYNFTNRKISVQRLASYRRITSSKCPKEAVIFKTIVA

KEICADPKQKWVQDSMDHLDKQTQTPXT-RESIN

X1=pyroGlu or Gln
X75=K(ivDde)

FmocLys(ivDde)-OH was incorporated as residue 75 to facilitate site-specific labelling at this position of the protein (SEQ ID NO: 248). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 249):

H-XPDAINAPVTCCYNFTNRKISVQRLASYRRITSSKCPKEAVIFKTIVA

KEICADPKQKWVQDSMDHLDKQTQTPXT-NH$_2$

X1=pyroGlu or Gln
X75=an amino acid residue that can be biotinylated, such as lysine, ornithine or diaminopropionic acid and optionally is biotinylated, optionally via a spacer molecule such as PEG, e.g. K(PEG-Biotin).

Electrospray ionisation with tandem mass spectrometry (ESI-TOF-MS) data of purified folded biotinMCP-1: obtained=9032.8 Da; expected 9034.4 Da.

Functional Assay Data:

biotinMCP-1 was tested for agonist activity in an Aequorin assay against hCCR2b, (Euroscreen) and an EC50 value of 9.6 nM was reported. c.f. EC50 for recombinant native MCP-1 is 3.1 nM.

Example 147

BiotinMCP-2 (CCL8)

Target Molecule:

MCP-2 derivatised at the e-amino side chain functionality of Lys(75) with PEG-Biotin (TFA salt)

Modifications:

Human MCP-2 corresponding to residues 1-76, is initially expressed as 99 amino acids comprising the chemokine fold, and a 23 amino acid signal peptide which is cleaved off. The Gln at the N-terminus of the protein is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 75 was modified through biotinylation on the resin. A PEG spacer was incorporated between the ε-amino functionality and the biotin.

The linear amino acid sequence (SEQ ID NO: 250) is shown, prior to attachment of the PEG spacer and biotin molecules at amino acid 75 (K):

H-XPDSVSIPITCCFNVINRKIPIQRLESYTRITNIQCPKEAVIFKTKRG

KEVCADPKERWVRDSMKHLDQIFQNLKP-NH$_2$

X=pyroGlu or Gln

The engineered MCP-2 sequence was assembled on a solid support (Rink Amide resin), using Fmoc protocols for solid-phase peptide synthesis as described in the general protocols section:

H-XPDSVSIPITCCFNVINRKIPIQRLESYTRITNIQCPKEAVIFKTKRG

KEVCADPKERWVRDSMKHLDQIFQNLXP-NH$_2$

X1=pyroGlu or Gln
X75=K(ivDde)

FmocLys(ivDde)-OH was incorporated as residue 75 to facilitate site-specific labelling at this position of the protein (SEQ ID NO: 251). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 252):

H-XPDSVSIPITCCFNVINRKIPIQRLESYTRITNIQCPKEAVIFKTKRG

KEVCADPKERWVRDSMKHLDQIFQNLXP-NH$_2$

X1=pyroGlu or gln
X75=an amino acid residue that can be biotinylated, such as lysine, ornithine or diaminopropionic acid and optionally is biotinylated, optionally via a spacer molecule such as PEG, e.g. K(PEG-Biotin).

Electrospray ionisation with tandem mass spectrometry (ESI-TOF-MS) data of purified folded biotinMCP-2: obtained=9263.6 Da; expected 9263.8 Da.

Functional Assay Data:

biotinMCP-2 was tested for activity in an Aequorin assay against hCCR2b, (Euroscreen) and was shown to be a partial agonist with an EC50 value of 50.9 nM. c.f. EC50 for recombinant native MCP-2 is 23.5 nM (partial agonist).

Example 148

BiotinRANTES (CCL5)

Target Molecule:

RANTES derivatised at the e-amino side chain functionality of Lys(67) with Biotin (TFA salt)

Modifications:

Human RANTES corresponding to residues 1-68, is initially expressed as 91 amino acids comprising the chemokine fold, and a 23 amino acid signal peptide which is cleaved off. The single methionine (Met67) within the sequence was mutated to lysine, to mitigate against oxidation of this residue during the chain assembly, which was observed during the synthesis of the natural sequence derivative. This Met to Lys substitution provided a lysine at position 67 which was modified through biotinylation on the resin.

The linear amino acid sequence (SEQ ID NO: 253) is shown, prior to attachment of the biotin molecule at amino acid 67 (K):

H-SPYSSDTTPCCFAYIARPLPRAHIKEYFYTSGKCSNPAVVFVTRKNRQ

VCANPEKKWVREYINSLEKS-OH

The engineered RANTES sequence was assembled on a solid support (Wang resin), using Fmoc protocols for solid-phase peptide synthesis as described in the general protocols section:

H-SPYSSDTTPCCFAYIARPLPRAHIKEYFYTSGKCSNPAVVFVTRKNRQ

VCANPEKKWVREYINSLEXS-RESIN

X is K(ivDde)

FmocLys(ivDde)-OH was incorporated as residue 67 to facilitate site-specific labelling at this position of the protein (SEQ ID NO: 254). Subsequent removal of the ivDde protecting group, followed by coupling of the Biotin, was carried out as described in the general protocol section. Cleavage, purification and folding protocols were carried out as described to furnish the desired active chemokine (SEQ ID NO: 255).

H-SPYSSDTTPCCFAYIARPLPRAHIKEYFYTSGKCSNPAVVFVTRKNRQ

VCANPEKKWVREYINSLEXS-OH

X is an amino acid residue that can be biotinylated, such as lysine, ornithine or diaminopropionic acid and optionally is biotinylated, optionally via a spacer molecule such as PEG (e.g. K(Biotin))

Electrospray ionisation with tandem mass spectrometry (ESI-TOF-MS) data of purified folded biotinRANTES: obtained=8068.9 Da; expected 8070.2 Da.

Functional Assay Data:

BiotinRANTES was tested for agonist activity in an Aequorin assay against hCCR5, (Euroscreen) and an EC50 value of 0.5 nM was reported.

Example 149

BiotinIL-8 (CXCL8)

Target Molecule:

IL-8 derivatised at the e-amino side chain functionality of Lys(78) with PEG-Biotin (TFA salt)

Modifications:

Human IL-8 corresponding to residues 1-77, is initially expressed as 99 amino acids comprising the chemokine fold, and a 22 amino acid signal peptide which is cleaved off. An additional lysine was inserted at the C-terminus at position 78, and modified through biotinylation on the resin. A PEG spacer was incorporated between the e-amino functionality and the biotin.

The linear amino acid sequence (SEQ ID NO: 256) is shown, prior to attachment of the PEG spacer and biotin molecules:

H-AVLPRSAKELRCQCIKTYSKPFHPKFIKELRVIESGPHCANTEIIVKL

SDGRELCLDPKENWVQRVVEKFLKRAENSX-NH$_2$

X is an amino acid residue that can be biotinylated, such as lysine, ornithine or diaminopropionic acid and optionally is biotinylated, optionally via a spacer molecule such as PEG The engineered IL-8 sequence was assembled on a solid support (Rink Amide resin), using Fmoc protocols for solid-phase peptide synthesis as described in the general protocols section:

H-AVLPRSAKELRCQCIKTYSKPFHPKFIKELRVIESGPHCANTEIIVKL

SDGRELCLDPKENWVQRVVEKFLKRAENSX-RESIN

X is K(ivDde)

FmocLys(ivDde)-OH was incorporated as residue 78 to facilitate site-specific labelling at this position of the protein (SEQ ID NO: 257). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 258):

H-AVLPRSAKELRCQCIKTYSKPFHPKFIKELRVIESGPHCANTEIIVKL

SDGRELCLDPKENWVQRVVEKFLKRAENSK(PEG-Biotin)-NH$_2$

Electrospray ionisation with tandem mass spectrometry (ESI-TOF-MS) data of purified folded biotinIL-8: obtained=9416.9 Da; expected 9417.0 Da.
Functional Assay Data:
BiotinIL-8 was tested for agonist activity in an Aequorin assay against hCXCR1, (Euroscreen) and an EC50 value of 18.9 nM was reported. c.f. EC50 for recombinant native IL-8 is 4.2 nM.

Example 150

BiotinIL-8 (6-78)

Target Molecule:
IL-8 (6-78) derivatised at the e-amino side chain functionality of Lys(78) with PEG-Biotin (TFA salt)
Modifications:
Truncated form of IL-8 corresponding to residues 6-77, the first five N-terminal residues have been removed and an additional lysine was inserted at the C-terminus at position 78, and modified through biotinylation on the resin. A PEG spacer was incorporated between the e-amino functionality and the biotin.
The linear amino acid sequence (SEQ ID NO: 259) is shown, prior to attachment of the PEG spacer and biotin molecules:

H-SAKELRCQCIKTYSKPFHPKFIKELRVIESGPHCANTEIIVKLSDGRE

LCLDPKENWVQRVVEKFLKRAENSX-NH$_2$

X is an amino acid residue that can be biotinylated, such as lysine, ornithine or diaminopropionic acid and optionally is biotinylated, optionally via a spacer molecule such as PEG
The engineered IL-8 sequence was assembled on a solid support (Rink Amide resin), using Fmoc protocols for solid-phase peptide synthesis as described in the general protocols section:

H-SAKELRCQCIKTYSKPFHPKFIKELRVIESGPHCANTEIIVKLSDGRE

LCLDPKENWVQRVVEKFLKRAENSX-RESIN

X is K(ivDde)
FmocLys(ivDde)-OH was incorporated as residue 78 to facilitate site-specific labelling at this position of the protein (SEQ ID NO: 260). Subsequent removal of the ivDde protecting group, followed by coupling of the PEG spacer and Biotin, was carried out as described in the general protocol section. Cleavage, purification and folding protocols were carried out as described to furnish the desired active chemokine (SEQ ID NO: 261):

H-SAKELRCQCIKTYSKPFHPKFIKELRVIESGPHCANTEIIVKLSDGRE

LCLDPKENWVQRVVEKFLKRAENSX-NH$_2$

X is K(PEG-Biotin)
Electrospray ionisation with tandem mass spectrometry (ESI-TOF-MS) data of purified folded biotinIL-8 (6-78): obtained=8880.50 Da; expected 8880.4 Da.
Functional Assay Data:
BiotinIL-8 (6-78) was tested for agonist activity in an Aequorin assay against hCXCR1, (Euroscreen) and an EC50 value of 6.1 nM was reported. c.f. EC50 for recombinant native IL-8 is 4.2 nM.

Example 151

Diagnosis and Treatment of RDS

Materials and Methods
1. Flow Cytometric Analysis of Peripheral Blood Peripheral blood from patients and healthy controls was collected in heparin tubes.
The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5) for 15 min at 37° C. The cells were washed in PBS with 2% Bovine Growth Serum, incubated with 10% human serum for 15 min at room temperature (RT) and stained with antibodies (Table 30) at 4° C. for 30 min. The cells were analysed with flow cytometry on a FACS Canto flow cytometer with the FACSDiva software (BD Biosciences).

TABLE 30

List of antibodies for flow cytometric analysis.

| Antibody | Fluorophore | Supplier |
|---|---|---|
| CD14 | FITC | Beckman Coulter |
| CCR5 | PE | Biolegend |
| CXCR2 | PE | Biolegend |
| Streptavidin | PE, APC | Biolegend |
| CD16 | PE Cy7 | BD Biosciences |
| CXCR1 | APC | Biolegend |
| CD3 | V450 | BD Biosciences |
| CD14 | V500 | BD Biosciences |

2. Chemokine Binding Test
Peripheral blood from patients and healthy controls was collected in heparin tubes. The red blood cells were lysed using Fix Buffer (Phosphate Buffer Saline (PBS) citrate with 4% paraformaldehyde) for four minutes at 37° C. and Lysing buffer (PBS with 10 mM Tris and 160 mM NH4Cl, pH 7.5) for 15 min at 37° C. The cells were washed in PBS with 2% Bovine Growth Serum, incubated with 10% human serum 15 min at room temperature (RT) and stained with cell specific antibodies together with biotinylated chemokine (1 µM) or the corresponding chemokine receptor antibody at 4° C. for 30 min (Table 30). The biotinylated chemokine was detected via the interaction between biotin and a fluorophore conjugated Streptavidin. The samples were analysed by flow cytometry on a FACS Canto flow cytometer with the FACSDiva software (BD Biosciences).
3. Cell Depletion with Antibody and Magnetic Activated Cell Sorting (MACS)
Cells were prepared from peripheral blood (section 1) and kept in MACS buffer (PBS pH 7.2 supplemented with 2 mM EDTA and 0.5% bovine serum albumin (BSA)). The cells were incubated with an anti-CXCR1-APC antibody for 30 min at 4° C. Next, the cells were incubated with anti-APC microbeads for 15 min, 4° C. (Miltenyi Biotec). The cells were run through MACS® columns (Miltenyi Biotec) to enable binding of the CXCR1 positive cells.
The cells were then analysed with flow cytometry.
Results and Discussion
1. Flow Cytometric Analysis of Peripheral Blood
White blood cells from patients with respiratory distress syndrome (RDS) were analysed for cell surface markers with flow cytometry. The patients exhibited an increased frequency of circulating neutrophils, 73% compared to 45% in healthy controls (FIG. 178).

2. Chemokine Binding Test

The neutrophils expressed the chemokine receptors CXCR1 and CXCR2 based upon flow cytometry data and binding by anti-CXCR1 and CXCR2 antibodies (FIG. 179). Both these receptors bind IL-8, a very important pro-inflammatory chemokine that mediates migration of neutrophils to site of infection.

Biotinylated IL-8 (bIL-8) could bind to the neutrophils to the same extent as the receptor-specific antibody anti-CXCR1 (FIG. 180).

3. Cell Depletion with Antibody and Magnetic Activated Cell Sorting (MACS)

Furthermore, the neutrophils could be efficiently depleted with an anti-CXCR1 antibody and Magnetic Activated Cell Sorting (MACS) (FIG. 181).

We conclude that the frequency of neutrophils is increased in sepsis patients. The neutrophils express the IL-8 receptors CXCR1 and CXCR2 and can bind the ligand IL-8. Furthermore, the neutrophils can be depleted with an anti-CXCR1-antibody and MACS.

Example 152

In-Vitro Depletion of Target Cell Populations (CCR5)

To investigate the ability to eliminate CCR5-expressing cells, in vitro tests have been performed on the biotinylated RANTES coupled matrix. Blood was collected from blood donors and passed through the column device containing biotinylated RANTES coupled matrix. Blood samples were taken before and after column passage and analyzed by flow cytometry (FACS) for the depletion of CCR5-expressing cells.

The RANTES molecule was synthesized by Almac. The amino acid sequence of the RANTES molecule, prior to biotinylation, is set forth as SEQ ID NO: 253:

H2N-SPYSSDTTPCCFAYIARPLPRAHIKEYFYTSGKCSNPAVVFVTRKN

RQVCANPEKKWVREYINSLEKS-CO2H

This molecule has the naturally occurring methionine at position 67 replaced with lysine to facilitate biotinylation at position 67. The biotinylated version is shown as SEQ ID NO: 16.

The side-chain of Lys 67 was directly biotinylated to given the protein primary structure shown in FIG. 185. The protein was folded and disulphide bonds formed between the first and third cysteine in the sequence and between the 2nd and 4th cysteines. The results demonstrate significant depletion of the target population chemokine receptor-expressing cells post matrix perfusion. Depletion tests were performed on blood from a healthy donor. The results are shown in FIG. 186.

The in-vitro results demonstrate a specific reduction of around 20% of the chemokine receptor-expressing cells by the column. Non-CCR5-expressing cells remained unaffected (data not shown).

The various embodiments of the present invention are not to be limited in scope by the specific embodiments described herein. Indeed, various modifications of the various embodiments of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

---

We claim:

1. A method for treating inflammatory bowel disease comprising:
applying peripheral blood from a patient diagnosed as having inflammatory bowel disease to an apheresis column loaded with a solid support comprising one or more binding reagents capable of specifically binding to a marker of CD14$^+$HLA-DR$^{hi}$ monocytes comprising CD14, wherein the one or more binding reagents are immobilized directly or indirectly on the support thus removing CD14$^+$HLA-DR$^{hi}$ monocytes from the peripheral blood of the patient; and
returning the peripheral blood from which CD14$^+$HLA-DR$^{hi}$ monocytes are removed to the patient.

2. The method of claim 1 wherein the inflammatory bowel disease is ulcerative colitis or Crohn's disease.

3. The method of claim 1 wherein the binding reagent is an antibody or a chemokine.

4. The method of claim 1, further comprising selecting a patient for treatment, the patient having an increase in the level of chemokine receptors comprising CD14+ cells, or an increased fraction/cell number of CD14+CCR9 positive cells.

5. The method of claim 1 wherein the apheresis column is loaded with a solid support comprising at least two binding reagents capable of specifically binding to at least two markers of CD14$^+$HLA-DR$^{hi}$ monocytes, wherein at least one of said markers comprises CD14.

6. The method of claim 1 wherein the binding reagents are selected from an anti-CD14 antibody or a modified version thereof.

7. A method for treating inflammatory bowel disease comprising:
applying peripheral blood from a patient diagnosed as having inflammatory bowel disease to an apheresis column loaded with a solid support comprising one or more binding reagents capable of specifically binding to a marker of CD14$^+$HLA-DR$^{hi}$ monocytes is selected from CD14, CCR7, and CCR9 wherein the binding reagent is immobilized directly or indirectly on the support thus removing CD14$^+$HLA-DR$^{hi}$ monocytes from the peripheral blood of the patient; and
returning the peripheral blood from which CD14$^+$HLA-DR$^{hi}$ monocytes are removed to the patient, and
wherein the binding reagents is selected from CCL19 or a modified version thereof, and wherein the modified CCL19 chemokine comprises the amino acid sequence of SEQ ID NO: 4, and
wherein the amino acid residue at position 78 of SEQ ID NO: 4 is biotinylated, optionally via a spacer group, to permit immobilization of the chemokine on a solid support.

8. The method of claim 7, wherein the amino acid residue at position 78 of SEQ ID NO: 4 is a lysine residue which is biotinylated via a polyethylene glycol (PEG) spacer group, to permit immobilization of the chemokine on a solid support.

9. The method of claim 8, wherein the PEG spacer is 3,6-dioxo aminooctanoic acid.

* * * * *